US008017612B2

(12) United States Patent
Abe et al.

(10) Patent No.: US 8,017,612 B2
(45) Date of Patent: Sep. 13, 2011

(54) PIPERAZINE COMPOUND AND USE THEREOF AS A HCV POLYMERASE INHIBITOR

(75) Inventors: Hiroyuki Abe, Takatsuki (JP); Masahiro Tanaka, Takatsuki (JP); Kazuyuki Sugimoto, Takatsuki (JP); Akira Suma, Takatsuki (JP); Masahiro Yokota, Takatsuki (JP); Makoto Shiozaki, Takatsuki (JP); Kiyosei Iio, Takatsuki (JP); Kazuhito Ueyama, Takatsuki (JP); Dai Motoda, Takatsuki (JP); Toru Noguchi, Takatsuki (JP); Tsuyoshi Adachi, Yokohama (JP); Junichiro Tsuruha, Yokohama (JP); Satoki Doi, Yokohama (JP)

(73) Assignee: Japan Tobacco Inc., Tokyo (JP)

( * ) Notice: Subject to any disclaimer, the term of this patent is extended or adjusted under 35 U.S.C. 154(b) by 1150 days.

(21) Appl. No.: 11/736,064

(22) Filed: Apr. 17, 2007

(65) Prior Publication Data
US 2008/0081818 A1    Apr. 3, 2008

Related U.S. Application Data

(60) Provisional application No. 60/796,565, filed on May 1, 2006.

(30) Foreign Application Priority Data

Apr. 18, 2006    (JP) .................................. 2006-115008

(51) Int. Cl.
*A61K 31/497* (2006.01)
*C07D 403/06* (2006.01)
*C07D 401/06* (2006.01)
*C07D 241/04* (2006.01)

(52) U.S. Cl. ......... 514/252.12; 514/252.13; 514/253.01; 514/253.02; 544/359; 544/360; 544/363; 544/390

(58) Field of Classification Search .................. 544/359, 544/360, 363, 390; 514/252.12, 252.13, 514/253.01, 253.02
See application file for complete search history.

(56) References Cited

U.S. PATENT DOCUMENTS

| | | | |
|---|---|---|---|
| 5,348,955 A * | 9/1994 | Greenlee et al. ........... 514/227.8 |
| 5,801,175 A | 9/1998 | Afonso et al. |
| 5,880,128 A | 3/1999 | Doll et al. |
| 6,211,182 B1 | 4/2001 | Vaccaro et al. |
| 6,432,947 B1 | 8/2002 | Arnaiz et al. |
| 6,525,042 B1 | 2/2003 | Kobayashi et al. |
| 6,645,939 B1 | 11/2003 | Durette et al. |
| 6,747,023 B1 | 6/2004 | Kobayashi et al. |
| 7,138,526 B1 | 11/2006 | Herpin et al. |
| 2001/0049373 A1 | 12/2001 | Chalquest |
| 2004/0229817 A1 | 11/2004 | Duggal et al. |
| 2005/0069541 A1 | 3/2005 | Karlik et al. |
| 2005/0197336 A1 | 9/2005 | Anandan et al. |
| 2005/0234033 A1 | 10/2005 | Anandan et al. |
| 2005/0250784 A1 | 11/2005 | Anandan et al. |
| 2006/0223813 A1 | 10/2006 | Magar et al. |

FOREIGN PATENT DOCUMENTS

| | | |
|---|---|---|
| CN | 1443191 A | 9/2003 |
| EP | 1 031 563 A1 | 8/2000 |
| EP | 1 104 754 A1 | 6/2001 |
| EP | 1 034 164 B1 | 5/2004 |
| EP | 1 140 909 B1 | 7/2005 |
| JP | 2001-294572 A | 10/2001 |
| JP | 2001-524465 A | 12/2001 |
| JP | 2002-533455 A | 10/2002 |
| JP | 2002-539121 A | 11/2002 |
| WO | WO 98/37079 A1 | 8/1998 |
| WO | WO 99/37304 A1 | 7/1999 |
| WO | WO 00/39119 A1 | 7/2000 |
| WO | WO 00/53596 A2 | 9/2000 |
| WO | WO 00/77519 A1 | 12/2000 |
| WO | WO 01/07436 A2 | 2/2001 |
| WO | WO 01/54504 A1 | 8/2001 |
| WO | 01/90121 A2 | 11/2001 |
| WO | WO 2004/031182 A1 | 4/2004 |
| WO | WO 2004/066931 A2 | 8/2004 |
| WO | WO 2004/071390 A2 | 8/2004 |
| WO | WO 2004/073599 A2 | 9/2004 |
| WO | WO 2005/086898 A2 | 9/2005 |
| WO | WO 2008-049919 A2 | 5/2008 |

OTHER PUBLICATIONS

Breitenbucher et al., *Tetrahedron Letters*, 39: 1295-1298 (1998).
Machida et al., *Journal of Virology*, 78(16): 8835-8843 (Aug. 2004).
Yoshida, *Nippon Rinsho: Japanese Journal of Clonical Medicine*, 53: 909-929 (1995).

* cited by examiner

*Primary Examiner* — James O Wilson
*Assistant Examiner* — Ebenezer Sackey
(74) *Attorney, Agent, or Firm* — Leydig, Voit & Mayer, Ltd.

(57) ABSTRACT

The present invention relates to a compound represented by the following formula [I]

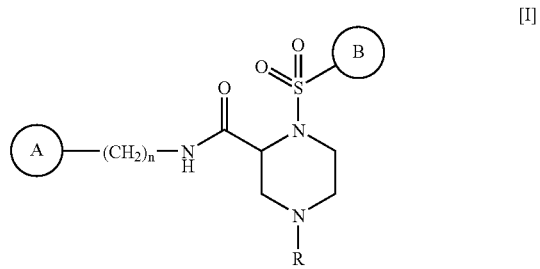

wherein each symbol is as defined in the specification, or a pharmaceutically acceptable salt thereof, or a solvate thereof and an anti-HCV agent and an HCV polymerase inhibitor containing this compound. The compound of the present invention shows an anti-HCV activity based on the HCV polymerase inhibitory activity, and useful as an agent for the prophylaxis or treatment of hepatitis C.

40 Claims, No Drawings

PIPERAZINE COMPOUND AND USE THEREOF AS A HCV POLYMERASE INHIBITOR

TECHNICAL FIELD

The present invention relates to a novel piperazine compound or a pharmaceutically acceptable salt thereof, or a solvate thereof, which is useful as a therapeutic agent for hepatitis C. The present invention relates to an anti-HCV agent, which contains a piperazine compound or a pharmaceutically acceptable salt thereof, or a solvate thereof, which is effective for the prophylaxis or treatment of hepatitis C and which shows anti-hepatitis C virus (HCV) activity, particularly anti-HCV activity based on an RNA-dependent RNA polymerase inhibitory activity.

BACKGROUND ART

In 1989, a main causative virus of non-A non-B posttransfusion hepatitis was found and named hepatitis C virus (HCV). Since then, several types of hepatitis viruses have been found besides type A, type B and type C, wherein hepatitis caused by HCV is called hepatitis C.

The patients infected with HCV are considered to involve several percent of the world population, and the infection with HCV characteristically becomes chronic.

HCV is an envelope RNA virus, wherein the genome is a single strand plus-strand RNA, and belongs to the genus Hepacivirus of Flavivirus. Of the same hepatitis viruses, for example, hepatitis B virus (HBV), which is a DNA virus, is eliminated by the immune system and the infection with this virus ends in an acute infection except for neonates and infants having yet immature immunological competence. In contrast, HCV somehow avoids the immune system of the host due to an unknown mechanism. Once infected with this virus, even an adult having a mature immune system frequently develops persistent infection.

When chronic hepatitis is associated with the persistent infection with HCV, it advances to cirrhosis or liver cancer in a high rate. Enucleation of tumor by operation does not help much, because the patient often develops recurrent liver cancer due to the sequela inflammation in non-cancerous parts. In addition, there is a report on the involvement of HCV infection in dermatosis such as chronic urticaria, lichen planus, cryoglobulinemic purpura and the like.

Thus, an effective therapeutic method of hepatitis C is desired. Apart from the symptomatic therapy to suppress inflammation with an anti-inflammatory agent, the development of a therapeutic agent that reduces HCV to a low level free from inflammation and that eradicates HCV has been strongly demanded.

At present, a treatment with interferon is the only effective method known for the eradication of HCV. However, interferon can eradicate the virus only in about one-third of the patient population. For the rest of the patients, it has no effect or provides only a temporary effect. In recent years, polyethylene glycolated interferon has been put to practical use, and enhanced effects and reduced side effects have been achieved. However, complete response rate still remains at a low level, and therefore, an anti-HCV drug to be used in the place of or concurrently with interferon is awaited in great expectation.

In recent years, Ribavirin (1-β-D-ribofuranosyl-1H-1,2,4-triazole-3-carboxamide) has become commercially available as a therapeutic agent for hepatitis C, which is to be used concurrently with interferon. It enhances the efficacy of interferon but only to a low efficacy rate, and a different novel therapeutic agent for hepatitis C is desired.

Also, an attempt has been made to potentiate the immunocompetence of the patient with an interferon agonist, an interleukin-12 agonist and the like, thereby to eradicate the virus, but an effective pharmaceutical agent has not been found yet.

In addition, the inhibition of HCV growth, wherein HCV-specific protein is targeted, has been drawing attention these days.

The gene of HCV encodes a protein such as serine protease, RNA helicase, RNA-dependent RNA polymerase and the like. These proteins function as a specific protein essential for the growth of HCV.

One of the specific proteins, RNA-dependent RNA polymerase (hereinafter to be also briefly referred to as an HCV polymerase), is an enzyme essential for the growth of the virus. The gene replication of HCV having a plus-strand RNA gene is considered to involve synthesis of a complementary minus-strand RNA by the use of the plus-strand RNA as a template and using the obtained minus-strand RNA as a template, amplifying the plus-strand RNA. The portion called NS5B of a protein precursor, that HCV codes for, has been found to show an RNA-dependent RNA polymerase activity, and is considered to play a central role in the HCV gene replication.

Therefore, an HCV polymerase inhibitor can be a target in the development of an anti-HCV drug, and the development thereof is eagerly awaited. However, an effective HCV polymerase inhibitor has not been developed yet, like in other attempts to develop an anti-HCV drug based on other action mechanisms. As the situation stands, no pharmaceutical agent can treat hepatitis C satisfactorily.

The following describes known compounds comparatively similar to the present invention.

WO2004/73599 (page 33, Table 1) discloses the following compound a and the like as anti-HCV agents (see patent document 1).

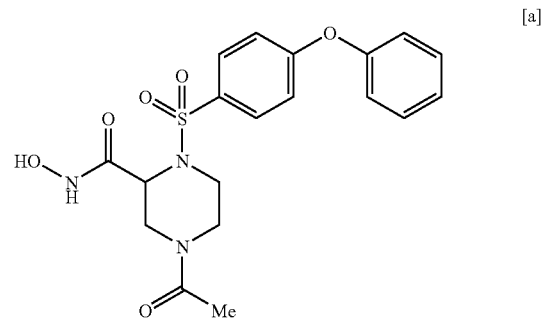

[a]

However, the compound of the present invention is not disclosed in the specification, and any description suggestive thereof is not found.

As references disclosing compounds other than for anti-HCV agents, which are comparatively similar to the compound of the present invention, the following can be mentioned.

WO2004/71390 (page 33, line 8) discloses the following compound b and the like as compounds usable for the treatment of dysmenorrhea and the like (see patent document 2).

[b]

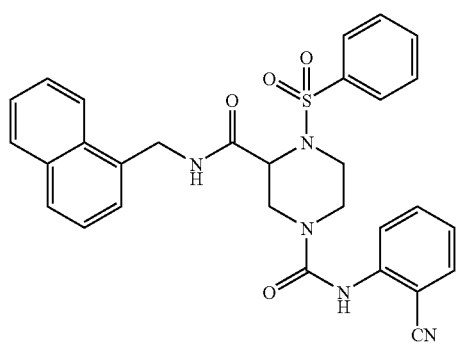

WO2004/31182 (page 25, line 4) discloses the following compound c and the like as compounds usable for the treatment of infertility (see patent document 3).

[c]

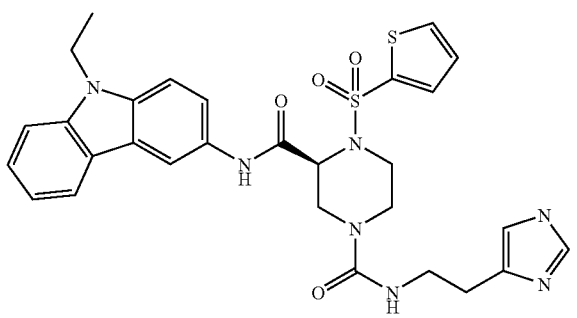

WO2000/39119 (page 42, Example 28L) discloses the following compound d and the like as compounds usable for inhibiting abnormal growth of cells (see patent document 4).

[d]

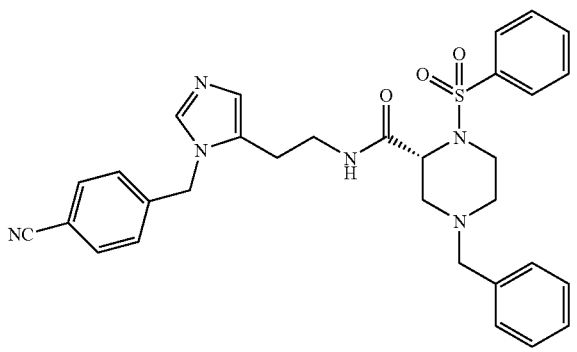

U.S. Pat. No. 5,880,128 (columns 67-68, Example 24) discloses the following compound e and the like as compounds usable for inhibiting abnormal growth of cells (see patent document 5).

[e]

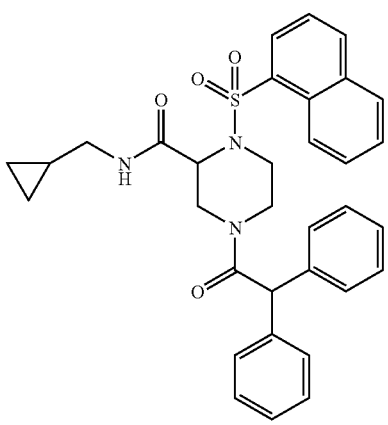

WO1999/37304 discloses the following compound f and the like as factor Xa inhibitors, and application to viral infections is exemplarily shown (see patent document 6).

[f]

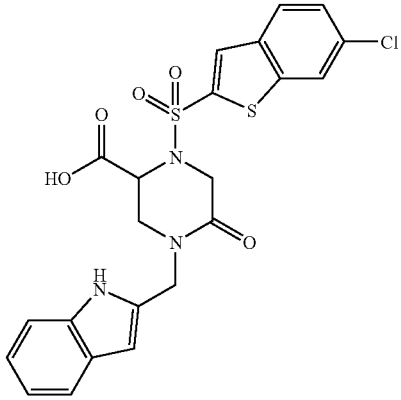

WO2001/07436 discloses the following compound g and the like as factor Xa inhibitors, and application to viral infections is exemplarily shown (see patent document 7).

[g]

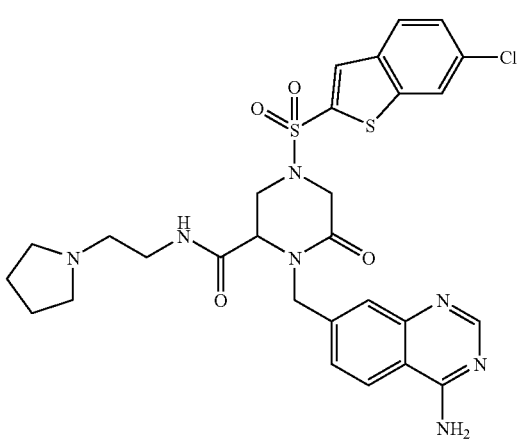

WO2005/86898 (page 95, Example 9) and US2005/234033 (page 37, Example 9) disclose the following compound h and the like as therapeutic agents for proliferative diseases (see patent document 8 and patent document 9).

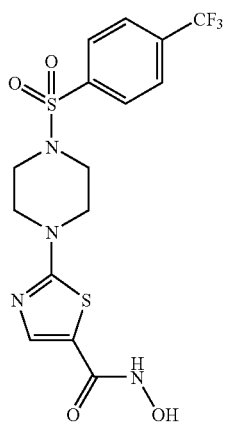

WO2000/53596 (page 42, in Table 2) discloses the following compound i and the like as compounds having activity for the central nervous system and activity for inflammatory diseases and allergic diseases (see patent document 10).

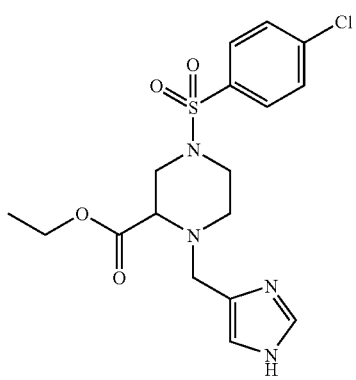

WO1998/37079 (page 138, lines 19-20) discloses the following compound j and the like as therapeutic agents for the diseases caused by abnormal nitric oxide production, such as multiple sclerosis and the like (see patent document 11).

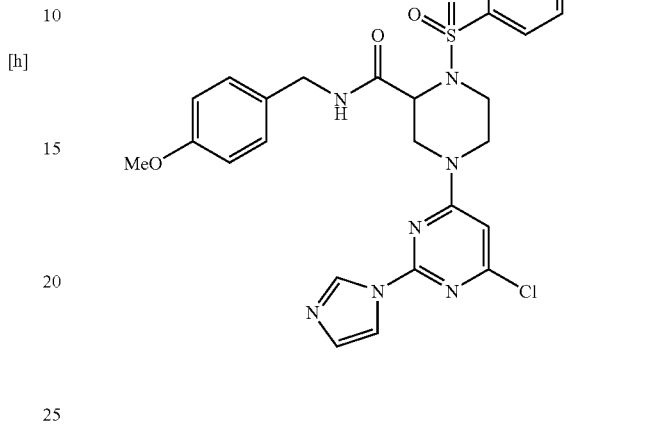

JP2001-294572 (page 297, Example 349) discloses the following compound k and the like as compounds having an antithrombotic effect (see patent document 12).

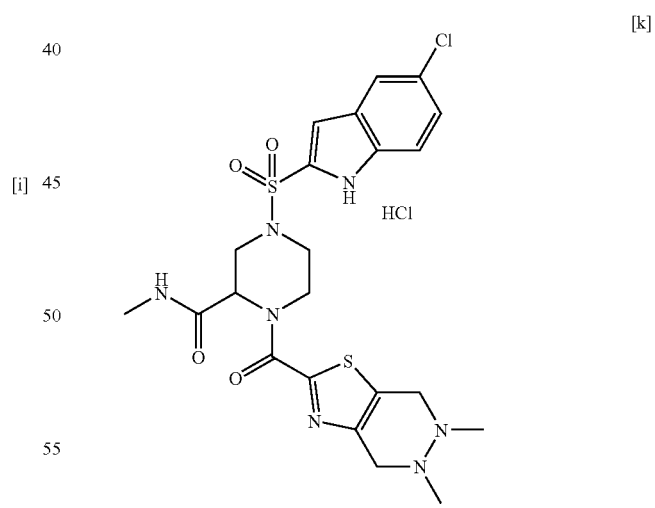

EP1104754 (Example A-33) and EP1031563 (Example 33) disclose the following compound l and the like as compounds having an antithrombotic effect (see patent document 3 and patent document 14).

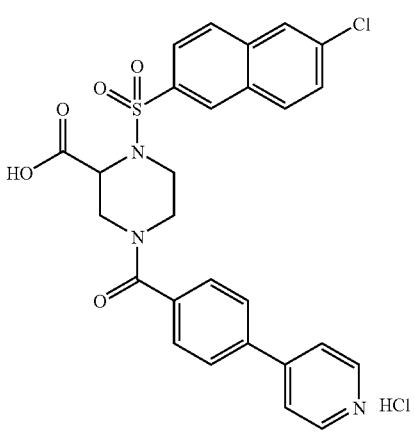

As compounds other than for a pharmaceutical use, which are comparatively similar to the compound of the present invention, the following can be mentioned.

WO2001/54504 (FIG. 55) discloses the following compound m and the like as anthelmintics (see patent document 15).

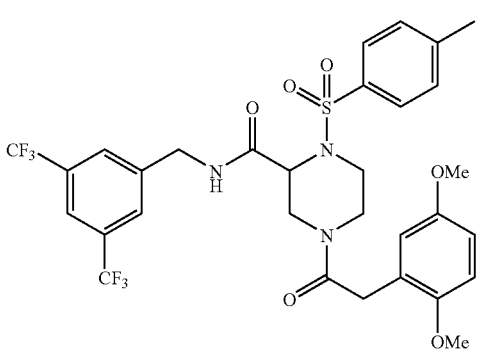

Other document (Tetrahedron Letters, 39, 1295-98, 1998; page 1297, Table II) discloses the following compound n and the like, and its synthetic method is described (see non-patent document 1).

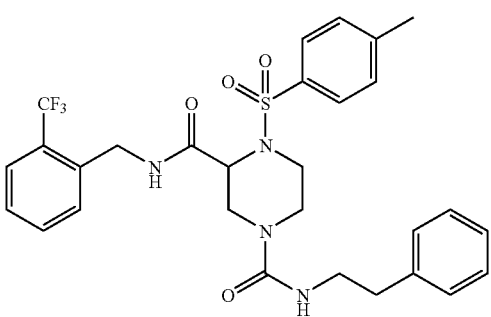

However, none of these references discloses the compound of the present invention, not to mention use of the compounds of these references as anti-HCV agents or description suggestive thereof.

[patent document 1] WO2004/73599 (page 33, Table 1)
[patent document 2] WO2004/71390 (page 33, line 8)
[patent document 3] WO2004/31182 (page 25, line 4)
[patent document 4] WO2000/39119 (page 42, Example 28L)
[patent document 5] U.S. Pat. No. 5,880,128 (columns 67-68, Example 24)
[patent document 6] WO1999/37304
[patent document 7] WO2001/07436
[patent document 8] WO2005/86898 (page 95, Example 9)
[patent document 9] US2005/234033 (page 37, Example 9)
[patent document 10] WO2000/53596 (page 42, in Table 2)
[patent document 11] WO1998/37079 (page 138, lines 19-20)
[patent document 12] JP2001-294572 (page 297, Example 349)
[patent document 13] EP1104754 (Example A-33)
[patent document 14] EP1031563 (Example 33)
[patent document 15] WO2001/54504 (FIG. 55)
[non-patent document 1] Tetrahedron Letters, Vol. 39, pages 1295-98, 1998 (page 1297, Table II)

DISCLOSURE OF THE INVENTION

Problems to be Solved by the Invention

Based on the findings from the preceding studies, it has been elucidated that a pharmaceutical agent having an anti-HCV activity is effective for the prophylaxis and treatment of hepatitis C, and particularly an anti-HCV agent having an inhibitory activity on RNA-dependent RNA polymerase of HCV can be a prophylactic and therapeutic agent effective against hepatitis C and a prophylactic and therapeutic agent for the disease caused by hepatitis C.

Accordingly, the present invention provides a pharmaceutical agent having an anti-HCV activity, particularly a pharmaceutical agent having an RNA-dependent RNA polymerase inhibitory activity.

Means for Solving the Problems

The present inventors have made an in-depth study of compounds having an anti-HCV activity, particularly RNA-dependent RNA polymerase inhibitory activity, and completed the present invention.

More particularly, the present invention provides the following.

[1] An anti-HCV agent comprising, as an active ingredient, a compound represented by the following formula [I] or a pharmaceutically acceptable salt thereof, or a solvate thereof:

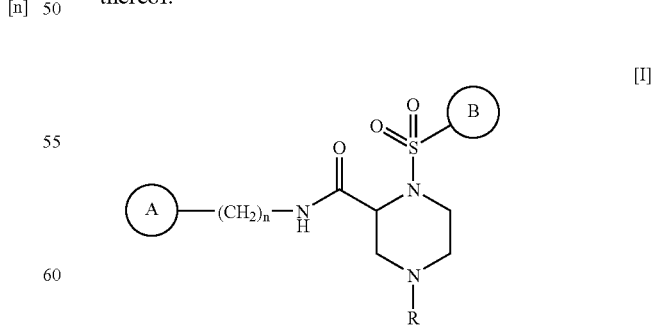

wherein
ring A is
a $C_{3-12}$ carbon ring group optionally substituted by 1 to 5 substituents selected from the following group A, or a heterocyclic group optionally substituted by 1 to 5 substituents selected from the following group A
(wherein the heterocyclic group has, besides carbon atom, 1 to 6 hetero atoms selected from nitrogen atom, oxygen atom and sulfur atom),
n is an integer of 1 to 6,
ring B is
a $C_{3-12}$ carbon ring group optionally substituted by 1 to 5 substituents selected from the following group A, or
a heterocyclic group optionally substituted by 1 to 5 substituents selected from the following group A
(wherein the heterocyclic group has, besides carbon atom, 1 to 6 hetero atoms selected from nitrogen atom, oxygen atom and sulfur atom), and
R is
a hydrogen atom,
—$COR^1$,
—$COOR^2$,
—$CONR^3R^4$,
—$SO_2R^5$,
—CO—$COOR^6$,
—CO—CH=CH—$COOR^{11}$,
—CO—$(CH_2)_a$—NH—$R^7$,
—CO—$(CH_2)_b$—$NHCOR^8$,
—CO—$(CH_2)_c$—$NHCOOR^9$
(wherein $R^1$ to $R^9$ and $R^{11}$ are the same or different and each is a hydrogen atom or a $C_{1-10}$ alkyl group optionally substituted by 1 to 5 substituents selected from the following group B, and a, b and c are the same or different and each is an integer of 1 to 4),
—CO—$CONH_2$,
—C(=NH)$NH_2$,
—C(=S)$NH_2$,
a $C_{1-10}$ alkyl group optionally substituted by 1 to 5 substituents selected from the following group B, or

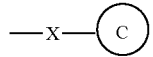

wherein X is
a bond,
$C_{1-4}$ alkylene,
—CO—$(CH_2)_p$—,
—$CONR^{10}$—$(CH_2)_q$—,
—CO—$(CH_2)_r$—O—$(CH_2)_s$—,
—CO—$(CH_2)_t$—NH—$(CH_2)_u$—,
—CO—$(CH_2)_v$—CONH—$(CH_2)_w$—, or
—CO—NH—$SO_2$—,
ring C is
a $C_{3-12}$ carbon ring group optionally substituted by 1 to 5 substituents selected from the following group A, or
a heterocyclic group optionally substituted by 1 to 5 substituents selected from the following group A
(wherein the heterocyclic group has, besides carbon atom, 1 to 6 hetero atoms selected from nitrogen atom, oxygen atom and sulfur atom),
$R^{10}$ is a hydrogen atom, or a $C_{1-10}$ alkyl group optionally substituted by 1 to 5 substituents selected from the following group B,
p, q, r, s, u, v and w are the same or different and each is 0 or an integer of 1 to 4, and t is an integer of 1 to 4, group A:
halogen atom, nitro group, cyano group,
—$OR^{a1}$,
—$SR^{a2}$,
—$NR^{a3}R^{a4}$,
—$NHCOR^{a5}$,
—$NHSO_2R^{a14}$,
—$COOR^{a6}$,
—$CONR^{a7}R^{a8}$,
—$SO_2NR^{a9}R^{a10}$,
—$SO_2NHCOR^{a15}$,
—$COR^{a11}$,
—$SO_2R^{a12}$,
—$CONHSO_2R^{a13}$,
—$COCOOR^{a16}$,
—$COCONR^{a17}R^{a18}$,
—$CONR^{a19}(OR^{a20})$
—$SF_5$
(wherein $R^{a1}$ to $R^{a20}$ are the same or different and each is a hydrogen atom,
a $C_{1-10}$ alkyl group optionally substituted by 1 to 5 substituents selected from the following group B,
a $C_{3-12}$ carbon ring group optionally substituted by 1 to 5 substituents selected from the following group C,
a heterocyclic group optionally substituted by 1 to 5 substituents selected from the following group C
(wherein the heterocyclic group has, besides carbon atom, 1 to 6 hetero atoms selected from nitrogen atom, oxygen atom and sulfur atom), or
a $C_{6-12}$ aryl-$C_{1-4}$ alkyl group optionally substituted by 1 to 5 substituents selected from the following group C),
a $C_{1-10}$ alkyl group optionally substituted by 1 to 5 substituents selected from the following group B,
a $C_{2-10}$ alkynyl group optionally substituted by 1 to 5 substituents selected from the following group B,
a $C_{3-12}$ carbon ring group optionally substituted by 1 to 5 substituents selected from the following group C,
a heterocyclic group optionally substituted by 1 to 5 substituents selected from the following group C
(wherein the heterocyclic group has, besides carbon atom, 1 to 6 hetero atoms selected from nitrogen atom, oxygen atom and sulfur atom),
a $C_{6-12}$ aryl-$C_{1-4}$ alkyl group optionally substituted by 1 to 5 substituents selected from the following group C,
a heterocyclyl-$C_{1-4}$ alkyl group optionally substituted by 1 to 5 substituents selected from the following group C
(wherein the heterocyclyl moiety has, besides carbon atom, 1 to 6 hetero atoms selected from nitrogen atom, oxygen atom and sulfur atom), and
a $C_{3-10}$ cycloalkyl-$C_{1-4}$ alkyl group optionally substituted by 1 to 5 substituents selected from the following group C,
group B:
halogen atom, cyano group, hydroxyl group,
$C_{1-4}$ alkoxy group,
amino group,
$C_{1-4}$ alkylamino group,
di($C_{1-4}$ alkyl)amino group,
carboxyl group,
$C_{1-4}$ alkoxy-carbonyl group,
carbamoyl group,
$C_{1-4}$ alkylamino-carbonyl group,
di($C_{1-4}$ alkyl)amino-carbonyl group,
heterocyclyl-carbonyl group, and
tri($C_{1-4}$ alkyl)ammoniumyl group
(wherein the heterocyclyl moiety has, besides carbon atom, 1 to 6 hetero atoms selected from nitrogen atom, oxygen atom and sulfur atom),
group C:
halogen atom, cyano group, hydroxyl group,
carboxyl group,
$C_{1-4}$ alkyl group,
halogeno $C_{1-4}$ alkyl group, hydroxy $C_{1-4}$ alkyl group,
carboxy $C_{1-4}$ alkyl group,
$C_{1-4}$ alkoxy $C_{1-4}$ alkyl group,
$C_{1-4}$ alkoxy group, and
carboxy $C_{1-4}$ alkoxy group.

[2] The anti-HCV agent of [1], which comprises a compound represented by the following formula [I'] or a pharmaceutically acceptable salt thereof as an active ingredient:

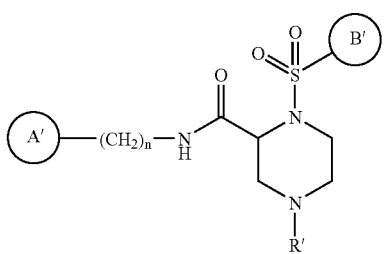

[I']

wherein ring A' is
a $C_{3-12}$ carbon ring group optionally substituted by 1 to 5 substituents selected from the following group A", or
a heterocyclic group optionally substituted by 1 to 5 substituents selected from the following group A"
(wherein the heterocyclic group has, besides carbon atom, 1 to 4 hetero atoms selected from nitrogen atom, oxygen atom and sulfur atom),
n is an integer of 1 to 6,
ring B' is
a $C_{3-12}$ carbon ring group optionally substituted by 1 to 5 substituents selected from the following group A", or
a heterocyclic group optionally substituted by 1 to 5 substituents selected from the following group A"
(wherein the heterocyclic group has, besides carbon atom, 1 to 4 hetero atoms selected from nitrogen atom, oxygen atom and sulfur atom), and
R' is
a hydrogen atom,
—$COR^{101}$,
—$COOR^{102}$,
—$CONR^{103}R^{104}$,
—$SO_2R^{105}$,
—CO—$COOR^{106}$
—CO—$(CH_2)_a$—NH—$R^{107}$,
—CO—$(CH_2)_b$—$NHCOR^{108}$,
—CO—$(CH_2)_c$—$NHCOOR^{109}$,
(wherein $R^{101}$ to $R^{109}$ are the same or different and each is a hydrogen atom, or a $C_{1-10}$ alkyl group optionally substituted by 1 to 5 substituents selected from the following group B', and a, b and c are the same or different and each is an integer of 1 to 4),
—CO—$CONH_2$,
—C(=NH)$NH_2$,
—C(=S)$NH_2$,
a $C_{1-10}$ alkyl group optionally substituted by 1 to 5 substituents selected from the following group B', or

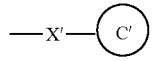

wherein X' is
a bond,
alkylene,
—CO—$(CH_2)_p$—,
—$CONR^{110}$—$(CH_2)_q$—,
—CO—$(CH_2)_r$—O—$(CH_2)_s$—,
—CO—$(CH_2)_t$—NH—$(CH_2)_u$—, or
—CO—NH—$SO_2$—,
ring C' is
a $C_{3-12}$ carbon ring group optionally substituted by 1 to 5 substituents selected from the following group A", or
a heterocyclic group optionally substituted by 1 to 5 substituents selected from the following group A"
(wherein the heterocyclic group has, besides carbon atom, 1 to 4 hetero atoms selected from nitrogen atom, oxygen atom and sulfur atom),
$R^{110}$ is a hydrogen atom, or a $C_{1-10}$ alkyl group optionally substituted by 1 to 5 substituents selected from the following group B',
p, q, r, s and u are the same or different and each is 0 or an integer of 1 to 4, and t is an integer of 1 to 4,
group A":
halogen atom, nitro group, cyano group,
—$OR^{a101}$,
—$SR^{a102}$,
—$NR^{a103}R^{a104}$,
—$NHCOR^{a105}$,
—$COOR^{a106}$,
—$CONR^{a107}R^{a108}$,
—$SO_2NR^{a109}R^{a110}$,
—$COR^{a111}$,
—$SO_2R^{a112}$,
—$CONHSO_2R^{a113}$
(wherein $R^{a101}$ to $R^{a113}$ are the same or different and each is
a hydrogen atom,
a $C_{1-10}$ alkyl group optionally substituted by 1 to 5 substituents selected from the following group B',
a $C_{3-12}$ carbon ring group optionally substituted by 1 to 5 substituents selected from the following group C',
a heterocyclic group optionally substituted by 1 to 5 substituents selected from the following group C'
(wherein the heterocyclic group has, besides carbon atom, 1 to 4 hetero atoms selected from nitrogen atom, oxygen atom and sulfur atom), or
a $C_{6-12}$ aryl-$C_{1-4}$ alkyl group optionally substituted by 1 to 5 substituents selected from the following group C'),
a $C_{1-10}$ alkyl group optionally substituted by 1 to 5 substituents selected from the following group B',
a $C_{3-12}$ carbon ring group optionally substituted by 1 to 5 substituents selected from the following group C',
a heterocyclic group optionally substituted by 1 to 5 substituents selected from the following group C'
(wherein the heterocyclic group has, besides carbon atom, 1 to 4 hetero atoms selected from nitrogen atom, oxygen atom and sulfur atom), and
a $C_{3-10}$ cycloalkyl-$C_{1-4}$ alkyl group optionally substituted by 1 to 5 substituents selected from the following group C',
group B':
halogen atom, cyano group, hydroxyl group, $C_{1-4}$ alkoxy group, amino group, $C_{1-4}$ alkylamino group, di($C_{1-4}$ alkyl) amino group, carboxyl group, $C_{1-4}$ alkoxy-carbonyl group, carbamoyl group, $C_{1-4}$ alkylamino-carbonyl group, di($C_{1-4}$ alkyl)amino-carbonyl group, and heterocyclyl-carbonyl group
(wherein the heterocyclyl moiety has, besides carbon atom, 1 to 4 hetero atoms selected from nitrogen atom, oxygen atom and sulfur atom), group C':
halogen atom, cyano group, hydroxyl group, $C_{1-4}$ alkyl group, halogeno $C_{1-4}$ alkyl group, and hydroxy $C_{1-4}$ alkyl group.
[3] The anti-HCV agent of [1], wherein the ring A is a $C_{3-12}$ carbon ring group optionally substituted by 1 to 5 substituents selected from group A.
[4] The anti-HCV agent of [1], wherein n is 1.
[5] The anti-HCV agent of [1], wherein ring B is a $C_{3-12}$ carbon ring group optionally substituted by 1 to 5 substituents selected from group A.
[6] The anti-HCV agent of [1], wherein R is

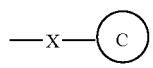

wherein each symbol is as defined in [1].
[7] The anti-HCV agent of [6], wherein X is a bond.
[8] The anti-HCV agent of [6], wherein X is —CO—$(CH_2)_p$— wherein p is as defined in [1].
[9] The anti-HCV agent of [8], wherein p is 1.
[10] The anti-HCV agent of [6], wherein X is —CONH—$(CH_2)_q$—wherein q is as defined in [1].
[11] The anti-HCV agent of [10], wherein q is 0.
[12] The anti-HCV agent of [10], wherein q is 1.
[13] The anti-HCV agent of [6], wherein ring C is a heterocyclic group optionally substituted by 1 to 5 substituents selected from group A.
[14] An HCV polymerase inhibitor comprising a compound of any one of [1] to [13] or a pharmaceutically acceptable salt thereof as an active ingredient.
[15] A compound represented by the following formula [I-A] or a pharmaceutically acceptable salt thereof, or a solvate thereof:

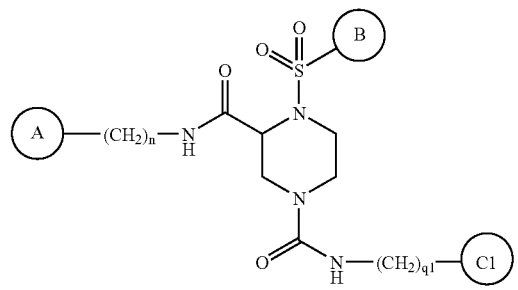

wherein ring C1 is a heterocyclic group optionally substituted by 1 to 5 substituents selected from group A (wherein the heterocyclic group has, besides carbon atom, 1 to 6 hetero atoms selected from nitrogen atom, oxygen atom and sulfur atom, and group A is as defined in [1]), q1 is an integer of 1 to 4, and other symbols are as defined in [1].
[16] A compound represented by the following formula [I-B] or a pharmaceutically acceptable salt thereof, or a solvate thereof:

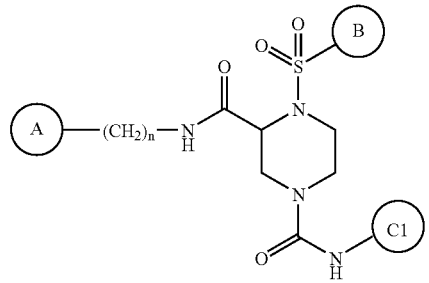

wherein ring C1 is a heterocyclic group optionally substituted by 1 to 5 substituents selected from group A (wherein the heterocyclic group has, besides carbon atom, 1 to 6 hetero atoms selected from nitrogen atom, oxygen atom and sulfur atom, and group A is as defined in [1]), and other symbols are as defined in [1].
[17] A compound represented by the following formula [I-C] or a pharmaceutically acceptable salt thereof, or a solvate thereof:

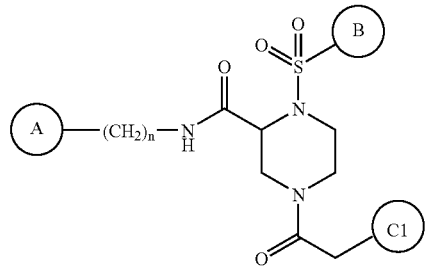

wherein ring C1 is a heterocyclic group optionally substituted by 1 to 5 substituents selected from group A (wherein the heterocyclic group has, besides carbon atom, 1 to 6 hetero atoms selected from nitrogen atom, oxygen atom and sulfur atom, and group A is as defined in [1]), and other symbols are as defined in [1].
[18.0] A compound represented by the following formula [I-D] or a pharmaceutically acceptable salt thereof:

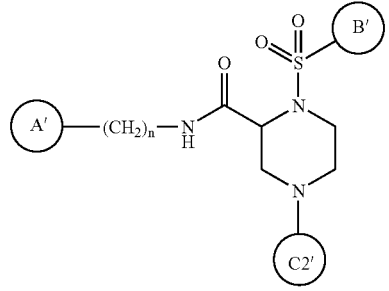

wherein ring C2' is a heterocyclic group optionally substituted by 1 to 5 substituents selected from the following group A'" (wherein the heterocyclic group has, besides carbon atom, 1 to 4 hetero atoms selected from nitrogen atom, oxygen atom and sulfur atom), and other symbols are as defined in [2].

group A''':
halogen atom, nitro group, cyano group,
—$OR^{a101}$,
—$SR^{a102}$,
—$NR^{a103}R^{a104}$,
—$NHCOR^{a105}$,
—$COOR^{a106}$,
—$CONR^{a107}R^{a108}$,
—$SO_2NR^{a109}R^{a110}$,
—$COR^{a111}$,
—$SO_2R^{a112}$,
—$CONHSO_2R^{a113}$,
(wherein $R^{a101}$ to $R^{a113}$ are the same or different and each is
a hydrogen atom,
a $C_{1-10}$ alkyl group optionally substituted by 1 to 5 substituents selected from the above-mentioned group B',
a $C_{3-12}$ carbon ring group optionally substituted by 1 to 5 substituents selected from the above-mentioned group C',
a heterocyclic group optionally substituted by 1 to 5 substituents selected from the above-mentioned group C'
(wherein the heterocyclic group has, besides carbon atom, 1 to 4 hetero atoms selected from nitrogen atom, oxygen atom and sulfur atom), or
a $C_{6-12}$ aryl-$C_{1-4}$ alkyl group optionally substituted by 1 to 5 substituents selected from the above-mentioned group C'),
a $C_{1-10}$ alkyl group optionally substituted by 1 to 5 substituents selected from the above-mentioned group B',
a $C_{3-12}$ carbon ring group optionally substituted by 1 to 5 substituents selected from the above-mentioned group C', and
a $C_{3-10}$ cycloalkyl-$C_{1-4}$ alkyl group optionally substituted by 1 to 5 substituents selected from the above-mentioned group C'.

[18] A compound represented by the following formula [I-D1] or a pharmaceutically acceptable salt thereof, or a solvate thereof:

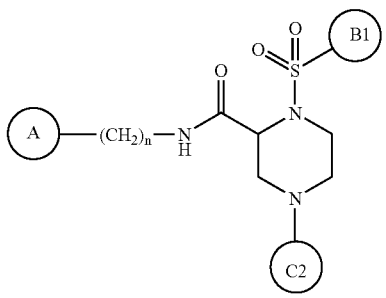

[I-D1]

wherein ring B1 is a phenyl group optionally substituted by 1 to 5 substituents selected from group A (wherein group A is as defined in [1]), ring C2 is a heterocyclic group optionally substituted by 1 to 5 substituents selected from the following group A' (wherein the heterocyclic group has, besides carbon atom, 1 to 6 hetero atoms selected from nitrogen atom, oxygen atom and sulfur atom), and other symbols are as defined in [1], group A':
halogen atom, nitro group, cyano group,
—$OR^{a1}$,
—$SR^{a2}$,
—$NR^{a3}R^{a4}$,
—$NHCOR^{a5}$,
—$NHSO_2R^{a14}$,
—$COOR^{a6}$,
—$CONR^{a7}R^{a8}$,
—$SO_2NR^{a9}R^{a10}$,
—$SO_2NHCOR^{a15}$,
—$COR^{a11}$,
—$SO_2R^{a12}$,
—$CONHSO_2R^{a13}$,
—$COCOOR^{a16}$,
—$COCONR^{a17}R^{a18}$,
—$CONR^{a19}(OR^{a20})$,
—$SF_5$
(wherein $R^{a1}$ to $R^{a20}$ are the same or different and each is
a hydrogen atom,
a $C_{1-10}$ alkyl group optionally substituted by 1 to 5 substituents selected from group B,
a $C_{3-12}$ carbon ring group optionally substituted by 1 to 5 substituents selected from group C,
a heterocyclic group optionally substituted by 1 to 5 substituents selected from group C
(wherein the heterocyclic group has, besides carbon atom, 1 to 6 hetero atoms selected from nitrogen atom, oxygen atom and sulfur atom), or
a $C_{6-12}$ aryl-$C_{1-4}$ alkyl group optionally substituted by 1 to 5 substituents selected from group C),
a $C_{1-10}$ alkyl group optionally substituted by 1 to 5 substituents selected from group B,
a $C_{2-10}$ alkynyl group optionally substituted by 1 to 5 substituents selected from group B,
a $C_{3-12}$ carbon ring group optionally substituted by 1 to 5 substituents selected from group C,
a $C_{6-12}$ aryl-$C_{1-4}$ alkyl group optionally substituted by 1 to 5 substituents selected from group C,
a heterocyclyl-$C_{1-4}$ alkyl group optionally substituted by 1 to 5 substituents selected from group C
(wherein the heterocyclyl moiety has, besides carbon atom, 1 to 6 hetero atoms selected from nitrogen atom, oxygen atom and sulfur atom), and
a $C_{3-10}$ cycloalkyl-$C_{1-4}$ alkyl group optionally substituted by 1 to 5 substituents selected from group C, and
group B and group C are as defined in [1].

[19] The compound of any one of [15] to [18], wherein ring A is a phenyl group optionally substituted by 1 to 5 substituents selected from group A, or a pharmaceutically acceptable salt thereof, or a solvate thereof.

[20] The compound of any one of [15] to [18], wherein n is 1, or a pharmaceutically acceptable salt thereof, or a solvate thereof.

[21] The compound of any one of [15] to [17], wherein the ring B is a phenyl group optionally substituted by 1 to 5 substituents selected from group A, or a pharmaceutically acceptable salt thereof, or a solvate thereof.

[22] The compound of any one of [15] to [17], wherein the ring C1 is a heterocyclic group optionally substituted by 1 to 5 substituents selected from group A, and the heterocyclic group is selected from the group consisting of piperidinyl group, morpholinyl group, pyrrolidinyl group, piperazinyl group, thiazolyl group, isothiazolyl group, pyrazolyl group, imidazolyl group, triazolyl group, tetrazolyl group, oxazolyl group, isoxazolyl group, thiadiazolyl group, oxadiazolyl group, pyridyl group and pyrimidinyl group, or a pharmaceutically acceptable salt thereof, or a solvate thereof.

[23] The compound of [16], wherein the ring C1 is a heterocyclic group optionally substituted by 1 to 5 substituents selected from group A, and the heterocyclic group is selected from the group consisting of thiazolyl group, isothiazolyl group, isoxazolyl group, thiadiazolyl group, oxadiazolyl group, pyrazolyl group, triazolyl group, tetrazolyl group, pyridyl group and pyrimidinyl group, or a pharmaceutically acceptable salt thereof, or a solvate thereof.

[24] The compound of [17], wherein the ring C1 is a heterocyclic group optionally substituted by 1 to 5 substituents selected from group A, and the heterocyclic group is selected from the group consisting of piperidinyl group, morpholinyl group, pyrrolidinyl group, piperazinyl group, pyrazolyl group, imidazolyl group, triazolyl group, tetrazolyl group, isoxazolyl group, pyridyl group and pyrimidinyl group, or a pharmaceutically acceptable salt thereof, or a solvate thereof.

[25] The compound of [18], wherein the ring C2 is a heterocyclic group optionally substituted by 1 to 5 substituents selected from group A', and the heterocyclic group is selected from the group consisting of imidazolinyl group, thiazolinyl group, oxazolinyl group, thienyl group, dioxopyrrolidinyl group, dioxopyrrolinyl group, oxopyrrolidinyl group, oxothiadiazolinyl group, tetrahydrobenzothiazolyl group, thiazolyl group, thiadiazolyl group, pyrazolyl group, imidazolyl group, triazolyl group, oxazolyl group, pyridyl group, pyrimidinyl group, pyrazinyl group, pyridazinyl group, quinolyl group,
[1,5]naphthyridinyl group,
[1,6]naphthyridinyl group,
oxopiperidinyl group,
oxodihydropyridinyl group,
[1,2,4]triazolo[1,5-a]pyrimidinyl group,
benzimidazolyl group,
imidazo[4,5-c]pyridinyl group,
quinoxalinyl group,
pyrido[2,3-b]pyrazinyl group,
pyrido[3,4-b]pyrazinyl group,
pteridinyl group,
pyrazino[2,3-b]pyrazinyl group,
imidazo[4,5-b]pyrazinyl group,
2,2-dioxo-1,2,3,4-tetrahydropyrazino[2,3-c][1,2,6]thiadiazinyl group,
2-oxo-1,4-dihydropyrazino[2,3-d][1,3]oxazinyl group,
2-oxo-2,3-dihydroimidazo[4,5-b]pyrazinyl group,
[1,2,5]thiadiazolo[3,4-b]pyrazinyl group,
benzothiazolyl group,
4,5,6,7-tetrahydrobenzothiazolyl group,
thiazolo[5,4-b]pyridinyl group,
thiazolo[5,4-c]pyridinyl group,
thiazolo[4,5-d]pyrimidinyl group,
thiazolo[5,4-d]pyrimidinyl group,
thiazolo[4,5-d]pyridazinyl group,
thiazolo[4,5-b]pyrazinyl group,
thiazolo[4,5-d][1,2,3]triazinyl group,
5-oxo-4,5-dihydrothiazolo[5,4-b]pyridinyl group,
pyrazolo[3,4-d]thiazolyl group,
4,6-dioxo-5,6-dihydropyrrolo[3,4-d]thiazolyl group,
4,5,6,7-tetrahydrothiazolo[5,4-c]pyridinyl group,
4-oxo-4,5,6,7-tetrahydrothiazolo[5,4-c]pyridinyl group,
4-oxo-4,5-dihydrothiazolo[5,4-c]pyridinyl group,
7-oxo-6,7-dihydrothiazolo[4,5-d]pyrimidinyl group,
4-oxo-4,5-dihydrothiazolo[4,5-d]pyridazinyl group,
7-oxo-6,7-dihydrothiazolo[4,5-d]pyridazinyl group,
4,7-dioxo-4,5,6,7-tetrahydrothiazolo[4,5-d]pyridazinyl group,
4-oxo-3,4-dihydrothiazolo[4,5-d][1,2,3]triazinyl group,
5-oxo-[1,3,4]thiadiazolo[3,2-a]pyrimidinyl group,
7-oxo-[1,3,4]thiadiazolo[3,2-a]pyrimidinyl group,
4-oxo-[1,3,4]thiadiazolo[2,3-c][1,2,4]triazinyl group,
[1,2,4]triazolo[3,4-b][1,3,4]thiadiazolyl group, and indenothiazolyl group, or a pharmaceutically acceptable salt thereof, or a solvate thereof.

[26] The compound of [25], wherein the ring C2 is a thiazol-2-yl group optionally substituted by 1 to 5 substituents selected from group A', or a pharmaceutically acceptable salt thereof, or a solvate thereof.

[27] The compound of [25], wherein the ring C2 is a heterocyclic group optionally substituted by 1 to 5 substituents selected from group A', and the heterocyclic group is selected from the group consisting of
benzothiazol-2-yl group,
4,5,6,7-tetrahydrobenzothiazol-2-yl group,
thiazolo[5,4-b]pyridin-2-yl group,
thiazolo[5,4-c]pyridin-2-yl group,
thiazolo[4,5-d]pyrimidin-2-yl group,
thiazolo[5,4-d]pyrimidin-2-yl group,
thiazolo[4,5-d]pyridazin-2-yl group,
thiazolo[4,5-b]pyrazin-2-yl group,
thiazolo[4,5-d][1,2,3]triazin-6-yl group,
5-oxo-4,5-dihydrothiazolo[5,4-b]pyridin-2-yl group,
1H-pyrazolo[3,4-d]thiazol-5-yl group,
4,6-dioxo-5,6-dihydro-4H-pyrrolo[3,4-d]thiazol-2-yl group,
4,5,6,7-tetrahydrothiazolo[5,4-c]pyridin-2-yl group,
4-oxo-4,5,6,7-tetrahydrothiazolo[5,4-c]pyridin-2-yl group,
4-oxo-4,5-dihydrothiazolo[5,4-c]pyridin-2-yl group,
7-oxo-6,7-dihydrothiazolo[4,5-d]pyrimidin-2-yl group,
4-oxo-4,5-dihydrothiazolo[4,5-d]pyridazin-2-yl group,
7-oxo-6,7-dihydrothiazolo[4,5-d]pyridazin-2-yl group,
4,7-dioxo-4,5,6,7-tetrahydrothiazolo[4,5-d]pyridazin-2-yl group,
4-oxo-3,4-dihydrothiazolo[4,5-d][1,2,3]triazin-6-yl group,
5-oxo-5H-[1,3,4]thiadiazolo[3,2-a]pyrimidin-2-yl group,
7-oxo-7H-[1,3,4]thiadiazolo[3,2-a]pyrimidin-2-yl group,
4-oxo-4H-[1,3,4]thiadiazolo[2,3-c][1,2,4]triazin-7-yl group,
[1,2,4]triazolo[3,4-b][1,3,4]thiadiazol-6-yl group, and indenothiazolyl group, or a pharmaceutically acceptable salt thereof, or a solvate thereof.

[28] The compound of [25], wherein the ring C2 is a pyrazin-2-yl group optionally substituted by 1 to 5 substituents selected from group A', or a pharmaceutically acceptable salt thereof, or a solvate thereof.

[29] The compound of [25], wherein the ring C2 is a heterocyclic group optionally substituted by 1 to 5 substituents selected from group A', and the heterocyclic group is selected from the group consisting of
quinoxalin-2-yl group,
pyrido[2,3-b]pyrazin-2-yl group,
pyrido[2,3-b]pyrazin-3-yl group,
pyrido[3,4-b]pyrazin-2-yl group,
pteridin-6-yl group,
pteridin-7-yl group,
pyrazino[2,3-b]pyrazin-2-yl group,
1H-imidazo[4,5-b]pyrazin-5-yl group,
2,2-dioxo-1,2,3,4-tetrahydropyrazino[2,3-c][1,2,6]thiadiazin-7-yl group,
2-oxo-1,4-dihydro-2H-pyrazino[2,3-d][1,3]oxazin-7-yl group,
2-oxo-2,3-dihydro-1H-imidazo[4,5-b]pyrazin-5-yl group, and
[1,2,5]thiadiazolo[3,4-b]pyrazinyl group, or a pharmaceutically acceptable salt thereof, or a solvate thereof.

[30] The compound of [16], which is selected from the group consisting of
(R)-4-(4-trifluoromethyl-benzenesulfonyl)-piperazine-1,3-dicarboxylic acid 3-(4-isopropyl-benzylamide) 1-pyridin-4-ylamide (Example 3), (R)-4-(4-trifluoromethyl-benzenesulfonyl)-piperazine-1,3-dicarboxylic acid 3-(4-isopropyl-benzylamide) 1-pyridin-3-ylamide (Example 211), (R)-4-(4-propyl-benzenesulfonyl)-piperazine-1,3-dicarboxylic acid 3-(4-isopropyl-benzylamide) 1-pyridin-4-ylamide (Example 295), (R)-4-(4-trifluoromethyl-benzenesulfonyl)-piperazine-1,3-dicarboxylic acid 3-(4-isopropyl-benzylamide) 1-pyrimidin-4-ylamide (Example 300), 4-{[(R)-3-(4-isopropyl-benzylcarbamoyl)-4-(4-trifluoromethyl-benzenesulfonyl)-piperazine-1-carbonyl]-amino}-pyridine-2-carboxylic acid tert-butyl ester (Example 301), 4-{[(R)-3-(4-isopropyl-benzylcarbamoyl)-4-(4-trifluoromethyl-benzenesulfonyl)-piperazine-1-carbonyl]-amino}-pyridine-2-carboxylic acid hydrochloride (Example 314), (R)-4-(4-trifluoromethoxy-benzenesulfonyl)-piperazine-1,3-dicarboxylic acid 3-(4-isopropyl-benzylamide) 1-pyridin-4-ylamide (Example 318), (R)-4-(4-trifluoromethyl-benzenesulfonyl)-piperazine-1,3-dicarboxylic acid 3-(4-isopropyl-benzylamide) 1-[1,3,4]thiadiazol-2-ylamide (Example 332), 5-{[(R)-3-(4-isopropyl-benzylcarbamoyl)-4-(4-trifluoromethyl-benzenesulfonyl)-piperazine-1-carbonyl]-amino}-[1,3,4]oxadiazole-2-carboxylic acid ethyl ester (Example 334), (R)-4-(4-trifluoromethyl-benzenesulfonyl)-piperazine-1,3-dicarboxylic acid 3-(4-isopropyl-benzylamide) 1-pyridin-4-ylamide (Example 347), (R)-4-(4-trifluoromethyl-benzenesulfonyl)-piperazine-1,3-dicarboxylic acid 3-(4-isopropyl-benzylamide) 1-[1,3,4]oxadiazol-2-ylamide (Example 348), (R)-4-(4-trifluoromethoxy-benzenesulfonyl)-piperazine-1,3-dicarboxylic acid 3-(4-propyl-benzylamide) 1-pyridin-4-ylamide (Example 436), (R)-4-(4-trifluoromethoxy-benzenesulfonyl)-piperazine-1,3-dicarboxylic acid 3-(4-propyl-benzylamide) 1-[1,3,4]thiadiazol-2-ylamide (Example 437), (2-{[(R)-3-(4-propyl-benzylcarbamoyl)-4-(4-trifluoromethoxy-benzenesulfonyl)-piperazine-1-carbonyl]-amino}-thiazol-4-yl)-acetic acid ethyl ester (Example 470), (R)-4-(4-trifluoromethoxy-benzenesulfonyl)-piperazine-1,3-dicarboxylic acid 1-{[4-(2-morpholin-4-yl-2-oxo-ethyl)-thiazol-2-yl]-amide} 3-(4-propyl-benzylamide) (Example 475), (R)-4-(4-trifluoromethoxy-benzenesulfonyl)-piperazine-1,3-dicarboxylic acid 1-{[4-(2-hydroxy-ethyl)-thiazol-2-yl]-amide} 3-(4-propyl-benzylamide) (Example 476), 5-{[(R)-3-[4-(1,1-difluoro-propyl)-benzylcarbamoyl]-4-(4-trifluoromethoxy-benzenesulfonyl)-piperazine-1-carbonyl]-amino}-[1,3,4]thiadiazole-2-carboxylic acid ethyl ester (Example 477), (R)-4-(4-trifluoromethoxy-benzenesulfonyl)-piperazine-1,3-dicarboxylic acid 3-[4-(1,1-difluoro-propyl)-benzylamide] 1-[(5-hydroxymethyl-[1,3,4]thiadiazol-2-yl)-amide] (Example 482), (R)-4-(4-trifluoromethoxy-benzenesulfonyl)-piperazine-1,3-dicarboxylic acid 1-[(5-acetyl-[1,3,4]thiadiazol-2-yl)-amide] 3-[4-(1,1-difluoro-propyl)-benzylamide] (Example 483), (R)-4-(4-trifluoromethoxy-benzenesulfonyl)-piperazine-1,3-dicarboxylic acid 3-[4-(1,1-difluoro-propyl)-benzylamide] 1-{[5-(1-hydroxy-1-methyl-ethyl)-[1,3,4]thiadiazol-2-yl]-amide} (Example 484), (R)-4-(4-trifluoromethoxy-benzenesulfonyl)-piperazine-1,3-dicarboxylic acid 3-[4-(1,1-difluoro-propyl)-benzylamide] 1-[(5-methyl-[1,3,4]thiadiazol-2-yl)-amide] (Example 488), (R)-4-(4-trifluoromethoxy-benzenesulfonyl)-piperazine-1,3-dicarboxylic acid 3-[4-(1,1-difluoro-propyl)-benzylamide] 1-[(5-trifluoromethyl-[1,3,4]thiadiazol-2-yl)-amide] (Example 489), (R)-4-(4-trifluoromethoxy-benzenesulfonyl)-piperazine-1,3-dicarboxylic acid 3-[4-(1,1-difluoro-propyl)-benzylamide] 1-[(2-methoxy-pyridin-4-yl)-amide] (Example 490), 4-{[(R)-3-[4-(1,1-difluoro-propyl)-benzylcarbamoyl]-4-(4-trifluoromethoxy-benzenesulfonyl)-piperazine-1-carbonyl]-amino}-pyridine-2-carboxylic acid tert-butyl ester (Example 491), (R)-4-(4-trifluoromethoxy-benzenesulfonyl)-piperazine-1,3-dicarboxylic acid 3-[4-(1,1-difluoro-propyl)-benzylamide] 1-{[5-((R)-3-hydroxy-pyrrolidine-1-carbonyl)-[1,3,4]thiadiazol-2-yl]-amide} (Example 495), (R)-4-(4-trifluoromethoxy-benzenesulfonyl)-piperazine-1,3-dicarboxylic acid 3-[4-(1,1-difluoro-propyl)-benzylamide] 1-{[5-(4-hydroxy-piperidine-1-carbonyl)-[1,3,4]thiadiazol-2-yl]-amide} (Example 496), (R)-4-(4-trifluoromethoxy-benzenesulfonyl)-piperazine-1,3-dicarboxylic acid 3-[4-(1,1-difluoro-propyl)-benzylamide] 1-{[5-(morpholine-4-carbonyl)-[1,3,4]thiadiazol-2-yl]-amide} (Example 497), 4-{[(R)-3-[4-(1,1-difluoro-propyl)-benzylcarbamoyl]-4-(4-trifluoromethoxy-benzenesulfonyl)-piperazine-1-carbonyl]-amino}-pyridine-2-carboxylic acid (Example 502), (R)-4-(4-trifluoromethoxy-benzenesulfonyl)-piperazine-1,3-dicarboxylic acid 1-[(2-carbamoyl-pyridin-4-yl)-amide] 3-[4-(1,1-difluoro-propyl)-benzylamide] (Example 503), (R)-4-(4-trifluoromethoxy-benzenesulfonyl)-piperazine-1,3-dicarboxylic acid 3-[4-(1,1-difluoro-propyl)-benzylamide] 1-[(2-dimethylcarbamoyl-pyridin-4-yl)-amide] (Example 504), (R)-4-(4-trifluoromethoxy-benzenesulfonyl)-piperazine-1,3-dicarboxylic acid 3-[4-(1,1-difluoro-propyl)-benzylamide] 1-[(2-hydroxymethyl-pyridin-4-yl)-amide] (Example 511), (R)-4-(4-trifluoromethoxy-benzenesulfonyl)-piperazine-1,3-dicarboxylic acid 1-[(2-cyclopropylcarbamoyl-pyridin-4-yl)-amide] 3-[4-(1,1-difluoro-propyl)-benzylamide] (Example 512), (R)-4-(4-trifluoromethoxy-benzenesulfonyl)-piperazine-1,3-dicarboxylic acid 3-[4-(1,1-difluoro-propyl)-benzylamide] 1-{[2-(morpholine-4-carbonyl)-pyridin-4-yl]-amide} (Example 513), (R)-4-(4-trifluoromethoxy-benzenesulfonyl)-piperazine-1,3-dicarboxylic acid 3-[4-(1,1-difluoro-propyl)-benzylamide] 1-{[2-(pyrrolidine-1-carbonyl)-pyridin-4-yl]-amide} (Example 514), (R)-4-(4-trifluoromethoxy-benzenesulfonyl)-piperazine-1,3-dicarboxylic acid 1-[(2-chloro-pyridin-4-yl)-amide] 3-[4-(1,1-difluoro-propyl)-benzylamide] (Example 517), (R)-4-(4-trifluoromethoxy-benzenesulfonyl)-piperazine-1,3-dicarboxylic acid 3-[4-(1,1-difluoro-propyl)-benzylamide] 1-thiazol-4-ylamide (Example 525), (R)-4-(4-trifluoromethoxy-benzenesulfonyl)-piperazine-1,3-dicarboxylic acid 3-[4-(1,1-difluoro-propyl)-benzylamide] 1-[(5-methyl-isoxazol-3-yl)-amide] (Example 526), (R)-4-(4-trifluoromethoxy-benzenesulfonyl)-piperazine-1,3-dicarboxylic acid 3-[4-(1,1-difluoro-propyl)-benzylamide] 1-[(3-methyl-[1,2,4]thiadiazol-5-yl)-amide] (Example 527), (R)-4-(4-trifluoromethoxy-benzenesulfonyl)-piperazine-1,
3-dicarboxylic acid 3-[4-(1,1-difluoro-propyl)-benzylamide] 1-[(3-methyl-isoxazol-5-yl)-amide] (Example 528),
(R)-4-(4-trifluoromethoxy-benzenesulfonyl)-piperazine-1,
3-dicarboxylic acid 3-[4-(1,1-difluoro-propyl)-benzylamide] 1-[1,2,4]triazol-4-ylamide (Example 539),
(R)-4-(4-trifluoromethoxy-benzenesulfonyl)-piperazine-1,
3-dicarboxylic acid 1-[(5-methyl-[1,3,4]thiadiazol-2-yl)-amide] 3-(4-pentafluoroethyl-benzylamide) (Example 552),
(R)-4-(4-trifluoromethoxy-benzenesulfonyl)-piperazine-1,
3-dicarboxylic acid 3-[4-(1,1-difluoro-propyl)-benzylamide] 1-[(3-methyl-isothiazol-5-yl)-amide] (Example 553),
(R)-4-(4-trifluoromethoxy-benzenesulfonyl)-piperazine-1,
3-dicarboxylic acid 3-[4-(1,1-difluoro-propyl)-benzylamide] 1-thiazol-2-ylamide (Example 554),
(R)-4-(4-trifluoromethoxy-benzenesulfonyl)-piperazine-1,
3-dicarboxylic acid 3-[4-(1,1-difluoro-propyl)-benzylamide] 1-[(2-trifluoromethyl-pyridin-4-yl)-amide] (Example 555),
(R)-4-(4-trifluoromethoxy-benzenesulfonyl)-piperazine-1,
3-dicarboxylic acid 3-[4-(1,1-difluoro-propyl)-benzylamide] 1-[(1H-[1,2,4]triazol-3-yl)-amide] (Example 565),
(R)-4-(4-trifluoromethoxy-benzenesulfonyl)-piperazine-1,
3-dicarboxylic acid 3-[4-(1,1-difluoro-propyl)-benzylamide] 1-[(2H-tetrazol-5-yl)-amide] (Example 566),
(R)-4-(4-trifluoromethoxy-benzenesulfonyl)-piperazine-1,
3-dicarboxylic acid 3-[4-(1,1-difluoro-propyl)-benzylamide] 1-[(2-methyl-thiazol-4-yl)-amide] (Example 567),
(R)-4-(4-trifluoromethoxy-benzenesulfonyl)-piperazine-1,
3-dicarboxylic acid 3-[4-(1,1-difluoro-propyl)-benzylamide] 1-[(1-methyl-1H-pyrazol-3-yl)-amide] (Example 569),
(R)-4-(4-trifluoromethoxy-benzenesulfonyl)-piperazine-1,
3-dicarboxylic acid 3-[4-(1,1-difluoro-propyl)-benzylamide] 1-thiazol-5-ylamide (Example 607),
(R)-4-(4-trifluoromethoxy-benzenesulfonyl)-piperazine-1,
3-dicarboxylic acid 3-[4-(1,1-difluoro-propyl)-benzylamide] 1-{[4-(1-hydroxy-1-methyl-ethyl)-thiazol-2-yl]-amide} (Example 612), and
(R)-4-(4-trifluoromethoxy-benzenesulfonyl)-piperazine-1,
3-dicarboxylic acid 1-[(5-bromo-[1,3,4]thiadiazol-2-yl)-amide] 3-(4-trifluoromethoxy-benzylamide) (Example 936),
or a pharmaceutically acceptable salt thereof, or a solvate thereof.
[31] The compound of [17], which is selected from the group consisting of
(R)-4-(2-pyridin-4-yl-acetyl)-1-(4-trifluoromethyl-benzenesulfonyl)-piperazine-2-carboxylic acid 4-isopropyl-benzylamide (Example 2),
1-(4-iodo-benzenesulfonyl)-4-(2-piperidin-1-yl-acetyl)-piperazine-2-carboxylic acid 4-dimethylamino-benzylamide (Example 102),
1-(4-iodo-benzenesulfonyl)-4-(2-morpholin-4-yl-acetyl)-piperazine-2-carboxylic acid 4-dimethylamino-benzylamide (Example 104),
1-(4-iodo-benzenesulfonyl)-4-(2-pyridin-2-yl-acetyl)-piperazine-2-carboxylic acid 4-dimethylamino-benzylamide (Example 153),
1-(4-iodo-benzenesulfonyl)-4-(2-pyridin-3-yl-acetyl)-piperazine-2-carboxylic acid 4-dimethylamino-benzylamide (Example 154),
(R)-1-(4-iodo-benzenesulfonyl)-4-(2-piperidin-1-yl-acetyl)-piperazine-2-carboxylic acid 4-dimethylamino-benzylamide (Example 158),
(R)-1-(4-iodo-benzenesulfonyl)-4-(2-pyrrolidin-1-yl-acetyl)-piperazine-2-carboxylic acid 4-dimethylamino-benzylamide (Example 159),
(R)-1-(4-iodo-benzenesulfonyl)-4-(2-morpholin-4-yl-acetyl)-piperazine-2-carboxylic acid 4-dimethylamino-benzylamide (Example 160),
(R)-4-(2-pyridin-3-yl-acetyl)-1-(4-trifluoromethyl-benzenesulfonyl)-piperazine-2-carboxylic acid 4-isopropyl-benzylamide (Example 175),
(R)-4-(2-morpholin-4-yl-acetyl)-1-(4-trifluoromethyl-benzenesulfonyl)-piperazine-2-carboxylic acid 4-isopropyl-benzylamide (Example 180),
(R)-4-(2-1H-imidazol-4-yl-acetyl)-1-(4-trifluoromethyl-benzenesulfonyl)-piperazine-2-carboxylic acid 4-isopropyl-benzylamide (Example 195),
(R)-4-(2-imidazol-1-yl-acetyl)-1-(4-trifluoromethyl-benzenesulfonyl)-piperazine-2-carboxylic acid 4-isopropyl-benzylamide (Example 219),
(R)-4-(2-[1,2,3]triazol-1-yl-acetyl)-1-(4-trifluoromethyl-benzenesulfonyl)-piperazine-2-carboxylic acid 4-isopropyl-benzylamide (Example 220),
(R)-4-(2-pyrazol-1-yl-acetyl)-1-(4-trifluoromethyl-benzenesulfonyl)-piperazine-2-carboxylic acid 4-isopropyl-benzylamide (Example 228),
(R)-4-(2-[1,2,4]triazol-1-yl-acetyl)-1-(4-trifluoromethyl-benzenesulfonyl)-piperazine-2-carboxylic acid 4-isopropyl-benzylamide (Example 229),
(R)-4-(2-[1,2,4]triazol-4-yl-acetyl)-1-(4-trifluoromethyl-benzenesulfonyl)-piperazine-2-carboxylic acid 4-isopropyl-benzylamide (Example 230),
(R)-4-(2-[1,2,3]triazol-2-yl-acetyl)-1-(4-trifluoromethyl-benzenesulfonyl)-piperazine-2-carboxylic acid 4-isopropyl-benzylamide (Example 242),
(R)-4-(2-tetrazol-1-yl-acetyl)-1-(4-trifluoromethyl-benzenesulfonyl)-piperazine-2-carboxylic acid 4-isopropyl-benzylamide (Example 257),
(R)-4-(2-1H-tetrazol-5-yl-acetyl)-1-(4-trifluoromethyl-benzenesulfonyl)-piperazine-2-carboxylic acid 4-isopropyl-benzylamide (Example 261),
(R)-4-(2-tetrazol-2-yl-acetyl)-1-(4-trifluoromethyl-benzenesulfonyl)-piperazine-2-carboxylic acid 4-isopropyl-benzylamide (Example 278),
(2-{2-[(R)-3-(4-isopropyl-benzylcarbamoyl)-4-(4-trifluoromethyl-benzenesulfonyl)-piperazin-1-yl]-2-oxo-ethyl}-2H-tetrazol-5-yl)-acetic acid ethyl ester (Example 309),
(2-{2-[(R)-3-(4-isopropyl-benzylcarbamoyl)-4-(4-trifluoromethyl-benzenesulfonyl)-piperazin-1-yl]-2-oxo-ethyl}-2H-tetrazol-5-yl)-acetic acid (Example 310),
(1-{2-[(R)-3-(4-isopropyl-benzylcarbamoyl)-4-(4-trifluoromethyl-benzenesulfonyl)-piperazin-1-yl]-2-oxo-ethyl}-1H-tetrazol-5-yl)-acetic acid ethyl ester (Example 311),
(1-{2-[(R)-3-(4-isopropyl-benzylcarbamoyl)-4-(4-trifluoromethyl-benzenesulfonyl)-piperazin-1-yl]-2-oxo-ethyl}-1H-tetrazol-5-yl)-acetic acid (Example 312),
1-(4-iodo-benzenesulfonyl)-4-[2-(4-methyl-piperazin-1-yl)-acetyl]-piperazine-2-carboxylic acid 4-dimethylamino-benzylamide (Example 346),
(R)-4-(2-pyridin-4-yl-acetyl)-1-(4-trifluoromethoxy-benzenesulfonyl)-piperazine-2-carboxylic acid 4-trifluoromethoxy-benzylamide (Example 409),
(R)-4-(2-pyridin-4-yl-acetyl)-1-(4-trifluoromethoxy-benzenesulfonyl)-piperazine-2-carboxylic acid 4-dimethylamino-benzylamide (Example 410),
(R)-4-(2-pyridin-4-yl-acetyl)-1-(4-trifluoromethoxy-benzenesulfonyl)-piperazine-2-carboxylic acid 4-propyl-benzylamide (Example 411), (R)-4-(2-pyridin-4-yl-acetyl)-1-(4-trifluoromethoxy-benzenesulfonyl)-piperazine-2-carboxylic acid 4-cyclopropyl-benzylamide (Example 412), (2-{2-oxo-2-[(R)-3-(4-propyl-benzylcarbamoyl)-4-(4-trifluoromethoxy-benzenesulfonyl)-piperazin-1-yl]-ethyl}-2H-tetrazol-5-yl)-acetic acid ethyl ester (Example 455), (R)-4-[2-(5-methyl-tetrazol-1-yl)-acetyl]-1-(4-trifluoromethoxy-benzenesulfonyl)-piperazine-2-carboxylic acid 4-propyl-benzylamide (Example 456), (R)-4-[2-(5-methyl-tetrazol-2-yl)-acetyl]-1-(4-trifluoromethoxy-benzenesulfonyl)-piperazine-2-carboxylic acid 4-propyl-benzylamide (Example 457), (R)-4-(2-tetrazol-2-yl-acetyl)-1-(4-trifluoromethoxy-benzenesulfonyl)-piperazine-2-carboxylic acid 4-propyl-benzylamide (Example 460), (R)-4-(2-tetrazol-1-yl-acetyl)-1-(4-trifluoromethoxy-benzenesulfonyl)-piperazine-2-carboxylic acid 4-propyl-benzylamide (Example 461), (R)-4-(2-imidazol-1-yl-acetyl)-1-(4-trifluoromethoxy-benzenesulfonyl)-piperazine-2-carboxylic acid 4-propyl-benzylamide (Example 462), (R)-4-(2-tetrazol-1-yl-acetyl)-1-(4-trifluoromethoxy-benzenesulfonyl)-piperazine-2-carboxylic acid 4-(1,1-difluoro-propyl)-benzylamide (Example 464), (2-{2-oxo-2-[(R)-3-(4-propyl-benzylcarbamoyl)-4-(4-trifluoromethoxy-benzenesulfonyl)-piperazin-1-yl]-ethyl}-2H-tetrazol-5-yl)-acetic acid (Example 465), (2-{2-[(R)-3-[4-(1,1-difluoro-propyl)-benzylcarbamoyl]-4-(4-trifluoromethoxy-benzenesulfonyl)-piperazin-1-yl]-2-oxo-ethyl}-2H-tetrazol-5-yl)-acetic acid ethyl ester (Example 466), (R)-4-[2-(5-methyl-tetrazol-1-yl)-acetyl]-1-(4-trifluoromethoxy-benzenesulfonyl)-piperazine-2-carboxylic acid 4-(1,1-difluoro-propyl)-benzylamide (Example 467), (R)-4-[2-(5-methyl-tetrazol-2-yl)-acetyl]-1-(4-trifluoromethoxy-benzenesulfonyl)-piperazine-2-carboxylic acid 4-(1,1-difluoro-propyl)-benzylamide (Example 468), (R)-4-[2-(5-phenyl-tetrazol-2-yl)-acetyl]-1-(4-trifluoromethoxy-benzenesulfonyl)-piperazine-2-carboxylic acid 4-(1,1-difluoro-propyl)-benzylamide (Example 479), (R)-4-[2-(3-methyl-isoxazol-5-yl)-acetyl]-1-(4-trifluoromethoxy-benzenesulfonyl)-piperazine-2-carboxylic acid 4-(1,1-difluoro-propyl)-benzylamide (Example 480), (R)-4-[2-(1-methyl-1H-imidazol-4-yl)-acetyl]-1-(4-trifluoromethoxy-benzenesulfonyl)-piperazine-2-carboxylic acid 4-(1,1-difluoro-propyl)-benzylamide (Example 498), (R)-4-(2-pyridin-4-yl-acetyl)-1-(4-trifluoromethoxy-benzenesulfonyl)-piperazine-2-carboxylic acid 4-tert-butyl-benzylamide (Example 500), (R)-4-(2-pyridin-4-yl-acetyl)-1-(4-trifluoromethoxy-benzenesulfonyl)-piperazine-2-carboxylic acid 4-(1,1-difluoro-propyl)-benzylamide (Example 508), (R)-4-[2-(2-methyl-2H-tetrazol-5-yl)-acetyl]-1-(4-trifluoromethoxy-benzenesulfonyl)-piperazine-2-carboxylic acid 4-(1,1-difluoro-propyl)-benzylamide (Example 518), (R)-4-[2-(1-methyl-1H-tetrazol-5-yl)-acetyl]-1-(4-trifluoromethoxy-benzenesulfonyl)-piperazine-2-carboxylic acid 4-(1,1-difluoro-propyl)-benzylamide (Example 519), (5-{2-[(R)-3-[4-(1,1-difluoro-propyl)-benzylcarbamoyl]-4-(4-trifluoromethoxy-benzenesulfonyl)-piperazin-1-yl]-2-oxo-ethyl}-tetrazol-2-yl)-acetic acid ethyl ester (Example 532), (5-{2-[(R)-3-[4-(1,1-difluoro-propyl)-benzylcarbamoyl]-4-(4-trifluoromethoxy-benzenesulfonyl)-piperazin-1-yl]-2-oxo-ethyl}-tetrazol-1-yl)-acetic acid ethyl ester (Example 533), (R)-4-[2-(5-isopropyl-tetrazol-1-yl)-acetyl]-1-(4-trifluoromethoxy-benzenesulfonyl)-piperazine-2-carboxylic acid 4-(1,1-difluoro-propyl)-benzylamide (Example 541), (R)-4-[2-(5-isopropyl-tetrazol-2-yl)-acetyl]-1-(4-trifluoromethoxy-benzenesulfonyl)-piperazine-2-carboxylic acid 4-(1,1-difluoro-propyl)-benzylamide (Example 542), (R)-4-{2-[5-(2-morpholin-4-yl-2-oxo-ethyl)-tetrazol-2-yl]-acetyl}-1-(4-trifluoromethoxy-benzenesulfonyl)-piperazine-2-carboxylic acid 4-(1,1-difluoro-propyl)-benzylamide (Example 543), (R)-4-[2-(5-methyl-tetrazol-2-yl)-acetyl]-1-(4-trifluoromethoxy-benzenesulfonyl)-piperazine-2-carboxylic acid 4-pentafluoroethyl-benzylamide (Example 551), (R)-4-(2-pyrimidin-4-yl-acetyl)-1-(4-trifluoromethoxy-benzenesulfonyl)-piperazine-2-carboxylic acid 4-(1,1-difluoro-propyl)-benzylamide (Example 590), (R)-4-[2-(5-amino-tetrazol-2-yl)-acetyl]-1-(4-trifluoromethoxy-benzenesulfonyl)-piperazine-2-carboxylic acid 4-(1,1-difluoro-propyl)-benzylamide (Example 1096), and (R)-4-[2-(5-amino-tetrazol-1-yl)-acetyl]-1-(4-trifluoromethoxy-benzenesulfonyl)-piperazine-2-carboxylic acid 4-(1,1-difluoro-propyl)-benzylamide (Example 1097), or a pharmaceutically acceptable salt thereof, or a solvate thereof.

[32] The compound of [18], which is selected from the group consisting of

2-[(R)-3-(4-isopropyl-benzylcarbamoyl)-4-(4-trifluoromethyl-benzenesulfonyl)-piperazin-1-yl]-4-methyl-thiazole-5-carboxylic acid tert-butyl ester (Example 5), 2-[(R)-3-(4-isopropyl-benzylcarbamoyl)-4-(4-trifluoromethyl-benzenesulfonyl)-piperazin-1-yl]-4-methyl-thiazole-5-carboxylic acid (Example 6), (R)-4-(5-carbamoyl-4-methyl-thiazol-2-yl)-1-(4-trifluoromethyl-benzenesulfonyl)-piperazine-2-carboxylic acid 4-isopropyl-benzylamide (Example 7), (R)-3-(4-isopropyl-benzylcarbamoyl)-4-(4-trifluoromethyl-benzenesulfonyl)-3,4,5,6-tetrahydro-2H-[1,2']bipyrazinyl-5'-carboxylic acid methyl ester (Example 8), (R)-3-(4-isopropyl-benzylcarbamoyl)-4-(4-trifluoromethyl-benzenesulfonyl)-3,4,5,6-tetrahydro-2H-[1,2']bipyrazinyl-5'-carboxylic acid (Example 9), 2-[(R)-3-[(6-isopropyl-pyridin-3-ylmethyl)-carbamoyl]-4-(4-trifluoromethoxy-benzenesulfonyl)-piperazin-1-yl]-4-methyl-thiazole-5-carboxylic acid (Example 13), 2-[(R)-3-(4-propyl-benzylcarbamoyl)-4-(2-fluoro-4-trifluoromethoxy-benzenesulfonyl)-piperazin-1-yl]-4-methyl-thiazole-5-carboxylic acid (Example 14), 4-(4,5-dihydro-1H-imidazol-2-yl)-1-(4-isopropyl-benzenesulfonyl)-piperazine-2-carboxylic acid 4-trifluoromethyl-benzylamide (Example 103), 4-(4,5-dihydro-thiazol-2-yl)-1-(4-isopropyl-benzenesulfonyl)-piperazine-2-carboxylic acid 4-trifluoromethyl-benzylamide (Example 112), 1-(4-isopropyl-benzenesulfonyl)-4-(4-methyl-thiazol-2-yl)-piperazine-2-carboxylic acid 4-trifluoromethyl-benzylamide (Example 115), 4-(4,5-dihydro-oxazol-2-yl)-1-(4-isopropyl-benzenesulfonyl)-piperazine-2-carboxylic acid 4-trifluoromethyl-benzylamide (Example 133), 4-benzothiazol-2-yl-1-(4-isopropyl-benzenesulfonyl)-piperazine-2-carboxylic acid 4-trifluoromethyl-benzylamide (Example 134), 1-(4-isopropyl-benzenesulfonyl)-4-(4-phenyl-thiazol-2-yl)-piperazine-2-carboxylic acid 4-trifluoromethyl-benzylamide (Example 135), (R)-4-(2,5-dioxo-pyrrolidin-3-yl)-1-(4-trifluoromethyl-benzenesulfonyl)-piperazine-2-carboxylic acid 4-isopropyl-benzylamide (Example 147), (R)-4-(2,5-dioxo-4-phenyl-2,5-dihydro-1H-pyrrol-3-yl)-1-(4-trifluoromethyl-benzenesulfonyl)-piperazine-2-carboxylic acid 4-isopropyl-benzylamide (Example 148), 4-(8H-indeno[1,2-d]thiazol-2-yl)-1-(4-isopropyl-benzenesulfonyl)-piperazine-2-carboxylic acid 4-trifluoromethyl-benzylamide (Example 155), 1-(4-isopropyl-benzenesulfonyl)-4-(4,5,6,7-tetrahydro-benzothiazol-2-yl)-piperazine-2-carboxylic acid 4-trifluoromethyl-benzylamide (Example 156), 2-[4-(4-isopropyl-benzenesulfonyl)-3-(4-trifluoromethyl-benzylcarbamoyl)-piperazin-1-yl]-thiazole-4-carboxylic acid ethyl ester (Example 170), 2-[4-(4-isopropyl-benzenesulfonyl)-3-(4-trifluoromethyl-benzylcarbamoyl)-piperazin-1-yl]-thiazole-4-carboxylic acid (Example 171), (R)-4-(4,5-dihydro-thiazol-2-yl)-1-(4-trifluoromethyl-benzenesulfonyl)-piperazine-2-carboxylic acid 4-isopropyl-benzylamide (Example 179), (R)-4-(4-methyl-thiazol-2-yl)-1-(4-trifluoromethyl-benzenesulfonyl)-piperazine-2-carboxylic acid 4-isopropyl-benzylamide (Example 184), (R)-4-benzothiazol-2-yl-1-(4-trifluoromethyl-benzenesulfonyl)-piperazine-2-carboxylic acid 4-isopropyl-benzylamide (Example 191), 2-[(R)-3-(4-isopropyl-benzylcarbamoyl)-4-(4-trifluoromethyl-benzenesulfonyl)-piperazin-1-yl]-thiazole-4-carboxylic acid (Example 244), 2-[(R)-3-(4-isopropyl-benzylcarbamoyl)-4-(4-trifluoromethyl-benzenesulfonyl)-piperazin-1-yl]-4-methyl-thiazole-5-carboxylic acid methyl ester (Example 254), {2-[(R)-3-(4-isopropyl-benzylcarbamoyl)-4-(4-trifluoromethyl-benzenesulfonyl)-piperazin-1-yl]-thiazol-4-yl}-acetic acid methyl ester (Example 255), {2-[(R)-3-(4-isopropyl-benzylcarbamoyl)-4-(4-trifluoromethyl-benzenesulfonyl)-piperazin-1-yl]-thiazol-4-yl}-acetic acid (Example 259), 2-[(R)-3-(4-isopropyl-benzylcarbamoyl)-4-(4-propyl-benzenesulfonyl)-piperazin-1-yl]-thiazole-4-carboxylic acid ethyl ester (Example 296), 2-[(R)-3-(4-isopropyl-benzylcarbamoyl)-4-(4-propyl-benzenesulfonyl)-piperazin-1-yl]-4-methyl-thiazole-5-carboxylic acid methyl ester (Example 297), 2-[(R)-3-(4-isopropyl-benzylcarbamoyl)-4-(4-propyl-benzenesulfonyl)-piperazin-1-yl]-thiazole-4-carboxylic acid (Example 298), 2-[(R)-3-(4-isopropyl-benzylcarbamoyl)-4-(4-propyl-benzenesulfonyl)-piperazin-1-yl]-4-methyl-thiazole-5-carboxylic acid (Example 299), 2-[(R)-3-(4-isopropyl-benzylcarbamoyl)-4-(4-trifluoromethyl-benzenesulfonyl)-piperazin-1-yl]-thiazole-5-carboxylic acid methyl ester (Example 302), 6-[(R)-3-(4-isopropyl-benzylcarbamoyl)-4-(4-trifluoromethyl-benzenesulfonyl)-piperazin-1-yl]-nicotinic acid methyl ester (Example 303), 2-[(R)-3-(4-isopropyl-benzylcarbamoyl)-4-(4-trifluoromethyl-benzenesulfonyl)-piperazin-1-yl]-thiazole-5-carboxylic acid (Example 315), 2-[(R)-3-(4-isopropyl-benzylcarbamoyl)-4-(4-propyl-benzenesulfonyl)-piperazin-1-yl]-4-methyl-thiazole-5-carboxylic acid tert-butyl ester (Example 319), 2-[(R)-3-(4-isopropyl-benzylcarbamoyl)-4-(4-trifluoromethoxy-benzenesulfonyl)-piperazin-1-yl]-4-methyl-thiazole-5-carboxylic acid tert-butyl ester (Example 320), 2-[(R)-3-(4-isopropyl-benzylcarbamoyl)-4-(4-trifluoromethoxy-benzenesulfonyl)-piperazin-1-yl]-4-methyl-thiazole-5-carboxylic acid (Example 322), 4-hydroxy-2-[(R)-3-(4-isopropyl-benzylcarbamoyl)-4-(4-trifluoromethyl-benzenesulfonyl)-piperazin-1-yl]-pyrimidine-5-carboxylic acid ethyl ester (Example 325), 6-[(R)-3-(4-isopropyl-benzylcarbamoyl)-4-(4-trifluoromethyl-benzenesulfonyl)-piperazin-1-yl]-nicotinic acid tert-butyl ester (Example 326), 6-[(R)-3-(4-isopropyl-benzylcarbamoyl)-4-(4-trifluoromethyl-benzenesulfonyl)-piperazin-1-yl]-nicotinic acid trifluoroacetate (Example 327), 2-[(R)-3-(4-isopropyl-benzylcarbamoyl)-4-(4-trifluoromethoxy-benzenesulfonyl)-piperazin-1-yl]-thiazole-5-carboxylic acid (Example 328), 2-[(R)-3-(4-isopropyl-benzylcarbamoyl)-4-(4-propyl-benzenesulfonyl)-piperazin-1-yl]-thiazole-5-carboxylic acid (Example 329), 2-[(R)-3-(4-isopropyl-2-methyl-benzylcarbamoyl)-4-(4-propyl-benzenesulfonyl)-piperazin-1-yl]-4-methyl-thiazole-5-carboxylic acid tert-butyl ester (Example 330), 2-[(R)-3-(4-isopropyl-2-methyl-benzylcarbamoyl)-4-(4-propyl-benzenesulfonyl)-piperazin-1-yl]-4-methyl-thiazole-5-carboxylic acid (Example 331), (R)-4-(5-carbamoyl-4-methyl-thiazol-2-yl)-1-(4-propyl-benzenesulfonyl)-piperazine-2-carboxylic acid 4-isopropyl-benzylamide (Example 333), 2-[(R)-3-(4-isopropyl-2-methyl-benzylcarbamoyl)-4-(4-trifluoromethyl-benzenesulfonyl)-piperazin-1-yl]-4-methyl-thiazole-5-carboxylic acid (Example 335), 2-[(R)-3-(4-isopropyl-benzylcarbamoyl)-4-(4-trifluoromethyl-benzenesulfonyl)-piperazin-1-yl]-4-methyl-pyrimidine-5-carboxylic acid benzyl ester (Example 336), 2-[(R)-3-(4-isopropyl-benzylcarbamoyl)-4-(4-trifluoromethyl-benzenesulfonyl)-piperazin-1-yl]-4-methyl-pyrimidine-5-carboxylic acid methyl ester (Example 337), 2-[(R)-3-(4-isopropyl-benzylcarbamoyl)-4-(4-trifluoromethyl-benzenesulfonyl)-piperazin-1-yl]-4-methyl-pyrimidine-5-carboxylic acid (Example 338), 4-methyl-2-[(R)-3-(4-propyl-benzylcarbamoyl)-4-(4-trifluoromethyl-benzenesulfonyl)-piperazin-1-yl]-thiazole-5-carboxylic acid (Example 339), (R)-4-(5-carbamoyl-4-methyl-thiazol-2-yl)-1-(4-trifluoromethoxy-benzenesulfonyl)-piperazine-2-carboxylic acid 4-isopropyl-benzylamide (Example 340), 4-methyl-2-[(R)-3-(2-methyl-4-propyl-benzylcarbamoyl)-4-(4-trifluoromethoxy-benzenesulfonyl)-piperazin-1-yl]-thiazole-5-carboxylic acid (Example 341), 2-[(R)-3-(4-isopropyl-benzylcarbamoyl)-4-(4-trifluoromethyl-benzenesulfonyl)-piperazin-1-yl]-pyrimidine-5-carboxylic acid (Example 342), 2-[(R)-3-(4-dimethylamino-benzylcarbamoyl)-4-(4-trifluoromethyl-benzenesulfonyl)-piperazin-1-yl]-4-methyl-thiazole-5-carboxylic acid (Example 343), 2-[(R)-4-(4-isopropyl-benzenesulfonyl)-3-(4-isopropyl-benzylcarbamoyl)-piperazin-1-yl]-4-methyl-thiazole-5-carboxylic acid (Example 344), (R)-4-(2-oxo-pyrrolidin-3-yl)-1-(4-trifluoromethyl-benzenesulfonyl)-piperazine-2-carboxylic acid 4-isopropyl-benzylamide (Example 345), 2-[(R)-3-(4-isopropyl-benzylcarbamoyl)-4-(4-trifluoromethyl-benzenesulfonyl)-piperazin-1-yl]-isonicotinic acid trifluoroacetate (Example 349), (R)-4-(1-methyl-1H-imidazol-2-yl)-1-(4-trifluoromethyl-benzenesulfonyl)-piperazine-2-carboxylic acid 4-isopropyl-benzylamide (Example 352), (R)-4-(1H-imidazol-2-yl)-1-(4-trifluoromethyl-benzenesulfonyl)-piperazine-2-carboxylic acid 4-isopropyl-benzylamide (Example 353), (R)-4-(4-methyl-5-methylcarbamoyl-thiazol-2-yl)-1-(4-trifluoromethoxy-benzenesulfonyl)-piperazine-2-carboxylic acid 4-isopropyl-benzylamide (Example 354), (R)-4-(5-dimethylcarbamoyl-4-methyl-thiazol-2-yl)-1-(4-trifluoromethoxy-benzenesulfonyl)-piperazine-2-carboxylic acid 4-isopropyl-benzylamide (Example 355), 2-[(R)-3-(4-cyclopropyl-2-methyl-benzylcarbamoyl)-4-(4-trifluoromethoxy-benzenesulfonyl)-piperazin-1-yl]-4-methyl-thiazole-5-carboxylic acid (Example 356), 4-hydroxy-2-[(R)-3-(4-isopropyl-benzylcarbamoyl)-4-(4-trifluoromethyl-benzenesulfonyl)-piperazin-1-yl]-pyrimidine-5-carboxylic acid (Example 357), ({2-[(R)-3-(4-isopropyl-benzylcarbamoyl)-4-(4-trifluoromethoxy-benzenesulfonyl)-piperazin-1-yl]-4-methyl-thiazole-5-carbonyl}-amino)-acetic acid tert-butyl ester (Example 358), 3-({2-[(R)-3-(4-isopropyl-benzylcarbamoyl)-4-(4-trifluoromethoxy-benzenesulfonyl)-piperazin-1-yl]-4-methyl-thiazole-5-carbonyl}-amino)-propionic acid tert-butyl ester (Example 359), ({2-[(R)-3-(4-isopropyl-benzylcarbamoyl)-4-(4-trifluoromethoxy-benzenesulfonyl)-piperazin-1-yl]-4-methyl-thiazole-5-carbonyl}-amino)-acetic acid (Example 360), 3-({2-[(R)-3-(4-isopropyl-benzylcarbamoyl)-4-(4-trifluoromethoxy-benzenesulfonyl)-piperazin-1-yl]-4-methyl-thiazole-5-carbonyl}-amino)-propionic acid (Example 361), (R)-4-(5-nitro-2H-[1,2,4]triazol-3-yl)-1-(4-trifluoromethyl-benzenesulfonyl)-piperazine-2-carboxylic acid 4-isopropyl-benzylamide (Example 362), 4-ethyl-2-[(R)-3-(2-methyl-4-propyl-benzylcarbamoyl)-4-(4-trifluoromethoxy-benzenesulfonyl)-piperazin-1-yl]-thiazole-5-carboxylic acid (Example 363), 2-[(R)-3-(4-isopropyl-2-methyl-benzylcarbamoyl)-4-(4-trifluoromethoxy-benzenesulfonyl)-piperazin-1-yl]-4-methyl-thiazole-5-carboxylic acid (Example 364), 4-methyl-2-[(R)-4-(4-trifluoromethoxy-benzenesulfonyl)-3-(4-trifluoromethoxy-benzylcarbamoyl)-piperazin-1-yl]-thiazole-5-carboxylic acid (Example 365), 2-[(R)-3-(4-ethyl-benzylcarbamoyl)-4-(4-trifluoromethoxy-benzenesulfonyl)-piperazin-1-yl]-4-methyl-thiazole-5-carboxylic acid (Example 366), 2-[(R)-3-(4-tert-butyl-benzylcarbamoyl)-4-(4-trifluoromethoxy-benzenesulfonyl)-piperazin-1-yl]-4-methyl-thiazole-5-carboxylic acid (Example 367), (R)-4-(5-amino-2H-[1,2,4]triazol-3-yl)-1-(4-trifluoromethyl-benzenesulfonyl)-piperazine-2-carboxylic acid 4-isopropyl-benzylamide (Example 368), (R)-2-({2-[(R)-3-(4-isopropyl-benzylcarbamoyl)-4-(4-trifluoromethoxy-benzenesulfonyl)-piperazin-1-yl]-4-methyl-thiazole-5-carbonyl}-amino)-propionic acid (Example 369), (S)-2-({2-[(R)-3-(4-isopropyl-benzylcarbamoyl)-4-(4-trifluoromethoxy-benzenesulfonyl)-piperazin-1-yl]-4-methyl-thiazole-5-carbonyl}-amino)-propionic acid (Example 370), 2-[(R)-3-(4-isopropyl-benzylcarbamoyl)-4-(4-trifluoromethyl-benzenesulfonyl)-piperazin-1-yl]-4-methyl-oxazole-5-carboxylic acid trifluoroacetate (Example 371), (R)-4-(5-bromo-2H-[1,2,4]triazol-3-yl)-1-(4-trifluoromethyl-benzenesulfonyl)-piperazine-2-carboxylic acid 4-isopropyl-benzylamide (Example 372), (R)-4-(2H-[1,2,4]triazol-3-yl)-1-(4-trifluoromethyl-benzenesulfonyl)-piperazine-2-carboxylic acid 4-isopropyl-benzylamide (Example 373), (R)-3-(4-propyl-benzylcarbamoyl)-4-(4-trifluoromethoxy-benzenesulfonyl)-3,4,5,6-tetrahydro-2H-[1,2']bipyrazinyl-5'-carboxylic acid (Example 374), 6-[(R)-3-(4-isopropyl-benzylcarbamoyl)-4-(4-trifluoromethyl-benzenesulfonyl)-piperazin-1-yl]-pyridazine-3-carboxylic acid (Example 376), (R)-4-(4-trifluoromethyl-benzenesulfonyl)-3,4,5,6-tetrahydro-2H-[1,2']bipyrazinyl-3',5'-dicarboxylic acid 5'-amide 3-(4-isopropyl-benzylamide) (Example 377), 4-methyl-2-[(R)-3-(4-propyl-benzylcarbamoyl)-4-(4-trifluoromethoxy-benzenesulfonyl)-piperazin-1-yl]-thiazole-5-carboxylic acid (Example 378), 2-[(R)-3-(4-dimethylamino-benzylcarbamoyl)-4-(4-trifluoromethoxy-benzenesulfonyl)-piperazin-1-yl]-4-methyl-thiazole-5-carboxylic acid hydrochloride (Example 379), 3-{2-[(R)-3-(4-isopropyl-benzylcarbamoyl)-4-(4-trifluoromethoxy-benzenesulfonyl)-piperazin-1-yl]-thiazol-4-yl}-propionic acid (Example 382), 2-[(R)-3-(4-cyclopropyl-benzylcarbamoyl)-4-(4-trifluoromethoxy-benzenesulfonyl)-piperazin-1-yl]-4-methyl-thiazole-5-carboxylic acid (Example 383), (R)-3-(4-isopropyl-benzylcarbamoyl)-4-(4-trifluoromethoxy-benzenesulfonyl)-3,4,5,6-tetrahydro-2H-[1,2']bipyrazinyl-5'-carboxylic acid (Example 385), (R)-4-(4-trifluoromethoxy-benzenesulfonyl)-3-(4-trifluoromethoxy-benzylcarbamoyl)-3,4,5,6-tetrahydro-2H-[1,2']bipyrazinyl-5'-carboxylic acid (Example 386), 2-[(R)-3-[(6-dimethylamino-pyridin-3-ylmethyl)-carbamoyl]-4-(4-trifluoromethoxy-benzenesulfonyl)-piperazin-1-yl]-4-methyl-thiazole-5-carboxylic acid (Example 387), 4-methyl-2-[(R)-3-[(6-propyl-pyridin-3-ylmethyl)-carbamoyl]-4-(4-trifluoromethoxy-benzenesulfonyl)-piperazin-1-yl]-thiazole-5-carboxylic acid (Example 388), 2-[(R)-3-[(6-azetidin-1-yl-pyridin-3-ylmethyl)-carbamoyl]-4-(4-trifluoromethoxy-benzenesulfonyl)-piperazin-1-yl]-4-methyl-thiazole-5-carboxylic acid (Example 389), 4-methyl-2-[(R)-3-[(6-pyrrolidin-1-yl-pyridin-3-ylmethyl)-carbamoyl]-4-(4-trifluoromethoxy-benzenesulfonyl)-piperazin-1-yl]-thiazole-5-carboxylic acid (Example 390), 2-[(R)-3-(4-isopropyl-benzylcarbamoyl)-4-(4-propyl-benzenesulfonyl)-piperazin-1-yl]-4-methoxymethyl-thiazole-5-carboxylic acid (Example 394), 2-[(R)-3-(4-azetidin-1-yl-benzylcarbamoyl)-4-(4-trifluoromethoxy-benzenesulfonyl)-piperazin-1-yl]-4-methyl-thiazole-5-carboxylic acid (Example 398), (R)-3-(4-dimethylamino-benzylcarbamoyl)-4-(4-trifluoromethoxy-benzenesulfonyl)-3,4,5,6-tetrahydro-2H-[1,2']bipyrazinyl-5'-carboxylic acid (Example 399), 2-[(R)-3-benzylcarbamoyl-4-(4-trifluoromethoxy-benzenesulfonyl)-piperazin-1-yl]-4-methyl-thiazole-5-carboxylic acid (Example 401), (R)-4-(5-carbamoyl-4-methyl-thiazol-2-yl)-1-(4-trifluoromethoxy-benzenesulfonyl)-piperazine-2-carboxylic acid 4-propyl-benzylamide (Example 406), (R)-3-[(6-dimethylamino-pyridin-3-ylmethyl)-carbamoyl]-4-(4-trifluoromethoxy-benzenesulfonyl)-3,4,5,6-tetrahydro-2H-[1,2']bipyrazinyl-5'-carboxylic acid (Example 407), (R)-3-[(6-isopropyl-pyridin-3-ylmethyl)-carbamoyl]-4-(4-trifluoromethoxy-benzenesulfonyl)-3,4,5,6-tetrahydro-2H-[1,2']bipyrazinyl-5'-carboxylic acid (Example 408), 2-[(R)-4-(4-ethyl-benzenesulfonyl)-3-(4-propyl-benzylcarbamoyl)-piperazin-1-yl]-4-methyl-thiazole-5-carboxylic acid (Example 414), (R)-4-(4-ethyl-benzenesulfonyl)-3-(4-propyl-benzylcarbamoyl)-3,4,5,6-tetrahydro-2H-[1,2']bipyrazinyl-5'-carboxylic acid (Example 415), 4-methyl-2-[(R)-3-(4-pyrrolidin-1-yl-benzylcarbamoyl)-4-(4-trifluoromethoxy-benzenesulfonyl)-piperazin-1-yl]-thiazole-5-carboxylic acid (Example 416), 6-[(R)-3-(4-propyl-benzylcarbamoyl)-4-(4-trifluoromethoxy-benzenesulfonyl)-piperazin-1-yl]-pyridazine-3-carboxylic acid (Example 417), 4-methyl-2-[(R)-3-phenethylcarbamoyl-4-(4-trifluoromethoxy-benzenesulfonyl)-piperazin-1-yl]-thiazole-5-carboxylic acid (Example 418), (R)-6'-amino-3'-chloro-3-(4-isopropyl-benzylcarbamoyl)-4-(4-trifluoromethyl-benzenesulfonyl)-3,4,5,6-tetrahydro-2H-[1,2']bipyrazinyl-5'-carboxylic acid methyl ester (Example 420), (R)-6'-bromo-3'-chloro-3-(4-isopropyl-benzylcarbamoyl)-4-(4-trifluoromethyl-benzenesulfonyl)-3,4,5,6-tetrahydro-2H-[1,2']bipyrazinyl-5'-carboxylic acid methyl ester (Example 421), (R)-3-(4-isopropyl-benzylcarbamoyl)-3',6'-dimethyl-4-(4-trifluoromethyl-benzenesulfonyl)-3,4,5,6-tetrahydro-2H-[1,2']bipyrazinyl-5'-carboxylic acid (Example 422), (R)-6'-amino-3-(4-isopropyl-benzylcarbamoyl)-4-(4-trifluoromethyl-benzenesulfonyl)-3,4,5,6-tetrahydro-2H-[1,2']bipyrazinyl-5'-carboxylic acid methyl ester (Example 423), 2-[(R)-3-[4-(ethyl-methyl-amino)-benzylcarbamoyl]-4-(4-trifluoromethoxy-benzenesulfonyl)-piperazin-1-yl]-4-methyl-thiazole-5-carboxylic acid (Example 424), 2-[(R)-3-(4-diethylamino-benzylcarbamoyl)-4-(4-trifluoromethoxy-benzenesulfonyl)-piperazin-1-yl]-4-methyl-thiazole-5-carboxylic acid (Example 425), 5-[(R)-3-(4-isopropyl-benzylcarbamoyl)-4-(4-trifluoromethyl-benzenesulfonyl)-piperazin-1-yl]-2H-pyrazole-3-carboxylic acid (Example 426), 4-chloro-5-[(R)-3-(4-isopropyl-benzylcarbamoyl)-4-(4-trifluoromethyl-benzenesulfonyl)-piperazin-1-yl]-2H-pyrazole-3-carboxylic acid (Example 427), (R)-3-(4-isopropyl-benzylcarbamoyl)-3'-methyl-4-(4-trifluoromethyl-benzenesulfonyl)-3,4,5,6-tetrahydro-2H-[1,2']bipyrazinyl-5'-carboxylic acid methyl ester (Example 431), (R)-3-(2-methyl-4-propyl-benzylcarbamoyl)-4-(4-trifluoromethoxy-benzenesulfonyl)-3,4,5,6-tetrahydro-2H-[1,2']bipyrazinyl-5'-carboxylic acid (Example 432), 2-[(R)-3-(4-isopropyl-benzylcarbamoyl)-4-(4-propyl-benzenesulfonyl)-piperazin-1-yl]-5-methyl-thiazole-4-carboxylic acid (Example 434), 5-[(R)-3-(4-isopropyl-benzylcarbamoyl)-4-(4-trifluoromethyl-benzenesulfonyl)-piperazin-1-yl]-1-methyl-1H-pyrazole-3-carboxylic acid (Example 439), (R)-4-(4-propyl-benzenesulfonyl)-3-(4-propyl-benzylcarbamoyl)-3,4,5,6-tetrahydro-2H-[1,2']bipyrazinyl-5'-carboxylic acid (Example 440), (R)-3-(2-methyl-4-propyl-benzylcarbamoyl)-4-(4-propyl-benzenesulfonyl)-3,4,5,6-tetrahydro-2H-[1,2']bipyrazinyl-5'-carboxylic acid (Example 441), 2-[(R)-3-(4-ethoxy-benzylcarbamoyl)-4-(4-trifluoromethoxy-benzenesulfonyl)-piperazin-1-yl]-4-methyl-thiazole-5-carboxylic acid (Example 442), (R)-6'-amino-3-(4-isopropyl-benzylcarbamoyl)-4-(4-trifluoromethyl-benzenesulfonyl)-3,4,5,6-tetrahydro-2H-[1,2']bipyrazinyl-5'-carboxylic acid (Example 443), 2-[(R)-3-(4-propyl-benzylcarbamoyl)-4-(4-trifluoromethoxy-benzenesulfonyl)-piperazin-1-yl]-4-trifluoromethyl-thiazole-5-carboxylic acid ethyl ester (Example 444), 5-[(R)-3-(4-isopropyl-benzylcarbamoyl)-4-(4-trifluoromethyl-benzenesulfonyl)-piperazin-1-yl]-2-methyl-2H-pyrazole-3-carboxylic acid (Example 445), (R)-4-(5-methanesulfonylaminocarbonyl-4-methyl-thiazol-2-yl)-1-(4-trifluoromethyl-benzenesulfonyl)-piperazine-2-carboxylic acid 4-isopropyl-benzylamide (Example 446), (R)-4-(5-methanesulfonylaminocarbonyl-4-methyl-thiazol-2-yl)-1-(4-trifluoromethoxy-benzenesulfonyl)-piperazine-2-carboxylic acid 4-propyl-benzylamide (Example 447), 2-[(R)-3-[4-(1,1-difluoro-propyl)-benzylcarbamoyl]-4-(4-trifluoromethoxy-benzenesulfonyl)-piperazin-1-yl]-4-methyl-thiazole-5-carboxylic acid (Example 448), (R)-6'-methyl-3-(4-propyl-benzylcarbamoyl)-4-(4-trifluoromethoxy-benzenesulfonyl)-3,4,5,6-tetrahydro-2H-[1,2']bipyrazinyl-5'-carboxylic acid (Example 449), 2-[(R)-3-(4-methoxymethyl-benzylcarbamoyl)-4-(4-trifluoromethoxy-benzenesulfonyl)-piperazin-1-yl]-4-methyl-thiazole-5-carboxylic acid (Example 451), (R)-4-(5-hydroxymethyl-4-methyl-thiazol-2-yl)-1-(4-trifluoromethoxy-benzenesulfonyl)-piperazine-2-carboxylic acid 4-propyl-benzylamide (Example 452), 2-[(R)-3-(4-propyl-benzylcarbamoyl)-4-(4-trifluoromethoxy-benzenesulfonyl)-piperazin-1-yl]-4-trifluoromethyl-thiazole-5-carboxylic acid (Example 453), (R)-4-(6-hydroxy-5-methyl-pyridazin-3-yl)-1-(4-trifluoromethoxy-benzenesulfonyl)-piperazine-2-carboxylic acid 4-propyl-benzylamide (Example 454), (R)-4-(5-amino-pyridin-2-yl)-1-(4-trifluoromethoxy-benzenesulfonyl)-piperazine-2-carboxylic acid 4-propyl-benzylamide (Example 458), (R)-5'-amino-4-(4-trifluoromethyl-benzenesulfonyl)-3,4,5,6-tetrahydro-2H-[1,2']bipyrazinyl-3-carboxylic acid 4-isopropyl-benzylamide (Example 471), (R)-4-(4-trifluoromethoxy-benzenesulfonyl)-3,4,5,6-tetrahydro-2H-[1,2']bipyrazinyl-3-carboxylic acid 4-propyl-benzylamide (Example 472), (R)-3-(4-methoxymethyl-benzylcarbamoyl)-4-(4-trifluoromethoxy-benzenesulfonyl)-3,4,5,6-tetrahydro-2H-[1,2']bipyrazinyl-5'-carboxylic acid (Example 473), (R)-3-(2-chloro-4-propyl-benzylcarbamoyl)-4-(4-trifluoromethoxy-benzenesulfonyl)-3,4,5,6-tetrahydro-2H-[1,2']bipyrazinyl-5'-carboxylic acid (Example 474), (R)-4-(4-ethyl-benzenesulfonyl)-5'-hydroxymethyl-3,4,5,6-tetrahydro-2H-[1,2']bipyrazinyl-3-carboxylic acid 4-propyl-benzylamide (Example 478), (R)-3-(2-chloro-4-propyl-benzylcarbamoyl)-4-(4-ethyl-benzenesulfonyl)-3,4,5,6-tetrahydro-2H-[1,2']bipyrazinyl-5'-carboxylic acid (Example 485), 4-methyl-6-[(R)-3-(4-propyl-benzylcarbamoyl)-4-(4-trifluoromethoxy-benzenesulfonyl)-piperazin-1-yl]-pyridazine-3-carboxylic acid methyl ester (Example 486), 4-methyl-6-[(R)-3-(4-propyl-benzylcarbamoyl)-4-(4-trifluoromethoxy-benzenesulfonyl)-piperazin-1-yl]-pyridazine-3-carboxylic acid (Example 487), {4-[(R)-3-(4-isopropyl-benzylcarbamoyl)-4-(4-trifluoromethyl-benzenesulfonyl)-piperazin-1-yl]-pyrazol-1-yl}-acetic acid (Example 493), 4-methyl-6-[(R)-3-(4-propyl-benzylcarbamoyl)-4-(4-trifluoromethoxy-benzenesulfonyl)-piperazin-1-yl]-pyridazine-3-carboxylic acid amide (Example 494), 4-methyl-2-[(R)-3-(4-propyl-benzylcarbamoyl)-4-(3-propyl-4-trifluoromethoxy-benzenesulfonyl)-piperazin-1-yl]-thiazole-5-carboxylic acid (Example 499), (R)-3-(4-tert-butyl-benzylcarbamoyl)-4-(4-trifluoromethoxy-benzenesulfonyl)-3,4,5,6-tetrahydro-2H-[1,2']bipyrazinyl-5'-carboxylic acid (Example 501), (R)-4-(5-dimethylaminomethyl-4-methyl-thiazol-2-yl)-1-(4-trifluoromethoxy-benzenesulfonyl)-piperazine-2-carboxylic acid 4-propyl-benzylamide (Example 505), (R)-4-(4-methyl-5-methylaminomethyl-thiazol-2-yl)-1-(4-trifluoromethoxy-benzenesulfonyl)-piperazine-2-carboxylic acid 4-propyl-benzylamide (Example 506), (R)-6'-amino-3-(4-propyl-benzylcarbamoyl)-4-(4-trifluoromethoxy-benzenesulfonyl)-3,4,5,6-tetrahydro-2H-[1,2']bipyrazinyl-5'-carboxylic acid methyl ester (Example 507), 2-[(R)-4-(3-fluoro-4-trifluoromethoxy-benzenesulfonyl)-3-(4-propyl-benzylcarbamoyl)-piperazin-1-yl]-4-methyl-thiazole-5-carboxylic acid (Example 509), (R)-4-(4-hydroxymethyl-thiazol-2-yl)-1-(4-trifluoromethoxy-benzenesulfonyl)-piperazine-2-carboxylic acid 4-propyl-benzylamide (Example 510), (R)-6'-acetylamino-3-(4-propyl-benzylcarbamoyl)-4-(4-trifluoromethoxy-benzenesulfonyl)-3,4,5,6-tetrahydro-2H-[1,2']bipyrazinyl-5'-carboxylic acid methyl ester (Example 515), (R)-4-(5-oxo-4,5-dihydro-[1,3,4]thiadiazol-2-yl)-1-(4-trifluoromethoxy-benzenesulfonyl)-piperazine-2-carboxylic acid 4-propyl-benzylamide (Example 516), (R)-4-(5-methyl-1H-pyrazol-3-yl)-1-(4-trifluoromethoxy-benzenesulfonyl)-piperazine-2-carboxylic acid 4-isopropyl-benzylamide (Example 523), (R)-3-(4-tert-butyl-benzylcarbamoyl)-4-(4-ethyl-benzenesulfonyl)-3,4,5,6-tetrahydro-2H-[1,2']bipyrazinyl-5'-carboxylic acid (Example 524)

(R)-5'-amino-4-(4-trifluoromethoxy-benzenesulfonyl)-3,4,5,6-tetrahydro-2H-[1,2']bipyrazinyl-3-carboxylic acid 4-propyl-benzylamide (Example 530), (R)-4-(4-methyl-5-pyrrolidin-1-ylmethyl-thiazol-2-yl)-1-(4-trifluoromethoxy-benzenesulfonyl)-piperazine-2-carboxylic acid 4-propyl-benzylamide (Example 531), 2-[(R)-3-(4-propyl-benzylcarbamoyl)-4-(4-trifluoromethoxy-benzenesulfonyl)-piperazin-1-yl]-6,7-dihydro-4H-thiazolo[5,4-c]pyridine-5-carboxylic acid benzyl ester (Example 534), 5-hydroxymethyl-2-[(R)-3-(4-isopropyl-benzylcarbamoyl)-4-(4-propyl-benzenesulfonyl)-piperazin-1-yl]-thiazole-4-carboxylic acid (Example 535), 5-methoxymethyl-2-[(R)-3-(4-propyl-benzylcarbamoyl)-4-(4-trifluoromethoxy-benzenesulfonyl)-piperazin-1-yl]-thiazole-4-carboxylic acid (Example 536), 5-hydroxymethyl-2-[(R)-3-(4-propyl-benzylcarbamoyl)-4-(4-trifluoromethoxy-benzenesulfonyl)-piperazin-1-yl]-thiazole-4-carboxylic acid (Example 537), (R)-5'-dimethylaminomethyl-4-(4-ethyl-benzenesulfonyl)-3,4,5,6-tetrahydro-2H-[1,2']bipyrazinyl-3-carboxylic acid 4-propyl-benzylamide (Example 538), (R)-5'-methanesulfonylamino-4-(4-trifluoromethoxy-benzenesulfonyl)-3,4,5,6-tetrahydro-2H-[1,2']bipyrazinyl-3-carboxylic acid 4-propyl-benzylamide (Example 544), (R)-5'-hydroxymethyl-4-(4-trifluoromethoxy-benzenesulfonyl)-3,4,5,6-tetrahydro-2H-[1,2']bipyrazinyl-3-carboxylic acid 4-tert-butyl-benzylamide (Example 545), (R)-4-(6-hydroxy-pyridazin-3-yl)-1-(4-trifluoromethoxy-benzenesulfonyl)-piperazine-2-carboxylic acid 4-propyl-benzylamide (Example 546), 6-[(R)-3-(4-propyl-benzylcarbamoyl)-4-(4-trifluoromethoxy-benzenesulfonyl)-piperazin-1-yl]-pyridazine-3-carboxylic acid amide (Example 547), (R)-4-(5-methyl-4,5,6,7-tetrahydro-thiazolo[5,4-c]pyridin-2-yl)-1-(4-trifluoromethoxy-benzenesulfonyl)-piperazine-2-carboxylic acid 4-propyl-benzylamide (Example 548), (R)-6'-amino-5'-hydroxymethyl-4-(4-trifluoromethoxy-benzenesulfonyl)-3,4,5,6-tetrahydro-2H-[1,2']bipyrazinyl-3-carboxylic acid 4-propyl-benzylamide (Example 549), (R)-4-(2-oxo-1,4-dihydro-2H-pyrazino[2,3-d][1,3]oxazin-7-yl)-1-(4-trifluoromethoxy-benzenesulfonyl)-piperazine-2-carboxylic acid 4-propyl-benzylamide (Example 556), (R)-4-(4,5,6,7-tetrahydro-thiazolo[5,4-c]pyridin-2-yl)-1-(4-trifluoromethoxy-benzenesulfonyl)-piperazine-2-carboxylic acid 4-propyl-benzylamide (Example 557), (R)-5'-pyrrolidin-1-ylmethyl-4-(4-trifluoromethoxy-benzenesulfonyl)-3,4,5,6-tetrahydro-2H-[1,2']bipyrazinyl-3-carboxylic acid 4-tert-butyl-benzylamide (Example 558), (R)-3-[4-(1,1-difluoro-propyl)-benzylcarbamoyl]-4-(4-trifluoromethoxy-benzenesulfonyl)-3,4,5,6-tetrahydro-2H-[1,2']bipyrazinyl-5'-carboxylic acid (Example 559), (R)-5'-hydroxymethyl-4-(4-trifluoromethoxy-benzenesulfonyl)-3,4,5,6-tetrahydro-2H-[1,2']bipyrazinyl-3-carboxylic acid 4-(1,1-difluoro-propyl)-benzylamide (Example 560), (R)-4-(5-benzyl-4,5,6,7-tetrahydro-thiazolo[5,4-c]pyridin-2-yl)-1-(4-trifluoromethoxy-benzenesulfonyl)-piperazine-2-carboxylic acid 4-propyl-benzylamide (Example 561), (R)-4-(4,5-bis-hydroxymethyl-thiazol-2-yl)-1-(4-trifluoromethoxy-benzenesulfonyl)-piperazine-2-carboxylic acid 4-propyl-benzylamide (Example 562), (R)-4-(3-methyl-[1,2,4]thiadiazol-5-yl)-1-(4-trifluoromethoxy-benzenesulfonyl)-piperazine-2-carboxylic acid 4-propyl-benzylamide (Example 563), (R)-3-[4-(1,1-difluoro-propyl)-benzylcarbamoyl]-4-(4-ethyl-benzenesulfonyl)-3,4,5,6-tetrahydro-2H-[1,2']bipyrazinyl-5'-carboxylic acid (Example 564), (R)-4-(5-hydroxymethyl-thiazol-2-yl)-1-(4-trifluoromethoxy-benzenesulfonyl)-piperazine-2-carboxylic acid 4-tert-butyl-benzylamide (Example 570), (R)-4-(6-chloro-pyrimidin-4-yl)-1-(4-trifluoromethoxy-benzenesulfonyl)-piperazine-2-carboxylic acid 4-propyl-benzylamide (Example 571), (R)-4-pyrimidin-4-yl-1-(4-trifluoromethoxy-benzenesulfonyl)-piperazine-2-carboxylic acid 4-propyl-benzylamide (Example 572), (R)-4-(4,6-dioxo-5,6-dihydro-4H-pyrrolo[3,4-d]thiazol-2-yl)-1-(4-trifluoromethoxy-benzenesulfonyl)-piperazine-2-carboxylic acid 4-tert-butyl-benzylamide (Example 573), (R)-4-pteridin-7-yl-1-(4-trifluoromethoxy-benzenesulfonyl)-piperazine-2-carboxylic acid 4-propyl-benzylamide (Example 574), (R)-6'-amino-5'-hydroxymethyl-4-(4-trifluoromethoxy-benzenesulfonyl)-3,4,5,6-tetrahydro-2H-[1,2']bipyrazinyl-3-carboxylic acid 4-tert-butyl-benzylamide (Example 575), (R)-4-(3-methyl-[1,2,4]thiadiazol-5-yl)-1-(4-trifluoromethoxy-benzenesulfonyl)-piperazine-2-carboxylic acid 4-(1,1-difluoro-propyl)-benzylamide (Example 576), (R)-4-(5-cyano-4-methyl-thiazol-2-yl)-1-(4-trifluoromethoxy-benzenesulfonyl)-piperazine-2-carboxylic acid 4-tert-butyl-benzylamide (Example 577), (R)-4-(4-oxo-4,5,6,7-tetrahydro-thiazolo[5,4-c]pyridin-2-yl)-1-(4-trifluoromethoxy-benzenesulfonyl)-piperazine-2-carboxylic acid 4-tert-butyl-benzylamide (Example 578), (R)-4-(2-oxo-1,4-dihydro-2H-pyrazino[2,3-d][1,3]oxazin-7-yl)-1-(4-trifluoromethoxy-benzenesulfonyl)-piperazine-2-carboxylic acid 4-tert-butyl-benzylamide (Example 579), (R)-4-pyrimidin-4-yl-1-(4-trifluoromethoxy-benzenesulfonyl)-piperazine-2-carboxylic acid 4-(1,1-difluoro-propyl)-benzylamide (Example 580), (R)-4-(2-hydroxy-pyrimidin-4-yl)-1-(4-trifluoromethoxy-benzenesulfonyl)-piperazine-2-carboxylic acid 4-tert-butyl-benzylamide (Example 581), 4-amino-2-[(R)-3-(4-tert-butyl-benzylcarbamoyl)-4-(4-trifluoromethoxy-benzenesulfonyl)-piperazin-1-yl]-thiazole-5-carboxylic acid ethyl ester (Example 582), (R)-4-(2-amino-pyrimidin-4-yl)-1-(4-trifluoromethoxy-benzenesulfonyl)-piperazine-2-carboxylic acid 4-(1,1-difluoro-propyl)-benzylamide (Example 584), (R)-4-(4-amino-pyrimidin-2-yl)-1-(4-trifluoromethoxy-benzenesulfonyl)-piperazine-2-carboxylic acid 4-(1,1-difluoro-propyl)-benzylamide (Example 585), (R)-4-(4-trifluoromethoxy-benzenesulfonyl)-3,4,5,6-tetrahydro-2H-[1,2']bipyrazinyl-3,5'-dicarboxylic acid 5'-amide 3-[4-(1,1-difluoro-propyl)-benzylamide] (Example 586), 2-[(R)-3-(4-tert-butyl-benzylcarbamoyl)-4-(4-trifluoromethoxy-benzenesulfonyl)-piperazin-1-yl]-6,7-dihydro-4H-thiazolo[5,4-c]pyridine-5-carboxylic acid tert-butyl ester (Example 587), (R)-4-(4,5,6,7-tetrahydro-thiazolo[5,4-c]pyridin-2-yl)-1-(4-trifluoromethoxy-benzenesulfonyl)-piperazine-2-carboxylic acid 4-tert-butyl-benzylamide (Example 588), (R)-4-(5-acetyl-4,5,6,7-tetrahydro-thiazolo[5,4-c]pyridin-2-yl)-1-(4-trifluoromethoxy-benzenesulfonyl)-piperazine-2-carboxylic acid 4-tert-butyl-benzylamide (Example 589), (R)-5'-cyano-4-(4-trifluoromethoxy-benzenesulfonyl)-3,4,5,6-tetrahydro-2H-[1,2']bipyrazinyl-3-carboxylic acid 4-(1,1-difluoro-propyl)-benzylamide (Example 591), (R)-5'-morpholin-4-ylmethyl-4-(4-trifluoromethoxy-benzenesulfonyl)-3,4,5,6-tetrahydro-2H-[1,2']bipyrazinyl-3-carboxylic acid 4-tert-butyl-benzylamide (Example 593), (R)-5'-(4-methyl-piperazin-1-ylmethyl)-4-(4-trifluoromethoxy-benzenesulfonyl)-3,4,5,6-tetrahydro-2H-[1,2']bipyrazinyl-3-carboxylic acid 4-tert-butyl-benzylamide (Example 594), (R)-5'-dimethylaminomethyl-4-(4-trifluoromethoxy-benzenesulfonyl)-3,4,5,6-tetrahydro-2H-[1,2']bipyrazinyl-3-carboxylic acid 4-(1,1-difluoro-propyl)-benzylamide (Example 595), (R)-4-(3-acetylamino-[1,2,4]thiadiazol-5-yl)-1-(4-trifluoromethoxy-benzenesulfonyl)-piperazine-2-carboxylic acid 4-(1,1-difluoro-propyl)-benzylamide (Example 596), (R)-4-(4-oxo-4,5-dihydro-thiazolo[5,4-c]pyridin-2-yl)-1-(4-trifluoromethoxy-benzenesulfonyl)-piperazine-2-carboxylic acid 4-tert-butyl-benzylamide (Example 597), (R)-4-(5-methanesulfonyl-4,5,6,7-tetrahydro-thiazolo[5,4-c]pyridin-2-yl)-1-(4-trifluoromethoxy-benzenesulfonyl)-piperazine-2-carboxylic acid 4-tert-butyl-benzylamide (Example 600), 2-[(R)-3-(4-tert-butyl-benzylcarbamoyl)-4-(4-trifluoromethoxy-benzenesulfonyl)-piperazin-1-yl]-6,7-dihydro-4H-thiazolo[5,4-c]pyridine-5-carboxylic acid ethylamide (Example 601), (R)-4-(7-oxo-6,7-dihydro-thiazolo[4,5-d]pyrimidin-2-yl)-1-(4-trifluoromethoxy-benzenesulfonyl)-piperazine-2-carboxylic acid 4-tert-butyl-benzylamide (Example 602), 2-[(R)-3-(4-tert-butyl-benzylcarbamoyl)-4-(4-trifluoromethoxy-benzenesulfonyl)-piperazin-1-yl]-4-hydroxymethyl-thiazole-5-carboxylic acid (Example 603), (R)-6'-amino-5'-hydroxymethyl-4-(4-trifluoromethoxy-benzenesulfonyl)-3,4,5,6-tetrahydro-2H-[1,2']bipyrazinyl-3-carboxylic acid 4-(1,1-difluoro-propyl)-benzylamide (Example 604), (R)-4-(6-amino-pyrimidin-4-yl)-1-(4-trifluoromethoxy-benzenesulfonyl)-piperazine-2-carboxylic acid 4-(1,1-difluoro-propyl)-benzylamide (Example 605), (R)-4-(3-methoxy-[1,2,4]thiadiazol-5-yl)-1-(4-trifluoromethoxy-benzenesulfonyl)-piperazine-2-carboxylic acid 4-tert-butyl-benzylamide (Example 606), (R)-4-pteridin-7-yl-1-(4-trifluoromethoxy-benzenesulfonyl)-piperazine-2-carboxylic acid 4-(1,1-difluoro-propyl)-benzylamide (Example 615), (R)-4-(2-oxo-1,4-dihydro-2H-pyrazino[2,3-d][1,3]oxazin-7-yl)-1-(4-trifluoromethoxy-benzenesulfonyl)-piperazine-2-carboxylic acid 4-(1,1-difluoro-propyl)-benzylamide (Example 616), (R)-4-pteridin-7-yl-1-(4-trifluoromethoxy-benzenesulfonyl)-piperazine-2-carboxylic acid 4-tert-butyl-benzylamide (Example 617), (R)-4-(4-oxo-3,4-dihydro-thiazolo[4,5-d][1,2,3]triazin-6-yl)-1-(4-trifluoromethoxy-benzenesulfonyl)-piperazine-2-carboxylic acid 4-tert-butyl-benzylamide (Example 618), (R)-4-pteridin-7-yl-1-(4-trifluoromethoxy-benzenesulfonyl)-piperazine-2-carboxylic acid 4-(ethyl-methyl-amino)-benzylamide (Example 619), 5-[(R)-3-(4-tert-butyl-benzylcarbamoyl)-4-(4-trifluoromethoxy-benzenesulfonyl)-piperazin-1-yl]-pyridine-2-carboxylic acid (Example 620), (R)-4-(3-methoxy-[1,2,4]thiadiazol-5-yl)-1-(4-trifluoromethoxy-benzenesulfonyl)-piperazine-2-carboxylic acid 4-(1,1-difluoro-propyl)-benzylamide (Example 625), (R)-4-[1,2,4]triazolo[1,5-a]pyrimidin-5-yl-1-(4-trifluoromethoxy-benzenesulfonyl)-piperazine-2-carboxylic acid 4-(1,1-difluoro-propyl)-benzylamide (Example 626), (R)-4-pteridin-7-yl-1-(4-trifluoromethoxy-benzenesulfonyl)-piperazine-2-carboxylic acid 4-trifluoromethoxy-benzylamide (Example 627), (R)-4-(2-oxo-2,3-dihydro-1H-imidazo[4,5-b]pyrazin-5-yl)-1-(4-trifluoromethoxy-benzenesulfonyl)-piperazine-2-carboxylic acid 4-propyl-benzylamide (Example 628), (R)-4-pteridin-7-yl-1-(4-trifluoromethoxy-benzenesulfonyl)-piperazine-2-carboxylic acid 4-chloro-benzylamide (Example 629), (R)-4-pteridin-7-yl-1-(4-trifluoromethoxy-benzenesulfonyl)-piperazine-2-carboxylic acid (6-dimethylamino-pyridin-3-ylmethyl)-amide (Example 630), 5-[(R)-3-(4-propyl-benzylcarbamoyl)-4-(4-trifluoromethoxy-benzenesulfonyl)-piperazin-1-yl]-pyridine-2-carboxylic acid (Example 631), (R)-4-quinoxalin-2-yl-1-(4-trifluoromethoxy-benzenesulfonyl)-piperazine-2-carboxylic acid 4-(1,1-difluoro-propyl)-benzylamide (Example 632), (R)-4-(7-oxo-6,7-dihydro-thiazolo[4,5-d]pyrimidin-2-yl)-1-(4-trifluoromethoxy-benzenesulfonyl)-piperazine-2-carboxylic acid 4-(1,1-difluoro-propyl)-benzylamide (Example 633), (R)-6'-amino-5'-aminomethyl-4-(4-trifluoromethoxy-benzenesulfonyl)-3,4,5,6-tetrahydro-2H-[1,2']bipyrazinyl-3-carboxylic acid 4-(1,1-difluoro-propyl)-benzylamide (Example 638), (R)-4-pteridin-7-yl-1-(4-trifluoromethoxy-benzenesulfonyl)-piperazine-2-carboxylic acid (benzoxazol-2-ylmethyl)-amide (Example 639), (R)-4-(4-oxo-3,4-dihydro-thiazolo[4,5-d][1,2,3]triazin-6-yl)-1-(4-trifluoromethoxy-benzenesulfonyl)-piperazine-2-carboxylic acid 4-(1,1-difluoro-propyl)-benzylamide (Example 640), (R)-4-(6-hydroxy-[1,2,5]thiadiazolo[3,4-b]pyrazin-5-yl)-1-(4-trifluoromethoxy-benzenesulfonyl)-piperazine-2-carboxylic acid 4-(1,1-difluoro-propyl)-benzylamide (Example 647), (R)-4-pyrido[3,4-b]pyrazin-2-yl-1-(4-trifluoromethoxy-benzenesulfonyl)-piperazine-2-carboxylic acid 4-(1,1-difluoro-propyl)-benzylamide (Example 648), (R)-4-(2,2-dioxo-1,2,3,4-tetrahydro-2$\lambda^6$-pyrazino[2,3-c][1,2,6]thiadiazin-7-yl)-1-(4-trifluoromethoxy-benzenesulfonyl)-piperazine-2-carboxylic acid 4-(1,1-difluoro-propyl)-benzylamide (Example 650), (R)-4-pteridin-7-yl-1-(4-trifluoromethoxy-benzenesulfonyl)-piperazine-2-carboxylic acid 4-ethoxy-benzylamide (Example 651), (R)-4-pteridin-7-yl-1-(4-trifluoromethoxy-benzenesulfonyl)-piperazine-2-carboxylic acid 4-thiophen-2-yl-benzylamide (Example 652), (R)-4-pteridin-7-yl-1-(4-trifluoromethoxy-benzenesulfonyl)-piperazine-2-carboxylic acid 4-bromo-benzylamide (Example 653), (R)-4-pteridin-7-yl-1-(4-trifluoromethoxy-benzenesulfonyl)-piperazine-2-carboxylic acid 4-cyclopropyl-benzylamide (Example 656), (R)-4-pteridin-7-yl-1-(4-trifluoromethoxy-benzenesulfonyl)-piperazine-2-carboxylic acid 4-methoxymethyl-benzylamide (Example 657), (R)-4-pteridin-7-yl-1-(4-trifluoromethoxy-benzenesulfonyl)-piperazine-2-carboxylic acid 4-methoxy-benzylamide (Example 658), (R)-4-pteridin-7-yl-1-(4-trifluoromethoxy-benzenesulfonyl)-piperazine-2-carboxylic acid ([2,2']bithiophenyl-5-ylmethyl)-amide (Example 659), (R)-4-pteridin-7-yl-1-(4-trifluoromethoxy-benzenesulfonyl)-piperazine-2-carboxylic acid 4-trifluoromethyl-benzylamide (Example 660), (R)-4-pteridin-7-yl-1-(4-trifluoromethoxy-benzenesulfonyl)-piperazine-2-carboxylic acid 4-methylsulfanyl-benzylamide (Example 661), (R)-4-pteridin-7-yl-1-(4-trifluoromethoxy-benzenesulfonyl)-piperazine-2-carboxylic acid (1-propyl-1,2,3,6-tetrahydro-pyridin-4-ylmethyl)-amide (Example 662), (R)-4-pteridin-7-yl-1-(4-trifluoromethoxy-benzenesulfonyl)-piperazine-2-carboxylic acid (biphenyl-4-ylmethyl)-amide (Example 663), (R)-4-(4-oxo-4,5-dihydro-thiazolo[4,5-d]pyridazin-2-yl)-1-(4-trifluoromethoxy-benzenesulfonyl)-piperazine-2-carboxylic acid 4-(1,1-difluoro-propyl)-benzylamide (Example 664), (R)-4-(1H-imidazo[4,5-b]pyrazin-5-yl)-1-(4-trifluoromethoxy-benzenesulfonyl)-piperazine-2-carboxylic acid 4-(1,1-difluoro-propyl)-benzylamide (Example 676), (R)-4-pteridin-7-yl-1-(4-trifluoromethoxy-benzenesulfonyl)-piperazine-2-carboxylic acid (2-oxo-1-propyl-1,2-dihydro-pyridin-4-ylmethyl)-amide (Example 680), (R)-1-(4-bromo-benzenesulfonyl)-4-pteridin-7-yl-piperazine-2-carboxylic acid 4-(1,1-difluoro-propyl)-benzylamide (Example 683), (R)-4-(6-bromo-quinoxalin-2-yl)-1-(4-trifluoromethoxy-benzenesulfonyl)-piperazine-2-carboxylic acid 4-(1,1-difluoro-propyl)-benzylamide (Example 684), (R)-4-(7-bromo-quinoxalin-2-yl)-1-(4-trifluoromethoxy-benzenesulfonyl)-piperazine-2-carboxylic acid 4-(1,1-difluoro-propyl)-benzylamide (Example 685), (R)-4-pteridin-7-yl-1-(4-trifluoromethyl-benzenesulfonyl)-piperazine-2-carboxylic acid 4-(1,1-difluoro-propyl)-benzylamide (Example 686), (R)-4-(4-bromo-benzenesulfonyl)-3-(4-propyl-benzylcarbamoyl)-3,4,5,6-tetrahydro-2H-[1,2']bipyrazinyl-5'-carboxylic acid (Example 687), (R)-4-(6-chloro-quinoxalin-2-yl)-1-(4-trifluoromethoxy-benzenesulfonyl)-piperazine-2-carboxylic acid 4-(1,1-difluoro-propyl)-benzylamide (Example 688), (R)-4-pyrido[3,4-b]pyrazin-2-yl-1-(4-trifluoromethoxy-benzenesulfonyl)-piperazine-2-carboxylic acid 4-tert-butyl-benzylamide (Example 689), (R)-4-pyrazino[2,3-b]pyrazin-2-yl-1-(4-trifluoromethoxy-benzenesulfonyl)-piperazine-2-carboxylic acid 4-(1,1-difluoro-propyl)-benzylamide (Example 690), (R)-4-[1,2,5]thiadiazolo[3,4-b]pyrazin-5-yl-1-(4-trifluoromethoxy-benzenesulfonyl)-piperazine-2-carboxylic acid 4-(1,1-difluoro-propyl)-benzylamide (Example 691), (R)-4-(2-methyl-pteridin-7-yl)-1-(4-trifluoromethoxy-benzenesulfonyl)-piperazine-2-carboxylic acid 4-(1,1-difluoro-propyl)-benzylamide (Example 692), 2-[(R)-3-[4-(1,1-difluoro-propyl)-benzylcarbamoyl]-4-(4-trifluoromethoxy-benzenesulfonyl)-piperazin-1-yl]-quinoxaline-6-carboxylic acid ethyl ester (Example 693), (R)-4-thiazolo[4,5-d]pyridazin-2-yl-1-(4-trifluoromethoxy-benzenesulfonyl)-piperazine-2-carboxylic acid 4-(1,1-difluoro-propyl)-benzylamide (Example 694), (R)-1-(4-tert-butyl-benzenesulfonyl)-4-pteridin-7-yl-piperazine-2-carboxylic acid 4-(1,1-difluoro-propyl)-benzylamide (Example 695), (R)-1-(biphenyl-4-sulfonyl)-4-pteridin-7-yl-piperazine-2-carboxylic acid 4-(1,1-difluoro-propyl)-benzylamide (Example 696), (R)-1-(4-chloro-benzenesulfonyl)-4-pteridin-7-yl-piperazine-2-carboxylic acid 4-(1,1-difluoro-propyl)-benzylamide (Example 697), (R)-1-(4-nitro-benzenesulfonyl)-4-pteridin-7-yl-piperazine-2-carboxylic acid 4-(1,1-difluoro-propyl)-benzylamide (Example 698), (R)-4-(4-tert-butyl-benzenesulfonyl)-3-(4-propyl-benzylcarbamoyl)-3,4,5,6-tetrahydro-2H-[1,2']bipyrazinyl-5'-carboxylic acid (Example 700), (R)-4-(biphenyl-4-sulfonyl)-3-(4-propyl-benzylcarbamoyl)-3,4,5,6-tetrahydro-2H-[1,2']bipyrazinyl-5'-carboxylic acid (Example 701), (R)-4-(4-oxo-4,5-dihydro-thiazol-2-yl)-1-(4-trifluoromethoxy-benzenesulfonyl)-piperazine-2-carboxylic acid 4-(1,1-difluoro-propyl)-benzylamide (Example 704), (R)-4-pteridin-6-yl-1-(4-trifluoromethoxy-benzenesulfonyl)-piperazine-2-carboxylic acid 4-(1,1-difluoro-propyl)-benzylamide (Example 707), (R)-1-(4-iodo-benzenesulfonyl)-4-pteridin-7-yl-piperazine-2-carboxylic acid 4-(1,1-difluoro-propyl)-benzylamide (Example 708), (R)-4-pteridin-7-yl-1-(4-thiophen-2-yl-benzenesulfonyl)-piperazine-2-carboxylic acid 4-(1,1-difluoro-propyl)-benzylamide (Example 709), 3-[(R)-3-[4-(1,1-difluoro-propyl)-benzylcarbamoyl]-4-(4-trifluoromethoxy-benzenesulfonyl)-piperazin-1-yl]-quinoxaline-6-carboxylic acid ethyl ester (Example 710), 3-[(R)-3-[4-(1,1-difluoro-propyl)-benzylcarbamoyl]-4-(4-trifluoromethoxy-benzenesulfonyl)-piperazin-1-yl]-quinoxaline-6-carboxylic acid (Example 711), 2-[(R)-3-[4-(1,1-difluoro-propyl)-benzylcarbamoyl]-4-(4-trifluoromethoxy-benzenesulfonyl)-piperazin-1-yl]-quinoxaline-6-carboxylic acid (Example 712), (R)-1-(4-chloro-benzenesulfonyl)-4-pyrido[3,4-b]pyrazin-2-yl-piperazine-2-carboxylic acid 4-(1,1-difluoro-propyl)-benzylamide (Example 713), (R)-1-(4-tert-butyl-benzenesulfonyl)-4-pyrido[3,4-b]pyrazin-2-yl-piperazine-2-carboxylic acid 4-(1,1-difluoro-propyl)-benzylamide (Example 714), (R)-4-thiazolo[5,4-c]pyridin-2-yl-1-(4-trifluoromethoxy-benzenesulfonyl)-piperazine-2-carboxylic acid 4-(1,1-difluoro-propyl)-benzylamide (Example 715), (R)-4-pteridin-7-yl-1-(4-trifluoromethoxy-benzenesulfonyl)-piperazine-2-carboxylic acid (6-propyl-pyridin-3-ylmethyl)-amide (Example 720), (R)-4-pteridin-7-yl-1-(4-trifluoromethoxy-benzenesulfonyl)-piperazine-2-carboxylic acid (5-methyl-pyrazin-2-ylmethyl)-amide (Example 721), (R)-4-pteridin-7-yl-1-(4-trifluoromethoxy-benzenesulfonyl)-piperazine-2-carboxylic acid 3-amino-4-propyl-benzylamide (Example 722), (R)-4-pteridin-7-yl-1-(4-trifluoromethoxy-benzenesulfonyl)-piperazine-2-carboxylic acid 3-hydroxy-4-propyl-benzylamide (Example 723), (R)-1-(2'-hydroxy-biphenyl-4-sulfonyl)-4-pteridin-7-yl-piperazine-2-carboxylic acid 4-(1,1-difluoro-propyl)-benzylamide (Example 724), (R)-1-(3'-hydroxy-biphenyl-4-sulfonyl)-4-pteridin-7-yl-piperazine-2-carboxylic acid 4-(1,1-difluoro-propyl)-benzylamide (Example 725), (R)-1-(4-nitro-benzenesulfonyl)-4-pyrido[3,4-b]pyrazin-2-yl-piperazine-2-carboxylic acid 4-(1,1-difluoro-propyl)-benzylamide (Example 726), (R)-1-(biphenyl-4-sulfonyl)-4-pyrido[3,4-b]pyrazin-2-yl-piperazine-2-carboxylic acid 4-(1,1-difluoro-propyl)-benzylamide (Example 727), 5-[(R)-3-(4-propyl-benzylcarbamoyl)-4-(4-trifluoromethoxy-benzenesulfonyl)-piperazin-1-yl]-thiophene-2-carboxylic acid tert-butyl ester (Example 728), (R)-4-pteridin-7-yl-1-(4-trifluoromethoxy-benzenesulfonyl)-piperazine-2-carboxylic acid (5-pyridin-2-yl-thiophen-2-ylmethyl)-amide (Example 730), (4'-{(R)-2-[4-(1,1-difluoro-propyl)-benzylcarbamoyl]-4-pteridin-7-yl-piperazine-1-sulfonyl}-biphenyl-2-yloxy)-acetic acid (Example 731), (4'-{(R)-2-[4-(1,1-difluoro-propyl)-benzylcarbamoyl]-4-pteridin-7-yl-piperazine-1-sulfonyl}-biphenyl-3-yloxy)-acetic acid (Example 732), (R)-4-pyrido[3,4-b]pyrazin-2-yl-1-(4-trifluoromethyl-benzenesulfonyl)-piperazine-2-carboxylic acid 4-(1,1-difluoro-propyl)-benzylamide (Example 735), (R)-1-(4-dimethylamino-benzenesulfonyl)-4-pyrido[3,4-b]pyrazin-2-yl-piperazine-2-carboxylic acid 4-(1,1-difluoro-propyl)-benzylamide (Example 736), (R)-4-thiazolo[5,4-b]pyridin-2-yl-1-(4-trifluoromethoxy-benzenesulfonyl)-piperazine-2-carboxylic acid 4-(1,1-difluoro-propyl)-benzylamide (Example 739), (R)-4-[1,6]naphthyridin-2-yl-1-(4-trifluoromethoxy-benzenesulfonyl)-piperazine-2-carboxylic acid 4-(1,1-difluoro-propyl)-benzylamide (Example 740), (R)-4-(5-chloro-quinoxalin-2-yl)-1-(4-trifluoromethoxy-benzenesulfonyl)-piperazine-2-carboxylic acid 4-(1,1-difluoro-propyl)-benzylamide (Example 741), (R)-4-(8-chloro-quinoxalin-2-yl)-1-(4-trifluoromethoxy-benzenesulfonyl)-piperazine-2-carboxylic acid 4-(1,1-difluoro-propyl)-benzylamide (Example 742), (R)-4-pyrido[3,4-b]pyrazin-2-yl-1-(4-pyrrolidin-1-yl-benzenesulfonyl)-piperazine-2-carboxylic acid 4-(1,1-difluoro-propyl)-benzylamide (Example 743), trans-[4-(4-{(R)-2-[4-(1,1-difluoro-propyl)-benzylcarbamoyl]-4-pteridin-7-yl-piperazine-1-sulfonyl}-phenyl)-cyclohexyl]-acetic acid (Example 744), (R)-4-pyrido[3,4-b]pyrazin-2-yl-1-(4-trifluoromethoxy-benzenesulfonyl)-piperazine-2-carboxylic acid 4-trifluoromethoxy-benzylamide (Example 745), (R)-1-(4-morpholin-4-yl-benzenesulfonyl)-4-pyrido[3,4-b]pyrazin-2-yl-piperazine-2-carboxylic acid 4-(1,1-difluoro-propyl)-benzylamide (Example 746), (R)-1-(4-methoxy-benzenesulfonyl)-4-pteridin-7-yl-piperazine-2-carboxylic acid 4-(1,1-difluoro-propyl)-benzylamide (Example 747), (R)-4-pyrido[2,3-b]pyrazin-6-yl-1-(4-trifluoromethoxy-benzenesulfonyl)-piperazine-2-carboxylic acid 4-(1,1-difluoro-propyl)-benzylamide (Example 748), (R)-4-pyrazino[2,3-b]pyrazin-2-yl-1-(4-trifluoromethoxy-benzenesulfonyl)-piperazine-2-carboxylic acid 4-trifluoromethoxy-benzylamide (Example 749), (R)-4-[1,2,4]triazolo[1,5-a]pyrimidin-5-yl-1-(4-trifluoromethoxy-benzenesulfonyl)-piperazine-2-carboxylic acid 4-trifluoromethoxy-benzylamide (Example 750), (R)-1-[4-(2-oxo-pyrrolidin-1-yl)-benzenesulfonyl]-4-pyrido[3,4-b]pyrazin-2-yl-piperazine-2-carboxylic acid 4-(1,1-difluoro-propyl)-benzylamide (Example 751), (R)-1-(4-chloro-benzenesulfonyl)-4-pyrido[3,4-b]pyrazin-2-yl-piperazine-2-carboxylic acid 4-trifluoromethoxy-benzylamide (Example 752), 4'-{(R)-2-[4-(1,1-difluoro-propyl)-benzylcarbamoyl]-4-pteridin-7-yl-piperazine-1-sulfonyl}-biphenyl-3-carboxylic acid (Example 753), (R)-1-(4-nitro-benzenesulfonyl)-4-pyrido[3,4-b]pyrazin-2-yl-piperazine-2-carboxylic acid 4-trifluoromethoxy-benzylamide (Example 754), (R)-4-pyrido[3,4-b]pyrazin-2-yl-1-(4-pyrrolidin-1-yl-benzenesulfonyl)-piperazine-2-carboxylic acid 4-trifluoromethoxy-benzylamide (Example 755), (R)-4-(3H-imidazo[4,5-c]pyridin-2-yl)-1-(4-trifluoromethoxy-benzenesulfonyl)-piperazine-2-carboxylic acid 4-(1,1-difluoro-propyl)-benzylamide (Example 756), (R)-4-pyrido[3,4-b]pyrazin-2-yl-1-(4-trifluoromethyl-benzenesulfonyl)-piperazine-2-carboxylic acid 4-trifluoromethoxy-benzylamide (Example 757), (R)-4-(1H-benzimidazol-2-yl)-1-(4-trifluoromethoxy-benzenesulfonyl)-piperazine-2-carboxylic acid 4-(1,1-difluoro-propyl)-benzylamide (Example 758), (R)-1-[4-(5-oxo-2,5-dihydro-[1,2,4]oxadiazol-3-yl)-benzenesulfonyl]-4-pteridin-7-yl-piperazine-2-carboxylic acid 4-(1,1-difluoro-propyl)-benzylamide (Example 759), (R)-4-pyrido[2,3-b]pyrazin-3-yl-1-(4-trifluoromethoxy-benzenesulfonyl)-piperazine-2-carboxylic acid 4-(1,1-difluoro-propyl)-benzylamide (Example 760), (R)-4-pyrido[2,3-b]pyrazin-2-yl-1-(4-trifluoromethoxy-benzenesulfonyl)-piperazine-2-carboxylic acid 4-(1,1-difluoro-propyl)-benzylamide (Example 761), (R)-4-pyrido[2,3-b]pyrazin-6-yl-1-(4-trifluoromethoxy-benzenesulfonyl)-piperazine-2-carboxylic acid 4-trifluoromethoxy-benzylamide (Example 762), (R)-4-pteridin-7-yl-1-(4-trifluoromethoxy-benzenesulfonyl)-piperazine-2-carboxylic acid 4-(2,2,2-trifluoroethoxy)-benzylamide (Example 763), (methyl-{4-[(R)-4-pyrido[3,4-b]pyrazin-2-yl-2-(4-trifluoromethoxy-benzylcarbamoyl)-piperazine-1-sulfonyl]-phenyl}-amino)-acetic acid ethyl ester (Example 764), (methyl-{4-[(R)-4-pyrido[3,4-b]pyrazin-2-yl-2-(4-trifluoromethoxy-benzylcarbamoyl)-piperazine-1-sulfonyl]-phenyl}-amino)-acetic acid (Example 765), (R)-4-(5-chloro-quinoxalin-2-yl)-1-(4-trifluoromethoxy-benzenesulfonyl)-piperazine-2-carboxylic acid 4-trifluoromethoxy-benzylamide (Example 766), (R)-4-(2-methyl-pteridin-7-yl)-1-(4-trifluoromethoxy-benzenesulfonyl)-piperazine-2-carboxylic acid 4-trifluoromethoxy-benzylamide (Example 767), (R)-4-thiazolo[5,4-c]pyridin-2-yl-1-(4-trifluoromethoxy-benzenesulfonyl)-piperazine-2-carboxylic acid 4-trifluoromethoxy-benzylamide (Example 768), (R)-4-pyrido[2,3-b]pyrazin-2-yl-1-(4-trifluoromethoxy-benzenesulfonyl)-piperazine-2-carboxylic acid 4-trifluoromethoxy-benzylamide (Example 769), (R)-4-pyrido[2,3-b]pyrazin-3-yl-1-(4-trifluoromethoxy-benzenesulfonyl)-piperazine-2-carboxylic acid 4-trifluoromethoxy-benzylamide (Example 770), (R)-4-[1,6]naphthyridin-2-yl-1-(4-trifluoromethoxy-benzenesulfonyl)-piperazine-2-carboxylic acid 4-trifluoromethoxy-benzylamide (Example 771), (R)-4-pteridin-7-yl-1-(4-trifluoromethoxy-benzenesulfonyl)-piperazine-2-carboxylic acid 4-trifluoromethylsulfanyl-benzylamide (Example 772), 4-{5-[(R)-2-(4-propyl-benzylcarbamoyl)-4-pteridin-7-yl-piperazine-1-sulfonyl]-2-trifluoromethoxy-phenyl}-butyric acid (Example 773), 6-[(R)-4-(4-trifluoromethoxy-benzenesulfonyl)-3-(4-trifluoromethoxy-benzylcarbamoyl)-piperazin-1-yl]-nicotinic acid (Example 774), (R)-4-thiazolo[5,4-b]pyridin-2-yl-1-(4-trifluoromethoxy-benzenesulfonyl)-piperazine-2-carboxylic acid 4-trifluoromethoxy-benzylamide (Example 776), (R)-1-(4-iodo-benzenesulfonyl)-4-pyrido[3,4-b]pyrazin-2-yl-piperazine-2-carboxylic acid 4-propyl-benzylamide (Example 777), (R)-1-(3'-hydroxy-biphenyl-4-sulfonyl)-4-pyrido[3,4-b]pyrazin-2-yl-piperazine-2-carboxylic acid 4-propyl-benzylamide (Example 778), {4'-[(R)-2-(4-propyl-benzylcarbamoyl)-4-pyrido[3,4-b]pyrazin-2-yl-piperazine-1-sulfonyl]-biphenyl-3-yloxy}-acetic acid (Example 779), 2-[(R)-4-(4-trifluoromethoxy-benzenesulfonyl)-3-(4-trifluoromethoxy-benzylcarbamoyl)-piperazin-1-yl]-quinoxaline-5-carboxylic acid (Example 780), 3-[(R)-4-(4-trifluoromethoxy-benzenesulfonyl)-3-(4-trifluoromethoxy-benzylcarbamoyl)-piperazin-1-yl]-quinoxaline-5-carboxylic acid (Example 781), (R)-4-quinoxalin-6-yl-1-(4-trifluoromethoxy-benzenesulfonyl)-piperazine-2-carboxylic acid 4-trifluoromethoxy-benzylamide (Example 782), (R)-4-(7-oxo-6,7-dihydro-thiazolo[4,5-d]pyrimidin-2-yl)-1-(4-trifluoromethoxy-benzenesulfonyl)-piperazine-2-carboxylic acid 4-trifluoromethoxy-benzylamide (Example 784), (R)-4-(4-oxo-3,4-dihydro-thiazolo[4,5-d][1,2,3]triazin-6-yl)-1-(4-trifluoromethoxy-benzenesulfonyl)-piperazine-2-carboxylic acid 4-trifluoromethoxy-benzylamide (Example 785), (R)-4-(4-ethyl-benzenesulfonyl)-3-(4-trifluoromethoxy-benzylcarbamoyl)-3,4,5,6-tetrahydro-2H-[1,2']bipyrazinyl-5'-carboxylic acid (Example 786), (R)-4-(4-pyrrolidin-1-yl-benzenesulfonyl)-3-(4-trifluoromethoxy-benzylcarbamoyl)-3,4,5,6-tetrahydro-2H-[1,2']bipyrazinyl-5'-carboxylic acid (Example 788), (R)-1-(4-nitro-benzenesulfonyl)-4-pteridin-7-yl-piperazine-2-carboxylic acid 4-trifluoromethoxy-benzylamide (Example 790), (R)-4-pteridin-7-yl-1-(4-trifluoromethyl-benzenesulfonyl)-piperazine-2-carboxylic acid 4-trifluoromethoxy-benzylamide (Example 791), (R)-4-[1,5]naphthyridin-2-yl-1-(4-trifluoromethoxy-benzenesulfonyl)-piperazine-2-carboxylic acid 4-trifluoromethoxy-benzylamide (Example 793), (R)-4-thiazolo[4,5-b]pyrazin-2-yl-1-(4-trifluoromethoxy-benzenesulfonyl)-piperazine-2-carboxylic acid 4-trifluoromethoxy-benzylamide (Example 794), (R)-4-pteridin-7-yl-1-(4-trifluoromethoxy-benzenesulfonyl)-piperazine-2-carboxylic acid 2,3,5,6-tetrafluoro-4-trifluoromethyl-benzylamide (Example 795), (R)-4-(4-ethyl-benzenesulfonyl)-5'-hydroxymethyl-3,4,5,6-tetrahydro-2H-[1,2']bipyrazinyl-3-carboxylic acid 4-trifluoromethoxy-benzylamide (Example 796), (R)-4-pteridin-7-yl-1-(4-trifluoromethoxy-benzenesulfonyl)-piperazine-2-carboxylic acid 2,4,6-trichloro-benzylamide (Example 797), (R)-1-(4-trifluoromethoxy-benzenesulfonyl)-4-(2-trifluoromethyl-pteridin-7-yl)-piperazine-2-carboxylic acid 4-trifluoromethoxy-benzylamide (Example 798), (R)-4-(8-bromo-pyrido[3,4-b]pyrazin-2-yl)-1-(4-trifluoromethoxy-benzenesulfonyl)-piperazine-2-carboxylic acid 4-trifluoromethoxy-benzylamide (Example 799), (R)-4-(5,7-dichloro-thiazolo[4,5-d]pyrimidin-2-yl)-1-(4-trifluoromethoxy-benzenesulfonyl)-piperazine-2-carboxylic acid 4-trifluoromethoxy-benzylamide (Example 800), (R)-4-thiazolo[4,5-d]pyrimidin-2-yl-1-(4-trifluoromethoxy-benzenesulfonyl)-piperazine-2-carboxylic acid 4-trifluoromethoxy-benzylamide (Example 801), (R)-4-(5-chloro-thiazolo[4,5-d]pyrimidin-2-yl)-1-(4-trifluoromethoxy-benzenesulfonyl)-piperazine-2-carboxylic acid 4-trifluoromethoxy-benzylamide (Example 802), (R)-4-(4,7-dioxo-4,5,6,7-tetrahydro-thiazolo[4,5-d]pyridazin-2-yl)-1-(4-trifluoromethoxy-benzenesulfonyl)-piperazine-2-carboxylic acid 4-trifluoromethoxy-benzylamide (Example 803), (R)-4-pteridin-7-yl-1-(4-trifluoromethoxy-benzenesulfonyl)-piperazine-2-carboxylic acid (adamantan-1-ylmethyl)-amide (Example 804), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-trifluoromethoxy-benzylamide (Example 805), 2-[(R)-4-(4-trifluoromethoxy-benzenesulfonyl)-3-(4-trifluoromethoxy-benzylcarbamoyl)-piperazin-1-yl]-pyrido[3,4-b]pyrazine-8-carboxylic acid (Example 806), 2-[(R)-4-(4-trifluoromethoxy-benzenesulfonyl)-3-(4-trifluoromethoxy-benzylcarbamoyl)-piperazin-1-yl]-pyrido[3,4-b]pyrazine-8-carboxylic acid amide (Example 807), 3-{2-[(R)-4-(4-trifluoromethoxy-benzenesulfonyl)-3-(4-trifluoromethoxy-benzylcarbamoyl)-piperazin-1-yl]-pyrido[3,4-b]pyrazin-8-yl}-propionic acid (Example 808), (R)-6'-methyl-4-(4-trifluoromethoxy-benzenesulfonyl)-3-(4-trifluoromethoxy-benzylcarbamoyl)-3,4,5,6-tetrahydro-2H-[1,2']bipyrazinyl-5'-carboxylic acid (Example 809), (R)-4-[8-(2-carbamoyl-ethyl)-pyrido[3,4-b]pyrazin-2-yl]-1-(4-trifluoromethoxy-benzenesulfonyl)-piperazine-2-carboxylic acid 4-trifluoromethoxy-benzylamide (Example 810), (R)-4-pteridin-7-yl-1-(4-trifluoromethoxy-benzenesulfonyl)-piperazine-2-carboxylic acid (3-phenyl-propyl)-amide (Example 811), (R)-1-(4-ethyl-benzenesulfonyl)-4-(7-oxo-6,7-dihydro-thiazolo[4,5-d]pyridazin-2-yl)-piperazine-2-carboxylic acid 4-propyl-benzylamide (Example 812), (R)-4-(8-bromo-pyrido[3,4-b]pyrazin-2-yl)-1-(4-ethyl-benzenesulfonyl)-piperazine-2-carboxylic acid 4-propyl-benzylamide (Example 813), 2-[(R)-4-(4-ethyl-benzenesulfonyl)-3-(4-propyl-benzylcarbamoyl)-piperazin-1-yl]-quinoxaline-5-carboxylic acid (Example 814), 2-[(R)-4-(4-ethyl-benzenesulfonyl)-3-(4-propyl-benzylcarbamoyl)-piperazin-1-yl]-pyrido[3,4-b]pyrazine-8-carboxylic acid (Example 815), 3-[(R)-4-(4-ethyl-benzenesulfonyl)-3-(4-propyl-benzylcarbamoyl)-piperazin-1-yl]-quinoxaline-5-carboxylic acid (Example 816), 2-[(R)-3-(4-propyl-benzylcarbamoyl)-4-(4-trifluoromethoxy-benzenesulfonyl)-piperazin-1-yl]-quinoxaline-5-carboxylic acid (Example 817), 2-[(R)-4-(4-ethyl-benzenesulfonyl)-3-(4-propyl-benzylcarbamoyl)-piperazin-1-yl]-benzothiazole-4-carboxylic acid (Example 818), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-propyl-benzylamide (Example 819), (R)-4-(7-oxo-6,7-dihydro-thiazolo[4,5-d]pyridazin-2-yl)-1-(4-trifluoromethyl-benzenesulfonyl)-piperazine-2-carboxylic acid 4-propyl-benzylamide (Example 820), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-(1,1-difluoro-propyl)-benzylamide (Example 821), 2-methyl-6-[(R)-3-(4-propyl-benzylcarbamoyl)-4-(4-trifluoromethoxy-benzenesulfonyl)-piperazin-1-yl]-nicotinic acid (Example 822), 5-fluoro-2-methyl-6-[(R)-3-(4-propyl-benzylcarbamoyl)-4-(4-trifluoromethoxy-benzenesulfonyl)-piperazin-1-yl]-nicotinic acid (Example 823), 2-[(R)-3-(4-propyl-benzylcarbamoyl)-4-(4-trifluoromethoxy-benzenesulfonyl)-piperazin-1-yl]-pyrido[3,4-b]pyrazine-8-carboxylic acid (Example 824), (R)-1-(4-nitro-benzenesulfonyl)-4-(7-oxo-6,7-dihydro-thiazolo[4,5-d]pyridazin-2-yl)-piperazine-2-carboxylic acid 4-propyl-benzylamide (Example 825), 3-{4-methyl-2-[(R)-3-(4-propyl-benzylcarbamoyl)-4-(4-trifluoromethoxy-benzenesulfonyl)-piperazin-1-yl]-thiazol-5-yl}-propionic acid (Example 826), (R)-4-(4-methyl-5-sulfamoyl-thiazol-2-yl)-1-(4-trifluoromethoxy-benzenesulfonyl)-piperazine-2-carboxylic acid 4-propyl-benzylamide (Example 827), (R)-4-(4-methyl-5-methylsulfamoyl-thiazol-2-yl)-1-(4-trifluoromethoxy-benzenesulfonyl)-piperazine-2-carboxylic acid 4-propyl-benzylamide (Example 828), (R)-4-(5-dimethylsulfamoyl-4-methyl-thiazol-2-yl)-1-(4-trifluoromethoxy-benzenesulfonyl)-piperazine-2-carboxylic acid 4-propyl-benzylamide (Example 829), (R)-4-(5-acetylsulfamoyl-4-methyl-thiazol-2-yl)-1-(4-trifluoromethoxy-benzenesulfonyl)-piperazine-2-carboxylic acid 4-propyl-benzylamide (Example 832), (R)-1-(4-nitro-benzenesulfonyl)-4-(7-oxo-6,7-dihydro-thiazolo[4,5-d]pyridazin-2-yl)-piperazine-2-carboxylic acid 4-trifluoromethoxy-benzylamide (Example 835), 2-[(R)-3-[4-(1,1-difluoro-propyl)-benzylcarbamoyl]-4-(4-trifluoromethoxy-benzenesulfonyl)-piperazin-1-yl]-pyrido[3,4-b]pyrazine-8-carboxylic acid (Example 836), (R)-4-(4-methyl-7-oxo-6,7-dihydro-thiazolo[4,5-d]pyridazin-2-yl)-1-(4-trifluoromethoxy-benzenesulfonyl)-piperazine-2-carboxylic acid 4-trifluoromethoxy-benzylamide (Example 839), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-(1,1-dimethyl-propyl)-benzylamide (Example 840), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-butyl-benzylamide (Example 841), 2-[(R)-3-(4-propyl-benzylcarbamoyl)-4-(4-trifluoromethyl-benzenesulfonyl)-piperazin-1-yl]-pyrido[3,4-b]pyrazine-8-carboxylic acid (Example 842), 2-[(R)-4-(4-nitro-benzenesulfonyl)-3-(4-propyl-benzylcarbamoyl)-piperazin-1-yl]-pyrido[3,4-b]pyrazine-8-carboxylic acid (Example 843), 2-[(R)-4-(4-tert-butyl-benzenesulfonyl)-3-(4-propyl-benzylcarbamoyl)-piperazin-1-yl]-pyrido[3,4-b]pyrazine-8-carboxylic acid (Example 844), 2-[(R)-4-(4-chloro-benzenesulfonyl)-3-(4-propyl-benzylcarbamoyl)-piperazin-1-yl]-pyrido[3,4-b]pyrazine-8-carboxylic acid (Example 845), {4-methyl-2-[(R)-3-(4-propyl-benzylcarbamoyl)-4-(4-trifluoromethoxy-benzenesulfonyl)-piperazin-1-yl]-thiazol-5-yl}-oxo-acetic acid ethyl ester (Example 846), 4-chloro-2-[(R)-3-(4-propyl-benzylcarbamoyl)-4-(4-trifluoromethoxy-benzenesulfonyl)-piperazin-1-yl]-thiazole-5-carboxylic acid (Example 847), {4-methyl-2-[(R)-3-(4-propyl-benzylcarbamoyl)-4-(4-trifluoromethoxy-benzenesulfonyl)-piperazin-1-yl]-thiazol-5-yl}-oxo-acetic acid (Example 848), (R)-4-pteridin-7-yl-1-(4-trifluoromethoxy-benzenesulfonyl)-piperazine-2-carboxylic acid (2-phenyl-cyclopropylmethyl)-amide (Example 849), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-(2-methoxy-1,1-dimethyl-ethyl)-benzylamide (Example 851), (R)-4-(4-trifluoromethoxy-benzenesulfonyl)-3,4,5,6-tetrahydro-2H-[1,2']bipyrazinyl-3,5'-dicarboxylic acid 5'-ethylamide 3-(4-trifluoromethoxy-benzylamide) (Example 852), (R)-4-(4-trifluoromethoxy-benzenesulfonyl)-3,4,5,6-tetrahydro-2H-[1,2']bipyrazinyl-3,5'-dicarboxylic acid 5'-tert-butylamide 3-(4-trifluoromethoxy-benzylamide) (Example 853), 2-[(R)-3-[4-(1,1-dimethyl-propyl)-benzylcarbamoyl]-4-(4-ethyl-benzenesulfonyl)-piperazin-1-yl]-pyrido[3,4-b]pyrazine-8-carboxylic acid (Example 854), 2-[(R)-3-(4-butyl-benzylcarbamoyl)-4-(4-ethyl-benzenesulfonyl)-piperazin-1-yl]-pyrido[3,4-b]pyrazine-8-carboxylic acid (Example 855), hydroxy-{4-methyl-2-[(R)-3-(4-propyl-benzylcarbamoyl)-4-(4-trifluoromethoxy-benzenesulfonyl)-piperazin-1-yl]-thiazol-5-yl}-acetic acid ethyl ester (Example 856), (R)-4-pteridin-7-yl-1-(4-trifluoromethoxy-benzenesulfonyl)-piperazine-2-carboxylic acid (5-propyl-thiophen-2-ylmethyl)-amide (Example 857), (R)-4-(4-methyl-5-methylaminooxalyl-thiazol-2-yl)-1-(4-trifluoromethoxy-benzenesulfonyl)-piperazine-2-carboxylic acid 4-propyl-benzylamide (Example 859), 2-[(R)-4-(4-ethyl-benzenesulfonyl)-3-(4-propyl-benzylcarbamoyl)-piperazin-1-yl]-7-oxo-6,7-dihydro-thiazolo[4,5-d]pyridazine-4-carboxylic acid ethyl ester (Example 862), 2-[(R)-4-(4-ethyl-benzenesulfonyl)-3-(4-propyl-benzylcarbamoyl)-piperazin-1-yl]-7-oxo-6,7-dihydro-thiazolo[4,5-d]pyridazine-4-carboxylic acid (Example 863), (R)-1-(4-fluoro-benzenesulfonyl)-4-(7-oxo-6,7-dihydro-thiazolo[4,5-d]pyridazin-2-yl)-piperazine-2-carboxylic acid 4-trifluoromethoxy-benzylamide (Example 864), 2-[(R)-4-(4-trifluoromethoxy-benzenesulfonyl)-3-(4-trifluoromethoxy-benzylcarbamoyl)-piperazin-1-yl]-pyrido[3,4-b]pyrazine-8-carboxylic acid methylamide (Example 865), 2-[(R)-4-(4-trifluoromethoxy-benzenesulfonyl)-3-(4-trifluoromethoxy-benzylcarbamoyl)-piperazin-1-yl]-pyrido[3,4-b]pyrazine-8-carboxylic acid dimethylamide (Example 866), (R)-4-pteridin-7-yl-1-(4-trifluoromethoxy-benzenesulfonyl)-piperazine-2-carboxylic acid (1-phenyl-azetidin-3-ylmethyl)-amide (Example 867), 4-chloro-2-[(R)-4-(4-ethyl-benzenesulfonyl)-3-(4-propyl-benzylcarbamoyl)-piperazin-1-yl]-thiazole-5-carboxylic acid (Example 868), (R)-4-(7-chloro-thiazolo[4,5-d]pyridazin-2-yl)-1-(4-trifluoromethoxy-benzenesulfonyl)-piperazine-2-carboxylic acid 4-trifluoromethoxy-benzylamide (Example 869), (R)-4-(4-hydroxymethyl-7-oxo-6,7-dihydro-thiazolo[4,5-d]pyridazin-2-yl)-1-(4-trifluoromethoxy-benzenesulfonyl)-piperazine-2-carboxylic acid 4-trifluoromethoxy-benzylamide (Example 870), 2-[(R)-4-(4-trifluoromethoxy-benzenesulfonyl)-3-(4-trifluoromethoxy-benzylcarbamoyl)-piperazin-1-yl]-pyrido[3,4-b]pyrazine-8-carboxylic acid isopropylamide (Example 871), (R)-4-(8-cyano-pyrido[3,4-b]pyrazin-2-yl)-1-(4-trifluoromethoxy-benzenesulfonyl)-piperazine-2-carboxylic acid 4-trifluoromethoxy-benzylamide (Example 872), (R)-1-(4-chloro-benzenesulfonyl)-4-(7-oxo-6,7-dihydro-thiazolo[4,5-d]pyridazin-2-yl)-piperazine-2-carboxylic acid 4-trifluoromethoxy-benzylamide (Example 873), 7-oxo-2-[(R)-4-(4-trifluoromethoxy-benzenesulfonyl)-3-(4-trifluoromethoxy-benzylcarbamoyl)-piperazin-1-yl]-6,7-dihydro-thiazolo[4,5-d]pyridazine-4-carboxylic acid (Example 874), 7-oxo-2-[(R)-4-(4-trifluoromethoxy-benzenesulfonyl)-3-(4-trifluoromethoxy-benzylcarbamoyl)-piperazin-1-yl]-6,7-dihydro-thiazolo[4,5-d]pyridazine-4-carboxylic acid methylamide (Example 875), 7-oxo-2-[(R)-4-(4-trifluoromethoxy-benzenesulfonyl)-3-(4-trifluoromethoxy-benzylcarbamoyl)-piperazin-1-yl]-6,7-dihydro-thiazolo[4,5-d]pyridazine-4-carboxylic acid amide (Example 876), (R)-4-(7-oxo-6,7-dihydro-thiazolo[4,5-d]pyridazin-2-yl)-1-(4-trifluoromethyl-benzenesulfonyl)-piperazine-2-carboxylic acid 4-trifluoromethoxy-benzylamide (Example 877), (R)-4-(5-hydroxy-thiazolo[5,4-d]pyrimidin-2-yl)-1-(4-trifluoromethoxy-benzenesulfonyl)-piperazine-2-carboxylic acid 4-trifluoromethoxy-benzylamide (Example 878), (R)-4-thiazolo[5,4-d]pyridazin-2-yl-1-(4-trifluoromethoxy-benzenesulfonyl)-piperazine-2-carboxylic acid 4-trifluoromethoxy-benzylamide (Example 879), 7-chloro-2-[(R)-4-(4-ethyl-benzenesulfonyl)-3-(4-propyl-benzylcarbamoyl)-piperazin-1-yl]-thiazolo[4,5-d]pyridazine-4-carboxylic acid ethyl ester (Example 880), (R)-1-(4-bromo-benzenesulfonyl)-4-(7-oxo-6,7-dihydro-thiazolo[4,5-d]pyridazin-2-yl)-piperazine-2-carboxylic acid 4-trifluoromethoxy-benzylamide (Example 881), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-(1-methoxymethyl-cyclopropyl)-benzylamide (Example 882), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-(ethyl-methyl-amino)-benzylamide (Example 883), (R)-1-(4-methoxy-benzenesulfonyl)-4-(7-oxo-6,7-dihydro-thiazolo[4,5-d]pyridazin-2-yl)-piperazine-2-carboxylic acid 4-trifluoromethoxy-benzylamide (Example 884), (R)-4-thiazolo[5,4-d]pyrimidin-2-yl-1-(4-trifluoromethoxy-benzenesulfonyl)-piperazine-2-carboxylic acid 4-trifluoromethoxy-benzylamide (Example 885), (R)-4-thiazolo[4,5-d]pyrimidin-2-yl-1-(4-trifluoromethyl-benzenesulfonyl)-piperazine-2-carboxylic acid 4-trifluoromethoxy-benzylamide (Example 886), (R)-4-(5-chloro-thiazolo[4,5-d]pyrimidin-2-yl)-1-(4-trifluoromethyl-benzenesulfonyl)-piperazine-2-carboxylic acid 4-trifluoromethoxy-benzylamide (Example 887), (R)-4-(5,7-dihydroxy-thiazolo[4,5-d]pyrimidin-2-yl)-1-(4-trifluoromethoxy-benzenesulfonyl)-piperazine-2-carboxylic acid 4-trifluoromethoxy-benzylamide (Example 888), 4-chloro-2-[(R)-3-[4-(1,1-dimethyl-propyl)-benzylcarbamoyl]-4-(4-trifluoromethoxy-benzenesulfonyl)-piperazin-1-yl]-thiazole-5-carboxylic acid (Example 890), 2-[(R)-4-(4-ethyl-benzenesulfonyl)-3-(4-propyl-benzylcarbamoyl)-piperazin-1-yl]-thiazolo[4,5-d]pyridazine-4-carboxylic acid ethyl ester (Example 891), 2-[(R)-4-(4-ethyl-benzenesulfonyl)-3-(4-propyl-benzylcarbamoyl)-piperazin-1-yl]-thiazolo[4,5-d]pyridazine-4-carboxylic acid (Example 892), (R)-4-(4-methyl-7-oxo-6,7-dihydro-thiazolo[4,5-d]pyridazin-2-yl)-1-(4-trifluoromethyl-benzenesulfonyl)-piperazine-2-carboxylic acid 4-trifluoromethoxy-benzylamide (Example 893), (R)-4-thiazolo[4,5-d]pyrimidin-2-yl-1-(4-trifluoromethoxy-benzenesulfonyl)-piperazine-2-carboxylic acid 4-(1,1-difluoro-propyl)-benzylamide (Example 894), (R)-4-(5-chloro-thiazolo[4,5-d]pyrimidin-2-yl)-1-(4-trifluoromethoxy-benzenesulfonyl)-piperazine-2-carboxylic acid 4-(1,1-difluoro-propyl)-benzylamide (Example 895), (R)-4-(7-chloro-thiazolo[4,5-d]pyridazin-2-yl)-1-(4-trifluoromethyl-benzenesulfonyl)-piperazine-2-carboxylic acid 4-trifluoromethoxy-benzylamide (Example 896), (R)-4-thiazolo[4,5-d]pyridazin-2-yl-1-(4-trifluoromethyl-benzenesulfonyl)-piperazine-2-carboxylic acid 4-trifluoromethoxy-benzylamide (Example 897), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-(1,1,2,2-tetrafluoro-ethoxy)-benzylamide (Example 898), (R)-4-(7-oxo-6,7-dihydro-thiazolo[4,5-d]pyridazin-2-yl)-1-(4-trifluoromethoxy-benzenesulfonyl)-piperazine-2-carboxylic acid (3-phenyl-cyclobutylmethyl)-amide (Example 899), (R)-4-(7-oxo-6,7-dihydro-thiazolo[4,5-d]pyridazin-2-yl)-1-(4-trifluoromethyl-benzenesulfonyl)-piperazine-2-carboxylic acid 4-(1,1-difluoro-propyl)-benzylamide (Example 900), (R)-4-(7-oxo-6,7-dihydro-thiazolo[4,5-d]pyridazin-2-yl)-1-(4-trifluoromethoxy-benzenesulfonyl)-piperazine-2-carboxylic acid (naphthalen-2-ylmethyl)-amide (Example 901), (R)-4-(5-chloro-thiazolo[4,5-d]pyrimidin-2-yl)-1-(4-trifluoromethyl-benzenesulfonyl)-piperazine-2-carboxylic acid 4-(1,1-difluoro-propyl)-benzylamide (Example 902), (R)-4-thiazolo[4,5-d]pyrimidin-2-yl-1-(4-trifluoromethyl-benzenesulfonyl)-piperazine-2-carboxylic acid 4-(1,1-difluoro-propyl)-benzylamide (Example 903), (R)-4-(6-methyl-7-oxo-6,7-dihydro-thiazolo[4,5-d]pyridazin-2-yl)-1-(4-trifluoromethoxy-benzenesulfonyl)-piperazine-2-carboxylic acid 4-trifluoromethoxy-benzylamide (Example 904), (R)-4-(5-methoxy-thiazolo[4,5-d]pyrimidin-2-yl)-1-(4-trifluoromethyl-benzenesulfonyl)-piperazine-2-carboxylic acid 4-trifluoromethoxy-benzylamide (Example 905), (R)-4-(7-chloro-4-methyl-thiazolo[4,5-d]pyridazin-2-yl)-1-(4-trifluoromethoxy-benzenesulfonyl)-piperazine-2-carboxylic acid 4-trifluoromethoxy-benzylamide (Example 906), (R)-4-(7-chloro-5-methyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 907), (R)-4-(5-methyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 908), (R)-4-(7-oxo-6,7-dihydro-thiazolo[4,5-d]pyridazin-2-yl)-1-(4-trifluoromethoxy-benzenesulfonyl)-piperazine-2-carboxylic acid (4-methyl-2-propyl-thiazol-5-ylmethyl)-amide (Example 909), (R)-4-(5-methyl-7-oxo-6,7-dihydro-thiazolo[4,5-d]pyrimidin-2-yl)-1-(4-trifluoromethoxy-benzenesulfonyl)-piperazine-2-carboxylic acid 4-trifluoromethoxy-benzylamide (Example 910), (R)-4-(5-methyl-7-oxo-6,7-dihydro-thiazolo[4,5-d]pyrimidin-2-yl)-1-(4-trifluoromethoxy-benzenesulfonyl)-piperazine-2-carboxylic acid 4-(1,1-difluoro-propyl)-benzylamide (Example 911), (R)-4-(5-bromo-thiazolo[4,5-d]pyrimidin-2-yl)-1-(4-trifluoromethoxy-benzenesulfonyl)-piperazine-2-carboxylic acid 4-trifluoromethoxy-benzylamide (Example 912), (R)-4-(5-chloro-thiazolo[4,5-d]pyrimidin-2-yl)-1-(4-trifluoromethoxy-benzenesulfonyl)-piperazine-2-carboxylic acid 4-propyl-benzylamide (Example 913), (R)-4-thiazolo[4,5-d]pyrimidin-2-yl-1-(4-trifluoromethoxy-benzenesulfonyl)-piperazine-2-carboxylic acid 4-propyl-benzylamide (Example 914), 2-[(R)-4-(4-trifluoromethoxy-benzenesulfonyl)-3-(4-trifluoromethoxy-benzylcarbamoyl)-piperazin-1-yl]-thiazolo[4,5-d]pyridazine-4-carboxylic acid amide (Example 915), 2-[(R)-4-(4-trifluoromethoxy-benzenesulfonyl)-3-(4-trifluoromethoxy-benzylcarbamoyl)-piperazin-1-yl]-thiazolo[4,5-d]pyridazine-4-carboxylic acid methylamide (Example 916), (R)-4-(4-methyl-thiazolo[4,5-d]pyridazin-2-yl)-1-(4-trifluoromethoxy-benzenesulfonyl)-piperazine-2-carboxylic acid 4-trifluoromethoxy-benzylamide (Example 917), (R)-4-(5-chloro-thiazolo[4,5-d]pyrimidin-2-yl)-1-(4-difluoromethoxy-benzenesulfonyl)-piperazine-2-carboxylic acid 4-trifluoromethoxy-benzylamide (Example 918), (R)-1-(4-difluoromethoxy-benzenesulfonyl)-4-thiazolo[4,5-d]pyrimidin-2-yl-piperazine-2-carboxylic acid 4-trifluoromethoxy-benzylamide (Example 919), (R)-4-(7-methyl-5-oxo-5H-[1,3,4]thiadiazolo[3,2-a]pyrimidin-2-yl)-1-(4-trifluoromethoxy-benzenesulfonyl)-piperazine-2-carboxylic acid 4-trifluoromethoxy-benzylamide (Example 920), (R)-4-(5-methyl-thiazolo[5,4-d]pyrimidin-2-yl)-1-(4-trifluoromethoxy-benzenesulfonyl)-piperazine-2-carboxylic acid 4-trifluoromethoxy-benzylamide (Example 921), (R)-4-[1,2,4]triazolo[3,4-b][1,3,4]thiadiazol-6-yl-1-(4-trifluoromethoxy-benzenesulfonyl)-piperazine-2-carboxylic acid 4-trifluoromethoxy-benzylamide (Example 922), (R)-4-(6-oxo-piperidin-3-yl)-1-(4-trifluoromethoxy-benzenesulfonyl)-piperazine-2-carboxylic acid 4-trifluoromethoxy-benzylamide (Example 923), (R)-4-(6-oxo-1,6-dihydro-pyridin-3-yl)-1-(4-trifluoromethoxy-benzenesulfonyl)-piperazine-2-carboxylic acid 4-trifluoromethoxy-benzylamide hydrochloride (Example 924), (R)-4-(5-methyl-thiazolo[4,5-d]pyrimidin-2-yl)-1-(4-trifluoromethyl-benzenesulfonyl)-piperazine-2-carboxylic acid 4-trifluoromethoxy-benzylamide (Example 925), (R)-4-(5-methyl-thiazolo[4,5-d]pyrimidin-2-yl)-1-(4-trifluoromethoxy-benzenesulfonyl)-piperazine-2-carboxylic acid 4-(1,1-difluoro-propyl)-benzylamide (Example 926), (R)-4-(7-chloro-5-methyl-thiazolo[4,5-d]pyrimidin-2-yl)-1-(4-trifluoromethyl-benzenesulfonyl)-piperazine-2-carboxylic acid 4-trifluoromethoxy-benzylamide (Example 927), (R)-4-(7-chloro-5-methyl-thiazolo[4,5-d]pyrimidin-2-yl)-1-(4-trifluoromethoxy-benzenesulfonyl)-piperazine-2-carboxylic acid 4-(1,1-difluoro-propyl)-benzylamide (Example 928), (R)-4-(5-methoxy-thiazolo[4,5-d]pyrimidin-2-yl)-1-(4-trifluoromethoxy-benzenesulfonyl)-piperazine-2-carboxylic acid 4-trifluoromethoxy-benzylamide (Example 929), 2-[(R)-4-(4-trifluoromethoxy-benzenesulfonyl)-3-(4-trifluoromethoxy-benzylcarbamoyl)-piperazin-1-yl]-thiazolo[4,5-d]pyridazine-4-carboxylic acid dimethylamide (Example 930), (R)-4-(5-chloro-thiazolo[4,5-d]pyrimidin-2-yl)-1-(4-trifluoromethoxy-benzenesulfonyl)-piperazine-2-carboxylic acid 4-difluoromethoxy-benzylamide (Example 931), (R)-4-thiazolo[4,5-d]pyrimidin-2-yl-1-(4-trifluoromethoxy-benzenesulfonyl)-piperazine-2-carboxylic acid 4-difluoromethoxy-benzylamide (Example 932), (R)-4-(3-methyl-[1,2,4]triazolo[3,4-b][1,3,4]thiadiazol-6-yl)-1-(4-trifluoromethoxy-benzenesulfonyl)-piperazine-2-carboxylic acid 4-trifluoromethoxy-benzylamide (Example 933), (R)-4-(7-chloro-5-methyl-thiazolo[4,5-d]pyrimidin-2-yl)-1-(4-trifluoromethyl-benzenesulfonyl)-piperazine-2-carboxylic acid 4-(1,1-difluoro-propyl)-benzylamide (Example 934), (R)-4-(5-methyl-thiazolo[4,5-d]pyrimidin-2-yl)-1-(4-trifluoromethyl-benzenesulfonyl)-piperazine-2-carboxylic acid 4-(1,1-difluoro-propyl)-benzylamide (Example 935), (R)-4-(4-oxo-4,5-dihydro-thiazolo[4,5-d]pyridazin-2-yl)-1-(4-trifluoromethoxy-benzenesulfonyl)-piperazine-2-carboxylic acid 4-trifluoromethoxy-benzylamide (Example 937), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-(difluoro-methoxy-methyl)-benzylamide (Example 938), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-methoxymethyl-benzylamide (Example 939), (R)-4-(4-hydroxymethyl-thiazolo[4,5-d]pyridazin-2-yl)-1-(4-trifluoromethoxy-benzenesulfonyl)-piperazine-2-carboxylic acid 4-trifluoromethoxy-benzylamide (Example 940),
(R)-4-(7-chloro-5-methyl-thiazolo[4,5-d]pyrimidin-2-yl)-1-(4-trifluoromethoxy-benzenesulfonyl)-piperazine-2-carboxylic acid 4-difluoromethoxy-benzylamide (Example 941),
(R)-4-(5-methyl-thiazolo[4,5-d]pyrimidin-2-yl)-1-(4-trifluoromethoxy-benzenesulfonyl)-piperazine-2-carboxylic acid 4-difluoromethoxy-benzylamide (Example 942),
(R)-4-(5-amino-thiazolo[4,5-d]pyrimidin-2-yl)-1-(4-trifluoromethoxy-benzenesulfonyl)-piperazine-2-carboxylic acid 4-trifluoromethoxy-benzylamide (Example 943),
(R)-4-(7-methoxy-thiazolo[4,5-d]pyridazin-2-yl)-1-(4-trifluoromethoxy-benzenesulfonyl)-piperazine-2-carboxylic acid 4-trifluoromethoxy-benzylamide (Example 944),
(R)-4-(5-dimethylamino-thiazolo[4,5-d]pyrimidin-2-yl)-1-(4-trifluoromethoxy-benzenesulfonyl)-piperazine-2-carboxylic acid 4-trifluoromethoxy-benzylamide (Example 945),
(R)-4-[5-(2-hydroxy-ethylamino)-thiazolo[4,5-d]pyrimidin-2-yl]-1-(4-trifluoromethoxy-benzenesulfonyl)-piperazine-2-carboxylic acid 4-trifluoromethoxy-benzylamide (Example 946),
7-oxo-2-[(R)-4-(4-trifluoromethoxy-benzenesulfonyl)-3-(4-trifluoromethoxy-benzylcarbamoyl)-piperazin-1-yl]-7H-[1,3,4]thiadiazolo[3,2-a]pyrimidine-5-carboxylic acid methyl ester (Example 948),
(R)-4-(5-ethyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 949),
(R)-4-(5-ethyl-thiazolo[4,5-d]pyrimidin-2-yl)-1-(4-trifluoromethyl-benzenesulfonyl)-piperazine-2-carboxylic acid 4-trifluoromethoxy-benzylamide (Example 950),
(R)-1-(4-trifluoromethoxy-benzenesulfonyl)-4-(3-trifluoromethyl-[1,2,4]triazolo[3,4-b][1,3,4]thiadiazol-6-yl)-piperazine-2-carboxylic acid 4-trifluoromethoxy-benzylamide (Example 951),
(R)-4-(5-methylamino-thiazolo[4,5-d]pyrimidin-2-yl)-1-(4-trifluoromethoxy-benzenesulfonyl)-piperazine-2-carboxylic acid 4-trifluoromethoxy-benzylamide (Example 952),
(R)-4-[1,2,4]triazolo[3,4-b][1,3,4]thiadiazol-6-yl-1-(4-trifluoromethyl-benzenesulfonyl)-piperazine-2-carboxylic acid 4-trifluoromethoxy-benzylamide (Example 953),
(R)-4-[1,2,4]triazolo[3,4-b][1,3,4]thiadiazol-6-yl-1-(4-trifluoromethyl-benzenesulfonyl)-piperazine-2-carboxylic acid 4-difluoromethoxy-benzylamide (Example 954),
(R)-4-(5-chloro-thiazolo[4,5-d]pyrimidin-2-yl)-1-(4-difluoromethoxy-benzenesulfonyl)-piperazine-2-carboxylic acid 4-difluoromethoxy-benzylamide (Example 955),
(R)-1-(4-difluoromethoxy-benzenesulfonyl)-4-thiazolo[4,5-d]pyrimidin-2-yl-piperazine-2-carboxylic acid 4-difluoromethoxy-benzylamide (Example 956),
(R)-4-(5-methyl-4-oxo-4,5-dihydro-thiazolo[4,5-d]pyridazin-2-yl)-1-(4-trifluoromethoxy-benzenesulfonyl)-piperazine-2-carboxylic acid 4-trifluoromethoxy-benzylamide (Example 957),
(R)-4-(5-chloro-thiazolo[4,5-d]pyrimidin-2-yl)-1-(4-trifluoromethoxy-benzenesulfonyl)-piperazine-2-carboxylic acid 4-(ethyl-methyl-amino)-benzylamide (Example 958),
(R)-4-(5-chloro-thiazolo[4,5-d]pyrimidin-2-yl)-1-[4-(1,1,2,2-tetrafluoro-ethoxy)-benzenesulfonyl]-piperazine-2-carboxylic acid 4-trifluoromethoxy-benzylamide (Example 959),
(R)-1-[4-(1,1,2,2-tetrafluoro-ethoxy)-benzenesulfonyl]-4-thiazolo[4,5-d]pyrimidin-2-yl-piperazine-2-carboxylic acid 4-trifluoromethoxy-benzylamide (Example 960),
(R)-1-(4-trifluoromethoxy-benzenesulfonyl)-4-(5-trifluoromethyl-thiazolo[4,5-d]pyrimidin-2-yl)-piperazine-2-carboxylic acid 4-trifluoromethoxy-benzylamide (Example 961),
(R)-4-(7-amino-5-chloro-thiazolo[4,5-d]pyrimidin-2-yl)-1-(4-trifluoromethoxy-benzenesulfonyl)-piperazine-2-carboxylic acid 4-trifluoromethoxy-benzylamide (Example 962),
(R)-4-(5-chloro-7-oxo-6,7-dihydro-thiazolo[4,5-d]pyrimidin-2-yl)-1-(4-trifluoromethoxy-benzenesulfonyl)-piperazine-2-carboxylic acid 4-trifluoromethoxy-benzylamide (Example 963),
(R)-4-(5-cyano-thiazolo[4,5-d]pyrimidin-2-yl)-1-(4-trifluoromethoxy-benzenesulfonyl)-piperazine-2-carboxylic acid 4-trifluoromethoxy-benzylamide (Example 964),
(R)-4-(5-chloro-thiazolo[4,5-d]pyrimidin-2-yl)-1-(4-trifluoromethoxy-benzenesulfonyl)-piperazine-2-carboxylic acid 4-methoxy-benzylamide (Example 965),
(R)-4-(5-chloro-thiazolo[4,5-d]pyrimidin-2-yl)-1-(4-trifluoromethoxy-benzenesulfonyl)-piperazine-2-carboxylic acid 4-fluoromethoxy-benzylamide (Example 966),
(R)-4-thiazolo[4,5-d]pyrimidin-2-yl-1-(4-trifluoromethoxy-benzenesulfonyl)-piperazine-2-carboxylic acid 4-fluoromethoxy-benzylamide (Example 967),
(R)-4-(5-chloro-thiazolo[4,5-d]pyrimidin-2-yl)-1-(4-trifluoromethyl-benzenesulfonyl)-piperazine-2-carboxylic acid 4-difluoromethoxy-benzylamide (Example 968),
(R)-4-thiazolo[4,5-d]pyrimidin-2-yl-1-(4-trifluoromethyl-benzenesulfonyl)-piperazine-2-carboxylic acid 4-difluoromethoxy-benzylamide (Example 969),
(R)-4-(5-methyl-thiazolo[4,5-d]pyrimidin-2-yl)-1-(4-trifluoromethyl-benzenesulfonyl)-piperazine-2-carboxylic acid 4-difluoromethoxy-benzylamide (Example 970),
(R)-4-(5-chloro-thiazolo[4,5-d]pyrimidin-2-yl)-1-(4-trifluoromethoxy-benzenesulfonyl)-piperazine-2-carboxylic acid 4-cyclopropyl-benzylamide (Example 971),
(R)-4-(5-fluoro-thiazolo[4,5-d]pyrimidin-2-yl)-1-(4-trifluoromethoxy-benzenesulfonyl)-piperazine-2-carboxylic acid 4-trifluoromethoxy-benzylamide (Example 972),
(R)-4-(5-isopropylamino-thiazolo[4,5-d]pyrimidin-2-yl)-1-(4-trifluoromethoxy-benzenesulfonyl)-piperazine-2-carboxylic acid 4-trifluoromethoxy-benzylamide (Example 973),
(R)-4-(5-bromo-7-diethylamino-thiazolo[4,5-d]pyrimidin-2-yl)-1-(4-trifluoromethyl-benzenesulfonyl)-piperazine-2-carboxylic acid 4-trifluoromethoxy-benzylamide (Example 974),
(R)-4-(5-cyclopropyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 975),
(R)-4-thiazolo[4,5-d]pyrimidin-2-yl-1-(4-trifluoromethoxy-benzenesulfonyl)-piperazine-2-carboxylic acid 4-cyclopropyl-benzylamide (Example 976),
(R)-4-(7-oxo-7H-[1,3,4]thiadiazolo[3,2-a]pyrimidin-2-yl)-1-(4-trifluoromethoxy-benzenesulfonyl)-piperazine-2-carboxylic acid 4-trifluoromethoxy-benzylamide (Example 977),
(R)-4-(5-acetyl-4-methyl-thiazol-2-yl)-1-(4-trifluoromethoxy-benzenesulfonyl)-piperazine-2-carboxylic acid 4-trifluoromethoxy-benzylamide (Example 978), 2-[(R)-4-(4-trifluoromethoxy-benzenesulfonyl)-3-(4-trifluoromethoxy-benzylcarbamoyl)-piperazin-1-yl]-thiazolo[4,5-d]pyrimidine-5-carboxylic acid amide (Example 979),
(R)-4-(1,3-dimethyl-1H-pyrazolo[3,4-d]thiazol-5-yl)-1-(4-trifluoromethoxy-benzenesulfonyl)-piperazine-2-carboxylic acid 4-trifluoromethoxy-benzylamide (Example 980),
(R)-1-(4-trifluoromethyl-benzenesulfonyl)-4-(5-trifluoromethyl-thiazolo[4,5-d]pyrimidin-2-yl)-piperazine-2-carboxylic acid 4-trifluoromethoxy-benzylamide (Example 981),
(R)-4-(7-amino-5-methyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 982),
(R)-4-(5-cyclopropyl-thiazolo[4,5-d]pyrimidin-2-yl)-1-(4-trifluoromethyl-benzenesulfonyl)-piperazine-2-carboxylic acid 4-trifluoromethoxy-benzylamide (Example 983),
(R)-4-(5-isopropyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 984),
(R)-4-(4-chloro-thiazolo[4,5-d]pyridazin-2-yl)-1-(4-trifluoromethoxy-benzenesulfonyl)-piperazine-2-carboxylic acid 4-trifluoromethoxy-benzylamide (Example 985),
(R)-4-(3-methyl-4-oxo-4H-[1,3,4]thiadiazolo[2,3-c][1,2,4]triazin-7-yl)-1-(4-trifluoromethoxy-benzenesulfonyl)-piperazine-2-carboxylic acid 4-trifluoromethoxy-benzylamide (Example 986),
(R)-4-thiazolo[4,5-d][1,2,3]triazin-6-yl-1-(4-trifluoromethoxy-benzenesulfonyl)-piperazine-2-carboxylic acid 4-trifluoromethoxy-benzylamide (Example 987),
(R)-4-thiazolo[4,5-d]pyrimidin-2-yl-1-(4-trifluoromethoxy-benzenesulfonyl)-piperazine-2-carboxylic acid (indolizin-2-ylmethyl)-amide (Example 989),
7-oxo-2-[(R)-4-(4-trifluoromethoxy-benzenesulfonyl)-3-(4-trifluoromethoxy-benzylcarbamoyl)-piperazin-1-yl]-7H-[1,3,4]thiadiazolo[3,2-a]pyrimidine-5-carboxylic acid methylamide (Example 990),
(R)-4-(5-isopropyl-thiazolo[4,5-d]pyrimidin-2-yl)-1-(4-trifluoromethyl-benzenesulfonyl)-piperazine-2-carboxylic acid 4-trifluoromethoxy-benzylamide (Example 991),
(R)-4-(5-cyclopropylmethyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 992),
(R)-4-(5-chloro-2-diethylamino-thiazolo[4,5-d]pyrimidin-7-yl)-1-(4-trifluoromethoxy-benzenesulfonyl)-piperazine-2-carboxylic acid 4-trifluoromethoxy-benzylamide (Example 993),
(R)-4-[5-(3-hydroxy-3-methyl-but-1-ynyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 994),
(R)-4-(5-ethynyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 995),
(R)-4-thiazolo[4,5-d]pyrimidin-2-yl-1-(4-trifluoromethoxy-benzenesulfonyl)-piperazine-2-carboxylic acid 4-pentafluorosulfanyl-benzylamide (Example 996),
(R)-4-(5-chloro-thiazolo[4,5-d]pyrimidin-2-yl)-1-(4-trifluoromethoxy-benzenesulfonyl)-piperazine-2-carboxylic acid 4-difluoromethoxy-2-fluoro-benzylamide (Example 997),
(R)-4-thiazolo[4,5-d]pyrimidin-2-yl-1-(4-trifluoromethoxy-benzenesulfonyl)-piperazine-2-carboxylic acid 4-difluoromethoxy-2-fluoro-benzylamide (Example 998),
(R)-1-(4-difluoromethoxy-benzenesulfonyl)-4-(5-trifluoromethyl-thiazolo[4,5-d]pyrimidin-2-yl)-piperazine-2-carboxylic acid 4-trifluoromethoxy-benzylamide (Example 999),
(R)-1-(4-trifluoromethoxy-benzenesulfonyl)-4-(5-trifluoromethyl-thiazolo[4,5-d]pyrimidin-2-yl)-piperazine-2-carboxylic acid 4-difluoromethoxy-benzylamide (Example 1000),
(R)-1-(4-trifluoromethyl-benzenesulfonyl)-4-(5-trifluoromethyl-thiazolo[4,5-d]pyrimidin-2-yl)-piperazine-2-carboxylic acid 4-difluoromethoxy-benzylamide (Example 1001),
(R)-4-[4-(2-hydroxy-ethylamino)-thiazolo[4,5-d][1,2,3]triazin-6-yl]-1-(4-trifluoromethoxy-benzenesulfonyl)-piperazine-2-carboxylic acid 4-trifluoromethoxy-benzylamide (Example 1002),
(R)-4-(7-oxo-5-trifluoromethyl-6,7-dihydro-thiazolo[4,5-d]pyrimidin-2-yl)-1-(4-trifluoromethoxy-benzenesulfonyl)-piperazine-2-carboxylic acid 4-trifluoromethoxy-benzylamide (Example 1003),
(R)-1-[4-(1,1,2,2-tetrafluoro-ethoxy)-benzenesulfonyl]-4-(5-trifluoromethyl-thiazolo[4,5-d]pyrimidin-2-yl)-piperazine-2-carboxylic acid 4-trifluoromethoxy-benzylamide (Example 1004),
(R)-1-(4-difluoromethoxy-benzenesulfonyl)-4-(5-trifluoromethyl-thiazolo[4,5-d]pyrimidin-2-yl)-piperazine-2-carboxylic acid 4-difluoromethoxy-benzylamide (Example 1005),
(R)-4-thiazolo[4,5-d][1,2,3]triazin-6-yl-1-(4-trifluoromethyl-benzenesulfonyl)-piperazine-2-carboxylic acid 4-trifluoromethoxy-benzylamide (Example 1006),
2-[(R)-4-(4-trifluoromethoxy-benzenesulfonyl)-3-(4-trifluoromethoxy-benzylcarbamoyl)-piperazin-1-yl]-thiazolo[4,5-d]pyrimidine-5-carboxylic acid ethyl ester (Example 1007),
(R)-4-(5-hydroxymethyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1008),
(R)-4-(4-methoxy-thiazolo[4,5-d]pyridazin-2-yl)-1-(4-trifluoromethoxy-benzenesulfonyl)-piperazine-2-carboxylic acid 4-trifluoromethoxy-benzylamide (Example 1009),
(R)-4-(5-cyano-thiazolo[4,5-d]pyrimidin-2-yl)-1-(4-trifluoromethoxy-benzenesulfonyl)-piperazine-2-carboxylic acid 4-trifluoromethoxy-benzylamide (Example 1010),
(R)-4-(5-cyano-thiazolo[4,5-d]pyrimidin-2-yl)-1-(4-trifluoromethoxy-benzenesulfonyl)-piperazine-2-carboxylic acid 4-difluoromethoxy-benzylamide (Example 1011),
(R)-4-(5-cyclopropylmethyl-thiazolo[4,5-d]pyrimidin-2-yl)-1-(4-trifluoromethyl-benzenesulfonyl)-piperazine-2-carboxylic acid 4-trifluoromethoxy-benzylamide (Example 1012),
2-[(R)-3-(4-trifluoromethoxy-benzylcarbamoyl)-4-(4-trifluoromethyl-benzenesulfonyl)-piperazin-1-yl]-thiazolo[4,5-d]pyrimidine-5-carboxylic acid amide (Example 1013),
(R)-4-(5-cyclopropyl-thiazolo[4,5-d]pyrimidin-2-yl)-1-(4-difluoromethoxy-benzenesulfonyl)-piperazine-2-carboxylic acid 4-difluoromethoxy-benzylamide (Example 1014),
(R)-1-[4-(1,1,2,2-tetrafluoro-ethoxy)-benzenesulfonyl]-4-(5-trifluoromethyl-thiazolo[4,5-d]pyrimidin-2-yl)-piperazine-2-carboxylic acid 4-difluoromethoxy-benzylamide (Example 1015), (R)-4-(5-cyclopropyl-thiazolo[4,5-d]pyrimidin-2-yl)-1-(4-difluoromethoxy-benzenesulfonyl)-piperazine-2-carboxylic acid 4-trifluoromethoxy-benzylamide (Example 1016), (R)-4-(5-cyclopropyl-thiazolo[4,5-d]pyrimidin-2-yl)-1-(4-trifluoromethoxy-benzenesulfonyl)-piperazine-2-carboxylic acid 4-difluoromethoxy-benzylamide (Example 1017), (R)-4-(5-cyclopropyl-thiazolo[4,5-d]pyrimidin-2-yl)-1-[4-(1,1,2,2-tetrafluoro-ethoxy)-benzenesulfonyl]-piperazine-2-carboxylic acid 4-difluoromethoxy-benzylamide (Example 1018), (R)-4-(5-methyl-7-oxo-7H-[1,3,4]thiadiazolo[3,2-a]pyrimidin-2-yl)-1-(4-trifluoromethoxy-benzenesulfonyl)-piperazine-2-carboxylic acid 4-trifluoromethoxy-benzylamide (Example 1019), (R)-4-(5-cyclopropyl-thiazolo[4,5-d]pyrimidin-2-yl)-1-[4-(1,1,2,2-tetrafluoro-ethoxy)-benzenesulfonyl]-piperazine-2-carboxylic acid 4-trifluoromethoxy-benzylamide (Example 1020), (R)-4-(7-amino-5-trifluoromethyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1021), (R)-4-(7-methoxy-5-trifluoromethyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1022), (R)-4-(5-cyclopropyl-thiazolo[4,5-d]pyrimidin-2-yl)-1-(4-trifluoromethyl-benzenesulfonyl)-piperazine-2-carboxylic acid 4-difluoromethoxy-benzylamide (Example 1023), (R)-4-(5-tert-butyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1024), (R)-4-(5-tert-butyl-thiazolo[4,5-d]pyrimidin-2-yl)-1-(4-trifluoromethyl-benzenesulfonyl)-piperazine-2-carboxylic acid 4-trifluoromethoxy-benzylamide (Example 1025), (R)-4-(6-chloro-5-methyl-7-oxo-7H-[1,3,4]thiadiazolo[3,2-a]pyrimidin-2-yl)-1-(4-trifluoromethoxy-benzenesulfonyl)-piperazine-2-carboxylic acid 4-trifluoromethoxy-benzylamide (Example 1026), (R)-4-(5-methyl-7-oxo-7H-[1,3,4]thiadiazolo[3,2-a]pyrimidin-2-yl)-1-(4-trifluoromethoxy-benzenesulfonyl)-piperazine-2-carboxylic acid 4-difluoromethoxy-benzylamide (Example 1027), (R)-4-(5-methyl-7-oxo-7H-[1,3,4]thiadiazolo[3,2-a]pyrimidin-2-yl)-1-(4-trifluoromethyl-benzenesulfonyl)-piperazine-2-carboxylic acid 4-trifluoromethoxy-benzylamide (Example 1028), 5-methyl-2-[(R)-4-(4-trifluoromethoxy-benzenesulfonyl)-3-(4-trifluoromethoxy-benzylcarbamoyl)-piperazin-1-yl]-thiazolo[4,5-d]pyrimidine-7-carboxylic acid amide (Example 1029), (R)-4-(5-methyl-4-oxo-4,5-dihydro-thiazolo[4,5-d]pyridazin-2-yl)-1-(4-trifluoromethyl-benzenesulfonyl)-piperazine-2-carboxylic acid 4-trifluoromethoxy-benzylamide (Example 1030), (R)-4-(4-oxo-3-trifluoromethyl-4H-[1,3,4]thiadiazolo[2,3-c][1,2,4]triazin-7-yl)-1-(4-trifluoromethoxy-benzenesulfonyl)-piperazine-2-carboxylic acid 4-trifluoromethoxy-benzylamide (Example 1031), (R)-4-(5-methyl-7-oxo-7H-[1,3,4]thiadiazolo[3,2-a]pyrimidin-2-yl)-1-(4-trifluoromethyl-benzenesulfonyl)-piperazine-2-carboxylic acid 4-difluoromethoxy-benzylamide (Example 1032), 2-[(R)-4-(4-trifluoromethoxy-benzenesulfonyl)-3-(4-trifluoromethoxy-benzylcarbamoyl)-piperazin-1-yl]-thiazolo[4,5-d]pyrimidine-5-carboxylic acid (Example 1033), (R)-4-(4-amino-thiazolo[4,5-d][1,2,3]triazin-6-yl)-1-(4-trifluoromethoxy-benzenesulfonyl)-piperazine-2-carboxylic acid 4-trifluoromethoxy-benzylamide (Example 1034), (R)-4-(4-methoxy-thiazolo[4,5-d][1,2,3]triazin-6-yl)-1-(4-trifluoromethoxy-benzenesulfonyl)-piperazine-2-carboxylic acid 4-trifluoromethoxy-benzylamide (Example 1035), (R)-4-(5-cyano-thiazolo[4,5-d]pyrimidin-2-yl)-1-(4-trifluoromethoxy-benzenesulfonyl)-piperazine-2-carboxylic acid 4-difluoromethoxy-benzylamide (Example 1036), (R)-4-(5-ethyl-4-oxo-4,5-dihydro-thiazolo[4,5-d]pyridazin-2-yl)-1-(4-trifluoromethyl-benzenesulfonyl)-piperazine-2-carboxylic acid 4-trifluoromethoxy-benzylamide (Example 1037), (R)-4-(5-oxo-7-trifluoromethyl-5H-[1,3,4]thiadiazolo[3,2-a]pyrimidin-2-yl)-1-(4-trifluoromethoxy-benzenesulfonyl)-piperazine-2-carboxylic acid 4-trifluoromethoxy-benzylamide (Example 1038), (R)-4-(5-methyl-thiazolo[4,5-d]pyrimidin-2-yl)-1-[4-(1,1,2,2-tetrafluoro-ethoxy)-benzenesulfonyl]-piperazine-2-carboxylic acid 4-difluoromethoxy-benzylamide (Example 1039), (R)-4-(5-cyclopropyl-thiazolo[4,5-d]pyrimidin-2-yl)-1-(4-trifluoromethyl-benzenesulfonyl)-piperazine-2-carboxylic acid 4-difluoromethoxy-2-fluoro-benzylamide (Example 1040), 2-[(R)-4-(4-trifluoromethoxy-benzenesulfonyl)-3-(4-trifluoromethoxy-benzylcarbamoyl)-piperazin-1-yl]-thiazolo[4,5-d]pyrimidine-5-carboxylic acid dimethylamide (Example 1041), (R)-1-(4-trifluoromethyl-benzenesulfonyl)-4-(5-trifluoromethyl-thiazolo[4,5-d]pyrimidin-2-yl)-piperazine-2-carboxylic acid 4-difluoromethoxy-2-fluoro-benzylamide (Example 1042), (R)-4-(5-methoxymethyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1043), (R)-1-(4-trifluoromethoxy-benzenesulfonyl)-4-(5-trifluoromethyl-thiazolo[4,5-d]pyrimidin-2-yl)-piperazine-2-carboxylic acid 4-difluoromethoxy-2-fluoro-benzylamide (Example 1044), (R)-4-(5-cyclopropyl-thiazolo[4,5-d]pyrimidin-2-yl)-1-(4-trifluoromethoxy-benzenesulfonyl)-piperazine-2-carboxylic acid 4-difluoromethoxy-2-fluoro-benzylamide (Example 1045), 2-[(R)-4-(4-trifluoromethoxy-benzenesulfonyl)-3-(4-trifluoromethoxy-benzylcarbamoyl)-piperazin-1-yl]-thiazolo[4,5-d]pyrimidine-5-carboxylic acid methylamide (Example 1046), (R)-4-[5-(1-hydroxy-1-methyl-ethyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 1047), (R)-4-(5-acetyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1048), (R)-4-(7-oxo-5-trifluoromethyl-7H-[1,3,4]thiadiazolo[3,2-a]pyrimidin-2-yl)-1-(4-trifluoromethoxy-benzenesulfonyl)-piperazine-2-carboxylic acid 4-trifluoromethoxy-benzylamide (Example 1049), (R)-4-(5-methoxy-thiazolo[5,4-b]pyridin-2-yl)-1-(4-trifluoromethoxy-benzenesulfonyl)-piperazine-2-carboxylic acid 4-trifluoromethoxy-benzylamide (Example 1050), (R)-4-(5-methyl-thiazolo[4,5-d]pyrimidin-2-yl)-1-[4-(1,1,2, 2-tetrafluoro-ethoxy)-benzenesulfonyl]-piperazine-2-carboxylic acid 4-trifluoromethoxy-benzylamide (Example 1051), (R)-4-(5-hydroxymethyl-thiazolo[4,5-d]pyrimidin-2-yl)-1-(4-trifluoromethyl-benzenesulfonyl)-piperazine-2-carboxylic acid 4-trifluoromethoxy-benzylamide (Example 1052), (R)-4-(7-oxo-7H-[1,3,4]thiadiazolo[3,2-a]pyrimidin-2-yl)-1-(4-trifluoromethoxy-benzenesulfonyl)-piperazine-2-carboxylic acid 4-difluoromethoxy-benzylamide (Example 1053), 2-[(R)-4-(4-trifluoromethoxy-benzenesulfonyl)-3-(4-trifluoromethoxy-benzylcarbamoyl)-piperazin-1-yl]-thiazolo[4,5-d]pyrimidine-5-carboxylic acid methoxy-methyl-amide (Example 1054), (R)-4-(7-amino-5-methoxymethyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1055), (R)-4-(5-pyrrolidin-1-ylmethyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1056), (R)-4-(7-oxo-7H-[1,3,4]thiadiazolo[3,2-a]pyrimidin-2-yl)-1-(4-trifluoromethyl-benzenesulfonyl)-piperazine-2-carboxylic acid 4-difluoromethoxy-benzylamide (Example 1057), (R)-1-(4-difluoromethoxy-benzenesulfonyl)-4-(7-oxo-7H-[1,3,4]thiadiazolo[3,2-a]pyrimidin-2-yl)-piperazine-2-carboxylic acid 4-trifluoromethoxy-benzylamide (Example 1058), (R)-4-(7-oxo-7H-[1,3,4]thiadiazolo[3,2-a]pyrimidin-2-yl)-1-(4-trifluoromethyl-benzenesulfonyl)-piperazine-2-carboxylic acid 4-trifluoromethoxy-benzylamide (Example 1059), (R)-4-[5-(1-hydroxy-ethyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 1060), (R)-1-(4-trifluoromethoxy-benzenesulfonyl)-4-(5-trifluoromethyl-thiazolo[4,5-d]pyrimidin-2-yl)-piperazine-2-carboxylic acid 4-difluoromethoxy-3-fluoro-benzylamide (Example 1061), (R)-4-(5-oxo-4,5-dihydro-thiazolo[5,4-b]pyridin-2-yl)-1-(4-trifluoromethoxy-benzenesulfonyl)-piperazine-2-carboxylic acid 4-trifluoromethoxy-benzylamide (Example 1062), (R)-1-(4-difluoromethoxy-benzenesulfonyl)-4-(7-oxo-7H-[1,3,4]thiadiazolo[3,2-a]pyrimidin-2-yl)-piperazine-2-carboxylic acid 4-difluoromethoxy-benzylamide (Example 1063), 2-[(R)-4-(4-ethyl-benzenesulfonyl)-3-(4-propyl-benzylcarbamoyl)-piperazin-1-yl]-thiazolo[5,4-c]pyridine-7-carboxylic acid ethyl ester (Example 1064), 2-[(R)-4-(4-ethyl-benzenesulfonyl)-3-(4-propyl-benzylcarbamoyl)-piperazin-1-yl]-thiazolo[5,4-c]pyridine-7-carboxylic acid (Example 1065), (R)-4-(7-oxo-5-trifluoromethyl-7H-[1,3,4]thiadiazolo[3,2-a]pyrimidin-2-yl)-1-(4-trifluoromethoxy-benzenesulfonyl)-piperazine-2-carboxylic acid 4-difluoromethoxy-benzylamide (Example 1066), (R)-4-(7-oxo-5-trifluoromethyl-7H-[1,3,4]thiadiazolo[3,2-a]pyrimidin-2-yl)-1-(4-trifluoromethyl-benzenesulfonyl)-piperazine-2-carboxylic acid 4-trifluoromethoxy-benzylamide (Example 1067), (R)-4-(7-oxo-5-trifluoromethyl-7H-[1,3,4]thiadiazolo[3,2-a]pyrimidin-2-yl)-1-(4-trifluoromethyl-benzenesulfonyl)-piperazine-2-carboxylic acid 4-difluoromethoxy-benzylamide (Example 1068), (R)-4-(5-cyclobutyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1069), (R)-4-[5-(2-methoxy-ethyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 1070), (R)-4-[5-(2-methoxy-ethyl)-4-oxo-4,5-dihydro-thiazolo[4,5-d]pyridazin-2-yl]-1-(4-trifluoromethoxy-benzenesulfonyl)-piperazine-2-carboxylic acid 4-trifluoromethoxy-benzylamide (Example 1071), (R)-4-(5-cyclobutyl-thiazolo[4,5-d]pyrimidin-2-yl)-1-(4-trifluoromethyl-benzenesulfonyl)-piperazine-2-carboxylic acid 4-trifluoromethoxy-benzylamide (Example 1072), (R)-4-(5-cyclopropyl-thiazolo[4,5-d]pyrimidin-2-yl)-1-(4-trifluoromethoxy-benzenesulfonyl)-piperazine-2-carboxylic acid 4-difluoromethoxy-3-fluoro-benzylamide (Example 1073), (R)-4-(5-cyclopropyl-thiazolo[4,5-d]pyrimidin-2-yl)-1-(4-trifluoromethyl-benzenesulfonyl)-piperazine-2-carboxylic acid 4-difluoromethoxy-3-fluoro-benzylamide (Example 1074), (R)-4-[5-(1-hydroxy-1-methyl-ethyl)-thiazolo[4,5-d]pyrimidin-2-yl]-1-(4-trifluoromethyl-benzenesulfonyl)-piperazine-2-carboxylic acid 4-trifluoromethoxy-benzylamide (Example 1075), (R)-4-[5-(1-methoxymethyl-cyclopropyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 1076), (R)-4-[5-(1-hydroxymethyl-cyclopropyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 1077), (R)-4-[5-(2-hydroxy-ethyl)-4-oxo-4,5-dihydro-thiazolo[4,5-d]pyridazin-2-yl]-1-(4-trifluoromethoxy-benzenesulfonyl)-piperazine-2-carboxylic acid 4-trifluoromethoxy-benzylamide (Example 1078), (R)-4-[5-(1-methoxy-cyclopropyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 1079), (R)-4-[5-(1-hydroxy-cyclopropyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 1080), 2-[(R)-3-(4-propyl-benzylcarbamoyl)-4-(4-trifluoromethoxy-benzenesulfonyl)-piperazin-1-yl]-thiazolo[5,4-c]pyridine-6-carboxylic acid tert-butyl ester (Example 1081), 2-[(R)-3-(4-propyl-benzylcarbamoyl)-4-(4-trifluoromethoxy-benzenesulfonyl)-piperazin-1-yl]-thiazolo[5,4-c]pyridine-6-carboxylic acid (Example 1082), 2-[(R)-3-(4-propyl-benzylcarbamoyl)-4-(4-trifluoromethoxy-benzenesulfonyl)-piperazin-1-yl]-thiazolo[5,4-c]pyridine-7-carboxylic acid ethyl ester (Example 1083), 2-[(R)-3-(4-propyl-benzylcarbamoyl)-4-(4-trifluoromethoxy-benzenesulfonyl)-piperazin-1-yl]-thiazolo[5,4-c]pyridine-7-carboxylic acid (Example 1084), (R)-1-(4-trifluoromethyl-benzenesulfonyl)-4-(5-trifluoromethyl-thiazolo[4,5-d]pyrimidin-2-yl)-piperazine-2-carboxylic acid 4-difluoromethoxy-3-fluoro-benzylamide (Example 1085),
(R)-4-(5-oxo-4,5-dihydro-thiazolo[5,4-b]pyridin-2-yl)-1-(4-trifluoromethyl-benzenesulfonyl)-piperazine-2-carboxylic acid 4-trifluoromethoxy-benzylamide (Example 1086),
(R)-4-(5-difluoromethoxy-thiazolo[4,5-d]pyrimidin-2-yl)-1-(4-trifluoromethoxy-benzenesulfonyl)-piperazine-2-carboxylic acid 4-trifluoromethoxy-benzylamide (Example 1087),
(R)-4-(5-isopropyl-7-oxo-7H-[1,3,4]thiadiazolo[3,2-a]pyrimidin-2-yl)-1-(4-trifluoromethoxy-benzenesulfonyl)-piperazine-2-carboxylic acid 4-trifluoromethoxy-benzylamide (Example 1088),
(R)-4-(5-isopropyl-7-oxo-7H-[1,3,4]thiadiazolo[3,2-a]pyrimidin-2-yl)-1-(4-trifluoromethoxy-benzenesulfonyl)-piperazine-2-carboxylic acid 4-difluoromethoxy-benzylamide (Example 1089),
(R)-4-(7-amino-5-cyclopropyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1090),
(R)-4-[7-amino-5-(1-hydroxy-1-methyl-ethyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 1091),
hydroxy-{4-methyl-2-[(R)-3-(4-propyl-benzylcarbamoyl)-4-(4-trifluoromethoxy-benzenesulfonyl)-piperazin-1-yl]-thiazol-5-yl}-acetic acid (Example 1092),
4-chloro-2-[(R)-3-[4-(ethyl-methyl-amino)-benzylcarbamoyl]-4-(4-trifluoromethoxy-benzenesulfonyl)-piperazin-1-yl]-thiazole-5-carboxylic acid (Example 1093),
{5-methyl-3-[(R)-3-(4-propyl-benzylcarbamoyl)-4-(4-trifluoromethoxy-benzenesulfonyl)-piperazin-1-yl]-pyrazol-1-yl}-acetic acid (Example 1094),
[(R)-3-(4-tert-butyl-benzylcarbamoyl)-4-(4-trifluoromethoxy-benzenesulfonyl)-3,4,5,6-tetrahydro-2H-[1,2']bipyrazinyl-5'-ylmethyl]-triethyl-ammonium trifluoromethanesulfonate (Example 1095),
(R)-4-[5-(2-hydroxy-ethyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 1098),
(R)-1-(4-cyclopropyl-benzenesulfonyl)-4-(5-cyclopropyl-thiazolo[4,5-d]pyrimidin-2-yl)-piperazine-2-carboxylic acid 4-trifluoromethoxy-benzylamide (Example 1099),
(R)-1-(4-cyclopropyl-benzenesulfonyl)-4-(5-trifluoromethyl-thiazolo[4,5-d]pyrimidin-2-yl)-piperazine-2-carboxylic acid 4-trifluoromethoxy-benzylamide (Example 1100),
(R)-4-(5-cyclopropyl-thiazolo[4,5-d]pyrimidin-2-yl)-1-(4-trifluoromethyl-benzenesulfonyl)-piperazine-2-carboxylic acid 3-fluoro-4-trifluoromethoxy-benzylamide (Example 1101),
(R)-4-(5-cyclopropyl-thiazolo[4,5-d]pyrimidin-2-yl)-1-(4-trifluoromethoxy-benzenesulfonyl)-piperazine-2-carboxylic acid 3-fluoro-4-trifluoromethoxy-benzylamide (Example 1102),
2-[(R)-4-(4-trifluoromethoxy-benzenesulfonyl)-3-(4-trifluoromethoxy-benzylcarbamoyl)-piperazin-1-yl]-thiazolo[5,4-c]pyridine-7-carboxylic acid (Example 1104),
(R)-4-(5-hydroxymethyl-7-oxo-7H-[1,3,4]thiadiazolo[3,2-a]pyrimidin-2-yl)-1-(4-trifluoromethoxy-benzenesulfonyl)-piperazine-2-carboxylic acid 4-trifluoromethoxy-benzylamide (Example 1105),
{4-oxo-2-[(R)-4-(4-trifluoromethoxy-benzenesulfonyl)-3-(4-trifluoromethoxy-benzylcarbamoyl)-piperazin-1-yl]-4H-thiazolo[4,5-d]pyridazin-5-yl}-acetic acid (Example 1106),
(R)-4-(5-cyclopropyl-7-oxo-6,7-dihydro-thiazolo[4,5-d]pyrimidin-2-yl)-1-(4-trifluoromethyl-benzenesulfonyl)-piperazine-2-carboxylic acid 4-trifluoromethoxy-benzylamide (Example 1107),
(R)-4-(5-cyclopropyl-7-oxo-6,7-dihydro-thiazolo[4,5-d]pyrimidin-2-yl)-1-(4-trifluoromethoxy-benzenesulfonyl)-piperazine-2-carboxylic acid 4-trifluoromethoxy-benzylamide (Example 1108),
2-[(R)-3-(4-difluoromethoxy-3-fluoro-benzylcarbamoyl)-4-(4-trifluoromethoxy-benzenesulfonyl)-piperazin-1-yl]-thiazolo[5,4-c]pyridine-7-carboxylic acid (Example 1109),
(R)-4-(5-cyclopropyl-thiazolo[4,5-d]pyrimidin-2-yl)-1-(2-fluoro-4-trifluoromethoxy-benzenesulfonyl)-piperazine-2-carboxylic acid 4-trifluoromethoxy-benzylamide (Example 1110),
(R)-3-(4-difluoromethoxy-3-fluoro-benzylcarbamoyl)-4-(4-trifluoromethoxy-benzenesulfonyl)-3,4,5,6-tetrahydro-2H-[1,2']bipyrazinyl-5'-carboxylic acid (Example 1111),
3-{4-oxo-2-[(R)-4-(4-trifluoromethoxy-benzenesulfonyl)-3-(4-trifluoromethoxy-benzylcarbamoyl)-piperazin-1-yl]-4H-thiazolo[4,5-d]pyridazin-5-yl}propionic acid (Example 1112),
(R)-4-(5-cyclopropyl-7-oxo-6,7-dihydro-thiazolo[4,5-d]pyrimidin-2-yl)-1-(4-trifluoromethoxy-benzenesulfonyl)-piperazine-2-carboxylic acid 4-difluoromethoxy-3-fluoro-benzylamide (Example 1113), and
(R)-4-(5-cyclopropyl-7-oxo-6,7-dihydro-thiazolo[4,5-d]pyrimidin-2-yl)-1-(4-trifluoromethyl-benzenesulfonyl)-piperazine-2-carboxylic acid 4-difluoromethoxy-3-fluoro-benzylamide (Example 1114),
or a pharmaceutically acceptable salt thereof, or a solvate thereof.

[33] A pharmaceutical composition comprising a compound of any one of [15] to [32] or a pharmaceutically acceptable salt thereof, or a solvate thereof, and a pharmaceutically acceptable carrier.

[34] An antiviral agent comprising a compound of any one of [15] to [32] or a pharmaceutically acceptable salt thereof, or a solvate thereof, and a pharmaceutically acceptable carrier.

[35] A therapeutic agent for hepatitis C comprising, as an active ingredient, a compound of any one of [15] to [32] or a pharmaceutically acceptable salt thereof, or a solvate thereof.

[36] A therapeutic agent for hepatitis C comprising (a) an HCV polymerase inhibitor of [14] and (b) at least one pharmaceutical agent selected from the group consisting of a different antiviral agent, an antiinflammatory agent and an immunostimulant in combination.

[37] A therapeutic agent for hepatitis C comprising (a) an HCV polymerase inhibitor of [14] and (b) interferon in combination.

[38] A pharmaceutical composition comprising (a) a compound of any one of [15] to [32] or a pharmaceutically acceptable salt thereof, or a solvate thereof, and (b) at least one pharmaceutical agent selected from the group consisting of a different antiviral agent, an antiinflammatory agent and an immunostimulant.

[39] A pharmaceutical composition comprising (a) a compound of any one of [15] to [32] or a pharmaceutically acceptable salt thereof, or a solvate thereof, and (b) interferon.

[40] Use of a compound represented by the formula [I] of [1], or a pharmaceutically acceptable salt thereof, or a solvate thereof, for the production of an anti-HCV agent.
[41] Use of a compound represented by the formula [I] of [1], or a pharmaceutically acceptable salt thereof, or a solvate thereof, for the production of an HCV polymerase inhibitor.
[42] Use of (a) a compound represented by the formula [I] of [1], or a pharmaceutically acceptable salt thereof, or a solvate thereof, and (b) at least one pharmaceutical agent selected from the group consisting of a different antiviral agent, an antiinflammatory agent and an immunostimulant, for the production of a therapeutic agent for hepatitis C.
[43] Use of (a) a compound represented by the formula [I] of [1], or a pharmaceutically acceptable salt thereof, or a solvate thereof, and (b) interferon, for the production of a therapeutic agent for hepatitis C.
[44] A method for treating hepatitis C in a mammal, comprising administering an effective amount of a compound represented by the formula [I] of [1], or a pharmaceutically acceptable salt thereof, or a solvate thereof to the mammal.
[45] The method of [44] further comprising administering an effective amount of at least one pharmaceutical agent selected from the group consisting of a different antiviral agent, an antiinflammatory agent and an immunostimulant to the mammal.
[46] The method of [44] further comprising administering an effective amount of interferon to the mammal.
[47] A method for inhibiting HCV polymerase in a mammal, comprising administering an effective amount of a compound represented by the formula [I] of [1], or a pharmaceutically acceptable salt thereof, or a solvate thereof to the mammal.
[48] The method of [47] further comprising administering an effective amount of at least one pharmaceutical agent selected from the group consisting of a different antiviral agent, an antiinflammatory agent and an immunostimulant to the mammal.
[49] The method of [47] further comprising administering an effective amount of interferon to the mammal.
[50] A pharmaceutical composition for the treatment of hepatitis C comprising a compound represented by the formula [I] of [1], or a pharmaceutically acceptable salt thereof, or a solvate thereof, and a pharmaceutically acceptable carrier.
[51] A pharmaceutical composition for inhibiting HCV polymerase comprising a compound represented by the formula [I] of [1], or a pharmaceutically acceptable salt thereof, or a solvate thereof, and a pharmaceutically acceptable carrier.

The definition of each substituent and moiety used in the specification is as follows.

The "halogen atom" is fluorine atom, chlorine atom, bromine atom or iodine atom.

The substituent (group A) on ring A or ring B is preferably a fluorine atom, and group B of the "$C_{1-10}$ alkyl group optionally substituted by 1 to 5 substituents selected from group B" is preferably a fluorine atom.

The "$C_{3-12}$ carbon ring group" is a saturated or unsaturated cyclic hydrocarbon group having 3 to 12 carbon atoms, specifically, $C_{6-12}$ aryl group, $C_{3-10}$ cycloalkyl group, $C_{3-10}$ cycloalkenyl group, a fused carbon ring group wherein two or more rings constituting them are fused and the like.

The "$C_{6-12}$ aryl group" is an aryl group having 6 to 12 carbon atoms and, for example, phenyl group, naphthyl group (e.g., naphthalen-2-yl etc.), azulenyl group, pentalenyl group and the like can be mentioned.

The "$C_{3-10}$ cycloalkyl group" is a cycloalkyl group having 3 to 10 carbon atoms and, for example, cyclopropyl group, cyclobutyl group, cyclopentyl group, cyclohexyl group, cycloheptyl group, cyclooctyl group etc., and bridged carbon rings such as adamantyl group (e.g., adamantan-1-yl etc.), norbornyl group (e.g., norbornan-2-yl) and the like can be mentioned. It is preferably cyclopropyl group, cyclobutyl group, cyclopentyl group, cyclohexyl group, cycloheptyl group or cyclooctyl group, more preferably cyclopropyl group, cyclobutyl group, cyclopentyl group or cyclohexyl group, further preferably cyclopropyl group or cyclobutyl group, and most preferably cyclopropyl group.

The "$C_{3-10}$ cycloalkenyl group" is a cycloalkenyl group having 3 to 10 carbon atoms and contains at least one, preferably 1 or 2, double bonds. For example, cyclopropenyl group, cyclobutenyl group, cyclopentenyl group, cyclopentadienyl group, cyclohexenyl group, cyclohexadienyl group (2,4-cyclohexadien-1-yl group, 2,5-cyclohexadien-1-yl group etc.), cycloheptenyl group, cyclooctenyl group and the like can be mentioned.

As the fused carbon ring group wherein two or more rings constituting the "$C_{6-12}$ aryl group", "$C_{3-10}$ cycloalkyl group" and "$C_{3-10}$ cycloalkenyl group" are fused, for example, indenyl group, indanyl group (e.g., indan-5-yl etc.), fluorenyl group, dihydronaphthyl group, tetrahydronaphthyl group (e.g., 1,2,3,4-tetrahydronaphthalen-2-yl, 5,6,7,8-tetrahydronaphthalen-2-yl etc.), perhydronaphthyl group, tetrahydrobenzocycloheptenyl group (e.g., 6,7,8,9-tetrahydro-5H-benzocycloheptenyl etc.) and the like can be mentioned.

The "heterocyclic group" has, as a ring-constituting atom besides carbon atom, 1 to 6 (preferably 1 to 4) hetero atoms selected from nitrogen atom, oxygen atom and sulfur atom, wherein the number of atoms constituting the ring is 3 to 14, and includes a saturated or unsaturated, monocyclic or fused ring.

As the "monocyclic heterocyclic group", specifically, pyridyl group (e.g., pyridin-2-yl, pyridin-3-yl, pyridin-4-yl), pyrazinyl group (e.g., pyrazin-2-yl etc.), pyrimidinyl group (e.g., pyrimidin-2-yl, pyrimidin-4-yl, pyrimidin-5-yl etc.), pyridazinyl group (e.g., pyridazin-3-yl etc.), triazinyl group, pyrrolyl group, pyrazolyl group (e.g., pyrazol-1-yl, 1H-pyrazol-3-yl, 2H-pyrazol-3-yl, 1H-pyrazol-4-yl etc.), imidazolyl group (e.g., imidazol-1-yl, 1H-imidazol-2-yl, 1H-imidazol-4-yl etc.), triazolyl group (e.g., 1,2,4-triazol-3-yl, 1,2,4-triazol-1-yl, 1,2,4-triazol-4-yl, 1,2,3-triazol-1-yl, 1,2,3-triazol-2-yl, 1,3,4-triazol-1-yl etc.), tetrazolyl group (e.g., tetrazol-1-yl, tetrazol-2-yl, 1H-tetrazol-5-yl, 2H-tetrazol-5-yl etc.), thienyl group (e.g., thiophen-2-yl, thiophen-3-yl etc.), furyl group (e.g., furan-3-yl etc.), oxazolyl group (e.g., oxazol-2-yl etc.), isoxazolyl group (e.g., isoxazol-5-yl, isoxazol-3-yl etc.), thiazolyl group (e.g., thiazol-2-yl, thiazol-4-yl, thiazol-5-yl etc.), isothiazolyl group (e.g., isothiazol-5-yl, isothiazol-3-yl etc.), thiadiazolyl group (e.g., 1,3,4-thiadiazol-2-yl, 1,2,3-thiadiazol-4-yl, 1,2,4-thiadiazol-3-yl, 1,2,4-thiadiazol-5-yl etc.), oxadiazolyl group (e.g., 1,3,4-oxadiazol-2-yl etc.), 2-oxo-1,2-dihydropyridyl group (e.g., 2-oxo-1,2-dihydropyridin-4-yl, 2-oxo-1,2-dihydropyridin-3-yl, 6-oxo-1,6-dihydropyridin-3-yl etc.), 1,2,3,6-tetrahydropyridyl group (e.g., 1,2,3,6-tetrahydropyridin-4-yl etc.), pyrrolinyl group (e.g., 2-pyrrolin-1-yl group, 3-pyrrolin-3-yl etc.), oxopyrrolinyl group (e.g., 2-oxo-3-pyrrolin-1-yl, 2-oxo-3-pyrrolin-3-yl etc.), dioxopyrrolinyl group (e.g., 2,5-dioxo-3-pyrrolin-3-yl etc.), imidazolinyl group (e.g., 2-imidazolin-2-yl etc.), thiazolinyl group (e.g., 2-thiazolin-2-yl etc.), oxothiazolinyl group (e.g., 4-oxo-4,5-dihydrothiazol-2-yl etc.), oxazolinyl group (e.g., 2-oxazolin-2-yl etc.), azetidinyl group (e.g., azetidin-1-yl, azetidin-3-yl etc.), pyrrolidinyl group (e.g., pyrrolidin-1-yl etc.), oxopyrrolidinyl group (e.g., 2-oxopyrrolidin-1-yl, 2-oxopyrrolidin-3-yl etc.), dioxopyrrolidinyl group (e.g., 2,5-dioxopyrrolidin-3-yl etc.), oxothiadiazolinyl group (e.g., 5-oxo-4,5-dihydro-1,3,4-thiadiazol-2-yl etc.), oxooxadiazolinyl group (e.g., 5-oxo-2,5-dihydro-1,2,4-oxadiazol-3-yl etc.), imidazolidinyl group, piperidinyl group (e.g., piperidin-1-yl, piperidin-4-yl etc.), oxopiperidinyl group (e.g., 6-oxopiperidin-3-yl group), piperazinyl group (e.g., piperazin-1-yl etc.), morpholinyl group (e.g., morpholin-4-yl etc.), thiomorpholinyl group, tetrahydropyranyl group and the like can be mentioned.

As the "fused heterocyclic group", specifically, quinolyl group, isoquinolyl group, quinazolinyl group, quinoxalyl group (e.g., quinoxalin-2-yl, quinoxalin-6-yl etc.), phthalazinyl group, cinnolinyl group, naphthyridinyl group (e.g., 1,5-naphthyridin-2-yl, 1,6-naphthyridin-2-yl etc.), indolyl group (e.g., 1H-indol-3-yl etc.), benzimidazolyl group (e.g., 1H-benzimidazol-2-yl etc.), indolinyl group, benzofuranyl group, benzothienyl group (e.g., benzothiophen-2-yl etc.), benzoxazolyl group (e.g., benzoxazol-2-yl etc.), benzodioxinyl group, benzothiazolyl group (e.g., benzothiazol-2-yl etc.), tetrahydroquinolyl group (e.g., 1,2,3,4-tetrahydroquinolin-7-yl etc.), dihydrobenzofuranyl group (e.g., 2,3-dihydrobenzofuran-5-yl etc.), dihydrobenzothienyl group, dihydrobenzodioxinyl group (e.g., 2,3-dihydrobenzo[1,4]dioxin-6-yl etc.), indenothiazolyl group (e.g., 8H-indeno[1,2-d]thiazol-2-yl etc.), tetrahydrobenzothiazolyl group (e.g., 4,5,6,7-tetrahydrobenzothiazol-2-yl etc.), indolizinyl group (e.g., indolizin-2-yl etc.) and the like can be mentioned.

The "fused heterocyclic group" includes a group bonded via carbon atom or nitrogen atom of a fused heterocycle represented by the following formula:

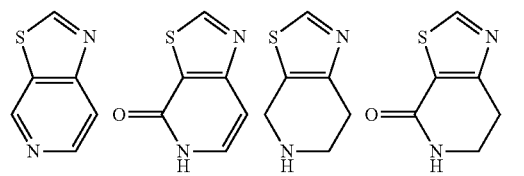

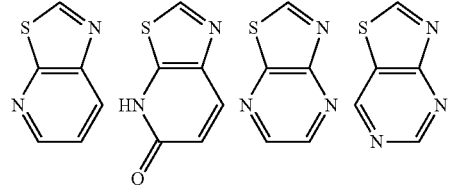

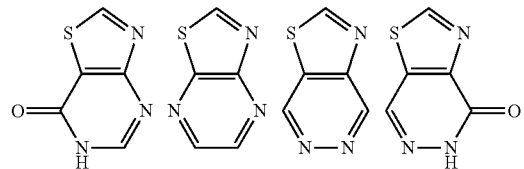

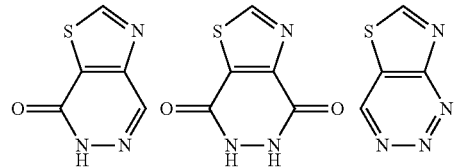

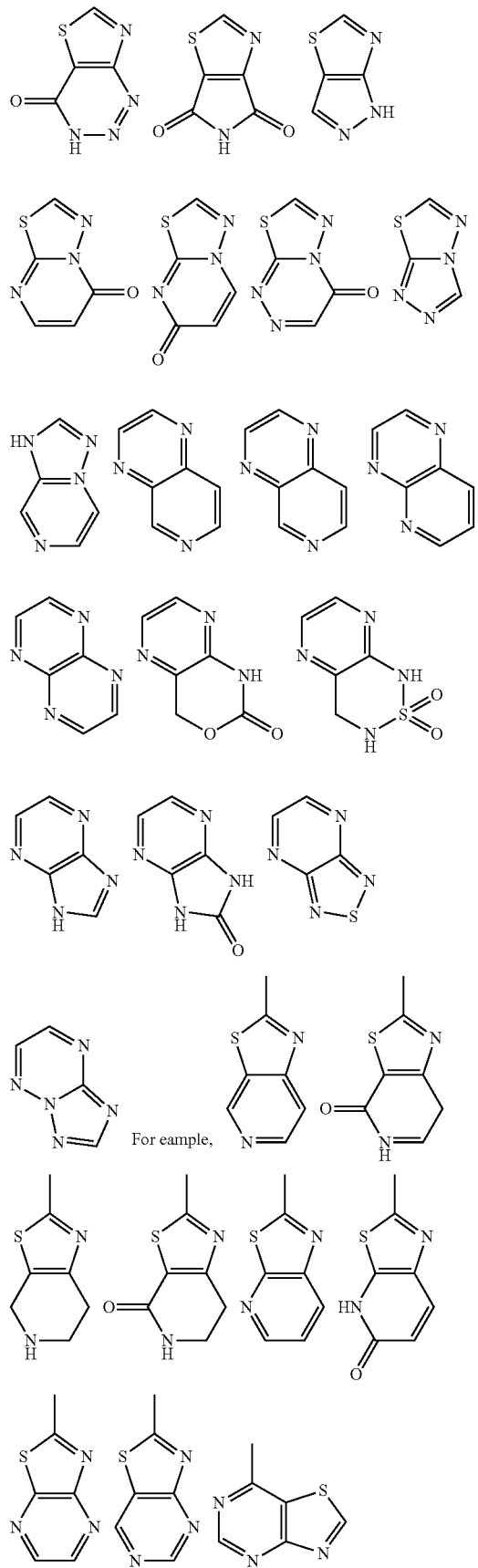

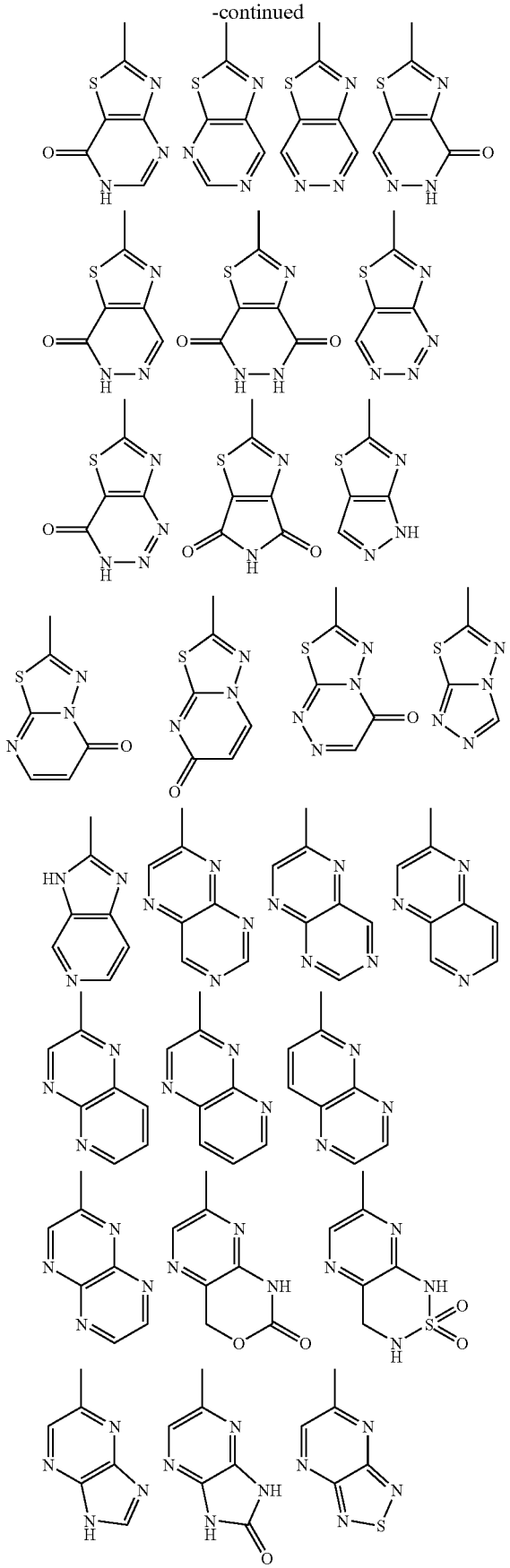
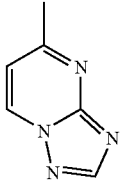

and the like can be mentioned.

The "fused heterocyclic group" is preferably a bicyclic fused ring, and a fused ring of a monocyclic heterocycle and a monocyclic heterocycle is preferable.

The "$C_{1-10}$ alkyl group" is a straight chain or branched chain alkyl group having 1 to 10 carbon atoms and, for example, methyl group, ethyl group, propyl group, isopropyl group, butyl group, isobutyl group, sec-butyl group, tert-butyl group, pentyl group, isopentyl group, tert-pentyl group, 1-ethylpropyl group, neopentyl group, hexyl group, heptyl group, 1-propylbutyl group, octyl group, nonyl group, decyl group and the like can be mentioned. It is preferably an alkyl group having 1 to 6 carbon atoms, more preferably an alkyl group having 1 to 4 carbon atoms.

The "$C_{1-4}$ alkyl group" is a straight chain or branched chain alkyl group having 1 to 4 carbon atoms and, for example, methyl group, ethyl group, propyl group, isopropyl group, butyl group, isobutyl group, sec-butyl group and tert-butyl group can be mentioned.

The "$C_{2-10}$ alkynyl group" is a straight chain or branched chain alkynyl group having 2 to 10 carbon atoms and, for example, ethynyl group, 1-propynyl group, 2-propynyl group, 1-butynyl group, 2-butynyl group, 3-butynyl group, 1-pentynyl group, 1-hexynyl group, 1-heptynyl group, 1-octynyl group, 3-methylbut-1-yn-1-yl group and the like can be mentioned. It is preferably an alkynyl group having 2 to 6 carbon atoms, more preferably an alkynyl group having 2 to 4 carbon atoms.

The "$C_{1-4}$ alkylene" is a straight chain or branched chain alkylene having 1 to 4 carbon atoms and, for example, methylene, ethylene, trimethylene, tetramethylene, —CH(CH$_3$)—, —C(CH$_3$)$_2$—, —CH(CH$_3$)—CH$_2$—, —CH$_2$—CH(CH$_3$)—, —C(CH$_3$)$_2$—CH$_2$—, —CH$_2$—C(CH$_3$)$_2$—, —CH(CH$_3$)—(CH$_2$)$_2$—, —CH$_2$—CH(CH$_3$)—CH$_2$—, —(CH$_2$)$_2$—CH(CH$_3$)— and the like can be mentioned.

The "halogeno $C_{1-4}$ alkyl group" is the above-defined "$C_{1-4}$ alkyl group" substituted by the above-defined "halogen atom" and, for example, fluoromethyl group, difluoromethyl group, trifluoromethyl group, bromomethyl group, chloromethyl group, 1,2-dichloroethyl group, 2,2-dichloroethyl group, 2,2,2-trifluoroethyl group and the like can be mentioned.

The "hydroxy $C_{1-4}$ alkyl group" is the above-defined "$C_{1-4}$ alkyl group" substituted by a hydroxy group and, for example, hydroxymethyl group, 1-hydroxyethyl group, 2-hydroxyethyl group, 3-hydroxypropyl group, 4-hydroxybutyl group and the like can be mentioned.

The "carboxy $C_{1-4}$ alkyl group" is the above-defined "$C_{1-4}$ alkyl group" substituted by a carboxy group and, for example, carboxymethyl group, 1-carboxyethyl group, 2-carboxyethyl group, 3-carboxypropyl group, 4-carboxybutyl group and the like can be mentioned.

The "$C_{6-12}$ aryl-$C_{1-14}$ alkyl group" is an aryl-alkyl group wherein the alkyl moiety is the above-defined "$C_{1-4}$ alkyl group", and the aryl moiety is the above-defined "$C_{6-12}$ aryl group" and, for example, benzyl group, 1-phenylethyl group, 2-phenylethyl group, 3-phenylpropyl group, 2-phenylpropyl group, 4-phenylbutyl group and the like can be mentioned.

The "heterocyclyl-$C_{1-4}$ alkyl group" is a heterocyclyl-alkyl group wherein the alkyl moiety is the above-defined "$C_{1-4}$ alkyl group" and the heterocyclyl moiety is the above-defined "heterocyclic group" and, for example, pyrrolidinylmethyl group (e.g., pyrrolidin-1-ylmethyl etc.), piperidinylmethyl group (e.g., piperidin-1-ylmethyl, piperidin-4-ylmethyl etc.), piperazinylmethyl group (e.g., piperazin-1-ylmethyl etc.), morpholinylmethyl group (e.g., morpholin-4-ylmethyl etc.), thiomorpholinylmethyl group and the like can be mentioned.

The "$C_{3-10}$ cycloalkyl-$C_{1-4}$ alkyl group" is a cycloalkyl-alkyl group wherein the alkyl moiety is the above-defined "$C_{1-4}$ alkyl group" and the cycloalkyl moiety is the above-defined "$C_{3-10}$ cycloalkyl group" and, for example, cyclopropylmethyl group, cyclobutylmethyl group, cyclopentylmethyl group, cyclohexylmethyl group, 2-cyclopropylethyl group and the like can be mentioned.

The "$C_{1-4}$ alkoxy group" is an alkyl-oxy group wherein the alkyl moiety is the above-defined "$C_{1-4}$ alkyl group" and, for example, methoxy group, ethoxy group, propoxy group, isopropyloxy group, butoxy group, isobutoxy group, tert-butoxy group and the like can be mentioned.

The "$C_{1-4}$ alkylamino group" is an alkyl-amino group wherein the alkyl moiety is the above-defined "$C_{1-4}$ alkyl group" and, for example, methylamino group, ethylamino group, propylamino group, isopropylamino group, butylamino group, isobutylamino group, sec-butylamino group, tert-butylamino group and the like can be mentioned.

The "di($C_{1-4}$ alkyl)amino group" is a dialkyl-amino group wherein the alkyl moiety is the above-defined "$C_{1-4}$ alkyl group" and, for example, dimethylamino group, diethylamino group, dipropylamino group, diisopropylamino group, dibutylamino group, diisobutylamino group, di-sec-butylamino group, di-tert-butylamino group, N-ethyl-N-methylamino group, N-methyl-N-propylamino group, N-butyl-N-methylamino group and the like can be mentioned.

The "$C_{1-4}$ alkoxy-carbonyl group" is an alkoxy-carbonyl group wherein the alkoxy moiety is the above-defined "$C_{1-4}$ alkoxy group" and, for example, methoxycarbonyl group, ethoxycarbonyl group, propoxycarbonyl group, isopropyloxycarbonyl group, butoxycarbonyl group, isobutyloxycarbonyl group, tert-butoxycarbonyl group and the like can be mentioned.

The "$C_{1-4}$ alkylamino-carbonyl group" is an alkylamino-carbonyl group wherein the alkylamino moiety is the above-defined "$C_{1-4}$ alkylamino group" and, for example, methylaminocarbonyl group, ethylaminocarbonyl group, propylaminocarbonyl group, isopropylaminocarbonyl group, butylaminocarbonyl group, isobutylaminocarbonyl group, sec-butylaminocarbonyl group, tert-butylaminocarbonyl, group and the like can be mentioned.

The "di($C_{1-4}$ alkyl)amino-carbonyl group" is a dialkylamino-carbonyl group wherein the dialkylamino moiety is the above-defined "di($C_{1-4}$ alkyl)amino group" and, for example, dimethylaminocarbonyl group, diethylaminocarbonyl group, dipropylaminocarbonyl group, diisopropylaminocarbonyl group, dibutylaminocarbonyl group, diisobutylaminocarbonyl group, di-sec-butylaminocarbonyl group, di-tert-butylaminocarbonyl group, N-ethyl-N-methylaminocarbonyl group, N-methyl-N-propylaminocarbonyl group, N-butyl-N-methylaminocarbonyl group and the like can be mentioned.

The "heterocyclyl-carbonyl group" is a heterocyclyl-carbonyl group wherein the heterocyclyl moiety is a ring constituting the above-defined "heterocyclic group" and, for example, pyrrolidinylcarbonyl group (e.g., pyrrolidin-1-ylcarbonyl etc.), piperidinylcarbonyl group (e.g., piperidin-1-ylcarbonyl etc.) and morpholinylcarbonyl group (e.g., morpholine-4-carbonyl etc.) can be mentioned.

The "tri($C_{1-4}$ alkyl)ammoniumyl group" is a trialkyl-ammoniumyl group (trialkyl-ammonio group) wherein the alkyl moiety is the above-defined "$C_{1-4}$ alkyl group" and, for example, trimethylammoniumyl group, triethylammoniumyl group, tripropylammoniumyl group, tributylammoniumyl group and the like can be mentioned.

The "$C_{1-4}$ alkoxy $C_{1-4}$ alkyl group" is the above-defined "$C_{1-4}$ alkyl group" substituted by the above-defined "$C_{1-4}$ alkoxy group" and, for example, methoxymethyl group, 1-methoxyethyl group, 2-methoxyethyl group, 3-methoxypropyl group, 4-methoxybutyl group, ethoxymethyl group, 2-ethoxyethyl group and the like can be mentioned.

The "carboxy $C_{1-4}$ alkoxy group" is the above-defined "$C_{1-4}$ alkoxy group" substituted by a carboxy group and, for example, carboxymethoxy group, 1-carboxyethoxy group, 2-carboxyethoxy group, 3-carboxypropoxy group, 4-carboxybutoxy group and the like can be mentioned.

The "a $C_{3-12}$ carbon ring group optionally substituted by 1 to 5 substituents selected from group A" is the above-defined "$C_{3-12}$ carbon ring group" optionally substituted by 1 to 5 substituents, and includes unsubstituted $C_{3-12}$ carbon ring group. The substituent is selected from group A.

Specifically, phenyl group, 4-methylphenyl group, 4-ethylphenyl group, 4-propylphenyl group, 4-isopropylphenyl group, 4-butylphenyl group, 4-isobutylphenyl group, 4-tert-butylphenyl group, 4-tert-pentylphenyl group, 4-neopentylphenyl group, 4-(1-ethylpropyl)phenyl group, 4-(1-propylbutyl)phenyl group, 2-trifluoromethylphenyl group, 3-trifluoromethylphenyl group, 4-trifluoromethylphenyl group, 4-(1,1-difluoroethyl)phenyl group, 4-(1,1-difluoropropyl)phenyl group, 4-pentafluoroethylphenyl group, 4-(1-cyano-1-methylethyl)phenyl group, 4-(hydroxymethyl)phenyl group, 4-(2-hydroxyethyl)phenyl group, 4-(3-hydroxypropyl)phenyl group, 4-(2-hydroxy-1,1-dimethylethyl)phenyl group, 4-(methoxymethyl)phenyl group, 4-(2-methoxy-1,1-dimethylethyl)phenyl group, 4-[difluoro(methoxy)methyl]phenyl group, 4-(2-methoxycarbonylethyl)phenyl group, 4-(1-methoxycarbonyl-1-methylethyl) phenyl group, 4-(1-carboxy-1-methylethyl)phenyl group, 4-(1-dimethylcarbamoyl-1-methylethyl)phenyl group, 2-fluorophenyl group, 3-fluorophenyl group, 4-fluorophenyl group, 2-chlorophenyl group, 3-chlorophenyl group, 4-chlorophenyl group, 3-bromophenyl group, 4-bromophenyl group, 4-iodophenyl group, 4-nitrophenyl group, 4-cyanophenyl group, 2-hydroxyphenyl group, 3-hydroxyphenyl group, 4-hydroxyphenyl group, 2-methoxyphenyl group, 3-methoxyphenyl group, 4-methoxyphenyl group, 4-ethoxyphenyl group, 4-propoxyphenyl group, 4-isopropoxyphenyl group, 4-fluoromethoxyphenyl group, 4-difluoromethoxyphenyl group, 3-trifluoromethoxyphenyl group, 4-trifluoromethoxyphenyl group, 4-(2,2,2-trifluoroethoxy)phenyl group, 4-(1,1,2,2-tetrafluoroethoxy)phenyl group, 3-carboxymethoxyphenyl group, 4-carboxymethoxyphenyl group, 4-methoxycarbonylmethoxyphenyl group, 4-(2-methoxycarbonylethoxy)phenyl group, 4-phenoxyphenyl group, 3-ethoxycarbonylmethoxyphenyl group, 4-ethoxycarbonylmethoxyphenyl group, 2-benzyloxyphenyl group, 4-methylsulfanylphenyl group, 4-trifluoromethylsulfanylphenyl group, 4-(4-chlorophenoxy)phenyl group, 4-(pyridin-3-yloxy)phenyl group, 4-aminophenyl group, 2-dimethylaminophenyl group, 3-dimethylaminophenyl group, 4-dimethylaminophenyl group, 4-diethylaminophenyl group, 4-(N-ethyl-N-methylamino)phenyl group, 4-(N-methyl-N-propylamino)phenyl group, 4-[N-(2-hydroxyethyl)-N- methylamino]phenyl group, 4-(N-carboxymethyl-N-methylamino)phenyl group, 4-(N-ethoxycarbonylmethyl-N-methylamino)phenyl group, 4-acetylaminophenyl group, 4-(2,2-dimethylpropionylamino)phenyl group, 2-carboxyphenyl group, 3-carboxyphenyl group, 4-carboxyphenyl group, 2-methoxycarbonylphenyl group, 4-methoxycarbonylphenyl group, 2-benzyloxycarbonylphenyl group, 4-sulfamoylphenyl group, 4-acetylphenyl group, 4-pentafluorosulfanylphenyl group, 4-cyclopropylphenyl group, 4-cyclohexylphenyl group, 4-(1-hydroxymethylcyclopropyl) phenyl group, 4-(1-methoxymethylcyclopropyl)phenyl group, 4-(4-carboxymethylcyclohexyl)phenyl group, 4-cyclopentylphenyl group, biphenyl-2-yl group, biphenyl-3-yl group, biphenyl-4-yl group, 2'-chlorobiphenyl-4-yl group, 3'-chlorobiphenyl-4-yl group, 4'-chlorobiphenyl-4-yl group, 2'-hydroxybiphenyl-4-yl group, 3'-hydroxybiphenyl-4-yl group, 2'-carboxymethoxybiphenyl-4-yl group, 3'-carboxymethoxybiphenyl-4-yl group, 3'-carboxybiphenyl-4-yl group, 4-(azetidin-1-yl)phenyl group, 4-cyclopropylmethylphenyl group, 4-(pyrrolidin-1-yl)phenyl group, 4-(2-oxopyrrolidin-1-yl)phenyl group, 4-(piperidin-1-yl)phenyl group, 4-(morpholin-4-yl)phenyl group, 4-(4-methylpiperazin-1-yl)phenyl group, 4-(1-methyl-1H-pyrazol-4-yl)phenyl group, 4-(furan-3-yl)phenyl group, 4-(1,2,3-thiadiazol-4-yl)phenyl group, 4-(thiophen-2-yl)phenyl group, 4-(5-oxo-2,5-dihydro-1,2,4-oxadiazol-3-yl)phenyl group, 4-ethyl-2-methylphenyl group, 2-methyl-4-propylphenyl group, 4-isopropyl-2-methylphenyl group, 4-cyclopropyl-2-methylphenyl group, 3,4-dichlorophenyl group, 2,4-dichlorophenyl group, 3,5-dichlorophenyl group, 4-bromo-2-chlorophenyl group, 2-chloro-4-propylphenyl group, 2-fluoro-4-isopropylphenyl group, 2,4-dimethoxyphenyl group, 3,4-dimethoxyphenyl group, 4-bromo-2-fluorophenyl group, 4-bromo-3-fluorophenyl group, 3-ethyl-4-methoxyphenyl group, 3-isopropyl-4-methoxyphenyl group, 3-tert-butyl-4-methoxyphenyl group, 3-chloro-4-methoxyphenyl group, 2-fluoro-4-trifluoromethoxyphenyl group, 3-fluoro-4-trifluoromethoxyphenyl group, 3-iodo-4-trifluoromethoxyphenyl group, 3-propyl-4-trifluoromethoxyphenyl group, 3-(2-carboxyethyl)-4-trifluoromethoxyphenyl group, 3-(3-carboxypropyl)-4-trifluoromethoxyphenyl group, 3-carboxy-4-methoxyphenyl group, 3-carboxy-4-trifluoromethoxyphenyl group, 4-methoxy-3-methoxycarbonylphenyl group, 4-methoxy-3-methoxycarbonylmethylphenyl group, 4-methoxy-3-(2-methoxycarbonylethyl)phenyl group, 3-carboxymethyl-4-methoxyphenyl group, 3-(2-carboxyethyl)-4-methoxyphenyl group, 3-cyano-4-methoxyphenyl group, 3-cyclopentyl-4-methoxyphenyl group, 4-methoxy-3-(2H-tetrazol-5-yl)phenyl group, 3-hydroxy-4-propylphenyl group, 3-amino-4-propylphenyl group, 3-hydroxy-4-methoxyphenyl group, 4-difluoromethoxy-2-fluorophenyl group, 4-difluoromethoxy-3-fluorophenyl group, 4-carboxy-3-fluorophenyl group, 2-(4-cyanophenoxy)-3,5-dimethylphenyl group, 2,4,6-trichlorophenyl group, 2,3,5,6-tetrafluoro-4-trifluoromethylphenyl group, cyclohexyl group, 1-hydroxycyclohexyl group, 4-carboxycyclohexyl group, 2-phenylcyclopropyl group, 3-phenylcyclobutyl group, adamantan-1-yl group, indan-5-yl group, 5,6,7,8-tetrahydronaphthalen-2-yl group, 6,7,8,9-tetrahydro-5H-benzocyclohepten-2-yl group, 7-carboxymethyl-6,7,8,9-tetrahydro-5H-benzocyclohepten-2-yl group, naphthalen-2-yl group and the like can be mentioned.

The "heterocyclic group optionally substituted by 1 to 5 substituents selected from group A" is the above-defined "heterocyclic group" optionally substituted by 1 to 5 substituents and includes unsubstituted heterocyclic group. The substituent is selected from group A.

Specifically, pyridin-2-yl group, pyridin-3-yl group, pyridin-4-yl group, 6-propylpyridin-3-yl group, 6-isopropylpyridin-3-yl group, 6-trifluoromethylpyridin-3-yl group, 6-dimethylaminopyridin-3-yl group, 6-(azetidin-1-yl)pyridin-3-yl group, 6-(pyrrolidin-1-yl)pyridin-3-yl group, 6-(morpholin-4-yl)pyridin-3-yl group, 5-bromo-6-chloropyridin-3-yl group, 6-methoxy-5-methylpyridin-2-yl group, 2-oxo-1-propyl-1,2-dihydropyridin-4-yl group, 2-oxo-6-propyl-1,2-dihydropyridin-3-yl group, 1-propyl-1,2,3,6-tetrahydropyridin-4-yl group, 5-methylpyrazin-2-yl group, 1H-indol-3-yl group, 1-propyl-1H-pyrazol-4-yl group, 1H-imidazol-4-yl group, 5-phenylthiophen-2-yl group, 5-(pyridin-2-yl)thiophen-2-yl group, 2,2'-bithiophenyl-5-yl group, 4-methyl-2-propylthiazol-5-yl group, 2-(thiophen-2-yl)thiazol-4-yl group, 1-phenylazetidin-3-yl group, piperidin-1-yl group, piperidin-4-yl group, 1-propylpiperidin-4-yl group, 1-tert-butoxycarbonylpiperidin-4-yl group, 1-acetylpiperidin-4-yl group, morpholin-4-yl group, benzoxazol-2-yl group, indolizin-2-yl group, 5-ethylthiophen-2-yl group, 5-propylthiophen-2-yl group, 5-isopropylthiophen-2-yl group, 5-trifluoromethylthiophen-2-yl group, 5-chlorothiophen-2-yl group, 5-bromothiophen-2-yl group, 5-carboxymethylthiophen-2-yl group, 5-(2-carboxyethyl)thiophen-2-yl group, 5-benzenesulfonylthiophen-2-yl group, 5-(4-chlorophenyl) thiophen-2-yl group, 5-(5-trifluoromethylisoxazol-3-yl) thiophen-2-yl group, 5-(4-chloropyrazol-1-yl)thiophen-2-yl group, 2,3-dihydrobenzofuran-5-yl group, benzothiophen-2-yl group, 2,2,3,3-tetrafluoro-2,3-dihydro-benzo[1,4]dioxin-6-yl group, 1-methyl-1,2,3,4-tetrahydroquinolin-7-yl group, 2-propylthiazol-5-yl group, 4-methylthiazol-2-yl group, 4-hydroxymethylthiazol-2-yl group, 5-hydroxymethylthiazol-2-yl group, 4-carboxymethylthiazol-2-yl group, 4-methoxycarbonylmethylthiazol-2-yl group, 4-(2-carboxyethyl)thiazol-2-yl group, 4-carboxythiazol-2-yl group, 5-carboxythiazol-2-yl group, 5-methoxycarbonylthiazol-2-yl group, 4-ethoxycarbonylthiazol-2-yl group, 4-phenylthiazol-2-yl group, 5-carboxy-4-methylthiazol-2-yl group, 4-carboxy-5-methylthiazol-2-yl group, 4-ethyl-5-carboxythiazol-2-yl group, 5-carboxy-4-trifluoromethylthiazol-2-yl group, 5-hydroxymethyl-4-methylthiazol-2-yl group, 5-methoxycarbonyl-4-methylthiazol-2-yl group, 5-tert-butoxycarbonyl-4-methylthiazol-2-yl group, 5-ethoxycarbonyl-4-trifluoromethylthiazol-2-yl group, 5-methylaminomethyl-4-methylthiazol-2-yl group, 5-dimethylaminomethyl-4-methylthiazol-2-yl group, 5-carbamoyl-4-methylthiazol-2-yl group, 5-methylcarbamoyl-4-methylthiazol-2-yl group, 5-dimethylcarbamoyl-4-methylthiazol-2-yl group, 5-carboxymethylcarbamoyl-4-methylthiazol-2-yl group, 5-tert-butoxycarbonylmethylcarbamoyl-4-methylthiazol-2-yl group, 5-(2-tert-butoxycarbonylethyl)carbamoyl-4-methylthiazol-2-yl group, 5-(2-carboxyethyl)carbamoyl-4-methylthiazol-2-yl group, 5-((R)-1-carboxyethyl)carbamoyl-4-methylthiazol-2-yl group, 5-((S)-1-carboxyethyl)carbamoyl-4-methylthiazol-2-yl group, 5-carboxy-4-methoxymethylthiazol-2-yl group, 5-methanesulfonylaminocarbonyl-4-methylthiazol-2-yl group, 5-(2-carboxyethyl)-4-methylthiazol-2-yl group, 5-(carboxy)(hydroxy)methyl-4-methylthiazol-2-yl group, 5-(ethoxycarbonyl)(hydroxy)methyl-4-methylthiazol-2-yl group, 5-cyano-4-methylthiazol-2-yl group, 4-methyl-5-sulfamoylthiazol-2-yl group, 4-methyl-5-methylsulfamoylthiazol-2-yl group, 5-dimethylsulfamoyl-4-methylthiazol-2-yl group, 5-acetylsulfamoyl-4-methylthiazol-2-yl group, 5-acetyl-4-methylthiazol-2-yl group, 5-carboxycarbonyl-4-methylthiazol-2-yl group, 5-ethoxycarbonylcarbonyl-4-methylthiazol-2-yl group, 5-methylcarbamoylcarbonyl-4-methylthiazol-2-yl group, 4-methyl-5-(1H-tetrazol-5-yl)thiazol- 2-yl group, 4-methyl-5-(pyrrolidin-1-ylmethyl)thiazol-2-yl group, 4,5-bis(hydroxymethyl)thiazol-2-yl group, 4-carboxy-5-hydroxymethylthiazol-2-yl group, 5-carboxy-4-hydroxymethylthiazol-2-yl group, 4-carboxy-5-methoxymethylthiazol-2-yl group, 5-carboxy-4-methoxymethylthiazol-2-yl group, 5-carboxy-4-chlorothiazol-2-yl group, 4-amino-5-ethoxycarbonylthiazol-2-yl group, pyrazin-2-yl group, 5-cyanopyrazin-2-yl group, 5-hydroxymethylpyrazin-2-yl group, 5-dimethylaminomethylpyrazin-2-yl group, 5-(triethylammoniumylmethyl)pyrazin-2-yl group, 5-methoxycarbonylpyrazin-2-yl group, 5-aminopyrazin-2-yl group, 5-methanesulfonylaminopyrazin-2-yl group, 5-carboxypyrazin-2-yl group, 5-carbamoylpyrazin-2-yl group, 5-ethylcarbamoylpyrazin-2-yl group, 5-tert-butylcarbamoylpyrazin-2-yl group, 5-(1H-tetrazol-5-yl)pyrazin-2-yl group, 5-(pyrrolidin-1-ylmethyl)pyrazin-2-yl group, 5-(morpholin-4-ylmethyl)pyrazin-2-yl group, 5-(4-methylpiperazin-1-ylmethyl)pyrazin-2-yl group, 5-methoxycarbonyl-3-methylpyrazin-2-yl group, 5-carboxy-6-methylpyrazin-2-yl group, 6-amino-5-hydroxymethylpyrazin-2-yl group, 6-amino-5-aminomethylpyrazin-2-yl group, 6-amino-5-carboxypyrazin-2-yl group, 6-amino-5-methoxycarbonylpyrazin-2-yl group, 6-acetylamino-5-methoxycarbonylpyrazin-2-yl group, 3,6-dimethyl-5-carboxypyrazin-2-yl group, 6-bromo-3-chloro-5-methoxycarbonylpyrazin-2-yl group, 6-amino-3-chloro-5-methoxycarbonylpyrazin-2-yl group, 5-aminopyridin-2-yl group, 5-carboxypyridin-2-yl group, 4-carboxypyridin-2-yl group, 5-methoxycarbonylpyridin-2-yl group, 5-tert-butoxycarbonylpyridin-2-yl group, 5-carboxy-6-methylpyridin-2-yl group, 5-carboxy-3-fluoro-6-methylpyridin-2-yl group, 6-carboxypyridin-3-yl group, 6-oxo-1,6-dihydropyridin-3-yl group, 5-carboxypyrimidin-2-yl group, 5-ethoxycarbonyl-4-hydroxypyrimidin-2-yl group, 5-carboxy-4-hydroxypyrimidin-2-yl group, 5-methoxycarbonyl-4-methylpyrimidin-2-yl group, 5-carboxy-4-methylpyrimidin-2-yl group, 5-benzyloxycarbonyl-4-methylpyrimidin-2-yl group, 4-aminopyrimidin-2-yl group, 6-chloropyrimidin-4-yl group, 2-hydroxypyrimidin-4-yl group, 2-aminopyrimidin-4-yl group, 6-aminopyrimidin-4-yl group, 6-hydroxypyridazin-3-yl group, 6-carboxypyridazin-3-yl group, 6-carbamoylpyridazin-3-yl group, 5-methyl-6-hydroxypyridazin-3-yl group, 6-carboxy-5-methylpyridazin-3-yl group, 6-methoxycarbonyl-5-methylpyridazin-3-yl group, 6-carbamoyl-5-methylpyridazin-3-yl group, 1-methyl-1H-pyrazol-3-yl group, 5-methyl-1H-pyrazol-3-yl group, 5-carboxy-1H-pyrazol-3-yl group, 1-carboxymethyl-5-methyl-1H-pyrazol-3-yl group, 5-carboxy-1-methyl-1H-pyrazol-3-yl group, 5-carboxy-2-methyl-2H-pyrazol-3-yl group, 4-chloro-5-carboxy-1H-pyrazol-3-yl group, 1H-imidazol-2-yl group, 1-methyl-1H-imidazol-2-yl group, 4-methyl-5-carboxyoxazol-2-yl group, 1,2,4-triazol-3-yl group, 1,2,4-triazol-4-yl group, 5-bromo-1,2,4-triazol-3-yl group, 5-nitro-1,2,4-triazol-3-yl group, 5-amino-1,2,4-triazol-3-yl group, 3-amino-1,2,4-triazol-1-yl group, 5-amino-3-methyl-1,2,4-triazol-1-yl group, benzothiazol-2-yl group, 4-carboxybenzothiazol-2-yl group, 8H-indeno[1,2-d]thiazol-2-yl group, 2-imidazolin-2-yl group, 2-thiazolin-2-yl group, 4-oxo-4,5-dihydrothiazol-2-yl group, 2-oxazolin-2-yl group, 2,5-dioxopyrrolidin-3-yl group, 4-phenyl-2,5-dioxo-3-pyrrolin-3-yl group, 2-oxopyrrolidin-3-yl group, 3-carboxyazetidin-1-yl group, 4-carboxypiperidin-1-yl group, 6-oxopiperidin-3-yl group, 5-oxo-4,5-dihydro-1,3,4-thiadiazol-2-yl group, 4,5,6,7-tetrahydrobenzothiazol-2-yl group, 5-methylisoxazol-3-yl group, 1H-imidazol-1-yl group, 1-methyl-1H-imidazol-4-yl group, 1,2,3-triazol-1-yl group, 1,2,4-triazol-1-yl group, 1,3,4-triazol-1-yl group, 1,2,3-triazol-2-yl group, pyrazol-1-yl group, tetrazol-1-yl group, 1H-tetrazol-5-yl group, 2H-tetrazol-5-yl group, tetrazol-2-yl group, 5-methyltetrazol-1-yl group, 5-methyltetrazol-2-yl group, 1-methyltetrazol-5-yl group, 2-methyltetrazol-5-yl group, 5-isopropyltetrazol-1-yl group, 5-isopropyltetrazol-2-yl group, 5-carboxymethyltetrazol-1-yl group, 5-carboxymethyltetrazol-2-yl group, 5-ethoxycarbonylmethyltetrazol-1-yl group, 5-ethoxycarbonylmethyltetrazol-2-yl group, 1-ethoxycarbonylmethyltetrazol-5-yl group, 2-ethoxycarbonylmethyltetrazol-5-yl group, 5-[2-(morpholin-4-yl)-2-oxoethyl]tetrazol-2-yl group, 5-aminotetrazol-1-yl group, 5-aminotetrazol-2-yl group, 5-phenyltetrazol-2-yl group, 3-methylisoxazol-5-yl group, 4-methylpiperazin-1-yl group, 2-trifluoromethylpyridin-4-yl group, 2-hydroxymethylpyridin-4-yl group, 2-carboxypyridin-4-yl group, 2-carbamoylpyridin-4-yl group, 2-dimethylcarbamoylpyridin-4-yl group, 2-(cyclopropylcarbamoyl)pyridin-4-yl group, 2-(morpholine-4-carbonyl)pyridin-4-yl group, 2-(pyrrolidine-1-carbonyl)pyridin-4-yl group, 2-chloropyridin-4-yl group, 2-methoxypyridin-4-yl group, 2-tert-butoxycarbonylpyridin-4-yl group, pyrimidin-4-yl group, thiazol-2-yl group, thiazol-4-yl group, thiazol-5-yl group, 2-methylthiazol-4-yl group, 4-(1-hydroxy-1-methylethyl)thiazol-2-yl group, 4-ethoxycarbonylmethylthiazol-2-yl group, 4-[2-(morpholin-4-yl)-2-oxoethyl]thiazol-2-yl group, 3-methylisothiazol-5-yl group, 1,3,4-thiadiazol-2-yl group, 5-methyl-1,3,4-thiadiazol-2-yl group, 5-bromo-1,3,4-thiadiazol-2-yl group, 5-ethoxycarbonyl-1,3,4-thiadiazol-2-yl group, 5-trifluoromethyl-1,3,4-thiadiazol-2-yl group, 5-hydroxymethyl-1,3,4-thiadiazol-2-yl group, 5-(1-hydroxy-1-methylethyl)-1,3,4-thiadiazol-2-yl group, 5-((R)-3-hydroxypyrrolidine-1-carbonyl)-1,3,4-thiadiazol-2-yl group, 5-(4-hydroxypiperidine-1-carbonyl)-1,3,4-thiadiazol-2-yl group, 5-(morpholine-4-carbonyl)-1,3,4-thiadiazol-2-yl group, 5-acetyl-1,3,4-thiadiazol-2-yl group, 1,3,4-oxadiazol-2-yl group, 3-methyl-1,2,4-thiadiazol-5-yl group, 3-methoxy-1,2,4-thiadiazol-5-yl group, 3-acetylamino-1,2,4-thiadiazol-5-yl group, 5-ethoxycarbonyl-1,3,4-oxadiazol-2-yl group, 5-tert-butoxycarbonylthiophen-2-yl group,
1H-benzimidazol-2-yl group,
quinoxalin-2-yl group,
quinoxalin-6-yl group,
5-chloroquinoxalin-2-yl group,
6-chloroquinoxalin-2-yl group,
8-chloroquinoxalin-2-yl group,
6-bromoquinoxalin-2-yl group,
7-bromoquinoxalin-2-yl group,
5-carboxyquinoxalin-2-yl group,
6-carboxyquinoxalin-2-yl group,
7-carboxyquinoxalin-2-yl group,
8-carboxyquinoxalin-2-yl group,
6-ethoxycarbonylquinoxalin-2-yl group,
7-ethoxycarbonylquinoxalin-2-yl group,
1,5-naphthyridin-2-yl group,
1,6-naphthyridin-2-yl group,
thiazolo[5,4-c]pyridin-2-yl group,
6-carboxy-thiazolo[5,4-c]pyridin-2-yl group,
7-carboxy-thiazolo[5,4-c]pyridin-2-yl group,
7-ethoxycarbonyl-thiazolo[5,4-c]pyridin-2-yl group,
6-tert-butoxycarbonyl-thiazolo[5,4-c]pyridin-2-yl group,
4-oxo-4,5-dihydrothiazolo[5,4-c]pyridin-2-yl group,
4,5,6,7-tetrahydrothiazolo[5,4-c]pyridin-2-yl group,
5-methyl-4,5,6,7-tetrahydrothiazolo[5,4-c]pyridin-2-yl group,
5-benzyl-4,5,6,7-tetrahydrothiazolo[5,4-c]pyridin-2-yl group,
5-tert-butoxycarbonyl-4,5,6,7-tetrahydrothiazolo[5,4-c]pyridin-2-yl group, 5-benzyloxycarbonyl-4,5,6,7-tetrahydrothiazolo[5,4-c]pyridin-2-yl group,
5-ethylcarbamoyl-4,5,6,7-tetrahydrothiazolo[5,4-c]pyridin-2-yl group,
5-acetyl-4,5,6,7-tetrahydrothiazolo[5,4-c]pyridin-2-yl group,
5-methanesulfonyl-4,5,6,7-tetrahydrothiazolo[5,4-c]pyridin-2-yl group,
4-oxo-4,5,6,7-tetrahydrothiazolo[5,4-c]pyridin-2-yl group,
thiazolo[5,4-b]pyridin-2-yl group,
5-methoxy-thiazolo[5,4-b]pyridin-2-yl group,
5-oxo-4,5-dihydrothiazolo[5,4-b]pyridin-2-yl group,
thiazolo[4,5-b]pyrazin-2-yl group,
thiazolo[4,5-d]pyrimidin-2-yl group,
5-methyl-thiazolo[4,5-d]pyrimidin-2-yl group,
5-ethyl-thiazolo[4,5-d]pyrimidin-2-yl group,
5-isopropyl-thiazolo[4,5-d]pyrimidin-2-yl group,
5-tert-butyl-thiazolo[4,5-d]pyrimidin-2-yl group,
5-trifluoromethyl-thiazolo[4,5-d]pyrimidin-2-yl group,
5-hydroxymethyl-thiazolo[4,5-d]pyrimidin-2-yl group,
5-(1-hydroxyethyl)-thiazolo[4,5-d]pyrimidin-2-yl group,
5-(2-hydroxyethyl)-thiazolo[4,5-d]pyrimidin-2-yl group,
5-(1-hydroxy-1-methylethyl)-thiazolo[4,5-d]pyrimidin-2-yl group,
5-methoxymethyl-thiazolo[4,5-d]pyrimidin-2-yl group,
5-(2-methoxyethyl)-thiazolo[4,5-d]pyrimidin-2-yl group,
5-ethynyl-thiazolo[4,5-d]pyrimidin-2-yl group,
5-(3-hydroxy-3-methyl-but-1-ynyl)-thiazolo[4,5-d]pyrimidin-2-yl group,
5-fluoro-thiazolo[4,5-d]pyrimidin-2-yl group,
5-chloro-thiazolo[4,5-d]pyrimidin-2-yl group,
5-bromo-thiazolo[4,5-d]pyrimidin-2-yl group,
5-cyano-thiazolo[4,5-d]pyrimidin-2-yl group,
5-hydroxy-thiazolo[4,5-d]pyrimidin-2-yl group,
5-methoxy-thiazolo[4,5-d]pyrimidin-2-yl group,
5-difluoromethoxy-thiazolo[4,5-d]pyrimidin-2-yl group,
5-amino-thiazolo[4,5-d]pyrimidin-2-yl group,
5-methylamino-thiazolo[4,5-d]pyrimidin-2-yl group,
5-isopropylamino-thiazolo[4,5-d]pyrimidin-2-yl group,
5-dimethylamino-thiazolo[4,5-d]pyrimidin-2-yl group,
5-(2-hydroxyethylamino)-thiazolo[4,5-d]pyrimidin-2-yl group,
5-carboxy-thiazolo[4,5-d]pyrimidin-2-yl group,
5-ethoxycarbonyl-thiazolo[4,5-d]pyrimidin-2-yl group,
5-carbamoyl-thiazolo[4,5-d]pyrimidin-2-yl group,
5-methylcarbamoyl-thiazolo[4,5-d]pyrimidin-2-yl group,
5-dimethylcarbamoyl-thiazolo[4,5-d]pyrimidin-2-yl group,
5-(N-methoxy-N-methylcarbamoyl)-thiazolo[4,5-d]pyrimidin-2-yl group,
5-acetyl-thiazolo[4,5-d]pyrimidin-2-yl group,
5-cyclopropyl-thiazolo[4,5-d]pyrimidin-2-yl group,
5-cyclobutyl-thiazolo[4,5-d]pyrimidin-2-yl group,
5-(1-hydroxymethylcyclopropyl)-thiazolo[4,5-d]pyrimidin-2-yl group,
5-(1-methoxymethylcyclopropyl)-thiazolo[4,5-d]pyrimidin-2-yl group,
5-(1-hydroxycyclopropyl)-thiazolo[4,5-d]pyrimidin-2-yl group,
5-(1-methoxycyclopropyl)-thiazolo[4,5-d]pyrimidin-2-yl group,
5-(pyrrolidin-1-ylmethyl)-thiazolo[4,5-d]pyrimidin-2-yl group,
cyclopropylmethyl-thiazolo[4,5-d]pyrimidin-2-yl group,
5,7-dichloro-thiazolo[4,5-d]pyrimidin-2-yl group,
7-chloro-5-methyl-thiazolo[4,5-d]pyrimidin-2-yl group,
5-bromo-7-diethylamino-thiazolo[4,5-d]pyrimidin-2-yl group,
5,7-dihydroxy-thiazolo[4,5-d]pyrimidin-2-yl group,
7-methoxy-5-trifluoromethyl-thiazolo[4,5-d]pyrimidin-2-yl group,
7-amino-5-chloro-thiazolo[4,5-d]pyrimidin-2-yl group,
7-amino-5-methyl-thiazolo[4,5-d]pyrimidin-2-yl group,
7-amino-5-trifluoromethyl-thiazolo[4,5-d]pyrimidin-2-yl group,
7-amino-5-(1-hydroxy-1-methylethyl)-thiazolo[4,5-d]pyrimidin-2-yl group,
7-amino-5-methoxymethyl-thiazolo[4,5-d]pyrimidin-2-yl group,
7-amino-5-cyclopropyl-thiazolo[4,5-d]pyrimidin-2-yl group,
7-carbamoyl-5-methyl-thiazolo[4,5-d]pyrimidin-2-yl group,
5-chloro-2-diethylamino-thiazolo[4,5-d]pyrimidin-7-yl group,
7-oxo-6,7-dihydrothiazolo[4,5-d]pyrimidin-2-yl group,
5-methyl-7-oxo-6,7-dihydrothiazolo[4,5-d]pyrimidin-2-yl group,
7-oxo-5-trifluoromethyl-6,7-dihydrothiazolo[4,5-d]pyrimidin-2-yl group,
5-chloro-7-oxo-6,7-dihydrothiazolo[4,5-d]pyrimidin-2-yl group,
thiazolo[5,4-d]pyrimidin-2-yl group,
5-methyl-thiazolo[5,4-d]pyrimidin-2-yl group,
thiazolo[4,5-d]pyridazin-2-yl group,
4-methyl-thiazolo[4,5-d]pyridazin-2-yl group,
4-hydroxymethyl-thiazolo[4,5-d]pyridazin-2-yl group,
4-chloro-thiazolo[4,5-d]pyridazin-2-yl group,
7-chloro-thiazolo[4,5-d]pyridazin-2-yl group,
4-methoxy-thiazolo[4,5-d]pyridazin-2-yl group,
7-methoxy-thiazolo[4,5-d]pyridazin-2-yl group,
4-carboxy-thiazolo[4,5-d]pyridazin-2-yl group,
4-ethoxycarbonyl-thiazolo[4,5-d]pyridazin-2-yl group,
4-carbamoyl-thiazolo[4,5-d]pyridazin-2-yl group,
4-methylcarbamoyl-thiazolo[4,5-d]pyridazin-2-yl group,
4-dimethylcarbamoyl-thiazolo[4,5-d]pyridazin-2-yl group,
7-chloro-4-methyl-thiazolo[4,5-d]pyridazin-2-yl group,
7-chloro-4-ethoxycarbonyl-thiazolo[4,5-d]pyridazin-2-yl group,
4-oxo-4,5-dihydrothiazolo[4,5-d]pyridazin-2-yl group,
5-methyl-4-oxo-4,5-dihydrothiazolo[4,5-d]pyridazin-2-yl group,
5-ethyl-4-oxo-4,5-dihydrothiazolo[4,5-d]pyridazin-2-yl group,
5-(2-hydroxyethyl)-4-oxo-4,5-dihydrothiazolo[4,5-d]pyridazin-2-yl group,
5-(2-methoxyethyl)-4-oxo-4,5-dihydrothiazolo[4,5-d]pyridazin-2-yl group,
7-oxo-6,7-dihydrothiazolo[4,5-d]pyridazin-2-yl group,
4-methyl-7-oxo-6,7-dihydrothiazolo[4,5-d]pyridazin-2-yl group,
6-methyl-7-oxo-6,7-dihydrothiazolo[4,5-d]pyridazin-2-yl group,
4-hydroxymethyl-7-oxo-6,7-dihydrothiazolo[4,5-d]pyridazin-2-yl group,
4-carboxy-7-oxo-6,7-dihydrothiazolo[4,5-d]pyridazin-2-yl group,
4-ethoxycarbonyl-7-oxo-6,7-dihydrothiazolo[4,5-d]pyridazin-2-yl group,
4-carbamoyl-7-oxo-6,7-dihydrothiazolo[4,5-d]pyridazin-2-yl group, 4-methylcarbamoyl-7-oxo-6,7-dihydrothiazolo[4,5-d]pyridazin-2-yl group,
4,7-dioxo-4,5,6,7-tetrahydrothiazolo[4,5-d]pyridazin-2-yl group,
thiazolo[4,5-d][1,2,3]triazin-6-yl group,
4-methoxy-thiazolo[4,5-d][1,2,3]triazin-6-yl group, 4-amino-thiazolo[4,5-d][1,2,3]triazin-6-yl group,
4-(2-hydroxyethylamino)-thiazolo[4,5-d][1,2,3]triazin-6-yl group,
4-oxo-3,4-dihydrothiazolo[4,5-d][1,2,3]triazin-6-yl group,
4,6-dioxo-5,6-dihydro-4H-pyrrolo[3,4-d]thiazol-2-yl group,
1,3-dimethyl-1H-pyrazolo[3,4-d]thiazol-5-yl group,
7-methyl-5-oxo-5H-[1,3,4]thiadiazolo[3,2-a]pyrimidin-2-yl group,
5-oxo-7-trifluoromethyl-5H-[1,3,4]thiadiazolo[3,2-a]pyrimidin-2-yl group,
7-oxo-7H-[1,3,4]thiadiazolo[3,2-a]pyrimidin-2-yl group,
5-methyl-7-oxo-7H-[1,3,4]thiadiazolo[3,2-a]pyrimidin-2-yl group,
5-isopropyl-7-oxo-7H-[1,3,4]thiadiazolo[3,2-a]pyrimidin-2-yl group,
7-oxo-5-trifluoromethyl-7H-[1,3,4]thiadiazolo[3,2-a]pyrimidin-2-yl group,
5-ethoxycarbonyl-7-oxo-7H-[1,3,4]thiadiazolo[3,2-a]pyrimidin-2-yl group,
5-methylcarbamoyl-7-oxo-7H-[1,3,4]thiadiazolo[3,2-a]pyrimidin-2-yl group,
6-chloro-5-methyl-7-oxo-7H-[1,3,4]thiadiazolo[3,2-a]pyrimidin-2-yl group,
3-methyl-4-oxo-4H-[1,3,4]thiadiazolo[2,3-c][1,2,4]triazin-7-yl group,
4-oxo-3-trifluoromethyl-4H-[1,3,4]thiadiazolo[2,3-c][1,2,4]triazin-7-yl group,
[1,2,4]triazolo[3,4-b][1,3,4]thiadiazol-6-yl group,
3-methyl-[1,2,4]triazolo[3,4-b][1,3,4]thiadiazol-6-yl group,
3-trifluoromethyl-[1,2,4]triazolo[3,4-b][1,3,4]thiadiazol-6-yl group,
3H-imidazo[4,5-c]pyridin-2-yl group,
pteridin-7-yl group,
pteridin-6-yl group,
2-methylpteridin-7-yl group,
2-trifluoromethylpteridin-7-yl group,
pyrido[3,4-b]pyrazin-2-yl group,
8-(2-carboxyethyl)-pyrido[3,4-b]pyrazin-2-yl group,
8-(2-carbamoylethyl)-pyrido[3,4-b]pyrazin-2-yl group,
8-bromo-pyrido[3,4-b]pyrazin-2-yl group,
8-cyano-pyrido[3,4-b]pyrazin-2-yl group,
8-carboxy-pyrido[3,4-b]pyrazin-2-yl group,
8-carbamoyl-pyrido[3,4-b]pyrazin-2-yl group,
8-methylcarbamoyl-pyrido[3,4-b]pyrazin-2-yl group,
8-isopropylcarbamoyl-pyrido[3,4-b]pyrazin-2-yl group,
8-dimethylcarbamoyl-pyrido[3,4-b]pyrazin-2-yl group,
pyrido[2,3-b]pyrazin-2-yl group,
pyrido[2,3-b]pyrazin-3-yl group,
pyrido[2,3-b]pyrazin-6-yl group,
pyrazino[2,3-b]pyrazin-2-yl group,
2-oxo-1,4-dihydro-2H-pyrazino[2,3-d][1,3]oxazin-7-yl group,
2,2-dioxo-1,2,3,4-tetrahydro-2$\lambda^6$-pyrazino[2,3-c][1,2,6]thiadiazin-7-yl group,
1H-imidazo[4,5-b]pyrazin-5-yl group,
2-oxo-2,3-dihydro-1H-imidazo[4,5-b]pyrazin-5-yl group,
6-hydroxy-[1,2,5]thiadiazolo[3,4-b]pyrazin-5-yl group,
[1,2,4]triazolo[1,5-a]pyrimidin-5-yl group
and the like can be mentioned.

The "$C_{1-10}$ alkyl group optionally substituted by 1 to 5 substituents selected from group B" is the above-defined "$C_{1-10}$ alkyl group" optionally substituted by 1 to 5 substituents and includes an unsubstituted $C_{1-10}$ alkyl group. The substituent is selected from group B.

Specifically, methyl group, ethyl group, propyl group, isopropyl group, tert-butyl group, 1-ethylpropyl group, 1-propylbutyl group, tert-pentyl group, neopentyl group, fluoromethyl group, difluoromethyl group, trifluoromethyl group, 1,1-difluoroethyl group, 1,1-difluoropropyl group, 2,2,2-trifluoroethyl group, 1,1,2,2-tetrafluoroethyl group, pentafluoroethyl group, cyanomethyl group, 1-cyano-1-methylethyl group, hydroxymethyl group, 1-hydroxyethyl group, 2-hydroxyethyl group, 3-hydroxypropyl group, 1-hydroxy-1-methylethyl group, 2-hydroxy-1,1-dimethylethyl group, methoxymethyl group, 2-methoxy-1,1-dimethylethyl group, difluoro(methoxy)methyl group, aminomethyl group, 2-aminoethyl group, methylaminomethyl group, dimethylaminomethyl group, dipropylaminomethyl group, 2-dipropylaminoethyl group, carboxymethyl group, 2-carboxyethyl group, (R)-1-carboxyethyl group, (S)-1-carboxyethyl group, 3-carboxypropyl group, 4-carboxybutyl group, 5-carboxypentyl group, methoxycarbonylmethyl group, ethoxycarbonylmethyl group, tert-butoxycarbonylmethyl group, 2-methoxycarbonylethyl group, 2-tert-butoxycarbonylethyl group, 3-methoxycarbonylpropyl group, 4-methoxycarbonylbutyl group, 5-ethoxycarbonylpentyl group, 1-methoxycarbonyl-1-methylethyl group, 1-carboxy-1-methylethyl group, carbamoylmethyl group, 2-carbamoylethyl group, 1-dimethylcarbamoyl-1-methylethyl group, 2-acetylaminoethyl group, 2-(morpholin-4-yl)-2-oxoethyl group, triethylammoniumylmethyl group, (carboxy)(hydroxy)methyl group, (ethoxycarbonyl)(hydroxy)methyl group and the like can be mentioned.

The "$C_{1-10}$ alkyl group optionally substituted by 1 to 5 substituents selected from group B" is more preferably an unsubstituted alkyl group and a $C_{1-10}$ alkyl group substituted by a halogen atom.

The "$C_{2-10}$ alkynyl group optionally substituted by 1 to 5 substituents selected from group B" is the above-defined "$C_{2-10}$ alkynyl group" optionally substituted by 1 to 5 substituents, and includes an unsubstituted $C_{2-10}$ alkynyl group. The substituent is selected from group B.

Specifically, ethynyl group, 1-propynyl group, 2-propynyl group, 1-butynyl group, 2-butynyl group, 3-butynyl group, 1-pentynyl group, 1-hexynyl group, 1-heptynyl group, 1-octynyl group, 3-methylbut-1-yn-1-yl group, 3-hydroxy-3-methylbut-1-yn-1-yl group and the like can be mentioned.

The "$C_{3-12}$ carbon ring group optionally substituted by 1 to 5 substituents selected from group C" is the above-defined "$C_{3-12}$ carbon ring group" optionally substituted by 1 to 5 substituents, and includes an unsubstituted $C_{3-12}$ carbon ring group. The substituent is selected from group C.

Specifically, phenyl group, 4-chlorophenyl group, 4-cyanophenyl group, 2-hydroxyphenyl group, 3-hydroxyphenyl group, 2-carboxymethoxyphenyl group, 3-carboxymethoxyphenyl group, 3-carboxyphenyl group, cyclopropyl group, 1-hydroxymethylcyclopropyl group, 1-methoxymethylcyclopropyl group, 1-hydroxycyclopropyl group, 1-methoxycyclopropyl group, cyclopentyl group, cyclohexyl group and the like can be mentioned.

The "heterocyclic group optionally substituted by 1 to 5 substituents selected from group C" is the above-defined "heterocyclic group" optionally substituted by 1 to 5 substituents, and includes an unsubstituted heterocyclic group. The substituent is selected from group C.

Specifically, azetidin-1-yl group, pyrrolidin-1-yl group, 2-oxopyrrolidin-1-yl group, piperidin-1-yl group, morpholin-4-yl group, 4-methylpiperazin-1-yl group, 1-methyl-1H-pyrazol-4-yl group, furan-3-yl group, 1,2,3-thiadiazol-4-yl group, thiophen-2-yl group, 1H-tetrazol-5-yl group, 2H-tetrazol-5-yl group, pyridin-2-yl group, pyridin-3-yl group, 5-trifluoromethylisoxazol-3-yl group, 4-chloropyrazol-1-yl group, 3-hydroxypyrrolidin-1-yl group, 4-hydroxypiperidin-1-yl group, 5-oxo-2,5-dihydro-1,2,4-oxadiazol-3-yl group and the like can be mentioned.

The "C$_{6-12}$ aryl-C$_{1-4}$ alkyl group optionally substituted by 1 to 5 substituents selected from group C" is the above-defined "C$_{6-12}$ aryl-C$_{1-4}$ alkyl group" optionally substituted by 1 to 5 substituents and includes unsubstituted C$_{6-12}$ aryl-C$_{1-4}$ alkyl group. The substituent is selected from group C. Specifically, benzyl group and the like can be mentioned.

The "heterocyclyl-C$_{1-4}$ alkyl group optionally substituted by 1 to 5 substituents selected from group C" is the above-defined "heterocyclyl-C$_{1-4}$ alkyl group" optionally substituted by 1 to 5 substituents and includes an unsubstituted heterocyclyl-C$_{1-4}$ alkyl group. The substituent is selected from group C. Specifically, pyrrolidin-1-ylmethyl group, 4-methylpiperazin-1-ylmethyl group, morpholin-4-ylmethyl group and the like can be mentioned.

The "C$_{3-10}$ cycloalkyl-C$_{1-4}$ alkyl group optionally substituted by 1 to 5 substituents selected from group C" is the above-defined "C$_{3-10}$ cycloalkyl-C$_{1-4}$ alkyl group" optionally substituted by 1 to 5 substituents and includes an unsubstituted C$_{3-10}$ cycloalkyl-C$_{1-4}$ alkyl group. The substituent is selected from group C. Specifically, cyclopropylmethyl group and the like can be mentioned.

Preferable groups of ring A, ring B and R are as follows.
Ring A is preferably
phenyl group,
4-methylphenyl group,
4-ethylphenyl group,
4-propylphenyl group,
4-isopropylphenyl group,
4-butylphenyl group,
4-tert-butylphenyl group,
4-tert-pentylphenyl group,
4-(1-ethylpropyl)phenyl group,
4-(1-propylbutyl)phenyl group,
2-trifluoromethylphenyl group,
3-trifluoromethylphenyl group,
4-trifluoromethylphenyl group,
4-(1,1-difluoroethyl)phenyl group,
4-(1,1-difluoropropyl)phenyl group,
4-pentafluoroethylphenyl group,
4-(1-cyano-1-methylethyl)phenyl group,
4-(hydroxymethyl)phenyl group,
4-(2-hydroxyethyl)phenyl group,
4-(3-hydroxypropyl)phenyl group,
4-(2-hydroxy-1,1-dimethylethyl)phenyl group,
4-(methoxymethyl)phenyl group,
4-(2-methoxy-1,1-dimethylethyl)phenyl group,
4-[difluoro(methoxy)methyl]phenyl group,
4-(1-methoxycarbonyl-1-methylethyl)phenyl group,
4-(1-carboxy-1-methylethyl)phenyl group,
4-(1-dimethylcarbamoyl-1-methylethyl)phenyl group,
2-fluorophenyl group,
3-fluorophenyl group,
2-chlorophenyl group,
3-chlorophenyl group,
4-chlorophenyl group,
4-bromophenyl group,
4-nitrophenyl group,
2-hydroxyphenyl group,
3-hydroxyphenyl group,
4-hydroxyphenyl group,
2-methoxyphenyl group,
3-methoxyphenyl group,
4-methoxyphenyl group,
4-ethoxyphenyl group,
4-isopropoxyphenyl group,
4-fluoromethoxyphenyl group,
4-difluoromethoxyphenyl group
3-trifluoromethoxyphenyl group,
4-trifluoromethoxyphenyl group,
4-(2,2,2-trifluoroethoxy)phenyl group,
4-(1,1,2,2-tetrafluoroethoxy)phenyl group,
4-phenoxyphenyl group,
4-methylsulfanylphenyl group,
4-trifluoromethylsulfanylphenyl group,
4-aminophenyl group,
2-dimethylaminophenyl group,
3-dimethylaminophenyl group,
4-dimethylaminophenyl group,
4-diethylaminophenyl group,
4-(N-ethyl-N-methylamino)phenyl group,
4-(N-methyl-N-propylamino)phenyl group,
4-[N-(2-hydroxyethyl)-N-methylamino]phenyl group,
4-(2,2-dimethylpropionylamino)phenyl group,
4-carboxyphenyl group,
4-methoxycarbonylphenyl group,
4-sulfamoylphenyl group,
4-pentafluorosulfanylphenyl group,
4-cyclopropylphenyl group,
4-(1-hydroxymethylcyclopropyl)phenyl group,
4-(1-methoxymethylcyclopropyl)phenyl group,
4-cyclopentylphenyl group,
biphenyl-2-yl group,
biphenyl-4-yl group,
2'-chlorobiphenyl-4-yl group,
3'-chlorobiphenyl-4-yl group,
4'-chlorobiphenyl-4-yl group,
4-(azetidin-1-yl)phenyl group,
4-(pyrrolidin-1-yl)phenyl group,
4-(piperidin-1-yl)phenyl group,
4-(morpholin-4-yl)phenyl group,
4-(4-methylpiperazin-1-yl)phenyl group,
4-(1-methyl-1H-pyrazol-4-yl)phenyl group,
4-(furan-3-yl)phenyl group,
4-(1,2,3-thiadiazol-4-yl)phenyl group,
4-(thiophen-2-yl)phenyl group,
4-ethyl-2-methylphenyl group,
2-methyl-4-propylphenyl group,
4-isopropyl-2-methylphenyl group,
4-cyclopropyl-2-methylphenyl group,
3,4-dichlorophenyl group,
2,4-dichlorophenyl group,
4-bromo-2-chlorophenyl group,
2-chloro-4-propylphenyl group,
2-fluoro-4-isopropylphenyl group,
2,4-dimethoxyphenyl group,
3,4-dimethoxyphenyl group,
3-hydroxy-4-propylphenyl group,
3-amino-4-propylphenyl group,
3-hydroxy-4-methoxyphenyl group,
4-difluoromethoxy-2-fluorophenyl group,
4-difluoromethoxy-3-fluorophenyl group,
3-fluoro-4-trifluoromethoxyphenyl group,
2,4,6-trichlorophenyl group,
2,3,5,6-tetrafluoro-4-trifluoromethylphenyl group,
cyclohexyl group,
1-hydroxycyclohexyl group,
4-carboxycyclohexyl group,
2-phenylcyclopropyl group,
3-phenylcyclobutyl group,
adamantan-1-yl group,
naphthalen-2-yl group,
pyridin-2-yl group,
pyridin-3-yl group,
pyridin-4-yl group, 6-propylpyridin-3-yl group,
6-isopropylpyridin-3-yl group,
6-trifluoromethylpyridin-3-yl group,
6-dimethylaminopyridin-3-yl group,
6-(azetidin-1-yl)pyridin-3-yl group,
6-(pyrrolidin-1-yl)pyridin-3-yl group,
6-methoxy-5-methylpyridin-2-yl group,
2-oxo-1-propyl-1,2-dihydropyridin-4-yl group,
2-oxo-6-propyl-1,2-dihydropyridin-3-yl group,
1-propyl-1,2,3,6-tetrahydropyridin-4-yl group,
5-methylpyrazin-2-yl group,
1H-indol-3-yl group,
1-propyl-1H-pyrazol-4-yl group,
1H-imidazol-4-yl group,
5-propylthiophen-2-yl group,
5-phenylthiophen-2-yl group,
5-(pyridin-2-yl)thiophen-2-yl group,
2,2'-bithiophenyl-5-yl group,
4-methyl-2-propylthiazol-5-yl group,
2-(thiophen-2-yl)thiazol-4-yl group,
1-phenylazetidin-3-yl group,
piperidin-1-yl group,
piperidin-4-yl group,
1-propylpiperidin-4-yl group,
1-tert-butoxycarbonylpiperidin-4-yl group,
1-acetylpiperidin-4-yl group,
morpholin-4-yl group,
benzoxazol-2-yl group,
indolizin-2-yl
or the like.

Another preferable embodiment of ring A is a phenyl group optionally substituted by 1 to 5 substituents selected from the above-mentioned group A, more preferably a phenyl group substituted by 1 to 5 substituents selected from the above-mentioned group A.

In this case, a preferable substituent on the phenyl group is the above-defined "halogen atom", —OR$^{a1}$ (wherein R$^{a1}$ is as defined above) and the above-defined "C$_{1-10}$ alkyl group optionally substituted by 1 to 5 substituents selected from group B".

The substitution position of the substituent on the phenyl group is preferably monosubstituted at 4-position, 2,4-disubstituted or 3,4-disubstituted, and the substituents at the 2-position, the 3-position and the 4-position may be the same or different. More preferred are monosubstituted at 4-position and 3,4-disubstituted.

n is preferably 1.

Ring B is preferably
phenyl group,
4-methylphenyl group,
4-ethylphenyl group,
4-propylphenyl group,
4-isopropylphenyl group,
4-butylphenyl group,
4-isobutylphenyl group,
4-tert-butylphenyl group,
4-tert-pentylphenyl group,
4-neopentylphenyl group,
4-(1-ethylpropyl)phenyl group,
3-trifluoromethylphenyl group,
4-trifluoromethylphenyl group,
4-hydroxymethylphenyl group,
4-methoxymethylphenyl group,
4-(2-methoxycarbonylethyl)phenyl group,
4-fluorophenyl group,
2-chlorophenyl group,
3-chlorophenyl group,
4-chlorophenyl group,
3-bromophenyl group,
4-bromophenyl group,
4-iodophenyl group,
4-nitrophenyl group,
4-cyanophenyl group,
4-hydroxyphenyl group,
3-methoxyphenyl group,
4-methoxyphenyl group,
4-ethoxyphenyl group,
4-propoxyphenyl group,
4-isopropoxyphenyl group,
4-difluoromethoxyphenyl group,
4-trifluoromethoxyphenyl group,
4-(2,2,2-trifluoroethoxy)phenyl group,
4-(1,1,2,2-tetrafluoroethoxy)phenyl group,
4-carboxymethoxyphenyl group,
4-methoxycarbonylmethoxyphenyl group,
4-(2-methoxycarbonylethoxy)phenyl group,
4-(4-chlorophenoxy)phenyl group,
4-(pyridin-3-yloxy)phenyl group,
4-aminophenyl group,
4-dimethylaminophenyl group,
4-(N-carboxymethyl-N-methylamino)phenyl group,
4-(N-ethoxycarbonylmethyl-N-methylamino)phenyl group,
4-acetylaminophenyl group,
3-carboxyphenyl group,
4-carboxyphenyl group,
4-methoxycarbonylphenyl group,
4-acetylphenyl group,
4-cyclopropylphenyl group,
4-cyclohexylphenyl group,
4-(4-carboxymethylcyclohexyl)phenyl group,
biphenyl-3-yl group,
biphenyl-4-yl group,
4'-chlorobiphenyl-4-yl group,
2'-hydroxybiphenyl-4-yl group,
3'-hydroxybiphenyl-4-yl group,
2'-carboxymethoxybiphenyl-4-yl group,
3'-carboxymethoxybiphenyl-4-yl group,
3'-carboxybiphenyl-4-yl group,
4-cyclopropylmethylphenyl group,
4-(pyrrolidin-1-yl)phenyl group,
4-(2-oxopyrrolidin-1-yl)phenyl group,
4-(morpholin-4-yl)phenyl group,
4-(thiophen-2-yl)phenyl group,
4-(5-oxo-2,5-dihydro-1,2,4-oxadiazol-3-yl)phenyl group,
3,4-dichlorophenyl group,
2,4-dichlorophenyl group,
3,5-dichlorophenyl group,
4-bromo-2-fluorophenyl group,
4-bromo-3-fluorophenyl group,
3,4-dimethoxyphenyl group,
3-ethyl-4-methoxyphenyl group,
3-isopropyl-4-methoxyphenyl group,
3-tert-butyl-4-methoxyphenyl group,
3-chloro-4-methoxyphenyl group,
2-fluoro-4-trifluoromethoxyphenyl group,
3-fluoro-4-trifluoromethoxyphenyl group,
3-iodo-4-trifluoromethoxyphenyl group,
3-propyl-4-trifluoromethoxyphenyl group,
3-(2-carboxyethyl)-4-trifluoromethoxyphenyl group,
3-(3-carboxypropyl)-4-trifluoromethoxyphenyl group,
3-carboxy-4-methoxyphenyl group,
3-carboxy-4-trifluoromethoxyphenyl group,
4-methoxy-3-methoxycarbonylphenyl group,
4-methoxy-3-methoxycarbonylmethylphenyl group, 4-methoxy-3-(2-methoxycarbonylethyl)phenyl group,
3-carboxymethyl-4-methoxyphenyl group,
3-(2-carboxyethyl)-4-methoxyphenyl group,
3-cyano-4-methoxyphenyl group,
3-cyclopentyl-4-methoxyphenyl group,
4-methoxy-3-(2H-tetrazol-5-yl)phenyl group,
4-carboxy-3-fluorophenyl group,
2-(4-cyanophenoxy)-3,5-dimethylphenyl group,
cyclohexyl group,
indan-5-yl group,
5,6,7,8-tetrahydronaphthalen-2-yl group,
6,7,8,9-tetrahydro-5H-benzocyclohepten-2-yl group,
7-carboxymethyl-6,7,8,9-tetrahydro-5H-benzocyclohepten-2-yl group,
naphthalen-2-yl group,
5-ethylthiophen-2-yl group,
5-propylthiophen-2-yl group,
5-isopropylthiophen-2-yl group,
5-trifluoromethylthiophen-2-yl group,
5-chlorothiophen-2-yl group,
5-bromothiophen-2-yl group,
5-carboxymethylthiophen-2-yl group,
5-(2-carboxyethyl)thiophen-2-yl group,
5-benzenesulfonylthiophen-2-yl group,
5-(4-chlorophenyl)thiophen-2-yl group,
5-(5-trifluoromethylisoxazol-3-yl)thiophen-2-yl group,
5-(4-chloropyrazol-1-yl)thiophen-2-yl group,
6-(morpholin-4-yl)pyridin-3-yl group,
5-bromo-6-chloropyridin-3-yl group,
2,3-dihydrobenzofuran-5-yl group,
benzothiophen-2-yl group,
2,2,3,3-tetrafluoro-2,3-dihydro-benzo[1,4]dioxin-6-yl group,
1-methyl-1,2,3,4-tetrahydroquinolin-7-yl group,
2-propylthiazol-5-yl group
or the like.

Another preferable embodiment of ring B is a phenyl group optionally substituted by 1 to 5 substituents selected from the above-mentioned group A, more preferably a phenyl group substituted by 1 to 5 substituents selected from the above-mentioned group A.

In this case, the substituent on the phenyl group is preferably the above-defined "halogen atom", —$OR^{a1}$ (wherein $R^{a1}$ is as defined above), the above-defined "$C_{1-10}$ alkyl group optionally substituted by 1 to 5 substituents selected from group B" or "$C_{3-12}$ carbon ring group optionally substituted by 1 to 5 substituents selected from group A" (particularly preferably the above-defined "$C_{3-10}$ cycloalkyl group").

The substitution position of the substituent on the phenyl group is preferably monosubstituted at 4-position, 2,4 disubstituted or 3,4-disubstituted, wherein the substituents at the 2-position, the 3-position and the 4-position may be the same or different. It is more preferably monosubstituted at 4-position.

R is preferably
hydrogen atom,
formyl group,
acetyl group,
propionyl group,
isobutyryl group,
2,2-dimethylpropionyl group,
2-cyanoacetyl group,
2-hydroxyacetyl group,
2-hydroxy-2-methylpropionyl group,
3-hydroxypropionyl group,
2-methoxyacetyl group,
2-aminoacetyl group,
3-aminopropionyl group,
2-dimethylaminoacetyl group,
2-dipropylaminoacetyl group,
3-dipropylaminopropionyl group,
2-carboxyacetyl group,
3-carboxypropionyl group
4-carboxybutyryl group,
5-carboxypentanoyl group,
6-carboxyhexanoyl group,
3-methoxycarbonylpropionyl group,
4-methoxycarbonylbutyryl group,
5-methoxycarbonylpentanoyl group,
6-ethoxycarbonylhexanoyl group,
methoxycarbonyl group,
tert-butoxycarbonyl group,
carbamoyl group,
ethylcarbamoyl group,
dimethylcarbamoyl group,
carboxymethylcarbamoyl group,
(3-carboxypropyl)carbamoyl group,
methanesulfonyl group,
carboxycarbonyl group,
2-ethoxy-2-oxoacetyl group,
(Z)-3-carboxyprop-2-enoyl group,
(E)-3-carboxyprop-2-enoyl group,
2-carboxymethylaminoacetyl group,
2-(2-carboxyethylamino)acetyl group,
acetylaminoacetyl group,
3-acetylaminopropionyl group,
2-(3-carboxypropionylamino)acetyl group,
2-(tert-butoxycarbonylamino)acetyl group,
3-(tert-butoxycarbonylamino)propionyl group,
2-(3-methoxycarbonylpropionylamino)acetyl group,
2-amino-2-oxoacetyl group,
carbamimidoyl group,
thiocarbamoyl group,
methyl group,
carboxymethyl group,
methoxycarbonylmethyl group,
carbamoylmethyl group,
4-carboxyphenyl group,
4-methylthiazol-2-yl group,
4-hydroxymethylthiazol-2-yl group,
5-hydroxymethylthiazol-2-yl group,
4-carboxymethylthiazol-2-yl group,
4-methoxycarbonylmethylthiazol-2-yl group,
4-(2-carboxyethyl)thiazol-2-yl group,
4-carboxythiazol-2-yl group,
5-carboxythiazol-2-yl group,
5-methoxycarbonylthiazol-2-yl group,
4-ethoxycarbonylthiazol-2-yl group,
4-phenylthiazol-2-yl group,
5-carboxy-4-methylthiazol-2-yl group,
4-carboxy-5-methylthiazol-2-yl group,
4-ethyl-5-carboxythiazol-2-yl group,
5-carboxy-4-trifluoromethylthiazol-2-yl group,
5-hydroxymethyl-4-methylthiazol-2-yl group,
5-methoxycarbonyl-4-methylthiazol-2-yl group,
5-tert-butoxycarbonyl-4-methylthiazol-2-yl group,
5-ethoxycarbonyl-4-trifluoromethylthiazol-2-yl group,
5-methylaminomethyl-4-methylthiazol-2-yl group,
5-dimethylaminomethyl-4-methylthiazol-2-yl group,
5-carbamoyl-4-methylthiazol-2-yl group,
5-methylcarbamoyl-4-methylthiazol-2-yl group,
5-dimethylcarbamoyl-4-methylthiazol-2-yl group,
5-carboxymethylcarbamoyl-4-methylthiazol-2-yl group, 5-tert-butoxycarbonylmethylcarbamoyl-4-methylthiazol-2-yl group,
5-(2-tert-butoxycarbonylethyl)carbamoyl-4-methylthiazol-2-yl group,
5-(2-carboxyethyl)carbamoyl-4-methylthiazol-2-yl group,
5-((R)-1-carboxyethyl)carbamoyl-4-methylthiazol-2-yl group,
5-((S)-1-carboxyethyl)carbamoyl-4-methylthiazol-2-yl group,
5-carboxy-4-methoxymethylthiazol-2-yl group,
5-methanesulfonylaminocarbonyl-4-methylthiazol-2-yl group,
5-(2-carboxyethyl)-4-methylthiazol-2-yl group,
5-(carboxy)(hydroxy)methyl-4-methylthiazol-2-yl group,
5-(ethoxycarbonyl)(hydroxy)methyl-4-methylthiazol-2-yl group,
5-cyano-4-methylthiazol-2-yl group,
4-methyl-5-sulfamoylthiazol-2-yl group,
4-methyl-5-methylsulfamoylthiazol-2-yl group,
5-dimethylsulfamoyl-4-methylthiazol-2-yl group,
5-acetylsulfamoyl-4-methylthiazol-2-yl group,
5-acetyl-4-methylthiazol-2-yl group,
5-carboxycarbonyl-4-methylthiazol-2-yl group,
5-ethoxycarbonylcarbonyl-4-methylthiazol-2-yl group,
5-methylcarbamoylcarbonyl-4-methylthiazol-2-yl group,
4-methyl-5-(1H-tetrazol-5-yl)thiazol-2-yl group,
4-methyl-5-(pyrrolidin-1-ylmethyl)thiazol-2-yl group,
4,5-bis(hydroxymethyl)thiazol-2-yl group,
4-carboxy-5-hydroxymethylthiazol-2-yl group,
5-carboxy-4-hydroxymethylthiazol-2-yl group,
4-carboxy-5-methoxymethylthiazol-2-yl group,
5-carboxy-4-chlorothiazol-2-yl group,
4-amino-5-ethoxycarbonylthiazol-2-yl group,
pyrazin-2-yl group,
5-cyanopyrazin-2-yl group,
5-hydroxymethylpyrazin-2-yl group,
5-dimethylaminomethylpyrazin-2-yl group,
5-(triethylammoniumylmethyl)pyrazin-2-yl group,
5-methoxycarbonylpyrazin-2-yl group,
5-aminopyrazin-2-yl group,
5-methanesulfonylaminopyrazin-2-yl group,
5-carboxypyrazin-2-yl group,
5-carbamoylpyrazin-2-yl group,
5-ethylcarbamoylpyrazin-2-yl group,
5-tert-butylcarbamoylpyrazin-2-yl group,
5-(1H-tetrazol-5-yl)pyrazin-2-yl group,
5-(pyrrolidin-1-ylmethyl)pyrazin-2-yl group,
5-(morpholin-4-ylmethyl)pyrazin-2-yl group,
5-(4-methylpiperazin-1-ylmethyl)pyrazin-2-yl group,
5-methoxycarbonyl-3-methylpyrazin-2-yl group,
5-carboxy-6-methylpyrazin-2-yl group,
6-amino-5-hydroxymethylpyrazin-2-yl group,
6-amino-5-aminomethylpyrazin-2-yl group,
6-amino-5-carboxypyrazin-2-yl group,
6-amino-5-methoxycarbonylpyrazin-2-yl group,
6-acetylamino-5-methoxycarbonylpyrazin-2-yl group,
3,6-dimethyl-5-carboxypyrazin-2-yl group,
6-bromo-3-chloro-5-methoxycarbonylpyrazin-2-yl group,
6-amino-3-chloro-5-methoxycarbonylpyrazin-2-yl group,
5-aminopyridin-2-yl group,
5-carboxypyridin-2-yl group,
4-carboxypyridin-2-yl group,
5-methoxycarbonylpyridin-2-yl group,
5-tert-butoxycarbonylpyridin-2-yl group,
5-carboxy-6-methylpyridin-2-yl group,
5-carboxy-3-fluoro-6-methylpyridin-2-yl group,
6-carboxypyridin-3-yl group,
6-oxo-1,6-dihydropyridin-3-yl group,
5-carboxypyrimidin-2-yl group,
5-ethoxycarbonyl-4-hydroxypyrimidin-2-yl group,
5-carboxy-4-hydroxypyrimidin-2-yl group,
5-methoxycarbonyl-4-methylpyrimidin-2-yl group,
5-carboxy-4-methylpyrimidin-2-yl group,
5-benzyloxycarbonyl-4-methylpyrimidin-2-yl group,
4-aminopyrimidin-2-yl group,
pyrimidin-4-yl group,
6-chloropyrimidin-4-yl group,
2-hydroxypyrimidin-4-yl group,
2-aminopyrimidin-4-yl group,
6-aminopyrimidin-4-yl group,
6-hydroxypyridazin-3-yl group,
6-carboxypyridazin-3-yl group,
6-carbamoylpyridazin-3-yl group,
5-methyl-6-hydroxypyridazin-3-yl group,
6-carboxy-5-methylpyridazin-3-yl group,
6-methoxycarbonyl-5-methylpyridazin-3-yl group,
6-carbamoyl-5-methylpyridazin-3-yl group,
5-methyl-1H-pyrazol-3-yl group,
5-carboxy-1H-pyrazol-3-yl group,
1-carboxymethyl-5-methyl-1H-pyrazol-3-yl group,
5-carboxy-1-methyl-1H-pyrazol-3-yl group,
5-carboxy-2-methyl-2H-pyrazol-3-yl group,
4-chloro-5-carboxy-1H-pyrazol-3-yl group,
1H-imidazol-2-yl group,
1-methyl-1H-imidazol-2-yl group,
4-methyl-5-carboxyoxazol-2-yl group,
1,2,4-triazol-3-yl group,
5-bromo-1,2,4-triazol-3-yl group,
5-nitro-1,2,4-triazol-3-yl group,
5-amino-1,2,4-triazol-3-yl group,
3-methyl-1,2,4-thiadiazol-5-yl group,
3-methoxy-1,2,4-thiadiazol-5-yl group,
3-acetylamino-1,2,4-thiadiazol-5-yl group,
5-tert-butoxycarbonylthiophen-2-yl group,
benzothiazol-2-yl group,
4-carboxybenzothiazol-2-yl group,
8H-indeno[1,2-d]thiazol-2-yl group,
2-imidazolin-2-yl group,
2-thiazolin-2-yl group,
4-oxo-4,5-dihydrothiazol-2-yl group,
2-oxazolin-2-yl group,
2,5-dioxopyrrolidin-3-yl group,
4-phenyl-2,5-dioxo-3-pyrrolin-3-yl group,
2-oxopyrrolidin-3-yl group,
6-oxopiperidin-3-yl group,
5-oxo-4,5-dihydro-1,3,4-thiadiazol-2-yl group,
4,5,6,7-tetrahydrobenzothiazol-2-yl group,
1H-benzimidazol-2-yl group,
quinoxalin-2-yl group,
quinoxalin-6-yl group,
5-chloroquinoxalin-2-yl group,
6-chloroquinoxalin-2-yl group,
8-chloroquinoxalin-2-yl group,
6-bromoquinoxalin-2-yl group,
7-bromoquinoxalin-2-yl group,
5-carboxyquinoxalin-2-yl group,
6-carboxyquinoxalin-2-yl group,
7-carboxyquinoxalin-2-yl group,
8-carboxyquinoxalin-2-yl group,
6-ethoxycarbonylquinoxalin-2-yl group,
7-ethoxycarbonylquinoxalin-2-yl group,
1,5-naphthyridin-2-yl group,
1,6-naphthyridin-2-yl group,
thiazolo[5,4-c]pyridin-2-yl group, 6-carboxy-thiazolo[5,4-c]pyridin-2-yl group,
7-carboxy-thiazolo[5,4-c]pyridin-2-yl group,
7-ethoxycarbonyl-thiazolo[5,4-c]pyridin-2-yl group,
6-tert-butoxycarbonyl-thiazolo[5,4-c]pyridin-2-yl group,
4-oxo-4,5-dihydrothiazolo[5,4-c]pyridin-2-yl group,
4,5,6,7-tetrahydrothiazolo[5,4-c]pyridin-2-yl group,
5-methyl-4,5,6,7-tetrahydrothiazolo[5,4-c]pyridin-2-yl group,
5-benzyl-4,5,6,7-tetrahydrothiazolo[5,4-c]pyridin-2-yl group,
5-tert-butoxycarbonyl-4,5,6,7-tetrahydrothiazolo[5,4-c]pyridin-2-yl group,
5-benzyloxycarbonyl-4,5,6,7-tetrahydrothiazolo[5,4-c]pyridin-2-yl group,
5-ethylcarbamoyl-4,5,6,7-tetrahydrothiazolo[5,4-c]pyridin-2-yl group,
5-acetyl-4,5,6,7-tetrahydrothiazolo[5,4-c]pyridin-2-yl group,
5-methanesulfonyl-4,5,6,7-tetrahydrothiazolo[5,4-c]pyridin-2-yl group,
4-oxo-4,5,6,7-tetrahydrothiazolo[5,4-c]pyridin-2-yl group,
thiazolo[5,4-b]pyridin-2-yl group,
5-methoxy-thiazolo[5,4-b]pyridin-2-yl group,
5-oxo-4,5-dihydrothiazolo[5,4-b]pyridin-2-yl group,
thiazolo[4,5-b]pyrazin-2-yl group,
thiazolo[4,5-d]pyrimidin-2-yl group,
5-methyl-thiazolo[4,5-d]pyrimidin-2-yl group,
5-ethyl-thiazolo[4,5-d]pyrimidin-2-yl group,
5-isopropyl-thiazolo[4,5-d]pyrimidin-2-yl group,
5-tert-butyl-thiazolo[4,5-d]pyrimidin-2-yl group,
5-trifluoromethyl-thiazolo[4,5-d]pyrimidin-2-yl group,
5-hydroxymethyl-thiazolo[4,5-d]pyrimidin-2-yl group,
5-(1-hydroxyethyl)-thiazolo[4,5-d]pyrimidin-2-yl group,
5-(2-hydroxyethyl)-thiazolo[4,5-d]pyrimidin-2-yl group,
5-(1-hydroxy-1-methylethyl)-thiazolo[4,5-d]pyrimidin-2-yl group,
5-methoxymethyl-thiazolo[4,5-d]pyrimidin-2-yl group,
5-(2-methoxyethyl)-thiazolo[4,5-d]pyrimidin-2-yl group,
5-ethynyl-thiazolo[4,5-d]pyrimidin-2-yl group,
5-(3-hydroxy-3-methyl-but-1-ynyl)-thiazolo[4,5-d]pyrimidin-2-yl group,
5-fluoro-thiazolo[4,5-d]pyrimidin-2-yl group,
5-chloro-thiazolo[4,5-d]pyrimidin-2-yl group,
5-bromo-thiazolo[4,5-d]pyrimidin-2-yl group,
5-cyano-thiazolo[4,5-d]pyrimidin-2-yl group,
5-hydroxy-thiazolo[4,5-d]pyrimidin-2-yl group,
5-methoxy-thiazolo[4,5-d]pyrimidin-2-yl group,
5-difluoromethoxy-thiazolo[4,5-d]pyrimidin-2-yl group,
5-amino-thiazolo[4,5-d]pyrimidin-2-yl group,
5-methylamino-thiazolo[4,5-d]pyrimidin-2-yl group,
5-isopropylamino-thiazolo[4,5-d]pyrimidin-2-yl group,
5-dimethylamino-thiazolo[4,5-d]pyrimidin-2-yl group,
5-(2-hydroxyethylamino)-thiazolo[4,5-d]pyrimidin-2-yl group,
5-carboxy-thiazolo[4,5-d]pyrimidin-2-yl group,
5-ethoxycarbonyl-thiazolo[4,5-d]pyrimidin-2-yl group,
5-carbamoyl-thiazolo[4,5-d]pyrimidin-2-yl group,
5-methylcarbamoyl-thiazolo[4,5-d]pyrimidin-2-yl group,
5-dimethylcarbamoyl-thiazolo[4,5-d]pyrimidin-2-yl group,
5-(N-methoxy-N-methylcarbamoyl)-thiazolo[4,5-d]pyrimidin-2-yl group,
5-acetyl-thiazolo[4,5-d]pyrimidin-2-yl group,
5-cyclopropyl-thiazolo[4,5-d]pyrimidin-2-yl group,
5-cyclobutyl-thiazolo[4,5-d]pyrimidin-2-yl group,
5-(1-hydroxymethylcyclopropyl)-thiazolo[4,5-d]pyrimidin-2-yl group,
5-(1-methoxymethylcyclopropyl)-thiazolo[4,5-d]pyrimidin-2-yl group,
5-(1-hydroxycyclopropyl)-thiazolo[4,5-d]pyrimidin-2-yl group,
5-(1-methoxycyclopropyl)-thiazolo[4,5-d]pyrimidin-2-yl group,
5-(pyrrolidin-1-ylmethyl)-thiazolo[4,5-d]pyrimidin-2-yl group,
5-cyclopropylmethyl-thiazolo[4,5-d]pyrimidin-2-yl group,
5,7-dichloro-thiazolo[4,5-d]pyrimidin-2-yl group,
7-chloro-5-methyl-thiazolo[4,5-d]pyrimidin-2-yl group,
5-bromo-7-diethylamino-thiazolo[4,5-d]pyrimidin-2-yl group,
5,7-dihydroxy-thiazolo[4,5-d]pyrimidin-2-yl group,
7-methoxy-5-trifluoromethyl-thiazolo[4,5-d]pyrimidin-2-yl group,
7-amino-5-chloro-thiazolo[4,5-d]pyrimidin-2-yl group,
7-amino-5-methyl-thiazolo[4,5-d]pyrimidin-2-yl group,
7-amino-5-trifluoromethyl-thiazolo[4,5-d]pyrimidin-2-yl group,
7-amino-5-(1-hydroxy-1-methylethyl)-thiazolo[4,5-d]pyrimidin-2-yl group,
7-amino-5-methoxymethyl-thiazolo[4,5-d]pyrimidin-2-yl group,
7-amino-5-cyclopropyl-thiazolo[4,5-d]pyrimidin-2-yl group,
7-carbamoyl-5-methyl-thiazolo[4,5-d]pyrimidin-2-yl group,
5-chloro-2-diethylamino-thiazolo[4,5-d]pyrimidin-7-yl group,
7-oxo-6,7-dihydrothiazolo[4,5-d]pyrimidin-2-yl group,
5-methyl-7-oxo-6,7-dihydrothiazolo[4,5-d]pyrimidin-2-yl group,
7-oxo-5-trifluoromethyl-6,7-dihydrothiazolo[4,5-d]pyrimidin-2-yl group,
5-chloro-7-oxo-6,7-dihydrothiazolo[4,5-d]pyrimidin-2-yl group,
thiazolo[5,4-d]pyrimidin-2-yl group,
5-methyl-thiazolo[5,4-d]pyrimidin-2-yl group,
thiazolo[4,5-d]pyridazin-2-yl group,
4-methyl-thiazolo[4,5-d]pyridazin-2-yl group,
4-hydroxymethyl-thiazolo[4,5-d]pyridazin-2-yl group,
4-chloro-thiazolo[4,5-d]pyridazin-2-yl group,
7-chloro-thiazolo[4,5-d]pyridazin-2-yl group,
4-methoxy-thiazolo[4,5-d]pyridazin-2-yl group,
7-methoxy-thiazolo[4,5-d]pyridazin-2-yl group,
4-carboxy-thiazolo[4,5-d]pyridazin-2-yl group,
4-ethoxycarbonyl-thiazolo[4,5-d]pyridazin-2-yl group,
4-carbamoyl-thiazolo[4,5-d]pyridazin-2-yl group,
4-methylcarbamoyl-thiazolo[4,5-d]pyridazin-2-yl group,
4-dimethylcarbamoyl-thiazolo[4,5-d]pyridazin-2-yl group,
7-chloro-4-methyl-thiazolo[4,5-d]pyridazin-2-yl group,
7-chloro-4-ethoxycarbonyl-thiazolo[4,5-d]pyridazin-2-yl group,
4-oxo-4,5-dihydrothiazolo[4,5-d]pyridazin-2-yl group,
5-methyl-4-oxo-4,5-dihydrothiazolo[4,5-d]pyridazin-2-yl group,
5-ethyl-4-oxo-4,5-dihydrothiazolo[4,5-d]pyridazin-2-yl group,
5-(2-hydroxyethyl)-4-oxo-4,5-dihydrothiazolo[4,5-d]pyridazin-2-yl group,
5-(2-methoxyethyl)-4-oxo-4,5-dihydrothiazolo[4,5-d]pyridazin-2-yl group,
7-oxo-6,7-dihydrothiazolo[4,5-d]pyridazin-2-yl group,
4-methyl-7-oxo-6,7-dihydrothiazolo[4,5-d]pyridazin-2-yl group,
6-methyl-7-oxo-6,7-dihydrothiazolo[4,5-d]pyridazin-2-yl group, 4-hydroxymethyl-7-oxo-6,7-dihydrothiazolo[4,5-d]pyridazin-2-yl group,
4-carboxy-7-oxo-6,7-dihydrothiazolo[4,5-d]pyridazin-2-yl group,
4-ethoxycarbonyl-7-oxo-6,7-dihydrothiazolo[4,5-d]pyridazin-2-yl group,
4-carbamoyl-7-oxo-6,7-dihydrothiazolo[4,5-d]pyridazin-2-yl group,
4-methylcarbamoyl-7-oxo-6,7-dihydrothiazolo[4,5-d]pyridazin-2-yl group,
4,7-dioxo-4,5,6,7-tetrahydrothiazolo[4,5-d]pyridazin-2-yl group,
thiazolo[4,5-d][1,2,3]triazin-6-yl group,
4-methoxy-thiazolo[4,5-d][1,2,3]triazin-6-yl group,
4-amino-thiazolo[4,5-d][1,2,3]triazin-6-yl group,
4-(2-hydroxyethylamino)-thiazolo[4,5-d][1,2,3]triazin-6-yl group,
4-oxo-3,4-dihydrothiazolo[4,5-d][1,2,3]triazin-6-yl group,
4,6-dioxo-5,6-dihydro-4H-pyrrolo[3,4-d]thiazol-2-yl group,
1,3-dimethyl-1H-pyrazolo[3,4-d]thiazol-5-yl group,
7-methyl-5-oxo-5H-[1,3,4]thiadiazolo[3,2-a]pyrimidin-2-yl group,
5-oxo-7-trifluoromethyl-5H-[1,3,4]thiadiazolo[3,2-a]pyrimidin-2-yl group,
7-oxo-7H-[1,3,4]thiadiazolo[3,2-a]pyrimidin-2-yl group,
5-methyl-7-oxo-7H-[1,3,4]thiadiazolo[3,2-a]pyrimidin-2-yl group,
5-isopropyl-7-oxo-7H-[1,3,4]thiadiazolo[3,2-a]pyrimidin-2-yl group,
7-oxo-5-trifluoromethyl-7H-[1,3,4]thiadiazolo[3,2-a]pyrimidin-2-yl group,
5-ethoxycarbonyl-7-oxo-7H-[1,3,4]thiadiazolo[3,2-a]pyrimidin-2-yl group,
5-methylcarbamoyl-7-oxo-7H-[1,3,4]thiadiazolo[3,2-a]pyrimidin-2-yl group,
6-chloro-5-methyl-7-oxo-7H-[1,3,4]thiadiazolo[3,2-a]pyrimidin-2-yl group,
3-methyl-4-oxo-4H-[1,3,4]thiadiazolo[2,3-c][1,2,4]triazin-7-yl group,
4-oxo-3-trifluoromethyl-4H-[1,3,4]thiadiazolo[2,3-c][1,2,4]triazin-7-yl group,
[1,2,4]triazolo[3,4-b][1,3,4]thiadiazol-6-yl group,
3-methyl-[1,2,4]triazolo[3,4-b][1,3,4]thiadiazol-6-yl group,
3-trifluoromethyl-[1,2,4]triazolo[3,4-b][1,3,4]thiadiazol-6-yl group,
3H-imidazo[4,5-c]pyridin-2-yl group,
pteridin-7-yl group,
pteridin-6-yl group,
2-methylpteridin-7-yl group,
2-trifluoromethylpteridin-7-yl group,
pyrido[3,4-b]pyrazin-2-yl group,
8-(2-carboxyethyl)-pyrido[3,4-b]pyrazin-2-yl group,
8-(2-carbamoylethyl)-pyrido[3,4-b]pyrazin-2-yl group,
8-bromo-pyrido[3,4-b]pyrazin-2-yl group,
8-cyano-pyrido[3,4-b]pyrazin-2-yl group,
8-carboxy-pyrido[3,4-b]pyrazin-2-yl group,
8-carbamoyl-pyrido[3,4-b]pyrazin-2-yl group,
8-methylcarbamoyl-pyrido[3,4-b]pyrazin-2-yl group,
8-isopropylcarbamoyl-pyrido[3,4-b]pyrazin-2-yl group,
8-dimethylcarbamoyl-pyrido[3,4-b]pyrazin-2-yl group,
pyrido[2,3-b]pyrazin-2-yl group,
pyrido[2,3-b]pyrazin-3-yl group,
pyrido[2,3-b]pyrazin-6-yl group,
pyrazino[2,3-b]pyrazin-2-yl group,
2-oxo-1,4-dihydro-2H-pyrazino[2,3-d][1,3]oxazin-7-yl group,
2,2-dioxo-1,2,3,4-tetrahydro-2$\lambda^6$-pyrazino[2,3-c][1,2,6]thiadiazin-7-yl group,
1H-imidazo[4,5-b]pyrazin-5-yl group,
2-oxo-2,3-dihydro-1H-imidazo[4,5-b]pyrazin-5-yl group,
6-hydroxy-[1,2,5]thiadiazolo[3,4-b]pyrazin-5-yl group,
[1,2,4]triazolo[1,5-a]pyrimidin-5-yl group,
2-(pyridin-4-yl)ethyl group,
benzoyl group,
cyclopropylcarbonyl group,
pyridine-4-carbonyl group
thiazole-4-carbonyl group,
5-methylisoxazole-3-carbonyl group,
3-amino-1,2,4-triazole-1-carbonyl group,
5-amino-3-methyl-1,2,4-triazole-1-carbonyl group,
3-carboxyazetidin-1-ylcarbonyl group,
4-carboxypiperidin-1-ylcarbonyl group,
phenylacetyl group,
2-(2-methoxyphenyl)acetyl group,
2-(3-methoxyphenyl)acetyl group,
2-(4-methoxyphenyl)acetyl group,
2-(pyridin-2-yl)acetyl group,
2-(pyridin-3-yl)acetyl group,
2-(pyridin-4-yl)acetyl group,
2-(pyrimidin-4-yl)acetyl group,
2-(1H-imidazol-1-yl)acetyl group,
2-(1H-imidazol-4-yl)acetyl group,
2-(1-methyl-1H-imidazol-4-yl)acetyl group,
2-(1,2,3-triazol-1-yl)acetyl group,
2-(1,2,4-triazol-1-yl)acetyl group,
2-(1,3,4-triazol-1-yl)acetyl group,
2-(1,2,3-triazol-2-yl)acetyl group,
2-(pyrazol-1-yl)acetyl group,
2-(tetrazol-1-yl)acetyl group,
2-(1H-tetrazol-5-yl)acetyl group,
2-(tetrazol-2-yl)acetyl group,
2-(5-methyltetrazol-1-yl)acetyl group,
2-(5-methyltetrazol-2-yl)acetyl group,
2-(1-methyltetrazol-5-yl)acetyl group,
2-(2-methyltetrazol-5-yl)acetyl group,
2-(5-isopropyltetrazol-1-yl)acetyl group,
2-(5-isopropyltetrazol-2-yl)acetyl group,
2-(5-carboxymethyltetrazol-1-yl)acetyl group,
2-(5-carboxymethyltetrazol-2-yl)acetyl group,
2-(5-ethoxycarbonylmethyltetrazol-1-yl)acetyl group,
2-(5-ethoxycarbonylmethyltetrazol-2-yl)acetyl group,
2-(1-ethoxycarbonylmethyltetrazol-5-yl)acetyl group,
2-(2-ethoxycarbonylmethyltetrazol-5-yl)acetyl group,
2-[5-[2-(morpholin-4-yl)-2-oxoethyl]tetrazol-2-yl]acetyl group,
2-(5-aminotetrazol-1-yl)acetyl group,
2-(5-aminotetrazol-2-yl)acetyl group,
2-(5-phenyltetrazol-2-yl)acetyl group,
2-(3-methylisoxazol-5-yl)acetyl group,
2-(4-methylpiperazin-1-yl)acetyl group,
2-(pyrrolidin-1-yl)acetyl group,
2-(piperidin-1-yl)acetyl group,
2-(morpholin-4-yl)acetyl group,
3-(morpholin-4-yl)propionyl group,
2-cyclohexylacetyl group,
phenylcarbamoyl group,
2-chlorophenylcarbamoyl group,
3-chlorophenylcarbamoyl group,
4-chlorophenylcarbamoyl group,
2-hydroxyphenylcarbamoyl group,
2-methoxyphenylcarbamoyl group,
3-methoxyphenylcarbamoyl group,
4-methoxyphenylcarbamoyl group, 2-benzyloxyphenylcarbamoyl group,
2-carboxyphenylcarbamoyl group,
3-carboxyphenylcarbamoyl group,
4-carboxyphenylcarbamoyl group,
(4-dimethylaminophenyl)carbamoyl group,
(3-ethoxycarbonylmethoxyphenyl)carbamoyl group,
(4-ethoxycarbonylmethoxyphenyl)carbamoyl group,
(3-carboxymethoxyphenyl)carbamoyl group,
(4-carboxymethoxyphenyl)carbamoyl group,
(2-methoxycarbonylphenyl)carbamoyl group,
(3-methoxycarbonylphenyl)carbamoyl group,
(4-methoxycarbonylphenyl)carbamoyl group,
(2-benzyloxycarbonylphenyl)carbamoyl group,
(pyridin-3-yl)carbamoyl group,
(pyridin-4-yl)carbamoyl group,
(2-trifluoromethylpyridin-4-yl)carbamoyl group,
(2-hydroxymethylpyridin-4-yl)carbamoyl group,
(2-carboxypyridin-4-yl)carbamoyl group,
(2-carbamoylpyridin-4-yl)carbamoyl group,
(2-dimethylcarbamoylpyridin-4-yl)carbamoyl group,
[2-(cyclopropylcarbamoyl)pyridin-4-yl]carbamoyl group,
[2-(morpholine-4-carbonyl)pyridin-4-yl]carbamoyl group,
[2-(pyrrolidine-1-carbonyl)pyridin-4-yl]carbamoyl group,
(2-chloropyridin-4-yl)carbamoyl group,
(2-methoxypyridin-4-yl)carbamoyl group,
(2-tert-butoxycarbonylpyridin-4-yl)carbamoyl group,
N-methyl-N-(pyridin-4-yl)carbamoyl group,
[4-(2-hydroxyethyl)thiazol-2-yl]carbamoyl group,
(pyrimidin-4-yl)carbamoyl group,
(1-methyl-1H-pyrazol-3-yl)carbamoyl group,
(1,2,4-triazol-3-yl)carbamoyl group,
(1,2,4-triazol-4-yl)carbamoyl group,
(2H-tetrazol-5-yl)carbamoyl group,
(thiazol-2-yl)carbamoyl group,
(thiazol-4-yl)carbamoyl group,
(thiazol-5-yl)carbamoyl group,
(2-methylthiazol-4-yl)carbamoyl group,
[4-(1-hydroxy-1-methylethyl)thiazol-2-yl]carbamoyl group,
(4-ethoxycarbonylmethylthiazol-2-yl)carbamoyl group,
[4-[2-(morpholin-4-yl)-2-oxoethyl]thiazol-2-yl]carbamoyl group,
(3-methylisothiazol-5-yl)carbamoyl group,
(3-methylisoxazol-5-yl)carbamoyl group,
(5-methylisoxazol-3-yl)carbamoyl group,
(1,3,4-thiadiazol-2-yl)carbamoyl group,
(5-methyl-1,3,4-thiadiazol-2-yl)carbamoyl group,
(5-bromo-1,3,4-thiadiazol-2-yl)carbamoyl group,
(5-ethoxycarbonyl-1,3,4-thiadiazol-2-yl)carbamoyl group,
(5-trifluoromethyl-1,3,4-thiadiazol-2-yl)carbamoyl group,
(5-hydroxymethyl-1,3,4-thiadiazol-2-yl)carbamoyl group,
[5-(1-hydroxy-1-methylethyl)-1,3,4-thiadiazol-2-yl]carbamoyl group,
[5-((R)-3-hydroxypyrrolidine-1-carbonyl)-1,3,4-thiadiazol-2-yl]carbamoyl group,
[5-(4-hydroxypiperidine-1-carbonyl)-1,3,4-thiadiazol-2-yl]carbamoyl group,
[5-(morpholine-4-carbonyl)-1,3,4-thiadiazol-2-yl]carbamoyl group,
(5-acetyl-1,3,4-thiadiazol-2-yl)carbamoyl group,
(3-methyl-1,2,4-thiadiazol-5-yl)carbamoyl group,
(1,3,4-oxadiazol-2-yl)carbamoyl group,
(5-ethoxycarbonyl-1,3,4-oxadiazol-2-yl)carbamoyl group,
benzylcarbamoyl group,
phenoxyacetyl group,
benzylaminoacetyl group,
2-(pyridin-3-ylamino)acetyl group,
2-(1-methyl-1H-pyrazol-3-ylamino)acetyl group,
2-(5-bromo-1,3,4-thiadiazol-2-ylcarbamoyl)acetyl group,
benzenesulfonylaminocarbonyl group
or the like.

Another preferable embodiment of R is a group other than a hydrogen atom, particularly preferably

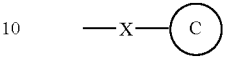

wherein each symbol is as defined above.

Here, X is preferably
a bond, —CO—$(CH_2)_p$— or —$CONR^{10}$—$(CH_2)_q$—, more preferably a bond.

Ring C is preferably the above-defined "heterocyclic group optionally substituted by 1 to 5 substituents selected from group A", more preferably the above-defined "heterocyclic group optionally substituted by 1 to 5 substituents selected from group A'".

The compound represented by the formula [I] or a pharmaceutically acceptable salt thereof, or a solvate thereof is preferably a compound represented by

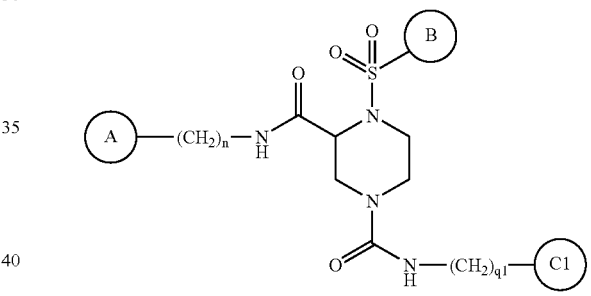

[I-A]

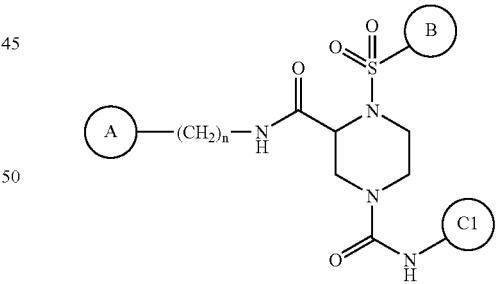

[I-B]

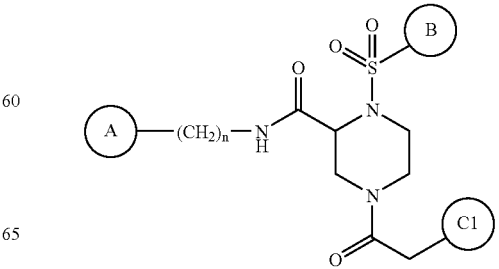

[I-C]

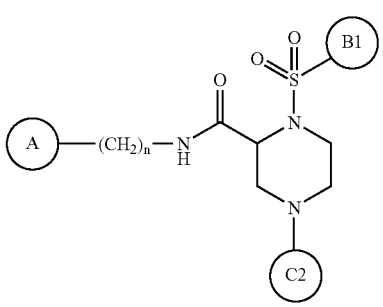

[I-D1]

wherein each symbol is as defined above,
or a pharmaceutically acceptable salt thereof, or a solvate thereof, particularly preferably a compound represented by the formula [I-D1], or a pharmaceutically acceptable salt thereof, or a solvate thereof.

Ring C2 is preferably, the above-defined "monocyclic heterocyclic group" substituted by 1 to 5 substituents selected from the above-mentioned "group A'", and the "monocyclic heterocyclic group" moiety is particularly preferably a thiazolyl group (particularly, thiazol-2-yl) or a pyrazinyl group (particularly, pyrazin-2-yl).

Here, the substituent (group A') on the "monocyclic heterocyclic group" is preferably cyano group, —COOR$^{a6}$, —CONR$^{a7}$R$^{a8}$, or —SO$_2$NR$^{a9}$R$^{a10}$, more preferably —COOR$^{a6}$ or —CONR$^{a7}$R$^{a8}$.

Another preferable embodiment of ring C2 is the above-defined "fused heterocyclic group" optionally substituted by 1 to 5 substituents selected from the above-mentioned "group A'". The "fused heterocyclic group" moiety is particularly preferably bicyclic fused heterocyclic group, particularly preferably a fused ring of a monocyclic heterocycle and a monocyclic heterocycle.

The "fused heterocyclic group" moiety is specifically preferably pyrido[2,3-b]pyrazin-2-yl group, pyrido[2,3-b]pyrazin-3-yl group, pyrido[3,4-b]pyrazin-2-yl group, pteridin-6-yl group, pteridin-7-yl group, pyrazino[2,3-b]pyrazin-2-yl group, 1H-imidazo[4,5-b]pyrazin-5-yl group, 2,2-dioxo-1,2,3,4-tetrahydropyrazino[2,3-c][1,2,6]thiadiazin-7-yl group, 2-oxo-1,4-dihydro-2H-pyrazino[2,3-d][1,3]oxazin-7-yl group, 2-oxo-2,3-dihydro-1H-imidazo[4,5-b]pyrazin-5-yl group or [1,2,5]thiadiazolo[3,4-b]pyrazinyl group, more preferably pyrido[2,3-b]pyrazin-2-yl group, pyrido[2,3-b]pyrazin-3-yl group, pyrido[3,4-b]pyrazin-2-yl group, pteridin-6-yl group, pteridin-7-yl group, pyrazino[2,3-b]pyrazin-2-yl group, 1H-imidazo[4,5-b]pyrazin-5-yl group or [1,2,5]thiadiazolo[3,4-b]pyrazinyl group, particularly preferably pyrido[3,4-b]pyrazin-2-yl group or pteridin-7-yl group.

Another preferable embodiment of the "fused heterocyclic group" moiety includes
benzothiazol-2-yl group,
4,5,6,7-tetrahydrobenzothiazol-2-yl group,
thiazolo[5,4-b]pyridin-2-yl group,
thiazolo[5,4-c]pyridin-2-yl group,
thiazolo[4,5-d]pyrimidin-2-yl group,
thiazolo[5,4-d]pyrimidin-2-yl group,
thiazolo[4,5-d]pyridazin-2-yl group,
thiazolo[4,5-b]pyrazin-2-yl group,
thiazolo[4,5-d][1,2,3]triazin-6-yl group,
5-oxo-4,5-dihydrothiazolo[5,4-b]pyridin-2-yl group,
1H-pyrazolo[3,4-d]thiazol-5-yl group,
4,6-dioxo-5,6-dihydro-4H-pyrrolo[3,4-d]thiazol-2-yl group,
4,5,6,7-tetrahydrothiazolo[5,4-c]pyridin-2-yl group,
4-oxo-4,5,6,7-tetrahydrothiazolo[5,4-c]pyridin-2-yl group,
4-oxo-4,5-dihydrothiazolo[5,4-c]pyridin-2-yl group,
7-oxo-6,7-dihydrothiazolo[4,5-d]pyrimidin-2-yl group,
4-oxo-4,5-dihydrothiazolo[4,5-d]pyridazin-2-yl group,
7-oxo-6,7-dihydrothiazolo[4,5-d]pyridazin-2-yl group,
4,7-dioxo-4,5,6,7-tetrahydrothiazolo[4,5-d]pyridazin-2-yl group,
4-oxo-3,4-dihydrothiazolo[4,5-d][1,2,3]triazin-6-yl group,
5-oxo-5H-[1,3,4]thiadiazolo[3,2-a]pyrimidin-2-yl group,
7-oxo-7H-[1,3,4]thiadiazolo[3,2-a]pyrimidin-2-yl group,
4-oxo-4H-[1,3,4]thiadiazolo[2,3-c][1,2,4]triazin-7-yl group, and
[1,2,4]triazolo[3,4-b][1,3,4]thiadiazol-6-yl group.

More preferably, it includes
thiazolo[5,4-b]pyridin-2-yl group,
thiazolo[5,4-c]pyridin-2-yl group,
thiazolo[4,5-d]pyrimidin-2-yl group,
thiazolo[5,4-d]pyrimidin-2-yl group,
thiazolo[4,5-d]pyridazin-2-yl group,
thiazolo[4,5-b]pyrazin-2-yl group,
thiazolo[4,5-d][1,2,3]triazin-6-yl group,
5-oxo-4,5-dihydrothiazolo[5,4-b]pyridin-2-yl group,
4,5,6,7-tetrahydrothiazolo[5,4-c]pyridin-2-yl group,
4-oxo-4,5,6,7-tetrahydrothiazolo[5,4-c]pyridin-2-yl group,
4-oxo-4,5-dihydrothiazolo[5,4-c]pyridin-2-yl group,
7-oxo-6,7-dihydrothiazolo[4,5-d]pyrimidin-2-yl group,
4-oxo-4,5-dihydrothiazolo[4,5-d]pyridazin-2-yl group,
7-oxo-6,7-dihydrothiazolo[4,5-d]pyridazin-2-yl group,
4,7-dioxo-4,5,6,7-tetrahydrothiazolo[4,5-d]pyridazin-2-yl group,
4-oxo-3,4-dihydrothiazolo[4,5-d][1,2,3]triazin-6-yl group,
5-oxo-5H-[1,3,4]thiadiazolo[3,2-a]pyrimidin-2-yl group,
7-oxo-7H-[1,3,4]thiadiazolo[3,2-a]pyrimidin-2-yl group, and
4-oxo-4H-[1,3,4]thiadiazolo[2,3-c][1,2,4]triazin-7-yl group.

Still more preferably, it includes thiazolo[4,5-d]pyrimidin-2-yl group, thiazolo[4,5-d]pyridazin-2-yl group, thiazolo[5,4-c]pyridin-2-yl group, 4-oxo-4,5-dihydrothiazolo[4,5-d]pyridazin-2-yl group and 7-oxo-7H-[1,3,4]thiadiazolo[3,2-a]pyrimidin-2-yl group, more preferably thiazolo[4,5-d]pyrimidin-2-yl group, 4-oxo-4,5-dihydrothiazolo[4,5-d]pyridazin-2-yl group and 7-oxo-7H-[1,3,4]thiadiazolo[3,2-a]pyrimidin-2-yl group.

Preferable embodiment of R$^{41}$ and R$^{42}$ includes halogen atom, nitro group, cyano group, —OR$^{a1}$, —SR$^{a2}$, —NR$^{a3}$R$^{a4}$, —NHCOR$^{a5}$, —COOR$^{a6}$, —CONR$^{a7}$R$^{a8}$, —COR$^{a11}$, —SO$_2$R$^{a12}$, a C$_{1-10}$ alkyl group optionally substituted by 1 to 5 substituents selected from group B, a C$_{3-12}$ carbon ring group optionally substituted by 1 to 5 substituents selected from group C, a heterocyclic group optionally substituted by 1 to 5 substituents selected from group C, and a C$_{3-10}$ cycloalkyl-C$_{1-4}$ alkyl group optionally substituted by 1 to 5 substituents selected from group C.

A still more preferable embodiment of R$^{41}$ includes —OR$^{a1}$, —NR$^{a3}$R$^{a4}$, —NHCOR$^{a5}$, —COOR$^{a6}$, —CONR$^{a7}$R$^{a8}$, —COR$^{a11}$, a C$_{1-10}$ alkyl group optionally substituted by 1 to 5 substituents selected from group B, a C$_{3-12}$ carbon ring group optionally substituted by 1 to 5 substituents selected from group C, a heterocyclic group optionally substituted by 1 to 5 substituents selected from group C, and a C$_{3-10}$ cycloalkyl-C$_{1-4}$ alkyl group optionally substituted by 1 to 5 substituents selected from group C.

A preferable embodiment of $R^{43}$, $R^{44}$ and $R^{45}$ includes halogen atom, nitro group, cyano group,
—$OR^{a1}$, —$SR^{a2}$, —$NR^{a3}R^{a4}$, —$NHCOR^{a5}$, —$COOR^{a6}$, —$CONR^{a7}R^{a8}$, —$COR^{a11}$, —$SO_2R^{a12}$,
a $C_{1-10}$ alkyl group optionally substituted by 1 to 5 substituents selected from group B,
a $C_{3-12}$ carbon ring group optionally substituted by 1 to 5 substituents selected from group C,
a heterocyclic group optionally substituted by 1 to 5 substituents selected from group C, and
a $C_{3-10}$ cycloalkyl-$C_{1-4}$ alkyl group optionally substituted by 1 to 5 substituents selected from group C.

A still more preferable embodiment of $R^{43}$ includes —$OR^{a1}$, —$NR^{a3}R^{a4}$, —$COOR^{a6}$, —$COR^{a11}$,
a $C_{1-10}$ alkyl group optionally substituted by 1 to 5 substituents selected from group B,
a $C_{3-12}$ carbon ring group optionally substituted by 1 to 5 substituents selected from group C,
a heterocyclic group optionally substituted by 1 to 5 substituents selected from group C, and
a $C_{3-10}$ cycloalkyl-$C_{1-4}$ alkyl group optionally substituted by 1 to 5 substituents selected from group C.

A still more preferable embodiment of $R^{44}$ includes halogen atom, nitro group, cyano group, —$OR^{a1}$, —$SR^{a2}$, —$NR^{a3}R^{a4}$, —$NHCOR^{a5}$, —$COOR^{a6}$, —$CONR^{a7}R^{a8}$, —$COR^{a11}$, —$SO_2R^{a12}$,
a $C_{1-10}$ alkyl group optionally substituted by 1 to 5 substituents selected from group B,
a $C_{3-12}$ carbon ring group optionally substituted by 1 to 5 substituents selected from group C,
a heterocyclic group optionally substituted by 1 to 5 substituents selected from group C, and
a $C_{3-10}$ cycloalkyl-$C_{1-4}$ alkyl group optionally substituted by 1 to 5 substituents selected from group C.

A still more preferable embodiment of $R^{45}$ includes —$OR^{a1}$, —$NR^{a3}R^{a4}$, —$NHCOR^{a5}$, —$CONR^{a7}R^{a8}$, —$COR^{a11}$,
a $C_{1-10}$ alkyl group optionally substituted by 1 to 5 substituents selected from group B,
a $C_{3-12}$ carbon ring group optionally substituted by 1 to 5 substituents selected from group C,
a heterocyclic group optionally substituted by 1 to 5 substituents selected from group C, and
a $C_{3-10}$ cycloalkyl-$C_{1-4}$ alkyl group optionally substituted by 1 to 5 substituents selected from group C.

A preferable embodiment of $R^{46}$ and $R^{47}$ includes hydrogen atom, halogen atom, cyano group, —$OR^{a1}$, $NR^{a3}R^{a4}$, —$COOR^{a6}$, $CONR^{a7}R^{a8}$, —$COR^{a11}$, —$CONR^{a19}(OR^{a20})$,
a $C_{1-10}$ alkyl group optionally substituted by 1 to 5 substituents selected from group B,
a $C_{2-10}$ alkynyl group optionally substituted by 1 to 5 substituents selected from group B,
a $C_{3-12}$ carbon ring group optionally substituted by 1 to 5 substituents selected from group C,
a heterocyclyl-$C_{1-4}$ alkyl group optionally substituted by 1 to 5 substituents selected from group C, and
a $C_{3-10}$ cycloalkyl-$C_{1-4}$ alkyl group optionally substituted by 1 to 5 substituents selected from group C.

A still more preferable embodiment of $R^{46}$ includes hydrogen atom, halogen atom, —$OR^{a1}$, —$NR^{a3}R^{a4}$ and —$CONR^{a7}R^{a8}$.

A still more preferable embodiment of $R^{47}$ includes hydrogen atom, halogen atom, cyano group, —$OR^{a1}$, —$NR^{a3}R^{a4}$, $COOR^{a6}$, $CONR^{a7}R^{a8}$, —$COR^{a11}$, —$CONR^{a19}(OR^{a20})$
a $C_{1-10}$ alkyl group optionally substituted by 1 to 5 substituents selected from group B,
a $C_{2-10}$ alkynyl group optionally substituted by 1 to 5 substituents selected from group B,
a $C_{3-12}$ carbon ring group optionally substituted by 1 to 5 substituents selected from group C,
a heterocyclyl-$C_{1-4}$ alkyl group optionally substituted by 1 to 5 substituents selected from group C, and
a $C_{3-10}$ cycloalkyl-$C_{1-4}$ alkyl group optionally substituted by 1 to 5 substituents selected from group C.

A preferable embodiment of $R^{414}$ includes —$OR^{a1}$, —$NR^{a3}R^{a4}$ and —$CONR^{a7}R^{a8}$.

A preferable embodiment of $R^{48}$ and $R^{49}$ includes hydrogen atom, and
a $C_{1-10}$ alkyl group optionally substituted by 1 to 5 substituents elected from group B.

A preferable embodiment of $R^{410}$ and $R^{411}$ includes hydrogen atom, halogen atom, —$COOR^{a6}$, —$CONR^{a7}R^{a8}$, and
a $C_{1-10}$ alkyl group optionally substituted by 1 to 5 substituents selected from group B.

A still more preferable embodiment of $R^{410}$ includes hydrogen atom, —$COOR^{a6}$, —$CONR^{a7}R^{a8}$, and
a $C_{1-10}$ alkyl group optionally substituted by 1 to 5 substituents selected from group B.

A still more preferable embodiment of $R^{411}$ includes hydrogen atom and halogen atom.

A preferable embodiment of $R^{412}$ and $R^{413}$ includes hydrogen atom, —$COOR^{a6}$, —$CONR^{a7}R^{a8}$, and
a $C_{1-10}$ alkyl group optionally substituted by 1 to 5 substituents selected from group B.

When the carbon atom at the following * moiety of a compound represented by the formula [I] is an asymmetric carbon atom, the compound is preferably an R form:

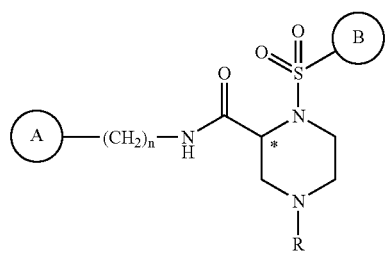

[I]

Examples of the compound represented by the formula [I] include the following compounds.
(R)-1-(4-trifluoromethyl-benzenesulfonyl)-piperazine-2-carboxylic acid 4-isopropyl-benzylamide hydrochloride (Example 1),
(R)-4-(2-pyridin-4-yl-acetyl)-1-(4-trifluoromethyl-benzenesulfonyl)-piperazine-2-carboxylic acid 4-isopropyl-benzylamide (Example 2),
(R)-4-(4-trifluoromethyl-benzenesulfonyl)-piperazine-1,3-dicarboxylic acid 3-(4-isopropyl-benzylamide) 1-pyridin-4-ylamide (Example 3),
(R)-4-thiocarbamoyl-1-(4-trifluoromethyl-benzenesulfonyl)-piperazine-2-carboxylic acid 4-isopropyl-benzylamide (Example 4),
2-[(R)-3-(4-isopropyl-benzylcarbamoyl)-4-(4-trifluoromethyl-benzenesulfonyl)-piperazin-1-yl]-4-methyl-thiazole-5-carboxylic acid tert-butyl ester (Example 5),
2-[(R)-3-(4-isopropyl-benzylcarbamoyl)-4-(4-trifluoromethyl-benzenesulfonyl)-piperazin-1-yl]-4-methyl-thiazole-5-carboxylic acid (Example 6), (R)-4-(5-carbamoyl-4-methyl-thiazol-2-yl)-1-(4-trifluoromethyl-benzenesulfonyl)-piperazine-2-carboxylic acid 4-isopropyl-benzylamide (Example 7),
(R)-3-(4-isopropyl-benzylcarbamoyl)-4-(4-trifluoromethyl-benzenesulfonyl)-3,4,5,6-tetrahydro-2H-[1,2']bipyrazinyl-5'-carboxylic acid methyl ester (Example 8),
(R)-3-(4-isopropyl-benzylcarbamoyl)-4-(4-trifluoromethyl-benzenesulfonyl)-3,4,5,6-tetrahydro-2H-[1,2']bipyrazinyl-5'-carboxylic acid (Example 9),
(R)-4-acetyl-1-(3-iodo-4-trifluoromethoxy-benzenesulfonyl)-piperazine-2-carboxylic acid 4-isopropyl-benzylamide (Example 10),
4-{5-[(R)-4-acetyl-2-(4-isopropyl-benzylcarbamoyl)-piperazine-1-sulfonyl]-2-trifluoromethoxy-phenyl}-butyric acid (Example 11),
(R)-4-acetyl-1-(4-isopropyl-benzenesulfonyl)-piperazine-2-carboxylic acid 2-methyl-4-propyl-benzylamide (Example 12),
2-[(R)-3-[(6-isopropyl-pyridin-3-ylmethyl)-carbamoyl]-4-(4-trifluoromethoxy-benzenesulfonyl)-piperazin-1-yl]-4-methyl-thiazole-5-carboxylic acid (Example 13),
2-[(R)-3-(4-propyl-benzylcarbamoyl)-4-(2-fluoro-4-trifluoromethoxy-benzenesulfonyl)-piperazin-1-yl]-4-methyl-thiazole-5-carboxylic acid (Example 14),
1-(4-isopropyl-benzenesulfonyl)-piperazine-2-carboxylic acid 4-trifluoromethyl-benzylamide hydrochloride (Example 15),
1-(4-isopropyl-benzenesulfonyl)-4-methyl-piperazine-2-carboxylic acid 4-trifluoromethyl-benzylamide (Example 16),
1-(4-isopropyl-benzenesulfonyl)-4-methanesulfonyl-piperazine-2-carboxylic acid 4-trifluoromethyl-benzylamide (Example 17),
(R)-4-acetyl-1-(4-isopropyl-benzenesulfonyl)-piperazine-2-carboxylic acid 4-trifluoromethyl-benzylamide (Example 18),
(S)-4-acetyl-1-(4-isopropyl-benzenesulfonyl)-piperazine-2-carboxylic acid 4-trifluoromethyl-benzylamide (Example 19),
4-acetyl-1-(4-chloro-benzenesulfonyl)-piperazine-2-carboxylic acid 4-trifluoromethyl-benzylamide (Example 20),
4-acetyl-1-(2-chloro-benzenesulfonyl)-piperazine-2-carboxylic acid 4-trifluoromethyl-benzylamide (Example 21),
4-acetyl-1-(4-bromo-benzenesulfonyl)-piperazine-2-carboxylic acid 4-trifluoromethyl-benzylamide (Example 22),
4-acetyl-1-(5-bromo-thiophene-2-sulfonyl)-piperazine-2-carboxylic acid 4-trifluoromethyl-benzylamide (Example 23),
4-acetyl-1-benzenesulfonyl-piperazine-2-carboxylic acid 4-trifluoromethyl-benzylamide (Example 24),
4-acetyl-1-[4-(4-chloro-phenoxy)-benzenesulfonyl]-piperazine-2-carboxylic acid 4-trifluoromethyl-benzylamide (Example 25),
4-acetyl-1-(4'-chloro-biphenyl-4-sulfonyl)-piperazine-2-carboxylic acid 4-trifluoromethyl-benzylamide (Example 26),
4-acetyl-1-[2-(4-cyano-phenoxy)-3,5-dimethyl-benzenesulfonyl]-piperazine-2-carboxylic acid 4-trifluoromethyl-benzylamide (Example 27),
4-acetyl-1-[5-(4-chloro-phenyl)-thiophene-2-sulfonyl]-piperazine-2-carboxylic acid 4-trifluoromethyl-benzylamide (Example 28),
4-acetyl-1-(3-chloro-benzenesulfonyl)-piperazine-2-carboxylic acid 4-trifluoromethyl-benzylamide (Example 29),
4-acetyl-1-(4-tert-butyl-benzenesulfonyl)-piperazine-2-carboxylic acid 4-trifluoromethyl-benzylamide (Example 30),
4-acetyl-1-(4-acetyl-benzenesulfonyl)-piperazine-2-carboxylic acid 4-trifluoromethyl-benzylamide (Example 31),
4-(4-isopropyl-benzenesulfonyl)-3-(4-trifluoromethyl-benzylcarbamoyl)-piperazine-1-carboxylic acid methyl ester (Example 32),
4-acetyl-1-(4-isopropyl-benzenesulfonyl)-piperazine-2-carboxylic acid 3-chloro-benzylamide (Example 33),
4-acetyl-1-(4-isopropyl-benzenesulfonyl)-piperazine-2-carboxylic acid 2-chloro-benzylamide (Example 34),
4-acetyl-1-(4-isopropyl-benzenesulfonyl)-piperazine-2-carboxylic acid 4-chloro-benzylamide (Example 35),
4-acetyl-1-(4-isopropyl-benzenesulfonyl)-piperazine-2-carboxylic acid (biphenyl-4-ylmethyl)-amide (Example 36),
4-acetyl-1-(4-isopropyl-benzenesulfonyl)-piperazine-2-carboxylic acid 4-dimethylamino-benzylamide (Example 37),
4-acetyl-1-(4-isopropyl-benzenesulfonyl)-piperazine-2-carboxylic acid 4-sulfamoyl-benzylamide (Example 38),
4-acetyl-1-(4-acetylamino-benzenesulfonyl)-piperazine-2-carboxylic acid 4-trifluoromethyl-benzylamide (Example 39),
4-acetyl-1-(4-nitro-benzenesulfonyl)-piperazine-2-carboxylic acid 4-trifluoromethyl-benzylamide (Example 40),
4-acetyl-1-(3,4-dichloro-benzenesulfonyl)-piperazine-2-carboxylic acid 4-trifluoromethyl-benzylamide (Example 41),
4-acetyl-1-(biphenyl-3-sulfonyl)-piperazine-2-carboxylic acid 4-trifluoromethyl-benzylamide (Example 42),
4-acetyl-1-[5-(5-trifluoromethyl-isoxazol-3-yl)-thiophene-2-sulfonyl]-piperazine-2-carboxylic acid 4-trifluoromethyl-benzylamide (Example 43),
4-acetyl-1-(4-methoxy-benzenesulfonyl)-piperazine-2-carboxylic acid 4-trifluoromethyl-benzylamide (Example 44),
4-acetyl-1-(4-trifluoromethyl-benzenesulfonyl)-piperazine-2-carboxylic acid 4-trifluoromethyl-benzylamide (Example 45),
4-acetyl-1-(4-cyano-benzenesulfonyl)-piperazine-2-carboxylic acid 4-trifluoromethyl-benzylamide (Example 46),
4-acetyl-1-(5-benzenesulfonyl-thiophene-2-sulfonyl)-piperazine-2-carboxylic acid 4-trifluoromethyl-benzylamide (Example 47),
4-acetyl-1-(2,3-dihydro-benzofuran-5-sulfonyl)-piperazine-2-carboxylic acid 4-trifluoromethyl-benzylamide (Example 48),
4-acetyl-1-(4-isopropyl-benzenesulfonyl)-piperazine-2-carboxylic acid benzylamide (Example 49),
4-acetyl-1-(4-isopropyl-benzenesulfonyl)-piperazine-2-carboxylic acid 2-methoxy-benzylamide (Example 50),
4-acetyl-1-(4-isopropyl-benzenesulfonyl)-piperazine-2-carboxylic acid 3-methoxy-benzylamide (Example 51),
4-acetyl-1-(4-isopropyl-benzenesulfonyl)-piperazine-2-carboxylic acid 4-methoxy-benzylamide (Example 52),
4-acetyl-1-(4-isopropyl-benzenesulfonyl)-piperazine-2-carboxylic acid 4-trifluoromethoxy-benzylamide (Example 53),
4-acetyl-1-(4-isopropyl-benzenesulfonyl)-piperazine-2-carboxylic acid 4-bromo-benzylamide (Example 54), 4-(2-hydroxy-acetyl)-1-(4-isopropyl-benzenesulfonyl)-piperazine-2-carboxylic acid 4-trifluoromethyl-benzylamide (Example 55),
4-(2-hydroxy-2-methyl-propionyl)-1-(4-isopropyl-benzenesulfonyl)-piperazine-2-carboxylic acid 4-trifluoromethyl-benzylamide (Example 56),
1-(4-isopropyl-benzenesulfonyl)-4-(2-methoxy-acetyl)-piperazine-2-carboxylic acid 4-trifluoromethyl-benzylamide (Example 57),
4-(3-hydroxy-propionyl)-1-(4-isopropyl-benzenesulfonyl)-piperazine-2-carboxylic acid 4-trifluoromethyl-benzylamide (Example 58),
4-(4-isopropyl-benzenesulfonyl)-piperazine-1,3-dicarboxylic acid 1-dimethylamide 3-(4-trifluoromethyl-benzylamide) (Example 59),
4-acetyl-1-(4-ethyl-benzenesulfonyl)-piperazine-2-carboxylic acid 4-trifluoromethyl-benzylamide (Example 60),
4-acetyl-1-(4-iodo-benzenesulfonyl)-piperazine-2-carboxylic acid 4-trifluoromethyl-benzylamide (Example 61),
4-acetyl-1-[5-(4-chloro-pyrazol-1-yl)-thiophene-2-sulfonyl]-piperazine-2-carboxylic acid 4-trifluoromethyl-benzylamide (Example 62),
4-formyl-1-(4-isopropyl-benzenesulfonyl)-piperazine-2-carboxylic acid 4-trifluoromethyl-benzylamide (Example 63),
4-acetyl-1-(toluene-4-sulfonyl)-piperazine-2-carboxylic acid 4-trifluoromethyl-benzylamide (Example 64),
4-acetyl-1-(4-trifluoromethoxy-benzenesulfonyl)-piperazine-2-carboxylic acid 4-trifluoromethyl-benzylamide (Example 65),
4-acetyl-1-[4-(pyridin-3-yloxy)-benzenesulfonyl]-piperazine-2-carboxylic acid 4-trifluoromethyl-benzylamide hydrochloride (Example 66),
4-acetyl-1-(4-isopropyl-benzenesulfonyl)-piperazine-2-carboxylic acid 2-fluoro-benzylamide (Example 67),
4-acetyl-1-(4-isopropyl-benzenesulfonyl)-piperazine-2-carboxylic acid 4-tert-butyl-benzylamide (Example 68),
4-acetyl-1-(5-bromo-6-chloro-pyridine-3-sulfonyl)-piperazine-2-carboxylic acid 4-trifluoromethyl-benzylamide hydrochloride (Example 69),
4-acetyl-1-(6-morpholin-4-yl-pyridine-3-sulfonyl)-piperazine-2-carboxylic acid 4-trifluoromethyl-benzylamide hydrochloride (Example 70),
4-acetyl-1-(3-methoxy-benzenesulfonyl)-piperazine-2-carboxylic acid 4-trifluoromethyl-benzylamide (Example 71),
4-acetyl-1-(4-propyl-benzenesulfonyl)-piperazine-2-carboxylic acid 4-trifluoromethyl-benzylamide (Example 72),
4-acetyl-1-(biphenyl-4-sulfonyl)-piperazine-2-carboxylic acid 4-trifluoromethyl-benzylamide (Example 73),
4-acetyl-1-(benzo[b]thiophene-2-sulfonyl)-piperazine-2-carboxylic acid 4-trifluoromethyl-benzylamide (Example 74),
4-acetyl-1-(5-isopropyl-thiophene-2-sulfonyl)-piperazine-2-carboxylic acid 4-trifluoromethyl-benzylamide (Example 75),
4-({[4-acetyl-1-(4-isopropyl-benzenesulfonyl)-piperazine-2-carbonyl]-amino}-methyl)-benzoic acid methyl ester (Example 76),
4-acetyl-1-(4-isopropyl-benzenesulfonyl)-piperazine-2-carboxylic acid 4-nitro-benzylamide (Example 77),
4-acetyl-1-(4-isopropyl-benzenesulfonyl)-piperazine-2-carboxylic acid 3-fluoro-benzylamide (Example 78),
4-acetyl-1-(4-isopropyl-benzenesulfonyl)-piperazine-2-carboxylic acid [2-(1H-indol-3-yl)-ethyl]-amide (Example 79),
4-acetyl-1-(4-isopropyl-benzenesulfonyl)-piperazine-2-carboxylic acid 4-morpholin-4-yl-benzylamide (Example 80),
4-acetyl-1-(4-isopropyl-benzenesulfonyl)-piperazine-2-carboxylic acid 4-(4-methyl-piperazin-1-yl)-benzylamide (Example 81),
3-(4-dimethylamino-benzylcarbamoyl)-4-(4-iodo-benzenesulfonyl)-piperazine-1-carboxylic acid tert-butyl ester (Example 82),
4-acetyl-1-(4-isopropoxy-benzenesulfonyl)-piperazine-2-carboxylic acid 4-trifluoromethyl-benzylamide (Example 83),
1-(4-iodo-benzenesulfonyl)-piperazine-2-carboxylic acid 4-dimethylamino-benzylamide hydrochloride (Example 84),
4-acetyl-1-(4-iodo-benzenesulfonyl)-piperazine-2-carboxylic acid 4-dimethylamino-benzylamide (Example 85),
{2-[3-(4-dimethylamino-benzylcarbamoyl)-4-(4-iodo-benzenesulfonyl)-piperazin-1-yl]-2-oxo-ethyl}-carbamic acid tert-butyl ester (Example 86),
{3-[3-(4-dimethylamino-benzylcarbamoyl)-4-(4-iodo-benzenesulfonyl)-piperazin-1-yl]-3-oxo-propyl}-carbamic acid tert-butyl ester (Example 87),
4-(2-amino-acetyl)-1-(4-iodo-benzenesulfonyl)-piperazine-2-carboxylic acid 4-dimethylamino-benzylamide hydrochloride (Example 88),
4-(3-amino-propionyl)-1-(4-iodo-benzenesulfonyl)-piperazine-2-carboxylic acid 4-dimethylamino-benzylamide hydrochloride (Example 89),
4-acetyl-1-(4-isopropyl-benzenesulfonyl)-piperazine-2-carboxylic acid 4-amino-benzylamide (Example 90),
4-acetyl-1-(4-butyl-benzenesulfonyl)-piperazine-2-carboxylic acid 4-trifluoromethyl-benzylamide (Example 91),
4-acetyl-1-(4-dimethylamino-benzenesulfonyl)-piperazine-2-carboxylic acid 4-trifluoromethyl-benzylamide (Example 92),
4-acetyl-1-(4-amino-benzenesulfonyl)-piperazine-2-carboxylic acid 4-trifluoromethyl-benzylamide hydrochloride (Example 93),
[3-(4-dimethylamino-benzylcarbamoyl)-4-(4-iodo-benzenesulfonyl)-piperazin-1-yl]-acetic acid methyl ester (Example 94),
4-(2-dimethylamino-acetyl)-1-(4-iodo-benzenesulfonyl)-piperazine-2-carboxylic acid 4-dimethylamino-benzylamide (Example 95),
[3-(4-dimethylamino-benzylcarbamoyl)-4-(4-iodo-benzenesulfonyl)-piperazin-1-yl]-acetic acid (Example 96),
4-acetyl-1-[4-(1,1-dimethyl-propyl)-benzenesulfonyl]-piperazine-2-carboxylic acid 4-trifluoromethyl-benzylamide (Example 97),
4-acetyl-1-(4-isopropyl-benzenesulfonyl)-piperazine-2-carboxylic acid 4-(2,2-dimethyl-propionylamino)-benzylamide (Example 98),
4-({[4-acetyl-1-(4-isopropyl-benzenesulfonyl)-piperazine-2-carbonyl]-amino}-methyl)-benzoic acid (Example 99),
4-acetyl-1-(4-isopropyl-benzenesulfonyl)-piperazine-2-carboxylic acid 3,4-dichloro-benzylamide (Example 100),
4-acetyl-1-(4-isopropyl-benzenesulfonyl)-piperazine-2-carboxylic acid 2,4-dichloro-benzylamide (Example 101),
1-(4-iodo-benzenesulfonyl)-4-(2-piperidin-1-yl-acetyl)-piperazine-2-carboxylic acid 4-dimethylamino-benzylamide (Example 102),
4-(4,5-dihydro-1H-imidazol-2-yl)-1-(4-isopropyl-benzenesulfonyl)-piperazine-2-carboxylic acid 4-trifluoromethyl-benzylamide (Example 103), 1-(4-iodo-benzenesulfonyl)-4-(2-morpholin-4-yl-acetyl)-piperazine-2-carboxylic acid 4-dimethylamino-benzylamide (Example 104), 4-(2-benzylamino-acetyl)-1-(4-iodo-benzenesulfonyl)-piperazine-2-carboxylic acid 4-dimethylamino-benzylamide (Example 105), 4-[4-acetyl-2-(4-trifluoromethyl-benzylcarbamoyl)-piperazine-1-sulfonyl]-benzoic acid methyl ester (Example 106), 4-[4-acetyl-2-(4-trifluoromethyl-benzylcarbamoyl)-piperazine-1-sulfonyl]-benzoic acid (Example 107), 4-acetyl-1-(4-isopropyl-benzenesulfonyl)-piperazine-2-carboxylic acid 4-(1-methyl-1H-pyrazol-4-yl)-benzylamide (Example 108), 4-acetyl-1-(4-isopropyl-benzenesulfonyl)-piperazine-2-carboxylic acid 4-piperidin-1-yl-benzylamide (Example 109), 4-(2-dipropylamino-acetyl)-1-(4-iodo-benzenesulfonyl)-piperazine-2-carboxylic acid 4-dimethylamino-benzylamide (Example 110), 1-(4-isopropyl-benzenesulfonyl)-4-thiocarbamoyl-piperazine-2-carboxylic acid 4-trifluoromethyl-benzylamide (Example 111), 4-(4,5-dihydro-thiazol-2-yl)-1-(4-isopropyl-benzenesulfonyl)-piperazine-2-carboxylic acid 4-trifluoromethyl-benzylamide (Example 112), 1-(4-iodo-benzenesulfonyl)-4-(3-morpholin-4-yl-propionyl)-piperazine-2-carboxylic acid 4-dimethylamino-benzylamide (Example 113), 4-(3-dipropylamino-propionyl)-1-(4-iodo-benzenesulfonyl)-piperazine-2-carboxylic acid 4-dimethylamino-benzylamide (Example 114), 1-(4-isopropyl-benzenesulfonyl)-4-(4-methyl-thiazol-2-yl)-piperazine-2-carboxylic acid 4-trifluoromethyl-benzylamide (Example 115), 4-acetyl-1-(4-isopropyl-benzenesulfonyl)-piperazine-2-carboxylic acid (4'-chloro-biphenyl-4-ylmethyl)-amide (Example 116), 4-acetyl-1-(4-isopropyl-benzenesulfonyl)-piperazine-2-carboxylic acid 4-isopropyl-benzylamide (Example 117), 4-acetyl-1-(4-isopropyl-benzenesulfonyl)-piperazine-2-carboxylic acid phenethyl-amide (Example 118), 4-acetyl-1-(4-isopropyl-benzenesulfonyl)-piperazine-2-carboxylic acid 3-trifluoromethyl-benzylamide (Example 119), 4-acetyl-1-(4-isopropyl-benzenesulfonyl)-piperazine-2-carboxylic acid 2-trifluoromethyl-benzylamide (Example 120), 4-acetyl-1-(4-isopropyl-benzenesulfonyl)-piperazine-2-carboxylic acid 3-trifluoromethoxy-benzylamide (Example 121), 4-(2-cyclohexyl-acetyl)-1-(4-iodo-benzenesulfonyl)-piperazine-2-carboxylic acid 4-dimethylamino-benzylamide (Example 122), 4-benzoyl-1-(4-isopropyl-benzenesulfonyl)-piperazine-2-carboxylic acid 4-trifluoromethyl-benzylamide (Example 123), 1-(4-isopropyl-benzenesulfonyl)-4-phenylacetyl-piperazine-2-carboxylic acid 4-trifluoromethyl-benzylamide (Example 124), 1-(4-isopropyl-benzenesulfonyl)-4-(2-phenoxy-acetyl)-piperazine-2-carboxylic acid 4-trifluoromethyl-benzylamide (Example 125), 4-acetyl-1-(4-isopropyl-benzenesulfonyl)-piperazine-2-carboxylic acid 4-phenoxy-benzylamide (Example 126), 4-acetyl-1-(4-isopropyl-benzenesulfonyl)-piperazine-2-carboxylic acid 4-isopropoxy-benzylamide (Example 127), 4-acetyl-1-(4-isopropyl-benzenesulfonyl)-piperazine-2-carboxylic acid 3-dimethylamino-benzylamide (Example 128), 4-acetyl-1-(4-isopropyl-benzenesulfonyl)-piperazine-2-carboxylic acid 2-dimethylamino-benzylamide (Example 129), 1-(4-iodo-benzenesulfonyl)-4-propionyl-piperazine-2-carboxylic acid 4-dimethylamino-benzylamide (Example 130), 1-(4-iodo-benzenesulfonyl)-4-phenylacetyl-piperazine-2-carboxylic acid 4-dimethylamino-benzylamide (Example 131), 4-acetyl-1-(4-hydroxymethyl-benzenesulfonyl)-piperazine-2-carboxylic acid 4-trifluoromethyl-benzylamide (Example 132), 4-(4,5-dihydro-oxazol-2-yl)-1-(4-isopropyl-benzenesulfonyl)-piperazine-2-carboxylic acid 4-trifluoromethyl-benzylamide (Example 133), 4-benzothiazol-2-yl-1-(4-isopropyl-benzenesulfonyl)-piperazine-2-carboxylic acid 4-trifluoromethyl-benzylamide (Example 134), 1-(4-isopropyl-benzenesulfonyl)-4-(4-phenyl-thiazol-2-yl)-piperazine-2-carboxylic acid 4-trifluoromethyl-benzylamide (Example 135), 4-acetyl-1-(3,4-dimethoxy-benzenesulfonyl)-piperazine-2-carboxylic acid 4-trifluoromethyl-benzylamide (Example 136), (R)-4-acetyl-1-(4-isopropyl-benzenesulfonyl)-piperazine-2-carboxylic acid 4-isopropyl-benzylamide (Example 137), (R)-4-acetyl-1-(4-isopropyl-benzenesulfonyl)-piperazine-2-carboxylic acid [2-(4-chloro-phenyl)-ethyl]-amide (Example 138), 4-acetyl-1-(4-isopropyl-benzenesulfonyl)-piperazine-2-carboxylic acid 4-cyclopentyl-benzylamide (Example 139), 4-acetyl-1-(4-isopropyl-benzenesulfonyl)-piperazine-2-carboxylic acid 4-(1-propyl-butyl)-benzylamide (Example 140), 4-acetyl-1-(4-isopropyl-benzenesulfonyl)-piperazine-2-carboxylic acid (3'-chloro-biphenyl-4-ylmethyl)-amide (Example 141), 4-acetyl-1-(4-isopropyl-benzenesulfonyl)-piperazine-2-carboxylic acid (2'-chloro-biphenyl-4-ylmethyl)-amide (Example 142), 4-acetyl-1-(4-methoxymethyl-benzenesulfonyl)-piperazine-2-carboxylic acid 4-trifluoromethyl-benzylamide (Example 143), 4-acetyl-1-(4-isopropyl-benzenesulfonyl)-piperazine-2-carboxylic acid 4-ethyl-benzylamide (Example 144), 4-acetyl-1-(4-isopropyl-benzenesulfonyl)-piperazine-2-carboxylic acid (3-phenyl-propyl)-amide (Example 145), (R)-4-carbamoylmethyl-1-(4-trifluoromethyl-benzenesulfonyl)-piperazine-2-carboxylic acid 4-isopropyl-benzylamide (Example 146), (R)-4-(2,5-dioxo-pyrrolidin-3-yl)-1-(4-trifluoromethyl-benzenesulfonyl)-piperazine-2-carboxylic acid 4-isopropyl-benzylamide (Example 147), (R)-4-(2,5-dioxo-4-phenyl-2,5-dihydro-1H-pyrrol-3-yl)-1-(4-trifluoromethyl-benzenesulfonyl)-piperazine-2-carboxylic acid 4-isopropyl-benzylamide (Example 148), (R)-4-acetyl-1-(4-isopropyl-benzenesulfonyl)-piperazine-2-carboxylic acid [2-(2-chloro-phenyl)-ethyl]-amide (Example 149), (R)-4-acetyl-1-(4-isopropyl-benzenesulfonyl)-piperazine-2-carboxylic acid [2-(3-chloro-phenyl)-ethyl]-amide (Example 150), 4-acetyl-1-(4-isopropyl-benzenesulfonyl)-piperazine-2-carboxylic acid (6-trifluoromethyl-pyridin-3-ylmethyl)-amide (Example 151), 4-acetyl-1-(4-isopropyl-benzenesulfonyl)-piperazine-2-carboxylic acid (pyridin-2-ylmethyl)-amide (Example 152), 1-(4-iodo-benzenesulfonyl)-4-(2-pyridin-2-yl-acetyl)-piperazine-2-carboxylic acid 4-dimethylamino-benzylamide (Example 153), 1-(4-iodo-benzenesulfonyl)-4-(2-pyridin-3-yl-acetyl)-piperazine-2-carboxylic acid 4-dimethylamino-benzylamide (Example 154), 4-(8H-indeno[1,2-d]thiazol-2-yl)-1-(4-isopropyl-benzenesulfonyl)-piperazine-2-carboxylic acid 4-trifluoromethyl-benzylamide (Example 155), 1-(4-isopropyl-benzenesulfonyl)-4-(4,5,6,7-tetrahydro-benzothiazol-2-yl)-piperazine-2-carboxylic acid 4-trifluoromethyl-benzylamide (Example 156), (R)-4-(2-amino-acetyl)-1-(4-iodo-benzenesulfonyl)-piperazine-2-carboxylic acid 4-dimethylamino-benzylamide hydrochloride (Example 157), (R)-1-(4-iodo-benzenesulfonyl)-4-(2-piperidin-1-yl-acetyl)-piperazine-2-carboxylic acid 4-dimethylamino-benzylamide (Example 158), (R)-1-(4-iodo-benzenesulfonyl)-4-(2-pyrrolidin-1-yl-acetyl)-piperazine-2-carboxylic acid 4-dimethylamino-benzylamide (Example 159), (R)-1-(4-iodo-benzenesulfonyl)-4-(2-morpholin-4-yl-acetyl)-piperazine-2-carboxylic acid 4-dimethylamino-benzylamide (Example 160), 4-acetyl-1-(2,4-dichloro-benzenesulfonyl)-piperazine-2-carboxylic acid 4-trifluoromethyl-benzylamide (Example 161), 4-acetyl-1-[4-(1-ethyl-propyl)-benzenesulfonyl]-piperazine-2-carboxylic acid 4-trifluoromethyl-benzylamide (Example 162), 4-acetyl-1-(4-isopropyl-benzenesulfonyl)-piperazine-2-carboxylic acid 4-(1-ethyl-propyl)-benzylamide (Example 163), 4-acetyl-1-(naphthalene-2-sulfonyl)-piperazine-2-carboxylic acid 4-trifluoromethyl-benzylamide (Example 164), 4-acetyl-1-(3-bromo-benzenesulfonyl)-piperazine-2-carboxylic acid 4-trifluoromethyl-benzylamide (Example 165), 3-{4-[4-acetyl-2-(4-trifluoromethyl-benzylcarbamoyl)-piperazine-1-sulfonyl]-phenyl}-propionic acid methyl ester (Example 166), 4-acetyl-1-(4-cyclohexyl-benzenesulfonyl)-piperazine-2-carboxylic acid 4-trifluoromethyl-benzylamide (Example 167), 3-[4-acetyl-2-(4-trifluoromethyl-benzylcarbamoyl)-piperazine-1-sulfonyl]-benzoic acid (Example 168), (R)-4-acetyl-1-(4-isopropyl-benzenesulfonyl)-piperazine-2-carboxylic acid 4-(2-hydroxy-1,1-dimethyl-ethyl)-benzylamide (Example 169), 2-[4-(4-isopropyl-benzenesulfonyl)-3-(4-trifluoromethyl-benzylcarbamoyl)-piperazin-1-yl]-thiazole-4-carboxylic acid ethyl ester (Example 170), 2-[4-(4-isopropyl-benzenesulfonyl)-3-(4-trifluoromethyl-benzylcarbamoyl)-piperazin-1-yl]-thiazole-4-carboxylic acid (Example 171), (R)-4-phenylacetyl-1-(4-trifluoromethyl-benzenesulfonyl)-piperazine-2-carboxylic acid 4-isopropyl-benzylamide (Example 172), 4-[(R)-3-(4-isopropyl-benzylcarbamoyl)-4-(4-trifluoromethyl-benzenesulfonyl)-piperazin-1-yl]-4-oxo-butyric acid methyl ester (Example 173), 5-[(R)-3-(4-isopropyl-benzylcarbamoyl)-4-(4-trifluoromethyl-benzenesulfonyl)-piperazin-1-yl]-5-oxo-pentanoic acid methyl ester (Example 174), (R)-4-(2-pyridin-3-yl-acetyl)-1-(4-trifluoromethyl-benzenesulfonyl)-piperazine-2-carboxylic acid 4-isopropyl-benzylamide (Example 175), (R)-4-acetyl-1-(4-trifluoromethyl-benzenesulfonyl)-piperazine-2-carboxylic acid 4-isopropyl-benzylamide (Example 176), (R)-4-(4-trifluoromethyl-benzenesulfonyl)-piperazine-1,3-dicarboxylic acid 1-ethylamide 3-(4-isopropyl-benzylamide) (Example 177), (R)-4-(4-trifluoromethyl-benzenesulfonyl)-piperazine-1,3-dicarboxylic acid 3-(4-isopropyl-benzylamide) 1-phenylamide (Example 178), (R)-4-(4,5-dihydro-thiazol-2-yl)-1-(4-trifluoromethyl-benzenesulfonyl)-piperazine-2-carboxylic acid 4-isopropyl-benzylamide (Example 179), (R)-4-(2-morpholin-4-yl-acetyl)-1-(4-trifluoromethyl-benzenesulfonyl)-piperazine-2-carboxylic acid 4-isopropyl-benzylamide (Example 180), 4-acetyl-1-(4-isopropyl-benzenesulfonyl)-piperazine-2-carboxylic acid 4-[(2-hydroxy-ethyl)-methyl-amino]-benzylamide (Example 181), (R)-4-acetyl-1-(4-isopropyl-benzenesulfonyl)-piperazine-2-carboxylic acid 4-bromo-2-chloro-benzylamide (Example 182), (R)-4-acetyl-1-(4-isopropyl-benzenesulfonyl)-piperazine-2-carboxylic acid 2-chloro-4-isopropyl-benzylamide (Example 183), (R)-4-(4-methyl-thiazol-2-yl)-1-(4-trifluoromethyl-benzenesulfonyl)-piperazine-2-carboxylic acid 4-isopropyl-benzylamide (Example 184), (R)-4-(2-acetylamino-acetyl)-1-(4-trifluoromethyl-benzenesulfonyl)-piperazine-2-carboxylic acid 4-isopropyl-benzylamide (Example 185), {3-[(R)-3-(4-isopropyl-benzylcarbamoyl)-4-(4-trifluoromethyl-benzenesulfonyl)-piperazin-1-yl]-3-oxo-propyl}-carbamic acid tert-butyl ester (Example 186), 4-[(R)-3-(4-isopropyl-benzylcarbamoyl)-4-(4-trifluoromethyl-benzenesulfonyl)-piperazin-1-yl]-4-oxo-butyric acid (Example 187), (R)-4-(3-acetylamino-propionyl)-1-(4-trifluoromethyl-benzenesulfonyl)-piperazine-2-carboxylic acid 4-isopropyl-benzylamide (Example 188), (R)-4-(3-amino-propionyl)-1-(4-trifluoromethyl-benzenesulfonyl)-piperazine-2-carboxylic acid 4-isopropyl-benzylamide hydrochloride (Example 189), 5-[(R)-3-(4-isopropyl-benzylcarbamoyl)-4-(4-trifluoromethyl-benzenesulfonyl)-piperazin-1-yl]-5-oxo-pentanoic acid (Example 190), (R)-4-benzothiazol-2-yl-1-(4-trifluoromethyl-benzenesulfonyl)-piperazine-2-carboxylic acid 4-isopropyl-benzylamide (Example 191), (R)-4-acetyl-1-(4-ethoxy-benzenesulfonyl)-piperazine-2-carboxylic acid 4-isopropyl-benzylamide (Example 192), (R)-4-acetyl-1-(4-propoxy-benzenesulfonyl)-piperazine-2-carboxylic acid 4-isopropyl-benzylamide (Example 193), (R)-4-acetyl-1-(4-isobutyl-benzenesulfonyl)-piperazine-2-carboxylic acid 4-isopropyl-benzylamide (Example 194), (R)-4-(2-1H-imidazol-4-yl-acetyl)-1-(4-trifluoromethyl-benzenesulfonyl)-piperazine-2-carboxylic acid 4-isopropyl-benzylamide (Example 195), 4-acetyl-1-cyclohexanesulfonyl-piperazine-2-carboxylic acid 4-trifluoromethyl-benzylamide (Example 196), 4-acetyl-1-(4-isopropyl-benzenesulfonyl)-piperazine-2-carboxylic acid 2,4-dimethoxy-benzylamide (Example 197), 4-acetyl-1-(4-isopropyl-benzenesulfonyl)-piperazine-2-carboxylic acid 3,4-dimethoxy-benzylamide (Example 198), 4-{[(R)-3-(4-isopropyl-benzylcarbamoyl)-4-(4-trifluoromethyl-benzenesulfonyl)-piperazine-1-carbonyl]-amino}-butyric acid (Example 199), (R)-4-(4-trifluoromethyl-benzenesulfonyl)-piperazine-1,3-dicarboxylic acid 1-[(4-dimethylamino-phenyl)-amide] 3-(4-isopropyl-benzylamide) (Example 200), (R)-4-(pyridine-4-carbonyl)-1-(4-trifluoromethyl-benzenesulfonyl)-piperazine-2-carboxylic acid 4-isopropyl-benzylamide (Example 201), 4-acetyl-1-(4-isopropyl-benzenesulfonyl)-piperazine-2-carboxylic acid 4-(methyl-propyl-amino)-benzylamide (Example 202), (R)-4-acetyl-1-(5,6,7,8-tetrahydro-naphthalene-2-sulfonyl)-piperazine-2-carboxylic acid 4-isopropyl-benzylamide (Example 203), (R)-4-acetyl-1-(indane-5-sulfonyl)-piperazine-2-carboxylic acid 4-isopropyl-benzylamide (Example 204), (R)-4-acetyl-1-(4-propyl-benzenesulfonyl)-piperazine-2-carboxylic acid 4-isopropyl-benzylamide (Example 205), (R)-4-acetyl-1-(biphenyl-4-sulfonyl)-piperazine-2-carboxylic acid 4-isopropyl-benzylamide (Example 206), (R)-4-acetyl-1-(4-trifluoromethoxy-benzenesulfonyl)-piperazine-2-carboxylic acid 4-isopropyl-benzylamide (Example 207), (R)-4-acetyl-1-(4-tert-butyl-benzenesulfonyl)-piperazine-2-carboxylic acid 4-isopropyl-benzylamide (Example 208), (R)-1-(4-trifluoromethyl-benzenesulfonyl)-piperazine-2-carboxylic acid 4-dimethylamino-benzylamide dihydrochloride (Example 209), 4-acetyl-1-(4-isopropyl-benzenesulfonyl)-piperazine-2-carboxylic acid 4-methyl-benzylamide (Example 210), (R)-4-(4-trifluoromethyl-benzenesulfonyl)-piperazine-1,3-dicarboxylic acid 3-(4-isopropyl-benzylamide) 1-pyridin-3-ylamide (Example 211), 6-[(R)-3-(4-isopropyl-benzylcarbamoyl)-4-(4-trifluoromethyl-benzenesulfonyl)-piperazin-1-yl]-6-oxo-hexanoic acid methyl ester (Example 212), 6-[(R)-3-(4-isopropyl-benzylcarbamoyl)-4-(4-trifluoromethyl-benzenesulfonyl)-piperazin-1-yl]-6-oxo-hexanoic acid (Example 213), (R)-4-acetyl-1-(4-methoxy-benzenesulfonyl)-piperazine-2-carboxylic acid 4-isopropyl-benzylamide (Example 214), (R)-4-acetyl-1-(3-isopropyl-4-methoxy-benzenesulfonyl)-piperazine-2-carboxylic acid 4-isopropyl-benzylamide (Example 215), (R)-4-acetyl-1-(3-chloro-4-methoxy-benzenesulfonyl)-piperazine-2-carboxylic acid 4-isopropyl-benzylamide (Example 216), {5-[(R)-4-acetyl-2-(4-isopropyl-benzylcarbamoyl)-piperazine-1-sulfonyl]-2-methoxy-phenyl}-acetic acid methyl ester (Example 217), 3-{5-[(R)-4-acetyl-2-(4-isopropyl-benzylcarbamoyl)-piperazine-1-sulfonyl]-2-methoxy-phenyl}-propionic acid methyl ester (Example 218), (R)-4-(2-imidazol-1-yl-acetyl)-1-(4-trifluoromethyl-benzenesulfonyl)-piperazine-2-carboxylic acid 4-isopropyl-benzylamide (Example 219), (R)-4-(2-[1,2,3]triazol-1-yl-acetyl)-1-(4-trifluoromethyl-benzenesulfonyl)-piperazine-2-carboxylic acid 4-isopropyl-benzylamide (Example 220), {5-[(R)-4-acetyl-2-(4-isopropyl-benzylcarbamoyl)-piperazine-1-sulfonyl]-2-methoxy-phenyl}-acetic acid (Example 221), 3-{5-[(R)-4-acetyl-2-(4-isopropyl-benzylcarbamoyl)-piperazine-1-sulfonyl]-2-methoxy-phenyl}-propionic acid (Example 222), 2-[4-({[(R)-4-acetyl-1-(4-isopropyl-benzenesulfonyl)-piperazine-2-carbonyl]-amino}-methyl)-phenyl]-2-methyl-propionic acid methyl ester (Example 223), (R)-4-acetyl-1-(4-isopropyl-benzenesulfonyl)-piperazine-2-carboxylic acid 4-(2-hydroxy-ethyl)-benzylamide (Example 224), (R)-4-(2-amino-acetyl)-1-(4-trifluoromethyl-benzenesulfonyl)-piperazine-2-carboxylic acid 4-isopropyl-benzylamide hydrochloride (Example 225), (R)-4-acetyl-1-(4-isopropyl-benzenesulfonyl)-piperazine-2-carboxylic acid 4-hydroxymethyl-benzylamide (Example 226), (R)-4-acetyl-1-(4-isopropyl-benzenesulfonyl)-piperazine-2-carboxylic acid 4-methylsulfanyl-benzylamide (Example 227), (R)-4-(2-pyrazol-1-yl-acetyl)-1-(4-trifluoromethyl-benzenesulfonyl)-piperazine-2-carboxylic acid 4-isopropyl-benzylamide (Example 228), (R)-4-(2-[1,2,4]triazol-1-yl-acetyl)-1-(4-trifluoromethyl-benzenesulfonyl)-piperazine-2-carboxylic acid 4-isopropyl-benzylamide (Example 229), (R)-4-(2-[1,2,4]triazol-4-yl-acetyl)-1-(4-trifluoromethyl-benzenesulfonyl)-piperazine-2-carboxylic acid 4-isopropyl-benzylamide (Example 230), 2-[4-({[(R)-4-acetyl-1-(4-isopropyl-benzenesulfonyl)-piperazine-2-carbonyl]-amino}-methyl)-phenyl]-2-methyl-propionic acid (Example 231), (R)-4-acetyl-1-(4-isopropyl-benzenesulfonyl)-piperazine-2-carboxylic acid 4-ethyl-benzylamide (Example 232), (R)-4-acetyl-1-(4-isopropyl-benzenesulfonyl)-piperazine-2-carboxylic acid 4-(1-dimethylcarbamoyl-1-methyl-ethyl)-benzylamide (Example 233), (R)-4-acetyl-1-(4-isopropyl-benzenesulfonyl)-piperazine-2-carboxylic acid 4-(1-hydroxymethyl-cyclopropyl)-benzylamide (Example 234), 5-[(R)-4-acetyl-2-(4-isopropyl-benzylcarbamoyl)-piperazine-1-sulfonyl]-2-methoxy-benzoic acid methyl ester (Example 235), (R)-4-acetyl-1-(3-ethyl-4-methoxy-benzenesulfonyl)-piperazine-2-carboxylic acid 4-isopropyl-benzylamide (Example 236), (R)-4-acetyl-1-[4-(2,2-dimethyl-propyl)-benzenesulfonyl]-piperazine-2-carboxylic acid 4-isopropyl-benzylamide (Example 237), {4-[(R)-4-acetyl-2-(4-isopropyl-benzylcarbamoyl)-piperazine-1-sulfonyl]-phenoxy}-acetic acid methyl ester (Example 238), (R)-4-acetyl-1-(3-cyano-4-methoxy-benzenesulfonyl)-piperazine-2-carboxylic acid 4-isopropyl-benzylamide (Example 239), (R)-4-acetyl-1-(3-tert-butyl-4-methoxy-benzenesulfonyl)-piperazine-2-carboxylic acid 4-isopropyl-benzylamide (Example 240), (R)-4-acetyl-1-(3-cyclopentyl-4-methoxy-benzenesulfonyl)-piperazine-2-carboxylic acid 4-isopropyl-benzylamide (Example 241), (R)-4-(2-[1,2,3]triazol-2-yl-acetyl)-1-(4-trifluoromethyl-benzenesulfonyl)-piperazine-2-carboxylic acid 4-isopropyl-benzylamide (Example 242), (R)-4-(4-trifluoromethyl-benzenesulfonyl)-piperazine-1,3-dicarboxylic acid 1-benzylamide 3-(4-isopropyl-benzylamide) (Example 243), 2-[(R)-3-(4-isopropyl-benzylcarbamoyl)-4-(4-trifluoromethyl-benzenesulfonyl)-piperazin-1-yl]-thiazole-4-carboxylic acid (Example 244),
(4-{[(R)-3-(4-isopropyl-benzylcarbamoyl)-4-(4-trifluoromethyl-benzenesulfonyl)-piperazine-1-carbonyl]-amino}-phenoxy)-acetic acid ethyl ester (Example 245),
(4-{[(R)-3-(4-isopropyl-benzylcarbamoyl)-4-(4-trifluoromethyl-benzenesulfonyl)-piperazine-1-carbonyl]-amino}-phenoxy)-acetic acid (Example 246),
(R)-4-acetyl-1-(4-propyl-benzenesulfonyl)-piperazine-2-carboxylic acid 4-ethyl-benzylamide (Example 247),
5-[(R)-4-acetyl-2-(4-isopropyl-benzylcarbamoyl)-piperazine-1-sulfonyl]-2-methoxy-benzoic acid (Example 248),
{4-[(R)-4-acetyl-2-(4-isopropyl-benzylcarbamoyl)-piperazine-1-sulfonyl]-phenoxy}-acetic acid (Example 249),
3-{4-[(R)-4-acetyl-2-(4-isopropyl-benzylcarbamoyl)-piperazine-1-sulfonyl]-phenoxy}-propionic acid methyl ester (Example 250),
(R)-4-acetyl-1-(4-hydroxy-benzenesulfonyl)-piperazine-2-carboxylic acid 4-isopropyl-benzylamide (Example 251),
N-{2-[(R)-3-(4-isopropyl-benzylcarbamoyl)-4-(4-trifluoromethyl-benzenesulfonyl)-piperazin-1-yl]-2-oxo-ethyl}-succinamic acid methyl ester (Example 252),
(R)-4-acetyl-1-(4-isopropyl-benzenesulfonyl)-piperazine-2-carboxylic acid 4-tert-butyl-benzylamide (Example 253),
2-[(R)-3-(4-isopropyl-benzylcarbamoyl)-4-(4-trifluoromethyl-benzenesulfonyl)-piperazin-1-yl]-4-methyl-thiazole-5-carboxylic acid methyl ester (Example 254),
{2-[(R)-3-(4-isopropyl-benzylcarbamoyl)-4-(4-trifluoromethyl-benzenesulfonyl)-piperazin-1-yl]-thiazol-4-yl}-acetic acid methyl ester (Example 255),
(3-{[(R)-3-(4-isopropyl-benzylcarbamoyl)-4-(4-trifluoromethyl-benzenesulfonyl)-piperazine-1-carbonyl]-amino}-phenoxy)-acetic acid ethyl ester (Example 256),
(R)-4-(2-tetrazol-1-yl-acetyl)-1-(4-trifluoromethyl-benzenesulfonyl)-piperazine-2-carboxylic acid 4-isopropyl-benzylamide (Example 257),
(R)-4-(2-cyano-acetyl)-1-(4-trifluoromethyl-benzenesulfonyl)-piperazine-2-carboxylic acid 4-isopropyl-benzylamide (Example 258),
{2-[(R)-3-(4-isopropyl-benzylcarbamoyl)-4-(4-trifluoromethyl-benzenesulfonyl)-piperazin-1-yl]-thiazol-4-yl}-acetic acid (Example 259),
(3-{[(R)-3-(4-isopropyl-benzylcarbamoyl)-4-(4-trifluoromethyl-benzenesulfonyl)-piperazine-1-carbonyl]-amino}-phenoxy)-acetic acid (Example 260),
(R)-4-(2-1H-tetrazol-5-yl-acetyl)-1-(4-trifluoromethyl-benzenesulfonyl)-piperazine-2-carboxylic acid 4-isopropyl-benzylamide (Example 261),
(R)-4-(2-amino-acetyl)-1-(4-trifluoromethyl-benzenesulfonyl)-piperazine-2-carboxylic acid 4-dimethylamino-benzylamide dihydrochloride (Example 262),
(R)-4-acetyl-1-(3-trifluoromethyl-benzenesulfonyl)-piperazine-2-carboxylic acid 4-isopropyl-benzylamide (Example 263),
(R)-4-acetyl-1-(6,7,8,9-tetrahydro-5H-benzocycloheptene-2-sulfonyl)-piperazine-2-carboxylic acid 4-isopropyl-benzylamide (Example 264),
(R)-4-benzenesulfonylaminocarbonyl-1-(4-trifluoromethyl-benzenesulfonyl)-piperazine-2-carboxylic acid 4-isopropyl-benzylamide (Example 265),
(R)-4-[2-(4-methoxy-phenyl)-acetyl]-1-(4-trifluoromethyl-benzenesulfonyl)-piperazine-2-carboxylic acid 4-isopropyl-benzylamide (Example 266),
(R)-4-[2-(2-methoxy-phenyl)-acetyl]-1-(4-trifluoromethyl-benzenesulfonyl)-piperazine-2-carboxylic acid 4-isopropyl-benzylamide (Example 267),
(R)-4-[2-(3-methoxy-phenyl)-acetyl]-1-(4-trifluoromethyl-benzenesulfonyl)-piperazine-2-carboxylic acid 4-isopropyl-benzylamide (Example 268),
(R)-4-(4-trifluoromethyl-benzenesulfonyl)-piperazine-1,3-dicarboxylic acid 1-[(2-chloro-phenyl)-amide] 3-(4-isopropyl-benzylamide) (Example 269),
(R)-4-(4-trifluoromethyl-benzenesulfonyl)-piperazine-1,3-dicarboxylic acid 1-[(3-chloro-phenyl)-amide] 3-(4-isopropyl-benzylamide) (Example 270),
(R)-4-(4-trifluoromethyl-benzenesulfonyl)-piperazine-1,3-dicarboxylic acid 1-[(4-chloro-phenyl)-amide] 3-(4-isopropyl-benzylamide) (Example 271),
(R)-4-(4-trifluoromethyl-benzenesulfonyl)-piperazine-1,3-dicarboxylic acid 3-(4-isopropyl-benzylamide) 1-[(2-methoxy-phenyl)-amide] (Example 272),
(R)-4-(4-trifluoromethyl-benzenesulfonyl)-piperazine-1,3-dicarboxylic acid 3-(4-isopropyl-benzylamide) 1-[(3-methoxy-phenyl)-amide] (Example 273),
N-{2-[(R)-3-(4-isopropyl-benzylcarbamoyl)-4-(4-trifluoromethyl-benzenesulfonyl)-piperazin-1-yl]-2-oxo-ethyl}-succinamic acid (Example 274),
3-{[(R)-3-(4-isopropyl-benzylcarbamoyl)-4-(4-trifluoromethyl-benzenesulfonyl)-piperazine-1-carbonyl]-amino}-benzoic acid methyl ester (Example 275),
4-{[(R)-3-(4-isopropyl-benzylcarbamoyl)-4-(4-trifluoromethyl-benzenesulfonyl)-piperazine-1-carbonyl]-amino}-benzoic acid methyl ester (Example 276),
(R)-4-(4-trifluoromethyl-benzenesulfonyl)-piperazine-1,3-dicarboxylic acid 3-(4-isopropyl-benzylamide) 1-[(4-methoxy-phenyl)-amide] (Example 277),
(R)-4-(2-tetrazol-2-yl-acetyl)-1-(4-trifluoromethyl-benzenesulfonyl)-piperazine-2-carboxylic acid 4-isopropyl-benzylamide (Example 278),
(R)-4-(2-methoxy-acetyl)-1-(4-trifluoromethyl-benzenesulfonyl)-piperazine-2-carboxylic acid 4-isopropyl-benzylamide (Example 279),
4-acetyl-1-(4-isopropyl-benzenesulfonyl)-piperazine-2-carboxylic acid 4-cyclopropyl-benzylamide (Example 280),
(3-{[(R)-3-(4-isopropyl-benzylcarbamoyl)-4-(4-propyl-benzenesulfonyl)-piperazine-1-carbonyl]-amino}-phenoxy)-acetic acid ethyl ester (Example 281),
(3-{[(R)-3-(4-isopropyl-benzylcarbamoyl)-4-(4-propyl-benzenesulfonyl)-piperazine-1-carbonyl]-amino}-phenoxy)-acetic acid (Example 282),
3-{5-[(R)-4-acetyl-2-(4-isopropyl-benzylcarbamoyl)-piperazine-1-sulfonyl]-thiophen-2-yl}-propionic acid (Example 283),
(R)-4-acetyl-1-[4-(2,2,2-trifluoro-ethoxy)-benzenesulfonyl]-piperazine-2-carboxylic acid 4-isopropyl-benzylamide (Example 284),
4-{[(R)-3-(4-isopropyl-benzylcarbamoyl)-4-(4-trifluoromethyl-benzenesulfonyl)-piperazine-1-carbonyl]-amino}-benzoic acid (Example 285),
3-{[(R)-3-(4-isopropyl-benzylcarbamoyl)-4-(4-trifluoromethyl-benzenesulfonyl)-piperazine-1-carbonyl]-amino}-benzoic acid (Example 286),
(R)-4-acetyl-1-(5-propyl-thiophene-2-sulfonyl)-piperazine-2-carboxylic acid 4-isopropyl-benzylamide (Example 287),
(R)-4-acetyl-1-[4-methoxy-3-(2H-tetrazol-5-yl)-benzenesulfonyl]-piperazine-2-carboxylic acid 4-isopropyl-benzylamide (Example 288),
{5-[(R)-4-acetyl-2-(4-isopropyl-benzylcarbamoyl)-piperazine-1-sulfonyl]-thiophen-2-yl}-acetic acid (Example 289),

[(R)-3-(4-isopropyl-benzylcarbamoyl)-4-(4-trifluoromethyl-benzenesulfonyl)-piperazin-1-yl]-oxo-acetic acid ethyl ester (Example 290), (R)-4-acetyl-1-(4-isopropyl-benzenesulfonyl)-piperazine-2-carboxylic acid 4-isopropyl-2-methyl-benzylamide (Example 291), (R)-4-acetyl-1-(4-isopropyl-benzenesulfonyl)-piperazine-2-carboxylic acid 2-fluoro-4-isopropyl-benzylamide (Example 292), (R)-4-acetyl-1-(4-isopropyl-benzenesulfonyl)-piperazine-2-carboxylic acid 4-(1,1-difluoro-ethyl)-benzylamide (Example 293), (R)-4-acetyl-1-(4-isopropyl-benzenesulfonyl)-piperazine-2-carboxylic acid 4-propyl-benzylamide (Example 294), (R)-4-(4-propyl-benzenesulfonyl)-piperazine-1,3-dicarboxylic acid 3-(4-isopropyl-benzylamide) 1-pyridin-4-ylamide (Example 295), 2-[(R)-3-(4-isopropyl-benzylcarbamoyl)-4-(4-propyl-benzenesulfonyl)-piperazin-1-yl]-thiazole-4-carboxylic acid ethyl ester (Example 296), 2-[(R)-3-(4-isopropyl-benzylcarbamoyl)-4-(4-propyl-benzenesulfonyl)-piperazin-1-yl]-4-methyl-thiazole-5-carboxylic acid methyl ester (Example 297), 2-[(R)-3-(4-isopropyl-benzylcarbamoyl)-4-(4-propyl-benzenesulfonyl)-piperazin-1-yl]-thiazole-4-carboxylic acid (Example 298), 2-[(R)-3-(4-isopropyl-benzylcarbamoyl)-4-(4-propyl-benzenesulfonyl)-piperazin-1-yl]-4-methyl-thiazole-5-carboxylic acid (Example 299), (R)-4-(4-trifluoromethyl-benzenesulfonyl)-piperazine-1,3-dicarboxylic acid 3-(4-isopropyl-benzylamide) 1-pyrimidin-4-ylamide (Example 300), 4-{[(R)-3-(4-isopropyl-benzylcarbamoyl)-4-(4-trifluoromethyl-benzenesulfonyl)-piperazine-1-carbonyl]-amino}-pyridine-2-carboxylic acid tert-butyl ester (Example 301), 2-[(R)-3-(4-isopropyl-benzylcarbamoyl)-4-(4-trifluoromethyl-benzenesulfonyl)-piperazin-1-yl]-thiazole-5-carboxylic acid methyl ester (Example 302), 6-[(R)-3-(4-isopropyl-benzylcarbamoyl)-4-(4-trifluoromethyl-benzenesulfonyl)-piperazin-1-yl]-nicotinic acid methyl ester (Example 303), (R)-4-(2-pyridin-4-yl-ethyl)-1-(4-trifluoromethyl-benzenesulfonyl)-piperazine-2-carboxylic acid 4-isopropyl-benzylamide (Example 304), 5-[(R)-4-acetyl-2-(4-isopropyl-benzylcarbamoyl)-piperazine-1-sulfonyl]-2-trifluoromethoxy-benzoic acid (Example 305), (R)-4-acetyl-1-(2,2,3,3-tetrafluoro-2,3-dihydro-benzo[1,4]dioxine-6-sulfonyl)-piperazine-2-carboxylic acid 4-isopropyl-benzylamide (Example 306), (R)-4-acetyl-1-(1-methyl-1,2,3,4-tetrahydro-quinoline-7-sulfonyl)-piperazine-2-carboxylic acid 4-isopropyl-benzylamide (Example 307), (R)-4-aminooxalyl-1-(4-trifluoromethyl-benzenesulfonyl)-piperazine-2-carboxylic acid 4-isopropyl-benzylamide (Example 308), (2-{2-[(R)-3-(4-isopropyl-benzylcarbamoyl)-4-(4-trifluoromethyl-benzenesulfonyl)-piperazin-1-yl]-2-oxo-ethyl}-2H-tetrazol-5-yl)-acetic acid ethyl ester (Example 309), (2-{2-[(R)-3-(4-isopropyl-benzylcarbamoyl)-4-(4-trifluoromethyl-benzenesulfonyl)-piperazin-1-yl]-2-oxo-ethyl}-2H-tetrazol-5-yl)-acetic acid (Example 310), (1-{2-[(R)-3-(4-isopropyl-benzylcarbamoyl)-4-(4-trifluoromethyl-benzenesulfonyl)-piperazin-1-yl]-2-oxo-ethyl}-1H-tetrazol-5-yl)-acetic acid ethyl ester (Example 311), (1-{2-[(R)-3-(4-isopropyl-benzylcarbamoyl)-4-(4-trifluoromethyl-benzenesulfonyl)-piperazin-1-yl]-2-oxo-ethyl}-1H-tetrazol-5-yl)-acetic acid (Example 312), (R)-4-carbamimidoyl-1-(4-trifluoromethyl-benzenesulfonyl)-piperazine-2-carboxylic acid 4-isopropyl-benzylamide hydrochloride (Example 313), 4-{[(R)-3-(4-isopropyl-benzylcarbamoyl)-4-(4-trifluoromethyl-benzenesulfonyl)-piperazine-1-carbonyl]-amino}-pyridine-2-carboxylic acid hydrochloride (Example 314), 2-[(R)-3-(4-isopropyl-benzylcarbamoyl)-4-(4-trifluoromethyl-benzenesulfonyl)-piperazin-1-yl]-thiazole-5-carboxylic acid (Example 315), 7-[(R)-3-(4-isopropyl-benzylcarbamoyl)-4-(4-trifluoromethyl-benzenesulfonyl)-piperazin-1-yl]-7-oxo-heptanoic acid ethyl ester (Example 316), 7-[(R)-3-(4-isopropyl-benzylcarbamoyl)-4-(4-trifluoromethyl-benzenesulfonyl)-piperazin-1-yl]-7-oxo-heptanoic acid (Example 317), (R)-4-(4-trifluoromethoxy-benzenesulfonyl)-piperazine-1,3-dicarboxylic acid 3-(4-isopropyl-benzylamide) 1-pyridin-4-ylamide (Example 318), 2-[(R)-3-(4-isopropyl-benzylcarbamoyl)-4-(4-propyl-benzenesulfonyl)-piperazin-1-yl]-4-methyl-thiazole-5-carboxylic acid tert-butyl ester (Example 319), 2-[(R)-3-(4-isopropyl-benzylcarbamoyl)-4-(4-trifluoromethoxy-benzenesulfonyl)-piperazin-1-yl]-4-methyl-thiazole-5-carboxylic acid tert-butyl ester (Example 320), (R)-4-acetyl-1-(4-isopropyl-benzenesulfonyl)-piperazine-2-carboxylic acid 4-ethyl-2-methyl-benzylamide (Example 321), 2-[(R)-3-(4-isopropyl-benzylcarbamoyl)-4-(4-trifluoromethoxy-benzenesulfonyl)-piperazin-1-yl]-4-methyl-thiazole-5-carboxylic acid (Example 322), (R)-4-acetyl-1-(4-isopropyl-benzenesulfonyl)-piperazine-2-carboxylic acid 4-cyclopropyl-2-methyl-benzylamide (Example 323), 3-{5-[(R)-4-acetyl-2-(4-isopropyl-benzylcarbamoyl)-piperazine-1-sulfonyl]-2-trifluoromethoxy-phenyl}-propionic acid (Example 324), 4-hydroxy-2-[(R)-3-(4-isopropyl-benzylcarbamoyl)-4-(4-trifluoromethyl-benzenesulfonyl)-piperazin-1-yl]-pyrimidine-5-carboxylic acid ethyl ester (Example 325), 6-[(R)-3-(4-isopropyl-benzylcarbamoyl)-4-(4-trifluoromethyl-benzenesulfonyl)-piperazin-1-yl]-nicotinic acid tert-butyl ester (Example 326), 6-[(R)-3-(4-isopropyl-benzylcarbamoyl)-4-(4-trifluoromethyl-benzenesulfonyl)-piperazin-1-yl]-nicotinic acid trifluoroacetate (Example 327), 2-[(R)-3-(4-isopropyl-benzylcarbamoyl)-4-(4-trifluoromethoxy-benzenesulfonyl)-piperazin-1-yl]-thiazole-5-carboxylic acid (Example 328), 2-[(R)-3-(4-isopropyl-benzylcarbamoyl)-4-(4-propyl-benzenesulfonyl)-piperazin-1-yl]-thiazole-5-carboxylic acid (Example 329), 2-[(R)-3-(4-isopropyl-2-methyl-benzylcarbamoyl)-4-(4-propyl-benzenesulfonyl)-piperazin-1-yl]-4-methyl-thiazole-5-carboxylic acid tert-butyl ester (Example 330), 2-[(R)-3-(4-isopropyl-2-methyl-benzylcarbamoyl)-4-(4-propyl-benzenesulfonyl)-piperazin-1-yl]-4-methyl-thiazole-5-carboxylic acid (Example 331), (R)-4-(4-trifluoromethyl-benzenesulfonyl)-piperazine-1,3-dicarboxylic acid 3-(4-isopropyl-benzylamide) 1-[1,3,4]thiadiazol-2-ylamide (Example 332), (R)-4-(5-carbamoyl-4-methyl-thiazol-2-yl)-1-(4-propyl-benzenesulfonyl)-piperazine-2-carboxylic acid 4-isopropyl-benzylamide (Example 333), 5-{[(R)-3-(4-isopropyl-benzylcarbamoyl)-4-(4-trifluoromethyl-benzenesulfonyl)-piperazine-1-carbonyl]-amino}-[1,3,4]oxadiazole-2-carboxylic acid ethyl ester (Example 334), 2-[(R)-3-(4-isopropyl-2-methyl-benzylcarbamoyl)-4-(4-trifluoromethyl-benzenesulfonyl)-piperazin-1-yl]-4-methyl-thiazole-5-carboxylic acid (Example 335), 2-[(R)-3-(4-isopropyl-benzylcarbamoyl)-4-(4-trifluoromethyl-benzenesulfonyl)-piperazin-1-yl]-4-methyl-pyrimidine-5-carboxylic acid benzyl ester (Example 336), 2-[(R)-3-(4-isopropyl-benzylcarbamoyl)-4-(4-trifluoromethyl-benzenesulfonyl)-piperazin-1-yl]-4-methyl-pyrimidine-5-carboxylic acid methyl ester (Example 337), 2-[(R)-3-(4-isopropyl-benzylcarbamoyl)-4-(4-trifluoromethyl-benzenesulfonyl)-piperazin-1-yl]-4-methyl-pyrimidine-5-carboxylic acid (Example 338), 4-methyl-2-[(R)-3-(4-propyl-benzylcarbamoyl)-4-(4-trifluoromethyl-benzenesulfonyl)-piperazin-1-yl]-thiazole-5-carboxylic acid (Example 339), (R)-4-(5-carbamoyl-4-methyl-thiazol-2-yl)-1-(4-trifluoromethoxy-benzenesulfonyl)-piperazine-2-carboxylic acid 4-isopropyl-benzylamide (Example 340), 4-methyl-2-[(R)-3-(2-methyl-4-propyl-benzylcarbamoyl)-4-(4-trifluoromethoxy-benzenesulfonyl)-piperazin-1-yl]-thiazole-5-carboxylic acid (Example 341), 2-[(R)-3-(4-isopropyl-benzylcarbamoyl)-4-(4-trifluoromethyl-benzenesulfonyl)-piperazin-1-yl]-pyrimidine-5-carboxylic acid (Example 342), 2-[(R)-3-(4-dimethylamino-benzylcarbamoyl)-4-(4-trifluoromethyl-benzenesulfonyl)-piperazin-1-yl]-4-methyl-thiazole-5-carboxylic acid (Example 343), 2-[(R)-4-(4-isopropyl-benzenesulfonyl)-3-(4-isopropyl-benzylcarbamoyl)-piperazin-1-yl]-4-methyl-thiazole-5-carboxylic acid (Example 344), (R)-4-(2-oxo-pyrrolidin-3-yl)-1-(4-trifluoromethyl-benzenesulfonyl)-piperazine-2-carboxylic acid 4-isopropyl-benzylamide (Example 345), 1-(4-iodo-benzenesulfonyl)-4-[2-(4-methyl-piperazin-1-yl)-acetyl]-piperazine-2-carboxylic acid 4-dimethylamino-benzylamide (Example 346), (R)-4-(4-trifluoromethyl-benzenesulfonyl)-piperazine-1,3-dicarboxylic acid 3-(4-isopropyl-benzylamide) 1-pyridin-4-ylamide (Example 347), (R)-4-(4-trifluoromethyl-benzenesulfonyl)-piperazine-1,3-dicarboxylic acid 3-(4-isopropyl-benzylamide) 1-[1,3,4]oxadiazol-2-ylamide (Example 348), 2-[(R)-3-(4-isopropyl-benzylcarbamoyl)-4-(4-trifluoromethyl-benzenesulfonyl)-piperazin-1-yl]-isonicotinic acid trifluoroacetate (Example 349), 4-(4-isopropyl-benzenesulfonyl)-piperazine-1,3-dicarboxylic acid 1-amide 3-(4-trifluoromethyl-benzylamide) (Example 350), 4-acetyl-1-(3,5-dichloro-benzenesulfonyl)-piperazine-2-carboxylic acid 4-trifluoromethyl-benzylamide (Example 351), (R)-4-(1-methyl-1H-imidazol-2-yl)-1-(4-trifluoromethyl-benzenesulfonyl)-piperazine-2-carboxylic acid 4-isopropyl-benzylamide (Example 352), (R)-4-(1H-imidazol-2-yl)-1-(4-trifluoromethyl-benzenesulfonyl)-piperazine-2-carboxylic acid 4-isopropyl-benzylamide (Example 353), (R)-4-(4-methyl-5-methylcarbamoyl-thiazol-2-yl)-1-(4-trifluoromethoxy-benzenesulfonyl)-piperazine-2-carboxylic acid 4-isopropyl-benzylamide (Example 354), (R)-4-(5-dimethylcarbamoyl-4-methyl-thiazol-2-yl)-1-(4-trifluoromethoxy-benzenesulfonyl)-piperazine-2-carboxylic acid 4-isopropyl-benzylamide (Example 355), 2-[(R)-3-(4-cyclopropyl-2-methyl-benzylcarbamoyl)-4-(4-trifluoromethoxy-benzenesulfonyl)-piperazin-1-yl]-4-methyl-thiazole-5-carboxylic acid (Example 356), 4-hydroxy-2-[(R)-3-(4-isopropyl-benzylcarbamoyl)-4-(4-trifluoromethyl-benzenesulfonyl)-piperazin-1-yl]-pyrimidine-5-carboxylic acid (Example 357), ({2-[(R)-3-(4-isopropyl-benzylcarbamoyl)-4-(4-trifluoromethoxy-benzenesulfonyl)-piperazin-1-yl]-4-methyl-thiazole-5-carbonyl}-amino)-acetic acid tert-butyl ester (Example 358), 3-({2-[(R)-3-(4-isopropyl-benzylcarbamoyl)-4-(4-trifluoromethoxy-benzenesulfonyl)-piperazin-1-yl]-4-methyl-thiazole-5-carbonyl}-amino)-propionic acid tert-butyl ester (Example 359), ({2-[(R)-3-(4-isopropyl-benzylcarbamoyl)-4-(4-trifluoromethoxy-benzenesulfonyl)-piperazin-1-yl]-4-methyl-thiazole-5-carbonyl}-amino)-acetic acid (Example 360), 3-({2-[(R)-3-(4-isopropyl-benzylcarbamoyl)-4-(4-trifluoromethoxy-benzenesulfonyl)-piperazin-1-yl]-4-methyl-thiazole-5-carbonyl}-amino)-propionic acid (Example 361), (R)-4-(5-nitro-2H-[1,2,4]triazol-3-yl)-1-(4-trifluoromethyl-benzenesulfonyl)-piperazine-2-carboxylic acid 4-isopropyl-benzylamide (Example 362), 4-ethyl-2-[(R)-3-(2-methyl-4-propyl-benzylcarbamoyl)-4-(4-trifluoromethoxy-benzenesulfonyl)-piperazin-1-yl]-thiazole-5-carboxylic acid (Example 363), 2-[(R)-3-(4-isopropyl-2-methyl-benzylcarbamoyl)-4-(4-trifluoromethoxy-benzenesulfonyl)-piperazin-1-yl]-4-methyl-thiazole-5-carboxylic acid (Example 364), 4-methyl-2-[(R)-4-(4-trifluoromethoxy-benzenesulfonyl)-3-(4-trifluoromethoxy-benzylcarbamoyl)-piperazin-1-yl]-thiazole-5-carboxylic acid (Example 365), 2-[(R)-3-(4-ethyl-benzylcarbamoyl)-4-(4-trifluoromethoxy-benzenesulfonyl)-piperazin-1-yl]-4-methyl-thiazole-5-carboxylic acid (Example 366), 2-[(R)-3-(4-tert-butyl-benzylcarbamoyl)-4-(4-trifluoromethoxy-benzenesulfonyl)-piperazin-1-yl]-4-methyl-thiazole-5-carboxylic acid (Example 367), (R)-4-(5-amino-2H-[1,2,4]triazol-3-yl)-1-(4-trifluoromethyl-benzenesulfonyl)-piperazine-2-carboxylic acid 4-isopropyl-benzylamide (Example 368), (R)-2-({2-[(R)-3-(4-isopropyl-benzylcarbamoyl)-4-(4-trifluoromethoxy-benzenesulfonyl)-piperazin-1-yl]-4-methyl-thiazole-5-carbonyl}-amino)-propionic acid (Example 369), (S)-2-({2-[(R)-3-(4-isopropyl-benzylcarbamoyl)-4-(4-trifluoromethoxy-benzenesulfonyl)-piperazin-1-yl]-4-methyl-thiazole-5-carbonyl}-amino)-propionic acid (Example 370), 2-[(R)-3-(4-isopropyl-benzylcarbamoyl)-4-(4-trifluoromethyl-benzenesulfonyl)-piperazin-1-yl]-4-methyl-oxazole-5-carboxylic acid trifluoroacetate (Example 371), (R)-4-(5-bromo-2H-[1,2,4]triazol-3-yl)-1-(4-trifluoromethyl-benzenesulfonyl)-piperazine-2-carboxylic acid 4-isopropyl-benzylamide (Example 372), (R)-4-(2H-[1,2,4]triazol-3-yl)-1-(4-trifluoromethyl-benzenesulfonyl)-piperazine-2-carboxylic acid 4-isopropyl-benzylamide (Example 373), (R)-3-(4-propyl-benzylcarbamoyl)-4-(4-trifluoromethoxy-benzenesulfonyl)-3,4,5,6-tetrahydro-2H-[1,2']bipyrazinyl-5'-carboxylic acid (Example 374), (R)-4-acetyl-1-(2-propyl-thiazole-5-sulfonyl)-piperazine-2-carboxylic acid 4-isopropyl-benzylamide (Example 375), 6-[(R)-3-(4-isopropyl-benzylcarbamoyl)-4-(4-trifluoromethyl-benzenesulfonyl)-piperazin-1-yl]-pyridazine-3-carboxylic acid (Example 376), (R)-4-(4-trifluoromethyl-benzenesulfonyl)-3,4,5,6-tetrahydro-2H-[1,2']bipyrazinyl-3,5'-dicarboxylic acid 5'-amide 3-(4-isopropyl-benzylamide) (Example 377), 4-methyl-2-[(R)-3-(4-propyl-benzylcarbamoyl)-4-(4-trifluoromethoxy-benzenesulfonyl)-piperazin-1-yl]-thiazole-5-carboxylic acid (Example 378), 2-[(R)-3-(4-dimethylamino-benzylcarbamoyl)-4-(4-trifluoromethoxy-benzenesulfonyl)-piperazin-1-yl]-4-methyl-thiazole-5-carboxylic acid hydrochloride (Example 379), 2-[(R)-3-(4-isopropyl-benzylcarbamoyl)-4-(5-propyl-thiophene-2-sulfonyl)-piperazin-1-yl]-4-methyl-thiazole-5-carboxylic acid (Example 380), 2-[(R)-3-(4-isopropyl-benzylcarbamoyl)-4-(6,7,8,9-tetrahydro-5H-benzocycloheptene-2-sulfonyl)-piperazin-1-yl]-4-methyl-thiazole-5-carboxylic acid (Example 381), 3-{2-[(R)-3-(4-isopropyl-benzylcarbamoyl)-4-(4-trifluoromethoxy-benzenesulfonyl)-piperazin-1-yl]-thiazol-4-yl}-propionic acid (Example 382), 2-[(R)-3-(4-cyclopropyl-benzylcarbamoyl)-4-(4-trifluoromethoxy-benzenesulfonyl)-piperazin-1-yl]-4-methyl-thiazole-5-carboxylic acid (Example 383), {2-[(R)-3-(4-isopropyl-benzylcarbamoyl)-4-(4-trifluoromethyl-benzenesulfonyl)-piperazin-1-yl]-2-oxo-ethylamino}-acetic acid hydrochloride (Example 384), (R)-3-(4-isopropyl-benzylcarbamoyl)-4-(4-trifluoromethoxy-benzenesulfonyl)-3,4,5,6-tetrahydro-2H-[1,2']bipyrazinyl-5'-carboxylic acid (Example 385), (R)-4-(4-trifluoromethoxy-benzenesulfonyl)-3-(4-trifluoromethoxy-benzylcarbamoyl)-3,4,5,6-tetrahydro-2H-[1,2']bipyrazinyl-5'-carboxylic acid (Example 386), 2-[(R)-3-[(6-dimethylamino-pyridin-3-ylmethyl)-carbamoyl]-4-(4-trifluoromethoxy-benzenesulfonyl)-piperazin-1-yl]-4-methyl-thiazole-5-carboxylic acid (Example 387), 4-methyl-2-[(R)-3-[(6-propyl-pyridin-3-ylmethyl)-carbamoyl]-4-(4-trifluoromethoxy-benzenesulfonyl)-piperazin-1-yl]-thiazole-5-carboxylic acid (Example 388), 2-[(R)-3-[(6-azetidin-1-yl-pyridin-3-ylmethyl)-carbamoyl]-4-(4-trifluoromethoxy-benzenesulfonyl)-piperazin-1-yl]-4-methyl-thiazole-5-carboxylic acid (Example 389), 4-methyl-2-[(R)-3-[(6-pyrrolidin-1-yl-pyridin-3-ylmethyl)-carbamoyl]-4-(4-trifluoromethoxy-benzenesulfonyl)-piperazin-1-yl]-thiazole-5-carboxylic acid (Example 390), 3-{2-[(R)-3-(4-isopropyl-benzylcarbamoyl)-4-(4-trifluoromethyl-benzenesulfonyl)-piperazin-1-yl]-2-oxo-ethylamino}-propionic acid hydrochloride (Example 391), (R)-4-acetyl-1-(4-isopropyl-benzenesulfonyl)-piperazine-2-carboxylic acid [2-(4-methoxy-phenyl)-ethyl]-amide (Example 392), 4-(2-{[(R)-4-acetyl-1-(4-isopropyl-benzenesulfonyl)-piperazine-2-carbonyl]-amino}-ethyl)-benzoic acid (Example 393), 2-[(R)-3-(4-isopropyl-benzylcarbamoyl)-4-(4-propyl-benzenesulfonyl)-piperazin-1-yl]-4-methoxymethyl-thiazole-5-carboxylic acid (Example 394), (R)-4-acetyl-1-(4-isopropyl-benzenesulfonyl)-piperazine-2-carboxylic acid (2-pyridin-4-yl-ethyl)-amide (Example 395), (R)-4-acetyl-1-(4-isopropyl-benzenesulfonyl)-piperazine-2-carboxylic acid (2-pyridin-2-yl-ethyl)-amide (Example 396), (R)-4-acetyl-1-(4-isopropyl-benzenesulfonyl)-piperazine-2-carboxylic acid (2-pyridin-3-yl-ethyl)-amide (Example 397), 2-[(R)-3-(4-azetidin-1-yl-benzylcarbamoyl)-4-(4-trifluoromethoxy-benzenesulfonyl)-piperazin-1-yl]-4-methyl-thiazole-5-carboxylic acid (Example 398), (R)-3-(4-dimethylamino-benzylcarbamoyl)-4-(4-trifluoromethoxy-benzenesulfonyl)-3,4,5,6-tetrahydro-2H-[1,2']bipyrazinyl-5'-carboxylic acid (Example 399), (R)-4-acetyl-1-(4-cyclopropyl-benzenesulfonyl)-piperazine-2-carboxylic acid 4-isopropyl-benzylamide (Example 400), 2-[(R)-3-benzylcarbamoyl-4-(4-trifluoromethoxy-benzenesulfonyl)-piperazin-1-yl]-4-methyl-thiazole-5-carboxylic acid (Example 401), (R)-4-acetyl-1-(4-isopropyl-benzenesulfonyl)-piperazine-2-carboxylic acid (2-piperidin-1-yl-ethyl)-amide (Example 402), (R)-4-acetyl-1-(4-isopropyl-benzenesulfonyl)-piperazine-2-carboxylic acid (2-morpholin-4-yl-ethyl)-amide (Example 403), (R)-4-acetyl-1-(4-isopropyl-benzenesulfonyl)-piperazine-2-carboxylic acid (3-morpholin-4-yl-propyl)-amide (Example 404), (R)-4-acetyl-1-(4-isopropyl-benzenesulfonyl)-piperazine-2-carboxylic acid (3-pyrrolidin-1-yl-propyl)-amide (Example 405), (R)-4-(5-carbamoyl-4-methyl-thiazol-2-yl)-1-(4-trifluoromethoxy-benzenesulfonyl)-piperazine-2-carboxylic acid 4-propyl-benzylamide (Example 406), (R)-3-[(6-dimethylamino-pyridin-3-ylmethyl)-carbamoyl]-4-(4-trifluoromethoxy-benzenesulfonyl)-3,4,5,6-tetrahydro-2H-[1,2']bipyrazinyl-5'-carboxylic acid (Example 407), (R)-3-[(6-isopropyl-pyridin-3-ylmethyl)-carbamoyl]-4-(4-trifluoromethoxy-benzenesulfonyl)-3,4,5,6-tetrahydro-2H-[1,2']bipyrazinyl-5'-carboxylic acid (Example 408), (R)-4-(2-pyridin-4-yl-acetyl)-1-(4-trifluoromethoxy-benzenesulfonyl)-piperazine-2-carboxylic acid 4-trifluoromethoxy-benzylamide (Example 409), (R)-4-(2-pyridin-4-yl-acetyl)-1-(4-trifluoromethoxy-benzenesulfonyl)-piperazine-2-carboxylic acid 4-dimethylamino-benzylamide (Example 410), (R)-4-(2-pyridin-4-yl-acetyl)-1-(4-trifluoromethoxy-benzenesulfonyl)-piperazine-2-carboxylic acid 4-propyl-benzylamide (Example 411), (R)-4-(2-pyridin-4-yl-acetyl)-1-(4-trifluoromethoxy-benzenesulfonyl)-piperazine-2-carboxylic acid 4-cyclopropyl-benzylamide (Example 412), 4-[(R)-3-(4-propyl-benzylcarbamoyl)-4-(4-trifluoromethoxy-benzenesulfonyl)-piperazin-1-yl]-benzoic acid (Example 413), 2-[(R)-4-(4-ethyl-benzenesulfonyl)-3-(4-propyl-benzylcarbamoyl)-piperazin-1-yl]-4-methyl-thiazole-5-carboxylic acid (Example 414), (R)-4-(4-ethyl-benzenesulfonyl)-3-(4-propyl-benzylcarbamoyl)-3,4,5,6-tetrahydro-2H-[1,2']bipyrazinyl-5'-carboxylic acid (Example 415), 4-methyl-2-[(R)-3-(4-pyrrolidin-1-yl-benzylcarbamoyl)-4-(4-trifluoromethoxy-benzenesulfonyl)-piperazin-1-yl]-thiazole-5-carboxylic acid (Example 416), 6-[(R)-3-(4-propyl-benzylcarbamoyl)-4-(4-trifluoromethoxy-benzenesulfonyl)-piperazin-1-yl]-pyridazine-3-carboxylic acid (Example 417), 4-methyl-2-[(R)-3-phenethylcarbamoyl-4-(4-trifluoromethoxy-benzenesulfonyl)-piperazin-1-yl]-thiazole-5-carboxylic acid (Example 418), (R)-4-acetyl-1-(4-bromo-2-fluoro-benzenesulfonyl)-piperazine-2-carboxylic acid 4-isopropyl-benzylamide (Example 419), (R)-6'-amino-3'-chloro-3-(4-isopropyl-benzylcarbamoyl)-4-(4-trifluoromethyl-benzenesulfonyl)-3,4,5,6-tetrahydro-2H-[1,2']bipyrazinyl-5'-carboxylic acid methyl ester (Example 420), (R)-6'-bromo-3'-chloro-3-(4-isopropyl-benzylcarbamoyl)-4-(4-trifluoromethyl-benzenesulfonyl)-3,4,5,6-tetrahydro-2H-[1,2']bipyrazinyl-5'-carboxylic acid methyl ester (Example 421), (R)-3-(4-isopropyl-benzylcarbamoyl)-3',6'-dimethyl-4-(4-trifluoromethyl-benzenesulfonyl)-3,4,5,6-tetrahydro-2H-[1,2']bipyrazinyl-5'-carboxylic acid (Example 422), (R)-6'-amino-3-(4-isopropyl-benzylcarbamoyl)-4-(4-trifluoromethyl-benzenesulfonyl)-3,4,5,6-tetrahydro-2H-[1,2']bipyrazinyl-5'-carboxylic acid methyl ester (Example 423), 2-[(R)-3-[4-(ethyl-methyl-amino)-benzylcarbamoyl]-4-(4-trifluoromethoxy-benzenesulfonyl)-piperazin-1-yl]-4-methyl-thiazole-5-carboxylic acid (Example 424), 2-[(R)-3-(4-diethylamino-benzylcarbamoyl)-4-(4-trifluoromethoxy-benzenesulfonyl)-piperazin-1-yl]-4-methyl-thiazole-5-carboxylic acid (Example 425), 5-[(R)-3-(4-isopropyl-benzylcarbamoyl)-4-(4-trifluoromethyl-benzenesulfonyl)-piperazin-1-yl]-2H-pyrazole-3-carboxylic acid (Example 426), 4-chloro-5-[(R)-3-(4-isopropyl-benzylcarbamoyl)-4-(4-trifluoromethyl-benzenesulfonyl)-piperazin-1-yl]-2H-pyrazole-3-carboxylic acid (Example 427), (R)-4-acetyl-1-(4-cyclopropylmethyl-benzenesulfonyl)-piperazine-2-carboxylic acid 4-isopropyl-benzylamide (Example 428), (R)-4-acetyl-1-(2-fluoro-4-propyl-benzenesulfonyl)-piperazine-2-carboxylic acid 4-isopropyl-benzylamide (Example 429), (R)-4-acetyl-1-(4-bromo-benzenesulfonyl)-piperazine-2-carboxylic acid 4-isopropyl-benzylamide (Example 430), (R)-3-(4-isopropyl-benzylcarbamoyl)-3'-methyl-4-(4-trifluoromethyl-benzenesulfonyl)-3,4,5,6-tetrahydro-2H-[1,2']bipyrazinyl-5'-carboxylic acid methyl ester (Example 431), (R)-3-(2-methyl-4-propyl-benzylcarbamoyl)-4-(4-trifluoromethoxy-benzenesulfonyl)-3,4,5,6-tetrahydro-2H-[1,2']bipyrazinyl-5'-carboxylic acid (Example 432), (R)-4-acetyl-1-(4-isopropyl-benzenesulfonyl)-piperazine-2-carboxylic acid [2-(1H-imidazol-4-yl)-ethyl]-amide hydrochloride (Example 433), 2-[(R)-3-(4-isopropyl-benzylcarbamoyl)-4-(4-propyl-benzenesulfonyl)-piperazin-1-yl]-5-methyl-thiazole-4-carboxylic acid (Example 434), (R)-3-(4-propyl-benzylcarbamoyl)-4-(6,7,8,9-tetrahydro-5H-benzenecycloheptene-2-sulfonyl)-3,4,5,6-tetrahydro-2H-[1,2']bipyrazinyl-5'-carboxylic acid (Example 435), (R)-4-(4-trifluoromethoxy-benzenesulfonyl)-piperazine-1,3-dicarboxylic acid 3-(4-propyl-benzylamide) 1-pyridin-4-ylamide (Example 436), (R)-4-(4-trifluoromethoxy-benzenesulfonyl)-piperazine-1,3-dicarboxylic acid 3-(4-propyl-benzylamide) 1-[1,3,4]thiadiazol-2-ylamide (Example 437), (R)-3-(4-propyl-benzylcarbamoyl)-4-(5-propyl-thiophene-2-sulfonyl)-3,4,5,6-tetrahydro-2H-[1,2']bipyrazinyl-5'-carboxylic acid (Example 438), 5-[(R)-3-(4-isopropyl-benzylcarbamoyl)-4-(4-trifluoromethyl-benzenesulfonyl)-piperazin-1-yl]-1-methyl-1H-pyrazole-3-carboxylic acid (Example 439), (R)-4-(4-propyl-benzenesulfonyl)-3-(4-propyl-benzylcarbamoyl)-3,4,5,6-tetrahydro-2H-[1,2']bipyrazinyl-5'-carboxylic acid (Example 440), (R)-3-(2-methyl-4-propyl-benzylcarbamoyl)-4-(4-propyl-benzenesulfonyl)-3,4,5,6-tetrahydro-2H-[1,2']bipyrazinyl-5'-carboxylic acid (Example 441), 2-[(R)-3-(4-ethoxy-benzylcarbamoyl)-4-(4-trifluoromethoxy-benzenesulfonyl)-piperazin-1-yl]-4-methyl-thiazole-5-carboxylic acid (Example 442), (R)-6'-amino-3-(4-isopropyl-benzylcarbamoyl)-4-(4-trifluoromethyl-benzenesulfonyl)-3,4,5,6-tetrahydro-2H-[1,2']bipyrazinyl-5'-carboxylic acid (Example 443), 2-[(R)-3-(4-propyl-benzylcarbamoyl)-4-(4-trifluoromethoxy-benzenesulfonyl)-piperazin-1-yl]-4-trifluoromethyl-thiazole-5-carboxylic acid ethyl ester (Example 444), 5-[(R)-3-(4-isopropyl-benzylcarbamoyl)-4-(4-trifluoromethyl-benzenesulfonyl)-piperazin-1-yl]-2-methyl-2H-pyrazole-3-carboxylic acid (Example 445), (R)-4-(5-methanesulfonylaminocarbonyl-4-methyl-thiazol-2-yl)-1-(4-trifluoromethyl-benzenesulfonyl)-piperazine-2-carboxylic acid 4-isopropyl-benzylamide (Example 446), (R)-4-(5-methanesulfonylaminocarbonyl-4-methyl-thiazol-2-yl)-1-(4-trifluoromethoxy-benzenesulfonyl)-piperazine-2-carboxylic acid 4-propyl-benzylamide (Example 447), 2-[(R)-3-[4-(1,1-difluoro-propyl)-benzylcarbamoyl]-4-(4-trifluoromethoxy-benzenesulfonyl)-piperazin-1-yl]-4-methyl-thiazole-5-carboxylic acid (Example 448), (R)-6'-methyl-3-(4-propyl-benzylcarbamoyl)-4-(4-trifluoromethoxy-benzenesulfonyl)-3,4,5,6-tetrahydro-2H-[1,2']bipyrazinyl-5'-carboxylic acid (Example 449), (R)-4-acetyl-1-(4-trifluoromethoxy-benzenesulfonyl)-piperazine-2-carboxylic acid 4-propyl-benzylamide (Example 450), 2-[(R)-3-(4-methoxymethyl-benzylcarbamoyl)-4-(4-trifluoromethoxy-benzenesulfonyl)-piperazin-1-yl]-4-methyl-thiazole-5-carboxylic acid (Example 451), (R)-4-(5-hydroxymethyl-4-methyl-thiazol-2-yl)-1-(4-trifluoromethoxy-benzenesulfonyl)-piperazine-2-carboxylic acid 4-propyl-benzylamide (Example 452), 2-[(R)-3-(4-propyl-benzylcarbamoyl)-4-(4-trifluoromethoxy-benzenesulfonyl)-piperazin-1-yl]-4-trifluoromethyl-thiazole-5-carboxylic acid (Example 453), (R)-4-(6-hydroxy-5-methyl-pyridazin-3-yl)-1-(4-trifluoromethoxy-benzenesulfonyl)-piperazine-2-carboxylic acid 4-propyl-benzylamide (Example 454), (2-{2-oxo-2-[(R)-3-(4-propyl-benzylcarbamoyl)-4-(4-trifluoromethoxy-benzenesulfonyl)-piperazin-1-yl]-ethyl}-2H-tetrazol-5-yl)-acetic acid ethyl ester (Example 455), (R)-4-[2-(5-methyl-tetrazol-1-yl)-acetyl]-1-(4-trifluoromethoxy-benzenesulfonyl)-piperazine-2-carboxylic acid 4-propyl-benzylamide (Example 456), (R)-4-[2-(5-methyl-tetrazol-2-yl)-acetyl]-1-(4-trifluoromethoxy-benzenesulfonyl)-piperazine-2-carboxylic acid 4-propyl-benzylamide (Example 457), (R)-4-(5-amino-pyridin-2-yl)-1-(4-trifluoromethoxy-benzenesulfonyl)-piperazine-2-carboxylic acid 4-propyl-benzylamide (Example 458), (R)-4-acetyl-1-(4-trifluoromethoxy-benzenesulfonyl)-piperazine-2-carboxylic acid 4-(1,1-difluoro-propyl)-benzylamide (Example 459), (R)-4-(2-tetrazol-2-yl-acetyl)-1-(4-trifluoromethoxy-benzenesulfonyl)-piperazine-2-carboxylic acid 4-propyl-benzylamide (Example 460), (R)-4-(2-tetrazol-1-yl-acetyl)-1-(4-trifluoromethoxy-benzenesulfonyl)-piperazine-2-carboxylic acid 4-propyl-benzylamide (Example 461), (R)-4-(2-imidazol-1-yl-acetyl)-1-(4-trifluoromethoxy-benzenesulfonyl)-piperazine-2-carboxylic acid 4-propyl-benzylamide (Example 462), (R)-4-(4-trifluoromethoxy-benzenesulfonyl)-piperazine-1,3-dicarboxylic acid 1-(methyl-pyridin-4-yl-amide) 3-(4-propyl-benzylamide) (Example 463), (R)-4-(2-tetrazol-1-yl-acetyl)-1-(4-trifluoromethoxy-benzenesulfonyl)-piperazine-2-carboxylic acid 4-(1,1-difluoro-propyl)-benzylamide (Example 464), (2-{2-oxo-2-[(R)-3-(4-propyl-benzylcarbamoyl)-4-(4-trifluoromethoxy-benzenesulfonyl)-piperazin-1-yl]-ethyl}-2H-tetrazol-5-yl)-acetic acid (Example 465), (2-{2-[(R)-3-[4-(1,1-difluoro-propyl)-benzylcarbamoyl]-4-(4-trifluoromethoxy-benzenesulfonyl)-piperazin-1-yl]-2-oxo-ethyl}-2H-tetrazol-5-yl)-acetic acid ethyl ester (Example 466), (R)-4-[2-(5-methyl-tetrazol-1-yl)-acetyl]-1-(4-trifluoromethoxy-benzenesulfonyl)-piperazine-2-carboxylic acid 4-(1,1-difluoro-propyl)-benzylamide (Example 467), (R)-4-[2-(5-methyl-tetrazol-2-yl)-acetyl]-1-(4-trifluoromethoxy-benzenesulfonyl)-piperazine-2-carboxylic acid 4-(1,1-difluoro-propyl)-benzylamide (Example 468), (R)-4-acetyl-1-(4-bromo-3-fluoro-benzenesulfonyl)-piperazine-2-carboxylic acid 4-isopropyl-benzylamide (Example 469), (2-{[(R)-3-(4-propyl-benzylcarbamoyl)-4-(4-trifluoromethoxy-benzenesulfonyl)-piperazine-1-carbonyl]-amino}-thiazol-4-yl)-acetic acid ethyl ester (Example 470), (R)-5'-amino-4-(4-trifluoromethyl-benzenesulfonyl)-3,4,5,6-tetrahydro-2H-[1,2']bipyrazinyl-3-carboxylic acid 4-isopropyl-benzylamide (Example 471), (R)-4-(4-trifluoromethoxy-benzenesulfonyl)-3,4,5,6-tetrahydro-2H-[1,2']bipyrazinyl-3-carboxylic acid 4-propyl-benzylamide (Example 472), (R)-3-(4-methoxymethyl-benzylcarbamoyl)-4-(4-trifluoromethoxy-benzenesulfonyl)-3,4,5,6-tetrahydro-2H-[1,2']bipyrazinyl-5'-carboxylic acid (Example 473), (R)-3-(2-chloro-4-propyl-benzylcarbamoyl)-4-(4-trifluoromethoxy-benzenesulfonyl)-3,4,5,6-tetrahydro-2H-[1,2']bipyrazinyl-5'-carboxylic acid (Example 474), (R)-4-(4-trifluoromethoxy-benzenesulfonyl)-piperazine-1,3-dicarboxylic acid 1-{[4-(2-morpholin-4-yl-2-oxo-ethyl)-thiazol-2-yl]-amide} 3-(4-propyl-benzylamide) (Example 475), (R)-4-(4-trifluoromethoxy-benzenesulfonyl)-piperazine-1,3-dicarboxylic acid 1-{[4-(2-hydroxy-ethyl)-thiazol-2-yl]-amide} 3-(4-propyl-benzylamide) (Example 476), 5-{[(R)-3-[4-(1,1-difluoro-propyl)-benzylcarbamoyl]-4-(4-trifluoromethoxy-benzenesulfonyl)-piperazine-1-carbonyl]-amino}-[1,3,4]thiadiazole-2-carboxylic acid ethyl ester (Example 477), (R)-4-(4-ethyl-benzenesulfonyl)-5'-hydroxymethyl-3,4,5,6-tetrahydro-2H-[1,2']bipyrazinyl-3-carboxylic acid 4-propyl-benzylamide (Example 478), (R)-4-[2-(5-phenyl-tetrazol-2-yl)-acetyl]-1-(4-trifluoromethoxy-benzenesulfonyl)-piperazine-2-carboxylic acid 4-(1,1-difluoro-propyl)-benzylamide (Example 479), (R)-4-[2-(3-methyl-isoxazol-5-yl)-acetyl]-1-(4-trifluoromethoxy-benzenesulfonyl)-piperazine-2-carboxylic acid 4-(1,1-difluoro-propyl)-benzylamide (Example 480), (R)-4-acetyl-1-(4-isopropyl-benzenesulfonyl)-piperazine-2-carboxylic acid 4-furan-3-yl-benzylamide (Example 481), (R)-4-(4-trifluoromethoxy-benzenesulfonyl)-piperazine-1,3-dicarboxylic acid 3-[4-(1,1-difluoro-propyl)-benzylamide] 1-[(5-hydroxymethyl-[1,3,4]thiadiazol-2-yl)-amide] (Example 482), (R)-4-(4-trifluoromethoxy-benzenesulfonyl)-piperazine-1,3-dicarboxylic acid 1-[(5-acetyl-[1,3,4]thiadiazol-2-yl)-amide] 3-[4-(1,1-difluoro-propyl)-benzylamide] (Example 483), (R)-4-(4-trifluoromethoxy-benzenesulfonyl)-piperazine-1,3-dicarboxylic acid 3-[4-(1,1-difluoro-propyl)-benzylamide] 1-{[5-(1-hydroxy-1-methyl-ethyl)-[1,3,4]thiadiazol-2-yl]-amide} (Example 484), (R)-3-(2-chloro-4-propyl-benzylcarbamoyl)-4-(4-ethyl-benzenesulfonyl)-3,4,5,6-tetrahydro-2H-[1,2']bipyrazinyl-5'-carboxylic acid (Example 485), 4-methyl-6-[(R)-3-(4-propyl-benzylcarbamoyl)-4-(4-trifluoromethoxy-benzenesulfonyl)-piperazin-1-yl]-pyridazine-3-carboxylic acid methyl ester (Example 486), 4-methyl-6-[(R)-3-(4-propyl-benzylcarbamoyl)-4-(4-trifluoromethoxy-benzenesulfonyl)-piperazin-1-yl]-pyridazine-3-carboxylic acid (Example 487), (R)-4-(4-trifluoromethoxy-benzenesulfonyl)-piperazine-1,3-dicarboxylic acid 3-[4-(1,1-difluoro-propyl)-benzylamide] 1-[(5-methyl-[1,3,4]thiadiazol-2-yl)-amide] (Example 488), (R)-4-(4-trifluoromethoxy-benzenesulfonyl)-piperazine-1,3-dicarboxylic acid 3-[4-(1,1-difluoro-propyl)-benzylamide] 1-[(5-trifluoromethyl-[1,3,4]thiadiazol-2-yl)-amide] (Example 489), (R)-4-(4-trifluoromethoxy-benzenesulfonyl)-piperazine-1,3-dicarboxylic acid 3-[4-(1,1-difluoro-propyl)-benzylamide] 1-[(2-methoxy-pyridin-4-yl)-amide] (Example 490), 4-{[(R)-3-[4-(1,1-difluoro-propyl)-benzylcarbamoyl]-4-(4-trifluoromethoxy-benzenesulfonyl)-piperazine-1-carbonyl]-amino}-pyridine-2-carboxylic acid tert-butyl ester (Example 491), (R)-4-acetyl-1-(4-isopropyl-benzenesulfonyl)-piperazine-2-carboxylic acid 4-[1,2,3]thiadiazol-4-yl-benzylamide (Example 492), {4-[(R)-3-(4-isopropyl-benzylcarbamoyl)-4-(4-trifluoromethoxy-benzenesulfonyl)-piperazin-1-yl]-pyrazol-1-yl}-acetic acid (Example 493), 4-methyl-6-[(R)-3-(4-propyl-benzylcarbamoyl)-4-(4-trifluoromethoxy-benzenesulfonyl)-piperazin-1-yl]-pyridazine-3-carboxylic acid amide (Example 494), (R)-4-(4-trifluoromethoxy-benzenesulfonyl)-piperazine-1,3-dicarboxylic acid 3-[4-(1,1-difluoro-propyl)-benzylamide] 1-{[5-((R)-3-hydroxy-pyrrolidine-1-carbonyl)-[1,3,4]thiadiazol-2-yl]-amide} (Example 495), (R)-4-(4-trifluoromethoxy-benzenesulfonyl)-piperazine-1,3-dicarboxylic acid 3-[4-(1,1-difluoro-propyl)-benzylamide] 1-{[5-(4-hydroxy-piperidine-1-carbonyl)-[1,3,4]thiadiazol-2-yl]-amide} (Example 496), (R)-4-(4-trifluoromethoxy-benzenesulfonyl)-piperazine-1,3-dicarboxylic acid 3-[4-(1,1-difluoro-propyl)-benzylamide] 1-{[5-(morpholine-4-carbonyl)-[1,3,4]thiadiazol-2-yl]-amide} (Example 497), (R)-4-[2-(1-methyl-1H-imidazol-4-yl)-acetyl]-1-(4-trifluoromethoxy-benzenesulfonyl)-piperazine-2-carboxylic acid 4-(1,1-difluoro-propyl)-benzylamide (Example 498), 4-methyl-2-[(R)-3-(4-propyl-benzylcarbamoyl)-4-(3-propyl-4-trifluoromethoxy-benzenesulfonyl)-piperazin-1-yl]-thiazole-5-carboxylic acid (Example 499), (R)-4-(2-pyridin-4-yl-acetyl)-1-(4-trifluoromethoxy-benzenesulfonyl)-piperazine-2-carboxylic acid 4-tert-butyl-benzylamide (Example 500), (R)-3-(4-tert-butyl-benzylcarbamoyl)-4-(4-trifluoromethoxy-benzenesulfonyl)-3,4,5,6-tetrahydro-2H-[1,2']bipyrazinyl-5'-carboxylic acid (Example 501), 4-{[(R)-3-[4-(1,1-difluoro-propyl)-benzylcarbamoyl]-4-(4-trifluoromethoxy-benzenesulfonyl)-piperazine-1-carbonyl]-amino}-pyridine-2-carboxylic acid (Example 502), (R)-4-(4-trifluoromethoxy-benzenesulfonyl)-piperazine-1,3-dicarboxylic acid 1-[(2-carbamoyl-pyridin-4-yl)-amide] 3-[4-(1,1-difluoro-propyl)-benzylamide] (Example 503), (R)-4-(4-trifluoromethoxy-benzenesulfonyl)-piperazine-1,3-dicarboxylic acid 3-[4-(1,1-difluoro-propyl)-benzylamide] 1-[(2-dimethylcarbamoyl-pyridin-4-yl)-amide] (Example 504), (R)-4-(5-dimethylaminomethyl-4-methyl-thiazol-2-yl)-1-(4-trifluoromethoxy-benzenesulfonyl)-piperazine-2-carboxylic acid 4-propyl-benzylamide (Example 505), (R)-4-(4-methyl-5-methylaminomethyl-thiazol-2-yl)-1-(4-trifluoromethoxy-benzenesulfonyl)-piperazine-2-carboxylic acid 4-propyl-benzylamide (Example 506), (R)-6'-amino-3-(4-propyl-benzylcarbamoyl)-4-(4-trifluoromethoxy-benzenesulfonyl)-3,4,5,6-tetrahydro-2H-[1,2']bipyrazinyl-5'-carboxylic acid methyl ester (Example 507), (R)-4-(2-pyridin-4-yl-acetyl)-1-(4-trifluoromethoxy-benzenesulfonyl)-piperazine-2-carboxylic acid 4-(1,1-difluoro-propyl)-benzylamide (Example 508), 2-[(R)-4-(3-fluoro-4-trifluoromethoxy-benzenesulfonyl)-3-(4-propyl-benzylcarbamoyl)-piperazin-1-yl]-4-methyl-thiazole-5-carboxylic acid (Example 509), (R)-4-(4-hydroxymethyl-thiazol-2-yl)-1-(4-trifluoromethoxy-benzenesulfonyl)-piperazine-2-carboxylic acid 4-propyl-benzylamide (Example 510), (R)-4-(4-trifluoromethoxy-benzenesulfonyl)-piperazine-1,3-dicarboxylic acid 3-[4-(1,1-difluoro-propyl)-benzylamide] 1-[(2-hydroxymethyl-pyridin-4-yl)-amide] (Example 511), (R)-4-(4-trifluoromethoxy-benzenesulfonyl)-piperazine-1,3-dicarboxylic acid 1-[(2-cyclopropylcarbamoyl-pyridin-4-yl)-amide] 3-[4-(1,1-difluoro-propyl)-benzylamide] (Example 512), (R)-4-(4-trifluoromethoxy-benzenesulfonyl)-piperazine-1,3-dicarboxylic acid 3-[4-(1,1-difluoro-propyl)-benzylamide] 1-{[2-(morpholine-4-carbonyl)-pyridin-4-yl]-amide} (Example 513), (R)-4-(4-trifluoromethoxy-benzenesulfonyl)-piperazine-1,3-dicarboxylic acid 3-[4-(1,1-difluoro-propyl)-benzylamide] 1-{[2-(pyrrolidine-1-carbonyl)-pyridin-4-yl]-amide} (Example 514), (R)-6'-acetylamino-3-(4-propyl-benzylcarbamoyl)-4-(4-trifluoromethoxy-benzenesulfonyl)-3,4,5,6-tetrahydro-2H-[1,2']bipyrazinyl-5'-carboxylic acid methyl ester (Example 515), (R)-4-(5-oxo-4,5-dihydro-[1,3,4]thiadiazol-2-yl)-1-(4-trifluoromethoxy-benzenesulfonyl)-piperazine-2-carboxylic acid 4-propyl-benzylamide (Example 516), (R)-4-(4-trifluoromethoxy-benzenesulfonyl)-piperazine-1,3-dicarboxylic acid 1-[(2-chloro-pyridin-4-yl)-amide] 3-[4-(1,1-difluoro-propyl)-benzylamide] (Example 517), (R)-4-[2-(2-methyl-2H-tetrazol-5-yl)-acetyl]-1-(4-trifluoromethoxy-benzenesulfonyl)-piperazine-2-carboxylic acid 4-(1,1-difluoro-propyl)-benzylamide (Example 518), (R)-4-[2-(1-methyl-1H-tetrazol-5-yl)-acetyl]-1-(4-trifluoromethoxy-benzenesulfonyl)-piperazine-2-carboxylic acid 4-(1,1-difluoro-propyl)-benzylamide (Example 519), (R)-4-(thiazole-4-carbonyl)-1-(4-trifluoromethoxy-benzenesulfonyl)-piperazine-2-carboxylic acid 4-(1,1-difluoro-propyl)-benzylamide (Example 520), (R)-4-(5-methyl-isoxazole-3-carbonyl)-1-(4-trifluoromethoxy-benzenesulfonyl)-piperazine-2-carboxylic acid 4-(1,1-difluoro-propyl)-benzylamide (Example 521), (R)-4-(5-ethyl-thiophene-2-sulfonyl)-3-(4-propyl-benzylcarbamoyl)-3,4,5,6-tetrahydro-2H-[1,2']bipyrazinyl-5'-carboxylic acid (Example 522), (R)-4-(5-methyl-1H-pyrazol-3-yl)-1-(4-trifluoromethoxybenzenesulfonyl)-piperazine-2-carboxylic acid 4-isopropyl-benzylamide (Example 523), (R)-3-(4-tert-butyl-benzylcarbamoyl)-4-(4-ethyl-benzenesulfonyl)-3,4,5,6-tetrahydro-2H-[1,2']bipyrazinyl-5'-carboxylic acid (Example 524), (R)-4-(4-trifluoromethoxy-benzenesulfonyl)-piperazine-1,3-dicarboxylic acid 3-[4-(1,1-difluoro-propyl)-benzylamide] 1-thiazol-4-ylamide (Example 525), (R)-4-(4-trifluoromethoxy-benzenesulfonyl)-piperazine-1,3-dicarboxylic acid 3-[4-(1,1-difluoro-propyl)-benzylamide] 1-[(5-methyl-isoxazol-3-yl)-amide] (Example 526), (R)-4-(4-trifluoromethoxy-benzenesulfonyl)-piperazine-1,3-dicarboxylic acid 3-[4-(1,1-difluoro-propyl)-benzylamide] 1-[(3-methyl-[1,2,4]thiadiazol-5-yl)-amide] (Example 527), (R)-4-(4-trifluoromethoxy-benzenesulfonyl)-piperazine-1,3-dicarboxylic acid 3-[4-(1,1-difluoro-propyl)-benzylamide] 1-[(3-methyl-isoxazol-5-yl)-amide] (Example 528), (R)-4-acetyl-1-(4-trifluoromethoxy-benzenesulfonyl)-piperazine-2-carboxylic acid 4-tert-butyl-benzylamide (Example 529), (R)-5'-amino-4-(4-trifluoromethoxy-benzenesulfonyl)-3,4,5,6-tetrahydro-2H-[1,2']bipyrazinyl-3-carboxylic acid 4-propyl-benzylamide (Example 530), (R)-4-(4-methyl-5-pyrrolidin-1-ylmethyl-thiazol-2-yl)-1-(4-trifluoromethoxy-benzenesulfonyl)-piperazine-2-carboxylic acid 4-propyl-benzylamide (Example 531), (5-{2-[(R)-3-[4-(1,1-difluoro-propyl)-benzylcarbamoyl]-4-(4-trifluoromethoxy-benzenesulfonyl)-piperazin-1-yl]-2-oxo-ethyl}-tetrazol-2-yl)-acetic acid ethyl ester (Example 532), (5-{2-[(R)-3-[4-(1,1-difluoro-propyl)-benzylcarbamoyl]-4-(4-trifluoromethoxy-benzenesulfonyl)-piperazin-1-yl]-2-oxo-ethyl}-tetrazol-1-yl)-acetic acid ethyl ester (Example 533), 2-[(R)-3-(4-propyl-benzylcarbamoyl)-4-(4-trifluoromethoxy-benzenesulfonyl)-piperazin-1-yl]-6,7-dihydro-4H-thiazolo[5,4-c]pyridine-5-carboxylic acid benzyl ester (Example 534), 5-hydroxymethyl-2-[(R)-3-(4-isopropyl-benzylcarbamoyl)-4-(4-propyl-benzenesulfonyl)-piperazin-1-yl]-thiazole-4-carboxylic acid (Example 535), 5-methoxymethyl-2-[(R)-3-(4-propyl-benzylcarbamoyl)-4-(4-trifluoromethoxy-benzenesulfonyl)-piperazin-1-yl]-thiazole-4-carboxylic acid (Example 536), 5-hydroxymethyl-2-[(R)-3-(4-propyl-benzylcarbamoyl)-4-(4-trifluoromethoxy-benzenesulfonyl)-piperazin-1-yl]-thiazole-4-carboxylic acid (Example 537), (R)-5'-dimethylaminomethyl-4-(4-ethyl-benzenesulfonyl)-3,4,5,6-tetrahydro-2H-[1,2']bipyrazinyl-3-carboxylic acid 4-propyl-benzylamide (Example 538), (R)-4-(4-trifluoromethoxy-benzenesulfonyl)-piperazine-1,3-dicarboxylic acid 3-[4-(1,1-difluoro-propyl)-benzylamide] 1-[1,2,4]triazol-4-ylamide (Example 539), (R)-4-(3-amino-[1,2,4]triazole-1-carbonyl)-1-(4-trifluoromethoxy-benzenesulfonyl)-piperazine-2-carboxylic acid 4-(1,1-difluoro-propyl)-benzylamide (Example 540), (R)-4-[2-(5-isopropyl-tetrazol-1-yl)-acetyl]-1-(4-trifluoromethoxy-benzenesulfonyl)-piperazine-2-carboxylic acid 4-(1,1-difluoro-propyl)-benzylamide (Example 541), (R)-4-[2-(5-isopropyl-tetrazol-2-yl)-acetyl]-1-(4-trifluoromethoxy-benzenesulfonyl)-piperazine-2-carboxylic acid 4-(1,1-difluoro-propyl)-benzylamide (Example 542), (R)-4-{2-[5-(2-morpholin-4-yl-2-oxo-ethyl)-tetrazol-2-yl]-acetyl}-1-(4-trifluoromethoxy-benzenesulfonyl)-piperazine-2-carboxylic acid 4-(1,1-difluoro-propyl)-benzylamide (Example 543), (R)-5'-methanesulfonylamino-4-(4-trifluoromethoxy-benzenesulfonyl)-3,4,5,6-tetrahydro-2H-[1,2']bipyrazinyl-3-carboxylic acid 4-propyl-benzylamide (Example 544), (R)-5'-hydroxymethyl-4-(4-trifluoromethoxy-benzenesulfonyl)-3,4,5,6-tetrahydro-2H-[1,2']bipyrazinyl-3-carboxylic acid 4-tert-butyl-benzylamide (Example 545), (R)-4-(6-hydroxy-pyridazin-3-yl)-1-(4-trifluoromethoxy-benzenesulfonyl)-piperazine-2-carboxylic acid 4-propyl-benzylamide (Example 546), 6-[(R)-3-(4-propyl-benzylcarbamoyl)-4-(4-trifluoromethoxy-benzenesulfonyl)-piperazin-1-yl]-pyridazine-3-carboxylic acid amide (Example 547), (R)-4-(5-methyl-4,5,6,7-tetrahydro-thiazolo[5,4-c]pyridin-2-yl)-1-(4-trifluoromethoxy-benzenesulfonyl)-piperazine-2-carboxylic acid 4-propyl-benzylamide (Example 548), (R)-6'-amino-5'-hydroxymethyl-4-(4-trifluoromethoxy-benzenesulfonyl)-3,4,5,6-tetrahydro-2H-[1,2']bipyrazinyl-3-carboxylic acid 4-propyl-benzylamide (Example 549), (R)-4-acetyl-1-(4-trifluoromethoxy-benzenesulfonyl)-piperazine-2-carboxylic acid 4-pentafluoroethyl-benzylamide (Example 550), (R)-4-[2-(5-methyl-tetrazol-2-yl)-acetyl]-1-(4-trifluoromethoxy-benzenesulfonyl)-piperazine-2-carboxylic acid 4-pentafluoroethyl-benzylamide (Example 551), (R)-4-(4-trifluoromethoxy-benzenesulfonyl)-piperazine-1,3-dicarboxylic acid 1-[(5-methyl-[1,3,4]thiadiazol-2-yl)-amide] 3-(4-pentafluoroethyl-benzylamide) (Example 552), (R)-4-(4-trifluoromethoxy-benzenesulfonyl)-piperazine-1,3-dicarboxylic acid 3-[4-(1,1-difluoro-propyl)-benzylamide] 1-[(3-methyl-isothiazol-5-yl)-amide] (Example 553), (R)-4-(4-trifluoromethoxy-benzenesulfonyl)-piperazine-1,3-dicarboxylic acid 3-[4-(1,1-difluoro-propyl)-benzylamide] 1-thiazol-2-ylamide (Example 554), (R)-4-(4-trifluoromethoxy-benzenesulfonyl)-piperazine-1,3-dicarboxylic acid 3-[4-(1,1-difluoro-propyl)-benzylamide] 1-[(2-trifluoromethyl-pyridin-4-yl)-amide] (Example 555), (R)-4-(2-oxo-1,4-dihydro-2H-pyrazino[2,3-d][1,3]oxazin-7-yl)-1-(4-trifluoromethoxy-benzenesulfonyl)-piperazine-2-carboxylic acid 4-propyl-benzylamide (Example 556), (R)-4-(4,5,6,7-tetrahydro-thiazolo[5,4-c]pyridin-2-yl)-1-(4-trifluoromethoxy-benzenesulfonyl)-piperazine-2-carboxylic acid 4-propyl-benzylamide (Example 557), (R)-5'-pyrrolidin-1-ylmethyl-4-(4-trifluoromethoxy-benzenesulfonyl)-3,4,5,6-tetrahydro-2H-[1,2']bipyrazinyl-3-carboxylic acid 4-tert-butyl-benzylamide (Example 558), (R)-3-[4-(1,1-difluoro-propyl)-benzylcarbamoyl]-4-(4-trifluoromethoxy-benzenesulfonyl)-3,4,5,6-tetrahydro-2H-[1,2']bipyrazinyl-5'-carboxylic acid (Example 559), (R)-5'-hydroxymethyl-4-(4-trifluoromethoxy-benzenesulfonyl)-3,4,5,6-tetrahydro-2H-[1,2']bipyrazinyl-3-carboxylic acid 4-(1,1-difluoro-propyl)-benzylamide (Example 560), (R)-4-(5-benzyl-4,5,6,7-tetrahydro-thiazolo[5,4-c]pyridin-2-yl)-1-(4-trifluoromethoxy-benzenesulfonyl)-piperazine-2-carboxylic acid 4-propyl-benzylamide (Example 561), (R)-4-(4,5-bis-hydroxymethyl-thiazol-2-yl)-1-(4-trifluoromethoxy-benzenesulfonyl)-piperazine-2-carboxylic acid 4-propyl-benzylamide (Example 562), (R)-4-(3-methyl-[1,2,4]thiadiazol-5-yl)-1-(4-trifluoromethoxy-benzenesulfonyl)-piperazine-2-carboxylic acid 4-propyl-benzylamide (Example 563), (R)-3-[4-(1,1-difluoro-propyl)-benzylcarbamoyl]-4-(4-ethyl-benzenesulfonyl)-3,4,5,6-tetrahydro-2H-[1,2']bipyrazinyl-5'-carboxylic acid (Example 564), (R)-4-(4-trifluoromethoxy-benzenesulfonyl)-piperazine-1,3-dicarboxylic acid 3-[4-(1,1-difluoro-propyl)-benzylamide] 1-[(1H-[1,2,4]triazol-3-yl)-amide] (Example 565), (R)-4-(4-trifluoromethoxy-benzenesulfonyl)-piperazine-1,3-dicarboxylic acid 3-[4-(1,1-difluoro-propyl)-benzylamide] 1-[(2H-tetrazol-5-yl)-amide] (Example 566), (R)-4-(4-trifluoromethoxy-benzenesulfonyl)-piperazine-1,3-dicarboxylic acid 3-[4-(1,1-difluoro-propyl)-benzylamide] 1-[(2-methyl-thiazol-4-yl)-amide] (Example 567), (R)-4-(5-amino-3-methyl-[1,2,4]triazole-1-carbonyl)-1-(4-trifluoromethoxy-benzenesulfonyl)-piperazine-2-carboxylic acid 4-(1,1-difluoro-propyl)-benzylamide (Example 568), (R)-4-(4-trifluoromethoxy-benzenesulfonyl)-piperazine-1,3-dicarboxylic acid 3-[4-(1,1-difluoro-propyl)-benzylamide] 1-[(1-methyl-1H-pyrazol-3-yl)-amide] (Example 569), (R)-4-(5-hydroxymethyl-thiazol-2-yl)-1-(4-trifluoromethoxy-benzenesulfonyl)-piperazine-2-carboxylic acid 4-tert-butyl-benzylamide (Example 570), (R)-4-(6-chloro-pyrimidin-4-yl)-1-(4-trifluoromethoxy-benzenesulfonyl)-piperazine-2-carboxylic acid 4-propyl-benzylamide (Example 571), (R)-4-pyrimidin-4-yl-1-(4-trifluoromethoxy-benzenesulfonyl)-piperazine-2-carboxylic acid 4-propyl-benzylamide (Example 572), (R)-4-(4,6-dioxo-5,6-dihydro-4H-pyrrolo[3,4-d]thiazol-2-yl)-1-(4-trifluoromethoxy-benzenesulfonyl)-piperazine-2-carboxylic acid 4-tert-butyl-benzylamide (Example 573), (R)-4-pteridin-7-yl-1-(4-trifluoromethoxy-benzenesulfonyl)-piperazine-2-carboxylic acid 4-propyl-benzylamide (Example 574), (R)-6'-amino-5'-hydroxymethyl-4-(4-trifluoromethoxy-benzenesulfonyl)-3,4,5,6-tetrahydro-2H-[1,2']bipyrazinyl-3-carboxylic acid 4-tert-butyl-benzylamide (Example 575), (R)-4-(3-methyl-[1,2,4]thiadiazol-5-yl)-1-(4-trifluoromethoxy-benzenesulfonyl)-piperazine-2-carboxylic acid 4-(1,1-difluoro-propyl)-benzylamide (Example 576), (R)-4-(5-cyano-4-methyl-thiazol-2-yl)-1-(4-trifluoromethoxy-benzenesulfonyl)-piperazine-2-carboxylic acid 4-tert-butyl-benzylamide (Example 577), (R)-4-(4-oxo-4,5,6,7-tetrahydro-thiazolo[5,4-c]pyridin-2-yl)-1-(4-trifluoromethoxy-benzenesulfonyl)-piperazine-2-carboxylic acid 4-tert-butyl-benzylamide (Example 578), (R)-4-(2-oxo-1,4-dihydro-2H-pyrazino[2,3-d][1,3]oxazin-7-yl)-1-(4-trifluoromethoxy-benzenesulfonyl)-piperazine-2-carboxylic acid 4-tert-butyl-benzylamide (Example 579), (R)-4-pyrimidin-4-yl-1-(4-trifluoromethoxy-benzenesulfonyl)-piperazine-2-carboxylic acid 4-(1,1-difluoro-propyl)-benzylamide (Example 580), (R)-4-(2-hydroxy-pyrimidin-4-yl)-1-(4-trifluoromethoxy-benzenesulfonyl)-piperazine-2-carboxylic acid 4-tert-butyl-benzylamide (Example 581), 4-amino-2-[(R)-3-(4-tert-butyl-benzylcarbamoyl)-4-(4-trifluoromethoxy-benzenesulfonyl)-piperazin-1-yl]-thiazole-5-carboxylic acid ethyl ester (Example 582), (R)-4-[4-methyl-5-(1H-tetrazol-5-yl)-thiazol-2-yl]-1-(4-trifluoromethoxy-benzenesulfonyl)-piperazine-2-carboxylic acid 4-tert-butyl-benzylamide (Example 583), (R)-4-(2-amino-pyrimidin-4-yl)-1-(4-trifluoromethoxy-benzenesulfonyl)-piperazine-2-carboxylic acid 4-(1,1-difluoro-propyl)-benzylamide (Example 584), (R)-4-(4-amino-pyrimidin-2-yl)-1-(4-trifluoromethoxy-benzenesulfonyl)-piperazine-2-carboxylic acid 4-(1,1-difluoro-propyl)-benzylamide (Example 585), (R)-4-(4-trifluoromethoxy-benzenesulfonyl)-3,4,5,6-tetrahydro-2H-[1,2']bipyrazinyl-3,5'-dicarboxylic acid 5'-amide 3-[4-(1,1-difluoro-propyl)-benzylamide] (Example 586), 2-[(R)-3-(4-tert-butyl-benzylcarbamoyl)-4-(4-trifluoromethoxy-benzenesulfonyl)-piperazin-1-yl]-6,7-dihydro-4H-thiazolo[5,4-c]pyridine-5-carboxylic acid tert-butyl ester (Example 587), (R)-4-(4,5,6,7-tetrahydro-thiazolo[5,4-c]pyridin-2-yl)-1-(4-trifluoromethoxy-benzenesulfonyl)-piperazine-2-carboxylic acid 4-tert-butyl-benzylamide (Example 588), (R)-4-(5-acetyl-4,5,6,7-tetrahydro-thiazolo[5,4-c]pyridin-2-yl)-1-(4-trifluoromethoxy-benzenesulfonyl)-piperazine-2-carboxylic acid 4-tert-butyl-benzylamide (Example 589), (R)-4-(2-pyrimidin-4-yl-acetyl)-1-(4-trifluoromethoxy-benzenesulfonyl)-piperazine-2-carboxylic acid 4-(1,1-difluoro-propyl)-benzylamide (Example 590), (R)-5'-cyano-4-(4-trifluoromethoxy-benzenesulfonyl)-3,4,5,6-tetrahydro-2H-[1,2']bipyrazinyl-3-carboxylic acid 4-(1,1-difluoro-propyl)-benzylamide (Example 591), (R)-5'-(1H-tetrazol-5-yl)-4-(4-trifluoromethoxy-benzenesulfonyl)-3,4,5,6-tetrahydro-2H-[1,2']bipyrazinyl-3-carboxylic acid 4-(1,1-difluoro-propyl)-benzylamide (Example 592), (R)-5'-morpholin-4-ylmethyl-4-(4-trifluoromethoxy-benzenesulfonyl)-3,4,5,6-tetrahydro-2H-[1,2']bipyrazinyl-3-carboxylic acid 4-tert-butyl-benzylamide (Example 593), (R)-5'-(4-methyl-piperazin-1-ylmethyl)-4-(4-trifluoromethoxy-benzenesulfonyl)-3,4,5,6-tetrahydro-2H-[1,2']bipyrazinyl-3-carboxylic acid 4-tert-butyl-benzylamide (Example 594), (R)-5'-dimethylaminomethyl-4-(4-trifluoromethoxy-benzenesulfonyl)-3,4,5,6-tetrahydro-2H-[1,2']bipyrazinyl-3-carboxylic acid 4-(1,1-difluoro-propyl)-benzylamide (Example 595), (R)-4-(3-acetylamino-[1,2,4]thiadiazol-5-yl)-1-(4-trifluoromethoxy-benzenesulfonyl)-piperazine-2-carboxylic acid 4-(1,1-difluoro-propyl)-benzylamide (Example 596), (R)-4-(4-oxo-4,5-dihydro-thiazolo[5,4-c]pyridin-2-yl)-1-(4-trifluoromethoxy-benzenesulfonyl)-piperazine-2-carboxylic acid 4-tert-butyl-benzylamide (Example 597), (R)-4-acetyl-1-(4-trifluoromethoxy-benzenesulfonyl)-piperazine-2-carboxylic acid (5-pyridin-2-yl-thiophen-2-yl-methyl)-amide (Example 598), (R)-4-acetyl-1-(4-trifluoromethoxy-benzenesulfonyl)-piperazine-2-carboxylic acid (2-thiophen-2-yl-thiazol-4-ylmethyl)-amide (Example 599), (R)-4-(5-methanesulfonyl-4,5,6,7-tetrahydro-thiazolo[5,4-c]pyridin-2-yl)-1-(4-trifluoromethoxy-benzenesulfonyl)-piperazine-2-carboxylic acid 4-tert-butyl-benzylamide (Example 600), 2-[(R)-3-(4-tert-butyl-benzylcarbamoyl)-4-(4-trifluoromethoxy-benzenesulfonyl)-piperazin-1-yl]-6,7-dihydro-4H-thiazolo[5,4-c]pyridine-5-carboxylic acid ethylamide (Example 601), (R)-4-(7-oxo-6,7-dihydro-thiazolo[4,5-d]pyrimidin-2-yl)-1-(4-trifluoromethoxy-benzenesulfonyl)-piperazine-2-carboxylic acid 4-tert-butyl-benzylamide (Example 602), 2-[(R)-3-(4-tert-butyl-benzylcarbamoyl)-4-(4-trifluoromethoxy-benzenesulfonyl)-piperazin-1-yl]-4-hydroxymethyl-thiazole-5-carboxylic acid (Example 603), (R)-6'-amino-5'-hydroxymethyl-4-(4-trifluoromethoxy-benzenesulfonyl)-3,4,5,6-tetrahydro-2H-[1,2']bipyrazinyl-3-carboxylic acid 4-(1,1-difluoro-propyl)-benzylamide (Example 604), (R)-4-(6-amino-pyrimidin-4-yl)-1-(4-trifluoromethoxy-benzenesulfonyl)-piperazine-2-carboxylic acid 4-(1,1-difluoro-propyl)-benzylamide (Example 605), (R)-4-(3-methoxy-[1,2,4]thiadiazol-5-yl)-1-(4-trifluoromethoxy-benzenesulfonyl)-piperazine-2-carboxylic acid 4-tert-butyl-benzylamide (Example 606), (R)-4-(4-trifluoromethoxy-benzenesulfonyl)-piperazine-1,3-dicarboxylic acid 3-[4-(1,1-difluoro-propyl)-benzylamide] 1-thiazol-5-ylamide (Example 607), (R)-4-acetyl-1-(4-trifluoromethoxy-benzenesulfonyl)-piperazine-2-carboxylic acid 4-methoxy-benzylamide (Example 608), (R)-4-isobutyryl-1-(4-trifluoromethoxy-benzenesulfonyl)-piperazine-2-carboxylic acid 4-(1,1-difluoro-propyl)-benzylamide (Example 609), (R)-4-cyclopropanecarbonyl-1-(4-trifluoromethoxy-benzenesulfonyl)-piperazine-2-carboxylic acid 4-(1,1-difluoro-propyl)-benzylamide (Example 610), (R)-4-(2,2-dimethyl-propionyl)-1-(4-trifluoromethoxy-benzenesulfonyl)-piperazine-2-carboxylic acid 4-(1,1-difluoro-propyl)-benzylamide (Example 611), (R)-4-(4-trifluoromethoxy-benzenesulfonyl)-piperazine-1,3-dicarboxylic acid 3-[4-(1,1-difluoro-propyl)-benzylamide] 1-{[4-(1-hydroxy-1-methyl-ethyl)-thiazol-2-yl]-amide} (Example 612), (R)-4-acetyl-1-(4-trifluoromethoxy-benzenesulfonyl)-piperazine-2-carboxylic acid 4-hydroxy-benzylamide (Example 613), (R)-4-acetyl-1-(4-trifluoromethoxy-benzenesulfonyl)-piperazine-2-carboxylic acid (5-phenyl-thiophen-2-ylmethyl)-amide (Example 614), (R)-4-pteridin-7-yl-1-(4-trifluoromethoxy-benzenesulfonyl)-piperazine-2-carboxylic acid 4-(1,1-difluoro-propyl)-benzylamide (Example 615), (R)-4-(2-oxo-1,4-dihydro-2H-pyrazino[2,3-d][1,3]oxazin-7-yl)-1-(4-trifluoromethoxy-benzenesulfonyl)-piperazine-2-carboxylic acid 4-(1,1-difluoro-propyl)-benzylamide (Example 616), (R)-4-pteridin-7-yl-1-(4-trifluoromethoxy-benzenesulfonyl)-piperazine-2-carboxylic acid 4-tert-butyl-benzylamide (Example 617), (R)-4-(4-oxo-3,4-dihydro-thiazolo[4,5-d][1,2,3]triazin-6-yl)-1-(4-trifluoromethoxy-benzenesulfonyl)-piperazine-2-carboxylic acid 4-tert-butyl-benzylamide (Example 618), (R)-4-pteridin-7-yl-1-(4-trifluoromethoxy-benzenesulfonyl)-piperazine-2-carboxylic acid 4-(ethyl-methyl-amino)-benzylamide (Example 619), 5-[(R)-3-(4-tert-butyl-benzylcarbamoyl)-4-(4-trifluoromethoxy-benzenesulfonyl)-piperazin-1-yl]-pyridine-2-carboxylic acid (Example 620), (R)-4-acetyl-1-(4-trifluoromethoxy-benzenesulfonyl)-piperazine-2-carboxylic acid (1-hydroxy-cyclohexylmethyl)-amide (Example 621),
(R)-4-acetyl-1-(4-trifluoromethoxy-benzenesulfonyl)-piperazine-2-carboxylic acid ([2,2']bithiophenyl-5-ylmethyl)-amide (Example 622),
(R)-4-acetyl-1-(4-trifluoromethoxy-benzenesulfonyl)-piperazine-2-carboxylic acid 4-thiophen-2-yl-benzylamide (Example 623),
(R)-4-acetyl-1-(4-trifluoromethoxy-benzenesulfonyl)-piperazine-2-carboxylic acid 3-hydroxy-4-propyl-benzylamide (Example 624),
(R)-4-(3-methoxy-[1,2,4]thiadiazol-5-yl)-1-(4-trifluoromethoxy-benzenesulfonyl)-piperazine-2-carboxylic acid 4-(1,1-difluoro-propyl)-benzylamide (Example 625),
(R)-4-[1,2,4]triazolo[1,5-a]pyrimidin-5-yl-1-(4-trifluoromethoxy-benzenesulfonyl)-piperazine-2-carboxylic acid 4-(1,1-difluoro-propyl)-benzylamide (Example 626),
(R)-4-pteridin-7-yl-1-(4-trifluoromethoxy-benzenesulfonyl)-piperazine-2-carboxylic acid 4-trifluoromethoxy-benzylamide (Example 627),
(R)-4-(2-oxo-2,3-dihydro-1H-imidazo[4,5-b]pyrazin-5-yl)-1-(4-trifluoromethoxy-benzenesulfonyl)-piperazine-2-carboxylic acid 4-propyl-benzylamide (Example 628),
(R)-4-pteridin-7-yl-1-(4-trifluoromethoxy-benzenesulfonyl)-piperazine-2-carboxylic acid 4-chloro-benzylamide (Example 629),
(R)-4-pteridin-7-yl-1-(4-trifluoromethoxy-benzenesulfonyl)-piperazine-2-carboxylic acid (6-dimethylamino-pyridin-3-ylmethyl)-amide (Example 630),
5-[(R)-3-(4-propyl-benzylcarbamoyl)-4-(4-trifluoromethoxy-benzenesulfonyl)-piperazin-1-yl]-pyridine-2-carboxylic acid (Example 631),
(R)-4-quinoxalin-2-yl-1-(4-trifluoromethoxy-benzenesulfonyl)-piperazine-2-carboxylic acid 4-(1,1-difluoro-propyl)-benzylamide (Example 632),
(R)-4-(7-oxo-6,7-dihydro-thiazolo[4,5-d]pyrimidin-2-yl)-1-(4-trifluoromethoxy-benzenesulfonyl)-piperazine-2-carboxylic acid 4-(1,1-difluoro-propyl)-benzylamide (Example 633),
(R)-4-acetyl-1-(4-trifluoromethoxy-benzenesulfonyl)-piperazine-2-carboxylic acid (2-oxo-1-propyl-1,2-dihydro-pyridin-4-ylmethyl)-amide (Example 634),
(R)-4-acetyl-1-(4-trifluoromethoxy-benzenesulfonyl)-piperazine-2-carboxylic acid 3-amino-4-propyl-benzylamide (Example 635),
(R)-4-acetyl-1-(4-trifluoromethoxy-benzenesulfonyl)-piperazine-2-carboxylic acid 3-methoxy-benzylamide (Example 636),
(R)-4-acetyl-1-(4-trifluoromethoxy-benzenesulfonyl)-piperazine-2-carboxylic acid 3-hydroxy-benzylamide (Example 637),
(R)-6'-amino-5'-aminomethyl-4-(4-trifluoromethoxy-benzenesulfonyl)-3,4,5,6-tetrahydro-2H-[1,2']bipyrazinyl-3-carboxylic acid 4-(1,1-difluoro-propyl)-benzylamide (Example 638),
(R)-4-pteridin-7-yl-1-(4-trifluoromethoxy-benzenesulfonyl)-piperazine-2-carboxylic acid (benzoxazol-2-ylmethyl)-amide (Example 639),
(R)-4-(4-oxo-3,4-dihydro-thiazolo[4,5-d][1,2,3]triazin-6-yl)-1-(4-trifluoromethoxy-benzenesulfonyl)-piperazine-2-carboxylic acid 4-(1,1-difluoro-propyl)-benzylamide (Example 640),
(R)-4-acetyl-1-(4-trifluoromethoxy-benzenesulfonyl)-piperazine-2-carboxylic acid 4-(cyano-dimethyl-methyl)-benzylamide (Example 641),
(R)-4-acetyl-1-(4-trifluoromethoxy-benzenesulfonyl)-piperazine-2-carboxylic acid (biphenyl-2-ylmethyl)-amide (Example 642),
(R)-4-acetyl-1-(4-trifluoromethoxy-benzenesulfonyl)-piperazine-2-carboxylic acid cyclohexylmethyl-amide (Example 643),
4-({[(R)-4-acetyl-1-(4-trifluoromethoxy-benzenesulfonyl)-piperazine-2-carbonyl]-amino}-methyl)-piperidine-1-carboxylic acid tert-butyl ester (Example 644),
(R)-4-acetyl-1-(4-trifluoromethoxy-benzenesulfonyl)-piperazine-2-carboxylic acid 3-hydroxy-4-methoxy-benzylamide (Example 645),
(R)-4-acetyl-1-(4-trifluoromethoxy-benzenesulfonyl)-piperazine-2-carboxylic acid (2-oxo-6-propyl-1,2-dihydro-pyridin-3-ylmethyl)-amide (Example 646),
(R)-4-(6-hydroxy-[1,2,5]thiadiazolo[3,4-b]pyrazin-5-yl)-1-(4-trifluoromethoxy-benzenesulfonyl)-piperazine-2-carboxylic acid 4-(1,1-difluoro-propyl)-benzylamide (Example 647),
(R)-4-pyrido[3,4-b]pyrazin-2-yl-1-(4-trifluoromethoxy-benzenesulfonyl)-piperazine-2-carboxylic acid 4-(1,1-difluoro-propyl)-benzylamide (Example 648),
(R)-4-acetyl-1-(4-trifluoromethoxy-benzenesulfonyl)-piperazine-2-carboxylic acid (6-methoxy-5-methyl-pyridin-2-ylmethyl)-amide (Example 649),
(R)-4-(2,2-dioxo-1,2,3,4-tetrahydro-2,6-pyrazino[2,3-c][1,2,6]thiadiazin-7-yl)-1-(4-trifluoromethoxy-benzenesulfonyl)-piperazine-2-carboxylic acid 4-(1,1-difluoro-propyl)-benzylamide (Example 650),
(R)-4-pteridin-7-yl-1-(4-trifluoromethoxy-benzenesulfonyl)-piperazine-2-carboxylic acid 4-ethoxy-benzylamide (Example 651),
(R)-4-pteridin-7-yl-1-(4-trifluoromethoxy-benzenesulfonyl)-piperazine-2-carboxylic acid 4-thiophen-2-yl-benzylamide (Example 652),
(R)-4-pteridin-7-yl-1-(4-trifluoromethoxy-benzenesulfonyl)-piperazine-2-carboxylic acid 4-bromo-benzylamide (Example 653),
(R)-4-acetyl-1-(4-trifluoromethoxy-benzenesulfonyl)-piperazine-2-carboxylic acid (piperidin-4-ylmethyl)-amide hydrochloride (Example 654),
(R)-4-acetyl-1-(4-trifluoromethoxy-benzenesulfonyl)-piperazine-2-carboxylic acid 4-bromo-benzylamide (Example 655),
(R)-4-pteridin-7-yl-1-(4-trifluoromethoxy-benzenesulfonyl)-piperazine-2-carboxylic acid 4-cyclopropyl-benzylamide (Example 656),
(R)-4-pteridin-7-yl-1-(4-trifluoromethoxy-benzenesulfonyl)-piperazine-2-carboxylic acid 4-methoxymethyl-benzylamide (Example 657),
(R)-4-pteridin-7-yl-1-(4-trifluoromethoxy-benzenesulfonyl)-piperazine-2-carboxylic acid 4-methoxy-benzylamide (Example 658),
(R)-4-pteridin-7-yl-1-(4-trifluoromethoxy-benzenesulfonyl)-piperazine-2-carboxylic acid ([2,2']bithiophenyl-5-ylmethyl)-amide (Example 659),
(R)-4-pteridin-7-yl-1-(4-trifluoromethoxy-benzenesulfonyl)-piperazine-2-carboxylic acid 4-trifluoromethyl-benzylamide (Example 660),
(R)-4-pteridin-7-yl-1-(4-trifluoromethoxy-benzenesulfonyl)-piperazine-2-carboxylic acid 4-methylsulfanyl-benzylamide (Example 661),
(R)-4-pteridin-7-yl-1-(4-trifluoromethoxy-benzenesulfonyl)-piperazine-2-carboxylic acid (1-propyl-1,2,3,6-tetrahydro-pyridin-4-ylmethyl)-amide (Example 662), (R)-4-pteridin-7-yl-1-(4-trifluoromethoxy-benzenesulfonyl)-piperazine-2-carboxylic acid (biphenyl-4-ylmethyl)-amide (Example 663), (R)-4-(4-oxo-4,5-dihydro-thiazolo[4,5-d]pyridazin-2-yl)-1-(4-trifluoromethoxy-benzenesulfonyl)-piperazine-2-carboxylic acid 4-(1,1-difluoro-propyl)-benzylamide (Example 664), (Z)-4-[(R)-3-(4-tert-butyl-benzylcarbamoyl)-4-(4-trifluoromethoxy-benzenesulfonyl)-piperazin-1-yl]-4-oxo-but-2-enoic acid (Example 665), (Z)-4-[(R)-3-[4-(1,1-difluoro-propyl)-benzylcarbamoyl]-4-(4-trifluoromethoxy-benzenesulfonyl)-piperazin-1-yl]-4-oxo-but-2-enoic acid (Example 666), (E)-4-[(R)-3-[4-(1,1-difluoro-propyl)-benzylcarbamoyl]-4-(4-trifluoromethoxy-benzenesulfonyl)-piperazin-1-yl]-4-oxo-but-2-enoic acid (Example 667), (E)-4-[(R)-3-(4-tert-butyl-benzylcarbamoyl)-4-(4-trifluoromethoxy-benzenesulfonyl)-piperazin-1-yl]-4-oxo-but-2-enoic acid (Example 668), trans-4-({[(R)-4-acetyl-1-(4-trifluoromethoxy-benzenesulfonyl)-piperazine-2-carbonyl]-amino}-methyl)-cyclohexanecarboxylic acid (Example 669), (R)-4-acetyl-1-(4-trifluoromethoxy-benzenesulfonyl)-piperazine-2-carboxylic acid (1-acetyl-piperidin-4-ylmethyl)-amide (Example 670), (R)-4-acetyl-1-(4-trifluoromethoxy-benzenesulfonyl)-piperazine-2-carboxylic acid [2-(2-methoxy-phenyl)-ethyl]-amide (Example 671), (R)-4-acetyl-1-(4-trifluoromethoxy-benzenesulfonyl)-piperazine-2-carboxylic acid [2-(3-methoxy-phenyl)-ethyl]-amide (Example 672), (R)-4-acetyl-1-(4-trifluoromethoxy-benzenesulfonyl)-piperazine-2-carboxylic acid [2-(4-methoxy-phenyl)-ethyl]-amide (Example 673), (R)-4-acetyl-1-(4-trifluoromethoxy-benzenesulfonyl)-piperazine-2-carboxylic acid [2-(3-hydroxy-phenyl)-ethyl]-amide (Example 674), (R)-4-acetyl-1-(4-trifluoromethoxy-benzenesulfonyl)-piperazine-2-carboxylic acid [2-(4-hydroxy-phenyl)-ethyl]-amide (Example 675), (R)-4-(1H-imidazo[4,5-b]pyrazin-5-yl)-1-(4-trifluoromethoxy-benzenesulfonyl)-piperazine-2-carboxylic acid 4-(1,1-difluoro-propyl)-benzylamide (Example 676), {[(R)-3-[4-(1,1-difluoro-propyl)-benzylcarbamoyl]-4-(4-trifluoromethoxy-benzenesulfonyl)-piperazine-1-carbonyl]-amino}-acetic acid (Example 677), 3-[(R)-3-[4-(1,1-difluoro-propyl)-benzylcarbamoyl]-4-(4-trifluoromethoxy-benzenesulfonyl)-piperazin-1-yl]-3-oxo-propionic acid (Example 678),

[(R)-3-[4-(1,1-difluoro-propyl)-benzylcarbamoyl]-4-(4-trifluoromethoxy-benzenesulfonyl)-piperazin-1-yl]-oxo-acetic acid (Example 679), (R)-4-pteridin-7-yl-1-(4-trifluoromethoxy-benzenesulfonyl)-piperazine-2-carboxylic acid (2-oxo-1-propyl-1,2-dihydro-pyridin-4-ylmethyl)-amide (Example 680), (R)-4-acetyl-1-(4-trifluoromethoxy-benzenesulfonyl)-piperazine-2-carboxylic acid (1-propyl-piperidin-4-ylmethyl)-amide (Example 681), (R)-4-acetyl-1-(4-trifluoromethoxy-benzenesulfonyl)-piperazine-2-carboxylic acid [2-(2-hydroxy-phenyl)-ethyl]-amide (Example 682), (R)-1-(4-bromo-benzenesulfonyl)-4-pteridin-7-yl-piperazine-2-carboxylic acid 4-(1,1-difluoro-propyl)-benzylamide (Example 683), (R)-4-(6-bromo-quinoxalin-2-yl)-1-(4-trifluoromethoxy-benzenesulfonyl)-piperazine-2-carboxylic acid 4-(1,1-difluoro-propyl)-benzylamide (Example 684), (R)-4-(7-bromo-quinoxalin-2-yl)-1-(4-trifluoromethoxy-benzenesulfonyl)-piperazine-2-carboxylic acid 4-(1,1-difluoro-propyl)-benzylamide (Example 685), (R)-4-pteridin-7-yl-1-(4-trifluoromethyl-benzenesulfonyl)-piperazine-2-carboxylic acid 4-(1,1-difluoro-propyl)-benzylamide (Example 686), (R)-4-(4-bromo-benzenesulfonyl)-3-(4-propyl-benzylcarbamoyl)-3,4,5,6-tetrahydro-2H-[1,2']bipyrazinyl-5'-carboxylic acid (Example 687), (R)-4-(6-chloro-quinoxalin-2-yl)-1-(4-trifluoromethoxy-benzenesulfonyl)-piperazine-2-carboxylic acid 4-(1,1-difluoro-propyl)-benzylamide (Example 688), (R)-4-pyrido[3,4-b]pyrazin-2-yl-1-(4-trifluoromethoxy-benzenesulfonyl)-piperazine-2-carboxylic acid 4-tert-butyl-benzylamide (Example 689), (R)-4-pyrazino[2,3-b]pyrazin-2-yl-1-(4-trifluoromethoxy-benzenesulfonyl)-piperazine-2-carboxylic acid 4-(1,1-difluoro-propyl)-benzylamide (Example 690), (R)-4-[1,2,5]thiadiazolo[3,4-b]pyrazin-5-yl-1-(4-trifluoromethoxy-benzenesulfonyl)-piperazine-2-carboxylic acid 4-(1,1-difluoro-propyl)-benzylamide (Example 691), (R)-4-(2-methyl-pteridin-7-yl)-1-(4-trifluoromethoxy-benzenesulfonyl)-piperazine-2-carboxylic acid 4-(1,1-difluoro-propyl)-benzylamide (Example 692), 2-[(R)-3-[4-(1,1-difluoro-propyl)-benzylcarbamoyl]-4-(4-trifluoromethoxy-benzenesulfonyl)-piperazin-1-yl]-quinoxaline-6-carboxylic acid ethyl ester (Example 693), (R)-4-thiazolo[4,5-d]pyridazin-2-yl-1-(4-trifluoromethoxy-benzenesulfonyl)-piperazine-2-carboxylic acid 4-(1,1-difluoro-propyl)-benzylamide (Example 694), (R)-1-(4-tert-butyl-benzenesulfonyl)-4-pteridin-7-yl-piperazine-2-carboxylic acid 4-(1,1-difluoro-propyl)-benzylamide (Example 695), (R)-1-(biphenyl-4-sulfonyl)-4-pteridin-7-yl-piperazine-2-carboxylic acid 4-(1,1-difluoro-propyl)-benzylamide (Example 696), (R)-1-(4-chloro-benzenesulfonyl)-4-pteridin-7-yl-piperazine-2-carboxylic acid 4-(1,1-difluoro-propyl)-benzylamide (Example 697), (R)-1-(4-nitro-benzenesulfonyl)-4-pteridin-7-yl-piperazine-2-carboxylic acid 4-(1,1-difluoro-propyl)-benzylamide (Example 698), (R)-4-(5-bromo-thiophene-2-sulfonyl)-3-(4-propyl-benzylcarbamoyl)-3,4,5,6-tetrahydro-2H-[1,2']bipyrazinyl-5'-carboxylic acid (Example 699), (R)-4-(4-tert-butyl-benzenesulfonyl)-3-(4-propyl-benzylcarbamoyl)-3,4,5,6-tetrahydro-2H-[1,2']bipyrazinyl-5'-carboxylic acid (Example 700), (R)-4-(biphenyl-4-sulfonyl)-3-(4-propyl-benzylcarbamoyl)-3,4,5,6-tetrahydro-2H-[1,2']bipyrazinyl-5'-carboxylic acid (Example 701), (R)-4-acetyl-1-(4-trifluoromethoxy-benzenesulfonyl)-piperazine-2-carboxylic acid 4-(3-hydroxy-propyl)-benzylamide (Example 702), (R)-4-acetyl-1-(4-trifluoromethoxy-benzenesulfonyl)-piperazine-2-carboxylic acid (1-propyl-1H-pyrazol-4-ylmethyl)-amide (Example 703), (R)-4-(4-oxo-4,5-dihydro-thiazol-2-yl)-1-(4-trifluoromethoxy-benzenesulfonyl)-piperazine-2-carboxylic acid 4-(1,1-difluoro-propyl)-benzylamide (Example 704), 1-[(R)-3-[4-(1,1-difluoro-propyl)-benzylcarbamoyl]-4-(4-trifluoromethoxy-benzenesulfonyl)-piperazine-1-carbonyl]-azetidine-3-carboxylic acid (Example 705), 1-[(R)-3-[4-(1,1-difluoro-propyl)-benzylcarbamoyl]-4-(4-trifluoromethoxy-benzenesulfonyl)-piperazine-1-carbonyl]-piperidine-4-carboxylic acid (Example 706), (R)-4-pteridin-6-yl-1-(4-trifluoromethoxy-benzenesulfo-nyl)-piperazine-2-carboxylic acid 4-(1,1-difluoro-propyl)-benzylamide (Example 707), (R)-1-(4-iodo-benzenesulfonyl)-4-pteridin-7-yl-piperazine-2-carboxylic acid 4-(1,1-difluoro-propyl)-benzylamide (Example 708), (R)-4-pteridin-7-yl-1-(4-thiophen-2-yl-benzenesulfonyl)-piperazine-2-carboxylic acid 4-(1,1-difluoro-propyl)-benzylamide (Example 709), 3-[(R)-3-[4-(1,1-difluoro-propyl)-benzylcarbamoyl]-4-(4-trifluoromethoxy-benzenesulfonyl)-piperazin-1-yl]-quinoxaline-6-carboxylic acid ethyl ester (Example 710), 3-[(R)-3-[4-(1,1-difluoro-propyl)-benzylcarbamoyl]-4-(4-trifluoromethoxy-benzenesulfonyl)-piperazin-1-yl]-quinoxaline-6-carboxylic acid (Example 711), 2-[(R)-3-[4-(1,1-difluoro-propyl)-benzylcarbamoyl]-4-(4-trifluoromethoxy-benzenesulfonyl)-piperazin-1-yl]-quinoxaline-6-carboxylic acid (Example 712), (R)-1-(4-chloro-benzenesulfonyl)-4-pyrido[3,4-b]pyrazin-2-yl-piperazine-2-carboxylic acid 4-(1,1-difluoro-propyl)-benzylamide (Example 713), (R)-1-(4-tert-butyl-benzenesulfonyl)-4-pyrido[3,4-b]pyrazin-2-yl-piperazine-2-carboxylic acid 4-(1,1-difluoro-propyl)-benzylamide (Example 714), (R)-4-thiazolo[5,4-c]pyridin-2-yl-1-(4-trifluoromethoxy-benzenesulfonyl)-piperazine-2-carboxylic acid 4-(1,1-difluoro-propyl)-benzylamide (Example 715), (R)-4-acetyl-1-(4-trifluoromethoxy-benzenesulfonyl)-piperazine-2-carboxylic acid [3-(3-hydroxy-phenyl)-propyl]-amide (Example 716), (R)-4-acetyl-1-(4-trifluoromethoxy-benzenesulfonyl)-piperazine-2-carboxylic acid [3-(3-hydroxy-phenyl)-propyl]-amide (Example 717), (R)-4-acetyl-1-(4-trifluoromethoxy-benzenesulfonyl)-piperazine-2-carboxylic acid (6-propyl-pyridin-3-ylmethyl)-amide (Example 718), (R)-4-acetyl-1-(4-trifluoromethoxy-benzenesulfonyl)-piperazine-2-carboxylic acid (5-methyl-pyrazin-2-ylmethyl)-amide (Example 719), (R)-4-pteridin-7-yl-1-(4-trifluoromethoxy-benzenesulfo-nyl)-piperazine-2-carboxylic acid (6-propyl-pyridin-3-ylmethyl)-amide (Example 720), (R)-4-pteridin-7-yl-1-(4-trifluoromethoxy-benzenesulfo-nyl)-piperazine-2-carboxylic acid (5-methyl-pyrazin-2-ylmethyl)-amide (Example 721), (R)-4-pteridin-7-yl-1-(4-trifluoromethoxy-benzenesulfo-nyl)-piperazine-2-carboxylic acid 3-amino-4-propyl-benzylamide (Example 722), (R)-4-pteridin-7-yl-1-(4-trifluoromethoxy-benzenesulfo-nyl)-piperazine-2-carboxylic acid 3-hydroxy-4-propyl-benzylamide (Example 723), (R)-1-(2'-hydroxy-biphenyl-4-sulfonyl)-4-pteridin-7-yl-piperazine-2-carboxylic acid 4-(1,1-difluoro-propyl)-benzylamide (Example 724), (R)-1-(3'-hydroxy-biphenyl-4-sulfonyl)-4-pteridin-7-yl-piperazine-2-carboxylic acid 4-(1,1-difluoro-propyl)-benzylamide (Example 725), (R)-1-(4-nitro-benzenesulfonyl)-4-pyrido[3,4-b]pyrazin-2-yl-piperazine-2-carboxylic acid 4-(1,1-difluoro-propyl)-benzylamide (Example 726), (R)-1-(biphenyl-4-sulfonyl)-4-pyrido[3,4-b]pyrazin-2-yl-piperazine-2-carboxylic acid 4-(1,1-difluoro-propyl)-benzylamide (Example 727), 5-[(R)-3-(4-propyl-benzylcarbamoyl)-4-(4-trifluoromethoxy-benzenesulfonyl)-piperazin-1-yl]-thiophene-2-carboxylic acid tert-butyl ester (Example 728), (2-{(R)-2-[4-(1,1-difluoro-propyl)-benzylcarbamoyl]-4-pteridin-7-yl-piperazine-1-sulfonyl}-6,7,8,9-tetrahydro-5H-benzocyclohepten-7-yl)-acetic acid (Example 729), (R)-4-pteridin-7-yl-1-(4-trifluoromethoxy-benzenesulfo-nyl)-piperazine-2-carboxylic acid (5-pyridin-2-yl-thiophen-2-ylmethyl)-amide (Example 730), (4'-{(R)-2-[4-(1,1-difluoro-propyl)-benzylcarbamoyl]-4-pteridin-7-yl-piperazine-1-sulfonyl}-biphenyl-2-yloxy)-acetic acid (Example 731), (4'-{(R)-2-[4-(1,1-difluoro-propyl)-benzylcarbamoyl]-4-pteridin-7-yl-piperazine-1-sulfonyl}-biphenyl-3-yloxy)-acetic acid (Example 732), (R)-4-[2-(pyridin-3-ylamino)-acetyl]-1-(4-trifluoromethoxy-benzenesulfonyl)-piperazine-2-carboxylic acid 4-(1,1-difluoro-propyl)-benzylamide (Example 733), (R)-4-[2-(1-methyl-1H-pyrazol-3-ylamino)-acetyl]-1-(4-trifluoromethoxy-benzenesulfonyl)-piperazine-2-carboxylic acid 4-(1,1-difluoro-propyl)-benzylamide (Example 734), (R)-4-pyrido[3,4-b]pyrazin-2-yl-1-(4-trifluoromethyl-benzenesulfonyl)-piperazine-2-carboxylic acid 4-(1,1-difluoro-propyl)-benzylamide (Example 735), (R)-1-(4-dimethylamino-benzenesulfonyl)-4-pyrido[3,4-b]pyrazin-2-yl-piperazine-2-carboxylic acid 4-(1,1-difluoro-propyl)-benzylamide (Example 736), (R)-1-(5-bromo-thiophene-2-sulfonyl)-4-pteridin-7-yl-piperazine-2-carboxylic acid 4-(1,1-difluoro-propyl)-benzylamide (Example 737), (R)-1-(benzo[b]thiophene-2-sulfonyl)-4-pteridin-7-yl-piperazine-2-carboxylic acid 4-(1,1-difluoro-propyl)-benzylamide (Example 738), (R)-4-thiazolo[5,4-b]pyridin-2-yl-1-(4-trifluoromethoxy-benzenesulfonyl)-piperazine-2-carboxylic acid 4-(1,1-difluoro-propyl)-benzylamide (Example 739), (R)-4-[1,6]naphthyridin-2-yl-1-(4-trifluoromethoxy-benzenesulfonyl)-piperazine-2-carboxylic acid 4-(1,1-difluoro-propyl)-benzylamide (Example 740), (R)-4-(5-chloro-quinoxalin-2-yl)-1-(4-trifluoromethoxy-benzenesulfonyl)-piperazine-2-carboxylic acid 4-(1,1-difluoro-propyl)-benzylamide (Example 741), (R)-4-(8-chloro-quinoxalin-2-yl)-1-(4-trifluoromethoxy-benzenesulfonyl)-piperazine-2-carboxylic acid 4-(1,1-difluoro-propyl)-benzylamide (Example 742), (R)-4-pyrido[3,4-b]pyrazin-2-yl-1-(4-pyrrolidin-1-yl-benzenesulfonyl)-piperazine-2-carboxylic acid 4-(1,1-difluoro-propyl)-benzylamide (Example 743), trans-[4-(4-{(R)-2-[4-(1,1-difluoro-propyl)-benzylcarbamoyl]-4-pteridin-7-yl-piperazine-1-sulfonyl}-phenyl)-cyclohexyl]-acetic acid (Example 744), (R)-4-pyrido[3,4-b]pyrazin-2-yl-1-(4-trifluoromethoxy-benzenesulfonyl)-piperazine-2-carboxylic acid 4-trifluoromethoxy-benzylamide (Example 745), (R)-1-(4-morpholin-4-yl-benzenesulfonyl)-4-pyrido[3,4-b]pyrazin-2-yl-piperazine-2-carboxylic acid 4-(1,1-difluoro-propyl)-benzylamide (Example 746), (R)-1-(4-methoxy-benzenesulfonyl)-4-pteridin-7-yl-piperazine-2-carboxylic acid 4-(1,1-difluoro-propyl)-benzylamide (Example 747), (R)-4-pyrido[2,3-b]pyrazin-6-yl-1-(4-trifluoromethoxy-benzenesulfonyl)-piperazine-2-carboxylic acid 4-(1,1-difluoro-propyl)-benzylamide (Example 748), (R)-4-pyrazino[2,3-b]pyrazin-2-yl-1-(4-trifluoromethoxy-benzenesulfonyl)-piperazine-2-carboxylic acid 4-trifluoromethoxy-benzylamide (Example 749), (R)-4-[1,2,4]triazolo[1,5-a]pyrimidin-5-yl-1-(4-trifluoromethoxy-benzenesulfonyl)-piperazine-2-carboxylic acid 4-trifluoromethoxy-benzylamide (Example 750), (R)-1-[4-(2-oxo-pyrrolidin-1-yl)-benzenesulfonyl]-4-pyrido [3,4-b]pyrazin-2-yl-piperazine-2-carboxylic acid 4-(1,1-difluoro-propyl)-benzylamide (Example 751),
(R)-1-(4-chloro-benzenesulfonyl)-4-pyrido[3,4-b]pyrazin-2-yl-piperazine-2-carboxylic acid 4-trifluoromethoxy-benzylamide (Example 752),
4'-{(R)-2-[4-(1,1-difluoro-propyl)-benzylcarbamoyl]-4-pteridin-7-yl-piperazine-1-sulfonyl}-biphenyl-3-carboxylic acid (Example 753),
(R)-1-(4-nitro-benzenesulfonyl)-4-pyrido[3,4-b]pyrazin-2-yl-piperazine-2-carboxylic acid 4-trifluoromethoxy-benzylamide (Example 754),
(R)-4-pyrido[3,4-b]pyrazin-2-yl-1-(4-pyrrolidin-1-yl-benzenesulfonyl)-piperazine-2-carboxylic acid 4-trifluoromethoxy-benzylamide (Example 755),
(R)-4-(3H-imidazo[4,5-c]pyridin-2-yl)-1-(4-trifluoromethoxy-benzenesulfonyl)-piperazine-2-carboxylic acid 4-(1,1-difluoro-propyl)-benzylamide (Example 756),
(R)-4-pyrido[3,4-b]pyrazin-2-yl-1-(4-trifluoromethyl-benzenesulfonyl)-piperazine-2-carboxylic acid 4-trifluoromethoxy-benzylamide (Example 757),
(R)-4-(1H-benzimidazol-2-yl)-1-(4-trifluoromethoxy-benzenesulfonyl)-piperazine-2-carboxylic acid 4-(1,1-difluoro-propyl)-benzylamide (Example 758),
(R)-1-[4-(5-oxo-2,5-dihydro-[1,2,4]oxadiazol-3-yl)-benzenesulfonyl]-4-pteridin-7-yl-piperazine-2-carboxylic acid 4-(1,1-difluoro-propyl)-benzylamide (Example 759),
(R)-4-pyrido[2,3-b]pyrazin-3-yl-1-(4-trifluoromethoxy-benzenesulfonyl)-piperazine-2-carboxylic acid 4-(1,1-difluoro-propyl)-benzylamide (Example 760),
(R)-4-pyrido[2,3-b]pyrazin-2-yl-1-(4-trifluoromethoxy-benzenesulfonyl)-piperazine-2-carboxylic acid 4-(1,1-difluoro-propyl)-benzylamide (Example 761),
(R)-4-pyrido[2,3-b]pyrazin-6-yl-1-(4-trifluoromethoxy-benzenesulfonyl)-piperazine-2-carboxylic acid 4-trifluoromethoxy-benzylamide (Example 762),
(R)-4-pteridin-7-yl-1-(4-trifluoromethoxy-benzenesulfonyl)-piperazine-2-carboxylic acid 4-(2,2,2-trifluoro-ethoxy)-benzylamide (Example 763),
(methyl-{4-[(R)-4-pyrido[3,4-b]pyrazin-2-yl-2-(4-trifluoromethoxy-benzylcarbamoyl)-piperazine-1-sulfonyl]-phenyl}-amino)-acetic acid ethyl ester (Example 764),
(methyl-{4-[(R)-4-pyrido[3,4-b]pyrazin-2-yl-2-(4-trifluoromethoxy-benzylcarbamoyl)-piperazine-1-sulfonyl]-phenyl}-amino)-acetic acid (Example 765),
(R)-4-(5-chloro-quinoxalin-2-yl)-1-(4-trifluoromethoxy-benzenesulfonyl)-piperazine-2-carboxylic acid 4-trifluoromethoxy-benzylamide (Example 766),
(R)-4-(2-methyl-pteridin-7-yl)-1-(4-trifluoromethoxy-benzenesulfonyl)-piperazine-2-carboxylic acid 4-trifluoromethoxy-benzylamide (Example 767),
(R)-4-thiazolo[5,4-c]pyridin-2-yl-1-(4-trifluoromethoxy-benzenesulfonyl)-piperazine-2-carboxylic acid 4-trifluoromethoxy-benzylamide (Example 768),
(R)-4-pyrido[2,3-b]pyrazin-2-yl-1-(4-trifluoromethoxy-benzenesulfonyl)-piperazine-2-carboxylic acid 4-trifluoromethoxy-benzylamide (Example 769),
(R)-4-pyrido[2,3-b]pyrazin-3-yl-1-(4-trifluoromethoxy-benzenesulfonyl)-piperazine-2-carboxylic acid 4-trifluoromethoxy-benzylamide (Example 770),
(R)-4-[1,6]naphthyridin-2-yl-1-(4-trifluoromethoxy-benzenesulfonyl)-piperazine-2-carboxylic acid 4-trifluoromethoxy-benzylamide (Example 771),
(R)-4-pteridin-7-yl-1-(4-trifluoromethoxy-benzenesulfonyl)-piperazine-2-carboxylic acid 4-trifluoromethylsulfanyl-benzylamide (Example 772),
4-{5-[(R)-2-(4-propyl-benzylcarbamoyl)-4-pteridin-7-yl-piperazine-1-sulfonyl]-2-trifluoromethoxy-phenyl}-butyric acid (Example 773),
6-[(R)-4-(4-trifluoromethoxy-benzenesulfonyl)-3-(4-trifluoromethoxy-benzylcarbamoyl)-piperazin-1-yl]-nicotinic acid (Example 774),
(R)-1-(5-bromo-thiophene-2-sulfonyl)-4-pyrido[3,4-b]pyrazin-2-yl-piperazine-2-carboxylic acid 4-trifluoromethoxy-benzylamide (Example 775),
(R)-4-thiazolo[5,4-b]pyridin-2-yl-1-(4-trifluoromethoxy-benzenesulfonyl)-piperazine-2-carboxylic acid 4-trifluoromethoxy-benzylamide (Example 776),
(R)-1-(4-iodo-benzenesulfonyl)-4-pyrido[3,4-b]pyrazin-2-yl-piperazine-2-carboxylic acid 4-propyl-benzylamide (Example 777),
(R)-1-(3'-hydroxy-biphenyl-4-sulfonyl)-4-pyrido[3,4-b]pyrazin-2-yl-piperazine-2-carboxylic acid 4-propyl-benzylamide (Example 778),
{4'-[(R)-2-(4-propyl-benzylcarbamoyl)-4-pyrido[3,4-b]pyrazin-2-yl-piperazine-1-sulfonyl]-biphenyl-3-yloxy}-acetic acid (Example 779),
2-[(R)-4-(4-trifluoromethoxy-benzenesulfonyl)-3-(4-trifluoromethoxy-benzylcarbamoyl)-piperazin-1-yl]-quinoxaline-5-carboxylic acid (Example 780),
3-[(R)-4-(4-trifluoromethoxy-benzenesulfonyl)-3-(4-trifluoromethoxy-benzylcarbamoyl)-piperazin-1-yl]-quinoxaline-5-carboxylic acid (Example 781),
(R)-4-quinoxalin-6-yl-1-(4-trifluoromethoxy-benzenesulfonyl)-piperazine-2-carboxylic acid 4-trifluoromethoxy-benzylamide (Example 782),
(R)-1-(4-trifluoromethoxy-benzenesulfonyl)-piperazine-2-carboxylic acid 4-trifluoromethoxy-benzylamide (Example 783),
(R)-4-(7-oxo-6,7-dihydro-thiazolo[4,5-d]pyrimidin-2-yl)-1-(4-trifluoromethoxy-benzenesulfonyl)-piperazine-2-carboxylic acid 4-trifluoromethoxy-benzylamide (Example 784),
(R)-4-(4-oxo-3,4-dihydro-thiazolo[4,5-d][1,2,3]triazin-6-yl)-1-(4-trifluoromethoxy-benzenesulfonyl)-piperazine-2-carboxylic acid 4-trifluoromethoxy-benzylamide (Example 785),
(R)-4-(4-ethyl-benzenesulfonyl)-3-(4-trifluoromethoxy-benzylcarbamoyl)-3,4,5,6-tetrahydro-2H-[1,2']bipyrazinyl-5'-carboxylic acid (Example 786),
(R)-4-(5-bromo-thiophene-2-sulfonyl)-3-(4-trifluoromethoxy-benzylcarbamoyl)-3,4,5,6-tetrahydro-2H-[1,2']bipyrazinyl-5'-carboxylic acid (Example 787),
(R)-4-(4-pyrrolidin-1-yl-benzenesulfonyl)-3-(4-trifluoromethoxy-benzylcarbamoyl)-3,4,5,6-tetrahydro-2H-[1,2']bipyrazinyl-5'-carboxylic acid (Example 788),
(R)-1-(5-bromo-thiophene-2-sulfonyl)-4-pteridin-7-yl-piperazine-2-carboxylic acid 4-trifluoromethoxy-benzylamide (Example 789),
(R)-1-(4-nitro-benzenesulfonyl)-4-pteridin-7-yl-piperazine-2-carboxylic acid 4-trifluoromethoxy-benzylamide (Example 790),
(R)-4-pteridin-7-yl-1-(4-trifluoromethyl-benzenesulfonyl)-piperazine-2-carboxylic acid 4-trifluoromethoxy-benzylamide (Example 791),
(R)-1-(5-chloro-thiophene-2-sulfonyl)-4-pteridin-7-yl-piperazine-2-carboxylic acid 4-trifluoromethoxy-benzylamide (Example 792),
(R)-4-[1,5]naphthyridin-2-yl-1-(4-trifluoromethoxy-benzenesulfonyl)-piperazine-2-carboxylic acid 4-trifluoromethoxy-benzylamide (Example 793), (R)-4-thiazolo[4,5-b]pyrazin-2-yl-1-(4-trifluoromethoxy-benzenesulfonyl)-piperazine-2-carboxylic acid 4-trifluoromethoxy-benzylamide (Example 794), (R)-4-pteridin-7-yl-1-(4-trifluoromethoxy-benzenesulfonyl)-piperazine-2-carboxylic acid 2,3,5,6-tetrafluoro-4-trifluoromethyl-benzylamide (Example 795), (R)-4-(4-ethyl-benzenesulfonyl)-5'-hydroxymethyl-3,4,5,6-tetrahydro-2H-[1,2']bipyrazinyl-3-carboxylic acid 4-trifluoromethoxy-benzylamide (Example 796), (R)-4-pteridin-7-yl-1-(4-trifluoromethoxy-benzenesulfonyl)-piperazine-2-carboxylic acid 2,4,6-trichloro-benzylamide (Example 797), (R)-1-(4-trifluoromethoxy-benzenesulfonyl)-4-(2-trifluoromethyl-pteridin-7-yl)-piperazine-2-carboxylic acid 4-trifluoromethoxy-benzylamide (Example 798), (R)-4-(8-bromo-pyrido[3,4-b]pyrazin-2-yl)-1-(4-trifluoromethoxy-benzenesulfonyl)-piperazine-2-carboxylic acid 4-trifluoromethoxy-benzylamide (Example 799), (R)-4-(5,7-dichloro-thiazolo[4,5-d]pyrimidin-2-yl)-1-(4-trifluoromethoxy-benzenesulfonyl)-piperazine-2-carboxylic acid 4-trifluoromethoxy-benzylamide (Example 800), (R)-4-thiazolo[4,5-d]pyrimidin-2-yl-1-(4-trifluoromethoxy-benzenesulfonyl)-piperazine-2-carboxylic acid 4-trifluoromethoxy-benzylamide (Example 801), (R)-4-(5-chloro-thiazolo[4,5-d]pyrimidin-2-yl)-1-(4-trifluoromethoxy-benzenesulfonyl)-piperazine-2-carboxylic acid 4-trifluoromethoxy-benzylamide (Example 802), (R)-4-(4,7-dioxo-4,5,6,7-tetrahydro-thiazolo[4,5-d]pyridazin-2-yl)-1-(4-trifluoromethoxy-benzenesulfonyl)-piperazine-2-carboxylic acid 4-trifluoromethoxy-benzylamide (Example 803), (R)-4-pteridin-7-yl-1-(4-trifluoromethoxy-benzenesulfonyl)-piperazine-2-carboxylic acid (adamantan-1-ylmethyl)-amide (Example 804), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-trifluoromethoxy-benzylamide (Example 805), 2-[(R)-4-(4-trifluoromethoxy-benzenesulfonyl)-3-(4-trifluoromethoxy-benzylcarbamoyl)-piperazin-1-yl]-pyrido[3,4-b]pyrazine-8-carboxylic acid (Example 806), 2-[(R)-4-(4-trifluoromethoxy-benzenesulfonyl)-3-(4-trifluoromethoxy-benzylcarbamoyl)-piperazin-1-yl]-pyrido[3,4-b]pyrazine-8-carboxylic acid amide (Example 807), 3-{2-[(R)-4-(4-trifluoromethoxy-benzenesulfonyl)-3-(4-trifluoromethoxy-benzylcarbamoyl)-piperazin-1-yl]-pyrido[3,4-b]pyrazin-8-yl}-propionic acid (Example 808), (R)-6'-methyl-4-(4-trifluoromethoxy-benzenesulfonyl)-3-(4-trifluoromethoxy-benzylcarbamoyl)-3,4,5,6-tetrahydro-2H-[1,2']bipyrazinyl-5'-carboxylic acid (Example 809), (R)-4-[8-(2-carbamoyl-ethyl)-pyrido[3,4-b]pyrazin-2-yl]-1-(4-trifluoromethoxy-benzenesulfonyl)-piperazine-2-carboxylic acid 4-trifluoromethoxy-benzylamide (Example 810), (R)-4-pteridin-7-yl-1-(4-trifluoromethoxy-benzenesulfonyl)-piperazine-2-carboxylic acid (3-phenyl-propyl)-amide (Example 811), (R)-1-(4-ethyl-benzenesulfonyl)-4-(7-oxo-6,7-dihydro-thiazolo[4,5-d]pyridazin-2-yl)-piperazine-2-carboxylic acid 4-propyl-benzylamide (Example 812), (R)-4-(8-bromo-pyrido[3,4-b]pyrazin-2-yl)-1-(4-ethyl-benzenesulfonyl)-piperazine-2-carboxylic acid 4-propyl-benzylamide (Example 813), 2-[(R)-4-(4-ethyl-benzenesulfonyl)-3-(4-propyl-benzylcarbamoyl)-piperazin-1-yl]-quinoxaline-5-carboxylic acid (Example 814), 2-[(R)-4-(4-ethyl-benzenesulfonyl)-3-(4-propyl-benzylcarbamoyl)-piperazin-1-yl]-pyrido[3,4-b]pyrazine-8-carboxylic acid (Example 815), 3-[(R)-4-(4-ethyl-benzenesulfonyl)-3-(4-propyl-benzylcarbamoyl)-piperazin-1-yl]-quinoxaline-5-carboxylic acid (Example 816), 2-[(R)-3-(4-propyl-benzylcarbamoyl)-4-(4-trifluoromethoxy-benzenesulfonyl)-piperazin-1-yl]-quinoxaline-5-carboxylic acid (Example 817), 2-[(R)-4-(4-ethyl-benzenesulfonyl)-3-(4-propyl-benzylcarbamoyl)-piperazin-1-yl]-benzothiazole-4-carboxylic acid (Example 818), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-propyl-benzylamide (Example 819), (R)-4-(7-oxo-6,7-dihydro-thiazolo[4,5-d]pyridazin-2-yl)-1-(4-trifluoromethyl-benzenesulfonyl)-piperazine-2-carboxylic acid 4-propyl-benzylamide (Example 820), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-(1,1-difluoro-propyl)-benzylamide (Example 821), 2-methyl-6-[(R)-3-(4-propyl-benzylcarbamoyl)-4-(4-trifluoromethoxy-benzenesulfonyl)-piperazin-1-yl]-nicotinic acid (Example 822), 5-fluoro-2-methyl-6-[(R)-3-(4-propyl-benzylcarbamoyl)-4-(4-trifluoromethoxy-benzenesulfonyl)-piperazin-1-yl]-nicotinic acid (Example 823), 2-[(R)-3-(4-propyl-benzylcarbamoyl)-4-(4-trifluoromethoxy-benzenesulfonyl)-piperazin-1-yl]-pyrido[3,4-b]pyrazine-8-carboxylic acid (Example 824), (R)-1-(4-nitro-benzenesulfonyl)-4-(7-oxo-6,7-dihydro-thiazolo[4,5-d]pyridazin-2-yl)-piperazine-2-carboxylic acid 4-propyl-benzylamide (Example 825), 3-{4-methyl-2-[(R)-3-(4-propyl-benzylcarbamoyl)-4-(4-trifluoromethoxy-benzenesulfonyl)-piperazin-1-yl]-thiazol-5-yl}-propionic acid (Example 826), (R)-4-(4-methyl-5-sulfamoyl-thiazol-2-yl)-1-(4-trifluoromethoxy-benzenesulfonyl)-piperazine-2-carboxylic acid 4-propyl-benzylamide (Example 827), (R)-4-(4-methyl-5-methylsulfamoyl-thiazol-2-yl)-1-(4-trifluoromethoxy-benzenesulfonyl)-piperazine-2-carboxylic acid 4-propyl-benzylamide (Example 828), (R)-4-(5-dimethylsulfamoyl-4-methyl-thiazol-2-yl)-1-(4-trifluoromethoxy-benzenesulfonyl)-piperazine-2-carboxylic acid 4-propyl-benzylamide (Example 829), (R)-4-(4-trifluoromethoxy-benzenesulfonyl)-piperazine-1,3-dicarboxylic acid 1-phenylamide 3-(4-propyl-benzylamide) (Example 830), 2-{[(R)-3-(4-propyl-benzylcarbamoyl)-4-(4-trifluoromethoxy-benzenesulfonyl)-piperazine-1-carbonyl]-amino}-benzoic acid methyl ester (Example 831), (R)-4-(5-acetylsulfamoyl-4-methyl-thiazol-2-yl)-1-(4-trifluoromethoxy-benzenesulfonyl)-piperazine-2-carboxylic acid 4-propyl-benzylamide (Example 832), (R)-4-(4-trifluoromethoxy-benzenesulfonyl)-piperazine-1,3-dicarboxylic acid 1-[(2-benzyloxy-phenyl)-amide] 3-(4-propyl-benzylamide) (Example 833), (R)-4-(4-trifluoromethoxy-benzenesulfonyl)-piperazine-1,3-dicarboxylic acid 1-[(2-hydroxy-phenyl)-amide] 3-(4-propyl-benzylamide) (Example 834), (R)-1-(4-nitro-benzenesulfonyl)-4-(7-oxo-6,7-dihydro-thiazolo[4,5-d]pyridazin-2-yl)-piperazine-2-carboxylic acid 4-trifluoromethoxy-benzylamide (Example 835), 2-[(R)-3-[4-(1,1-difluoro-propyl)-benzylcarbamoyl]-4-(4-trifluoromethoxy-benzenesulfonyl)-piperazin-1-yl]-pyrido[3,4-b]pyrazine-8-carboxylic acid (Example 836), 2-{[(R)-3-(4-propyl-benzylcarbamoyl)-4-(4-trifluoromethoxy-benzenesulfonyl)-piperazine-1-carbonyl]-amino}-benzoic acid benzyl ester (Example 837), 2-{[(R)-3-(4-propyl-benzylcarbamoyl)-4-(4-trifluoromethoxy-benzenesulfonyl)-piperazine-1-carbonyl]-amino}-benzoic acid (Example 838), (R)-4-(4-methyl-7-oxo-6,7-dihydro-thiazolo[4,5-d]pyridazin-2-yl)-1-(4-trifluoromethoxy-benzenesulfonyl)-piperazine-2-carboxylic acid 4-trifluoromethoxy-benzylamide (Example 839), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-(1,1-dimethyl-propyl)-benzylamide (Example 840), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-butyl-benzylamide (Example 841), 2-[(R)-3-(4-propyl-benzylcarbamoyl)-4-(4-trifluoromethyl-benzenesulfonyl)-piperazin-1-yl]-pyrido[3,4-b]pyrazine-8-carboxylic acid (Example 842), 2-[(R)-4-(4-nitro-benzenesulfonyl)-3-(4-propyl-benzylcarbamoyl)-piperazin-1-yl]-pyrido[3,4-b]pyrazine-8-carboxylic acid (Example 843), 2-[(R)-4-(4-tert-butyl-benzenesulfonyl)-3-(4-propyl-benzylcarbamoyl)-piperazin-1-yl]-pyrido[3,4-b]pyrazine-8-carboxylic acid (Example 844), 2-[(R)-4-(4-chloro-benzenesulfonyl)-3-(4-propyl-benzylcarbamoyl)-piperazin-1-yl]-pyrido[3,4-b]pyrazine-8-carboxylic acid (Example 845), {4-methyl-2-[(R)-3-(4-propyl-benzylcarbamoyl)-4-(4-trifluoromethoxy-benzenesulfonyl)-piperazin-1-yl]-thiazol-5-yl}-oxo-acetic acid ethyl ester (Example 846), 4-chloro-2-[(R)-3-(4-propyl-benzylcarbamoyl)-4-(4-trifluoromethoxy-benzenesulfonyl)-piperazin-1-yl]-thiazole-5-carboxylic acid (Example 847), {4-methyl-2-[(R)-3-(4-propyl-benzylcarbamoyl)-4-(4-trifluoromethoxy-benzenesulfonyl)-piperazin-1-yl]-thiazol-5-yl}-oxo-acetic acid (Example 848), (R)-4-pteridin-7-yl-1-(4-trifluoromethoxy-benzenesulfonyl)-piperazine-2-carboxylic acid (2-phenyl-cyclopropylmethyl)-amide (Example 849), (R)-1-(5-chloro-thiophene-2-sulfonyl)-4-(7-oxo-6,7-dihydro-thiazolo[4,5-d]pyridazin-2-yl)-piperazine-2-carboxylic acid 4-trifluoromethoxy-benzylamide (Example 850), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-(2-methoxy-1,1-dimethyl-ethyl)-benzylamide (Example 851), (R)-4-(4-trifluoromethoxy-benzenesulfonyl)-3,4,5,6-tetrahydro-2H-[1,2']bipyrazinyl-3,5'-dicarboxylic acid 5'-ethylamide 3-(4-trifluoromethoxy-benzylamide) (Example 852), (R)-4-(4-trifluoromethoxy-benzenesulfonyl)-3,4,5,6-tetrahydro-2H-[1,2']bipyrazinyl-3,5'-dicarboxylic acid 5'-tert-butylamide 3-(4-trifluoromethoxy-benzylamide) (Example 853), 2-[(R)-3-[4-(1,1-dimethyl-propyl)-benzylcarbamoyl]-4-(4-ethyl-benzenesulfonyl)-piperazin-1-yl]-pyrido[3,4-b]pyrazine-8-carboxylic acid (Example 854), 2-[(R)-3-(4-butyl-benzylcarbamoyl)-4-(4-ethyl-benzenesulfonyl)-piperazin-1-yl]-pyrido[3,4-b]pyrazine-8-carboxylic acid (Example 855), hydroxy-{4-methyl-2-[(R)-3-(4-propyl-benzylcarbamoyl)-4-(4-trifluoromethoxy-benzenesulfonyl)-piperazin-1-yl]-thiazol-5-yl}-acetic acid ethyl ester (Example 856), (R)-4-pteridin-7-yl-1-(4-trifluoromethoxy-benzenesulfonyl)-piperazine-2-carboxylic acid (5-propyl-thiophen-2-ylmethyl)-amide (Example 857), 2-{(R)-4-(5-chloro-thiophene-2-sulfonyl)-3-[4-(1,1-dimethyl-propyl)-benzylcarbamoyl]-piperazin-1-yl}-pyrido[3,4-b]pyrazine-8-carboxylic acid (Example 858), (R)-4-(4-methyl-5-methylaminooxalyl-thiazol-2-yl)-1-(4-trifluoromethoxy-benzenesulfonyl)-piperazine-2-carboxylic acid 4-propyl-benzylamide (Example 859), 2-[(R)-4-(5-chloro-thiophene-2-sulfonyl)-3-(4-propyl-benzylcarbamoyl)-piperazin-1-yl]-pyrido[3,4-b]pyrazine-8-carboxylic acid (Example 860), 2-[(R)-4-(5-chloro-thiophene-2-sulfonyl)-3-(4-trifluoromethoxy-benzylcarbamoyl)-piperazin-1-yl]-pyrido[3,4-b]pyrazine-8-carboxylic acid (Example 861), 2-[(R)-4-(4-ethyl-benzenesulfonyl)-3-(4-propyl-benzylcarbamoyl)-piperazin-1-yl]-7-oxo-6,7-dihydro-thiazolo[4,5-d]pyridazine-4-carboxylic acid ethyl ester (Example 862), 2-[(R)-4-(4-ethyl-benzenesulfonyl)-3-(4-propyl-benzylcarbamoyl)-piperazin-1-yl]-7-oxo-6,7-dihydro-thiazolo[4,5-d]pyridazine-4-carboxylic acid (Example 863), (R)-1-(4-fluoro-benzenesulfonyl)-4-(7-oxo-6,7-dihydro-thiazolo[4,5-d]pyridazin-2-yl)-piperazine-2-carboxylic acid 4-trifluoromethoxy-benzylamide (Example 864), 2-[(R)-4-(4-trifluoromethoxy-benzenesulfonyl)-3-(4-trifluoromethoxy-benzylcarbamoyl)-piperazin-1-yl]-pyrido[3,4-b]pyrazine-8-carboxylic acid methylamide (Example 865), 2-[(R)-4-(4-trifluoromethoxy-benzenesulfonyl)-3-(4-trifluoromethoxy-benzylcarbamoyl)-piperazin-1-yl]-pyrido[3,4-b]pyrazine-8-carboxylic acid dimethylamide (Example 866), (R)-4-pteridin-7-yl-1-(4-trifluoromethoxy-benzenesulfonyl)-piperazine-2-carboxylic acid (1-phenyl-azetidin-3-ylmethyl)-amide (Example 867), 4-chloro-2-[(R)-4-(4-ethyl-benzenesulfonyl)-3-(4-propyl-benzylcarbamoyl)-piperazin-1-yl]-thiazole-5-carboxylic acid (Example 868), (R)-4-(7-chloro-thiazolo[4,5-d]pyridazin-2-yl)-1-(4-trifluoromethoxy-benzenesulfonyl)-piperazine-2-carboxylic acid 4-trifluoromethoxy-benzylamide (Example 869), (R)-4-(4-hydroxymethyl-7-oxo-6,7-dihydro-thiazolo[4,5-d]pyridazin-2-yl)-1-(4-trifluoromethoxy-benzenesulfonyl)-piperazine-2-carboxylic acid 4-trifluoromethoxy-benzylamide (Example 870), 2-[(R)-4-(4-trifluoromethoxy-benzenesulfonyl)-3-(4-trifluoromethoxy-benzylcarbamoyl)-piperazin-1-yl]-pyrido[3,4-b]pyrazine-8-carboxylic acid isopropylamide (Example 871), (R)-4-(8-cyano-pyrido[3,4-b]pyrazin-2-yl)-1-(4-trifluoromethoxy-benzenesulfonyl)-piperazine-2-carboxylic acid 4-trifluoromethoxy-benzylamide (Example 872), (R)-1-(4-chloro-benzenesulfonyl)-4-(7-oxo-6,7-dihydro-thiazolo[4,5-d]pyridazin-2-yl)-piperazine-2-carboxylic acid 4-trifluoromethoxy-benzylamide (Example 873), 7-oxo-2-[(R)-4-(4-trifluoromethoxy-benzenesulfonyl)-3-(4-trifluoromethoxy-benzylcarbamoyl)-piperazin-1-yl]-6,7-dihydro-thiazolo[4,5-d]pyridazine-4-carboxylic acid (Example 874), 7-oxo-2-[(R)-4-(4-trifluoromethoxy-benzenesulfonyl)-3-(4-trifluoromethoxy-benzylcarbamoyl)-piperazin-1-yl]-6,7-dihydro-thiazolo[4,5-d]pyridazine-4-carboxylic acid methylamide (Example 875), 7-oxo-2-[(R)-4-(4-trifluoromethoxy-benzenesulfonyl)-3-(4-trifluoromethoxy-benzylcarbamoyl)-piperazin-1-yl]-6,7-dihydro-thiazolo[4,5-d]pyridazine-4-carboxylic acid amide (Example 876), (R)-4-(7-oxo-6,7-dihydro-thiazolo[4,5-d]pyridazin-2-yl)-1-(4-trifluoromethyl-benzenesulfonyl)-piperazine-2-carboxylic acid 4-trifluoromethoxy-benzylamide (Example 877), (R)-4-(5-hydroxy-thiazolo[4,5-d]pyrimidin-2-yl)-1-(4-trifluoromethoxy-benzenesulfonyl)-piperazine-2-carboxylic acid 4-trifluoromethoxy-benzylamide (Example 878), (R)-4-thiazolo[4,5-d]pyridazin-2-yl-1-(4-trifluoromethoxy-benzenesulfonyl)-piperazine-2-carboxylic acid 4-trifluoromethoxy-benzylamide (Example 879), 7-chloro-2-[(R)-4-(4-ethyl-benzenesulfonyl)-3-(4-propyl-benzylcarbamoyl)-piperazin-1-yl]-thiazolo[4,5-d]pyridazine-4-carboxylic acid ethyl ester (Example 880), (R)-1-(4-bromo-benzenesulfonyl)-4-(7-oxo-6,7-dihydro-thiazolo[4,5-d]pyridazin-2-yl)-piperazine-2-carboxylic acid 4-trifluoromethoxy-benzylamide (Example 881), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-(1-methoxymethyl-cyclopropyl)-benzylamide (Example 882), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-(ethyl-methyl-amino)-benzylamide (Example 883), (R)-1-(4-methoxy-benzenesulfonyl)-4-(7-oxo-6,7-dihydro-thiazolo[4,5-d]pyridazin-2-yl)-piperazine-2-carboxylic acid 4-trifluoromethoxy-benzylamide (Example 884), (R)-4-thiazolo[5,4-d]pyrimidin-2-yl-1-(4-trifluoromethoxy-benzenesulfonyl)-piperazine-2-carboxylic acid 4-trifluoromethoxy-benzylamide (Example 885), (R)-4-thiazolo[4,5-d]pyrimidin-2-yl-1-(4-trifluoromethyl-benzenesulfonyl)-piperazine-2-carboxylic acid 4-trifluoromethoxy-benzylamide (Example 886), (R)-4-(5-chloro-thiazolo[4,5-d]pyrimidin-2-yl)-1-(4-trifluoromethyl-benzenesulfonyl)-piperazine-2-carboxylic acid 4-trifluoromethoxy-benzylamide (Example 887), (R)-4-(5,7-dihydroxy-thiazolo[4,5-d]pyrimidin-2-yl)-1-(4-trifluoromethoxy-benzenesulfonyl)-piperazine-2-carboxylic acid 4-trifluoromethoxy-benzylamide (Example 888), 4-[(R)-4-(4-ethyl-benzenesulfonyl)-3-(4-propyl-benzylcarbamoyl)-piperazin-1-yl]-2-fluoro-benzoic acid (Example 889), 4-chloro-2-[(R)-3-[4-(1,1-dimethyl-propyl)-benzylcarbamoyl]-4-(4-trifluoromethoxy-benzenesulfonyl)-piperazin-1-yl]-thiazole-5-carboxylic acid (Example 890), 2-[(R)-4-(4-ethyl-benzenesulfonyl)-3-(4-propyl-benzylcarbamoyl)-piperazin-1-yl]-thiazolo[4,5-d]pyridazine-4-carboxylic acid ethyl ester (Example 891), 2-[(R)-4-(4-ethyl-benzenesulfonyl)-3-(4-propyl-benzylcarbamoyl)-piperazin-1-yl]-thiazolo[4,5-d]pyridazine-4-carboxylic acid (Example 892), (R)-4-(4-methyl-7-oxo-6,7-dihydro-thiazolo[4,5-d]pyridazin-2-yl)-1-(4-trifluoromethyl-benzenesulfonyl)-piperazine-2-carboxylic acid 4-trifluoromethoxy-benzylamide (Example 893), (R)-4-thiazolo[4,5-d]pyrimidin-2-yl-1-(4-trifluoromethoxy-benzenesulfonyl)-piperazine-2-carboxylic acid 4-(1,1-difluoro-propyl)-benzylamide (Example 894), (R)-4-(5-chloro-thiazolo[4,5-d]pyrimidin-2-yl)-1-(4-trifluoromethoxy-benzenesulfonyl)-piperazine-2-carboxylic acid 4-(1,1-difluoro-propyl)-benzylamide (Example 895), (R)-4-(7-chloro-thiazolo[4,5-d]pyridazin-2-yl)-1-(4-trifluoromethoxy-benzenesulfonyl)-piperazine-2-carboxylic acid 4-trifluoromethoxy-benzylamide (Example 896), (R)-4-thiazolo[4,5-d]pyridazin-2-yl)-1-(4-trifluoromethyl-benzenesulfonyl)-piperazine-2-carboxylic acid 4-trifluoromethoxy-benzylamide (Example 897), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-(1,1,2,2-tetrafluoro-ethoxy)-benzylamide (Example 898), (R)-4-(7-oxo-6,7-dihydro-thiazolo[4,5-d]pyridazin-2-yl)-1-(4-trifluoromethoxy-benzenesulfonyl)-piperazine-2-carboxylic acid (3-phenyl-cyclobutylmethyl)-amide (Example 899), (R)-4-(7-oxo-6,7-dihydro-thiazolo[4,5-d]pyridazin-2-yl)-1-(4-trifluoromethyl-benzenesulfonyl)-piperazine-2-carboxylic acid 4-(1,1-difluoro-propyl)-benzylamide (Example 900), (R)-4-(7-oxo-6,7-dihydro-thiazolo[4,5-d]pyridazin-2-yl)-1-(4-trifluoromethoxy-benzenesulfonyl)-piperazine-2-carboxylic acid (naphthalen-2-ylmethyl)-amide (Example 901), (R)-4-(5-chloro-thiazolo[4,5-d]pyrimidin-2-yl)-1-(4-trifluoromethyl-benzenesulfonyl)-piperazine-2-carboxylic acid 4-(1,1-difluoro-propyl)-benzylamide (Example 902), (R)-4-thiazolo[4,5-d]pyrimidin-2-yl-1-(4-trifluoromethyl-benzenesulfonyl)-piperazine-2-carboxylic acid 4-(1,1-difluoro-propyl)-benzylamide (Example 903), (R)-4-(6-methyl-7-oxo-6,7-dihydro-thiazolo[4,5-d]pyridazin-2-yl)-1-(4-trifluoromethoxy-benzenesulfonyl)-piperazine-2-carboxylic acid 4-trifluoromethoxy-benzylamide (Example 904), (R)-4-(5-methoxy-thiazolo[4,5-d]pyrimidin-2-yl)-1-(4-trifluoromethyl-benzenesulfonyl)-piperazine-2-carboxylic acid 4-trifluoromethoxy-benzylamide (Example 905), (R)-4-(7-chloro-4-methyl-thiazolo[4,5-d]pyridazin-2-yl)-1-(4-trifluoromethoxy-benzenesulfonyl)-piperazine-2-carboxylic acid 4-trifluoromethoxy-benzylamide (Example 906), (R)-4-(7-chloro-5-methyl-thiazolo[4,5-d]pyridazin-2-yl)-1-(4-trifluoromethoxy-benzenesulfonyl)-piperazine-2-carboxylic acid 4-trifluoromethoxy-benzylamide (Example 907), (R)-4-(5-methyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 908), (R)-4-(7-oxo-6,7-dihydro-thiazolo[4,5-d]pyridazin-2-yl)-1-(4-trifluoromethoxy-benzenesulfonyl)-piperazine-2-carboxylic acid (4-methyl-2-propyl-thiazol-5-ylmethyl)-amide (Example 909), (R)-4-(5-methyl-7-oxo-6,7-dihydro-thiazolo[4,5-d]pyrimidin-2-yl)-1-(4-trifluoromethoxy-benzenesulfonyl)-piperazine-2-carboxylic acid 4-trifluoromethoxy-benzylamide (Example 910), (R)-4-(5-methyl-7-oxo-6,7-dihydro-thiazolo[4,5-d]pyrimidin-2-yl)-1-(4-trifluoromethoxy-benzenesulfonyl)-piperazine-2-carboxylic acid 4-(1,1-difluoro-propyl)-benzylamide (Example 911), (R)-4-(5-bromo-thiazolo[4,5-d]pyrimidin-2-yl)-1-(4-trifluoromethoxy-benzenesulfonyl)-piperazine-2-carboxylic acid 4-trifluoromethoxy-benzylamide (Example 912), (R)-4-(5-chloro-thiazolo[4,5-d]pyrimidin-2-yl)-1-(4-trifluoromethoxy-benzenesulfonyl)-piperazine-2-carboxylic acid 4-propyl-benzylamide (Example 913), (R)-4-thiazolo[4,5-d]pyrimidin-2-yl-1-(4-trifluoromethoxy-benzenesulfonyl)-piperazine-2-carboxylic acid 4-propyl-benzylamide (Example 914), 2-[(R)-4-(4-trifluoromethoxy-benzenesulfonyl)-3-(4-trifluoromethoxy-benzylcarbamoyl)-piperazin-1-yl]-thiazolo[4,5-d]pyridazine-4-carboxylic acid amide (Example 915), 2-[(R)-4-(4-trifluoromethoxy-benzenesulfonyl)-3-(4-trifluoromethoxy-benzylcarbamoyl)-piperazin-1-yl]-thiazolo[4,5-d]pyridazine-4-carboxylic acid methylamide (Example 916), (R)-4-(4-methyl-thiazolo[4,5-d]pyridazin-2-yl)-1-(4-trifluoromethoxy-benzenesulfonyl)-piperazine-2-carboxylic acid 4-trifluoromethoxy-benzylamide (Example 917), (R)-4-(5-chloro-thiazolo[4,5-d]pyrimidin-2-yl)-1-(4-difluoromethoxy-benzenesulfonyl)-piperazine-2-carboxylic acid 4-trifluoromethoxy-benzylamide (Example 918), (R)-1-(4-difluoromethoxy-benzenesulfonyl)-4-thiazolo[4,5-d]pyrimidin-2-yl-piperazine-2-carboxylic acid 4-trifluoromethoxy-benzylamide (Example 919), (R)-4-(7-methyl-5-oxo-5H-[1,3,4]thiadiazolo[3,2-a]pyrimidin-2-yl)-1-(4-trifluoromethoxy-benzenesulfonyl)-piperazine-2-carboxylic acid 4-trifluoromethoxy-benzylamide (Example 920), (R)-4-(5-methyl-thiazolo[5,4-d]pyrimidin-2-yl)-1-(4-trifluoromethoxy-benzenesulfonyl)-piperazine-2-carboxylic acid 4-trifluoromethoxy-benzylamide (Example 921), (R)-4-[1,2,4]triazolo[3,4-b][1,3,4]thiadiazol-6-yl-1-(4-trifluoromethoxy-benzenesulfonyl)-piperazine-2-carboxylic acid 4-trifluoromethoxy-benzylamide (Example 922), (R)-4-(6-oxo-piperidin-3-yl)-1-(4-trifluoromethoxy-benzenesulfonyl)-piperazine-2-carboxylic acid 4-trifluoromethoxy-benzylamide (Example 923), (R)-4-(6-oxo-1,6-dihydro-pyridin-3-yl)-1-(4-trifluoromethoxy-benzenesulfonyl)-piperazine-2-carboxylic acid 4-trifluoromethoxy-benzylamide hydrochloride (Example 924), (R)-4-(5-methyl-thiazolo[4,5-d]pyrimidin-2-yl)-1-(4-trifluoromethyl-benzenesulfonyl)-piperazine-2-carboxylic acid 4-trifluoromethoxy-benzylamide (Example 925), (R)-4-(5-methyl-thiazolo[4,5-d]pyrimidin-2-yl)-1-(4-trifluoromethoxy-benzenesulfonyl)-piperazine-2-carboxylic acid 4-(1,1-difluoro-propyl)-benzylamide (Example 926), (R)-4-(7-chloro-5-methyl-thiazolo[4,5-d]pyrimidin-2-yl)-1-(4-trifluoromethyl-benzenesulfonyl)-piperazine-2-carboxylic acid 4-trifluoromethoxy-benzylamide (Example 927), (R)-4-(7-chloro-5-methyl-thiazolo[4,5-d]pyrimidin-2-yl)-1-(4-trifluoromethoxy-benzenesulfonyl)-piperazine-2-carboxylic acid 4-(1,1-difluoro-propyl)-benzylamide (Example 928), (R)-4-(5-methoxy-thiazolo[4,5-d]pyrimidin-2-yl)-1-(4-trifluoromethoxy-benzenesulfonyl)-piperazine-2-carboxylic acid 4-trifluoromethoxy-benzylamide (Example 929), 2-[(R)-4-(4-trifluoromethoxy-benzenesulfonyl)-3-(4-trifluoromethoxy-benzylcarbamoyl)-piperazin-1-yl]-thiazolo[4,5-d]pyridazine-4-carboxylic acid dimethylamide (Example 930), (R)-4-(5-chloro-thiazolo[4,5-d]pyrimidin-2-yl)-1-(4-trifluoromethoxy-benzenesulfonyl)-piperazine-2-carboxylic acid 4-difluoromethoxy-benzylamide (Example 931), (R)-4-thiazolo[4,5-d]pyrimidin-2-yl-1-(4-trifluoromethoxy-benzenesulfonyl)-piperazine-2-carboxylic acid 4-difluoromethoxy-benzylamide (Example 932), (R)-4-(3-methyl-[1,2,4]triazolo[3,4-b][1,3,4]thiadiazol-6-yl)-1-(4-trifluoromethoxy-benzenesulfonyl)-piperazine-2-carboxylic acid 4-trifluoromethoxy-benzylamide (Example 933), (R)-4-(7-chloro-5-methyl-thiazolo[4,5-d]pyrimidin-2-yl)-1-(4-trifluoromethyl-benzenesulfonyl)-piperazine-2-carboxylic acid 4-(1,1-difluoro-propyl)-benzylamide (Example 934), (R)-4-(5-methyl-thiazolo[4,5-d]pyrimidin-2-yl)-1-(4-trifluoromethyl-benzenesulfonyl)-piperazine-2-carboxylic acid 4-(1,1-difluoro-propyl)-benzylamide (Example 935), (R)-4-(4-trifluoromethoxy-benzenesulfonyl)-piperazine-1,3-dicarboxylic acid 1-[(5-bromo-[1,3,4]thiadiazol-2-yl)-amide] 3-(4-trifluoromethoxy-benzylamide) (Example 936), (R)-4-(4-oxo-4,5-dihydro-thiazolo[4,5-d]pyridazin-2-yl)-1-(4-trifluoromethoxy-benzenesulfonyl)-piperazine-2-carboxylic acid 4-trifluoromethoxy-benzylamide (Example 937), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-(difluoro-methoxy-methyl)-benzylamide (Example 938), (R)-4-(7-oxo-6,7-dihydro-thiazolo[4,5-d]pyridazin-2-yl)-1-(4-trifluoromethoxy-benzenesulfonyl)-piperazine-2-carboxylic acid 4-methoxymethyl-benzylamide (Example 939), (R)-4-(4-hydroxymethyl-thiazolo[4,5-d]pyridazin-2-yl)-1-(4-trifluoromethoxy-benzenesulfonyl)-piperazine-2-carboxylic acid 4-trifluoromethoxy-benzylamide (Example 940), (R)-4-(7-chloro-5-methyl-thiazolo[4,5-d]pyrimidin-2-yl)-1-(4-trifluoromethoxy-benzenesulfonyl)-piperazine-2-carboxylic acid 4-difluoromethoxy-benzylamide (Example 941), (R)-4-(5-methyl-thiazolo[4,5-d]pyrimidin-2-yl)-1-(4-trifluoromethoxy-benzenesulfonyl)-piperazine-2-carboxylic acid 4-difluoromethoxy-benzylamide (Example 942), (R)-4-(5-amino-thiazolo[4,5-d]pyrimidin-2-yl)-1-(4-trifluoromethoxy-benzenesulfonyl)-piperazine-2-carboxylic acid 4-trifluoromethoxy-benzylamide (Example 943), (R)-4-(7-methoxy-thiazolo[4,5-d]pyridazin-2-yl)-1-(4-trifluoromethoxy-benzenesulfonyl)-piperazine-2-carboxylic acid 4-trifluoromethoxy-benzylamide (Example 944), (R)-4-(5-dimethylamino-thiazolo[4,5-d]pyrimidin-2-yl)-1-(4-trifluoromethoxy-benzenesulfonyl)-piperazine-2-carboxylic acid 4-trifluoromethoxy-benzylamide (Example 945), (R)-4-[5-(2-hydroxy-ethylamino)-thiazolo[4,5-d]pyrimidin-2-yl]-1-(4-trifluoromethoxy-benzenesulfonyl)-piperazine-2-carboxylic acid 4-trifluoromethoxy-benzylamide (Example 946), (R)-4-(5-chloro-thiazolo[4,5-d]pyrimidin-2-yl)-1-(5-trifluoromethyl-thiophene-2-sulfonyl)-piperazine-2-carboxylic acid 4-trifluoromethoxy-benzylamide (Example 947), 7-oxo-2-[(R)-4-(4-trifluoromethoxy-benzenesulfonyl)-3-(4-trifluoromethoxy-benzylcarbamoyl)-piperazin-1-yl]-7H-[1,3,4]thiadiazolo[3,2-a]pyrimidine-5-carboxylic acid methyl ester (Example 948), (R)-4-(5-ethyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 949), (R)-4-(5-ethyl-thiazolo[4,5-d]pyrimidin-2-yl)-1-(4-trifluoromethyl-benzenesulfonyl)-piperazine-2-carboxylic acid 4-trifluoromethoxy-benzylamide (Example 950), (R)-1-(4-trifluoromethoxy-benzenesulfonyl)-4-(3-trifluoromethyl-[1,2,4]triazolo[3,4-b][1,3,4]thiadiazol-6-yl)-piperazine-2-carboxylic acid 4-trifluoromethoxy-benzylamide (Example 951), (R)-4-(5-methylamino-thiazolo[4,5-d]pyrimidin-2-yl)-1-(4-trifluoromethoxy-benzenesulfonyl)-piperazine-2-carboxylic acid 4-trifluoromethoxy-benzylamide (Example 952), (R)-4-[1,2,4]triazolo[3,4-b][1,3,4]thiadiazol-6-yl-1-(4-trifluoromethyl-benzenesulfonyl)-piperazine-2-carboxylic acid 4-trifluoromethoxy-benzylamide (Example 953), (R)-4-[1,2,4]triazolo[3,4-b][1,3,4]thiadiazol-6-yl-1-(4-trifluoromethoxy-benzenesulfonyl)-piperazine-2-carboxylic acid 4-difluoromethoxy-benzylamide (Example 954), (R)-4-(5-chloro-thiazolo[4,5-d]pyrimidin-2-yl)-1-(4-difluoromethoxy-benzenesulfonyl)-piperazine-2-carboxylic acid 4-difluoromethoxy-benzylamide (Example 955), (R)-1-(4-difluoromethoxy-benzenesulfonyl)-4-thiazolo[4,5-d]pyrimidin-2-yl-piperazine-2-carboxylic acid 4-difluoromethoxy-benzylamide (Example 956), (R)-4-(5-methyl-4-oxo-4,5-dihydro-thiazolo[4,5-d]pyridazin-2-yl)-1-(4-trifluoromethoxy-benzenesulfonyl)-piperazine-2-carboxylic acid 4-trifluoromethoxy-benzylamide (Example 957), (R)-4-(5-chloro-thiazolo[4,5-d]pyrimidin-2-yl)-1-(4-trifluoromethoxy-benzenesulfonyl)-piperazine-2-carboxylic acid 4-(ethyl-methyl-amino)-benzylamide (Example 958), (R)-4-(5-chloro-thiazolo[4,5-d]pyrimidin-2-yl)-1-[4-(1,1,2,2-tetrafluoro-ethoxy)-benzenesulfonyl]-piperazine-2-carboxylic acid 4-trifluoromethoxy-benzylamide (Example 959), (R)-1-[4-(1,1,2,2-tetrafluoro-ethoxy)-benzenesulfonyl]-4-thiazolo[4,5-d]pyrimidin-2-yl-piperazine-2-carboxylic acid 4-trifluoromethoxy-benzylamide (Example 960), (R)-1-(4-trifluoromethoxy-benzenesulfonyl)-4-(5-trifluoromethyl-thiazolo[4,5-d]pyrimidin-2-yl)-piperazine-2-carboxylic acid 4-trifluoromethoxy-benzylamide (Example 961), (R)-4-(7-amino-5-chloro-thiazolo[4,5-d]pyrimidin-2-yl)-1-(4-trifluoromethoxy-benzenesulfonyl)-piperazine-2-carboxylic acid 4-trifluoromethoxy-benzylamide (Example 962), (R)-4-(5-chloro-7-oxo-6,7-dihydro-thiazolo[4,5-d]pyrimidin-2-yl)-1-(4-trifluoromethoxy-benzenesulfonyl)-piperazine-2-carboxylic acid 4-trifluoromethoxy-benzylamide (Example 963), (R)-4-(5-cyano-thiazolo[4,5-d]pyrimidin-2-yl)-1-(4-trifluoromethoxy-benzenesulfonyl)-piperazine-2-carboxylic acid 4-trifluoromethoxy-benzylamide (Example 964), (R)-4-(5-chloro-thiazolo[4,5-d]pyrimidin-2-yl)-1-(4-trifluoromethoxy-benzenesulfonyl)-piperazine-2-carboxylic acid 4-methoxy-benzylamide (Example 965), (R)-4-(5-chloro-thiazolo[4,5-d]pyrimidin-2-yl)-1-(4-trifluoromethoxy-benzenesulfonyl)-piperazine-2-carboxylic acid 4-fluoromethoxy-benzylamide (Example 966), (R)-4-thiazolo[4,5-d]pyrimidin-2-yl-1-(4-trifluoromethoxy-benzenesulfonyl)-piperazine-2-carboxylic acid 4-fluoromethoxy-benzylamide (Example 967), (R)-4-(5-chloro-thiazolo[4,5-d]pyrimidin-2-yl)-1-(4-trifluoromethyl-benzenesulfonyl)-piperazine-2-carboxylic acid 4-difluoromethoxy-benzylamide (Example 968), (R)-4-thiazolo[4,5-d]pyrimidin-2-yl-1-(4-trifluoromethyl-benzenesulfonyl)-piperazine-2-carboxylic acid 4-difluoromethoxy-benzylamide (Example 969), (R)-4-(5-methyl-thiazolo[4,5-d]pyrimidin-2-yl)-1-(4-trifluoromethyl-benzenesulfonyl)-piperazine-2-carboxylic acid 4-difluoromethoxy-benzylamide (Example 970), (R)-4-(5-chloro-thiazolo[4,5-d]pyrimidin-2-yl)-1-(4-trifluoromethoxy-benzenesulfonyl)-piperazine-2-carboxylic acid 4-cyclopropyl-benzylamide (Example 971), (R)-4-(5-fluoro-thiazolo[4,5-d]pyrimidin-2-yl)-1-(4-trifluoromethoxy-benzenesulfonyl)-piperazine-2-carboxylic acid 4-trifluoromethoxy-benzylamide (Example 972), (R)-4-(5-isopropylamino-thiazolo[4,5-d]pyrimidin-2-yl)-1-(4-trifluoromethoxy-benzenesulfonyl)-piperazine-2-carboxylic acid 4-trifluoromethoxy-benzylamide (Example 973), (R)-4-(5-bromo-7-diethylamino-thiazolo[4,5-d]pyrimidin-2-yl)-1-(4-trifluoromethyl-benzenesulfonyl)-piperazine-2-carboxylic acid 4-trifluoromethoxy-benzylamide (Example 974), (R)-4-(5-cyclopropyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 975), (R)-4-thiazolo[4,5-d]pyrimidin-2-yl-1-(4-trifluoromethoxy-benzenesulfonyl)-piperazine-2-carboxylic acid 4-cyclopropyl-benzylamide (Example 976), (R)-4-(7-oxo-7H-[1,3,4]thiadiazolo[3,2-a]pyrimidin-2-yl)-1-(4-trifluoromethoxy-benzenesulfonyl)-piperazine-2-carboxylic acid 4-trifluoromethoxy-benzylamide (Example 977), (R)-4-(5-acetyl-4-methyl-thiazol-2-yl)-1-(4-trifluoromethoxy-benzenesulfonyl)-piperazine-2-carboxylic acid 4-trifluoromethoxy-benzylamide (Example 978), 2-[(R)-4-(4-trifluoromethoxy-benzenesulfonyl)-3-(4-trifluoromethoxy-benzylcarbamoyl)-piperazin-1-yl]-thiazolo[4,5-d]pyrimidine-5-carboxylic acid amide (Example 979), (R)-4-(1,3-dimethyl-1H-pyrazolo[3,4-d]thiazol-5-yl)-1-(4-trifluoromethoxy-benzenesulfonyl)-piperazine-2-carboxylic acid 4-trifluoromethoxy-benzylamide (Example 980), (R)-1-(4-trifluoromethyl-benzenesulfonyl)-4-(5-trifluoromethyl-thiazolo[4,5-d]pyrimidin-2-yl)-piperazine-2-carboxylic acid 4-trifluoromethoxy-benzylamide (Example 981), (R)-4-(7-amino-5-methyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 982), (R)-4-(5-cyclopropyl-thiazolo[4,5-d]pyrimidin-2-yl)-1-(4-trifluoromethyl-benzenesulfonyl)-piperazine-2-carboxylic acid 4-trifluoromethoxy-benzylamide (Example 983), (R)-4-(5-isopropyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 984), (R)-4-(4-chloro-thiazolo[4,5-d]pyridazin-2-yl)-1-(4-trifluoromethoxy-benzenesulfonyl)-piperazine-2-carboxylic acid 4-trifluoromethoxy-benzylamide (Example 985), (R)-4-(3-methyl-4-oxo-4H-[1,3,4]thiadiazolo[2,3-c][1,2,4]triazin-7-yl)-1-(4-trifluoromethoxy-benzenesulfonyl)-piperazine-2-carboxylic acid 4-trifluoromethoxy-benzylamide (Example 986), (R)-4-thiazolo[4,5-d][1,2,3]triazin-6-yl-1-(4-trifluoromethoxy-benzenesulfonyl)-piperazine-2-carboxylic acid 4-trifluoromethoxy-benzylamide (Example 987), (R)-4-[2-(5-bromo-[1,3,4]thiadiazol-2-ylcarbamoyl)-acetyl]-1-(4-trifluoromethoxy-benzenesulfonyl)-piperazine-2-carboxylic acid 4-trifluoromethoxy-benzylamide (Example 988), (R)-4-thiazolo[4,5-d]pyrimidin-2-yl-1-(4-trifluoromethoxy-benzenesulfonyl)-piperazine-2-carboxylic acid (indolizin-2-ylmethyl)-amide (Example 989), 7-oxo-2-[(R)-4-(4-trifluoromethoxy-benzenesulfonyl)-3-(4-trifluoromethoxy-benzylcarbamoyl)-piperazin-1-yl]-7H-

[1,3,4]thiadiazolo[3,2-a]pyrimidine-5-carboxylic acid methylamide (Example 990), (R)-4-(5-isopropyl-thiazolo[4,5-d]pyrimidin-2-yl)-1-(4-trifluoromethyl-benzenesulfonyl)-piperazine-2-carboxylic acid 4-trifluoromethoxy-benzylamide (Example 991), (R)-4-(5-cyclopropylmethyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 992), (R)-4-(5-chloro-2-diethylamino-thiazolo[4,5-d]pyrimidin-7-yl)-1-(4-trifluoromethoxy-benzenesulfonyl)-piperazine-2-carboxylic acid 4-trifluoromethoxy-benzylamide (Example 993), (R)-4-[5-(3-hydroxy-3-methyl-but-1-ynyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 994), (R)-4-(5-ethynyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 995), (R)-4-thiazolo[4,5-d]pyrimidin-2-yl-1-(4-trifluoromethoxy-benzenesulfonyl)-piperazine-2-carboxylic acid 4-pentafluorosulfanyl-benzylamide (Example 996), (R)-4-(5-chloro-thiazolo[4,5-d]pyrimidin-2-yl)-1-(4-trifluoromethoxy-benzenesulfonyl)-piperazine-2-carboxylic acid 4-difluoromethoxy-2-fluoro-benzylamide (Example 997), (R)-4-thiazolo[4,5-d]pyrimidin-2-yl-1-(4-trifluoromethoxy-benzenesulfonyl)-piperazine-2-carboxylic acid 4-difluoromethoxy-2-fluoro-benzylamide (Example 998), (R)-1-(4-difluoromethoxy-benzenesulfonyl)-4-(5-trifluoromethyl-thiazolo[4,5-d]pyrimidin-2-yl)-piperazine-2-carboxylic acid 4-trifluoromethoxy-benzylamide (Example 999), (R)-1-(4-trifluoromethoxy-benzenesulfonyl)-4-(5-trifluoromethyl-thiazolo[4,5-d]pyrimidin-2-yl)-piperazine-2-carboxylic acid 4-difluoromethoxy-benzylamide (Example 1000), (R)-1-(4-trifluoromethyl-benzenesulfonyl)-4-(5-trifluoromethyl-thiazolo[4,5-d]pyrimidin-2-yl)-piperazine-2-carboxylic acid 4-difluoromethoxy-benzylamide (Example 1001), (R)-4-[4-(2-hydroxy-ethylamino)-thiazolo[4,5-d][1,2,3]triazin-6-yl]-1-(4-trifluoromethoxy-benzenesulfonyl)-piperazine-2-carboxylic acid 4-trifluoromethoxy-benzylamide (Example 1002), (R)-4-(7-oxo-5-trifluoromethyl-6,7-dihydro-thiazolo[4,5-d]pyrimidin-2-yl)-1-(4-trifluoromethoxy-benzenesulfonyl)-piperazine-2-carboxylic acid 4-trifluoromethoxy-benzylamide (Example 1003), (R)-1-[4-(1,1,2,2-tetrafluoro-ethoxy)-benzenesulfonyl]-4-(5-trifluoromethyl-thiazolo[4,5-d]pyrimidin-2-yl)-piperazine-2-carboxylic acid 4-trifluoromethoxy-benzylamide (Example 1004), (R)-1-(4-difluoromethoxy-benzenesulfonyl)-4-(5-trifluoromethyl-thiazolo[4,5-d]pyrimidin-2-yl)-piperazine-2-carboxylic acid 4-difluoromethoxy-benzylamide (Example 1005), (R)-4-thiazolo[4,5-d][1,2,3]triazin-6-yl-1-(4-trifluoromethyl-benzenesulfonyl)-piperazine-2-carboxylic acid 4-trifluoromethoxy-benzylamide (Example 1006), 2-[(R)-4-(4-trifluoromethoxy-benzenesulfonyl)-3-(4-trifluoromethoxy-benzylcarbamoyl)-piperazin-1-yl]-thiazolo[4,5-d]pyrimidine-5-carboxylic acid ethyl ester (Example 1007), (R)-4-(5-hydroxymethyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1008), (R)-4-(4-methoxy-thiazolo[4,5-d]pyridazin-2-yl)-1-(4-trifluoromethoxy-benzenesulfonyl)-piperazine-2-carboxylic acid 4-trifluoromethoxy-benzylamide (Example 1009), (R)-4-(5-cyano-thiazolo[4,5-d]pyrimidin-2-yl)-1-(4-trifluoromethyl-benzenesulfonyl)-piperazine-2-carboxylic acid 4-trifluoromethoxy-benzylamide (Example 1010), (R)-4-(5-cyano-thiazolo[4,5-d]pyrimidin-2-yl)-1-(4-trifluoromethyl-benzenesulfonyl)-piperazine-2-carboxylic acid 4-difluoromethoxy-benzylamide (Example 1011), (R)-4-(5-cyclopropylmethyl-thiazolo[4,5-d]pyrimidin-2-yl)-1-(4-trifluoromethyl-benzenesulfonyl)-piperazine-2-carboxylic acid 4-trifluoromethoxy-benzylamide (Example 1012), 2-[(R)-3-(4-trifluoromethoxy-benzylcarbamoyl)-4-(4-trifluoromethyl-benzenesulfonyl)-piperazin-1-yl]-thiazolo[4,5-d]pyrimidine-5-carboxylic acid amide (Example 1013), (R)-4-(5-cyclopropyl-thiazolo[4,5-d]pyrimidin-2-yl)-1-(4-difluoromethoxy-benzenesulfonyl)-piperazine-2-carboxylic acid 4-difluoromethoxy-benzylamide (Example 1014), (R)-1-[4-(1,1,2,2-tetrafluoro-ethoxy)-benzenesulfonyl]-4-(5-trifluoromethyl-thiazolo[4,5-d]pyrimidin-2-yl)-piperazine-2-carboxylic acid 4-difluoromethoxy-benzylamide (Example 1015), (R)-4-(5-cyclopropyl-thiazolo[4,5-d]pyrimidin-2-yl)-1-(4-difluoromethoxy-benzenesulfonyl)-piperazine-2-carboxylic acid 4-trifluoromethoxy-benzylamide (Example 1016), (R)-4-(5-cyclopropyl-thiazolo[4,5-d]pyrimidin-2-yl)-1-(4-trifluoromethoxy-benzenesulfonyl)-piperazine-2-carboxylic acid 4-difluoromethoxy-benzylamide (Example 1017), (R)-4-(5-cyclopropyl-thiazolo[4,5-d]pyrimidin-2-yl)-1-[4-(1,1,2,2-tetrafluoro-ethoxy)-benzenesulfonyl]-piperazine-2-carboxylic acid 4-difluoromethoxy-benzylamide (Example 1018), (R)-4-(5-methyl-7-oxo-7H-[1,3,4]thiadiazolo[3,2-a]pyrimidin-2-yl)-1-(4-trifluoromethoxy-benzenesulfonyl)-piperazine-2-carboxylic acid 4-trifluoromethoxy-benzylamide (Example 1019), (R)-4-(5-cyclopropyl-thiazolo[4,5-d]pyrimidin-2-yl)-1-[4-(1,1,2,2-tetrafluoro-ethoxy)-benzenesulfonyl]-piperazine-2-carboxylic acid 4-trifluoromethoxy-benzylamide (Example 1020), (R)-4-(7-amino-5-trifluoromethyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1021), (R)-4-(7-methoxy-5-trifluoromethyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1022), (R)-4-(5-cyclopropyl-thiazolo[4,5-d]pyrimidin-2-yl)-1-(4-trifluoromethyl-benzenesulfonyl)-piperazine-2-carboxylic acid 4-difluoromethoxy-benzylamide (Example 1023), (R)-4-(5-tert-butyl-thiazolo[4,5-d]pyrimidin-2-yl)-1-(4-trifluoromethyl-benzenesulfonyl)-piperazine-2-carboxylic acid 4-trifluoromethoxy-benzylamide (Example 1024), (R)-4-(5-tert-butyl-thiazolo[4,5-d]pyrimidin-2-yl)-1-(4-trifluoromethyl-benzenesulfonyl)-piperazine-2-carboxylic acid 4-trifluoromethoxy-benzylamide (Example 1025), (R)-4-(6-chloro-5-methyl-7-oxo-7H-[1,3,4]thiadiazolo[3,2-a]pyrimidin-2-yl)-1-(4-trifluoromethoxy-benzenesulfonyl)-piperazine-2-carboxylic acid 4-trifluoromethoxy-benzylamide (Example 1026), (R)-4-(5-methyl-7-oxo-7H-[1,3,4]thiadiazolo[3,2-a]pyrimidin-2-yl)-1-(4-trifluoromethoxy-benzenesulfonyl)-piperazine-2-carboxylic acid 4-difluoromethoxy-benzylamide (Example 1027), (R)-4-(5-methyl-7-oxo-7H-[1,3,4]thiadiazolo[3,2-a]pyrimidin-2-yl)-1-(4-trifluoromethyl-benzenesulfonyl)-piperazine-2-carboxylic acid 4-trifluoromethoxy-benzylamide (Example 1028), 5-methyl-2-[(R)-4-(4-trifluoromethoxy-benzenesulfonyl)-3-(4-trifluoromethoxy-benzylcarbamoyl)-piperazin-1-yl]-thiazolo[4,5-d]pyrimidine-7-carboxylic acid amide (Example 1029), (R)-4-(5-methyl-4-oxo-4,5-dihydro-thiazolo[4,5-d]pyridazin-2-yl)-1-(4-trifluoromethyl-benzenesulfonyl)-piperazine-2-carboxylic acid 4-trifluoromethoxy-benzylamide (Example 1030), (R)-4-(4-oxo-3-trifluoromethyl-4H-[1,3,4]thiadiazolo[2,3-c][1,2,4]triazin-7-yl)-1-(4-trifluoromethoxy-benzenesulfonyl)-piperazine-2-carboxylic acid 4-trifluoromethoxy-benzylamide (Example 1031), (R)-4-(5-methyl-7-oxo-7H-[1,3,4]thiadiazolo[3,2-a]pyrimidin-2-yl)-1-(4-trifluoromethyl-benzenesulfonyl)-piperazine-2-carboxylic acid 4-difluoromethoxy-benzylamide (Example 1032), 2-[(R)-4-(4-trifluoromethoxy-benzenesulfonyl)-3-(4-trifluoromethoxy-benzylcarbamoyl)-piperazin-1-yl]-thiazolo[4,5-d]pyrimidine-5-carboxylic acid (Example 1033), (R)-4-(4-amino-thiazolo[4,5-d][1,2,3]triazin-6-yl)-1-(4-trifluoromethoxy-benzenesulfonyl)-piperazine-2-carboxylic acid 4-trifluoromethoxy-benzylamide (Example 1034), (R)-4-(4-methoxy-thiazolo[4,5-d][1,2,3]triazin-6-yl)-1-(4-trifluoromethoxy-benzenesulfonyl)-piperazine-2-carboxylic acid 4-trifluoromethoxy-benzylamide (Example 1035), (R)-4-(5-cyano-thiazolo[4,5-d]pyrimidin-2-yl)-1-(4-trifluoromethoxy-benzenesulfonyl)-piperazine-2-carboxylic acid 4-difluoromethoxy-benzylamide (Example 1036), (R)-4-(5-ethyl-4-oxo-4,5-dihydro-thiazolo[4,5-d]pyridazin-2-yl)-1-(4-trifluoromethyl-benzenesulfonyl)-piperazine-2-carboxylic acid 4-trifluoromethoxy-benzylamide (Example 1037), (R)-4-(5-oxo-7-trifluoromethyl-5H-[1,3,4]thiadiazolo[3,2-a]pyrimidin-2-yl)-1-(4-trifluoromethoxy-benzenesulfonyl)-piperazine-2-carboxylic acid 4-trifluoromethoxy-benzylamide (Example 1038), (R)-4-(5-methyl-thiazolo[4,5-d]pyrimidin-2-yl)-1-[4-(1,1,2,2-tetrafluoro-ethoxy)-benzenesulfonyl]-piperazine-2-carboxylic acid 4-difluoromethoxy-benzylamide (Example 1039), (R)-4-(5-cyclopropyl-thiazolo[4,5-d]pyrimidin-2-yl)-1-(4-trifluoromethyl-benzenesulfonyl)-piperazine-2-carboxylic acid 4-difluoromethoxy-2-fluoro-benzylamide (Example 1040), 2-[(R)-4-(4-trifluoromethoxy-benzenesulfonyl)-3-(4-trifluoromethoxy-benzylcarbamoyl)-piperazin-1-yl]-thiazolo[4,5-d]pyrimidine-5-carboxylic acid dimethylamide (Example 1041), (R)-1-(4-trifluoromethyl-benzenesulfonyl)-4-(5-trifluoromethyl-thiazolo[4,5-d]pyrimidin-2-yl)-piperazine-2-carboxylic acid 4-difluoromethoxy-2-fluoro-benzylamide (Example 1042), (R)-4-(5-methoxymethyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1043), (R)-1-(4-trifluoromethoxy-benzenesulfonyl)-4-(5-trifluoromethyl-thiazolo[4,5-d]pyrimidin-2-yl)-piperazine-2-carboxylic acid 4-difluoromethoxy-2-fluoro-benzylamide (Example 1044), (R)-4-(5-cyclopropyl-thiazolo[4,5-d]pyrimidin-2-yl)-1-(4-trifluoromethoxy-benzenesulfonyl)-piperazine-2-carboxylic acid 4-difluoromethoxy-2-fluoro-benzylamide (Example 1045), 2-[(R)-4-(4-trifluoromethoxy-benzenesulfonyl)-3-(4-trifluoromethoxy-benzylcarbamoyl)-piperazin-1-yl]-thiazolo[4,5-d]pyrimidine-5-carboxylic acid methylamide (Example 1046), (R)-4-[5-(1-hydroxy-1-methyl-ethyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 1047), (R)-4-(5-acetyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1048), (R)-4-(7-oxo-5-trifluoromethyl-7H-[1,3,4]thiadiazolo[3,2-a]pyrimidin-2-yl)-1-(4-trifluoromethoxy-benzenesulfonyl)-piperazine-2-carboxylic acid 4-trifluoromethoxy-benzylamide (Example 1049), (R)-4-(5-methoxy-thiazolo[5,4-b]pyridin-2-yl)-1-(4-trifluoromethoxy-benzenesulfonyl)-piperazine-2-carboxylic acid 4-trifluoromethoxy-benzylamide (Example 1050), (R)-4-(5-methyl-thiazolo[4,5-d]pyrimidin-2-yl)-1-[4-(1,1,2,2-tetrafluoro-ethoxy)-benzenesulfonyl]-piperazine-2-carboxylic acid 4-trifluoromethoxy-benzylamide (Example 1051), (R)-4-(5-hydroxymethyl-thiazolo[4,5-d]pyrimidin-2-yl)-1-(4-trifluoromethyl-benzenesulfonyl)-piperazine-2-carboxylic acid 4-trifluoromethoxy-benzylamide (Example 1052), (R)-4-(7-oxo-7H-[1,3,4]thiadiazolo[3,2-a]pyrimidin-2-yl)-1-(4-trifluoromethoxy-benzenesulfonyl)-piperazine-2-carboxylic acid 4-difluoromethoxy-benzylamide (Example 1053), 2-[(R)-4-(4-trifluoromethoxy-benzenesulfonyl)-3-(4-trifluoromethoxy-benzylcarbamoyl)-piperazin-1-yl]-thiazolo[4,5-d]pyrimidine-5-carboxylic acid methoxy-methyl-amide (Example 1054), (R)-4-(7-amino-5-methoxymethyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1055), (R)-4-(5-pyrrolidin-1-ylmethyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1056), (R)-4-(7-oxo-7H-[1,3,4]thiadiazolo[3,2-a]pyrimidin-2-yl)-1-(4-trifluoromethyl-benzenesulfonyl)-piperazine-2-carboxylic acid 4-difluoromethoxy-benzylamide (Example 1057), (R)-1-(4-difluoromethoxy-benzenesulfonyl)-4-(7-oxo-7H-[1,3,4]thiadiazolo[3,2-a]pyrimidin-2-yl)-piperazine-2-carboxylic acid 4-trifluoromethoxy-benzylamide (Example 1058), (R)-4-(7-oxo-7H-[1,3,4]thiadiazolo[3,2-a]pyrimidin-2-yl)-1-(4-trifluoromethyl-benzenesulfonyl)-piperazine-2-carboxylic acid 4-trifluoromethoxy-benzylamide (Example 1059), (R)-4-[5-(1-hydroxy-ethyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 1060), (R)-1-(4-trifluoromethoxy-benzenesulfonyl)-4-(5-trifluoromethyl-thiazolo[4,5-d]pyrimidin-2-yl)-piperazine-2-carboxylic acid 4-difluoromethoxy-3-fluoro-benzylamide (Example 1061), (R)-4-(5-oxo-4,5-dihydro-thiazolo[5,4-b]pyridin-2-yl)-1-(4-trifluoromethoxy-benzenesulfonyl)-piperazine-2-carboxylic acid 4-trifluoromethoxy-benzylamide (Example 1062), (R)-1-(4-difluoromethoxy-benzenesulfonyl)-4-(7-oxo-7H-[1,3,4]thiadiazolo[3,2-a]pyrimidin-2-yl)-piperazine-2-carboxylic acid 4-difluoromethoxy-benzylamide (Example 1063), 2-[(R)-4-(4-ethyl-benzenesulfonyl)-3-(4-propyl-benzylcarbamoyl)-piperazin-1-yl]-thiazolo[5,4-c]pyridine-7-carboxylic acid ethyl ester (Example 1064), 2-[(R)-4-(4-ethyl-benzenesulfonyl)-3-(4-propyl-benzylcarbamoyl)-piperazin-1-yl]-thiazolo[5,4-c]pyridine-7-carboxylic acid (Example 1065), (R)-4-(7-oxo-5-trifluoromethyl-7H-[1,3,4]thiadiazolo[3,2-a]pyrimidin-2-yl)-1-(4-trifluoromethoxy-benzenesulfonyl)-piperazine-2-carboxylic acid 4-difluoromethoxy-benzylamide (Example 1066), (R)-4-(7-oxo-5-trifluoromethyl-7H-[1,3,4]thiadiazolo[3,2-a]pyrimidin-2-yl)-1-(4-trifluoromethyl-benzenesulfonyl)-piperazine-2-carboxylic acid 4-trifluoromethoxy-benzylamide (Example 1067), (R)-4-(7-oxo-5-trifluoromethyl-7H-[1,3,4]thiadiazolo[3,2-a]pyrimidin-2-yl)-1-(4-trifluoromethyl-benzenesulfonyl)-piperazine-2-carboxylic acid 4-difluoromethoxy-benzylamide (Example 1068), (R)-4-(5-cyclobutyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1069), (R)-4-[5-(2-methoxy-ethyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 1070), (R)-4-[5-(2-methoxy-ethyl)-4-oxo-4,5-dihydro-thiazolo[4,5-d]pyridazin-2-yl]-1-(4-trifluoromethoxy-benzenesulfonyl)-piperazine-2-carboxylic acid 4-trifluoromethoxy-benzylamide (Example 1071), (R)-4-(5-cyclobutyl-thiazolo[4,5-d]pyrimidin-2-yl)-1-(4-trifluoromethyl-benzenesulfonyl)-piperazine-2-carboxylic acid 4-trifluoromethoxy-benzylamide (Example 1072), (R)-4-(5-cyclopropyl-thiazolo[4,5-d]pyrimidin-2-yl)-1-(4-trifluoromethoxy-benzenesulfonyl)-piperazine-2-carboxylic acid 4-difluoromethoxy-3-fluoro-benzylamide (Example 1073), (R)-4-(5-cyclopropyl-thiazolo[4,5-d]pyrimidin-2-yl)-1-(4-trifluoromethyl-benzenesulfonyl)-piperazine-2-carboxylic acid 4-difluoromethoxy-3-fluoro-benzylamide (Example 1074), (R)-4-[5-(1-hydroxy-1-methyl-ethyl)-thiazolo[4,5-d]pyrimidin-2-yl]-1-(4-trifluoromethyl-benzenesulfonyl)-piperazine-2-carboxylic acid 4-trifluoromethoxy-benzylamide (Example 1075), (R)-4-[5-(1-methoxymethyl-cyclopropyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 1076), (R)-4-[5-(1-hydroxymethyl-cyclopropyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 1077), (R)-4-[5-(2-hydroxy-ethyl)-4-oxo-4,5-dihydro-thiazolo[4,5-d]pyridazin-2-yl]-1-(4-trifluoromethoxy-benzenesulfonyl)-piperazine-2-carboxylic acid 4-trifluoromethoxy-benzylamide (Example 1078), (R)-4-[5-(1-methoxy-cyclopropyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 1079), (R)-4-[5-(1-hydroxy-cyclopropyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 1080), 2-[(R)-3-(4-propyl-benzylcarbamoyl)-4-(4-trifluoromethoxy-benzenesulfonyl)-piperazin-1-yl]-thiazolo[5,4-c]pyridine-6-carboxylic acid tert-butyl ester (Example 1081), 2-[(R)-3-(4-propyl-benzylcarbamoyl)-4-(4-trifluoromethoxy-benzenesulfonyl)-piperazin-1-yl]-thiazolo[5,4-c]pyridine-6-carboxylic acid (Example 1082), 2-[(R)-3-(4-propyl-benzylcarbamoyl)-4-(4-trifluoromethoxy-benzenesulfonyl)-piperazin-1-yl]-thiazolo[5,4-c]pyridine-7-carboxylic acid ethyl ester (Example 1083), 2-[(R)-3-(4-propyl-benzylcarbamoyl)-4-(4-trifluoromethoxy-benzenesulfonyl)-piperazin-1-yl]-thiazolo[5,4-c]pyridine-7-carboxylic acid (Example 1084), (R)-1-(4-trifluoromethyl-benzenesulfonyl)-4-(5-trifluoromethyl-thiazolo[4,5-d]pyrimidin-2-yl)-piperazine-2-carboxylic acid 4-difluoromethoxy-3-fluoro-benzylamide (Example 1085), (R)-4-(5-oxo-4,5-dihydro-thiazolo[5,4-b]pyridin-2-yl)-1-(4-trifluoromethyl-benzenesulfonyl)-piperazine-2-carboxylic acid 4-trifluoromethoxy-benzylamide (Example 1086), (R)-4-(5-difluoromethoxy-thiazolo[4,5-d]pyrimidin-2-yl)-1-(4-trifluoromethoxy-benzenesulfonyl)-piperazine-2-carboxylic acid 4-trifluoromethoxy-benzylamide (Example 1087), (R)-4-(5-isopropyl-7-oxo-7H-[1,3,4]thiadiazolo[3,2-a]pyrimidin-2-yl)-1-(4-trifluoromethoxy-benzenesulfonyl)-piperazine-2-carboxylic acid 4-trifluoromethoxy-benzylamide (Example 1088), (R)-4-(5-isopropyl-7-oxo-7H-[1,3,4]thiadiazolo[3,2-a]pyrimidin-2-yl)-1-(4-trifluoromethoxy-benzenesulfonyl)-piperazine-2-carboxylic acid 4-difluoromethoxy-benzylamide (Example 1089), (R)-4-(7-amino-5-cyclopropyl-thiazolo[4,5-d]pyrimidin-2-yl)-1-(4-trifluoromethoxy-benzenesulfonyl)-piperazine-2-carboxylic acid 4-trifluoromethoxy-benzylamide (Example 1090), (R)-4-[7-amino-5-(1-hydroxy-1-methyl-ethyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 1091), hydroxy-{4-methyl-2-[(R)-3-(4-propyl-benzylcarbamoyl)-4-(4-trifluoromethoxy-benzenesulfonyl)-piperazin-1-yl]-thiazol-5-yl}-acetic acid (Example 1092), 4-chloro-2-[(R)-3-[4-(ethyl-methyl-amino)-benzylcarbamoyl]-4-(4-trifluoromethoxy-benzenesulfonyl)-piperazin-1-yl]-thiazole-5-carboxylic acid (Example 1093), {5-methyl-3-[(R)-3-(4-propyl-benzylcarbamoyl)-4-(4-trifluoromethoxy-benzenesulfonyl)-piperazin-1-yl]-pyrazol-1-yl}-acetic acid (Example 1094),

[(R)-3-(4-tert-butyl-benzylcarbamoyl)-4-(4-trifluoromethoxy-benzenesulfonyl)-3,4,5,6-tetrahydro-2H-[1,2']bipyrazinyl-5'-ylmethyl]-triethyl-ammonium trifluoromethanesulfonate (Example 1095), (R)-4-[2-(5-amino-tetrazol-2-yl)-acetyl]-1-(4-trifluoromethoxy-benzenesulfonyl)-piperazine-2-carboxylic acid 4-(1,1-difluoro-propyl)-benzylamide (Example 1096), (R)-4-[2-(5-amino-tetrazol-1-yl)-acetyl]-1-(4-trifluoromethoxy-benzenesulfonyl)-piperazine-2-carboxylic acid 4-(1,1-difluoro-propyl)-benzylamide (Example 1097), (R)-4-[5-(2-hydroxy-ethyl)-thiazolo[4,5-d]pyrimidin-2-yl]-1-(4-trifluoromethoxy-benzenesulfonyl)-piperazine-2-carboxylic acid 4-trifluoromethoxy-benzylamide (Example 1098), (R)-1-(4-cyclopropyl-benzenesulfonyl)-4-(5-cyclopropyl-thiazolo[4,5-d]pyrimidin-2-yl)-piperazine-2-carboxylic acid 4-trifluoromethoxy-benzylamide (Example 1099), (R)-1-(4-cyclopropyl-benzenesulfonyl)-4-(5-trifluoromethyl-thiazolo[4,5-d]pyrimidin-2-yl)-piperazine-2-carboxylic acid 4-trifluoromethoxy-benzylamide (Example 1100), (R)-4-(5-cyclopropyl-thiazolo[4,5-d]pyrimidin-2-yl)-1-(4-trifluoromethyl-benzenesulfonyl)-piperazine-2-carboxylic acid 3-fluoro-4-trifluoromethoxy-benzylamide (Example 1101), (R)-4-(5-cyclopropyl-thiazolo[4,5-d]pyrimidin-2-yl)-1-(4-trifluoromethoxy-benzenesulfonyl)-piperazine-2-carboxylic acid 3-fluoro-4-trifluoromethoxy-benzylamide (Example 1102)

(R)-4-acetyl-1-(4-trifluoromethoxy-benzenesulfonyl)-piperazine-2-carboxylic acid 3-fluoro-4-trifluoromethoxy-benzylamide (Example 1103), 2-[(R)-4-(4-trifluoromethoxy-benzenesulfonyl)-3-(4-trifluoromethoxy-benzylcarbamoyl)-piperazin-1-yl]-thiazolo[5,4-c]pyridine-7-carboxylic acid (Example 1104), (R)-4-(5-hydroxymethyl-7-oxo-7H-[1,3,4]thiadiazolo[3,2-a]pyrimidin-2-yl)-1-(4-trifluoromethoxy-benzenesulfonyl)-piperazine-2-carboxylic acid 4-trifluoromethoxy-benzylamide (Example 1105), {4-oxo-2-[(R)-4-(4-trifluoromethoxy-benzenesulfonyl)-3-(4-trifluoromethoxy-benzylcarbamoyl)-piperazin-1-yl]-4H-thiazolo[4,5-d]pyridazin-5-yl}-acetic acid (Example 1106), (R)-4-(5-cyclopropyl-7-oxo-6,7-dihydro-thiazolo[4,5-d]pyrimidin-2-yl)-1-(4-trifluoromethyl-benzenesulfonyl)-piperazine-2-carboxylic acid 4-trifluoromethoxy-benzylamide (Example 1107), (R)-4-(5-cyclopropyl-7-oxo-6,7-dihydro-thiazolo[4,5-d]pyrimidin-2-yl)-1-(4-trifluoromethoxy-benzenesulfonyl)-piperazine-2-carboxylic acid 4-trifluoromethoxy-benzylamide (Example 1108), 2-[(R)-3-(4-difluoromethoxy-3-fluoro-benzylcarbamoyl)-4-(4-trifluoromethoxy-benzenesulfonyl)-piperazin-1-yl]-thiazolo[5,4-c]pyridine-7-carboxylic acid (Example 1109), (R)-4-(5-cyclopropyl-thiazolo[4,5-d]pyrimidin-2-yl)-1-(2-fluoro-4-trifluoromethoxy-benzenesulfonyl)-piperazine-2-carboxylic acid 4-trifluoromethoxy-benzylamide (Example 1110), (R)-3-(4-difluoromethoxy-3-fluoro-benzylcarbamoyl)-4-(4-trifluoromethoxy-benzenesulfonyl)-3,4,5,6-tetrahydro-2H-[1,2']bipyrazinyl-5'-carboxylic acid (Example 1111), 3-{4-oxo-2-[(R)-4-(4-trifluoromethoxy-benzenesulfonyl)-3-(4-trifluoromethoxy-benzylcarbamoyl)-piperazin-1-yl]-4H-thiazolo[4,5-d]pyridazin-5-yl}propionic acid (Example 1112), (R)-4-(5-cyclopropyl-7-oxo-6,7-dihydro-thiazolo[4,5-d]pyrimidin-2-yl)-1-(4-trifluoromethoxy-benzenesulfonyl)-piperazine-2-carboxylic acid 4-difluoromethoxy-3-fluoro-benzylamide (Example 1113), (R)-4-(5-cyclopropyl-7-oxo-6,7-dihydro-thiazolo[4,5-d]pyrimidin-2-yl)-1-(4-trifluoromethyl-benzenesulfonyl)-piperazine-2-carboxylic acid 4-difluoromethoxy-3-fluoro-benzylamide (Example 1114), 4-acetyl-1-(4-isopropyl-benzenesulfonyl)-piperazine-2-carboxylic acid 4-trifluoromethyl-benzylamide (Example 1115), (R)-4-acetyl-1-(4-isopropyl-benzenesulfonyl)-piperazine-2-carboxylic acid 4-trifluoromethyl-benzylamide (Example 1116), and (S)-4-acetyl-1-(4-isopropyl-benzenesulfonyl)-piperazine-2-carboxylic acid 4-trifluoromethyl-benzylamide (Example 1117).

The "pharmaceutically acceptable salt" of the compound represented by the formula [I] (hereinafter to be also referred to as the compound of the present invention) may be any salt as long as it forms a nontoxic salt with a compound of the present invention. Examples thereof include a salt with an inorganic acid, a salt with an organic acid, a salt with an inorganic base, a salt with an organic base, a salt with an amino acid and the like.

As the salt with an inorganic acid, for example, salts with hydrochloric acid, nitric acid, sulfuric acid, phosphoric acid, hydrobromic acid and the like can be mentioned.

As the salt with an organic acid, for example, salts with oxalic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid and the like can be mentioned.

As the salt with an inorganic base, for example, sodium salt, potassium salt, calcium salt, magnesium salt, ammonium salt and the like can be mentioned.

As the salt with an organic base, for example, salts with methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline, choline, cinchonine, meglumine and the like can be mentioned.

As the salt with an amino acid, for example, salts with lysine, arginine, aspartic acid, glutamic acid and the like can be mentioned.

Each salt can be obtained by reacting a compound represented by the formula [I] with an inorganic base, an organic base, an inorganic acid, an organic acid or an amino acid according to a method known per se.

The "solvate" is a compound represented by the formula [I] or a pharmaceutically acceptable salt thereof, with which a molecule of a solvent is coordinated, and also encompasses hydrates (also referred to as water-containing compound). The solvate is preferably a pharmaceutically acceptable solvate, such as a monohydrate, a ½ hydrate, a dihydrate, a monohydrate of sodium salt, a monomethanolate, a monoethanolate, a monoacetonitrilate, a ⅔ ethanolate of dihydrochloride of the compound represented by the formula [I] and the like.

A solvate of a compound represented by the formula [I] or a pharmaceutically acceptable salt thereof can be obtained according to a method known per se.

In addition, there are various "isomers" of a compound represented by the above-mentioned formula [I]. For example, E form and Z form are present as geometric isomers. When an asymmetric carbon atom is present, an enantiomer and a diastereomer can be present as stereoisomers based thereon.

When an axial asymmetry is present, a stereoisomer based thereon is present. In some cases, a tautomer may be present. Accordingly, all of such isomers and mixtures thereof are encompassed in the scope of the present invention.

In addition, a compound represented by the formula [I] may be labeled with an isotope (e.g., $^3$H, $^{14}$C, $^{35}$S etc.).

The compound represented by the formula [I], or a pharmaceutically acceptable salt thereof, or a solvate thereof is preferably a substantially purified compound represented by the formula [I], or a pharmaceutically acceptable salt thereof, or a solvate thereof. It is more preferably a compound represented by the formula [I], or a pharmaceutically acceptable salt thereof, or a solvate thereof, which is purified to a purity of not less than 80%.

In the present invention, a prodrug of a compound represented by the formula [I] can also be a useful pharmaceutical agent. By the "prodrug" is meant a derivative of the compound of the present invention, which has a chemically or metabolically decomposable group and which restores to the original compound to show its inherent efficacy after administration to the body by, for example, hydrolysis, solvolysis or decomposition under physiological conditions. It includes a complex and a salt, not involving a covalent bond. The prodrug is utilized, for example, for improving absorption by oral administration or targeting of a target site.

As the site to be modified, highly reactive functional groups in the compound of the present invention, such as hydroxyl group, carboxyl group, amino group, thiol group and the like, are mentioned.

Examples of the hydroxyl-modifying group include acetyl group, propionyl group, isobutyryl group, pivaloyl group, palmitoyl group, benzoyl group, 4-methylbenzoyl group, dimethylcarbamoyl group, dimethylaminomethylcarbonyl group, sulfo group, alanyl group, fumaryl group and the like. In addition, a sodium salt of 3-carboxybenzoyl group, 2-carboxyethylcarbonyl group and the like can be mentioned.

Examples of the carboxyl-modifying group include methyl group, ethyl group, propyl group, isopropyl group, butyl group, isobutyl group, tert-butyl group, pivaloyloxymethyl group, carboxymethyl group, dimethylaminomethyl group, 1-(acetyloxy)ethyl group, 1-(ethoxycarbonyloxy)ethyl group, 1-(isopropyloxycarbonyloxy)ethyl group, 1-(cyclohexyloxycarbonyloxy)ethyl group, (5-methyl-2-oxo-1,3-dioxol-4-yl)methyl group, benzyl group, phenyl group, o-tolyl group, morpholinoethyl group, N,N-diethylcarbamoylmethyl group, phthalidyl group and the like.

Examples of the amino-modifying group include tert-butyl group, docosanoyl group, pivaloylmethyloxy group, alanyl group, hexylcarbamoyl group, pentylcarbamoyl group, 3-methylthio-1-(acetylamino)propylcarbonyl group, 1-sulfo-1-(3-ethoxy-4-hydroxyphenyl)methyl group, (5-methyl-2-oxo-1,3-dioxol-4-yl)methyl group, (5-methyl-2-oxo-1,3-dioxol-4-yl)methoxycarbonyl group, tetrahydrofuranyl group, pyrrolidylmethyl group and the like.

As a pharmaceutical composition containing the compound of the present invention or a salt thereof, or a solvate thereof, oral preparations such as tablet, capsule, granule, powder, troche, syrup, emulsion, suspension and the like, parenteral agents such as external preparation, suppository, injection, eye drop, transnasal agent, pulmonary preparation and the like can be mentioned.

The pharmaceutical composition is produced by appropriately admixing a suitable amount of the compound of the present invention or a salt thereof, or a solvate thereof with at least one kind of a pharmaceutically acceptable carrier according to a method known per se in the technical field of pharmaceutical preparations. The content of the compound of the present invention or a salt thereof in the pharmaceutical composition varies depending on the dosage form, the dose of the compound of the present invention or a salt thereof, and the like. It is, for example, 0.1 to 100 wt % of the whole composition.

As the "pharmaceutically acceptable carrier", various organic or inorganic carrier substances conventionally used as preparation materials can be mentioned. For example, excipient, disintegrant, binder, glidant, lubricant and the like for solid dosage forms, and solvent, solubilizing agent, suspending agent, isotonicity agent, buffer, soothing agent and the like for liquid preparations can be mentioned. Where necessary, additives such as preservative, antioxidant, colorant, sweetening agent and the like are used.

As the "excipient", for example, lactose, sucrose, D-mannitol, D-sorbitol, cornstarch, dextrin, microcrystalline cellulose, crystalline cellulose, carmellose, carmellose calcium, carboxymethyl starch sodium, low-substituted hydroxypropylcellulose, gum arabic and the like can be mentioned.

As the "disintegrant", for example, carmellose, carmellose calcium, carmellose sodium, carboxymethyl starch sodium, croscarmellose sodium, crospovidone, low-substituted hydroxypropylcellulose, hydroxypropylmethylcellulose, crystalline cellulose and the like can be mentioned.

As the "binder", for example, hydroxypropylcellulose, hydroxypropylmethylcellulose, povidone, crystalline cellulose, sucrose, dextrin, starch, gelatin, carmellose sodium, gum arabic and the like can be mentioned.

As the "glidant", for example, light anhydrous silicic acid, magnesium stearate and the like can be mentioned.

As the "lubricant", for example, magnesium stearate, calcium stearate, talc and the like can be mentioned.

As the "solvent", for example, purified water, ethanol, propylene glycol, macrogol, sesame oil, corn oil, olive oil and the like can be mentioned.

As the "solubilizing agent", for example, propylene glycol, D-mannitol, benzyl benzoate, ethanol, triethanolamine, sodium carbonate, sodium citrate and the like can be mentioned.

As the "suspending agent", for example, benzalkonium chloride, carmellose, hydroxypropylcellulose, propylene glycol, povidone, methylcellulose, glyceryl monostearate and the like can be mentioned.

As the "isotonicity agent", for example, glucose, D-sorbitol, sodium chloride, D-mannitol and the like can be mentioned.

As the "buffer", for example, sodium hydrogen phosphate, sodium acetate, sodium carbonate, sodium citrate and the like can be mentioned.

As the "soothing agent", for example, benzyl alcohol and the like can be mentioned.

As the "preservative", for example, ethyl p-hydroxybenzoate, chlorobutanol, benzyl alcohol, sodium dehydroacetate, sorbic acid and the like can be mentioned.

As the "antioxidant", for example, sodium sulfite, ascorbic acid and the like can be mentioned.

As the "colorant", for example, foodcolor (e.g., Food Red No. 2 or No. 3, Food Yellow No. 4 or No. 5 etc.), β-carotene and the like can be mentioned.

As the "sweetening agent", for example, saccharin sodium, dipotassium glycyrrhizinate, aspartame and the like can be mentioned.

While the dose varies depending on the age, body weight, general condition, treatment effect, administration route and the like, it is from 0.01 mg to 3 g, preferably 0.1 mg to 1 g, for an adult per dose, which is given one to several times a day.

The "prophylaxis of hepatitis C" means, for example, administration of a pharmaceutical agent to an individual found to carry an HCV by a test and the like but without a symptom of hepatitis C, or to an individual who shows an improved disease state of hepatitis after a treatment of hepatitis C, but who still carries an HCV and is associated with a risk of recurrence of hepatitis.

The piperazine compound of the present invention can be used for the improvement of viremia in hepatitis C and/or maintenance of improved condition thereof, treatment of viral infections, particularly, an HCV infection and/or maintenance of improved condition thereof.

HCV is known to be a virus with many gene mutations. Therefore, its effect varies depending on the genotype, so is with interferon. Accordingly, a compound showing an effect for many genotypes is one of the preferable embodiments. HCV type 1a and type 1b are widely distributed all over the world and found in high proportions. Therefore, a compound showing a high effect for the both is particularly preferable.

As an index of the "treatment", "improvement" or "effect", a decrease in the virus level or HCV RNA level in the body, particularly in blood, can be used.

The therapeutic agent for hepatitis C of the present invention is expected to provide a synergistic effect when concurrently used with other antiviral agents, antiinflammatory agents or immunostimulants.

The medicaments with the prospect of synergistic effect include, for example, interferon-α, interferon-β, interferon-γ, interleukin-2, interleukin-8, interleukin-10, interleukin-12, TNFα, recombinant or modified products thereof, agonists, antibodies, vaccines, ribozymes, antisense nucleotides and the like.

As evidenced in the combination therapy of anti-HIV agents, which is also called a cocktail therapy, the combined use of various anti-virus agents against viruses showing frequent genetic mutations is expected to show effect for suppressing emergence and increase of drug tolerant viruses. For example, two or three agents from HCV-IRES inhibitors, HCV-NS3 protease inhibitors, HCV-NS2NS3 protease inhibitors, HCV-NS5A inhibitors and HCV polymerase inhibitors may be used in combination. Specifically, the combined use with Ribavirin(R), interferon-α (IFN-α, Roferon (R), IntronA(R), Sumiferon(R), MultiFeron(R), Infergen(R), Omniferon(R), Pegasys(R), PEG-Intron A(R)), interferon-β (Frone(R), Rebif(R), AvoneX(R), IFNβMOCHIDA(R)), interferon-γ, interferon-δ, interferon-ω, interferon-τ, consensus interferon, asialointerferon, and Reg interferons thereof, 1-β-L-ribofuranosyl-1H-1,2,4-triazole-3-carboxamide, 16α-bromo-3β-hydroxy-5α-androstan-17-one, 1H-imidazole-4-ethanamide dihydrochloride, HCV ribozyme Heptazyme(R), polyclonal antibody Civacir(R), lactoferrin GPX-400, (1S, 2R,8R,8aR)-1,2,8-trihydroxyoctahydroindolizidinium chloride, HCV vaccine (MTH-68/B, Innivax C(R), Engerix B(R)), antisense oligonucleotide ISIS-14803, HCV-RNA transcriptase inhibitor VP-50406, tetrachlorodecaoxide (high concentration Oxoferin(R)), tetrahydrofuran-3-yl (S)-N-3-[3-(3-methoxy-4-oxazol-5-ylphenyl)ureido]benzylcarbamate, 4-amino-2-ethoxymethyl-α,α-dimethyl-1H-imidazo[4,5-c]quinoline-1-ethanol, interleukin-2 (Proleukin(R)), thymosin α1, VX-497, VX-950, JTK-003, HCV796, R-1626, NM283 and the like is exemplified, wherein (R) shows trade names.

Furthermore, the combined use with the compounds disclosed in JP-A-08-268890, JP-A-10-101591, JP-A-07-069899, WO99/61613 and the like as HCV-IRES inhibitors; the compounds disclosed in WO98/22496, WO99/7733, WO99/7734, WO00/9543, WO00/9558, WO01/59929, WO98/17679, EP932617, WO99/50230, WO00/74768, WO97/43310, U.S. Pat. No. 5,990,276, WO01/58929, WO01/77113, WO02/8198, WO02/8187, WO02/8244, WO02/8256, WO01/7407, WO01/40262, WO01/64678, WO98/46630, JP-A-11-292840, JP-A-10-298151, JP-A-11-127861, JP-A-2001-103993, WO98/46597, WO99/64442, WO00/31129, WO01/32961, WO93/15730, U.S. Pat. No. 7,832,236, WO00/200400, WO02/8251, WO01/16379, WO02/7761 and the like as HCV protease inhibitors; the compounds disclosed in WO97/36554, U.S. Pat. No. 5,830,905, WO97/36866, U.S. Pat. No. 5,633,388, WO01/7027, WO00/24725 and the like as HCV helicase inhibitors; the compounds disclosed in WO00/10573, WOO/13708, WO00/18231, WO00/6529, WO02/6246, WO01/32153, WO01/60315, WO01/77091, WO02/4425, WO02/20497, WO00/4141 and the like as HCV polymerase inhibitors; the compounds disclosed in WO01/58877, JP-A-11-180981, WO01/12214 and the like as interferon agonists or enhancers; and the like is also exemplified.

In the case of combined administration, the compound of the present invention can be administered simultaneously with a pharmaceutical agent to be used in combination (hereinafter combination drug) or administered at certain time intervals. In the case of combined administration, a pharmaceutical composition containing the compound of the present invention and a combination drug can be administered. Alternatively, a pharmaceutical composition containing the compound of the present invention and a pharmaceutical composition containing a combination drug may be administered separately. The administration route of the compound of the present invention and that of the combination drug may be the same or different.

In the case of a combined administration, the compound of the present invention can be administered once a day or several times a day in a single dose of 0.01 mg to 3 g, preferably 0.1 mg to 1 g, or may be administered at a smaller dose. The combination drug can be administered at a dose generally used for the prevention or treatment of hepatitis C, for example, at a single dose of 0.01 mg to 2 mg. Alternatively, it may be administered at a smaller dose.

Examples of the production method of the compound of the present invention to be used for the practice of the present invention are given in the following. However, the production method of the compound of the present invention is not limited to these examples.

Even if no directly corresponding disclosure is found in the following Production Methods, the steps may be modified for efficient production of the compound, such as introduction of a protecting group into a functional group with deprotection in a subsequent step, and changing the order of Production Methods and steps.

The treatment after reaction in each step may be conventional ones, for which typical methods, such as isolation and purification, crystallization, recrystallization, silica gel chromatography, preparative HPLC and the like, can be appropriately selected and combined.

Production Method 1-1

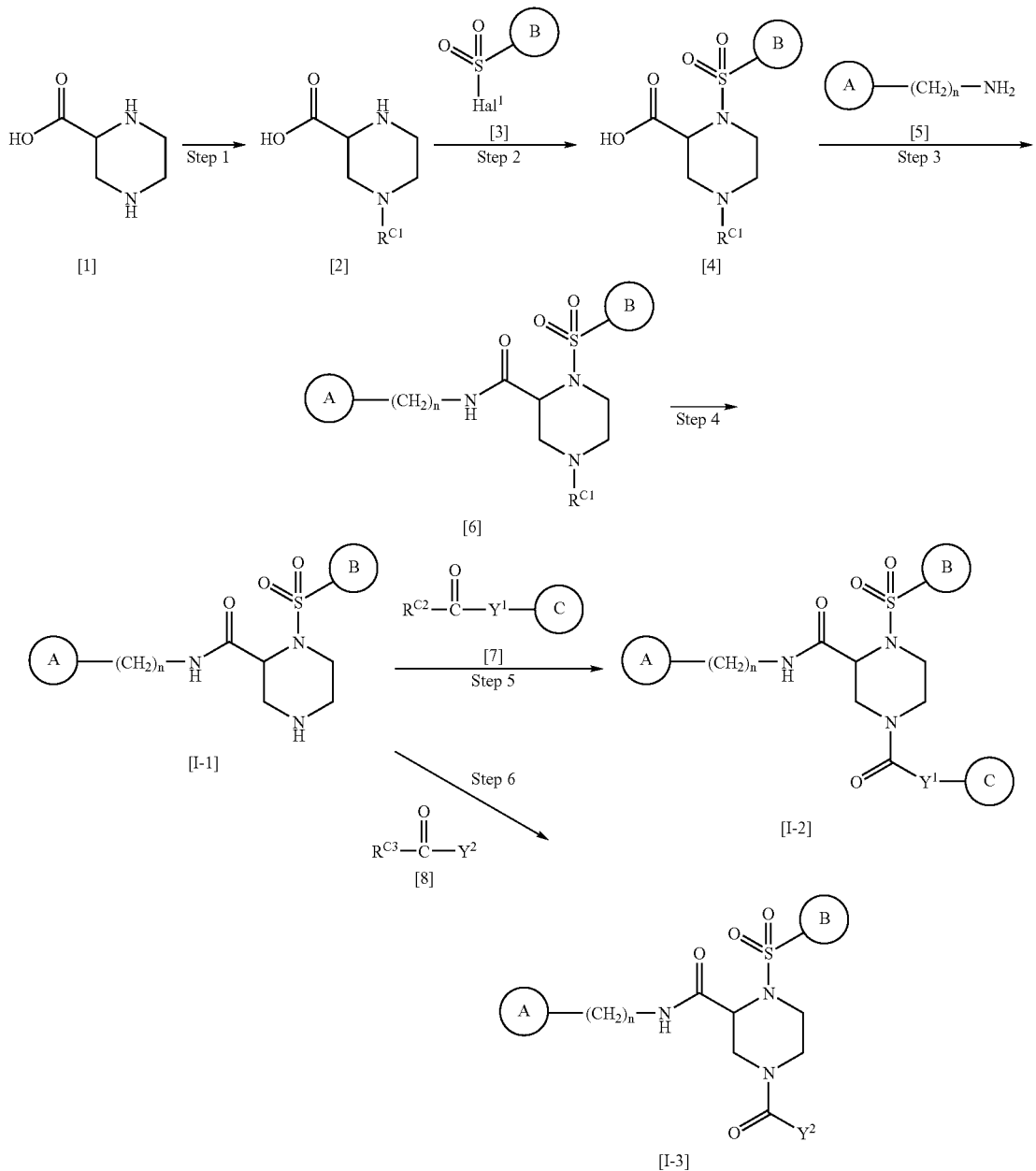

wherein $R^{C1}$ is an amine protecting group, $Hal^1$ is a halogen atom, $R^{C2}$ and $R^{C3}$ are the same or different and each is a hydroxyl group or a leaving group, wherein compound [7] and compound [8] may be an acid anhydride represented by ring $C-Y^1-C(=O)-O-C(=O)-Y^1$-ring C or $Y^2-C(=O)-O-C(=O)-Y^2$, respectively, $Y^1$ is *—$(CH_2)_p$—, *—$NR^{10}$—$(CH_2)_q$—, *—$(CH_2)_r$—O—$(CH_2)_s$—, *—$(CH_2)_t$—NH—$(CH_2)_u$—, —$(CH_2)_v$—CONH—$(CH_2)_w$— or *—NH—$SO_2$—, $Y^2$ is a hydrogen atom, a $C_{1-10}$ alkyl group optionally substituted by 1 to 5 substituents selected from group B,

*—$OR^2$, *—$COOR^6$, —CH=CH—$COOR^{11}$, *—$(CH_2)_a$—NH—$R^7$, *—$(CH_2)_b$—$NHCOR^8$, *—$(CH_2)_c$—NH-$COOR^9$ or *—$CONH_2$, wherein * shows the side bonded to the carbonyl group, and other symbols are as defined above.

As the leaving group, fluorine atom, chlorine atom, bromine atom, iodine atom, p-nitrophenyloxy group, azido group and the like can be mentioned.

As the amine protecting group, benzoyl group, tert-butyl group, tert-butylcarbonyl group, tert-butoxycarbonyl group, benzyloxycarbonyl group, trifluoroacetyl group, fluorenylmethoxycarbonyl group and the like can be mentioned.

Step 1

Compound [2] can be obtained by introducing a protecting group into compound [1] according to a conventional method.

For example, when $R^{C1}$ is tert-butoxycarbonyl group, compound [1] is treated with tert-butoxycarbonyl chloride, 2-tert-butyloxycarbonyl-oxyimino-2-phenylacetonitrile or di-tertbutyl dicarbonate under cooling to room temperature in a solvent such as tetrahydrofuran (THF), 1,4-dioxane, a mixed solvent thereof with water and the like in the presence or absence of a base such as sodium hydroxide and the like.
Step 2

Compound [4] can be obtained by reacting compound [2] with compound [3] in a solvent in the presence of a base in the presence or absence of a catalyst such as 4-(dimethylamino)pyridine and the like.

As the solvent, a single or mixed solvent of water, 1,4-dioxane, acetonitrile, THF, chloroform, ethyl acetate, methylene chloride, toluene, pyridine, N,N-dimethylformamide (DMF) and the like can be mentioned, with preference given to chloroform and a mixed solvent of 1,4-dioxane and water.

As the base, triethylamine, pyridine, 2,6-lutidine, 2,4,6-collidine, sodium hydroxide, potassium carbonate and the like can be mentioned, preferably, triethylamine.

As the $Hal^1$, preferred is a chlorine atom.
Step 3

Compound [6] can be obtained by amide condensation of carboxylic acid compound [4] with amine compound [5] in a solvent in the presence of a condensing agent.

Compound [6] can also be obtained by a method including affording a reactive derivative of carboxylic acid compound [4] by converting carboxylic acid compound [4] to an acid halide induced with thionyl chloride, oxalyl chloride etc. (optionally adding a catalytic amount of DMF), or converting to a mixed acid anhydride induced with ethyl chlorocarbonate etc., and the like, and then reacting the reactive derivative with amine compound [5] in the presence of a base.

As the solvent, DMF, acetonitrile, THF, chloroform, ethyl acetate, methylene chloride, toluene and the like can be mentioned, with preference given to DMF.

As the condensing agent, dicyclohexylcarbodiimide, 1-ethyl-3-(3-dimethylaminopropyl)carbodiimide hydrochloride, diphenylphosphoryl azide and the like can be mentioned. As necessary, N-hydroxysuccinimide, 1-hydroxybenzotriazole and the like can be added.

As the base, potassium carbonate, triethylamine, pyridine, 4-(dimethylamino)pyridine, N-methylmorpholine, diisopropylethylamine and the like can be mentioned, with preference given to triethylamine.
Step 4

Compound [I-1] can be obtained by eliminating the amine protecting group of compound [6] by a conventional method.

For example, when $R^{C1}$ is tert-butoxycarbonyl group, deprotection can be performed by a method including treatment with a hydrogen chloride-ethyl acetate solution at room temperature in an ethyl acetate or methanol solution; treatment with hydrochloric acid in tetrahydrofuran at room temperature; treatment with a hydrogen chloride-1,4-dioxane solution in a methanol or chloroform solvent at room temperature; treatment with trifluoroacetic acid in a chloroform solution and the like.
Step 5

In this step, $R^{C2}$ is a hydroxyl group or a leaving group, and a preferable leaving group is chlorine atom.

When $R^{C2}$ is a hydroxyl group, compound [I-2] can be obtained in the same manner as in production method I-1, step 3, by reacting compound [I-1] with compound [7]

When $R^{C2}$ is a leaving group, compound [I-2] can be obtained by reacting compound [I-1] with compound [7] in a solvent in the presence of a base.

As the solvent, DMF, acetonitrile, THF, chloroform, ethyl acetate, methylene chloride, toluene and the like can be mentioned, with preference given to DMF, THF and chloroform.

As the base, potassium carbonate, triethylamine, pyridine, N-methylmorpholine, diisopropylethylamine and the like can be mentioned, with preference given to triethylamine.
Step 6

In this step, $R^{C3}$ is a hydroxyl group or a leaving group, and the leaving group is preferably chlorine atom. Compound [8] which is an acid anhydride represented by $Y^2-C(=O)-O-C(=O)-Y^2$ is one of the preferable embodiments.

Compound [I-3] can be obtained by reacting compound [I-1] with compound [8] in the same manner as in the previous step.
Production Method 1-2

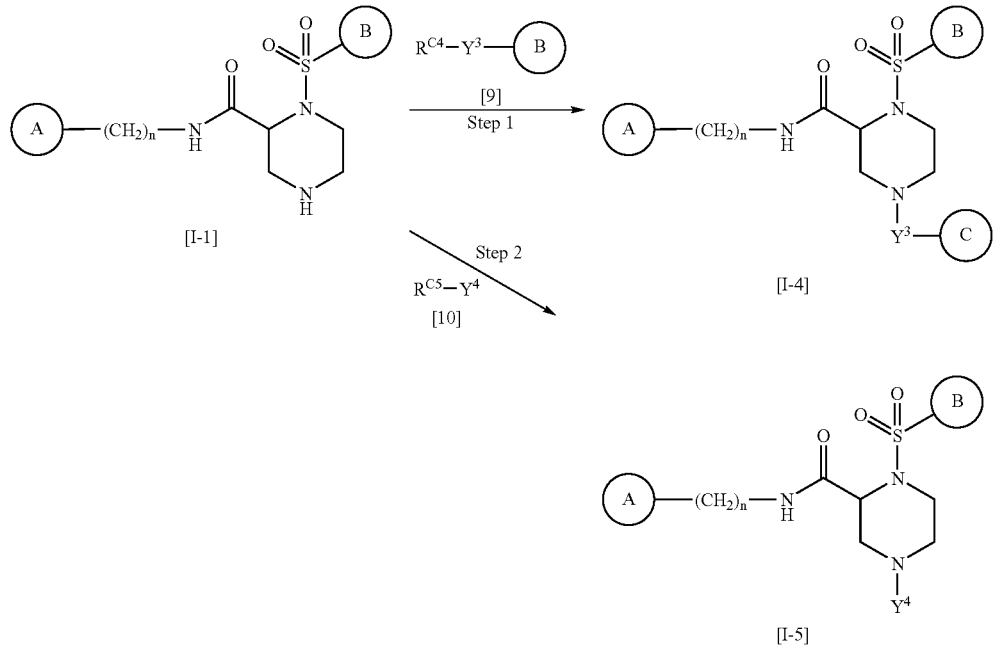

wherein $R^{C4}$ and $R^{C5}$ are the same or different and each is a leaving group,
$Y^3$ is a bond or $C_{1-4}$ alkylene,
$Y^4$ is $-SO_2R^5$ or a $C_{1-10}$ alkyl group optionally substituted by 1 to 5 substituents selected from group B, and other symbols are as defined above.

Step 1

In this step, $R^{C4}$ is a leaving group, preferably, fluorine atom, chlorine atom, bromine atom, iodine atom, methylthio group, methylsulfinyl group, methylsulfonyl group, methanesulfonyloxy group, p-toluenesulfonyloxy group, trifluoromethanesulfonyloxy group and the like, more preferably, fluorine atom, chlorine atom, bromine atom, iodine atom, methylthio group or methylsulfonyl group.

Compound [I-4] can be obtained by reacting compound [I-1] with compound [9] in a solvent in the presence of a base.

As the solvent, alcohol solvents such as ethanol, isopropanol and the like, DMF, acetonitrile, THF, chloroform, ethyl acetate, methylene chloride, toluene and the like can be mentioned.

As the base, potassium carbonate, triethylamine, pyridine, 4-(dimethylamino)pyridine, diisopropylethylamine and the like can be mentioned.

Step 2

In this step, $R^{C5}$ is a leaving group, with preference given to chlorine atom, bromine atom and iodine atom.

In the same manner as in the previous step, compound [I-5] can be obtained by reacting compound [I-1] with compound [10].

Production Method 1-3

Step 1

Compound [I-6] can be obtained by reacting compound [11] with carbonyldiimidazole or triphosgene in a solvent in the presence or absence of a base, and then by reacting with compound [I-1] in the presence of a base.

As the solvent, chloroform, DMF, acetonitrile, THF, ethyl acetate, methylene chloride, toluene and the like can be mentioned, with preference given to chloroform.

As the base, triethylamine, potassium carbonate, pyridine, 4-(dimethylamino)pyridine, diisopropylethylamine and the like can be mentioned, with preference given to triethylamine.

Step 2

In the same manner as in the previous step, compound [I-7] can be obtained by reacting compound [12] with compound [I-1].

Production Method 1-4

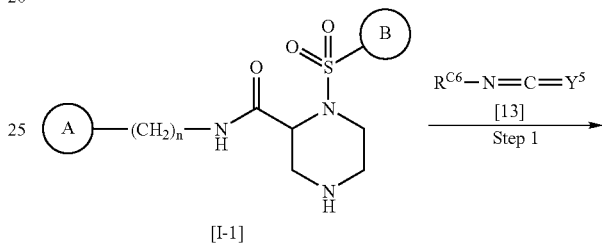

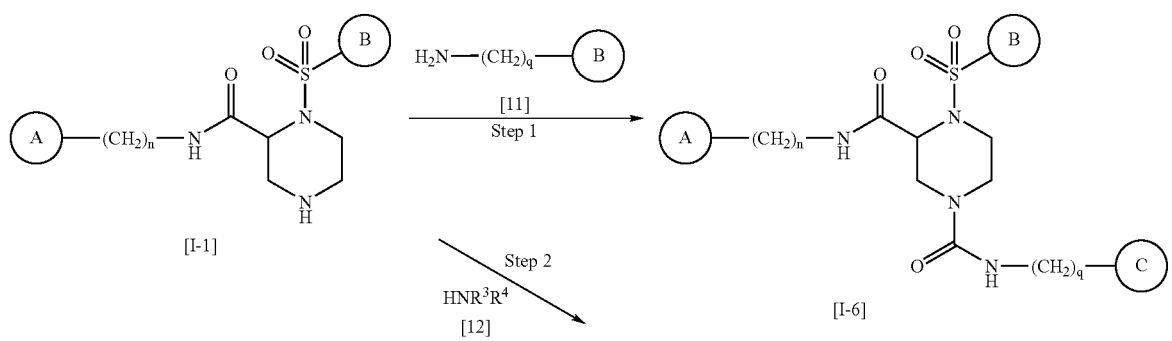

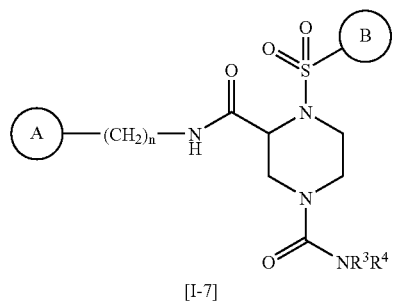

wherein each symbol is as defined above.

-continued

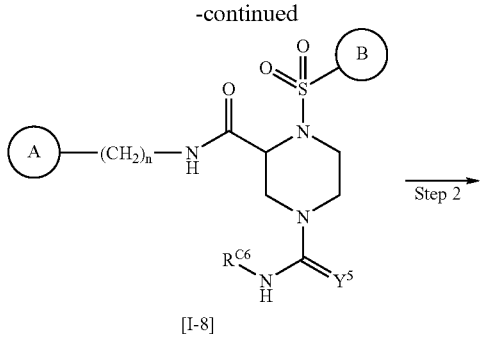

[I-8]

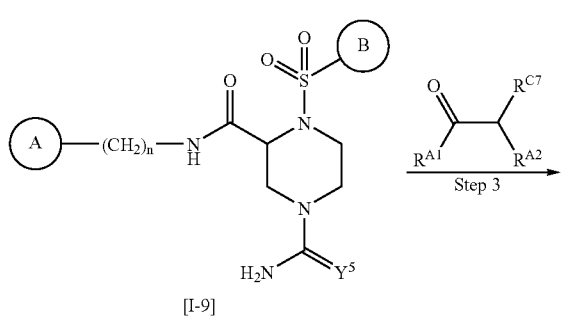

[I-9]

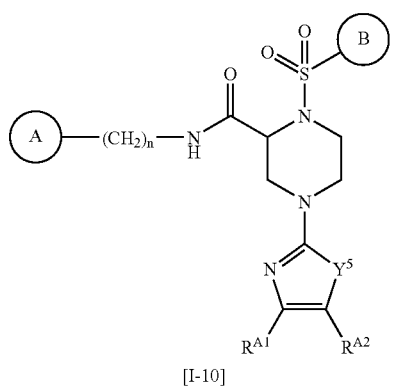

[I-10]

wherein $R^{C6}$ is an amine protecting group, $R^{C7}$ is a halogen atom, $Y^5$ is an oxygen atom or a sulfur atom, $R^{A1}$ and $R^{A2}$ are the same or different and each is a substituent selected from group A, and other symbols are as defined above.

Using, as compound [14], a compound wherein $R^{A1}$ and $R^{A2}$ in combination form a ring, a fused ring such as 4,5,6,7-tetrahydrobenzothiazole, 4,5,6,7-tetrahydrobenzoxazole, 8H-indeno[1,2-d]thiazole and the like can also be formed.

Step 1

Compound [I-8] can be obtained by reacting compound [I-1] with compound [13] in a solvent in the presence of a base.

As the solvent, chloroform, DMF, acetonitrile, THF, ethyl acetate, methylene chloride, toluene and the like can be mentioned, with preference given to chloroform.

As the base, potassium carbonate, triethylamine, pyridine, 4-(dimethylamino)pyridine, diisopropylethylamine and the like can be mentioned, with preference given to triethylamine.

Step 2

Compound [I-9] can be obtained by deprotecting compound [I-8] by a conventional method.

For example, when $R^{C6}$ is fluorenylmethoxycarbonyl group, compound [I-9] can be obtained by reacting compound [I-8] in the presence of a base.

As the base, piperidine, 4-(dimethylamino)pyridine, morpholine, dicyclohexylamine, diisopropylethylamine, tetrabutylammonium fluoride and the like can be mentioned, with preference given to piperidine.

Step 3

Compound [I-10] can be obtained by reacting compound [I-9] with compound [14] in a solvent under heating.

As the solvent, acetonitrile, methanol, ethanol, isopropanol, DMF, N-methylpyrrolidone, THF, toluene and the like can be mentioned, with preference given to acetonitrile.

Production Method 1-5

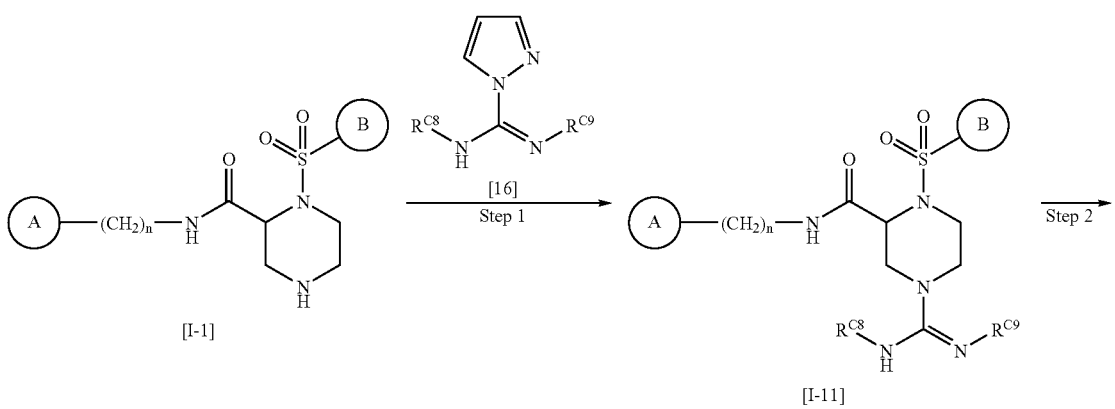

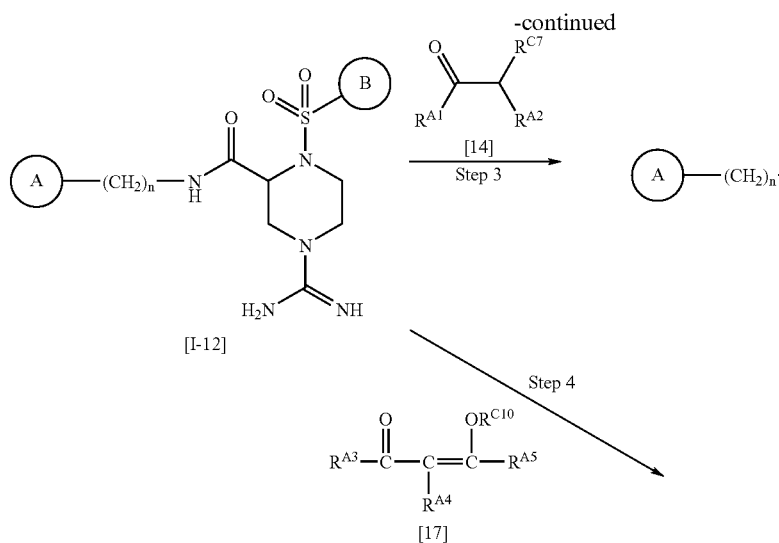

[I-12]

[14] Step 3

[I-13]

Step 4

[17]

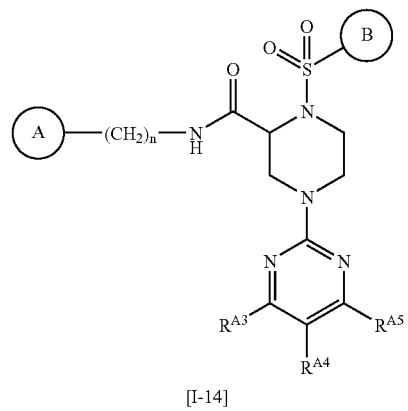

[I-14]

wherein $R^{C8}$ and $R^{C9}$ are amine protecting groups, $R^{C10}$ is a $C_{1-4}$ alkyl group such as methyl group, ethyl group and the like, $R^{A3}$, $R^{A4}$ and $R^{A5}$ are the same or different and each is a substituent selected from group A, and other symbols are as defined above.

Step 1

Compound [I-11] can be obtained by reacting compound [I-1] with compound [16] in a solvent in the presence or absence of a base.

As the solvent, acetonitrile, methanol, ethanol, isopropanol, DMF, THF, toluene and the like can be mentioned, with preference given to acetonitrile and DMF.

As the base, potassium carbonate, triethylamine, pyridine, 4-(dimethylamino)pyridine, diisopropylethylamine and the like can be mentioned, with preference given to diisopropylethylamine.

Step 2

Compound [I-12] can be obtained by eliminating the amine protecting group of compound [I-11] by a conventional method.

$R^{C8}$ and $R^{C9}$ are preferably tert-butoxycarbonyl groups.

Step 3

Compound [I-13] can be obtained by reacting compound [I-12] with compound [14] in a solvent in the presence or absence of a base.

As the solvent, acetonitrile, methanol, ethanol, isopropanol, DMF, THF, toluene, 1,4-dioxane and the like can be mentioned, with preference given to methanol and ethanol.

As the base, sodium ethoxide, sodium methoxide, potassium carbonate, potassium hydrogen carbonate, sodium acetate, ammonia and the like can be mentioned, with preference given to sodium ethoxide and sodium methoxide.

Step 4

In the same manner as in production method 1-5, step 3, compound [I-14] can be obtained by reacting compound [I-12] with compound [17].

Production Method 2

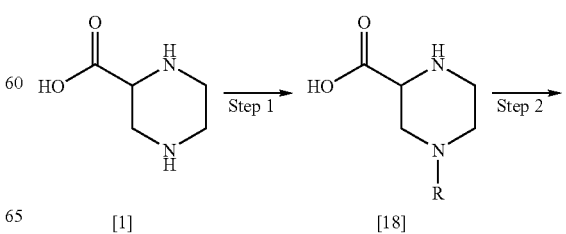

[1]　　　　　　　　　　　　[18]

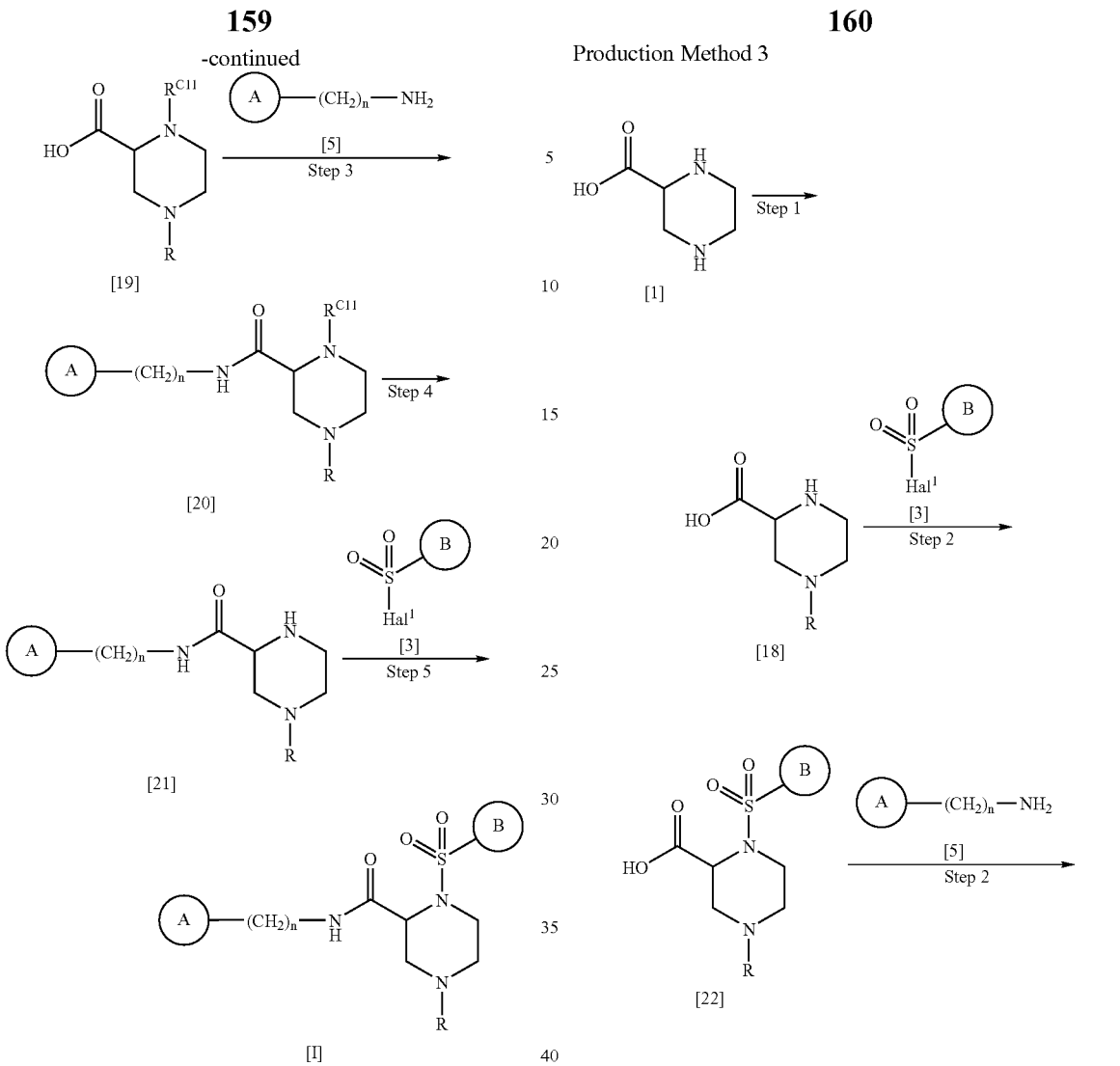

Production Method 3 wherein $R^{C11}$ is an amine protecting group, and other symbols are as defined above.

Step 1

Compound [18] can be obtained from compound [1] in the same manner as in production methods 1-1 to 1-5, or by a conventional method.

Step 2

Compound [19] can be obtained by introducing a protecting group into compound [18] according to a conventional method.

$R^{C11}$ is preferably tert-butoxycarbonyl group.

Step 3

Compound [20] can be obtained by reacting compound [19] with compound [5] in the same manner as in production method 1-1, step 3.

Step 4

Compound [21] can be obtained by eliminating the amine protecting group of compound [20] by a conventional method.

Step 5

Compound [I] can be obtained by reacting compound [21] with compound [3] in the same manner as in production method 1-1, step 2.

wherein each symbol is as defined above.

Step 1

Compound [18] can be obtained from compound [1] in the same manner as in production methods 1-1 to 1-5, or by a conventional method.

Step 2

Compound [22] can be obtained by reacting compound [18] with compound [3] in the same manner as in production method 1-1, step 2.

Step 3

Compound [I] can be obtained by reacting compound [22] with compound [5] in the same manner as in production method 1-1, step 3.

Production Method 4

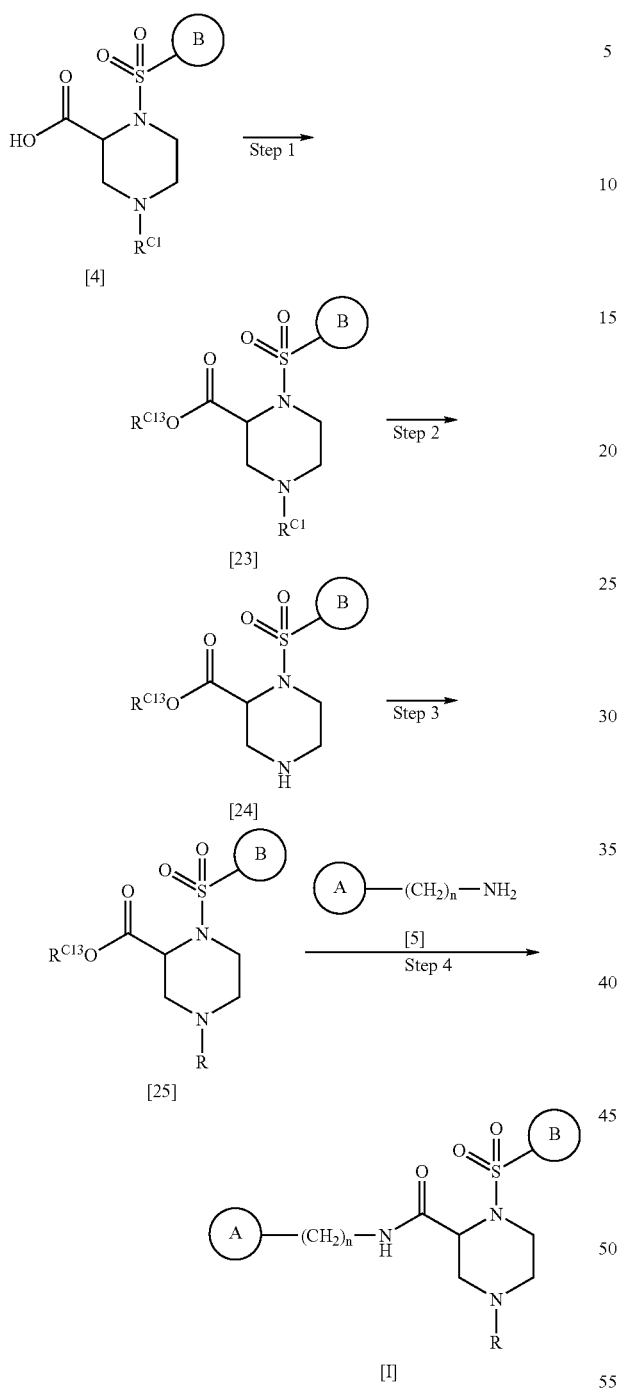

wherein $R^{C13}$ is a carboxylic acid protecting group, and other symbols are as defined above.

As the carboxylic acid protecting group, methyl group, ethyl group, tert-butyl group, benzyl group, allyl group, tetrahydropyranyl group and the like can be mentioned.

Step 1

Compound [23] can be obtained by introducing a protecting group into the carboxyl group of compound [4] according to a conventional method.

For example, when $R^{C13}$ is benzyl group, compound [23] can be obtained by reacting compound [4] with benzyl alcohol in a chloroform solvent in the presence or absence of a catalyst such as 4-(dimethylamino)pyridine and the like in the presence of a condensing agent such as 1-ethyl-3-(3-dimethylaminopropyl)carbodiimide hydrochloride and the like.

Step 2

Compound [24] can be obtained by eliminating an amine protecting group of compound [23] by a conventional method.

$R^{C1}$ is preferably tert-butoxycarbonyl group.

Step 3

Compound [25] can be obtained from compound [24] in the same manner as in production methods 1-1 to 1-5, or by a conventional method.

Step 4

After removing $R^{C13}$ by a conventional method, compound [I] can be obtained by reacting compound [25] with compound [5] in the same manner as in production method 1-1, step 3.

Production Method 5

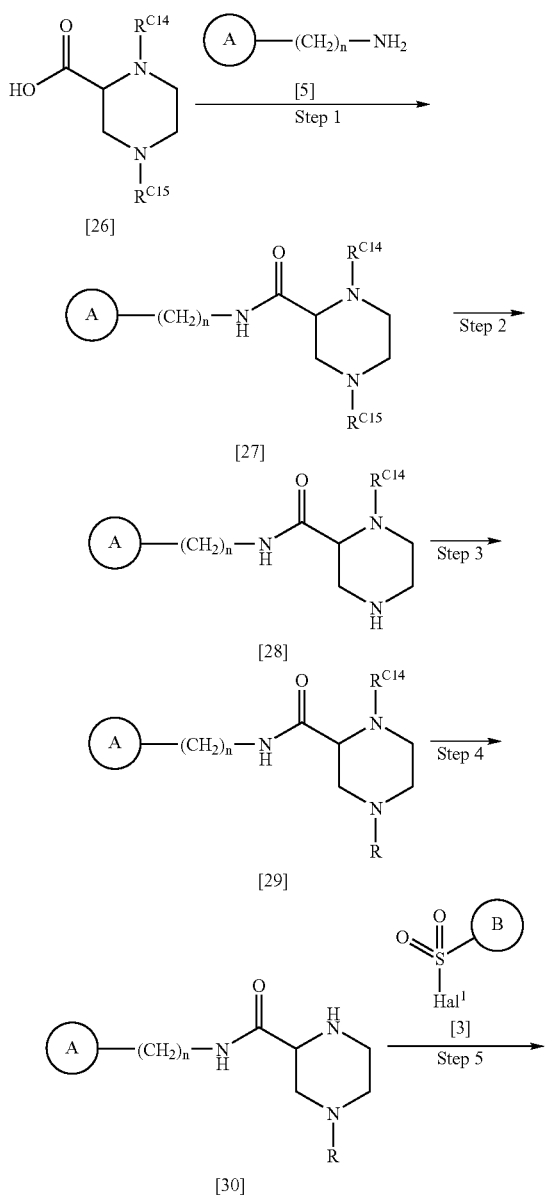

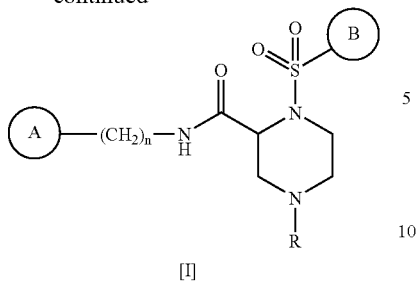

[I]

wherein $R^{C14}$ and $R^{C15}$ are the same or different and each is an amine protecting group, and other symbols are as defined above.

Step 1
Compound [27] can be obtained by reacting compound [26] obtained by a conventional method with compound [5] in the same manner as in production method 1-1, step 3.

Step 2
Compound [28] can be obtained by eliminating the amine protecting group of compound [27] by a conventional method.

The combination of $R^{C14}$ and $R^{C15}$ refers to the combination of benzyloxycarbonyl group and tert-butoxycarbonyl group, trifluoroacetyl group and benzyloxycarbonyl group, trifluoroacetyl group and tert-butoxycarbonyl group, 9-fluorenylmethyloxycarbonyl group and benzyloxycarbonyl group, 9-fluorenylmethyloxycarbonyl group and tert-butoxycarbonyl group and the like can be mentioned, with preference given to a combination of benzyloxycarbonyl group and tert-butoxycarbonyl group.

Step 3
Compound [29] can be obtained from compound [28] in the same manner as in production methods 1-1 to 1-5, or by a conventional method.

Step 4
Compound [30] can be obtained by eliminating the amine protecting group of compound [29] by a conventional method.

Step 5
Compound [I] can be obtained by reacting compound [30] with compound [3] in the same manner as in production method 1-1, step 2.

Production Method 1-2-1
When, in $R^{C4}$—$Y^3$-ring C (compound [9]), $Y^3$ is a bond and ring C is thiazolo[4,5-d]pyrimidin-2-yl optionally substituted by a substituent selected from group A, compound [I] can also be produced by the following method.

This production method is applicable even when the pyrimidine moiety of thiazolo[4,5-d]pyrimidin-2-yl is, for example, other aryl group.

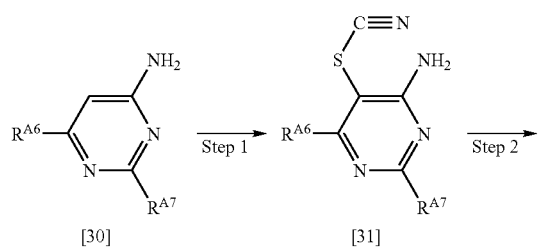

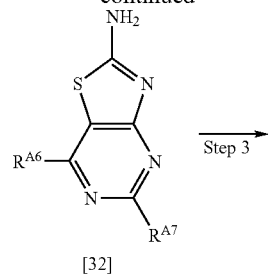

[32]

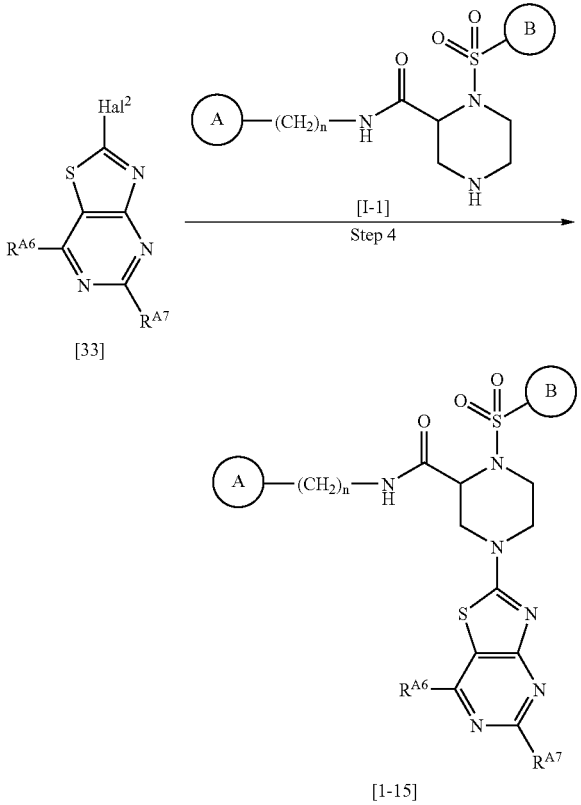

wherein $R^{A6}$ and $R^{A7}$ are the same or different and each is a hydrogen atom or a substituent selected from group A, $Hal^2$ is a halogen atom such as a bromine atom, a chlorine atom and the like, and other symbols are as defined above.

Step 1
Compound [31] can be obtained by reacting compound [30] with thiocyanate such as potassium thiocyanate, sodium thiocyanate, ammonium thiocyanate and the like and halogen in a solvent in the presence of a base.

As the solvent, an alcohol solvent such as methanol, ethanol and the like, or DMF, THF, toluene and the like can be mentioned, with preference given to DMF and methanol.

As the base, pyridine, 4-(dimethylamino)pyridine and the like can be mentioned, with preference given to pyridine.

As the halogen, bromine is preferable.

Step 2
Compound [32] can be obtained by heating compound [31] in a solvent.

As the solvent, hydrous or anhydrous DMF, dimethyl sulfoxide (DMSO) and the like can be mentioned, with preference given to anhydrous DMF.

In addition, compound [32] can also be obtained by heating compound [31] with acetic anhydride, and treating the obtained compound with an alkali solution such as aqueous sodium carbonate solution, aqueous sodium hydroxide solution and the like.

Step 3

Compound [33] can be obtained by substituting the amino group of compound [32] by a leaving group by a conventional method.

For example, when $Hal^2$ is a chlorine atom, compound [33] can be obtained by adding sodium nitrite to compound [32] suspended in an aqueous sodium hydroxide solution, then adding hydrochloric acid, or adding sodium nitrite to a solution of compound [32] in hydrochloric acid, or adding hydrochloric acid to a solution of compound [32] in acetic acid and then adding sodium nitrite.

$Hal^2$ is preferably a chlorine atom.

Step 4

Compound [I-15] can be obtained by reacting compound [33] with compound [I-1] in the same manner as in production method 1-2, step 1.

Production Method 1-2-1-1

Production example for converting substituent on thiazolo[4,5-d]pyrimidin-2-yl group

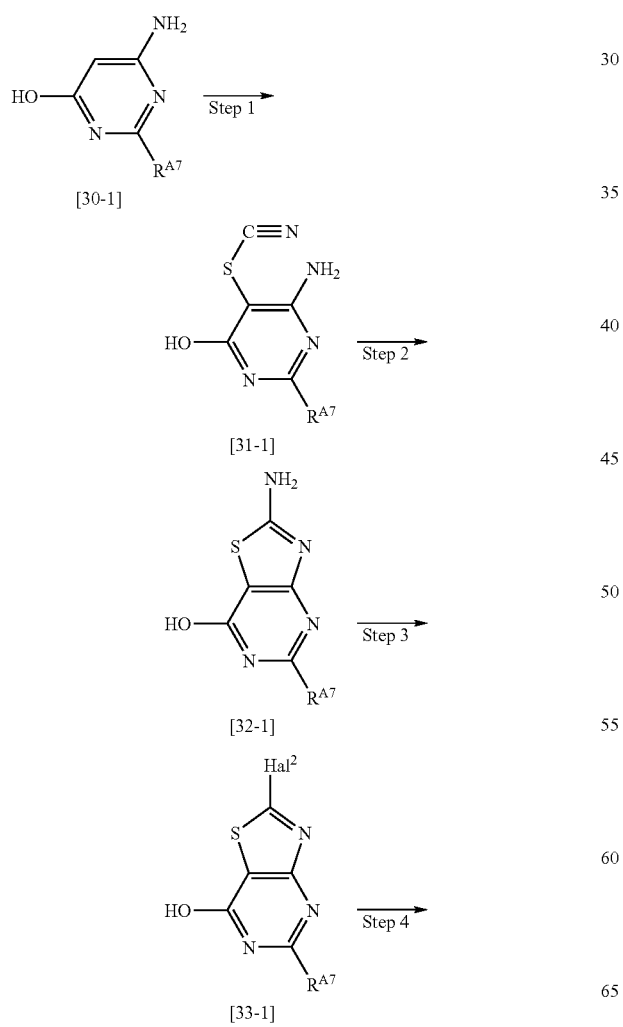

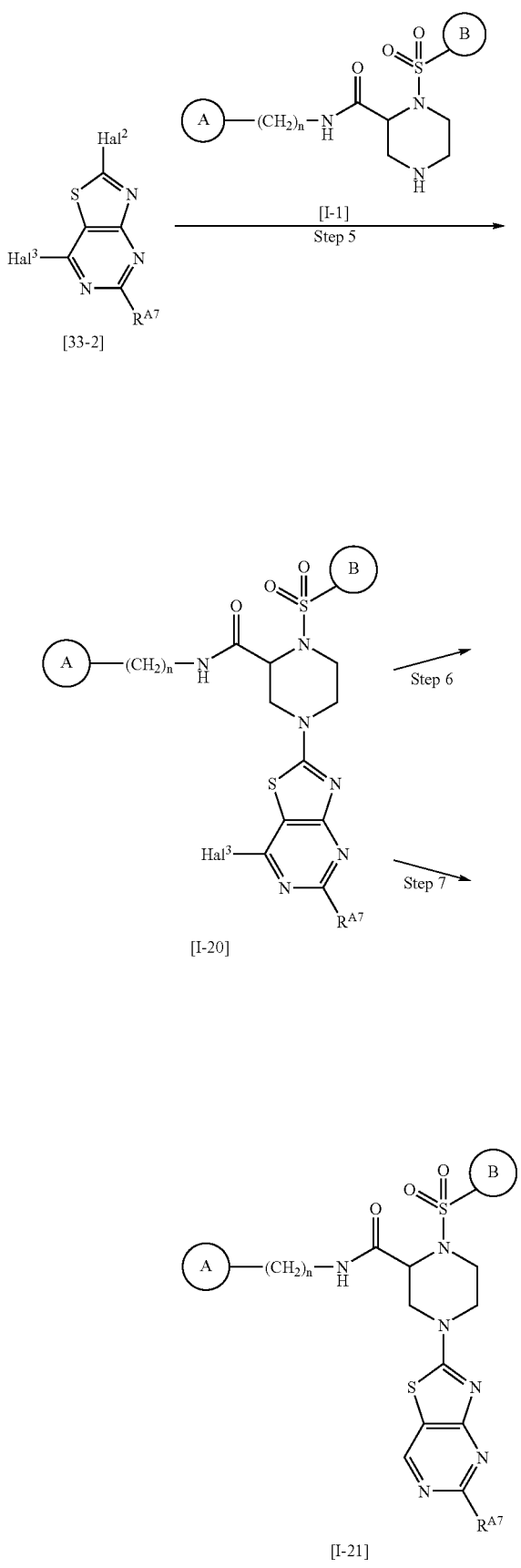

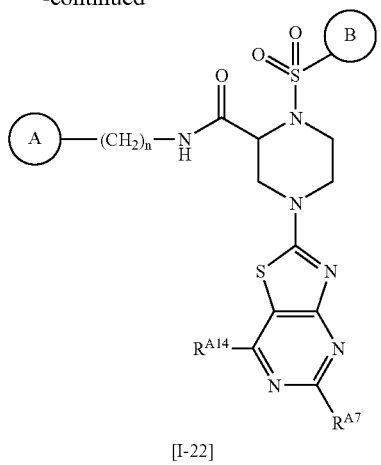

[I-22]

wherein Hal³ is a halogen atom, $R^{A14}$ is a substituent selected from the following group A1, and other symbols are as defined above:

group A1:
nitro group, cyano group,
—$OR^{a1}$,
$SR^{a2}$,
$NR^{a3}R^{a4}$,
—$NHCOR^{a5}$,
—$NHSO_2R^{a14}$,
—$COOR^{a6}$,
—$CONR^{a7}R^{a8}$,
—$SO_2NR^{a9}R^{a10}$,
—$SO_2NHCOR^{a15}$,
—$COR^{a11}$,
—$SO_2R^{a12}$,
—$CONHSO_2R^{a13}$,
a $C_{1-10}$ alkyl group optionally substituted by 1 to 5 substituents selected from group B,
a $C_{2-10}$ alkynyl group optionally substituted by 1 to 5 substituents selected from group B,
a $C_{3-12}$ carbon ring group optionally substituted by 1 to 5 substituents selected from group C,
a heterocyclic group optionally substituted by 1 to 5 substituents selected from group C,
a $C_{6-12}$ aryl-$C_{1-4}$ alkyl group optionally substituted by 1 to 5 substituents selected from group C,
a heterocyclyl-$C_{1-4}$ alkyl group optionally substituted by 1 to 5 substituents selected from group C, and,
a $C_{3-10}$ cycloalkyl-$C_{1-4}$ alkyl group optionally substituted by 1 to 5 substituents selected from group C.

Step 1
Compound [31-1] can be obtained from compound [30-1] in the same manner as in production method 1-2-1, step 1.

Step 2
Compound [32-1] can be obtained from compound [31-1] in the same manner as in production method 1-2-1, step 2.

Step 3
Compound [33-1] can be obtained by substituting the amino group of compound [32-1] by a halogen atom by a conventional method in the same manner as in production method 1-2-1, step 3.

Step 4
Compound [33-2] can be obtained by substituting the hydroxyl group of compound [33-1] by a halogen atom by a conventional method.

For example, compound [33-2] can be obtained by reacting compound [33-1] without a solvent or in a solvent in the presence of a halogenating agent such as phosphorus oxychloride, phosphorus pentachloride and the like under heating conditions.

To promote the reaction, water or a base such as N,N-dimethylaniline, triethylamine, N,N-diisopropylethylamine and the like may be added.

As the solvent, dichloromethane, chloroform, 1,4-dioxane, THF and the like can be mentioned.

Step 5
Compound [I-20] can be obtained by reacting compound [33-2] with compound [I-1] in the same manner as in production method 1-2, step 1.

Step 6
Compound [I-21] can be obtained by reducing Hal³ of compound [I-20] by a conventional method.

For example, compound [I-21] can be obtained by reacting compound [I-20] in an alcohol solvent such as methanol, ethanol and the like in the presence of ammonium formate using a catalyst such as palladium carbon, palladium hydroxide and the like under heating conditions.

Step 7
Compound [I-22] can be obtained by introducing and substituting a substituent into Hal³ of compound [I-20] by a conventional method.

Production Method 1-2-2

When, in $R^{C4}$—$Y^3$-ring C (compound [9]), $Y^3$ is a bond, and ring C is pteridin-7-yl optionally substituted by a substituent selected from group A, compound [I] can alo be produced by the following method.

This production method is applicable even when the pyrimidine moiety of pteridin-7-yl is, for example, other aryl group.

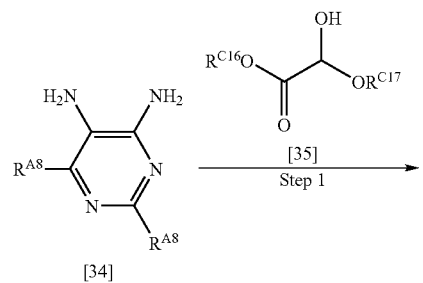

[34]

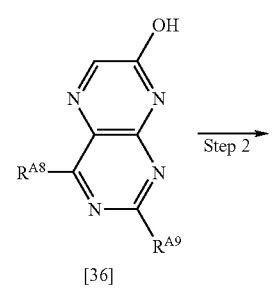

[36]

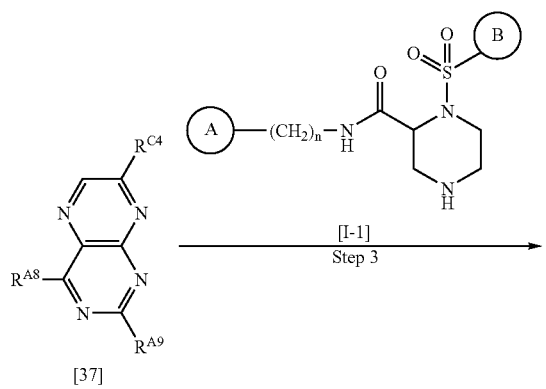

[37]

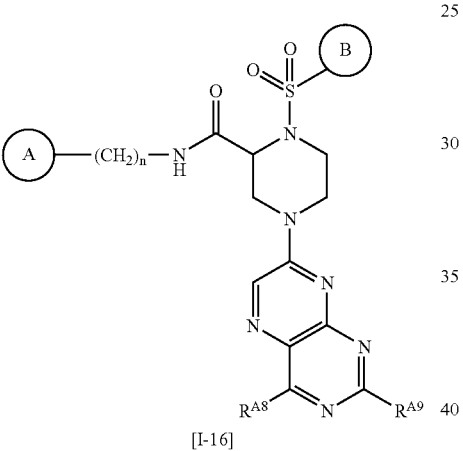

[I-16]

wherein $R^{A8}$ and $R^{A9}$ are the same or different and each is a hydrogen atom or a substituent selected from group A, $R^{C16}$ and $R^{C17}$ are the same or different and each is a $C_{1-4}$ alkyl group such as methyl group, ethyl group and the like, and other symbols are as defined above.

Step 1

Compound [36] can be obtained by reacting compound [34] with compound [35] in a solvent in the presence of a base under heating conditions.

As the combination of solvent and base, a combination of a mixed solvent of acetic acid and water and sodium acetate is preferable.

Step 2

Compound [37] can be obtained by substituting the hydroxyl group of compound [36] by a leaving group by a conventional method.

For example, when $R^{C4}$ is a chlorine atom, compound [37] can be obtained by heating compound [36] in a solvent in the presence of a halogenating agent such as phosphorus oxychloride, phosphorus pentachloride and the like.

As the solvent, pentachloroethane, DMF, xylene, pyridine and the like can be mentioned, with preference given to pentachloroethane.

Step 3

Compound [I-16] can be obtained by reacting compound [37] with compound [I-1] in the same manner as in production method 1-2, step 1.

Production Method 1-2-3-1

When, in $R^{C4}$—$Y^3$-ring C (compound [9]), $Y^3$ is a bond and ring C is 7-oxo-7H-[1,3,4]thiadiazolo[3,2-a]pyrimidin-2-yl optionally substituted by a substituent selected from group A, compound [I] can also be produced by the following method.

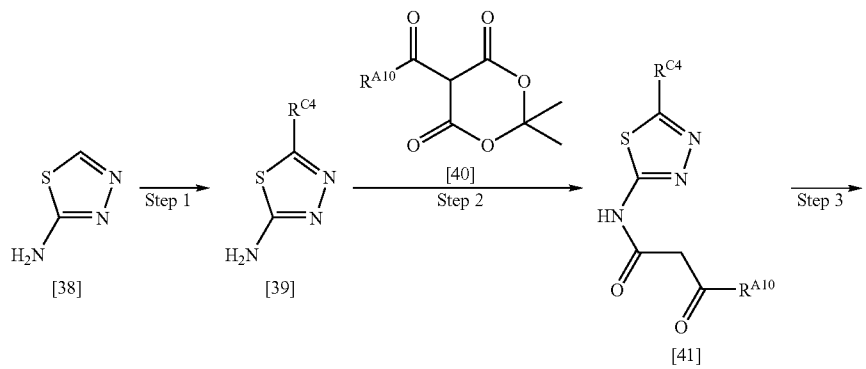

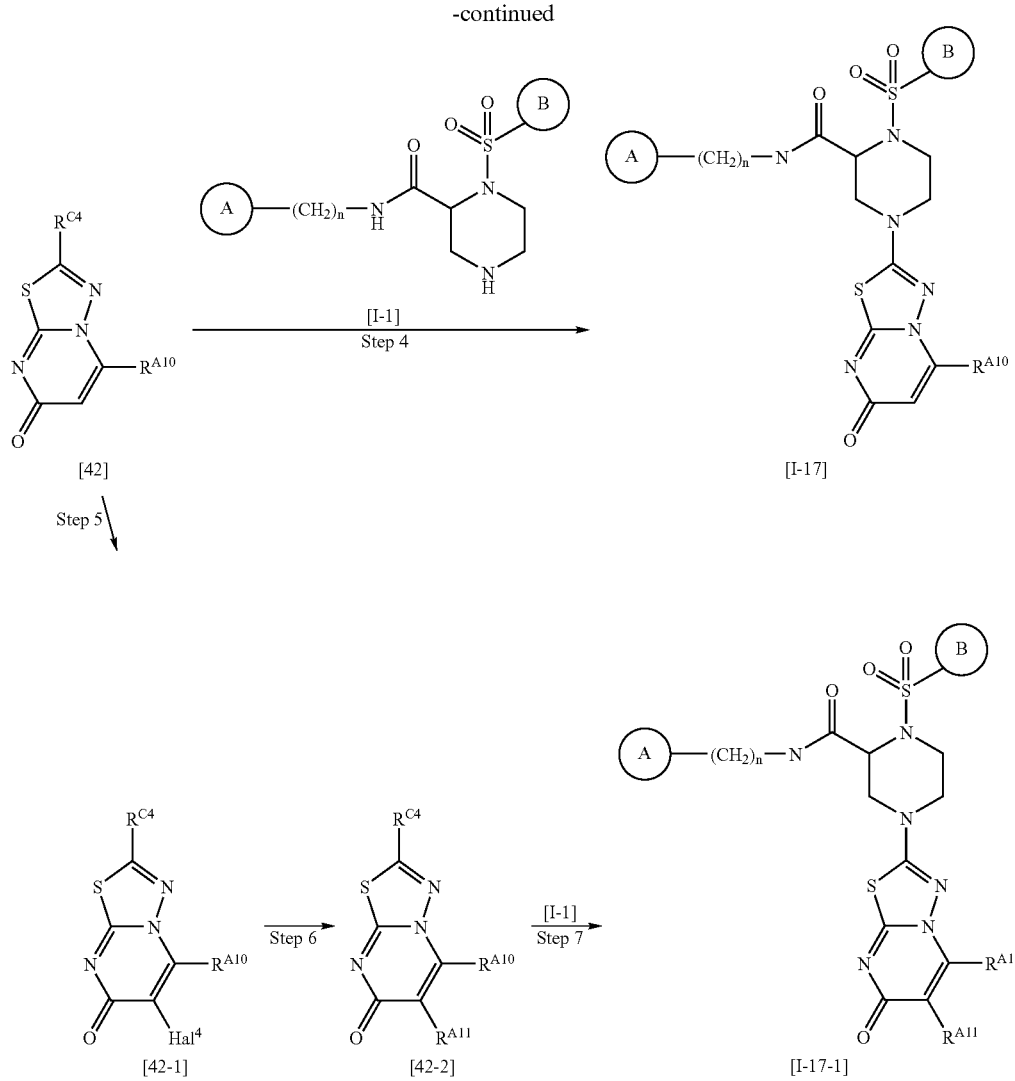

wherein $R^{A10}$ and $R^{A11}$ are the same or different and each is a substituent selected from the above-mentioned group A1, $Hal^4$ is a halogen atom such as bromine atom, chlorine atom and the like, and other symbols are as defined above.

Step 1

Compound [39] can be obtained by introducing a leaving group into compound [38] by a conventional method.

For example, when $R^{C4}$ is a halogen atom, Compound [39] can be obtained by reacting compound [38] with halogen in the presence of acetic acid and sodium acetate.

Step 2

Compound [41] can be obtained by reacting compound [39] with compound [40] in a solvent under heating conditions.

In addition, compound [41] wherein $R^{A10}$ is methyl group can be obtained by using 4-methyleneoxetan-2-one instead of compound [40].

As the solvent, DMF, THF, toluene and the like can be mentioned, with preference given to toluene.

Step 3

Compound [42] can be obtained by reacting compound [41] in the presence of an acid such as concentrated sulfuric acid, concentrated hydrochloric acid, acetic acid, trifluoroacetic acid and the like under heating conditions.

Step 4

Compound [I-17] can be obtained by reacting compound [42] with compound [I-1] in the same manner as in production method 1-2, step 1.

Step 5

Compound [42-1] can be obtained by halogenating compound [42] by a conventional method.

Step 6

Compound [42-2] can be obtained by introducing and substituting a substituent into $Hal^4$ of compound [42-1] by a conventional method.

Step 7

Compound [I-17-1] can be obtained by reacting compound [42-2] with compound [I-1] in the same manner as in production method 1-2, step 1.

Production Method 1-2-3-2

When, in $R^{C4}$—$Y^3$-ring C (compound [9]), $Y^3$ is a bond and ring C is 7-oxo-7H-[1,3,4]thiadiazolo[3,2-a]pyrimidin-2-yl optionally substituted by a substituent selected from group A, compound [I] can also be produced by the following method.

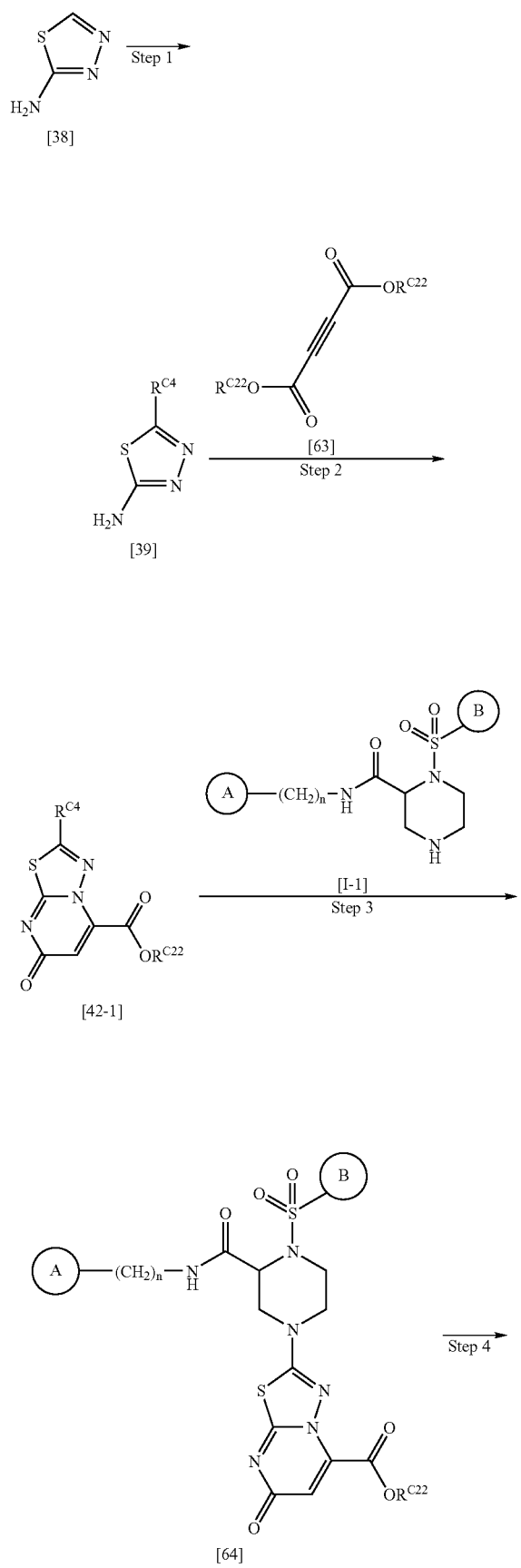
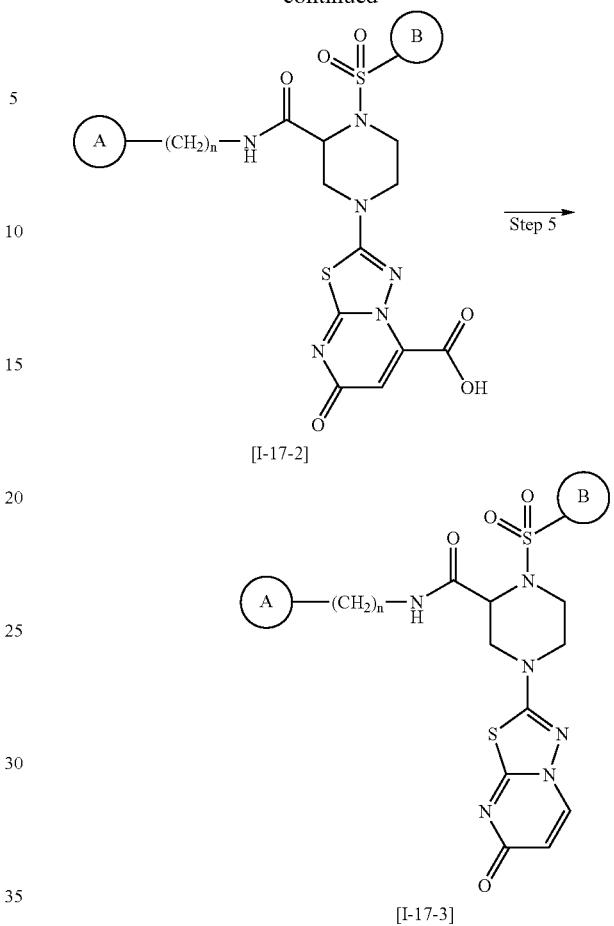

wherein $R^{C22}$ is a carboxylic acid protecting group, and other symbols are as defined above.

Step 1

Compound [39] can be obtained by introducing a leaving group into compound [38] by a conventional method in the same manner as in production method 1-2-3-1, step 1.

Step 2

Compound [42-1] can be obtained by reacting compound [39] with compound [63] in an alcohol solvent such as methanol, tert-butyl alcohol and the like under heating conditions.

Step 3

Compound [64] can be obtained by reacting compound [42-1] with compound [I-1] in the same manner as in production method 1-2, step 1.

Step 4

Compound [I-17-2] can be obtained by eliminating the carboxylic acid protecting group of compound [64] by a conventional method.

Step 5

Compound [I-17-3] can be obtained by heating compound [I-17-2] in a solvent.

As the solvent, diphenyl ether, diethylene glycol and the like can be mentioned.

Production Method 1-2-4

When, in $R^{C4}$—$Y^3$-ring C (compound [9]), $Y^3$ is a bond, and ring C is 7-oxo-6,7-dihydrothiazolo[4,5-d]pyridazin-2-yl optionally substituted by a substituent selected from group A, compound [I] can also be produced by the following method.

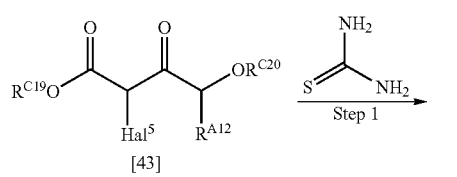

[43]

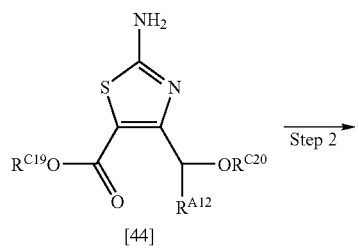

[44]

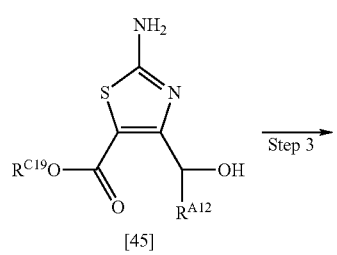

[45]

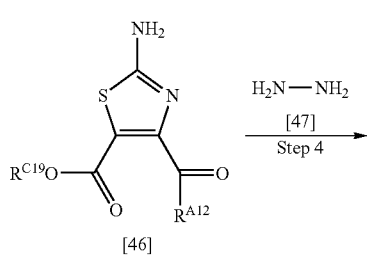

[46]

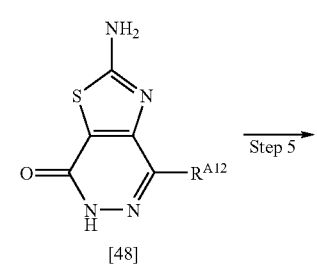

[48]

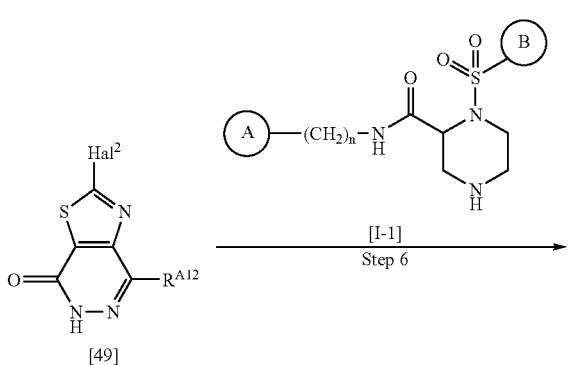

[49]

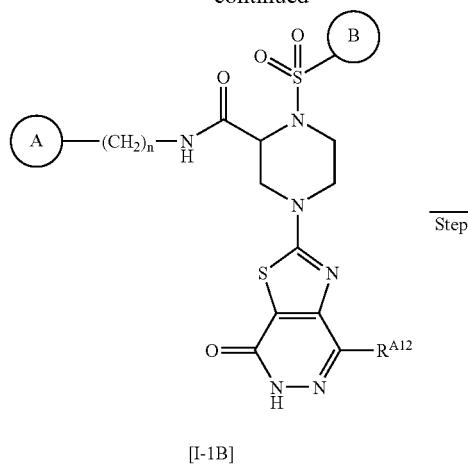

[I-1B]

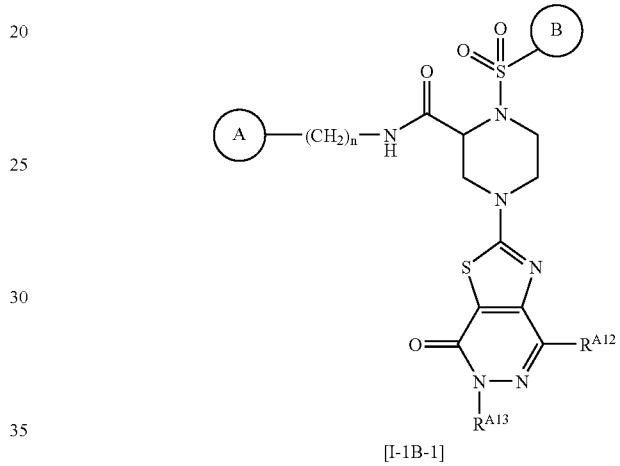

[I-1B-1]

wherein $R^{A12}$ is a hydrogen atom or a substituent selected from group A, $R^{A13}$ is a substituent selected from group A, $R^{C19}$ is a carboxylic acid protecting group, $R^{C20}$ is a hydroxyl protecting group, $Hal^5$ is a halogen atom such as a chlorine atom, a bromine atom and the like, and other symbols are as defined above.

As the hydroxyl protecting group, methyl group, ethyl group, tert-butyldimethylsilyl group, acetyl group, benzyl group, methoxyethoxymethyl group and the like can be mentioned.

Step 1

Compound [44] can be obtained by reacting compound [43] with thiourea in an alcohol solvent such as methanol, ethanol and the like, or in an acetonitrile solvent, under heating conditions.

Step 2

Compound [45] can be obtained by eliminating the hydroxyl protecting group of compound [44] by a conventional method.

For example, when $R^{C20}$ is methyl group, compound [45] can be obtained by adding boron tribromide to compound [44] in a dichloromethane solvent, and then adding aqueous sodium hydroxide solution.

Step 3

Compound [46] can be obtained by oxidizing compound [45] by a conventional method.

For example, compound [46] can be obtained by treating compound [45] with manganese dioxide in a solvent such as chloroform, dichloroethane, 1,4-dioxane, DMF and the like, or a mixed solvent thereof.

Step 4

Compound [48] can be obtained by reacting compound [46] with compound [47] in an alcohol solvent such as methanol, ethanol and the like under heating conditions.

To promote the reaction, acetic acid may be added.

Step 5

In the same manner as in production method 1-2-1, step 3, compound [49] can be obtained by converting the amino group of compound [48] to a leaving group.

Step 6

Compound [I-18] can be obtained by reacting compound [49] with compound [I-1] in the same manner as in production method 1-2, step 1.

Step 7

Compound [I-18-1] can be obtained by introducing a substituent selected from group A into the nitrogen atom on compound [I-18] by a conventional method.

Compound [I-18-1] can also be obtained by performing the production methods of step 5 and step 6 using $R^{A13}$—NH—$NH_2$ instead of compound [47].

Production Method 1-2-5

When, in $R^{C4}$—$Y^3$-ring C (compound [9]), $Y^3$ is a bond and ring C is 4-oxo-4,5-dihydrothiazolo[4,5-d]pyridazin-2-yl optionally substituted by a substituent selected from group A, compound [I] can also be produced by the following method.

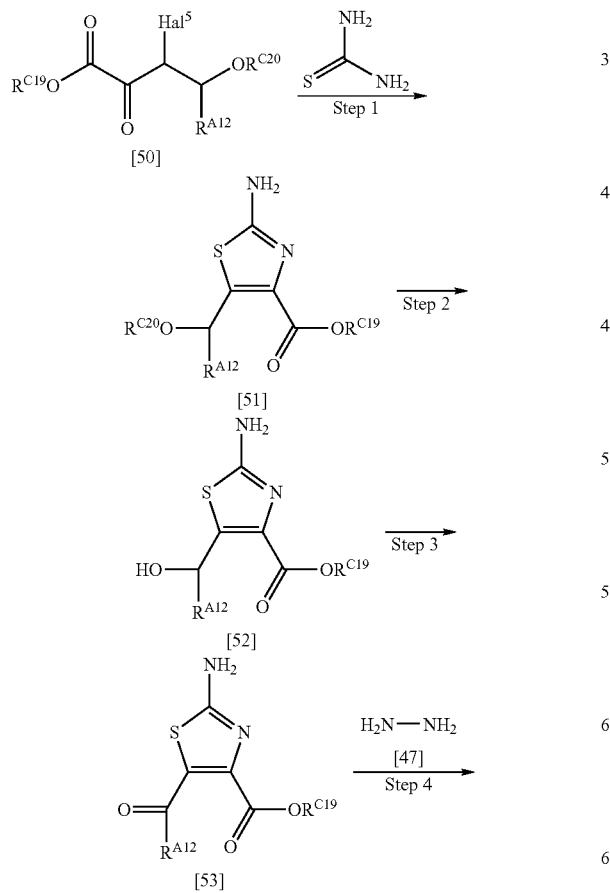

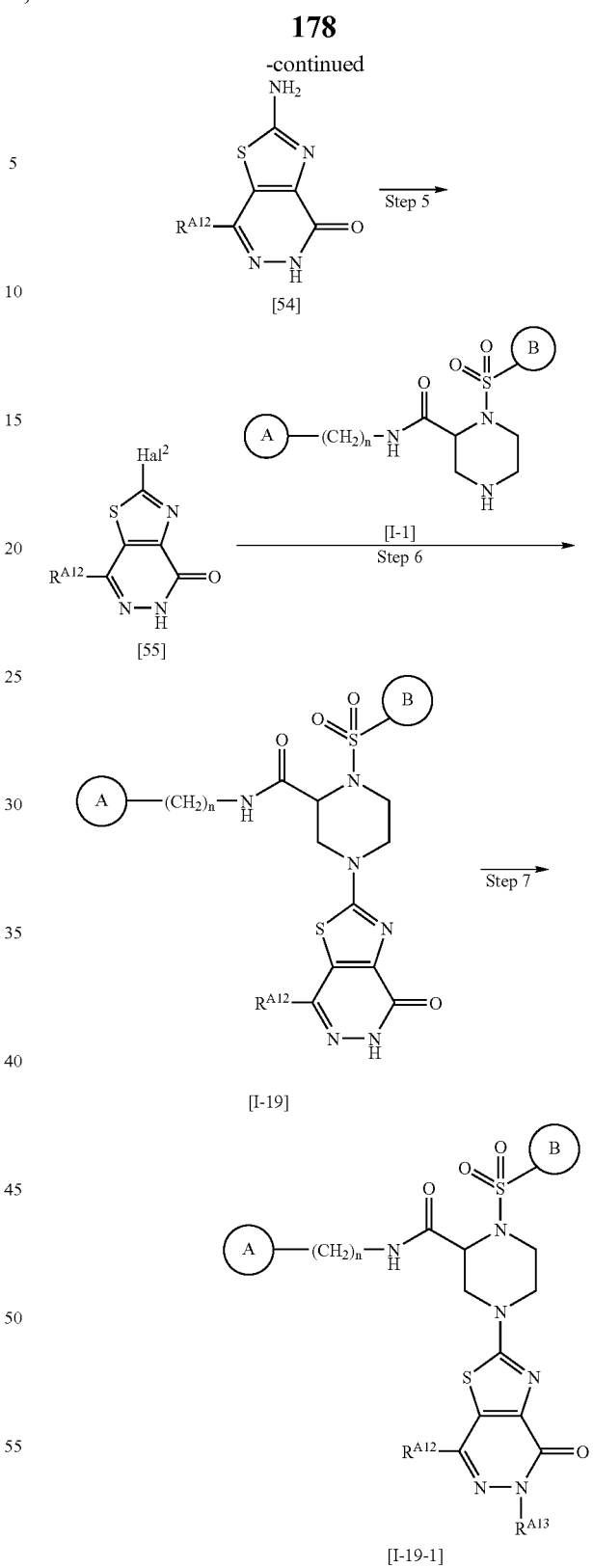

wherein each symbol is as defined above.

Step 1

Compound [51] can be obtained by reacting compound [50] with thiourea in the same manner as in production method 1-2-4, step 1.

Step 2

In the same manner as in production method 1-2-4, step 2, compound [52] can be obtained by eliminating the hydroxyl protecting group of compound [51] by a conventional method.

Step 3

In the same manner as in production method 1-2-4, step 3, compound [53] can be obtained by oxidizing compound [52] by a conventional method.

Step 4

In the same manner as in production method 1-2-4, step 4, compound [54] can be obtained by reacting compound [53] with compound [47].

Step 5

In the same manner as in production method 1-2-1, step 3, compound [55] can be obtained by converting the amino group of compound [54] to a leaving group.

Step 6

In the same manner as in production method 1-2, step 1, compound [I-19] can be obtained by reacting compound [55] with compound [I-1].

Step 7

Compound [I-19-1] can be obtained by introducing a substituent selected from group A into the nitrogen atom on compound [I-19] by a conventional method.

Compound [I-19-1] can also be obtained by performing the production methods of step 5 and step 6 using $R^{A13}$—NH—$NH_2$ instead of compound [47].

Production Method 1-2-6

Production Example of Compound [30] ($R^{A6}$ is a Hydroxyl Group)

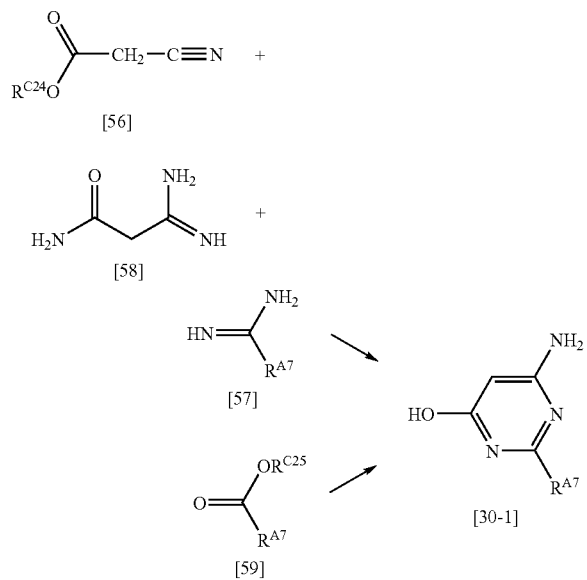

wherein $R^{C24}$ and $R^{C25}$ are the same or different and each is a carboxylic acid protecting group, and other symbols are as defined above.

Compound [30-1] can be obtained by reacting compound [56] with compound [57] in a methanol solvent under heating under reflux in the presence of sodium methoxide.

In addition, compound [30-1] can be obtained by reacting compound [58] with compound [59] in a solvent in the presence of a base.

As the solvent, dichloromethane, chloroform, THF, toluene and the like can be mentioned.

As the base, triethylamine, N,N-diisopropylethylamine, N-methylmorpholine, 1,8-diazabicyclo[5.4.0]undec-7-ene, 1,5-diazabicyclo[4.3.0]non-5-ene and the like can be mentioned.

Production Method 1-2-7

Production Example of Compound [43] and Compound [44]

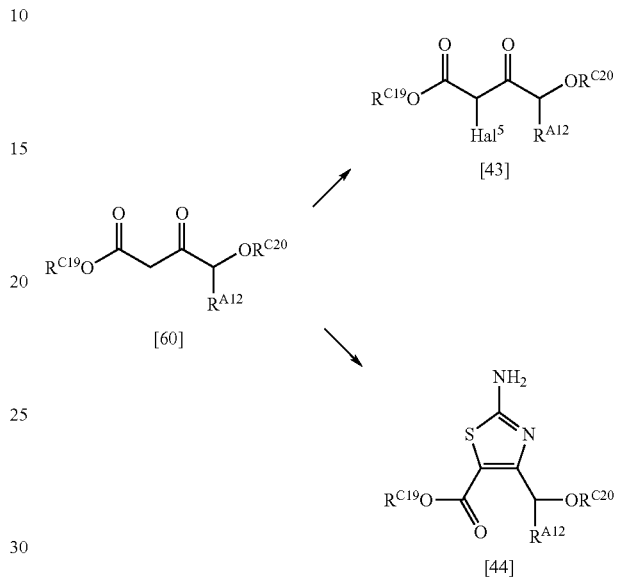

wherein each symbol is as defined above.

Compound [43] can be obtained by halogenating compound [60] by a conventional method.

For example, compound [43] can be obtained by brominating compound [60] using copper (II) bromide and hydroxy(tosyloxy)iodobenzene in an acetonitrile solvent.

In addition, compound [44] can also be obtained by reacting compound [60] with hydroxy(tosyloxy)iodobenzene in an acetonitrile solvent under heating conditions, and then reacting the obtained compound with thiourea under heating conditions.

Production Method 1-2-8

Production Example of Compound [50]

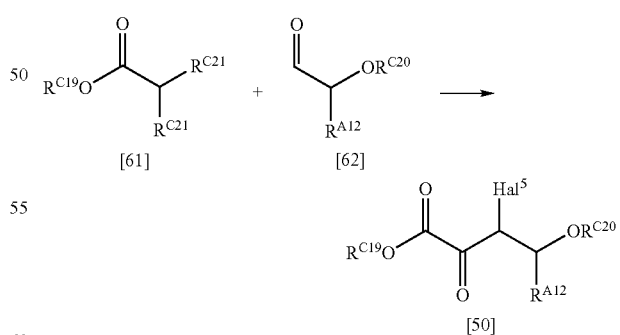

wherein $R^{C21}$ is a halogen atom such as a chlorine atom, a bromine atom and the like, and other symbols are as defined above.

Compound [50] can be obtained by reacting compound [61] with compound [62] in an alcohol solvent such as methanol, ethanol and the like or an ether solvent such as diethyl

EXAMPLES

The compound represented by the formula [I] of the present invention and production methods thereof are explained in detail in the following byeferring to Examples. However, the present invention is not limited by these Examples.

Example 1

Step 1

(R)-4-(4-trifluoromethyl-benzenesulfonyl)-piperazine-1,3-dicarboxylic acid 1-tert-butyl ester

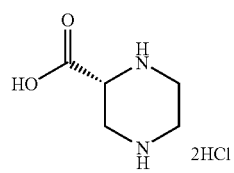

(R)-piperazine-2-carboxylic acid dihydrochloride (4.98 g) was suspended in a mixed solvent of 1,4-dioxane (50 ml) and water (25 ml) and, with stirring under ice-cooling, 50% aqueous sodium hydroxide solution (3.79 ml) and then di-tert-butyl dicarbonate (6.19 ml) were added. After stirring overnight at room temperature, triethylamine (6.83 ml), 4-trifluoromethylbenzenesulfonyl chloride (5.99 g) and 4-dimethylaminopyridine (60 mg) were added, and the mixture was stirred overnight at room temperature. The reaction mixture was concentrated under reduced pressure, and the residue was partitioned by adding ethyl acetate and 1N aqueous hydrochloric acid solution. The aqueous layer was re-extracted twice with ethyl acetate. The organic layers were combined, washed with saturated brine, dried over anhydrous sodium sulfate, filtrated, and concentrated under reduced pressure to give a crude product (9.16 g) containing the title compound as a main component.

ether, THF and the like or a mixed solvent thereof in the presence of sodium methoxide.

$R^{C21}$ is preferably a chlorine atom.

Step 2

(R)-3-(4-isopropyl-benzylcarbamoyl)-4-(4-trifluoromethyl-benzenesulfonyl)-piperazine-1-carboxylic acid tert-butyl ester To a mixed solution of the compound (2.19 g) obtained in Step 1,4-isopropylbenzylamine (761 mg) and 1-hydroxybenzotriazole hydrate (804 mg) in N,N-dimethylformamide (10 ml) was added, with stirring at room temperature, 1-ethyl-3-(3-dimethylaminopropyl)carbodiimide hydrochloride (1.00 g). After stirring at room temperature for 3 days, the reaction mixture was partitioned by adding 1N aqueous hydrochloric acid solution and ethyl acetate. The organic layer was washed successively with water, saturated aqueous sodium hydrogen carbonate solution and saturated brine, dried over anhydrous sodium sulfate, filtrated, and concentrated under reduced pressure. The residue was purified by column chromatography (ethyl acetate:n-hexane=1:2) to give the title compound (973 mg).

Step 3

(R)-1-(4-trifluoromethyl-benzenesulfonyl)-piperazine-2-carboxylic acid 4-isopropyl-benzylamide hydrochloride

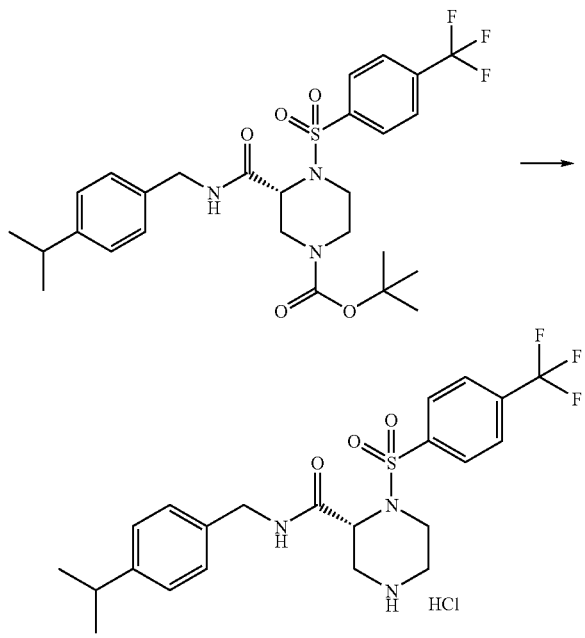

To a solution of the compound (973 mg) obtained in Step 2 in ethyl acetate (10 ml) was added, with stirring at room temperature, 4N hydrogen chloride/ethyl acetate solution (4.73 ml). After stirring at room temperature for 4 hr, the reaction mixture was concentrated under reduced pressure. Toluene was added to the residue, and the mixture was concentrated again under reduced pressure. The obtained crude crystals were suspended in a mixed solvent of ethyl acetate and diisopropyl ether, collected by filtration and dried to give the title compound (742 mg).

Example 2

(R)-4-(2-pyridin-4-yl-acetyl)-1-(4-trifluoromethyl-benzenesulfonyl)-piperazine-2-carboxylic acid 4-isopropyl-benzylamide

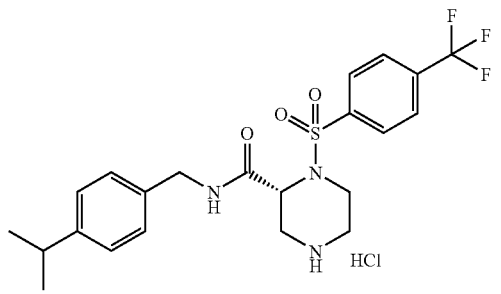

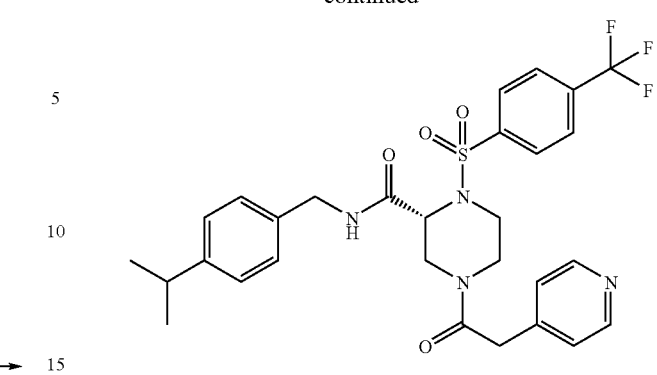

To a mixed solution of the compound (20 mg) obtained in Example 1 4-pyridylacetic acid hydrochloride (7.5 mg), 1-hydroxybenzotriazole hydrate (6.6 mg) and triethylamine (12 µl) in N,N-dimethylformamide (0.4 ml) was added, with stirring at room temperature, 1-ethyl-3-(3-dimethylaminopropyl)carbodiimide hydrochloride (8.3 mg). After stirring overnight at room temperature, aqueous sodium hydrogen carbonate solution and methanol were added to the reaction mixture and the mixture was stirred at room temperature. The precipitated crystals were collected by filtration, washed with water and dried to give the title compound (14 mg).

Example 3

(R)-4-(4-trifluoromethyl-benzenesulfonyl)-piperazine-1,3-dicarboxylic acid 3-(4-isopropyl-benzylamide) 1-pyridin-4-ylamide

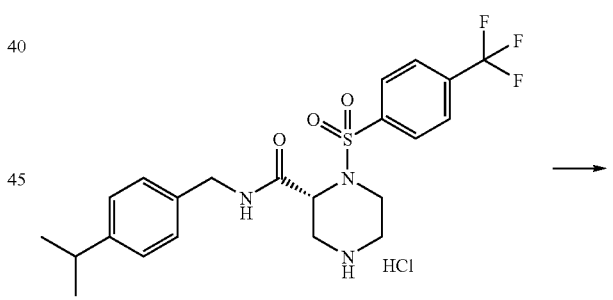

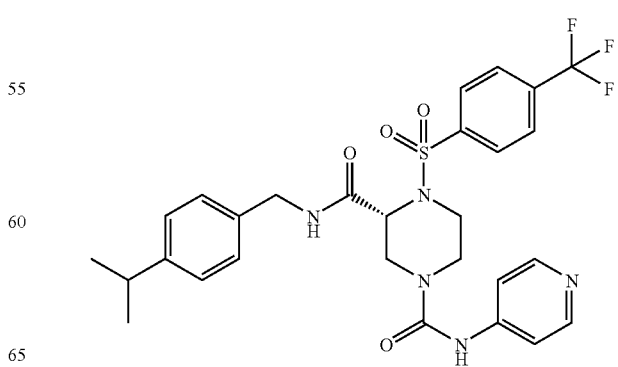

185

To a solution of 4-aminopyridine (94 mg) in chloroform (2.0 ml) was added, with stirring at room temperature, N,N'-carbonyldiimidazole (178 mg), and the mixture was stirred overnight at room temperature to give the reaction mixture A.

In a separate container, to a solution of the compound (30 mg) obtained in Example 1 in chloroform (1 ml) was added, with stirring at room temperature, triethylamine (12.5 μl), the reaction mixture A (240 μl) was added, and the mixture was stirred overnight at room temperature. The reaction mixture was concentrated under reduced pressure, and the residue was purified by thin layer chromatography (10% methanol/chloroform) to give the title compound (31 mg).

Example 4

(R)-4-thiocarbamoyl-1-(4-trifluoromethyl-benzenesulfonyl)-piperazine-2-carboxylic acid 4-isopropyl-benzylamide To a solution of the compound (506 mg) obtained in Example 1 in chloroform (5 ml) was added, with stirring at room temperature, triethylamine (167 μl), and 9-fluorenyl-methoxycarbonyl isothiocyanate (281 mg) was added. After stirring overnight at room temperature, piperidine (198 μl) was added. After stirring overnight at room temperature, the reaction mixture was concentrated under reduced pressure, and purified by column chromatography (3% methanol/chloroform) to give the title compound (442 mg).

Example 5

2-[(R)-3-(4-isopropyl-benzylcarbamoyl)-4-(4-trifluoromethyl-benzenesulfonyl)-piperazin-1-yl]-4-methyl-thiazole-5-carboxylic acid tert-butyl ester

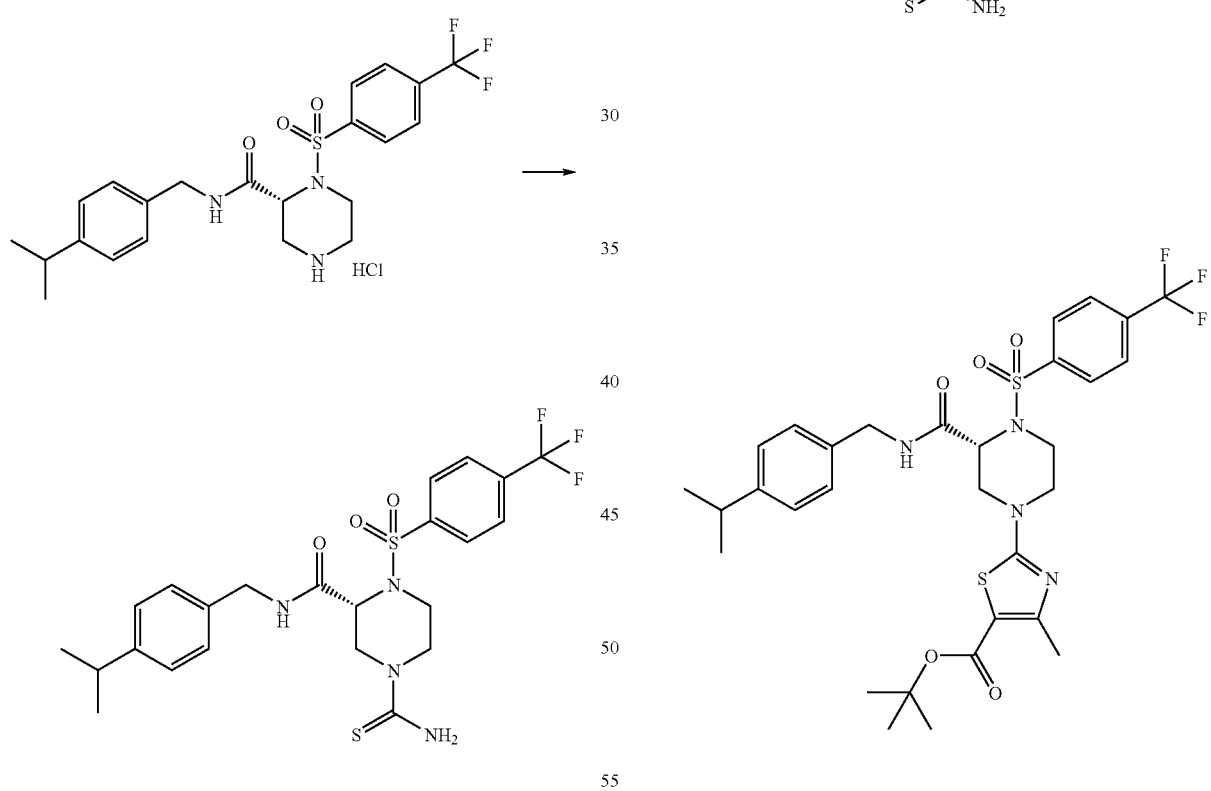

A mixture of the compound (250 mg) obtained in Example 4 and 2-bromo-3-oxobutyric acid tert-butyl ester (168 mg) in acetonitrile (1.25 ml) was stirred at 80° C. for 20 min. The reaction mixture was concentrated under reduced pressure, and the residue was purified by thin layer chromatography (ethyl acetate:n-hexane=2:3) to give the title compound (268 mg).

Example 6

2-[(R)-3-(4-isopropyl-benzylcarbamoyl)-4-(4-trifluoromethyl-benzenesulfonyl)-piperazin-1-yl]-4-methyl-thiazole-5-carboxylic acid

Example 7

(R)-4-(5-carbamoyl-4-methyl-thiazol-2-yl)-1-(4-trifluoromethyl-benzenesulfonyl)-piperazine-2-carboxylic acid 4-isopropyl-benzylamide

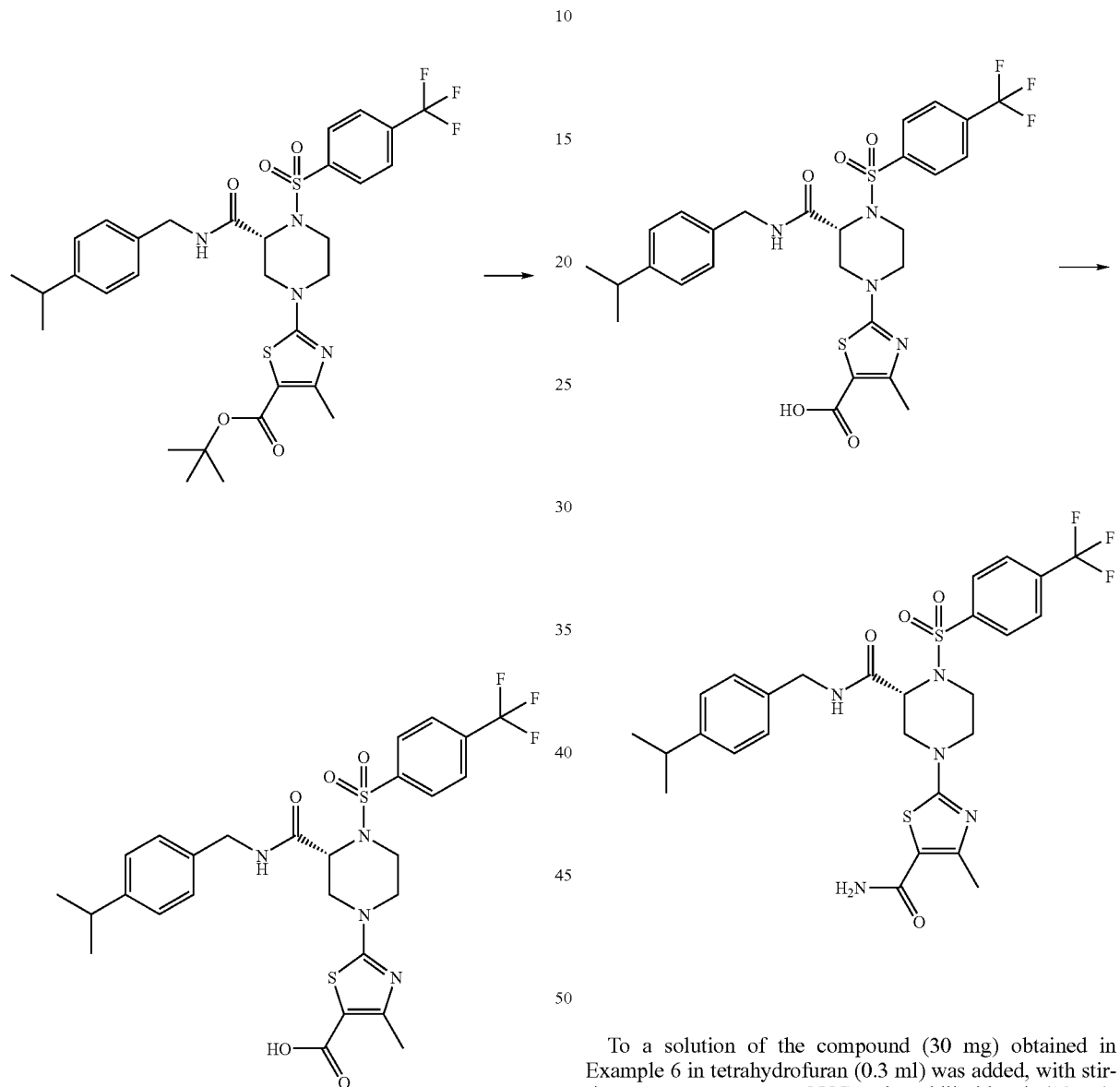

A solution of the compound (224 mg) obtained in Example 5 in trifluoroacetic acid (1.1 ml) was stirred at room temperature for 1 hr. The reaction mixture was concentrated under reduced pressure, toluene was added to the residue, and the mixture was concentrated again under reduced pressure. Diisopropyl ether was added to the residue, and the mixture was stirred at room temperature. The precipitated crystals were collected by filtration, and dried to give the title compound (97 mg).

To a solution of the compound (30 mg) obtained in Example 6 in tetrahydrofuran (0.3 ml) was added, with stirring at room temperature, N,N'-carbonyldiimidazole (10 mg). After stirring at room temperature for 3 hr, 28% aqueous ammonia solution (10 µl) was added. After stirring at room temperature for 2.5 hr, 28% aqueous ammonia solution (10 µl) was added. After stirring at room temperature for 2.5 hr, 28% aqueous ammonia solution (10 µl) was added. After stirring overnight at room temperature, the reaction mixture was partitioned by adding ethyl acetate and saturated aqueous sodium hydrogen carbonate solution. The organic layer was washed successively with water and saturated brine, dried over anhydrous magnesium sulfate, filtrated, and concentrated under reduced pressure. The residue was purified by thin layer chromatography (10% methanol/chloroform) to give the title compound (20 mg).

Example 8

(R)-3-(4-isopropyl-benzylcarbamoyl)-4-(4-trifluoromethyl-benzenesulfonyl)-3,4,5,6-tetrahydro-2H-[1,2']bipyrazinyl-5'-carboxylic acid methyl ester

Example 9

(R)-3-(4-isopropyl-benzylcarbamoyl)-4-(4-trifluoromethyl-benzenesulfonyl)-3,4,5,6-tetrahydro-2H-[1,2']bipyrazinyl-5'-carboxylic acid

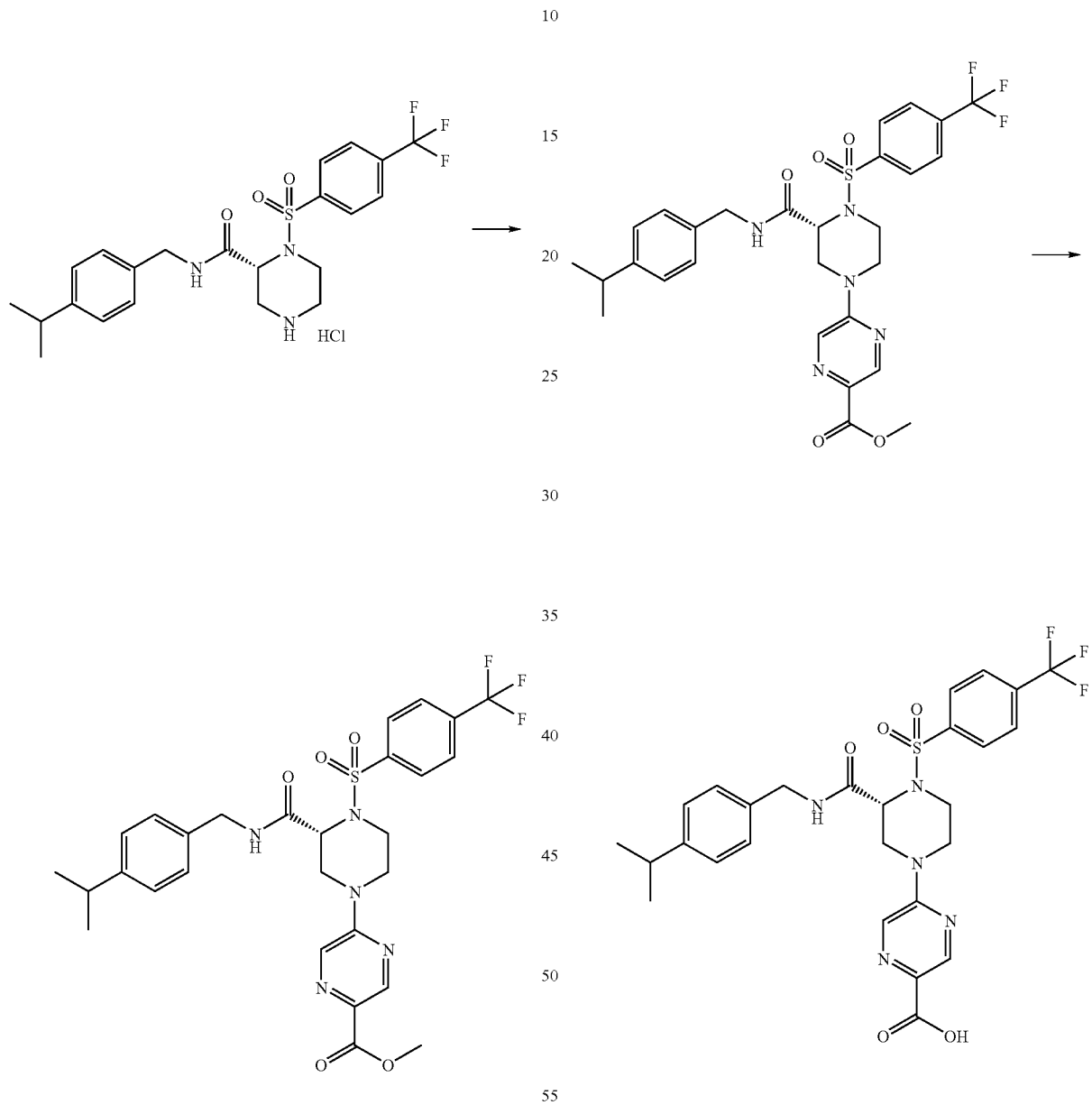

A mixture of the compound (61 mg) obtained in Example 1, 5-chloropyrazine-2-carboxylic acid methyl ester (25 mg) and triethylamine (42 μl) in N,N-dimethylformamide (0.3 ml) was stirred at 60° C. for 14 hr. The reaction mixture was concentrated under reduced pressure, and the residue was purified by thin layer chromatography (5% methanol/chloroform) to give the title compound (75 mg).

To a mixed solution of the compound (75 mg) obtained in Example 8 in tetrahydrofuran (400 μl) and methanol (400 μl) was added, with stirring at room temperature, 2N aqueous sodium hydroxide solution (186 μl). After stirring at room temperature for 30 min, 2N aqueous hydrochloric acid solution (186 μl) was added, and the mixture was concentrated under reduced pressure. Methanol and water were added to the residue, and the mixture was stirred at room temperature. The precipitated crystals were collected by filtration, and dried to give the title compound (61 mg).

Example 10

Step 1

(R)-4-acetyl-piperazine-1,2-dicarboxylic acid 1-tert-butyl ester

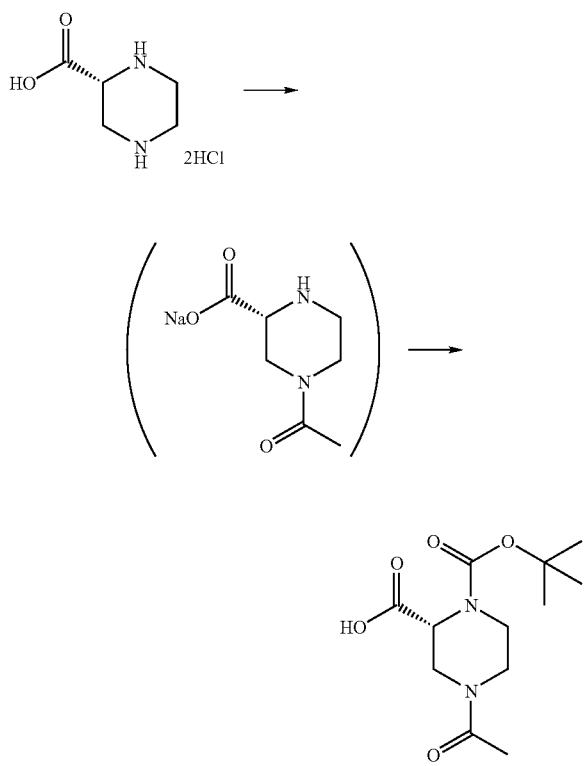

(R)-piperazine-2-carboxylic acid dihydrochloride (5.0 g) was suspended in a mixed solvent of 1,4-dioxane (25 ml) and water (28 ml) and, with stirring under ice-cooling, 4N aqueous sodium hydroxide solution (22 ml) was added and a solution of p-nitrophenol acetate (4.69 g) in 1,4-dioxane (25 ml) was added dropwise over 30 min. After stirring at room temperature for 3 hr, the reaction mixture was concentrated under reduced pressure to evaporate 1,4-dioxane. The precipitated insoluble material was filtered off, and a solution of di-tert-butyl dicarbonate (8.5 ml) in 1,4-dioxane (30 ml) was added dropwise to the obtained filtrate (about 70 ml) with stirring under ice-cooling. After stirring at room temperature for 3 hr, the reaction mixture was partitioned by adding saturated aqueous sodium hydrogen carbonate solution and diethyl ether. The aqueous layer was adjusted to pH 2 with 2N aqueous hydrochloric acid solution, saturated brine was added, and the mixture was extracted with tetrahydrofuran. The organic layer was dried over anhydrous magnesium sulfate, filtrated, and concentrated under reduced pressure. Toluene was added to the residue, and the mixture was concentrated again under reduced pressure to give a crude product (4.83 g) containing the title compound as a main component.

Step 2

(R)-4-acetyl-2-(4-isopropyl-benzylcarbamoyl)-piperazine-1-carboxylic acid tert-butyl ester

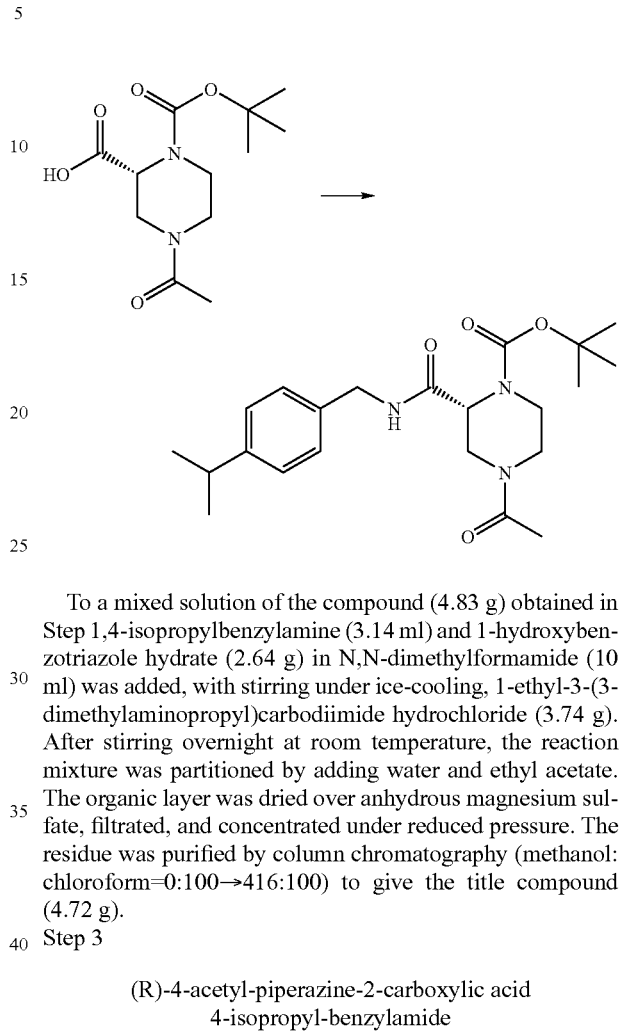

To a mixed solution of the compound (4.83 g) obtained in Step 1,4-isopropylbenzylamine (3.14 ml) and 1-hydroxybenzotriazole hydrate (2.64 g) in N,N-dimethylformamide (10 ml) was added, with stirring under ice-cooling, 1-ethyl-3-(3-dimethylaminopropyl)carbodiimide hydrochloride (3.74 g). After stirring overnight at room temperature, the reaction mixture was partitioned by adding water and ethyl acetate. The organic layer was dried over anhydrous magnesium sulfate, filtrated, and concentrated under reduced pressure. The residue was purified by column chromatography (methanol:chloroform=0:100→416:100) to give the title compound (4.72 g).

Step 3

(R)-4-acetyl-piperazine-2-carboxylic acid 4-isopropyl-benzylamide

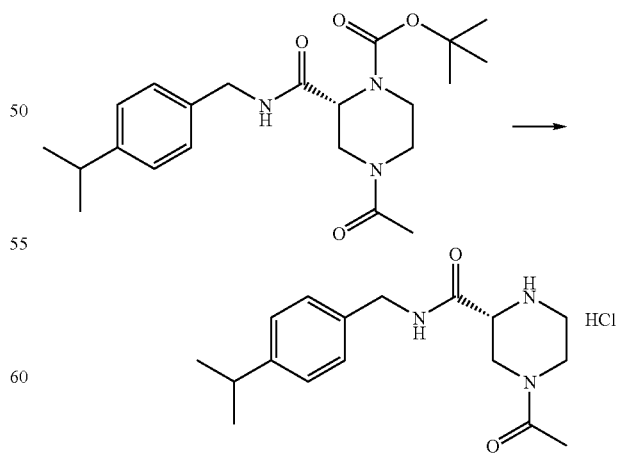

To a solution of the compound (4.72 g) obtained in Step 2 in chloroform (5 ml) was added, with stirring at room temperature, 4N hydrogen chloride/1,4-dioxane solution (20 ml).

After stirring at room temperature for 3 hr, the reaction mixture was concentrated under reduced pressure. Toluene was added to the residue, and the mixture was concentrated again under reduced pressure. The obtained crude crystals were suspended in diisopropyl ether, collected by filtration and dried to give the title compound (3.23 g).

Step 4

(R)-4-acetyl-1-(3-iodo-4-trifluoromethoxy-benzene-sulfonyl)-piperazine-2-carboxylic acid 4-isopropyl-benzylamide

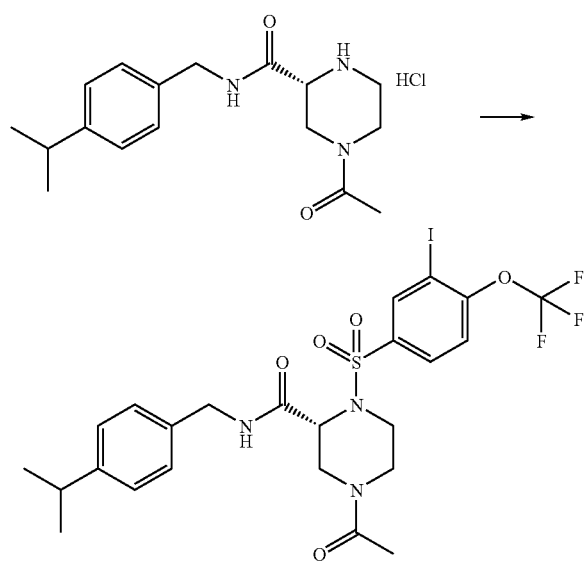

To a solution of the compound (40 mg) obtained in Step 3 and triethylamine (66 µl) in chloroform (0.4 ml) was added, with stirring at room temperature, 3-iodo-4-trifluoromethoxybenzenesulfonyl chloride (68 mg). After stirring at room temperature for 1 hr, the reaction mixture was directly purified by thin layer chromatography (methanol:chloroform=1:15) and recrystallized from water-containing methanol to give the title compound (53 mg).

Example 11

4-{5-[(R)-4-acetyl-2-(4-isopropyl-benzylcarbamoyl)-piperazine-1-sulfonyl]-2-trifluoromethoxy-phenyl}-butyric acid

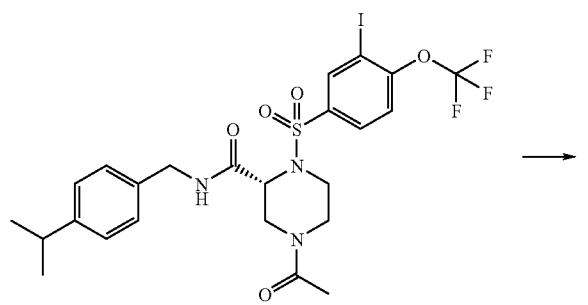

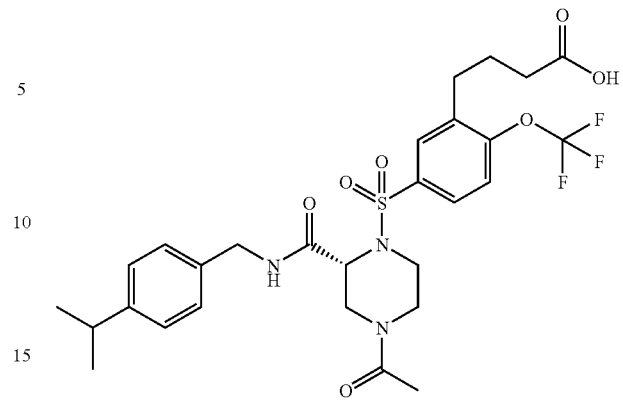

Under an argon stream, to a suspension of the compound (46 mg) obtained in Example 10, 1,2,3,4,5-pentaphenyl-1'-(di-tert-butylphosphino)ferrocene (5 mg) and bis(dibenzylideneacetone)palladium(0) (4 mg) in tetrahydrofuran was added, with stirring under ice-cooling, 0.5M 4-ethoxy-4-oxobutylzinc bromide/tetrahydrofuran solution (422 µl). After stirring at room temperature for 24 hr, 1N aqueous hydrochloric acid solution was added, and the mixture was extracted with ethyl acetate. The organic layer was dried over magnesium sulfate, filtrated and concentrated under reduced pressure. Methanol (0.5 ml) was added to the residue, and 4N aqueous sodium hydroxide solution (35 µl) was added with stirring under ice-cooling. After stirring at room temperature for 3 hr, 2N aqueous hydrochloric acid solution (70 µl) was added, and the mixture was concentrated under reduced pressure. The residue was purified by thin layer chromatography (chloroform:methanol:acetic acid=90:10:1) and recrystallized from water-containing methanol to give the title compound (2.4 mg).

Example 12

Step 1

(R)-4-acetyl-1-(4-isopropyl-benzenesulfonyl)-piperazine-2-carboxylic acid

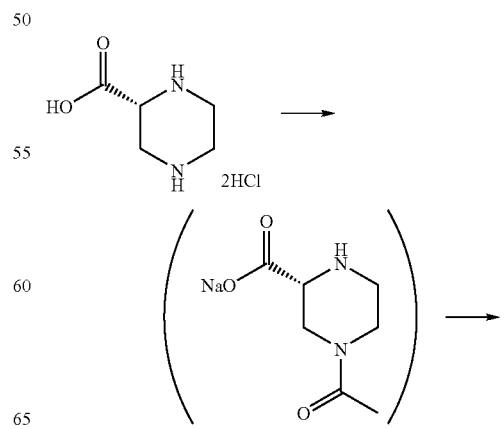

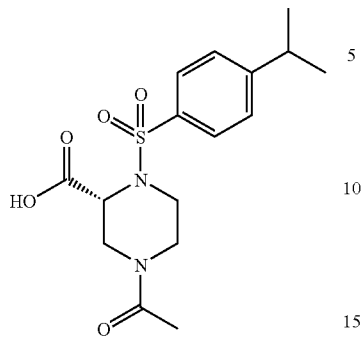

(R)-piperazine-2-carboxylic acid dihydrochloride (4.06 g) was suspended in a mixed solvent of 1,4-dioxane (20 ml) and water (20 ml), 4N aqueous sodium hydroxide solution (18 ml) was added, with stirring under ice-cooling, and a solution of p-nitrophenol acetate (3.99 g) in 1,4-dioxane (20 ml) was added dropwise. After stirring overnight at room temperature, the reaction mixture was concentrated under reduced pressure to evaporate 1,4-dioxane. The precipitated insoluble material was filtered off, and washed with water. 1,4-Dioxane (40 ml) and triethylamine (5.57 ml) were added to the obtained filtrate, and 4-isopropylbenzenesulfonyl chloride (3.59 ml) was added dropwise with stirring under ice-cooling. After stirring overnight at room temperature, the reaction mixture was adjusted to pH 2 with 2N aqueous hydrochloric acid solution and 1,4-dioxane was evaporated by concentration under reduced pressure. The obtained aqueous solution was extracted 4 times with chloroform. The organic layers were combined, dried over anhydrous magnesium sulfate, filtrated, and concentrated under reduced pressure. The obtained crude crystals were suspended in ethyl acetate, collected by filtration and dried to give a crude product (3.10 g) containing the title compound as a main component.

Step 2

(R)-4-acetyl-1-(4-isopropyl-benzenesulfonyl)-piperazine-2-carboxylic acid 2-methyl-4-propyl-benzylamide

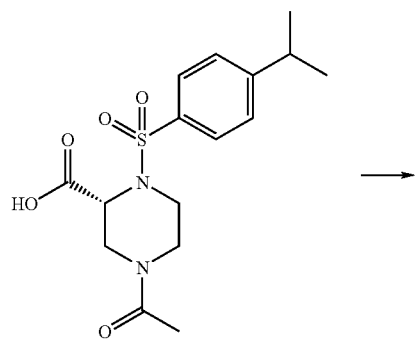

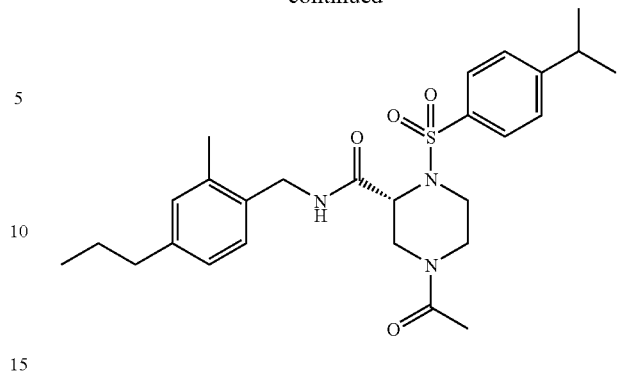

To a mixed solution of the compound (35.4 mg) obtained in Step 1,2-methyl-4-propylbenzylamine hydrochloride (22.0 mg), 1-hydroxybenzotriazole hydrate (18.4 mg) and triethylamine (17.4 µl) in N,N-dimethylformamide (0.2 ml) was added, with stirring under ice-cooling, 1-ethyl-3-(3-dimethylaminopropyl)carbodiimide hydrochloride (23.0 mg). After stirring overnight at room temperature, the reaction mixture was partitioned by adding saturated aqueous sodium hydrogen carbonate solution and chloroform. The organic layer was washed twice with water, dried over anhydrous magnesium sulfate, filtrated, and concentrated under reduced pressure. The residue was purified by thin layer chromatography (methanol:chloroform=1:20) to give the title compound (40.5 mg).

Example 13

Step 1

(R)-4-(4-trifluoromethoxy-benzenesulfonyl)-piperazine-1,3-dicarboxylic acid 1-tert-butyl ester

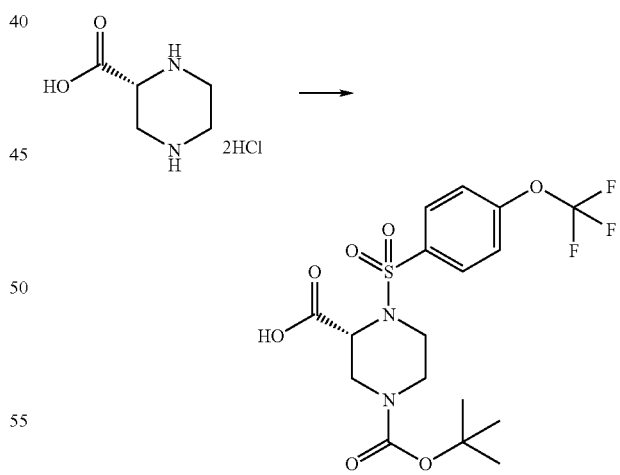

(R)-piperazine-2-carboxylic acid dihydrochloride (5.08 g) was suspended in a mixed solvent of 1,4-dioxane (40 ml) and water (25 ml), 50% aqueous sodium hydroxide solution (3.87 ml) was added with stirring under ice-cooling, and a solution of di-tert-butyl dicarbonate (6.32 ml) in 1,4-dioxane (10 ml) was added dropwise. After stirring overnight at room temperature, triethylamine (6.97 ml), 4-trifluoromethoxybenzenesulfonyl chloride (4.24 ml) and 4-dimethylaminopyridine (61 mg) were added, and the mixture was stirred overnight at room temperature. The reaction mixture was concentrated under reduced pressure to evaporate 1,4-dioxane. The residue was partitioned by adding ethyl acetate and 1N aqueous hydrochloric acid solution. The aqueous layer was re-extracted twice with ethyl acetate. The organic layers were combined, dried over anhydrous sodium sulfate, filtrated, and concentrated under reduced pressure to give a crude product (10.2 g) containing the title compound as a main component.

Step 2

(R)-4-(4-trifluoromethoxy-benzenesulfonyl)-piperazine-1,3-dicarboxylic acid 3-benzyl ester 1-tert-butyl ester

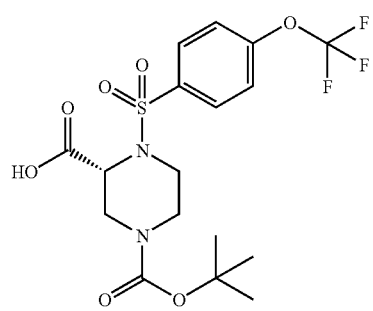

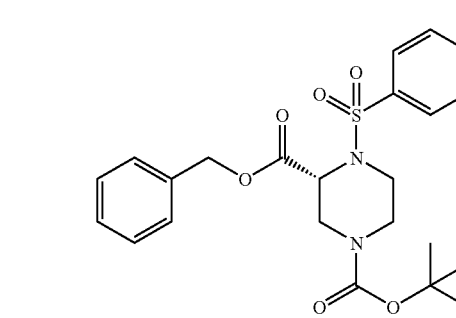

To a mixed solution of the compound (5.77 g) obtained in Step 1, benzyl alcohol (1.45 ml) and 4-dimethylaminopyridine (77 mg) in chloroform (60 ml) was added, with stirring under ice-cooling, 1-ethyl-3-(3-dimethylaminopropyl)carbodiimide hydrochloride (2.68 g). After stirring at room temperature for 3 hr, the mixture was concentrated under reduced pressure. The residue was partitioned by adding water and ethyl acetate. The organic layer was washed successively with water and saturated brine, dried over anhydrous sodium sulfate, filtrated, and concentrated under reduced pressure. The residue was purified by column chromatography (ethyl acetate:n-hexane=1:2) to give a crude product (3.66 g) containing the title compound as a main component.

Step 3

(R)-1-(4-trifluoromethoxy-benzenesulfonyl)-piperazine-2-carboxylic acid benzyl ester hydrochloride

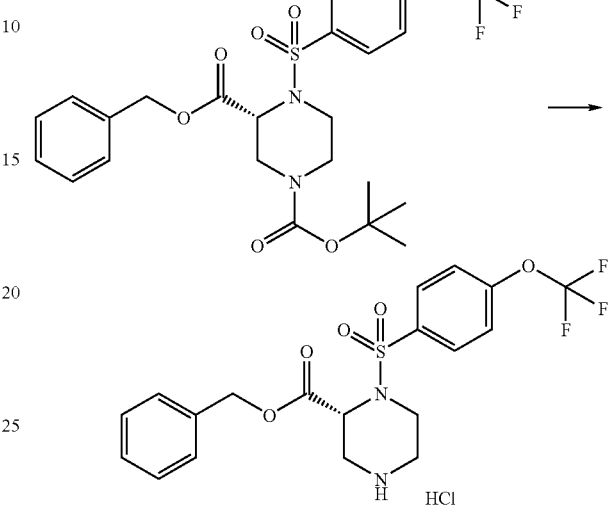

To a solution of the compound (3.66 g) obtained in Step 2 in ethyl acetate (10 ml) was added, with stirring at room temperature, 4N hydrogen chloride/ethyl acetate solution (16.8 ml). After stirring at room temperature for 4 hr, the insoluble material was filtered off, and the filtrate was concentrated under reduced pressure to give a crude product (2.58 g) containing the title compound as a main component.

Step 4

(R)-4-thiocarbamoyl-1-(4-trifluoromethoxy-benzenesulfonyl)-piperazine-2-carboxylic acid benzyl ester

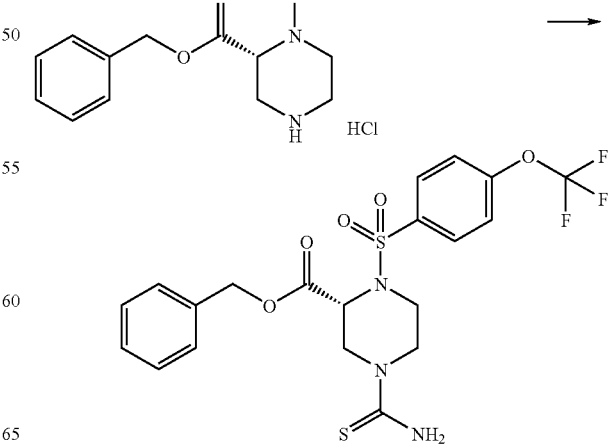

To a solution of the compound (2.58 g) obtained in Step 3 in chloroform (26 ml) was added, with stirring at room temperature, triethylamine (896 µl), and 9-fluorenylmethoxycarbonyl isothiocyanate (1.66 g) was added. After stirring overnight at room temperature, piperidine (1.11 ml) was added. After stirring overnight at room temperature, the reaction mixture was concentrated under reduced pressure, and purified by column chromatography (5% methanol/chloroform) to give the title compound (2.12 g).

Step 5

(R)-4-(5-tert-butoxycarbonyl-4-methyl-thiazol-2-yl)-1-(4-trifluoromethoxy-benzenesulfonyl)-piperazine-2-carboxylicacid benzyl ester

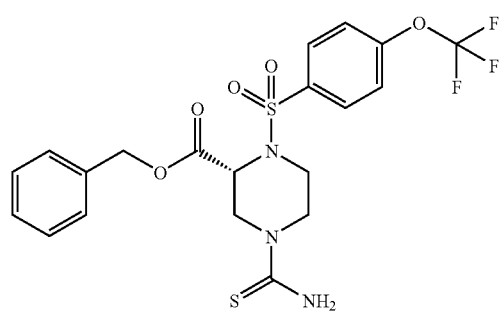

A mixture of the compound (2.12 g) obtained in Step 4 and 2-bromo-3-oxobutyric acid tert-butyl ester (2.0 g) in acetonitrile (20 ml) was stirred at 80° C. for 30 min. The reaction mixture was concentrated under reduced pressure, and the residue was partitioned by adding ethyl acetate and saturated aqueous sodium carbonate solution. The organic layer was washed successively with saturated aqueous sodium carbonate solution and saturated brine, dried over anhydrous sodium sulfate, filtrated, and concentrated under reduced pressure. The residue was purified by column chromatography (ethyl acetate:n-hexane=1:2) to give the title compound (1.82 g).

Step 6

(R)-4-(5-tert-butoxycarbonyl-4-methyl-thiazol-2-yl)-1-(4-trifluoromethoxy-benzenesulfonyl)-piperazine-2-carboxylic acid

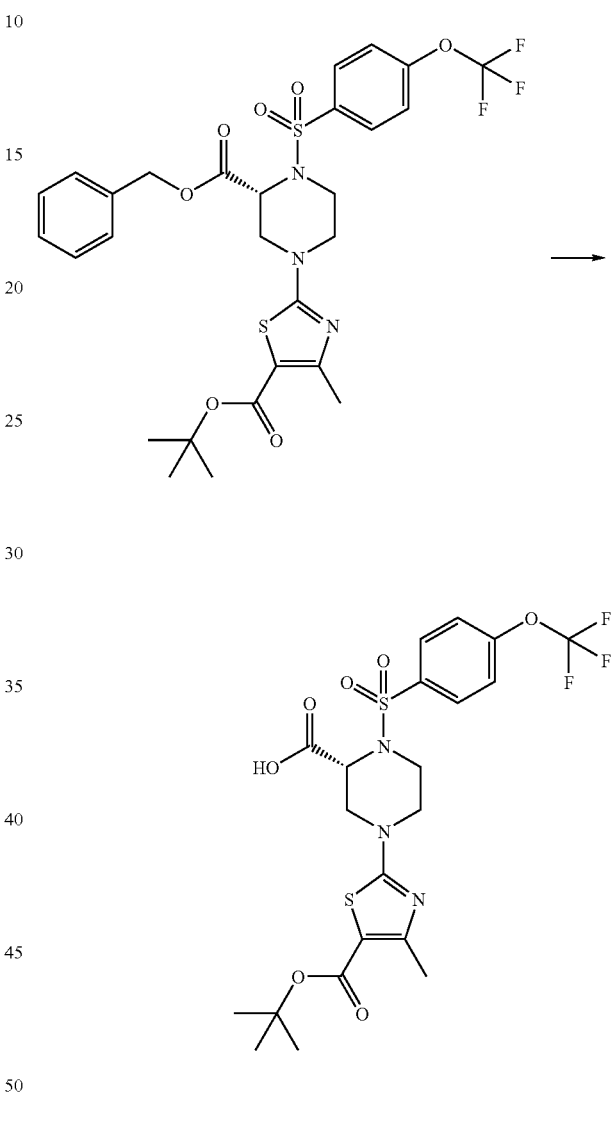

A mixture of the compound (1.82 g) obtained in Step 5, 10% palladium carbon (250 mg) and acetic acid (4.0 ml) in methanol (50 ml) was stirred under a hydrogen atmosphere (4 atm) at room temperature for 3 hr. The reaction mixture was filtered through celite, and concentrated under reduced pressure. 10% Palladium carbon (1.8 g), acetic acid (4.0 ml) and methanol (50 ml) were added again to the residue, and the mixture was stirred under a hydrogen atmosphere (4 atm) at room temperature for 30 min. The reaction mixture was filtered through celite, and the filtrate was concentrated under reduced pressure. Toluene was added to the residue, and the mixture was concentrated under reduced pressure (repeated 4 times). The obtained powder was suspended in water, collected by filtration and dried to give the title compound (1.24 g).

Step 7

2-[(R)-3-[(6-isopropyl-pyridin-3-ylmethyl)-carbamoyl]-4-(4-trifluoromethoxy-benzenesulfonyl)-piperazin-1-yl]-4-methyl-thiazole-5-carboxylic acid tert-butyl ester Step 8

2-[(R)-3-[(6-isopropyl-pyridin-3-ylmethyl)-carbamoyl]-4-(4-trifluoromethoxy-benzenesulfonyl)-piperazin-1-yl]-4-methyl-thiazole-5-carboxylic acid

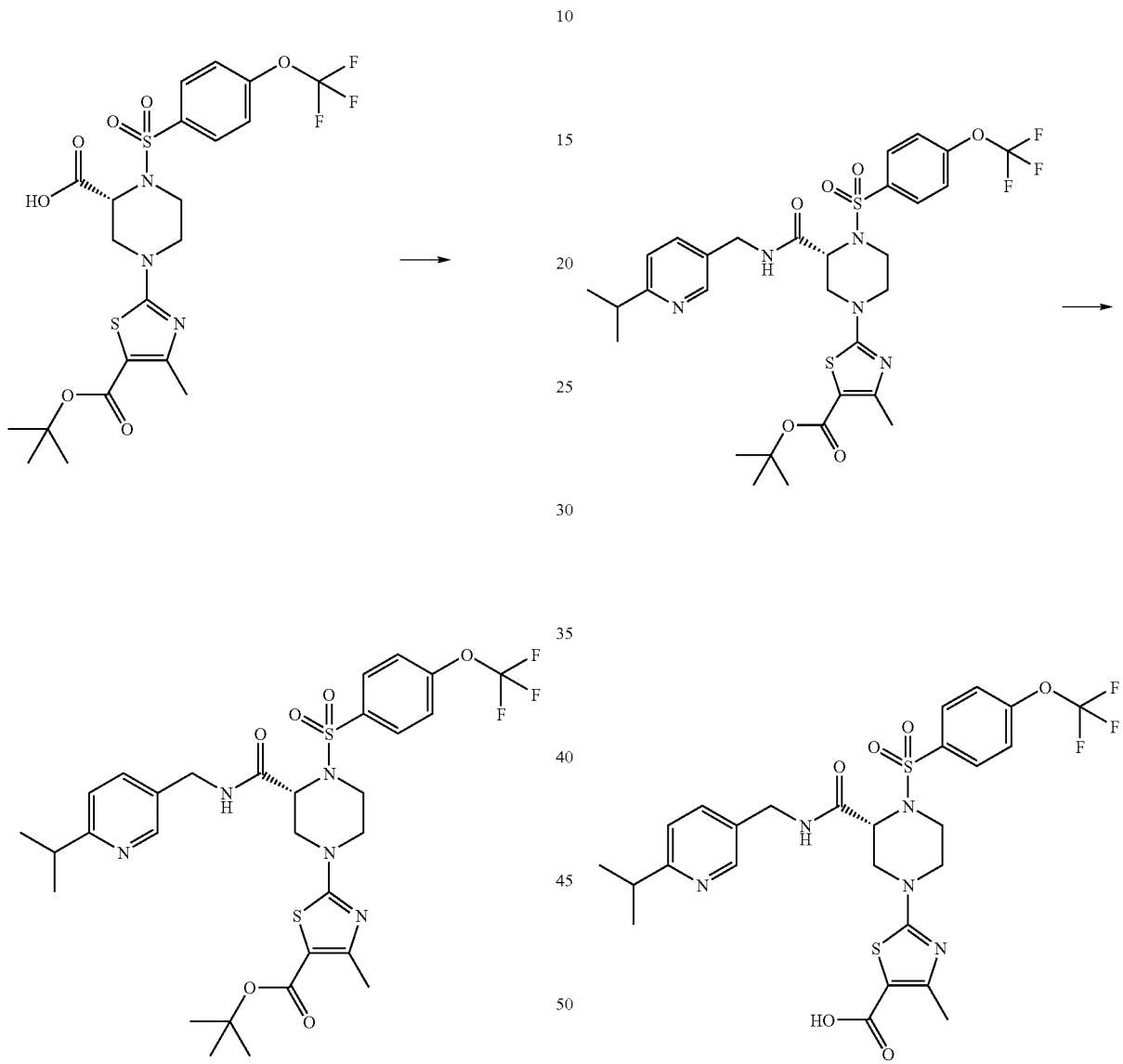

To a mixed solution of the compound (55 mg) obtained in Step 6, [(6-isopropylpyridin-3-yl)methyl]amine (24 mg) and 1-hydroxybenzotriazole hydrate (23 mg) in N,N-dimethylformamide (660 μl) was added, with stirring at room temperature, 1-ethyl-3-(3-dimethylaminopropyl)carbodiimide hydrochloride (29 mg). After stirring at room temperature for 3 hr, the reaction mixture was partitioned by adding saturated aqueous sodium hydrogen carbonate solution and ethyl acetate. The organic layer was washed with saturated brine, dried over anhydrous sodium sulfate, filtrated, and concentrated under reduced pressure. The residue was purified by thin layer chromatography (ethyl acetate:n-hexane=3:2) to give the title compound (59 mg).

A solution of the compound (55 mg) obtained in Step 7 in trifluoroacetic acid (330 μl) was stirred at room temperature for 1 hr. The reaction mixture was concentrated under reduced pressure, chloroform was added to the residue, and the mixture was concentrated again under reduced pressure. The residue was purified by thin layer chromatography (methanol:chloroform=1:10) to give the title compound (43 mg).

Example 14

Step 1

(R)-piperazine-1,2,4-tricarboxylic acid 1-benzyl ester 4-tert-butyl ester

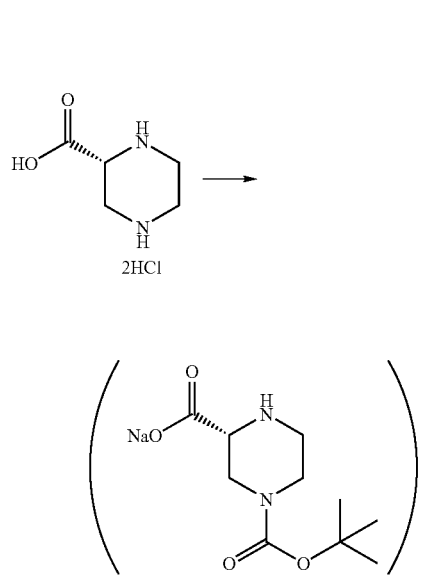

(R)-Piperazine-2-carboxylic acid dihydrochloride (10.0 g) was suspended in a mixed solvent of 1,4-dioxane (50 ml) and water (50 ml) and 50% aqueous sodium hydroxide solution (7.62 ml) was added with stirring under ice-cooling. After stirring under ice-cooling for 30 min, a solution of di-tert-butyl dicarbonate (11.8 g) in 1,4-dioxane (50 ml) was added dropwise. After stirring at room temperature for 7 hr, the reaction mixture was stirred again under ice-cooling, triethylamine (13.7 ml) was added, and benzyl chloroformate (7.03 ml) was added dropwise. After stirring overnight at room temperature, triethylamine (6.85 ml) and benzyl chloroformate (3.52 ml) were added. After stirring at room temperature for 4 hr, the mixture was concentrated under reduced pressure to evaporate 1,4-dioxane. The residue was adjusted to pH 5-6 with 0.5N aqueous hydrochloric acid solution, and extracted 3 times with ethyl acetate. The organic layer was washed with saturated brine, and the insoluble material in the organic layer was filtered off. The filtrate was dried over anhydrous magnesium sulfate, filtrated, and concentrated under reduced pressure to give a crude product (17.1 g) containing the title compound as a main component.

Step 2

(R)-2-(4-propyl-benzylcarbamoyl)-piperazine-1,4-dicarboxylic acid 1-benzyl ester 4-tert-butyl ester

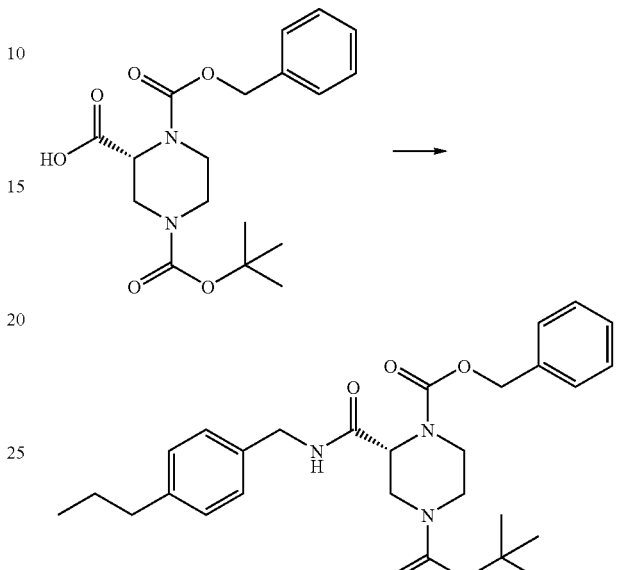

To a mixed solution of the compound (3.41 g) obtained in Step 1, 4-n-propylbenzylamine hydrochloride (1.74 g) and 1-hydroxybenzotriazole hydrate (1.43 g) in N,N-dimethylformamide (34 ml) was added, with stirring at room temperature, triethylamine (1.96 ml), and 1-ethyl-3-(3-dimethylaminopropyl) carbodiimide hydrochloride (1.80 g) was added. After stirring at room temperature for 4 hr, the reaction mixture was partitioned by adding saturated aqueous sodium hydrogen carbonate solution and ethyl acetate. The organic layer was washed successively with water and saturated brine, dried over anhydrous magnesium sulfate, filtrated, and concentrated under reduced pressure. The residue was purified by thin layer chromatography (ethyl acetate:n-hexane=2:5) to give a crude product (2.64 g) containing the title compound as a main component.

Step 3

(R)-2-(4-propyl-benzylcarbamoyl)-piperazine-1-carboxylic acid benzyl ester

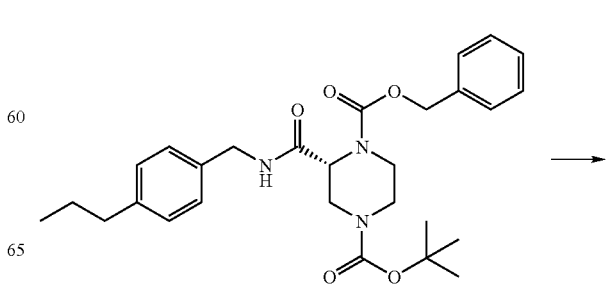

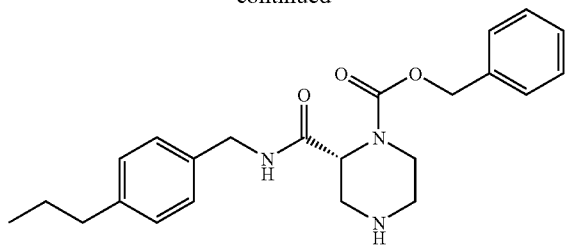

To the compound (2.64 g) obtained in Step 2 in 1,4-dioxane (13 ml) was added, with stirring at room temperature, 4N hydrogen chloride/1,4-dioxane (13 ml). After stirring at room temperature for 3 hr, the reaction mixture was concentrated under reduced pressure. Toluene was added to the residue, and the mixture was concentrated again under reduced pressure. The residue was partitioned by adding ethyl acetate and saturated aqueous sodium hydrogen carbonate solution. The organic layer was washed successively with water and saturated brine, dried over anhydrous magnesium sulfate, filtrated, and concentrated under reduced pressure. The residue was purified by column chromatography (5%-10% methanol/chloroform) to give the title compound (1.59 g).

Step 4

(R)-2-(4-propyl-benzylcarbamoyl)-4-thiocarbamoyl-piperazine-1-carboxylic acid benzyl ester

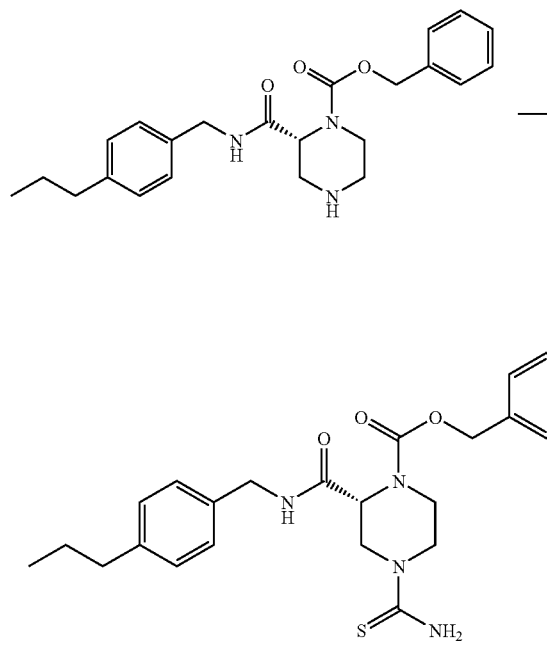

To a solution of the compound (1.59 g) obtained in Step 3 in chloroform (16 ml) was added, with stirring at room temperature, triethylamine (840 μl), and 9-fluorenylmethoxycarbonyl isothiocyanate (1.13 g) was added. After stirring at room temperature for 4 hr, piperidine (805 μl) was added. After stirring overnight at room temperature, the reaction mixture was concentrated under reduced pressure. The residue was partitioned by adding ethyl acetate and water. The organic layer was washed with saturated brine, dried over anhydrous magnesium sulfate, filtrated, and concentrated under reduced pressure. The residue was purified by column chromatography (ethyl acetate:n-hexane=1:1-4:1) to give the title compound (1.62 g).

Step 5

(R)-4-(5-tert-butoxycarbonyl-4-methyl-thiazol-2-yl)-2-(4-propyl-benzylcarbamoyl)-piperazine-1-carboxylic acid benzyl ester

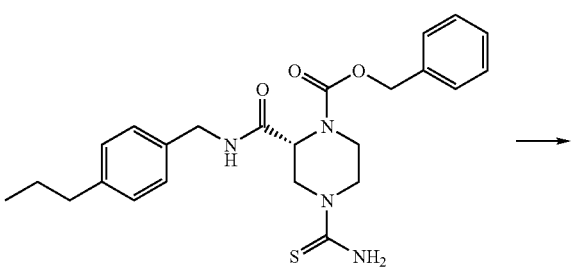

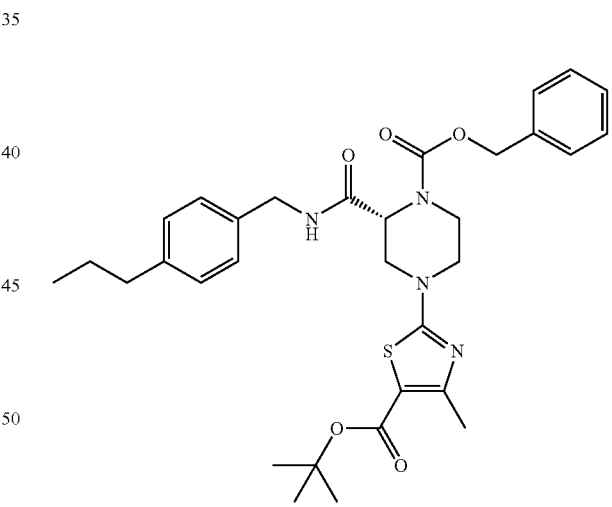

A mixture of the compound (1.51 g) obtained in Step 4 and 2-bromo-3-oxobutyric acid tert-butyl ester (1.58 g) in acetonitrile (15 ml) was stirred at 80° C. for 15 min. The reaction mixture was concentrated under reduced pressure, and the residue was partitioned by adding ethyl acetate and water. The organic layer was washed with saturated brine, dried over anhydrous magnesium sulfate, filtrated, and concentrated under reduced pressure. The residue was purified by column chromatography (ethyl acetate:n-hexane=1:2-2:3) to give the title compound (1.29 g).

207

Step 6

4-methyl-2-[(R)-3-(4-propyl-benzylcarbamoyl)-piperazin-1-yl]-thiazole-5-carboxylic acid tert-butyl ester

208

Step 7

2-[(R)-4-(2-fluoro-4-trifluoromethoxy-benzenesulfonyl)-3-(4-propyl-benzylcarbamoyl)-piperazin-1-yl]-4-methyl-thiazole-5-carboxylic acid tert-butyl ester

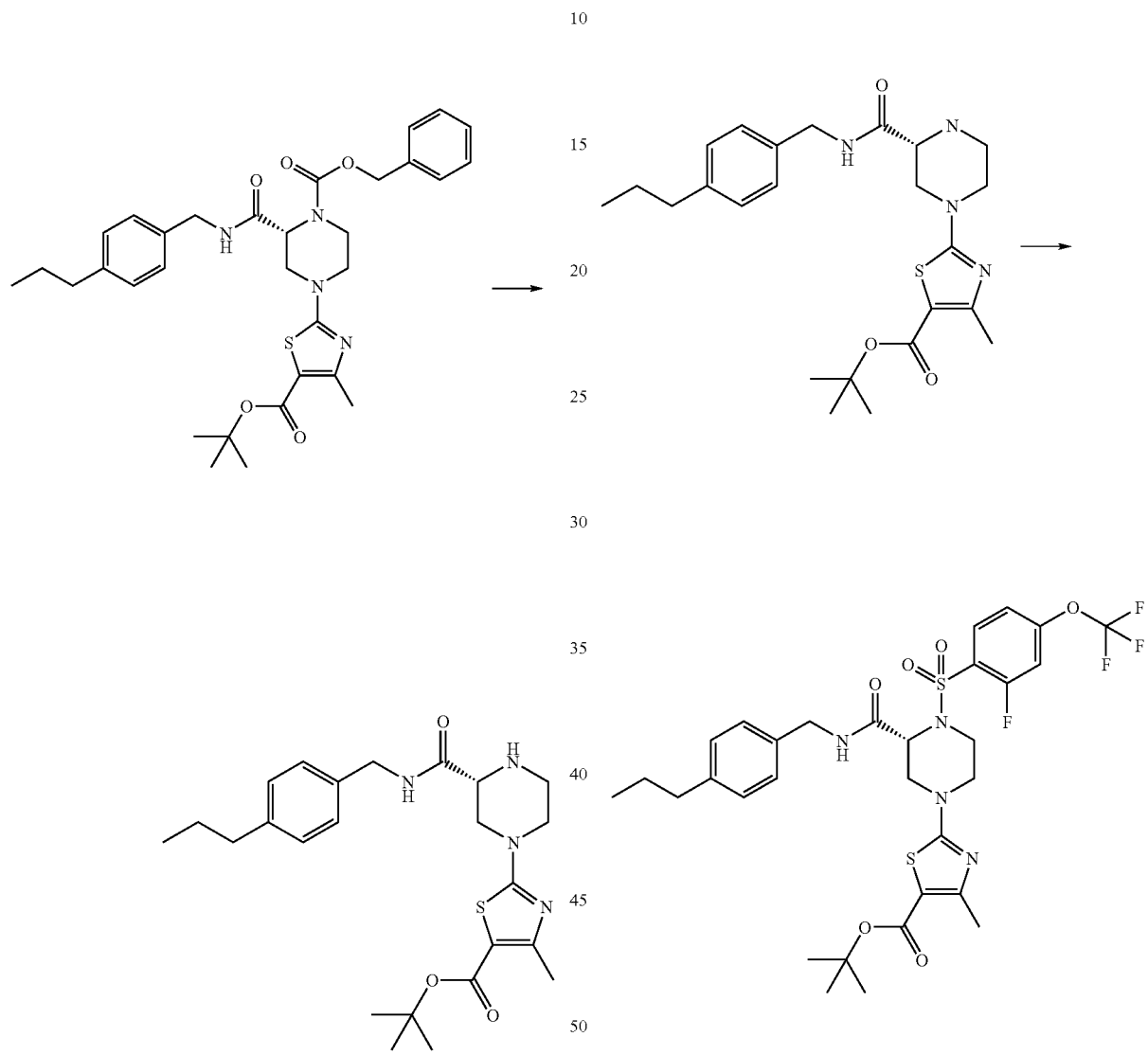

A mixture of the compound (1.00 g) obtained in Step 5 and 7.5% palladium carbon (1.0 g) in methanol (15 ml) was stirred under a hydrogen atmosphere (5 atm) at room temperature for 4 hr. The reaction mixture was filtered through celite, and concentrated under reduced pressure. 10% Palladium carbon (500 mg) and methanol (15 ml) were added again to the residue, and the mixture was stirred under a hydrogen atmosphere (5 atm) at room temperature for 6 hr. The reaction mixture was filtered through celite, and the filtrate was concentrated under reduced pressure. The residue was purified by column chromatography (3%-5% methanol/chloroform) to give the title compound (688 mg).

To a solution of the compound (50 mg) obtained in Step 6 in pyridine (0.5 ml) was added, with stirring at room temperature, 2-fluoro-4-trifluoromethoxybenzenesulfonyl chloride (46 mg). After stirring overnight at room temperature, the reaction mixture was concentrated under reduced pressure. The residue was partitioned by adding ethyl acetate and water. The organic layer was washed successively with 1N aqueous hydrochloric acid solution, saturated aqueous sodium hydrogen carbonate solution and saturated brine, dried over anhydrous magnesium sulfate, filtrated, and concentrated under reduced pressure. The residue was purified by thin layer chromatography (ethyl acetate:n-hexane=1:2) to give the title compound (59 mg).

Step 8

2-[(R)-4-(2-fluoro-4-trifluoromethoxy-benzenesulfonyl)-3-(4-propyl-benzylcarbamoyl)-piperazin-1-yl]-4-methyl-thiazole-5-carboxylic acid

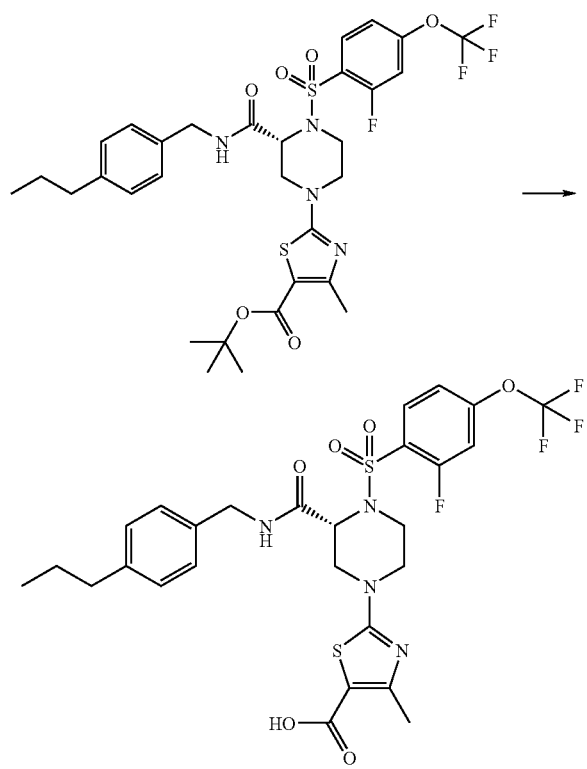

To a solution of the compound (59 mg) obtained in Step 7 in chloroform (0.3 ml) was added, with stirring at room temperature, trifluoroacetic acid (0.3 ml). After stirring at room temperature for 7 hr, the reaction mixture was concentrated under reduced pressure, toluene was added to the residue, and the mixture was concentrated again under reduced pressure. The residue was purified by column chromatography (ethyl acetate:n-hexane=1:2-10% methanol/chloroform) to give the title compound (45 mg).

Example 783

Step 1 sodium (R)-4-tert-butoxycarbonyl-piperazine-2-carboxylate

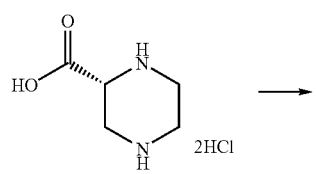

-continued

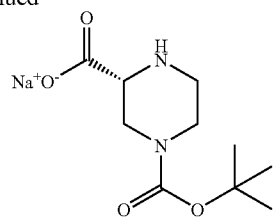

(R)-piperazine-2-carboxylic acid dihydrochloride (20.0 g) was suspended in a mixed solvent of 1,4-dioxane (140 ml) and water (60 ml) and, with stirring under ice-cooling, 50% aqueous sodium hydroxide solution (15.2 ml) was added dropwise, and then a solution of di-tert-butyl dicarbonate (23.6 g) in 1,4-dioxane (60 ml) was added dropwise. The mixture was stirred under ice-cooling for 15 min, and the mixture was stirred at room temperature for 7 hr. Ethyl acetate (60 ml) was added to the reaction mixture, and the mixture was stirred at room temperature for 30 min. The precipitated crystals were collected by filtration, washed with ethyl acetate (40 ml), and dried to give a crude product (13.3 g) containing the title compound as a main component.

$^1$H-NMR (D$_2$O, 400 MHz) δ: 1.49 (9H, s), 3.02-3.13 (1H, m), 3.21-3.44 (3H, m), 3.66-3.73 (1H, m), 3.89-4.12 (1H, br m), 4.28 (1H, dd, J=14.2, 4.1 Hz).

Step 2

(R)-4-(4-trifluoromethoxy-benzenesulfonyl)-piperazine-1,3-dicarboxylic acid 1-tert-butyl ester The compound (6.8 g) obtained in Step 1 was suspended in a mixed solvent of 1,4-dioxane (68 ml) and water (20 ml) and, with stirring under ice-cooling, triethylamine (5.6 g) and 4-dimethylaminopyridine (66 mg) were added, and 4-trifluoromethoxybenzenesulfonyl chloride (7.4 g) was added dropwise. The mixture was stirred under ice-cooling for 20 min, and the mixture was stirred at room temperature for 5.5 hr. With stirring under ice-cooling again, the reaction mixture was adjusted to pH 3 by adding 2N aqueous hydrochloric acid solution (23.5 ml) and saturated aqueous sodium hydrogen carbonate solution (about 5 ml). Ethyl acetate (70 ml) and water (30 ml) were added. The reaction mixture was partitioned, and the aqueous layer was re-extracted twice with ethyl acetate (50 ml). The organic layers were combined, washed twice with water (20 ml), washed with saturated brine (20 ml), dried over anhydrous magnesium sulfate, filtrated, and concentrated under reduced pressure to give a crude product (9.01 g) containing the title compound as a main component.

$^1$H-NMR (DMSO-d$_6$, 400 MHz) δ: 1.33 (9H, s), 2.66-2.87 (1H, br m), 3.03-3.17 (1H, br m), 3.21-3.31 (1H, m), 3.58-3.64 (1H, m), 3.83-3.99 (1H, br m), 4.31 (1H, d, J=13.9 Hz), 4.49 (1H, d, J=3.3 Hz), 7.56 (2H, d, J=8.9 Hz), 7.91 (2H, d, J=8.9 Hz), 13.05 (1H, s).

Step 3

(R)-4-(4-trifluoromethoxy-benzenesulfonyl)-3-(4-trifluoromethoxy-benzylcarbamoyl)-piperazine-1-carboxylic acid tert-butyl ester

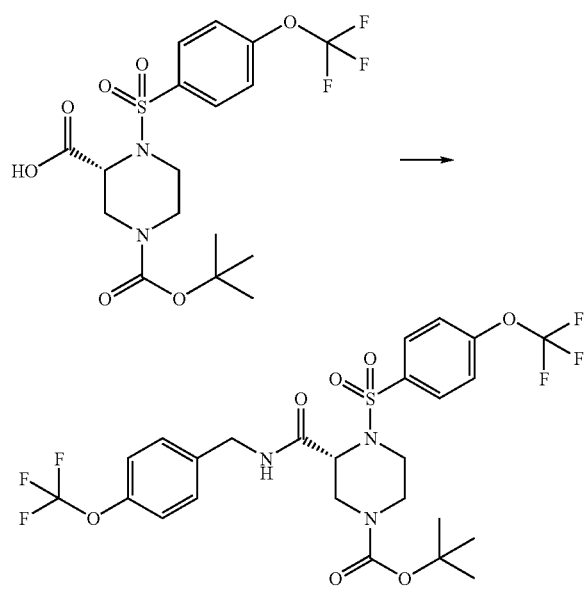

To a solution of the compound (2.40 g) obtained in Step 2, 4-trifluoromethoxybenzylamine (1.21 g) and 1-hydroxybenzotriazole hydrate (1.21 g) in N,N-dimethylformamide (24 ml) was added, with stirring under ice-cooling, 1-ethyl-3-(3-dimethylaminopropyl) carbodiimide hydrochloride (1.21 g). After stirring overnight at room temperature, and the reaction mixture was partitioned by adding ethyl acetate and water. The organic layer was washed successively with saturated aqueous sodium hydrogen carbonate solution, 10% aqueous citric acid solution and saturated brine, dried over anhydrous magnesium sulfate, filtrated, and concentrated under reduced pressure. The obtained crude crystals were suspended in a mixed solution of diisopropyl ether and n-hexane, collected by filtration and dried to give the title compound (2.20 g).

$^1$H-NMR (CDCl$_3$, 300 MHz) δ: 1.39 (9H, s), 2.60-3.10 (2H, br m), 3.31 (1H, m), 3.69 (1H, m), 3.84 (1H, d, J=14.0 Hz), 4.35-4.50 (3H, m), 4.56 (1H, d, J=13.6 Hz), 6.83 (1H, br s), 7.18 (2H, d, J=8.1 Hz), 7.27 (2H, d, J=8.1 Hz), 7.35 (2H, d, J=8.7 Hz), 7.91 (2H, d, J=8.7 Hz).

Step 4

(R)-1-(4-trifluoromethoxy-benzenesulfonyl)-piperazine-2-carboxylic acid 4-trifluoromethoxy-benzylamide

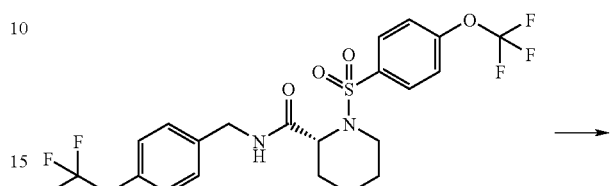

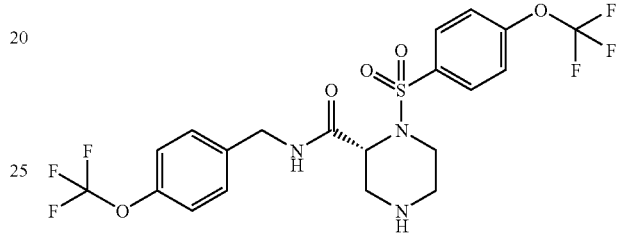

4N Hydrogen chloride/1,4-dioxane solution (40 ml) was added to the compound (2.20 g) obtained in Step 3, and the mixture was stirred at room temperature for 1.5 hr. The reaction mixture was concentrated under reduced pressure, and the residue was partitioned by adding chloroform and saturated aqueous sodium hydrogen carbonate solution. The organic layer was dried over anhydrous sodium carbonate, filtrated, and concentrated under reduced pressure. The residue was crystallized from a mixed solvent of diisopropyl ether and n-hexane, collected by filtration and dried to give the title compound (1.57 g).

$^1$H-NMR (CDCl$_3$, 300 MHz) δ: 2.45-2.58 (2H, m), 2.86 (1H, d, J=13.2 Hz), 3.16 (1H, dt, J=3.3, 6.8 Hz), 3.54 (1H, d, J=12.9 Hz), 3.76 (1H, d, J=13.7 Hz), 4.35 (1H, d, J=3.9 Hz), 4.40-4.55 (2H, m), 7.18 (2H, d, J=8.1 Hz), 7.20 (1H, m), 7.28 (2H, d, J=8.9 Hz), 7.35 (2H, d, J=8.1 Hz), 7.90 (2H, d, J=8.9 Hz).

Example 975

Step 1

6-amino-2-cyclopropyl-pyrimidin-4-ol

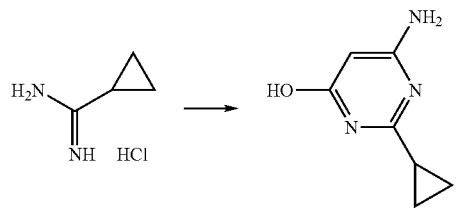

A mixed solution of cyclopropanecarboxamidine hydrochloride (0.30 g), ethyl cyanoacetate (0.27 ml) and methanol (1.5 ml) was added to 28% sodium methoxide methanol solution (2.0 ml) under ice-cooling. After heating under reflux for 1 hr, the mixture was cooled to room temperature. The reaction mixture was concentrated under reduced pressure, and the obtained residue was adjusted to pH 5 with water and acetic acid. The precipitated solid was collected by filtration, washed with water and dried to give the title compound (0.30 g).

$^1$H-NMR (DMSO-$d_6$, 300 MHz) δ: 0.91 (4H, d, J=6.0 Hz), 1.73-1.81 (1H, m), 4.79 (1H, s), 6.21 (2H, s), 11.53 (1H, br s).

Step 2

6-amino-2-cyclopropyl-5-thiocyanato-pyrimidin-4-ol

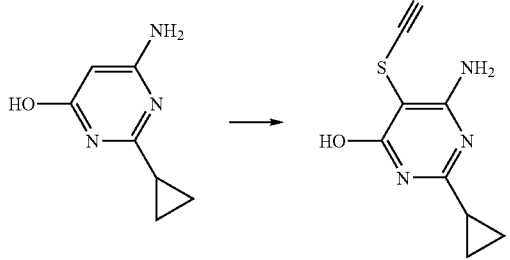

To a mixed solution of the compound (0.30 g) obtained in Step 1, potassium thiocyanate (0.77 g) and N,N-dimethylformamide (6.0 ml) was added pyridine (0.29 ml) at 90° C. After allowing to cool to 40° C., a mixed solution of bromine (0.15 ml) and N,N-dimethylformamide (1.0 ml) was added, and the mixture was stirred at room temperature for 1 hr. Under ice-cooling, water (12 ml) was added to the reaction solution, and the precipitated solid was collected by filtration, washed with water and dried to give the title compound (0.40 g).

$^1$H-NMR (DMSO-$d_6$, 300 MHz) δ: 0.97-1.05 (4H, m), 1.76-1.87 (1H, m), 7.42 (2H, br s), 12.21 (1H, br s).

Step 3

2-amino-5-cyclopropyl-thiazolo[4,5-d]pyrimidin-7-ol

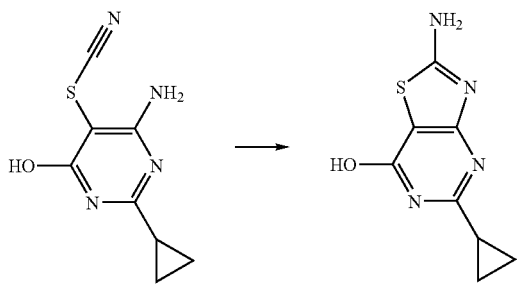

A solution of the compound (0.20 g) obtained in Step 2 in N,N-dimethylformamide (7.0 ml) was stirred overnight under heating at 135° C. The reaction mixture was cooled to room temperature, and water (7.0 ml) was added under ice-cooling. The precipitated solid was collected by filtration, washed with water and dried to give the title compound (0.15 g).

$^1$H-NMR (DMSO-$d_6$, 300 MHz) δ: 0.96-1.03 (4H, m), 1.88-1.98 (1H, m), 8.02 (2H, s), 12.40 (1H, br s).

Step 4

2-chloro-5-cyclopropyl-thiazolo[4,5-d]pyrimidin-7-ol

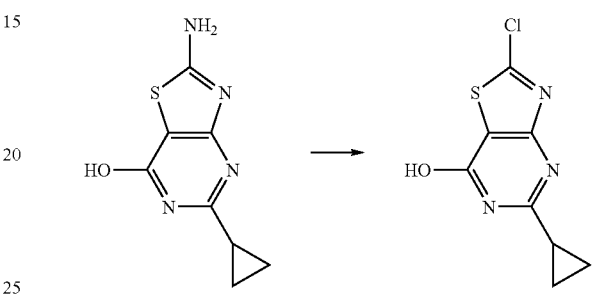

The compound (1.2 g) obtained in Step 3 was suspended in 2N aqueous sodium hydroxide solution (18 ml) and, under ice-cooling, sodium nitrite (1.2 g) was added in several portions. The obtained suspension was slowly added dropwise to a concentrated aqueous hydrochloric acid solution (18 ml) heated to 80° C., and the mixture was stirred at the same temperature for 1 hr. The reaction mixture was cooled to room temperature, and the precipitated solid was collected by filtration, washed with water and dried to give the title compound (0.60 g). The filtrate was extracted with ethyl acetate, and the organic layer was washed with saturated brine, dried over anhydrous sodium sulfate, filtrated, and concentrated under reduced pressure to give a crude product (0.34 g) containing the title compound as a main component. The obtained crude crystals were suspended in a mixed solvent of hexane and ethyl acetate, collected by filtration and dried to give the title compound (0.26 g).

$^1$H-NMR (DMSO-$d_6$, 300 MHz) δ: 1.08-1.13 (4H, m), 2.01-2.06 (1H, m), 13.15 (1H, br s).

Step 5

2,7-dichloro-5-cyclopropyl-thiazolo[4,5-d]pyrimidine

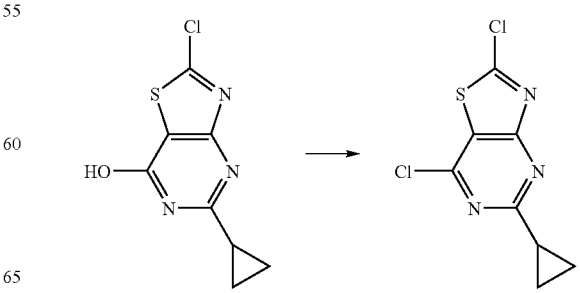

To a solution of the compound (0.82 g) obtained in Step 4 in phosphorus oxychloride (2.5 ml) was added N,N-diisopropylethylamine (0.25 ml) under ice-cooling, and the mixture was heated under reflux for 2 hr. The reaction mixture was concentrated under reduced pressure, toluene was added to the residue, and the mixture was concentrated again under reduced pressure. The obtained residue was dissolved in ethyl acetate, poured into ice water and partitioned. The organic layer was washed successively with saturated aqueous sodium hydrogen carbonate solution and saturated brine, dried over anhydrous sodium sulfate, filtrated, and concentrated under reduced pressure. The residue was purified by silica gel column chromatography (ethyl acetate:n-hexane=1:8) to give the title compound (0.79 g).

$^1$H-NMR (CDCl$_3$, 300 MHz) δ: 1.15-1.31 (4H, m), 2.32-2.43 (1H, m).

Step 6

(R)-4-(7-chloro-5-cyclopropyl-thiazolo[4,5-d]pyrimidin-2-yl)-1-(4-trifluoromethoxy-benzenesulfonyl)-piperazine-2-carboxylic acid 4-trifluoromethoxy-benzylamide

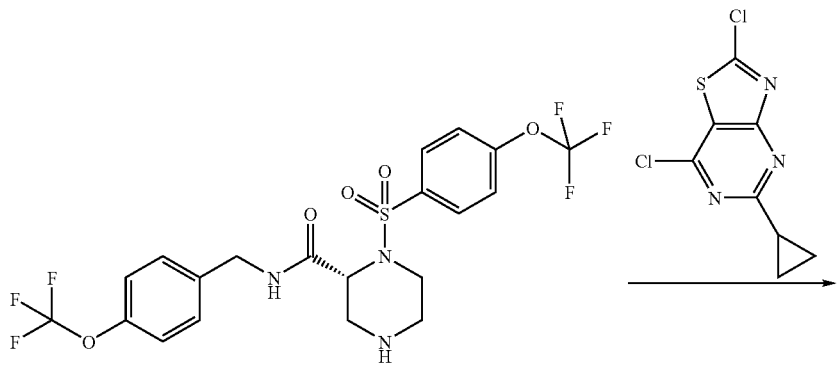

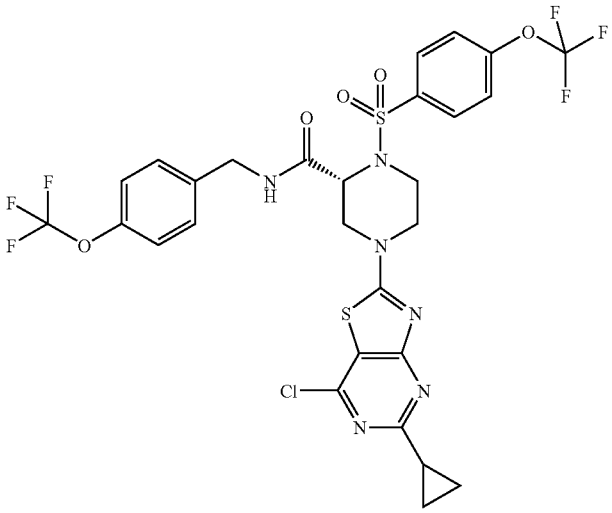

To a mixed solution of the compound (0.94 g) obtained in Example 783, the compound (0.48 g) obtained in Step 5 and chloroform (2.8 ml) was added N,N-diisopropylethylamine (0.30 ml) at room temperature. The mixture was stirred at room temperature for 30 min, and concentrated under reduced pressure. The residue was purified by silica gel column chromatography (ethyl acetate:chloroform=1:2) to give the title compound (1.3 g).

$^1$H-NMR (CDCl$_3$, 300 MHz) δ: 1.03-1.24 (4H, m), 2.16-2.28 (1H, m), 3.11-3.37 (2H, m), 3.39-3.54 (1H, m), 3.92 (1H, d, J=14.3 Hz), 4.23-4.60 (4H, m), 4.64 (1H, s), 6.90 (1H, t, J=5.8 Hz), 7.12 (2H, d, J=8.3 Hz), 7.21 (2H, d, J=8.7 Hz), 7.37 (2H, d, J=8.3 Hz), 7.93 (2H, d, J=8.7 Hz).

217

Step 7

(R)-4-(5-cyclopropyl-thiazolo[4,5-d]pyrimidin-2-yl)-
1-(4-trifluoromethoxy-benzenesulfonyl)-piperazine-
2-carboxylic acid 4-trifluoromethoxy-benzylamide

218

Example 1001

Step 1

(R)-4-(4-trifluoromethyl-benzenesulfonyl)-pipera-
zine-1,3-dicarboxylic acid 1-tert-butyl ester

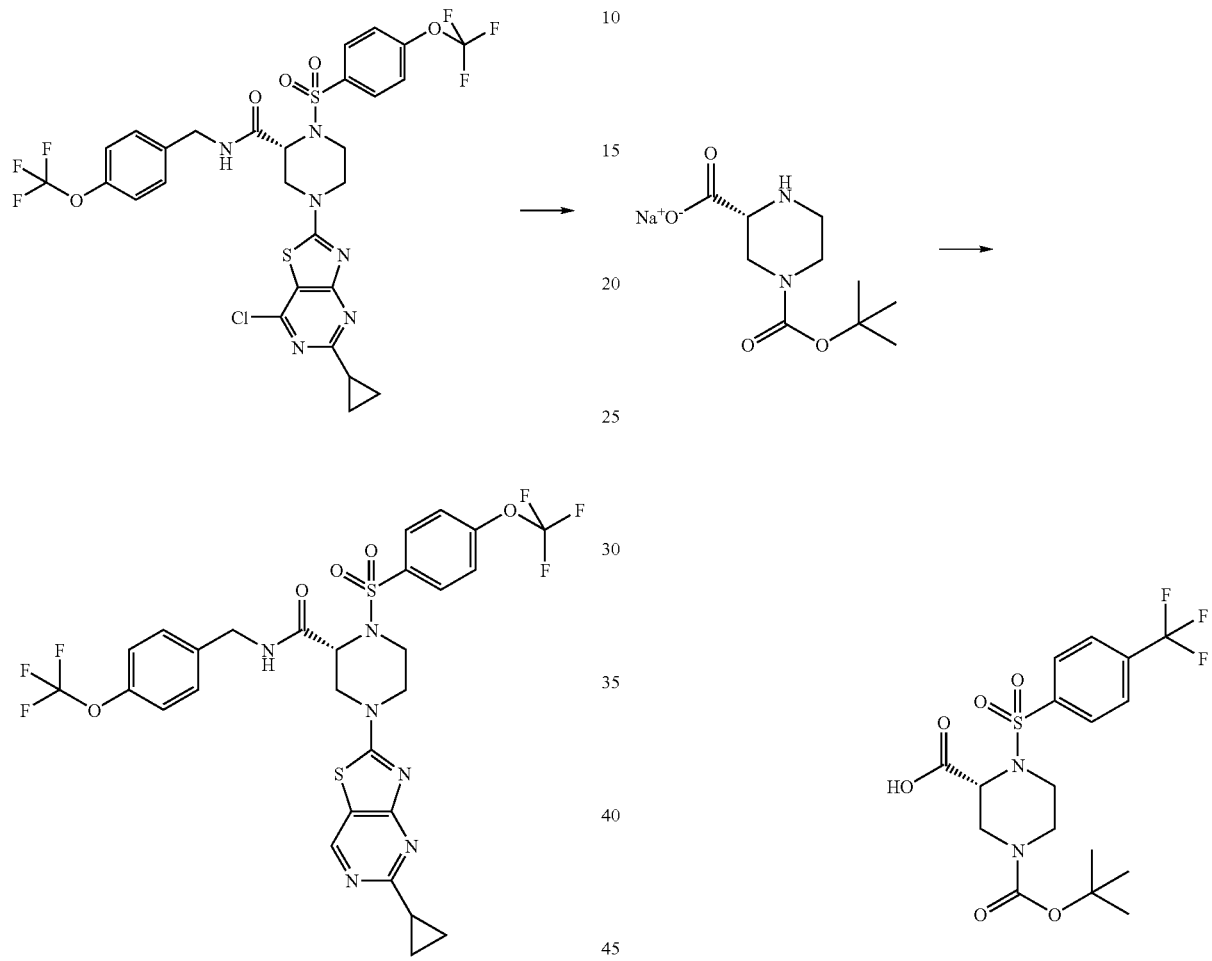

To a mixed solution of the compound (1.3 g) obtained in Step 6, ammonium formate (1.2 g) and ethanol (13 ml) was added 10% palladium carbon (1.3 g) at 80° C. After stirring at the same temperature for 30 min, ammonium formate (1.3 g) and 10% palladium carbon (0.50 g) were added. After stirring at 80° C. for 30 min, ammonium formate (1.2 g) and 10% palladium carbon (0.65 g) were further added. After stirring at the same temperature for 1.5 hr, the reaction mixture was allowed to return to room temperature and diluted with chloroform. The mixture was filtered through celite, and the filtrate was concentrated under reduced pressure. The residue was purified by silica gel column chromatography (ethyl acetate:chloroform=1:2) to give the title compound (0.91 g).

$^1$H-NMR (CDCl$_3$, 300 MHz) δ: 1.01-1.09 (2H, m), 1.16-1.21 (2H, m), 2.21-2.30 (1H, m), 3.12-3.36 (2H, m), 3.42-3.51 (1H, m), 3.91 (1H, d, J=13.6 Hz), 4.24-4.52 (3H, m), 4.55-4.67 (2H, m), 6.90-6.98 (1H, m), 7.09 (2H, d, J=9.0 Hz), 7.19 (2H, d, J=8.7 Hz), 7.36 (2H, d, J=8.7 Hz), 7.93 (2H, d, J=8.7 Hz), 8.61 (1H, s).

Sodium (R)-4-tert-butoxycarbonyl-piperazine-2-carboxy-late (10.0 g) was suspended in a mixed solvent of 1,4-dioxane (100 ml) and water (30 ml) and, with stirring under ice-cooling, triethylamine (11.3 ml) and 4-dimethylaminopyridine (97 mg) were added, and 4-trifluoromethylbenzene-sulfonyl chloride (10.2 g) was added dropwise. After stirring overnight at room temperature, 2N aqueous hydrochloric acid solution was added with stirring under ice-cooling to adjust the reaction mixture to pH 3, and ethyl acetate and water were added. The reaction mixture was partitioned, the organic layer was washed successively with water and saturated brine, dried over anhydrous magnesium sulfate, filtrated, and concentrated under reduced pressure to give a crude product (10.2 g) containing the title compound as a main component.

$^1$H-NMR (DMSO-d$_6$, 400 MHz) δ: 1.32 (9H, s), 2.68-2.87 (1H, m), 3.01-3.17 (1H, m), 3.25 (1H, d, J=13.6 Hz), 3.64 (1H, d, J=10.2 Hz), 3.84-4.03 (1H, m), 4.32 (1H, d, J=13.6 Hz), 4.51 (1H, s), 7.97 (4H, s), 13.08 (1H, s).

Step 2

(R)-3-(4-difluoromethoxy-benzylcarbamoyl)-4-(4-trifluoromethyl-benzenesulfonyl)-piperazine-1-carboxylic acid tert-butyl ester

Step 3

(R)-1-(4-trifluoromethyl-benzenesulfonyl)-piperazine-2-carboxylic acid 4-difluoromethoxy-benzylamide

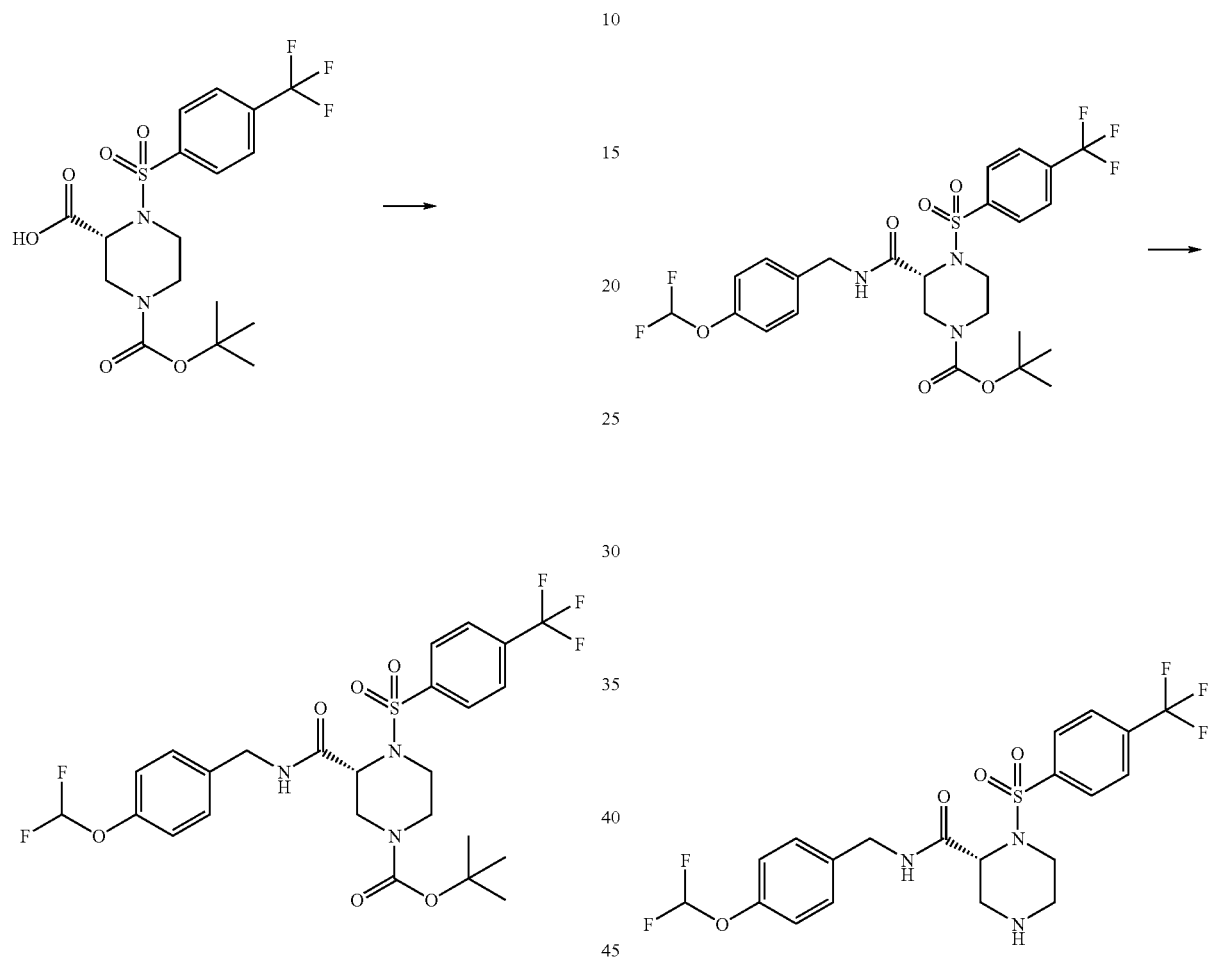

To a solution of the compound (1.00 g) obtained in Step 1, 4-difluoromethoxybenzylamine (474 mg) and 1-hydroxybenzotriazole hydrate (420 mg) in N,N-dimethylformamide (10 ml) was added, with stirring under ice-cooling, 1-ethyl-3-(3-dimethylaminopropyl) carbodiimide hydrochloride (524 mg). After stirring overnight at room temperature, the reaction mixture was partitioned by adding ethyl acetate and water. The organic layer was washed successively with saturated aqueous sodium hydrogen carbonate solution, 10% aqueous citric acid solution and saturated brine, dried over anhydrous magnesium sulfate, filtrated, and concentrated under reduced pressure. The obtained crude crystals were suspended in a mixed solution of diisopropyl ether and n-hexane, collected by filtration and dried to give the title compound (956 mg).

$^1$H-NMR (DMSO-$d_6$, 300 MHz) δ: 1.39 (9H, s), 2.60-3.20 (2H, br m), 3.20-3.40 (1H, m), 3.65-3.80 (1H, m), 3.86 (1H, d, J=13.6 Hz), 4.35-4.55 (3H, m), 4.56 (1H, d, J=14.0 Hz), 6.50 (1H, t, J=73.8 Hz), 6.77 (1H, br s), 7.09 (2H, d, J=8.5 Hz), 7.24 (2H, d, J=8.5 Hz), 7.79 (2H, d, J=8.3 Hz), 7.98 (2H, d, J=8.3 Hz).

4N Hydrogen chloride/1,4-dioxane solution (20 ml) was added to the compound (950 mg) obtained in Step 2, and the mixture was stirred at room temperature for 1.5 hr. The reaction mixture was concentrated under reduced pressure, and the residue was partitioned by adding chloroform and saturated aqueous sodium hydrogen carbonate solution. The organic layer was dried over anhydrous sodium carbonate, filtrated, and concentrated under reduced pressure to give a crude product (807 mg) containing the title compound as a main component.

$^1$H-NMR (CDCl$_3$, 300 MHz) δ: 2.45-2.60 (2H, m), 2.87 (1H, d, J=12.4 Hz), 3.18 (1H, dt, J=3.3, 13.1 Hz), 3.53 (1H, d, J=12.7 Hz), 3.77 (1H, d, J=13.3 Hz), 4.35-4.50 (3H, m), 6.50 (1H, t, J=73.8 Hz), 7.08 (2H, d, J=8.5 Hz), 7.19 (1H, br s), 7.24 (2H, d, J=8.5 Hz), 7.80 (2H, d, J=8.4 Hz), 7.98 (2H, d, J=8.4 Hz).

Step 4

6-amino-2-trifluoromethyl-pyrimidin-4-ol

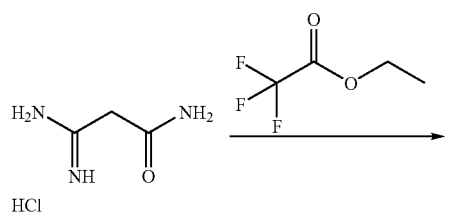

Under stirring at room temperature, malonamidine hydrochloride (406 g) and 1,8-diazabicyclo[5.4.0]undec-7-ene (870 ml) were added to tetrahydrofuran (2 L), and ethyl trifluoroacetate (1040 ml) was added dropwise. After stirring under heating at a bath temperature of 65° C. for 17.5 hr, water (200 ml) was added, and the reaction mixture was concentrated. Water (1 L) was added to the concentrated residue, concentrated hydrochloric acid (485 ml) was added dropwise with stirring at room temperature and the mixture was stirred for 1 hr. After cooling the inside temperature to 0° C. or below, the precipitated crystals were collected by filtration, washed twice with water (600 ml), and dried to give the title compound (251 g).

$^1$H-NMR (DMSO-$d_6$, 300 MHz) δ: 5.68 (1H, s), 7.10 (2H, br s), 11.64 (1H, br s).

Step 5

6-amino-5-thiocyanato-2-trifluoromethyl-pyrimidin-4-ol

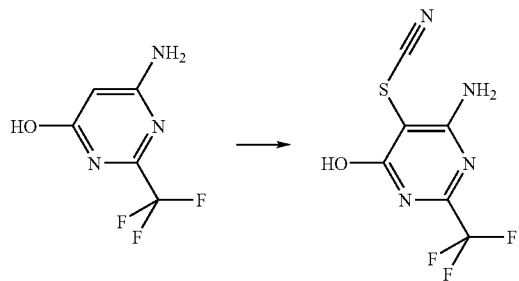

To a solution of potassium thiocyanate (6.78 g) and pyridine (3.37 ml) in N,N-dimethylformamide (75 ml) was added dropwise bromine (1.72 ml) with stirring under ice-cooling. After stirring under ice-cooling for 1 hr, a solution of the compound (5.00 g) obtained in Step 4 in N,N-dimethylformamide (25 ml) was added dropwise. After further stirring under ice-cooling for 1 hr, water was added, and the insoluble material was filtered off. The filtrate was extracted with ethyl acetate. The organic layer was washed successively with water and saturated brine, dried over anhydrous magnesium sulfate, filtrated, and concentrated under reduced pressure to give a crude product (4.40 g) containing the title compound as a main component.

$^1$H-NMR (DMSO-$d_6$, 400 MHz) δ: 8.17 (2H, br s), 13.58 (1H, br s).

Step 6

2-amino-5-trifluoromethyl-thiazolo[4,5-d]pyrimidin-7-ol

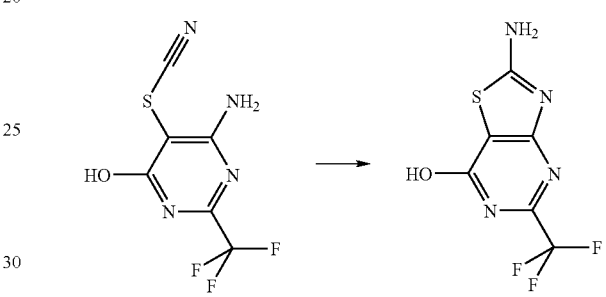

A solution of the compound (4.25 g) obtained in Step 5 in N,N-dimethylformamide (128 ml) was stirred at 130° C. for 14 hr. The reaction mixture was concentrated under reduced pressure, xylene was added to the residue, and the mixture was concentrated again under reduced pressure. The obtained crude crystals were suspended in ethyl acetate, collected by filtration and dried to give the title compound (3.35 g).

$^1$H-NMR (DMSO-$d_6$, 400 MHz) δ: 8.58 (2H, s)

Step 7

2-chloro-5-trifluoromethyl-thiazolo[4,5-d]pyrimidin-7-ol

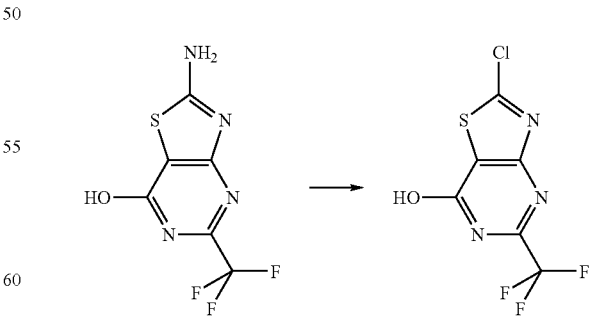

To a solution of the compound (3.00 g) obtained in Step 6 in 6N hydrochloric acid (45 ml) was added sodium nitrite (8.76 g) in several portions with stirring at room temperature, and the mixture was further stirred at room temperature for 30 min. The precipitated crystals were collected by filtration, washed with water and dried to give the title compound (1.46 g).

Step 8

2,7-dichloro-5-trifluoromethyl-thiazolo[4,5-d]pyrimidine

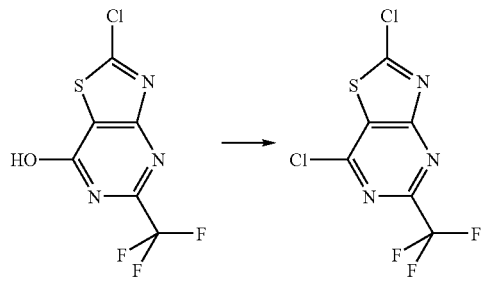

To a solution of the compound (1.35 g) obtained in Step 7 in phosphorus oxychloride (20 ml) was added water (190 mg) with stirring under ice-cooling, and the mixture was stirred at 100° C. for 3 hr. The reaction mixture was concentrated under reduced pressure, and partitioned by adding chloroform and water. The organic layer was washed successively with water and saturated brine, dried over anhydrous magnesium sulfate, filtrated, and concentrated under reduced pressure. The residue was purified by silica gel column chromatography (ethyl acetate:n-hexane=1:10) to give the title compound (1.17 g).

Step 9

(R)-4-(7-chloro-5-trifluoromethyl-thiazolo[4,5-d]pyrimidin-2-yl)-1-(4-trifluoromethyl-benzenesulfonyl)-piperazine-2-carboxylic acid 4-difluoromethoxy-benzylamide

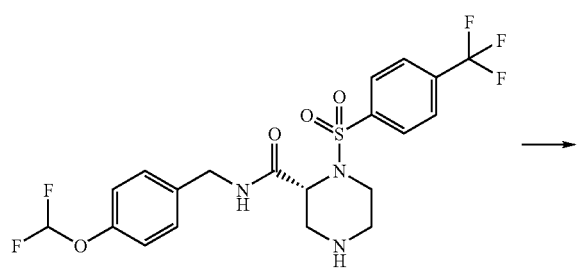

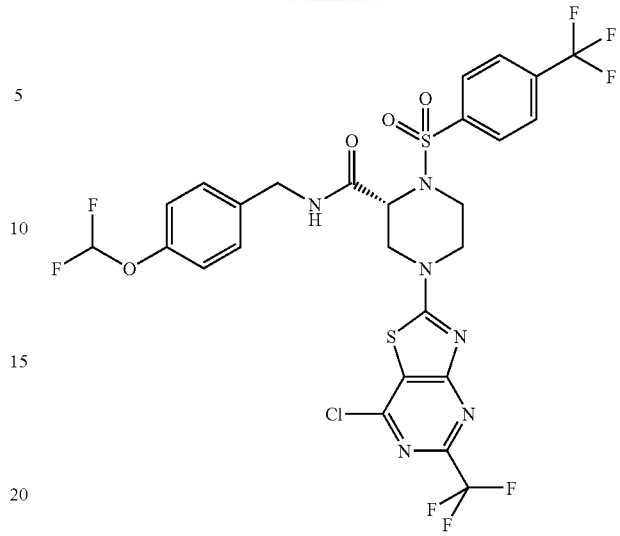

To a solution of the compound (700 mg) obtained in Step 3 and N,N-diisopropylethylamine (371 mg) in chloroform (11 ml) was added the compound (389 mg) obtained in Step 8 with stirring under ice-cooling. After stirring at room temperature for 1 hr, the reaction mixture was partitioned by adding chloroform and water. The organic layer was washed successively with water and saturated brine, dried over anhydrous magnesium sulfate, filtrated, and concentrated under reduced pressure to give a crude product (1.09 g) containing the title compound as a main component.

$^1$H-NMR (CDCl$_3$, 300 MHz) δ: 3.45-3.48 (3H, m), 3.99 (1H, d, J=13.9 Hz), 4.44-4.59 (5H, m), 6.49 (1H, t, J=73.5 Hz), 6.81 (1H, t, J=10.0 Hz), 7.03 (2H, d, J=8.7 Hz), 7.18 (2H, d, J=8.3 Hz), 7.84 (2H, d, J=8.7 Hz), 8.02 (2H, d, J=8.3 Hz).

Step 10

(R)-1-(4-trifluoromethyl-benzenesulfonyl)-4-(5-trifluoromethyl-thiazolo[4,5-d]pyrimidin-2-yl)-piperazine-2-carboxylic acid 4-difluoromethoxy-benzylamide

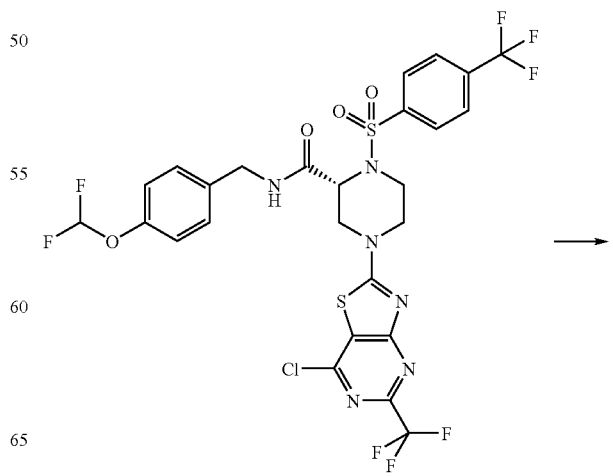

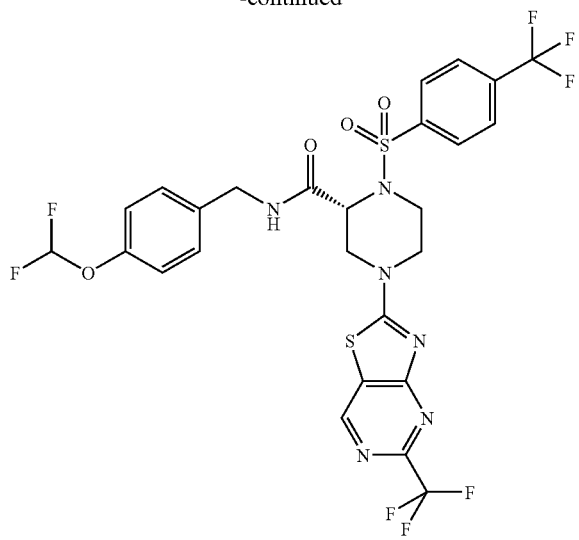

Under a nitrogen atmosphere, to a solution of the compound (1.09 g) obtained in Step 9 and ammonium formate (895 mg) in ethanol (15 ml)-methanol (5 ml) was added 10% palladium carbon (1.0 g). After stirring at 85° C. for 1 hr, the catalyst was filtered off. The filtrate was concentrated under reduced pressure, and the residue was partitioned by adding ethyl acetate and water. The organic layer was washed successively with water and saturated brine, dried over anhydrous magnesium sulfate, filtrated, and concentrated under reduced pressure. The residue was purified by silica gel column chromatography (ethyl acetate:n-hexane=1:1) to give the title compound (596 mg).

$^1$H-NMR (CDCl$_3$, 400 MHz) δ: 3.34-3.50 (3H, m), 3.98 (1H, d, J=14.1 Hz), 4.42-4.58 (5H, m), 6.47 (1H, t, J=73.7 Hz), 6.88 (1H, t, J=10.0 Hz), 7.00 (2H, d, J=8.4 Hz), 7.16 (2H, d, J=8.6 Hz), 7.82 (2H, d, J=8.4 Hz), 8.01 (2H, d, J=8.2 Hz), 8.87 (1H, s).

Example 983

Step 1

(R)-3-(4-trifluoromethoxy-benzylcarbamoyl)-4-(4-trifluoromethyl-benzenesulfonyl)-piperazine-1-carboxylic acid tert-butyl ester

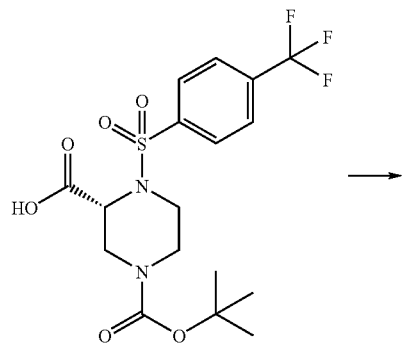

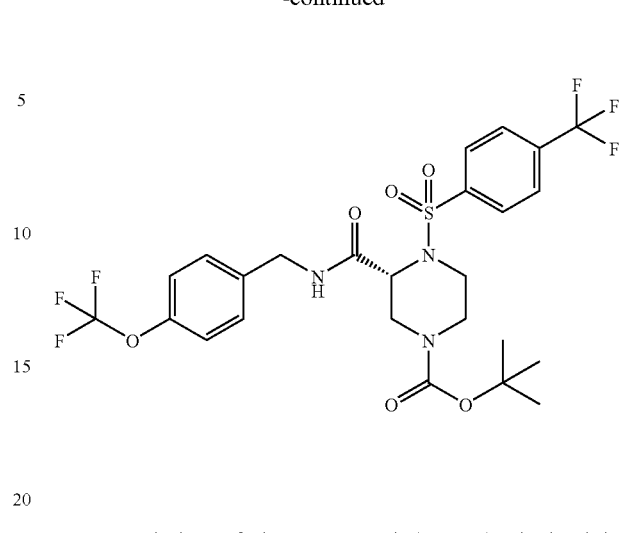

To a solution of the compound (2.98 g) obtained in Example 1001, Step 1, 4-trifluoromethoxybenzylamine (1.56 g) and 1-hydroxybenzotriazole hydrate (1.25 g) in N,N-dimethylformamide (30 ml) was added 1-ethyl-3-(3-dimethylaminopropyl)carbodiimide hydrochloride (1.56 g) with stirring under ice-cooling. After stirring overnight at room temperature, the reaction mixture was partitioned by adding ethyl acetate and water. The organic layer was washed successively with saturated aqueous sodium hydrogen carbonate solution, 10% aqueous citric acid solution and saturated brine, dried over anhydrous magnesium sulfate, filtrated, and concentrated under reduced pressure. The obtained crude crystals were suspended in a mixed solution of diisopropyl ether and n-hexane, collected by filtration and dried to give the title compound (2.79 g).

$^1$H-NMR (CDCl$_3$, 300 MHz) δ: 1.39 (9H, s), 2.60-3.20 (2H, br m), 3.20-3.40 (1H, br m), 3.65-3.80 (1H, br m), 3.86 (1H, d, J=13.3 Hz), 4.35-4.55 (3H, m), 4.56 (1H, d, J=14.0 Hz), 6.80 (1H, br s), 7.18 (2H, d, J=8.4 Hz), 7.27 (2H, d, J=8.4 Hz), 7.79 (2H, d, J=8.4 Hz), 7.99 (2H, d, J=8.4 Hz).

Step 2

(R)-1-(4-trifluoromethyl-benzenesulfonyl)-piperazine-2-carboxylic acid 4-trifluoromethoxy-benzylamide

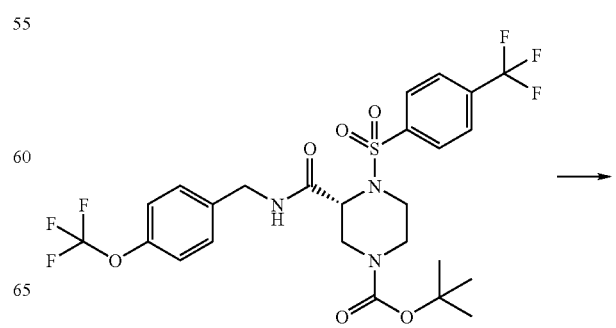

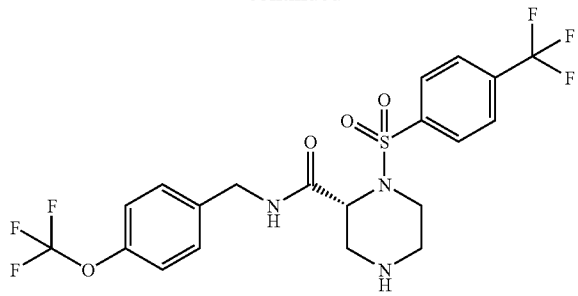

4N Hydrogen chloride/1,4-dioxane solution (30 ml) was added to the compound (2.78 g) obtained in Step 1, and the mixture was stirred at room temperature for 1.5 hr. The reaction mixture was concentrated under reduced pressure, and the residue was partitioned by adding chloroform and saturated aqueous sodium hydrogen carbonate solution. The organic layer was dried over anhydrous sodium carbonate, filtrated, and concentrated under reduced pressure to give a crude product (2.31 g) containing the title compound as a main component.

$^1$H-NMR (CDCl$_3$, 300 MHz) δ: 2.45-2.56 (2H, m), 2.87 (1H, d, J=13.0 Hz), 3.17 (1H, dt, J=3.2, 13.1 Hz), 3.53 (1H, d, J=12.9 Hz), 3.78 (1H, d, J=11.6 Hz), 4.38 (1H, d, J=3.9 Hz), 4.38-4.53 (2H, m), 7.18 (2H, d, J=8.5 Hz), 7.23 (1H, br s), 7.27 (2H, d, J=8.5 Hz), 7.80 (2H, d, J=8.4 Hz), 7.98 (2H, d, J=8.4 Hz).

Step 3

(R)-4-(7-chloro-5-cyclopropyl-thiazolo[4,5-d]pyrimidin-2-yl)-1-(4-trifluoromethyl-benzenesulfonyl)-piperazine-2-carboxylic acid 4-trifluoromethoxy-benzylamide

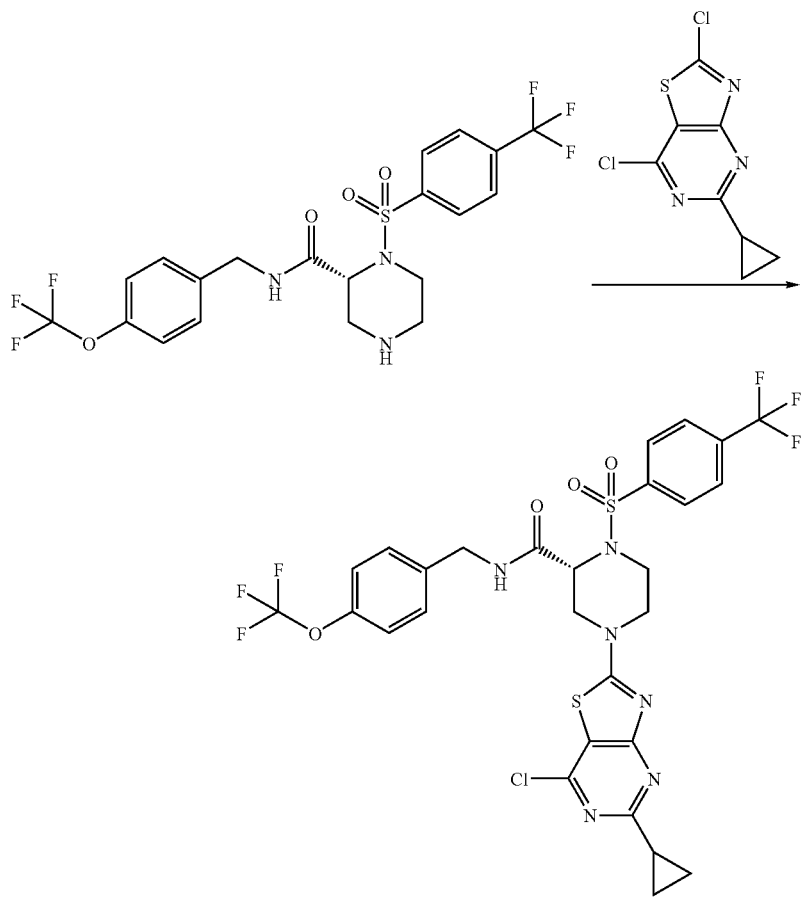

To a mixed solution of the compound (0.75 g) obtained in Step 2 and 2,7-dichloro-5-cyclopropyl-thiazolo[4,5-d]pyrimidine (0.36 g) in chloroform (7.5 ml) was added at room temperature N,N-diisopropylethylamine (0.31 ml). After stirring overnight at room temperature, the reaction mixture was concentrated under reduced pressure, and the residue was purified by silica gel column chromatography (ethyl acetate: n-hexane=2:3-3:2) to give the title compound (0.99 g).

$^1$H-NMR (CDCl$_3$, 300 MHz) δ: 1.03-1.10 (2H, m), 1.17-1.22 (2H, m), 2.17-2.27 (1H, m), 3.13-3.35 (2H, m), 3.42-3.53 (1H, m), 3.94 (1H, d, J=13.9 Hz), 4.23-4.38 (2H, m), 4.48 (1H, dd, J=15.1, 6.0 Hz), 4.54-4.68 (2H, m), 6.88 (1H, t,

J=5.8 Hz), 7.12 (2H, d, J=8.3 Hz), 7.21 (2H, d, J=8.3 Hz), 7.82 (2H, d, J=8.3 Hz), 8.01 (2H, d, J=7.9 Hz).

Step 4

(R)-4-(5-cyclopropyl-thiazolo[4,5-d]pyrimidin-2-yl)-1-(4-trifluoromethyl-benzenesulfonyl)-piperazine-2-carboxylic acid 4-trifluoromethoxy-benzylamide

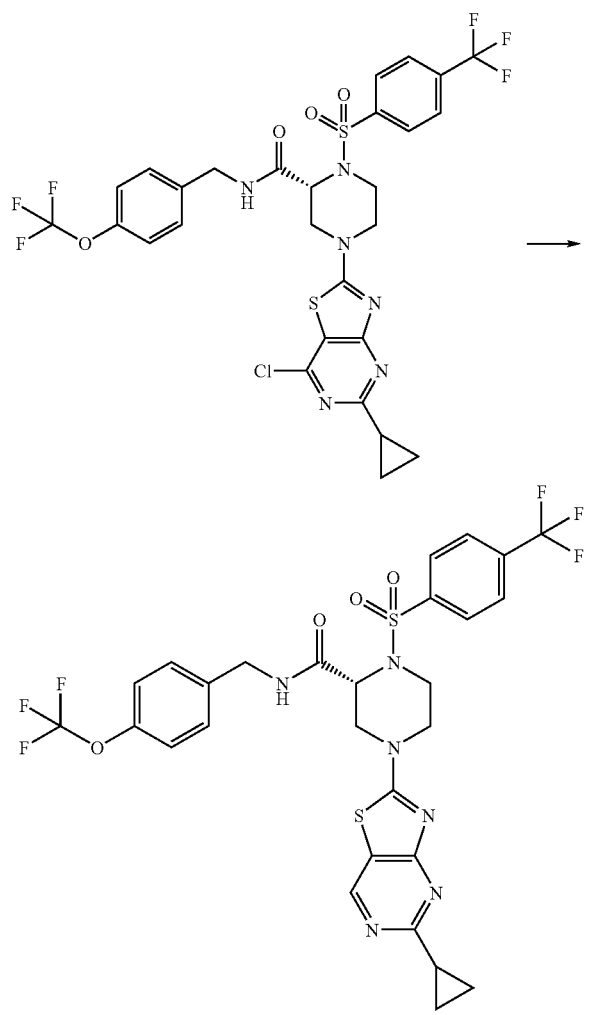

To a mixture of the compound (0.99 g) obtained in Step 3 and ammonium formate (0.86 g) in ethanol (10 ml) was added 10% palladium carbon (0.50 g) at 80° C. After stirring at 80° C. for 30 min, ammonium formate (0.43 g) and 10% palladium carbon (0.50 g) were added. After stirring at 80° C. for 30 min, ammonium formate (0.43 g) and 10% palladium carbon (0.50 g) were added. After stirring at 80° C. for 30 min, the reaction mixture was allowed to return to room temperature, and the reaction mixture was diluted with ethyl acetate. The mixture was filtered through celite, and the filtrate was concentrated under reduced pressure. The residue was purified by silica gel column chromatography (ethyl acetate:n-hexane=7:3-8:2) to give the title compound (0.71 g).

$^1$H-NMR (CDCl$_3$, 300 MHz) δ: 1.03-1.08 (2H, m), 1.17-1.21 (2H, m), 2.22-2.29 (1H, m), 3.21 (1H, t, J=10.9 Hz), 3.32 (1H, d, J=11.6 Hz), 3.46-3.53 (1H, m), 3.90-3.98 (1H, m), 4.22-4.52 (3H, m), 4.59-4.73 (2H, m), 7.00 (1H, t, J=5.9 Hz), 7.09 (2H, d, J=8.1 Hz), 7.19 (2H, d, J=8.1 Hz), 7.81 (2H, d, J=8.3 Hz), 8.01 (2H, d, J=8.3 Hz), 8.62 (1H, s).

Example 1061

Step 1

4-difluoromethoxy-3-fluoro-benzonitrile

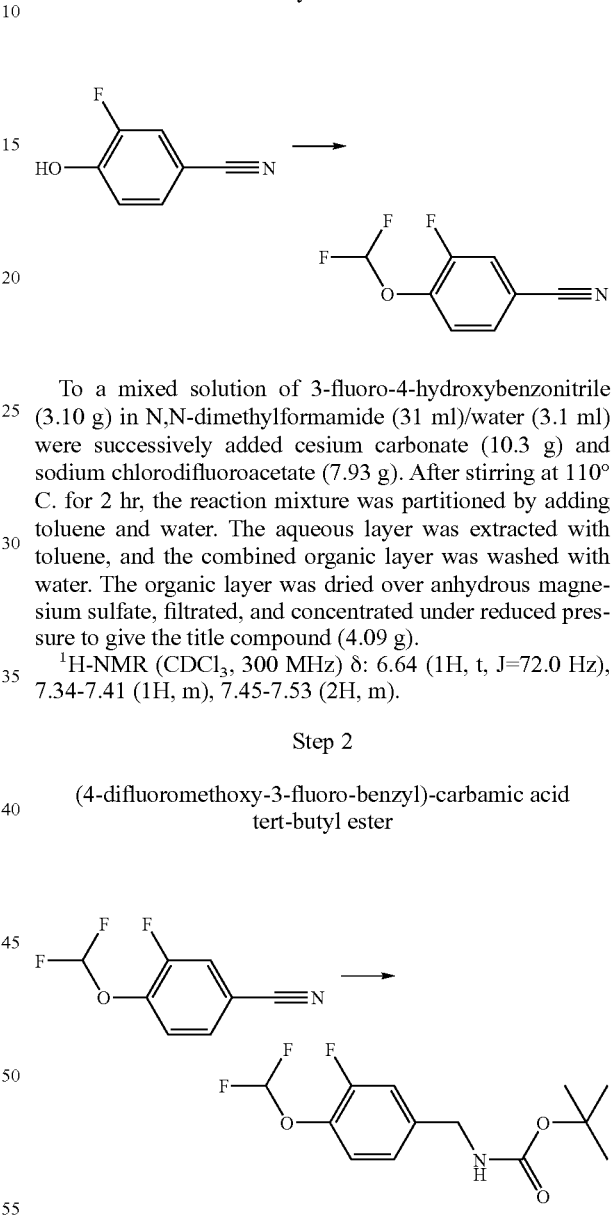

To a mixed solution of 3-fluoro-4-hydroxybenzonitrile (3.10 g) in N,N-dimethylformamide (31 ml)/water (3.1 ml) were successively added cesium carbonate (10.3 g) and sodium chlorodifluoroacetate (7.93 g). After stirring at 110° C. for 2 hr, the reaction mixture was partitioned by adding toluene and water. The aqueous layer was extracted with toluene, and the combined organic layer was washed with water. The organic layer was dried over anhydrous magnesium sulfate, filtrated, and concentrated under reduced pressure to give the title compound (4.09 g).

$^1$H-NMR (CDCl$_3$, 300 MHz) δ: 6.64 (1H, t, J=72.0 Hz), 7.34-7.41 (1H, m), 7.45-7.53 (2H, m).

Step 2

(4-difluoromethoxy-3-fluoro-benzyl)-carbamic acid tert-butyl ester

Under an argon atmosphere, to a solution of the compound (4.09 g) obtained in Step 1 in methanol (30 ml) were added a solution of di-tert-butyl dicarbonate (10.5 g) in methanol (10 ml) and nickel (II) chloride hexahydrate (520 mg). With stirring under ice-cooling, sodium borohydride (4.96 g) was added by small portions over about 30 min, and methanol (8 ml) was added. After stirring overnight at room temperature, diethylenetriamine (5.2 ml) and methanol (8 ml) were added. After stirring for 1 hr, the reaction mixture was concentrated. Ethyl acetate and aqueous sodium hydrogen carbonate solution were added to the residue and, after stirring at room temperature for 1 hr, the mixture was partitioned. The aqueous layer was extracted with ethyl acetate, and the combined organic layer was washed successively with saturated aqueous sodium hydrogen carbonate solution and saturated brine. The organic layer was dried over anhydrous magnesium sulfate, filtrated, and concentrated under reduced pressure. The residue was purified by silica gel column chromatography (ethyl acetate:n-hexane=10:1-4:1) to give the title compound (4.52 g).

$^1$H-NMR (CDCl$_3$, 400 MHz) δ: 1.46 (9H, s), 4.29 (2H, d, J=6.0 Hz), 4.89 (1H, br s), 6.52 (1H, t, J=73.6 Hz), 7.04 (1H, d, J=8.4 Hz), 7.11 (1H, dd, J=11.0, 2.0 Hz), 7.19 (1H, t, J=8.0 Hz).

Step 3

4-difluoromethoxy-3-fluoro-benzylamine

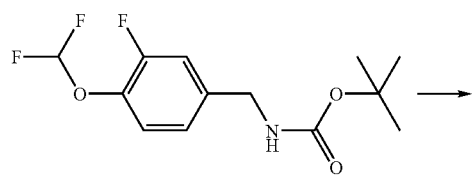

To a solution of the compound (4.52 g) obtained in Step 2 in 1,4-dioxane (5 ml) was added 4N hydrogen chloride/1,4-dioxane (15 ml) solution, and the mixture was stirred at room temperature for 1 hr. Diisopropyl ether (40 ml) was added to the reaction mixture, and the mixture was stirred at room temperature for 30 min. The precipitated solid was collected by filtration, washed with diisopropyl ether, and dried to give a white solid (2.80 g). With stirring under ice-cooling, the obtained white solid was suspended in ethyl acetate, and neutralized with aqueous sodium hydrogen carbonate solution. After partitioning, the organic layer was washed with saturated brine. The organic layer was dried over anhydrous magnesium sulfate, filtrated, and concentrated under reduced pressure to give the title compound (2.03 g).

$^1$H-NMR (CDCl$_3$, 300 MHz) δ: 3.87 (2H, s), 6.53 (1H, t, J=73.7 Hz), 7.07 (1H, d, J=8.3 Hz), 7.14-7.23 (2H, m).

Step 4

(R)-3-(4-difluoromethoxy-3-fluoro-benzylcarbamoyl)-4-(4-trifluoromethoxy-benzenesulfonyl)-piperazine-1-carboxylic acid ter-butyl ester To a solution of the compound (1.83 g) obtained in Example 783, Step 2 in N,N-dimethylformamide (10 ml) were successively added, with stirring under ice-cooling, 1-hydroxybenzotriazole hydrate (677 mg), 1-ethyl-3-(3-dimethylaminopropyl)carbodiimide hydrochloride (847 mg) and a solution of 4-difluoromethoxy-3-fluorobenzylamine (806 mg) in N,N-dimethylformamide (3 ml). After stirring overnight at room temperature, the mixture was partitioned by adding ethyl acetate and saturated aqueous sodium hydrogen carbonate solution. The aqueous layer was extracted with ethyl acetate, the combined organic layer was washed successively with saturated aqueous sodium hydrogen carbonate solution and water. The organic layer was dried over anhydrous magnesium sulfate, filtrated, and concentrated under reduced pressure to give the title compound (2.76 g).

Step 5

(R)-1-(4-trifluoromethoxy-benzenesulfonyl)-piperazine-2-carboxylic acid 4-difluoromethoxy-3-fluoro-benzylamide

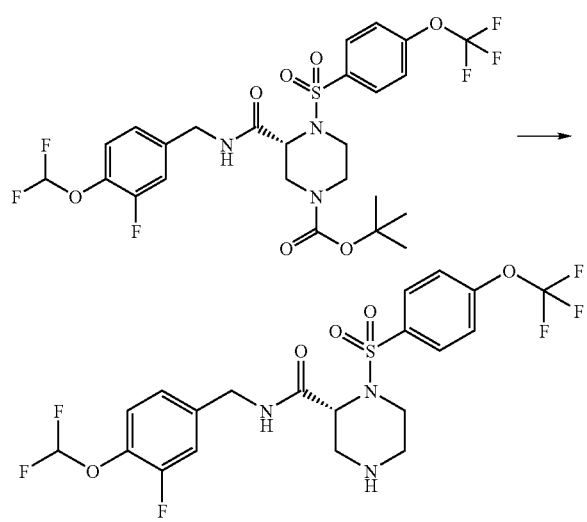

To a solution of the compound (2.76 g) obtained in Step 4 in ethyl acetate (4 ml) was added 4N hydrogen chloride/ethyl acetate solution (20 ml), and the mixture was stirred at room temperature for 2.5 hr. The reaction mixture was concentrated under reduced pressure, and the residue was partitioned by adding ethyl acetate and saturated aqueous sodium hydrogen carbonate solution. The aqueous layer was extracted with ethyl acetate, and the combined organic layer was washed with saturated brine. The organic layer was dried over anhydrous magnesium sulfate, filtrated, and concentrated under reduced pressure to give a crude product (1.94 g) containing the title compound as a main component.

$^1$H-NMR (CDCl$_3$, 400 MHz) δ: 2.46-2.59 (2H, m), 2.86 (1H, d, J=13.0 Hz), 3.13-3.21 (1H, m), 3.53 (1H, d, J=13.0 Hz), 3.76 (1H, d, J=13.9 Hz), 4.32-4.50 (3H, m), 6.54 (1H, t, J=73.4 Hz), 7.01 (1H, d, J=8.4 Hz), 7.08 (1H, dd, J=10.9, 2.1 Hz), 7.19 (1H, t, J=8.2 Hz), 7.28 (1H, br s), 7.36 (2H, d, J=8.2 Hz), 7.91 (2H, dt, J=9.3, 2.4 Hz).

Step 6

(R)-4-(7-chloro-5-trifluoromethyl-thiazolo[4,5-d]pyrimidin-2-yl)-1-(4-trifluoromethoxy-benzenesulfonyl)-piperazine-2-carboxylic acid 4-difluoromethoxy-3-fluoro-benzylamide

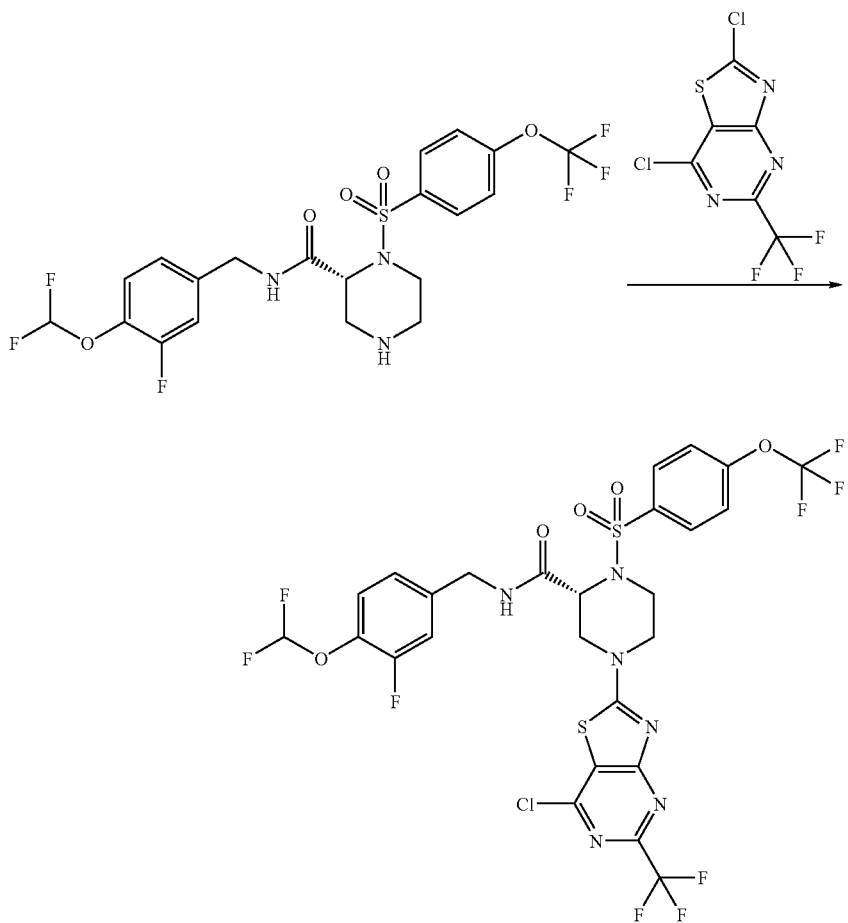

To a solution of the compound (796 mg) obtained in Step 5 in chloroform (8 ml) were successively added, with stirring under ice-cooling, N,N-diisopropylethylamine (234 mg) and 2,7-dichloro-5-trifluoromethyl-thiazolo[4,5-d]pyrimidine (414 mg). After stirring at room temperature for 1 hr, the mixture was partitioned by adding chloroform and water. The aqueous layer was extracted with chloroform, and the organic layer was dried over anhydrous magnesium sulfate, filtrated, and concentrated under reduced pressure. The residue was purified by silica gel column chromatography (ethyl acetate: n-hexane=6:1-1:2) to give the title compound (912 mg).

Step 7

(R)-1-(4-trifluoromethoxy-benzenesulfonyl)-4-(5-trifluoromethyl-thiazolo[4,5-d]pyrimidin-2-yl)-piperazine-2-carboxylic acid 4-difluoromethoxy-3-fluoro-benzylamide

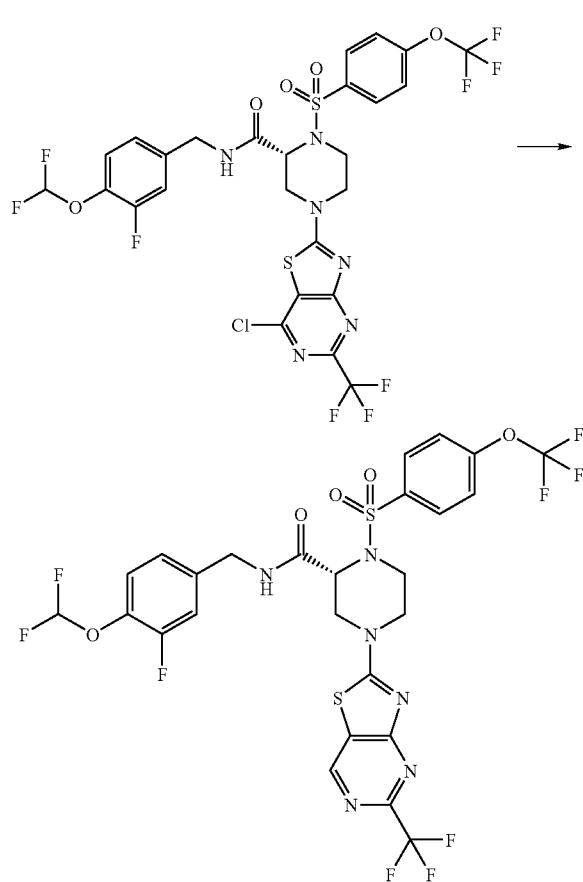

Under an argon atmosphere, to a solution of the compound (912 mg) obtained in Step 6 and ammonium formate (750 mg) in ethanol (18 ml) was added 10% palladium carbon (912 mg). After stirring under refluxing conditions for 1 hr, the catalyst was filtered off. The filtrate was concentrated under reduced pressure, and the residue was partitioned by adding ethyl acetate and water. The organic layer was washed with water, dried over anhydrous magnesium sulfate, filtrated, and concentrated under reduced pressure. The residue was purified by silica gel column chromatography (ethyl acetate:n-hexane=10:1-1:2) to give the title compound (625 mg).

$^1$H-NMR (CDCl$_3$, 400 MHz) δ: 3.16-3.42 (2H, m), 3.47 (1H, t, J=12.4 Hz), 3.97 (1H, d, J=14.3 Hz), 4.22-4.77 (2H, br m), 4.28 (1H, dd, J=15.1, 5.4 Hz), 4.48 (1H, dd, J=15.1, 6.7 Hz), 4.68 (1H, d, J=2.4 Hz), 6.51 (1H, t, J=73.3 Hz), 6.93-7.00 (3H, m), 7.13 (1H, t, J=8.0 Hz), 7.39 (2H, d, J=8.2 Hz), 7.95 (2H, dt, J=9.4, 2.4 Hz), 8.88 (1H, s).

Example 1101

Step 1

(3-fluoro-4-trifluoromethoxy-phenyl)-methanol

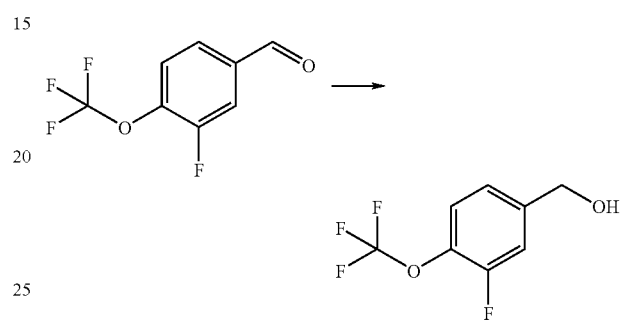

To a solution of 3-fluoro-4-trifluoromethoxybenzaldehyde (3.00 g) in THF (15 ml) was added, with stirring under ice-cooling, sodium borohydride (655 mg). After stirring at room temperature for 1 hr, the mixture was partitioned by adding ethyl acetate and saturated aqueous ammonium chloride solution. The organic layer was washed successively with saturated aqueous sodium hydrogen carbonate solution, water and saturated brine, dried over anhydrous sodium sulfate, filtrated, and concentrated under reduced pressure to give a crude product (2.99 g) containing the title compound as a main component.

$^1$H-NMR (CDCl$_3$, 300 MHz) δ: 1.80 (1H, t, J=5.8 Hz), 4.71 (2H, d, J=5.3 Hz), 7.14 (1H, d, J=8.3 Hz), 7.23-7.32 (2H, m).

Step 2

2-(3-fluoro-4-trifluoromethoxy-benzyl)-isoindole-1,3-dione

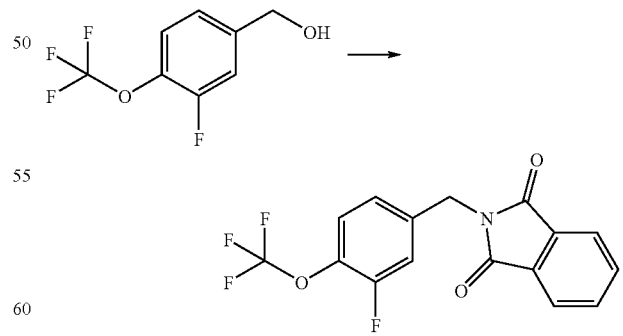

To a solution of the compound (2.95 g) obtained in Step 1 in THF (30 ml) were added phthalimide (3.10 g) and triphenylphosphine (5.52 g) with stirring at room temperature, and the mixture was stirred under ice-cooling. With stirring under ice-cooling, diisopropyl azodicarboxylate (4.15 ml) was added, and the mixture was stirred overnight at room temperature. The reaction mixture was concentrated under reduced pressure, and the residue was purified by silica gel column chromatography (ethyl acetate:n-hexane=2:8-3:7) to give the title compound (4.30 g).

¹H-NMR (CDCl₃, 300 MHz) δ: 4.83 (2H, s), 7.21-7.31 (3H, m), 7.71-7.77 (2H, m), 7.84-7.90 (2H, m).

Step 3

3-fluoro-4-trifluoromethoxy-benzylamine

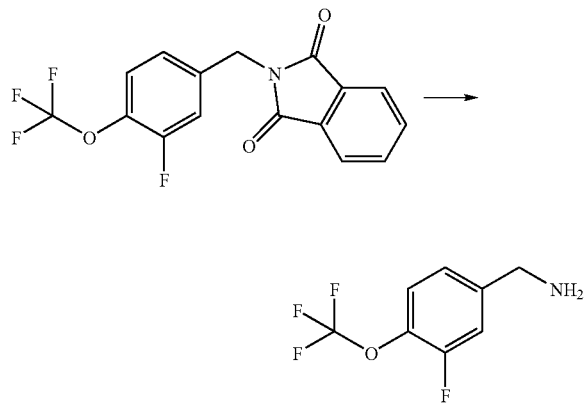

To a suspension of the compound (4.30 g) obtained in Step 2 in ethanol (65 ml) was added hydrazine monohydrate (1.84 ml) at room temperature. With heating under reflux, the mixture was stirred for 1 hr. The insoluble material was filtered off, and the filtrate was concentrated under reduced pressure to give a crude product (1.28 g) containing the title compound as a main component.

¹H-NMR (CDCl₃, 300 MHz) δ: 1.48 (2H, br s), 3.89 (2H, s), 7.11 (1H, d, J=8.3 Hz), 7.19-7.29 (2H, m).

Step 4

(R)-3-(3-fluoro-4-trifluoromethoxy-benzylcarbamoyl)-4-(4-trifluoromethyl-benzenesulfonyl)-piperazine-1-carboxylic acid tert-butyl ester

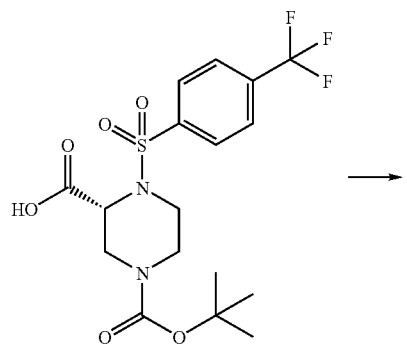

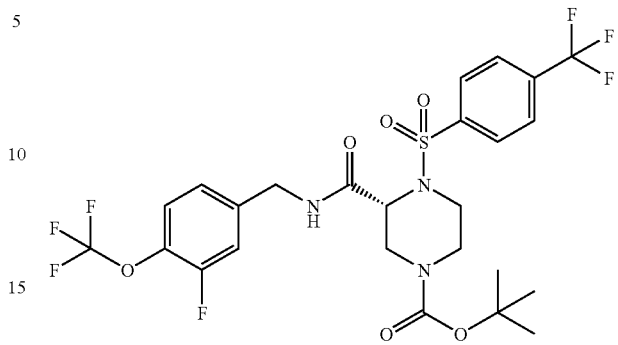

To a solution of the compound (1.24 g) obtained in Example 1001, Step 1 in N,N-dimethylformamide (12 ml) were added, with stirring under ice-cooling, 1-ethyl-3-(3-dimethylaminopropyl) carbodiimide hydrochloride (0.65 g), 1-hydroxybenzotriazole hydrate (0.52 g) and the compound (0.59 g) obtained in Step 3. After stirring overnight at room temperature, the reaction mixture was partitioned by adding saturated aqueous sodium hydrogen carbonate solution and ethyl acetate. The organic layer was washed successively with water and saturated brine, dried over anhydrous sodium sulfate, filtered, and concentrated under reduced pressure. The residue was purified by silica gel column chromatography (methanol:chloroform=4:96-6:94) to give the title compound (1.70 g).

¹H-NMR (CDCl₃, 300 MHz) δ: 1.38 (9H, s), 2.63-3.12 (3H, m), 3.20-3.37 (1H, m), 3.64-3.79 (1H, m), 3.87 (1H, d, J=13.6 Hz), 4.32-4.62 (3H, m), 6.93 (1H, t, J=6.6 Hz), 7.02-7.13 (2H, m), 7.24-7.29 (1H, m), 7.81 (2H, d, J=8.3 Hz), 8.00 (2H, d, J=8.7 Hz).

Step 5

(R)-1-(4-trifluoromethyl-benzenesulfonyl)-piperazine-2-carboxylic acid 3-fluoro-4-trifluoromethoxy-benzylamide hydrochloride

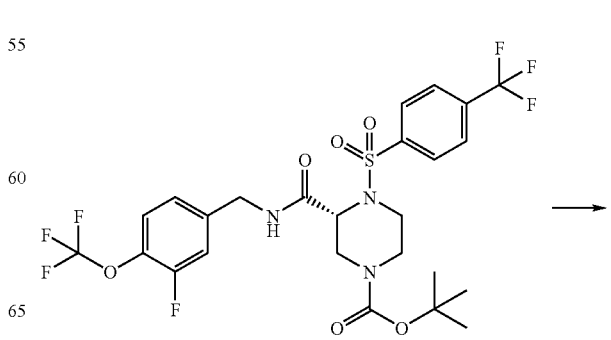

239
-continued

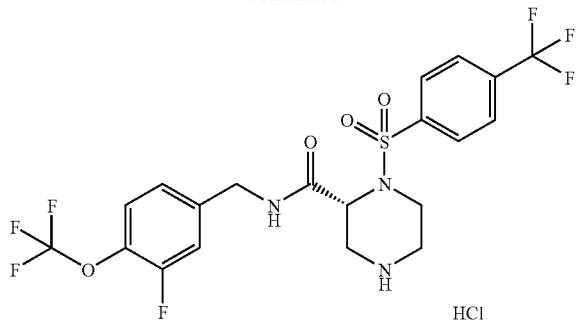

To a solution of the compound (60 mg) obtained in Step 4 in 1,4-dioxane (0.6 ml) was added 4N hydrogen chloride/1,

240

4-dioxane solution (0.6 ml) with stirring at room temperature. After stirring at room temperature for 2 days, the reaction mixture was concentrated under reduced pressure. Toluene was added to the residue, and the mixture was concentrated again under reduced pressure to give a crude product (about 0.095 mmol) containing the title compound as a main component. The obtained crude product was directly used for the next reaction.

Step 6

(R)-4-(7-chloro-5-cyclopropyl-thiazolo[4,5-d]pyrimidin-2-yl)-1-(4-trifluoromethyl-benzenesulfonyl)-piperazine-2-carboxylic acid 3-fluoro-4-trifluoromethoxy-benzylamide

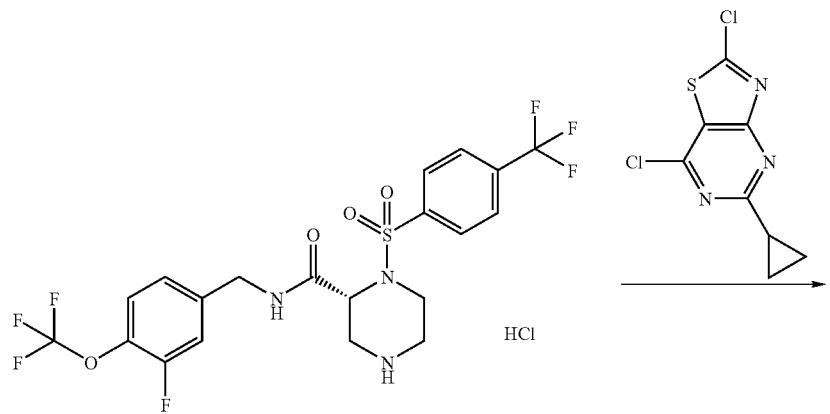

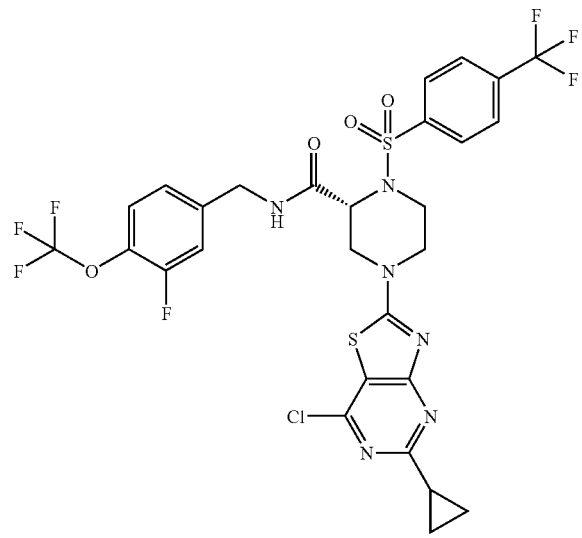

To a mixture of the crude product (about 0.095 mmol) obtained in Step 5 and 2,7-dichloro-5-cyclopropyl-thiazolo[4,5-d]pyrimidine (24 mg) in chloroform (1.0 ml) was added N,N-diisopropylethylamine (42 μl) at room temperature. After stirring at room temperature for 2 hr, the reaction mixture was concentrated under reduced pressure, and the residue was purified by thin layer silica gel chromatography (methanol:chloroform=1:10) to give the title compound (52 mg). $^1$H-NMR (CDCl$_3$, 300 MHz) δ: 1.03-1.09 (2H, m), 1.17-1.22 (2H, m), 2.18-2.27 (1H, m), 3.14-3.35 (2H, m), 3.43-3.53 (1H, m), 3.96 (1H, d, J=13.6 Hz), 4.22-4.36 (2H, m), 4.45-4.69 (3H, m), 6.97-7.06 (3H, m), 7.20 (1H, t, J=8.5 Hz), 7.83 (2H, d, J=8.3 Hz), 8.02 (2H, d, J=8.3 Hz).

Step 7

(R)-4-(5-cyclopropyl-thiazolo[4,5-d]pyrimidin-2-yl)-1-(4-trifluoromethyl-benzenesulfonyl)-piperazine-2-carboxylic acid 3-fluoro-4-trifluoromethoxy-benzylamide To a mixture of the compound (49 mg) obtained in Step 6 and ammonium formate (42 mg) in ethanol (1.0 ml) was added 10% palladium carbon (25 mg) at 80° C. After stirring at 80° C. for 30 min, 10% palladium carbon (25 mg) was added. After stirring at 80° C. for 30 min, ammonium formate (42 mg) and 10% palladium carbon (25 mg) were added. After stirring at 80° C. for 30 min, 10% palladium carbon (25 mg) was added. After stirring at 80° C. for 30 min, the reaction mixture was allowed to return to room temperature, and the reaction mixture was diluted with ethyl acetate. The mixture was filtered through celite, and the filtrate was concentrated under reduced pressure. The residue was purified by thin layer silica gel chromatography (methanol:chloroform=1:10) to give the title compound (29 mg).

$^1$H-NMR (CDCl$_3$, 300 MHz) δ: 1.02-1.08 (2H, m), 1.15-1.20 (2H, m), 2.20-2.29 (1H, m), 3.16-3.27 (1H, m), 3.29-3.37 (1H, m), 3.44-3.54 (1H, m), 3.95 (1H, d, J=13.9 Hz), 4.20-4.33 (2H, m), 4.50 (1H, dd, J=15.3, 6.6 Hz), 4.59-4.71 (2H, m), 6.94-7.04 (2H, m), 7.08 (1H, t, J=5.8 Hz), 7.16 (1H, t, J=7.5 Hz), 7.82 (2H, d, J=8.7 Hz), 8.02 (2H, d, J=8.3 Hz), 8.61 (1H, s).

Example 1102

Step 1

(R)-3-(3-fluoro-4-trifluoromethoxy-benzylcarbamoyl)-4-(4-trifluoromethoxy-benzenesulfonyl)-piperazine-1-carboxylic acid tert-butyl ester

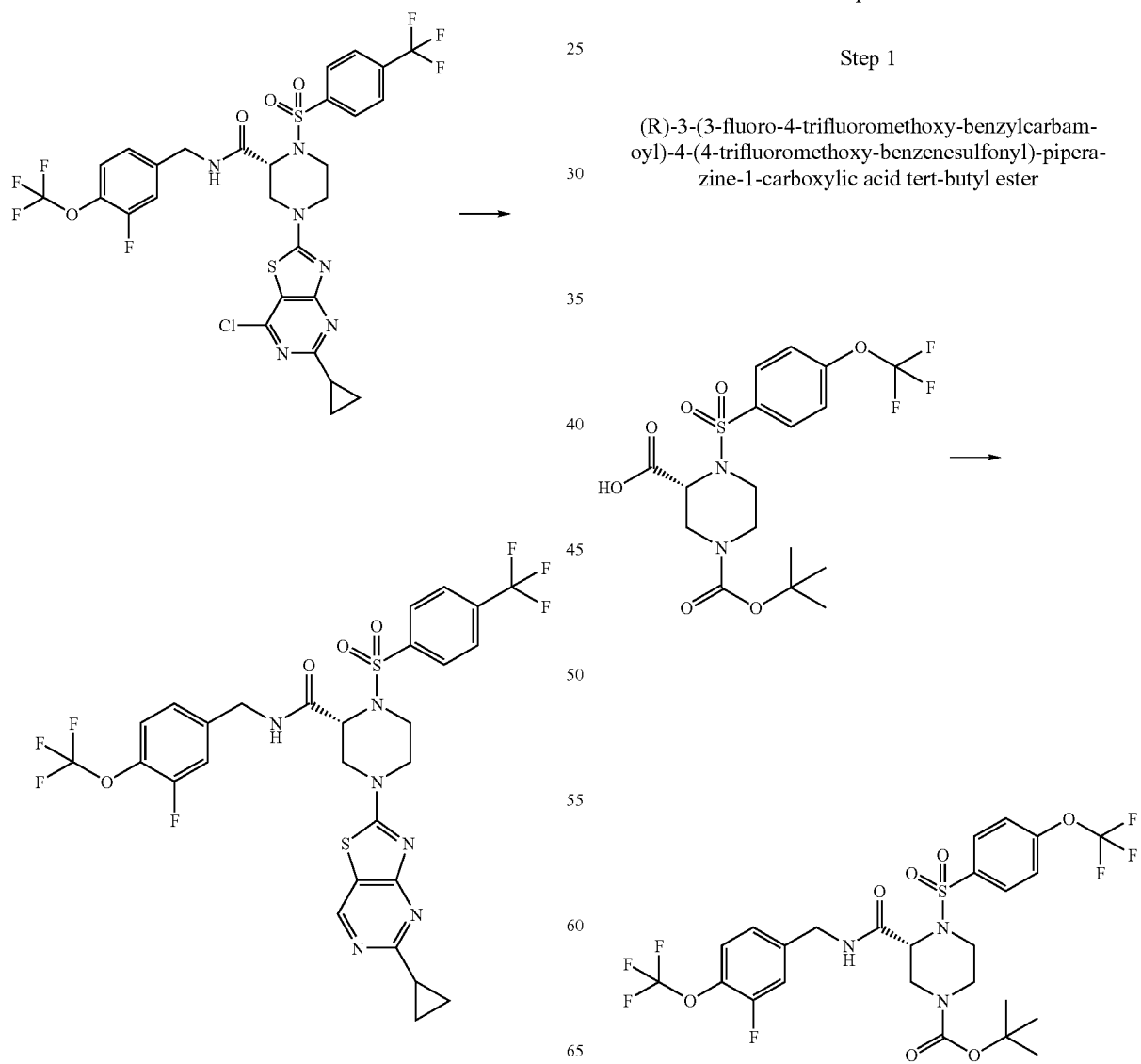

To a solution of the compound (1.35 g) obtained in Example 783, Step 2 in chloroform (15 ml) were added 1-ethyl-3-(3-dimethylaminopropyl) carbodiimide hydrochloride (625 mg), 1-hydroxybenzotriazole hydrate (499 mg) and 3-fluoro-4-trifluoromethoxybenzylamine (620 mg) with stirring under ice-cooling. After stirring overnight at room temperature, the reaction mixture was partitioned by adding saturated aqueous sodium hydrogen carbonate solution and chloroform, and the aqueous layer was re-extracted twice with chloroform. The organic layers were combined, dried over anhydrous magnesium sulfate, filtrated, and concentrated under reduced pressure. The residue was purified by silica gel column chromatography (hexane:ethyl acetate=1:1) to give the title compound (1.50 g).

Step 2

(R)-1-(4-trifluoromethoxy-benzenesulfonyl)-piperazine-2-carboxylic acid 3-fluoro-4-trifluoromethoxy-benzylamide

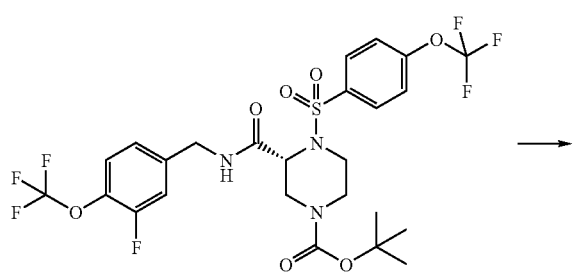

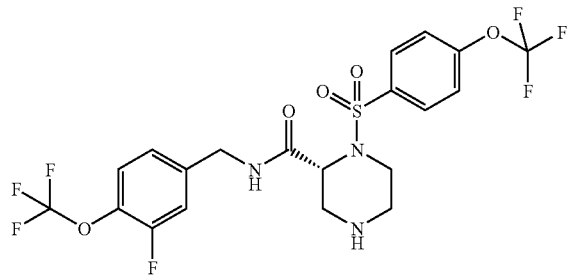

After stirring the compound (1.50 g) obtained in Step 1 in 4N hydrogen chloride/1,4-dioxane solution (20 ml) at room temperature for 2 days, the reaction mixture was concentrated under reduced pressure. The residue was partitioned by adding chloroform and saturated aqueous sodium hydrogen carbonate solution and the aqueous layer was re-extracted twice with chloroform. The organic layers were combined, dried over anhydrous magnesium sulfate, filtrated, and concentrated under reduced pressure to give a crude product (1.36 g) containing the title compound as a main component. A part thereof was used for the next reaction.

$^1$H-NMR (CDCl$_3$, 400 MHz) δ: 2.46-2.58 (2H, m), 2.87 (1H, d, J=11.6 Hz), 3.12-3.22 (1H, m), 3.54 (1H, d, J=12.8 Hz), 3.74-3.81 (1H, m), 4.34-4.52 (3H, m), 7.01-7.14 (2H, m), 7.29-7.40 (3H, m), 7.92 (2H, dt, J=9.4, 2.5 Hz).

Step 3

(R)-4-(7-chloro-5-cyclopropyl-thiazolo[4,5-d]pyrimidin-2-yl)-1-(4-trifluoromethoxy-benzenesulfonyl)-piperazine-2-carboxylic acid 3-fluoro-4-trifluoromethoxy-benzylamide

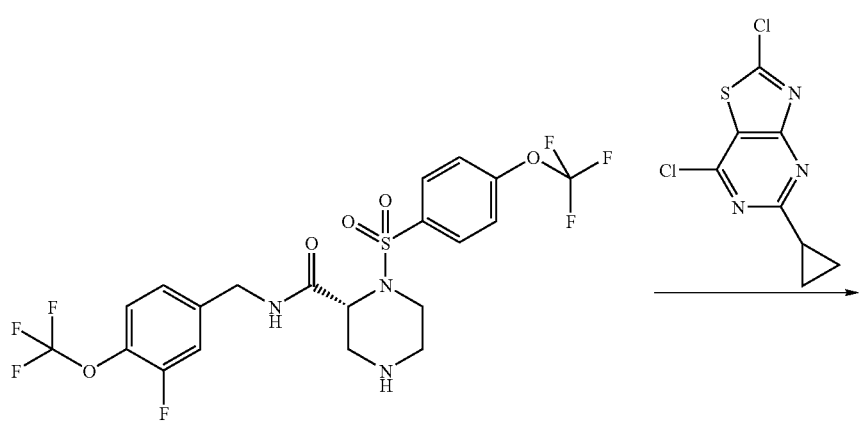

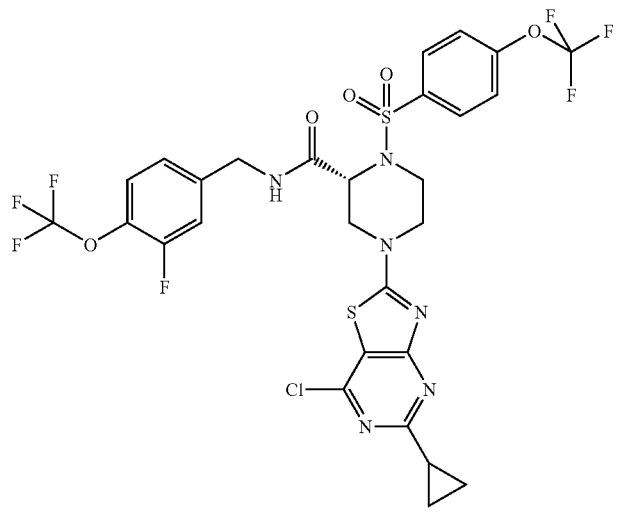

To a solution of the crude product (38 mg) obtained in Step 2 and 2,7-dichloro-5-cyclopropyl-thiazolo[4,5-d]pyrimidine (18 mg) in chloroform (1.0 ml) was added at room temperature N,N-diisopropylethylamine (15 μl). After stirring at room temperature for 2 hr, the reaction mixture was concentrated under reduced pressure to give a crude product (about 0.070 mmol) containing the title compound as a main component. The crude product was directly used for the next reaction.

Step 4

(R)-4-(5-cyclopropyl-thiazolo[4,5-d]pyrimidin-2-yl)-1-(4-trifluoromethoxy-benzenesulfonyl)-piperazine-2-carboxylic acid 3-fluoro-4-trifluoromethoxy-benzylamide

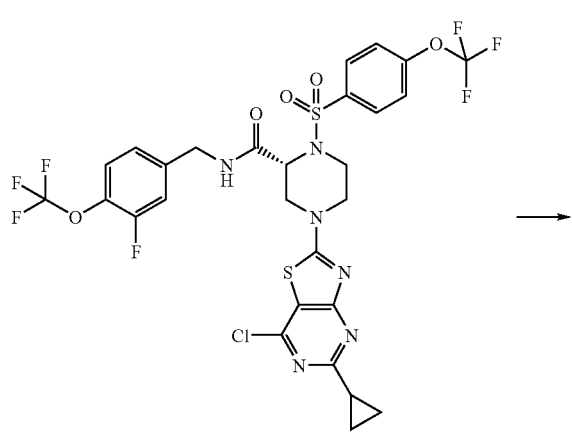

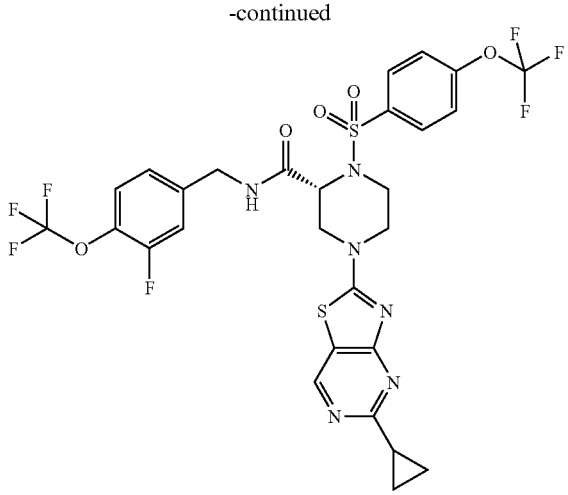

To a solution of the compound (about 0.070 mmol) obtained in Step 3 and a large excess of ammonium formate in ethanol (2.0 ml) was added, with heating under reflux, 10% palladium carbon (25 mg). Thereafter, 10% palladium carbon (25 mg) was added twice every 10 min with heating under reflux. The mixture was heated under reflux for 30 min in total, and the reaction mixture was allowed to return to room temperature, and diluted with chloroform. The mixture was filtered through celite, and the filtrate was concentrated under reduced pressure. The residue was partitioned by adding chloroform and water, and the organic layer was dried over anhydrous magnesium sulfate, filtrated, and concentrated under reduced pressure. The residue was purified by thin layer silica gel chromatography (methanol:chloroform=1:20) to give the title compound (21 mg).

$^1$H-NMR (CDCl$_3$, 400 MHz) δ: 1.01-1.08 (2H, m), 1.15-1.21 (2H, m), 2.25 (1H, tt, J=8.1, 3.9 Hz), 3.15-3.37 (2H, m), 3.43-3.53 (1H, m), 3.92 (1H, dt, J=14.1, 3.1 Hz), 4.21-4.69

(5H, m), 6.96 (1H, d, J=8.3 Hz), 7.03 (1H, dd, J=10.3, 2.0 Hz), 7.08-7.21 (2H, m), 7.37 (2H, d, J=8.1 Hz), 7.94 (2H, dt, J=9.5, 2.4 Hz), 8.62 (1H, s).

Example 574

Step 1

(R)-1-(4-trifluoromethoxy-benzenesulfonyl)-piperazine-2-carboxylic acid 4-propyl-benzylamide

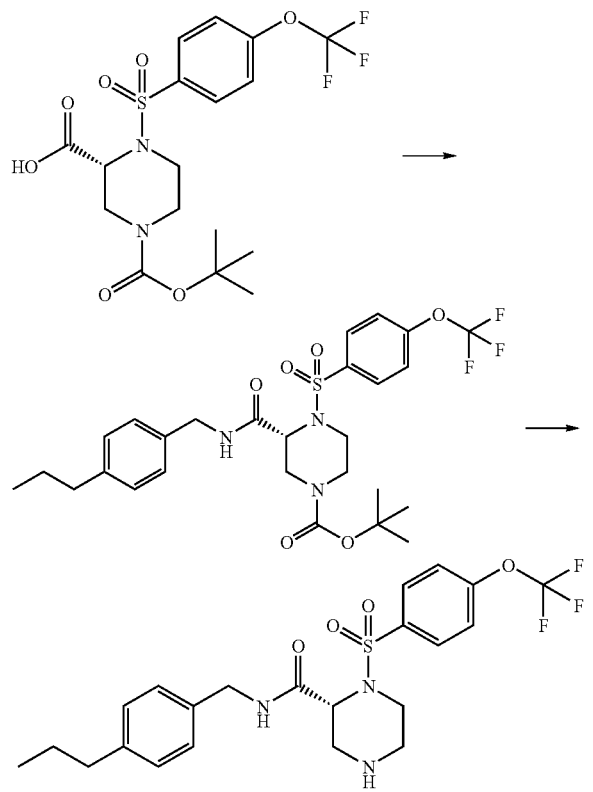

To a solution of the compound (6.65 g) obtained in Example 783, Step 2,4-propylbenzylamine (3.26 g) and 1-hydroxybenzotriazole hydrate (2.69 g) in N,N-dimethylformamide (33 ml) was added, with stirring under ice-cooling, 1-ethyl-3-(3-dimethylaminopropyl) carbodiimide hydrochloride (3.37 g). After stirring overnight at room temperature, saturated aqueous sodium hydrogen carbonate solution and water were added under ice-cooling, and the mixture was stirred at room temperature. The precipitated solid was collected by filtration, washed with water, and dried under reduced pressure to give a crude product (7.40 g). This was purified by silica gel column chromatography (ethyl acetate: n-hexane=1:2) to give a crude product containing (R)-3-(4-propyl-benzylcarbamoyl)-4-(4-trifluoromethoxy-benzenesulfonyl)-piperazine-1-carboxylic acid tert-butyl ester as a main component. The obtained crude product was dissolved in 1,4-dioxane (40 ml), 4N hydrogen chloride/1,4-dioxane solution (50 ml) was added at room temperature, and the mixture was stirred at room temperature for 2 hr. Further, 4N hydrogen chloride/1,4-dioxane solution (20 ml) was added, and the mixture was stirred at room temperature for 1 hr. The reaction mixture was concentrated under reduced pressure, and the residue was partitioned by adding saturated aqueous sodium hydrogen carbonate solution and ethyl acetate. The organic layer was washed with saturated brine, dried over anhydrous sodium carbonate, filtrated, and concentrated under reduced pressure to give a crude product (3.70 g) containing the title compound as a main component. The residue was crystallized from a mixed solvent of diisopropyl ether and n-hexane, and collected by filtration. The obtained crude crystals were suspended in diisopropyl ether, collected by filtration and dried to give the title compound (3.0 g).

$^1$H-NMR (CDCl$_3$, 300 MHz) δ: 0.94 (3H, t, J=7.3 Hz), 1.58-1.71 (2H, m), 2.48-2.63 (4H, m), 2.86 (1H, d, J=12.1 Hz), 3.11-3.24 (1H, m), 3.53 (1H, d, J=13.2 Hz), 3.74 (1H, d, J=12.4 Hz), 4.34 (1H, d, J=4.1 Hz), 4.40 (2H, d, J=5.7 Hz), 6.97-7.05 (1H, br m), 7.14 (4H, s), 7.33 (2H, d, J=8.3 Hz), 7.89 (2H, d, J=8.7 Hz).

Step 2 puteridin-7-ol

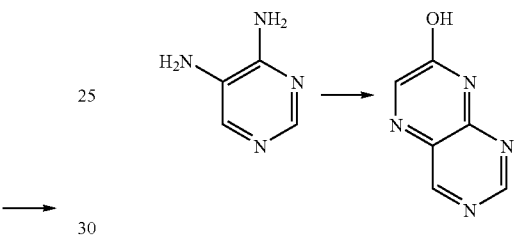

To a mixed solution of pyrimidine-4,5-diamine (4.4 g), sodium acetate (6.1 g), water (40 ml) and 5N aqueous acetic acid solution (10 ml) was added methyl 2-hydroxy-2-methoxyacetate (7.2 g) at 90° C. and the mixture was stirred under heating at the same temperature for 1 hr. The reaction mixture was cooled to room temperature, and adjusted to pH 2 with 5N aqueous sulfuric acid solution (9.0 ml). The precipitated solid was collected by filtration, washed with water and dried to give the title compound (4.7 g).

$^1$H-NMR (DMSO-d$_6$, 300 MHz) δ: 8.26 (1H, s), 8.99 (1H, s), 9.13 (1H, s), 13.20 (1H, br s).

Step 3

7-chloro-puteridine

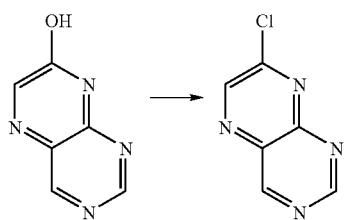

A mixed solution of the compound (0.50 g) obtained in Step 2 and pentachloroethane (27.5 ml) was heated under reflux. Phosphorus pentachloride (8.7 g) was added, and the mixture was heated under reflux for 15 min. The reaction mixture was cooled to room temperature, and the precipitated solid was collected by filtration, and dried to give the title compound (0.42 g).

$^1$H-NMR (DMSO-d$_6$, 300 MHz) δ: 9.28 (1H, s), 9.61 (1H, s), 9.88 (1H, s).

Step 4

(R)-4-pteridin-7-yl-1-(4-trifluoromethoxy-benzene-sulfonyl)-piperazine-2-carboxylic acid 4-propyl-benzylamide

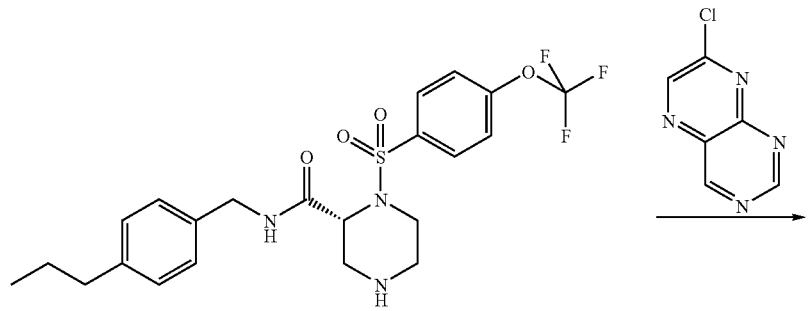

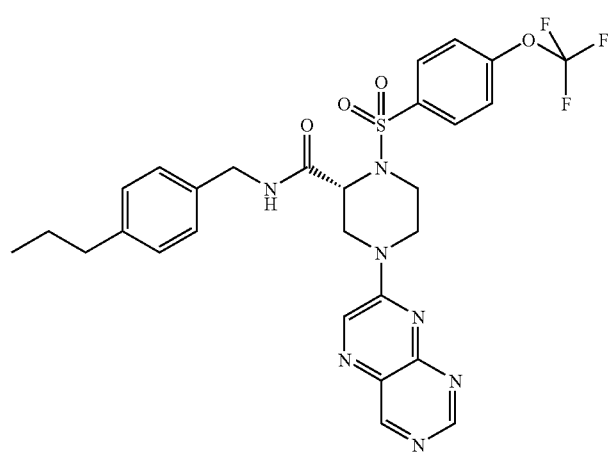

To a mixed solution of the compound (0.050 g) obtained in Step 1, the compound (0.034 g) obtained in Step 3 and isopropanol (1.0 ml) was added triethylamine (0.016 ml) at room temperature and the mixture was heated under reflux for 3.5 hr. The reaction mixture was cooled to room temperature, and concentrated under reduced pressure. Ethyl acetate was added to the obtained residue, water was poured, and the mixture was partitioned. The organic layer was washed successively with saturated aqueous sodium hydrogen carbonate solution and saturated brine, dried over anhydrous sodium sulfate, filtrated, and concentrated under reduced pressure. The residue was purified by thin layer silica gel chromatography (methanol:ethyl acetate=1:20) and the obtained residue was suspended in a mixed solvent of hexane and diisopropyl ether, collected by filtration and dried to give the title compound (0.026 g).

$^1$H-NMR (CDCl$_3$, 300 MHz) δ: 0.91 (3H, t, J=7.3 Hz), 1.51-1.65 (2H, m), 2.50 (2H, t, J=7.7 Hz), 2.92-3.07 (1H, m), 3.20 (1H, dd, J=13.6, 3.4 Hz), 3.36-3.50 (1H, m), 3.90-4.00 (1H, m), 4.25-4.38 (2H, m), 4.66 (1H, s), 4.77-4.90 (1H, m), 5.08 (1H, d, J=13.6 Hz), 6.82 (1H, t, J=5.3 Hz), 6.97 (2H, d, J=8.3 Hz), 7.00 (2H, d, J=8.3 Hz), 7.37 (2H, d, J=8.3 Hz), 7.95 (2H, d, J=8.3 Hz), 8.79 (1H, s), 9.22 (1H, s), 9.26 (1H, s).

Example 805

Step 1

2-bromo-4-methoxy-3-oxo-butyric acid methyl ester

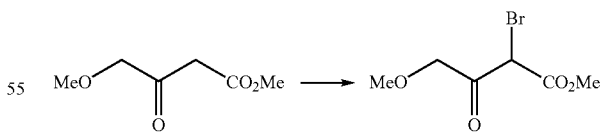

Copper (II) bromide (7.37 g) was suspended in acetonitrile (39 ml), and 4-methoxy-3-oxobutyric acid methyl ester (3.88 ml, 30 mmol) and hydroxy(tosyloxy)iodobenzene (11.8 g) were added with stirring under ice-cooling. The reaction mixture was directly stirred for 3 hr, and water and chloroform were added. The reaction mixture was partitioned, and the aqueous layer was re-extracted twice with chloroform. The organic layers were combined, dried over anhydrous magnesium sulfate, filtrated, and concentrated under reduced pressure to give a crude product (about 30 mmol) containing the title compound as a main component. The obtained crude product was directly used for the next reaction.

Step 2

2-amino-4-methoxymethylthiazole-5-carboxylic acid methyl ester

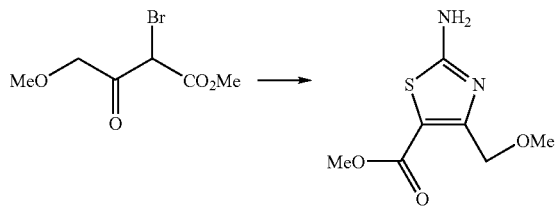

A solution of the crude product (about 30 mmol) obtained in Step 1 and thiourea (2.28 g) in ethanol (60 ml) was heated under reflux overnight. After cooling to room temperature, the reaction mixture was partitioned by adding ethyl acetate and water. The organic layer was washed successively with water and saturated brine, dried over anhydrous magnesium sulfate, filtrated, and concentrated under reduced pressure. Then, suitable amounts of isopropanol, chloroform, ethyl acetate and diisopropyl ether were added, and the mixture was stirred at room temperature for 30 min. The precipitated crystals were collected by filtration and dried to give the title compound (3.27 g).

$^1$H-NMR (CDCl$_3$, 400 MHz) δ: 3.47 (3H, s), 3.81 (3H, s), 4.74 (2H, s), 5.45 (2H, br s).

Step 3

2-amino-4-hydroxymethylthiazole-5-carboxylic acid methyl ester

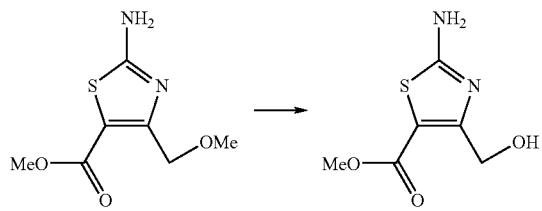

The compound (4.68 g) obtained in Step 2 was suspended in dichloromethane (160 ml), and boron tribromide (1.0M dichloromethane solution, 35 ml) was added dropwise with stirring under ice-cooling. The reaction mixture was stirred under ice-cooling for 90 min, 4N aqueous sodium hydroxide solution (26 ml) was added dropwise with stirring under ice-cooling, and the mixture was stirred at room temperature for 30 min. The precipitated solid was collected by filtration, washed with water and acetone, and dried to give the title compound (3.15 g).

$^1$H-NMR (CD$_3$OD, 400 MHz) δ: 3.78 (3H, s), 4.73 (2H, s).

Step 4

2-amino-4-formylthiazole-5-carboxylic acid methyl ester

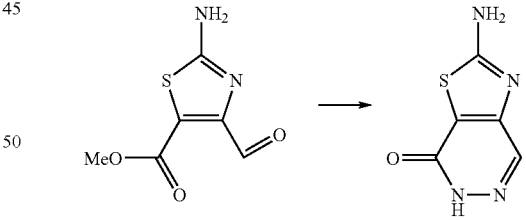

To a solution of the compound (1.35 g) obtained in Step 3 in 1,4-dioxane (68 ml)/N,N-dimethylformamide (13 ml) was added manganese dioxide (3.68 g) at room temperature and the mixture was stirred at room temperature for 40 hr. The insoluble material was filtered off, and the filtrate was concentrated under reduced pressure to give the title compound (1.20 g).

$^1$H-NMR (DMSO-d$_6$, 400 MHz) δ: 3.81 (3H, s), 8.05 (2H, br s), 10.28 (1H, s)

Step 5

2-amino-6H-thiazolo[4,5-d]pyridazin-7-one

To a solution of the compound (1.20 g) obtained in Step 4 in ethanol (120 ml) was added hydrazine monohydrate (374 μl), and the mixture was heated under reflux for 24 hr. Since the reaction was not completed, acetic acid (1.0 ml) was added, and the mixture was further heated under reflux for 20 hr. The reaction mixture was concentrated under reduced pressure to an amount of 5 ml, a small amount of ethanol was added, and the mixture was stirred at room temperature for 30 min. The precipitated solid was collected by filtration, washed with a small amount of ethanol, and dried to give the title compound (822 mg).

¹H-NMR (DMSO-d₆, 400 MHz) δ: 8.08 (1H, s), 8.26 (2H, br s), 12.75 (1H, br s).

Step 6

2-chloro-6H-thiazolo[4,5-d]pyridazin-7-one

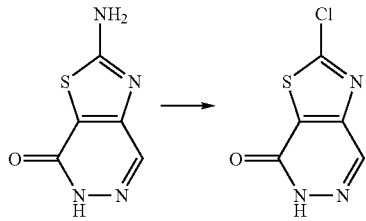

The compound (822 mg) obtained in Step 5 was suspended in 6N aqueous hydrochloric acid solution (6.6 ml), and sodium nitrite (1.69 g) was added in several portions at room temperature. After stirring the obtained suspension at room temperature for 30 min, the reaction mixture was diluted with water, and the solid was collected by filtration, washed with water and a small amount of acetone, and dried to give the title compound (770 mg).

¹H-NMR (DMSO-d₆, 400 MHz) δ: 8.61 (1H, s), 13.41 (1H, br s).

Step 7

(R)-4-(7-oxo-6,7-dihydrothiazolo[4,5-d]pyridazin-2-yl)-1-(4-trifluoromethoxy-benzenesulfonyl)-piperazine-2-carboxylic acid 4-trifluoromethoxy-benzylamide

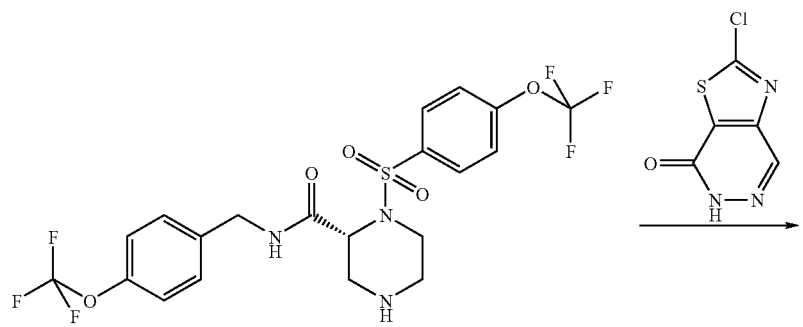

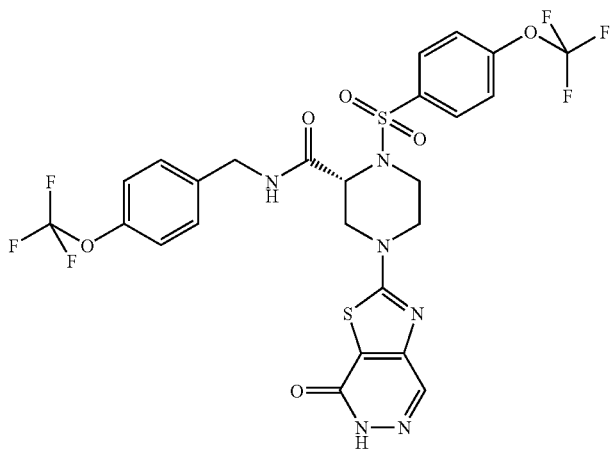

To a mixed solution of the compound (26 mg) obtained in Example 783, the compound (10 mg) obtained in Step 6 and isopropanol (1.0 ml) was added triethylamine (14 μl) at room temperature, and the mixture was heated under reflux overnight. The reaction mixture was concentrated under reduced pressure, and the residue was purified by thin layer silica gel chromatography (methanol:chloroform=1:20, developed twice) to give the title compound (31 mg).

$^1$H-NMR (DMSO-d$_6$, 400 MHz) δ: 3.33-3.40 (1H, m), 3.60-3.85 (3H, m), 3.95-4.20 (3H, m), 4.39 (1H, d, J=13.0 Hz), 4.64 (1H, dd, J=4.8, 2.4 Hz), 7.23 (4H, dd, J=22.3, 8.6 Hz), 7.50 (2H, d, J=8.6 Hz), 7.93 (2H, dt, J=9.7, 2.5 Hz), 8.13 (1H, s), 8.81 (1H, t, J=5.9 Hz), 12.87 (1H, s).

Example 1019

Step 1

5-bromo-[1,3,4]thiadiazol-2-ylamine

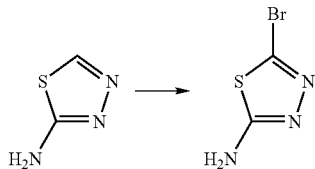

To a suspension of [1,3,4]-thiadiazol-2-ylamine (11 g) and sodium acetate (36 g) in acetic acid (160 ml) was slowly added dropwise a solution of bromine (6.0 ml) in acetic acid (40 ml) at room temperature over 30 min. After dropwise addition, the mixture was further stirred for 3 hr, and water (200 ml) was added to the reaction mixture. The precipitated solid was collected by filtration, washed with water and dried to give the title compound (17 g).

$^1$H-NMR (DMSO-d$_6$, 300 MHz) δ: 7.51 (2H, br s).

Step 2

N-(5-bromo-[1,3,4]thiadiazol-2-yl)-3-oxo-butylamide

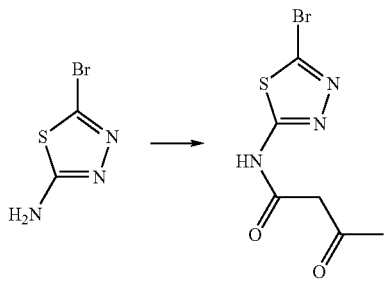

To a suspension of the compound (2.8 g) obtained in Step 1 in toluene (200 ml) was slowly added dropwise 4-methyleneoxetan-2-one (10 ml) at 100° C., and the mixture was stirred at the same temperature for 6 hr. The reaction mixture was concentrated under reduced pressure, and the obtained crude product (3.5 g) containing the title compound as a main component was washed with water-containing methanol, and dried to give the title compound (2.0 g).

$^1$H-NMR (DMSO-d$_6$, 300 MHz) δ: 2.21 (3H, s), 3.79 (2H, s), 12.95 (1H, s).

Step 3

2-bromo-5-methyl-[1,3,4]thiadiazolo[3,2-a]pyrimidin-7-one

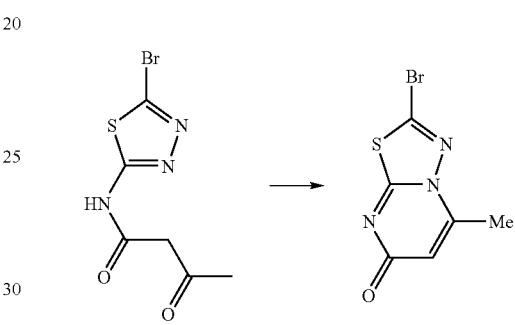

To concentrated sulfuric acid (10 ml) heated to 60° C. was added the compound (1.3 g) obtained in Step 2 in divided portions, and the mixture was stirred at the same temperature for 3 hr. The reaction mixture was poured into ice (100 g), and the mixture was neutralized with an aqueous solution (100 ml) of sodium carbonate (20 g). The organic layer was extracted with chloroform (50 ml), and dried to give the title compound (810 mg).

$^1$H-NMR (CDCl$_3$, 300 MHz) δ: 2.52 (3H, s), 6.14 (1H, s).

Step 4

(R)-4-(5-methyl-7-oxo-7H-[1,3,4]thiadiazolo[3,2-a]pyrimidin-2-yl)-1-(4-trifluoromethoxy-benzenesulfonyl)-piperazine-2-carboxylic acid 4-trifluoromethoxy-benzylamide

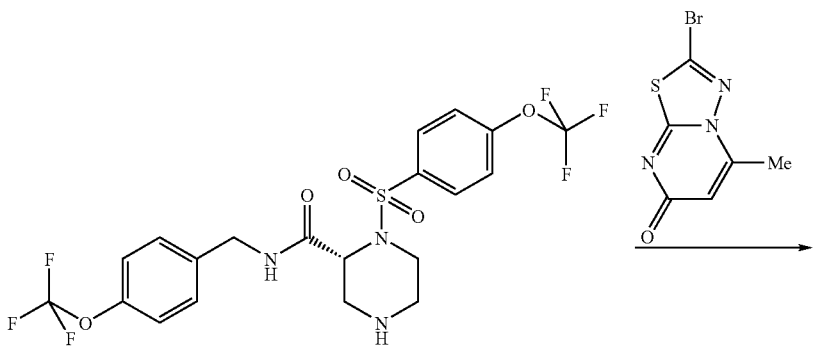

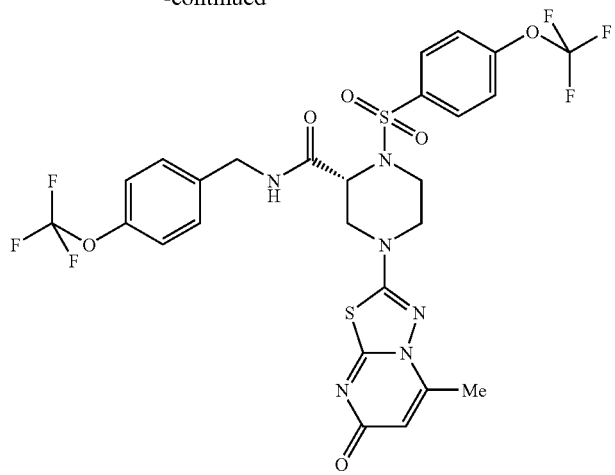

To a mixed solution of the compound (0.038 g) obtained in Example 783, the compound (0.023 g) obtained in Step 3 and ethanol (1.0 ml) was added N,N-diisopropylethylamine (0.019 ml) at room temperature. After stirring at 100° C. for 3 hr, the reaction mixture was concentrated under reduced pressure, and the residue was purified by thin layer silica gel chromatography (methanol:chloroform=1:9) to give the title compound (0.032 g).

$^1$H-NMR (CDCl$_3$, 300 MHz) δ: 2.36 (3H, s), 3.01 (1H, td, J=12.2, 3.1 Hz), 3.15 (1H, dd, J=13.2, 4.1 Hz), 3.57 (1H, ddd, J=13.8, 10.7, 2.4 Hz), 3.90 (2H, tt, J=16.4, 3.0 Hz), 4.28 (1H, d, J=13.2 Hz), 4.36 (1H, dd, J=13.6, 5.3 Hz), 4.43 (1H, dd, J=14.1, 5.5 Hz), 4.66 (1H, d, J=1.9 Hz), 6.05 (1H, d, J=0.8 Hz), 7.15 (2H, d, J=7.9 Hz), 7.26 (2H, d, J=8.7 Hz), 7.32 (2H, d, J=8.3 Hz), 7.57 (1H, t, J=5.7 Hz), 7.88 (2H, d, J=8.7 Hz).

Example 1030

Step 1

2-amino-5-(tert-butyldimethylsilyloxymethyl)-thiazole-4-carboxylic acid methyl ester

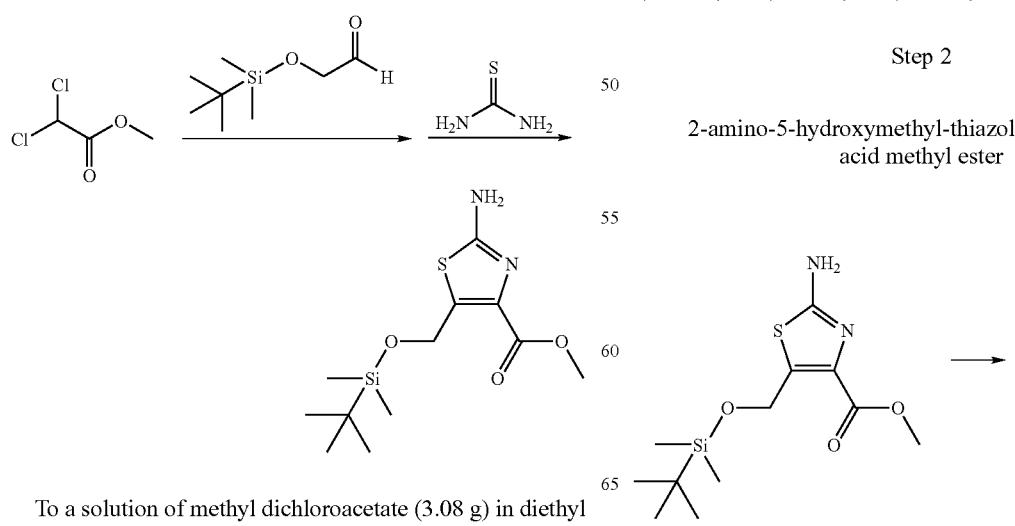

To a solution of methyl dichloroacetate (3.08 g) in diethyl ether (12 ml)-methanol (6 ml) was added (tert-butyldimethylsilyloxy)acetaldehyde (5.0 g) with stirring under ice-cooling. With stirring under ice-cooling, 28% sodium methoxide methanol solution (4.83 ml) was added dropwise, and the mixture was further stirred for 3 hr. With stirring under ice-cooling, water was added, and the temperature of the mixture was raised to room temperature. The mixture was partitioned by adding diethyl ether, and the organic layer was washed with saturated brine. The obtained organic layer was dried over anhydrous magnesium sulfate, filtrated, and concentrated under reduced pressure. To a solution of the concentrated residue in acetonitrile (30 ml) was added thiourea (1.64 g) with stirring at room temperature. After stirring at bath temperature of 70° C. for 3 hr, the reaction mixture was returned to room temperature. The reaction mixture was concentrated under reduced pressure, and ethyl acetate and water were added to the concentrated residue, and the insoluble material was filtered off. The filtrate was partitioned by adding sodium chloride. The obtained organic layer was dried over anhydrous magnesium sulfate, filtrated, and concentrated under reduced pressure. The concentrated residue was purified by silica gel column chromatography (ethyl acetate:n-hexane=3:7) to give the title compound (2.05 g).

$^1$H-NMR (DMSO-d$_6$, 300 MHz) δ: 0.08 (6H, s), 0.89 (9H, s), 3.72 (3H, s), 4.99 (2H, s), 7.02 (2H, br s).

Step 2

2-amino-5-hydroxymethyl-thiazole-4-carboxylic acid methyl ester

-continued

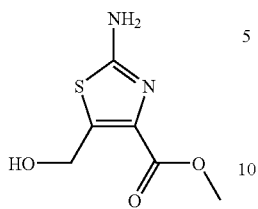

To a solution of the compound (2.03 g) obtained in Step 1 in tetrahydrofuran (40 ml) was added dropwise, with stirring under ice-cooling, 1.0M tetrabutylammonium fluoride tetrahydrofuran solution (7.38 ml). After stirring at room temperature for 1 hr, the reaction mixture was concentrated under reduced pressure. The concentrated residue was purified by silica gel column chromatography (ethyl acetate:methanol=9:1) to give the title compound (1.06 g).

$^1$H-NMR (CDCl$_3$, 300 MHz) δ: 3.42 (1H, t, J=7.0 Hz), 3.93 (3H, s), 4.87 (2H, d, J=7.0 Hz), 4.98 (2H, br s).

Step 3

2-amino-5-formyl-thiazole-4-carboxylic acid methyl ester

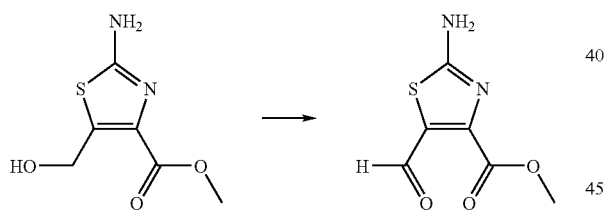

The compound (1.05 g) obtained in Step 2 was suspended in chloroform (50 ml), manganese dioxide (4.86 g) was added, with stirring at room temperature, and the mixture was stirred at the same temperature for 3 days. The reaction mixture was concentrated, tetrahydrofuran (150 ml) and activated carbon were added, and the mixture was heated under reflux. The insoluble material was filtered off when it was hot, and the insoluble material was washed with a heated mixed solvent (tetrahydrofuran:N,N-dimethylformamide:methanol=8:1:1). The filtrate was concentrated under reduced pressure, and the obtained crude crystals were suspended in diethyl ether, collected by filtration and dried to give the title compound (782 mg).

$^1$H-NMR (DMSO-d$_6$, 300 MHz) δ: 3.85 (3H, s), 8.41 (2H, br s), 10.14 (1H, s)

Step 4

2-amino-5H-thiazolo[4,5-d]pyridazin-4-one

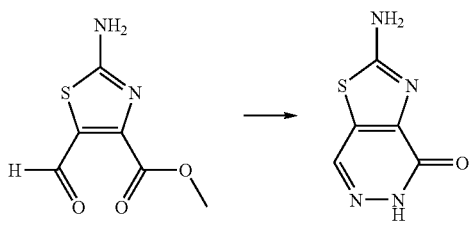

The compound (788 mg) obtained in Step 3 was suspended in ethanol (7.8 ml), and hydrazine monohydrate (243 μl) and acetic acid (780 μl) were added, with stirring at room temperature. The mixture was stirred overnight at a bath temperature of 100° C. and returned to room temperature. The reaction mixture was concentrated under reduced pressure, and the obtained crude crystals were suspended in methanol, collected by filtration and dried to give the title compound (690 mg).

$^1$H-NMR (DMSO-d$_6$, 300 MHz) δ: 8.07 (2H, br s), 8.25 (1H, s), 12.67 (1H, br s).

Step 5

2-chloro-5H-thiazolo[4,5-d]pyridazin-4-one

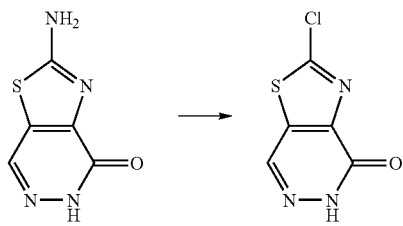

The compound (688 mg) obtained in Step 4 was suspended in 6N aqueous hydrochloric acid solution (10 ml), and sodium nitrite (1.41 g) was added in several portions with stirring at room temperature, and the mixture was further stirred at room temperature for 1 hr. Water was added, with stirring at room temperature, and the solid was collected by filtration, washed with water, and dried to give the title compound (571 mg).

$^1$H-NMR (DMSO-d$_6$, 300 MHz) δ: 8.61 (1H, s), 13.25 (1H, br s).

Step 6

(R)-4-(4-oxo-4,5-dihydro-thiazolo[4,5-d]pyridazin-2-yl)-1-(4-trifluoromethyl-benzenesulfonyl)-piperazine-2-carboxylic acid 4-trifluoromethoxy-benzylamide

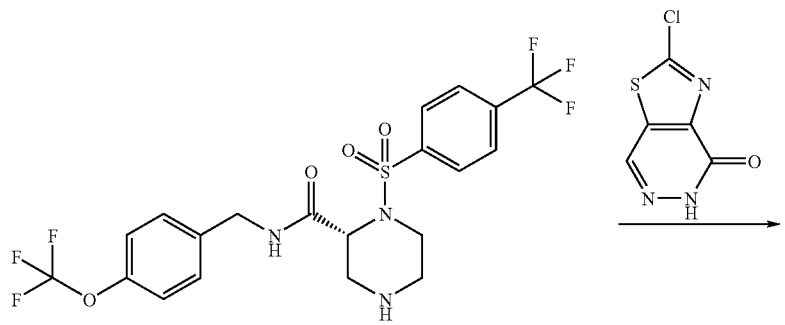

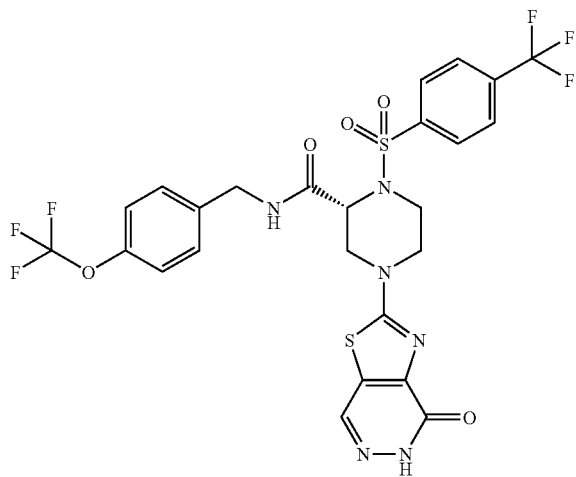

To a mixture of the compound (87 mg) obtained in Example 983, Step 2 and the compound (32 mg) obtained in Step 5 in isopropanol (0.9 ml) was added N,N-diisopropylethylamine (30 μl) at room temperature. After stirring overnight at room temperature, and the mixture was stirred with heating under reflux for 5 hr. The reaction mixture was concentrated under reduced pressure, and the residue was purified by thin layer silica gel chromatography (methanol:chloroform=5:95) to give the title compound (84 mg).

$^1$H-NMR (CDCl$_3$, 300 MHz) δ: 3.07-3.17 (1H, m), 3.27 (1H, dd, J=13.4, 4.3 Hz), 3.44-3.54 (1H, m), 3.95 (1H, d, J=14.3 Hz), 4.28-4.39 (2H, m), 4.47 (1H, dd, J=15.3, 6.2 Hz), 4.56 (1H, d, J=12.8 Hz), 4.67 (1H, br s), 6.99 (1H, t, J=5.7

Hz), 7.13 (2H, d, J=7.9 Hz), 7.22 (2H, d, J=9.0 Hz), 7.81 (2H, d, J=8.3 Hz), 8.01 (2H, d, J=8.3 Hz), 8.04 (1H, s), 10.28 (1H, br s).

Step 7

(R)-4-(5-methyl-4-oxo-4,5-dihydro-thiazolo[4,5-d]pyridazin-2-yl)-1-(4-trifluoromethyl-benzenesulfonyl)-piperazine-2-carboxylic acid 4-trifluoromethoxy-benzylamide

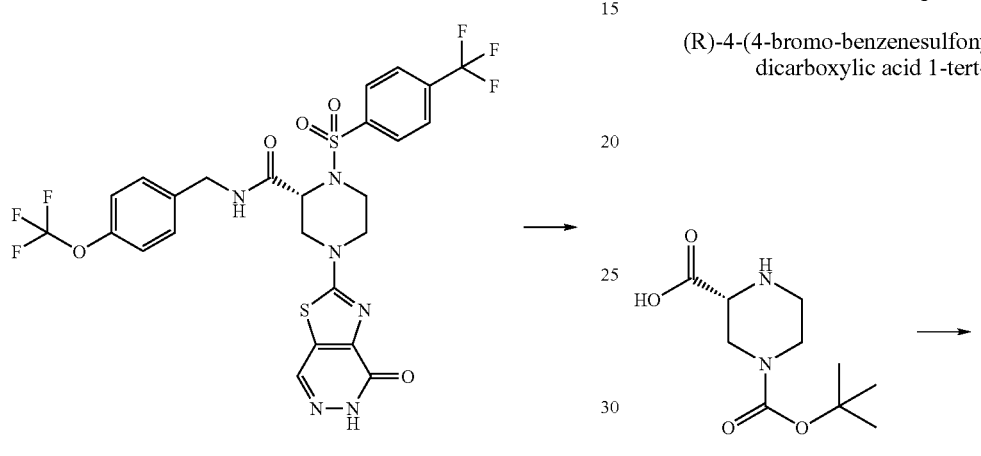

To a solution of the compound (40 mg) obtained in Step 6 in THF (0.8 ml) were added methanol (3.7 μl), triphenylphosphine (24 mg) and diisopropyl azodicarboxylate (18 μl) with stirring under ice-cooling, and the mixture was stirred overnight at room temperature. Methanol (1.2 μl), triphenylphosphine (8 mg) and diisopropyl azodicarboxylate (6 μl) was added at room temperature, and the mixture was stirred for 3 hr. The reaction mixture was concentrated under reduced pressure, and the residue was purified by silica gel column chromatography (methanol:chloroform=5:95) to give the title compound (29 mg).

$^1$H-NMR (CDCl$_3$, 300 MHz) δ: 3.08-3.17 (1H, m), 3.27 (1H, dd, J=13.4, 4.3 Hz), 3.45-3.55 (1H, m), 3.85 (3H, s), 3.93 (1H, d, J=14.3 Hz), 4.25-4.37 (2H, m), 4.46 (1H, dd, J=15.1, 6.4 Hz), 4.56 (1H, d, J=13.6 Hz), 4.68 (1H, br s), 7.05-7.13 (3H, m), 7.20 (2H, d, J=8.7 Hz), 7.80 (2H, d, J=8.7 Hz), 7.98-8.02 (3H, m).

Example 1100

Step 1

(R)-4-(4-bromo-benzenesulfonyl)-piperazine-1,3-dicarboxylic acid 1-tert-butyl ester

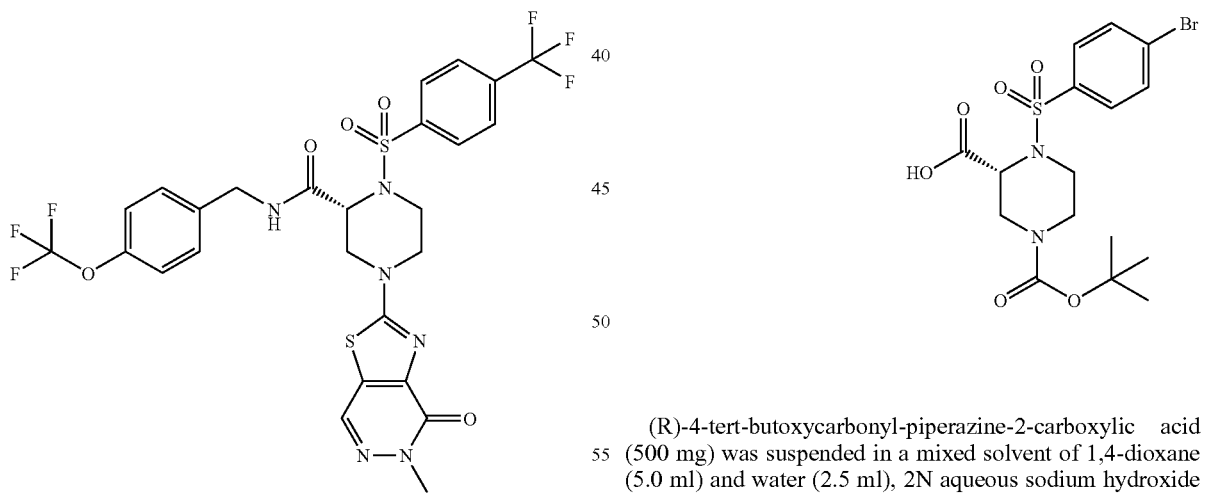

(R)-4-tert-butoxycarbonyl-piperazine-2-carboxylic acid (500 mg) was suspended in a mixed solvent of 1,4-dioxane (5.0 ml) and water (2.5 ml), 2N aqueous sodium hydroxide solution (1.1 ml) and triethylamine (440 mg) were successively added with stirring under ice-cooling, and a solution of 4-bromobenzenesulfonyl chloride (610 mg) in 1,4-dioxane (1.0 ml) was added dropwise. After stirring overnight at room temperature, 10% aqueous citric acid solution and ethyl acetate were added with stirring under ice-cooling. The reaction mixture was partitioned, and the organic layer was washed with water and saturated brine, and concentrated under reduced pressure to give a crude product (548 mg) containing the title compound as a main component. A part thereof was directly used for the next reaction.

265
Step 2

(R)-4-(4-cyclopropyl-benzenesulfonyl)-piperazine-1,3-dicarboxylic acid 1-tert-butyl ester

266
Step 3

(R)-4-(4-cyclopropyl-benzenesulfonyl)-3-(4-trifluoromethoxy-benzylcarbamoyl)-piperazine-1-carboxylic acid tert-butyl ester

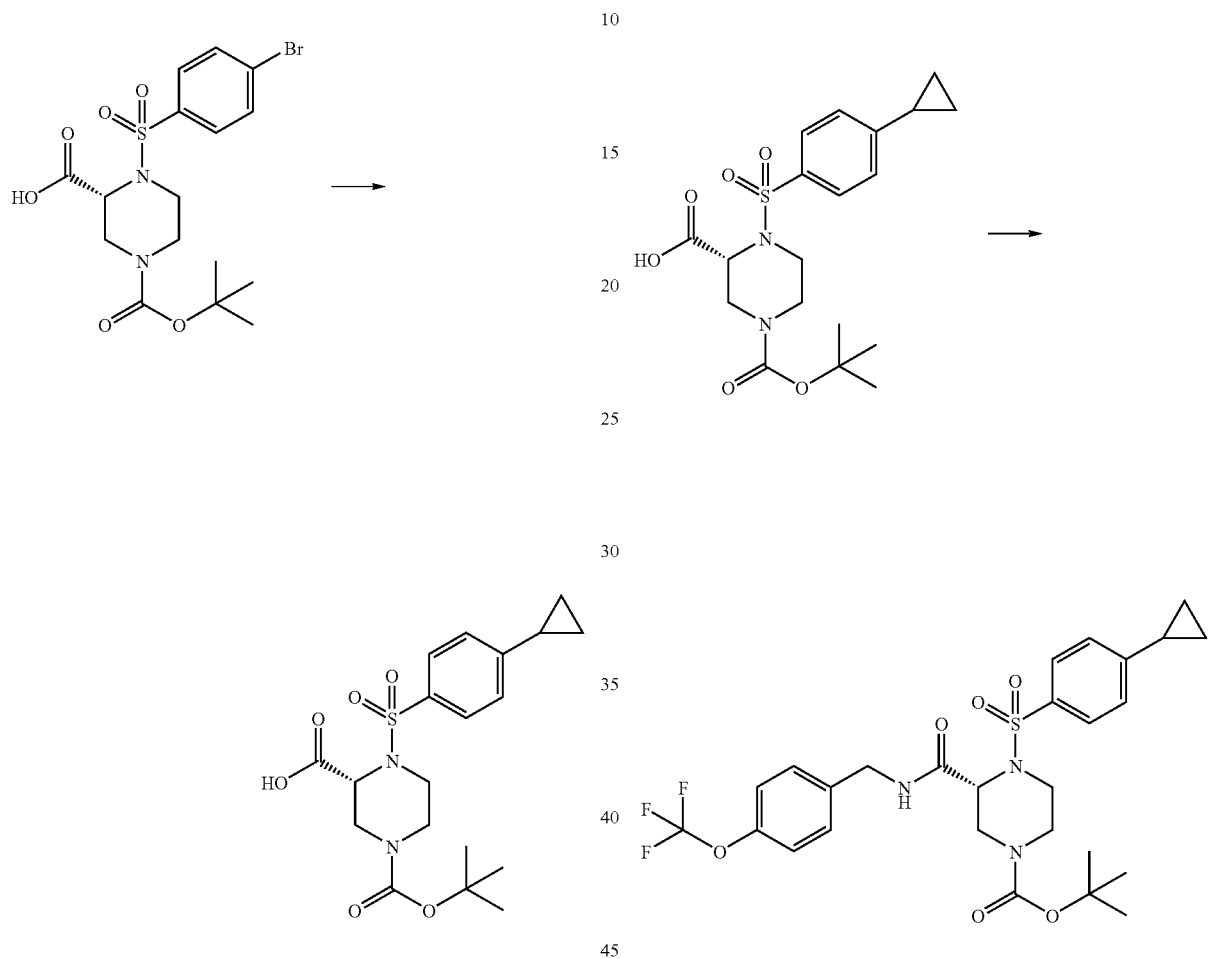

Under an argon atmosphere, to a suspension of palladium diacetate (15 mg) and 2-dicyclohexylphosphino-2',4',6'-triisopropylbiphenyl (61 mg) in toluene (5.8 ml) were successively added the compound (290 mg) obtained in Step 1, cyclopropylboronic acid (83 mg) and tripotassium phosphate (1.21 g). The mixture was stirred at 100° C. for 1 hr. Ethyl acetate was added at room temperature and the reaction mixture was adjusted to pH 4 by adding 1N aqueous hydrochloric acid solution with stirring under ice-cooling. The obtained suspension was filtered through celite and partitioned. The organic layer was washed with saturated brine, dried over anhydrous magnesium sulfate, filtrated, and concentrated under reduced pressure to give a crude product (328 mg) containing the title compound as a main component.

$^1$H-NMR (CDCl$_3$, 300 MHz) δ: 0.72-0.81 (2H, m), 1.02-1.13 (2H, m), 1.29-1.45 (9H, m), 1.88-2.01 (1H, m), 2.75-2.96 (1H, m), 3.01-3.16 (1H, m), 3.29-3.46 (1H, m), 3.58-3.69 (1H, m), 3.93-4.12 (1H, m), 4.46-4.67 (2H, m), 7.13 (2H, d, J=8.3 Hz), 7.64 (2H, d, J=8.3 Hz).

To a solution of the compound (168 mg) obtained in Step 2 in N,N-dimethylformamide (1.7 ml) were successively added, with stirring under ice-cooling, 1-ethyl-3-(3-dimethylaminopropyl) carbodiimide hydrochloride (94 mg), 1-hydroxybenzotriazole hydrate (75 mg) and 4-trifluoromethoxybenzylamine (85 mg). After stirring overnight at room temperature, the mixture was partitioned by adding ethyl acetate, saturated aqueous sodium hydrogen carbonate solution and water. The organic layer was washed with saturated brine, dried over anhydrous magnesium sulfate, filtrated, and concentrated under reduced pressure. The residue was purified by thin layer silica gel chromatography (hexane:ethyl acetate=1:1) to give the title compound (132 mg).

$^1$H-NMR (CDCl$_3$, 400 MHz) δ: 0.78-0.84 (2H, m), 1.10-1.17 (2H, m), 1.93-2.01 (1H, m), 2.62-2.82 (2H, br m), 3.24-3.35 (1H, m), 3.60-3.83 (2H, br m), 4.37-4.64 (4H, m), 6.94-7.01 (1H, m), 7.16-7.21 (4H, m), 7.25-7.30 (2H, m), 7.71 (2H, d, J=8.6 Hz).

Step 4

(R)-1-(4-cyclopropyl-benzenesulfonyl)-piperazine-2-carboxylic acid 4-trifluoromethoxy-benzylamide

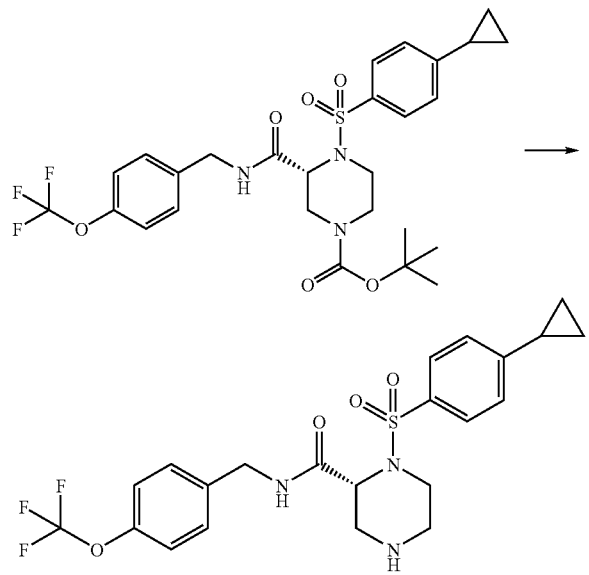

4N Hydrogen chloride/1,4-dioxane solution (1.3 ml) was added to the compound (130 mg) obtained in Step 3, and the mixture was stirred at room temperature for 6 hr. The reaction mixture was concentrated under reduced pressure, and the residue was partitioned by adding ethyl acetate, saturated aqueous sodium hydrogen carbonate solution and water. The organic layer was dried over anhydrous magnesium sulfate, filtrated, and concentrated under reduced pressure. The residue was purified by thin layer silica gel chromatography (chloroform:methanol=9:1) to give the title compound (88 mg).

$^1$H-NMR (CDCl$_3$, 300 MHz) δ: 0.74-0.83 (2H, m), 1.08-1.17 (2H, m), 1.90-2.01 (1H, m), 2.38-2.50 (2H, m), 2.76 (1H, d, J=12.8 Hz), 3.04-3.17 (1H, m), 3.54 (1H, d, J=12.8 Hz), 3.71-3.80 (1H, m), 4.31 (1H, d, J=3.8 Hz), 4.40-4.55 (2H, m), 7.11-7.21 (5H, m), 7.28 (2H, t, J=5.8 Hz), 7.69-7.72 (2H, m).

Step 5

(R)-4-(7-chloro-5-trifluoromethyl-thiazolo[4,5-d]pyrimidin-2-yl)-1-(4-cyclopropyl-benzenesulfonyl)-piperazine-2-carboxylic acid 4-trifluoromethoxy-benzylamide

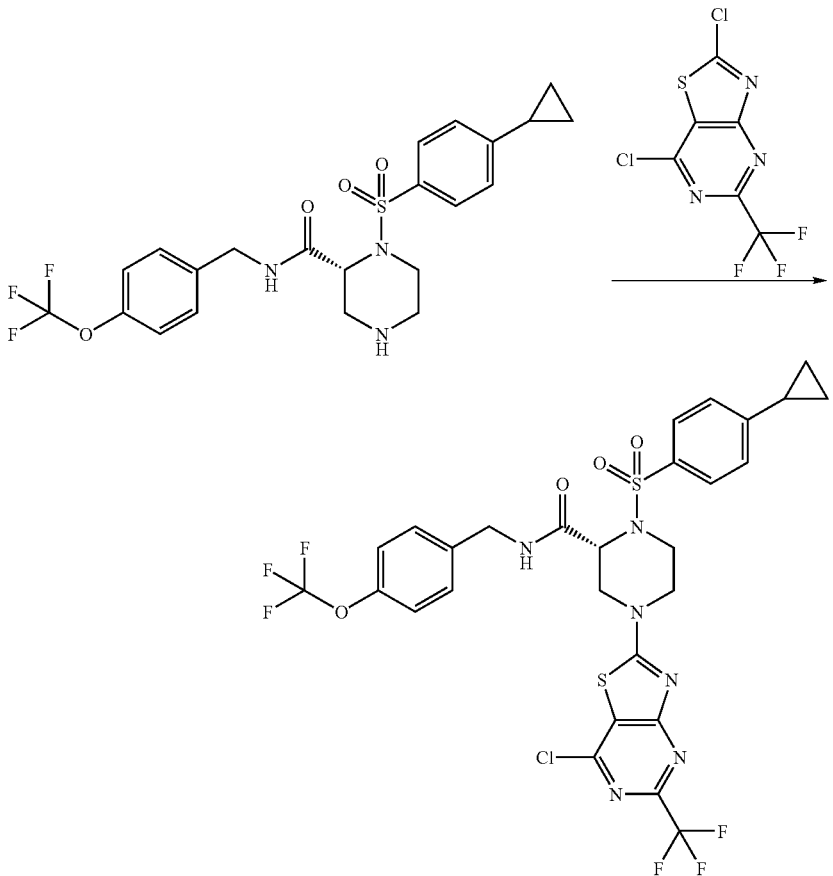

To a mixed solution of the compound (27 mg) obtained in Example 1001, Step 8, the compound (43 mg) obtained in Step 4 and chloroform (0.50 ml) was added N,N-diisopropylethylamine (19 μl) under ice-cooling. After stirring overnight at room temperature, the reaction mixture was purified by silica gel column chromatography (chloroform:methanol=20:1) to give the title compound (66 mg).

Step 6

(R)-4-(5-trifluoromethyl-thiazolo[4,5-d]pyrimidin-2-yl)-1-(4-cyclopropyl-benzenesulfonyl)-piperazine-2-carboxylic acid 4-trifluoromethoxy-benzylamide

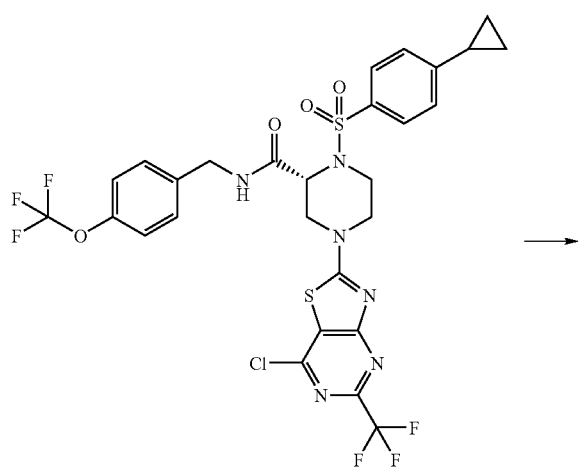

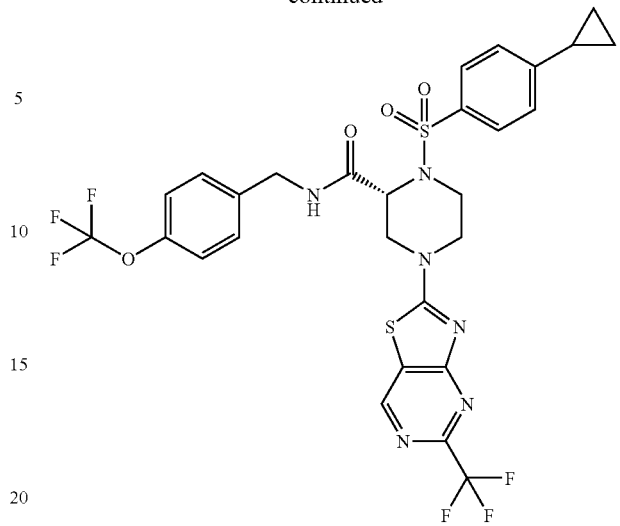

To a mixed solution of the compound (66 mg) obtained in Step 5, ammonium formate (28 mg) and ethanol (1.3 ml) was added 10% palladium carbon (33 mg) with heating under reflux. The mixture was stirred at the same temperature for 10 min and ammonium formate (28 mg) and 10% palladium carbon (33 mg) were added and the mixture was stirred for 10 min. Ammonium formate (28 mg) and 10% palladium carbon (33 mg) were further added. The reaction mixture was allowed to return to room temperature, and diluted with ethanol. The mixture was filtered through celite, and the filtrate was concentrated under reduced pressure. The residue was partitioned by adding ethyl acetate and water. The organic layer was dried over anhydrous magnesium sulfate, filtrated, and concentrated under reduced pressure. The residue was purified by silica gel column chromatography (chloroform:methanol=20:1), and the obtained crude product was suspended in hexane, collected by filtration, and dried to give the title compound (31 mg).

$^1$H-NMR (CDCl$_3$, 300 MHz) δ: 0.74-0.82 (2H, m), 1.07-1.18 (2H, m), 1.89-1.99 (1H, m), 3.07-3.30 (2H, m), 3.33-3.48 (1H, m), 3.98 (1H, d, J=13.9 Hz), 4.30-4.54 (4H, m),

Example 1099

Step 1

(R)-4-(7-chloro-5-cyclopropyl-thiazolo[4,5-d]pyrimidin-2-yl)-1-(4-cyclopropyl-benzenesulfonyl)-piperazine-2-carboxylic acid 4-trifluoromethoxy-benzylamide

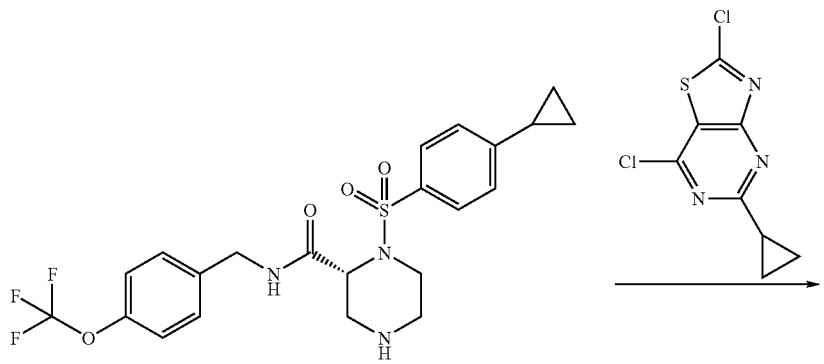

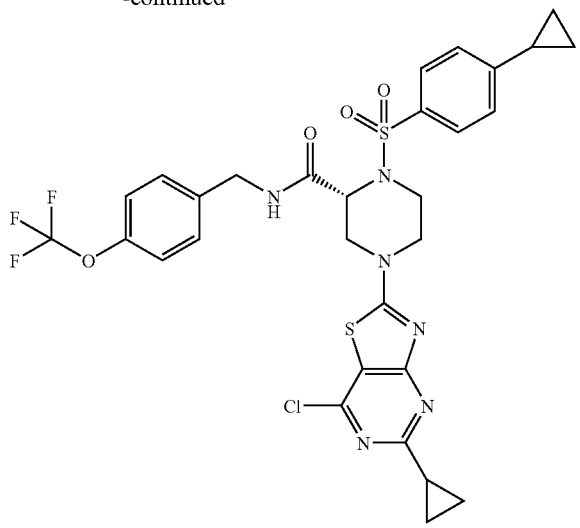

To a mixture of (R)-1-(4-cyclopropyl-benzenesulfonyl)-piperazine-2-carboxylic acid 4-trifluoromethoxy-benzylamide (39 mg) obtained in Example 1100, Step 4 and 2,7-dichloro-5-cyclopropyl-thiazolo [4,5-d]pyrimidine (20 mg) in chloroform (1.0 ml) was added N,N-diisopropylethylamine (20 μl) at room temperature. After stirring overnight at room temperature, the reaction mixture was diluted with ethyl acetate, and the mixture was partitioned by adding water. The organic layer was dried over anhydrous sodium sulfate, filtrated, and concentrated under reduced pressure. The residue was purified by silica gel column chromatography (ethyl acetate:n-hexane=1:1) to give the title compound (54 mg).

Step 2

(R)-1-(4-cyclopropyl-benzenesulfonyl)-4-(5-cyclopropyl-thiazolo [4,5-d]pyrimidin-2-yl)-piperazine-2-carboxylic acid 4-trifluoromethoxy-benzylamide

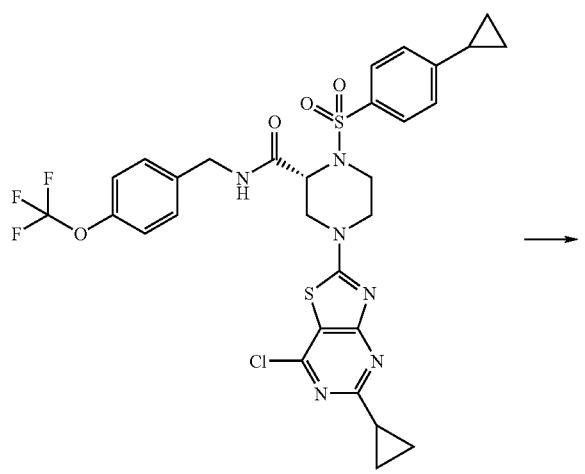

→

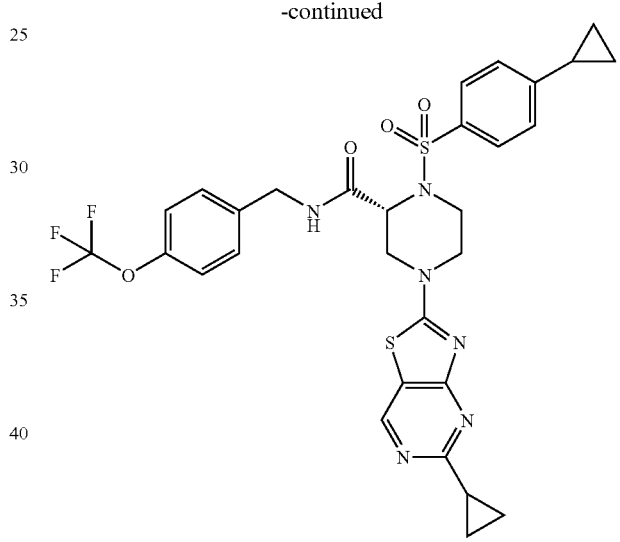

To a mixture of the compound (54 mg) obtained in Step 1 and ammonium formate (49 mg) in ethanol (2.0 ml) was added 10% palladium carbon (50 mg) at 80° C. After stirring at 80° C. for 30 min, ammonium formate (49 mg) and 10% palladium carbon (50 mg) were added. After stirring at 80° C. for 30 min, the reaction mixture was allowed to return to room temperature, and the reaction mixture was diluted with ethyl acetate. The mixture was filtered through celite, and the filtrate was concentrated under reduced pressure. The residue was purified by thin layer silica gel chromatography (ethyl acetate) to give the title compound (24 mg).

$^1$H-NMR (CDCl$_3$, 400 MHz) δ: 0.76-0.80 (2H, m), 1.02-1.07 (2H, m), 1.10-1.16 (2H, m), 1.17-1.22 (2H, m), 1.89-1.97 (1H, m), 2.21-2.29 (1H, m), 3.06-3.14 (1H, m), 3.17-3.25 (1H, m), 3.37-3.45 (1H, m), 3.93 (1H, d, J=14.1 Hz), 4.27-4.51 (4H, m), 4.62 (1H, br s), 7.05 (1H, br s), 7.12 (2H, d, J=8.1 Hz), 7.19 (2H, d, J=8.8 Hz), 7.21 (2H, d, J=8.8 Hz), 7.73 (2H, d, J=8.6 Hz), 8.61 (1H, s).

The compounds obtained in the above-mentioned Examples and the compounds synthesized by a method similar thereto and other conventional methods where necessary are shown in Table 1-Table 226.

The NMR data and mass spectrum data of the compounds of the present invention are shown in Table 227-Table 459.
TABLE 1
| Ex. No. | Structural Formula |
|---|---|
| 1 | 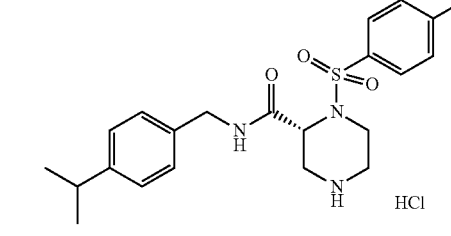 |
| 2 | 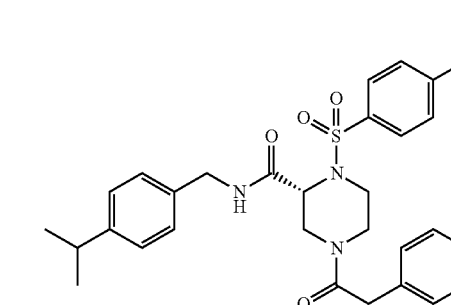 |
| 3 | 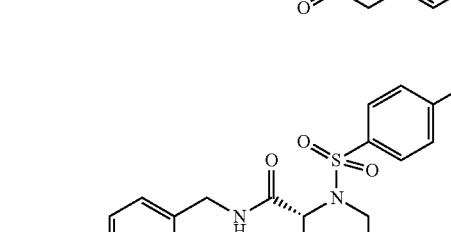 |
TABLE 1-continued
| Ex. No. | Structural Formula |
|---|---|
| 4 | 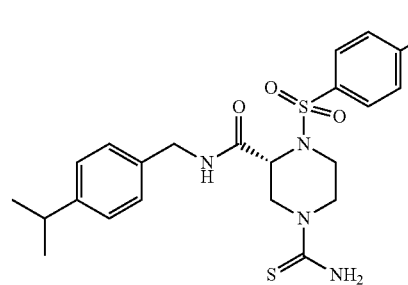 |
| 5 | 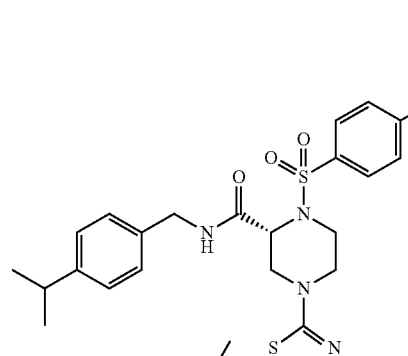 |
TABLE 2
| Ex. No. | Structural Formula |
|---|---|
| 6 | 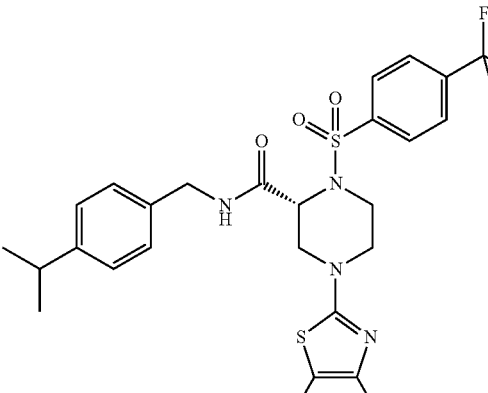 |

TABLE 2-continued
| Ex. No. | Structural Formula |
| --- | --- |
| 7 | 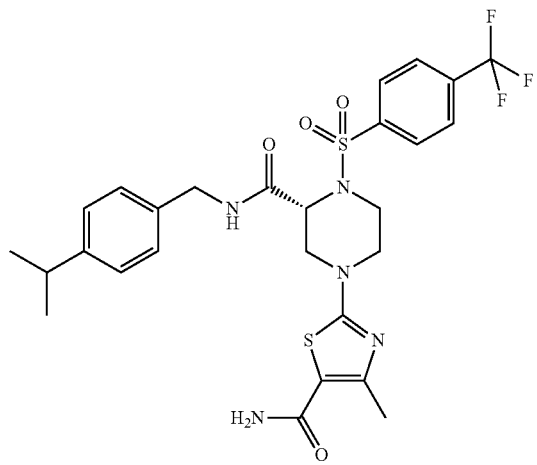 |
| 8 | 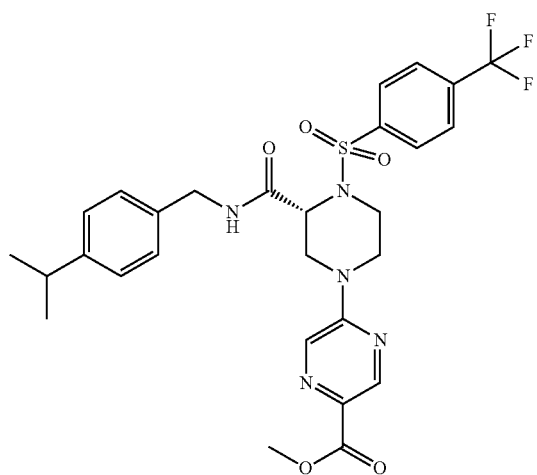 |
| 9 | 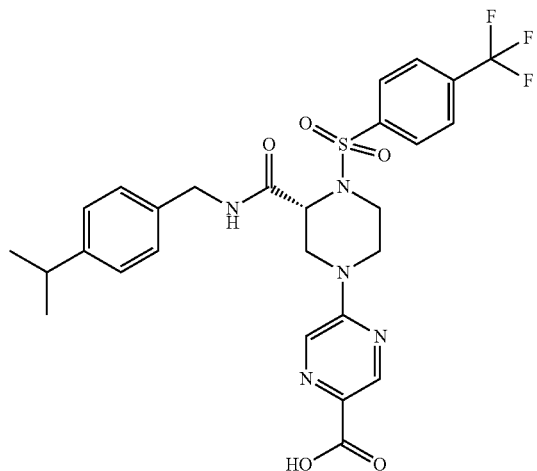 |

TABLE 2-continued

| Ex. No. | Structural Formula |
|---|---|
| 10 | (structure) |

TABLE 3

| Ex. No. | Structural Formula |
|---|---|
| 11 | (structure) |
| 12 | (structure) |
| 13 | (structure) |

TABLE 3-continued
| Ex. No. | Structural Formula |
|---|---|
| 14 | 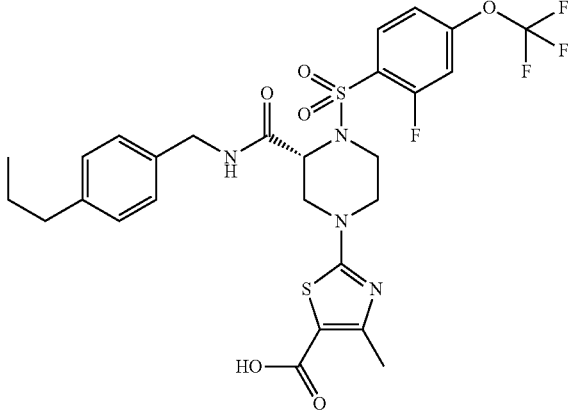 |
| 15 | 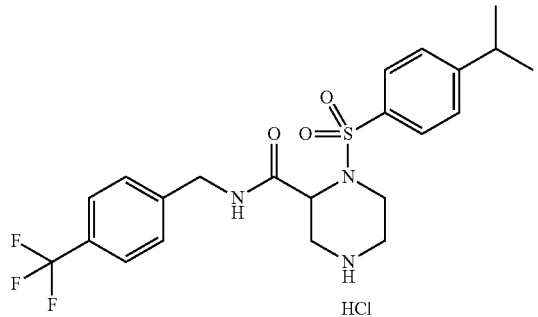 |
TABLE 4
| Ex. No. | Structural Formula |
|---|---|
| 16 | 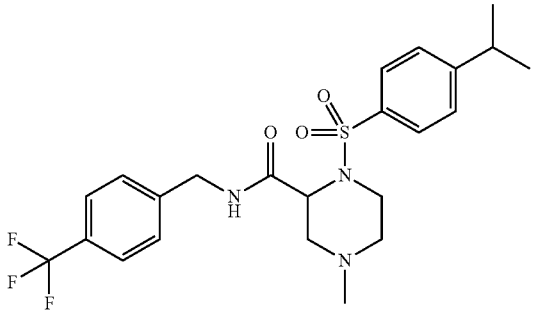 |
| 17 | 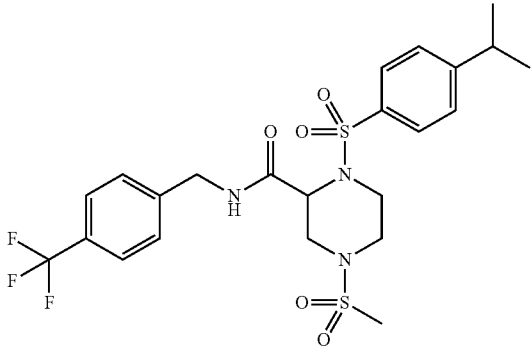 |
TABLE 4-continued
| Ex. No. | Structural Formula |
|---|---|
| 18 | 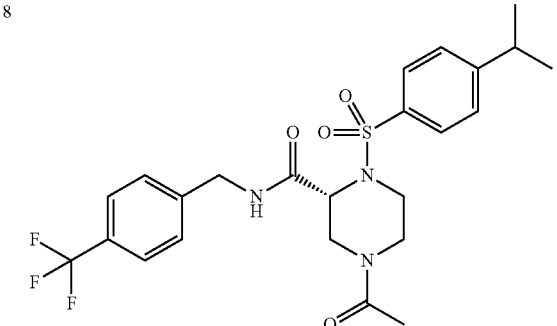 |
| 19 | 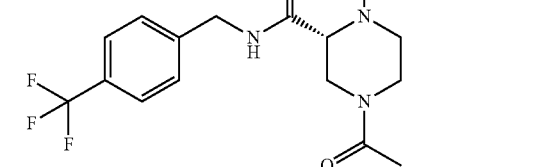 |

TABLE 5

| Ex. No. | Structural Formula |
|---|---|
| 21 | *(4-(trifluoromethyl)benzyl)amide of 1-(2-chlorophenylsulfonyl)-4-acetylpiperazine-2-carboxylic acid)* |
| 22 | *(4-(trifluoromethyl)benzyl)amide of 1-(4-bromophenylsulfonyl)-4-acetylpiperazine-2-carboxylic acid)* |
| 23 | *(4-(trifluoromethyl)benzyl)amide of 1-(5-bromothiophen-2-ylsulfonyl)-4-acetylpiperazine-2-carboxylic acid)* |
| 24 | *(4-(trifluoromethyl)benzyl)amide of 1-(phenylsulfonyl)-4-acetylpiperazine-2-carboxylic acid)* |
| 25 | *(4-(trifluoromethyl)benzyl)amide of 1-(4-(4-chlorophenoxy)phenylsulfonyl)-4-acetylpiperazine-2-carboxylic acid)* |

TABLE 6
| Ex. No. | Structural Formula |
|---------|-------------------|
| 26 | 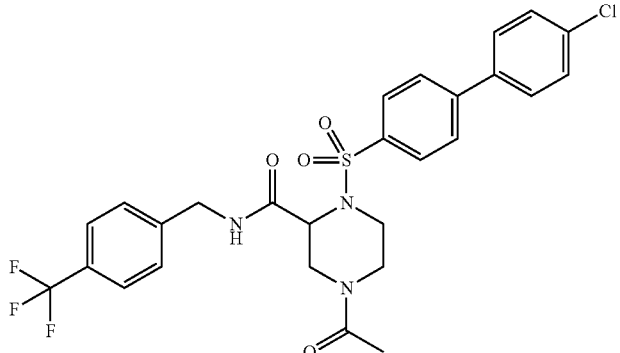 |
| 27 | 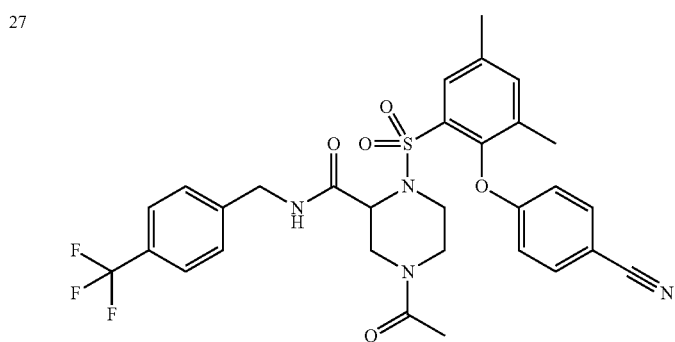 |
| 28 | 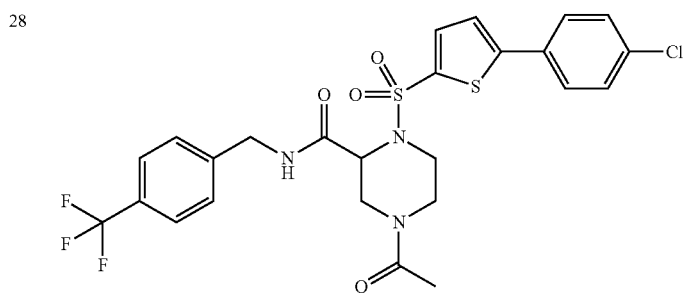 |
| 29 | 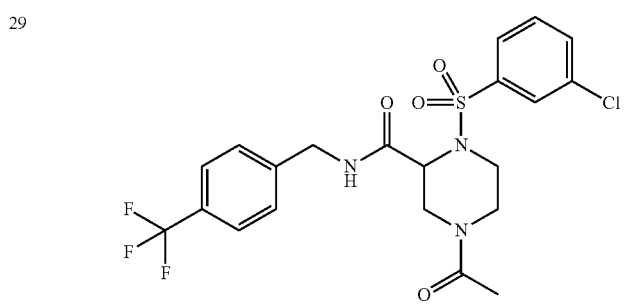 |

TABLE 6-continued
| Ex. No. | Structural Formula |
|---|---|
| 30 | 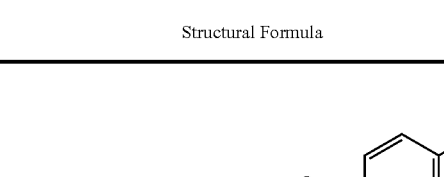 |
TABLE 7
| Ex. No. | Structural Formula |
|---|---|
| 31 | |
| 32 | |
TABLE 7-continued
| Ex. No. | Structural Formula |
|---|---|
| 33 | |
| 34 | |
| 35 | |

TABLE 8
| Ex. No. | Structural Formula |
|---|---|
| 36 | 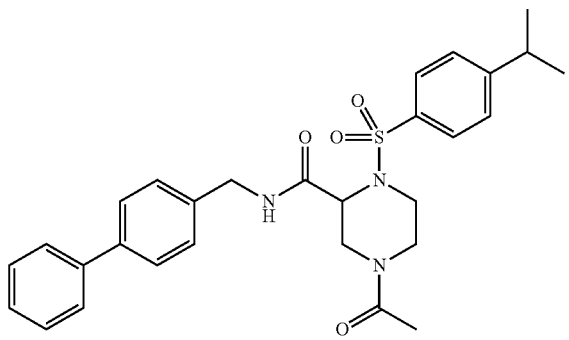 |
| 37 | 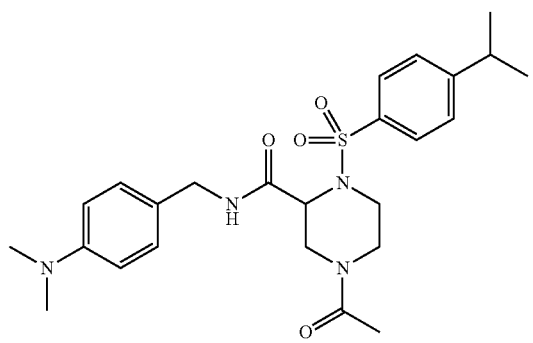 |
| 38 | 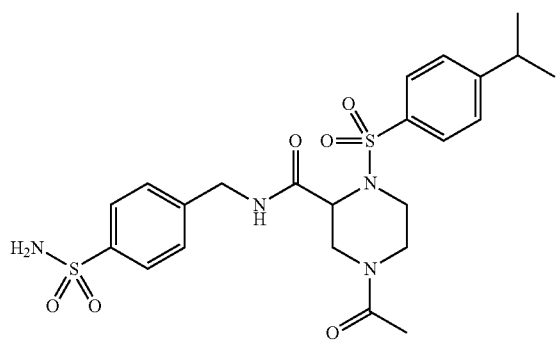 |
| 39 | 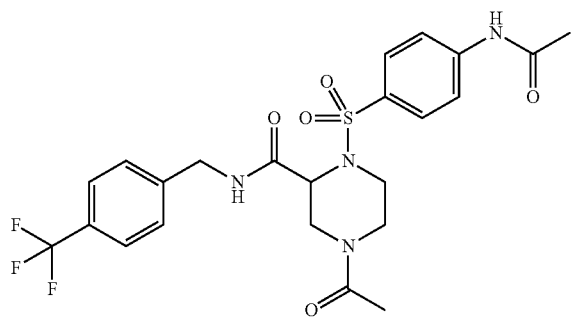 |

TABLE 8-continued

| Ex. No. | Structural Formula |
|---|---|
| 40 | *(structure: 4-(trifluoromethyl)benzyl amide of 1-(4-nitrophenylsulfonyl)-4-acetylpiperazine-2-carboxamide)* |

TABLE 9

| Ex. No. | Structural Formula |
|---|---|
| 41 | *(structure: 4-(trifluoromethyl)benzyl amide of 1-(3,4-dichlorophenylsulfonyl)-4-acetylpiperazine-2-carboxamide)* |
| 42 | *(structure: 4-(trifluoromethyl)benzyl amide of 1-(biphenyl-3-ylsulfonyl)-4-acetylpiperazine-2-carboxamide)* |
| 43 | *(structure: 4-(trifluoromethyl)benzyl amide of 1-{[5-(5-(trifluoromethyl)isoxazol-3-yl)thiophen-2-yl]sulfonyl}-4-acetylpiperazine-2-carboxamide)* |

TABLE 9-continued
| Ex. No. | Structural Formula |
|---|---|
| 44 | 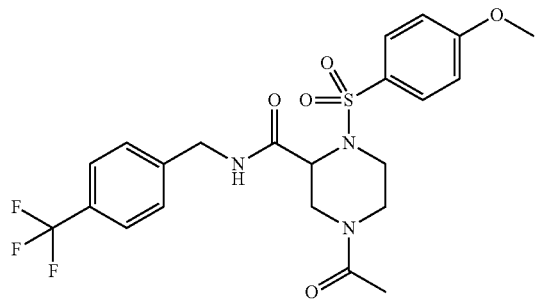 |
| 45 | 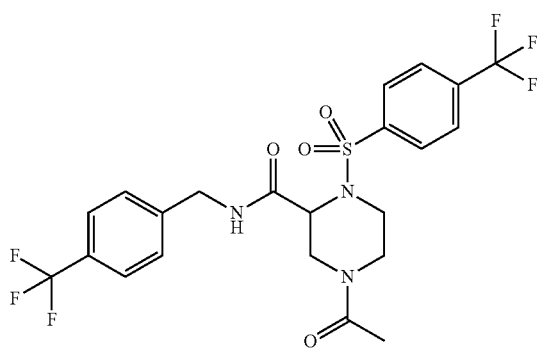 |
TABLE 10
| Ex. No. | Structural Formula |
|---|---|
| 46 | 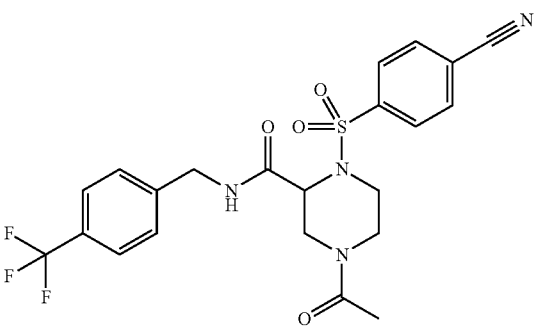 |
| 47 | 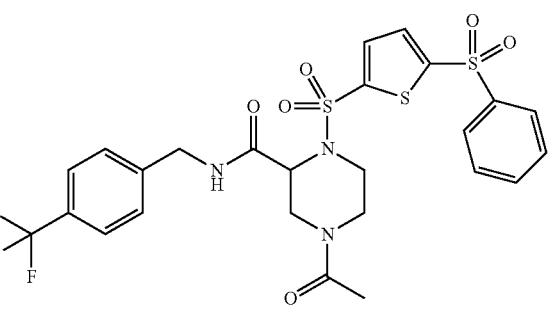 |

TABLE 10-continued

| Ex. No. | Structural Formula |
| --- | --- |
| 48 | |
| 49 | |
| 50 | |

TABLE 11

| Ex. No. | Structural Formula |
| --- | --- |
| 51 | |

TABLE 11-continued
| Ex. No. | Structural Formula |
|---|---|
| 52 | 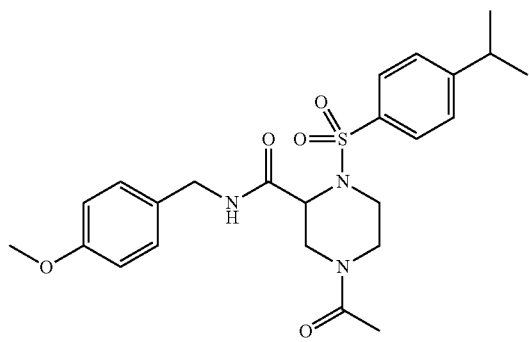 |
| 53 | 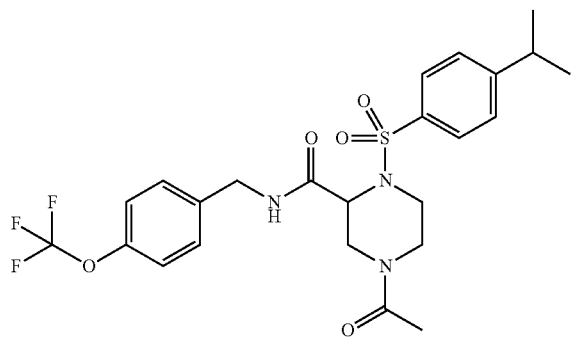 |
| 54 | 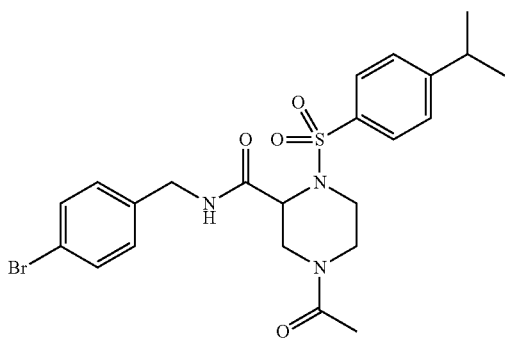 |
| 55 | 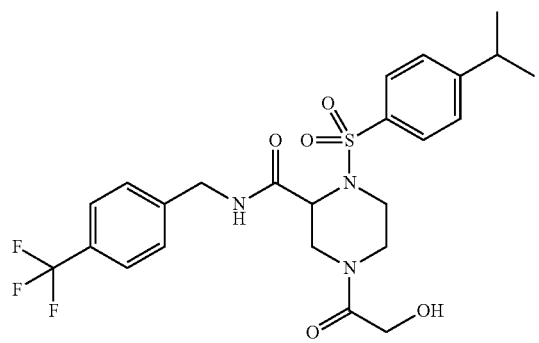 |

TABLE 12
| Ex. No. | Structural Formula |
|---|---|
| 56 | 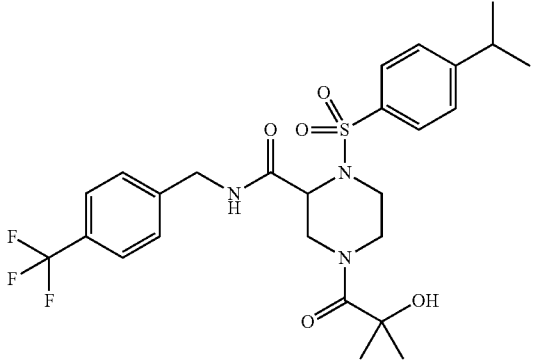 |
| 57 | 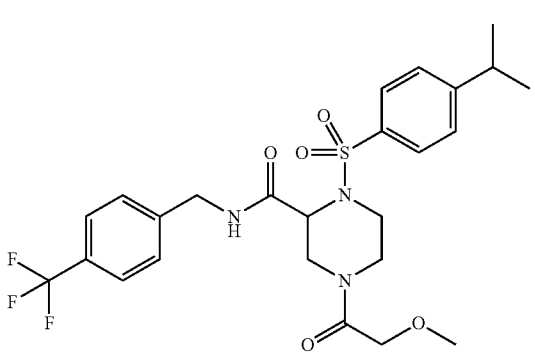 |
| 58 | 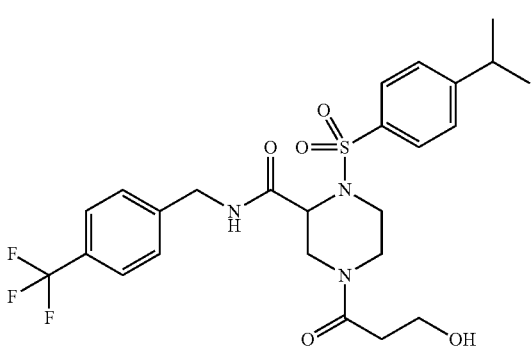 |
TABLE 12-continued
| Ex. No. | Structural Formula |
|---|---|
| 59 | 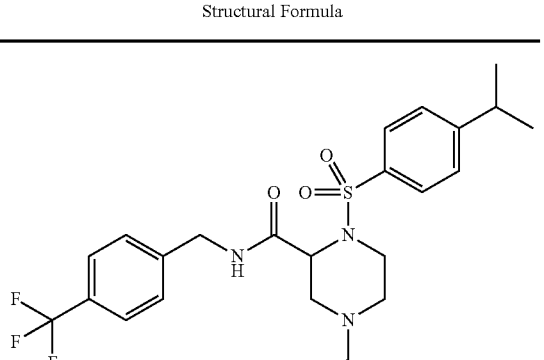 |
| 60 |  |
TABLE 13
| Ex. No. | Structural Formula |
|---|---|
| 61 | 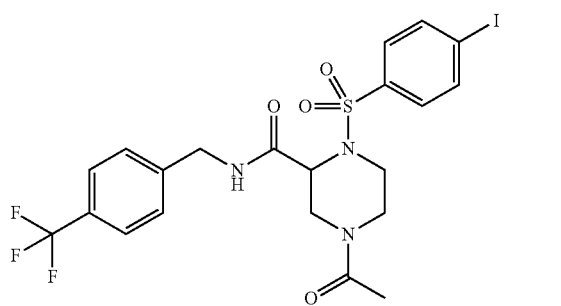 |

TABLE 13-continued
| Ex. No. | Structural Formula |
|---|---|
| 62 | 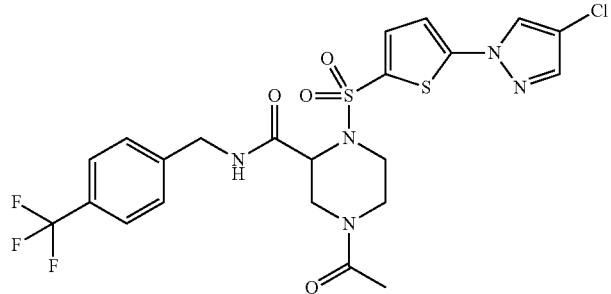 |
| 63 | 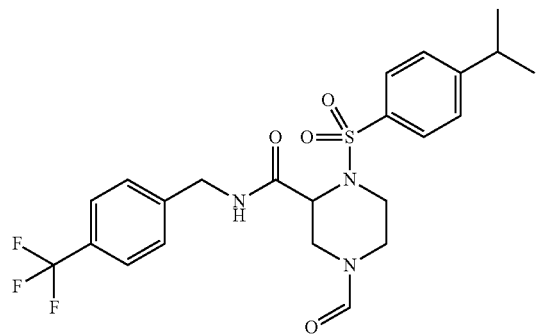 |
| 64 | 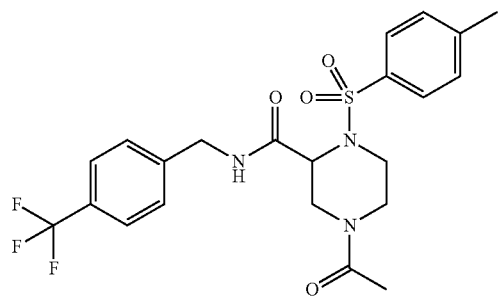 |
| 65 | 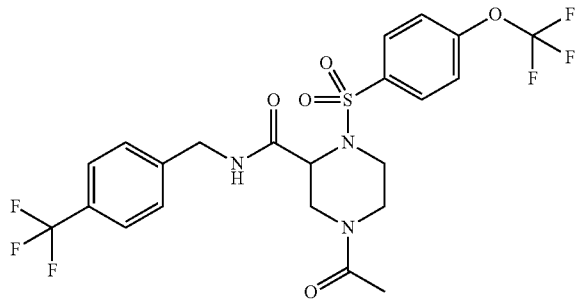 |

TABLE 14

| Ex. No. | Structural Formula |
| --- | --- |
| 66 | (4-trifluoromethylbenzyl)amide of 1-[4-(pyridin-3-yloxy)phenylsulfonyl]-4-acetylpiperazine-2-carboxylic acid · HCl |
| 67 | (2-fluorobenzyl)amide of 1-(4-isopropylphenylsulfonyl)-4-acetylpiperazine-2-carboxylic acid |
| 68 | (4-tert-butylbenzyl)amide of 1-(4-isopropylphenylsulfonyl)-4-acetylpiperazine-2-carboxylic acid |
| 69 | (4-trifluoromethylbenzyl)amide of 1-[(5-bromo-6-chloropyridin-3-yl)sulfonyl]-4-acetylpiperazine-2-carboxylic acid · HCl |

TABLE 14-continued

| Ex. No. | Structural Formula |
|---|---|
| 70 | (structure: 4-(trifluoromethyl)benzyl amide of 4-acetyl-1-[(6-morpholinopyridin-3-yl)sulfonyl]piperazine-2-carboxamide, HCl salt) |

TABLE 15

| Ex. No. | Structural Formula |
|---|---|
| 71 | (structure: 4-(trifluoromethyl)benzyl amide of 4-acetyl-1-[(3-methoxyphenyl)sulfonyl]piperazine-2-carboxamide) |
| 72 | (structure: 4-(trifluoromethyl)benzyl amide of 4-acetyl-1-[(4-propylphenyl)sulfonyl]piperazine-2-carboxamide) |
| 73 | (structure: 4-(trifluoromethyl)benzyl amide of 4-acetyl-1-([1,1'-biphenyl]-4-ylsulfonyl)piperazine-2-carboxamide) |

TABLE 15-continued

| Ex. No. | Structural Formula |
|---|---|
| 74 | |
| 75 | |

TABLE 16

| Ex. No. | Structural Formula |
|---|---|
| 76 | |
| 77 | |

TABLE 16-continued
| Ex. No. | Structural Formula |
|---|---|
| 78 | 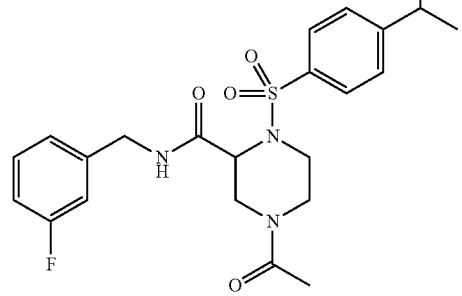 |
| 79 | |
| 80 | |
TABLE 17
| Ex. No. | Structural Formula |
|---|---|
| 81 | 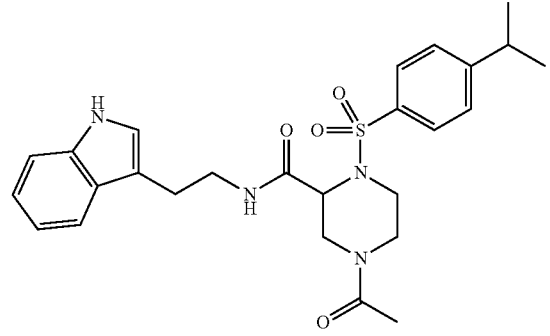 |

TABLE 17-continued
| Ex. No. | Structural Formula |
|---|---|
| 82 | 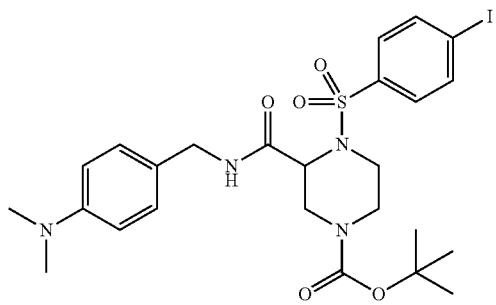 |
| 83 | 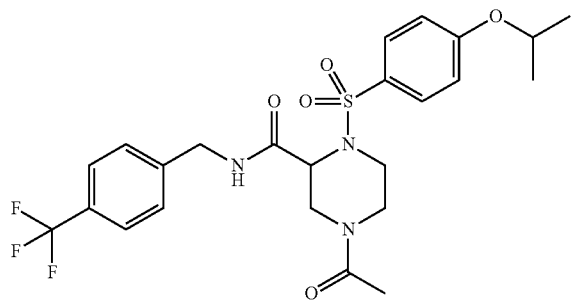 |
| 84 | 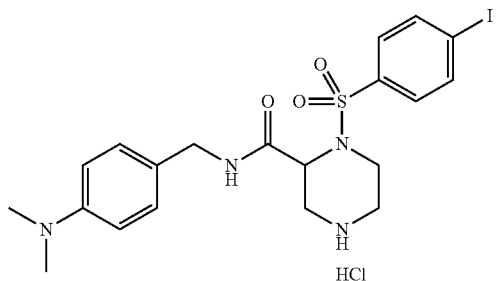
HCl |
| 85 | 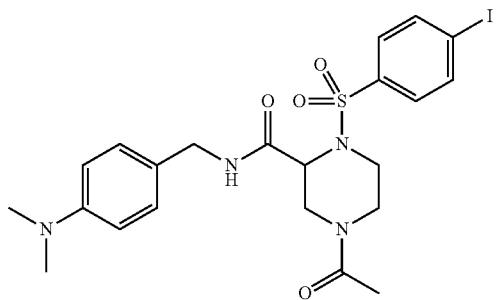 |

TABLE 18

| Ex. No. | Structural Formula |
|---|---|
| 86 | (structure: N,N-dimethylaminobenzyl-NH-C(O)-piperazine with N-sulfonyl-(4-iodophenyl) and N-C(O)-CH2-NH-Boc substituents) |
| 87 | (structure: N,N-dimethylaminobenzyl-NH-C(O)-piperazine with N-sulfonyl-(4-iodophenyl) and N-C(O)-CH2CH2-NH-Boc substituents) |
| 88 | (structure: N,N-dimethylaminobenzyl-NH-C(O)-piperazine with N-sulfonyl-(4-iodophenyl) and N-C(O)-CH2-NH2 substituents) · HCl |
| 89 | (structure: N,N-dimethylaminobenzyl-NH-C(O)-piperazine with N-sulfonyl-(4-iodophenyl) and N-C(O)-CH2CH2-NH2 substituents) · HCl |
| 90 | (structure: 4-aminobenzyl-NH-C(O)-piperazine with N-sulfonyl-(4-iodophenyl) and N-acetyl substituents) · HCl |

TABLE 19
| Ex. No. | Structural Formula |
|---|---|
| 91 | 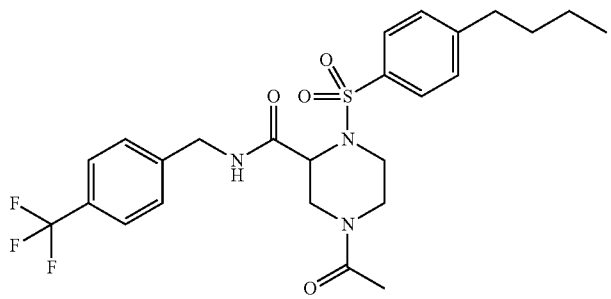 |
| 92 | 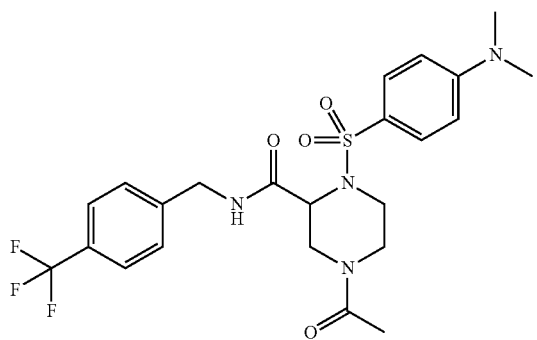 |
| 93 | 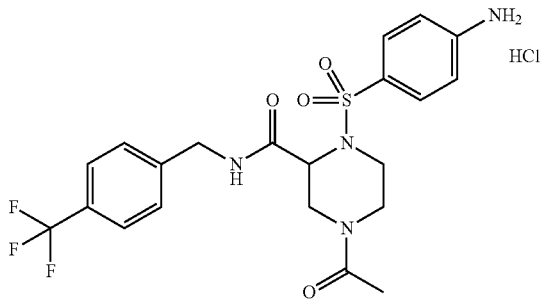 |
| 94 | 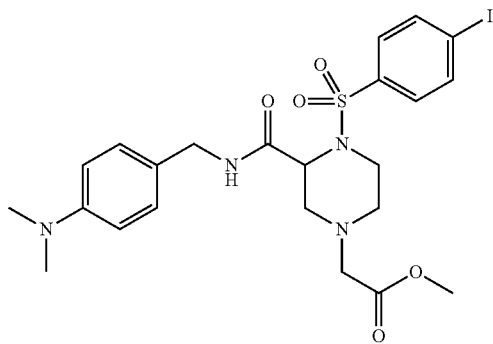 |

TABLE 19-continued

| Ex. No. | Structural Formula |
|---|---|
| 95 | |

TABLE 20

| Ex. No. | Structural Formula |
|---|---|
| 96 | |
| 97 | |
| 98 | |

TABLE 20-continued

| Ex. No. | Structural Formula |
|---|---|
| 99 | |
| 100 | |

TABLE 21

| Ex. No. | Structural Formula |
|---|---|
| 101 | |
| 102 | |
| 103 | |

TABLE 21-continued

| Ex. No. | Structural Formula |
|---|---|
| 104 | (structure) |
| 105 | (structure) |

TABLE 22

| Ex. No. | Structural Formula |
|---|---|
| 106 | (structure) |
| 107 | (structure) |
| 108 | (structure) |

TABLE 22-continued

| Ex. No. | Structural Formula |
|---|---|
| 109 | |
| 110 | |

TABLE 23

| Ex. No. | Structural Formula |
|---|---|
| 111 | |
| 112 | |

TABLE 23-continued
| Ex. No. | Structural Formula |
|---|---|
| 113 | 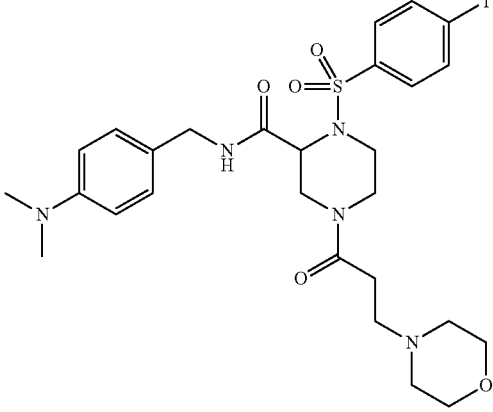 |
| 114 | 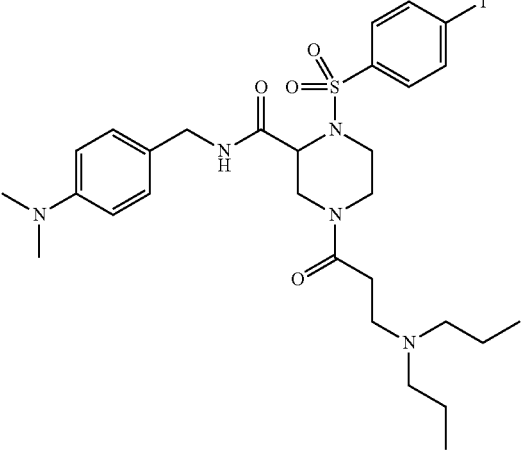 |
| 115 | 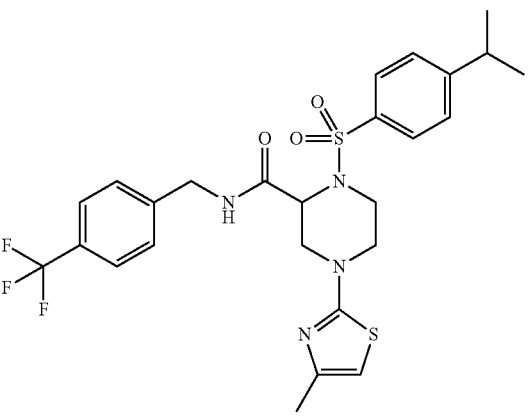 |
TABLE 24
| Ex. No. | Structural Formula |
|---|---|
| 116 | 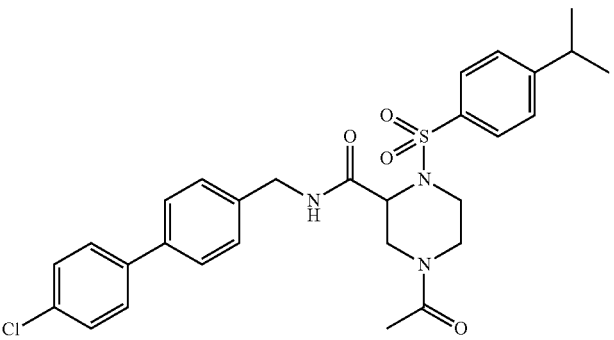 |

TABLE 24-continued
| Ex. No. | Structural Formula |
|---|---|
| 117 | 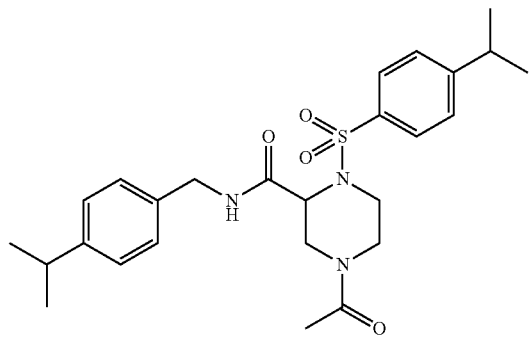 |
| 118 | 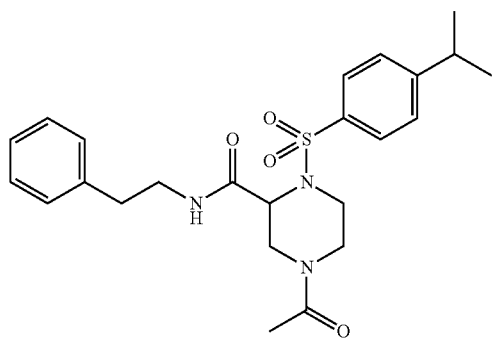 |
| 119 | 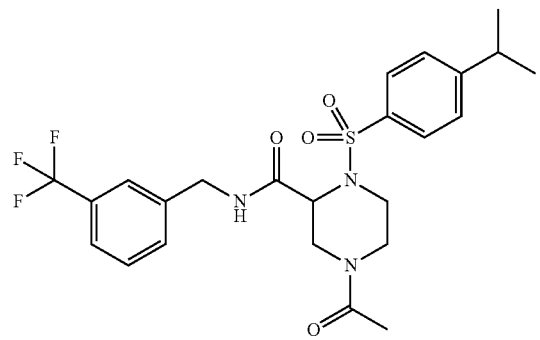 |

TABLE 24-continued
| Ex. No. | Structural Formula |
|---|---|
| 120 | 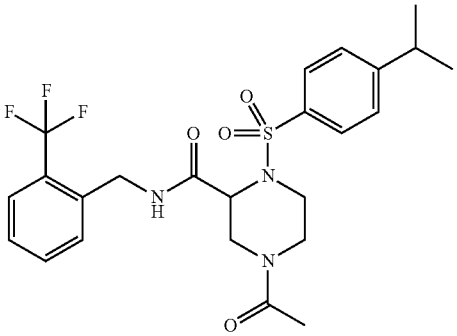 |
TABLE 25
| Ex. No. | Structural Formula |
|---|---|
| 121 | 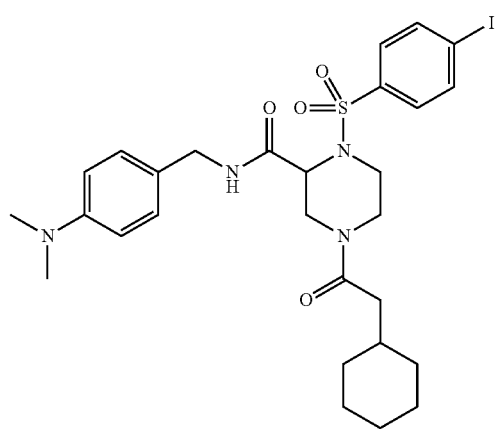 |
| 122 | 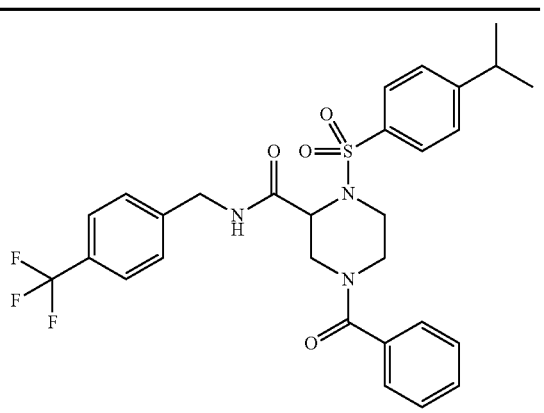 |
TABLE 25-continued
| Ex. No. | Structural Formula |
|---|---|
| 123 | 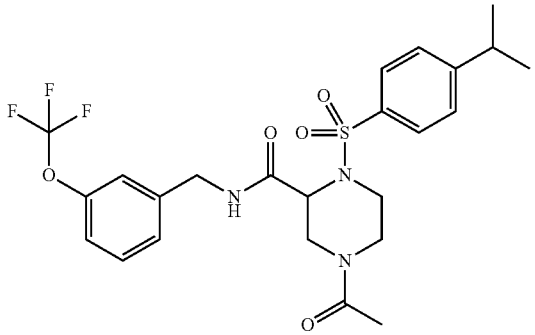 |
| 124 | 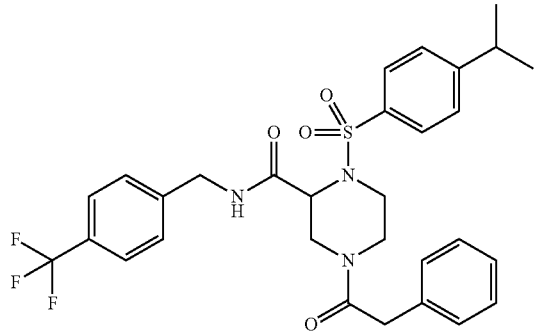 |
| 125 | 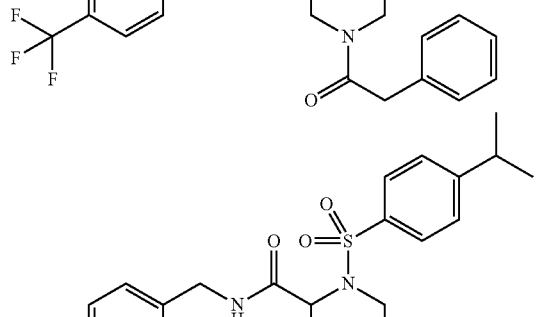 |

TABLE 26
| Ex. No. | Structural Formula |
|---|---|
| 126 | 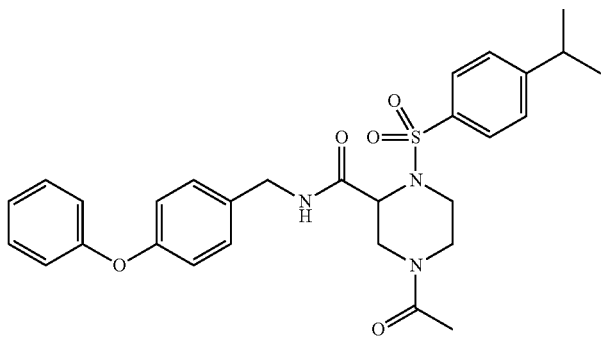 |
| 127 | 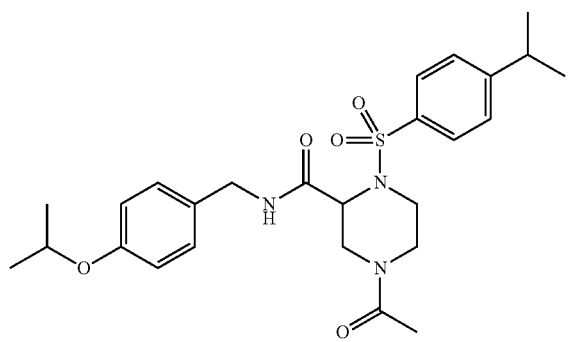 |
| 128 | 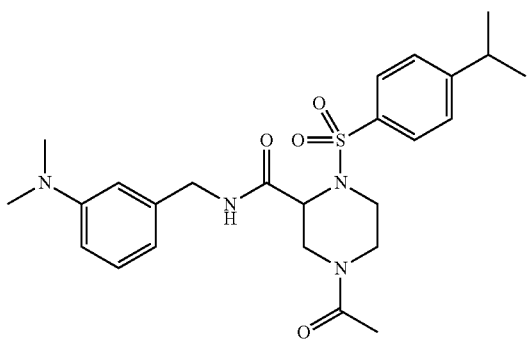 |
| 129 | 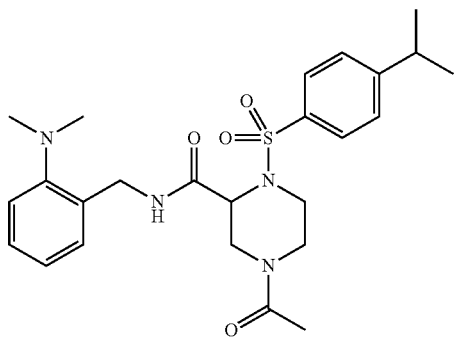 |

TABLE 26-continued
| Ex. No. | Structural Formula |
|---|---|
| 130 |  |
TABLE 27
| Ex. No. | Structural Formula |
|---|---|
| 131 | 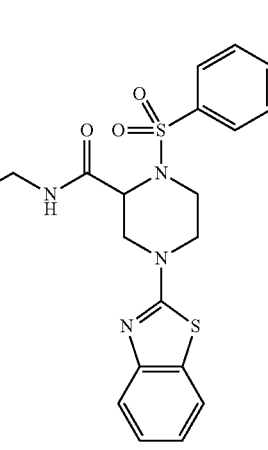 |
| 132 | |
| 133 | |
TABLE 27-continued
| Ex. No. | Structural Formula |
|---|---|
| 134 | 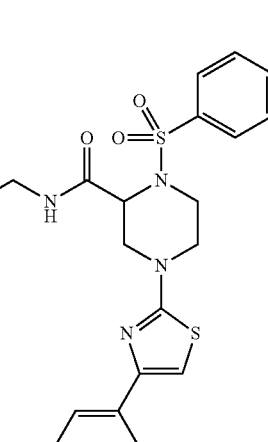 |
| 135 | |

TABLE 28
| Ex. No. | Structural Formula |
|---|---|
| 136 | 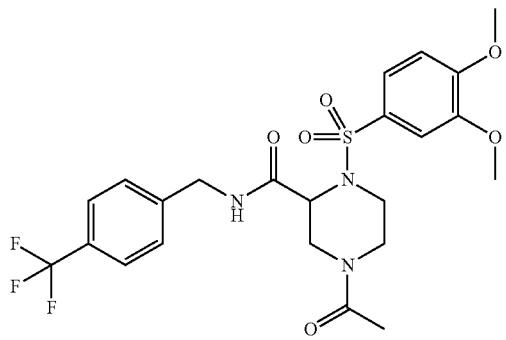 |
| 137 | 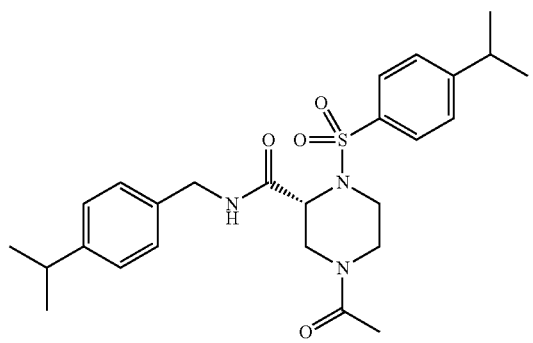 |
| 138 | 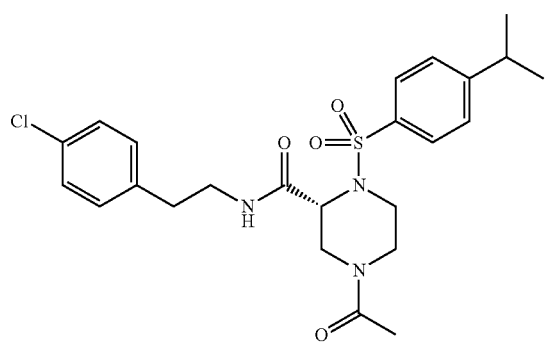 |
| 139 | 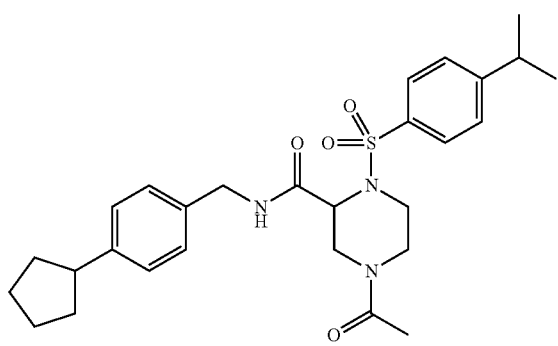 |

TABLE 28-continued

| Ex. No. | Structural Formula |
| --- | --- |
| 140 | |

TABLE 29

| Ex. No. | Structural Formula |
| --- | --- |
| 141 | |
| 142 | |
| 143 | |

TABLE 29-continued

| Ex. No. | Structural Formula |
| --- | --- |
| 144 | |
| 145 | |

TABLE 30
| Ex. No. | Structural Formula |
|---|---|
| 146 | 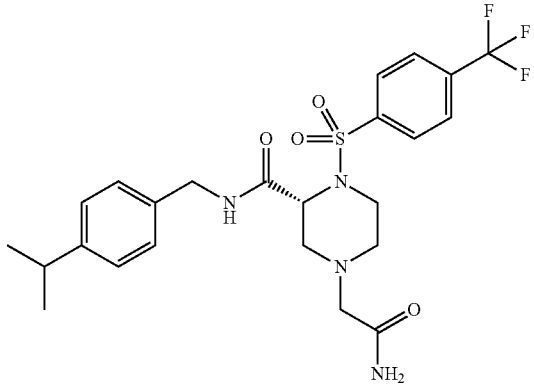 |
| 147 | 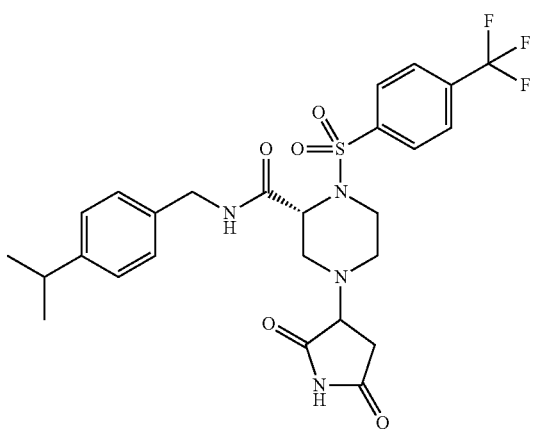 |
| 148 | 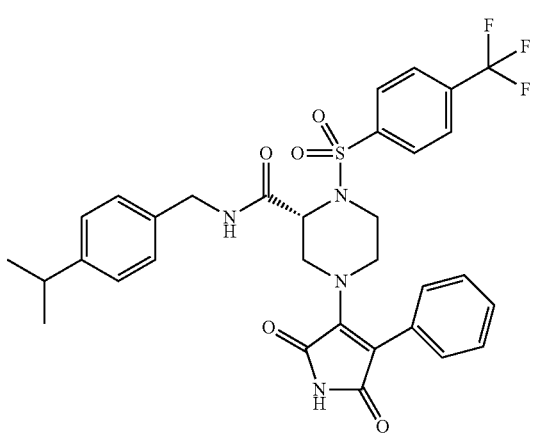 |
| 149 | 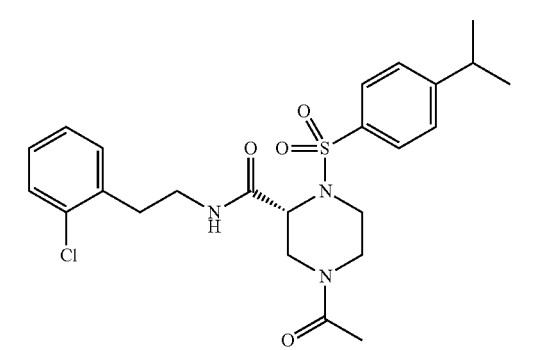 |
TABLE 30-continued
| Ex. No. | Structural Formula |
|---|---|
| 150 | 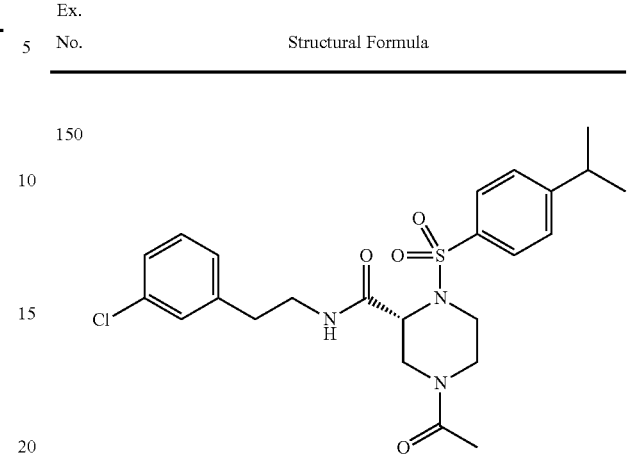 |
TABLE 31
| Ex. No. | Structural Formula |
|---|---|
| 151 | 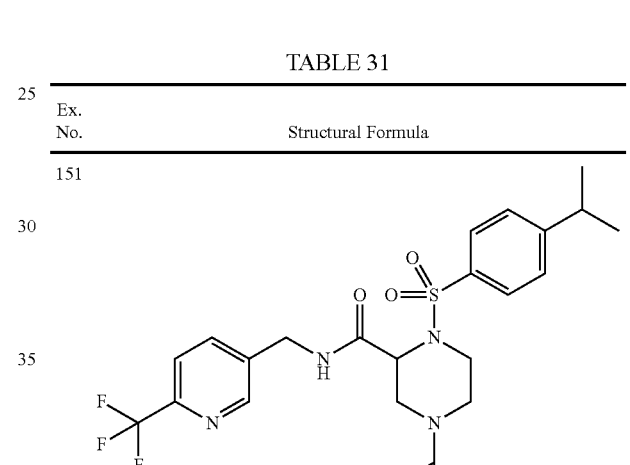 |
| 152 | 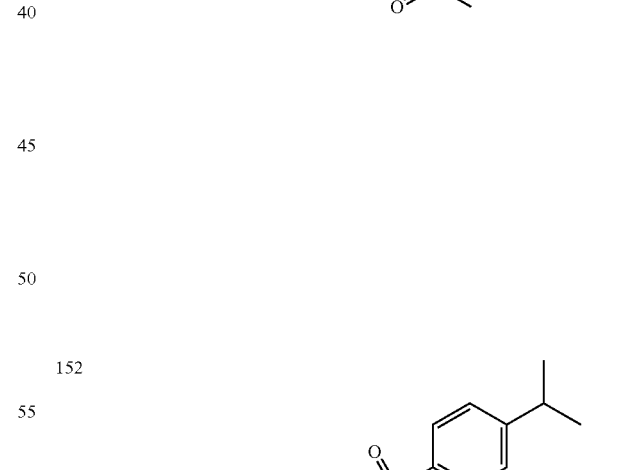 |

TABLE 31-continued

| Ex. No. | Structural Formula |
|---|---|
| 153 | |
| 154 | |
| 155 | |

TABLE 32

| Ex. No. | Structural Formula |
|---|---|
| 156 | |
| 157 | |
| 158 | |
| 159 | |

TABLE 32-continued

| Ex. No. | Structural Formula |
|---|---|
| 160 | |

TABLE 33

| Ex. No. | Structural Formula |
|---|---|
| 161 | |
| 162 | |
| 163 | |

TABLE 33-continued

| Ex. No. | Structural Formula |
|---|---|
| 164 | |
| 165 | |

TABLE 34

| Ex. No. | Structural Formula |
|---|---|
| 166 | |
| 167 | |

TABLE 34-continued

| Ex. No. | Structural Formula |
|---|---|
| 168 | |
| 169 | |
| 170 | |

TABLE 35

| Ex. No. | Structural Formula |
|---|---|
| 171 | |
| 172 | |
| 173 | |
| 174 | |

TABLE 35-continued

| Ex. No. | Structural Formula |
|---|---|
| 175 | |

TABLE 36

| Ex. No. | Structural Formula |
|---|---|
| 176 | |
| 177 | |
| 178 | |

TABLE 36-continued

| Ex. No. | Structural Formula |
|---|---|
| 179 | |
| 180 | |

TABLE 37
| Ex. No. | Structural Formula |
| --- | --- |
| 181 | 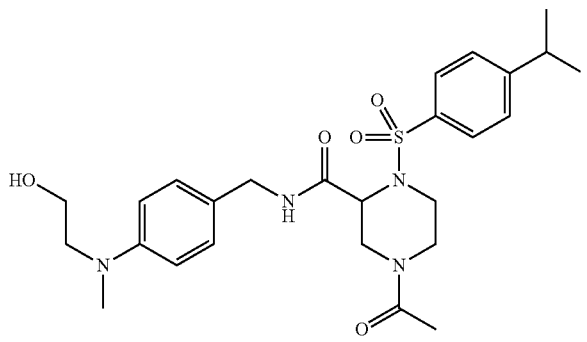 |
| 182 | 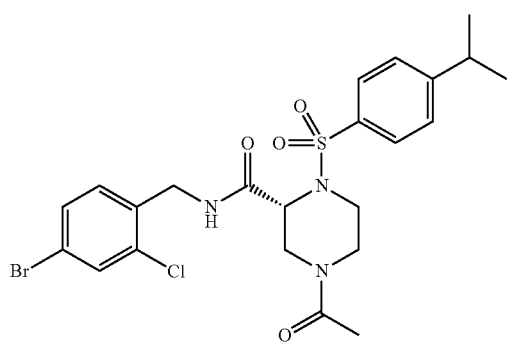 |
| 183 | 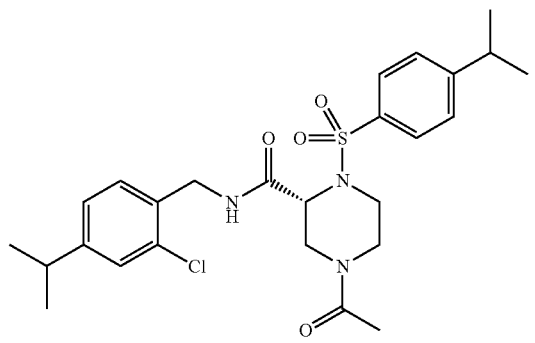 |
| 184 | 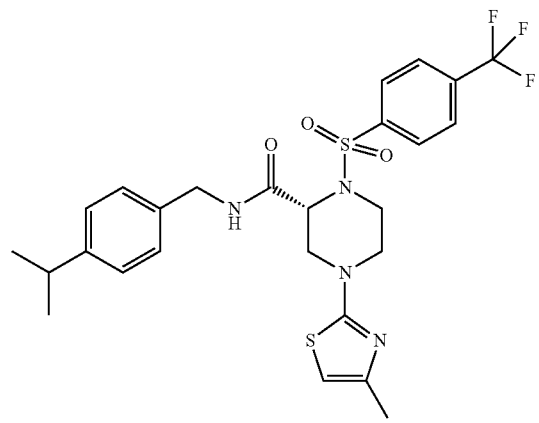 |

TABLE 37-continued
| Ex. No. | Structural Formula |
|---|---|
| 185 | 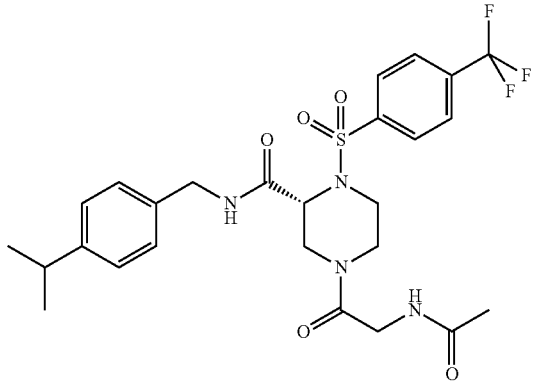 |
TABLE 38
| Ex.No. | Structural Formula |
|---|---|
| 186 | 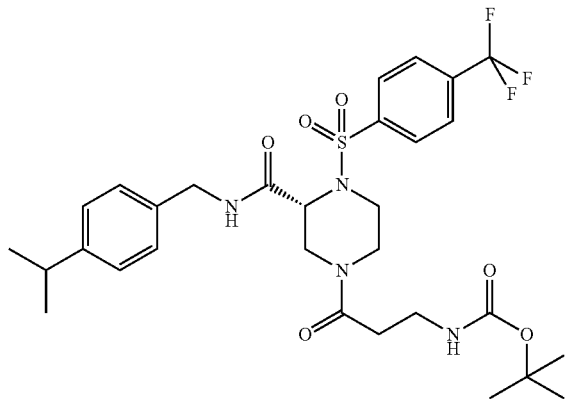 |
| 187 | 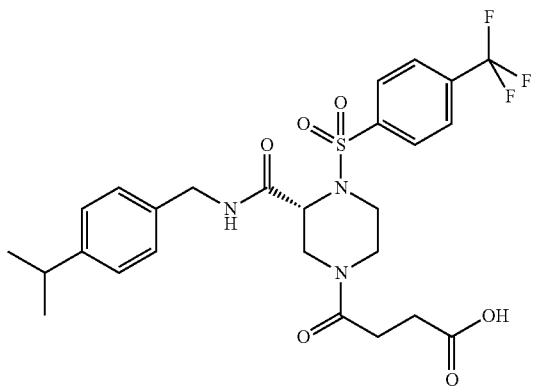 |

TABLE 38-continued
| Ex.No. | Structural Formula |
|---|---|
| 188 | 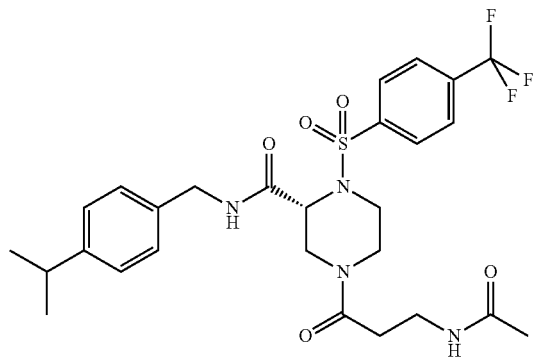 |
| 189 | 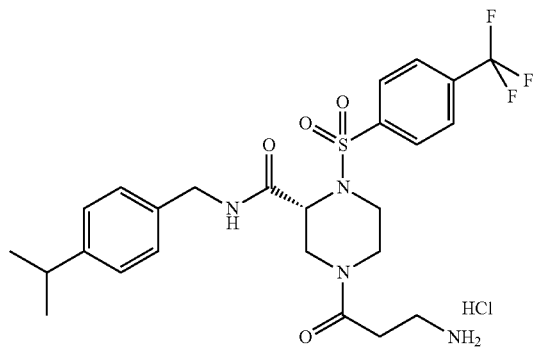 |
| 190 | 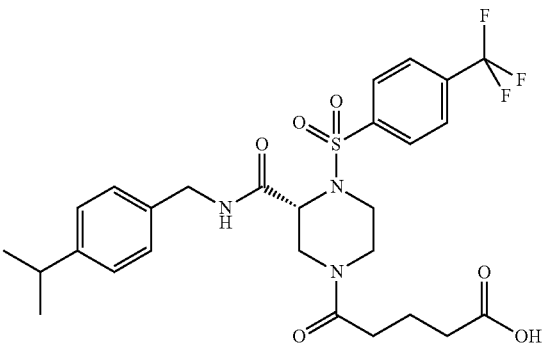 |

TABLE 39
| Ex. No. | Structural Formula |
|---|---|
| 191 | 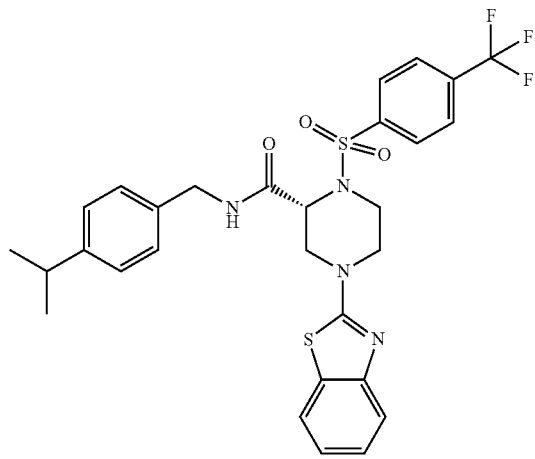 |
| 192 | 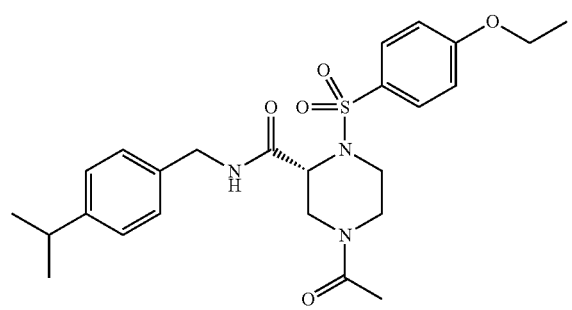 |
| 193 | 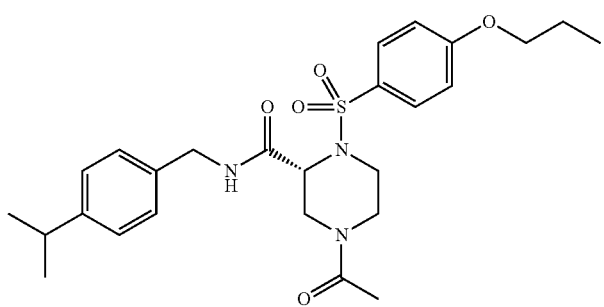 |
| 194 | 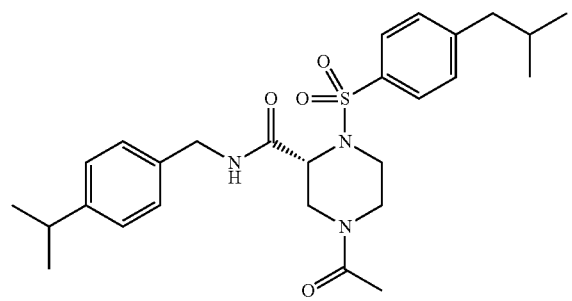 |

TABLE 39-continued
| Ex. No. | Structural Formula |
|---|---|
| 195 | 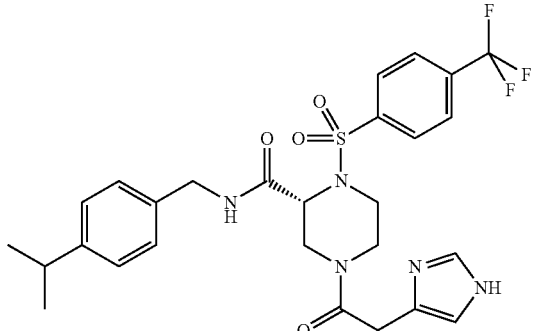 |
TABLE 40
| Ex. No. | Structural Formula |
|---|---|
| 196 | 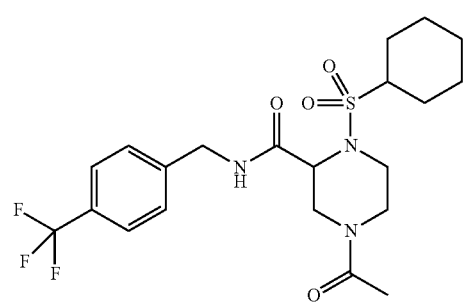 |
| 197 | 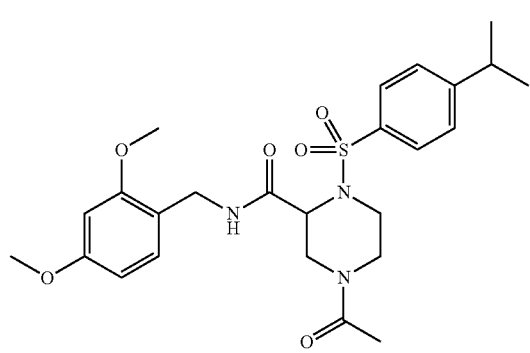 |
| 198 | 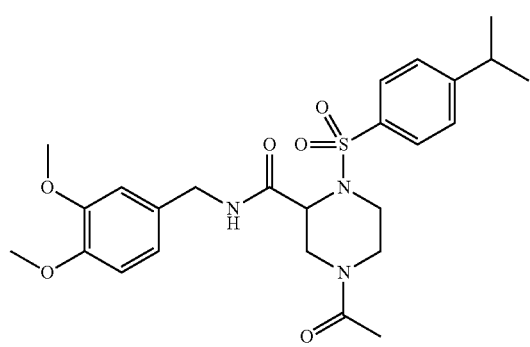 |

TABLE 40-continued
| Ex. No. | Structural Formula |
|---|---|
| 199 | |
| 200 | |
TABLE 41
| Ex. No. | Structural Formula |
|---|---|
| 201 | |
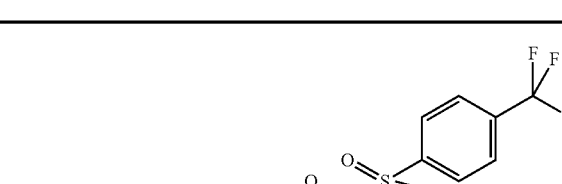

TABLE 41-continued
| Ex. No. | Structural Formula |
|---|---|
| 202 | 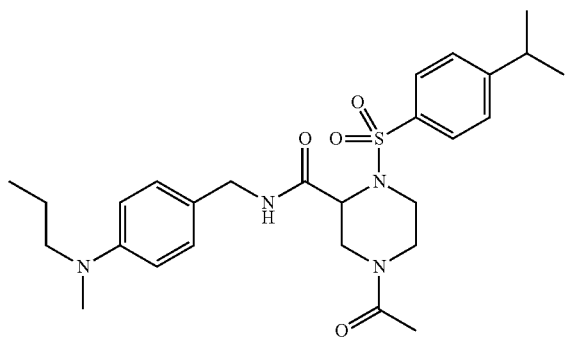 |
| 203 | 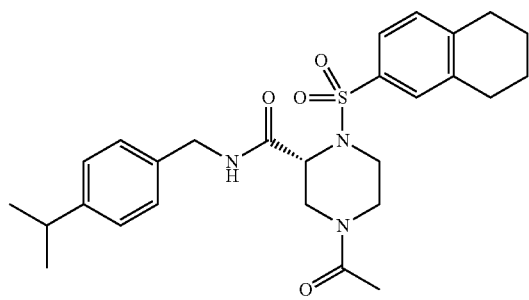 |
| 204 | 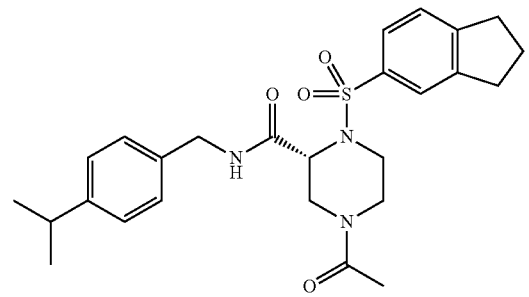 |
| 205 | 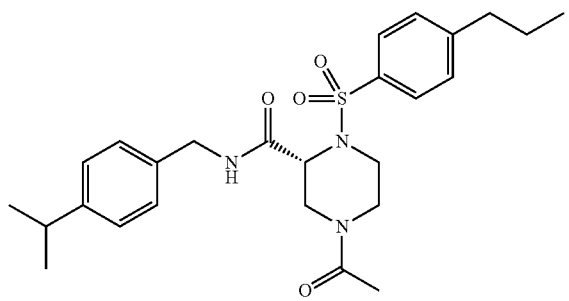 |

TABLE 42
| Ex. No. | Structural Formula |
|---|---|
| 206 | 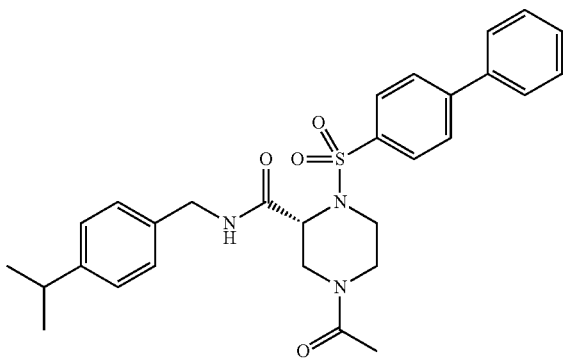 |
| 207 | 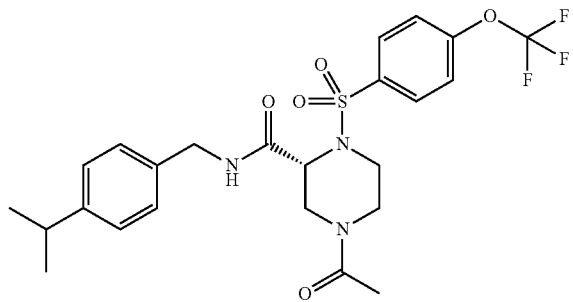 |
| 208 | 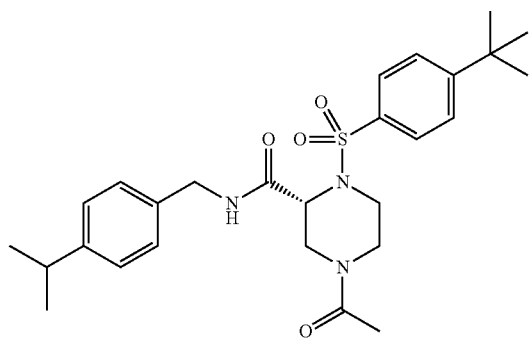 |
| 209 | 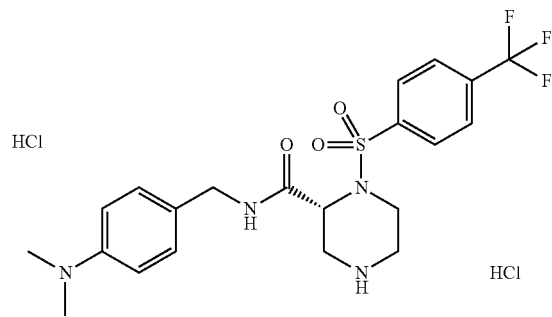 |

TABLE 42-continued
| Ex. No. | Structural Formula |
| --- | --- |
| 210 | 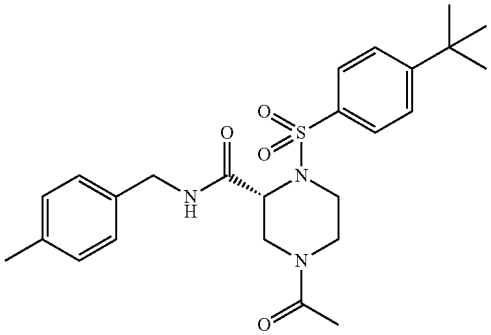 |
TABLE 43
| Ex. No. | Structural Formula |
| --- | --- |
| 211 | 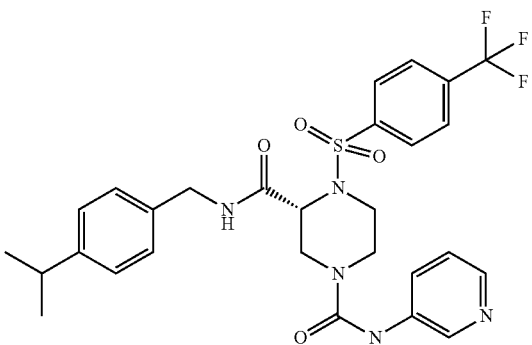 |
| 212 | 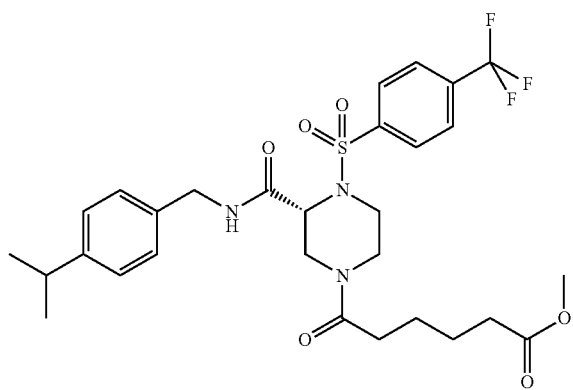 |

369
TABLE 43-continued
| Ex. No. | Structural Formula |
|---|---|
| 213 | 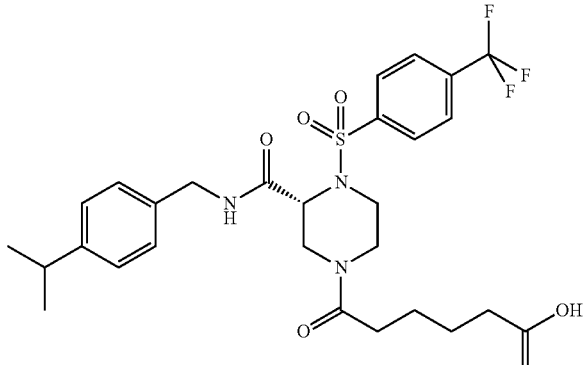 |
| 214 | 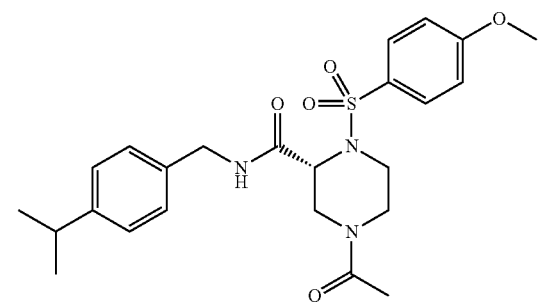 |
| 215 | 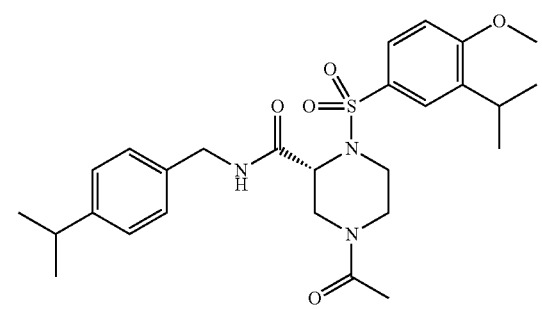 |
TABLE 44
| Ex. No. | Structural Formula |
|---|---|
| 216 | 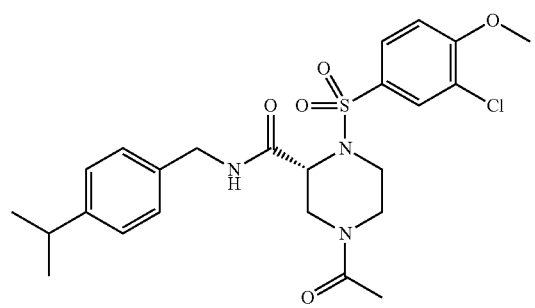 |

TABLE 44-continued

| Ex. No. | Structural Formula |
|---|---|
| 217 | |
| 218 | |
| 219 | |
| 220 | |

TABLE 45
| Ex. No. | Structural Formula |
|---|---|
| 221 | 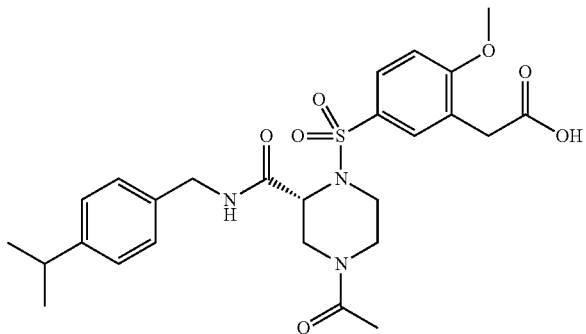 |
| 222 | 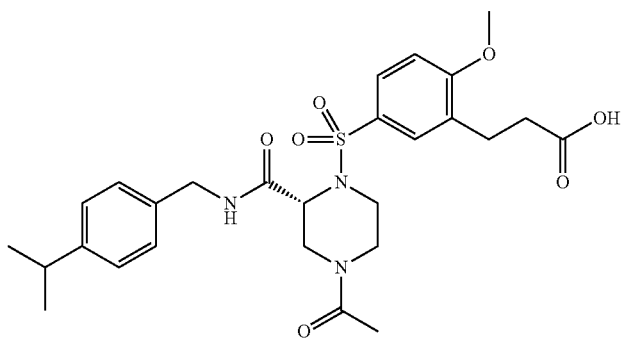 |
| 223 | 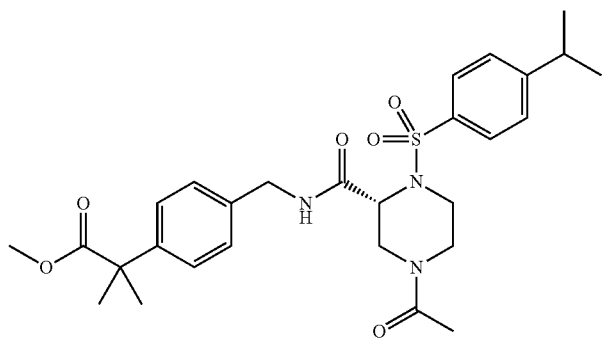 |
| 224 | 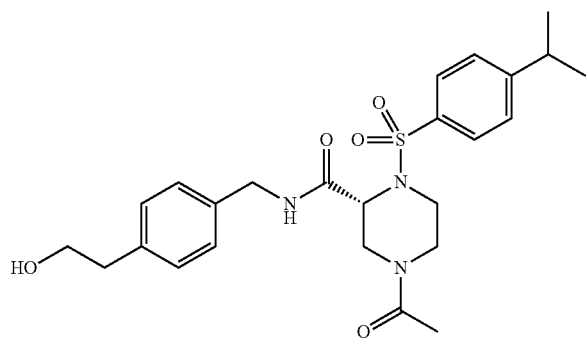 |

TABLE 45-continued

| Ex. No. | Structural Formula |
|---|---|
| 225 | (structure: N-(4-isopropylbenzyl) piperazine-2-carboxamide with 4-(trifluoromethyl)phenylsulfonyl group and glycyl (NH2CH2C(O)-) substituent; HCl salt) |

TABLE 46

| Ex. No. | Structural Formula |
|---|---|
| 226 | (structure: N-(4-hydroxymethylbenzyl) piperazine-2-carboxamide with 4-isopropylphenylsulfonyl group and acetyl group) |
| 227 | (structure: N-(4-methylthiobenzyl) piperazine-2-carboxamide with 4-isopropylphenylsulfonyl group and acetyl group) |
| 228 | (structure: N-(4-isopropylbenzyl) piperazine-2-carboxamide with 4-(trifluoromethyl)phenylsulfonyl group and pyrazol-1-ylacetyl substituent) |

TABLE 46-continued

| Ex. No. | Structural Formula |
|---|---|
| 229 | (structure: N-(4-isopropylbenzyl) piperazine-2-carboxamide with 4-(trifluoromethyl)phenylsulfonyl group and 1,2,4-triazol-1-ylacetyl substituent) |
| 230 | (structure: N-(4-isopropylbenzyl) piperazine-2-carboxamide with 4-(trifluoromethyl)phenylsulfonyl group and 1,2,4-triazol-4-ylacetyl substituent) |

TABLE 47
| Ex. No. | Structural Formula |
|---|---|
| 231 | 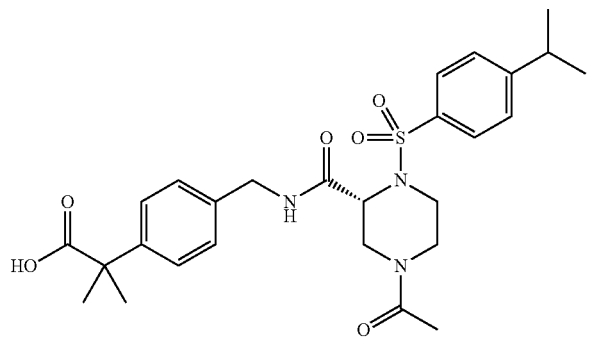 |
| 232 | 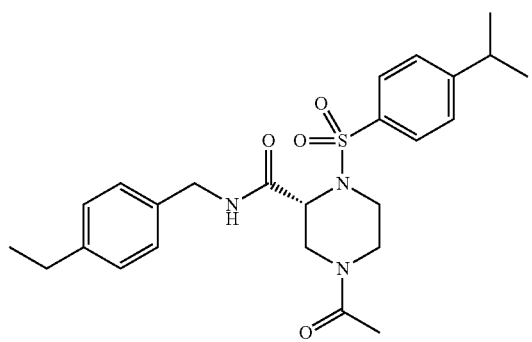 |
| 233 | 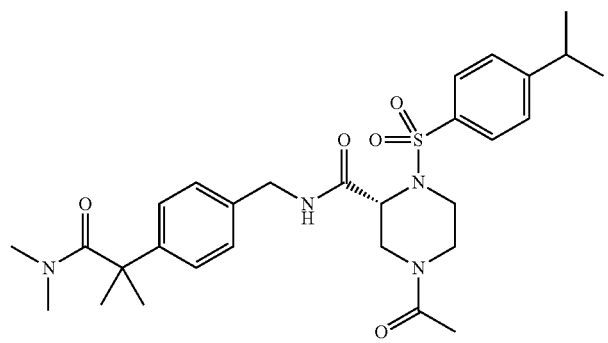 |
| 234 | 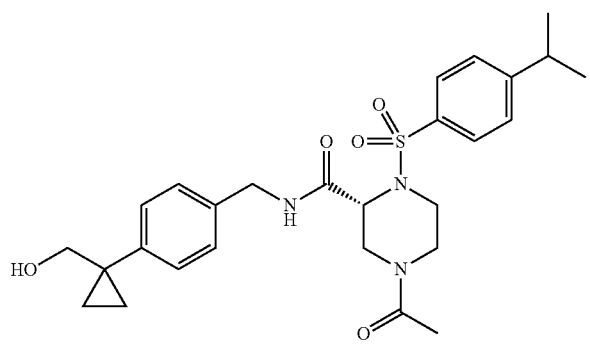 |

TABLE 47-continued
| Ex. No. | Structural Formula |
|---|---|
| 235 | |
TABLE 48
| Ex. No. | Structural Formula |
|---|---|
| 236 | 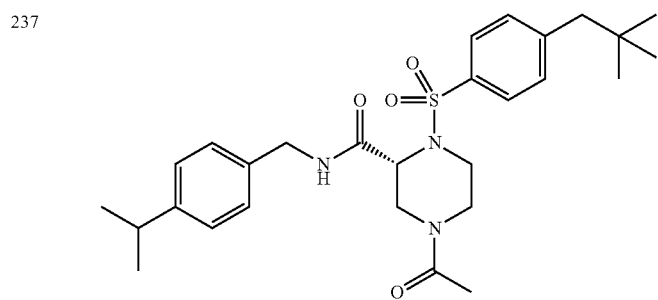 |
| 237 | |
| 238 | 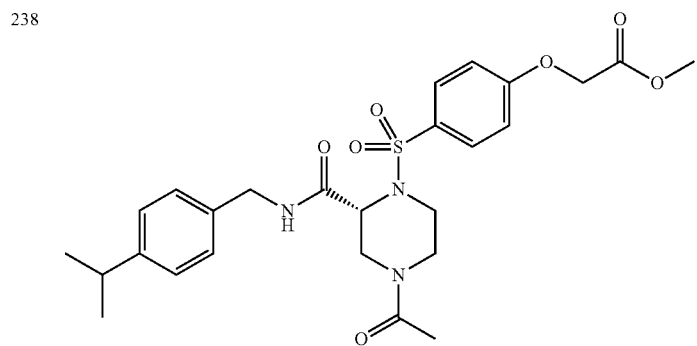 |

TABLE 48-continued
| Ex. No. | Structural Formula |
|---|---|
| 239 | 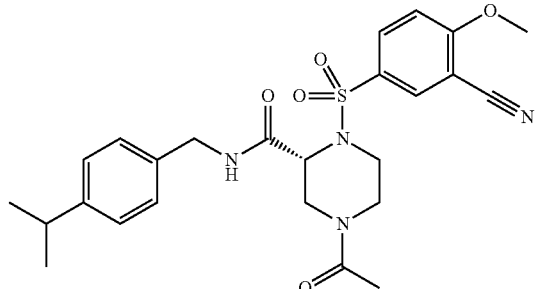 |
| 240 | 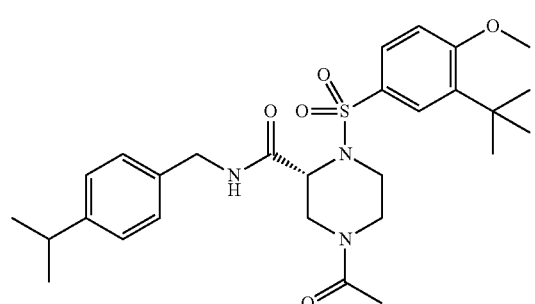 |
TABLE 49
| Ex. No. | Structural Formula |
|---|---|
| 241 | 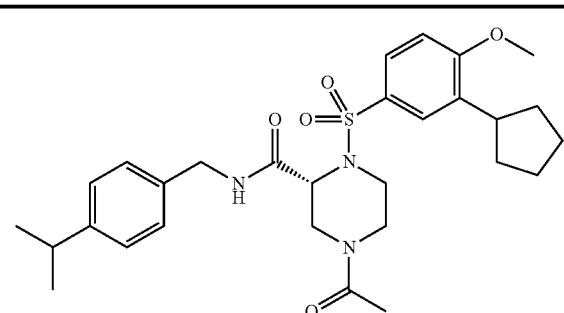 |
| 242 | 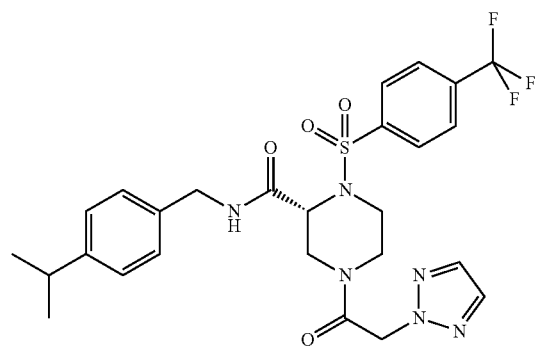 |

TABLE 49-continued

| Ex. No. | Structural Formula |
|---|---|
| 243 | |
| 244 | |
| 245 | |

TABLE 50
| Ex. No. | Structural Formula |
|---|---|
| 246 | 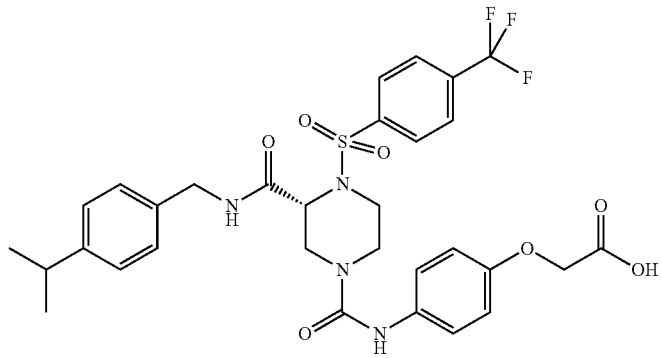 |
| 247 | 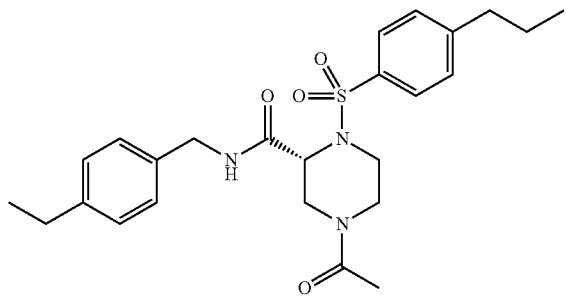 |
| 248 | 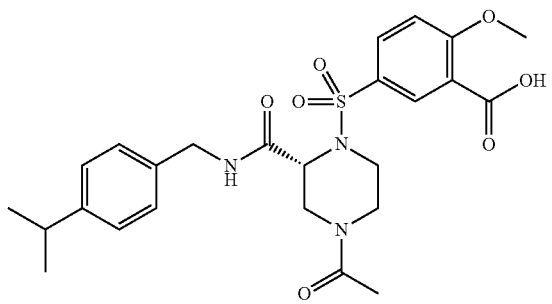 |
| 249 | 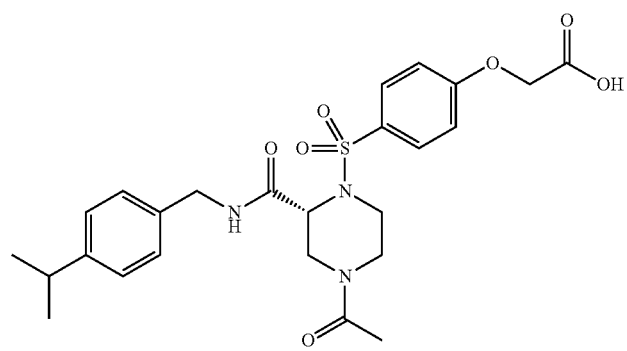 |

TABLE 50-continued
| Ex. No. | Structural Formula |
|---|---|
| 250 | 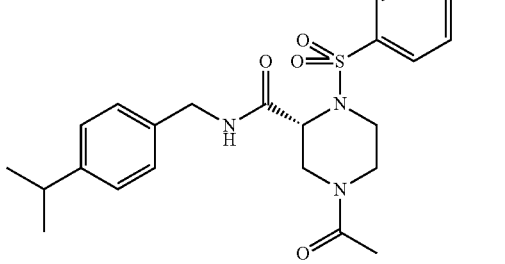 |
TABLE 51
| Ex. No. | Structural Formula |
|---|---|
| 251 | 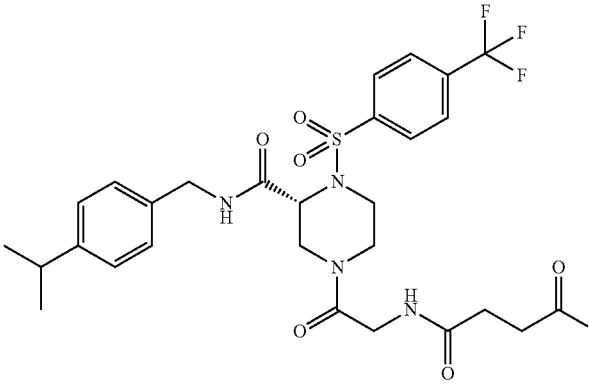 |
| 252 | |
| 253 | 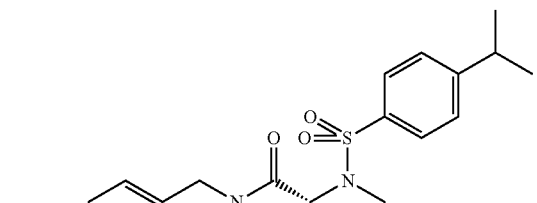 |

TABLE 51-continued
| Ex. No. | Structural Formula |
|---|---|
| 254 | 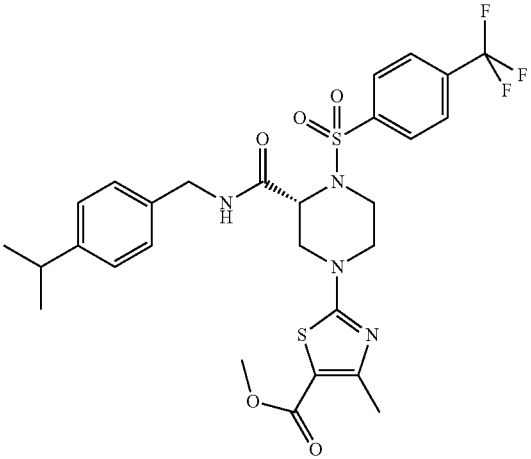 |
| 255 | 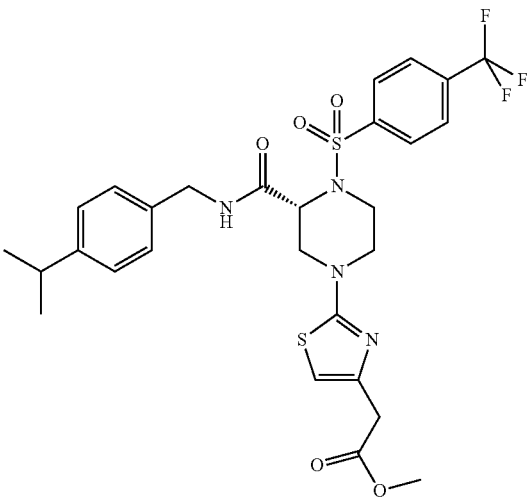 |
TABLE 52
| Ex. No. | Structural Formula |
|---|---|
| 256 | 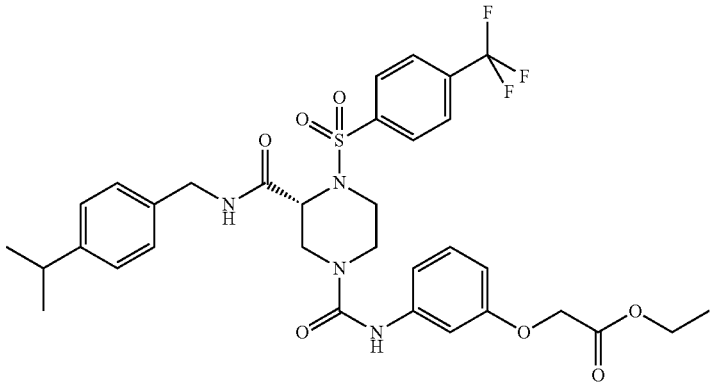 |

TABLE 52-continued
| Ex. No. | Structural Formula |
|---|---|
| 257 | 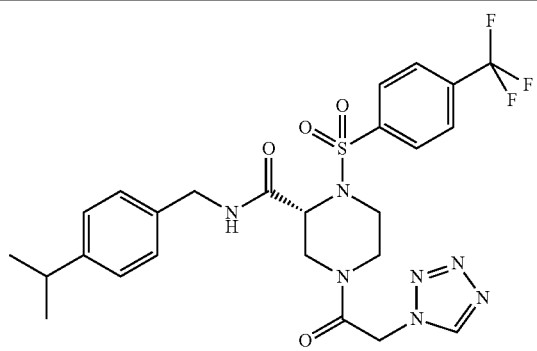 |
| 258 | 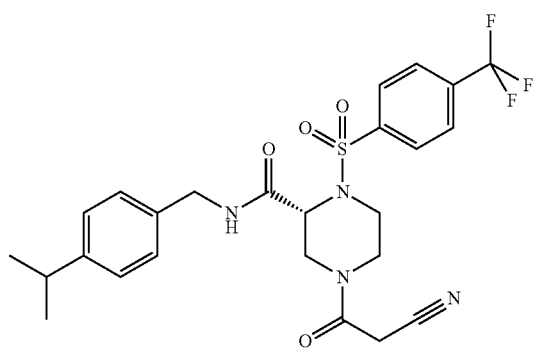 |
| 259 | 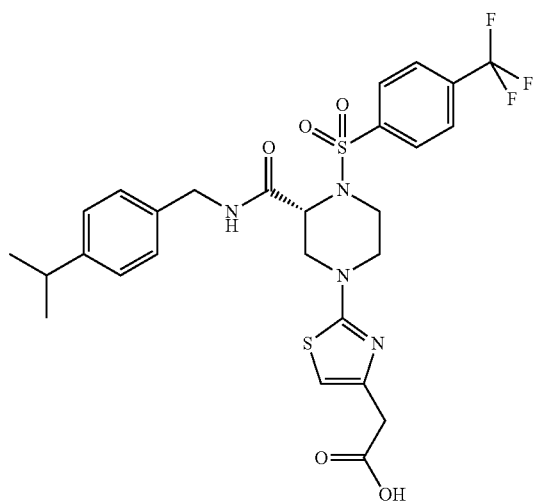 |
| 260 | 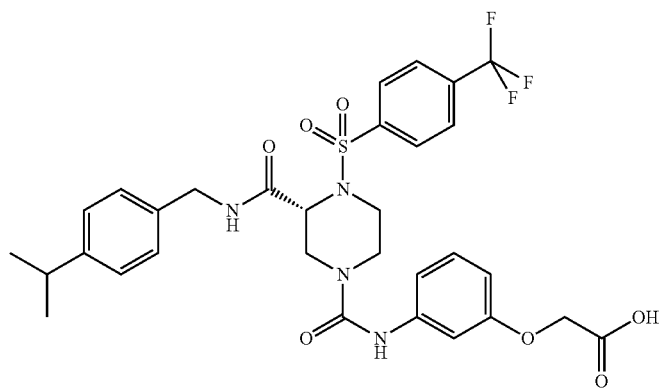 |

TABLE 53
| Ex. No. | Structural Formula |
|---|---|
| 261 | 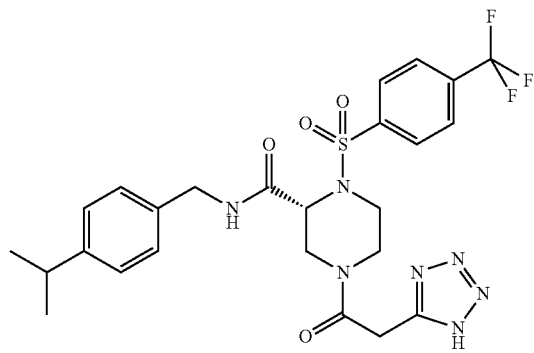 |
| 262 | 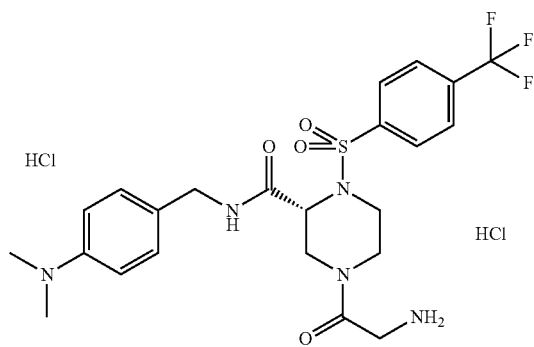 |
| 263 | 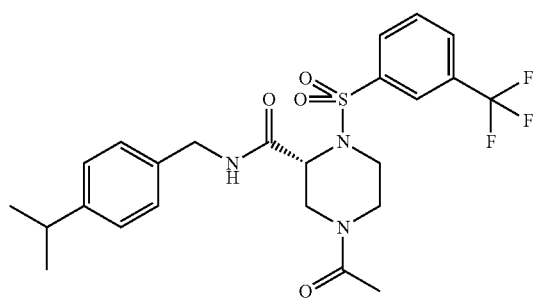 |
| 264 | 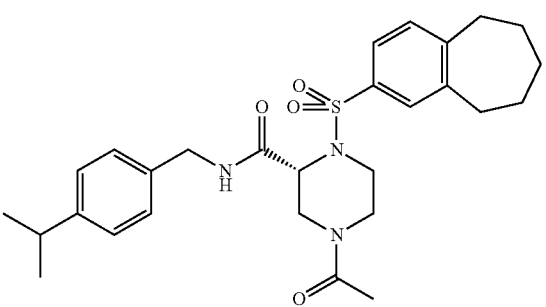 |

TABLE 53-continued
| Ex. No. | Structural Formula |
|---|---|
| 265 | 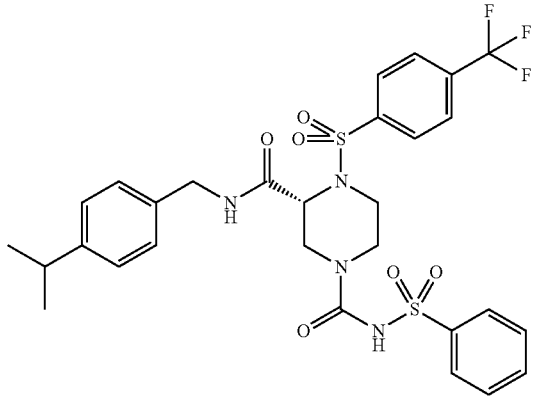 |
TABLE 54
| Ex. No. | Structural Formula |
|---|---|
| 266 | 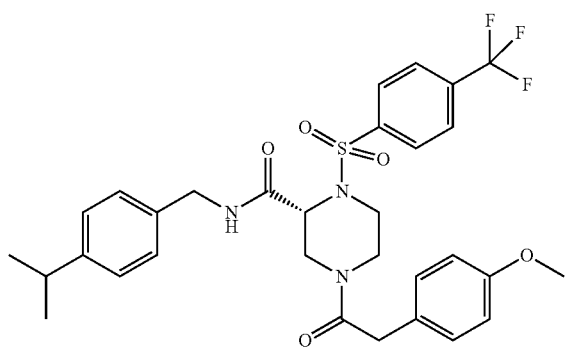 |
| 267 | 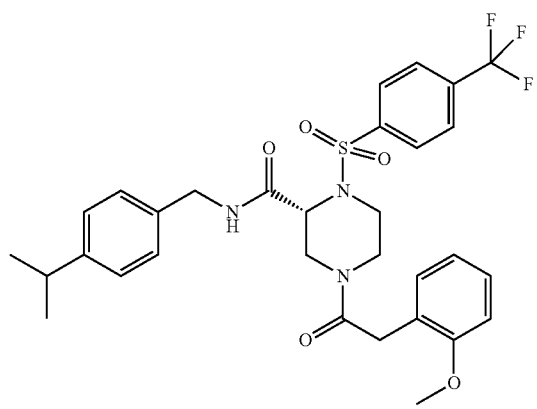 |

TABLE 54-continued
| Ex. No. | Structural Formula |
|---|---|
| 268 | 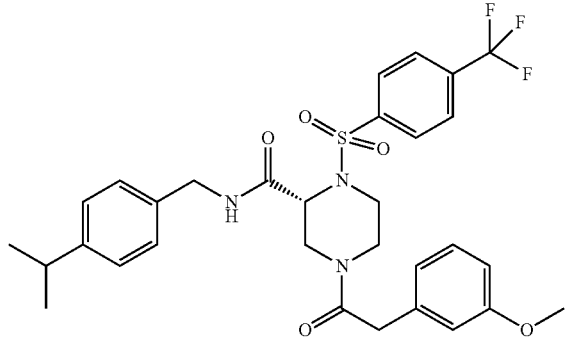 |
| 269 | 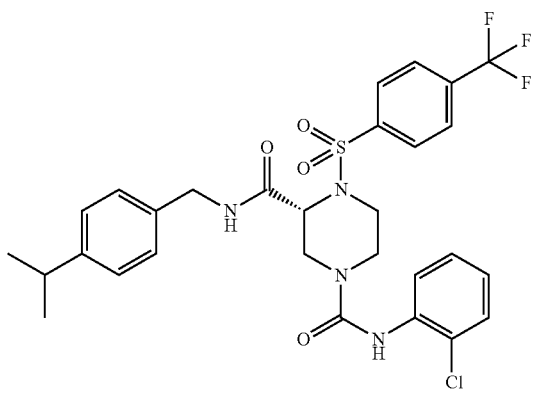 |
| 270 | 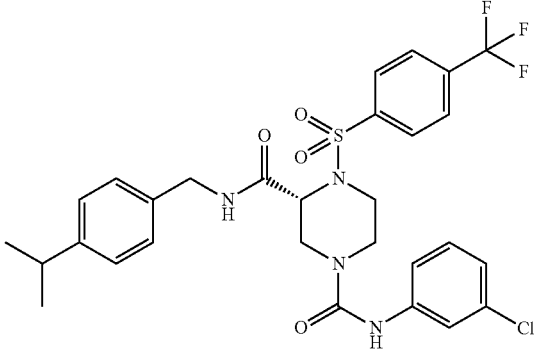 |

TABLE 55
| Ex. No. | Structural Formula |
|---|---|
| 271 | 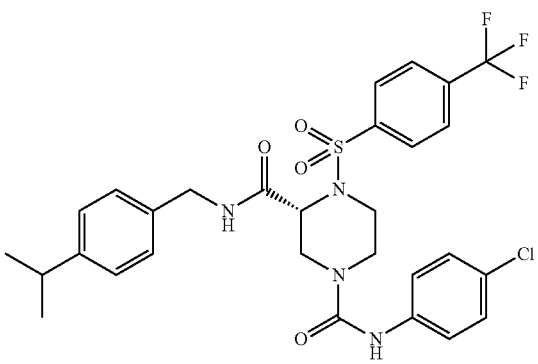 |
| 272 | 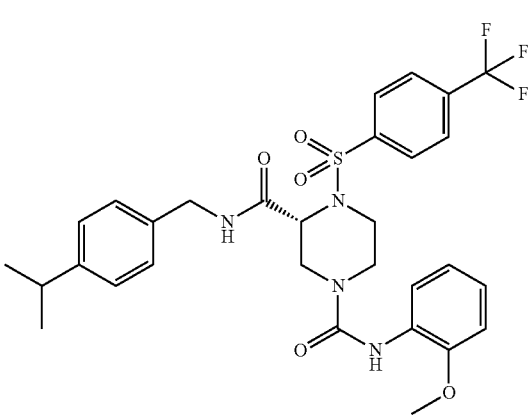 |
| 273 | 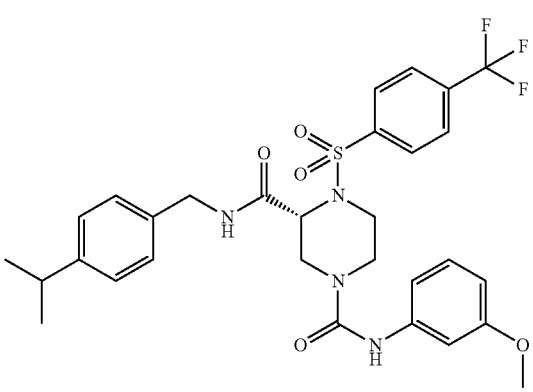 |
| 274 | 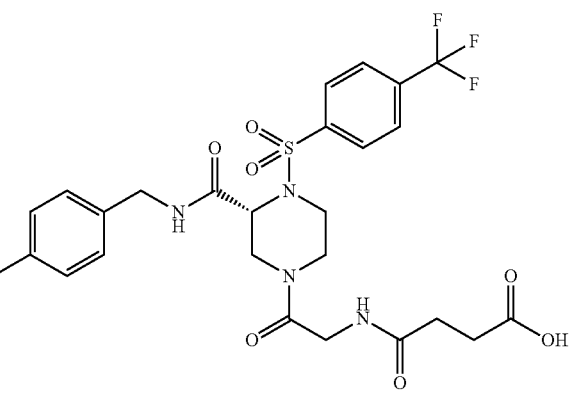 |

TABLE 55-continued

| Ex. No. | Structural Formula |
| --- | --- |
| 275 | (structure) |

TABLE 56

| Ex. No. | Structural Formula |
| --- | --- |
| 276 | (structure) |
| 277 | (structure) |

TABLE 56-continued
| Ex. No. | Structural Formula |
|---|---|
| 278 | 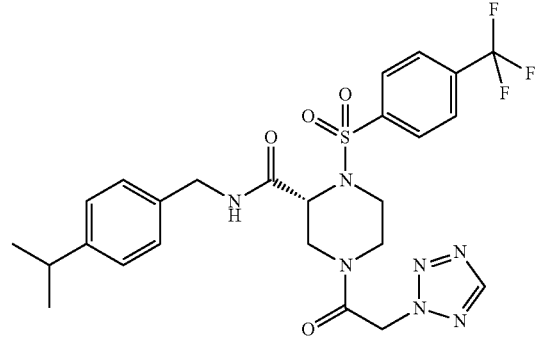 |
| 279 | 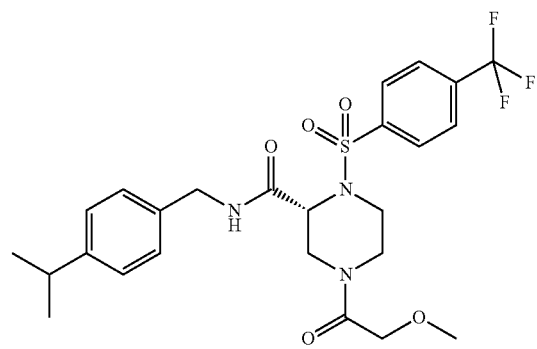 |
| 280 | 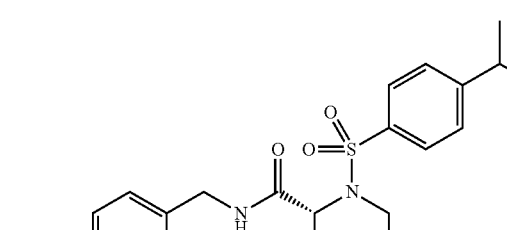 |
TABLE 57
| Ex. No. | Structural Formula |
|---|---|
| 281 | 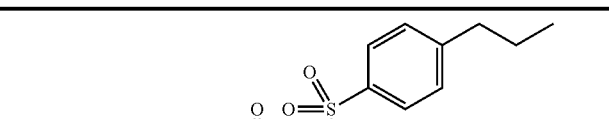 |

TABLE 57-continued
| Ex. No. | Structural Formula |
|---|---|
| 282 | 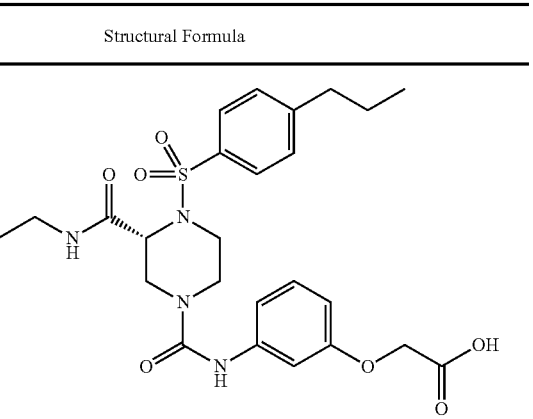 |
| 283 | 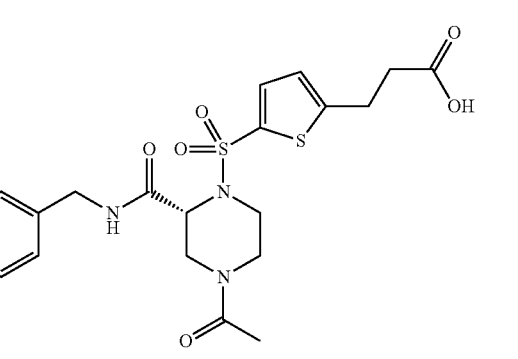 |
| 284 | 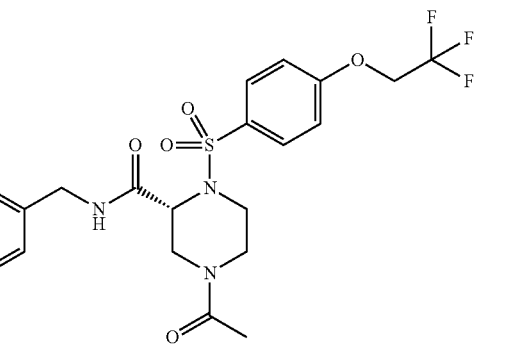 |
| 285 | 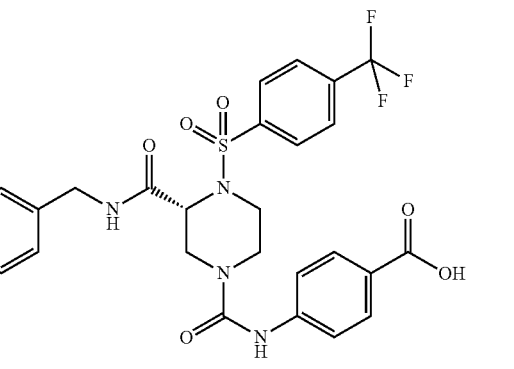 |

TABLE 58
| Ex. No. | Structural Formula |
|---|---|
| 286 | 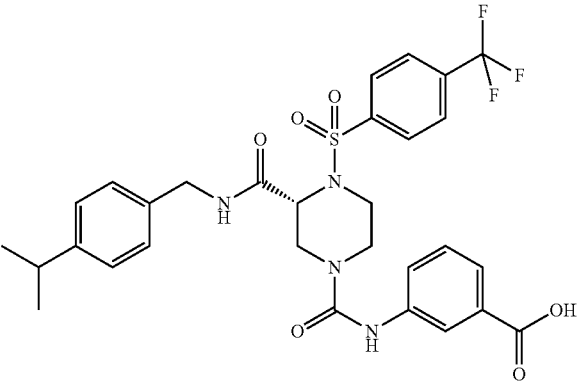 |
| 287 | 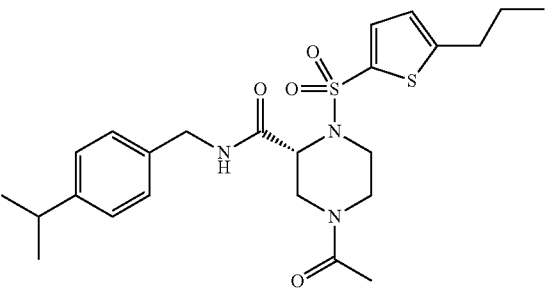 |
| 288 | 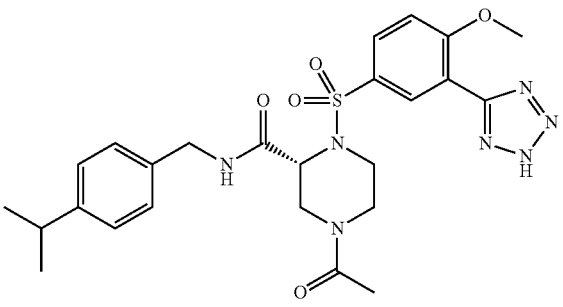 |
| 289 | 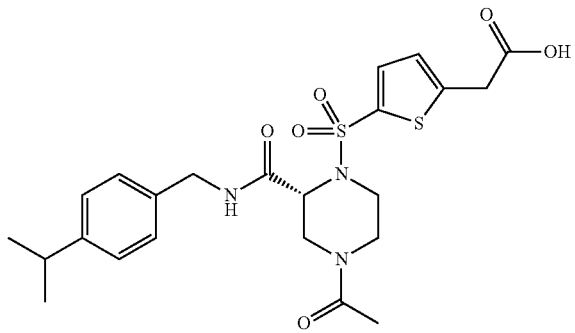 |

TABLE 58-continued
| Ex. No. | Structural Formula |
| --- | --- |
| 290 | 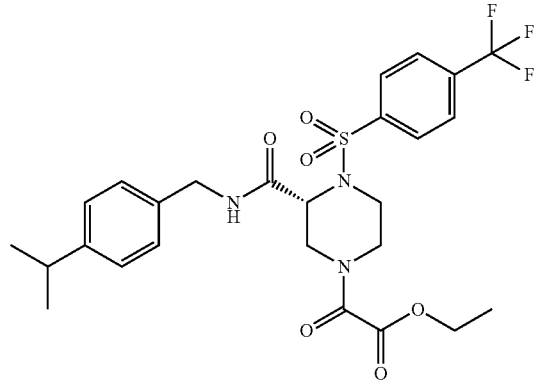 |
TABLE 59
| Ex. No. | Structural Formula |
| --- | --- |
| 291 | 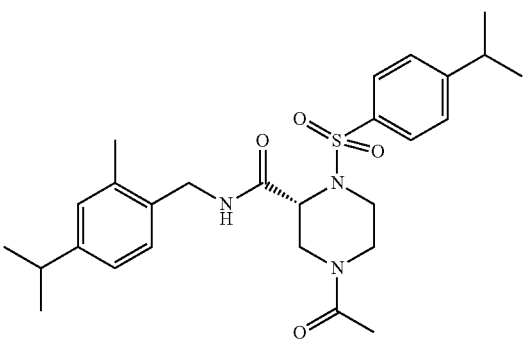 |
| 292 | 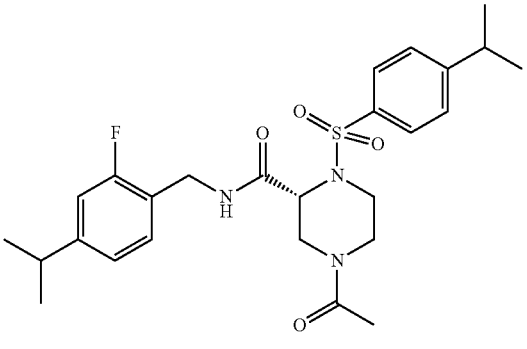 |
| 293 | 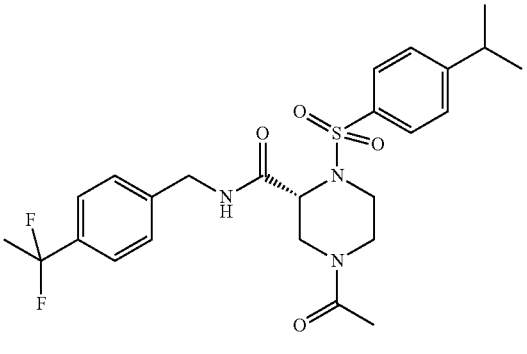 |

TABLE 59-continued
| Ex. No. | Structural Formula |
|---|---|
| 294 | 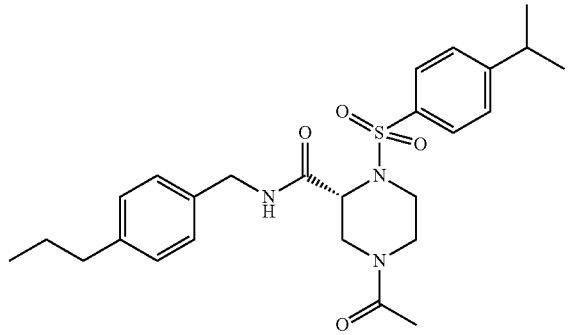 |
| 295 | 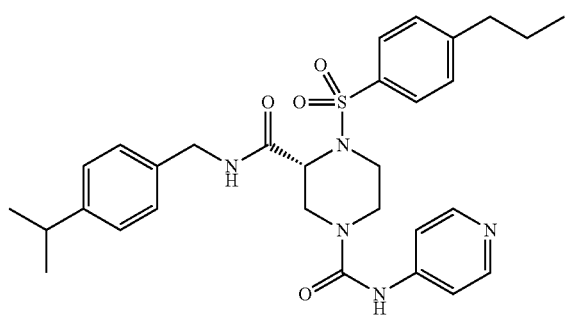 |
TABLE 60
| Ex. No. | Structural Formula |
|---|---|
| 296 | 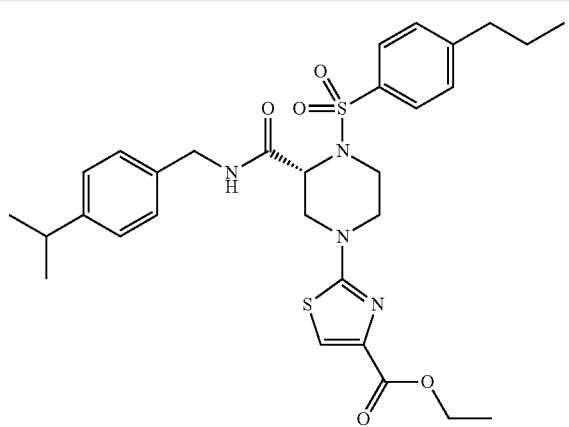 |

TABLE 60-continued
| Ex. No. | Structural Formula |
|---|---|
| 297 | 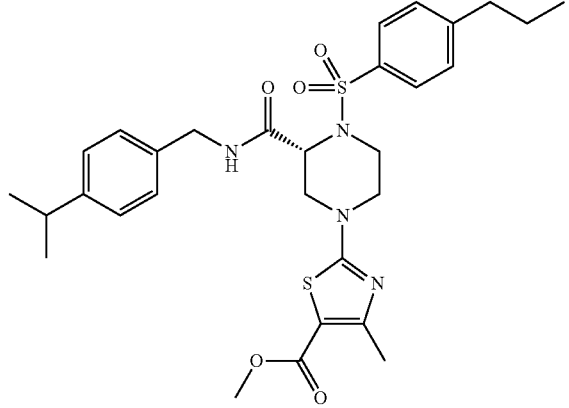 |
| 298 | 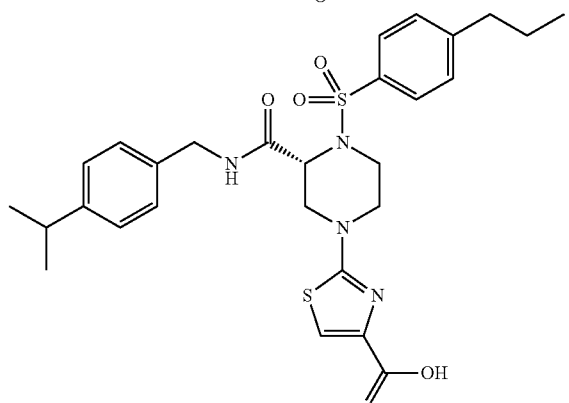 |
| 299 | 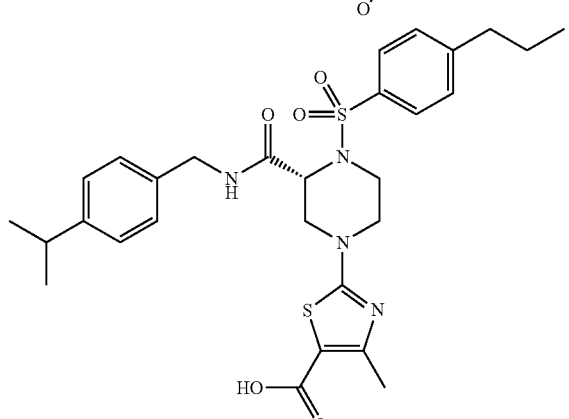 |
| 300 | 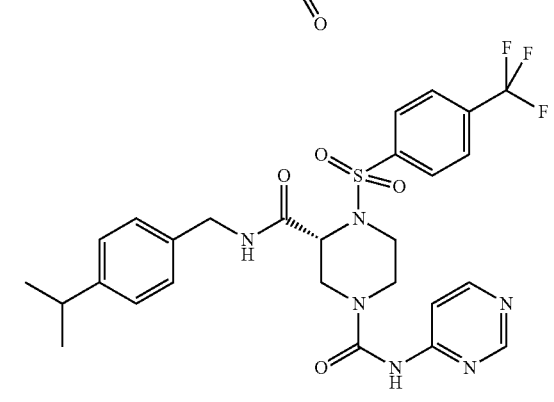 |

US 8,017,612 B2
415
416
TABLE 61
| Ex. No. | Structural Formula |
|---|---|
| 301 | 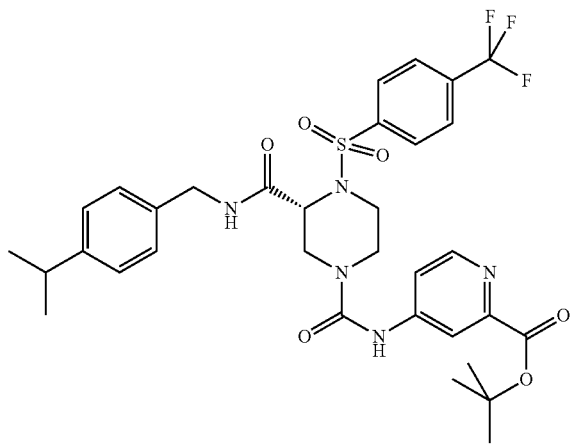 |
| 302 | 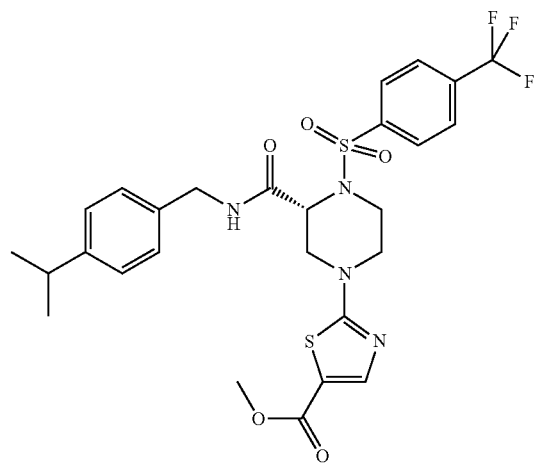 |
| 303 | 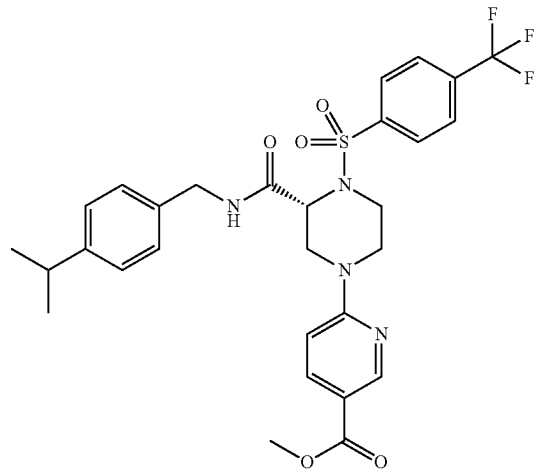 |

TABLE 61-continued
| Ex. No. | Structural Formula |
|---|---|
| 304 | 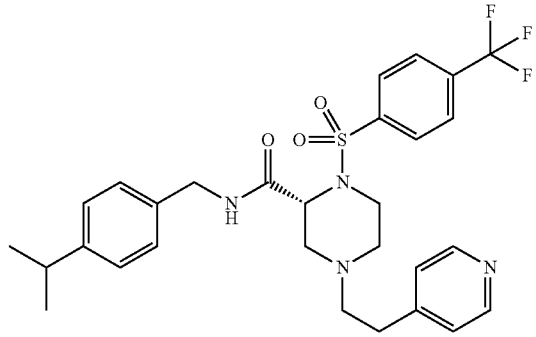 |
| 305 | 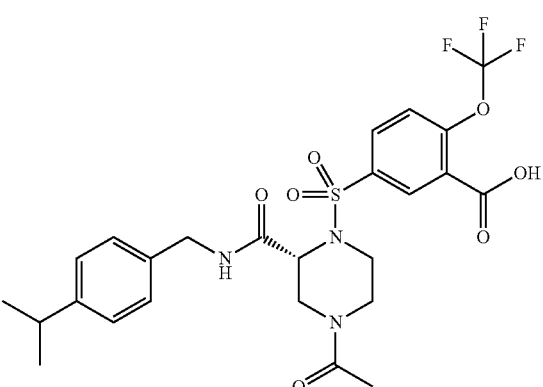 |
TABLE 62
| Ex. No. | Structural Formula |
|---|---|
| 306 | 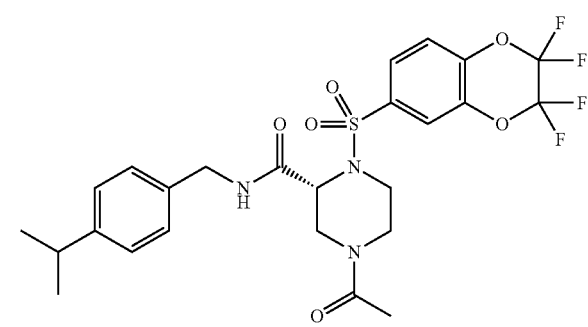 |
| 307 | 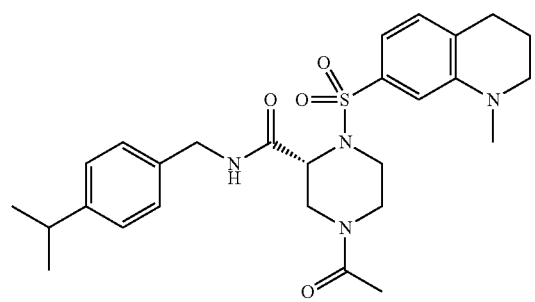 |

TABLE 62-continued
| Ex. No. | Structural Formula |
|---|---|
| 308 | 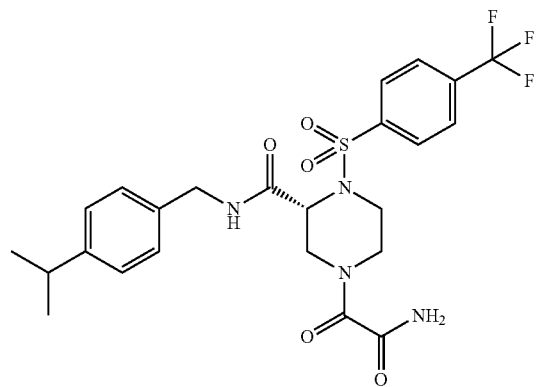 |
| 309 | 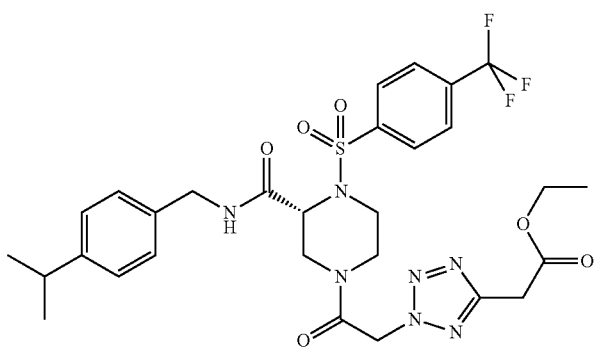 |
| 310 | 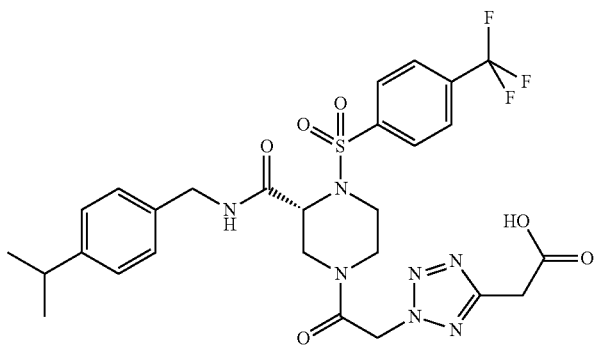 |

421 422
TABLE 63
| Ex. No. | Structural Formula |
|---|---|
| 311 | 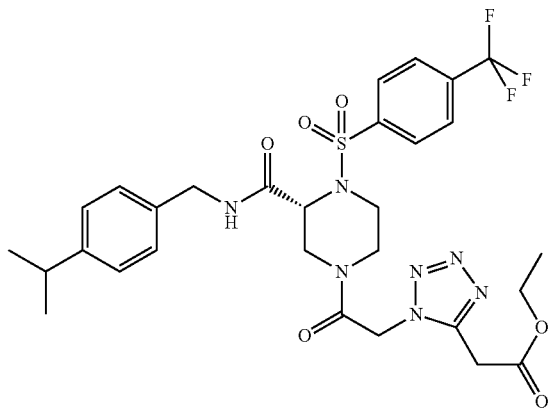 |
| 312 | 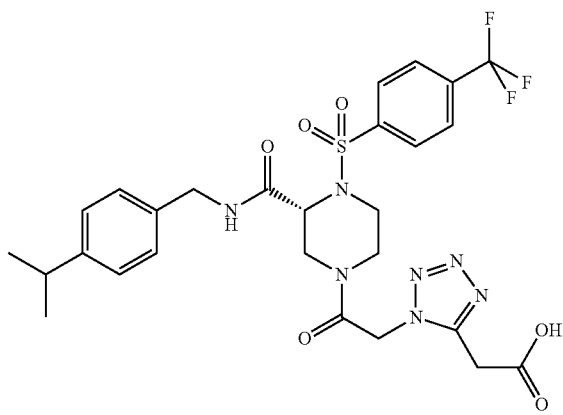 |
| 313 | 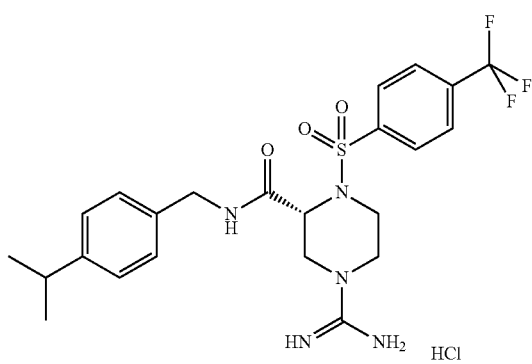 |
| 314 | 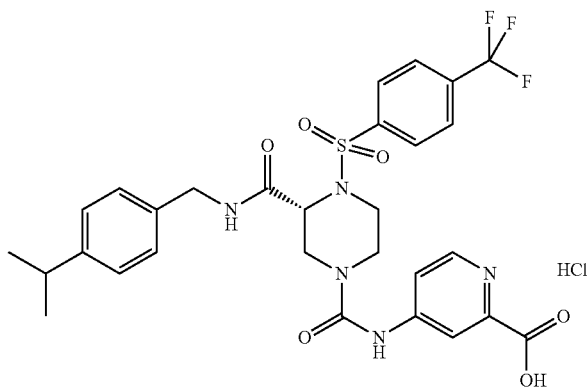 |

TABLE 63-continued
| Ex. No. | Structural Formula |
|---|---|
| 315 | 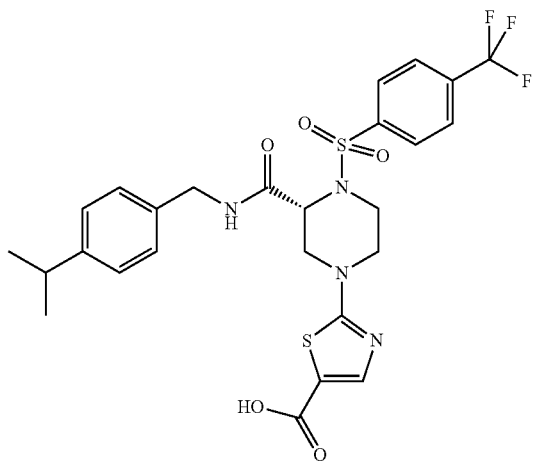 |
TABLE 64
| Ex. No. | Structural Formula |
|---|---|
| 316 | 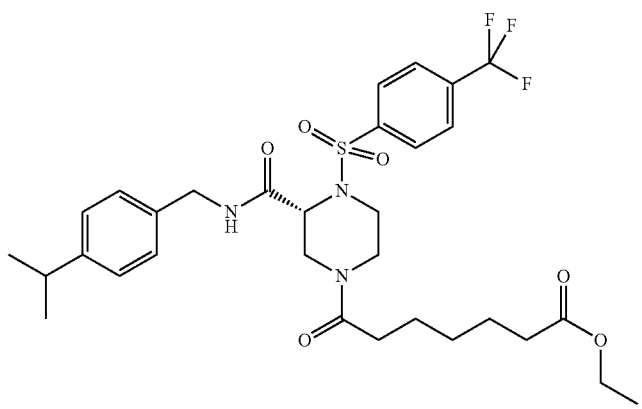 |
| 317 | 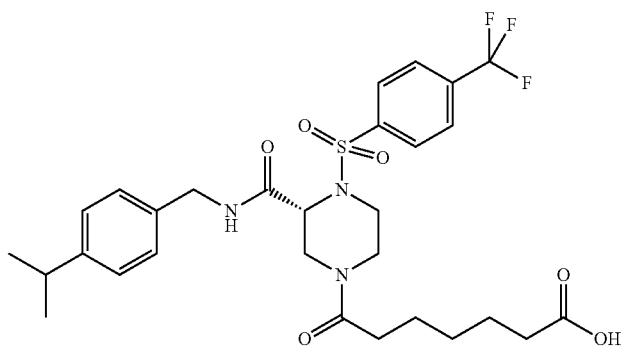 |

TABLE 64-continued
| Ex. No. | Structural Formula |
|---|---|
| 318 | 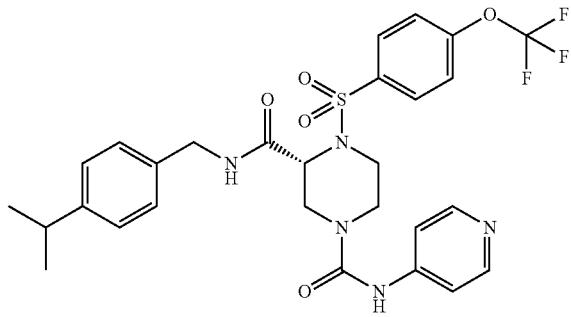 |
| 319 | 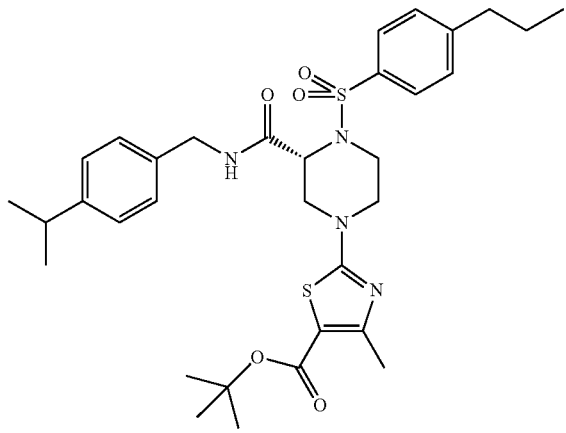 |
| 320 | 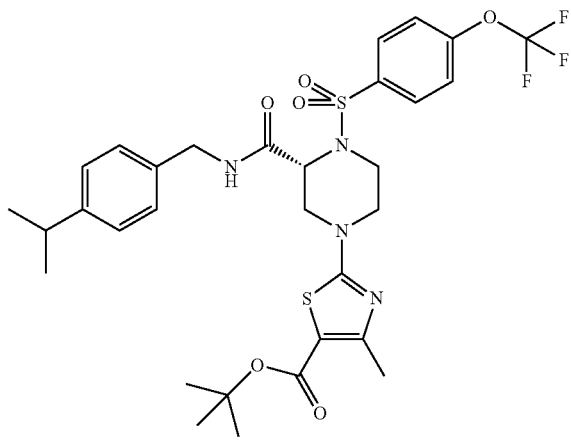 |

TABLE 65
| Ex. No. | Structural Formula |
|---|---|
| 321 | 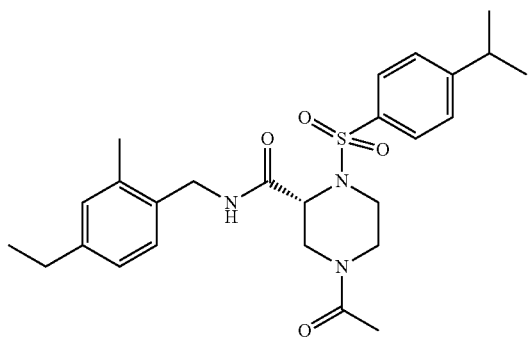 |
| 322 | 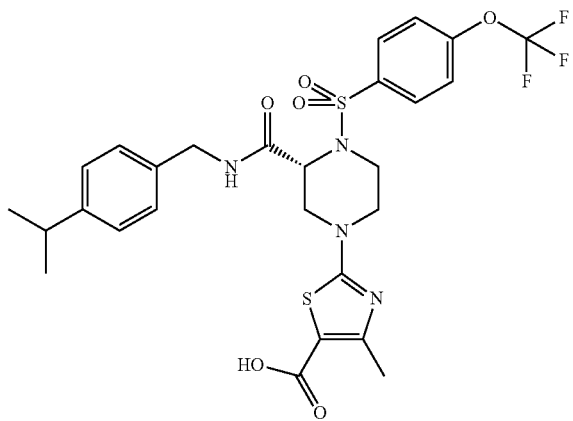 |
| 323 | 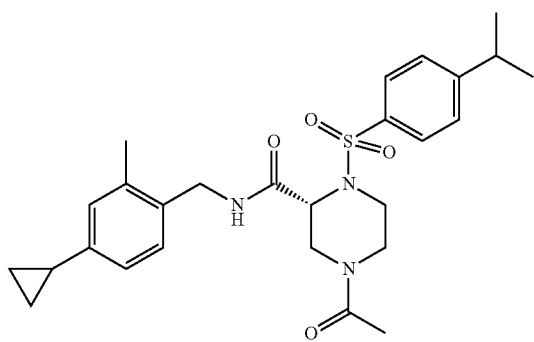 |
| 324 | 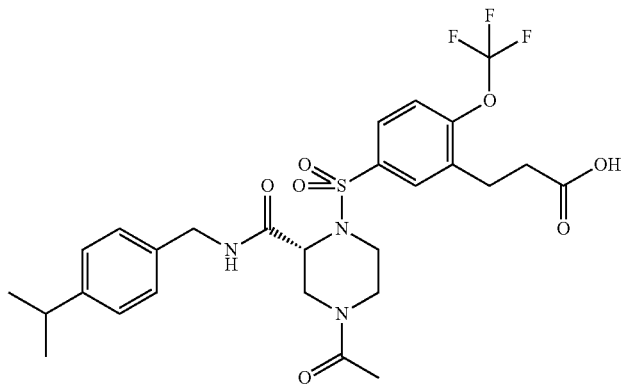 |

TABLE 65-continued
| Ex. No. | Structural Formula |
| --- | --- |
| 325 | 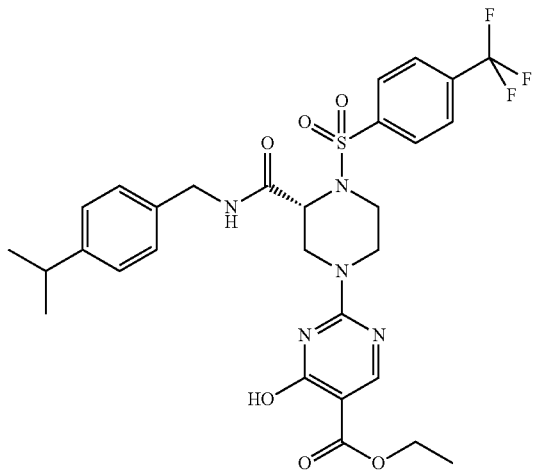 |
TABLE 66
| Ex. No. | Structural Formula |
| --- | --- |
| 326 | 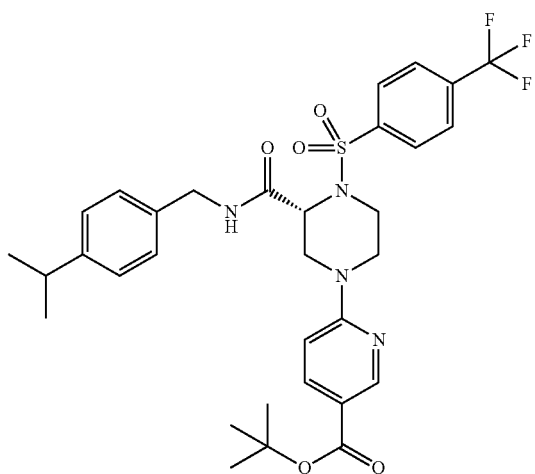 |
| 327 | 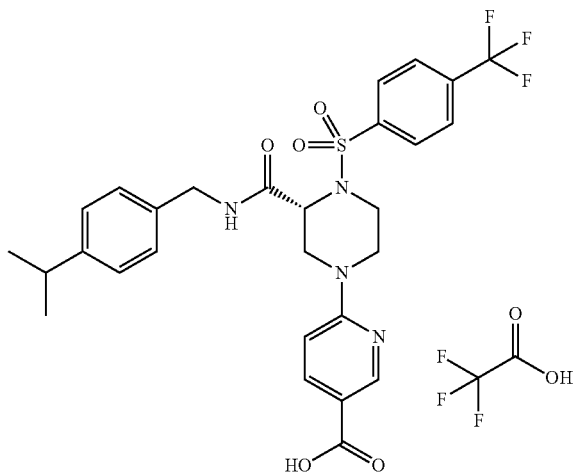 |

TABLE 66-continued
| Ex. No. | Structural Formula |
|---|---|
| 328 | 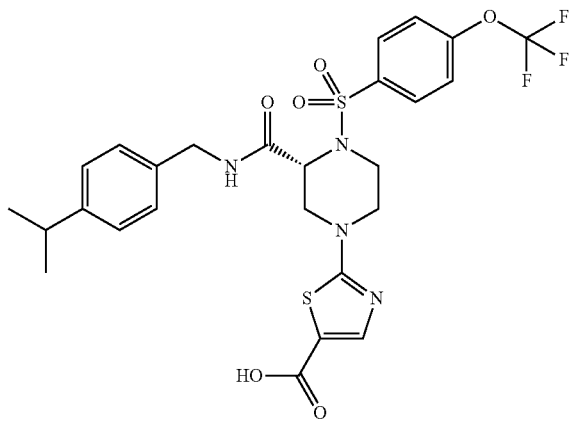 |
| 329 | 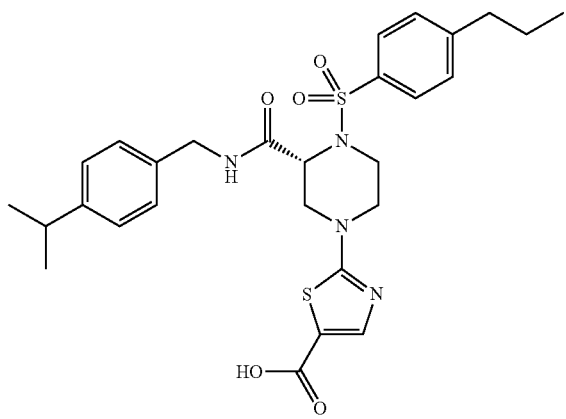 |
| 330 | 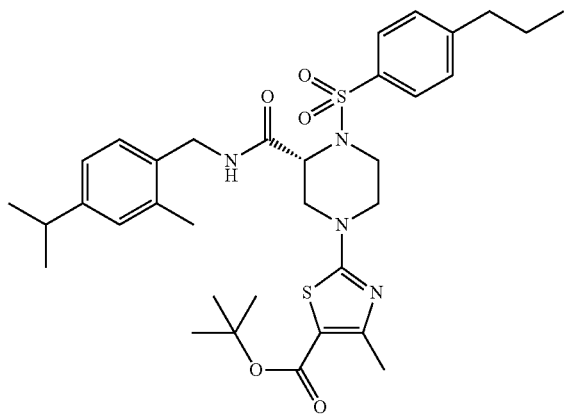 |

TABLE 67
| Ex. No. | Structural Formula |
|---|---|
| 331 | 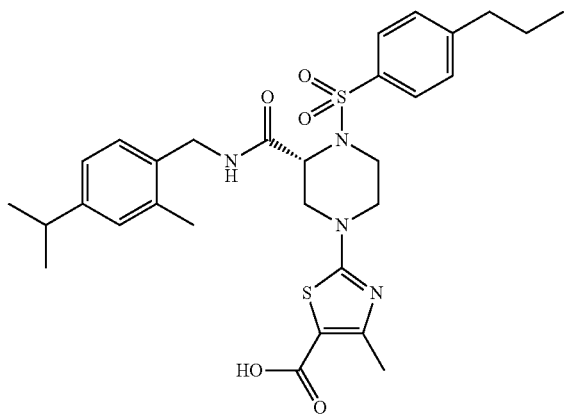 |
| 332 | 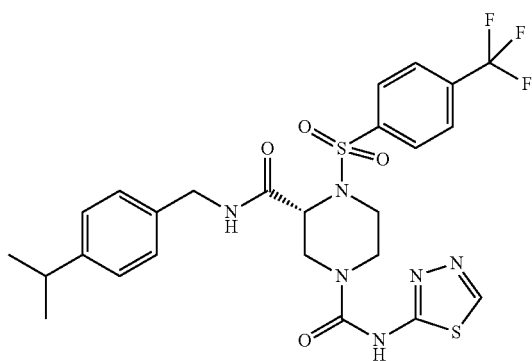 |
| 333 | 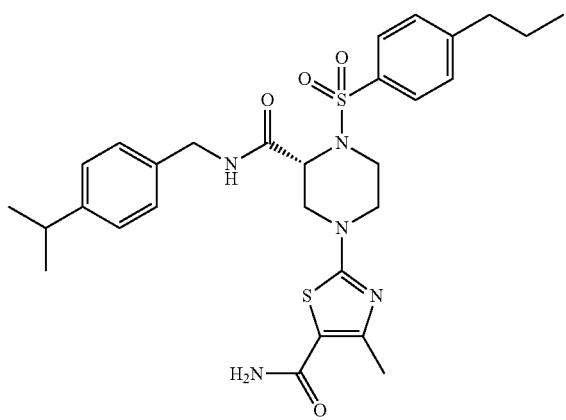 |

TABLE 67-continued
| Ex. No. | Structural Formula |
|---|---|
| 334 | 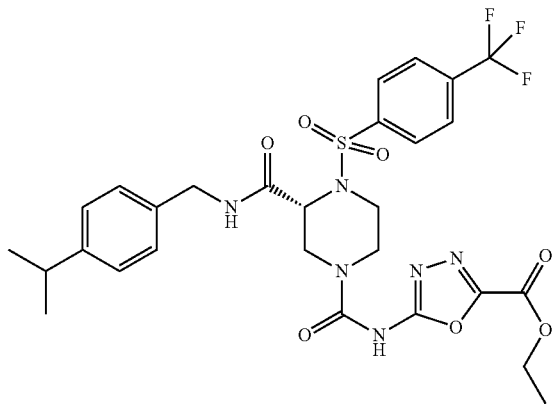 |
| 335 | 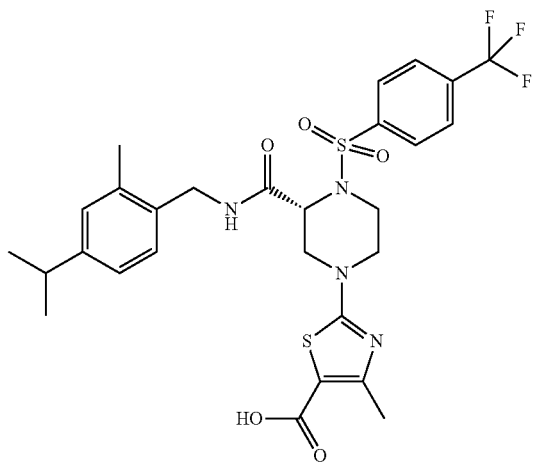 |
TABLE 68
| Ex. No. | Structural Formula |
|---|---|
| 336 | 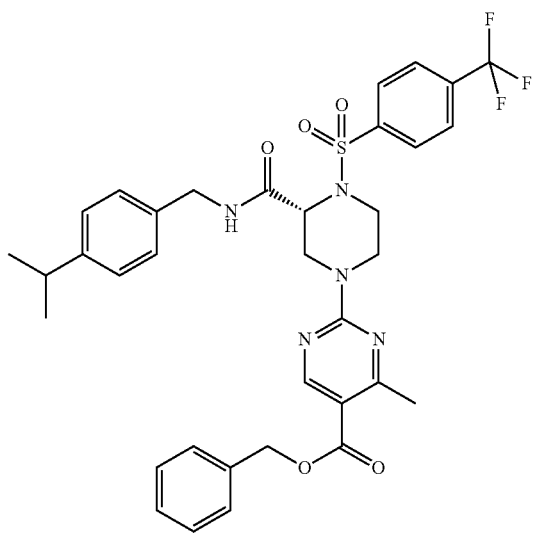 |

TABLE 68-continued
| Ex. No. | Structural Formula |
|---|---|
| 337 | 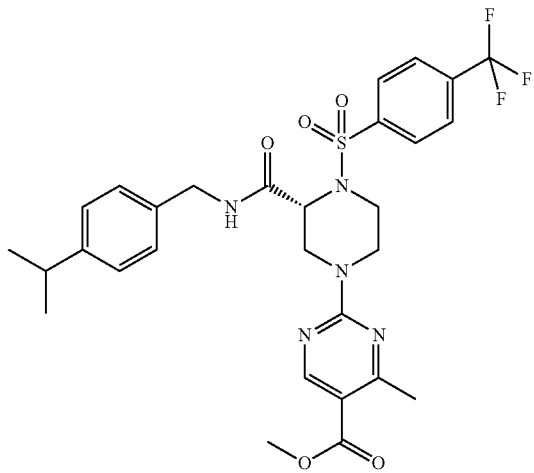 |
| 338 | 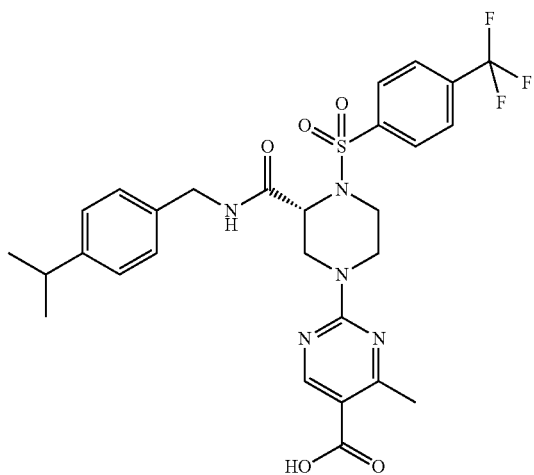 |
| 339 | 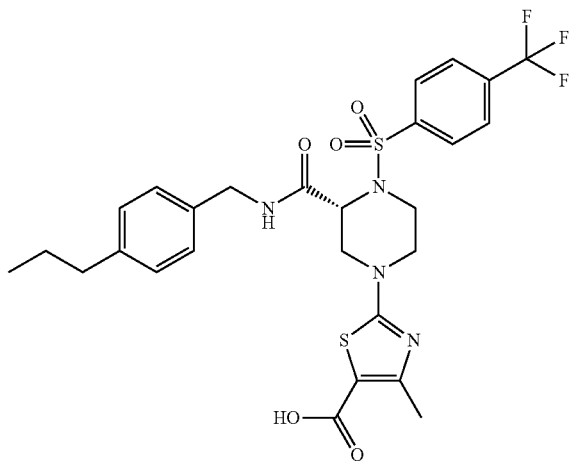 |

TABLE 68-continued
| Ex. No. | Structural Formula |
|---|---|
| 340 | 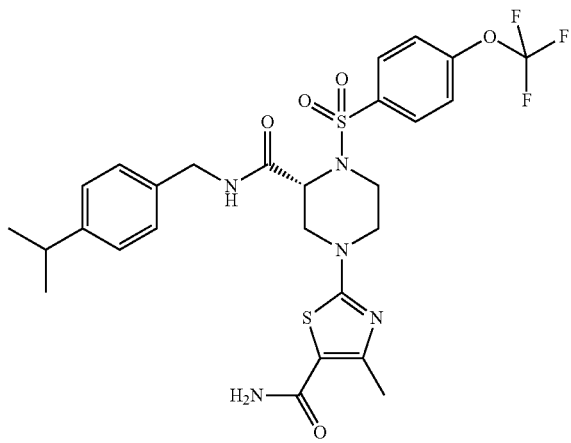 |
TABLE 69
| Ex. No. | Structural Formula |
|---|---|
| 341 | 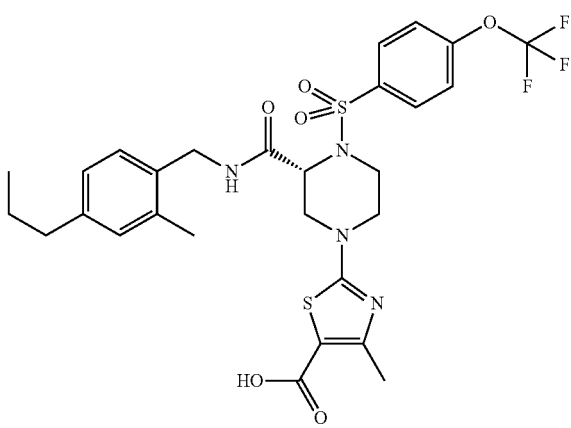 |
| 342 | 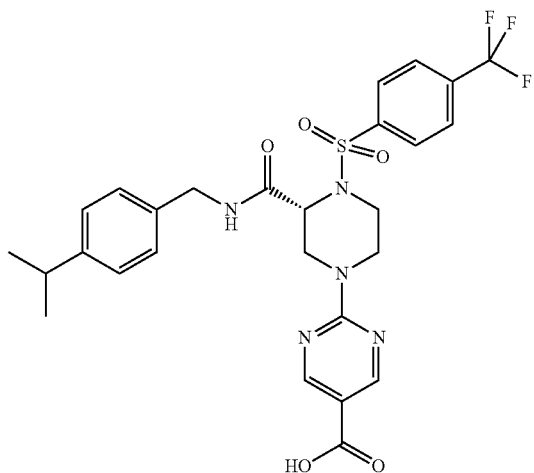 |

TABLE 69-continued
| Ex. No. | Structural Formula |
|---|---|
| 343 | 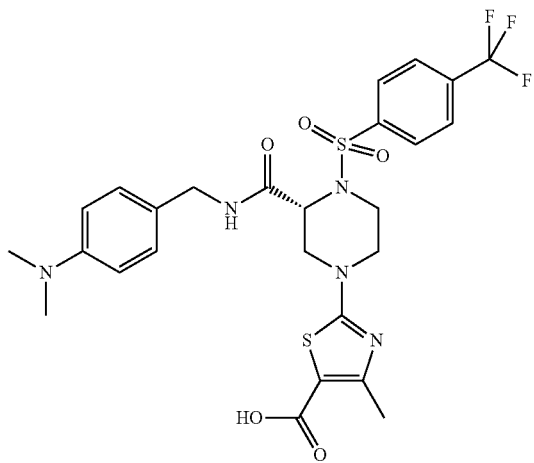 |
| 344 | 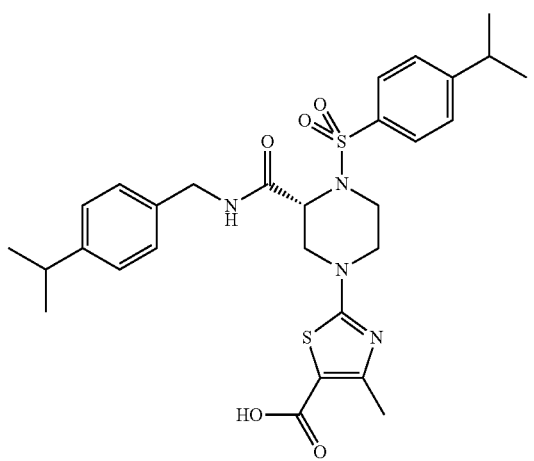 |
| 345 | 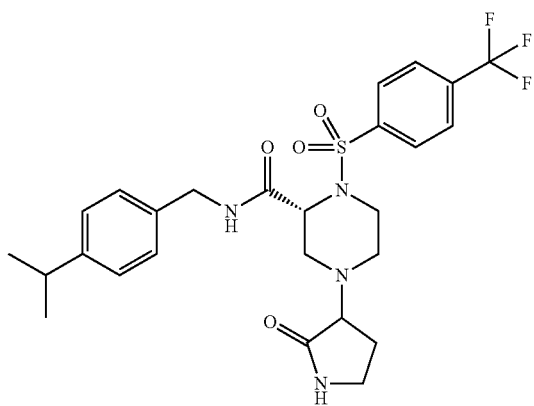 |

TABLE 70
| Ex. No. | Structural Formula |
|---|---|
| 346 | 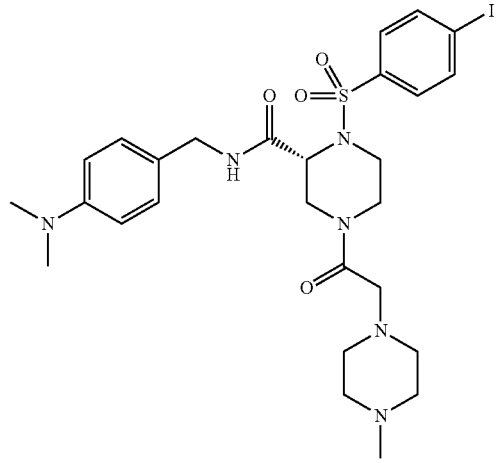 |
| 347 | 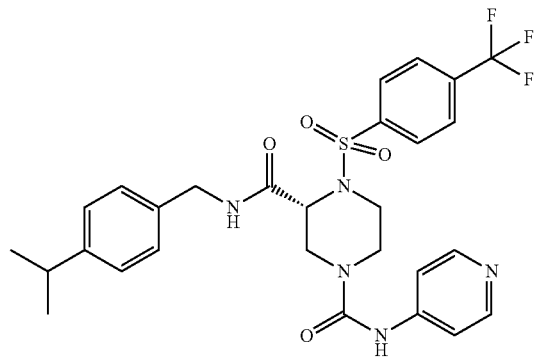 |
| 348 | 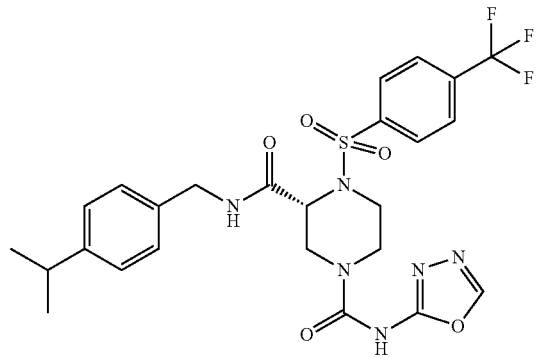 |

TABLE 70-continued
| Ex. No. | Structural Formula |
| --- | --- |
| 349 | 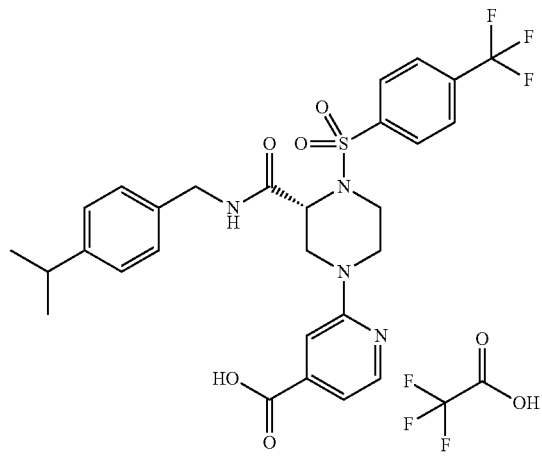 |
| 350 | 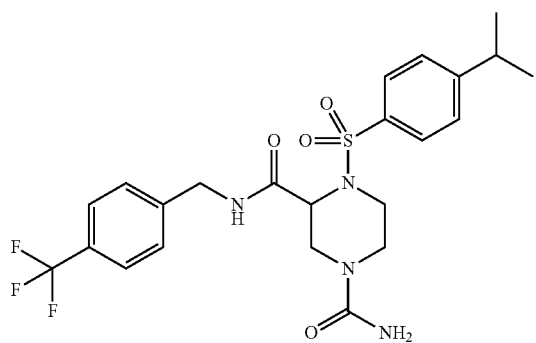 |
TABLE 71
| Ex. No. | Structural Formula |
| --- | --- |
| 351 | 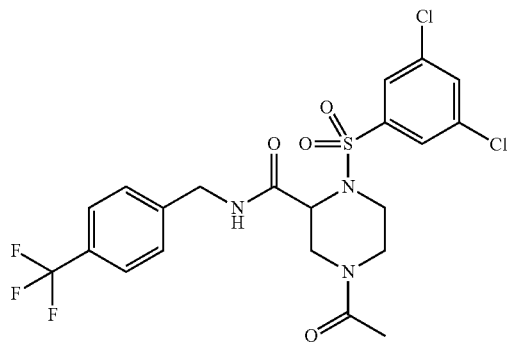 |

TABLE 71-continued
| Ex. No. | Structural Formula |
|---|---|
| 352 | 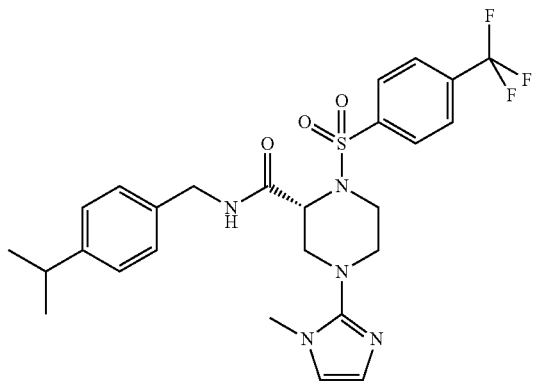 |
| 353 | 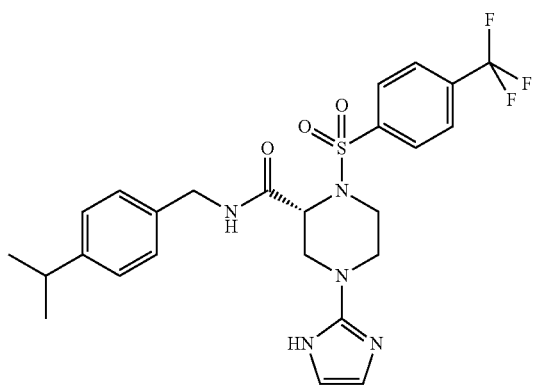 |
| 354 | 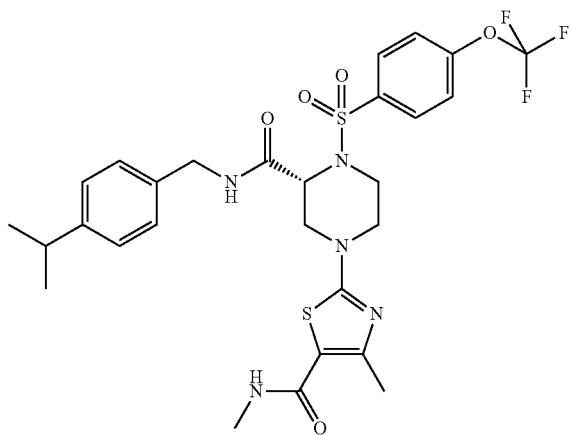 |

TABLE 71-continued
| Ex. No. | Structural Formula |
|---|---|
| 355 | 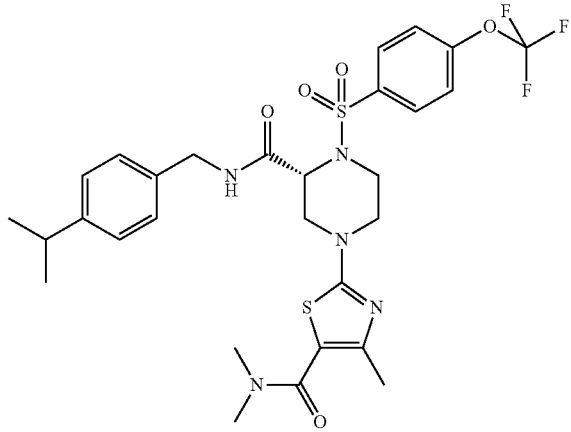 |
TABLE 72
| Ex. No. | Structural Formula |
|---|---|
| 356 | 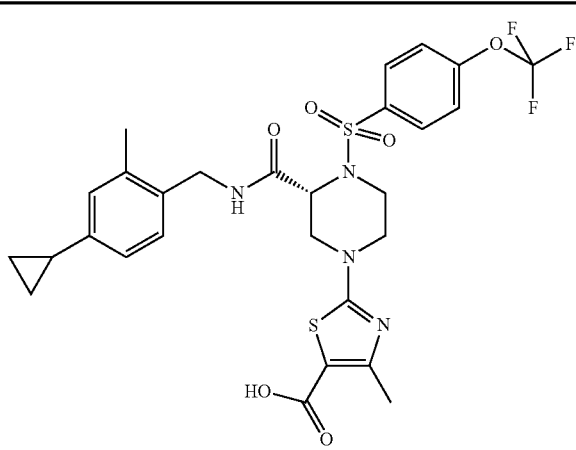 |
| 357 | 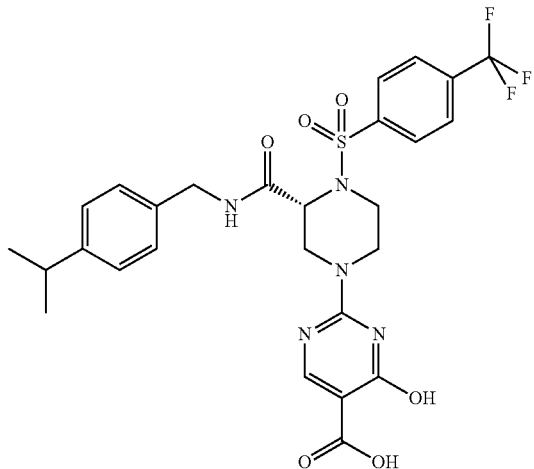 |

TABLE 72-continued
Ex. No. Structural Formula
358
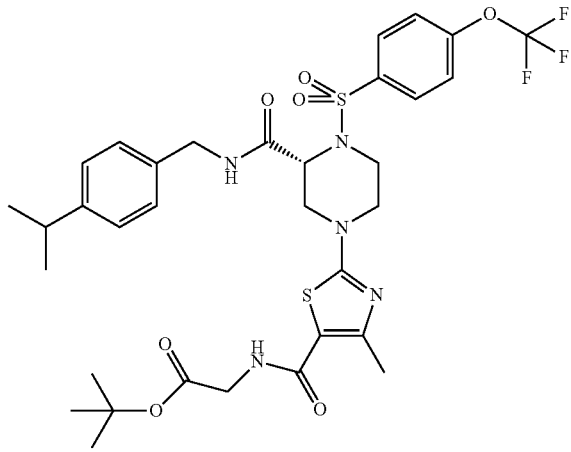
359
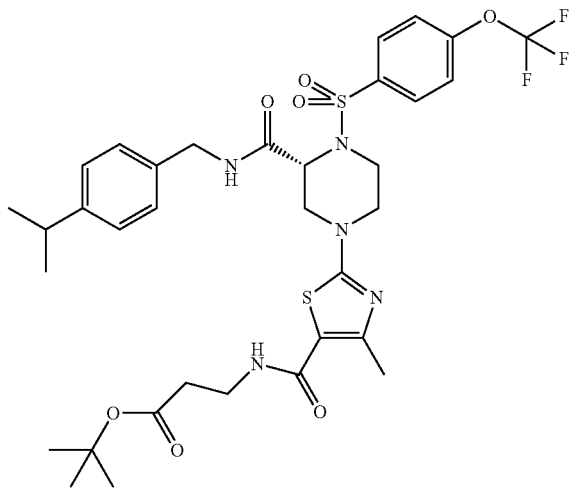
360
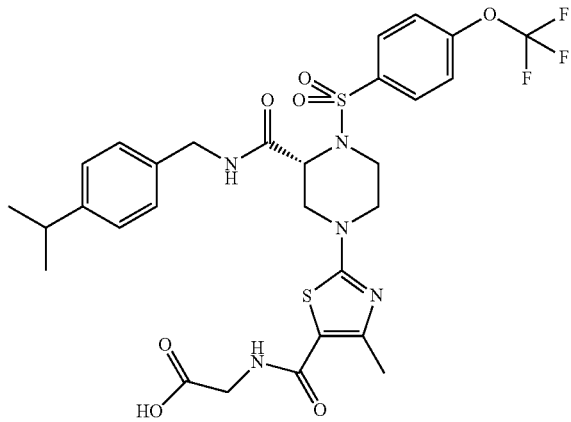

TABLE 73
| Ex. No. | Structural Formula |
|---|---|
| 361 | 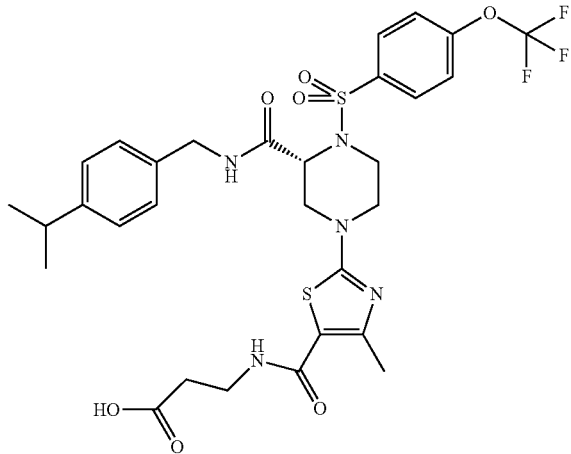 |
| 362 | 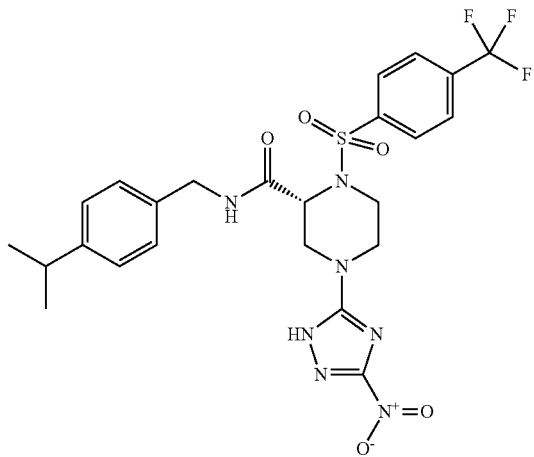 |
| 363 | 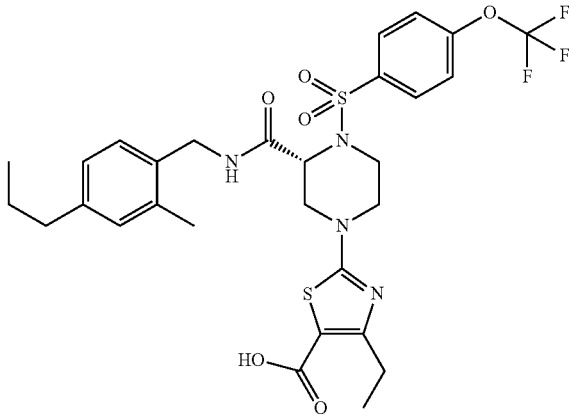 |

TABLE 73-continued
| Ex. No. | Structural Formula |
| --- | --- |
| 364 | 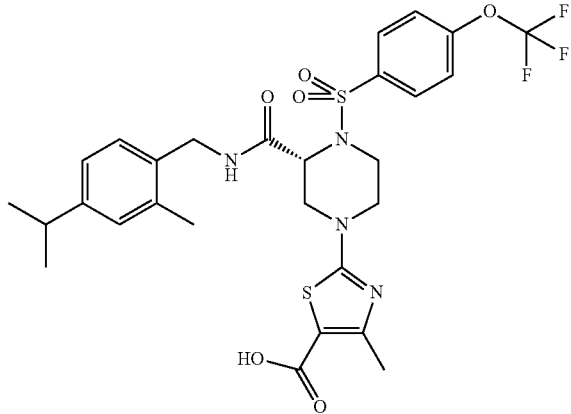 |
| 365 | 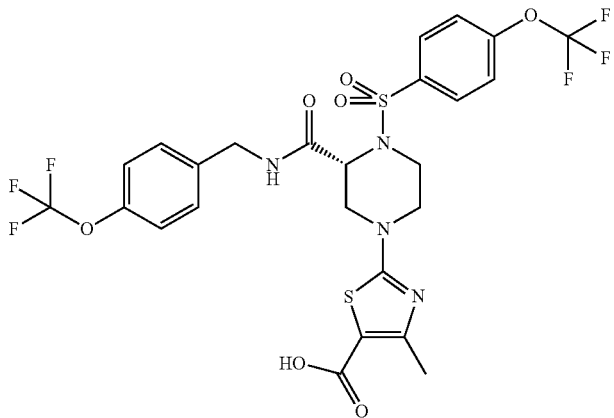 |
TABLE 74
| Ex. No. | Structural Formula |
| --- | --- |
| 366 | 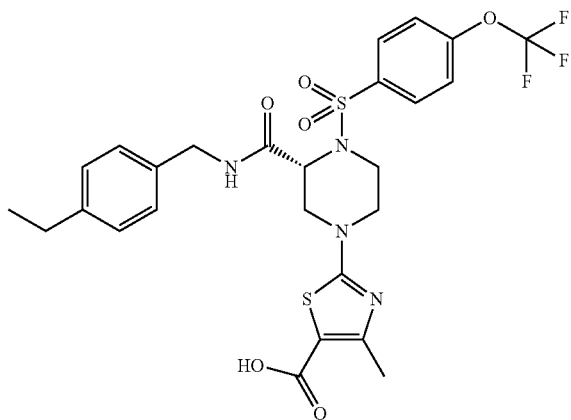 |

US 8,017,612 B2
457
458
TABLE 74-continued
Ex. No. Structural Formula
367
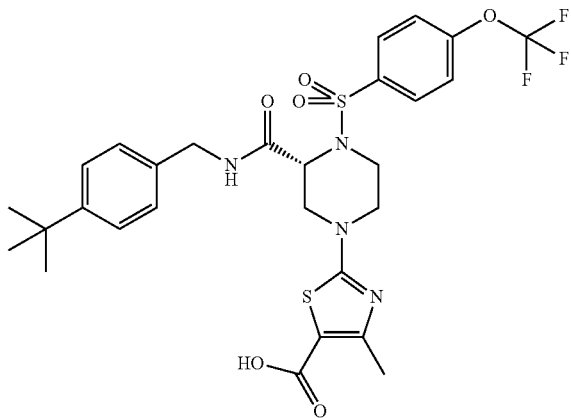
368
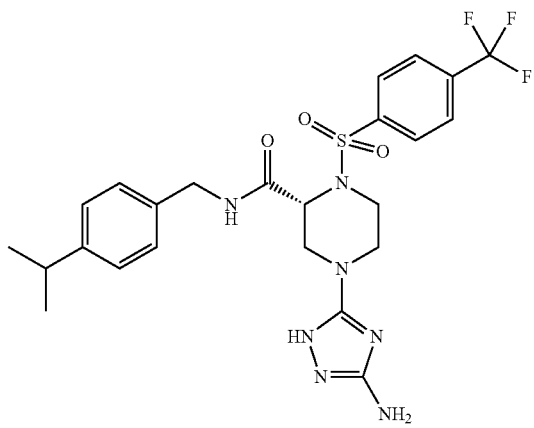
369
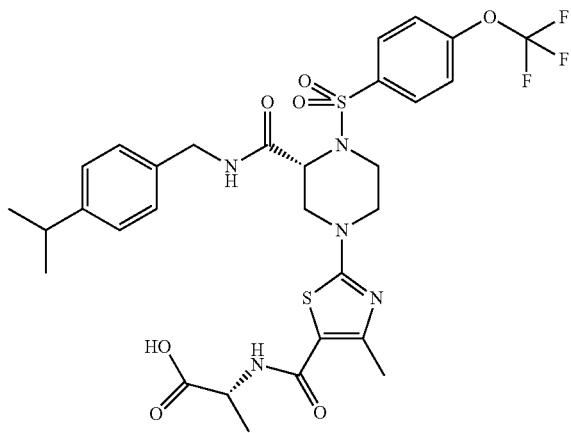

TABLE 74-continued
| Ex. No. | Structural Formula |
|---|---|
| 370 | 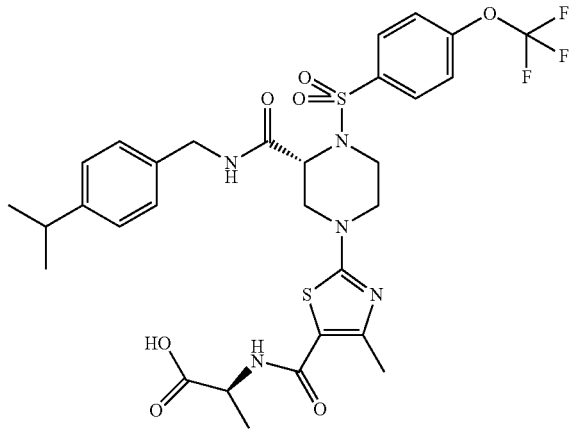 |
TABLE 75
| Ex. No. | Structural Formula |
|---|---|
| 371 | 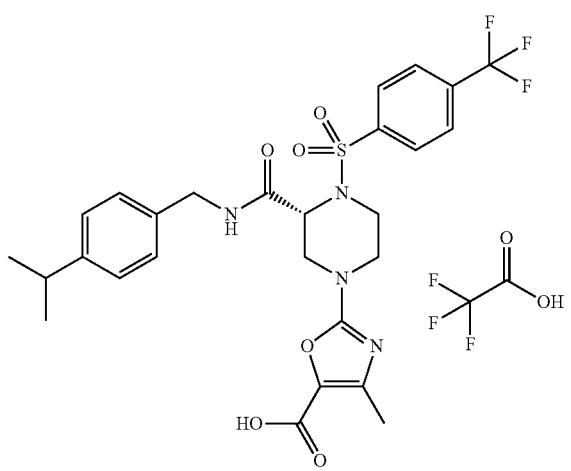 |
| 372 | 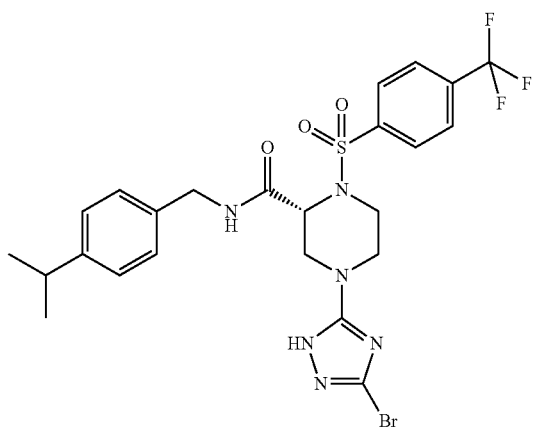 |

TABLE 75-continued
| Ex. No. | Structural Formula |
|---|---|
| 373 | 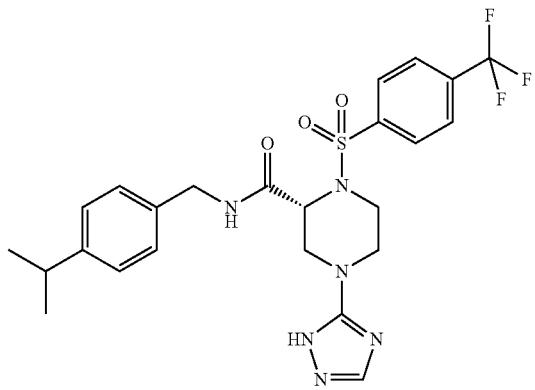 |
| 374 | 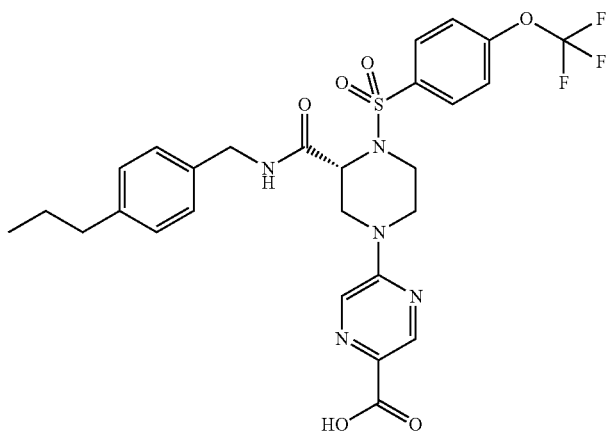 |
| 375 | 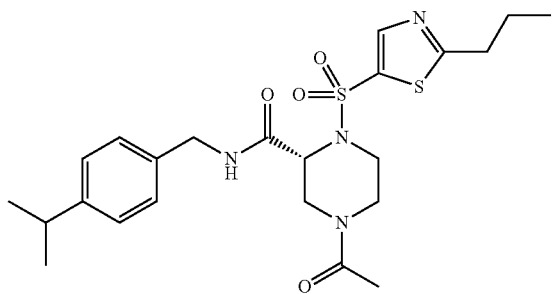 |

TABLE 76
| Ex. No. | Structural Formula |
| --- | --- |
| 376 | 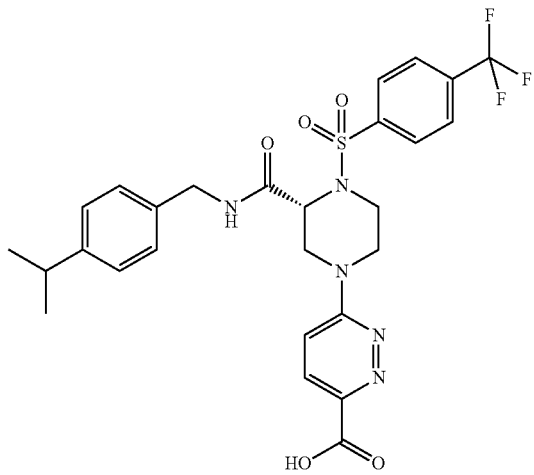 |
| 377 | 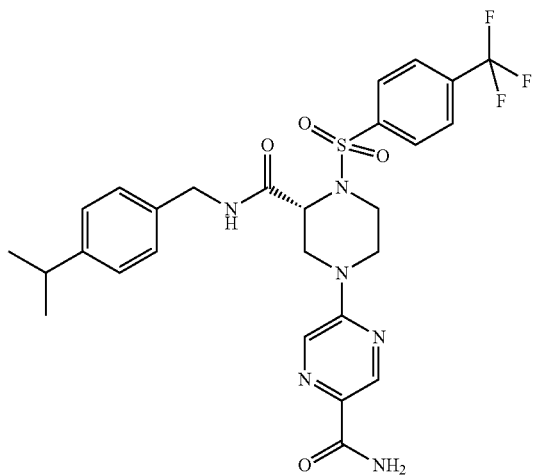 |
| 378 | 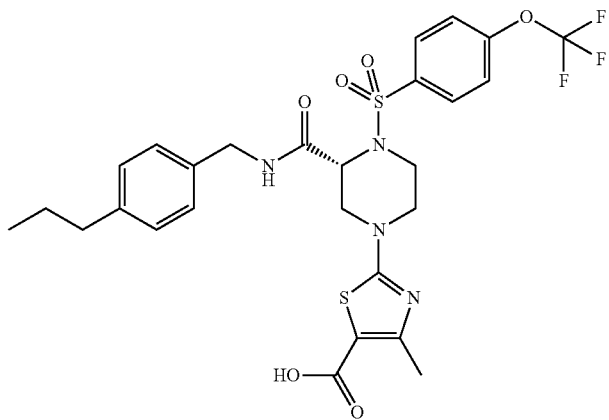 |

TABLE 76-continued
| Ex. No. | Structural Formula |
|---|---|
| 379 | 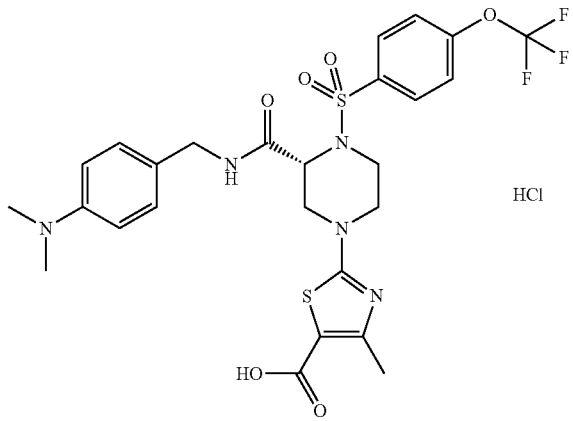 |
| 380 | 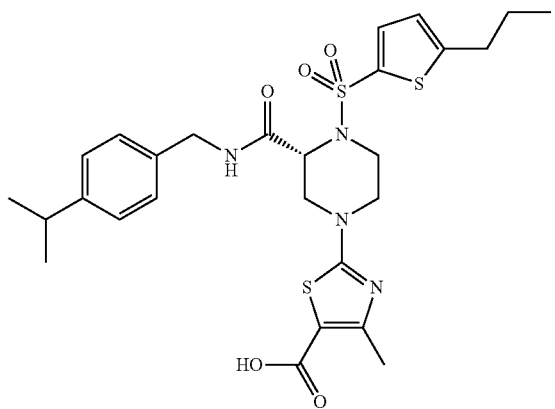 |
TABLE 77
| Ex. No. | Structural Formula |
|---|---|
| 381 | 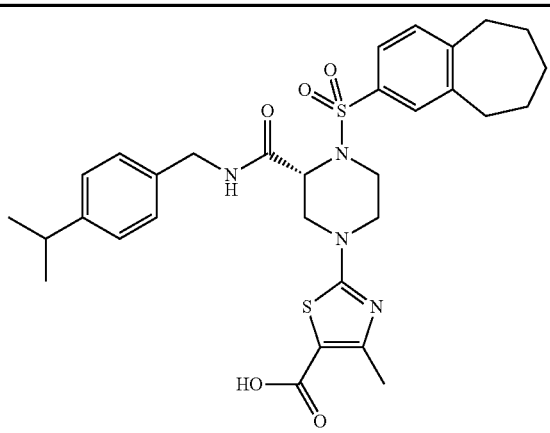 |

TABLE 77-continued
| Ex. No. | Structural Formula |
|---|---|
| 382 | 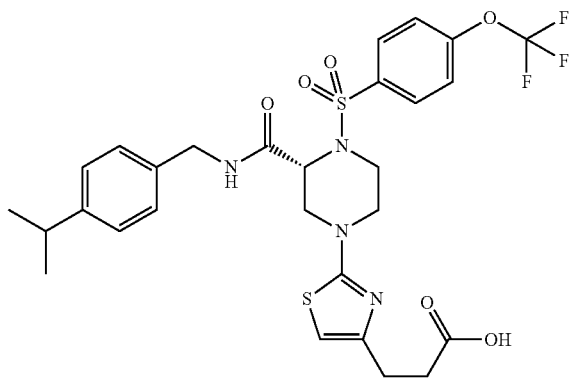 |
| 383 | 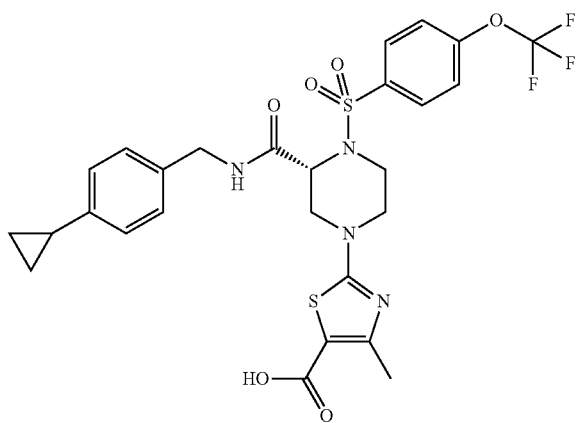 |
| 384 | 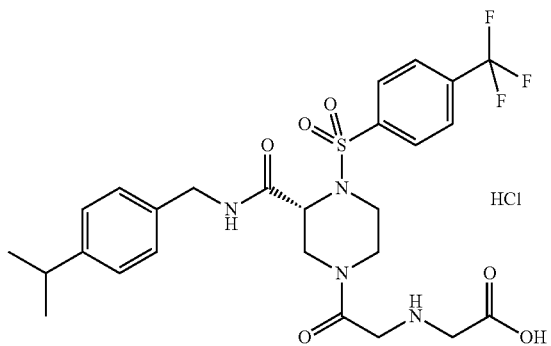 |
| 385 | 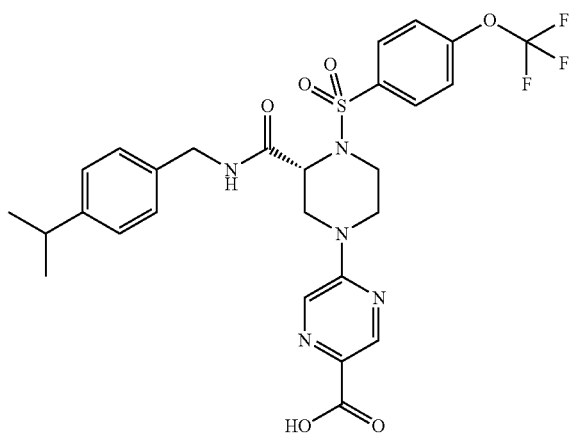 |

TABLE 78
| Ex. No. | Structural Formula |
|---|---|
| 386 | 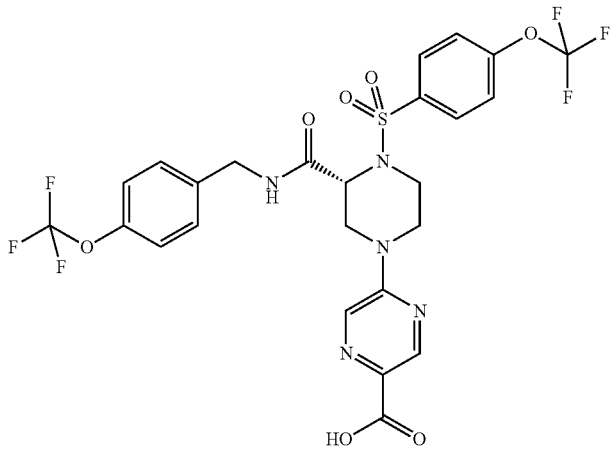 |
| 387 | 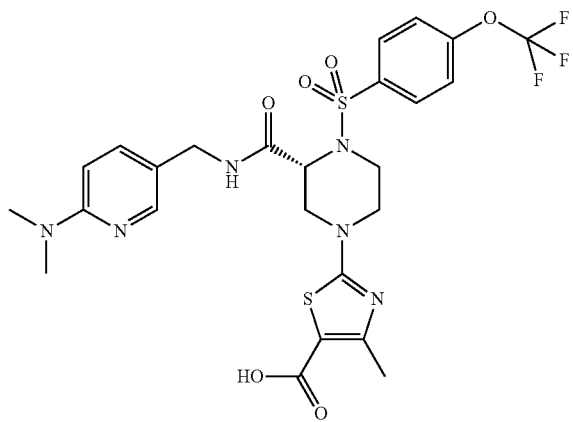 |
| 388 | 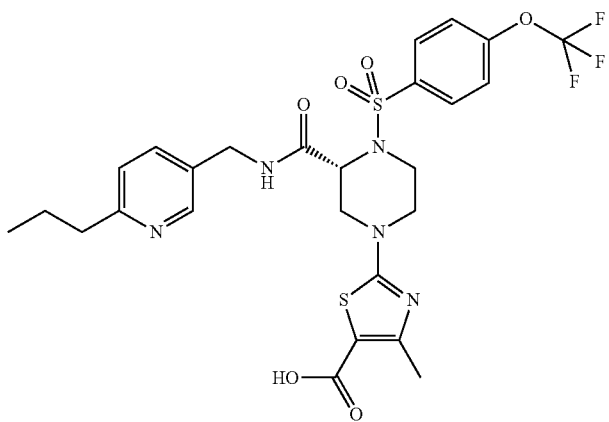 |

TABLE 78-continued
| Ex. No. | Structural Formula |
|---|---|
| 389 | 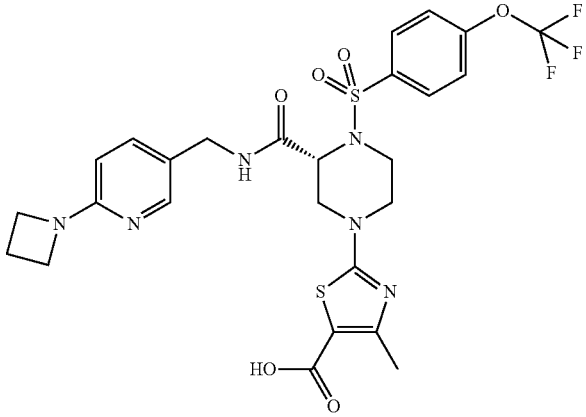 |
| 390 | 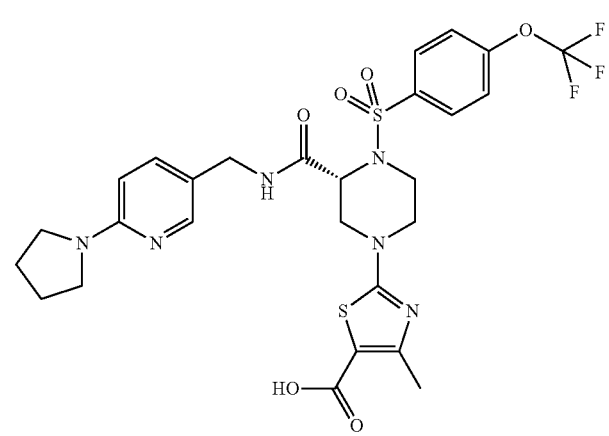 |
TABLE 79
| Ex. No. | Structural Formula |
|---|---|
| 391 | 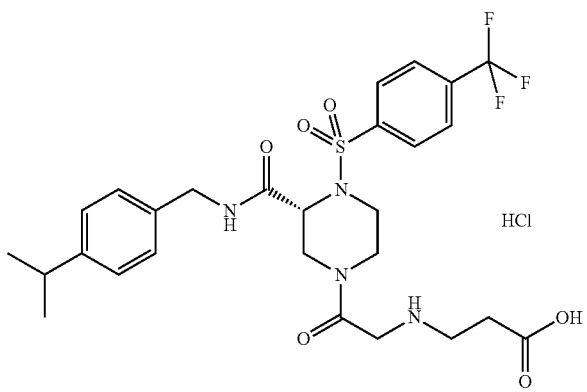 |

TABLE 79-continued
| Ex. No. | Structural Formula |
|---|---|
| 392 | 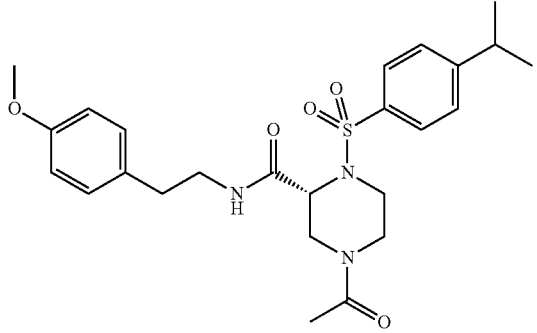 |
| 393 | 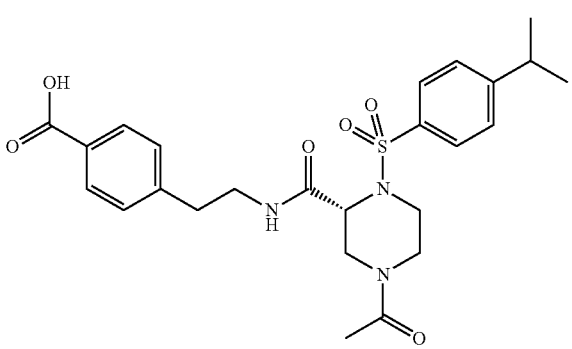 |
| 394 | 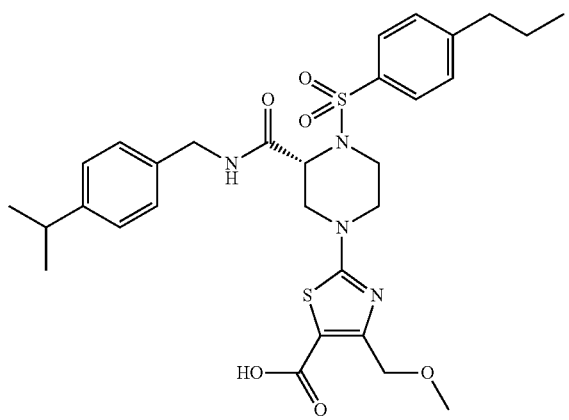 |
| 395 | 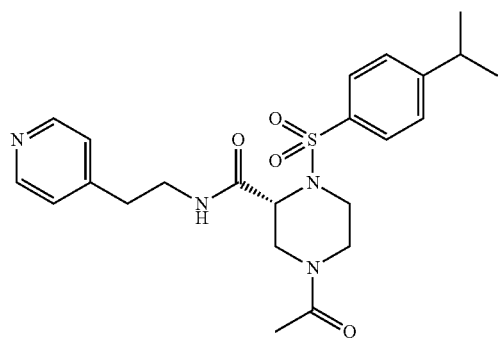 |

TABLE 80
| Ex. No. | Structural Formula |
|---|---|
| 396 | 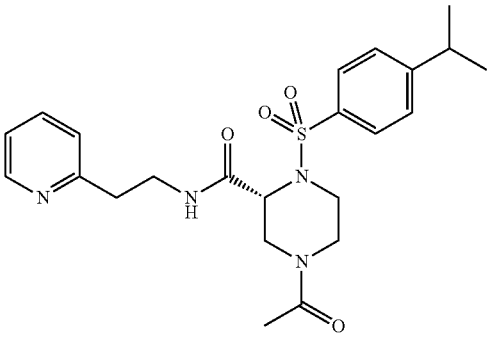 |
| 397 | 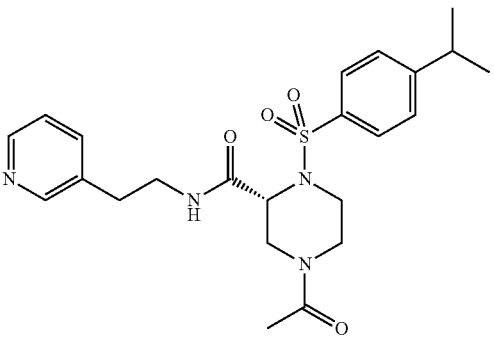 |
| 398 | 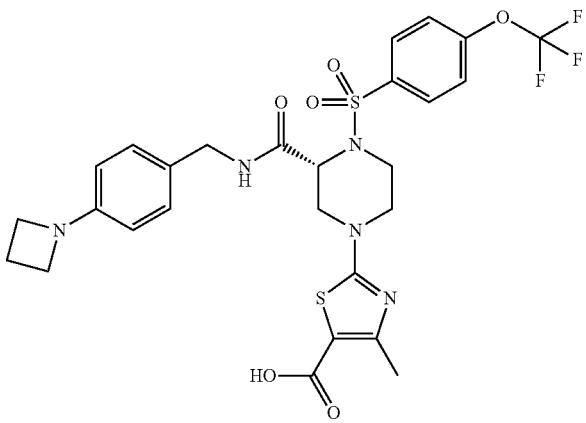 |
| 399 | 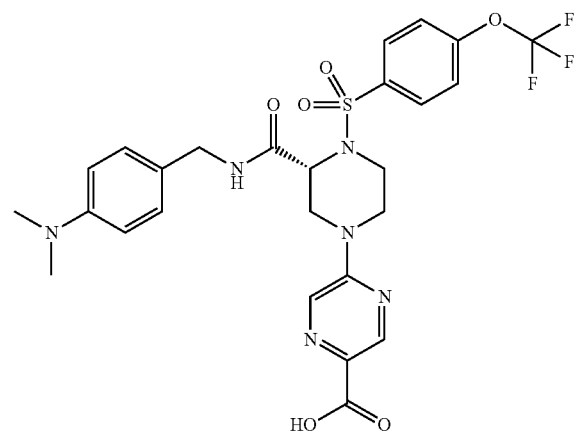 |

TABLE 80-continued

| Ex. No. | Structural Formula |
|---|---|
| 400 | (structure) |

TABLE 81

| Ex. No. | Structural Formula |
|---|---|
| 401 | (structure) |
| 402 | (structure) |
| 403 | (structure) |

TABLE 81-continued

| Ex. No. | Structural Formula |
|---|---|
| 404 | (structure) |
| 405 | (structure) |

TABLE 82
| Ex. No. | Structural Formula |
|---|---|
| 406 | 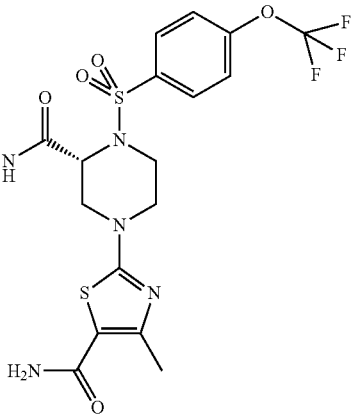 |
| 407 | 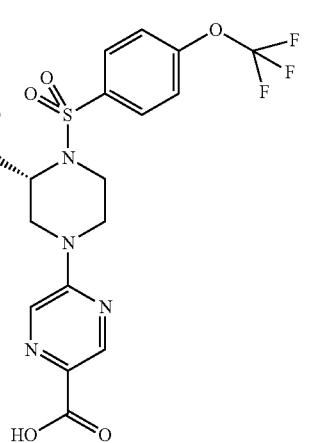 |
| 408 | 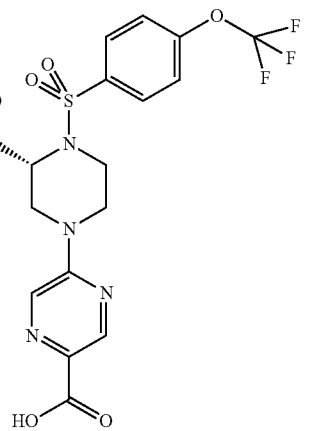 |
| 409 | 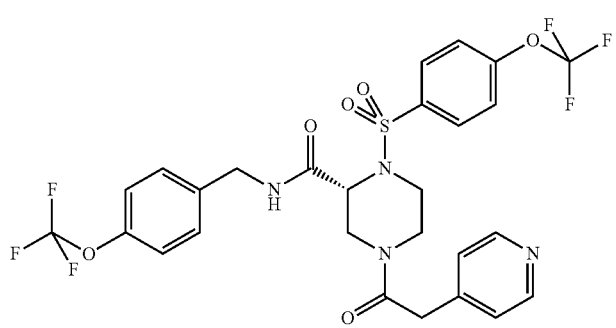 |

TABLE 82-continued
| Ex. No. | Structural Formula |
|---|---|
| 410 | 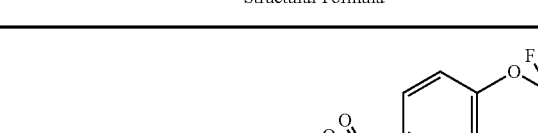 |
TABLE 83
| Ex. No. | Structural Formula |
|---|---|
| 411 | |
| 412 | |
| 413 | |

TABLE 83-continued
| Ex. No. | Structural Formula |
| --- | --- |
| 414 | 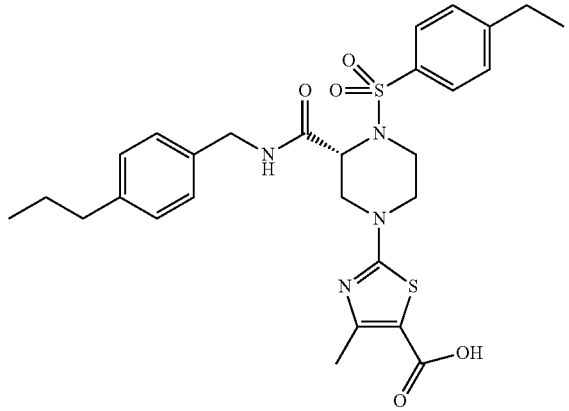 |
| 415 | 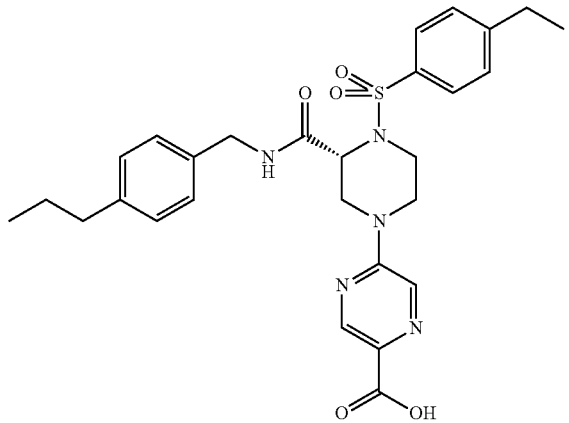 |
TABLE 84
| Ex. No. | Structural Formula |
| --- | --- |
| 416 | 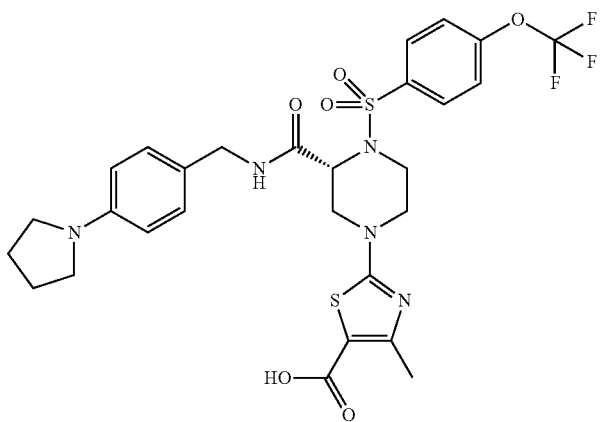 |

TABLE 84-continued
| Ex. No. | Structural Formula |
|---|---|
| 417 | 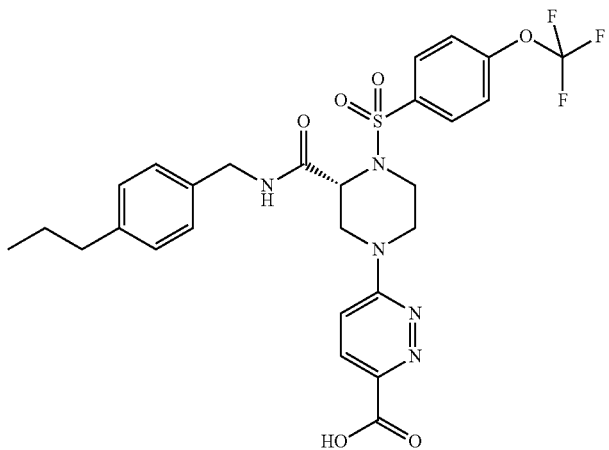 |
| 418 | 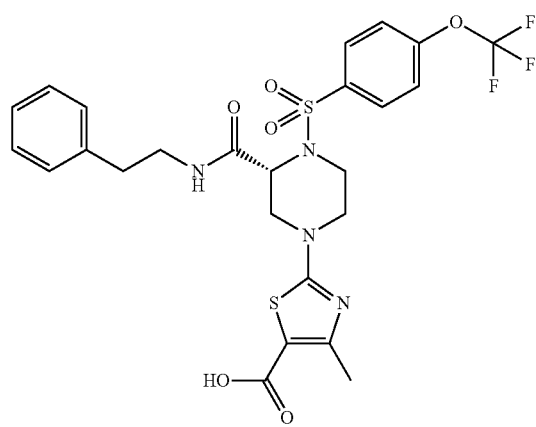 |
| 419 | 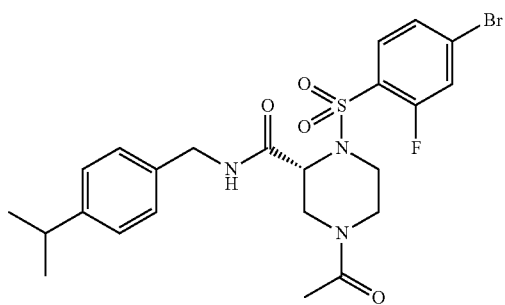 |

TABLE 84-continued

| Ex. No. | Structural Formula |
|---|---|
| 420 | |

TABLE 85

| Ex. No. | Structural Formula |
|---|---|
| 421 | |
| 422 | |

TABLE 85-continued
| Ex. No. | Structural Formula |
|---|---|
| 423 | 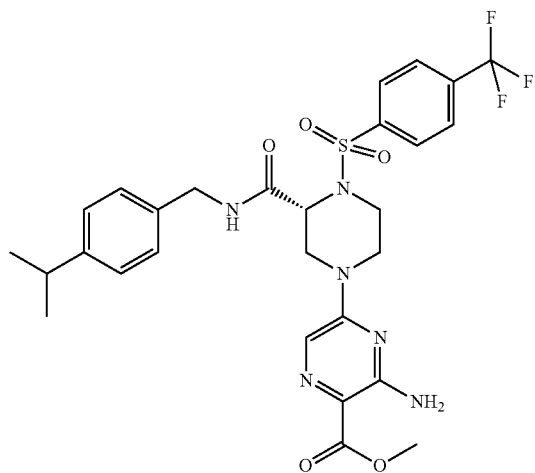 |
| 424 | 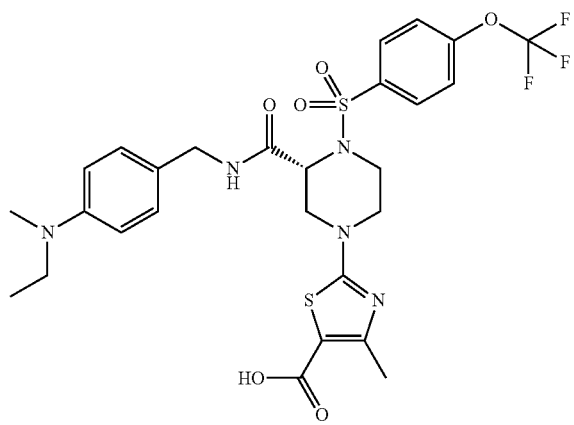 |
| 425 | 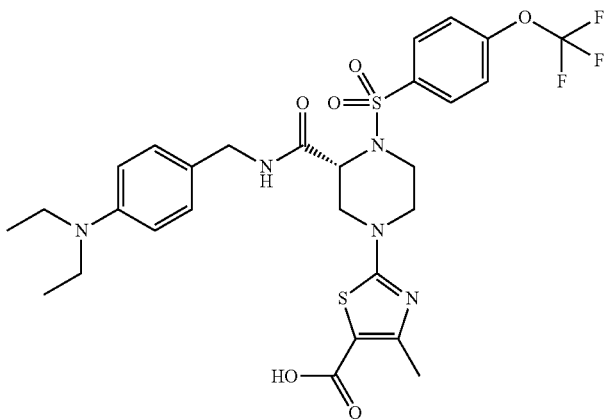 |

TABLE 86
| Ex. No. | Structural Formula |
|---|---|
| 426 | 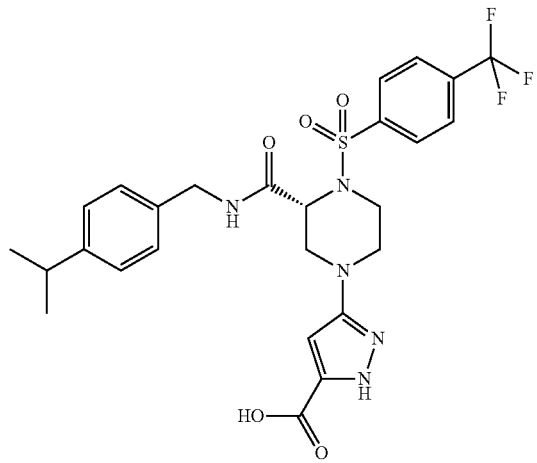 |
| 427 | 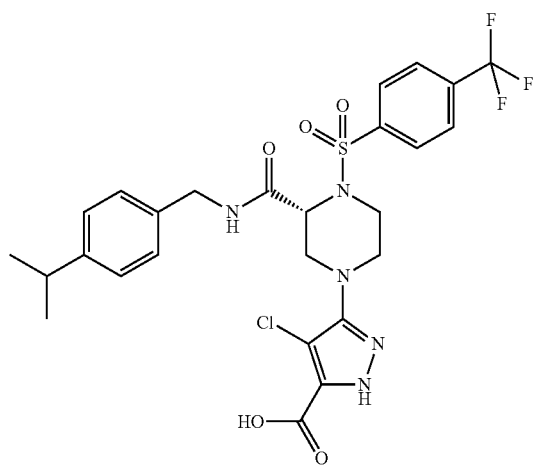 |
| 428 | 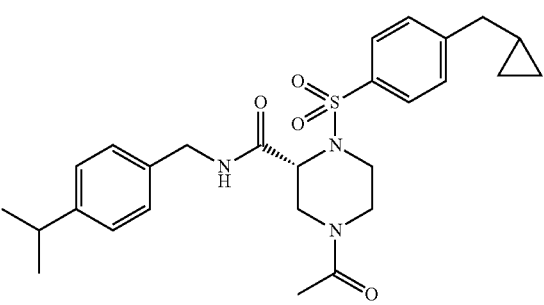 |
| 429 | 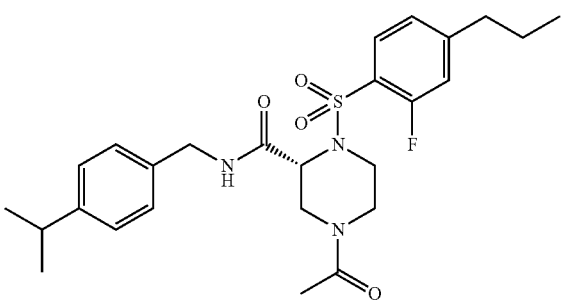 |

TABLE 86-continued
| Ex. No. | Structural Formula |
|---|---|
| 430 | |
TABLE 87
| Ex. No. | Structural Formula |
|---|---|
| 431 | |
| 432 | 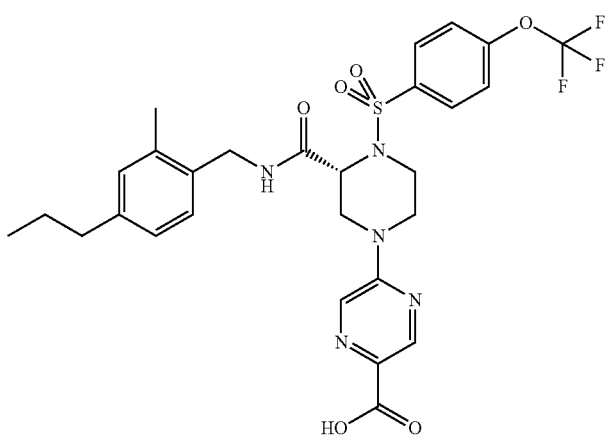 |

495
TABLE 87-continued
| Ex. No. | Structural Formula |
|---|---|
| 433 | 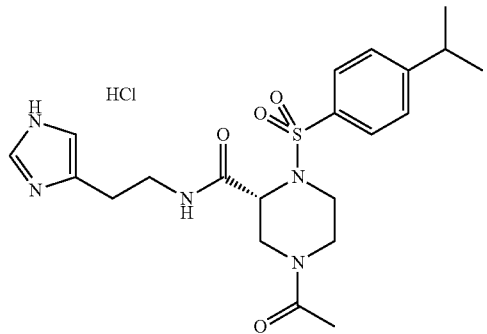 |
| 434 | 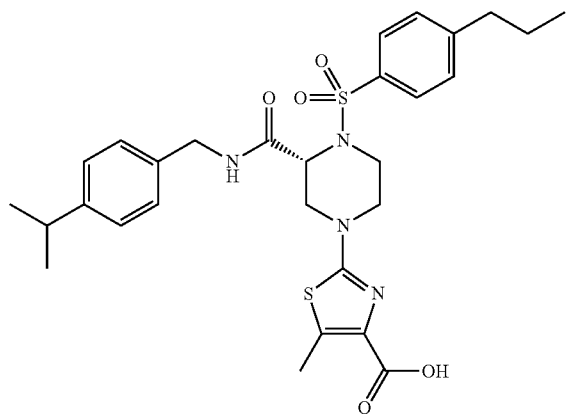 |
| 435 | 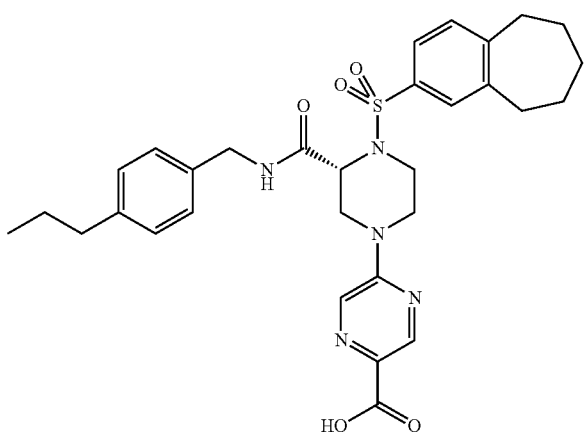 |

TABLE 88
| Ex. No. | Structural Formula |
|---|---|
| 436 | 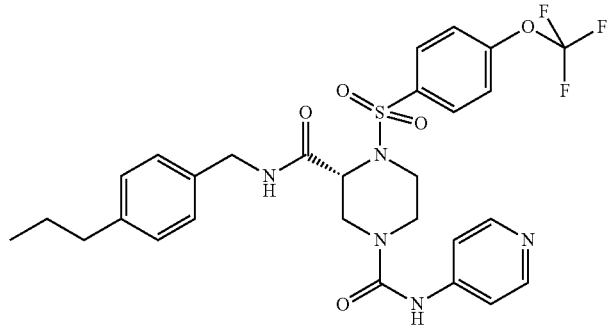 |
| 437 | 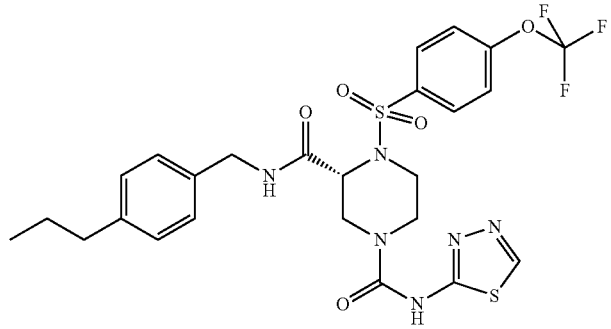 |
| 438 | 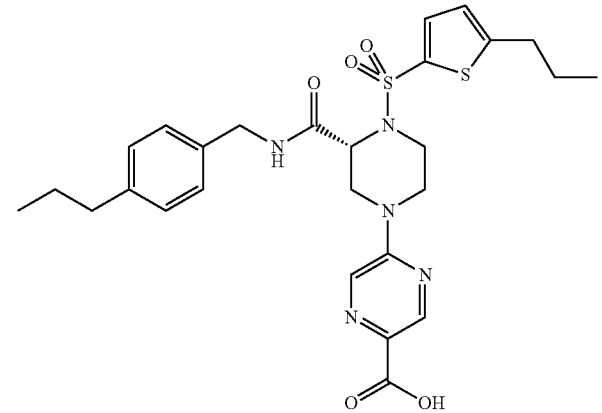 |
| 439 | 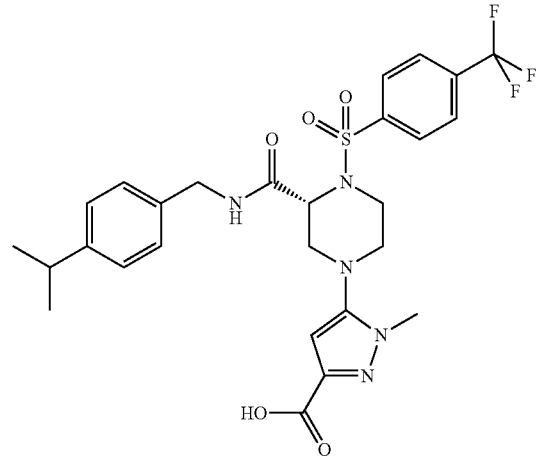 |

TABLE 88-continued
| Ex. No. | Structural Formula |
|---|---|
| 440 | 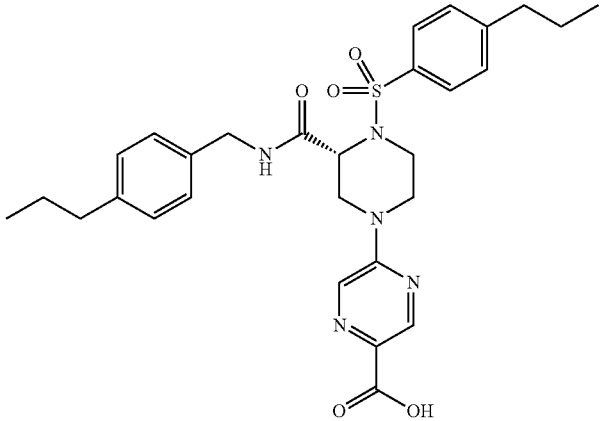 |
TABLE 89
| Ex. No. | Structural Formula |
|---|---|
| 441 | 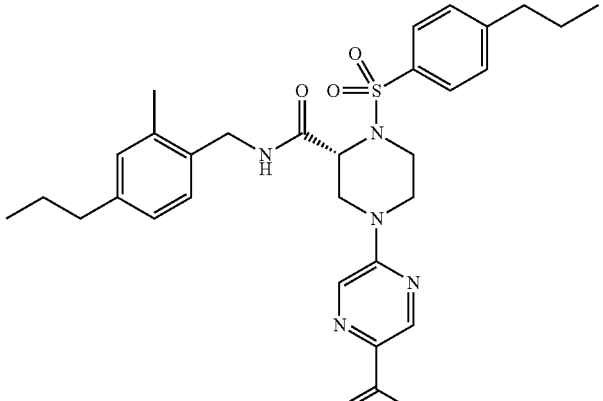 |
| 442 | 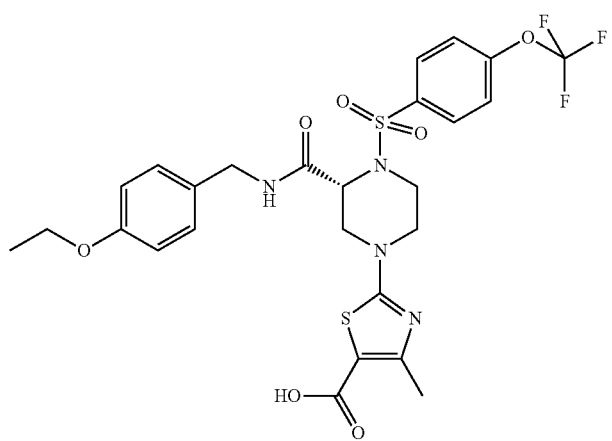 |

TABLE 89-continued
| Ex. No. | Structural Formula |
|---|---|
| 443 | 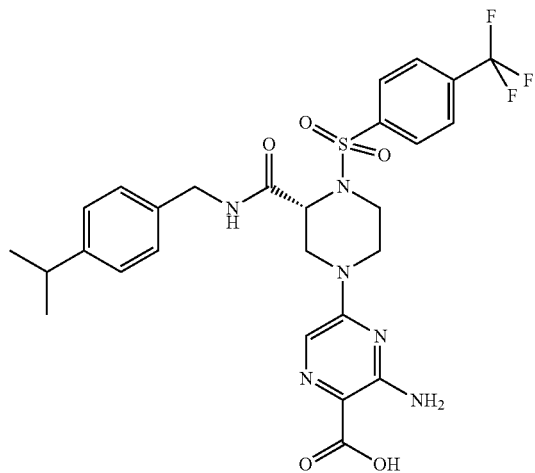 |
| 444 | 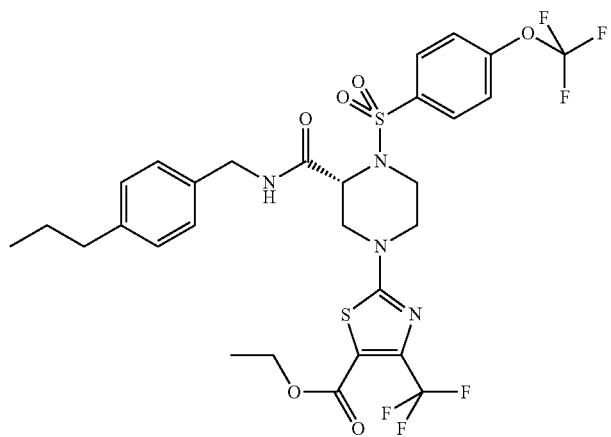 |
| 445 | 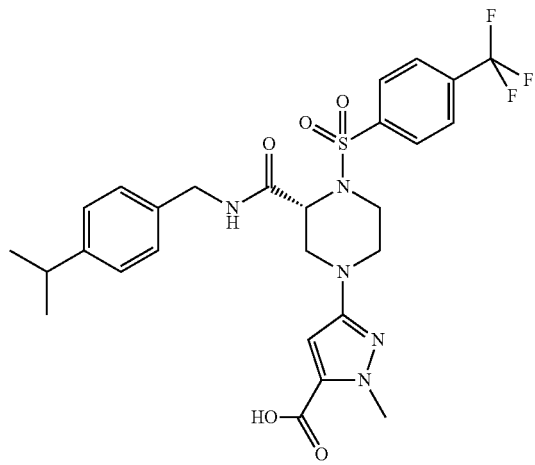 |

TABLE 90
| Ex. No. | Structural Formula |
|---|---|
| 446 | 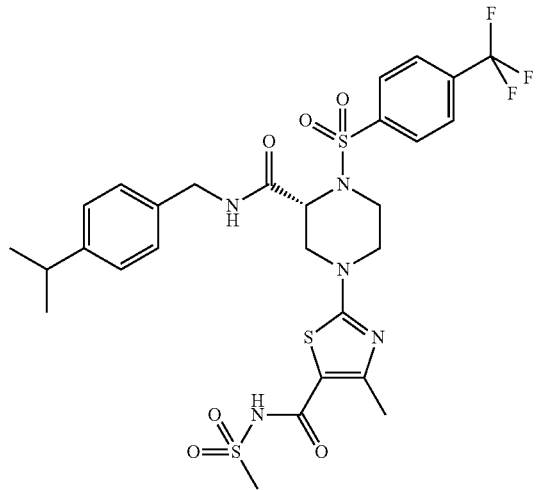 |
| 447 | 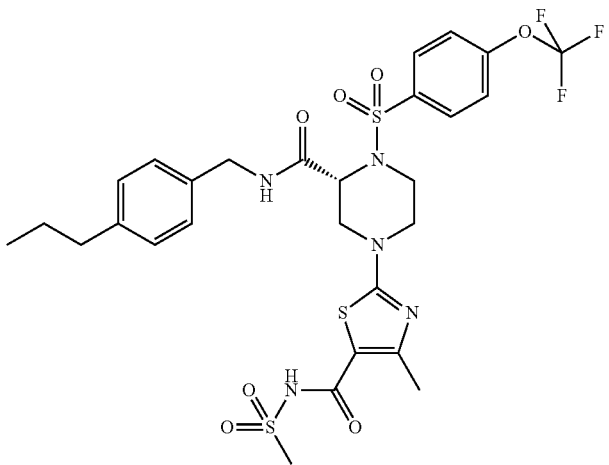 |
| 448 | 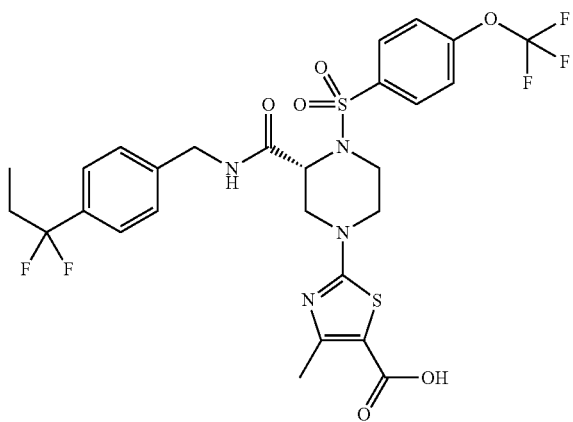 |

505
TABLE 90-continued
| Ex. No. | Structural Formula |
| --- | --- |
| 449 | 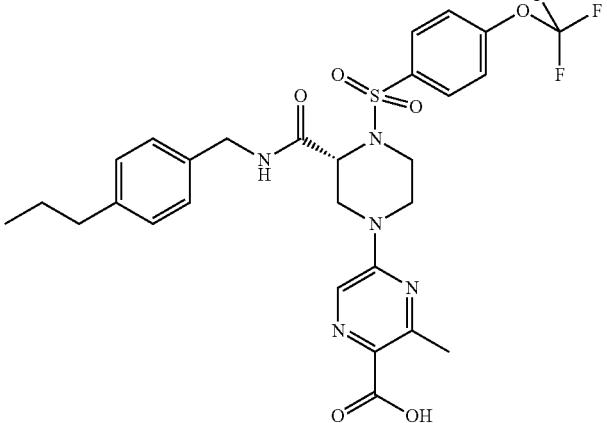 |
| 450 | 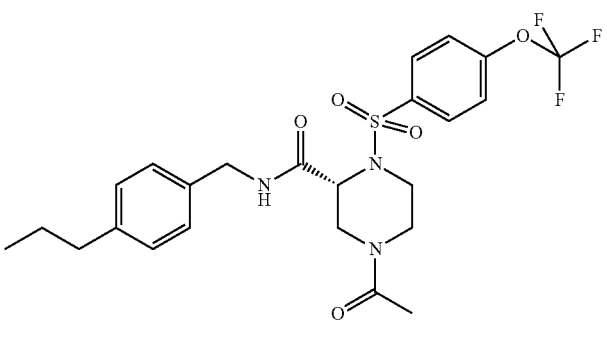 |
TABLE 91
| Ex. No. | Structural Formula |
| --- | --- |
| 451 | 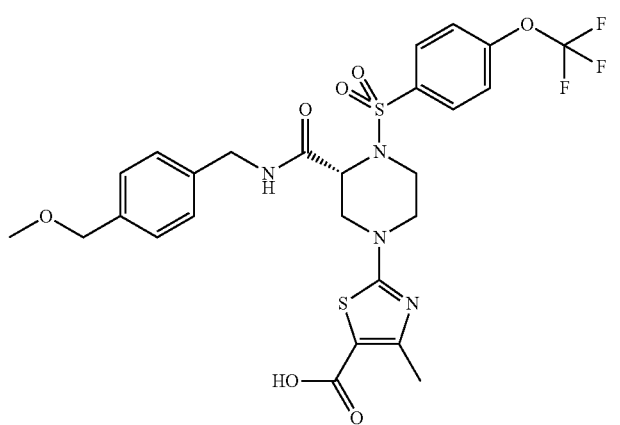 |

TABLE 91-continued

| Ex. No. | Structural Formula |
|---|---|
| 452 | |
| 453 | |
| 454 | |
| 455 | |

TABLE 92
| Ex. No. | Structural Formula |
|---|---|
| 456 | 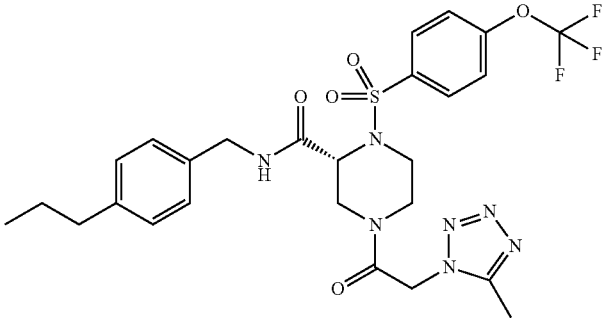 |
| 457 | 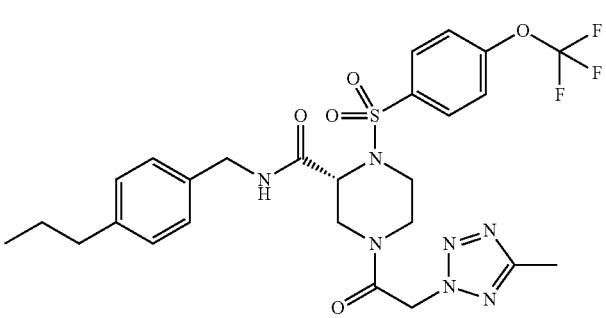 |
| 458 | 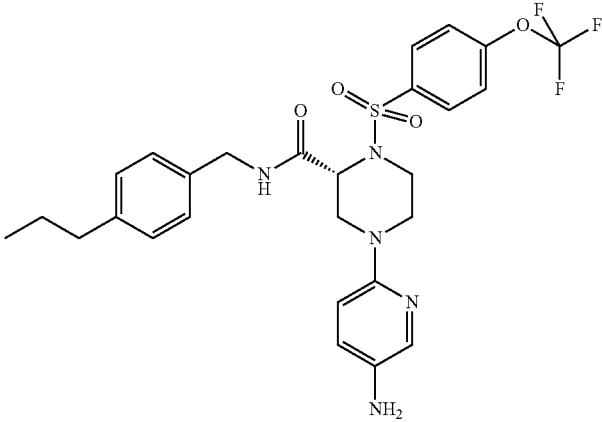 |
| 459 | 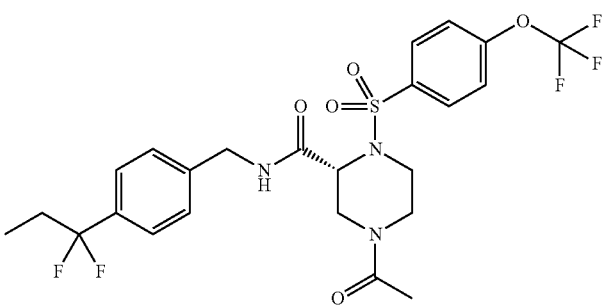 |

TABLE 92-continued
| Ex. No. | Structural Formula |
|---|---|
| 460 | 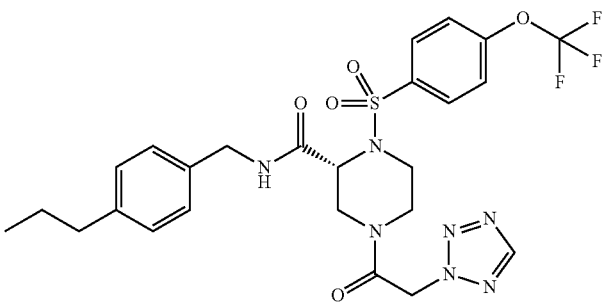 |
TABLE 93
| Ex. No. | Structural Formula |
|---|---|
| 461 | 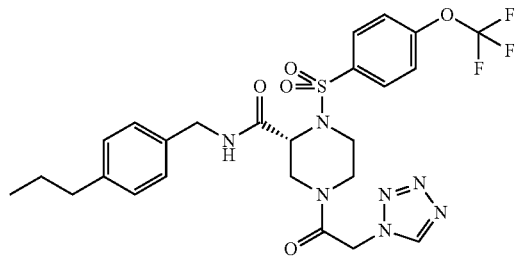 |
| 462 | 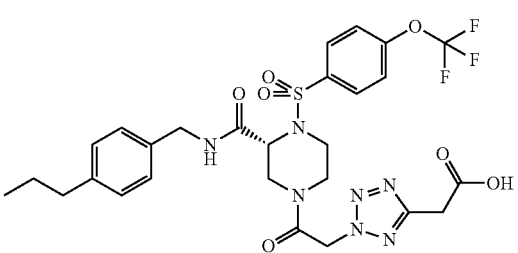 |
| 463 | 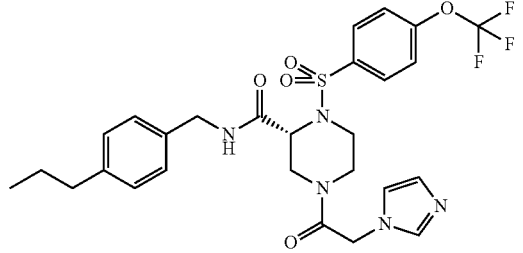 |
| 464 | 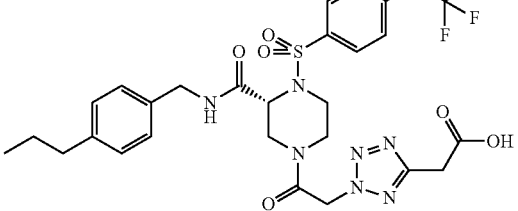 |
| 465 | 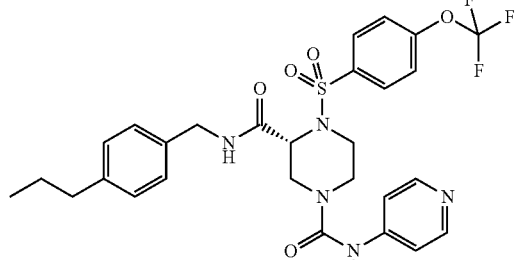 |
TABLE 94
| Ex. No. | Structural Formula |
|---|---|
| 466 | 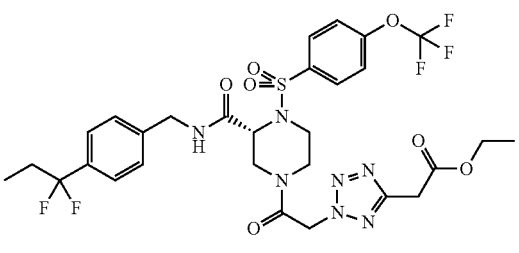 |
| 467 | 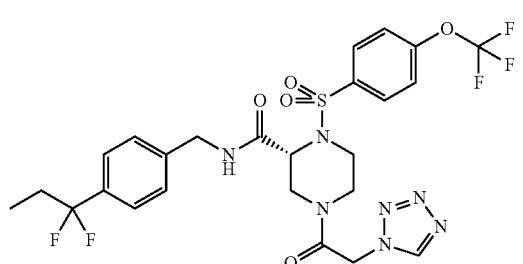 |

US 8,017,612 B2
513
TABLE 94-continued
| Ex. No. | Structural Formula |
|---|---|
| 468 | 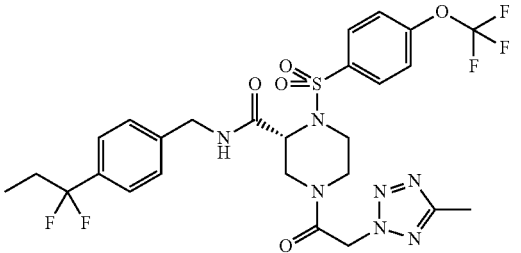 |
| 469 | 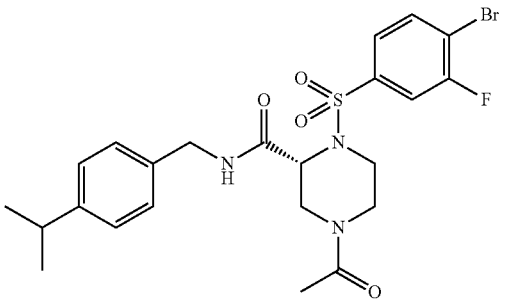 |
| 470 | 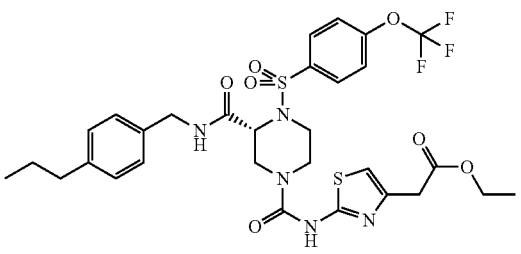 |
TABLE 95
| Ex. No. | Structural Formula |
|---|---|
| 471 | 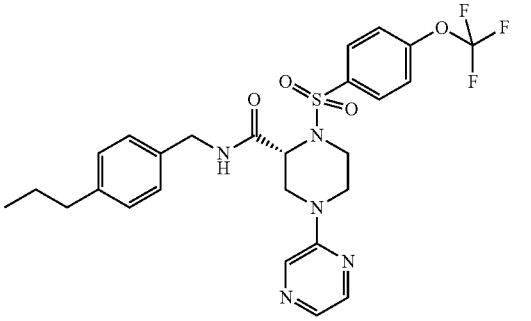 |
514
TABLE 95-continued
| Ex. No. | Structural Formula |
|---|---|
| 472 |  |
| 473 | 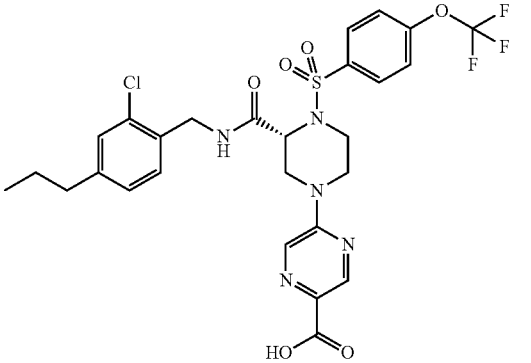 |
| 474 | 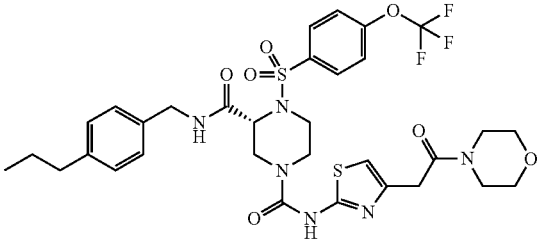 |
| 475 | 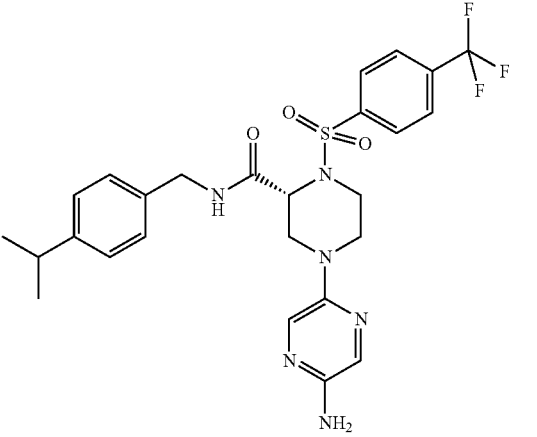 |

TABLE 96
| Ex. No. | Structural Formula |
|---|---|
| 476 | 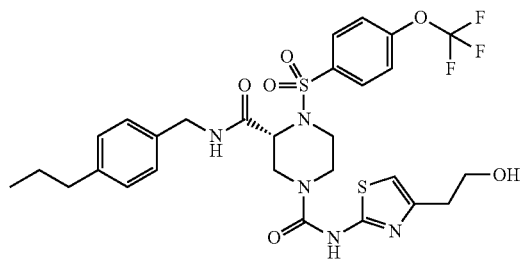 |
| 477 | 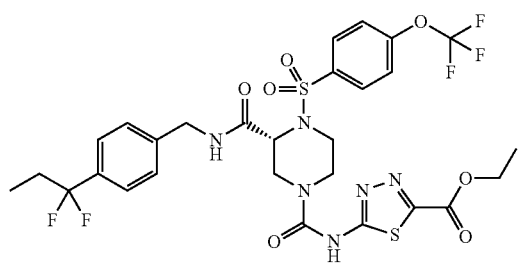 |
| 478 | 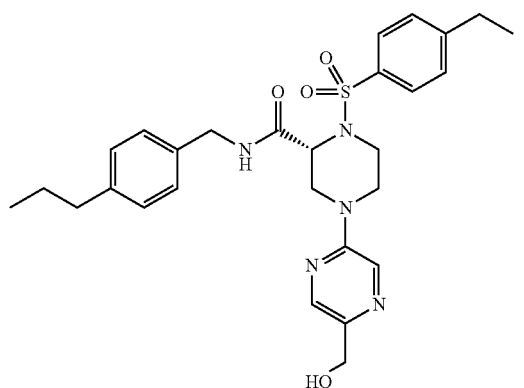 |
| 479 | 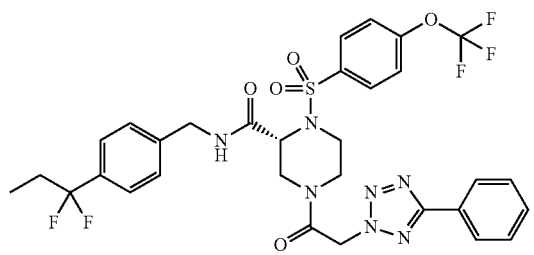 |
| 480 | 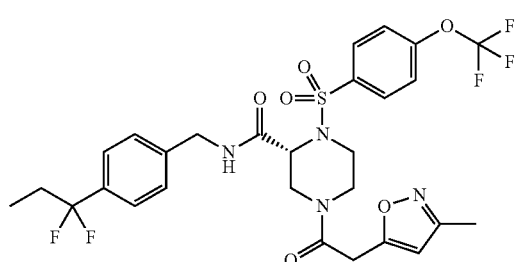 |
TABLE 97
| Ex. No. | Structural Formula |
|---|---|
| 481 | 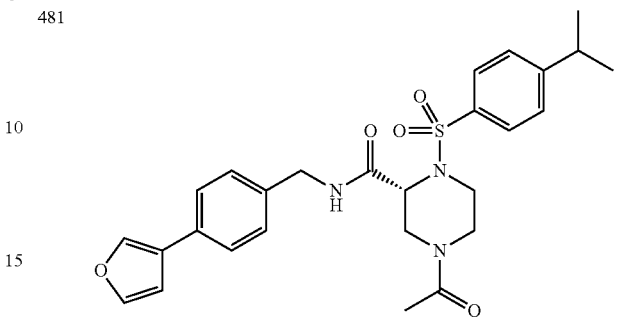 |
| 482 | 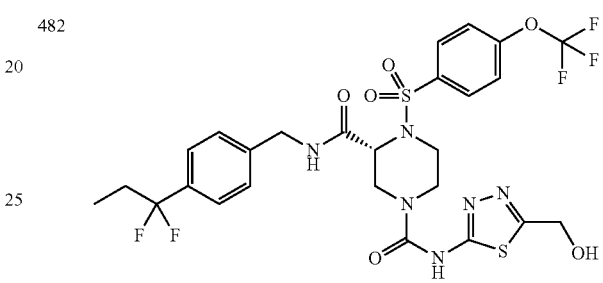 |
| 483 | 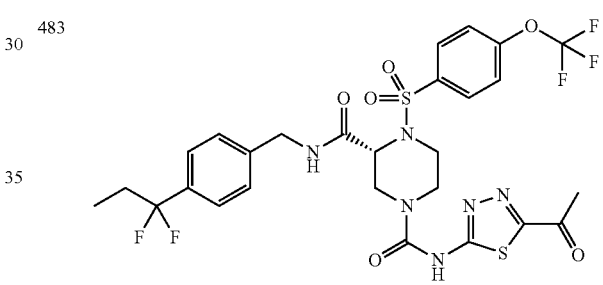 |
| 484 | 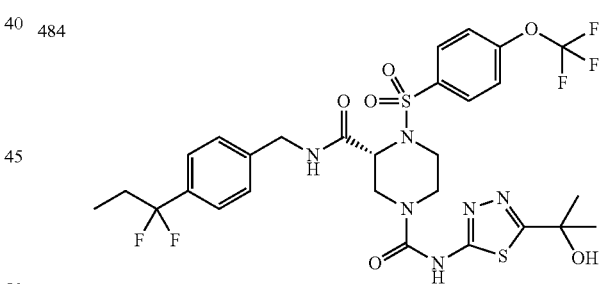 |
| 485 | 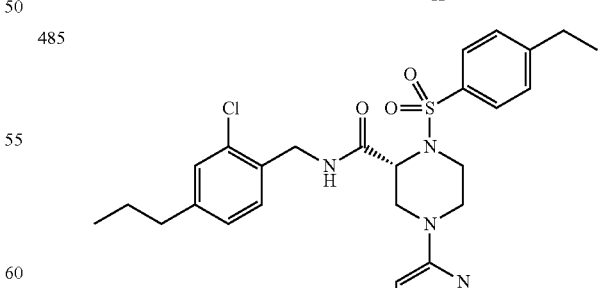 |

TABLE 98
| Ex. No. | Structural Formula |
|---|---|
| 486 | 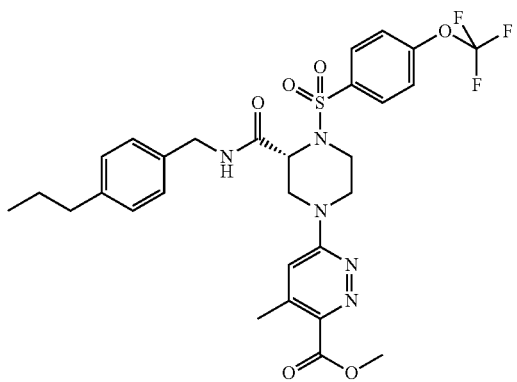 |
| 487 | 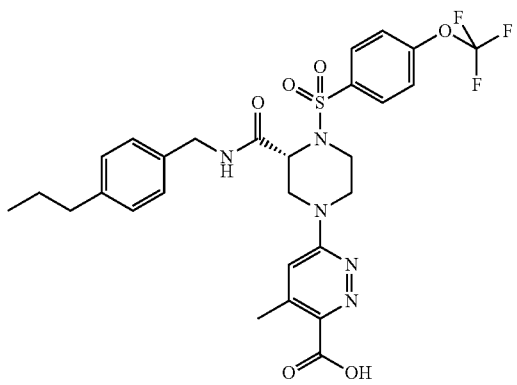 |
| 488 | 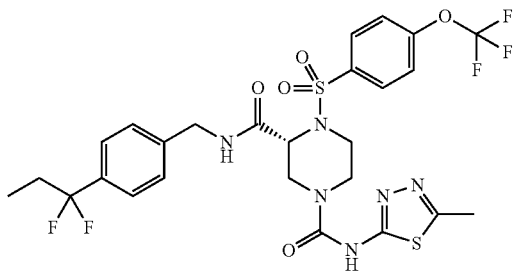 |
| 489 | 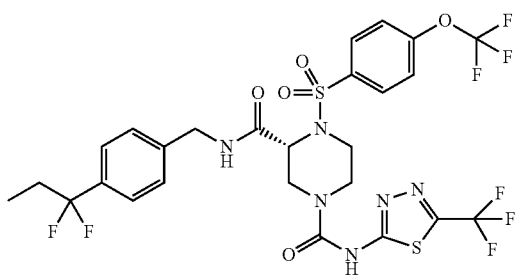 |
TABLE 98-continued
| Ex. No. | Structural Formula |
|---|---|
| 490 | 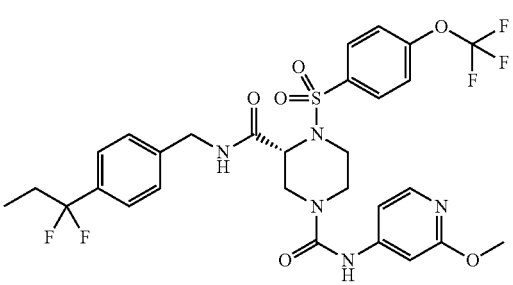 |
TABLE 99
| Ex. No. | Structural Formula |
|---|---|
| 491 | 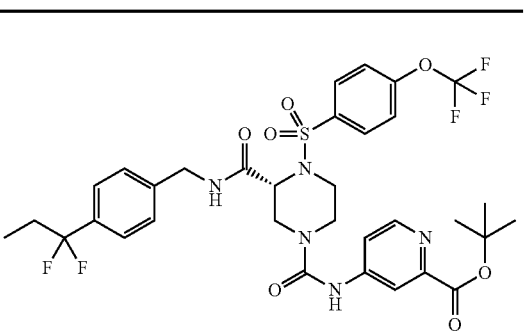 |
| 492 | |
| 493 | 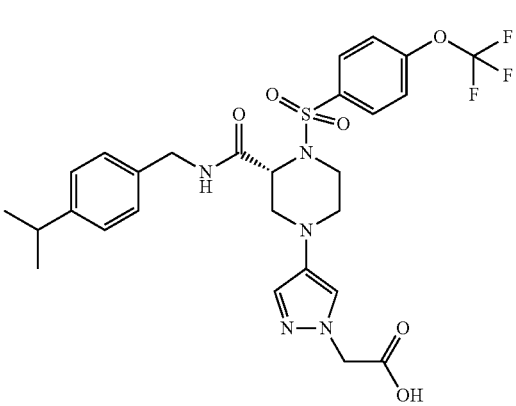 |

TABLE 99-continued
| Ex. No. | Structural Formula |
|---|---|
| 494 | 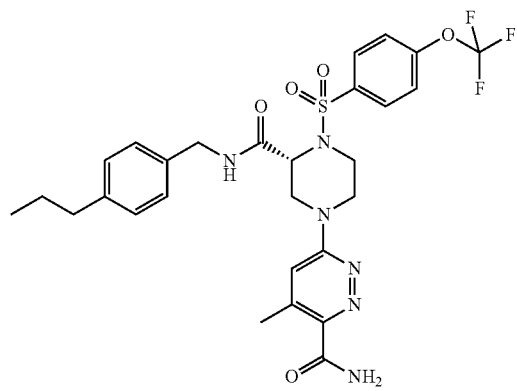 |
| 495 | 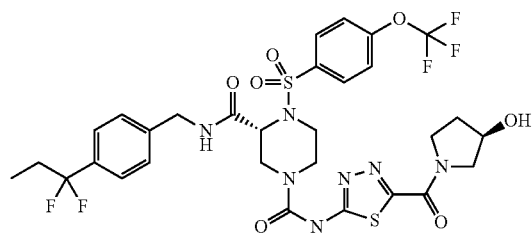 |
TABLE 100
| Ex. No. | Structural Formula |
|---|---|
| 496 | 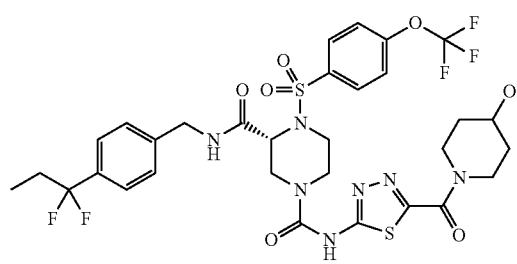 |
| 497 | 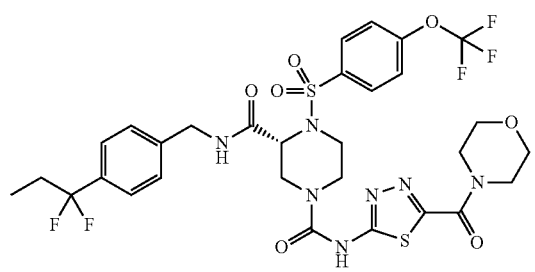 |
TABLE 100-continued
| Ex. No. | Structural Formula |
|---|---|
| 498 | 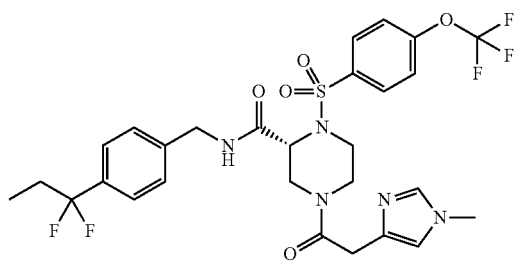 |
| 499 | 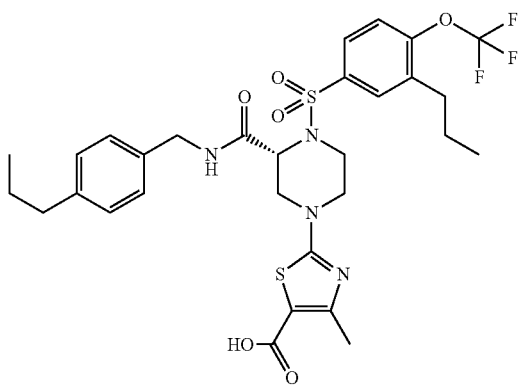 |
| 500 | 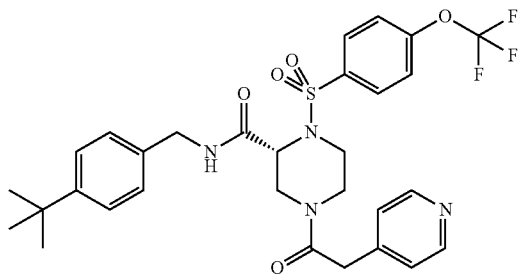 |
TABLE 101
| Ex. No. | Structural Formula |
|---|---|
| 501 | 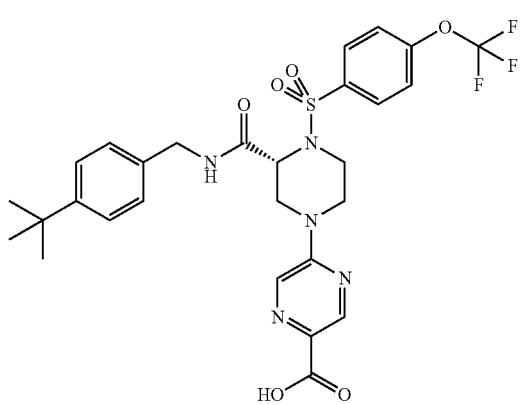 |

TABLE 101-continued
| Ex. No. | Structural Formula |
|---|---|
| 502 | 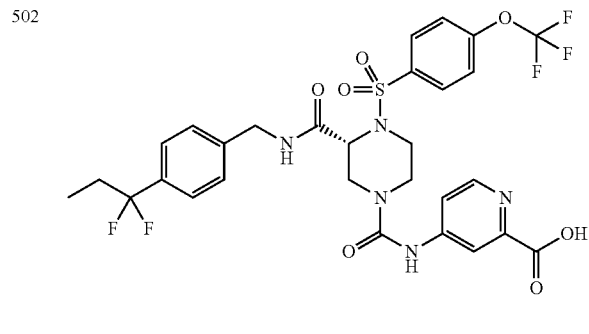 |
| 503 | 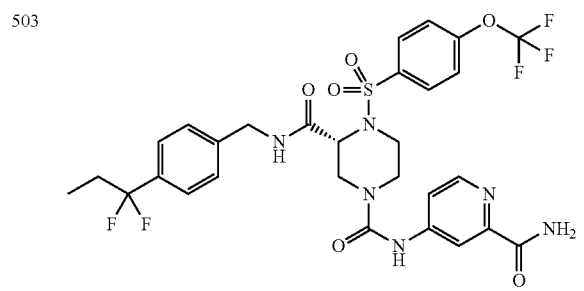 |
| 504 | 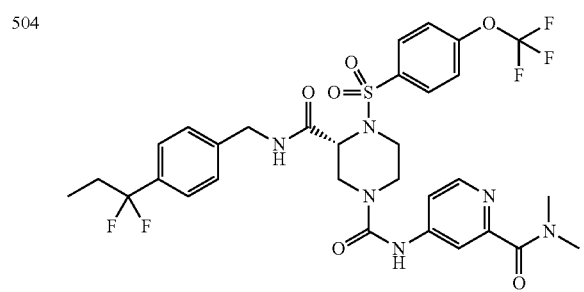 |
| 505 | 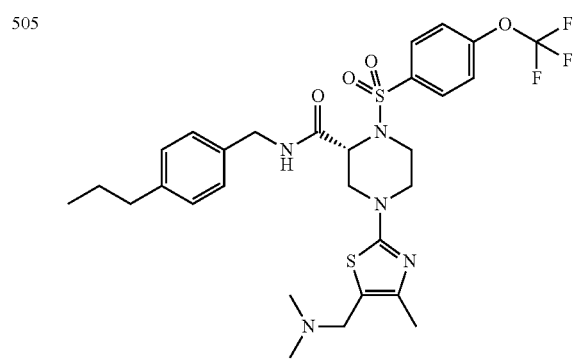 |
TABLE 102
| Ex. No. | Structural Formula |
|---|---|
| 506 | 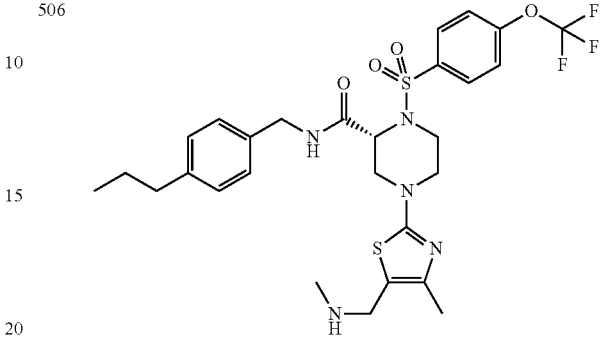 |
| 507 | 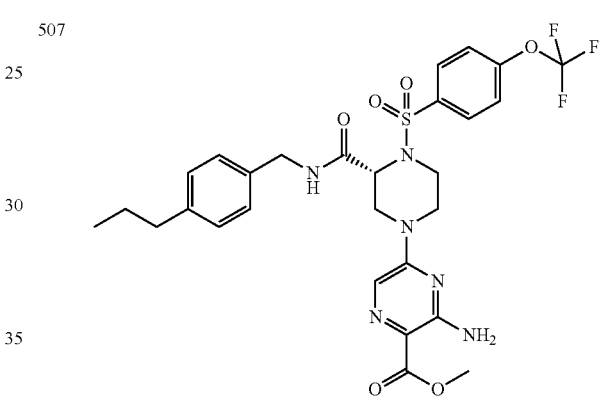 |
| 508 | 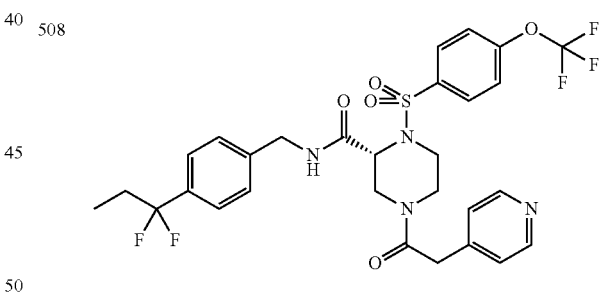 |
| 509 | 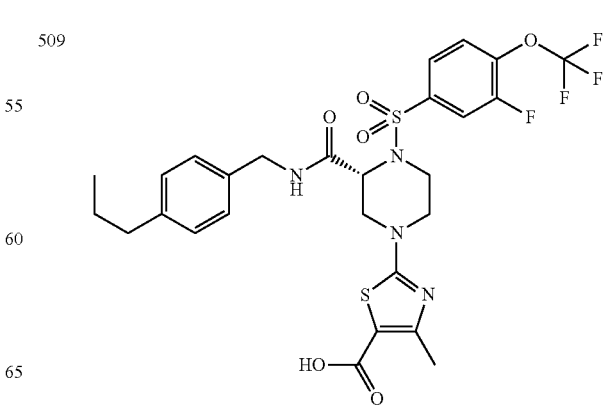 |

TABLE 102-continued
| Ex. No. | Structural Formula |
|---|---|
| 510 | 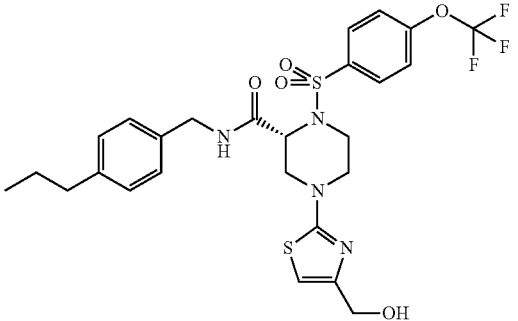 |
TABLE 103
| Ex. No. | Structural Formula |
|---|---|
| 511 | 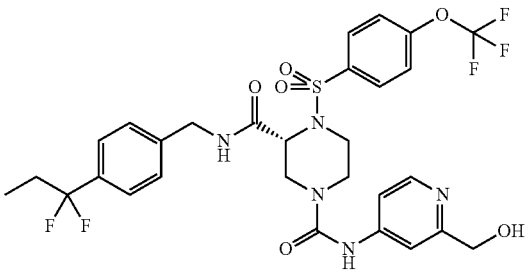 |
| 512 | 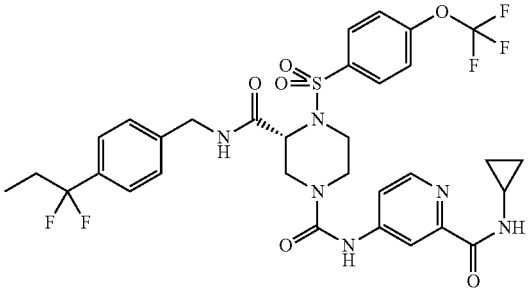 |
| 513 | 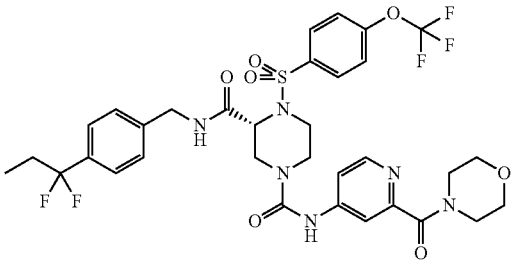 |
TABLE 103-continued
| Ex. No. | Structural Formula |
|---|---|
| 514 | 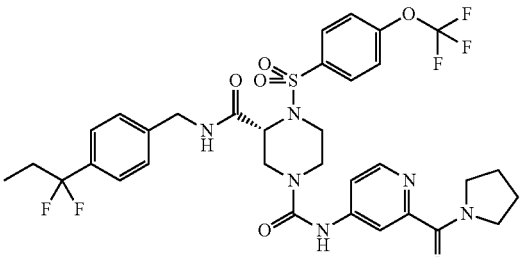 |
| 515 | 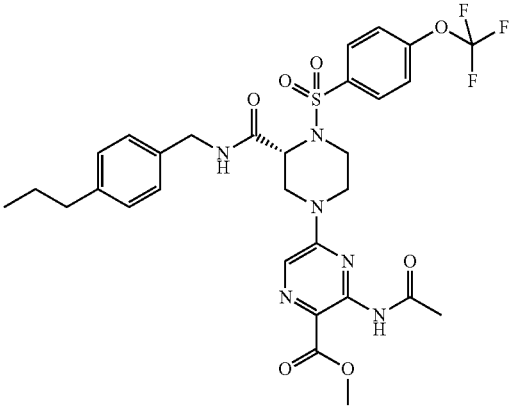 |
TABLE 104
| Ex. No. | Structural Formula |
|---|---|
| 516 | 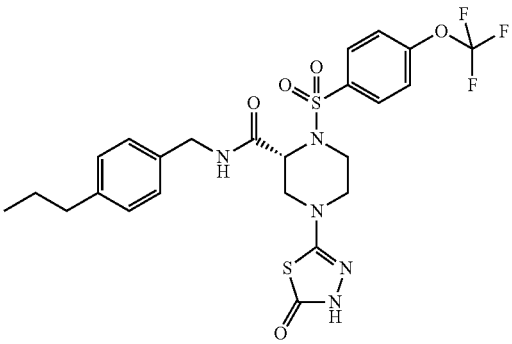 |
| 517 | 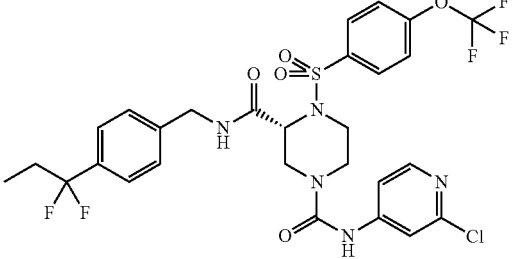 |

TABLE 104-continued
| Ex. No. | Structural Formula |
|---|---|
| 518 | 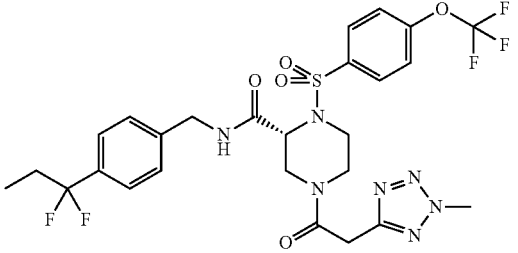 |
| 519 | 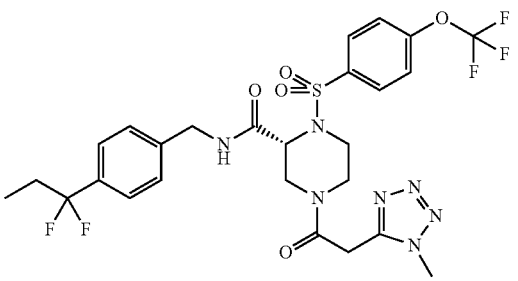 |
| 520 | 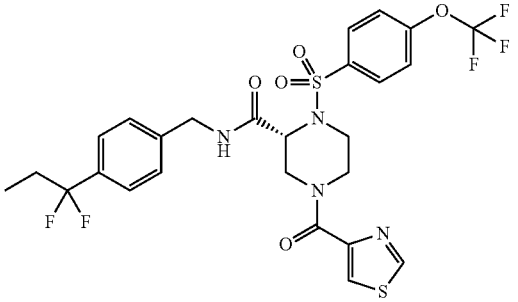 |
TABLE 105
| Ex. No. | Structural Formula |
|---|---|
| 521 | 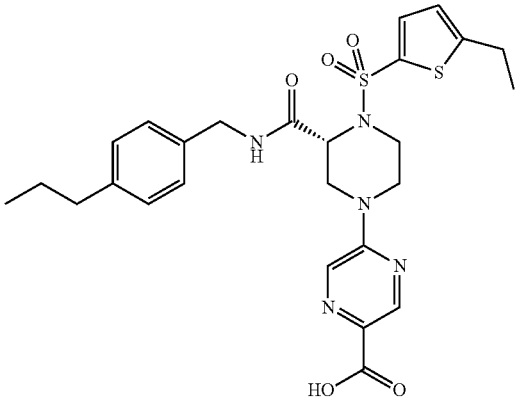 |
TABLE 105-continued
| Ex. No. | Structural Formula |
|---|---|
| 522 | 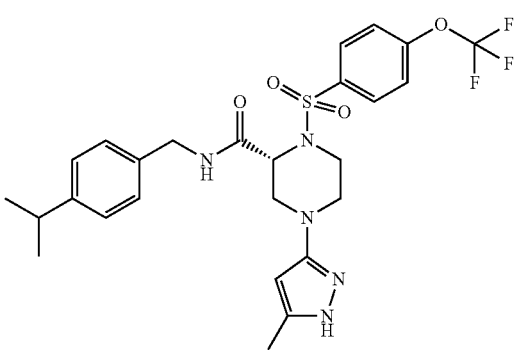 |
| 523 | 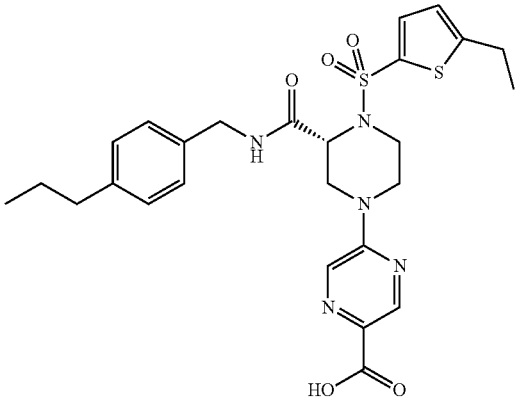 |
| 524 | 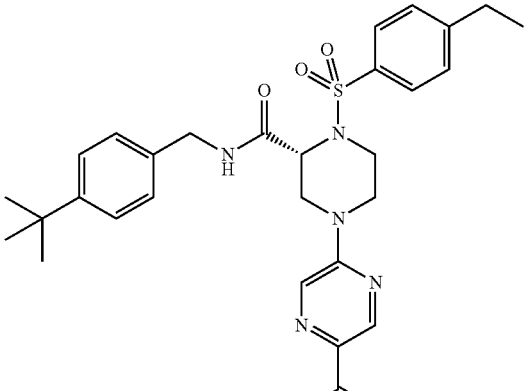 |

TABLE 106
| Ex. No. | Structural Formula |
|---|---|
| 525 | 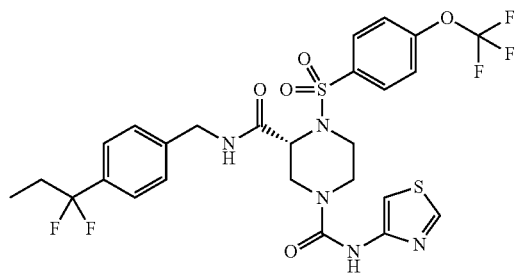 |
| 526 | 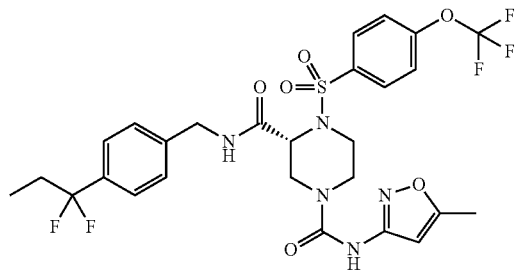 |
| 527 | 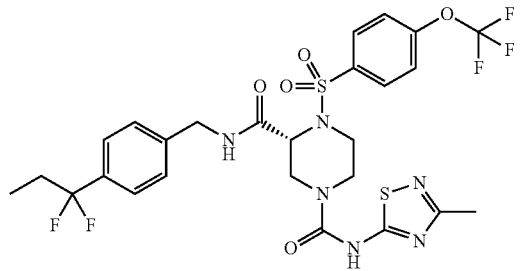 |
| 528 | 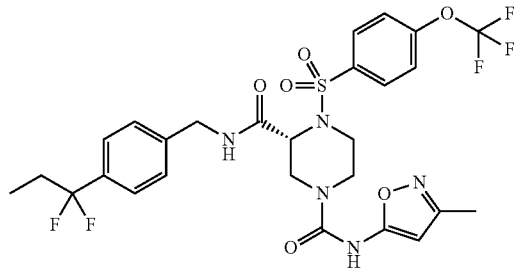 |
| 529 | 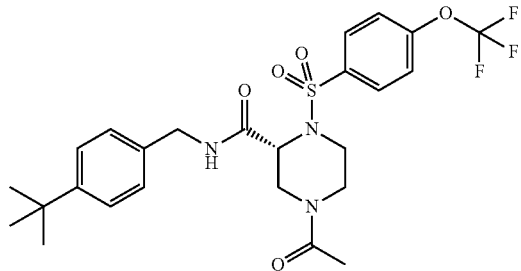 |
TABLE 107
| Ex. No. | Structural Formula |
|---|---|
| 530 | 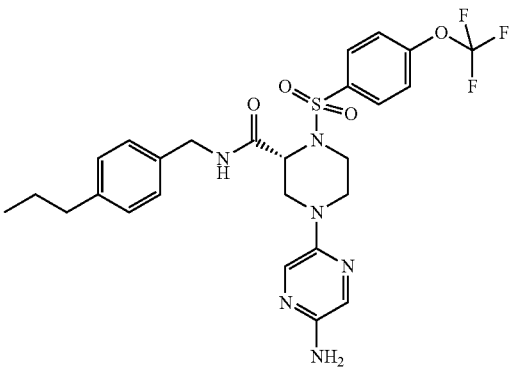 |
| 531 | 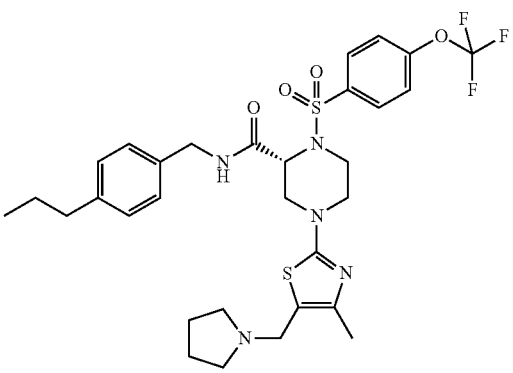 |
| 532 | 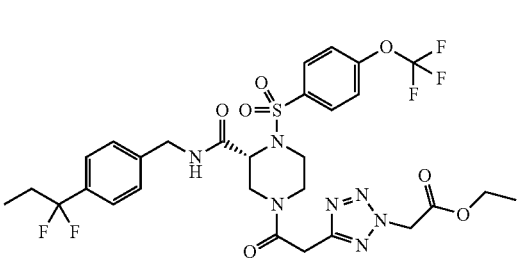 |

TABLE 107-continued
| Ex. No. | Structural Formula |
|---|---|
| 533 | 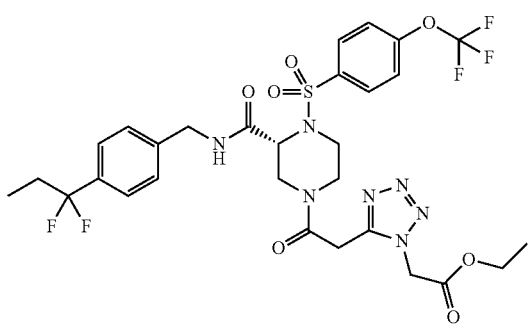 |
| 534 | 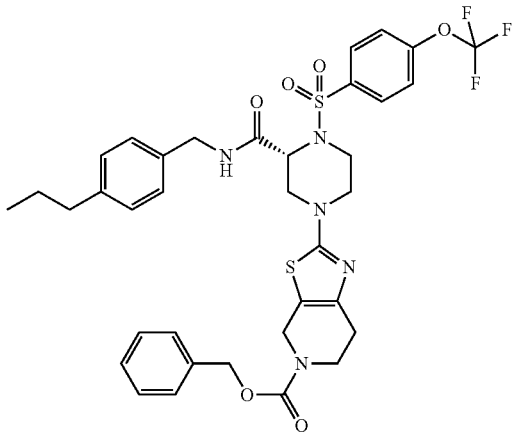 |
TABLE 108
| Ex. No. | Structural Formula |
|---|---|
| 535 | 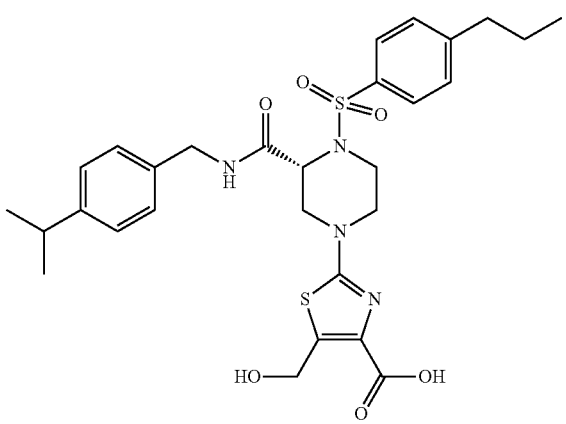 |
| 536 | 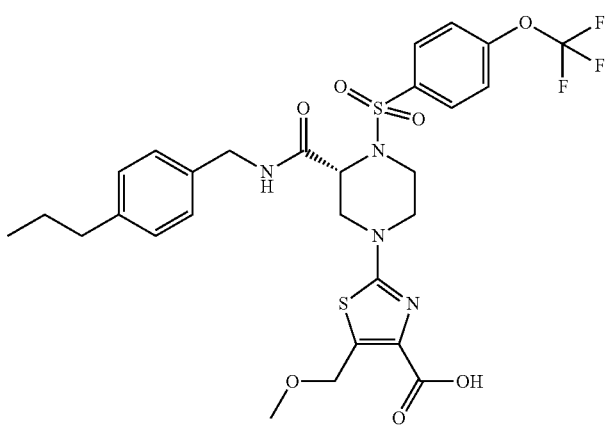 |

TABLE 108-continued
| Ex. No. | Structural Formula |
|---|---|
| 537 | 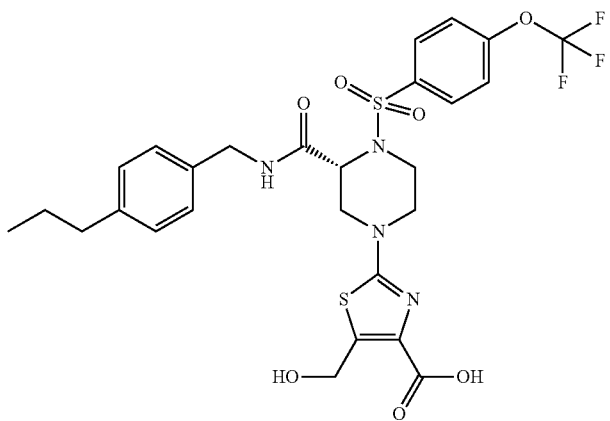 |
| 538 | 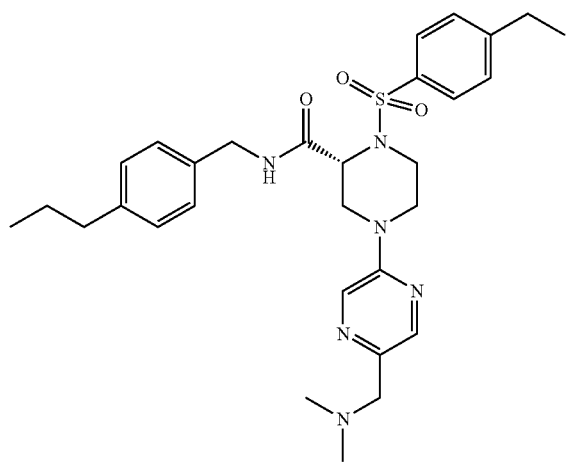 |
| 539 | 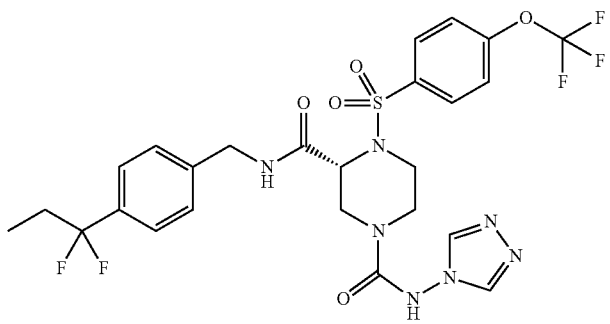 |

TABLE 109
| Ex. No. | Structural Formula |
|---|---|
| 540 | 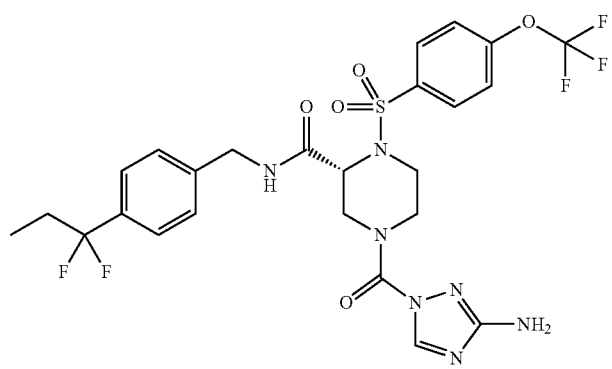 |
| 541 | 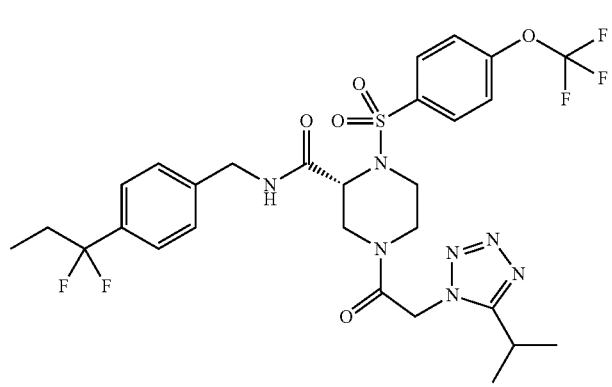 |
| 542 | 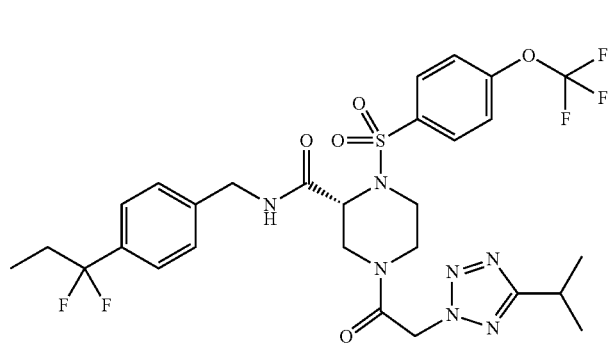 |
| 543 | 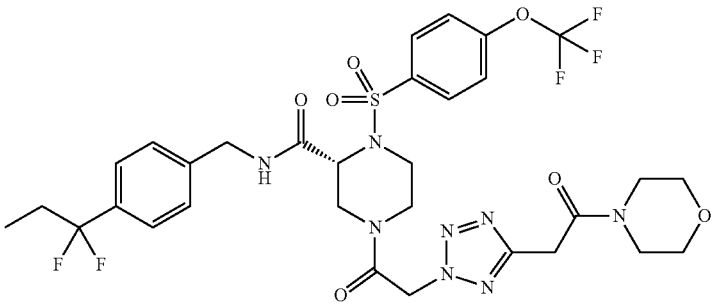 |

TABLE 109-continued
| Ex. No. | Structural Formula |
|---|---|
| 544 | 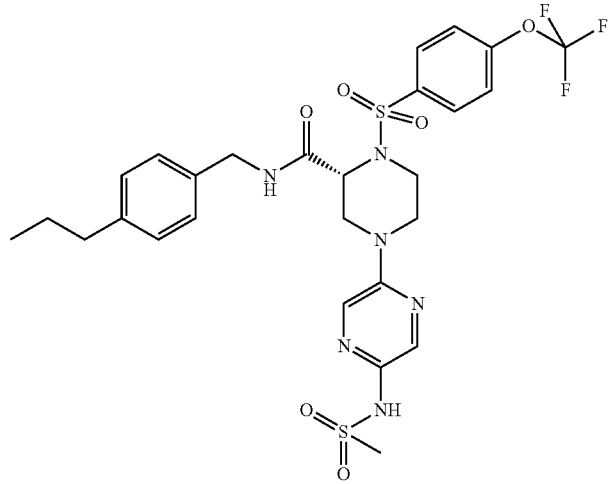 |
TABLE 110
| Ex. No. | Structural Formula |
|---|---|
| 545 | 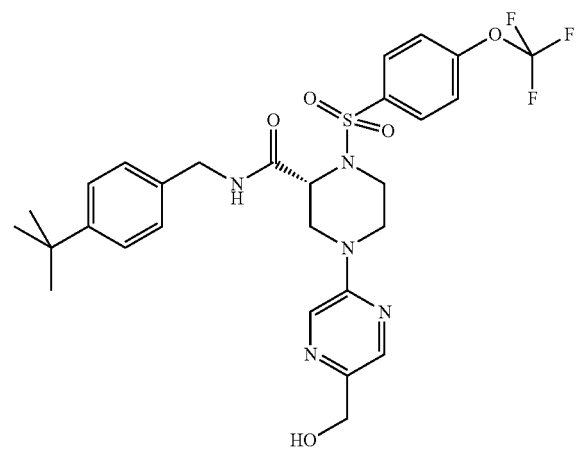 |
| 546 | 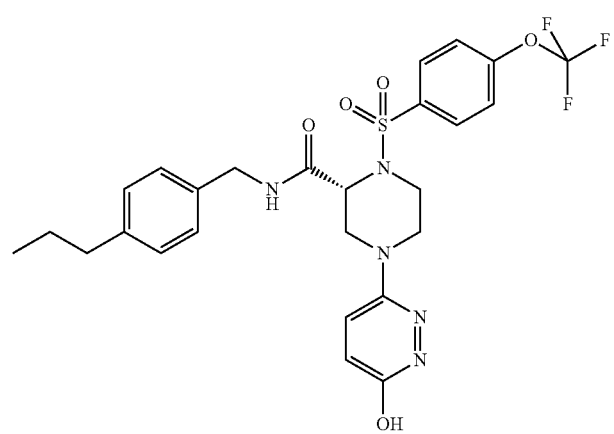 |

TABLE 110-continued
| Ex. No. | Structural Formula |
|---|---|
| 547 | 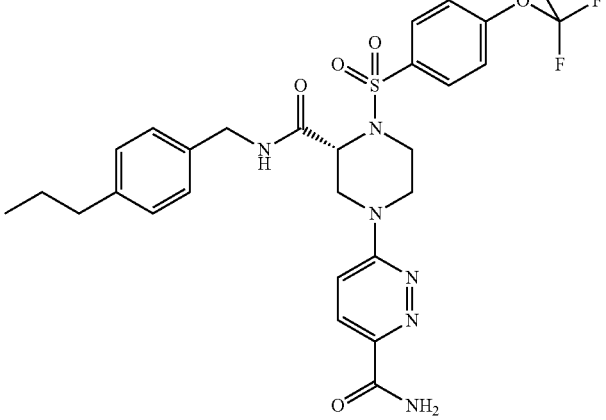 |
| 548 | 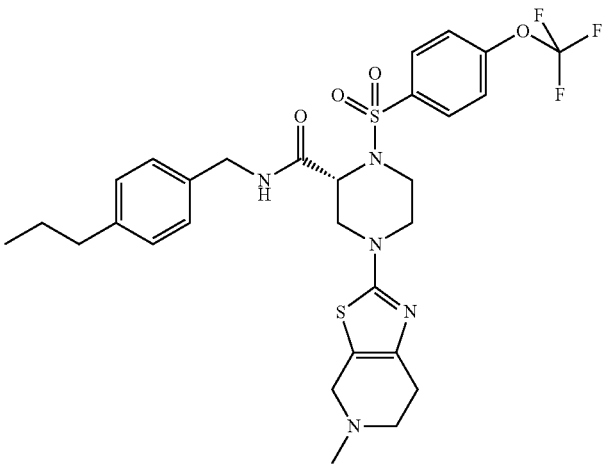 |
| 549 | 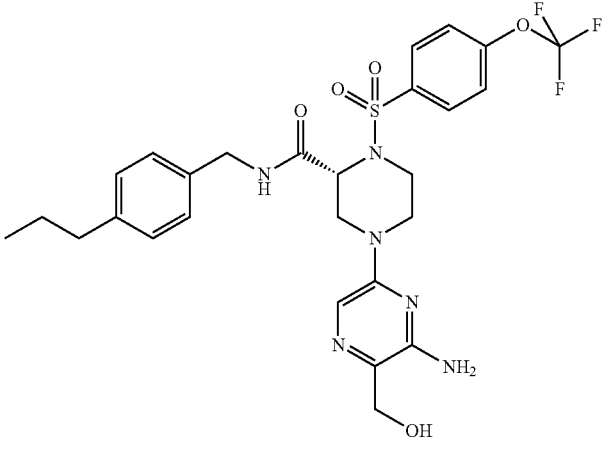 |

TABLE 111
| Ex. No. | Structural Formula |
|---|---|
| 550 | 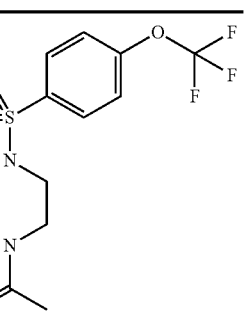 |
| 551 | 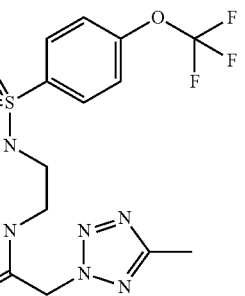 |
| 552 | 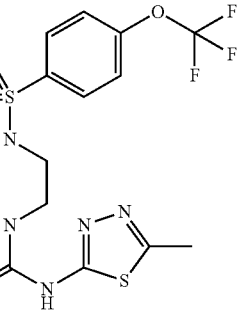 |
| 553 | 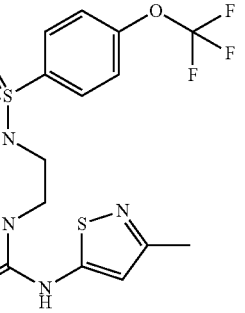 |
| 554 | 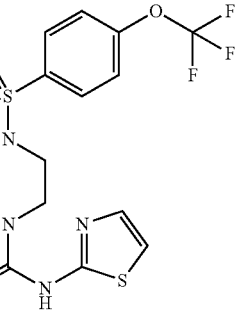 |

TABLE 112
| Ex. No. | Structural Formula |
|---|---|
| 555 | 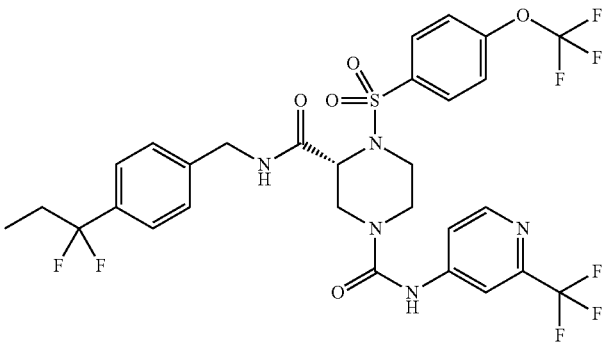 |
| 556 | 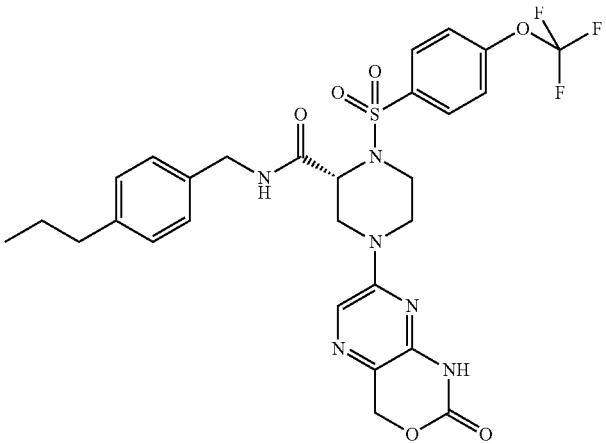 |
| 557 | 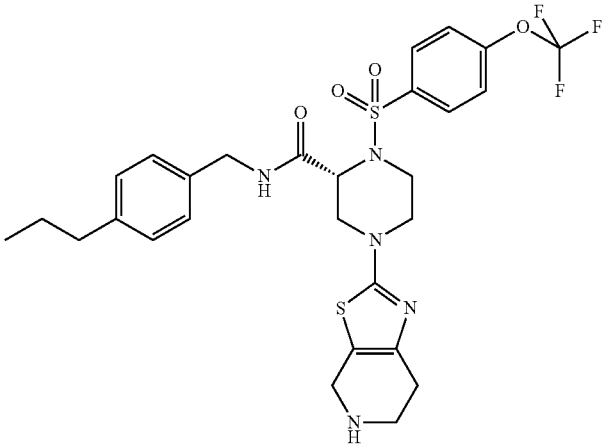 |

543
TABLE 112-continued
| Ex. No. | Structural Formula |
| --- | --- |
| 558 | 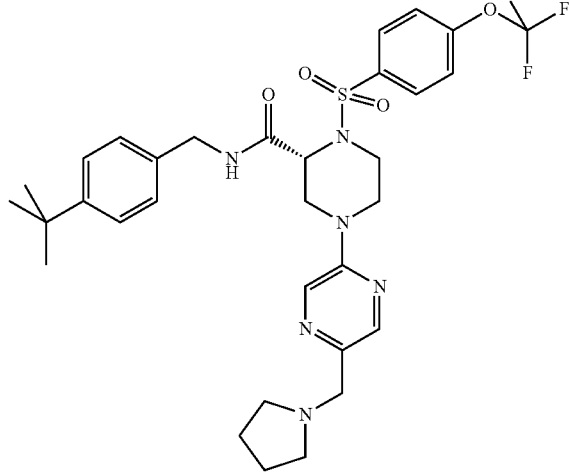 |
| 559 | 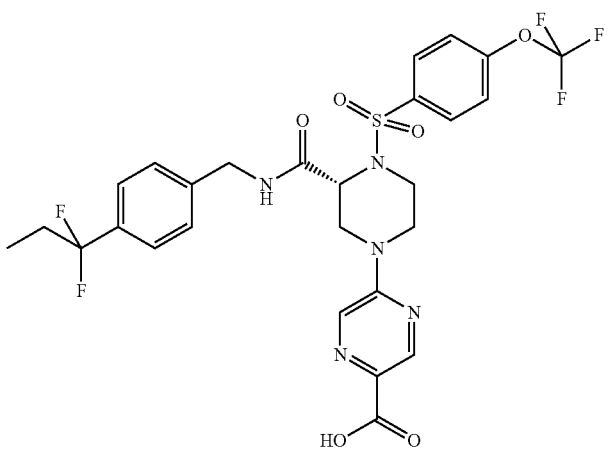 |
TABLE 113
| Ex. No. | Structural Formula |
| --- | --- |
| 560 | 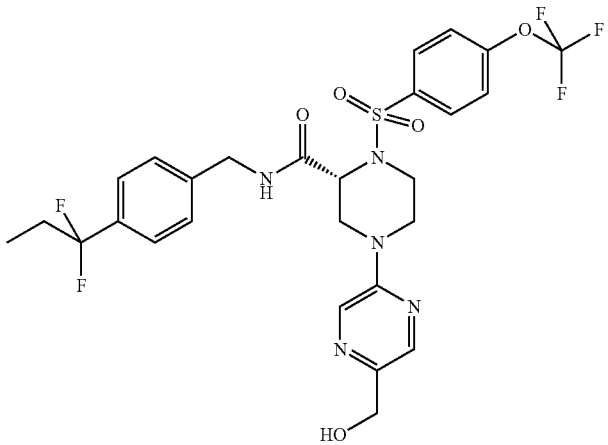 |

TABLE 113-continued
| Ex. No. | Structural Formula |
|---|---|
| 561 | 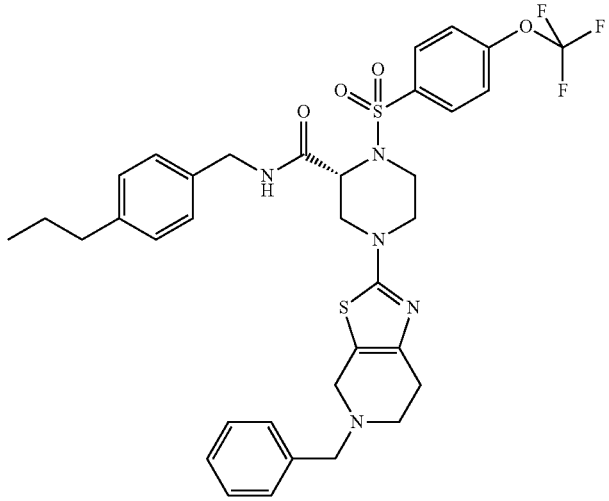 |
| 562 | 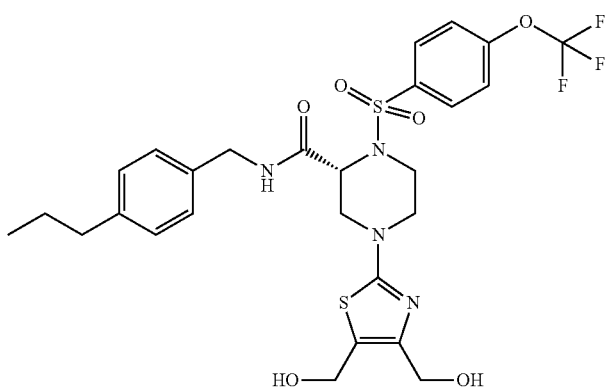 |
| 563 | 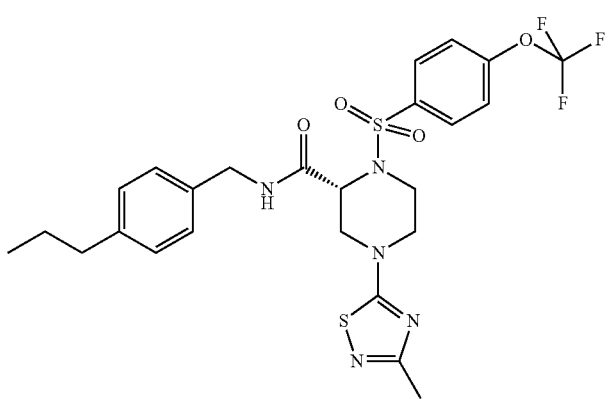 |

TABLE 113-continued
| Ex. No. | Structural Formula |
|---|---|
| 564 | 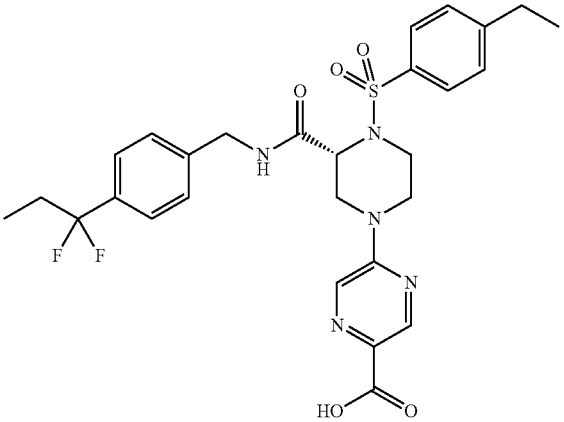 |
TABLE 114
| Ex. No. | Structural Formula |
|---|---|
| 565 | 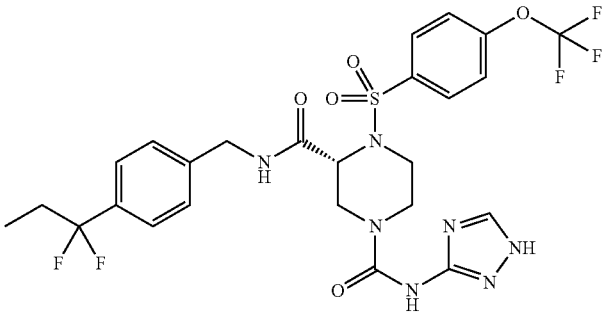 |
| 566 | 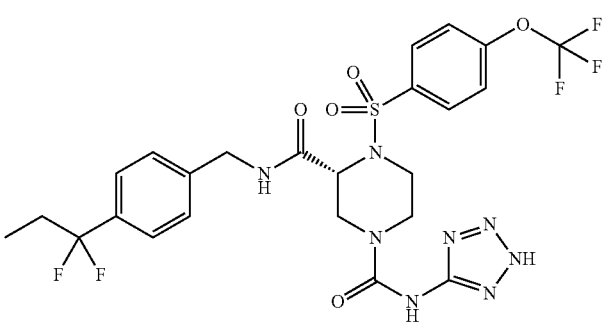 |
| 567 | 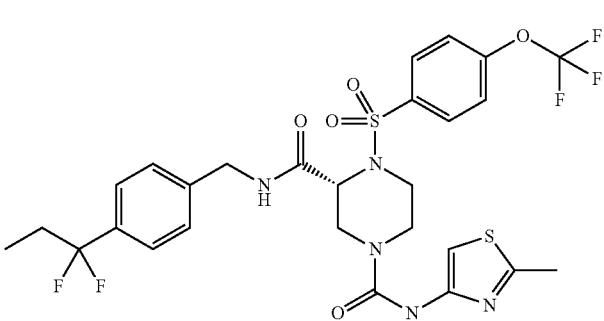 |

TABLE 114-continued
| Ex. No. | Structural Formula |
|---|---|
| 568 | |
| 569 | 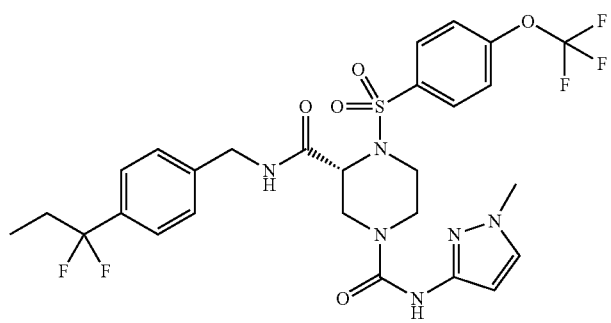 |
TABLE 115
| Ex. No. | Structural Formula |
|---|---|
| 570 | |

TABLE 115-continued
| Ex. No. | Structural Formula |
|---|---|
| 571 | 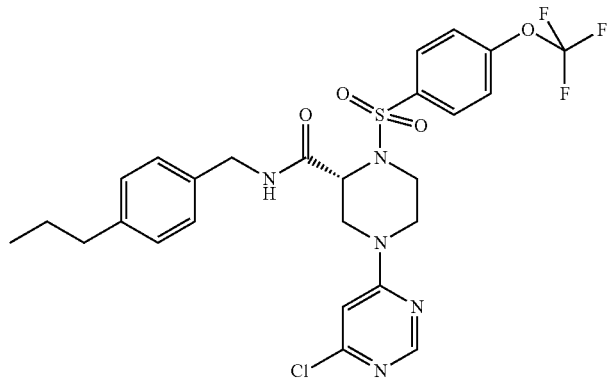 |
| 572 | 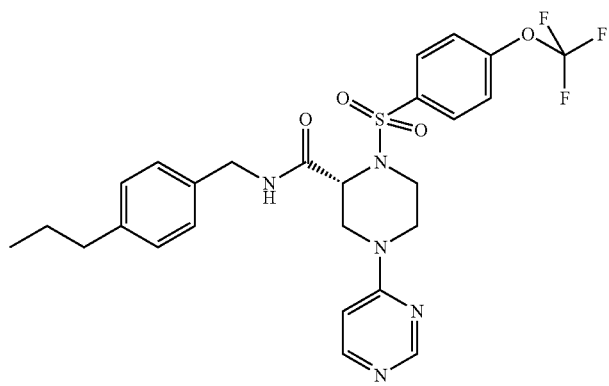 |
| 573 | 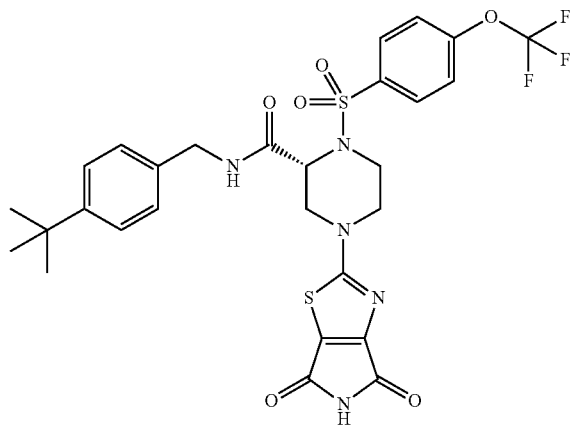 |

TABLE 115-continued
| Ex. No. | Structural Formula |
|---|---|
| 574 | 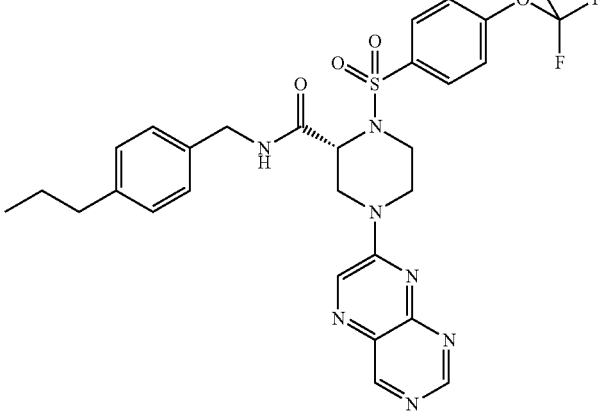 |
TABLE 116
| Ex. No. | Structural Formula |
|---|---|
| 575 | 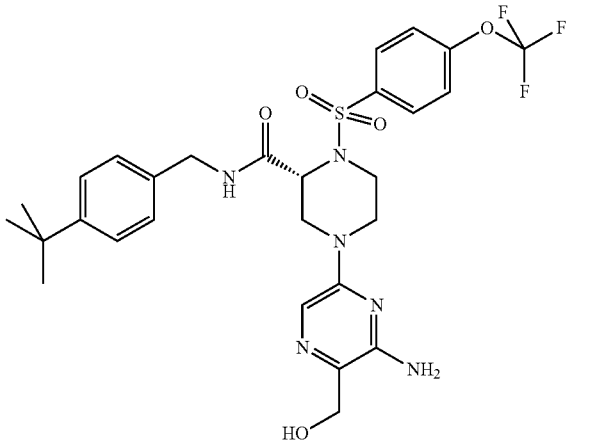 |
| 576 | 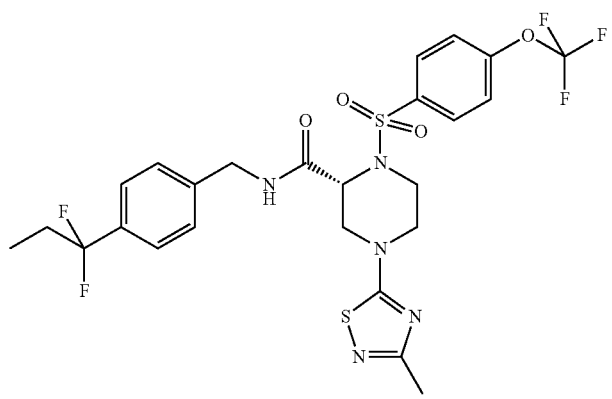 |

TABLE 116-continued
| Ex. No. | Structural Formula |
| --- | --- |
| 577 | 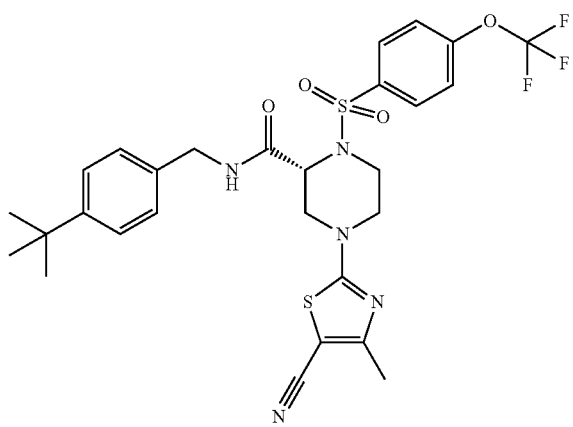 |
| 578 | 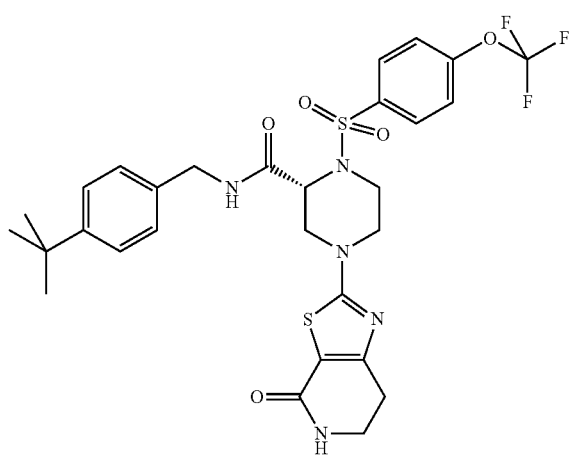 |
| 579 | 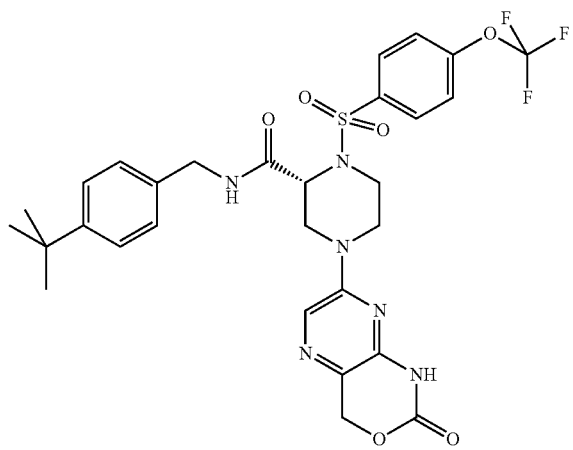 |

TABLE 117
| Ex. No. | Structural Formula |
|---|---|
| 580 | 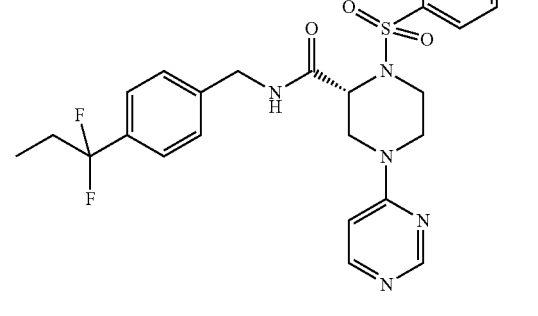 |
| 581 | 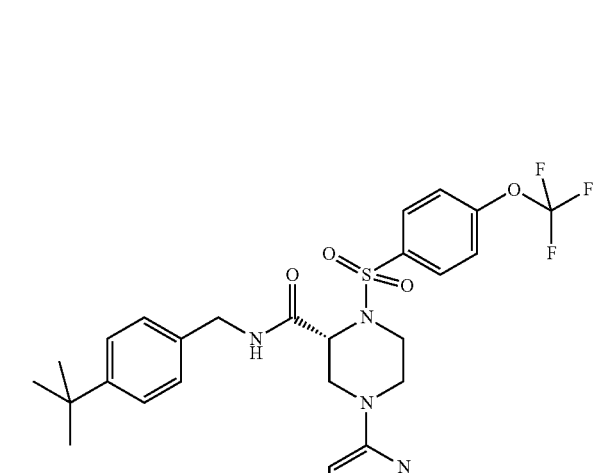 |
| 582 | 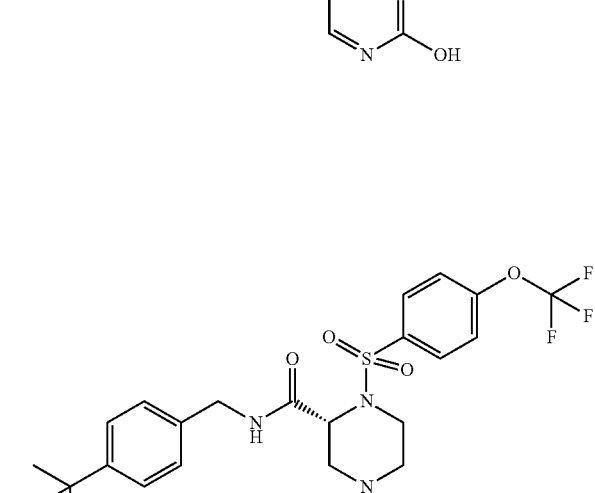 |

TABLE 117-continued
| Ex. No. | Structural Formula |
|---|---|
| 583 | 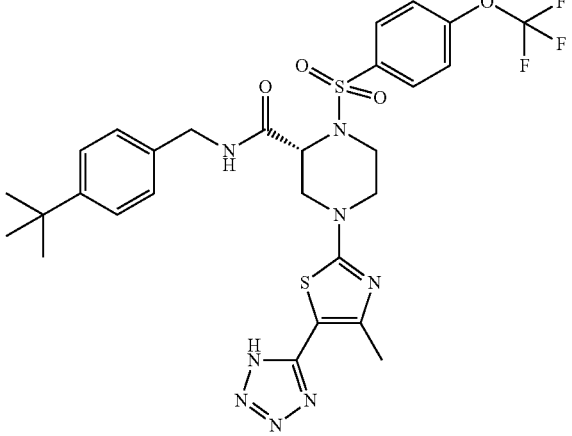 |
| 584 | 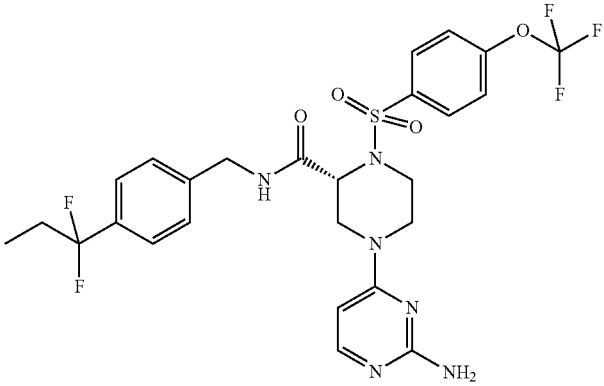 |
TABLE 118
| Ex. No. | Structural Formula |
|---|---|
| 585 | 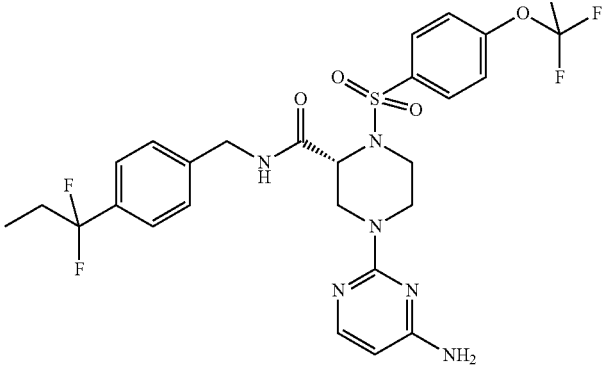 |

TABLE 118-continued
| Ex. No. | Structural Formula |
| --- | --- |
| 586 | 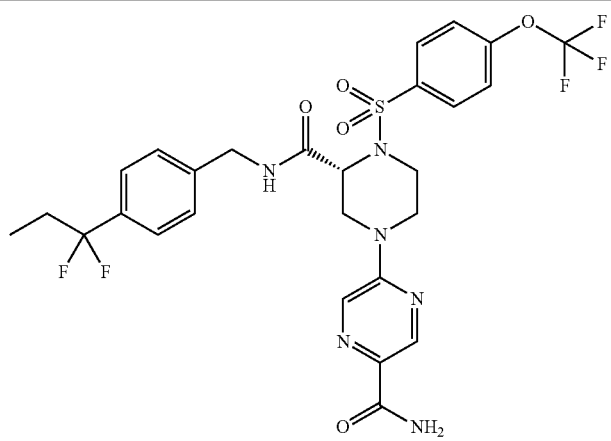 |
| 587 | 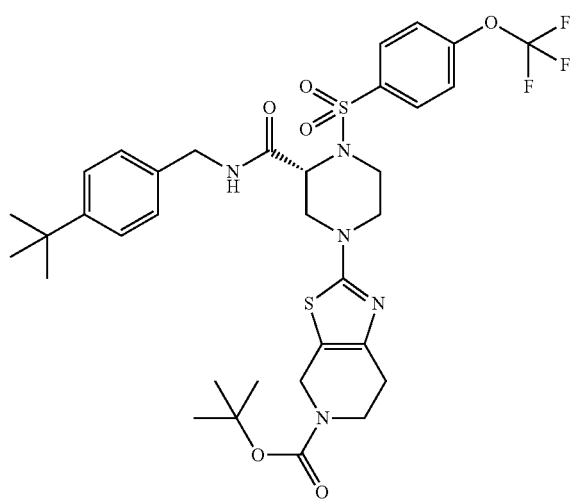 |
| 588 | 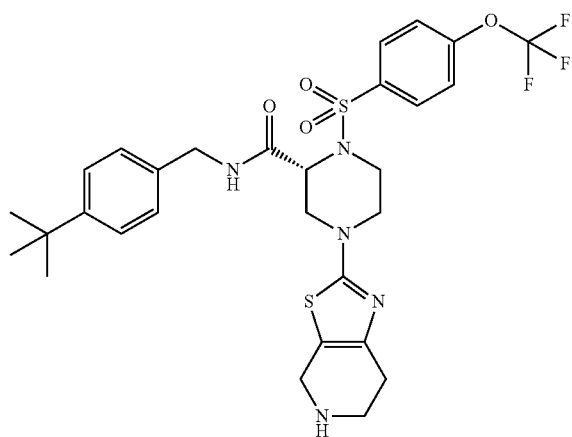 |

TABLE 118-continued
| Ex. No. | Structural Formula |
|---|---|
| 589 | 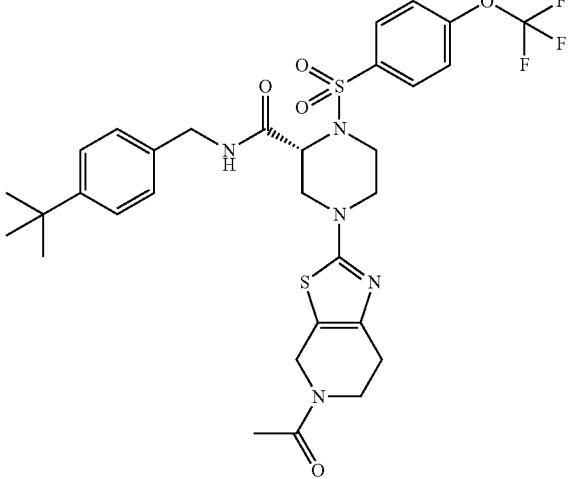 |
TABLE 119
| Ex. No. | Structural Formula |
|---|---|
| 590 | 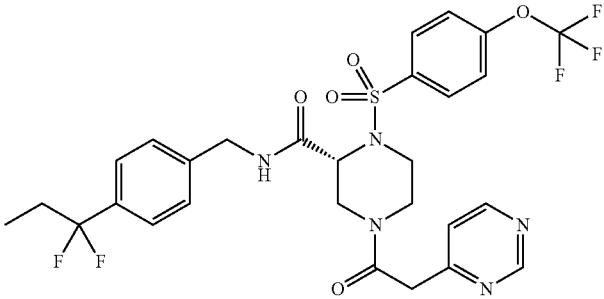 |
| 591 | 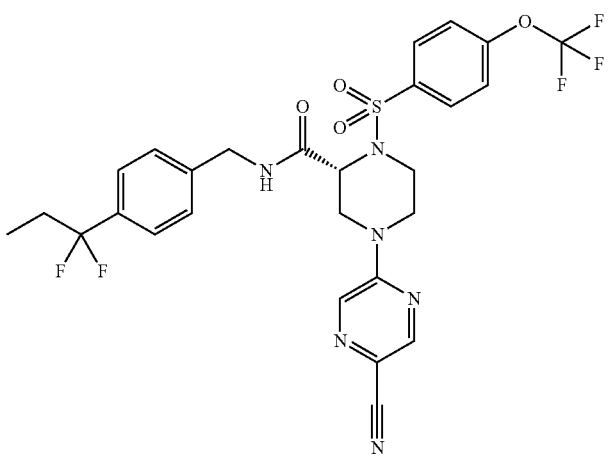 |

TABLE 119-continued
| Ex. No. | Structural Formula |
|---|---|
| 592 | 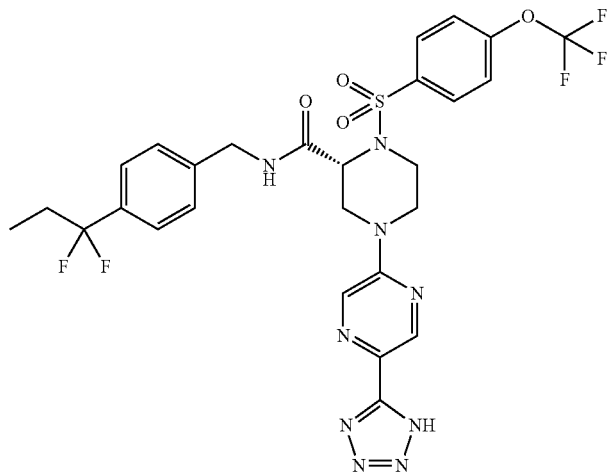 |
| 593 | 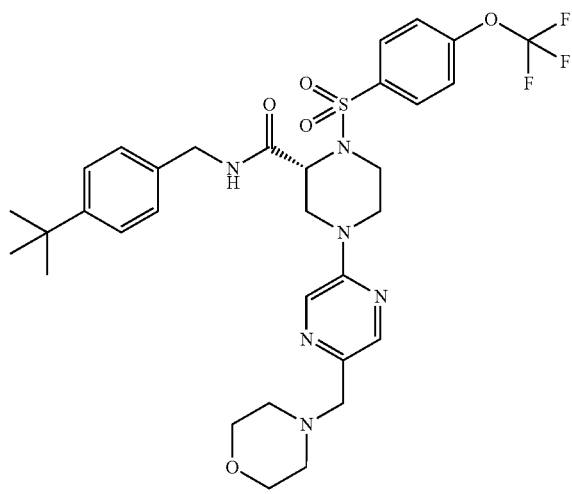 |
| 594 | 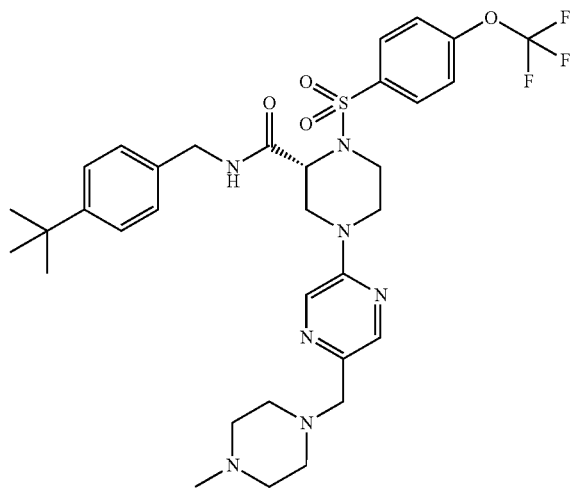 |

TABLE 120
| Ex. No. | Structural Formula |
|---|---|
| 595 | 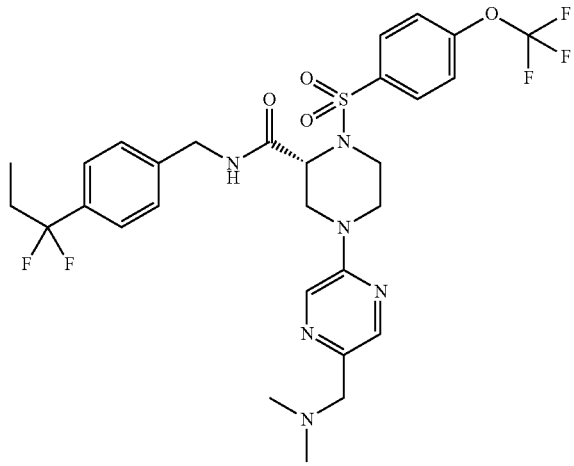 |
| 596 | 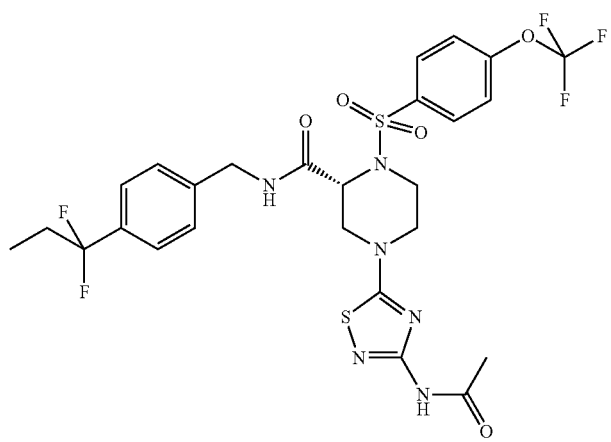 |
| 597 | 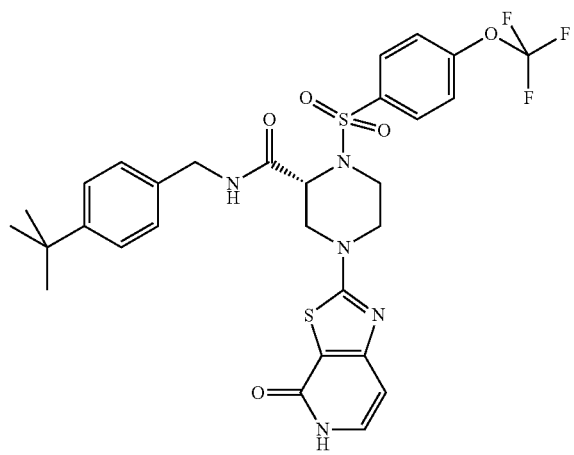 |

TABLE 120-continued
| Ex. No. | Structural Formula |
|---|---|
| 598 | |
| 599 | |
TABLE 121
| Ex. No. | Structural Formula |
|---|---|
| 600 | 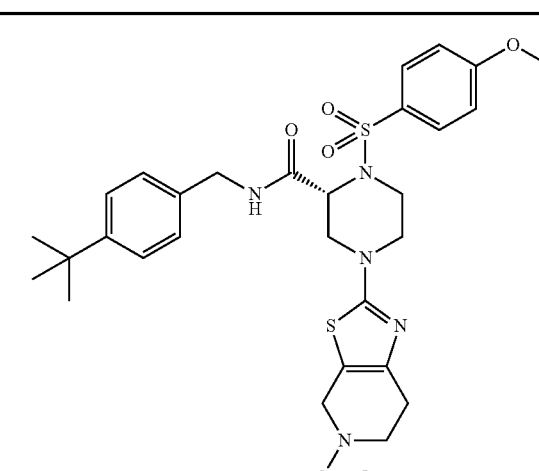 |

TABLE 121-continued
| Ex. No. | Structural Formula |
|---|---|
| 601 | 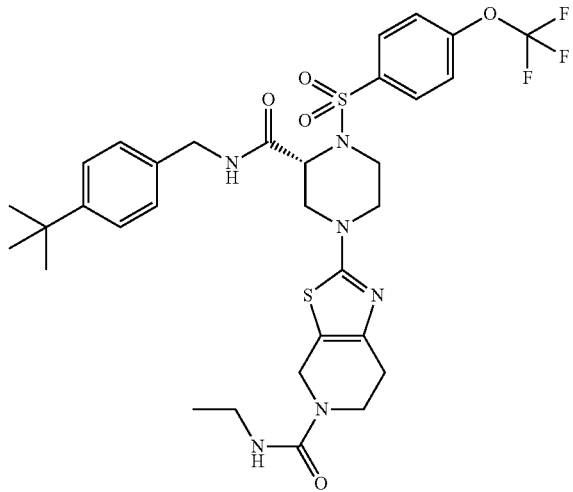 |
| 602 | 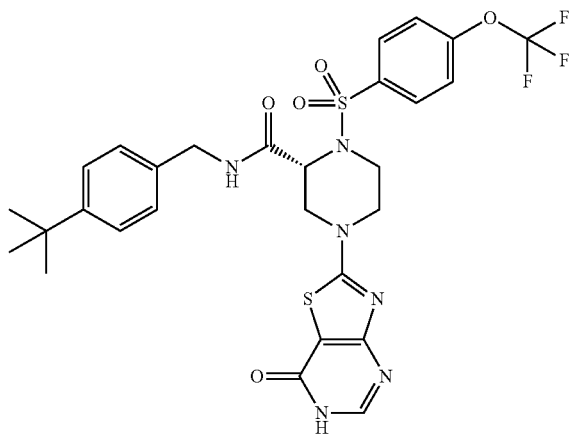 |
| 603 | 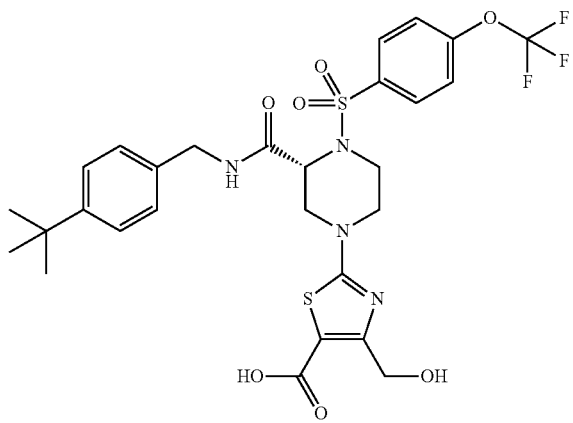 |

TABLE 121-continued

| Ex. No. | Structural Formula |
|---|---|
| 604 | |

TABLE 122

| Ex. No. | Structural Formula |
|---|---|
| 605 | |
| 606 | |

TABLE 122-continued
| Ex. No. | Structural Formula |
|---|---|
| 607 | 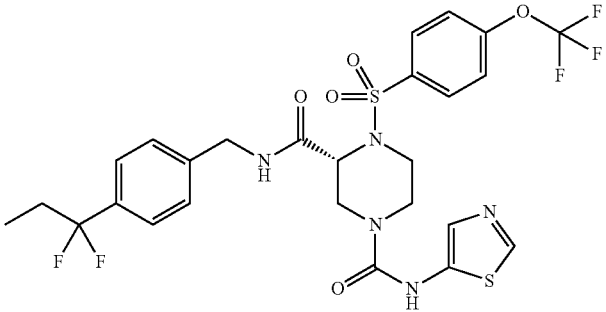 |
| 608 | 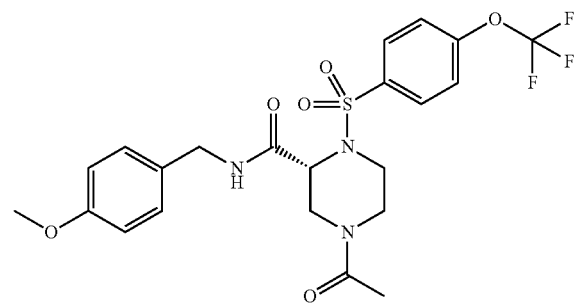 |
| 609 | 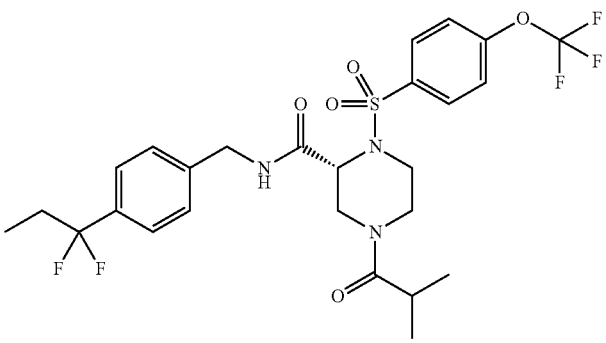 |
TABLE 123
| Ex. No. | Structural Formula |
|---|---|
| 610 | 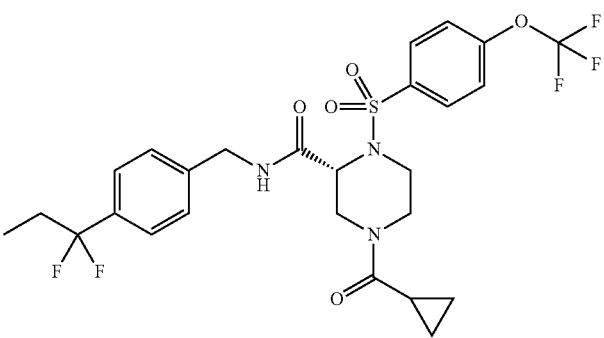 |

TABLE 123-continued
| Ex. No. | Structural Formula |
|---|---|
| 611 | 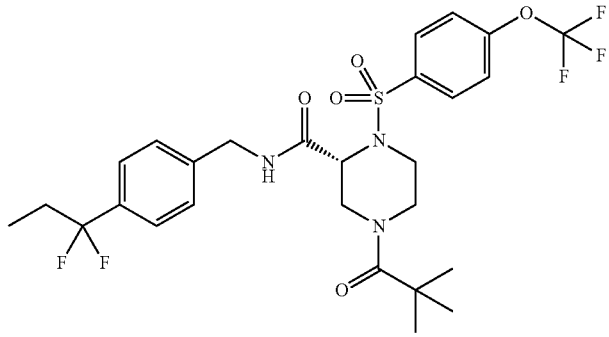 |
| 612 | 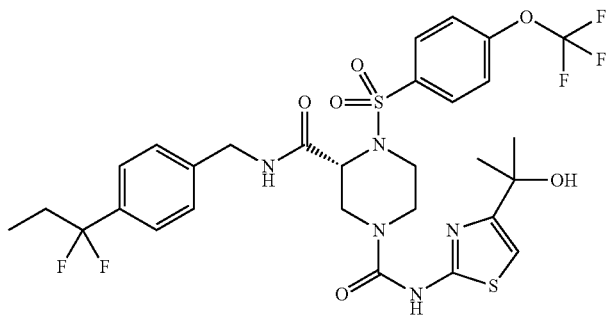 |
| 613 | 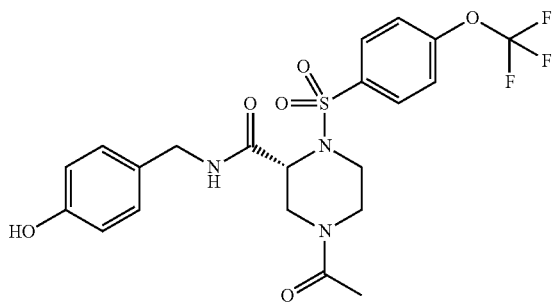 |
| 614 | 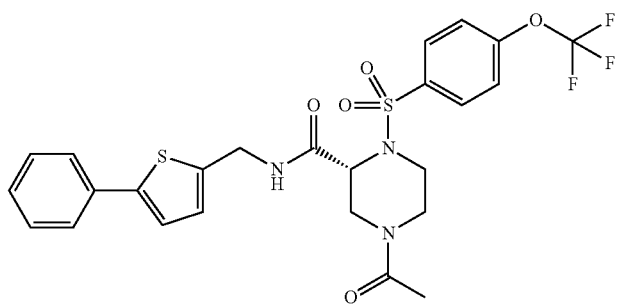 |

TABLE 124
| Ex. No. | Structural Formula |
|---|---|
| 615 | 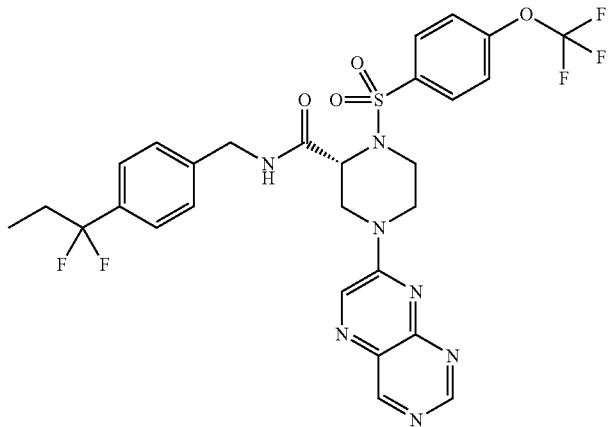 |
| 616 | 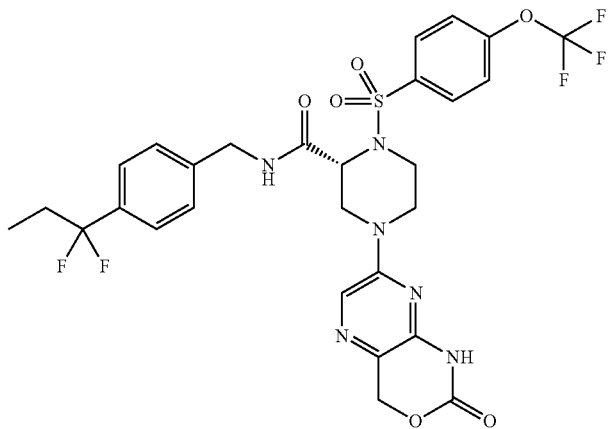 |
| 617 | 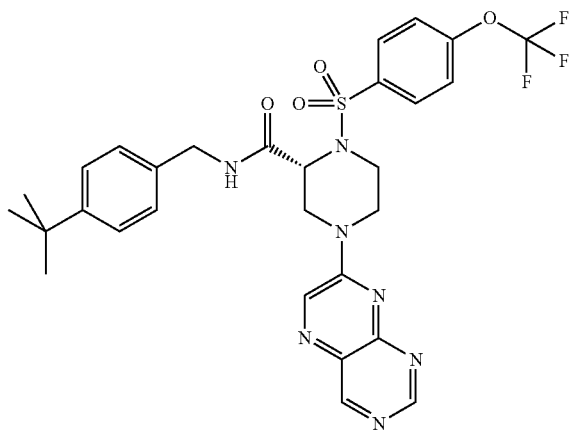 |

TABLE 124-continued
Ex. No. Structural Formula
618
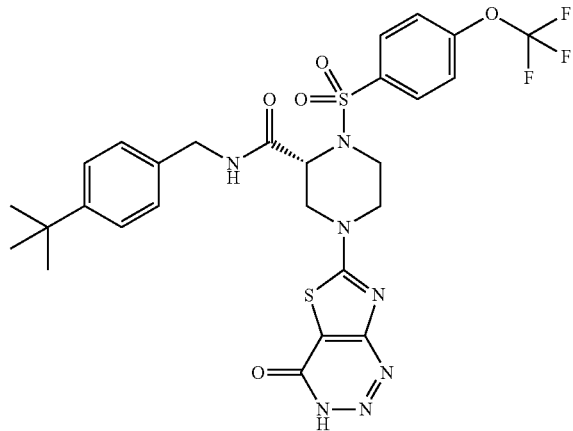
619
TABLE 125
Ex. No. Structural Formula
620
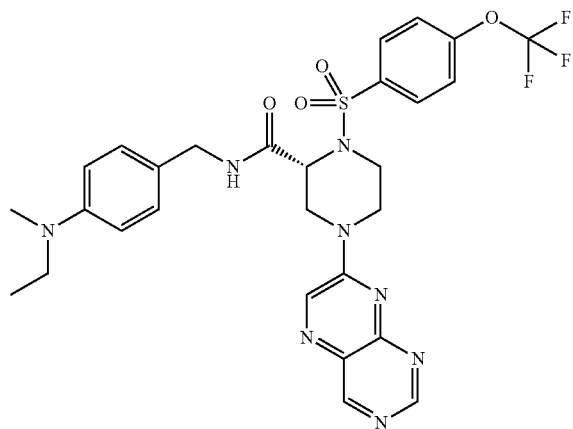

TABLE 125-continued
| Ex. No. | Structural Formula |
|---|---|
| 621 | 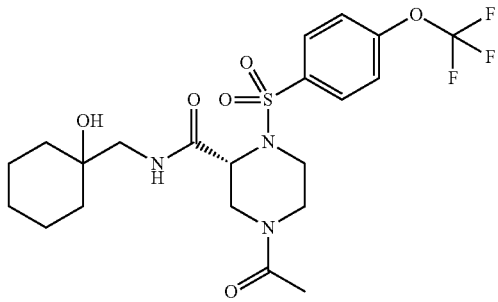 |
| 622 | 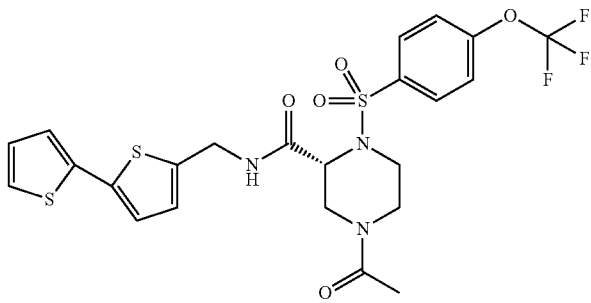 |
| 623 | 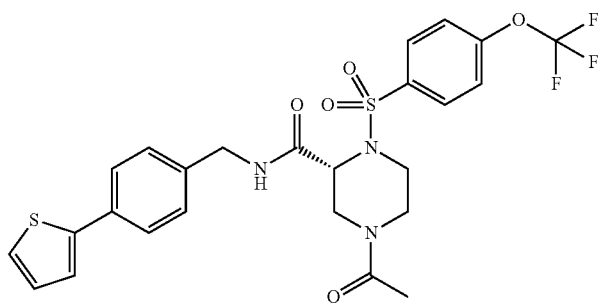 |
| 624 | 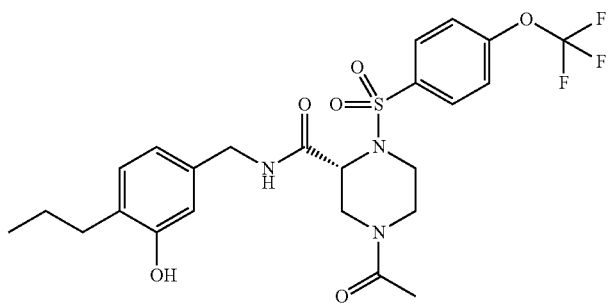 |

TABLE 126
| Ex. No. | Structural Formula |
|---|---|
| 625 | 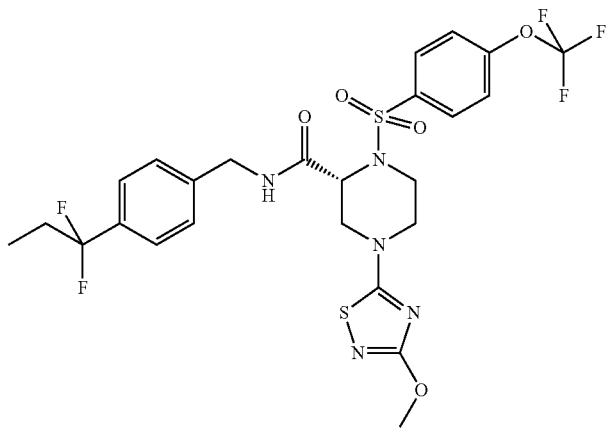 |
| 626 | 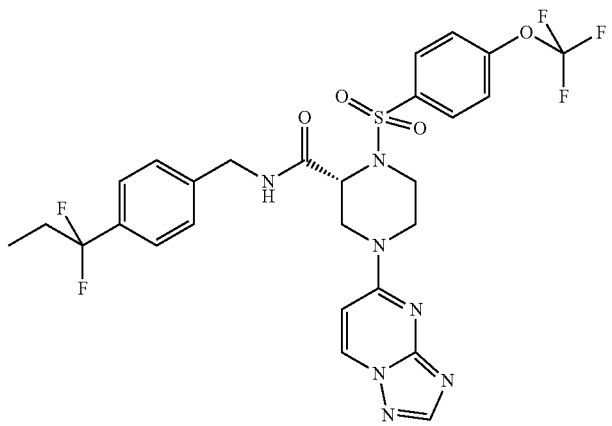 |
| 627 | 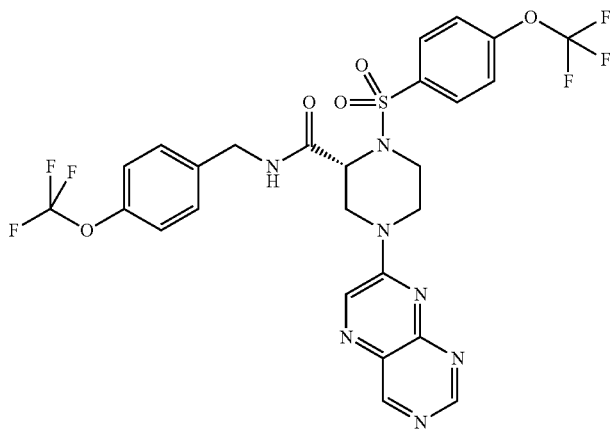 |

TABLE 126-continued
Ex. No. Structural Formula
628
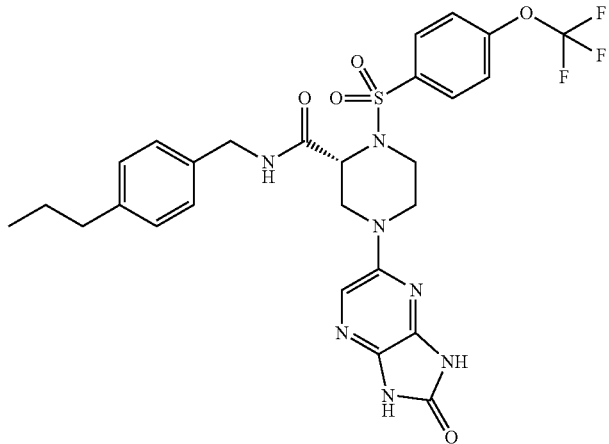
629
TABLE 127
Ex. No. Structural Formula
630
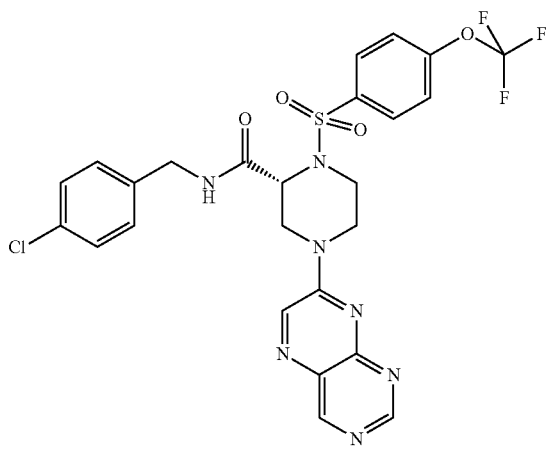

TABLE 127-continued
| Ex. No. | Structural Formula |
|---|---|
| 631 | 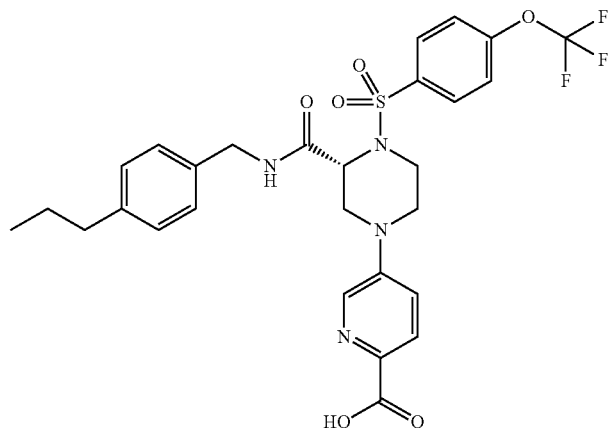 |
| 632 | 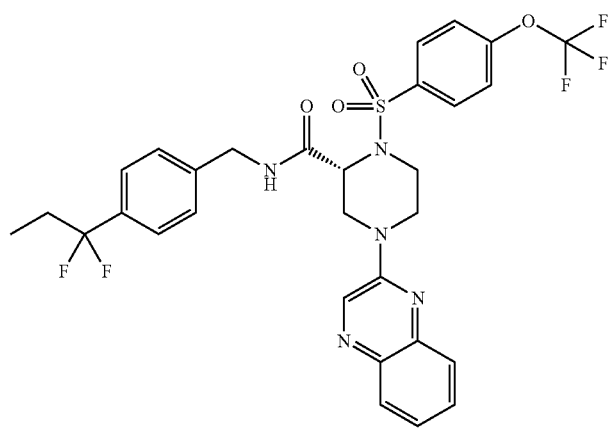 |
| 633 | 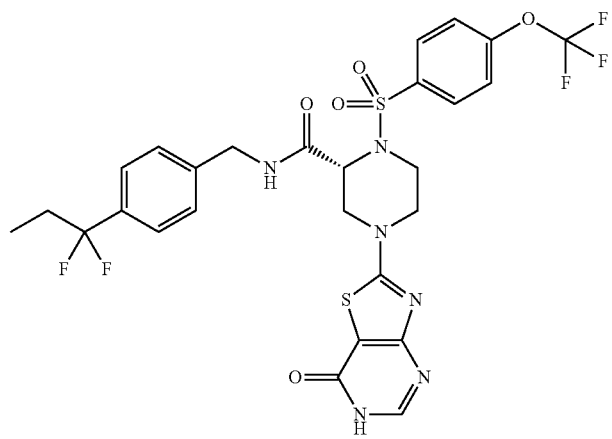 |
| 634 | 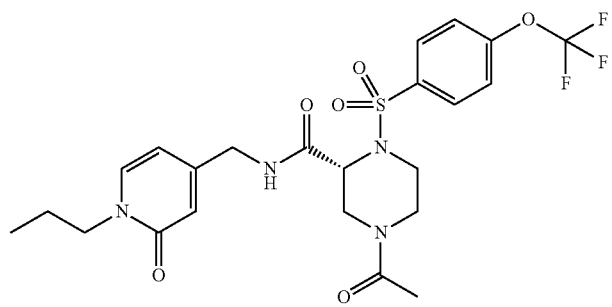 |

TABLE 128
| Ex. No. | Structural Formula |
|---|---|
| 635 | 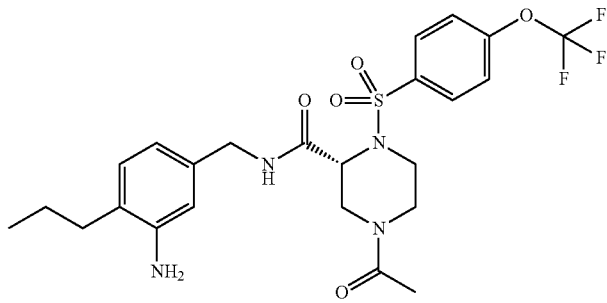 |
| 636 | 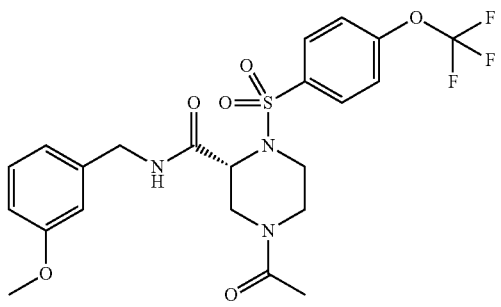 |
| 637 | 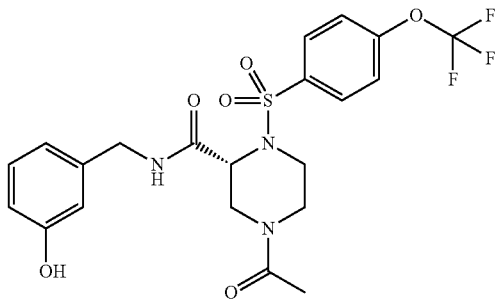 |
| 638 | 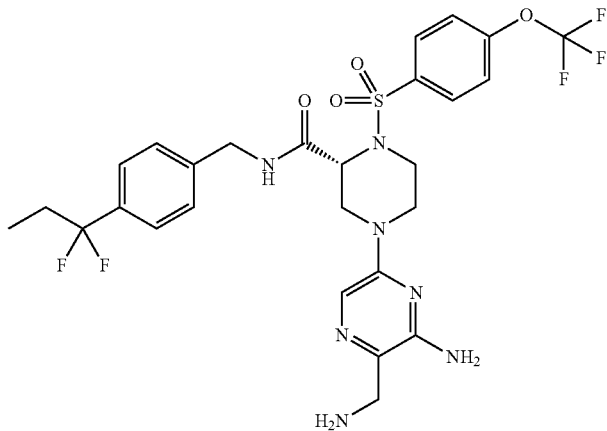 |

TABLE 128-continued
| Ex. No. | Structural Formula |
|---|---|
| 639 | 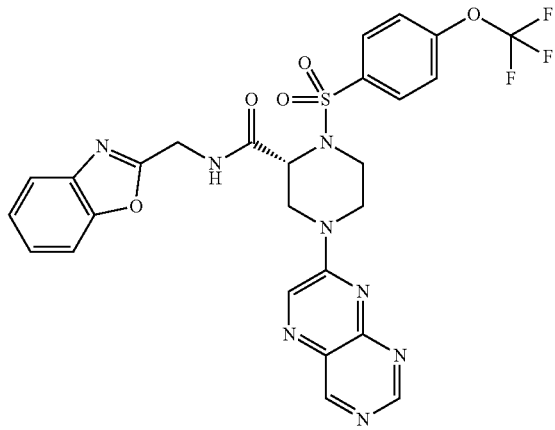 |
TABLE 129
| Ex. No. | Structural Formula |
|---|---|
| 640 | 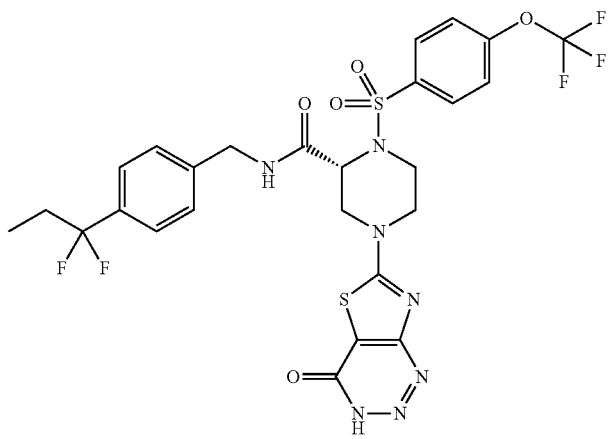 |
| 641 | 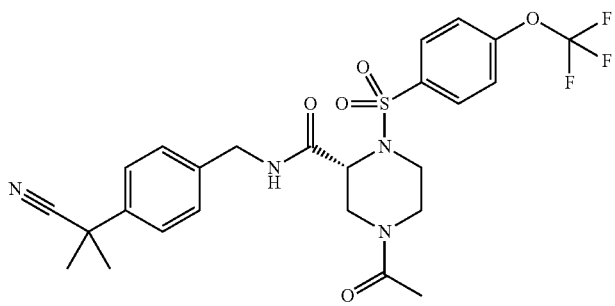 |

TABLE 129-continued
| Ex. No. | Structural Formula |
|---|---|
| 642 | 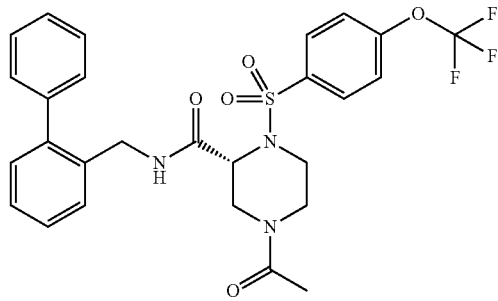 |
| 643 | 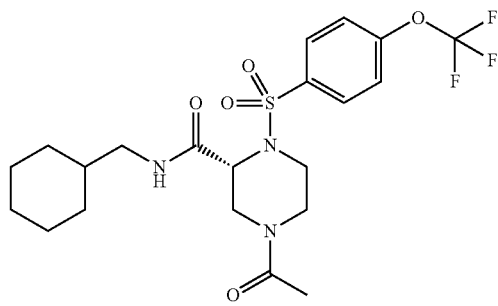 |
| 644 | 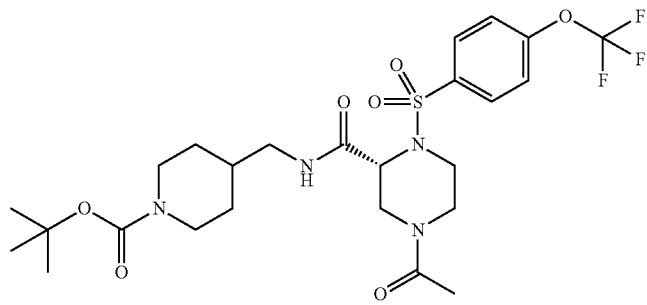 |
TABLE 130
| Ex. No. | Structural Formula |
|---|---|
| 645 | 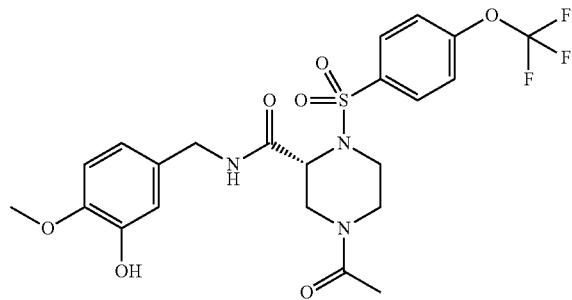 |

TABLE 130-continued
| Ex. No. | Structural Formula |
|---|---|
| 646 | 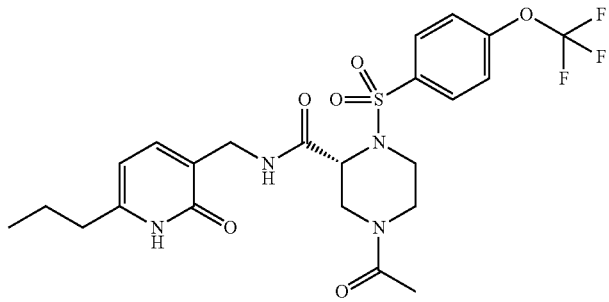 |
| 647 | 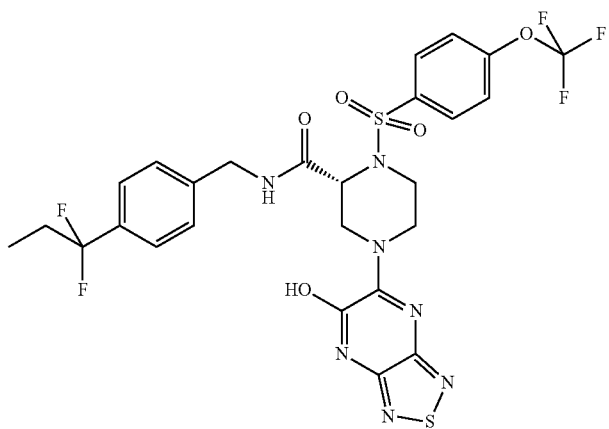 |
| 648 | 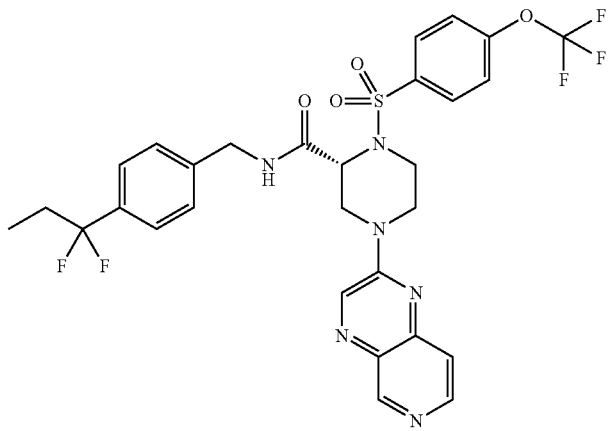 |
| 649 | 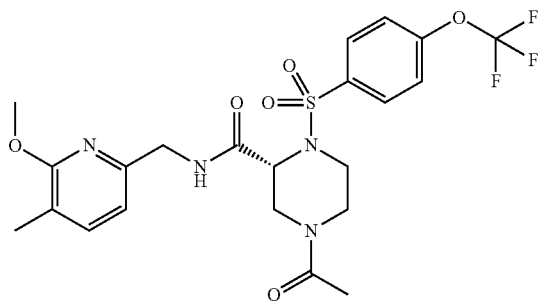 |

US 8,017,612 B2
TABLE 131
| Ex. No. | Structural Formula |
|---|---|
| 650 | 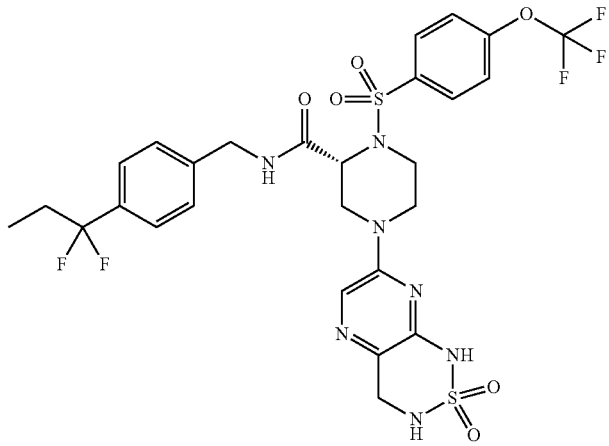 |
| 651 | 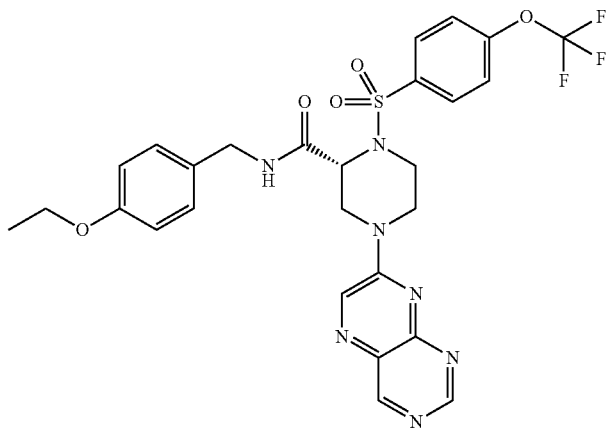 |
| 652 | 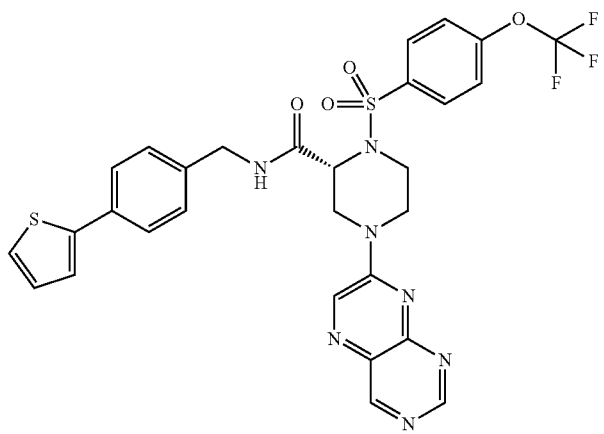 |

TABLE 131-continued
| Ex. No. | Structural Formula |
|---|---|
| 653 | 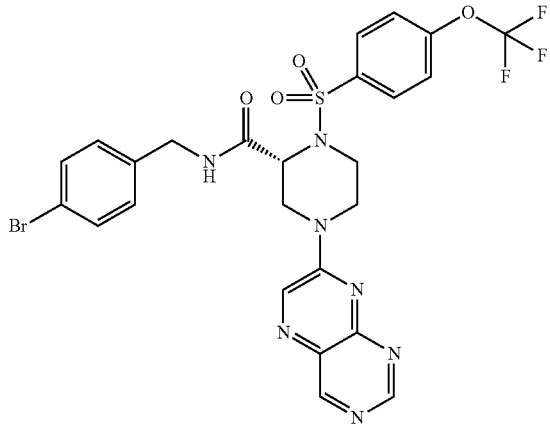 |
| 654 | 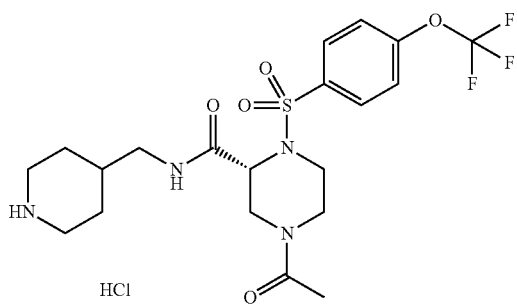 |
TABLE 132
| Ex. No. | Structural Formula |
|---|---|
| 655 | 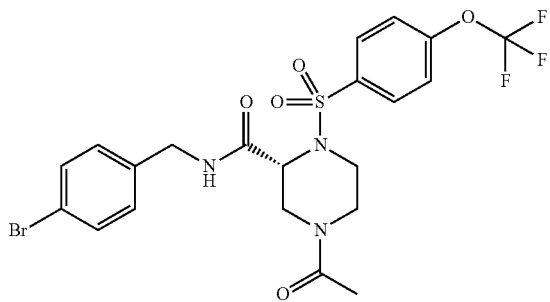 |

TABLE 132-continued
| Ex. No. | Structural Formula |
| --- | --- |
| 656 | 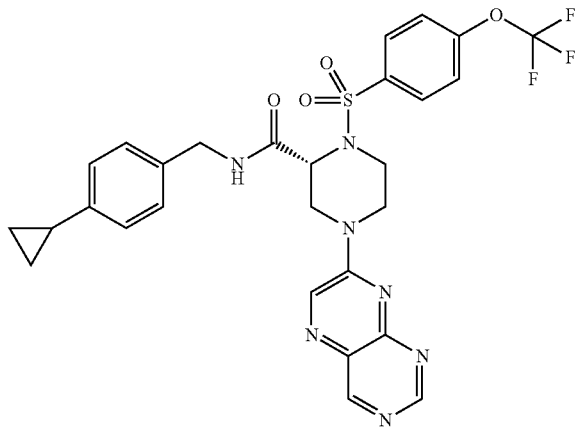 |
| 657 | 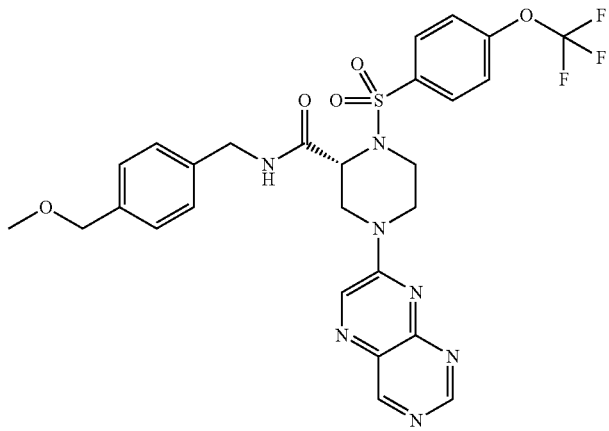 |
| 658 | 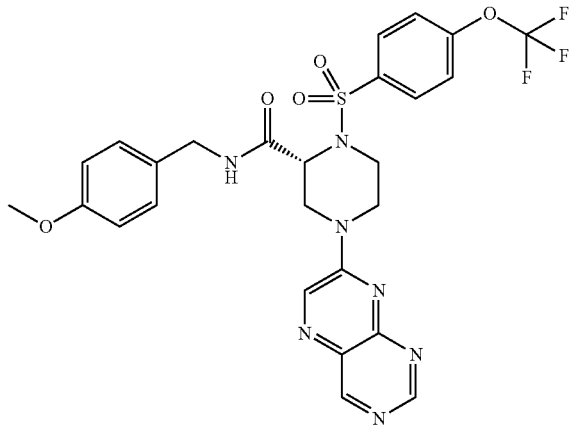 |

605
TABLE 132-continued
| Ex. No. | Structural Formula |
|---|---|
| 659 | 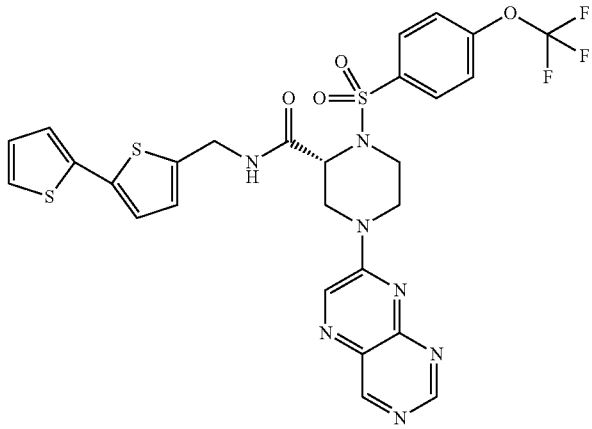 |
TABLE 133
| Ex. No. | Structural Formula |
|---|---|
| 660 | 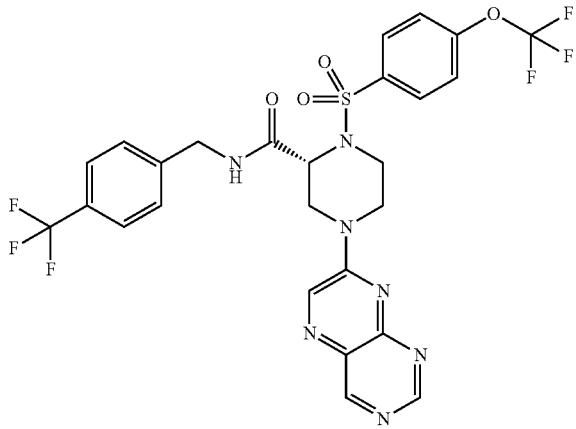 |
| 661 | 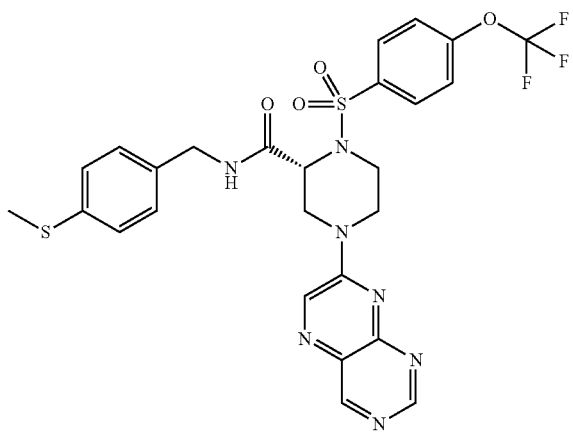 |

TABLE 133-continued
| Ex. No. | Structural Formula |
|---|---|
| 662 | 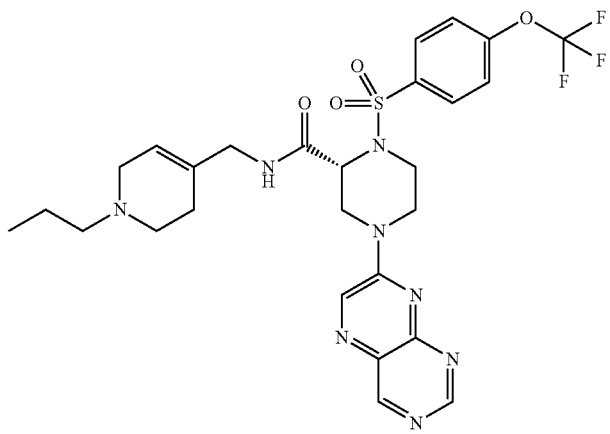 |
| 663 | 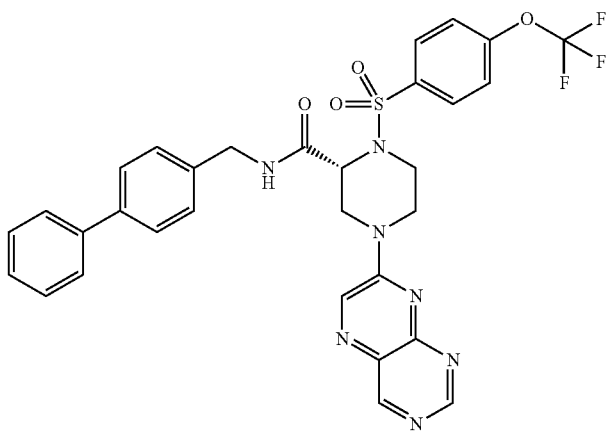 |
| 664 | 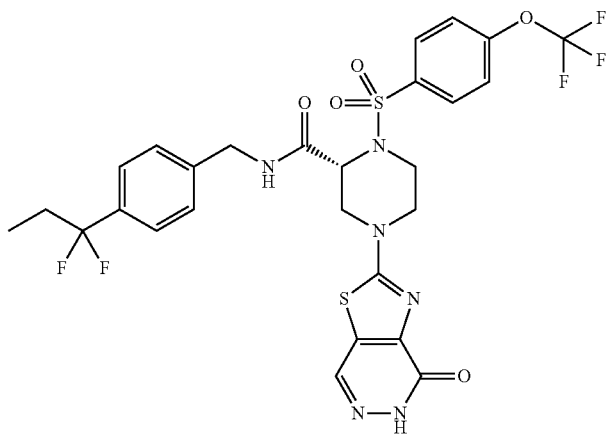 |

TABLE 134
| Ex. No. | Structural Formula |
|---|---|
| 665 | 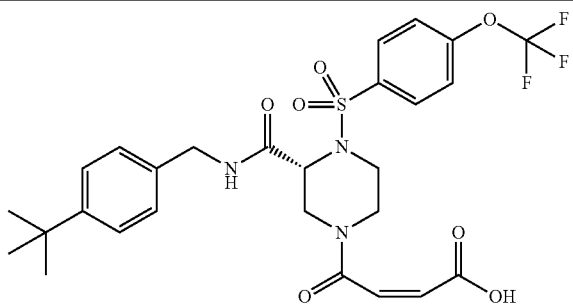 |
| 666 | 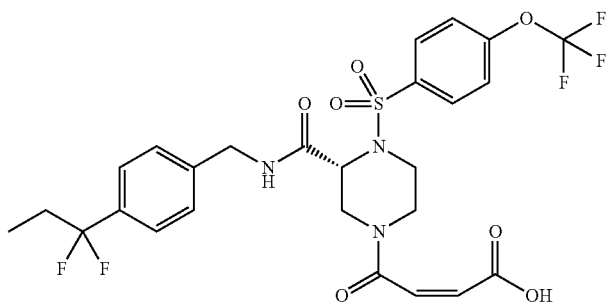 |
| 667 | 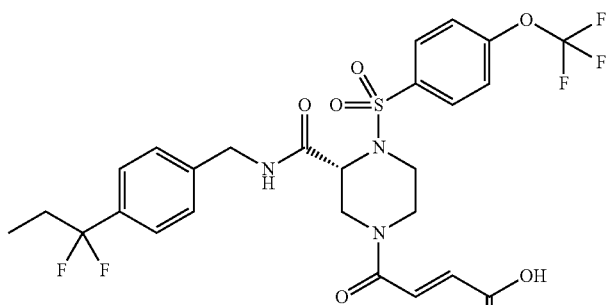 |
| 668 | 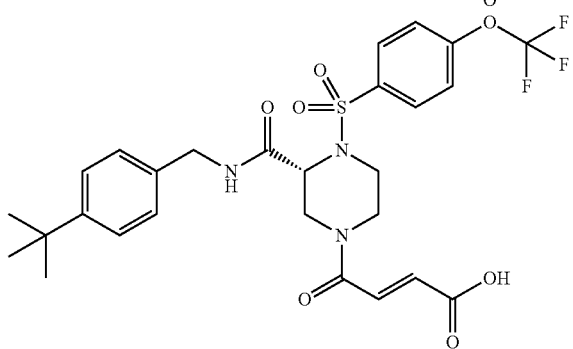 |
| 669 | 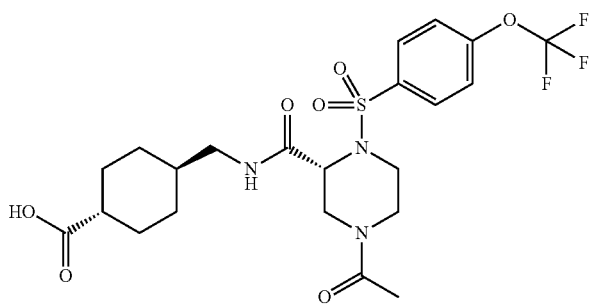 |

TABLE 135
| Ex. No. | Structural Formula |
|---|---|
| 670 | 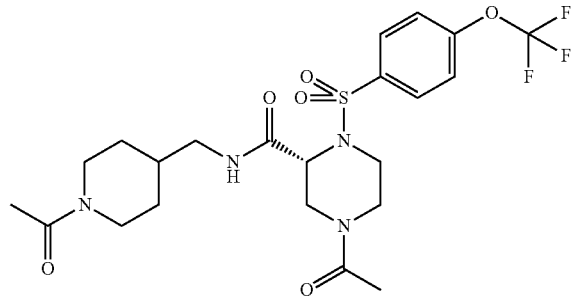 |
| 671 | 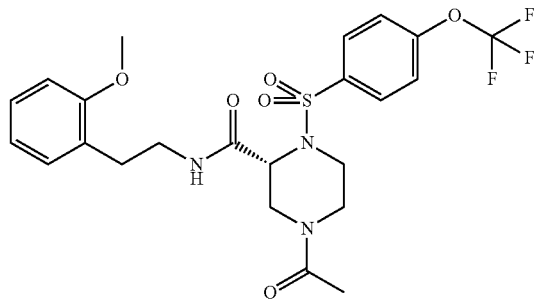 |
| 672 | 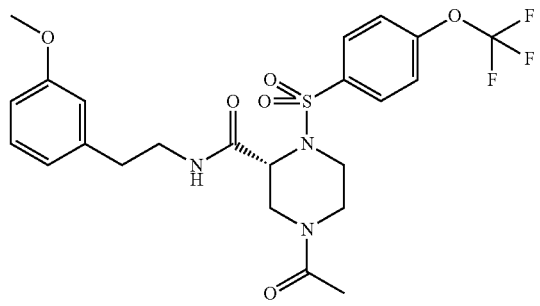 |
| 673 | 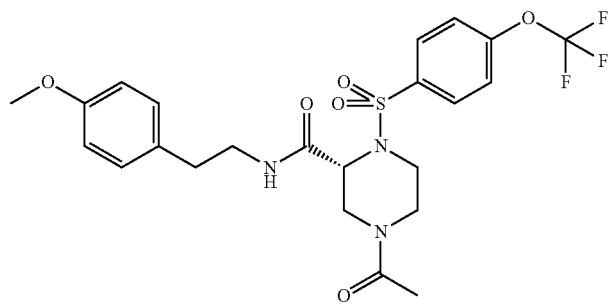 |

TABLE 135-continued
| Ex. No. | Structural Formula |
|---|---|
| 674 | 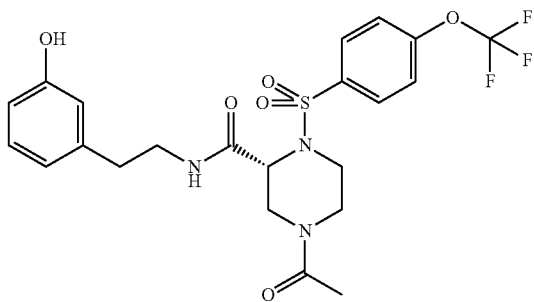 |
TABLE 136
| Ex. No. | Structural Formula |
|---|---|
| 675 | 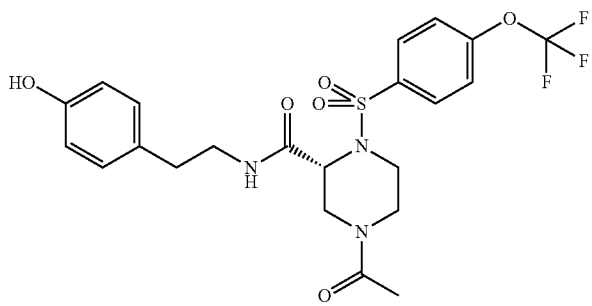 |
| 676 | 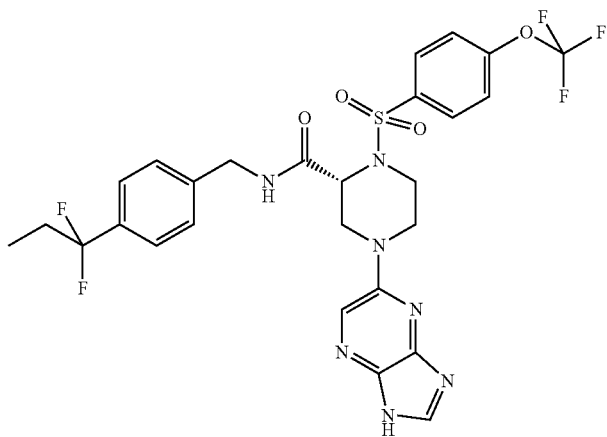 |
| 677 | 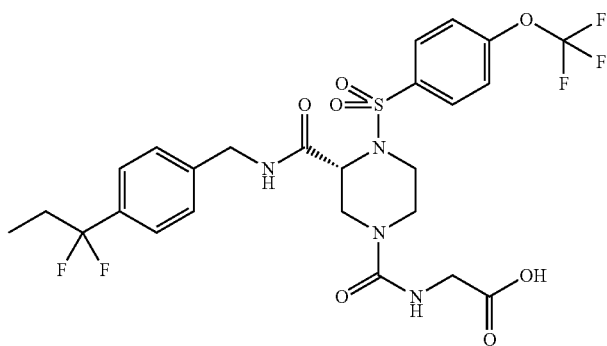 |

TABLE 136-continued
| Ex. No. | Structural Formula |
|---|---|
| 678 | 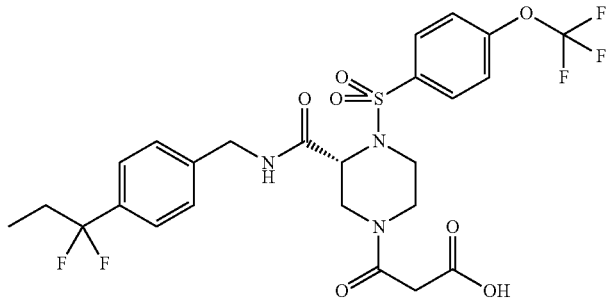 |
| 679 | 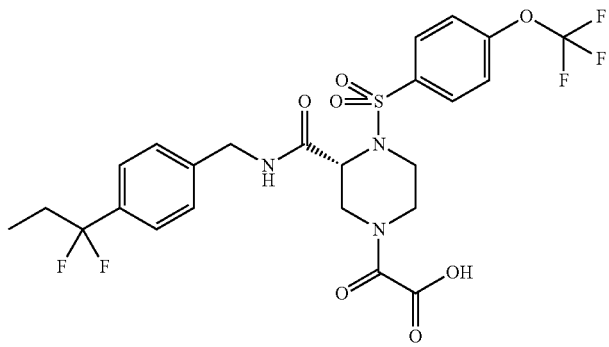 |
TABLE 137
| Ex. No. | Structural Formula |
|---|---|
| 680 | 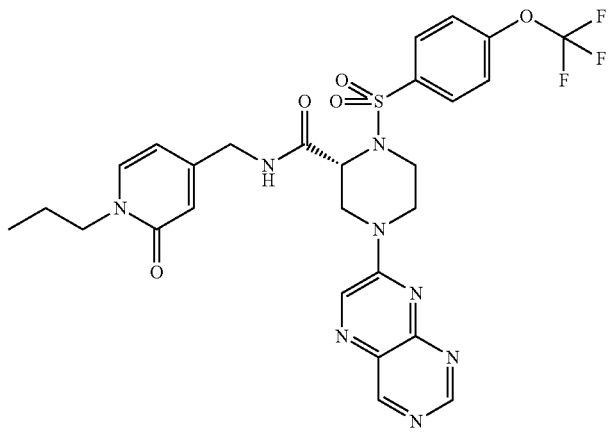 |
| 681 | 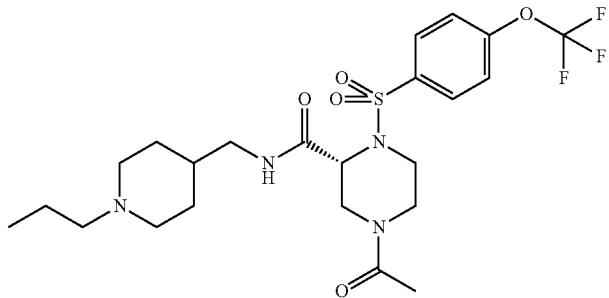 |

TABLE 137-continued
| Ex. No. | Structural Formula |
|---|---|
| 682 | 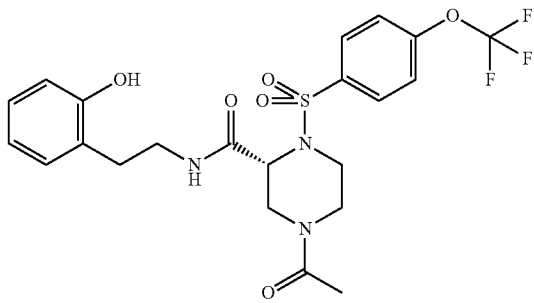 |
| 683 | 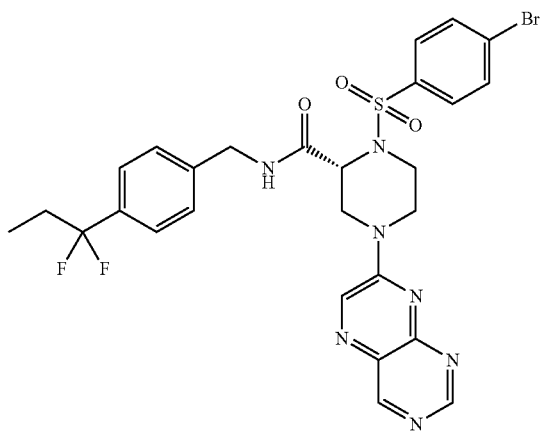 |
| 684 | 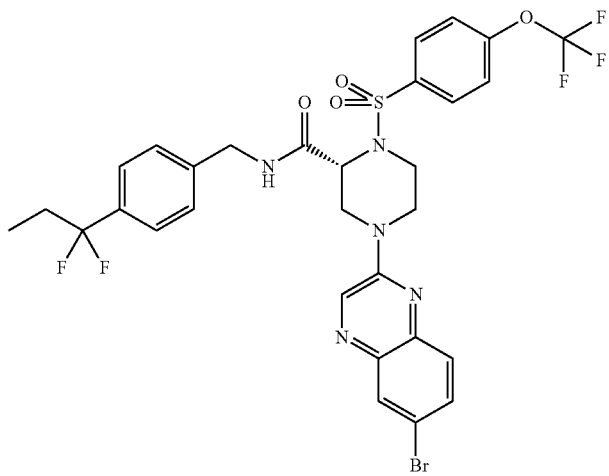 |

TABLE 138
| Ex. No. | Structural Formula |
| --- | --- |
| 685 | 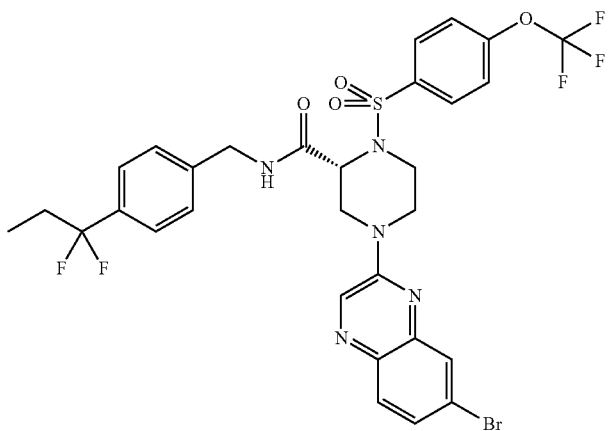 |
| 686 | 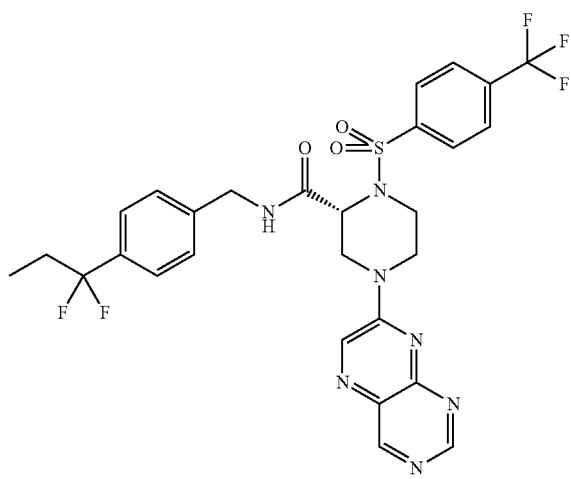 |
| 687 | 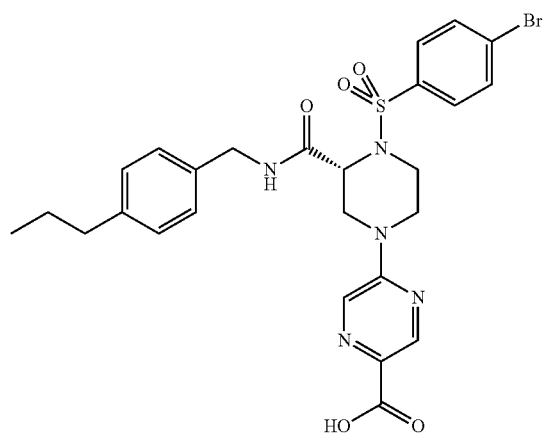 |

TABLE 138-continued
| Ex. No. | Structural Formula |
|---|---|
| 688 | 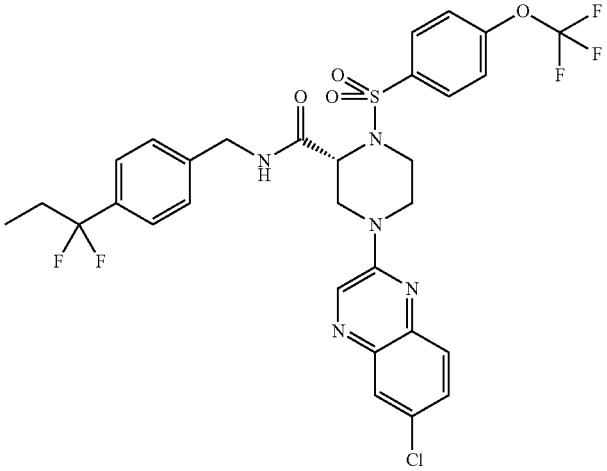 |
| 689 | 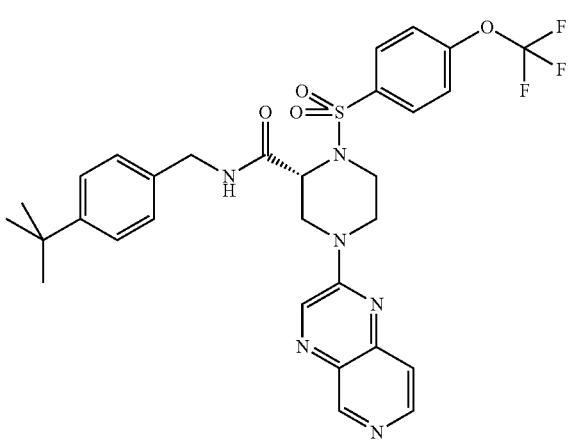 |
TABLE 139
| Ex. No. | Structural Formula |
|---|---|
| 690 | 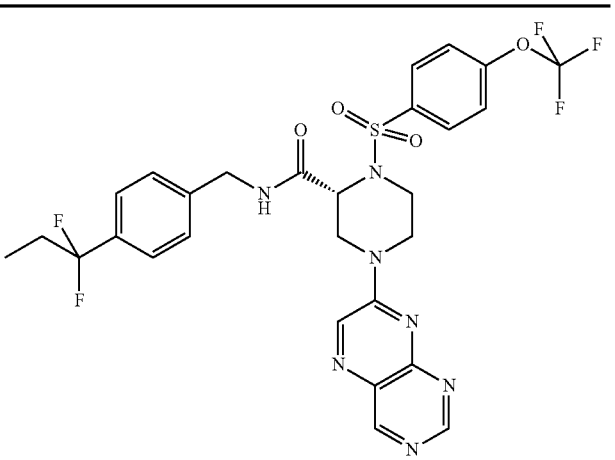 |

TABLE 139-continued
| Ex. No. | Structural Formula |
| --- | --- |
| 691 | 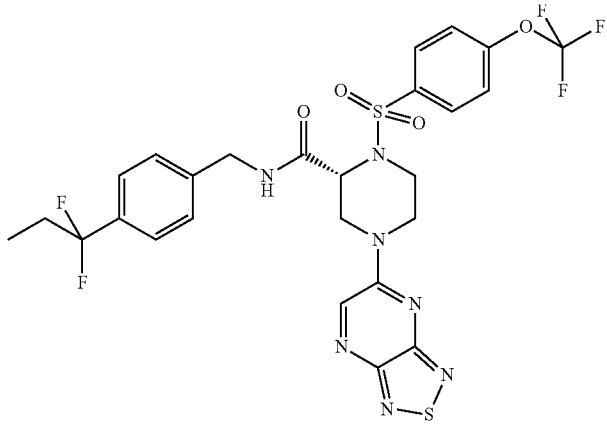 |
| 692 | 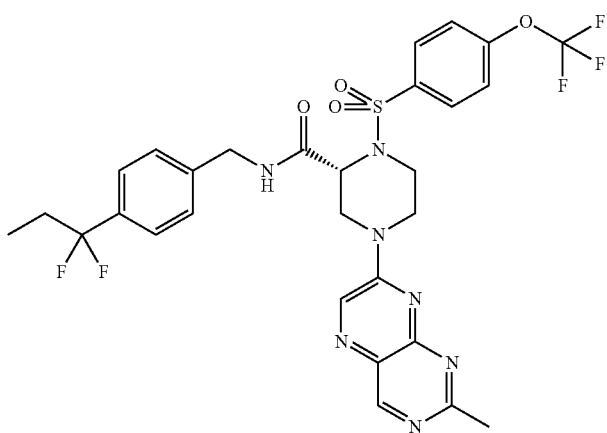 |
| 693 | 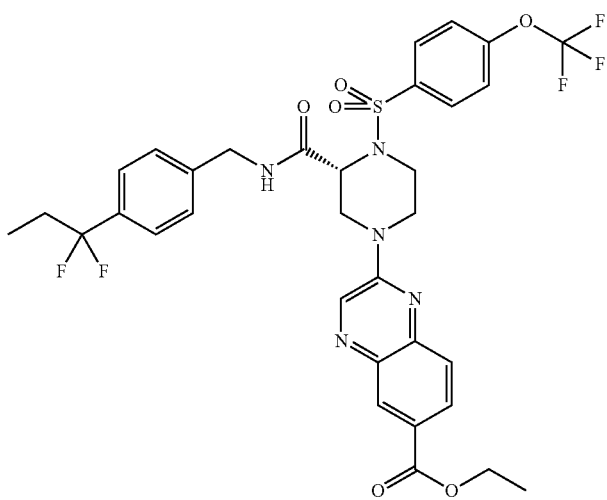 |

TABLE 139-continued

| Ex. No. | Structural Formula |
|---|---|
| 694 | |

TABLE 140

| Ex. No. | Structural Formula |
|---|---|
| 695 | |
| 696 | |

TABLE 140-continued
| Ex. No. | Structural Formula |
|---|---|
| 697 | 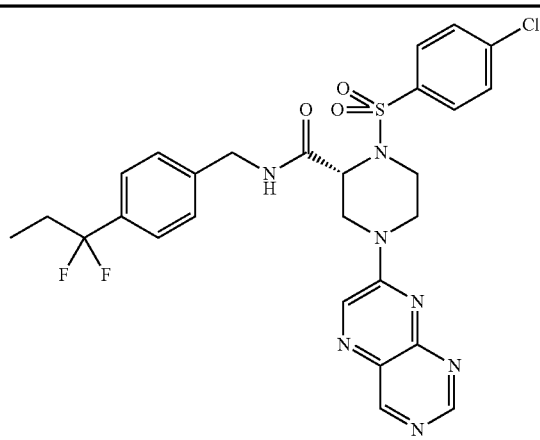 |
| 698 | 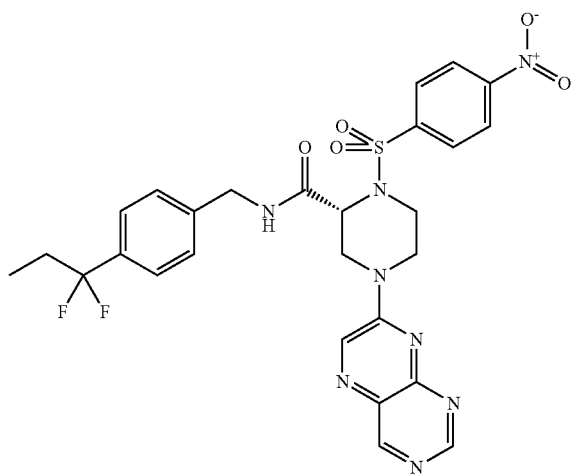 |
| 699 | 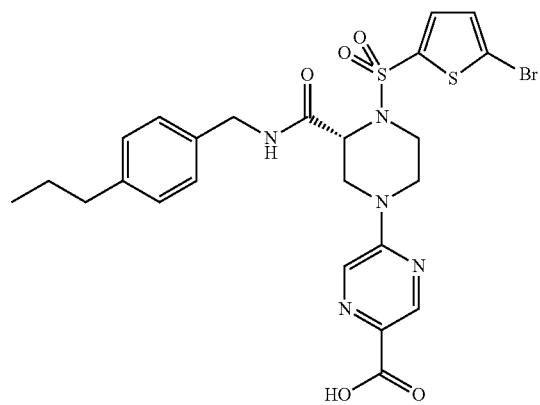 |

TABLE 141
| Ex. No. | Structural Formula |
|---|---|
| 700 | 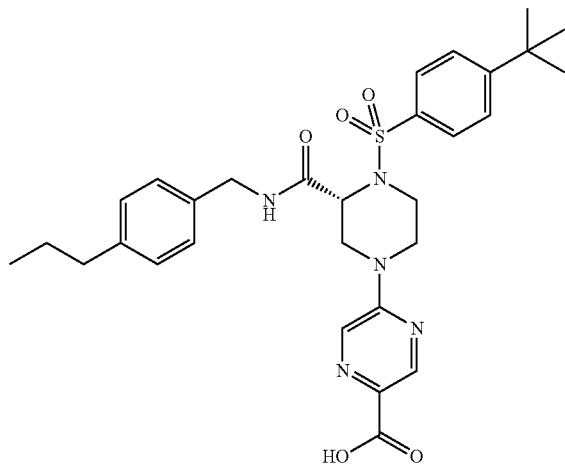 |
| 701 | 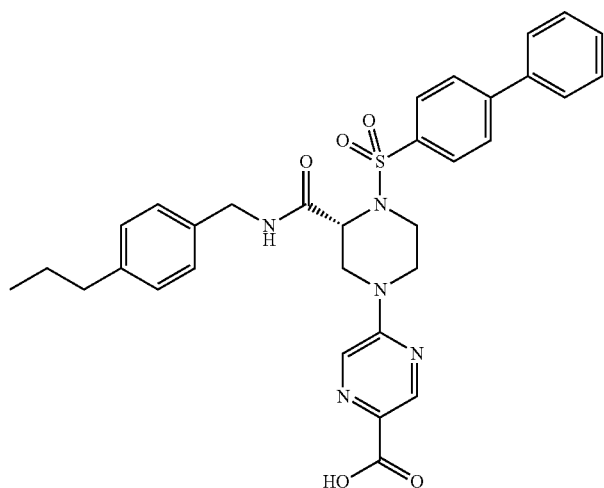 |
| 702 | 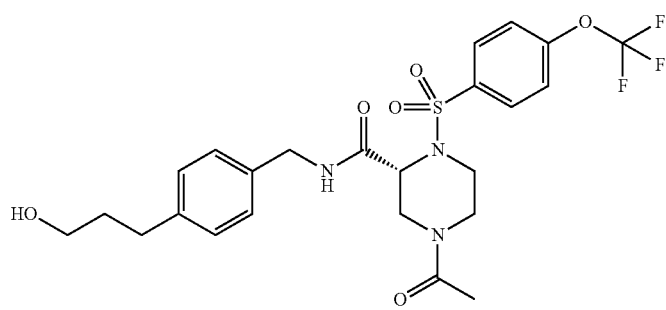 |
| 703 | 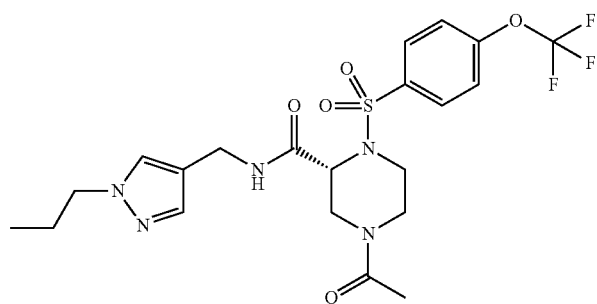 |

TABLE 141-continued
| Ex. No. | Structural Formula |
|---|---|
| 704 | 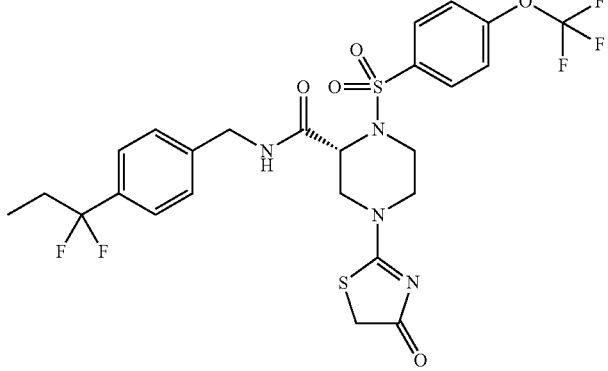 |
TABLE 142
| Ex. No. | Structural Formula |
|---|---|
| 705 | 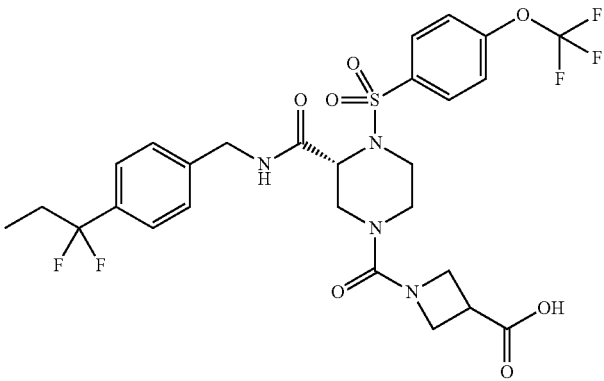 |
| 706 | 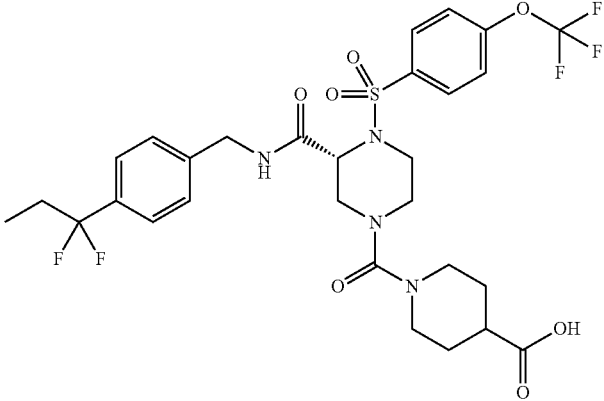 |

TABLE 142-continued
| Ex. No. | Structural Formula |
|---|---|
| 707 | 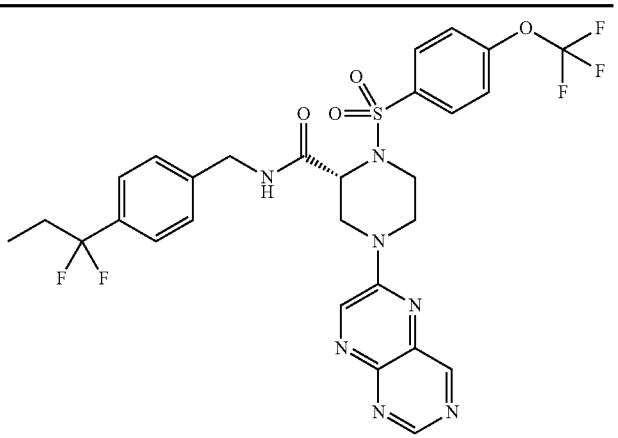 |
| 708 | 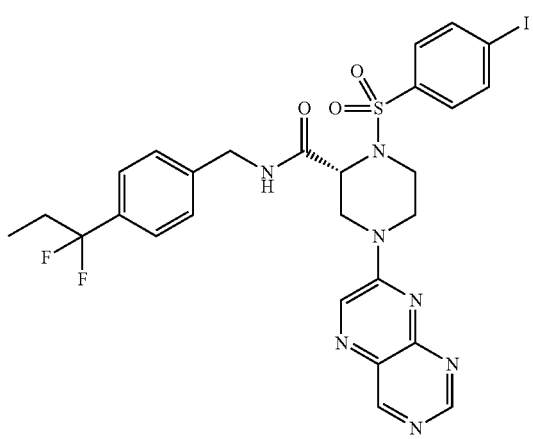 |
| 709 | 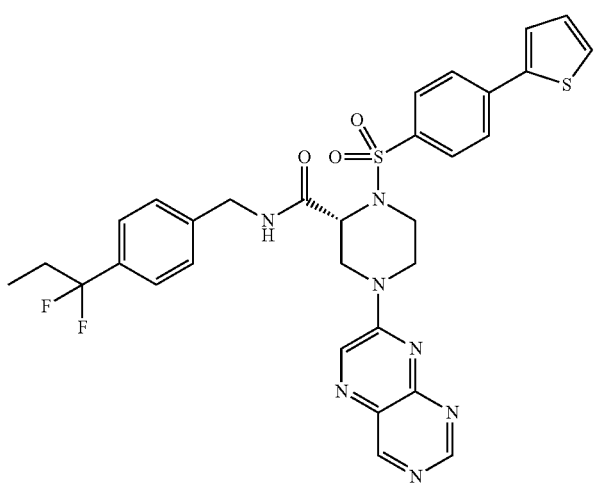 |

TABLE 143
| Ex. No. | Structural Formula |
|---|---|
| 710 | 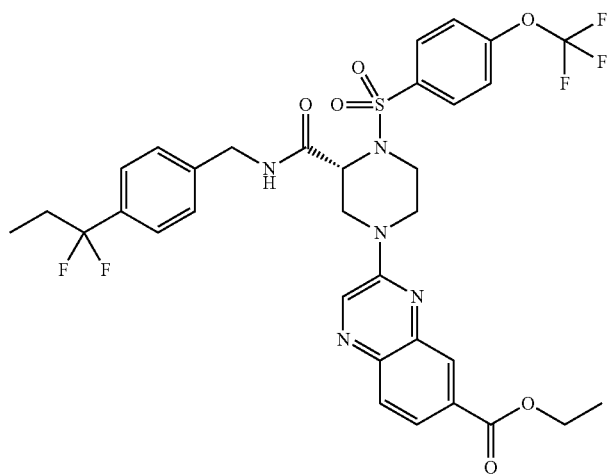 |
| 711 | 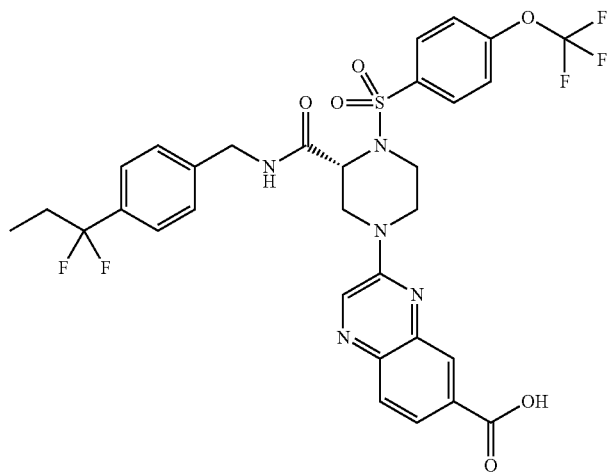 |
| 712 | 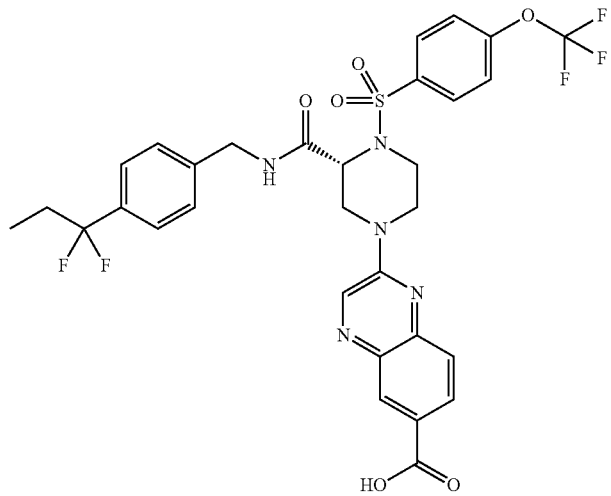 |

TABLE 143-continued
| Ex. No. | Structural Formula |
|---|---|
| 713 | 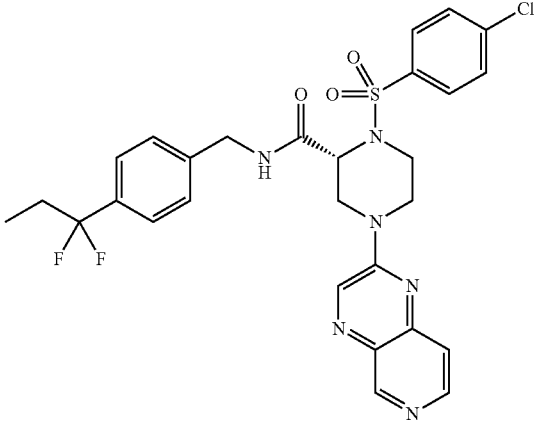 |
| 714 | 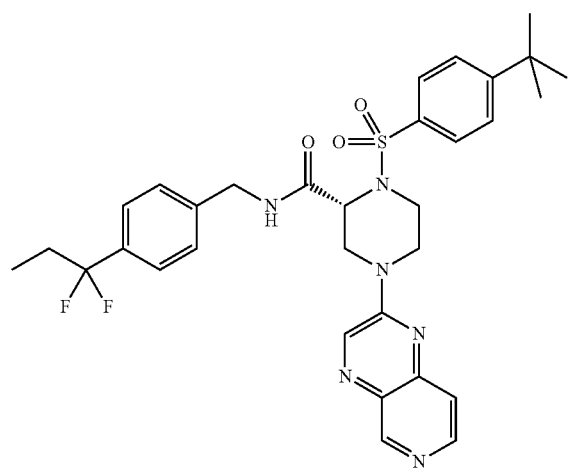 |
TABLE 144
| Ex. No. | Structural Formula |
|---|---|
| 715 | 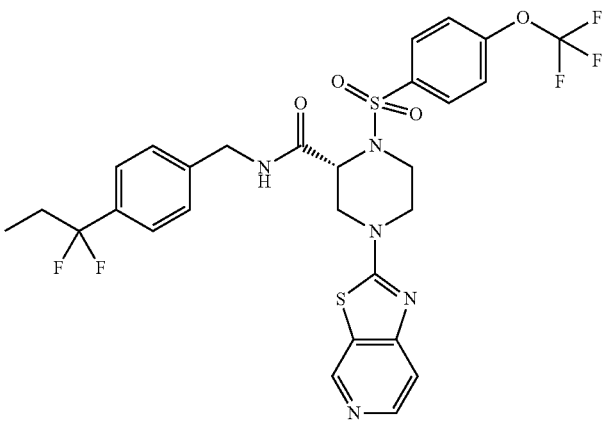 |

TABLE 144-continued
| Ex. No. | Structural Formula |
|---|---|
| 716 | 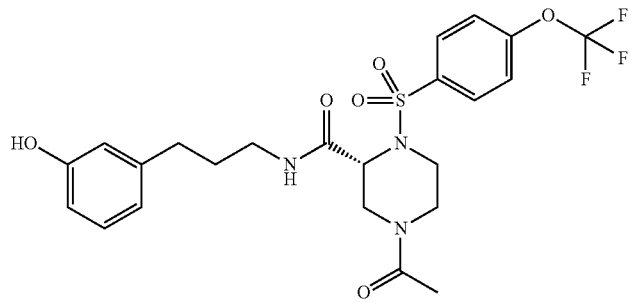 |
| 717 | 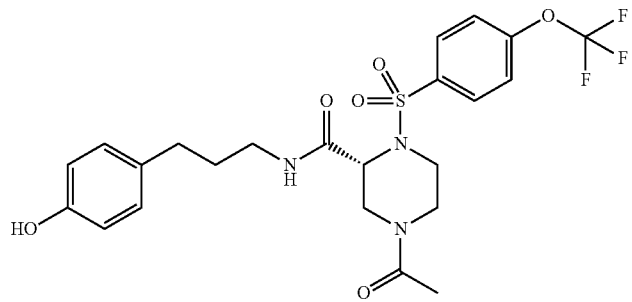 |
| 718 | 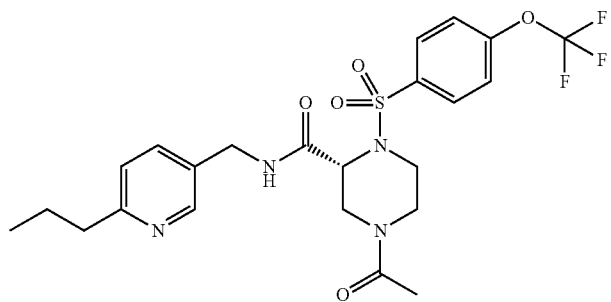 |
| 719 | 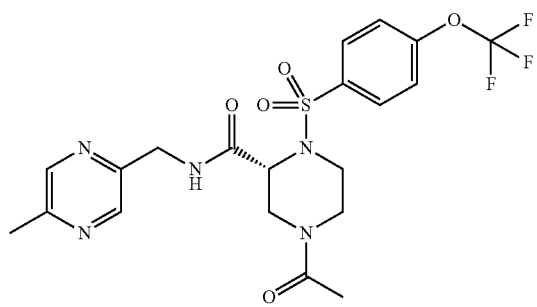 |

TABLE 145
| Ex. No. | Structural Formula |
|---|---|
| 720 | 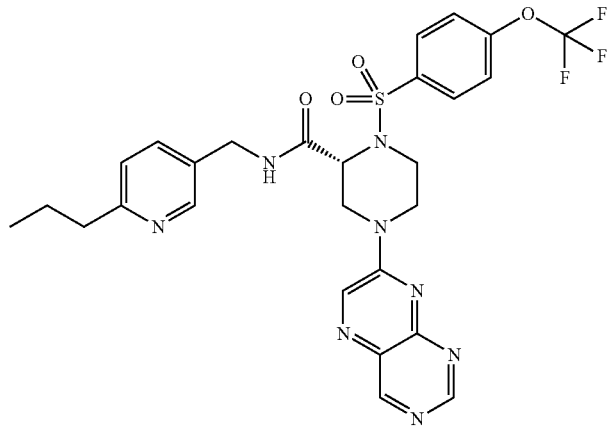 |
| 721 | 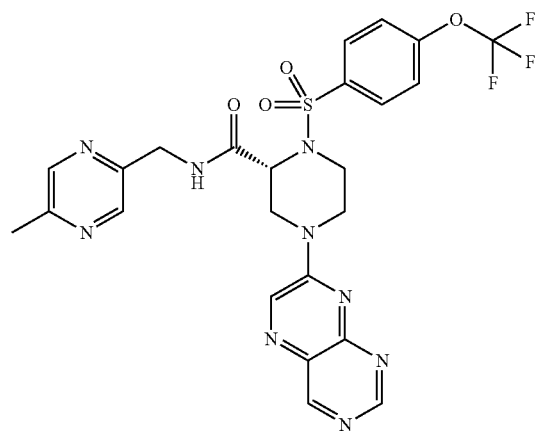 |
| 722 | 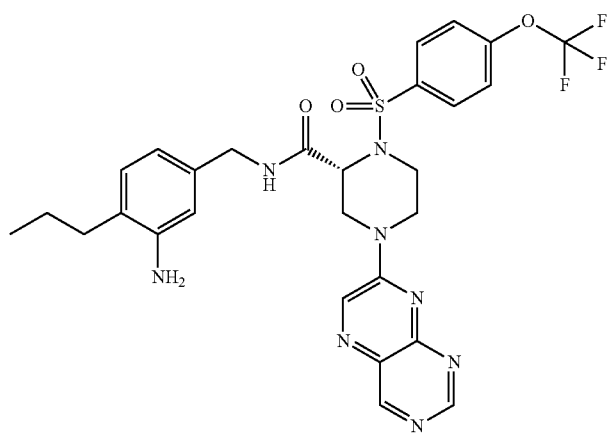 |

TABLE 145-continued
| Ex. No. | Structural Formula |
|---|---|
| 723 | 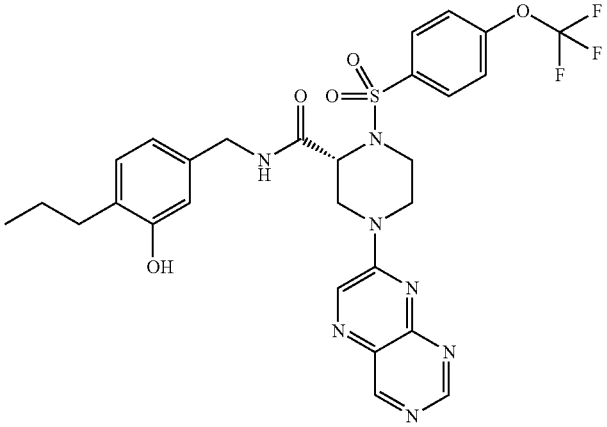 |
| 724 | 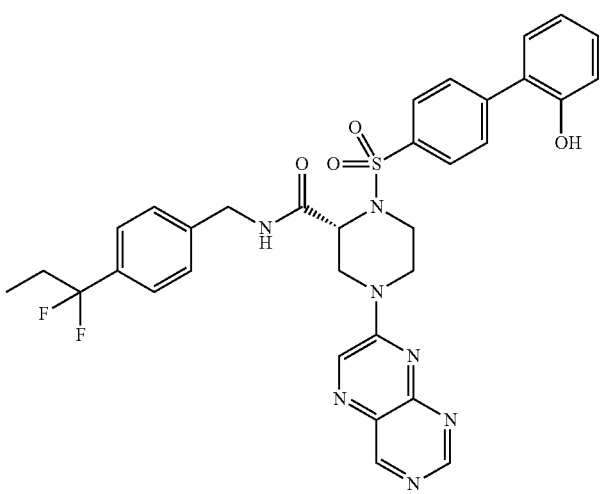 |
TABLE 146
| Ex. No. | Structural Formula |
|---|---|
| 725 | 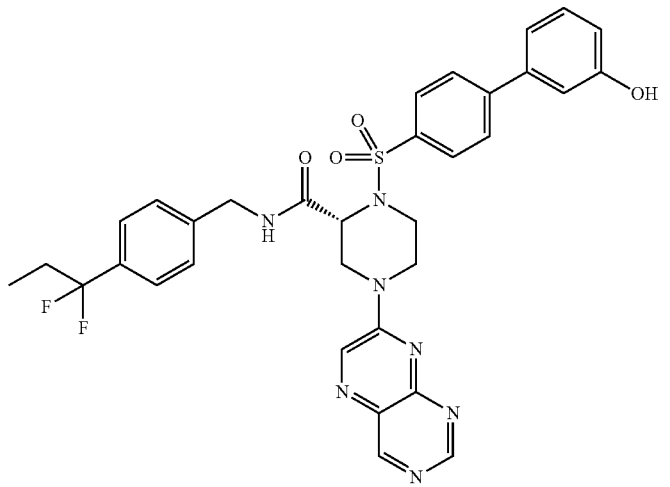 |

TABLE 146-continued
| Ex. No. | Structural Formula |
|---|---|
| 726 | 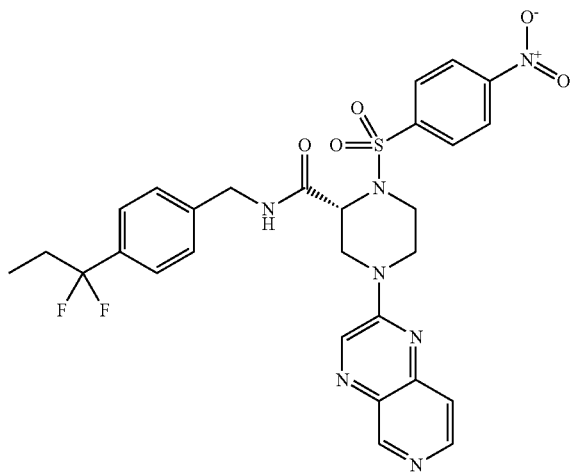 |
| 727 | 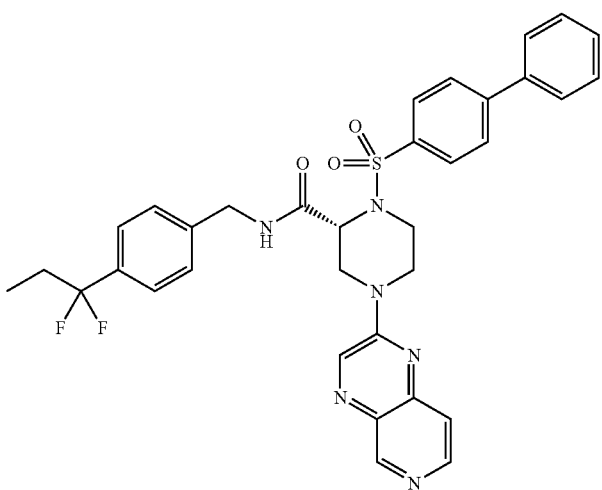 |
| 728 | 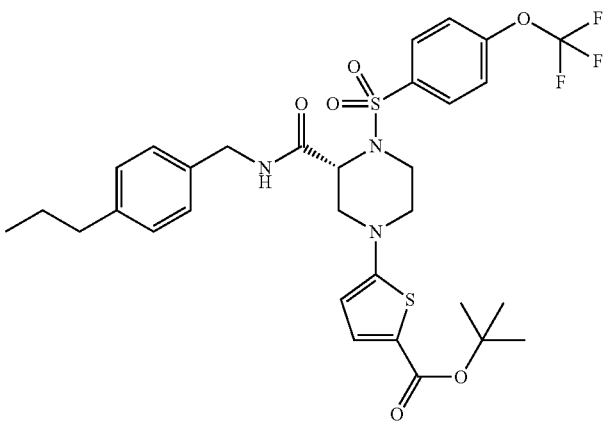 |

TABLE 146-continued
| Ex. No. | Structural Formula |
|---|---|
| 729 | 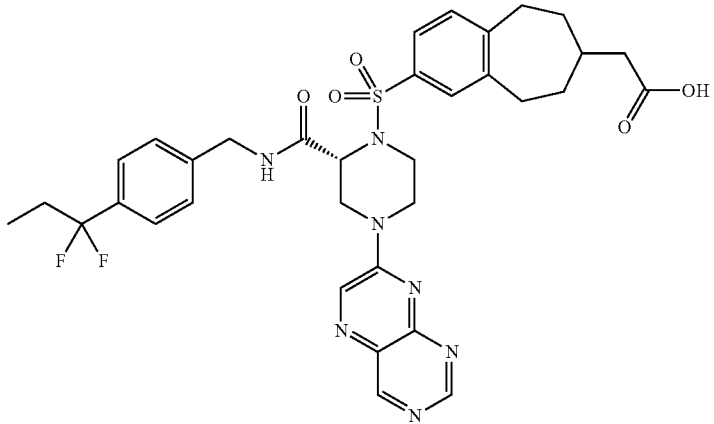 |
TABLE 147
| Ex. No. | Structural Formula |
|---|---|
| 730 | 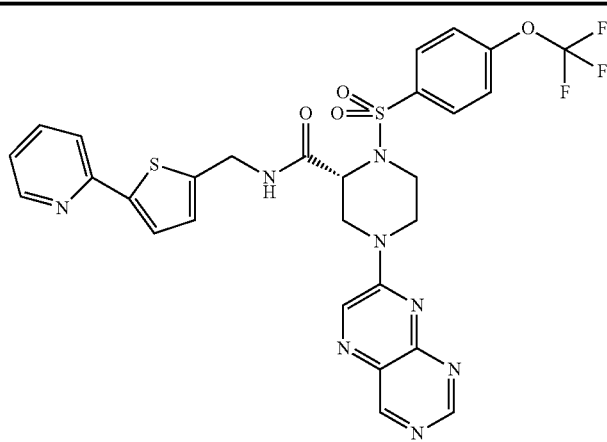 |
| 731 | 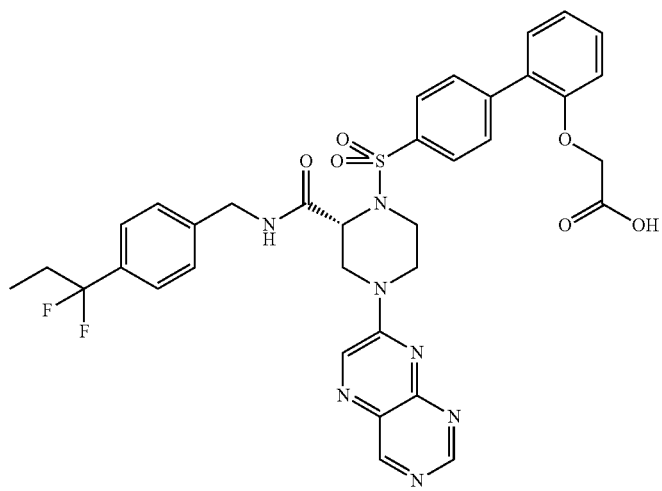 |

TABLE 147-continued

| Ex. No. | Structural Formula |
|---------|-------------------|
| 732 | |
| 733 | |
| 734 | |

TABLE 148
| Ex. No. | Structural Formula |
|---|---|
| 735 | 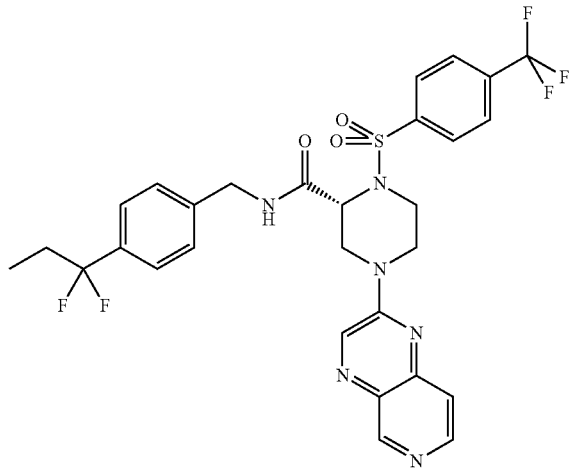 |
| 736 | 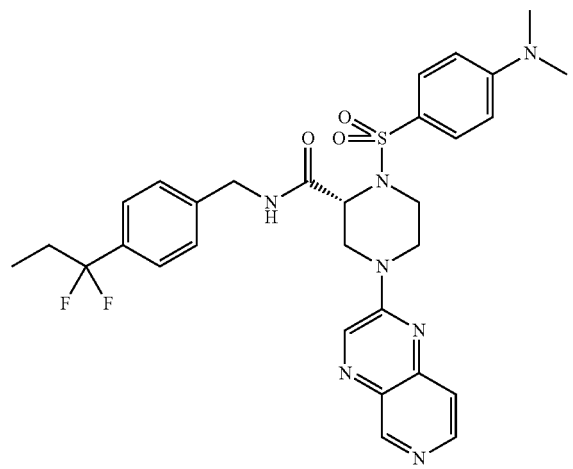 |
| 737 | 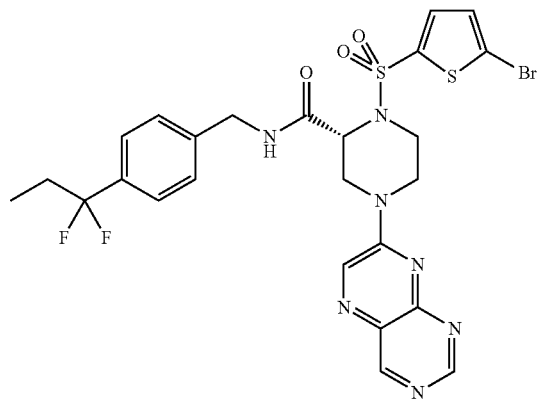 |

653
TABLE 148-continued
| Ex. No. | Structural Formula |
|---------|-------------------|
| 738 | 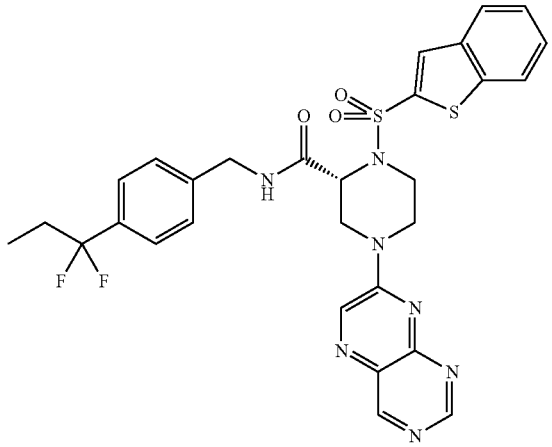 |
| 739 | 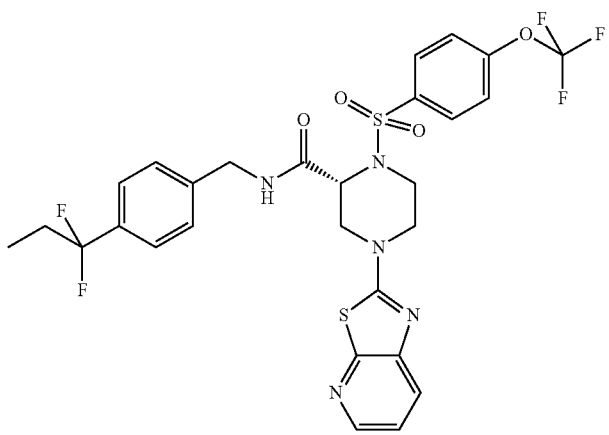 |
TABLE 149
| Ex. No. | Structural Formula |
|---------|-------------------|
| 740 | 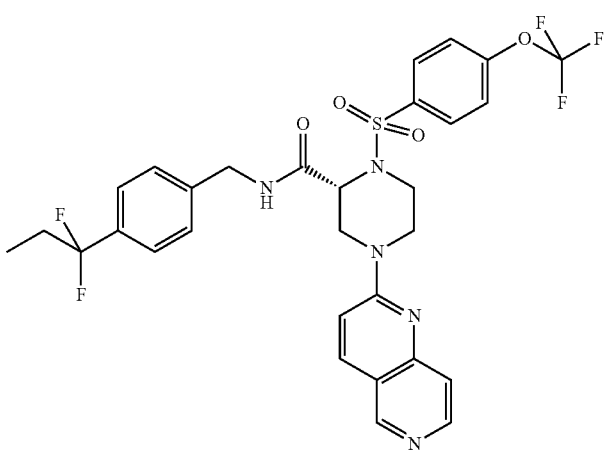 |

TABLE 149-continued
| Ex. No. | Structural Formula |
|---------|--------------------|
| 741 | 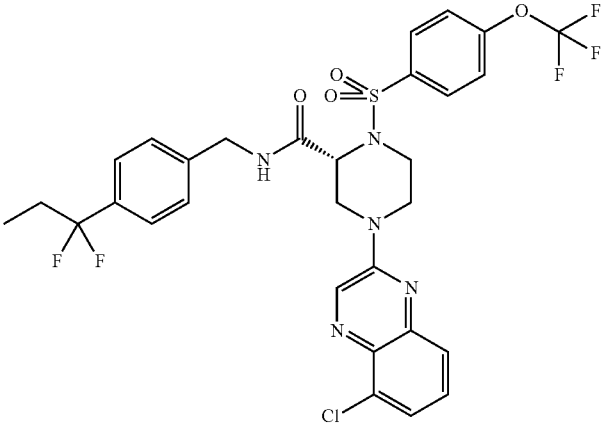 |
| 742 | 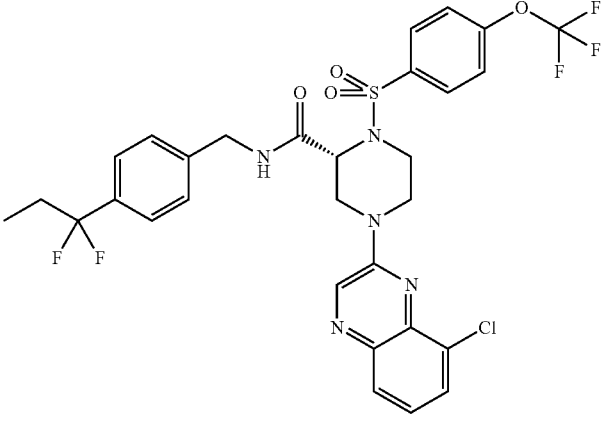 |
| 743 | 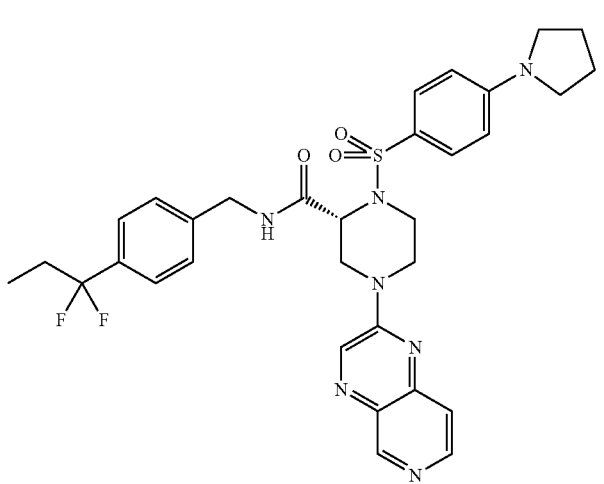 |

TABLE 149-continued
| Ex. No. | Structural Formula |
|---|---|
| 744 | 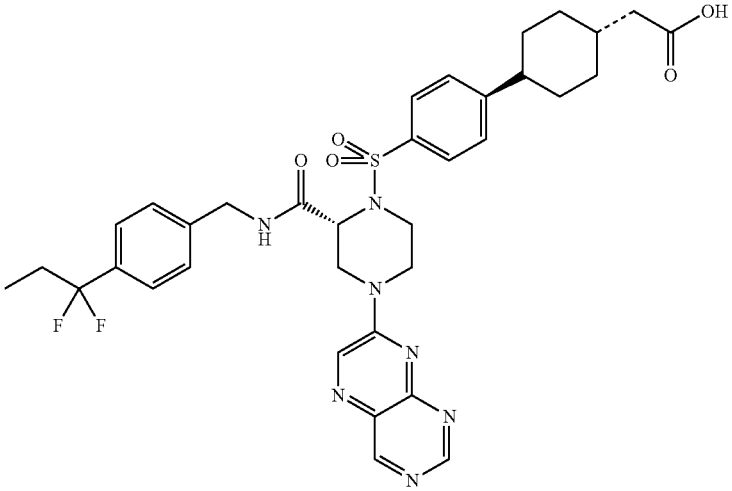 |
TABLE 150
| Ex. No. | Structural Formula |
|---|---|
| 745 | 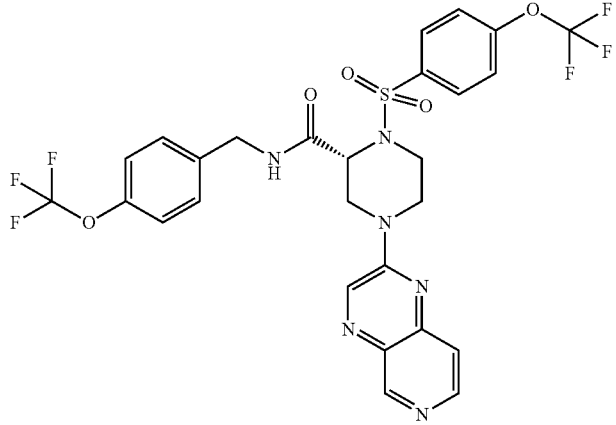 |
| 746 | 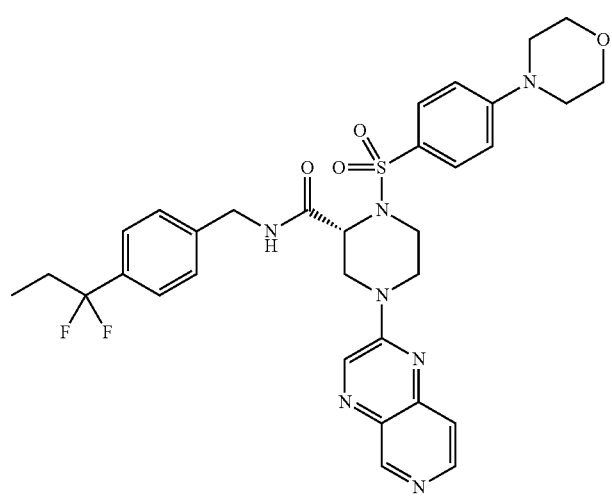 |

TABLE 150-continued
| Ex. No. | Structural Formula |
|---|---|
| 747 | 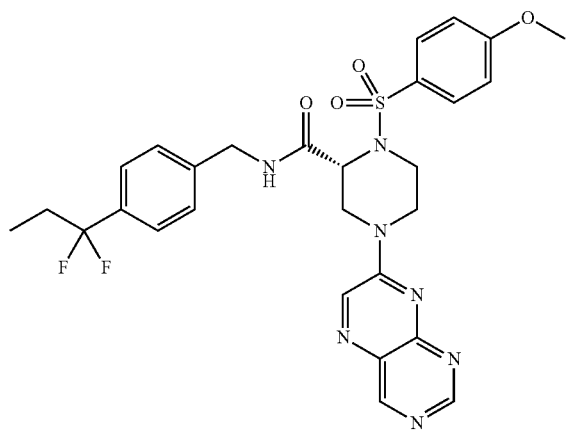 |
| 748 | 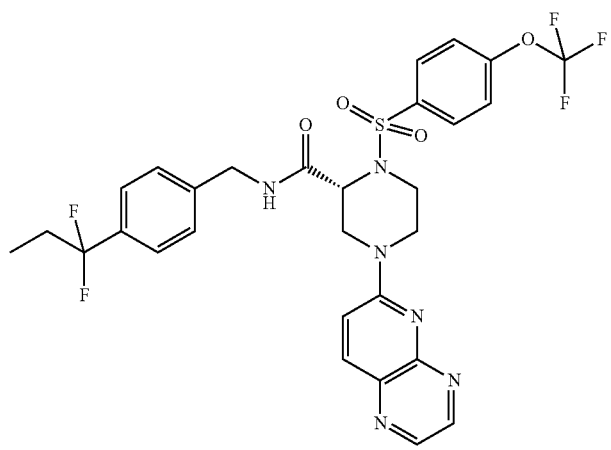 |
| 749 | 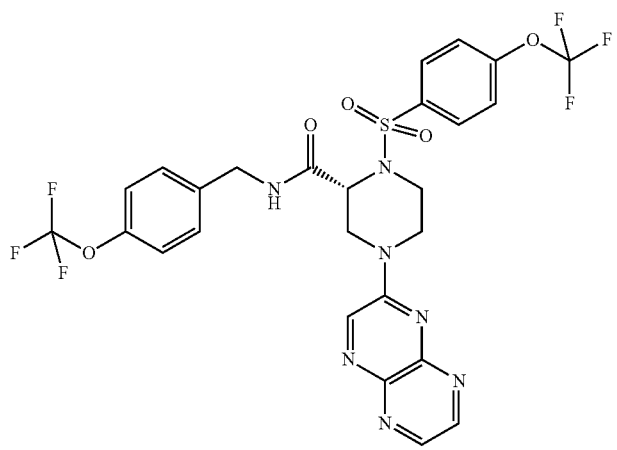 |

TABLE 151
| Ex. No. | Structural Formula |
| --- | --- |
| 750 | 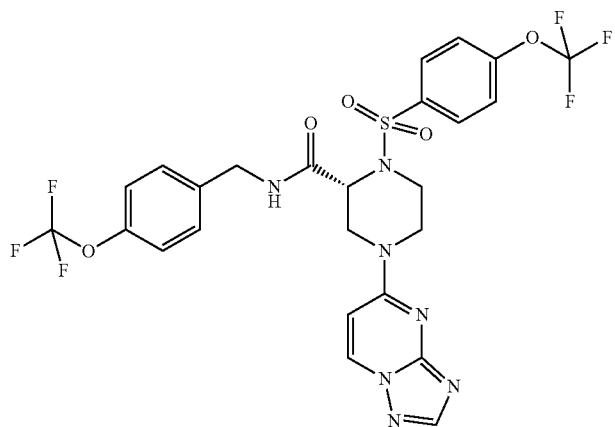 |
| 751 | 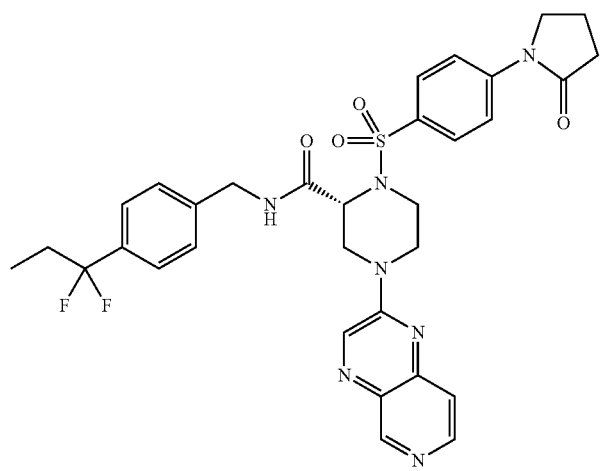 |
| 752 | 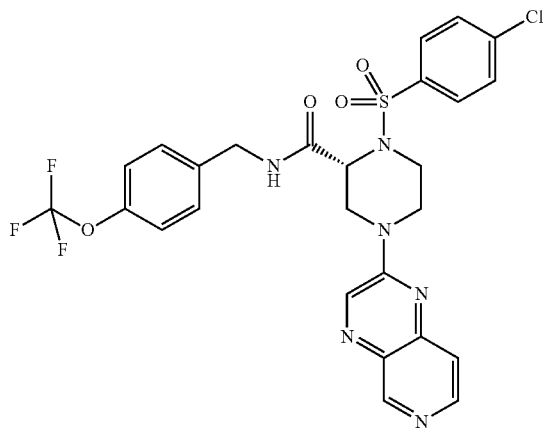 |

663
TABLE 151-continued
| Ex. No. | Structural Formula |
|---|---|
| 753 | 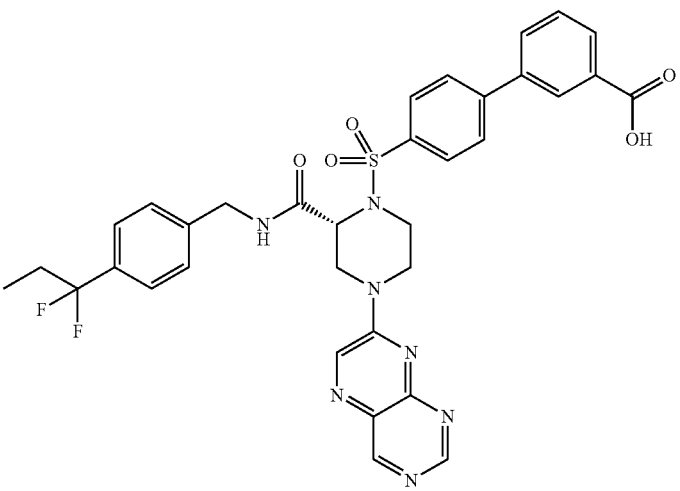 |
| 754 | 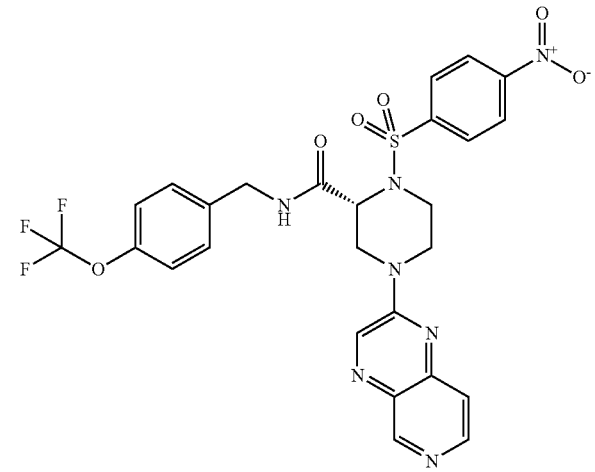 |
TABLE 152
| Ex. No. | Structural Formula |
|---|---|
| 755 | 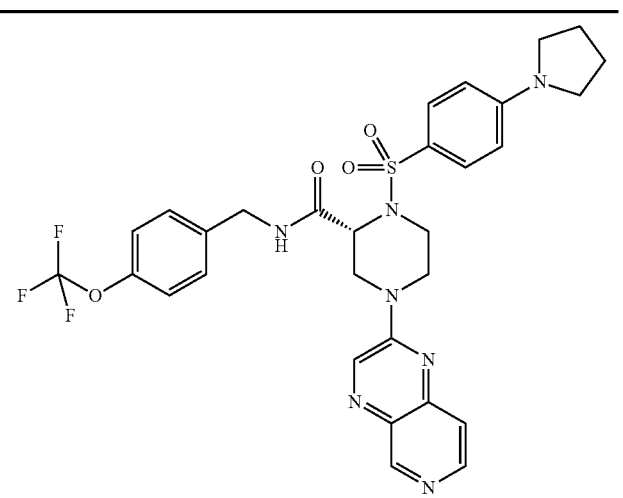 |

TABLE 152-continued
| Ex. No. | Structural Formula |
| --- | --- |
| 756 | 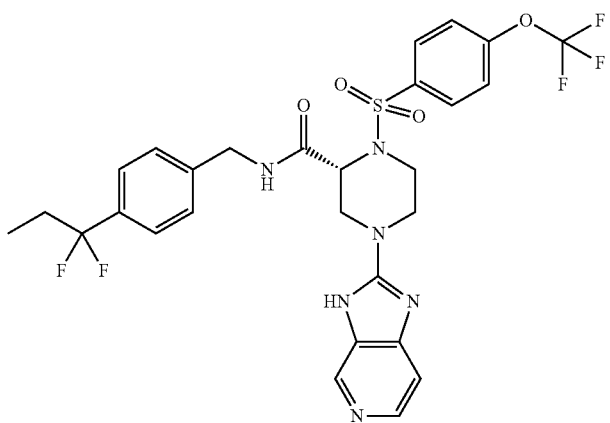 |
| 757 | 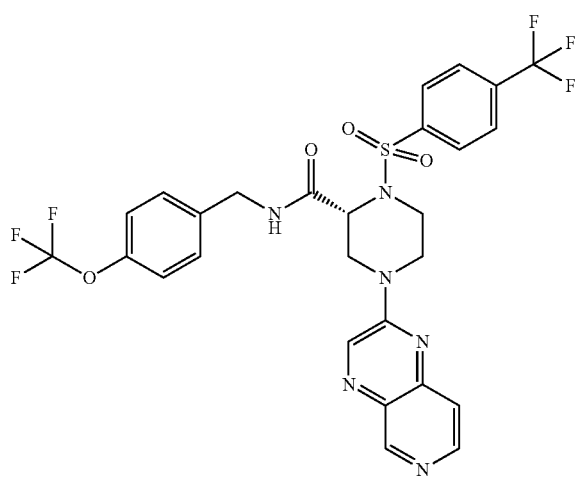 |
| 758 | 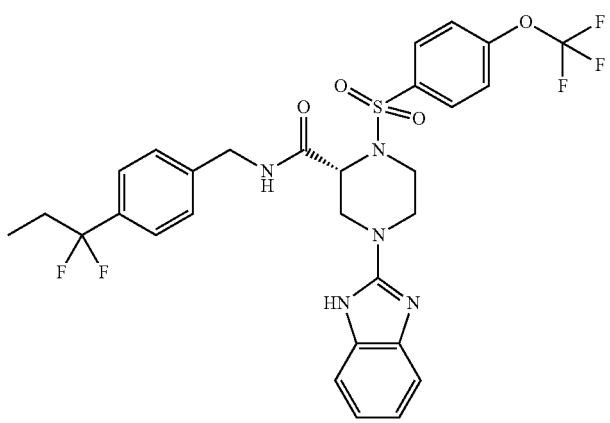 |

TABLE 152-continued
| Ex. No. | Structural Formula |
|---|---|
| 759 | 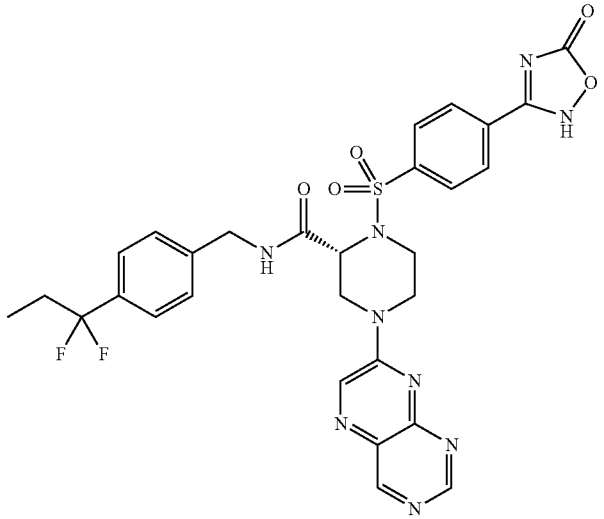 |
TABLE 153
| Ex. No. | Structural Formula |
|---|---|
| 760 | 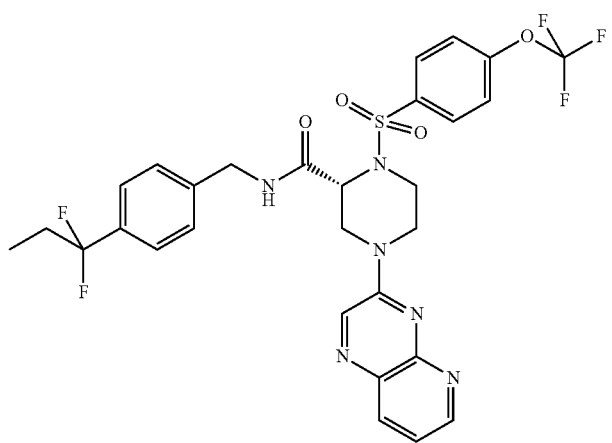 |
| 761 | 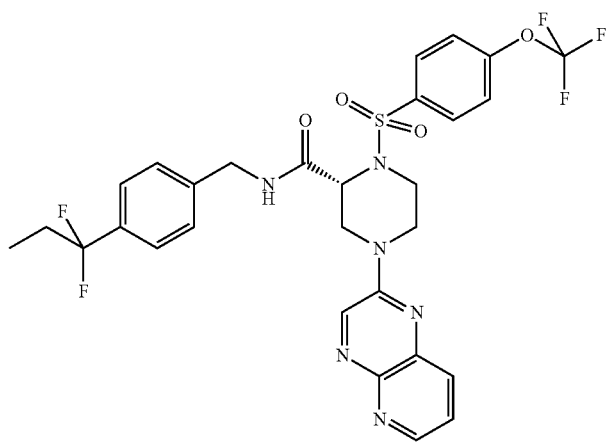 |

TABLE 153-continued
| Ex. No. | Structural Formula |
|---|---|
| 762 | 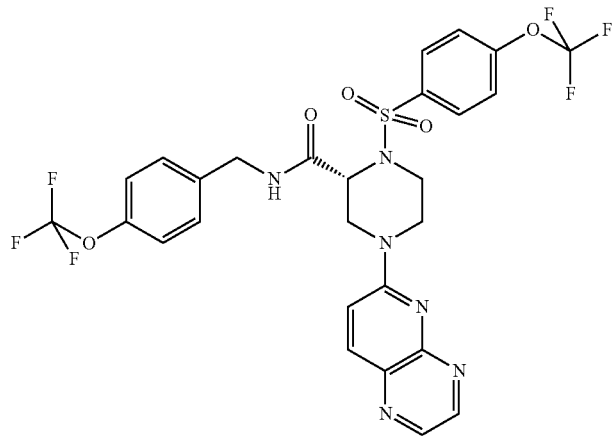 |
| 763 | 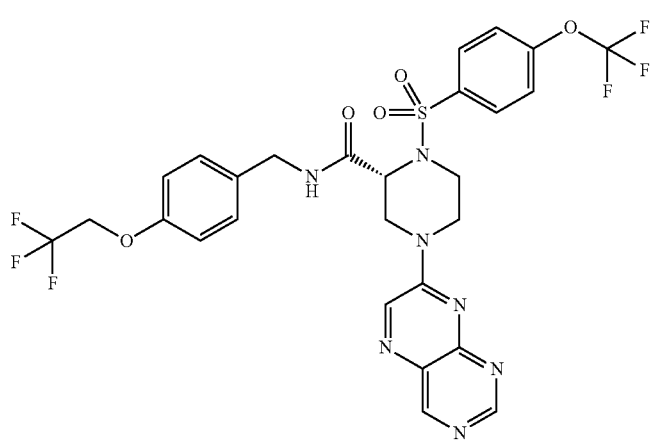 |
| 764 | 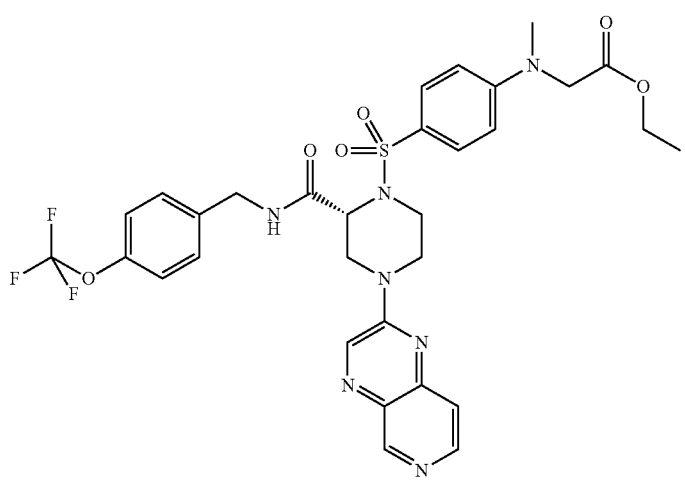 |

TABLE 154

| Ex. No. | Structural Formula |
|---|---|
| 765 | |
| 766 | |
| 767 | |

TABLE 154-continued
| Ex. No. | Structural Formula |
|---|---|
| 768 | 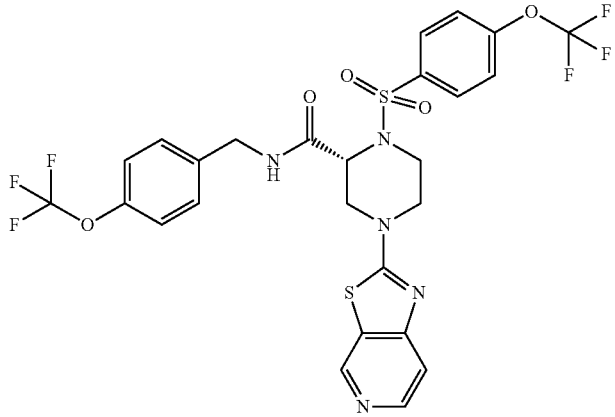 |
| 769 | 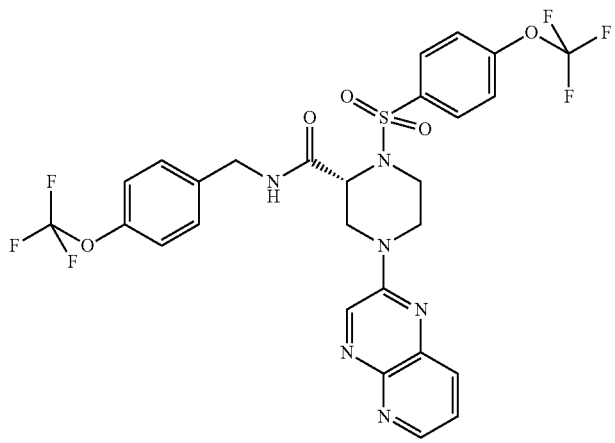 |
TABLE 155
| Ex. No. | Structural Formula |
|---|---|
| 770 | 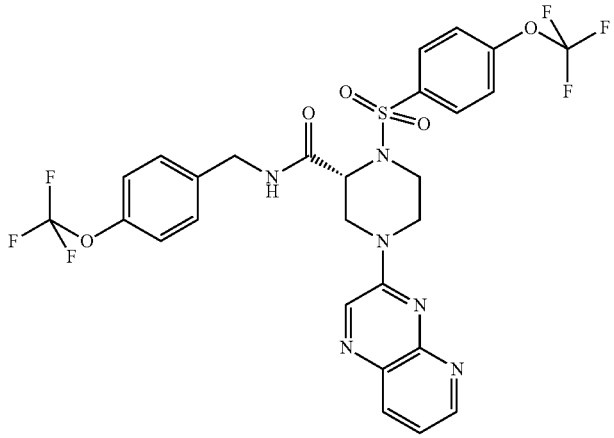 |

TABLE 155-continued
| Ex. No. | Structural Formula |
|---------|--------------------|
| 771 | 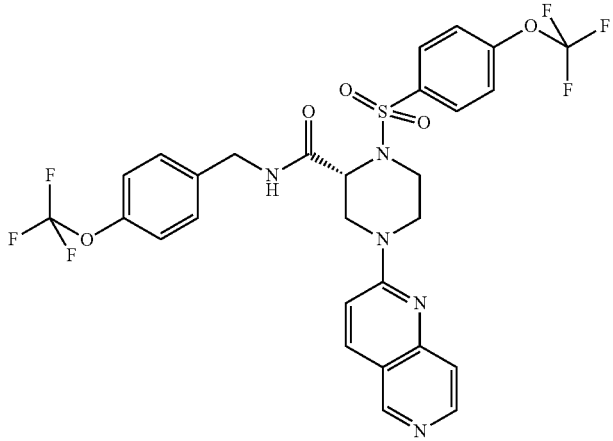 |
| 772 | 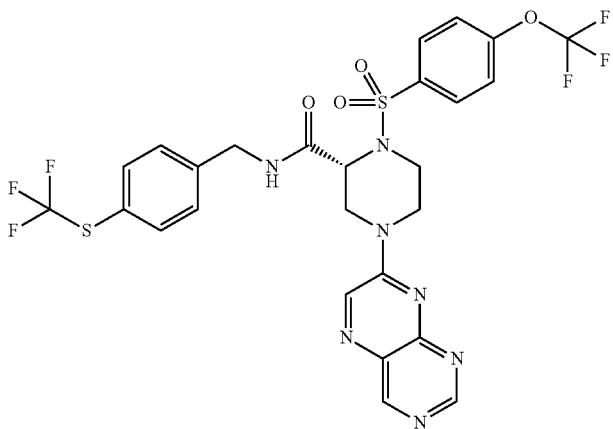 |
| 773 | 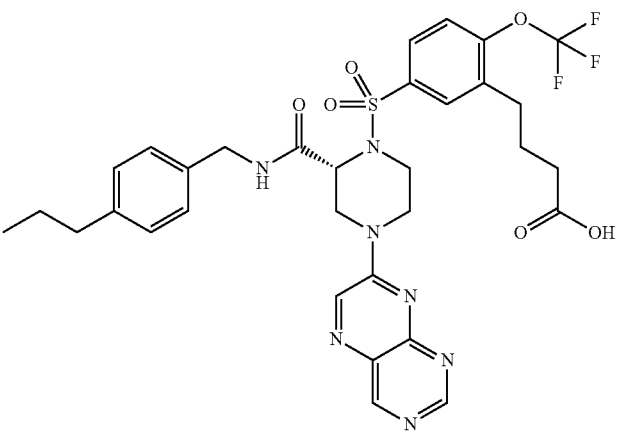 |

TABLE 155-continued
| Ex. No. | Structural Formula |
|---|---|
| 774 | 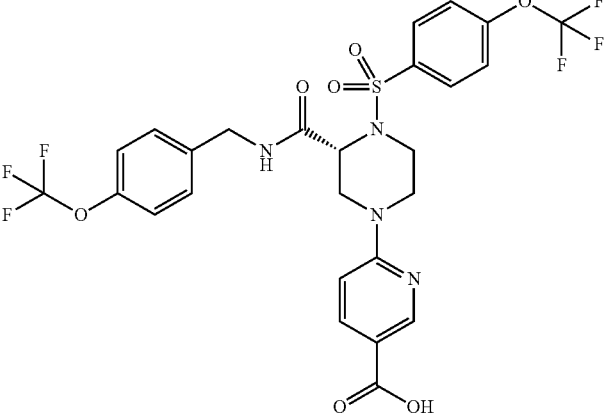 |
TABLE 156
| Ex. No. | Structural Formula |
|---|---|
| 775 | 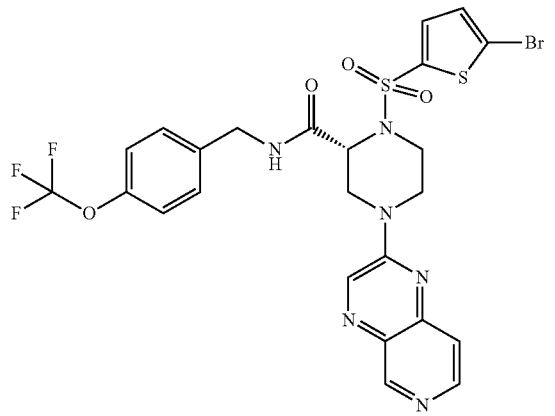 |
| 776 | 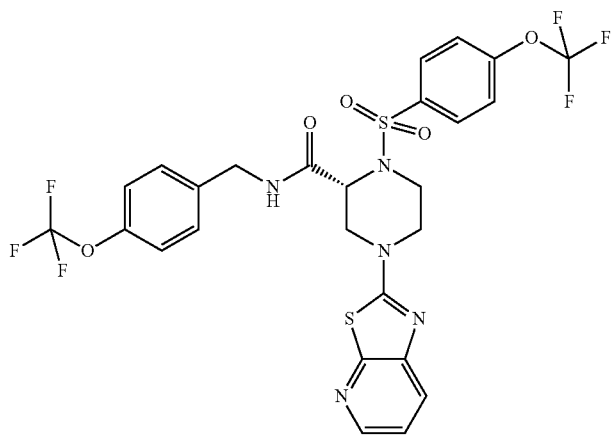 |

TABLE 156-continued
| Ex. No. | Structural Formula |
|---|---|
| 777 | 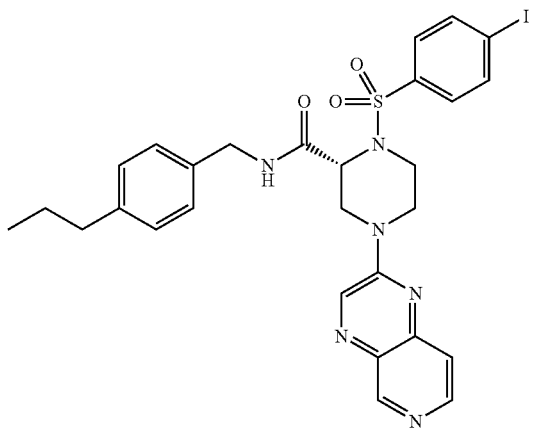 |
| 778 | 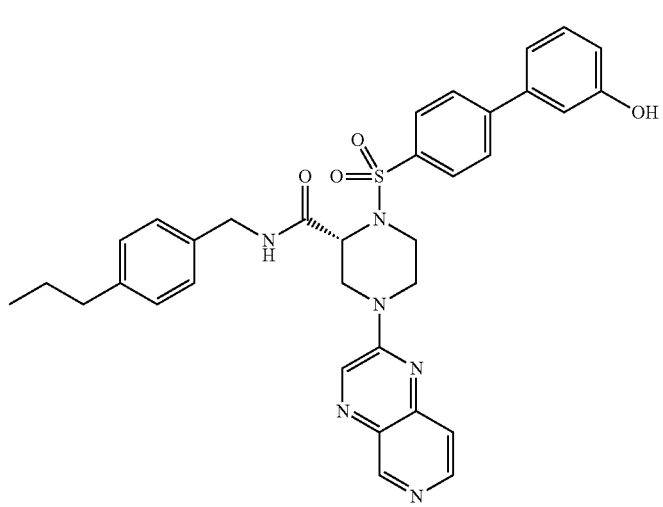 |
| 779 | 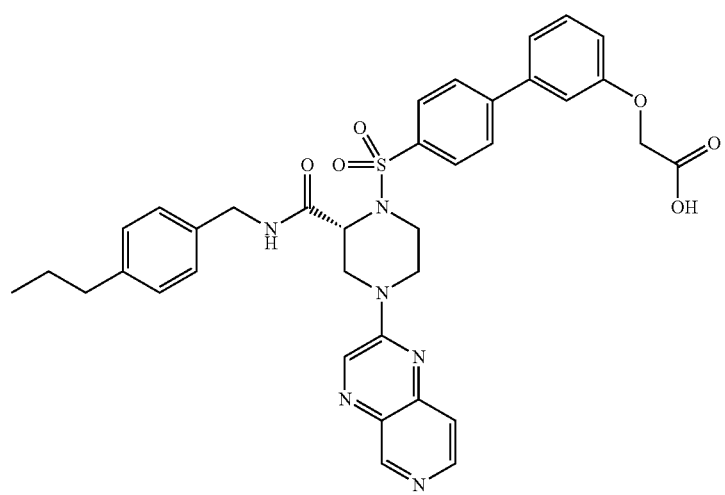 |

TABLE 157

| Ex. No. | Structural Formula |
|---------|--------------------|
| 780 | |
| 781 | |
| 782 | |
| 783 | |

TABLE 157-continued
| Ex. No. | Structural Formula |
|---|---|
| 784 | |
TABLE 158
| Ex. No. | Structural Formula |
|---|---|
| 785 | |
| 786 | 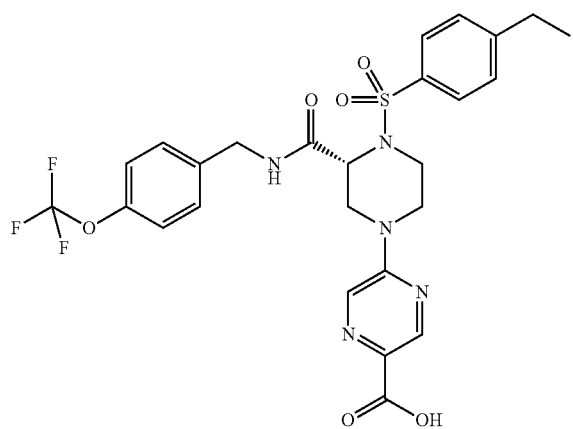 |

TABLE 158-continued
| Ex. No. | Structural Formula |
|---|---|
| 787 | 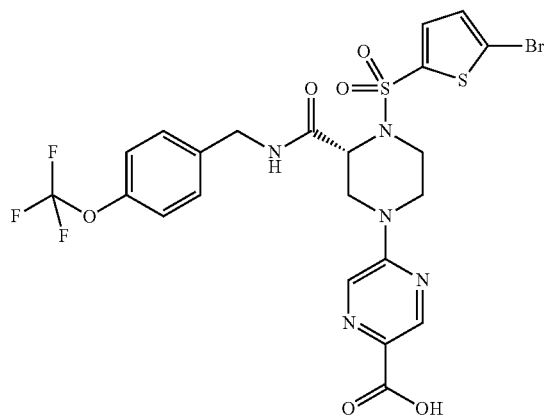 |
| 788 | 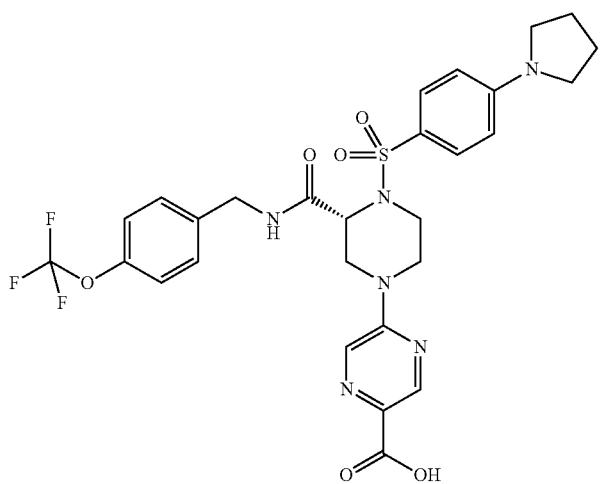 |
| 789 | 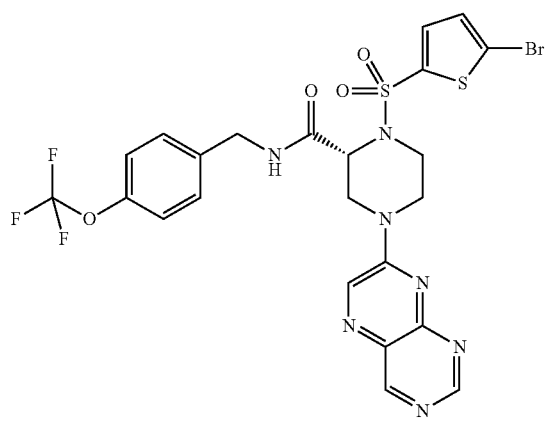 |

TABLE 159
| Ex. No. | Structural Formula |
| --- | --- |
| 790 | 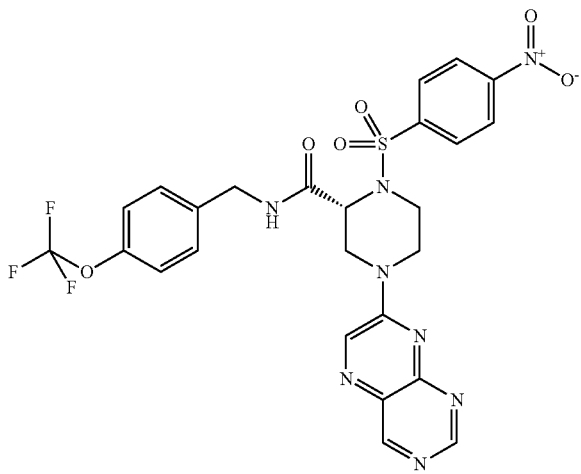 |
| 791 | 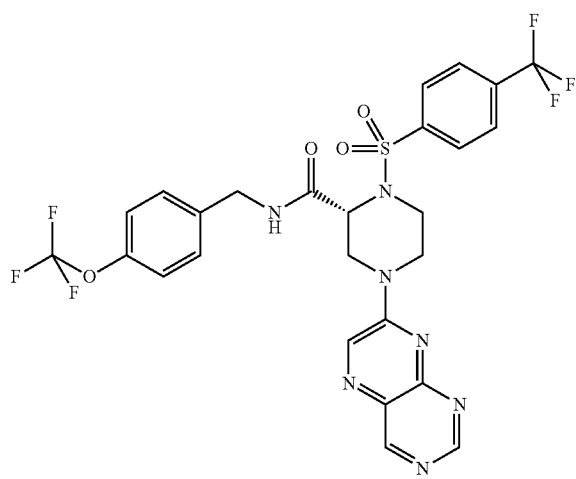 |
| 792 | 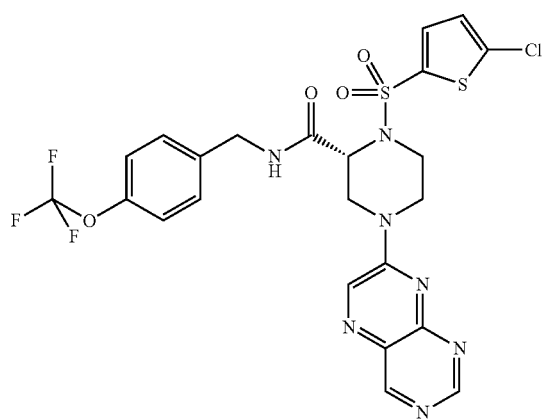 |

TABLE 159-continued

| Ex. No. | Structural Formula |
|---|---|
| 793 | |
| 794 | |

TABLE 160

| Ex. No. | Structural Formula |
|---|---|
| 795 | |

TABLE 160-continued
| Ex. No. | Structural Formula |
|---|---|
| 796 | 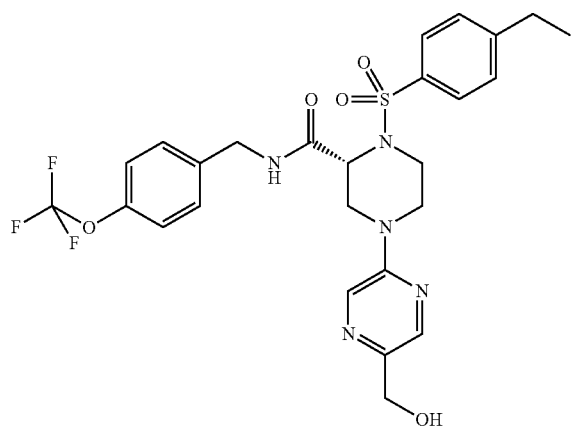 |
| 797 | 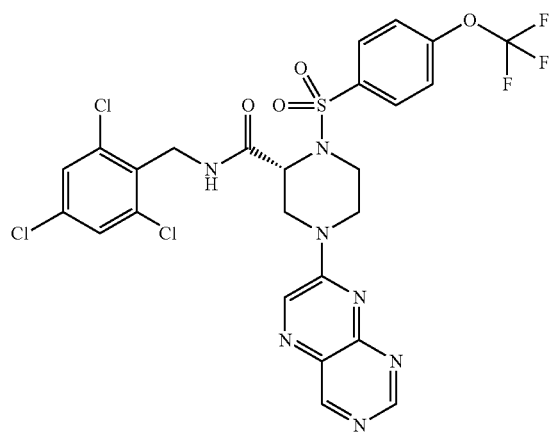 |
| 798 | 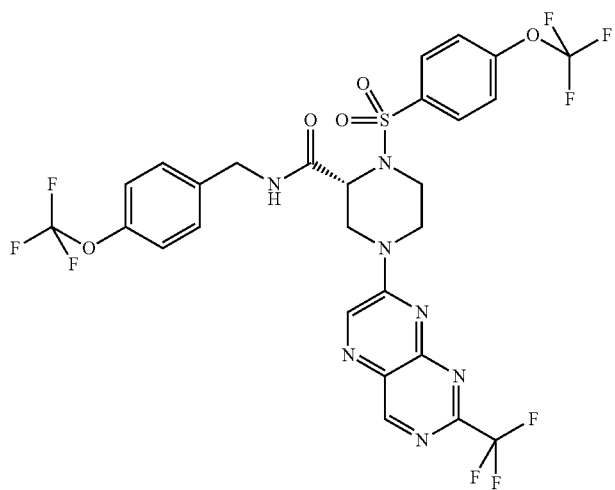 |

TABLE 160-continued

| Ex. No. | Structural Formula |
|---|---|
| 799 | |

TABLE 161

| Ex. No. | Structural Formula |
|---|---|
| 800 | |
| 801 | |

TABLE 161-continued
| Ex. No. | Structural Formula |
|---|---|
| 802 | 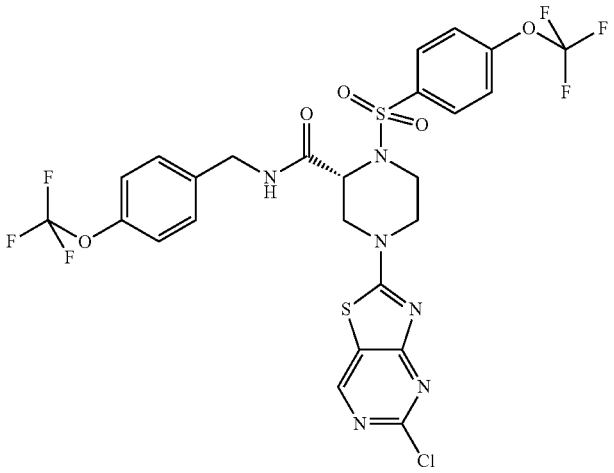 |
| 803 | 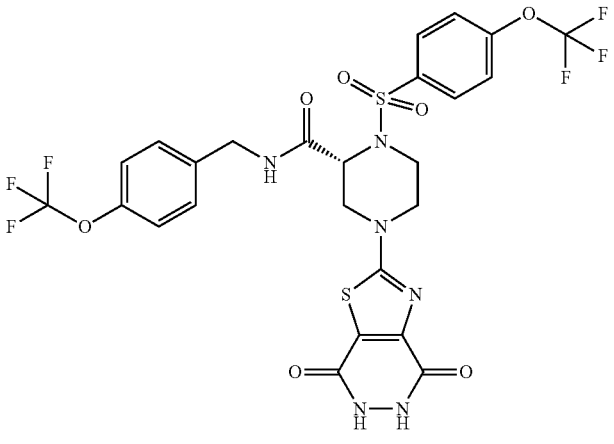 |
| 804 | 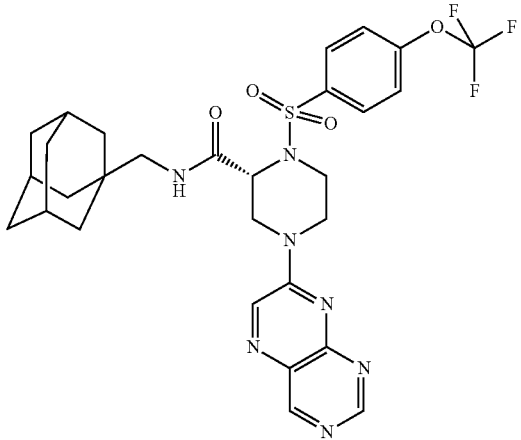 |

TABLE 162
| Ex. No. | Structural Formula |
|---|---|
| 805 | 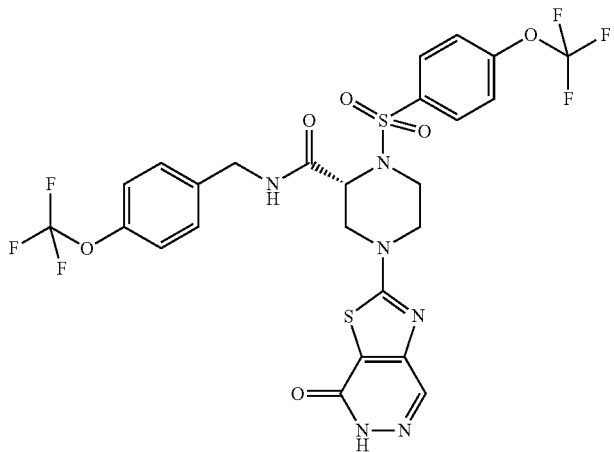 |
| 806 | 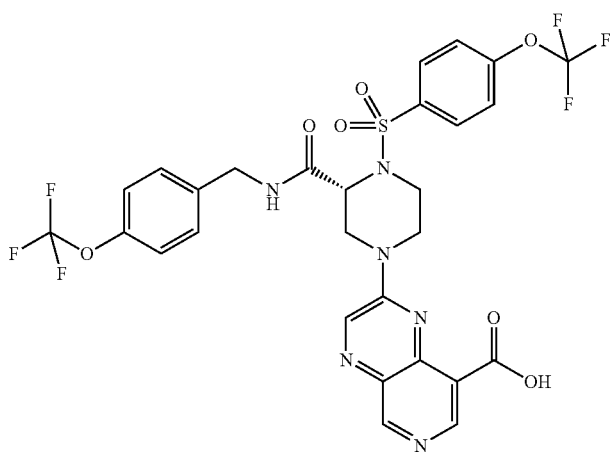 |
| 807 | 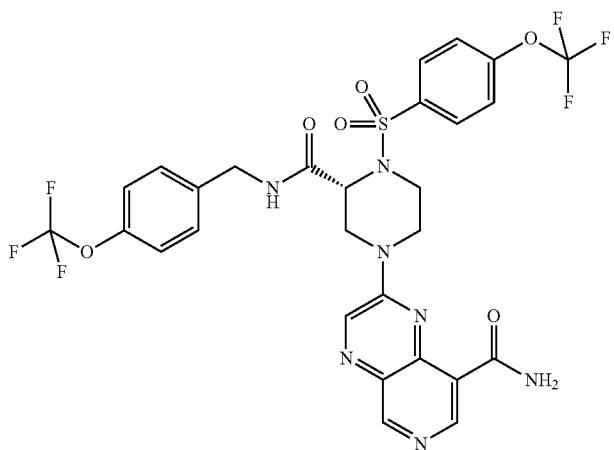 |

TABLE 162-continued
| Ex. No. | Structural Formula |
|---|---|
| 808 | 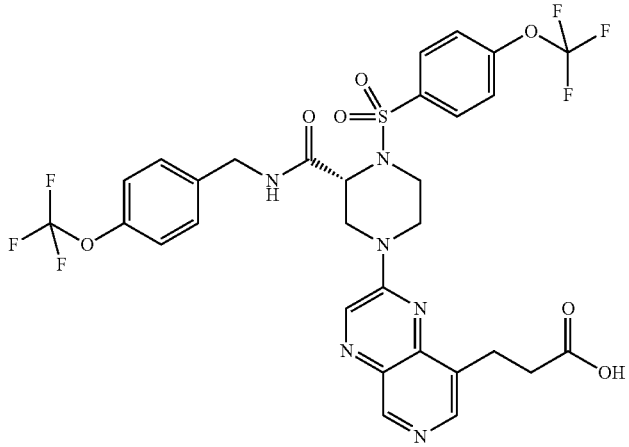 |
| 809 | 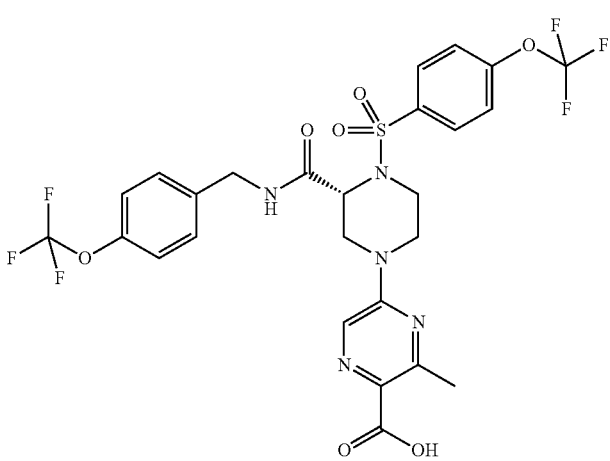 |
TABLE 163
| Ex. No. | Structural Formula |
|---|---|
| 810 | 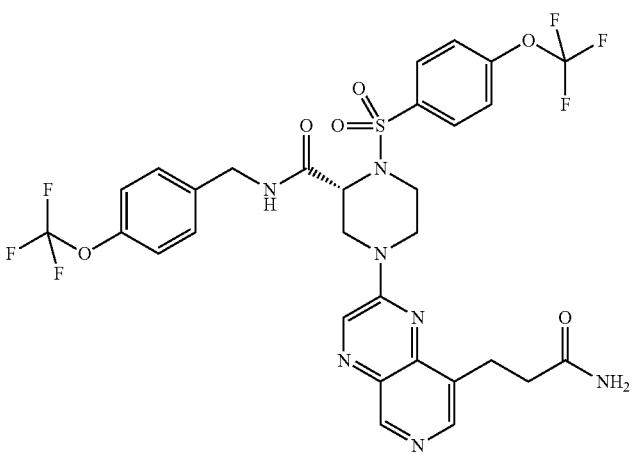 |

TABLE 163-continued
| Ex. No. | Structural Formula |
|---|---|
| 811 | 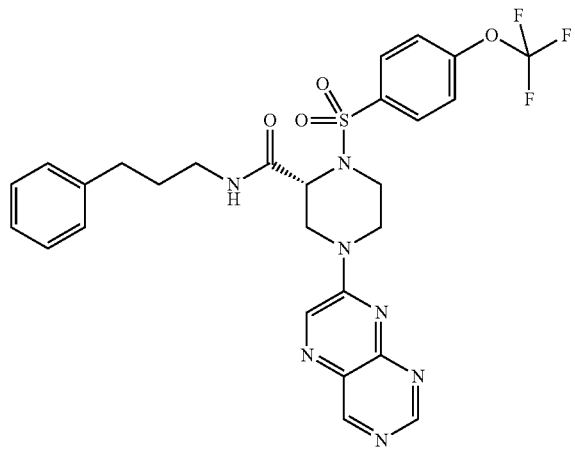 |
| 812 | 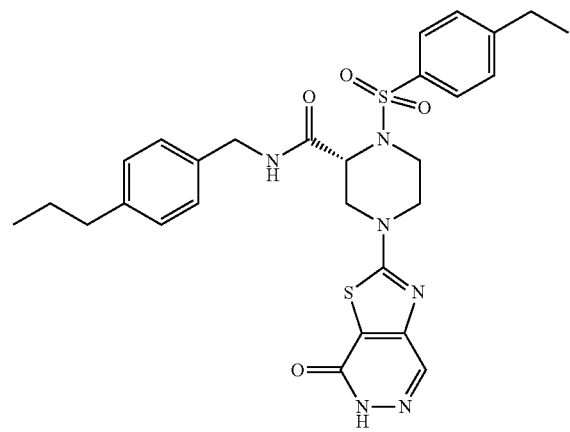 |
| 813 | 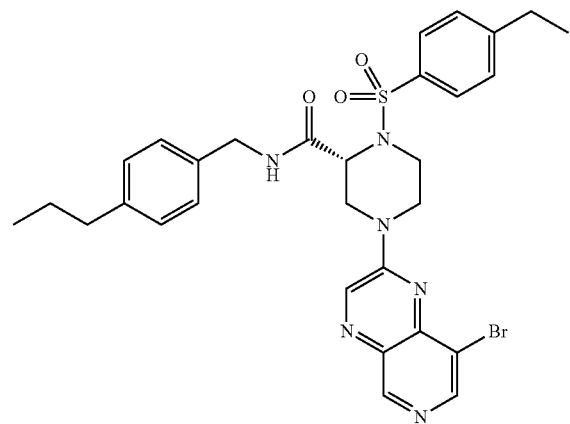 |

703
TABLE 163-continued
| Ex. No. | Structural Formula |
| --- | --- |
| 814 | 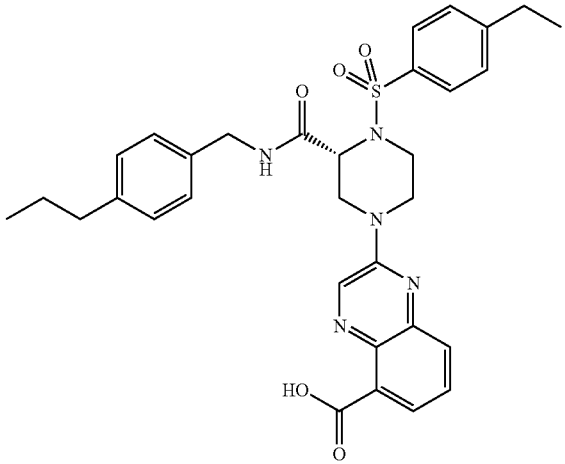 |
704
TABLE 164
| Ex. No. | Structural Formula |
| --- | --- |
| 815 | 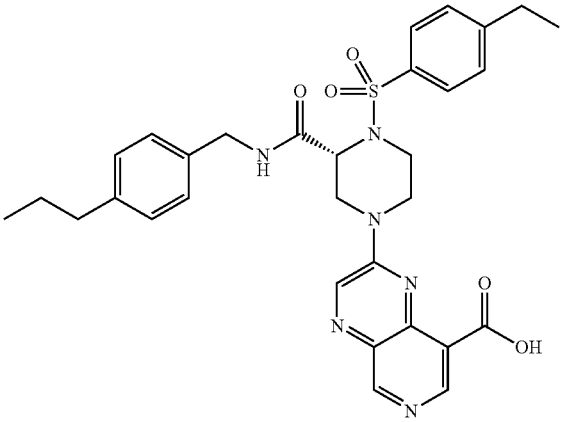 |
| 816 | 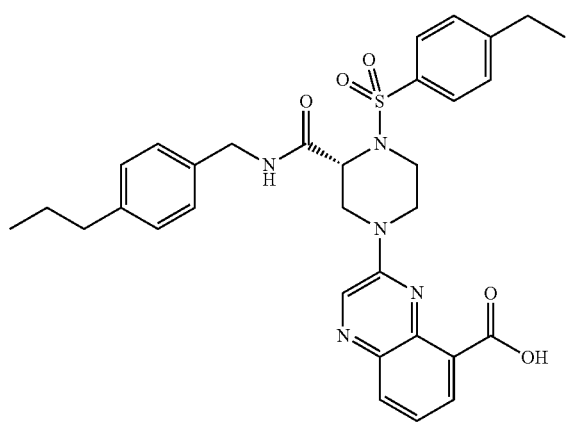 |

TABLE 164-continued
| Ex. No. | Structural Formula |
|---|---|
| 817 | 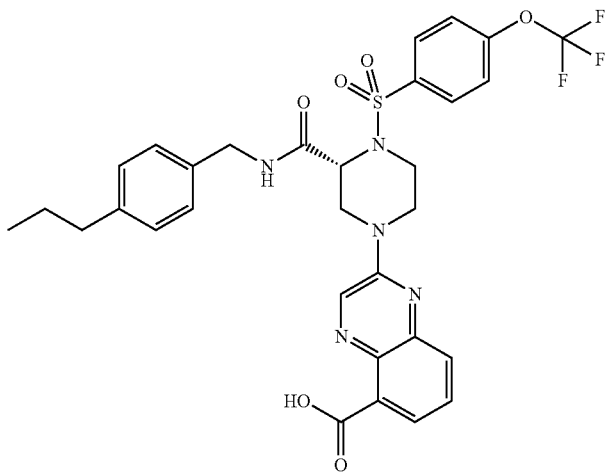 |
| 818 | 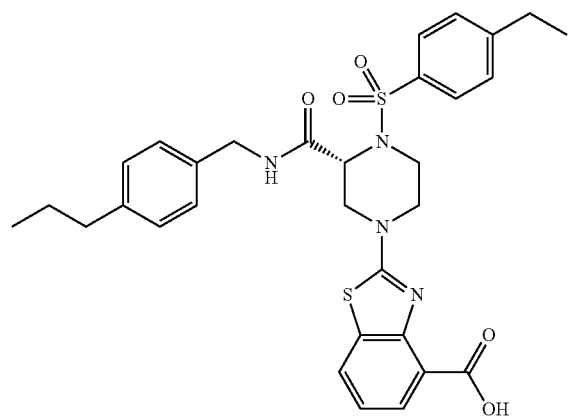 |
| 819 | 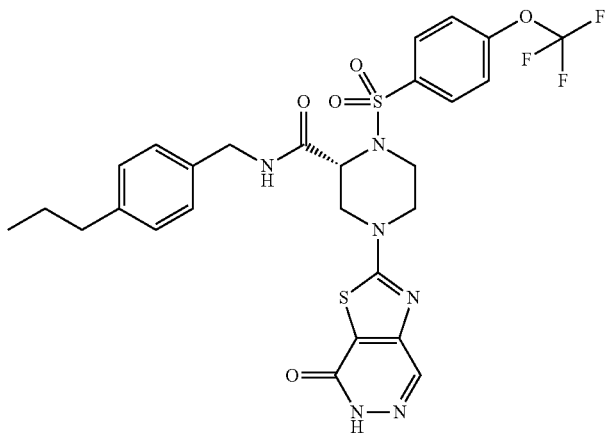 |

TABLE 165
| Ex. No. | Structural Formula |
|---|---|
| 820 | 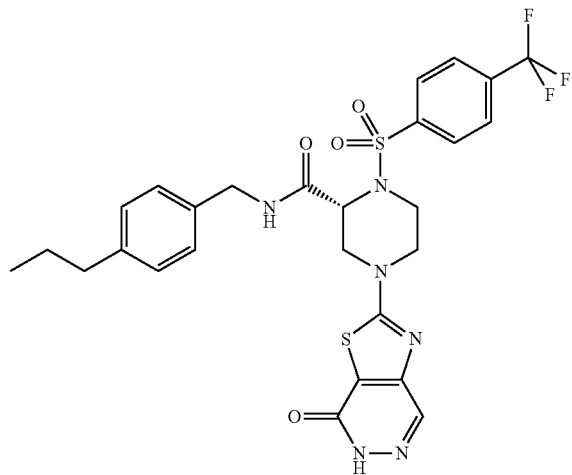 |
| 821 | 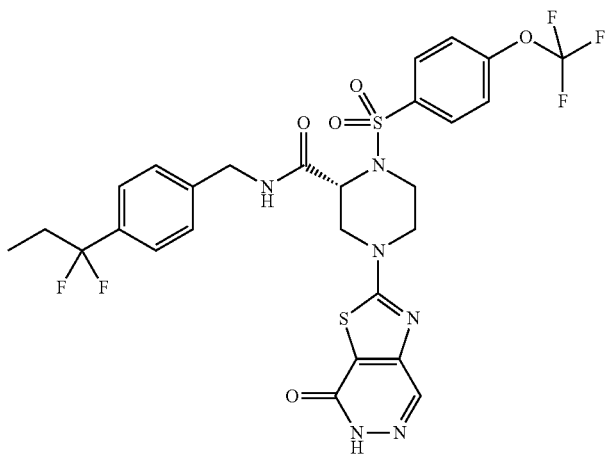 |
| 822 | 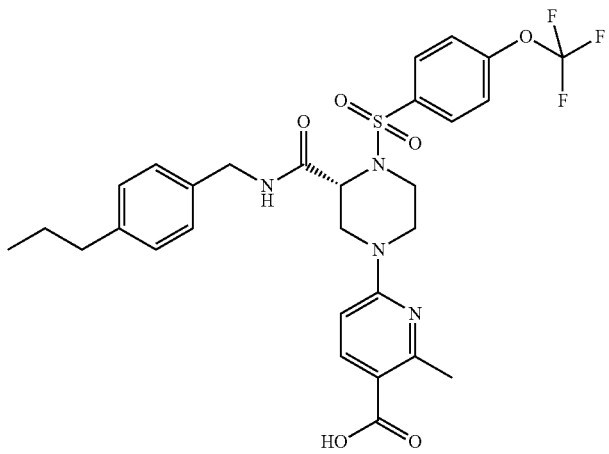 |

TABLE 165-continued
| Ex. No. | Structural Formula |
|---|---|
| 823 | 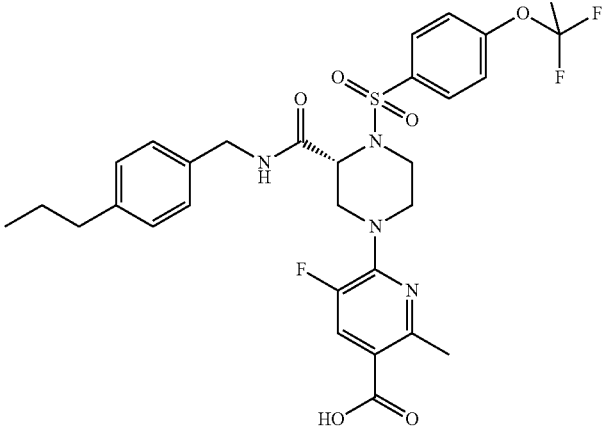 |
| 824 | 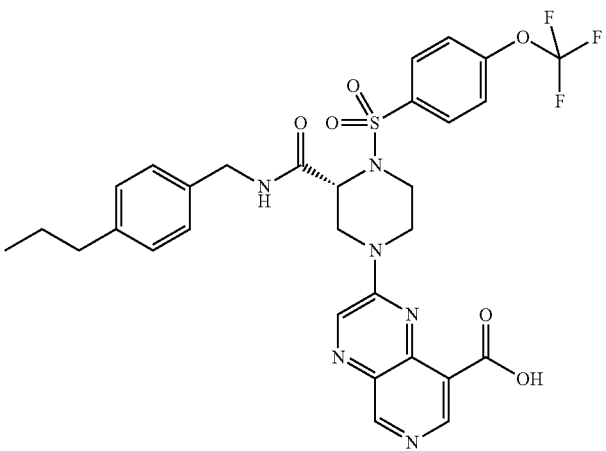 |
TABLE 166
| Ex. No. | Structural Formula |
|---|---|
| 825 | 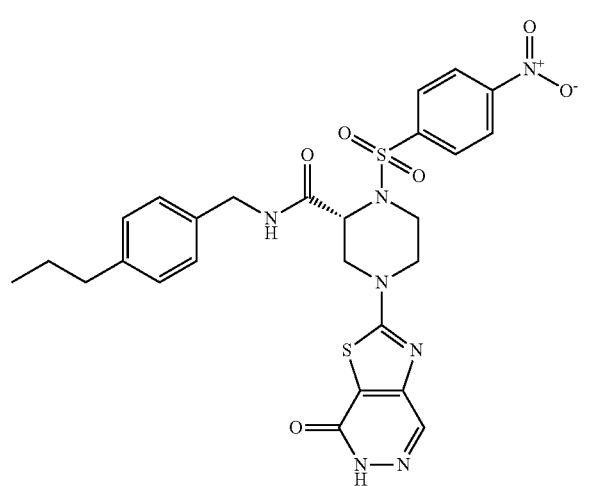 |

TABLE 166-continued
| Ex. No. | Structural Formula |
|---|---|
| 826 | 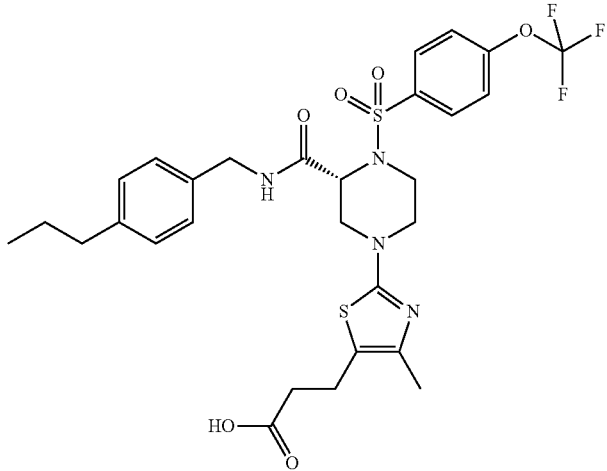 |
| 827 | 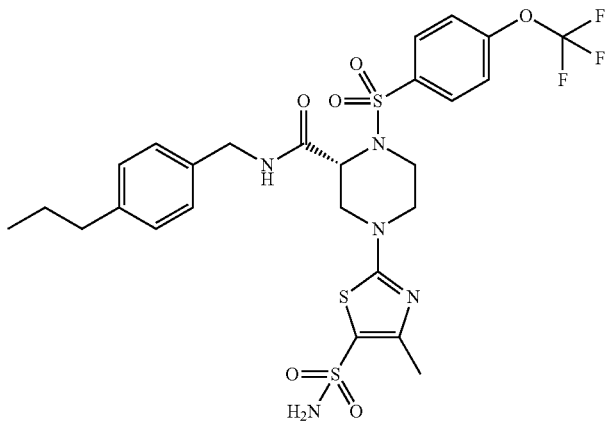 |
| 828 | 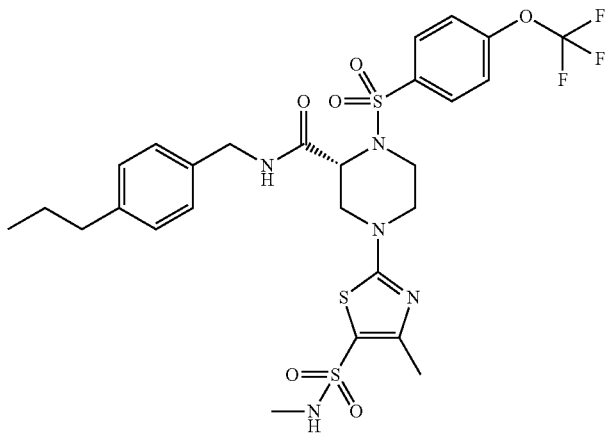 |

TABLE 166-continued
| Ex. No. | Structural Formula |
|---|---|
| 829 | 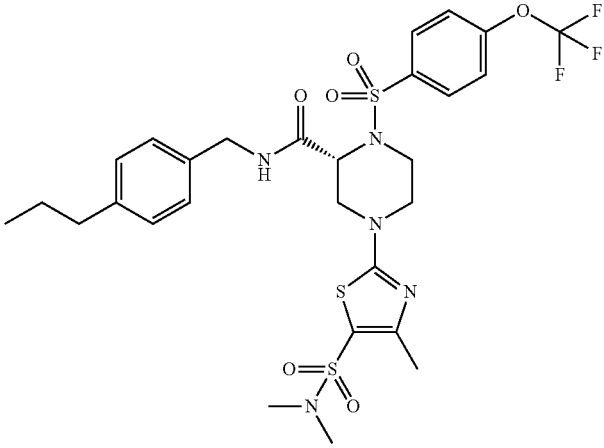 |
TABLE 167
| Ex. No. | Structural Formula |
|---|---|
| 830 | 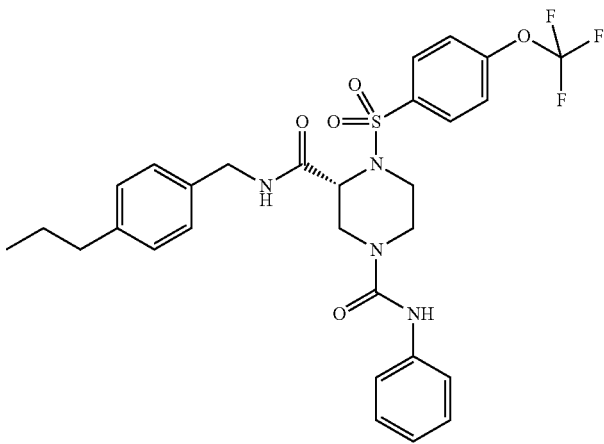 |
| 831 | 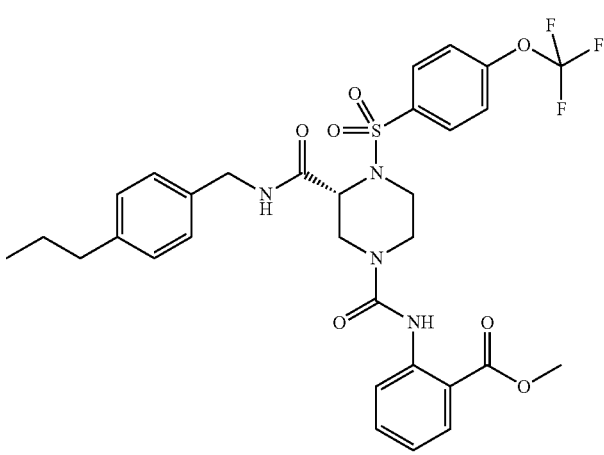 |

715
TABLE 167-continued
| Ex. No. | Structural Formula |
|---|---|
| 832 | 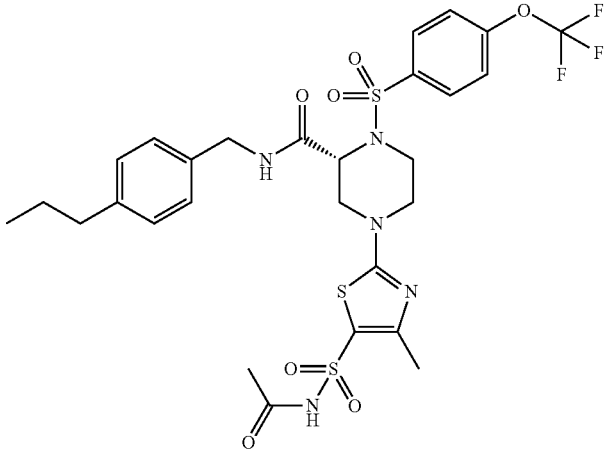 |
| 833 | 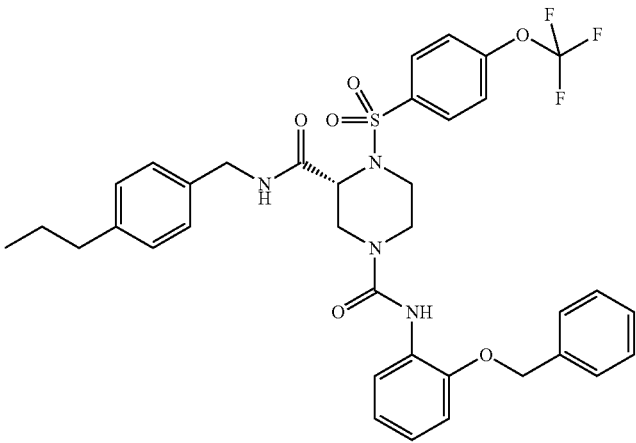 |
| 834 | 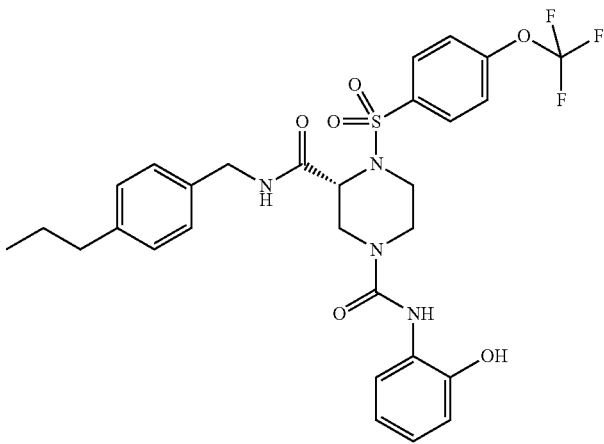 |

TABLE 168

| Ex. No. | Structural Formula |
| --- | --- |
| 835 | |
| 836 | |
| 837 | |

TABLE 168-continued
| Ex. No. | Structural Formula |
|---|---|
| 838 | 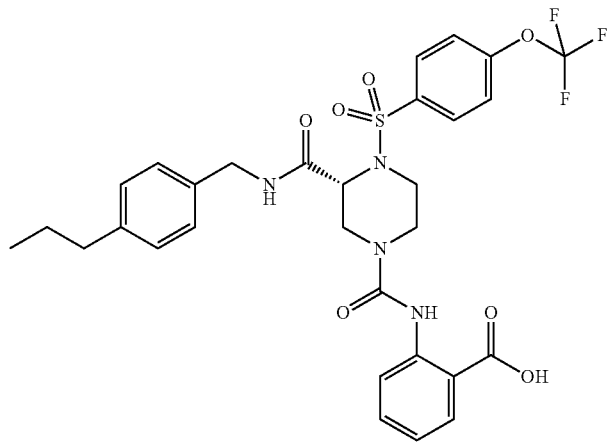 |
| 839 | 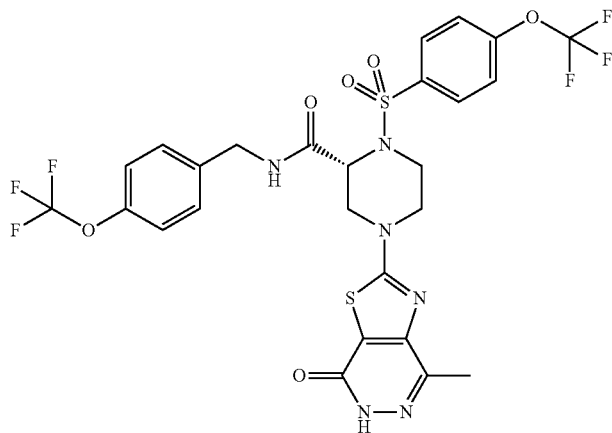 |
TABLE 169
| Ex. No. | Structural Formula |
|---|---|
| 840 | 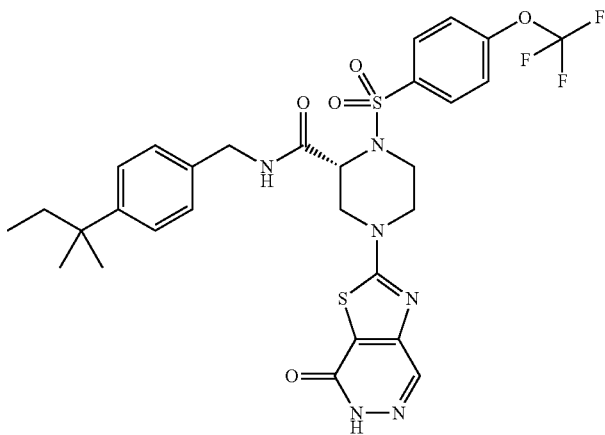 |

TABLE 169-continued
| Ex. No. | Structural Formula |
|---|---|
| 841 | 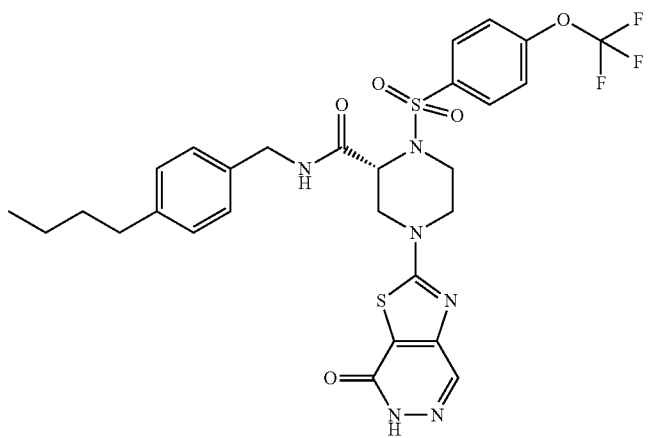 |
| 842 | 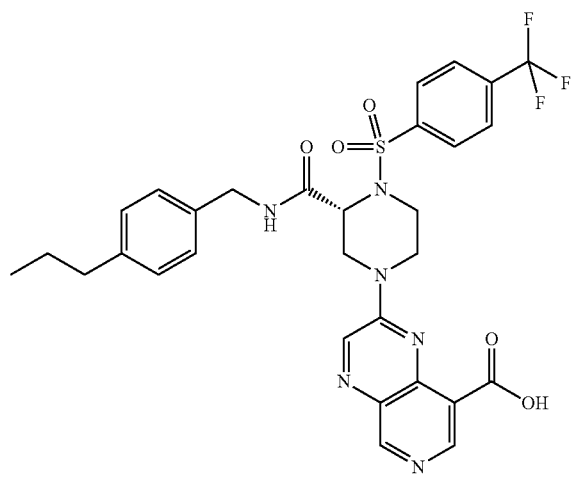 |
| 843 | 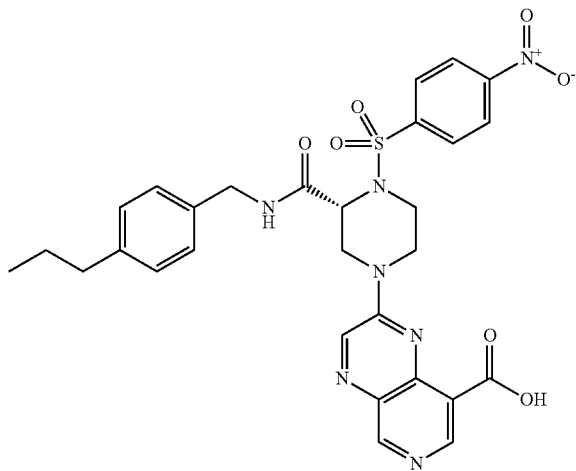 |

TABLE 169-continued
| Ex. No. | Structural Formula |
|---|---|
| 844 | 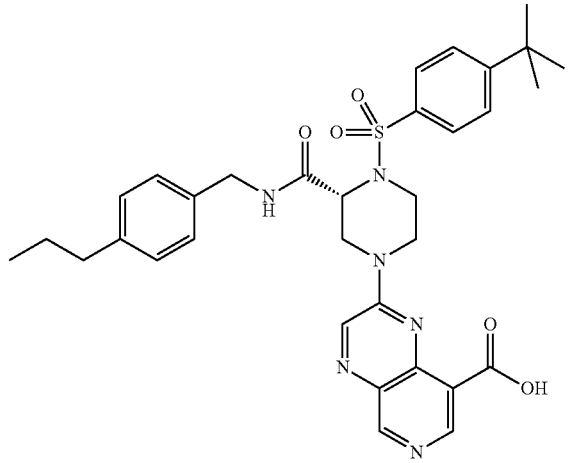 |
TABLE 170
| Ex. No. | Structural Formula |
|---|---|
| 845 | 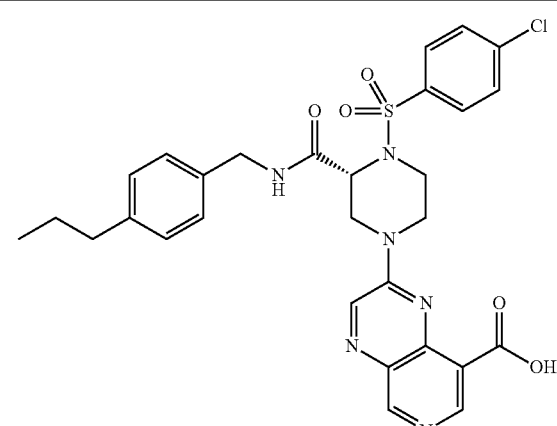 |
| 846 | 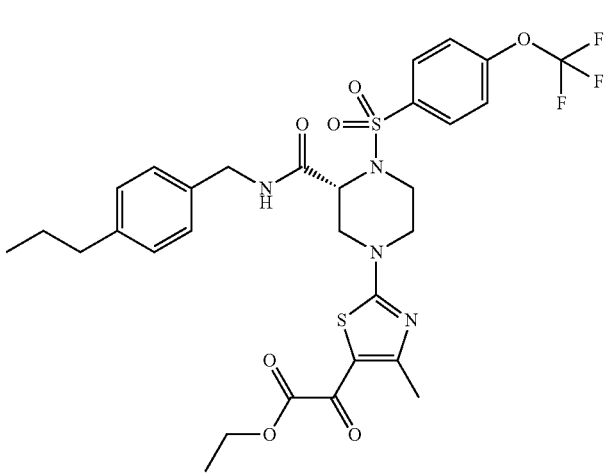 |

TABLE 170-continued
| Ex. No. | Structural Formula |
|---|---|
| 847 | 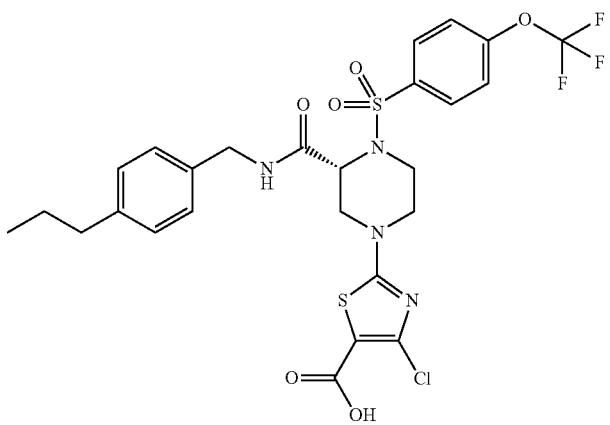 |
| 848 | 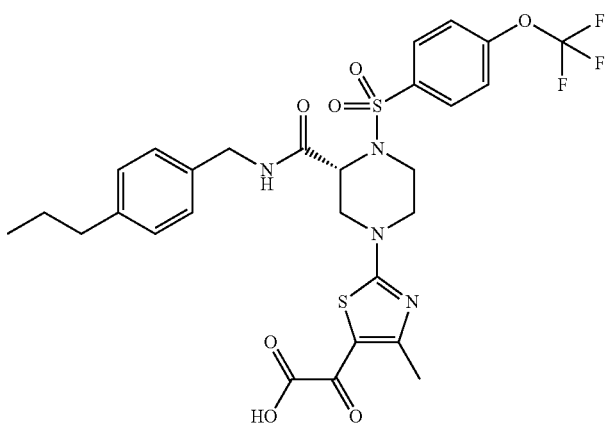 |
| 849 | 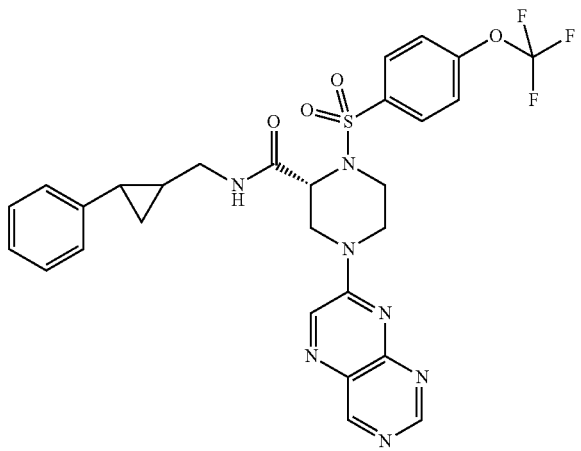 |

TABLE 171
| Ex. No. | Structural Formula |
|---|---|
| 850 | 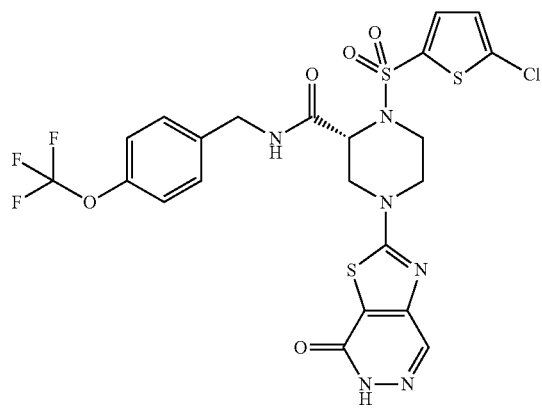 |
| 851 | 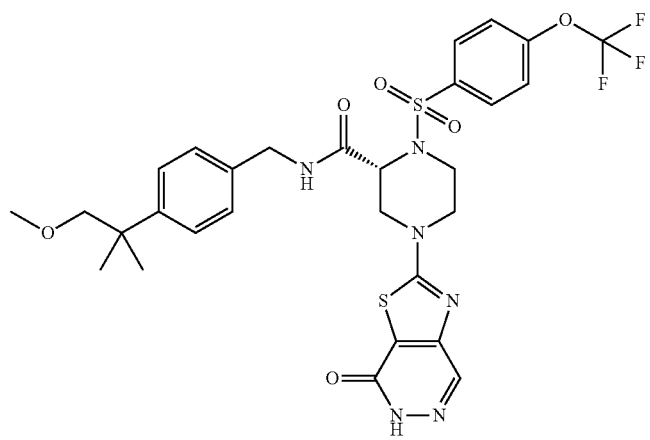 |
| 852 | 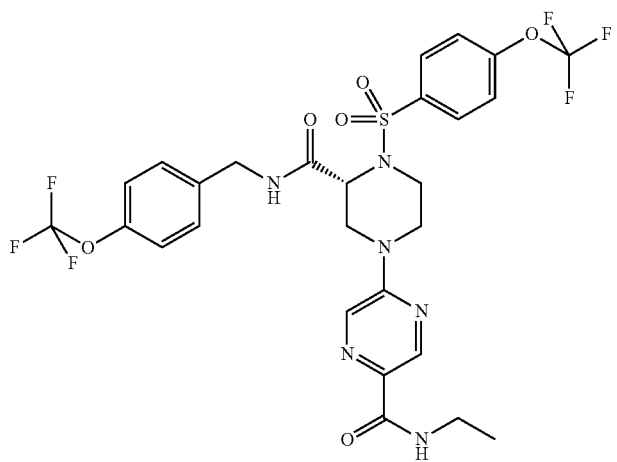 |

TABLE 171-continued

| Ex. No. | Structural Formula |
|---------|--------------------|
| 853 | |
| 854 | |

TABLE 172

| Ex. No. | Structural Formula |
|---------|--------------------|
| 855 | |

TABLE 172-continued
| Ex. No. | Structural Formula |
|---|---|
| 856 | 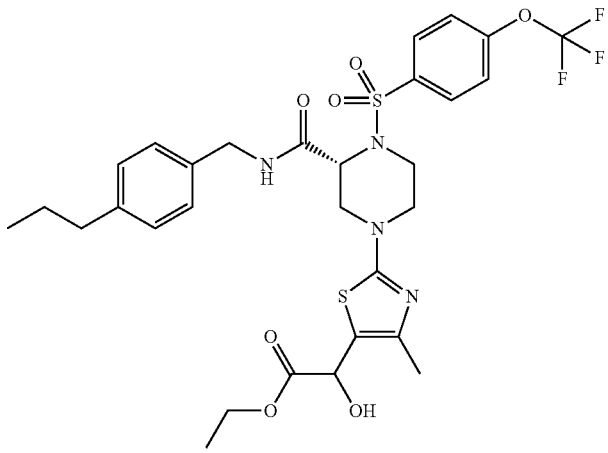 |
| 857 | 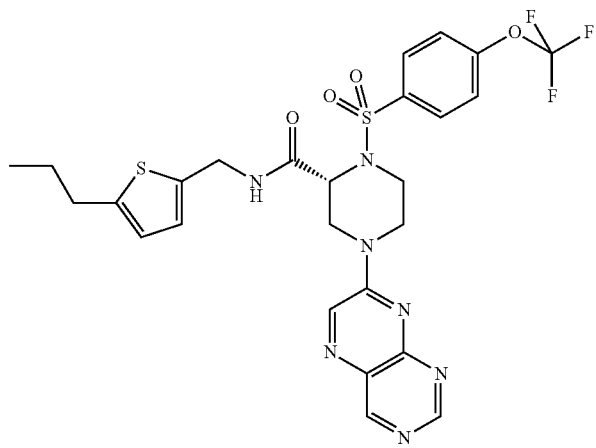 |
| 858 | 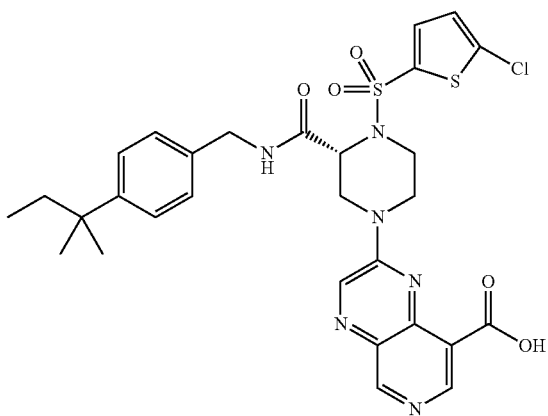 |

TABLE 172-continued
| Ex. No. | Structural Formula |
|---|---|
| 859 | |
TABLE 173
| Ex. No. | Structural Formula |
|---|---|
| 860 | |
| 861 | 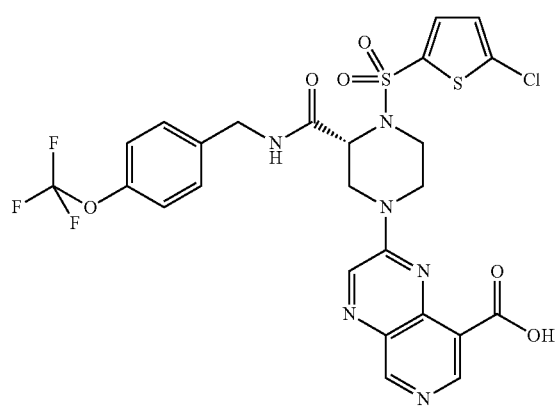 |

TABLE 173-continued
| Ex. No. | Structural Formula |
|---|---|
| 862 | 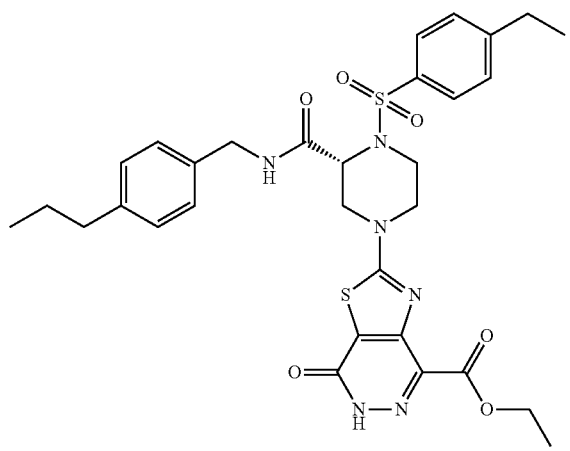 |
| 863 | 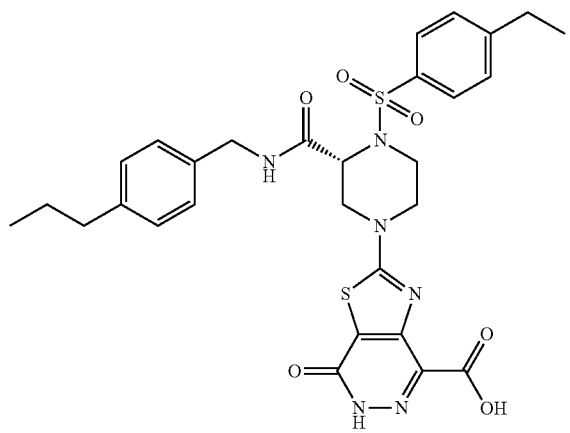 |
| 864 | 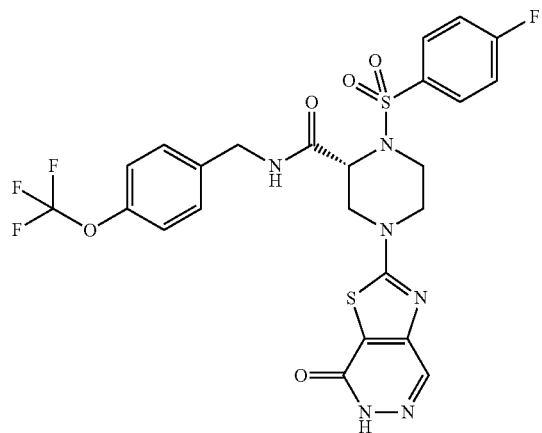 |

TABLE 174
| Ex. No. | Structural Formula |
| --- | --- |
| 865 | 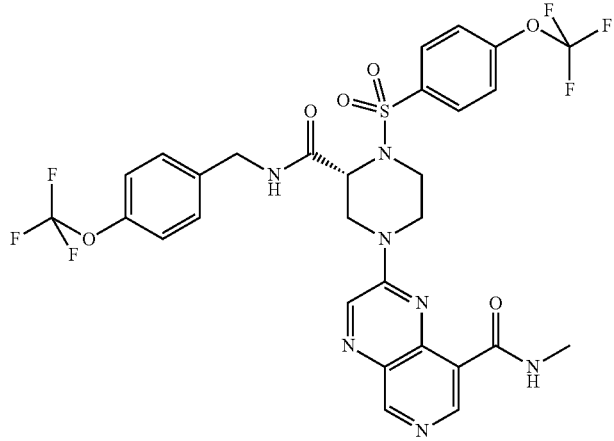 |
| 866 | 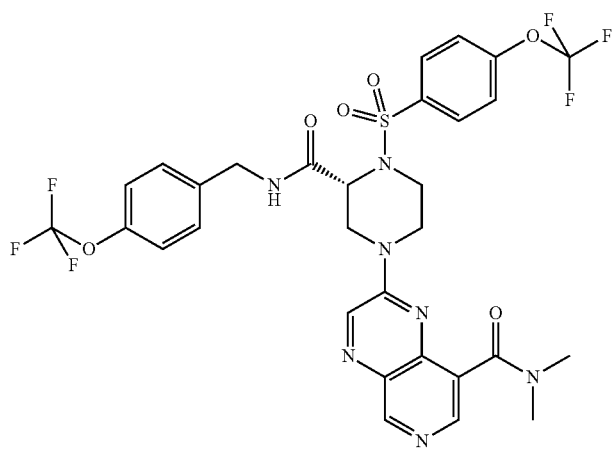 |
| 867 | 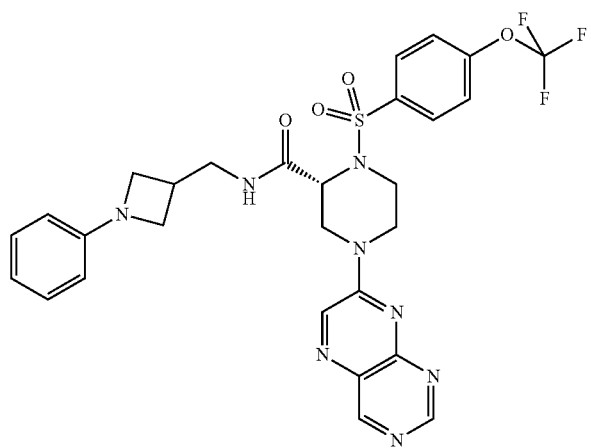 |

TABLE 174-continued
| Ex. No. | Structural Formula |
|---|---|
| 868 | |
| 869 | |
TABLE 175
| Ex. No. | Structural Formula |
|---|---|
| 870 | 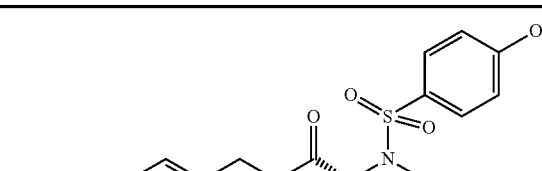 |

TABLE 175-continued
| Ex. No. | Structural Formula |
|---|---|
| 871 | 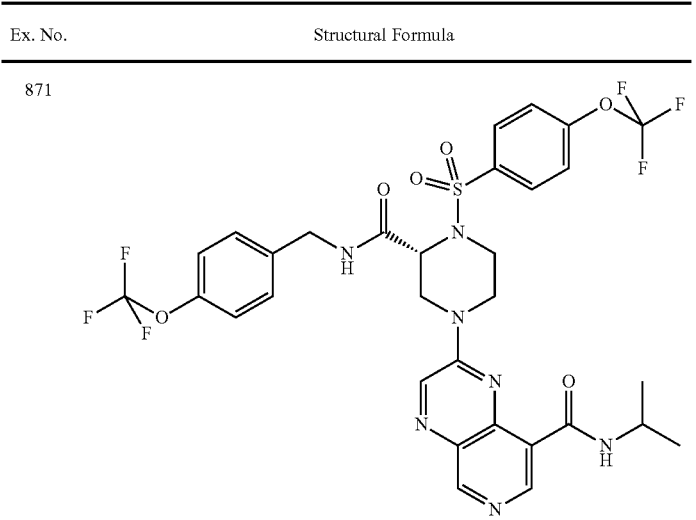 |
| 872 | 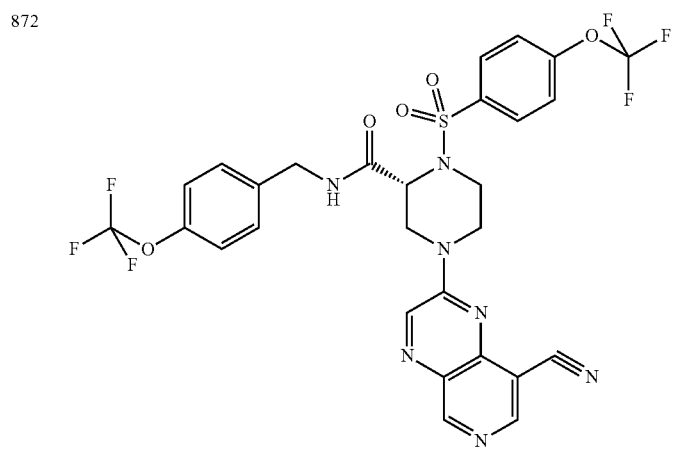 |
| 873 | 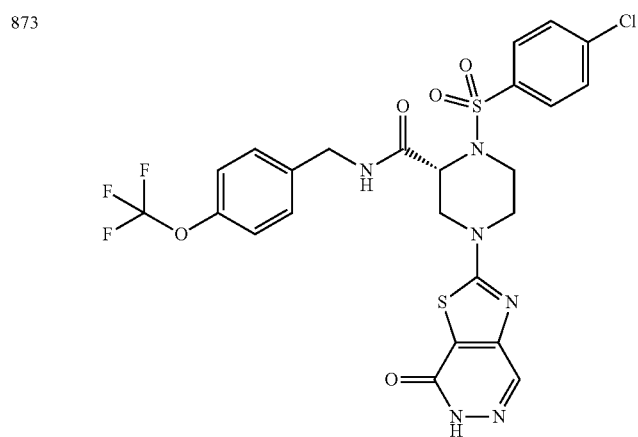 |

TABLE 175-continued
| Ex. No. | Structural Formula |
| --- | --- |
| 874 | 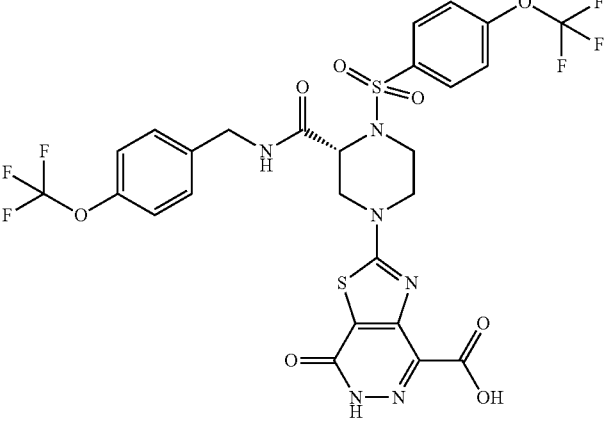 |
TABLE 176
| Ex. No. | Structural Formula |
| --- | --- |
| 875 | 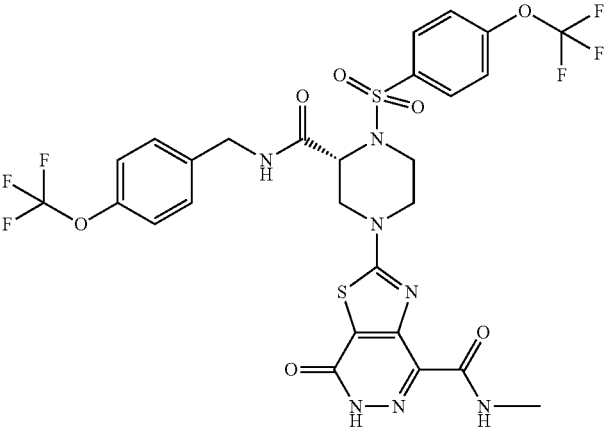 |
| 876 | 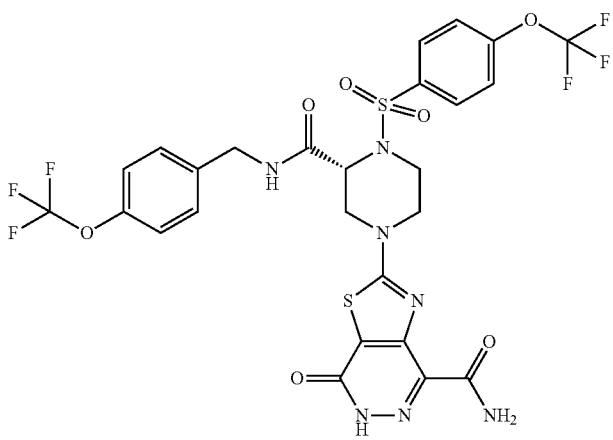 |

TABLE 176-continued
| Ex. No. | Structural Formula |
|---|---|
| 877 | 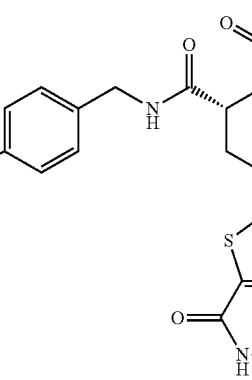 |
| 878 | 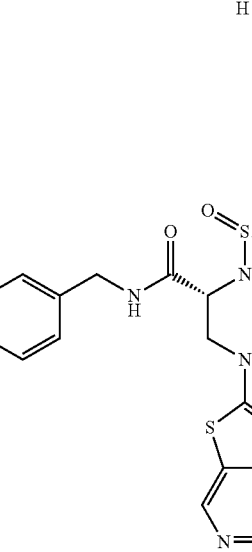 |
| 879 | 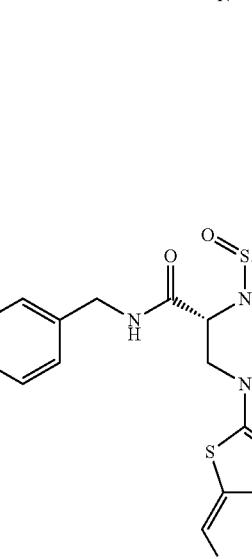 |

TABLE 177

| Ex. No. | Structural Formula |
|---|---|
| 880 | |
| 881 | |
| 882 | |

749
TABLE 177-continued
| Ex. No. | Structural Formula |
|---|---|
| 883 | |
| 884 | |
TABLE 178
| Ex. No. | Structural Formula |
|---|---|
| 885 | 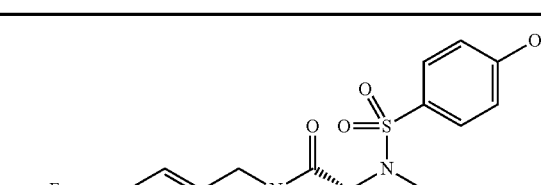 |

TABLE 178-continued
| Ex. No. | Structural Formula |
|---|---|
| 886 | 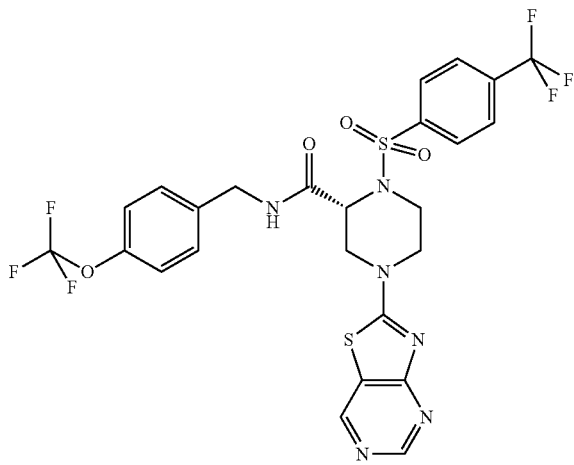 |
| 887 | 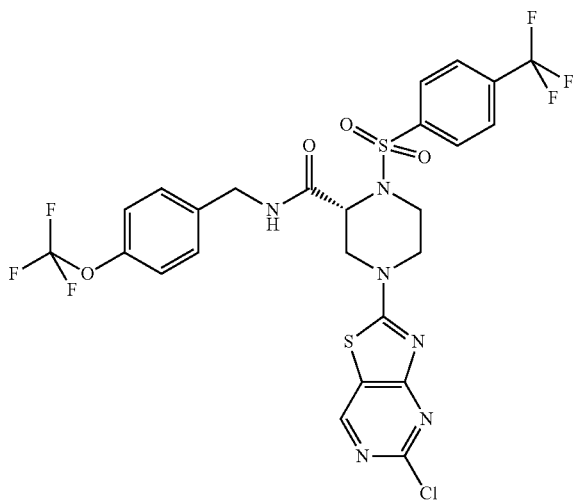 |
| 888 | 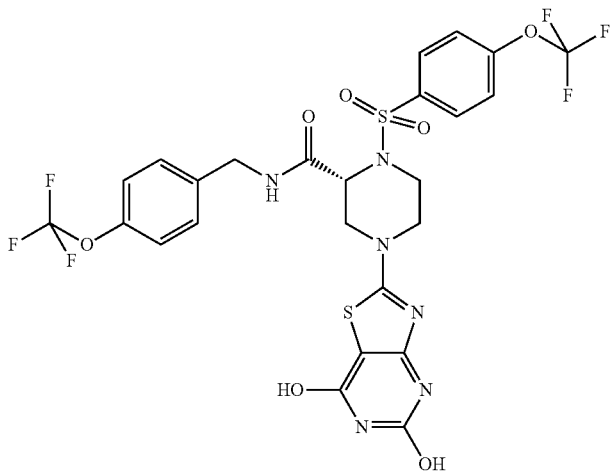 |

TABLE 178-continued
| Ex. No. | Structural Formula |
|---|---|
| 889 | 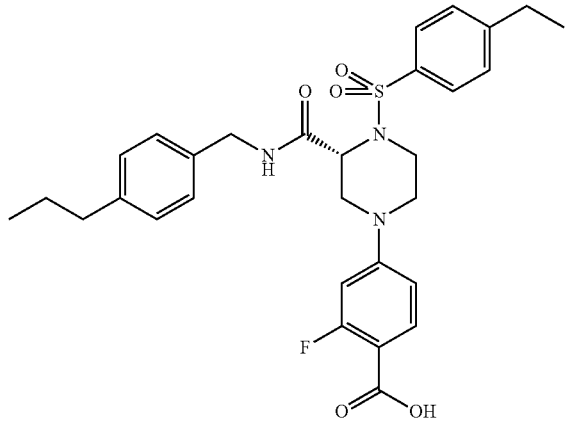 |
TABLE 179
| Ex. No. | Structural Formula |
|---|---|
| 890 | 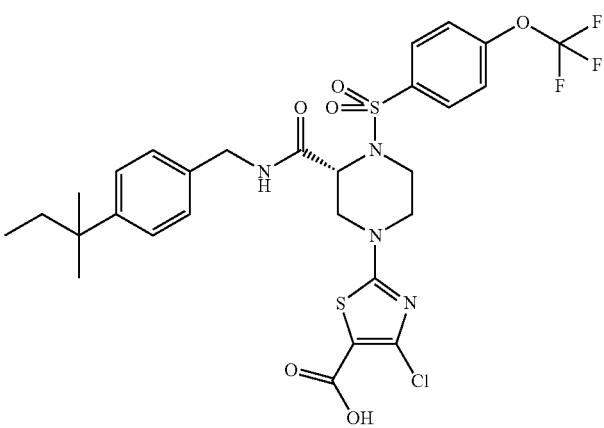 |
| 891 | 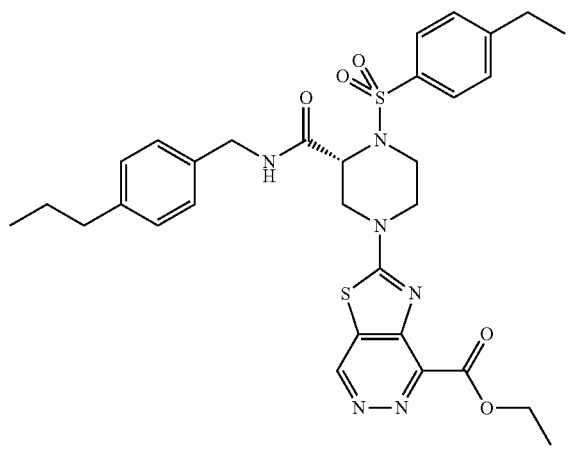 |

TABLE 179-continued
| Ex. No. | Structural Formula |
|---|---|
| 892 | 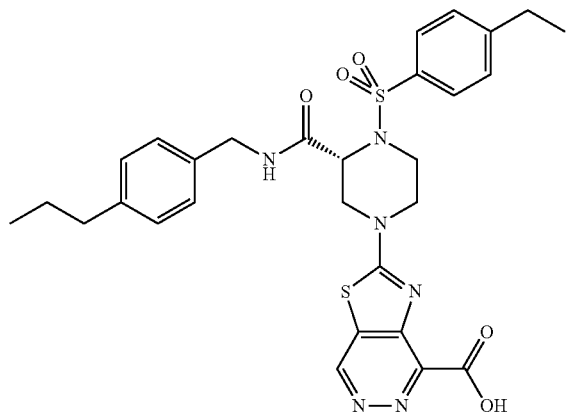 |
| 893 | 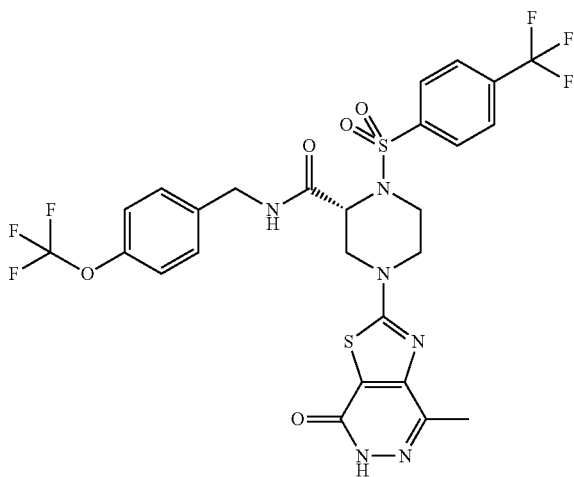 |
| 894 | 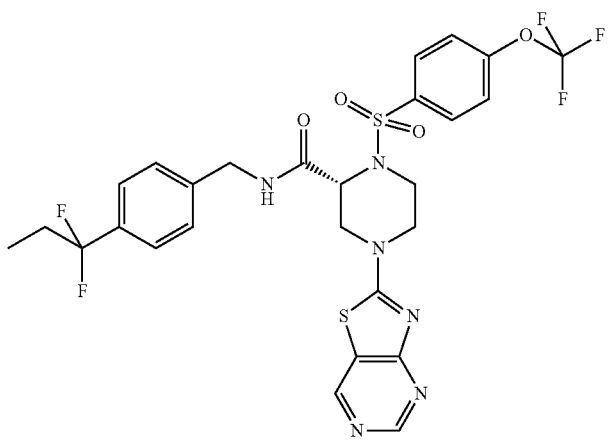 |

TABLE 180
| Ex. No. | Structural Formula |
|---|---|
| 895 | 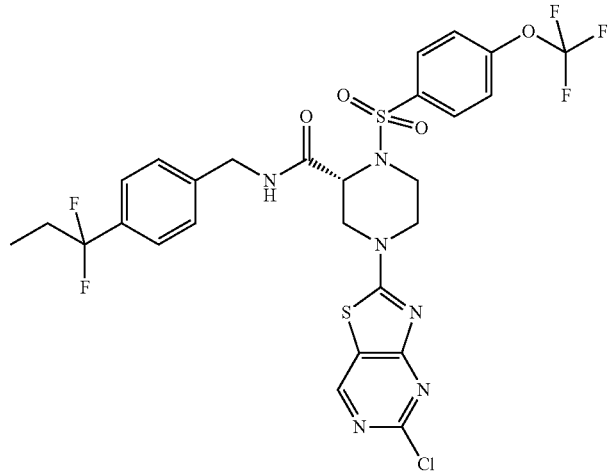 |
| 896 | 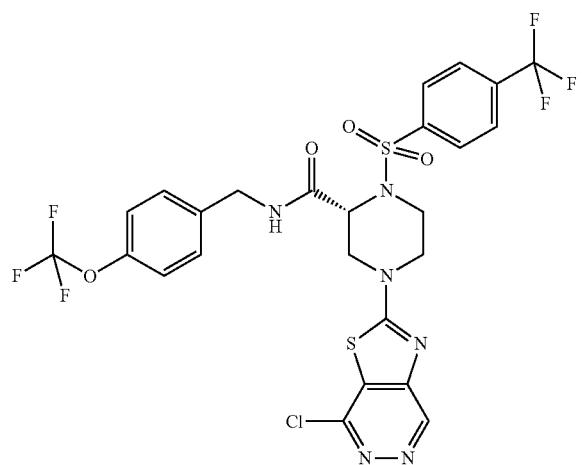 |
| 897 | 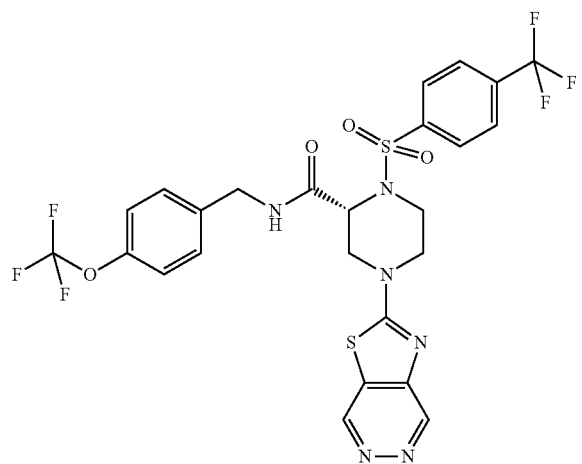 |

TABLE 180-continued
| Ex. No. | Structural Formula |
|---|---|
| 898 | |
| 899 | |
TABLE 181
| Ex. No. | Structural Formula |
|---|---|
| 900 | |
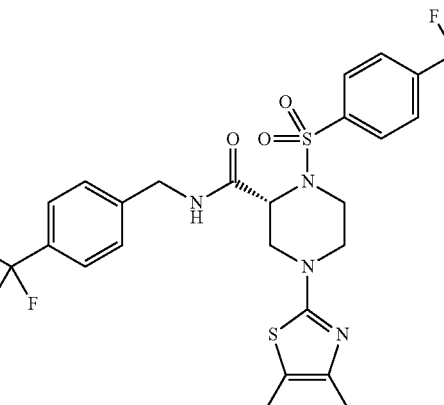

TABLE 181-continued
| Ex. No. | Structural Formula |
|---|---|
| 901 | 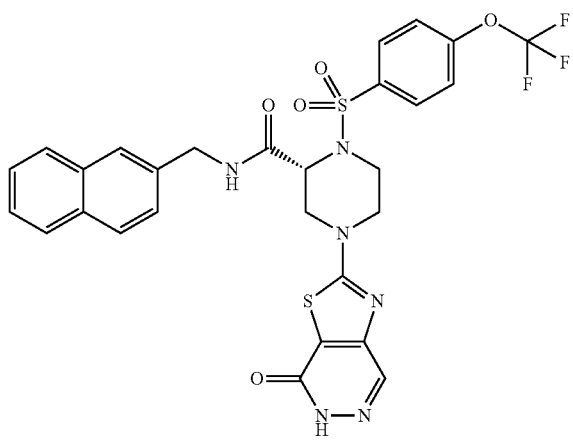 |
| 902 | 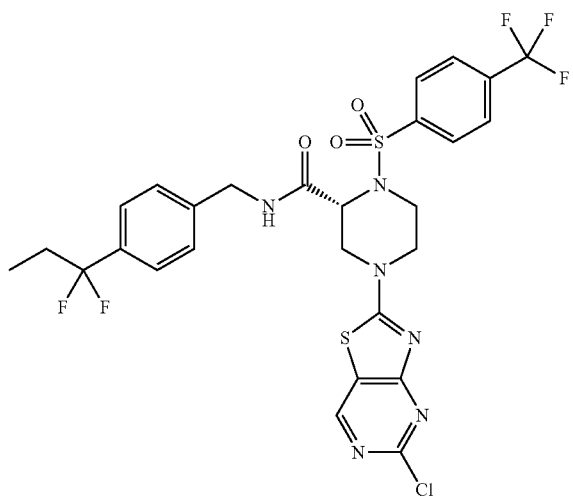 |
| 903 | 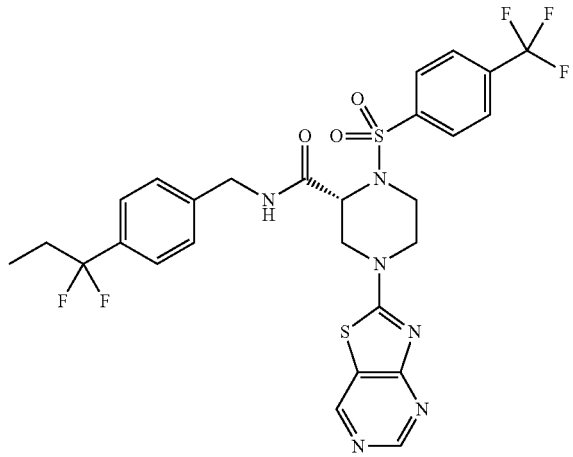 |

TABLE 181-continued

| Ex. No. | Structural Formula |
|---|---|
| 904 | |

TABLE 182

| Ex. No. | Structural Formula |
|---|---|
| 905 | |
| 906 | |

TABLE 182-continued
| Ex. No. | Structural Formula |
|---|---|
| 907 | 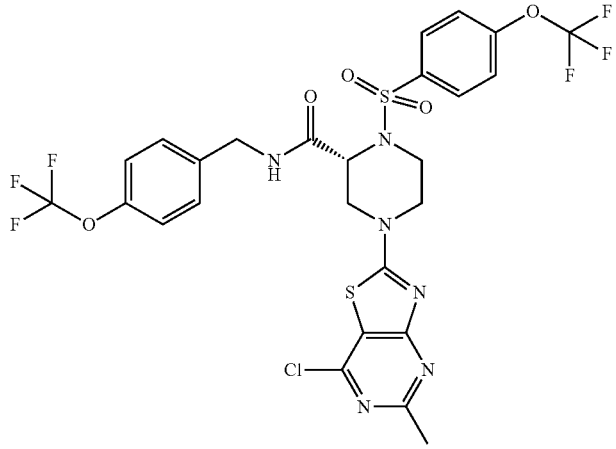 |
| 908 | 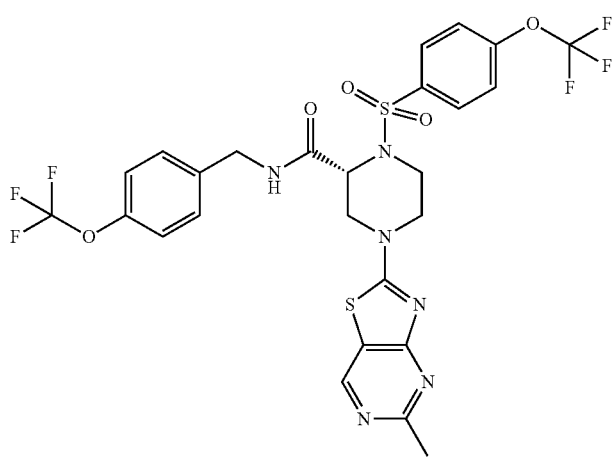 |
| 909 | 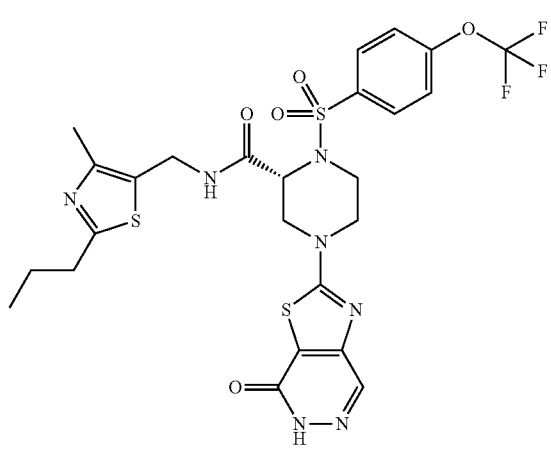 |

TABLE 183
| Ex. No. | Structural Formula |
| --- | --- |
| 910 | 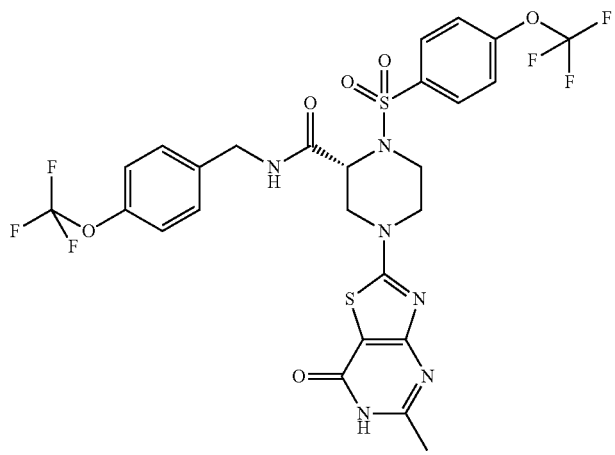 |
| 911 | 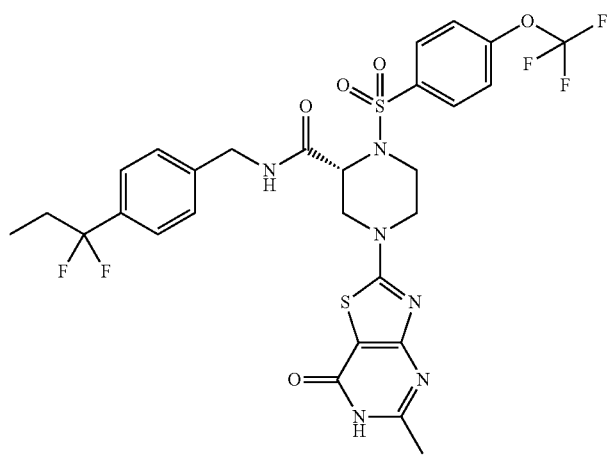 |
| 912 | 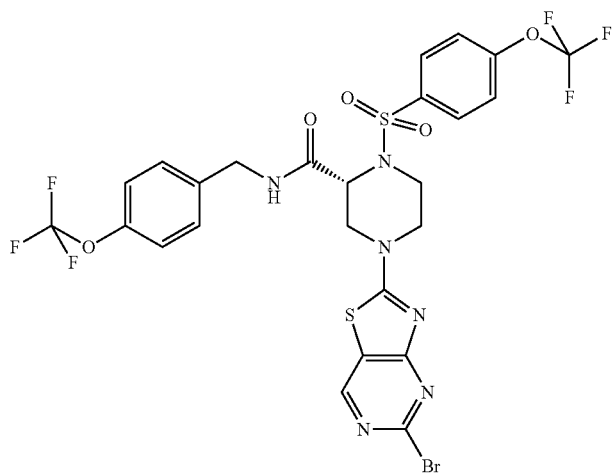 |

TABLE 183-continued
| Ex. No. | Structural Formula |
|---|---|
| 913 | 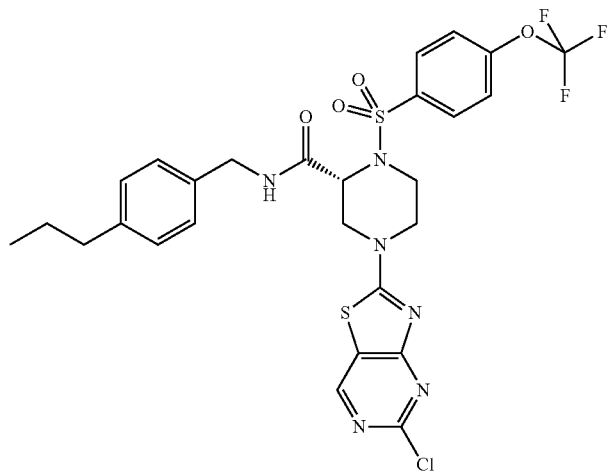 |
| 914 | 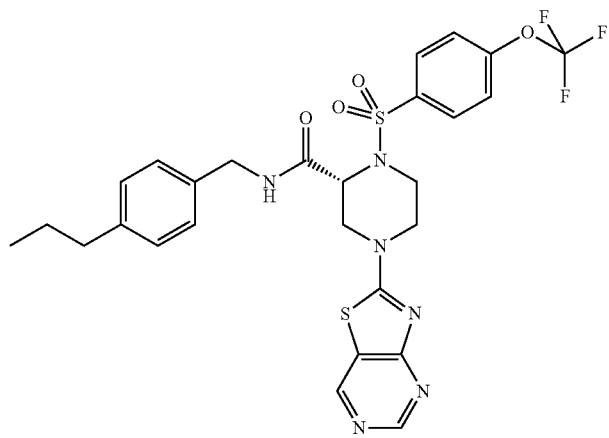 |
TABLE 184
| Ex. No. | Structural Formula |
|---|---|
| 915 | 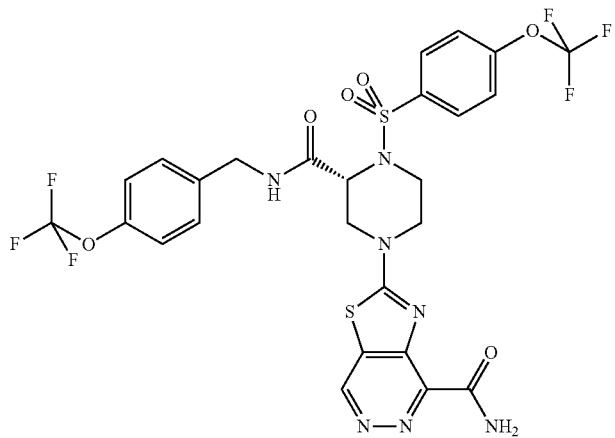 |

TABLE 184-continued
| Ex. No. | Structural Formula |
|---|---|
| 916 | 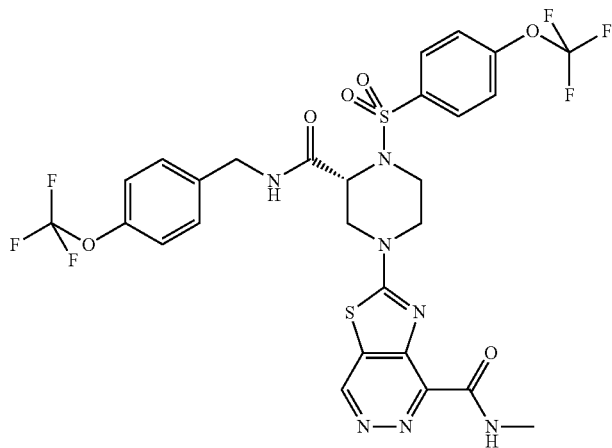 |
| 917 | 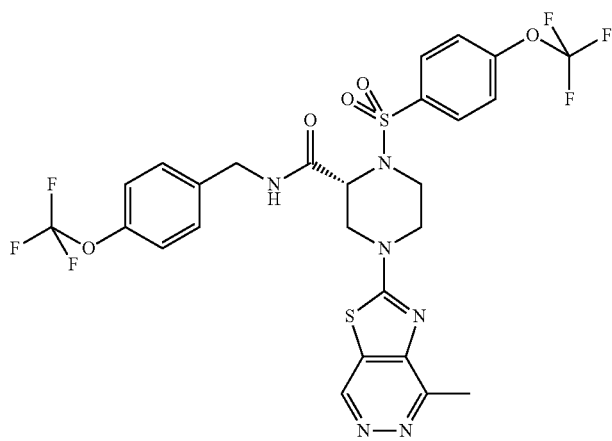 |
| 918 | 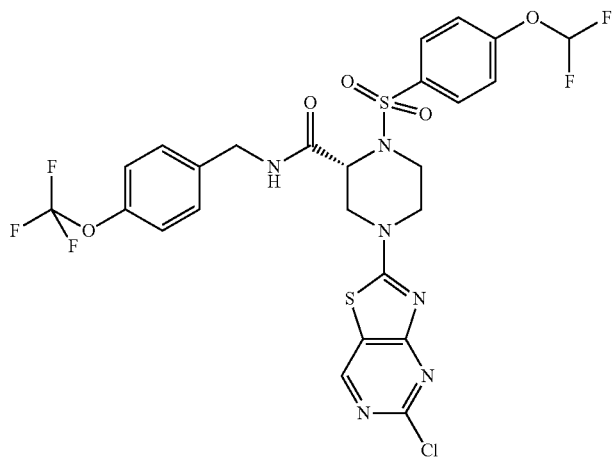 |

TABLE 184-continued
| Ex. No. | Structural Formula |
|---|---|
| 919 | 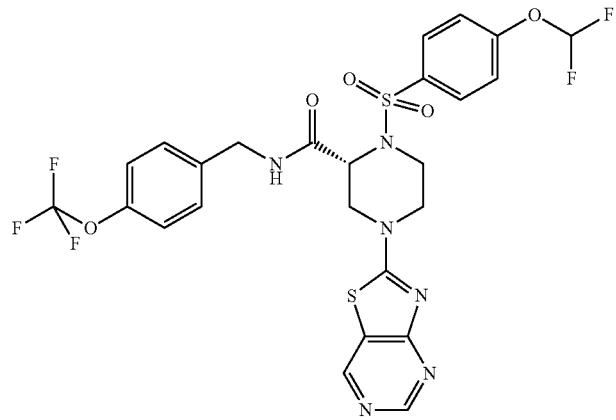 |
TABLE 185
| Ex. No. | Structural Formula |
|---|---|
| 920 | 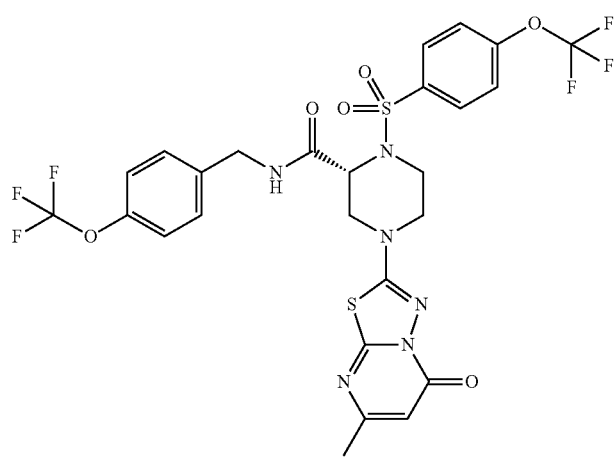 |
| 921 | 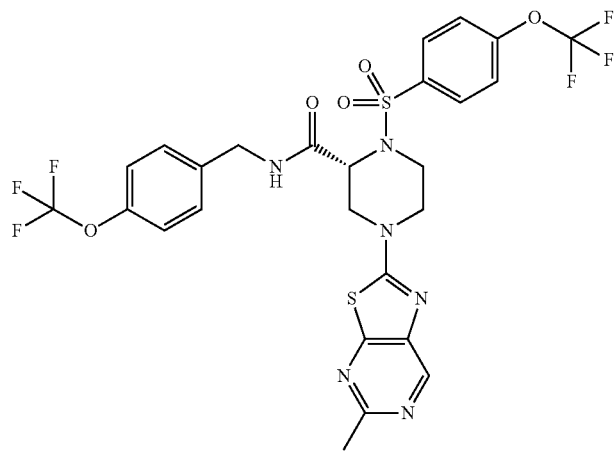 |

TABLE 185-continued
| Ex. No. | Structural Formula |
|---|---|
| 922 | 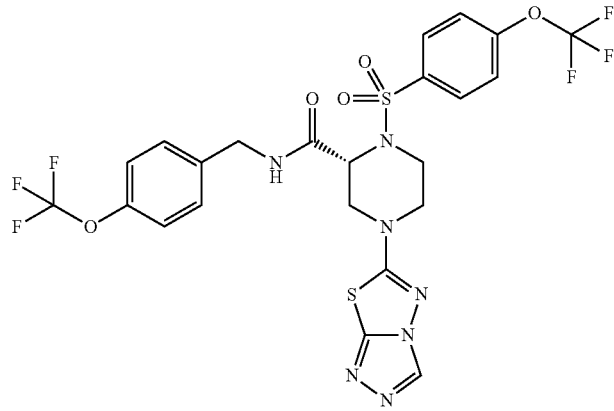 |
| 923 | 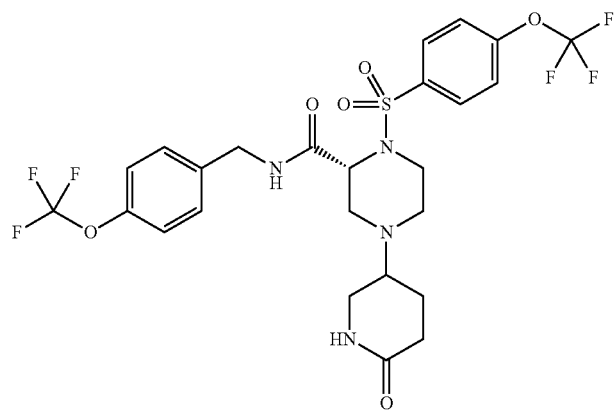 |
| 924 | 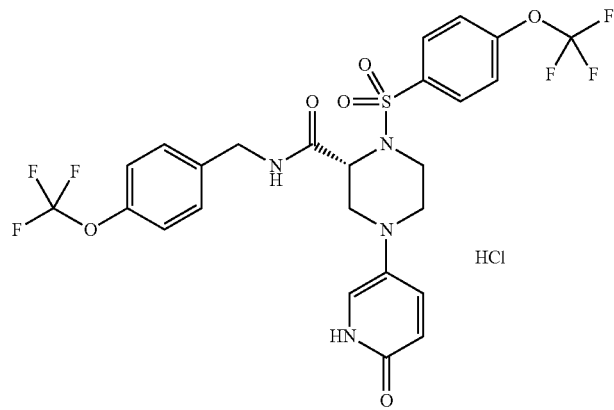 |

TABLE 186
| Ex. No. | Structural Formula |
|---|---|
| 925 | 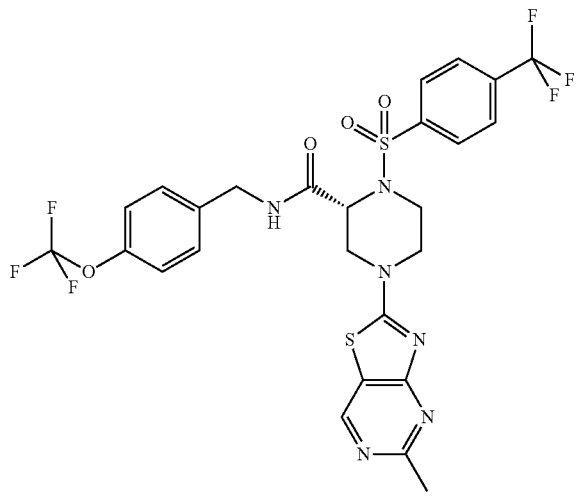 |
| 926 | 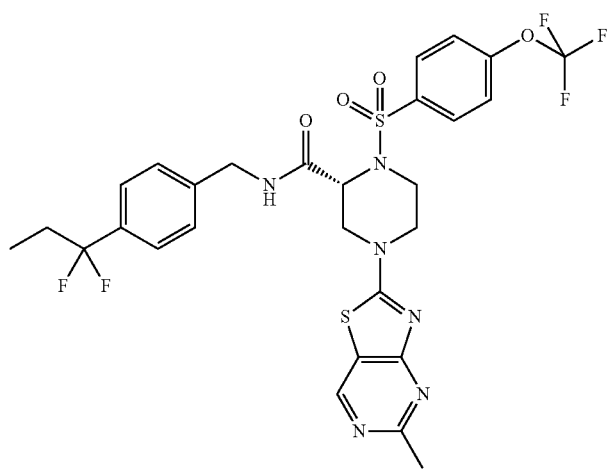 |
| 927 | 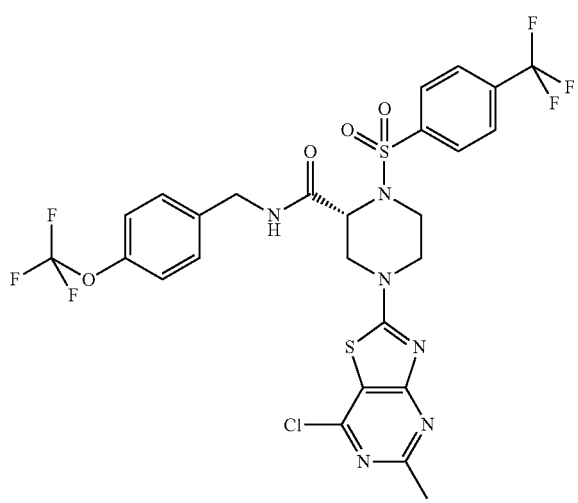 |

TABLE 186-continued
| Ex. No. | Structural Formula |
|---|---|
| 928 | 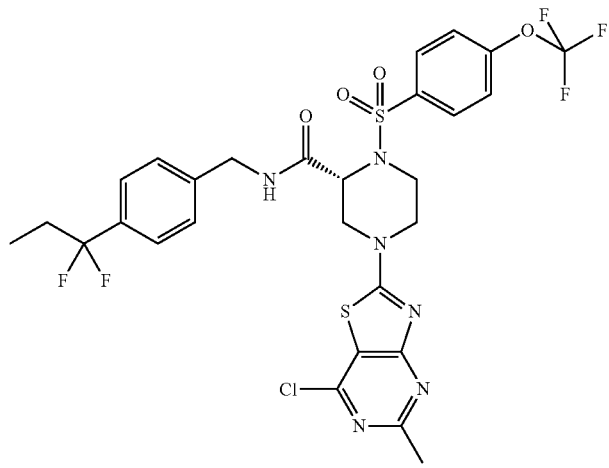 |
| 929 | 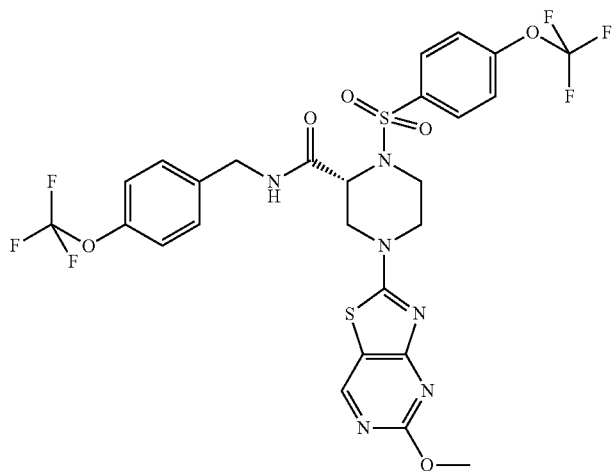 |
TABLE 187
| Ex. No. | Structural Formula |
|---|---|
| 930 | 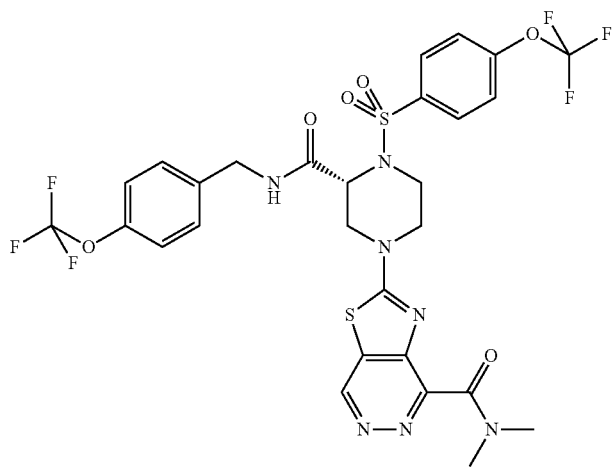 |

US 8,017,612 B2
TABLE 187-continued
| Ex. No. | Structural Formula |
|---|---|
| 931 | 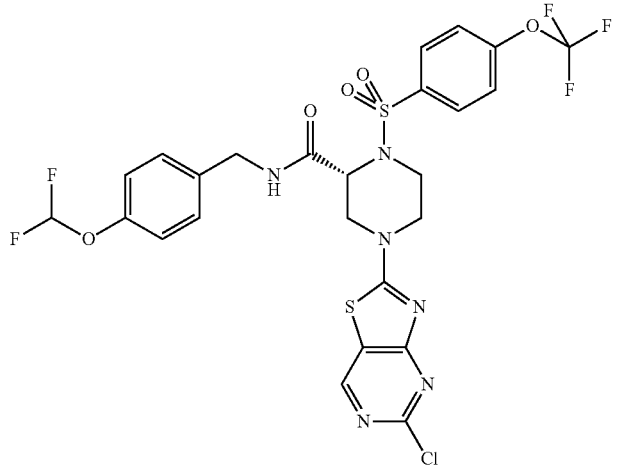 |
| 932 | 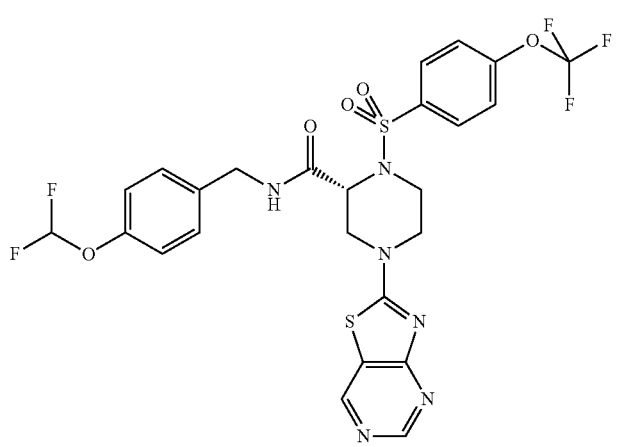 |
| 933 | 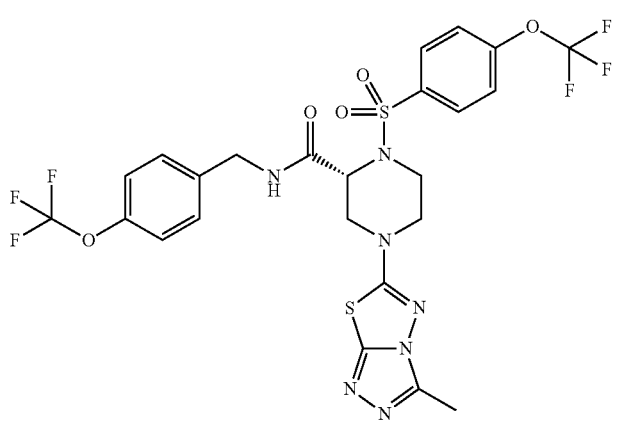 |

TABLE 187-continued
| Ex. No. | Structural Formula |
| --- | --- |
| 934 | 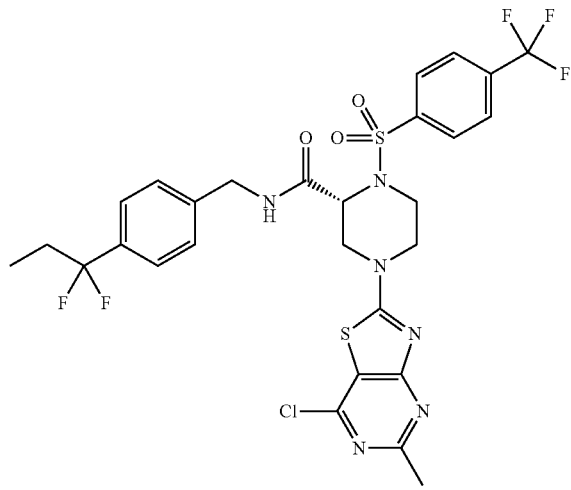 |
TABLE 188
| Ex. No. | Structural Formula |
| --- | --- |
| 935 | 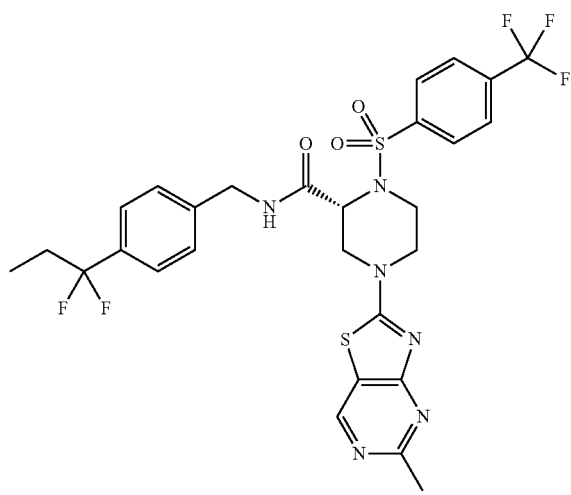 |
| 936 | 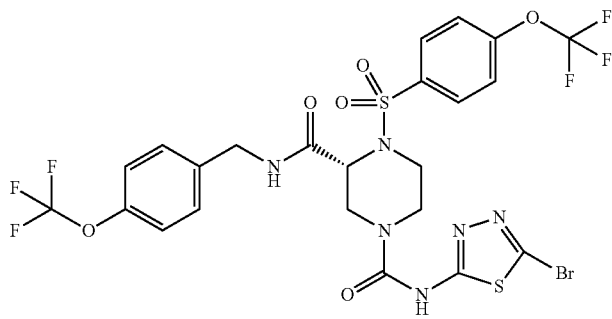 |

TABLE 188-continued
| Ex. No. | Structural Formula |
| --- | --- |
| 937 | 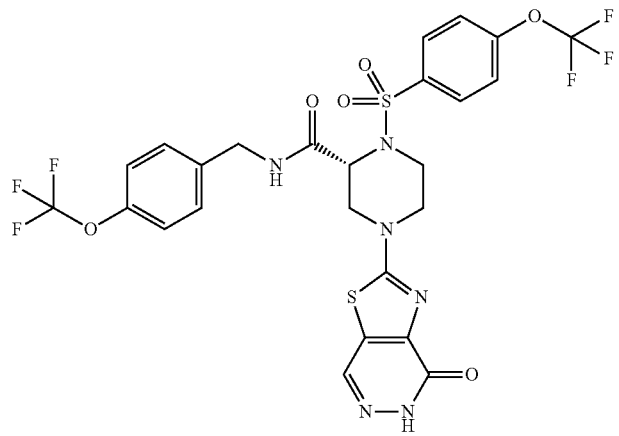 |
| 938 | 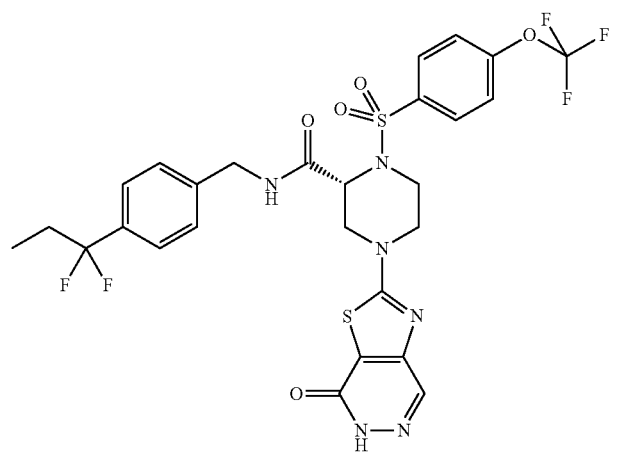 |
| 939 | 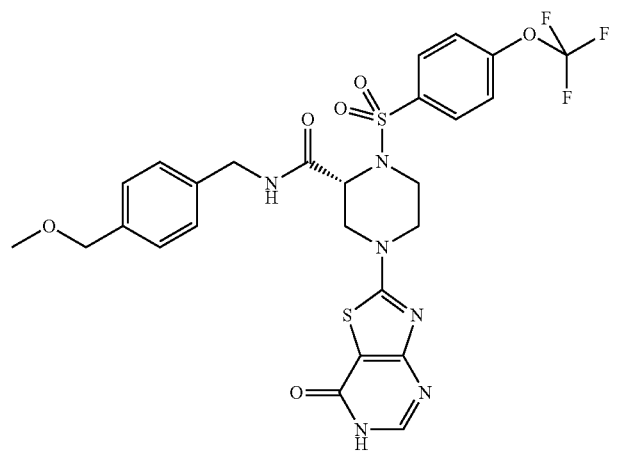 |

TABLE 189
| Ex. No. | Structural Formula |
|---|---|
| 940 | 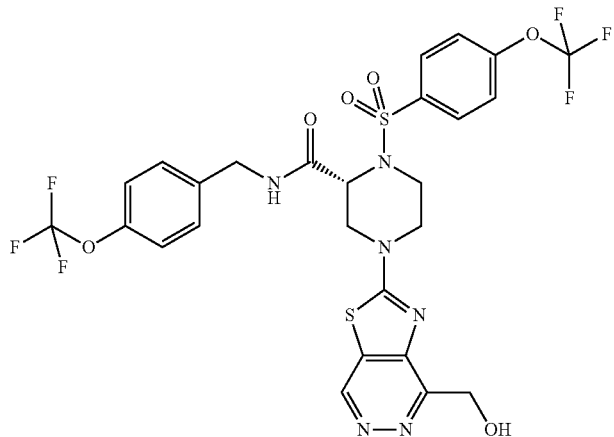 |
| 941 | 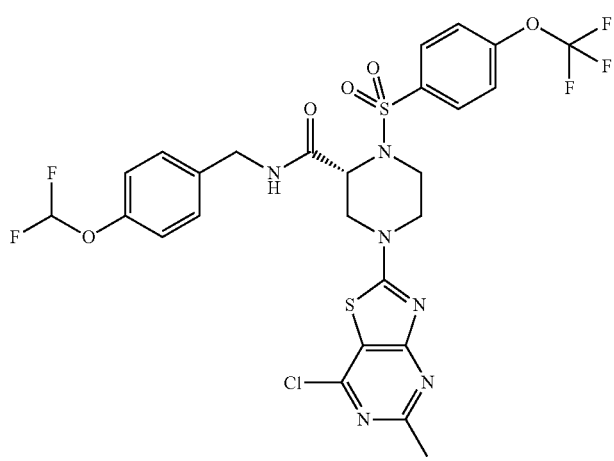 |
| 942 | 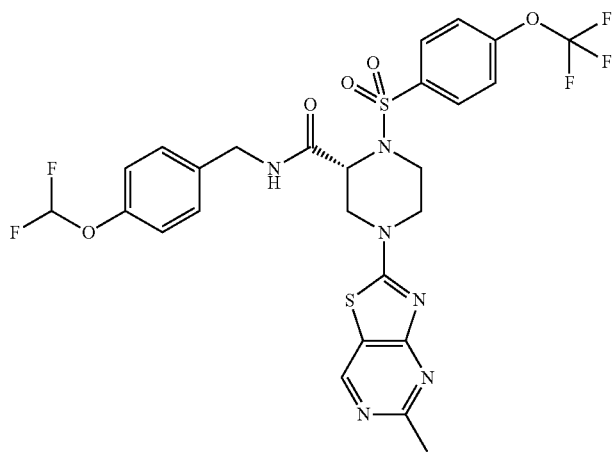 |

TABLE 189-continued
| Ex. No. | Structural Formula |
|---|---|
| 943 | 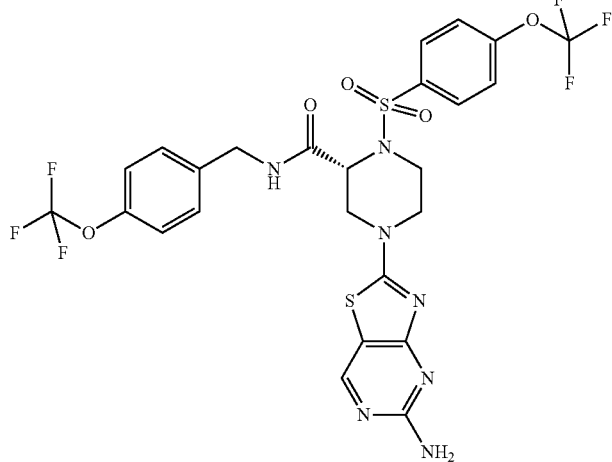 |
| 944 | 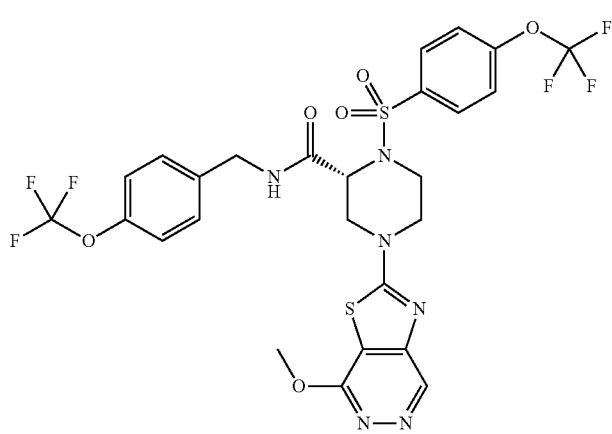 |
TABLE 190
| Ex. No. | Structural Formula |
|---|---|
| 945 | 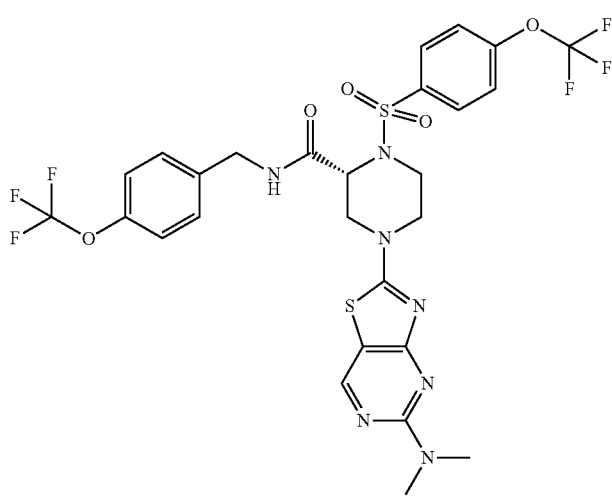 |

TABLE 190-continued
| Ex. No. | Structural Formula |
|---|---|
| 946 | 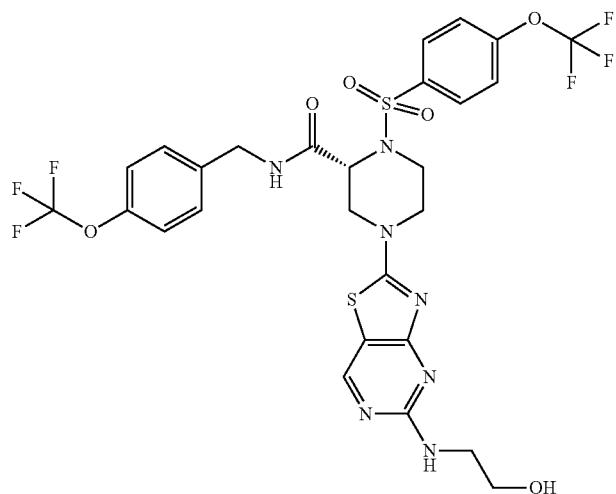 |
| 947 | 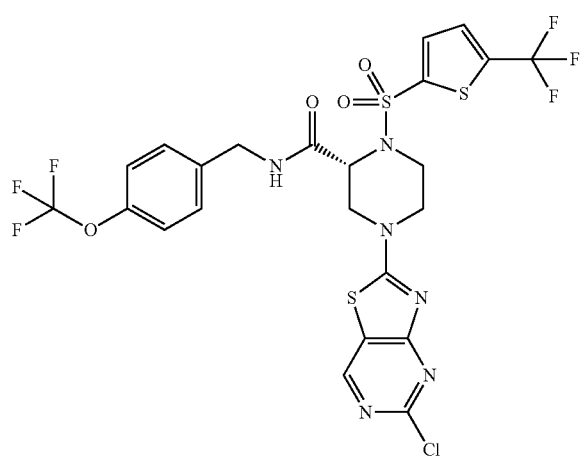 |
| 948 | 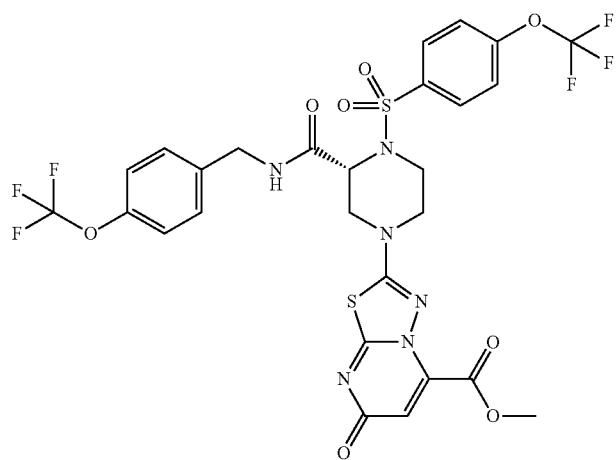 |

TABLE 190-continued
| Ex. No. | Structural Formula |
|---|---|
| 949 | 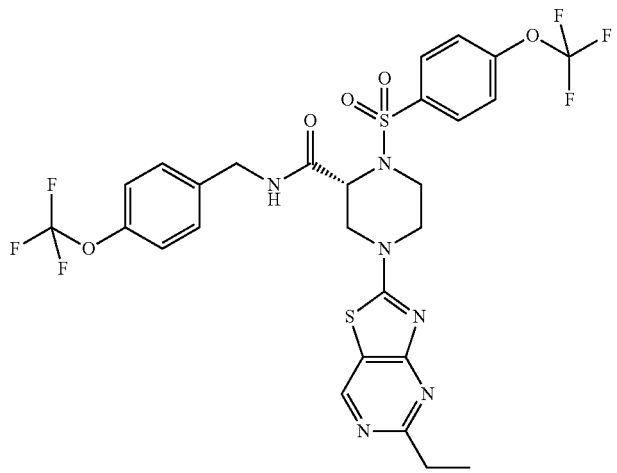 |
TABLE 191
| Ex. No. | Structural Formula |
|---|---|
| 950 | 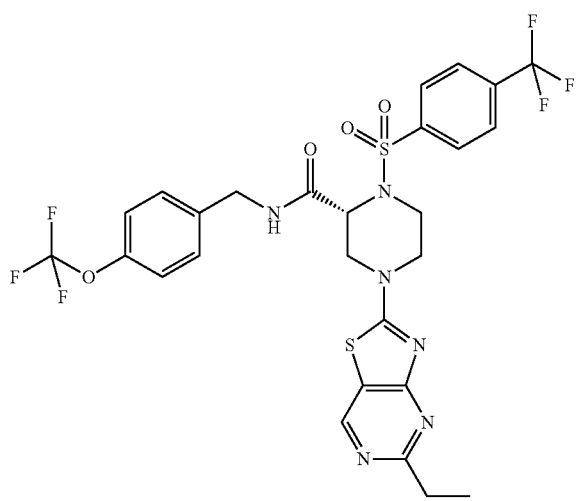 |
| 951 | 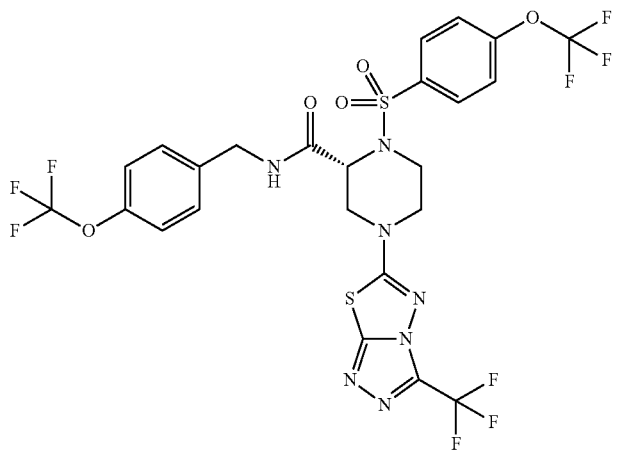 |

TABLE 191-continued
| Ex. No. | Structural Formula |
| --- | --- |
| 952 | 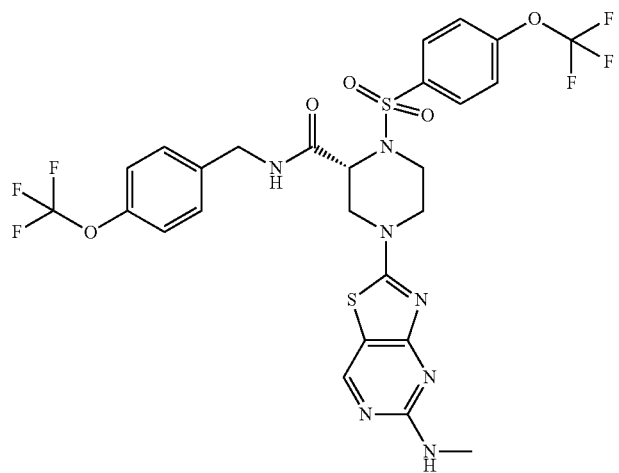 |
| 953 | 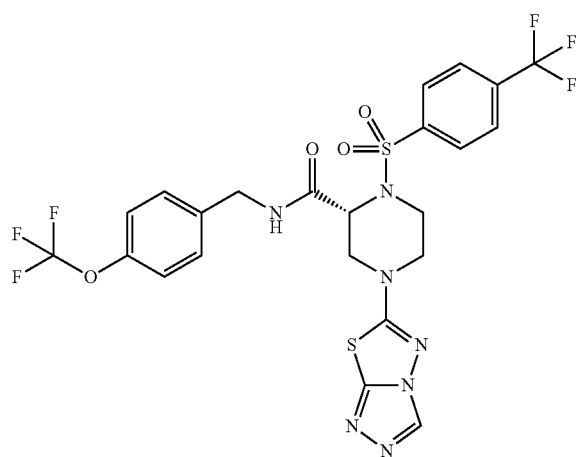 |
| 954 | 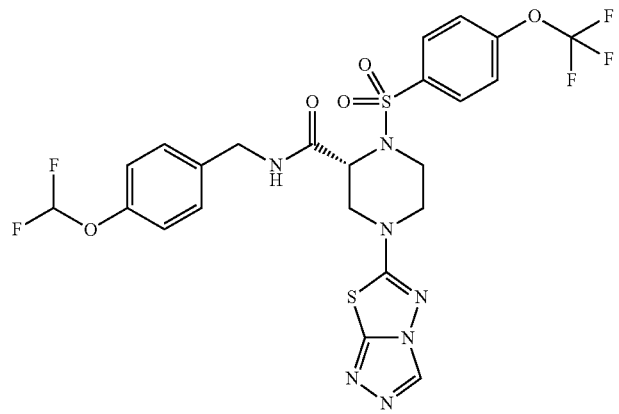 |

//
TABLE 192
| Ex. No. | Structural Formula |
|---|---|
| 955 | 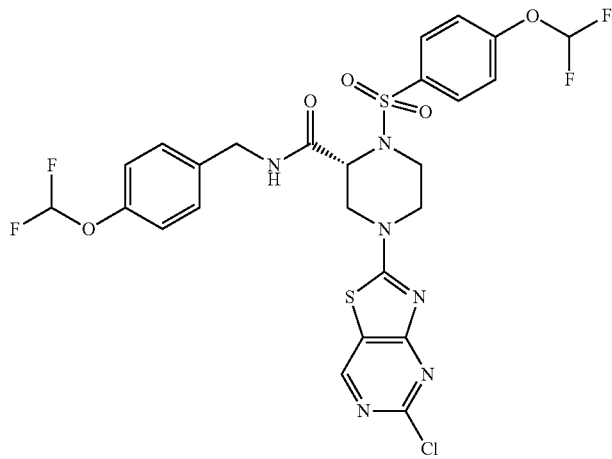 |
| 956 | 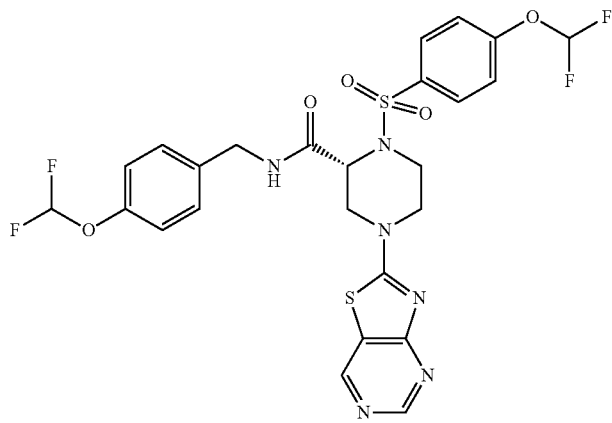 |
| 957 | 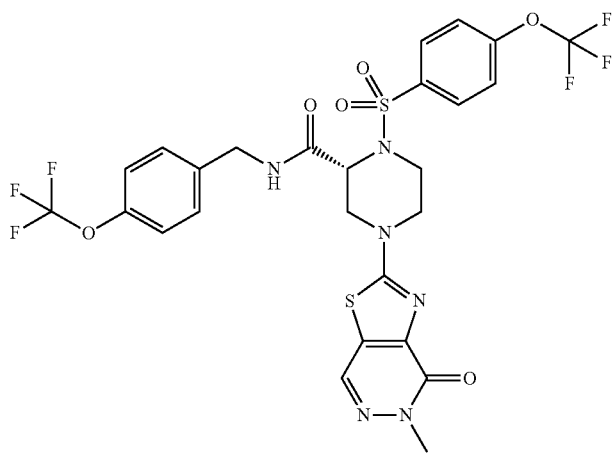 |

TABLE 192-continued
| Ex. No. | Structural Formula |
|---|---|
| 958 | 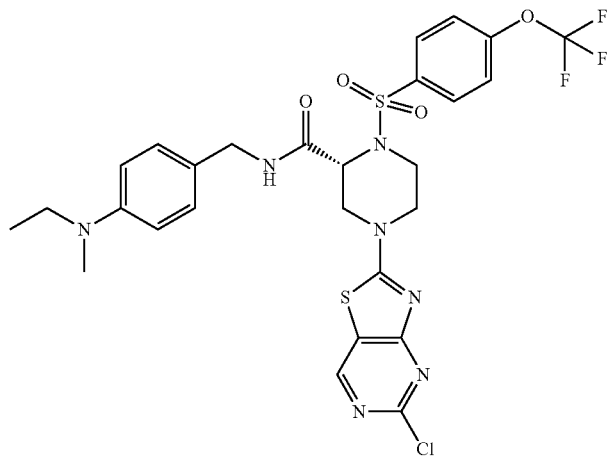 |
| 959 | 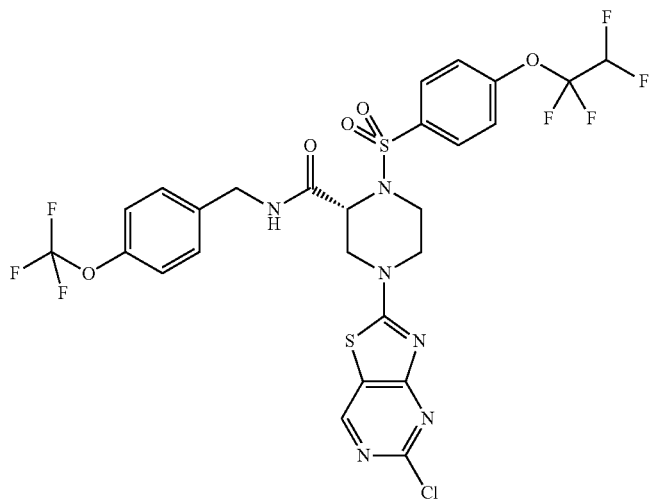 |
TABLE 193
| Ex. No. | Structural Formula |
|---|---|
| 960 | 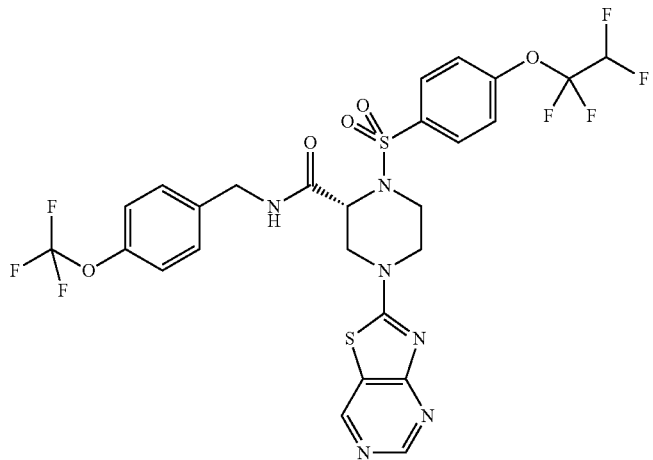 |

US 8,017,612 B2
TABLE 193-continued
| Ex. No. | Structural Formula |
|---|---|
| 961 | 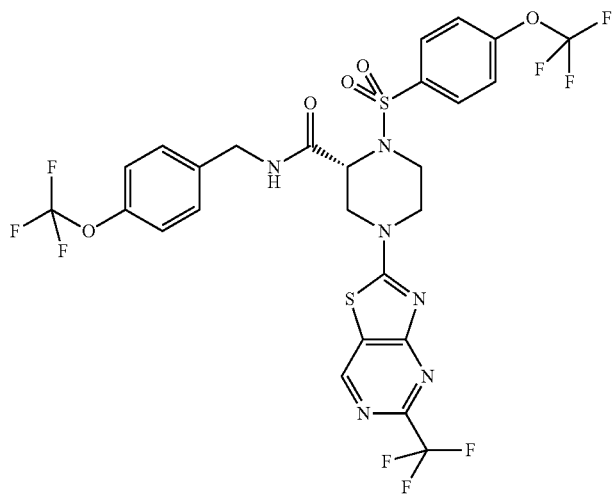 |
| 962 | 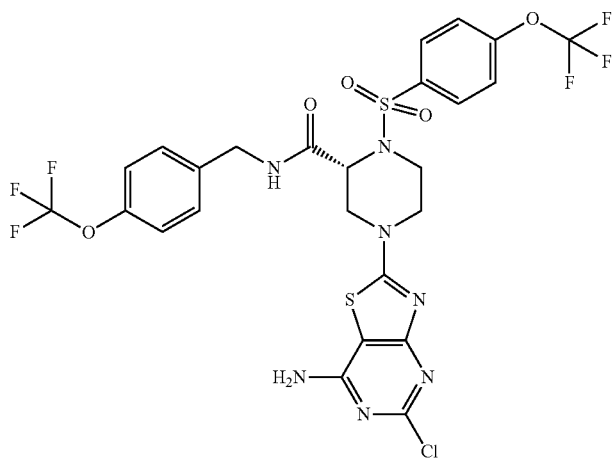 |
| 963 | 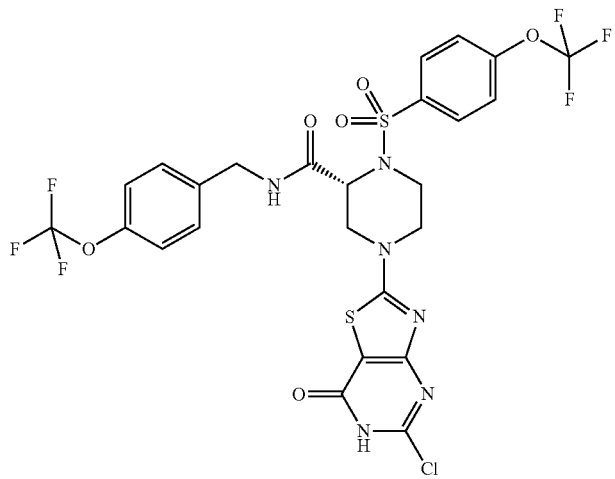 |

TABLE 193-continued
| Ex. No. | Structural Formula |
|---|---|
| 964 | 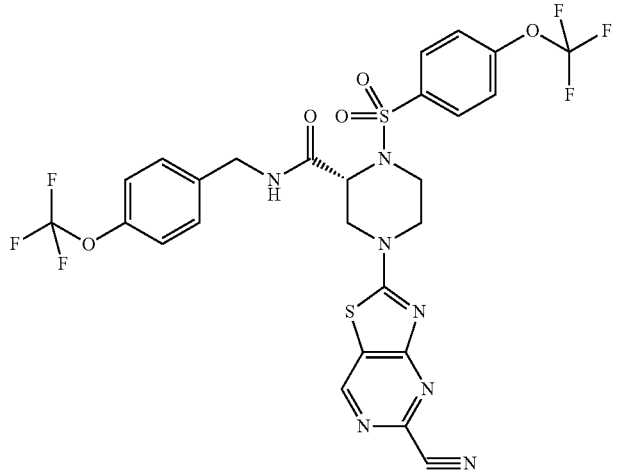 |
TABLE 194
| Ex. No. | Structural Formula |
|---|---|
| 965 | 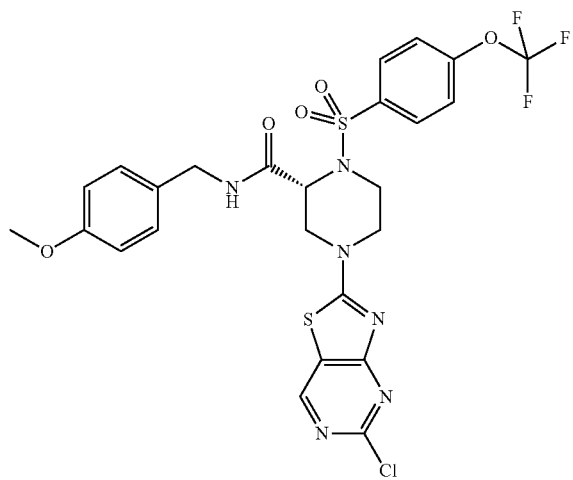 |
| 966 | 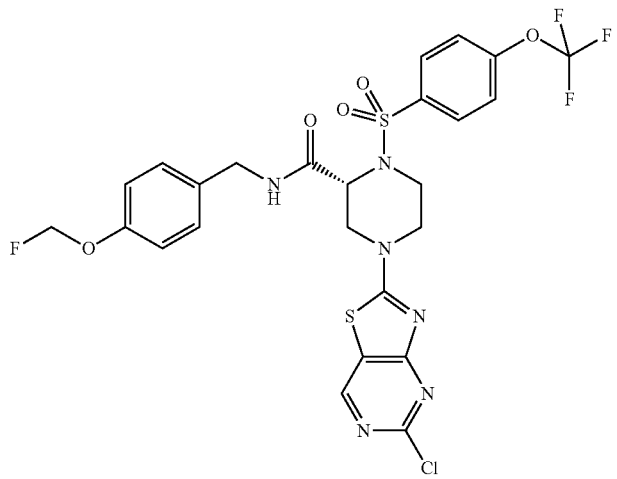 |

TABLE 194-continued
| Ex. No. | Structural Formula |
|---|---|
| 967 | 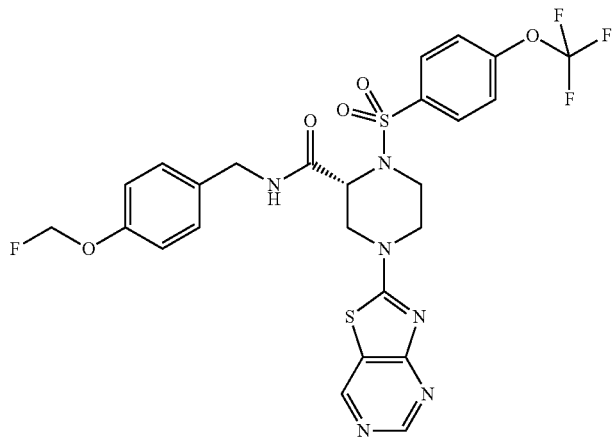 |
| 968 | 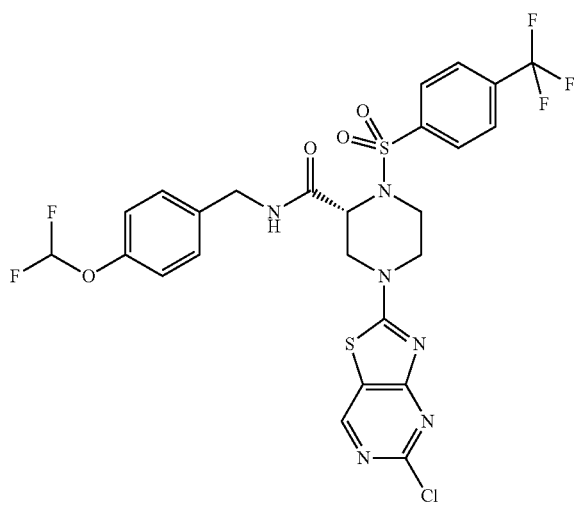 |
| 969 | 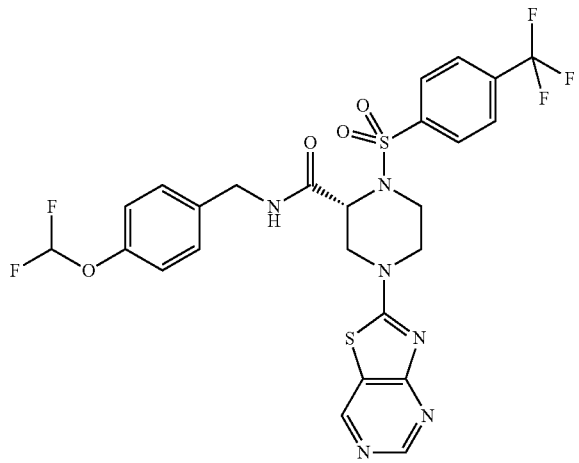 |

TABLE 195
| Ex. No. | Structural Formula |
|---|---|
| 970 | 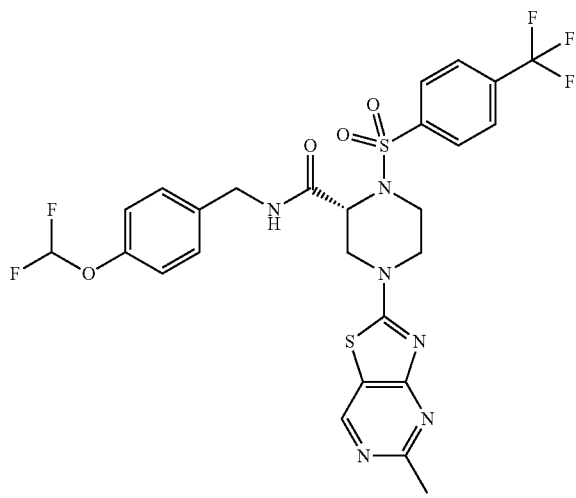 |
| 971 | 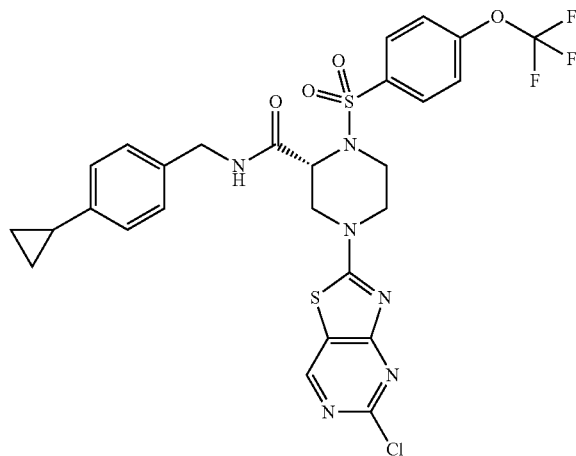 |
| 972 | 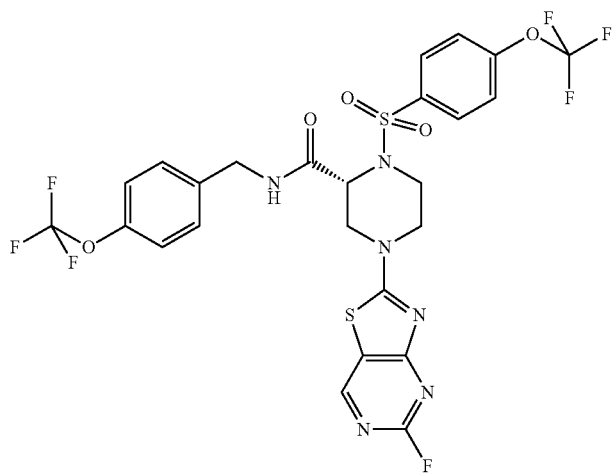 |

TABLE 195-continued
| Ex. No. | Structural Formula |
|---|---|
| 973 | 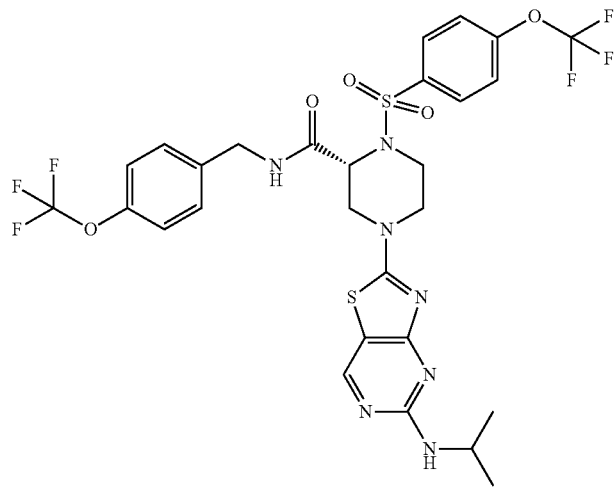 |
| 974 | 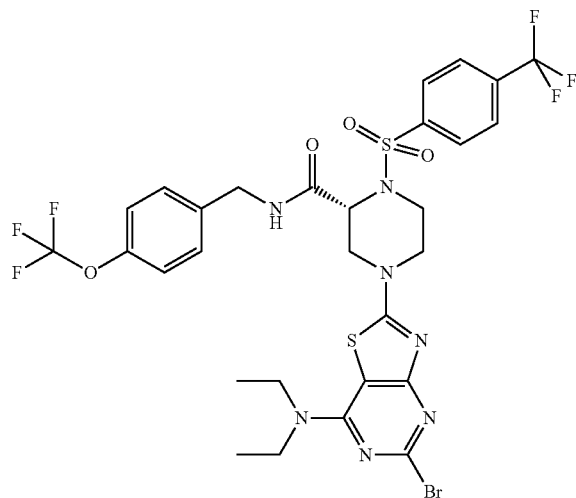 |
TABLE 196
| Ex. No. | Structural Formula |
|---|---|
| 975 | 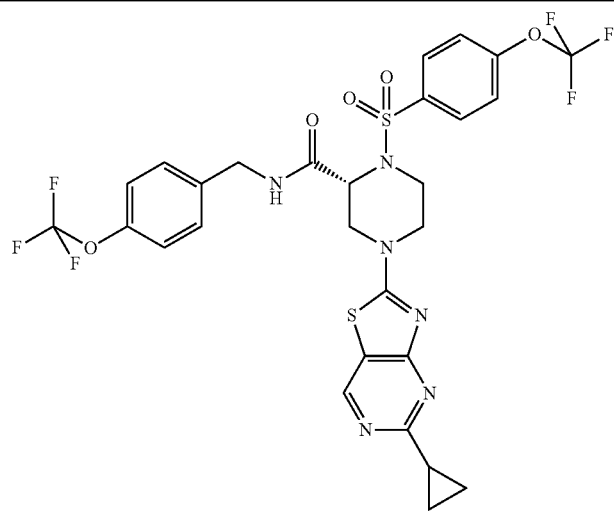 |

811
TABLE 196-continued
| Ex. No. | Structural Formula |
|---|---|
| 976 | 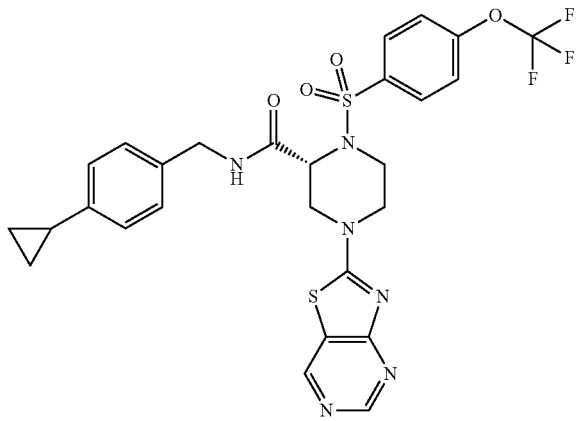 |
| 977 | 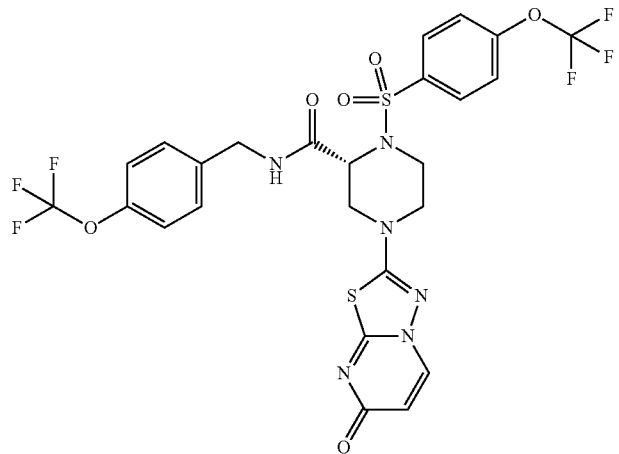 |
| 978 | 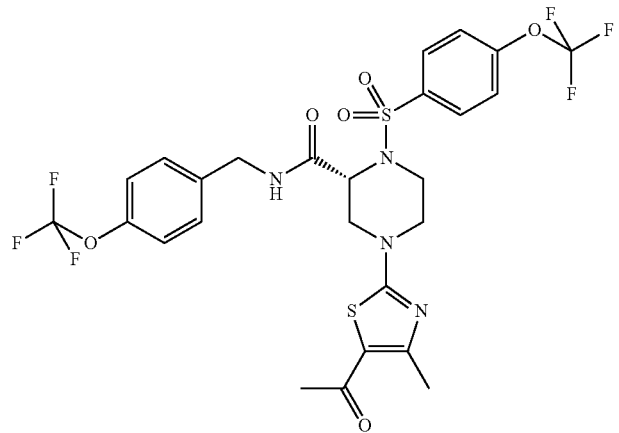 |

TABLE 196-continued
| Ex. No. | Structural Formula |
|---|---|
| 979 | 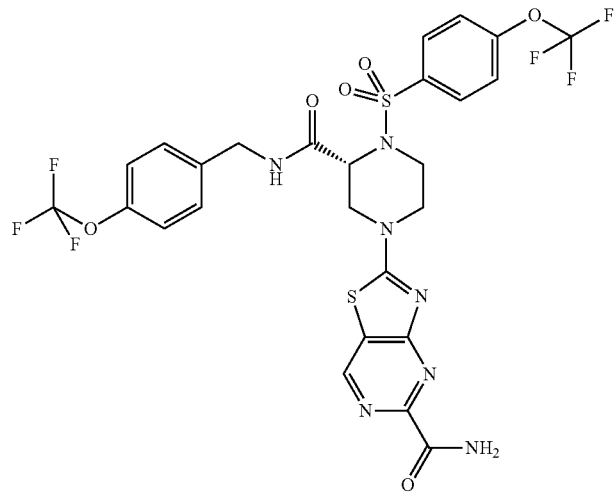 |
TABLE 197
| Ex. No. | Structural Formula |
|---|---|
| 980 | 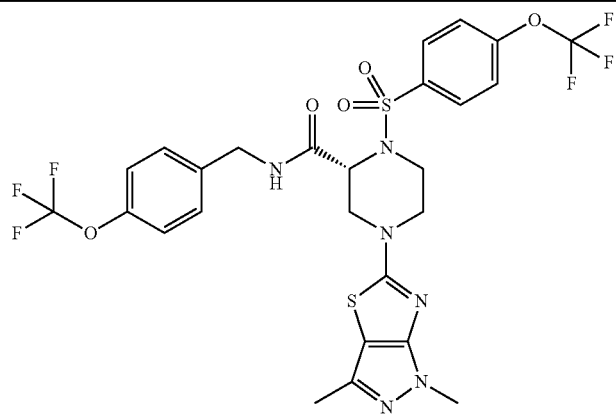 |
| 981 | 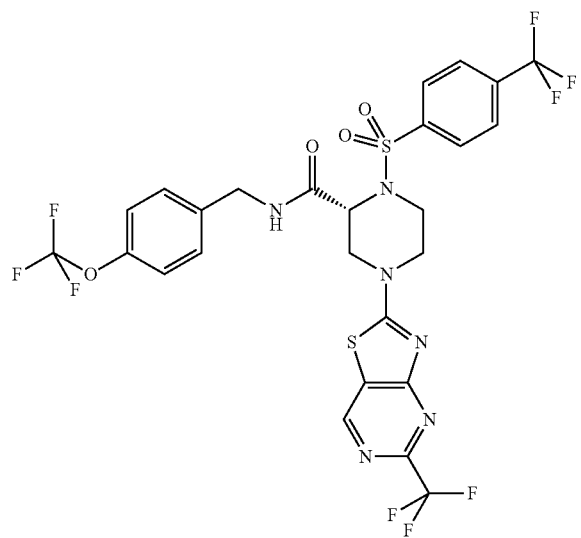 |

TABLE 197-continued
| Ex. No. | Structural Formula |
|---|---|
| 982 | 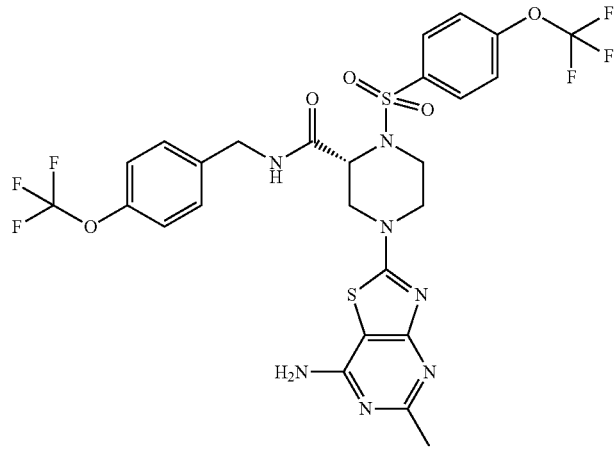 |
| 983 | 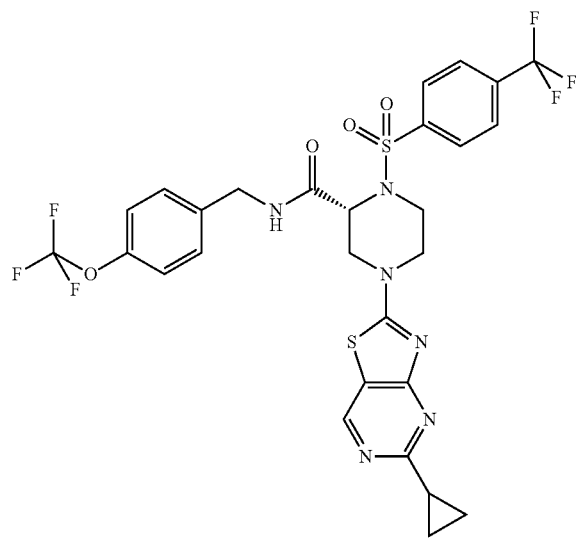 |
| 984 | 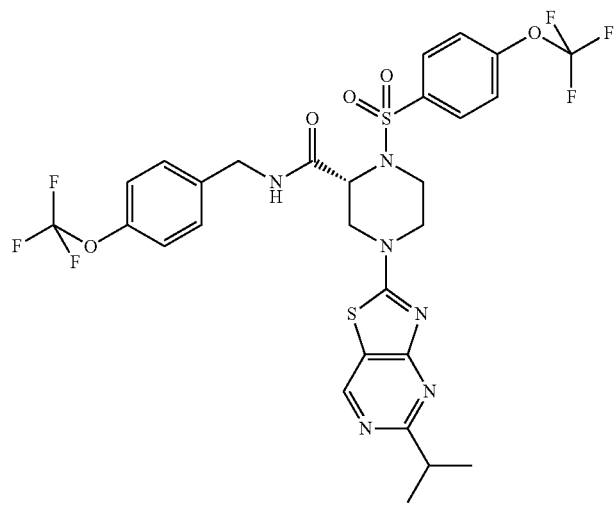 |

TABLE 198
| Ex. No. | Structural Formula |
|---|---|
| 985 | 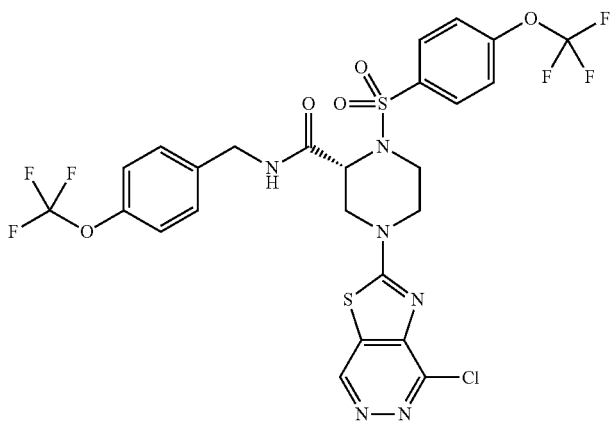 |
| 986 | 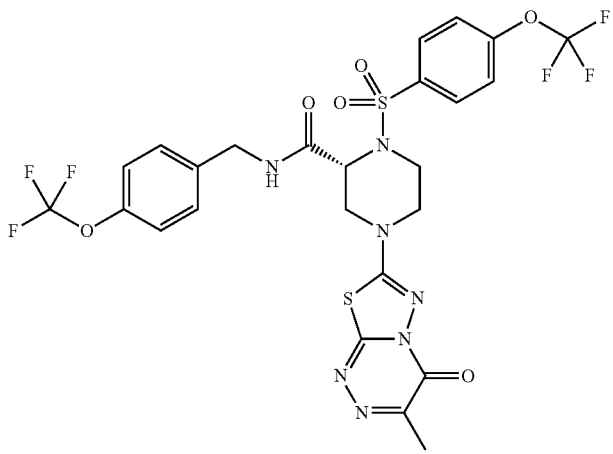 |
| 987 | 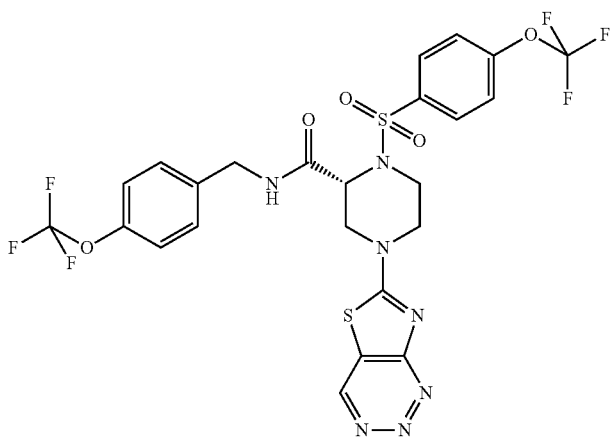 |

988
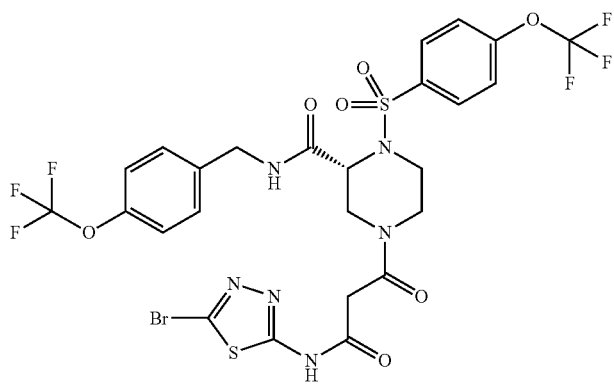
989
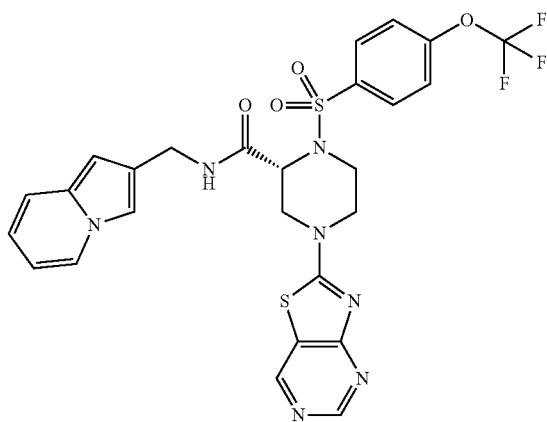
TABLE 199
| Ex. No. | Structural Formula |
|---|---|
| 990 | 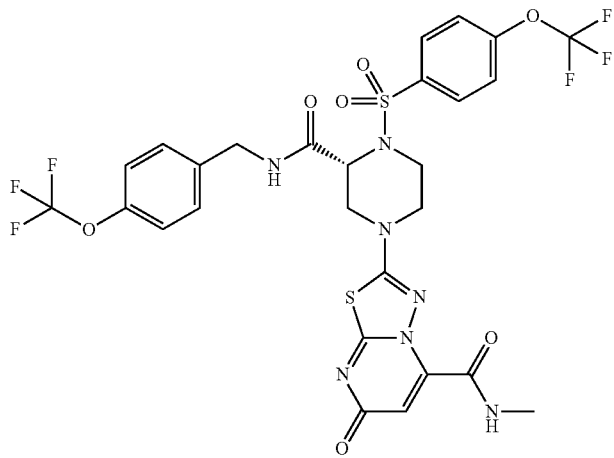 |

TABLE 199-continued
| Ex. No. | Structural Formula |
|---|---|
| 991 | 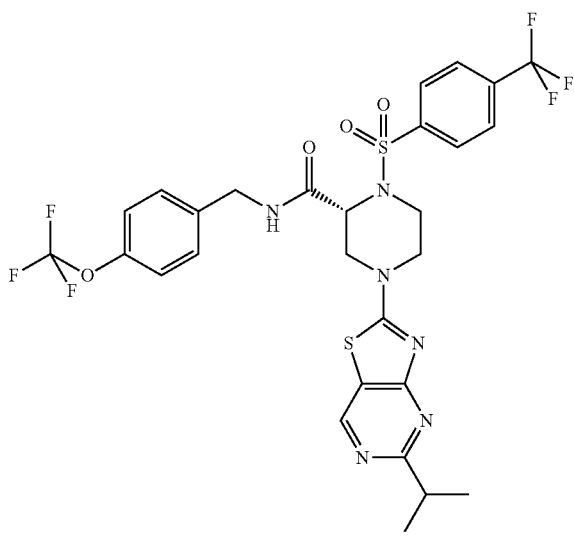 |
| 992 | 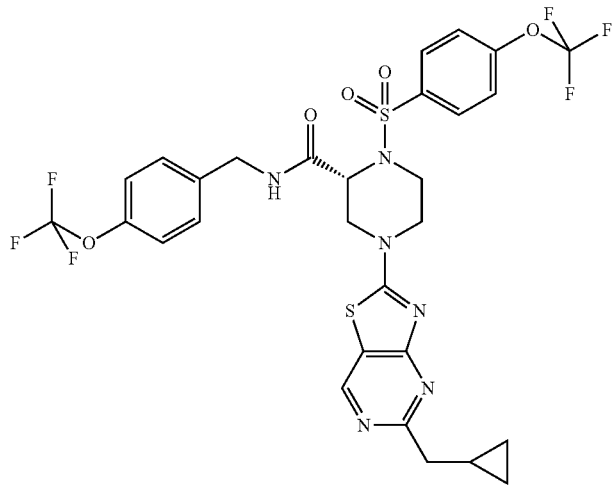 |
| 993 | 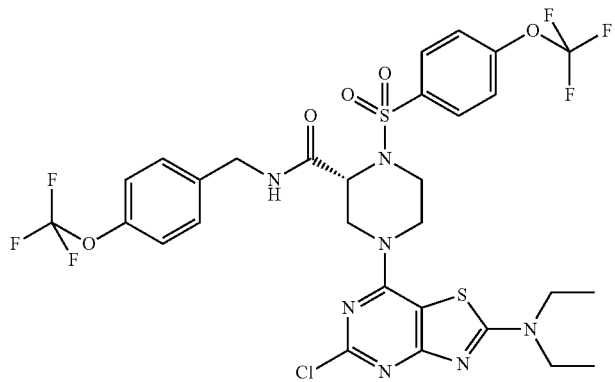 |

TABLE 199-continued

| Ex. No. | Structural Formula |
|---|---|
| 994 | |

TABLE 200

| Ex. No. | Structural Formula |
|---|---|
| 995 | |
| 996 | |

TABLE 200-continued

| Ex. No. | Structural Formula |
|---|---|
| 997 | |
| 998 | |
| 999 | |

TABLE 201
| Ex. No. | Structural Formula |
|---|---|
| 1000 | 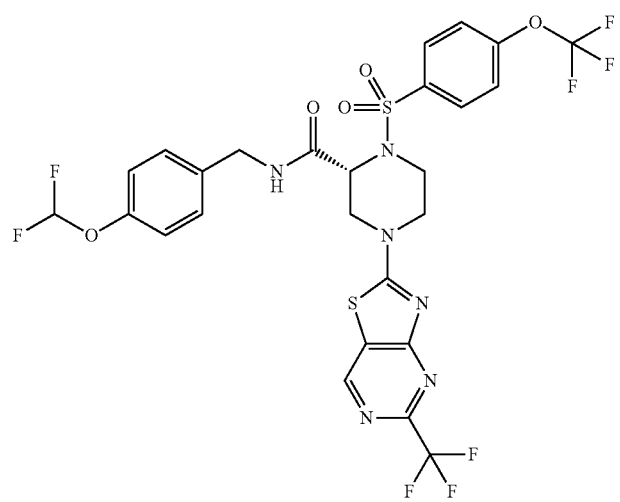 |
| 1001 | 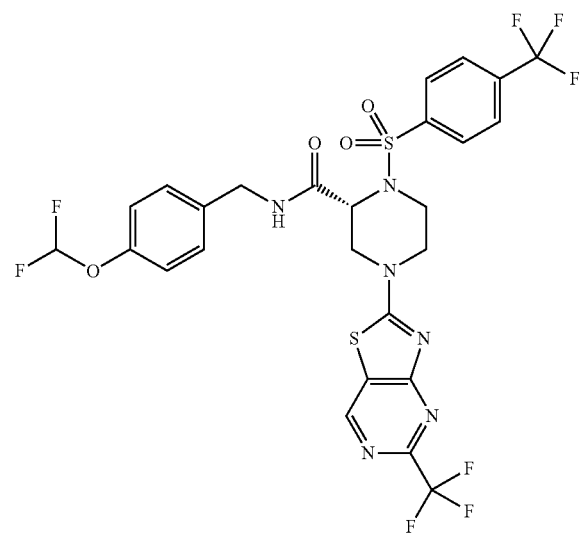 |
| 1002 | 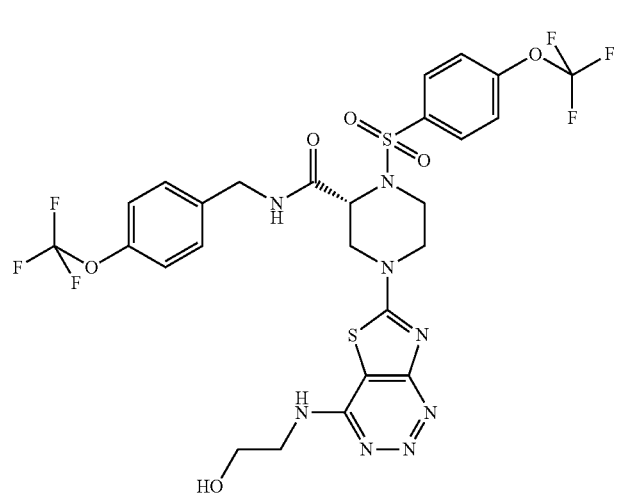 |

TABLE 201-continued
| Ex. No. | Structural Formula |
|---|---|
| 1003 | 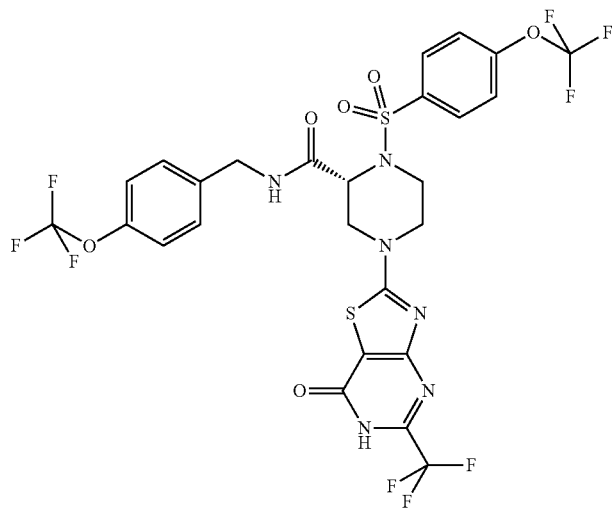 |
| 1004 | 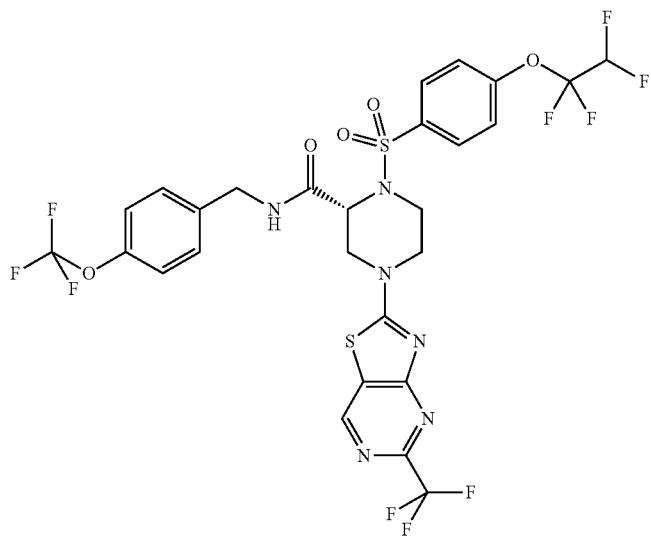 |

831
832
TABLE 202
| Ex. No. | Structural Formula |
|---|---|
| 1005 | 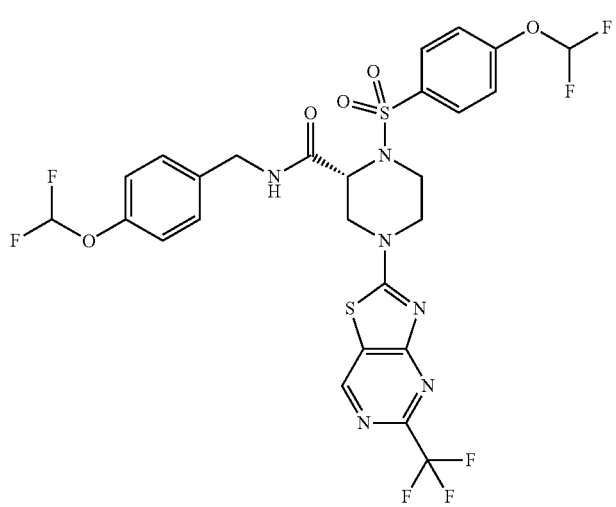 |
| 1006 | 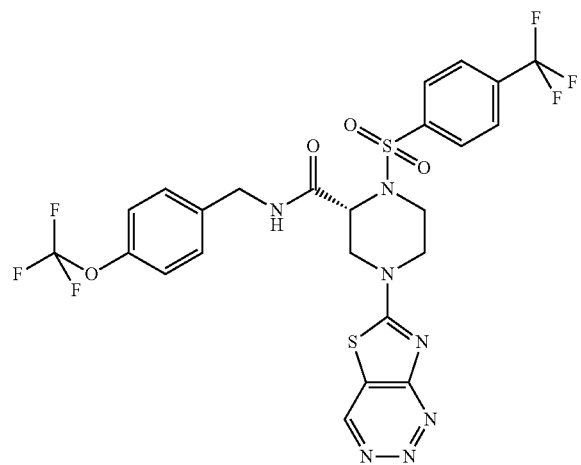 |
| 1007 | 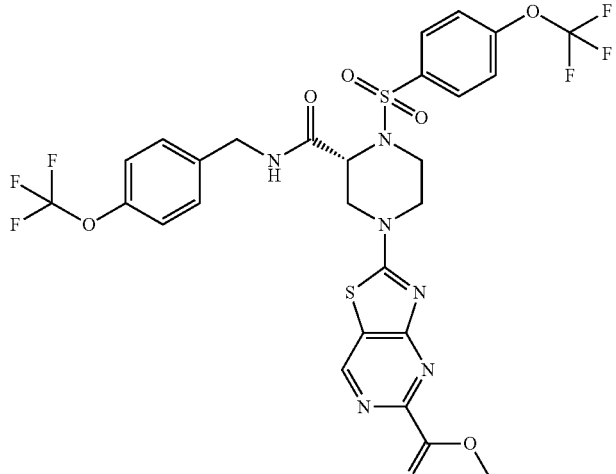 |

TABLE 202-continued
| Ex. No. | Structural Formula |
|---|---|
| 1008 | |
| 1009 | |
TABLE 203
| Ex. No. | Structural Formula |
|---|---|
| 1010 | |
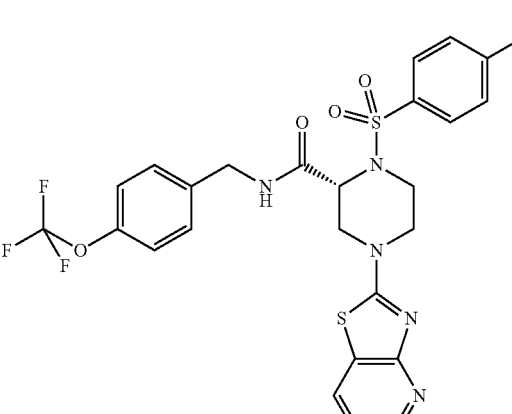

TABLE 203-continued

| Ex. No. | Structural Formula |
|---|---|
| 1011 | |
| 1012 | |
| 1013 | |

TABLE 203-continued
| Ex. No. | Structural Formula |
|---|---|
| 1014 | 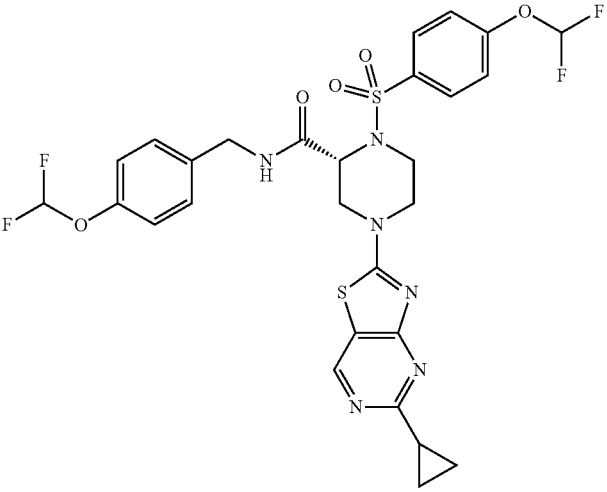 |
TABLE 204
| Ex. No. | Structural Formula |
|---|---|
| 1015 | 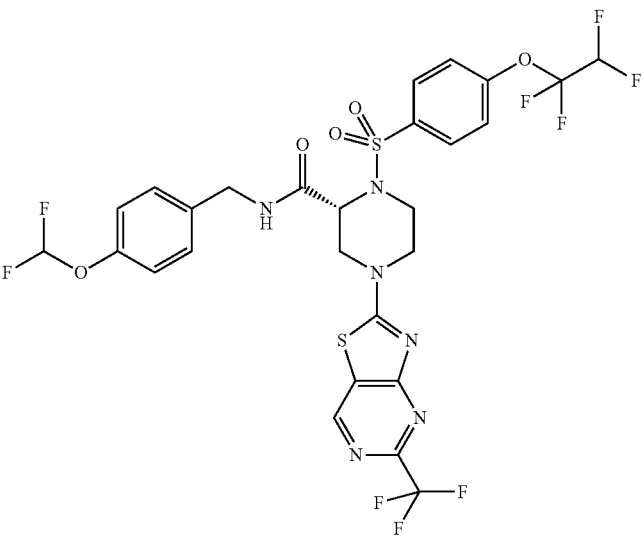 |

TABLE 204-continued
| Ex. No. | Structural Formula |
| --- | --- |
| 1016 | 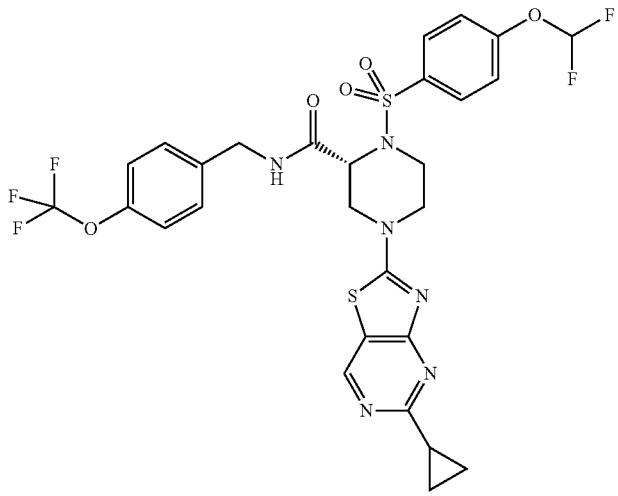 |
| 1017 | 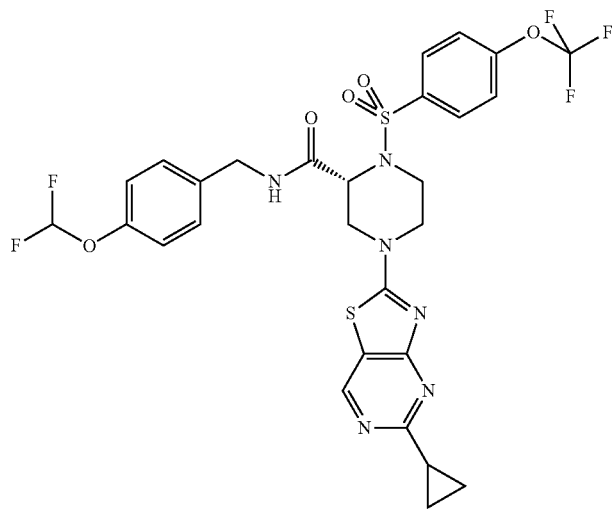 |
| 1018 | 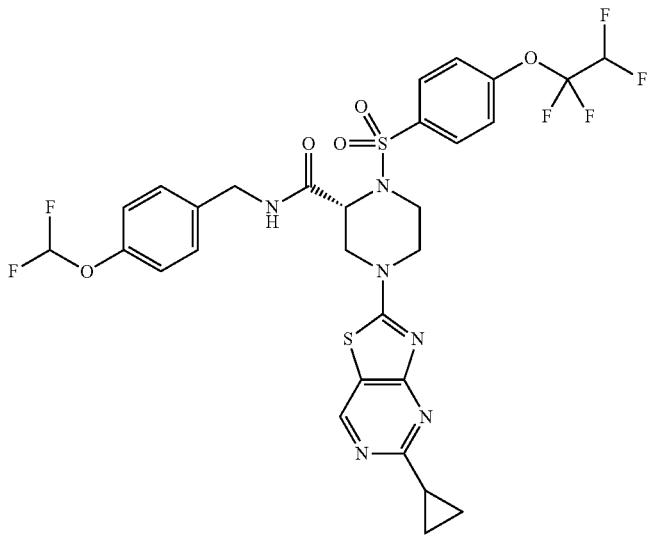 |

TABLE 204-continued
| Ex. No. | Structural Formula |
|---|---|
| 1019 | 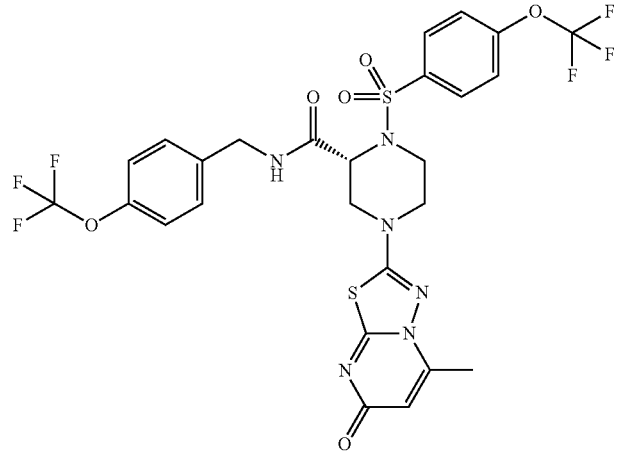 |
TABLE 205
| Ex. No. | Structural Formula |
|---|---|
| 1020 | 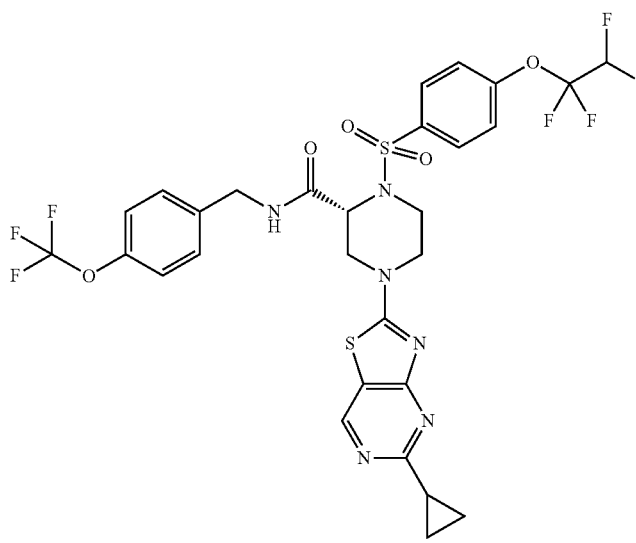 |

TABLE 205-continued
| Ex. No. | Structural Formula |
|---|---|
| 1021 | 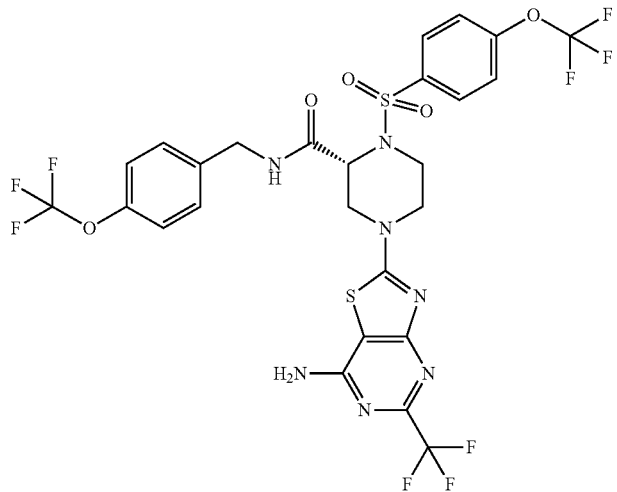 |
| 1022 | 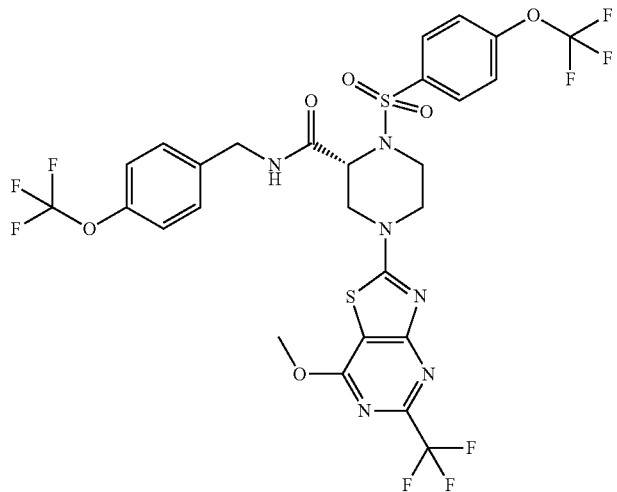 |
| 1023 | 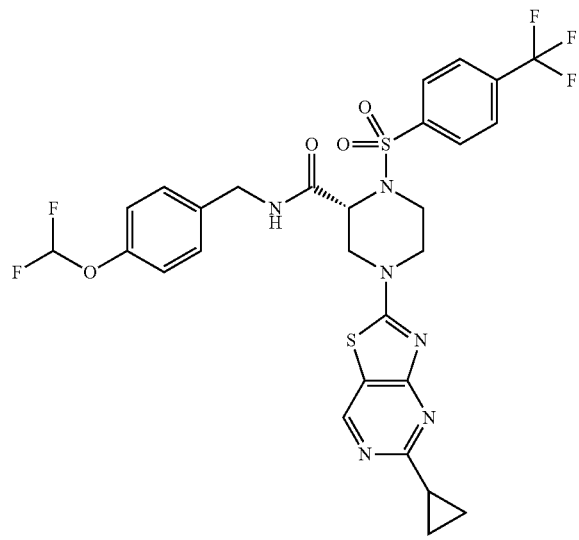 |

TABLE 205-continued
| Ex. No. | Structural Formula |
|---|---|
| 1024 | 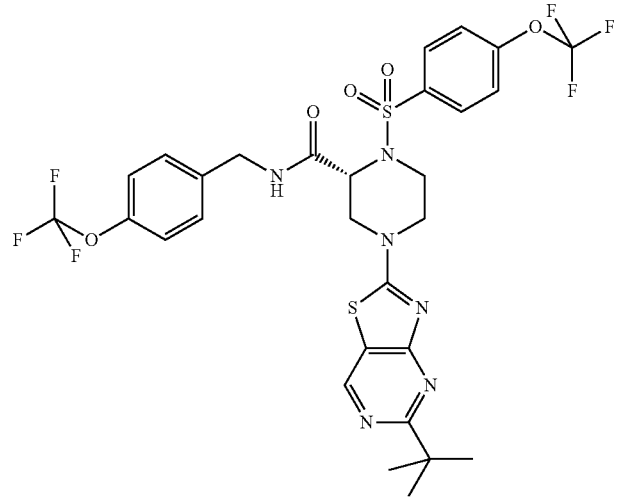 |
TABLE 206
| Ex. No. | Structural Formula |
|---|---|
| 1025 | 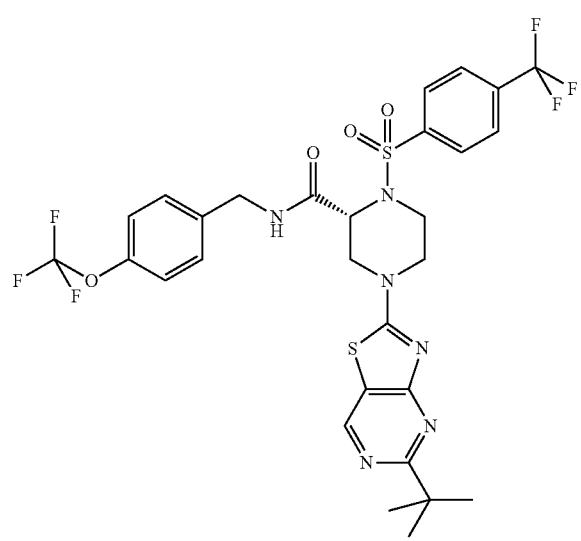 |

TABLE 206-continued
| Ex. No. | Structural Formula |
|---|---|
| 1026 | 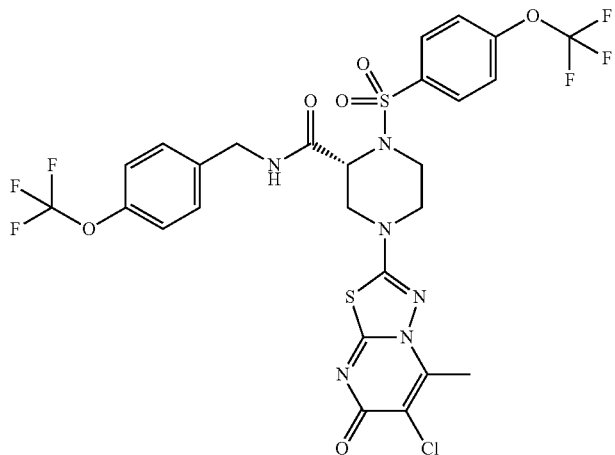 |
| 1027 | 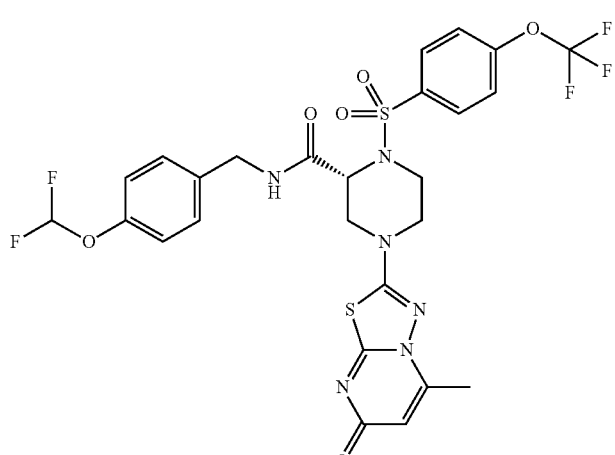 |
| 1028 | 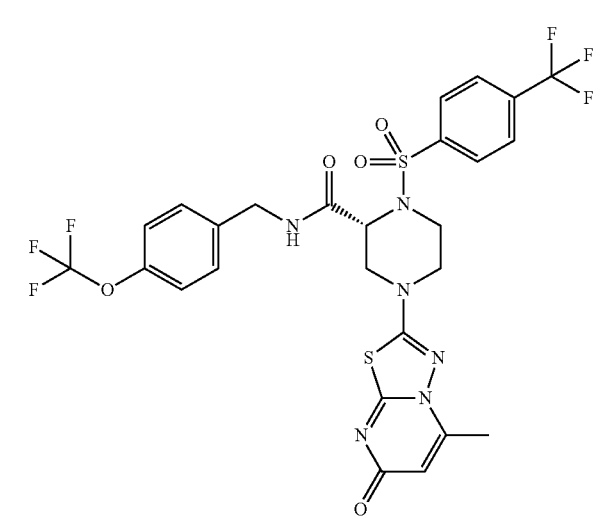 |

TABLE 206-continued

| Ex. No. | Structural Formula |
|---|---|
| 1029 | |

TABLE 207

| Ex. No. | Structural Formula |
|---|---|
| 1030 | |
| 1031 | |

TABLE 207-continued

| Ex. No. | Structural Formula |
|---|---|
| 1032 | |
| 1033 | |
| 1034 | |

TABLE 208
| Ex. No. | Structural Formula |
|---|---|
| 1035 | 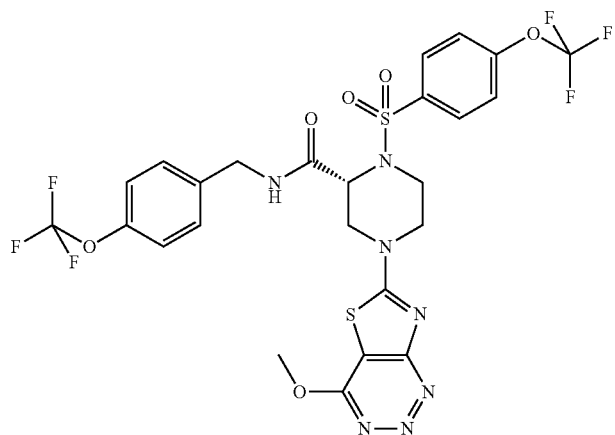 |
| 1036 | 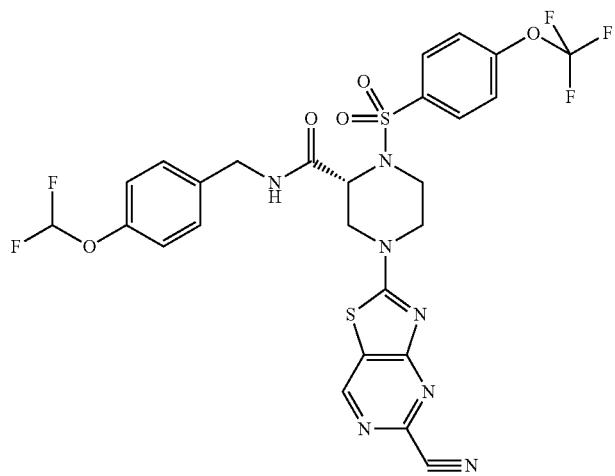 |
| 1037 | 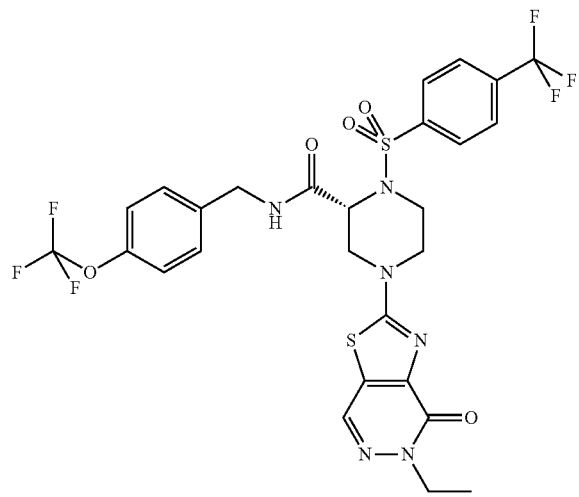 |

TABLE 208-continued
| Ex. No. | Structural Formula |
| --- | --- |
| 1038 | 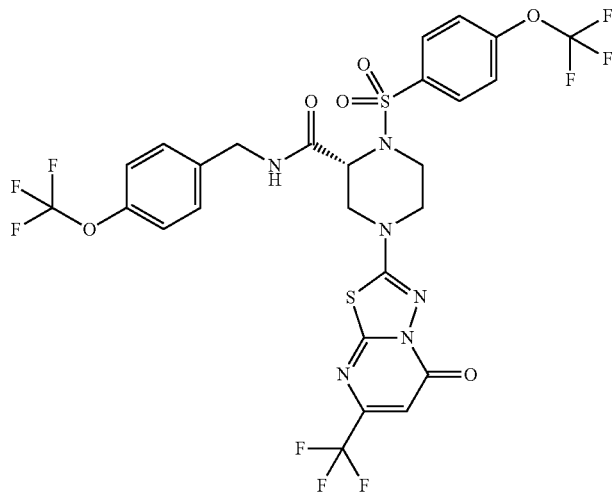 |
| 1039 | 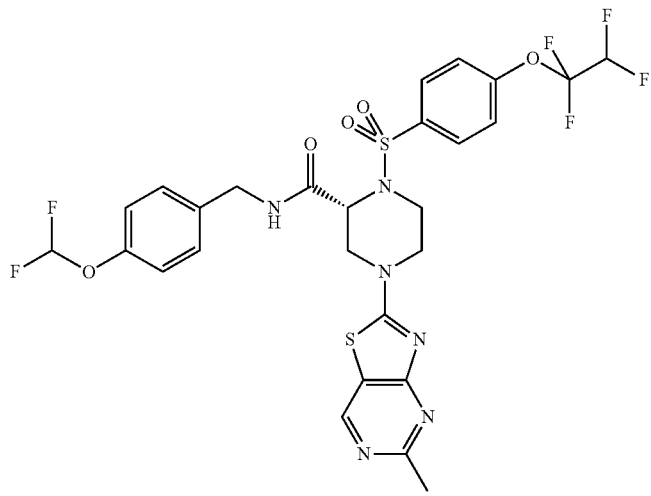 |

TABLE 209

| Ex. No. | Structural Formula |
|---|---|
| 1040 | |
| 1041 | |
| 1042 | |

TABLE 209-continued
| Ex. No. | Structural Formula |
|---|---|
| 1043 | 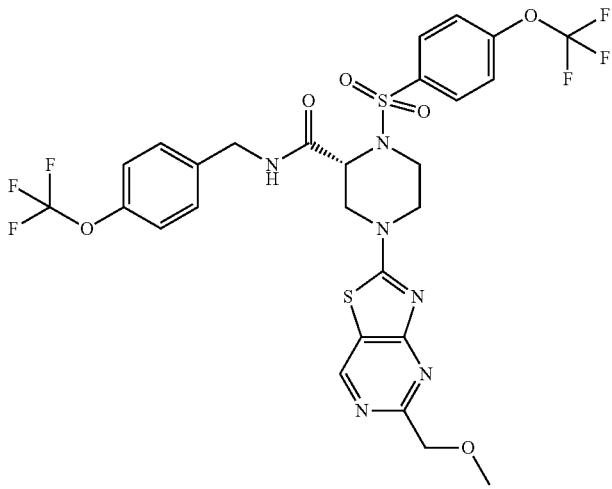 |
| 1044 | 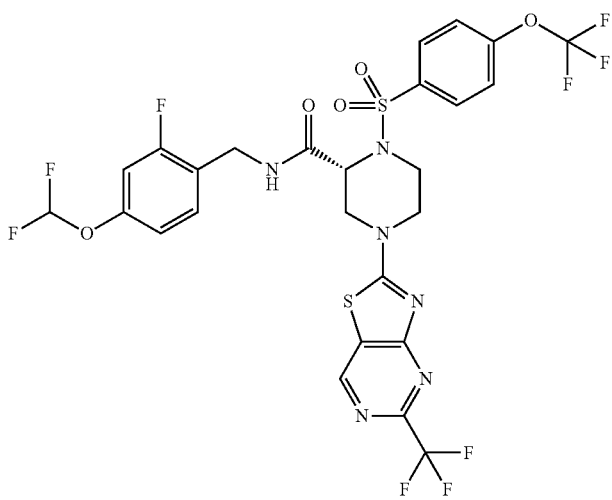 |

TABLE 210
| Ex. No. | Structural Formula |
|---|---|
| 1045 | 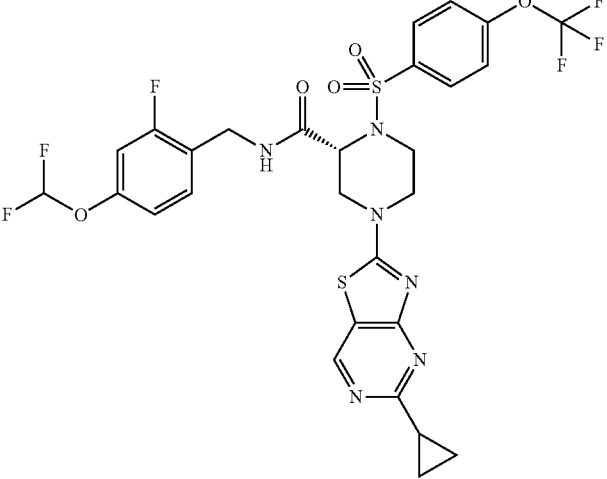 |
| 1046 | 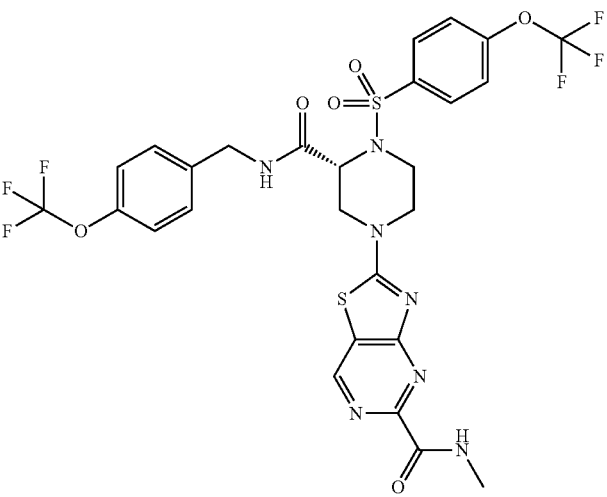 |
| 1047 | 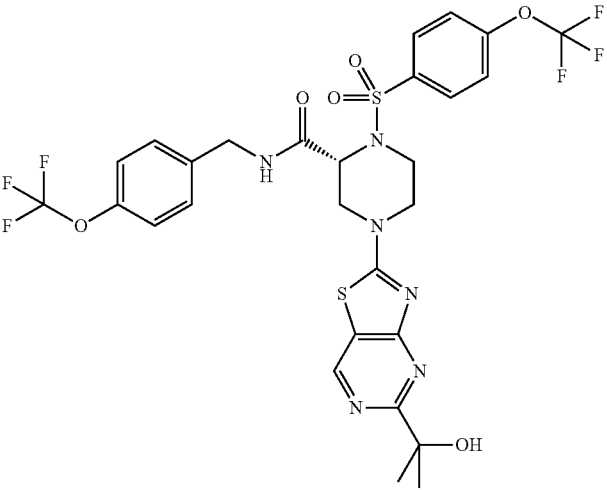 |

TABLE 210-continued
| Ex. No. | Structural Formula |
|---|---|
| 1048 | 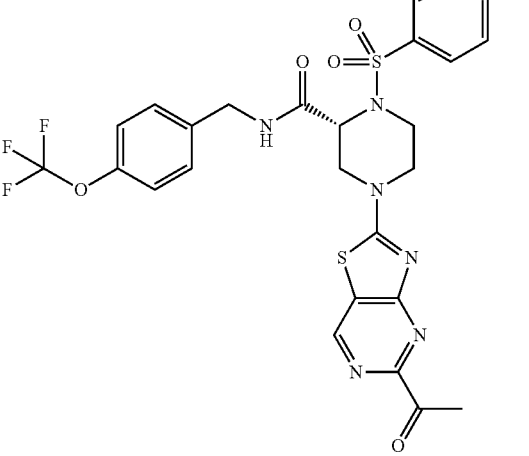 |
| 1049 | |
TABLE 211
| Ex. No. | Structural Formula |
|---|---|
| 1050 | 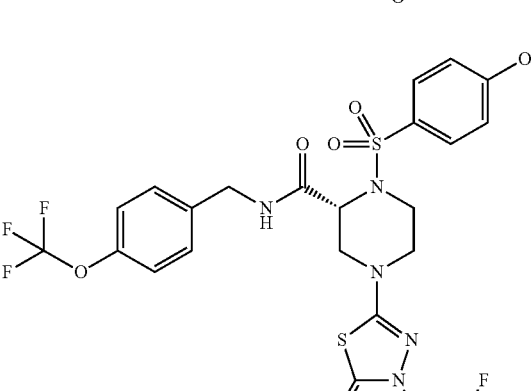 |

TABLE 211-continued
| Ex. No. | Structural Formula |
|---|---|
| 1051 | 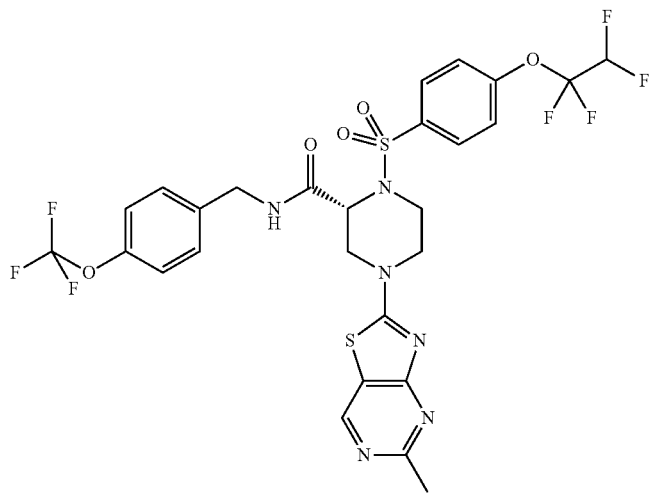 |
| 1052 | 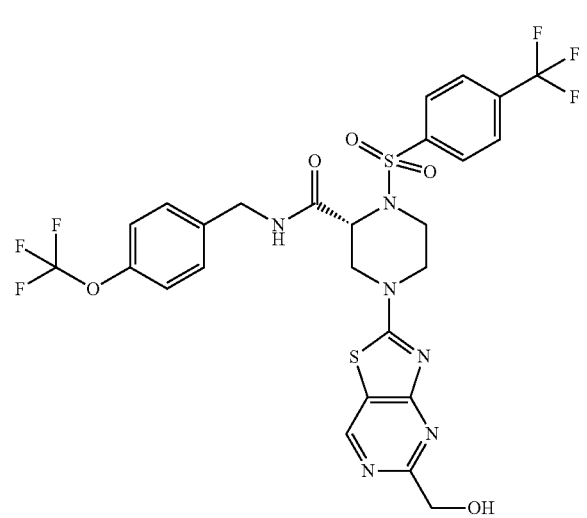 |
| 1053 | 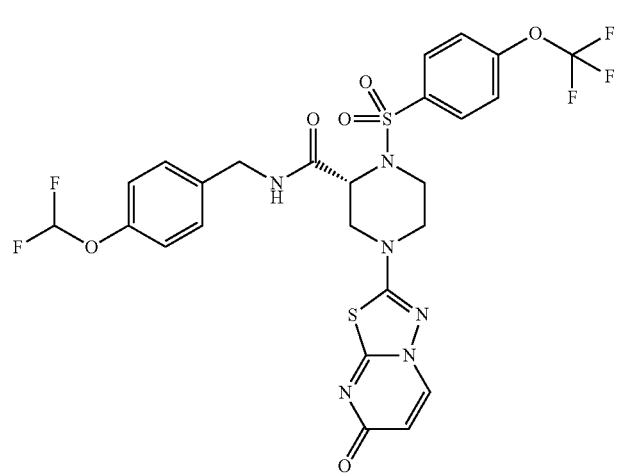 |

TABLE 211-continued

| Ex. No. | Structural Formula |
|---|---|
| 1054 | |

TABLE 212

| Ex. No. | Structural Formula |
|---|---|
| 1055 | |
| 1056 | |

TABLE 212-continued
| Ex. No. | Structural Formula |
|---|---|
| 1057 | 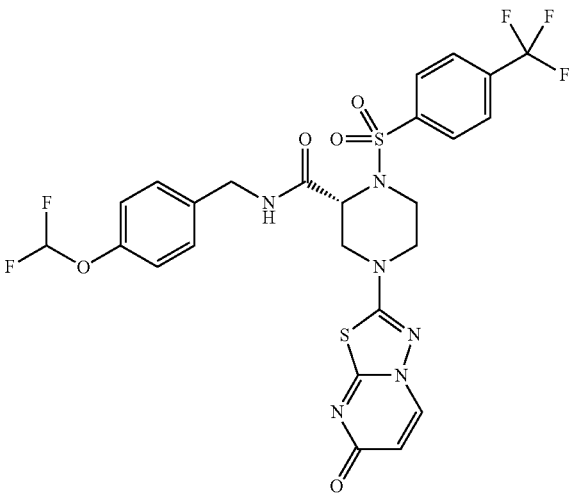 |
| 1058 | 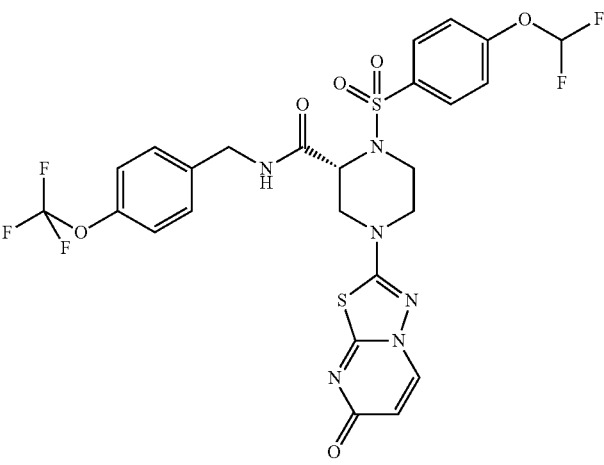 |
| 1059 | 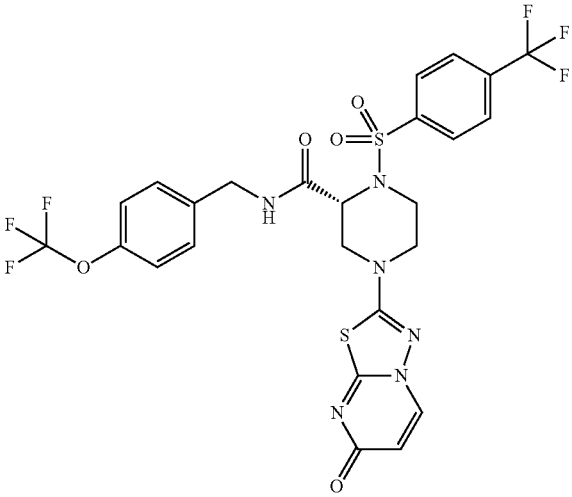 |

TABLE 213

| Ex. No. | Structural Formula |
| --- | --- |
| 1060 | |
| 1061 | |
| 1062 | |

873
TABLE 213-continued
| Ex. No. | Structural Formula |
|---|---|
| 1063 | 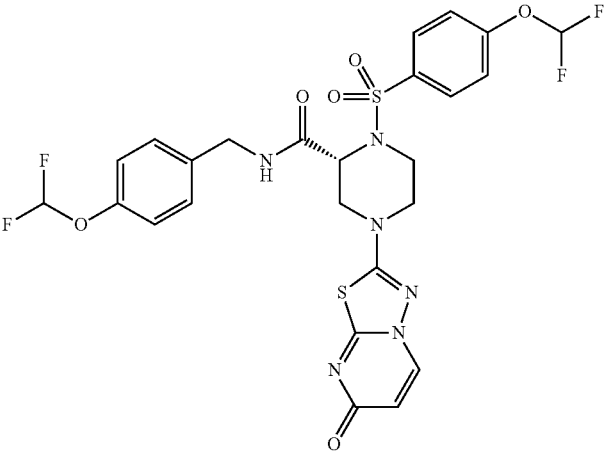 |
| 1064 | 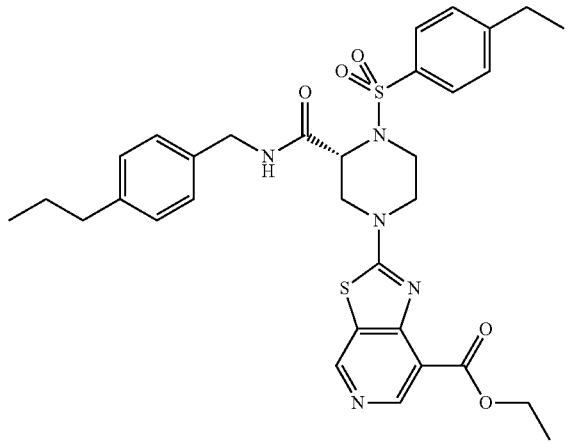 |
TABLE 214
| Ex. No. | Structural Formula |
|---|---|
| 1065 | 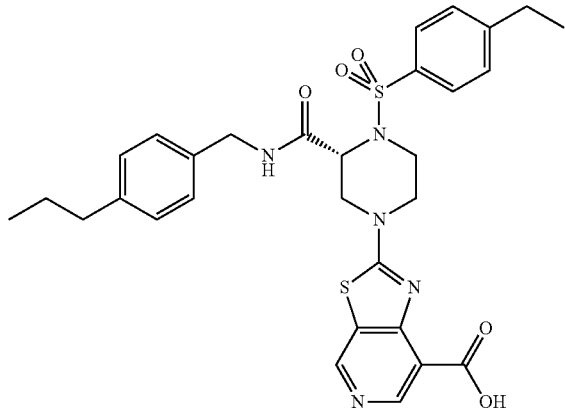 |

TABLE 214-continued
| Ex. No. | Structural Formula |
|---|---|
| 1066 | 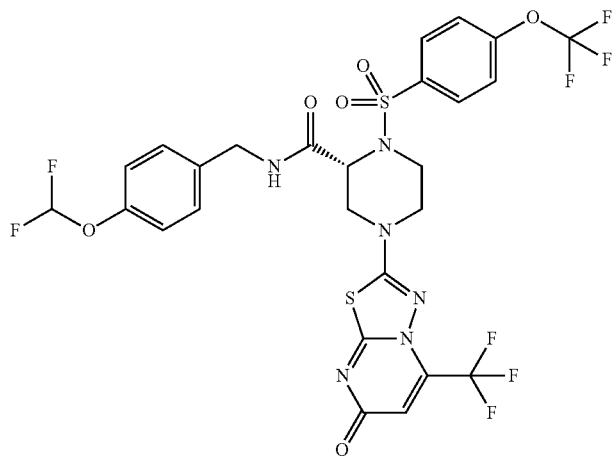 |
| 1067 | 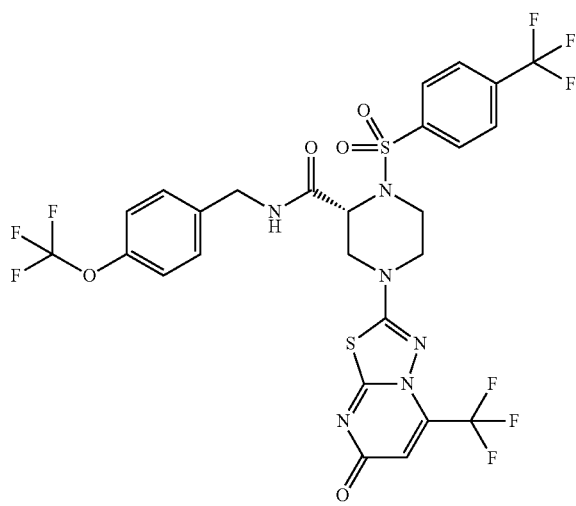 |
| 1068 | 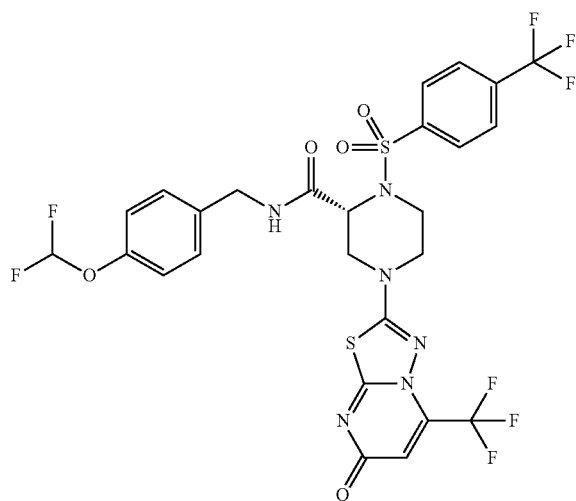 |

TABLE 214-continued
| Ex. No. | Structural Formula |
|---|---|
| 1069 | 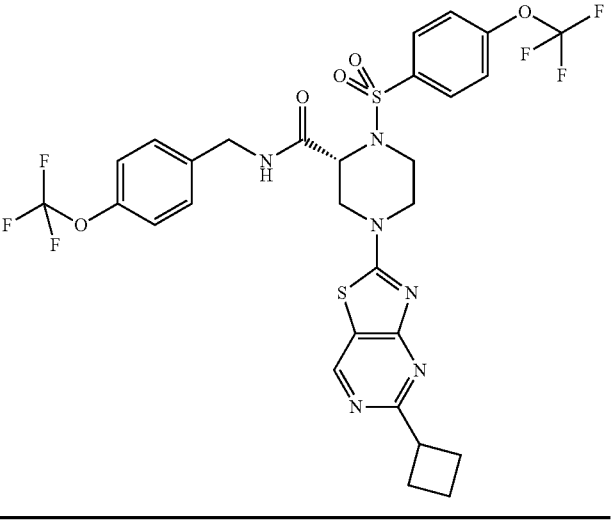 |
TABLE 215
| Ex. No. | Structural Formula |
|---|---|
| 1070 | 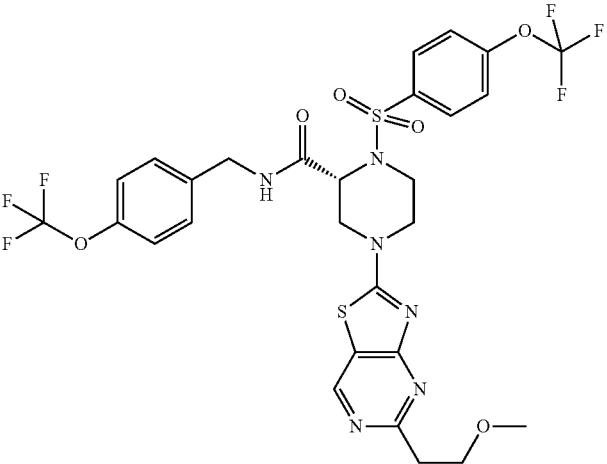 |
| 1071 | 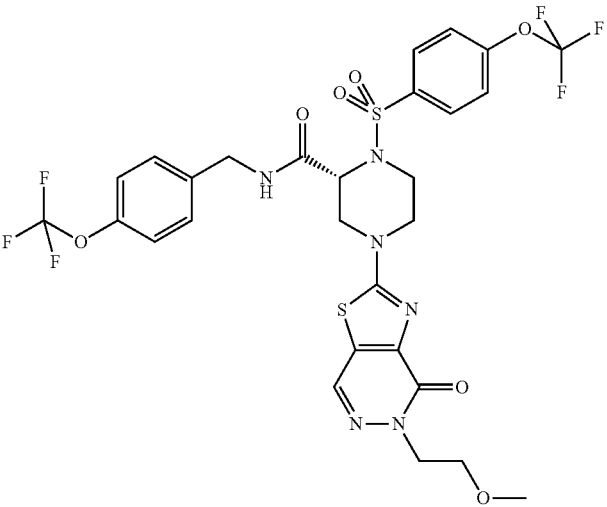 |

TABLE 215-continued
| Ex. No. | Structural Formula |
|---|---|
| 1072 | 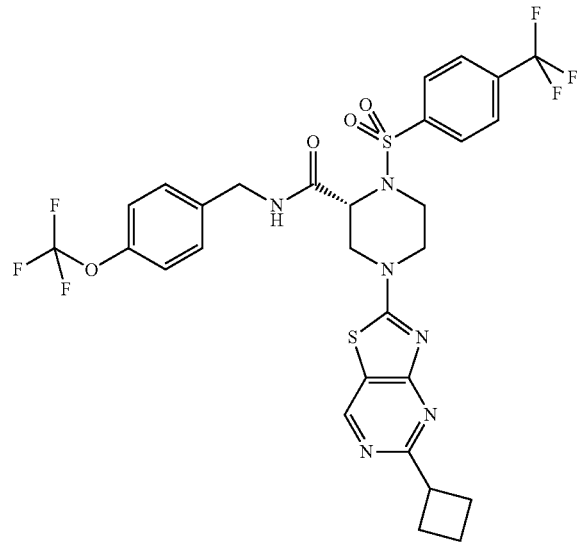 |
| 1073 | 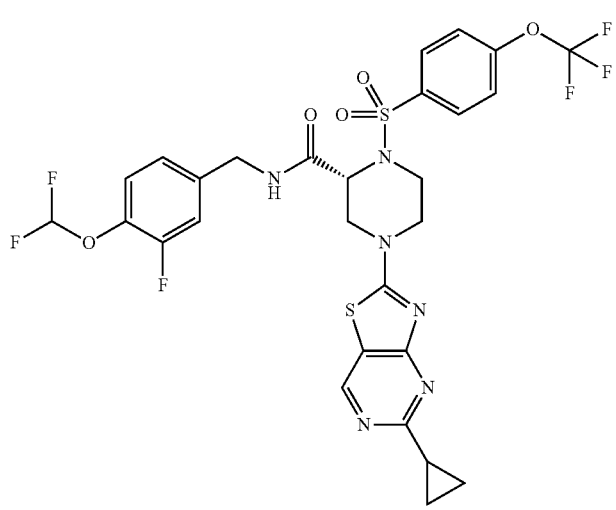 |
| 1074 | 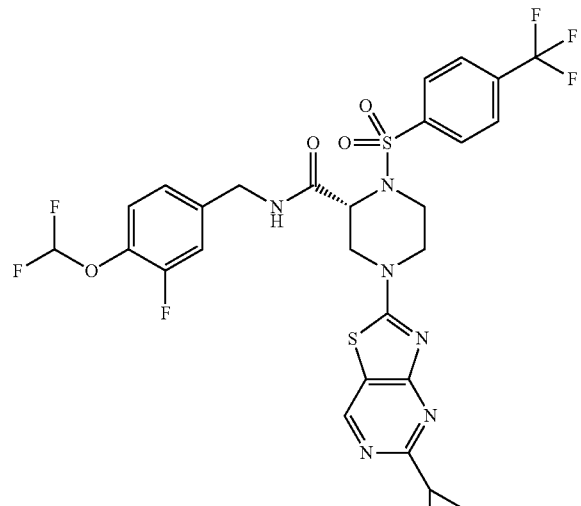 |

TABLE 216
| Ex. No. | Structural Formula |
|---|---|
| 1075 | 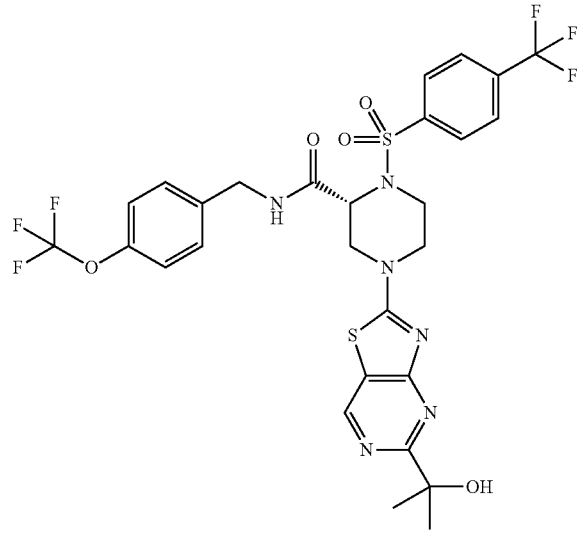 |
| 1076 | 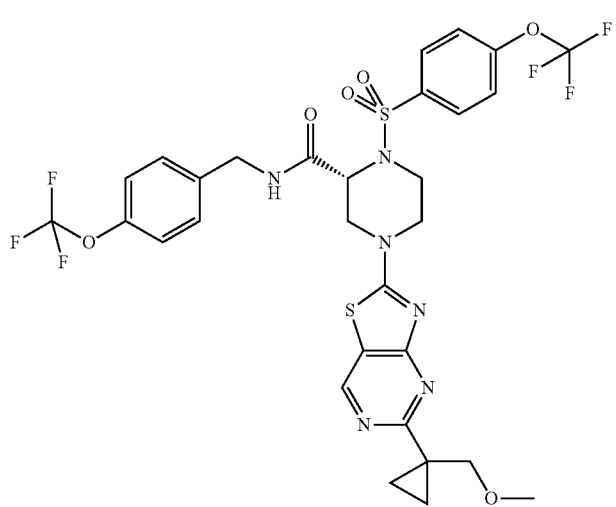 |
| 1077 | 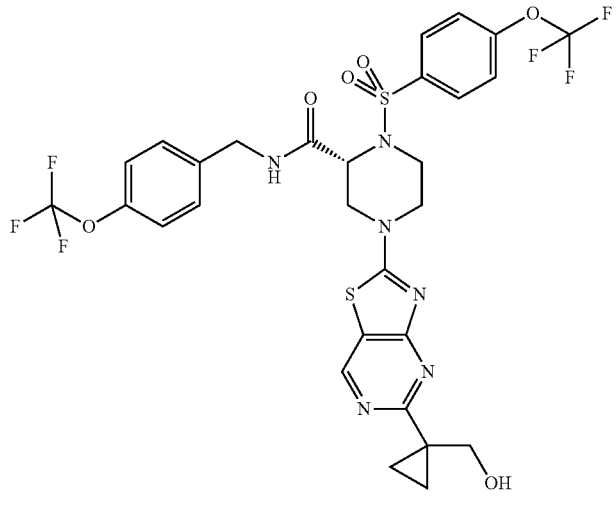 |

TABLE 216-continued
| Ex. No. | Structural Formula |
|---|---|
| 1078 | 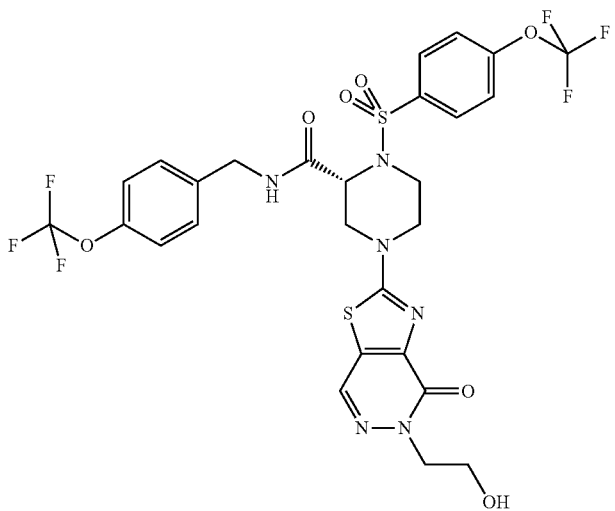 |
| 1079 | 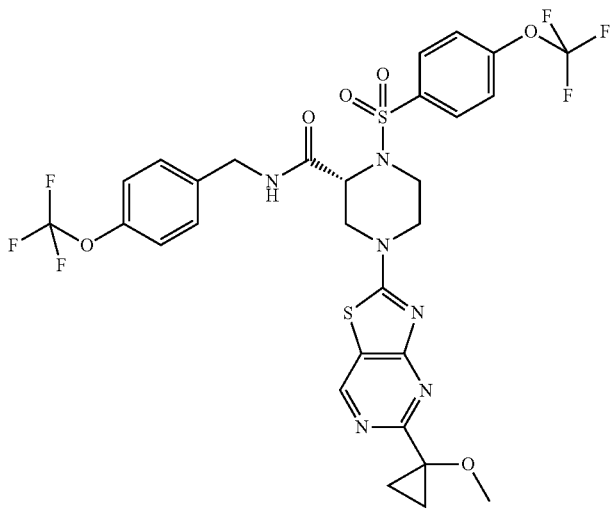 |

TABLE 217
| Ex. No. | Structural Formula |
|---|---|
| 1080 | 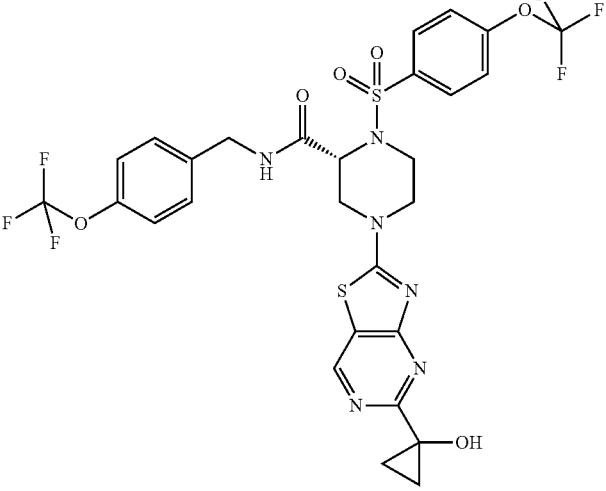 |
| 1081 | 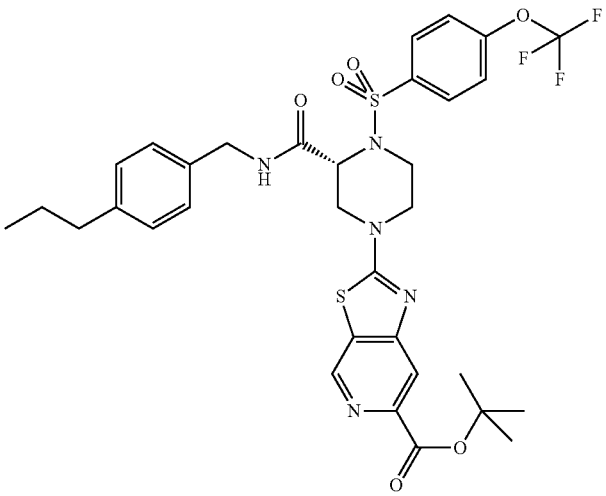 |
| 1082 | 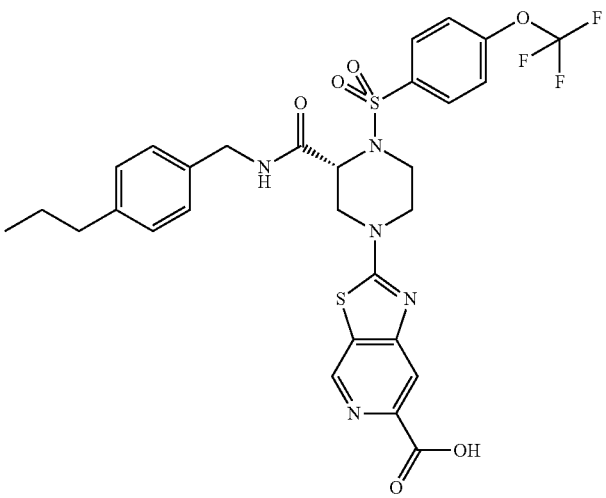 |

TABLE 217-continued

| Ex. No. | Structural Formula |
|---|---|
| 1083 | |
| 1084 | |

TABLE 218

| Ex. No. | Structural Formula |
|---|---|
| 1085 | |

TABLE 218-continued
| Ex. No. | Structural Formula |
| --- | --- |
| 1086 | 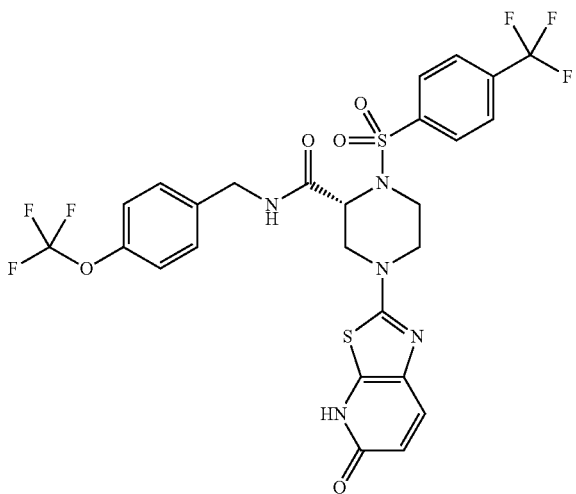 |
| 1087 | 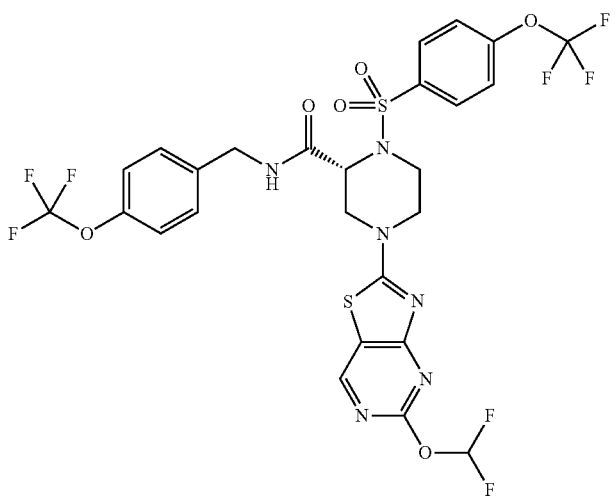 |
| 1088 | 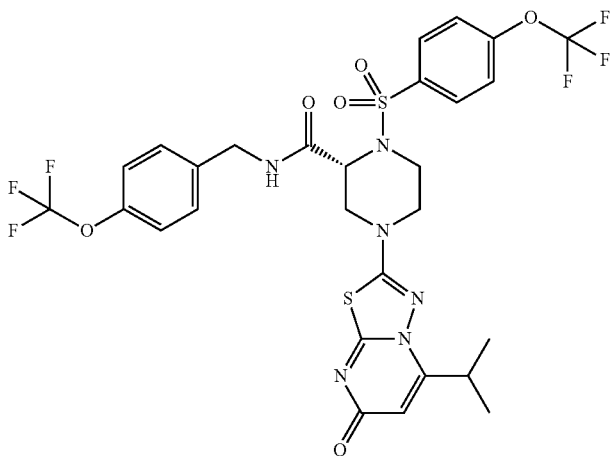 |

TABLE 218-continued
| Ex. No. | Structural Formula |
|---|---|
| 1089 | 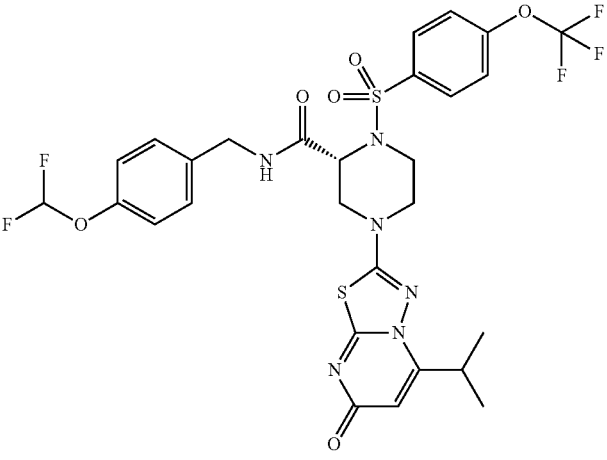 |
TABLE 219
| Ex. No. | Structural Formula |
|---|---|
| 1090 | 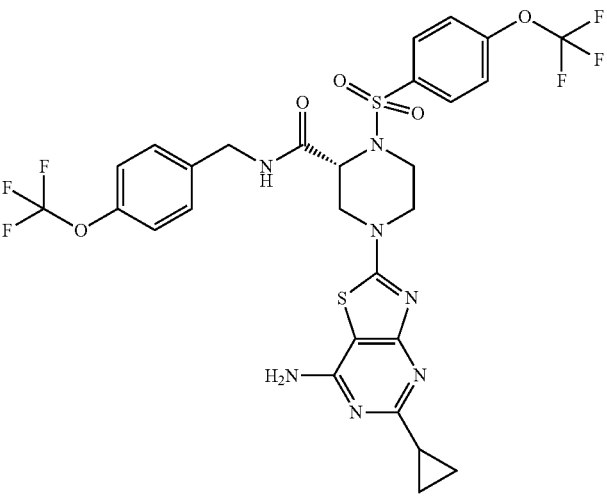 |
| 1091 | 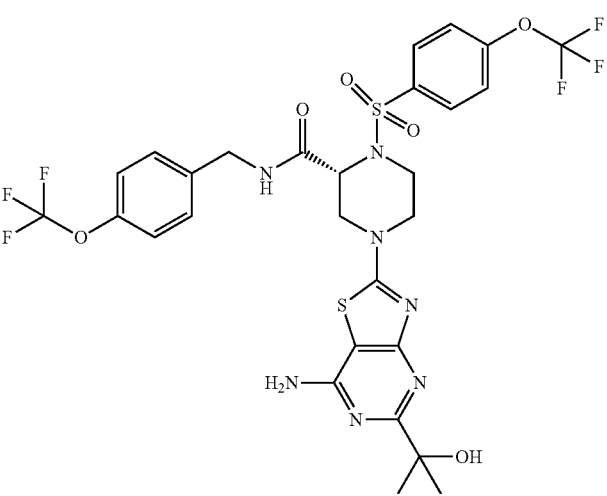 |

TABLE 219-continued
| Ex. No. | Structural Formula |
|---|---|
| 1092 | 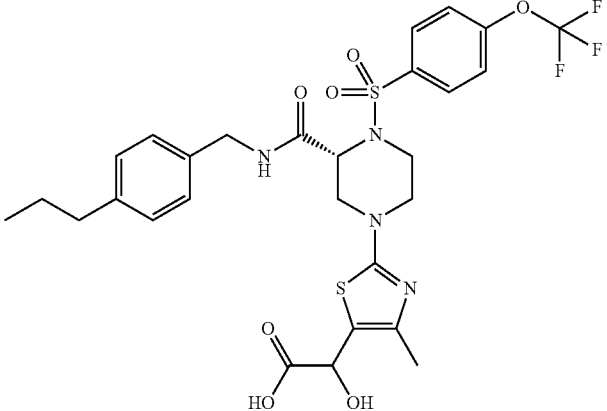 |
| 1093 | 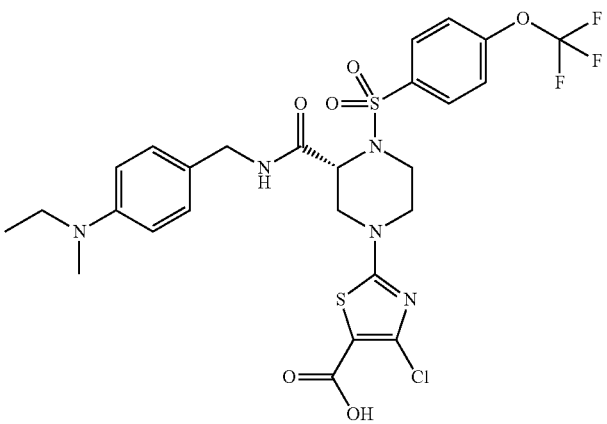 |
| 1094 | 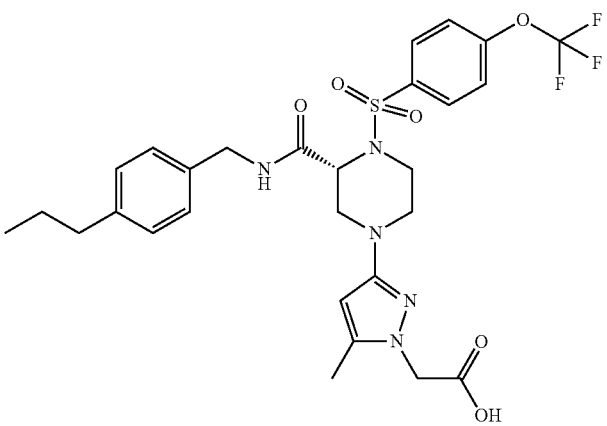 |

TABLE 220
| Ex. No. | Structural Formula |
|---|---|
| 1095 | 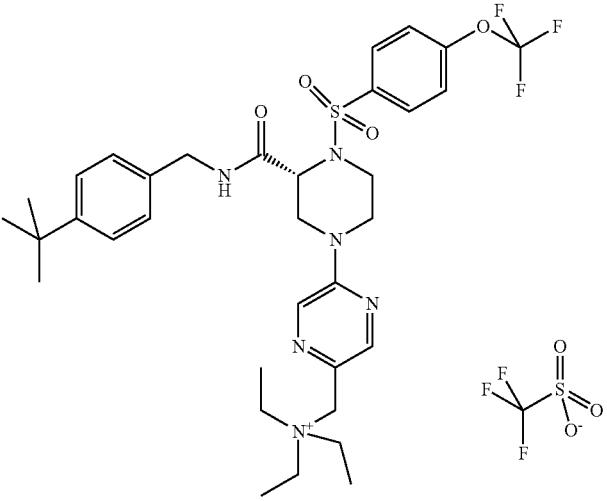 |
| 1096 | 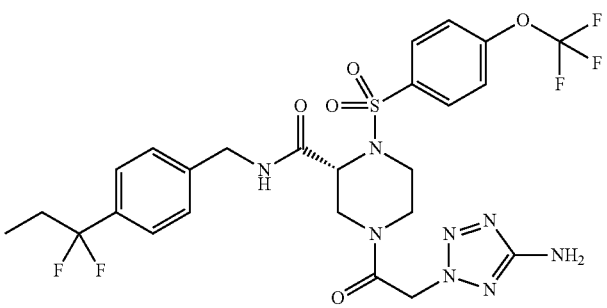 |
| 1097 | 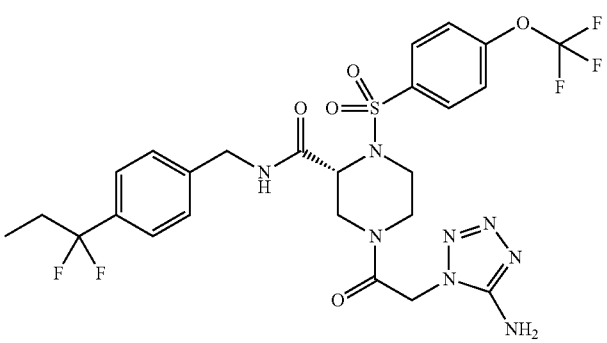 |
| 1098 | 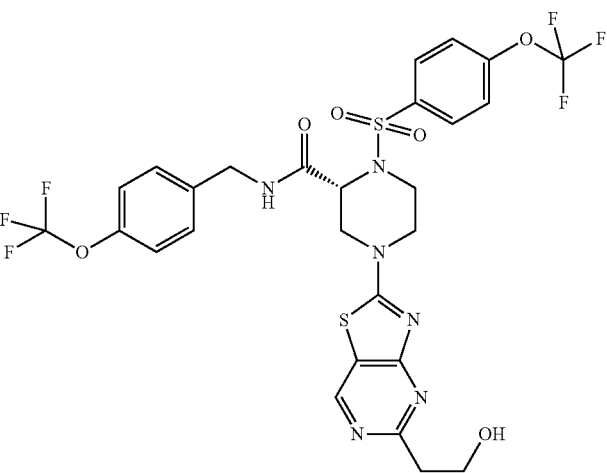 |

TABLE 220-continued
| Ex. No. | Structural Formula |
|---|---|
| 1099 | 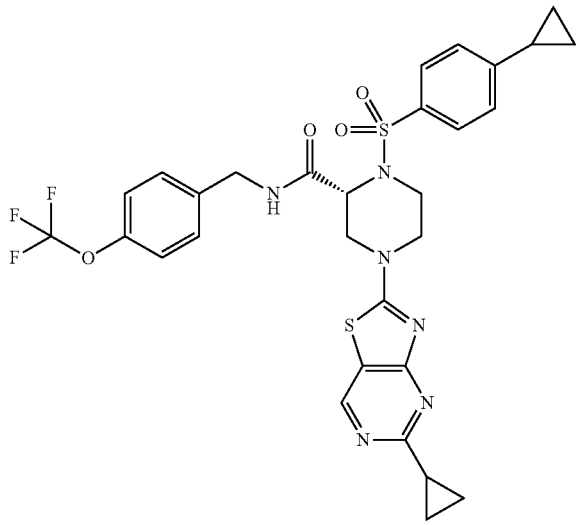 |
TABLE 221
| Ex. No. | Structural Formula |
|---|---|
| 1100 | 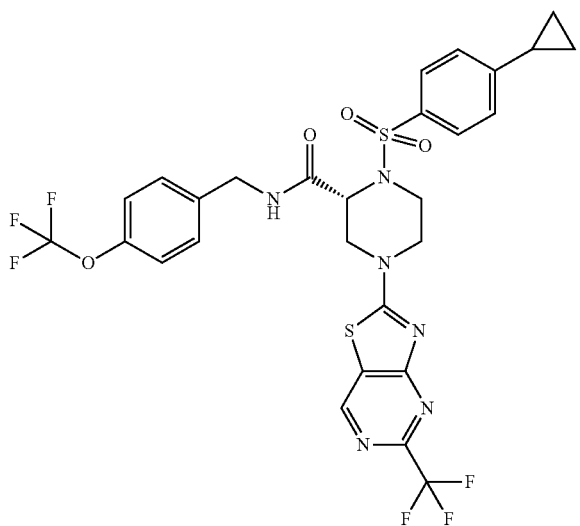 |

TABLE 221-continued
| Ex. No. | Structural Formula |
|---|---|
| 1101 | 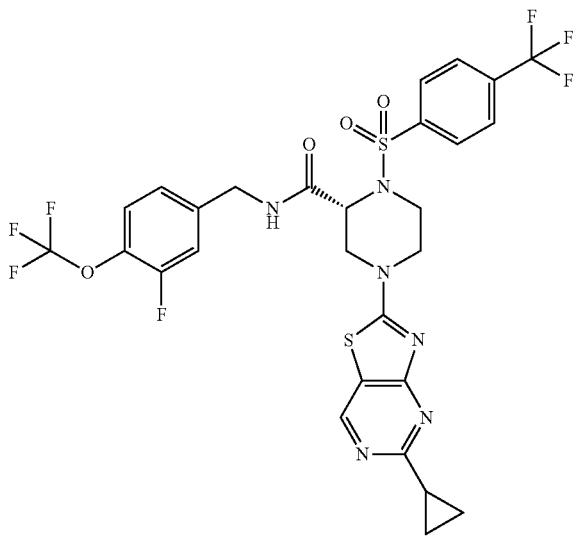 |
| 1102 | 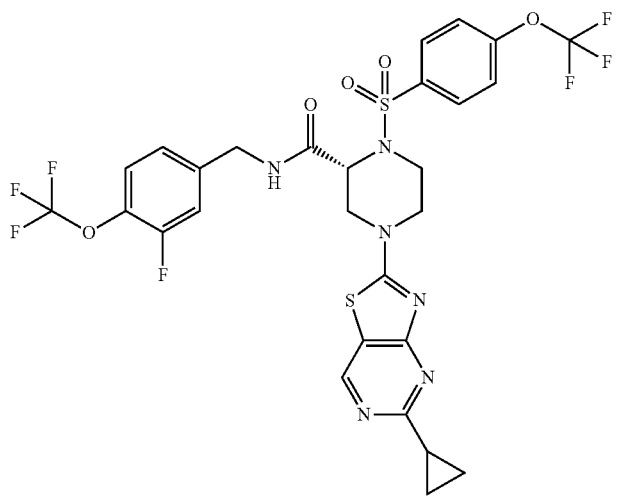 |
| 1103 | 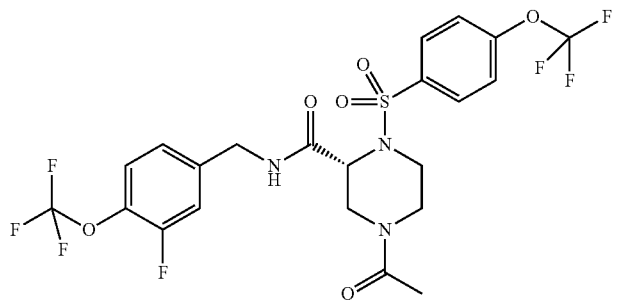 |

TABLE 221-continued
| Ex. No. | Structural Formula |
|---|---|
| 1104 | |
TABLE 222
| Ex. No. | Structural Formula |
|---|---|
| 1105 | |
| 1106 | |
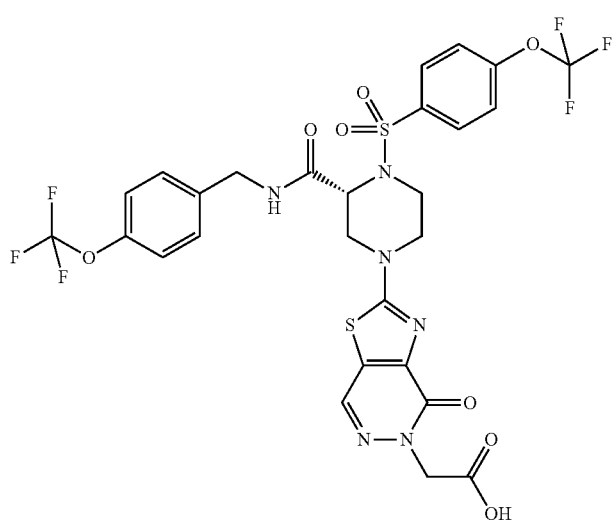

TABLE 222-continued
| Ex. No. | Structural Formula |
|---|---|
| 1107 | 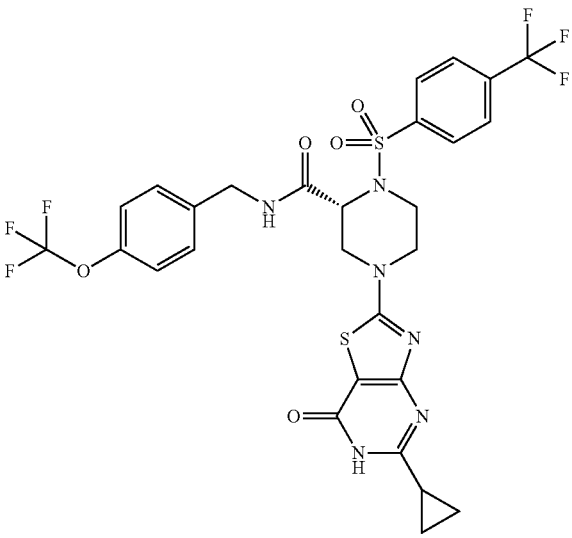 |
| 1108 | 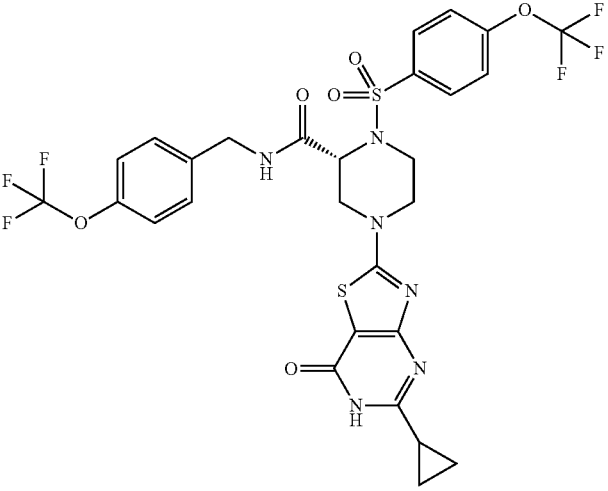 |
| 1109 | 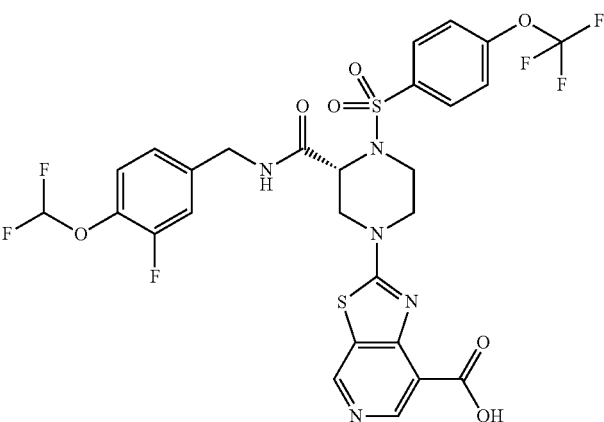 |

TABLE 223
| Ex. No. | Structural Formula |
|---|---|
| 1110 | 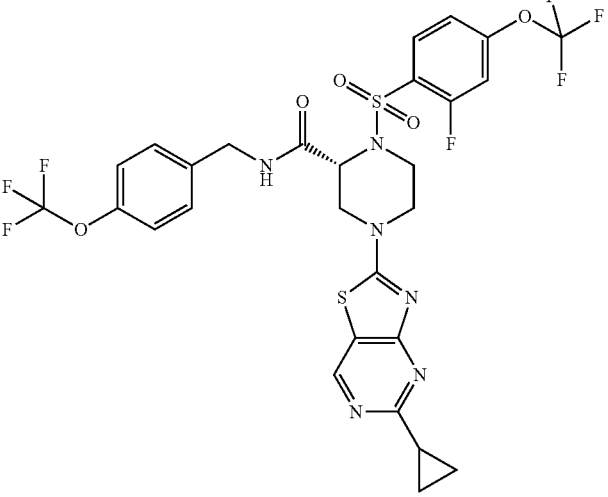 |
| 1111 | 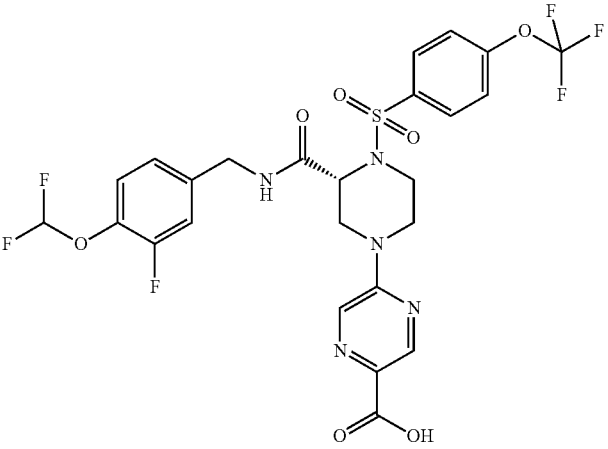 |
| 1112 | 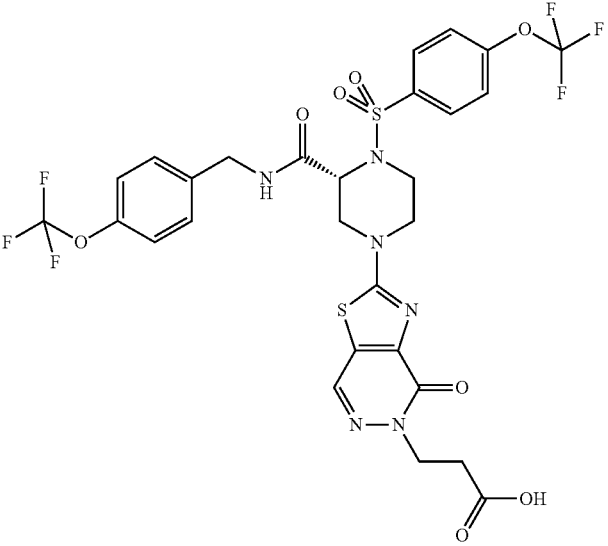 |

TABLE 223-continued
| Ex. No. | Structural Formula |
|---|---|
| 1113 | 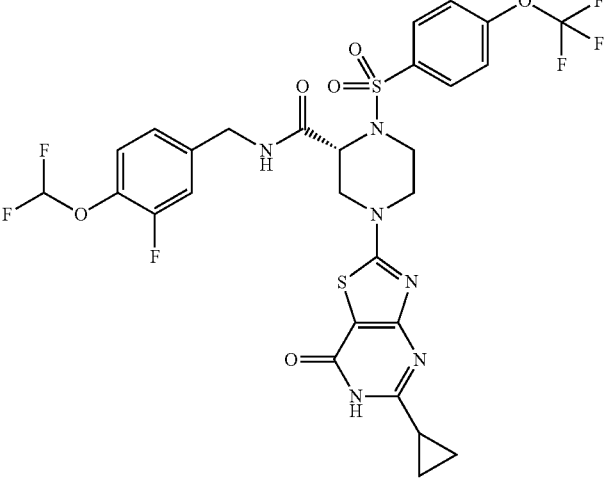 |
| 1114 | 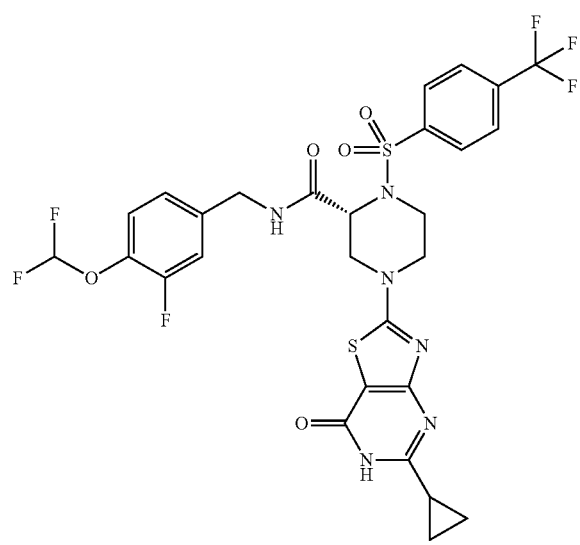 |
TABLE 224
| Ex. No. | Structural Formula |
|---|---|
| 1115 | 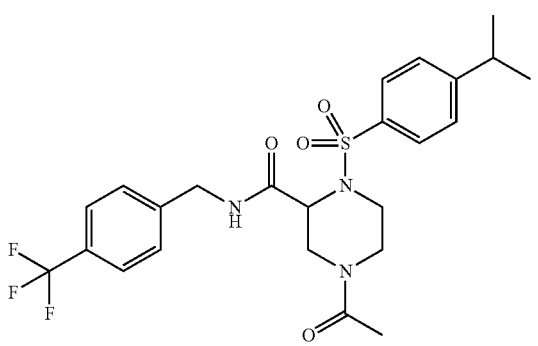 |

TABLE 224-continued
| Ex. No. | Structural Formula |
|---|---|
| 1116 | 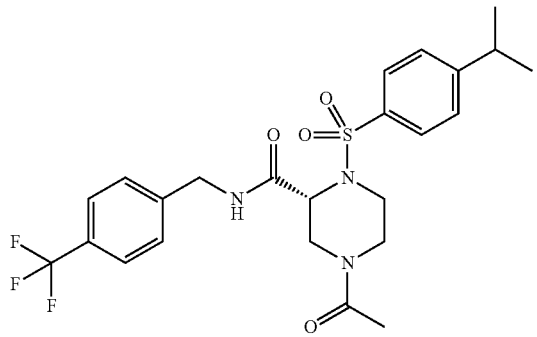 |
| 1117 | 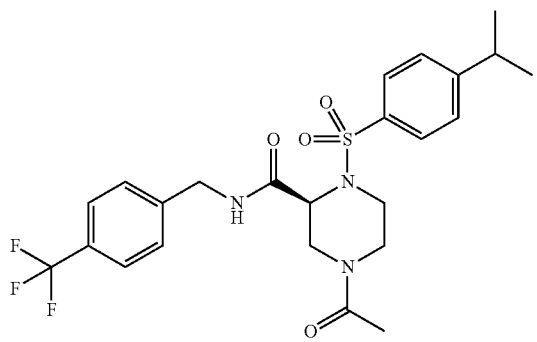 |
| 1118 | 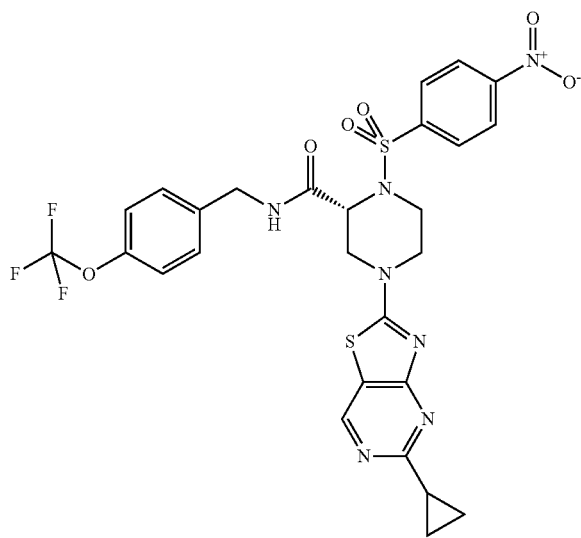 |

TABLE 224-continued
| Ex. No. | Structural Formula |
|---|---|
| 1119 | |
TABLE 225
| Ex. No. | Structural Formula |
|---|---|
| 1120 | 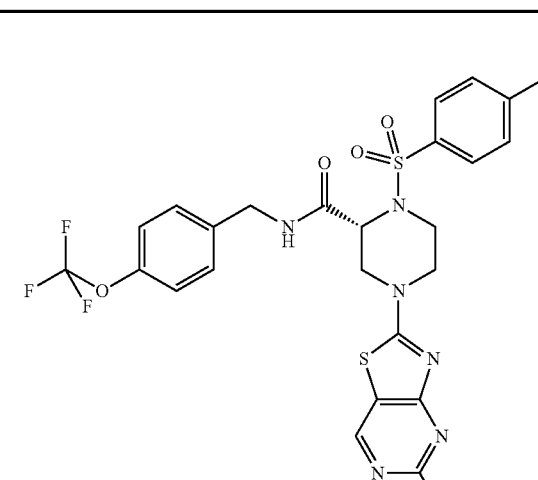 |

TABLE 225-continued
| Ex. No. | Structural Formula |
|---|---|
| 1121 | 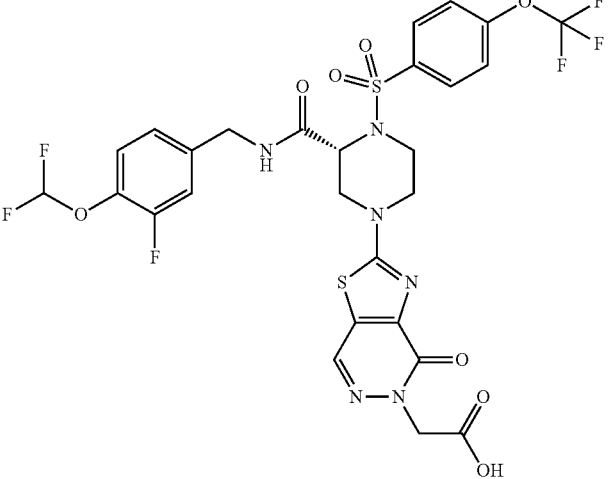 |
| 1122 | 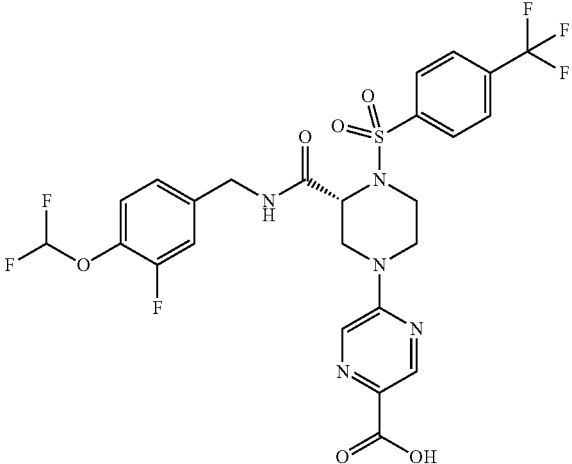 |
| 1123 | 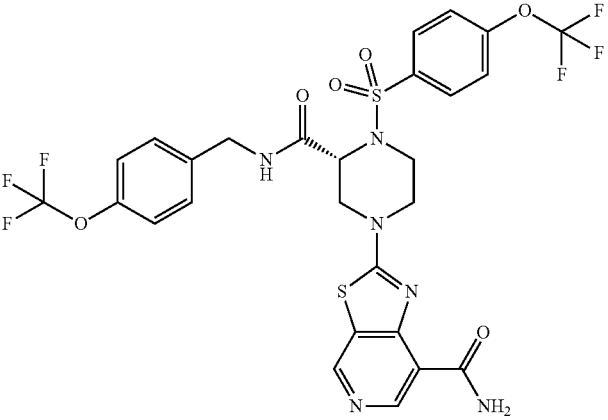 |

TABLE 225-continued
| Ex. No. | Structural Formula |
|---|---|
| 1124 | 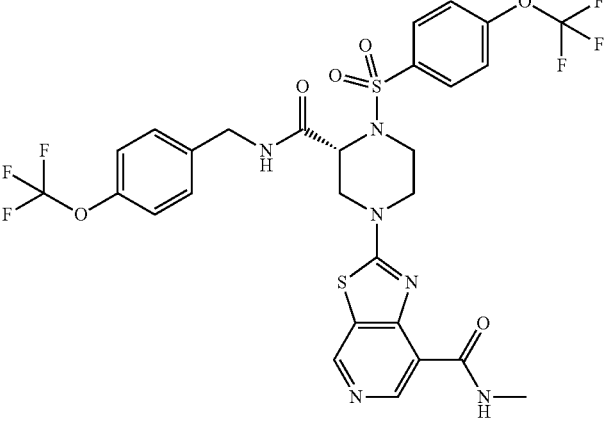 |
TABLE 226
| Ex. No. | Structural Formula |
|---|---|
| 1125 | 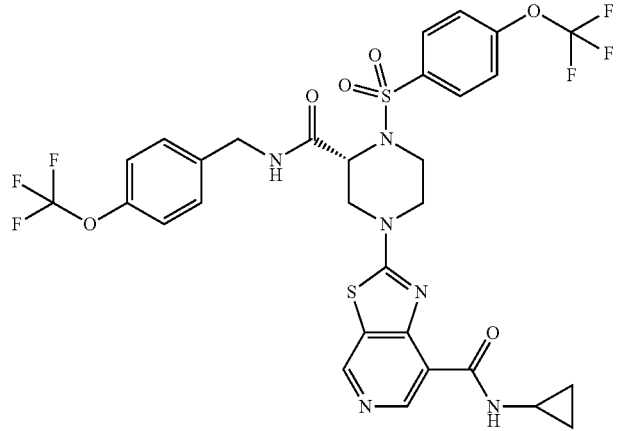 |
| 1126 | 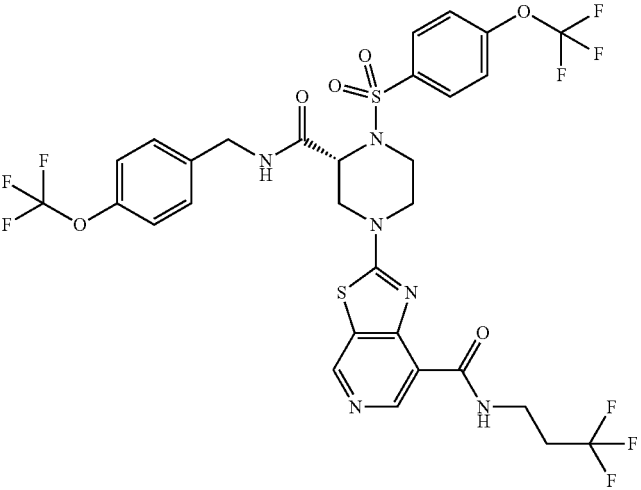 |

TABLE 226-continued
| Ex. No. | Structural Formula |
|---|---|
| 1127 | 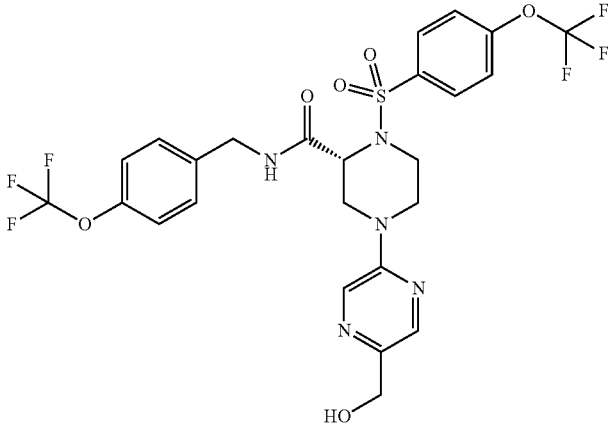 |
| 1128 | 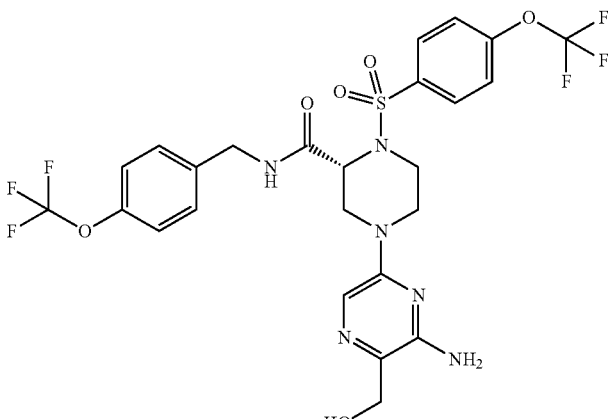 |
| 1129 | 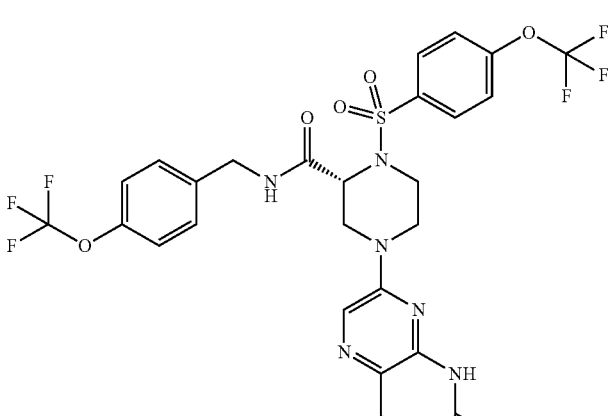 |
TABLE 227
| Example No. | MS ESI m/e: | NMR |
|---|---|---|
| 1 | 470 (M + H). | 1H-NMR (CDCl$_3$, 400 MHz) δ: 1.23 (6H, d, J = 7.1 Hz), 2.89-2.96 (3H, br m), 3.42-3.46 (1H, br m), 3.70-3.86 (2H, m), 4.08-4.11 (1H, br m), 4.36 (2H, s), 4.78 (1H, br s), 7.18 (4H, s), 7.67 (2H, d, J = 7.5 Hz), 7.90 (2H, d, J = 7.7 Hz). |
| 2 | 589 (M + H). | 1H-NMR (CDCl$_3$, 400 MHz) δ: 1.26 (6.5H, d, J = 6.7 Hz), 2.36-2.45 (1.0H, m), 2.77 (0.9H, dd, J = 13.7, 3.9 Hz), 2.83-3.03 |

TABLE 227-continued

| Example No. | MS ESI m/e: | NMR |
|---|---|---|
| | | (1.3H, m), 3.16-3.27 (1.3H, m), 3.45-3.72 (0.8H, m), 3.78-3.97 (3.0H, m), 4.31-4.45 (3.4H, m), 4.52 (0.9H, d, J = 3.2 Hz), 4.61 (1.1H, d, J = 13.4 Hz), 4.94-5.01 (0.1H, m), 7.71-7.77 (0.2H, m), 7.81 (1.7H, d, J = 8.3 Hz), 7.97 (2.0H, d, J = 8.1 Hz), 8.51 (1.8H, dd, J = 4.4, 1.6 Hz). |
| 3 | 590 (M + H). | 1H-NMR (CDCl$_3$, 400 MHz) δ: 1.24 (6H, d, J = 7.1 Hz), 2.48 (1H, td, J = 13.2, 3.0 Hz), 2.71 (1H, dd, J = 14.3, 3.3 Hz), 2.84-2.95 (1H, m), 3.10 (1H, ddd, J = 15.0, 11.9, 3.1 Hz), 3.95 (1H, d, J = 13.7 Hz), 4.17 (1H, d, J = 13.7 Hz), 4.40-4.63 (4H, m), 6.99 (1H, t, J = 5.2 Hz), 7.14 (2H, d, J = 8.2 Hz), 7.20 (2H, d, J = 8.2 Hz), 7.24-7.28 (2H, m), 7.84 (2H, d, J = 8.6 Hz), 8.00 (2H, d, J = 7.9 Hz), 8.40 (2H, dd, J = 4.9, 1.5 Hz), 8.54 (1H, s). |
| 4 | 529 (M + H). | 1H-NMR (CDCl$_3$, 400 MHz) δ: 1.26 (6H, d, J = 6.8 Hz), 2.67-2.78 (1H, m), 2.86-2.97 (1H, m), 3.12-3.23 (1H, m), 3.95 (1H, d, J = 14.8 Hz), 4.43 (1H, d, J = 5.7 Hz), 4.58-4.69 (2H, m), 5.03 (1H, d, J = 14.6 Hz), 6.36 (2H, s), 6.90 (1H, s), 7.13 (4H, d, J = 8.2 Hz), 7.23 (4H, d, J = 7.9 Hz), 7.83 (2H, d, J = 8.2 Hz), 7.99 (2H, d, J = 8.2 Hz). |
| 5 | 667 (M + H). | 1H-NMR (CDCl$_3$, 300 MHz) δ: 1.25 (6H, d, J = 6.8 Hz), 1.51 (9H, s), 2.42 (3H, s), 2.91-2.99 (2H, m), 3.11 (1H, dd, J = 13.2, 4.5 Hz), 3.40-3.46 (1H, m), 3.87 (2H, d, J = 10.2 Hz), 4.39 (2H, d, J = 5.7 Hz), 4.48 (1H, d, J = 12.8 Hz), 4.62 (1H, br s), 6.76 (1H, t, J = 5.5 Hz), 7.11 (2H, d, J = 8.3 Hz), 7.18 (2H, d, J = 7.9 Hz), 7.77 (2H, d, J = 8.7 Hz), 7.99 (2H, d, J = 8.3 Hz). |

TABLE 228

| Example No. | MS ESI m/e: | NMR |
|---|---|---|
| 6 | 611 (M + H). | 1H-NMR (CD$_3$OD, 300 MHz) δ: 1.27 (6H, t, J = 6.2 Hz), 2.90 (1H, h J = 6.2 Hz), 3.25-3.30 (1H, m), 3.52 (1H, dd, J = 13.9, 4.5 Hz), 3.87-3.93 (3H, m), 4.22-4.28 (2H, m), 4.44 (1H, d, J = 13.6 Hz), 4.69-4.70 (1H, m), 7.14 (2H, d, J = 9.0 Hz), 7.18 (2H, d, J = 9.0 Hz), 7.83 (2H, d, J = 8.3 Hz), 8.04 (2H, d, J = 8.3 Hz), 8.62-8.64 (1H, br m). |
| 7 | 610 (M + H). | 1H-NMR (CDCl$_3$, 300 MHz) δ: 1.25 (6H, d, J = 6.8 Hz), 2.44 (3H, s), 2.85-3.11 (3H, m), 3.42-3.49 (1H, m), 3.90 (2H, d, J = 9.8 Hz), 4.39 (2H, d, J = 5.3 Hz), 4.47 (1H, t, J = 10.4 Hz), 4.62 (1H, br s), 5.34 (2H, br s), 6.77 (1H, t, J = 5.3 Hz), 7.11 (2H, d, J = 8.3 Hz), 7.19 (2H, d, J = 8.3 Hz), 7.78 (2H, d, J = 8.3 Hz), 7.99 (2H, d, J = 8.3 Hz). |
| 8 | 606 (M + H). | 1H-NMR (CDCl$_3$, 400 MHz) δ: 1.24 (6H, d, J = 7.1 Hz), 2.83-2.94 (1H, m), 3.01-3.18 (2H, m), 3.42-3.53 (1H, m), 3.84-3.99 (4H, m), 4.19-4.42 (3H, m), 4.62 (1H, t, J = 3.0 Hz), 4.87 (1H, d, J = 12.8 Hz), 6.78 (1H, t, J = 5.5 Hz), 7.04-7.18 (4H, m), 7.78 (2H, d, J = 8.4 Hz), 7.99 (2H, d, J = 8.2 Hz), 8.16 (1H, d, J = 1.3 Hz), 8.70 (1H, d, J = 1.1 Hz). |
| 9 | 592 (M + H). | 1H-NMR (CD$_3$OD, 400 MHz) δ: 1.21 (6H, d, J = 6.8 Hz), 2.80-2.91 (1H, m), 3.45 (1H, dd, J = 14.0, 4.3 Hz), 3.72-3.94 (2H, m), 4.17 (2H, s), 4.34 (1H, d, J = 13.5 Hz), 4.66 (1H, br s), 7.02-7.12 (4H, m), 7.79 (2H, d, J = 8.4 Hz), 8.02 (3H, d, J = 8.4 Hz), 8.12 (3H, s), 8.63 (1H, s). |
| 10 | 654 (M + H). | 1H-NMR (CDCl$_3$, 400 MHz) δ: 1.25 (6H, d, J = 6.8 Hz), 2.16 (3H, s), 2.45 (1H, ddd, J = 14.4, 11.6, 2.9 Hz), 2.86-2.93 (2H, m), 3.20 (1H, ddd, J = 14.7, 11.5, 3.4 Hz), 3.82 (1H, dt, J = 15.0, 2.7 Hz), 4.31-4.59 (5H, m), 6.70 (1H, t, J = 7.1 Hz), 7.13 (2H, d, J = 7.9 Hz), 7.21 (2H, d, J = 8.2 Hz), 7.37 (1H, d, J = 8.4 Hz), 7.84 (1H, dd, J = 8.8, 2.0 Hz), 8.34 (1H, d, J = 2.4 Hz). |

TABLE 229

| Example No. | MS ESI m/e | NMR |
|---|---|---|
| 11 | 614 (M + H). | 1H-NMR (CDCl$_3$, 400 MHz) δ: 1.25 (6H, d, J = 6.8 Hz), 1.94-2.05 (2H, m), 2.14 (3H, s), 2.38 (2H, t, J = 6.8 Hz), 2.49 (1H, td, J = 12.3, 3.6 Hz), 2.80 (2H, t, J = 7.5 Hz), 2.85-2.95 (2H, m), 3.21 (1H, ddd, J = 14.4, 11.4, 3.3 Hz), 3.82 (1H, dt, J = 14.7, 3.2 Hz), 4.30 (1H, dt, J = 12.2, 2.6 Hz), 4.42 (2H, d, J = 5.7 Hz), 4.45-4.58 (2H, m), 6.85 (1H, t, J = 4.9 Hz), 7.13 (2H, d, J = 7.9 Hz), 7.21 (2H, d, J = 7.9 Hz), 7.37 (1H, d, J = 7.5 Hz), 7.73 (1H, dd, J = 8.7, 2.6 Hz), 7.79 (1H, d, J = 1.9 Hz), 11.10 (1H, br s). |

TABLE 229-continued

| Example No. | MS ESI m/e | NMR |
|---|---|---|
| 12 | 500 (M + H). | 1H-NMR (CDCl$_3$, 400 MHz) δ: 0.95 (3H, t, J = 7.3 Hz), 1.28 (6H, d, J = 6.8 Hz), 1.59-1.69 (2H, m), 2.15 (3H, s), 2.25 (3H, s), 2.36-2.43 (1H, m), 2.54 (2H, t, J = 7.6 Hz), 2.81 (1H, dd, J = 13.6, 3.6 Hz), 2.93-3.17 (2H, m), 3.81 (1H, d, J = 14.3 Hz), 4.29 (1H, d, J = 13.9 Hz), 4.34-4.56 (4H, m), 6.72 (1H, t, J = 4.7 Hz), 6.96-7.08 (3H, m), 7.38 (2H, d, J = 8.4 Hz), 7.74 (2H, d, J = 8.2 Hz). |
| 13 | 628 (M + H). | 1H-NMR (DMSO-d$_6$, 400 MHz) δ: 1.20 (6H, d, J = 7.0 Hz), 2.37 (3H, s), 2.91-3.03 (1H, m), 3.10-3.20 (1H, m), 3.38-3.46 (1H, m), 3.67-3.78 (2H, m), 3.79-3.87 (1H, m), 4.03-4.19 (2H, m), 4.23-4.31 (1H, m), 4.53-4.58 (1H, m), 7.13 (1H, d, J = 8.1 Hz), 7.43 (1H, dd, J = 8.1, 2.3 Hz), 7.52 (2H, d, J = 8.8 Hz), 7.90 (2H, d, J = 8.8 Hz), 8.31 (1H, d, J = 2.3 Hz), 8.72 (1H, br t, J = 5.8 Hz), 12.52 (1H, br s). |
| 14 | 645 (M + H). | 1H-NMR (CD$_3$OD, 400 MHz) δ: 0.90 (3H, t, J = 7.4 Hz), 1.59 (2H, td, J = 15.0, 7.6 Hz), 2.42 (3H, s), 2.53 (2H, t, J = 7.5 Hz), 3.17-3.29 (1H, m), 3.51 (1H, dd, J = 13.8, 4.5 Hz), 3.85-4.03 (3H, m), 4.09 (1H, dd, J = 14.7, 5.4 Hz), 4.22 (1H, dd, J = 15.1, 6.3 Hz), 4.48 (1H, d, J = 13.7 Hz), 4.66 (1H, s), 7.01-7.09 (4H, m), 7.20-7.28 (2H, m), 7.95 (1H, t, J = 8.4 Hz), 8.47-8.53 (1H, br m). |

TABLE 230

| Example No. | MS ESI m/e: | NMR |
|---|---|---|
| 15 | 470 (M + H). | 1H-NMR (DMSO-d$_6$, 300 MHz) δ: 1.21 (6H, d, J = 6.8 Hz), 2.68 (1H, t, J = 10.0 Hz), 2.87-3.05 (2H, m), 3.17 (1H, d, J = 12.8 Hz), 3.50-3.63 (2H, m), 3.85 (1H, d, J = 13.9 Hz), 4.30 (2H, d, J = 4.5 Hz), 4.73 (1H, d, J = 3.8 Hz), 7.45 (2H, d, J = 6.4 Hz), 7.48 (2H, d, J = 5.7 Hz), 7.70 (2H, d, J = 8.3 Hz), 7.79 (2H, d, J = 8.7 Hz), 8.42 (1H, br s), 8.92 (1H, t, J = 5.7 Hz), 9.55 (1H, br s). |
| 16 | 484 (M + H). | 1H-NMR (DMSO-d$_6$, 300 MHz) δ: 1.21 (6H, d, J = 7.2 Hz), 1.60 (1H, t, J = 9.2 Hz), 1.80 (1H, dd, J = 11.7, 4.1 Hz), 2.02 (3H, s), 2.54-2.60 (1H, m), 2.93-3.02 (1H, m), 3.10 (1H, d, J = 11.7 Hz), 3.49 (1H, d, J = 15.1 Hz), 3.63 (1H, d, J = 12.8 Hz), 4.25-4.44 (3H, m), 7.39-7.46 (4H, m), 7.68 (2H, d, J = 7.9 Hz), 7.72 (2H, d, J = 8.3 Hz), 8.50 (1H, t, J = 5.5 Hz). |
| 17 | 548 (M + H). | 1H-NMR (DMSO-d$_6$, 300 MHz) δ: 1.20 (6H, d, J = 6.8 Hz), 2.62 (1H, dd, J = 13.0, 9.2 Hz), 2.80 (3H, s), 2.87 (1H, dd, J = 12.2, 3.6 Hz), 2.92-3.03 (1H, m), 3.48 (1H, d, J = 10.9 Hz), 3.61 (1H, t, J = 12.1 Hz), 3.75 (1H, d, J = 12.4 Hz), 3.95 (1H, d, J = 12.4 Hz), 4.32 (2H, ddd, J = 30.7, 16.0, 5.8 Hz), 4.61 (1H, d, J = 2.6 Hz), 7.41 (2H, d, J = 6.4 Hz), 7.44 (2H, d, J = 6.0 Hz), 7.65 (2H, d, J = 7.9 Hz), 7.71 (2H, d, J= 8.3 Hz), 8.69 (1H, t, J = 6.0 Hz). |
| 18 | 512 (M + H). | 1H-NMR (CDCl$_3$, 400 MHz) δ: 1.29 (6H, d, J = 7.1 Hz), 2.13 (3H, s), 2.36-2.47 (1H, m), 2.82 (1H, dd, J = 13.7, 4.4 Hz), 2.95-3.05 (1H, m), 3.12-3.22 (1H, m), 3.82 (1H, d, J = 14.1 Hz), 4.28 (1H, d, J = 13.5 Hz), 4.44-4.59 (4H, m), 7.14 (1H, t, J = 5.8 Hz), 7.34 (2H, d, J = 8.2 Hz), 7.41 (2H, d, J = 8.4 Hz), 7.60 (2H, d, J = 8.2 Hz), 7.77 (2H, d, J = 8.6 Hz). |

TABLE 231

| Example No. | MS ESI m/e: | NMR |
|---|---|---|
| 19 | 512 (M + H). | 1H-NMR (CDCl$_3$, 300 MHz) δ: 1.29 (6.3H, d, J = 6.8 Hz), 1.90 (0.4H, s), 2.13 (2.7H, s), 2.35-2.48 (1.0H, m), 2.81 (1.0H, dd, J = 13.8, 4.3 Hz), 2.93-3.07 (1.3H, m), 3.11-3.25 (1.2H, m), 3.83 (1.1H, d, J = 14.3 Hz), 4.28 (1.0H, d, J = 13.2 Hz), 4.43-4.61 (4.1H, m), 7.09-7.18 (1.0H, m), 7.34 (4.1H, d, J = 8.3 Hz), 7.41 (4.1H, d, J = 8.3 Hz), 7.61 (2.0H, d, J = 8.3 Hz), 7.77 (1.9H, d, J = 8.3 Hz). |
| 20 | 504 (M + H). | 1H-NMR (CDCl$_3$, 400 MHz) δ: 2.14 (3H, s), 2.40 (1H, ddd, J = 14.5, 11.2, 3.1 Hz), 2.83 (1H, dd, J = 13.3, 3.9 Hz), 3.19 (1H, ddd, J = 14.5, 11.2, 2.8 Hz), 3.83 (1H, dt, J = 14.4, 2.5 Hz), 4.33 (1H, dt, J = 13.2, 3.0 Hz), 4.44-4.60 (4H, m), 7.01 (1H, t, J = 5.0 Hz), 7.34 (2H, d, J = 7.7 Hz), 7.55 (2H, d, J = 8.4 Hz), 7.62 (2H, d, J = 8.2 Hz), 7.80 (2H, d, J = 8.6 Hz). |
| 21 | 504 (M + H). | 1H-NMR (CDCl$_3$, 400 MHz) δ: 2.20 (3H, s), 2.60 (1H, td, J = 12.8, 3.4 Hz), 3.12 (1H, ddd, J = 14.4, 12.0, 2.4 Hz), 3.25 (1H, dd, J = 13.3, |

TABLE 231-continued

| Example No. | MS ESI m/e: | NMR |
|---|---|---|
| | | 4.1 Hz), 3.82 (1H, dt, J = 14.1, 1.9 Hz), 4.40 (1H, dd, J = 15.1, 5.4 Hz), 4.49-4.67 (4H, m), 7.04 (1H, t, J = 5.4 Hz), 7.28 (2H, d, J = 8.2 Hz), 7.47 (2H, t, J = 7.1 Hz), 7.54 (1H, dd, J = 8.0, 1.2 Hz), 7.57 (2H, t, J = 8.3 Hz), 8.14 (1H, dd, J = 8.0, 1.7 Hz). |
| 22 | 548, 550 (M + H). | 1H-NMR (CDCl$_3$, 400 MHz) δ: 2.14 (3H, s), 2.40 (1H, ddd, J = 14.1, 11.4, 2.9 Hz), 2.83 (1H, dd, J = 13.5, 4.2 Hz), 3.19 (1H, ddd, J = 14.6, 11.4, 3.2 Hz), 3.82 (1H, dt, J = 14.7, 2.8 Hz), 4.33 (1H, d, J = 14.6 Hz), 4.44-4.60 (4H, m), 7.00 (1H, t, J = 5.5 Hz), 7.34 (2H, d, J = 7.9 Hz), 7.62 (2H, d, J = 8.2 Hz), 7.71-7.73 (4H, m). |
| 23 | 554, 556 (M + H). | 1H-NMR (CDCl$_3$, 400 MHz) δ: 2.17 (3H, s), 2.62 (1H, ddd, J = 13.8, 11.1, 2.6 Hz), 3.02 (1H, dd, J = 13.7, 4.2 Hz), 3.23 (1H, ddd, J = 14.4, 11.1, 3.1 Hz), 3.84(1H, dt, J = 14.0, 3.4 Hz), 4.33 (1H, d, J = 14.1 Hz), 4.44-4.61 (4H, m), 6.97 (1H, t, J = 6.3 Hz), 7.13 (1H, d, J = 3.7 Hz), 7.34 (2H, d, J = 7.9 Hz), 7.42 (1H, d, J = 4.0 Hz), 7.61 (2H, d, J = 8.2 Hz). |

TABLE 232

| Example No. | MS ESI m/e: | NMR |
|---|---|---|
| 24 | 470 (M + H). | 1H-NMR (CDCl$_3$, 300 MHz) δ: 2.13 (3H, s), 2.38 (1H, ddd, J = 14.5, 10.9, 3.0 Hz), 2.79 (1H, dd, J = 13.9, 4.1 Hz), 3.18 (1H, ddd, J = 13.9, 11.3, 2.8 Hz), 3.86 (1H, dt, J = 13.6, 2.8 Hz), 4.30 (1H, d, J = 12.8 Hz), 4.44-4.59 (4H, m), 7.05 (1H, t, J = 5.7 Hz), 7.34 (2H, d, J = 8.7 Hz), 7.54-7.68 (5H, m), 7.87 (2H, d, J = 7.5 Hz). |
| 25 | 596 (M + H). | 1H-NMR (CDCl$_3$, 400 MHz) δ: 2.15 (3H, s), 2.43 (1H, ddd, J = 13.9, 11.4, 2.8 Hz), 2.86 (1H, dd, J = 13.7, 4.2 Hz), 3.18 (1H, ddd, J = 14.7, 11.5, 3.3 Hz), 3.81 (1H, dt, J = 12.9, 2.4 Hz), 4.29 (1H, dt, J = 13.7, 2.6 Hz), 4.44-4.60 (4H, m), 7.03 (2H, d, J = 8.8 Hz), 7.07 (2H, d, J = 8.6 Hz), 7.12 (1H, t, J = 5.8 Hz), 7.34 (2H, d, J = 8.2 Hz), 7.41 (2H, d, J = 8.8 Hz), 7.61 (2H, d, J = 7.9 Hz), 7.80 (2H, d, J = 8.6 Hz). |
| 26 | 580 (M + H). | 1H-NMR (CDCl$_3$, 400 MHz) δ: 2.14 (3H, s), 2.45 (1H, ddd, J = 13.7, 11.2, 2.7 Hz), 2.86 (1H, dd, J = 14.0, 4.5 Hz), 3.21 (1H, ddd, J = 14.7, 11.7, 2.9 Hz), 3.88 (1H, dt, J = 14.2, 3.0 Hz), 4.32 (1H, d, J = 13.8, 2.7 Hz), 4.46-4.61 (4H, m), 7.09 (1H, t, J = 5.8 Hz), 7.34 (2H, d, J = 7.9 Hz), 7.48 (2H, d, J = 8.6 Hz), 7.54 (2H, d, J = 8.6 Hz), 7.60 (2H, d, J = 8.2 Hz), 7.74 (2H, d, J = 8.4 Hz), 7.92 (2H, d, J = 8.4 Hz). |
| 27 | 615 (M + H). | 1H-NMR (CDCl$_3$, 400 MHz) δ: 2.19 (3H, s), 2.23 (3H, s), 2.47 (1H, td, J = 12.7, 3.3 Hz), 2.57 (3H, s), 2.59-2.62 (1H, m), 3.04-3.13 (1H, m), 3.59 (1H, d, J = 13.5 Hz), 4.42-4.58 (4H, m), 4.66 (1H, d, J = 13.5 Hz), 6.90 (2H, d, J = 8.8 Hz), 7.08 (1H, t, J = 5.4 Hz), 7.25 (2H, d, J = 3.7 Hz), 7.31 (2H, d, J = 7.9 Hz), 7.60 (2H, d, J = 9.5 Hz), 7.62 (2H, d, J = 9.0 Hz). |

TABLE 233

| Example No. | MS ESI m/e: | NMR |
|---|---|---|
| 28 | 586 (M + H). | 1H-NMR (CDCl$_3$, 400 MHz) δ: 2.15 (3H, s), 2.66 (1H, ddd, J = 13.9, 10.9, 3.1 Hz), 3.05 (1H, dd, J = 14.1, 4.4 Hz), 3.26 (1H, ddd, J = 14.3, 10.4, 3.0 Hz), 3.90 (1H, dt, J = 14.5, 3.3 Hz), 4.32 (1H, dt, J = 13.5, 3.2 Hz), 4.45-4.61 (4H, m), 7.05 (1H, t, J = 5.4 Hz), 7.27 (1H, d, J = 4.0 Hz), 7.34 (2H, d, J = 8.2 Hz), 7.43 (2H, d, J = 8.4 Hz), 7.51 (2H, d, J = 8.6 Hz), 7.59 (2H, d, J = 8.2 Hz), 7.62 (1H, d, J = 3.5 Hz). |
| 29 | 504 (M + H). | 1H-NMR (CDCl$_3$, 400 MHz) δ: 2.14 (3H, s), 2.42 (1H, ddd, J = 14.8, 11.4, 3.4 Hz), 2.85 (1H, dd, J = 13.6, 3.4 Hz), 3.20 (1H, ddd, J = 15.1, 11.2, 3.2 Hz), 3.85 (1H, dt, J = 14.1, 2.5 Hz), 4.34 (1H, dt, J = 14.3, 3.3 Hz), 4.44-4.60 (4H, m), 6.97 (1H, t, J = 6.0 Hz), 7.34 (2H, d, J = 7.9 Hz), 7.52 (1H, t, J = 8.0 Hz), 7.58-7.65 (3H, m), 7.74 (1H, d, J = 7.7 Hz), 7.85 (1H, t, J = 2.0 Hz). |
| 30 | 526 (M + H). | 1H-NMR (CDCl$_3$, 400 MHz) δ: 1.35 (9H, s), 2.14 (3H, s), 2.42 (1H, ddd, J = 13.9, 10.7, 2.4 Hz), 2.82 (1H, dd, J = 13.3, 4.5 Hz), 3.18 (1H, ddd, J = 13.8, 11.3, 2.8 Hz), 3.83 (1H, dt, J = 14.5, 2.9 Hz), 4.28 (1H, dt, J = 13.4, 3.0 Hz), 4.45-4.59 (4H, m), 7.14 (1H, t, J = 5.3 Hz), 7.35 (2H, d, J = 7.9 Hz), 7.57 (2H, d, J = 7.9 Hz), 7.61 (2H, d, J = 7.9 Hz), 7.78 (2H, d, J = 7.7 Hz). |

TABLE 233-continued

| Example No. | MS ESI m/e: | NMR |
|---|---|---|
| 31 | 512 (M + H). | 1H-NMR (CDCl$_3$, 400 MHz) δ: 2.13 (3H, s), 2.35 (1H, ddd, J = 13.8, 10.9, 3.0 Hz), 2.67 (3H, s), 2.78 (1H, dd, J = 14.1, 4.6 Hz), 3.20 (1H, ddd, J = 14.8, 12.1, 3.3 Hz), 3.86 (1H, dt, J = 14.6, 2.5 Hz), 4.33 (1H, dt, J = 13.5, 2.9 Hz), 4.45-4.60 (4H, m), 7.03 (1H, t, J = 5.7 Hz), 7.34 (2H, d, J = 7.9 Hz), 7.61 (2H, d, J = 8.2 Hz), 7.97 (2H, d, J = 8.4 Hz), 8.12 (2H, d, J = 8.4 Hz). |

TABLE 234

| Example No. | MS ESI m/e: | NMR |
|---|---|---|
| 32 | 528 (M + H). | 1H-NMR (CDCl$_3$, 400 MHz) δ: 1.28 (6H, d, J = 6.8 Hz), 2.70-2.81 (1H, m), 2.96-3.03 (1H, m), 3.31 (1H, ddd, J = 14.7, 11.1, 4.1 Hz), 3.65 (3H, s), 3.68-3.82 (2H, m), 4.42-4.62 (5H, m), 7.04 (1H, t, J = 6.6 Hz), 7.37 (2H, d, J = 8.6 Hz), 7.39 (2H, d, J = 7.9 Hz), 7.60 (2H, d, J = 7.9 Hz), 7.75 (2H, d, J = 8.4 Hz). |
| 33 | 478 (M + H). | 1H-NMR (CDCl$_3$, 400 MHz) δ: 1.29 (6H, d, J = 7.0 Hz), 2.12 (3H, s), 2.36-2.47 (1H, m), 2.85 (1H, dd, J = 13.6, 4.5 Hz), 2.98-3.04 (1H, m), 3.15 (1H, t, J = 18.4 Hz), 3.84 (1H, d, J = 14.6 Hz), 4.30 (1H, d, J = 13.9 Hz), 4.45-4.62 (4H, m), 7.05 (1H, t, J = 10.0 Hz), 7.22-7.33 (3H, m), 7.38-7.42 (3H, m), 7.78 (2H, d, J = 8.6 Hz). |
| 34 | 478 (M + H). | 1H-NMR (CDCl$_3$, 400 MHz) δ: 1.29 (6H, d, J = 7.0 Hz), 2.12 (3H, s), 2.38-2.46 (1H, m), 2.85 (1H, dd, J = 13.6, 4.5 Hz), 2.98-3.04 (1H, m), 3.11-3.18 (1H, m), 3.84 (1H, d, J = 14.6 Hz), 4.30 (1H, d, J = 13.9 Hz), 4.48-4.59 (4H, m), 7.04 (1H, br s), 7.22-7.33 (3H, m), 7.37-7.40 (3H, m), 7.78 (2H, d, J = 10.7 Hz). |
| 35 | 478 (M + H). | 1H-NMR (CDCl$_3$, 400 MHz) δ: 1.30 (6H, d, J = 7.0 Hz), 2.15 (3H, s), 2.36-2.45 (1H, m), 2.82 (1H, dd, J = 13.7, 4.4 Hz), 2.97-3.05 (1H, m), 3.11-3.19 (1H, m), 3.83 (1H, d, J = 14.8 Hz), 4.28 (1H, d, J = 13.7 Hz), 4.37-4.53 (4H, m), 7.03 (1H, br s), 7.17 (2H, d, J = 8.6 Hz), 7.33 (2H, d, J = 8.3 Hz), 7.42 (2H, d, J = 8.3 Hz), 7.77 (2H, d, J = 8.3 Hz). |
| 36 | 520 (M + H). | 1H-NMR (CDCl$_3$, 400 MHz) δ: 1.29 (6H, d, J = 7.0 Hz), 2.18 (3H, s), 2.36-2.47 (1H, m), 2.83 (1H, dd, J = 13.6, 4.3 Hz), 2.96-3.05 (1H, m), 3.17-3.21 (1H, m), 3.85 (1H, d, J = 14.1 Hz), 4.31 (1H, d, J = 13.9 Hz), 4.44-4.58 (4H, m), 7.02 (1H, t, J = 4.9 Hz), 7.29-7.47 (7H, m), 7.59-7.61 (4H, m), 7.78 (2H, d, J = 6.6 Hz). |

TABLE 235

| Example No. | MS ESI m/e: | NMR |
|---|---|---|
| 37 | 487 (M + H). | 1H-NMR (CDCl$_3$, 400 MHz) δ: 1.29 (6H, d, J = 7.0 Hz), 2.17 (3H, s), 2.36-2.45 (1H, m), 2.78-2.86 (1H, m), 2.96 (6H, s), 2.98-3.05 (1H, m), 3.07-3.17 (1H, m), 3.82 (1H, d, J = 14.4 Hz), 4.25-4.43 (3H, m), 4.46-4.55 (2H, m), 6.78 (3H, br s), 7.10 (2H, d, J = 8.8 Hz), 7.39 (2H, d, J = 8.3 Hz), 7.75 (2H, d, J = 8.6 Hz). |
| 38 | 523 (M + H). | 1H-NMR (CDCl$_3$, 400 MHz) δ: 1.30 (6H, d, J = 7.0 Hz), 2.10 (3H, s), 2.37-2.46 (1H, m), 2.80 (1H, dd, J = 13.4, 4.2 Hz), 2.97-3.06 (1H, m), 3.15-3.24 (1H, m), 3.76-3.85 (1H, m), 4.18-4.25 (1H, m), 4.41-4.58 (4H, m), 5.03 (2H, s), 7.38 (2H, d, J = 8.3 Hz), 7.44 (2H, d, J = 8.3 Hz), 7.79 (2H, d, J = 8.3 Hz), 7.88 (2H, d, J = 8.3 Hz). |
| 39 | 527 (M + H). | 1H-NMR (CDCl$_3$, 400 MHz) δ: 2.15 (3H, s), 2.25 (3H, s), 2.42 (1H, ddd, J = 13.7, 10.9, 3.1 Hz), 2.85 (1H, dd, J = 14.3, 4.8 Hz), 3.14-3.28 (1H, m), 3.83 (1H, dt, J = 14.3, 2.8 Hz), 4.29 (1H, dt, J = 13.6, 3.0 Hz), 4.45-4.61 (4H, m), 7.10 (1H, t, J = 5.6 Hz), 7.34 (2H, d, J = 8.1 Hz), 7.51 (1H, br s), 7.61 (2H, d, J = 7.7 Hz), 7.74 (2H, d, J = 8.8 Hz), 7.81 (2H, d, J = 8.3 Hz). |
| 40 | 515 (M + H). | 1H-NMR (CDCl$_3$, 400 MHz) δ: 1.99 (1.2H, s), 2.15 (1.8H, s), 2.38 (0.6H, ddd, J = 14.1, 11.2, 3.0 Hz), 2.83 (0.6H, dd, J = 13.9, 4.9 Hz), 3.03-3.42 (1.8H, m), 3.73-3.92 (1H, m), 4.28-4.64 (5H, m), 6.97 (0.6H, t, J = 5.7 Hz), 7.04 (0.4H, t, J = 5.3 Hz), 7.34 (0.8H, d, J = 7.2 Hz), 7.36 (1.2H, d, J = 8.1 Hz), 7.59 (0.8H, d, J = 7.7 Hz), 7.63 (1.2H, d, J = 9.0 Hz), 8.06 (0.8H, d, J = 8.6 Hz), 8.08 (1.2H, d, J = 9.7 Hz), 8.34 (0.8H, d, J = 9.3 Hz), 8.43 (1.2H, d, J = 9.7 Hz). |

TABLE 236

| Example No. | MS ESI m/e: | NMR |
|---|---|---|
| 41 | 538 (M + H). | 1H-NMR (CDCl₃, 400 MHz) δ: 2.16 (3H, s), 2.45 (1H, ddd, J = 14.0, 11.1, 3.1 Hz), 2.89 (1H, dd, J = 13.8, 4.3 Hz), 3.22 (1H, ddd, J = 14.4, 11.1, 3.5 Hz), 3.84 (1H, dt, J = 14.1, 2.8 Hz), 4.34-4.64 (5H, m), 6.98 (1H, t, J = 5.6 Hz), 7.35 (2H, d, J = 7.7 Hz), 7.58-7.71 (4H, m), 7.96 (1H, d, J = 2.6 Hz). |
| 42 | 546 (M + H). | 1H-NMR (CDCl₃, 400 MHz) δ: 2.14 (3H, s), 2.44 (1H, ddd, J = 13.9, 10.8, 2.8 Hz), 2.86 (1H, dd, J = 12.5, 4.2 Hz), 3.21 (1H, ddd, J = 14.6, 11.5, 3.4 Hz), 3.91 (1H, dt, J = 14.7, 3.1 Hz), 4.33 (1H, dt, J = 13.5, 3.1 Hz), 4.45-4.61 (4H, m), 7.09 (1H, t, J = 6.5 Hz), 7.34 (2H, d, J = 8.3 Hz), 7.44-7.54 (3H, m), 7.59 (2H, d, J = 2.6 Hz), 7.61 (2H, d, J = 3.7 Hz), 7.65 (1H, t, J = 7.8 Hz), 7.84 (1H, dt, J = 8.0, 1.0 Hz), 7.89 (1H, dt, J = 7.5, 1.2 Hz), 8.08 (1H, t, J = 1.5 Hz). |
| 43 | 611 (M + H). | 1H-NMR (CDCl₃, 400 MHz) δ: 2.17 (3H, s), 2.62 (1H, ddd, J = 14.6, 11.1, 3.3 Hz), 3.05 (1H, dd, J = 13.6, 4.8 Hz), 3.29 (1H, ddd, J = 15.4, 10.6, 3.5 Hz), 3.92 (1H, dt, J = 14.0, 3.0 Hz), 4.36 (1H, dt, J = 13.8, 3.1 Hz), 4.46-4.65 (4H, m), 6.97-7.00 (1H, m), 7.00 (1H, s), 7.36 (2H, d, J = 7.9 Hz), 7.51 (1H, d, J = 3.7 Hz), 7.61 (2H, d, J = 7.9 Hz), 7.69 (1H, d, J = 4.4 Hz). |
| 44 | 500 (M + H). | 1H-NMR (CDCl₃, 400 MHz) δ: 2.13 (3H, s), 2.42 (1H, ddd, J = 13.9, 10.8, 3.0 Hz), 2.83 (1H, dd, J = 14.1, 4.6 Hz), 3.16 (1H, ddd, J = 14.6, 11.5, 3.0 Hz), 3.81 (1H, dt, J = 13.8, 2.9 Hz), 3.89 (3H, s), 4.28 (1H, dt, J = 13.3, 3.0 Hz), 4.45-4.59 (4H, m), 7.02 (2H, d, J = 8.8 Hz), 7.11 (1H, t, J = 6.0 Hz), 7.33 (2H, d, J = 7.9 Hz), 7.60 (2H, d, J = 8.2 Hz), 7.78 (2H, d, J = 9.0 Hz). |
| 45 | 538 (M + H). | 1H-NMR (CDCl₃, 400 MHz) δ: 2.14 (3H, s), 2.38 (1H, ddd, J = 14.3, 11.4, 3.1 Hz), 2.81 (1H, dd, J = 13.2, 3.7 Hz), 3.22 (1H, ddd, J = 14.4, 11.5, 3.1 Hz), 3.85 (1H, dt, J = 14.3, 2.8 Hz), 4.36 (1H, dt, J = 14.1, 2.5 Hz), 4.43-4.61 (4H, m), 6.98 (1H, t, J = 6.0 Hz), 7.35 (2H, d, J = 7.9 Hz), 7.62 (2H, d, J = 8.2 Hz), 7.85 (2H, d, J = 8.4 Hz), 8.00 (2H, d, J = 8.2 Hz). |

Table 237

| Example No. | MS ESI m/e: | NMR |
|---|---|---|
| 46 | 495 (M + H). | 1H-NMR (CDCl₃, 400 MHz) δ: 1.98 (0.9H, s), 2.14 (2.1H, s), 2.36 (0.7H, ddd, J = 14.1, 11.0, 3.2 Hz), 2.80 (0.7H, dd, J = 13.6, 4.1 Hz), 3.04 (0.3H, dd, J = 14.8, 3.7 Hz), 3.16 (0.3H, td, J = 11.8, 2.9 Hz), 3.23 (0.7H, ddd, J = 14.0, 11.4, 2.9 Hz), 3.35 (0.3H, ddd, J = 14.3, 11.3, 3.5 Hz), 3.70-3.78 (0.3H, m), 3.84 (0.7H, dt, J = 13.7, 2.7 Hz), 4.32-4.61 (5H, m), 6.95 (0.7H, t, J = 5.7 Hz), 7.01 (0.3H, t, J = 5.4 Hz), 7.35 (2H, d, J = 7.9 Hz), 7.58 (0.6H, d, J = 8.4 Hz), 7.62 (1.4H, d, J = 7.9 Hz), 7.77 (0.6H, d, J = 8.4 Hz), 7.88 (1.4H, d, J = 8.6 Hz), 7.99 (2H, d, J = 7.1 Hz). |
| 47 | 616 (M + H). | 1H-NMR (CDCl₃, 400 MHz) δ: 2.15 (3H, s), 2.56 (1H, ddd, J = 14.1, 11.0, 3.1 Hz), 2.96 (1H, dd, J = 13.5, 4.0 Hz), 3.27(1H, ddd, J = 14.3, 11.4, 3.5 Hz), 3.84 (1H, dt, J = 14.3, 3.0 Hz), 4.35 (1H, dt, J = 13.2, 3.4 Hz), 4.40-4.63 (4H, m), 6.88 (1H, t, J = 6.7 Hz), 7.34 (2H, d, J = 7.7 Hz), 7.53-7.71 (7H, m), 8.00 (2H, d, J = 7.3 Hz). |
| 48 | 512(M + H). | 1H-NMR (CDCl₃, 400 MHz) δ: 2.14 (3H, s), 2.48 (1H, ddd, J = 13.9, 10.8, 3.1 Hz), 2.87 (1H, dd, J = 13.2, 4.0 Hz), 3.16 (1H, ddd, J = 14.7, 11.5, 3.4 Hz), 3.27 (2H, t, J = 8.9 Hz), 3.80 (1H, dt, J = 14.0, 3.0 Hz), 4.28 (1H, dt, J = 13.9, 3.1 Hz), 4.44-4.60 (4H, m), 4.72 (2H, t, J = 8.8 Hz), 6.88 (1H, d, J = 8.4 Hz), 7.13 (1H, t, J = 5.1 Hz), 7.34 (2H, d, J = 7.9 Hz), 7.61 (2H, d, J = 8.2 Hz), 7.64 (1H, d, J = 8.6 Hz), 7.66 (1H, s). |
| 49 | 444 (M + H). | 1H-NMR (CDCl₃, 400 MHz) δ: 1.28 (6H, d, J = 6.8 Hz), 2.15 (3H, s), 2.35-2.45 (1H, m), 2.77-2.85 (1H, m), 2.92-3.05 (1H, m), 3.09-3.19 (1H, m), 3.82(1H, d, J = 14.3 Hz), 4.28 (1H, d, J = 14.3 Hz), 4.40-4.54 (4H, m), 6.95 (1H, t, J = 5.6 Hz), 7.21 (2H, d, J = 7.7 Hz), 7.28-7.40 (5H, m), 7.75 (2H, d, J = 7.7 Hz). |

TABLE 238

| Example No. | MS ESI m/e: | NMR |
|---|---|---|
| 50 | 474 (M + H). | 1H-NMR. (CDCl$_3$, 400 MHz) δ: 1.29 (6H, d, J = 7.0 Hz), 2.13 (3H, s), 2.29-2.38 (1H, m), 2.73-2.81 (1H, m), 2.94-3.05 (1H, m), 3.06-3.17 (1H, m), 3.82 (1H, d, J = 14.4 Hz), 3.88 (3H, s), 4.26 (1H, d, J = 13.7 Hz), 4.37-4.52 (4H, m), 6.89-6.95 (2H, m), 7.21 (1H, d, J = 7.7 Hz), 7.28-7.33 (1H, m), 7.39 (2H, d, J = 8.3 Hz), 7.76 (2H, d, J = 8.3 Hz). |
| 51 | 474 (M + H). | 1H-NMR (CDCl$_3$, 400 MHz) δ: 1.30 (6H, d, J = 7.0 Hz), 2.16 (3H, s), 2.37-2.46 (1H, m), 2.83 (1H, dd, J = 13.7, 4.4 Hz), 2.96-3.05 (1H, m), 3.11-3.20 (1H, m), 3.82 (3H, s), 3.84-3.88 (1H, m), 4.29 (1H, d, J = 13.4 Hz), 4.44 (2H, d, J = 5.8 Hz), 4.49-4.54 (2H, m), 6.77-6.87 (3H, m), 6.97 (1H, br s), 7.27 (1H, s), 7.41 (2H, d, J = 8.3 Hz), 7.77 (2H, d, J = 8.3 Hz). |
| 52 | 474 (M + H). | 1H-NMR (CDCl$_3$, 400 MHz) δ: 1.29 (6H, d, J = 7.0 Hz), 2.16 (3H, s), 2.35-2.45 (1H, m), 2.82 (1H, dd, J = 13.2, 3.9 Hz), 2.96-3.05 (1H, m), 3.08-3.18 (1H, m), 3.79-3.86 (1H, m), 3.82 (3H, s), 4.29 (1H, d, J = 14.1 Hz), 4.33-4.54 (4H, m), 6.85-6.91 (3H, m), 7.15 (2H, d, J = 8.8 Hz), 7.40 (2H, d, J = 8.3 Hz), 7.76 (2H, d, J = 8.3 Hz). |
| 53 | 528 (M + H). | 1H-NMR (CDCl$_3$, 400 MHz) δ: 1.30 (6H, d, J = 7.0 Hz), 2.15 (3H, s), 2.36-2.47 (1H, m), 2.81 (1H, dd, J = 13.7, 4.4 Hz), 2.94-3.07 (1H, m), 3.12-3.22 (1H, m), 3.84 (1H, d, J = 14.6 Hz), 4.29 (1H, d, J = 14.6 Hz), 4.40-4.55 (4H, m), 7.08 (1H, br s), 7.21 (2H, d, J = 8.1 Hz), 7.21 (2H, s), 7.27 (2H, d, J = 8.8 Hz), 7.42 (2H, d, J = 8.1 Hz), 7.78 (2H, d, J = 8.3 Hz). |
| 54 | 523, 525 (M + H). | 1H-NMR (CDCl$_3$, 400 MHz) δ: 1.30 (6H, d, J = 7.0 Hz), 2.15 (3H, s), 2.36-2.45 (1H, m), 2.82 (1H, dd, J = 13.7, 4.4 Hz), 2.97-3.06 (1H, m), 3.11-3.19 (1H, m), 3.83 (1H, d, J = 14.1 Hz), 4.28 (1H, d, J = 14.6 Hz), 4.36-4.52 (4H, m), 7.03 (1H, br s), 7.11 (2H, d, J = 8.3 Hz), 7.42 (2H, d, J = 8.3 Hz), 7.48 (2H, d, J = 8.6 Hz), 7.77 (2H, d, J = 8.6 Hz). |

TABLE 239

| Example No. | MS ESI m/e: | NMR |
|---|---|---|
| 55 | 528 (M + H). | 1H-NMR (CDCl$_3$, 400 MHz) δ: 1.28 (6H, d, J = 6.8 Hz), 2.50-2.59 (1H, m), 2.75 (1H, dd, J = 13.3, 4.1 Hz), 2.95-3.05 (1H, m), 3.14-3.28 (2H, m), 3.88 (1H, d, J = 14.3 Hz), 4.06 (1H, d, J = 15.2 Hz), 4.18 (1H, d, J = 13.0 Hz), 4.26 (1H, d, J = 13.7 Hz), 4.41-4.60 (4H, m), 7.11 (1H, t, J = 6.0 Hz), 7.34 (2H, d, J = 7.9 Hz), 7.42 (2H, d, J = 8.4 Hz), 7.61 (2H, d, J = 7.9 Hz), 7.77 (2H, d, J = 8.4 Hz). |
| 56 | 556 (M + H). | 1H-NMR (CDCl$_3$, 400 MHz) δ: 1.29 (6H, d, J = 6.8 Hz), 1.38 (3H, s), 1.42 (3H, s), 2.75-2.90 (2H, m), 2.94-3.07 (1H, m), 3.28-3.38 (1H, m), 3.77 (1H, dt, J = 13.9, 3.6 Hz), 4.10-4.38 (2H, m), 4.45 (1H, s), 4.51 (2H, d, J = 5.3 Hz), 5.34 (1H, d, J = 13.2 Hz), 7.36 (2H, d, J = 7.9 Hz), 7.41 (2H, d, J = 8.2 Hz), 7.60 (2H, d, J = 7.9 Hz), 7.76 (2H, d, J = 8.6 Hz). |
| 57 | 542 (M + H). | 1H-NMR (CDCl$_3$, 400 MHz) δ: 1.29 (6H, d, J = 7.1 Hz), 2.47 (1H, t, J = 11.0 Hz), 2.82 (1H, dd, J = 13.7, 4.0 Hz), 2.95-3.05 (1H, m), 3.14-3.29 (1H, m), 3.37 (3H, s), 3.84 (1H, d, J = 14.6 Hz), 4.15 (1H, d, J = 13.7 Hz), 4.22-4.31 (2H, m), 4.40-4.59 (4H, m), 7.16 (1H, br s), 7.34 (2H, d, J = 7.5 Hz), 7.41 (2H, d, J = 8.2 Hz), 7.60 (2H, d, J = 7.9 Hz), 7.77 (2H, d, J = 8.6 Hz). |
| 58 | 542 (M + H). | 1H-NMR (CDCl$_3$, 400 MHz) δ: 1.29 (6H, d, J = 6.8 Hz), 2.38-2.50 (2H, m), 2.77 (1H, dd, J = 13.8, 4.3 Hz), 2.87 (1H, dq, J = 16.9, 3.0 Hz), 2.94-3.08 (2H, m), 3.12-3.23 (1H, m), 3.69-3.93 (3H, m), 4.29 (1H, d, J = 13.7 Hz), 4.43-4.59 (4H, m), 7.16 (1H, br s), 7.34 (2H, d, J = 7.9 Hz), 7.42 (2H, d, J = 8.4 Hz), 7.60 (2H, d, J = 8.2 Hz), 7.77 (2H, d, J = 8.4 Hz). |
| 59 | 541 (M + H). | 1H-NMR (CDCl$_3$, 400 MHz) δ: 1.28 (6H, d, J = 6.8 Hz), 2.51-2.61 (1H, m), 2.64 (1H, dd, J = 13.2, 4.4 Hz), 2.79 (6H, s), 2.93-3.05 (1H, m), 3.29-3.38 (2H, m), 3.80 (1H, d, J = 13.7 Hz), 4.15 (1H, d, J = 13.0 Hz), 4.44-4.51 (2H, m), 4.60 (1H, dd, J = 15.4, 6.0 Hz), 7.34 (1H, br s), 7.36-7.41 (4H, m), 7.59 (2H, d, J = 7.9 Hz), 7.76 (2H, d, J = 8.4 Hz). |

TABLE 240

| Example No. | MS ESI m/e: | NMR |
|---|---|---|
| 60 | 498 (M + H). | 1H-NMR (CDCl$_3$, 400 MHz) δ: 1.28 (3H, t, J = 7.6 Hz), 2.13 (3H, s), 2.40 (114, ddd, J = 14.3, 11.1, 3.3 Hz), 2.75 (2H, q, J = 7.6 Hz), 2.81 (1H, dd, J = 13.5, 4.2 Hz), 3.17 (1H, ddd, J = 14.8, 11.2, 3.0 Hz), 3.83 (1H, dt, J = 14.6, 2.6 Hz), 4.28 (1H, dt, J = 14.6, 2.6 Hz), 4.45-4.59 (4H, m), 7.12 (1H, t, J = 5.3 Hz), 7.34 (2H, d, J = 7.9 Hz), 7.38 (2H, d, J = 8.4 Hz), 7.61 (2H, d, J = 7.9 Hz), 7.76 (2H, d, J = 8.2 Hz). |
| 61 | 596 (M + H). | 1H-NMR (CDCl$_3$, 400 MHz) δ: 2.14 (3H, s), 2.40 (1H, ddd, J = 14.0, 11.1, 3.1 Hz), 2.83 (1H, dd, J = 14.0, 3.9 Hz), 3.18 (1H, ddd, J = 14.9, 11.4, 3.3 Hz), 3.82 (1H, dt, J = 13.7, 2.9 Hz), 4.33 (1H, dt, J = 13.9, 3.1 Hz), 4.44-4.59 (4H, m), 7.03 (1H, t, J = 5.1 Hz), 7.34 (2H, d, J = 8.2 Hz), 7.56 (2H, d, J = 8.6 Hz), 7.62 (2H, d, J = 7.9 Hz), 7.93 (2H, d, J = 8.6 Hz). |
| 62 | 576 (M + H). | 1H-NMR. (CDCl$_3$, 400 MHz) δ: 2.16 (3H, s), 2.65 (1H, ddd, J = 14.1, 11.3, 2.9 Hz), 3.08 (1H, dd, J = 13.3, 4.1 Hz), 3.25 (1H, ddd, J = 14.5, 11.0, 3.4 Hz), 3.87 (1H, dt, J = 14.3, 2.9 Hz), 4.33 (1H, dt, J = 14.0, 3.1 Hz), 4.45-4.61 (4H, m), 6.94 (1H, d, J = 4.2 Hz), 7.02 (1H, t, J = 5.3 Hz), 7.34 (2H, d, J = 8.2 Hz), 7.52 (1H, d, J = 4.0 Hz), 7.59 (2H, d, J = 7.9 Hz), 7.64 (1H, s), 7.86 (1H, s). |
| 63 | 498 (M + H). | 1H-NMR (CDCl$_3$, 400 MHz) δ: 1.28 (6H, d, J = 7.1 Hz), 2.45 (1H, td, J = 13.5, 4.0 Hz), 2.86 (1H, dd, J = 13.3, 4.3 Hz), 2.96-3.05 (1H, m), 3.10 (1H, ddd, J = 14.8, 11.7, 3.3 Hz), 3.88 (1H, d, J = 14.3 Hz), 4.14 (1H, d, J = 13.5 Hz), 4.28 (1H, d, J = 13.5 Hz), 4.45-4.53 (3H, m), 7.05 (1H, t, J = 6.1 Hz), 7.34 (2H, d, J = 8.2 Hz), 7.42 (2H, d, J = 8.4 Hz), 7.60 (2H, d, J = 8.2 Hz), 7.78 (2H, d, J = 8.4 Hz), 8.02 (1H, s). |

TABLE 241

| Example No. | MS ESI m/e: | NMR |
|---|---|---|
| 64 | 484 (M + H). | 1H-NMR (CDCl$_3$, 400 MHz) δ: 2.13 (3H, s), 2.39 (1H, ddd, J = 13.9, 11.3, 2.7 Hz), 2.46 (3H, s), 2.80 (1H, dd, J = 13.7, 4.4 Hz), 3.16 (1H, ddd, J = 14.6, 11.5, 3.4 Hz), 3.83 (1H, dt, J = 14.8, 2.8 Hz), 4.28 (1H, dt, J = 13.8, 2.8 Hz), 4.44-4.59 (4H, m), 7.09 (1H, t, J = 5.5 Hz), 7.34 (2H, d, J = 8.6 Hz), 7.36 (2H, d, J = 8.6 Hz), 7.61 (2H, d, J = 8.2 Hz), 7.74 (2H, d, J = 8.2 Hz). |
| 65 | 554 (M + H). | 1H-NMR (CDCl$_3$, 400 MHz) δ: 2.14 (3H, s), 2.42 (1H, ddd, J = 13.7, 11.0, 3.1 Hz), 2.84 (1H, dd, J = 13.3, 4.1 Hz), 3.21 (1H, ddd, J = 14.6, 11.5, 2.9 Hz), 3.83 (1H, dt, J = 13.9, 2.7 Hz), 4.34 (1H, dt, J = 14.2, 3.0 Hz), 4.43-4.60 (4H, m), 7.03 (1H, t, J = 5.5 Hz), 7.34 (2H, d, J = 8.2 Hz), 7.39 (2H, d, J = 8.2 Hz), 7.61 (2H, d, J = 8.2 Hz), 7.92 (2H, d, J = 8.6 Hz). |
| 66 | 563 (M + H). | 1H-NMR (DMSO-d$_6$, 300 MHz) δ: 1.76 (1.5H, s), 1.91 (1.5H, s), 2.52-2.61 (0.5H, m), 2.93 (0.5H, dd, J = 13.4, 5.1 Hz), 3.08-3.23 (1H, m), 3.40 (0.5H, td, J = 12.5, 4.4 Hz), 3.53-3.85 (2H, m), 3.98-4.32 (3H, m), 4.42-4.64 (1.5H, m), 7.12-7.19 (2H, m), 7.39-7.44 (2H, m), 7.53-7.73 (4H, m), 7.77 (1H, d, J = 7.9 Hz), 7.85 (1H, d, J = 7.9 Hz), 8.49-8.55 (2H, m), 8.71 (0.5H, t, J = 5.8 Hz), 8.81 (0.5H, t, J = 5.5 Hz). |
| 67 | 462 (M + H). | 1H-NMR (CDCl$_3$, 300 MHz) δ 1.28 (6H, d, J = 6.9 Hz), 2.12 (3H, s), 2.30-2.50 (1H, m), 2.90-3.05 (1H, m), 3.05-3.20 (1H, m), 3.83 (1H, d, J = 14.1 Hz), 4.28 (1H, d, J = 13.8 Hz), 4.40-4.60 (4H, m), 6.95 (1H, brs), 7.00-7.15 (2H, m), 7.20-7.30 (2H, m), 7.40 (2H, d, J = 8.4 Hz), 7.76 (2H, d, J = 8.3 Hz). |
| 68 | 500 (M + H). | 1H-NMR (CDCl$_3$, 300 MHz) δ: 1.28 (6H, d, J = 7.2 Hz), 1.32 (9H, s), 2.15 (3H, s), 2.32-2.47 (1H, m), 2.80 (1H, dd, J = 13.9, 4.5 Hz), 2.93-3.06 (1H, m), 3.09-3.23 (1H, m), 3.83 (1H, d, J = 13.9 Hz), 4.29 (1H, d, J = 13.6 Hz), 4.35-4.56 (4H, m), 6.89 (1H, br s), 7.15 (2H, d, J = 7.9 Hz), 7.33-7.44 (4H, m), 7.76 (2H, d, J = 7.9 Hz). |

Table 242

| Example No. | MS ESI m/e: | NMR |
|---|---|---|
| 69 | 583, 585 (M + H). | 1H-NMR (CDCl$_3$, 400 MHz) δ: 2.00 (1.5H, s), 2.15 (1.5H, s), 2.49 (0.5H, t, J = 11.8 Hz), 2.96 (0.5H, t, J = 6.7 Hz), 3.03-3.17 (1H, m), |

Table 242-continued

| Example No. | MS ESI m/e: | NMR |
|---|---|---|
| | | 3.28 (0.5H, t, J = 11.1 Hz), 3.39 (0.5H, t, J = 10.5 Hz), 3.73-3.87 (1.5H, m), 4.27-4.62 (3.5H, m), 4.69-4.73 (0.5H, m), 4.95-5.03 (0.5H, m), 6.90 (0.5H, t, J = 6.1 Hz), 7.01 (0.5H, t, J = 6.5 Hz), 7.35 (2H, d, J = 7.3 Hz), 7.58 (1H, d, J = 7.7 Hz), 7.62 (1H, d, J = 7.7 Hz), 8.34 (1H, d, J = 9.7 Hz), 8.74 (1H, d, J = 13.9 Hz). |
| 70 | 556 (M + H). | 1H-NMR (CDCl$_3$, 400 MHz) δ: 2.14 (3H, s), 2.52 (1H, t, J = 10.9 Hz), 2.96 (1H, d, J = 13.2 Hz), 3.20 (1H, t, J = 12.1 Hz), 3.67-3.87 (9H, m), 4.30 (1H, d, J = 13.2 Hz), 4.45-4.62 (4H, m), 6.63 (1H, d, J = 8.8 Hz), 7.18 (1H, t, J = 6.0 Hz), 7.35 (2H, d, J = 8.4 Hz), 7.61 (2H, d, J = 8.4 Hz), 7.79 (1H, d, J = 9.5 Hz), 8.58 (1H, s). |
| 71 | 500 (M + H). | 1H-NMR (CDCl$_3$, 400 MHz) δ: 2.14 (3H, s), 2.43 (1H, ddd, J = 14.2, 11.3, 2.9 Hz), 2.83 (1H, dd, J = 13.8, 4.3 Hz), 3.17 (1H, ddd, J = 14.4, 11.4, 2.9 Hz), 3.86 (3H, s), 3.86-3.90 (1H, m), 4.31 (1H, dt, J = 13.2, 2.7 Hz), 4.43-4.59 (4H, m), 7.03 (1H, t, J = 5.3 Hz), 7.16 (1H, d, J = 8.6 Hz), 7.31-7.37 (3H, m), 7.40-7.50 (2H, m), 7.61 (2H, d, J = 8.2 Hz). |
| 72 | 512 (M + H). | 1H-NMR (CDCl$_3$, 400 MHz) δ: 0.96 (3H, t, J = 7.3 Hz), 1.68 (2H, dd, J = 15.0, 7.5 Hz), 2.13 (3H, s), 2.40 (1H, ddd, J = 13.9, 11.0, 2.7 Hz), 2.68 (2H, t, J = 7.7 Hz), 2.80 (1H, dd, J = 13.6, 4.5 Hz), 3.17 (1H, ddd, J = 14.7, 11.2, 3.4 Hz), 3.83 (1H, dt, J = 14.1, 3.0 Hz), 4.28 (1H, dt, J = 13.3, 2.3 Hz), 4.45-4.59 (4H, m), 7.10 (1H, t, J = 6.1 Hz), 7.34 (2H, d, J = 9.0 Hz), 7.36 (2H, d, J = 8.6 Hz), 7.61 (2H, d, J = 7.9 Hz), 7.76 (2H, d, J = 8.4 Hz). |

TABLE 243

| Example No. | MS ESI m/e: | NMR |
|---|---|---|
| 73 | 546 (M + H). | 1H-NMR. (CDCl$_3$, 400 MHz) 6: 2.14 (3H, s), 2.47 (1H, ddd, J = 14.1, 11.0, 3.0 Hz), 2.87 (1H, dd, J = 13.7, 4.2 Hz), 3.21 (1H, ddd, J = 14.6, 11.0, 3.3 Hz), 3.89 (1H, dt, J = 14.4, 3.0 Hz), 4.32 (1H, dt, J = 13.8, 3.5 Hz), 4.46-4.61 (4H, m), 7.10 (1H, t, J = 5.4 Hz), 7.34 (2H, d, J = 8.4 Hz), 7.44-7.53 (3H, m), 7.59 (2H, d, J = 7.3 Hz), 7.61 (2H, d, J = 6.6 Hz), 7.77 (2H, d, J = 8.4 Hz), 7.92 (2H, d, J = 8.6 Hz). |
| 74 | 526 (M + H). | 1H-NMR (CDCl$_3$, 400 MHz) δ: 2.14 (3H, s), 2.63 (1H, ddd, J = 14.3, 11.0, 3.3 Hz), 3.04 (1H, dd, J = 13.8, 4.1 Hz), 3.24 (1H, ddd, J = 14.3, 11.2, 3.4 Hz), 3.95 (1H, dt, J = 14.6, 2.9 Hz), 4.35 (1H, dt, J = 13.4, 2.9 Hz), 4.44-4.61 (4H, m), 7.01 (1H, t, J = 5.5 Hz), 7.30 (2H, d, J = 7.9 Hz), 7.50-7.60 (4H, m), 7.87 (1H, d, J = 8.2 Hz), 7.92 (1H, d, J = 7.1 Hz), 7.94 (1H, s). |
| 75 | 518 (M + H). | 1H-NMR (CDCl$_3$, 400 MHz) δ: 1.35 (6H, d, J = 6.6 Hz), 2.16 (3H, s), 2.61 (1H, ddd, J = 14.3, 10.4, 3.0 Hz), 2.99 (1H, dd, J = 12.8, 3.5 Hz), 3.17-3.27 (2H, m), 3.84 (1H, dt, J = 14.8, 3.0 Hz), 4.28 (1H, dt, J = 13.5, 3.1 Hz), 4.47-4.59 (4H, m), 6.85 (1H, d, J = 3.1 Hz), 7.10 (1H, t, J = 5.5 Hz), 7.35 (2H, d, J = 7.5 Hz), 7.50 (1H, s), 7.61 (2H, d, J = 8.2 Hz). |
| 76 | 502 (M + H). | 1H-NMR (CDCl$_3$, 300 MHz) δ: 1.28 (6H, d, J = 6.8 Hz), 2.14 (3H, s), 2.33-2.47 (1H, m), 2.82 (1H, dd, J = 13.6, 4.1 Hz), 2.92-3.06 (1H, m), 3.09-3.23 (1H, m), 3.83 (1H, d, 3 = 14.3 Hz), 3.92 (3H, s), 4.28 (1H, d, J = 13.6 Hz), 4.43-4.59 (4H, m), 7.08 (1H, br s), 7.28 (2H, d, J = 8.3 Hz), 7.41 (2H, d, J = 8.3 Hz), 7.77 (2H, d, J = 8.3 Hz), 8.02 (2H, d, J = 8.3 Hz). |
| 77 | 489 (M + H). | 1H-NMR (CDCl$_3$, 300 MHz) δ: 1.29 (6H, d, J = 6.8 Hz), 2.12 (3H, s), 2.36-2.49 (1H, m), 2.76-2.86 (1H, m), 2.94-3.09 (1H, m), 3.13-3.27 (1H, m), 3.83 (1H, d, J = 14.3 Hz), 4.27 (1H, d, J = 13.6 Hz), 4.42-4.58 (2H, m), 4.63 (1H, dd, J = 15.8, 6.4 Hz), 7.29 (1H, br s), 7.40-7.43 (4H, m), 7.78 (2H, d, J = 8.3 Hz), 8.21 (2H, d, J = 8.7 Hz). |

TABLE 244

| Example No. | MS ESI m/e: | NMR |
|---|---|---|
| 78 | 462 (M + H). | 1H-NMR (CDCl$_3$, 400 MHz) δ: 1.30 (6H, d, J = 7.0 Hz), 2.15 (3H, s), 2.37-2.45 (1H, m), 2.83 (1H, dd, J = 13.7, 4.4 Hz), 2.97-3.05 |

TABLE 244-continued

| Example No. | MS ESI m/e: | NMR |
|---|---|---|
| | | (1H, m), 3.12-3.21 (1H, m), 3.85 (1H, d, J = 14.4 Hz), 4.30 (1H, d, J = 14.1 Hz), 4.38-4.54 (4H, m), 6.91-7.08 (4H, m), 7.32 (1H, td, J = 7.9, 6.0 Hz), 7.42 (2H, d, J = 8.3 Hz), 7.78 (2H, d, J = 8.6 Hz). |
| 79 | 497 (M + H). | 1H-NMR (CDCl$_3$, 400 MHz) δ: 1.28 (6H, d, J = 7.0 Hz), 2.16 (3H, s), 2.21-2.31 (1H, m), 2.56-2.66 (1H, m), 2.75 (1H, dd, J = 13.4, 4.2 Hz), 2.92-3.09 (3H, m), 3.48-3.60 (2H, m), 3.67-3.78 (1H, m), 4.12 (1H, d, J = 13.2 Hz), 4.39 (1H, d, J = 3.7 Hz), 4.47 (1H, d, J = 13.4 Hz), 6.53-6.59 (1H, m), 6.98-7.00 (1H, m), 7.13-7.18 (1H, m), 7.21-7.26 (1H, m), 7.33 (2H, d, J = 8.3 Hz), 7.40 (1H, d, J = 8.1 Hz), 7.59 (1H, d, J = 7.7 Hz), 7.65 (2H, d, J = 8.3 Hz), 8.19 (1H, br s). |
| 80 | 529 ( M + H). | 1H-NMR (CDCl$_3$, 400 MHz) δ: 1.28 (6H, d, J = 6.8 Hz), 2.15 (3H, s), 2.33-2.42 (1H, m), 2.79 (1H, dd, J = 13.2, 4.0 Hz), 2.95-3.05 (1H, m), 3.08-3.16 (1H, m), 3.14-3.18 (4H, m), 3.80 (1H, d, J = 14.6 Hz), 3.84-3.89 (4H, m), 4.23-4.53 (5H, m), 6.83-6.88 (1H, m), 6.88 (2H, d, J = 8.6 Hz), 7.13 (2H, d, J = 8.8 Hz), 7.39 (2H, d, J = 8.2 Hz), 7.75 (2H, d, J = 8.4 Hz). |
| 81 | 542 (M + H) | 1H-NMR (CDCl$_3$, 400 MHz) δ: 1.28 (6H, d, J = 7.1 Hz), 2.15 (3H, s), 2.34-2.44 (1H, m), 2.47 (3H, s), 2.71-2.77 (4H, m), 2.77-2.84 (1H, m), 2.94-3.04 (1H, m), 3.07-3.17 (1H, m), 3.27-3.33 (4H, m), 3.79 (1H, d, J = 14.3 Hz), 4.22-4.34 (2H, m), 4.38-4.52 (3H, m), 6.70 (1H, s), 6.88 (2H, d, J = 8.6 Hz), 7.11(2H, d, J = 8.6 Hz), 7.39 (2H, d, J =8.4 Hz), 7.75 (2H, d, J =8.4 Hz). |
| 82 | 629 (M + H). | 1H-NMR (CDCl$_3$, 300 MHz) δ: 1.42 (9H, s), 2.65-2.91 (2H, m), 2.95 (6H, s), 3.28 (1H, ddd, J = 13.8, 10.9, 3.2 Hz), 3.62-187 (2H, m), 4.23 (1H, dd, J = 14.9, 5.1 Hz), 4.33-4.42 (2H, m), 4.52-4.60 (1H, m), 6.48 (1H, t, J = 5.5 Hz), 6.71 (2H, d, J = 7.9 Hz), 7.09 (2H, d, J = 8.7 Hz), 7.52 (2H, d, J = 8.7 Hz), 7.85 (2H, d, J = 8.7 Hz). |

TABLE 245

| Example No. | MS ESI m/e: | NMR |
|---|---|---|
| 83 | 528 (M + H). | 1H-NMR (CDCl$_3$, 400 MHz) δ: 1.39 (6H, d, J = 6.0 Hz), 2.14 (3H, s), 2.44 (1H, ddd, J = 14.1, 11.3, 3.0 Hz), 2.85 (1H, dd, J = 13.9, 4.6 Hz), 3.16 (1H, ddd, J = 14.4, 11.6, 3.1 Hz), 3.80(1H, dt, J = 14.4, 2.9 Hz), 4.27 (1H, dt, J = 13.7, 3.0 Hz), 4.45-4.59 (4H, m), 4.60-4.67 (1H, m), 6.98 (2H, d, J = 8.8 Hz), 7.14 (1H, t, J = 5.8 Hz), 7.33 (2H, d, J = 8.2 Hz), 7.60 (2H, d, J = 8.2 Hz), 7.75 (2H, d, J = 8.8 Hz). |
| 84 | 529 M + H). | 1H-NMR (DMSO-d$_6$, 300 MHz) δ: 2.72 (1H, t, J = 10.0 Hz), 2.99-3.03 (1H, m), 3.02 (6H, s), 3.19 (1H, d, J = 11.7 Hz), 3.53-3.66 (2H, m), 3.86 (1H, d, J = 12.1 Hz), 4.19 (2H, d, J = 5.3 Hz), 4.71 (1H, d, J = 4.1 Hz), 7.21-7.32 (4H, m), 7.60 (2H, d, J = 8.7 Hz), 7.97 (2H, d, J = 8.7 Hz), 8.46 (1H, br s), 8.78 (1H, br s), 9.68 (1H, br s). |
| 85 | 571 (M + H). | 1H-NMR (CDCl$_3$, 300 MHz) δ: 2.16 (3H, s), 2.41 (1H, ddd, J = 14.1, 11.1, 3.0 Hz), 2.85 (1H, dd, J = 13.6, 4.1 Hz), 3.00 (6H, s), 3.12(1H, ddd, J = 14.4, 11.4, 3.3 Hz), 3.79 (1H, dt, J = 14.9, 3.0 Hz), 4.27-4.56 (5H, m), 6.56-7.01 (3H, m), 7.12 (2H, d, J = 6.8 Hz), 7.53 (2H, d, J = 8.7 Hz), 7.89 (2H, d, J = 8.7 Hz). |
| 86 | 686 (M + H). | 1H-NMR (DMSO-d$_6$, 400 MHz, 120° C.) δ: 1.37 (9H, s), 2.90 (6H, s), 2.91-2.95 (1H, m), 3.13 (1H, dd, J = 13.9, 4.2 Hz), 3.51-3.77 (4H, m), 3.95 (1H, d, J = 12.6 Hz), 4.08 (2H, dd, J = 5.3, 2.9 Hz), 4.21 (1H, d, J = 13.0 Hz), 4.45 (1H, dd, J = 4.0, 2.5 Hz), 5.99 (1H, t, J = 8.3 Hz), 6.68 (2H, d, J = 8.7 Hz), 7.03 (2H, d, J = 8.7 Hz), 7.52 (2H, d, J = 8.5 Hz), 7.89 (2H, d, J = 8.5 Hz), 7.90 (1H, br s). |
| 87 | 700 (M + H). | 1H-NMR (DMSO-d$_6$, 400 MHz, 120° C.) δ: 1.36 (9H, s), 2.34 (2H, ddd, J = 32.9, 14.8, 7.4 Hz), 2.88 (6H, s), 3.07-3.14 (4H, m), 3.57-3.61 (2H, m), 3.95-4.12 (3H, m), 4.21-4.32 (1H, m), 4.44 (1H, dd, J = 4.7, 2.5 Hz), 5.98 (1H, br s), 6.68 (2H, d, J = 8.7 Hz), 7.02 (2H, d, J = 8.7 Hz), 7.51 (2H, d, J = 8.5 Hz), 7.88 (2H, d, J = 8.5 Hz), 7.91 (1H, br s). |

TABLE 246

| Example No. | MS ESI m/e: | NMR |
|---|---|---|
| 88 | 586 (M + H). | 1H-NMR (DMSO-d$_6$, 400 MHz, 120° C.) δ: 2.90 (6H, s), 3.10-3.18 (1H, m), 3.64-3.71 (2H, m), 3.77-4.15 (8H, m), 4.53 (1H, dd, J = 4.3, 1.9 Hz), 6.75 (2H, d, J = 8.5 Hz), 7.05 (2H, d, J = 8.7 Hz), 7.54 (2H, d, J = 8.2 Hz), 7.90 (2H, d, J = 8.5 Hz), 7.93-8.05 (3H, m). |
| 89 | 600 (M + H). | 1H-NMR (DMSO-d$_6$, 400 MHz, 120° C.) δ: 2.52-2.69 (2H, m), 2.90 (6H, s), 2.93-2.98 (2H, m), 3.12-3.20 (2H, m), 3.25-3.33 (2H, m), 3.65 (1H, d, J = 12.6 Hz), 3.98-4.12 (4H, m), 4.49 (1H, dd, J = 4.2, 2.3 Hz), 6.78 (2H, d, J = 8.7 Hz), 7.06 (2H, d, J = 8.7 Hz), 7.53 (2H, d, J = 8.5 Hz), 7.71 (2H, br s), 7.90 (2H, d, J = 8.7 Hz), 8.04 (1H, t, J = 5.6 Hz). |
| 90 | 459 (M + H). | 1H-NMR (CDCl$_3$, 400 MHz) δ: 1.28 (6H, d, J = 7.1 Hz), 2.15 (3H, s), 2.35-2.43 (1H, m), 2.79-2.84 (1H, m), 2.95-3.04 (1H, m), 3.05-3.15 (1H, m), 3.80 (1H, d, J = 14.3 Hz), 4.22-4.39 (2H, m), 4.44-4.53 (2H, m), 6.65 (2H, d, J = 8.4 Hz), 6.78 (1H, br s), 7.00 (2H, d, J = 8.4 Hz), 7.38 (2H, d, J = 8.2 Hz), 7.74 (2H, d, J = 8.4 Hz). |
| 91 | 526 (M + H). | 1H-NMR (CDCl$_3$, 300 MHz) δ: 0.94 (3H, t, J = 7.2 Hz), 1.30-1.43 (2H, m), 1.59-1.68 (2H, m), 2.13 (3H, s), 2.40 (1H, ddd, J = 13.8, 11.4, 3.1 Hz), 70 (2H, t, J = 7.7 Hz), 2.80 (1H, dd, J = 13.8, 4.3 Hz), 3.17 (1H, ddd, J = 14.0, 11.2, 2.9 Hz), 3.83 (1H, dt, J = 14.3, 2.8 Hz), 4.28 (1H, dt, J = 13.6, 2.6 Hz), 4.43-4.55 (4H, m), 7.13 (1H, t, J = 6.0 Hz), 7.34 (2H, d, J = 7.5 Hz), 7.36 (2H, d, J = 7.9 Hz), 7.61 (2H, d, J = 8.3 Hz), 7.75 (2H, d, J = 8.3 Hz). |
| 92 | 513 (M + H). | 1H-NMR (CDCl$_3$, 300 MHz) δ: 2.13 (3H, s), 2.45 (1H, ddd, J = 13.9, 11.1, 3.0 Hz), 2.86 (1H, dd, J = 13.6, 4.5 Hz), 3.07 (6H, s), 3.13 (1H, ddd, J = 14.6, 10.8, 3.3 Hz), 3.79 (1H, dt, J = 14.4, 3.3 Hz), 4.24 (1H, dt, J = 13.7, 2.8 Hz), 4.42-4.55 (4H, m), 6.67 (2H, d, J = 9.0 Hz), 7.22 (1H, t, J = 6.2 Hz), 7.33 (2H, d, J = 8.3 Hz), 7.59 (2H, d, J = 8.3 Hz), 7.64 (2H, d, J = 9.0 Hz). |

TABLE 247

| Example No. | MS ESI m/e: | NMR |
|---|---|---|
| 93 | 485 (M + H). | 1H-NMR (DMSO-d$_6$, 400 MHz, 120° C.) δ: 1.83 (3H, s), 2.77-3.27 (5H, m), 3.40-3.58 (2H, m), 3.81-3.93 (1H, m), 4.16-4.25 (1H, m), 4.31-4.36 (3H, m), 6.65 (2H, d, J = 8.7 Hz), 7.43 (2H, d, J = 8.2 Hz), 7.46 (2H, d, J = 8.7 Hz), 7.60 (2H, d, J = 8.2 Hz), 8.14 (1H, t, J = 5.2 Hz). |
| 94 | 601 (M + H). | 1H-NMR (CDCl$_3$, 300 MHz) δ: 2.42 (2H, dd, J = 11.7, 3.8 Hz), 2.67 (1H, d, J = 10.5 Hz), 2.96 (6H, s), 3.09-3.19 (1H, m), 3.17 (1H, d, J = 17.0 Hz), 3.27 (1H, d, J = 17.0 Hz), 3.35 (1H, dt, J = 12.1, 1.4 Hz), 3.65 (3H, s), 3.68-3.76 (1H, m), 4.28 (1H, d, J = 5.3 Hz), 4.38 (1H, d, J = 6.0 Hz), 4.50 (1H, dt, J = 3.5, 1.8 Hz), 6.72 (2H, d, J = 5.7 Hz), 7.07 (2H, d, J = 8.7 Hz), 7.60 (2H, d, J = 8.7 Hz), 7.62-7.66 (1H, m), 7.86 (2H, d, J = 8.7 Hz). |
| 95 | 614 (M + H). | 1H-NMR (CDCl$_3$, 300 MHz) δ: 2.52 (6H, s), 2.87-2.94 (1H, m), 2.95 (6H, s), 3.13 (1H, ddd, J = 14.5, 11.5, 3.0 Hz), 3.53-3.73 (2H, m), 3.81 (1H, d, J = 13.6 Hz), 4.20-4.55 (6H, m), 6.69 (2H, d, J = 8.7 Hz), 6.80 (1H, t, J = 5.1 Hz), 7.05 (2H, d, J = 8.7 Hz), 7.53 (2H, d, J = 8.3 Hz), 7.88 (2H, d, J = 8.3 Hz). |
| 96 | 587 (M + H). | 1H-NMR (CDCl$_3$, 300 MHz) δ: 1.99 (1H, dd, J = 11.5, 2.8 Hz), 2.25 (1H, td, J = 11.8, 3.1 Hz), 2.63 (1H, d, J = 10.5 Hz), 2.96 (6H, s), 3.05 (1H, d, J = 17.7 Hz), 3.19 (1H, d, J = 17.7 Hz), 3.19-3.33 (2H, m), 3.86 (1H, d, J = 14.3 Hz), 4.34-4.43 (3H, m), 6.71 (2H, d, J = 8.7 Hz), 6.89 (1H, t, J = 4.3 Hz), 7.12 (2H, d, J = 8.7 Hz), 7.51 (2H, d, J = 8.7 Hz), 7.88 (2H, d, J = 8.7 Hz), 11.20 (1H, br s). |
| 97 | 540 (M + H). | 1H-NMR (CDCl$_3$, 300 MHz) δ: 1.32 (6.0H, s), 1.67 (2.0H, q, J = 7.3 Hz), 1.91 (0.3H, s), 2.13 (2.7H, s), 2.36-2.46 (0.7H, m), 2.80 (0.7H, dd, J = 13.8, 4.3 Hz), 3.13-3.22 (0.8H, m), 3.83 (0.7H, d, J = 14.7 Hz), 4.28 (0.7H, d, J = 12.4 Hz), 4.46-4.59 (3.7H, m), 7.11-7.15 (0.7H, m), 7.35 (1.8H, d, J = 7.5 Hz), 7.52 (1.9H, d, J = 8.7 Hz), 7.61 (1.9H, d, J = 7.9 Hz), 7.78 (1.9H, d, J = 8.3 Hz). |

TABLE 248

| Example No. | MS ESI m/e: | NMR |
|---|---|---|
| 98 | 543 M + H). | 1H-NMR (CDCl₃, 400 MHz) δ: 1.29 (6H, d, J = 7.0 Hz), 1.33 (9H, s), 2.16 (3H, s), 2.37-2.46 (1H, m), 2.83 (1H, dd, J = 13.1, 3.8 Hz), 2.96-3.05 (1H, m), 3.07-3.16 (1H, m), 3.81 (1H, d, J = 14.1 Hz), 4.27 (1H, d, J = 13.0 Hz), 4.34-4.54 (4H, m), 6.91 (1H, br s), 7.18 (2H, d, J = 8.3 Hz), 7.32 (1H, br s), 7.41 (2H, d, J = 8.1 Hz), 7.52 (2H, d, J = 8.6 Hz), 7.76 (2H, d, J = 8.3 Hz). |
| 99 | 48 488 (M + H). | 1H-NMR (CDCl₃, 400 MHz) δ: 1.29 (6H, d, J = 6.8 Hz), 2.14 (3H, s), 2.39-2.46 (1H, m), 2.83 (1H, dd, J = 13.5, 4.0 Hz), 2.96-3.05 (1H, m), 3.14-3.22 (1H, m), 3.83 (1H, d, J = 14.6 Hz), 4.30 (1H, d, J = 13.7 Hz), 4.48-4.54 (4H, m), 7.11 (1H, t, J = 5.8 Hz), 7.31 (2H, d, J = 7.9 Hz), 7.41 (2H, d, J = 7.9 Hz), 7.77 (2H, d, J = 8.2 Hz), 8.05 (2H, d, J = 7.9 Hz). |
| 100 | 512 (M + H). | 1H-NMR (CDCl₃, 400 MHz) δ: 1.29 (6H, d, J = 7.1 Hz), 1.92 (0.3H, s), 2.13 (2.6H, s), 2.37-2.45 (1H, m), 2.81 (1H, dd, J = 13.7, 4.4 Hz), 2.97-3.04 (1H, m), 3.10-3.18 (1H, m), 3.83 (1H, d, J = 14.3 Hz), 4.24-4.40 (2H, m), 4.42-4.50 (3H, m), 7.07 (2H, d, J = 7.9 Hz), 7.34 (4H, d, J = 2.0 Hz), 7.41 (4H, d, J = 8.2 Hz), 7.77 (2H, d, J = 8.4 Hz). |
| 101 | 512 (M + H). | 1H-NMR (CDCl₃, 400 MHz) δ: 1.29 (6H, d, J = 7.1 Hz), 2.11 (3H, s), 2.35-2.46 (1H, m), 2.81-2.88 (1H, m), 2.95-3.04 (1H, m), 3.10-3.17 (1H, m), 3.82 (1H, d, J = 14.3 Hz), 4.28 (1H, d, J = 13.7 Hz), 4.44-4.49 (4H, m), 7.06-7.08 (1H, br m), 7.24 (2H, s), 7.41 (3H, d, J = 8.2 Hz), 7.77 (2H, d, J = 8.2 Hz). |
| 102 | 654 (M + H). | 1H-NMR (CDCl₃, 300 MHz) δ: 1.34-1.45 (2H, m), 2.23-2.59 (5H, m), 2.86-3.22 (9H, m), 3.53 (1H, d, J = 13.6 Hz), 3.76 (1H, d, J = 13.6 Hz), 4.17-4.58 (4H, m), 4.76-4.95 (1H, m), 6.49-6.61 (1H, m), 6.64-6.75 (2H, m), 6.99-7.14 (2H, m), 7.46-7.63 (2H, m), 7.81-7.92 (2H, m). |

TABLE 249

| Example No. | MS ESI m/e: | NMR |
|---|---|---|
| 103 | 538 (M + H). | 1H-NMR (CDCl₃, 400 MHz) δ: 1.29 (6H, d, J = 7.1 Hz), 2.89 (1H, dd, J = 14.1, 3.7 Hz), 2.95-3.08 (2H, m), 3.22-3.33 (1H, m), 3.62-3.81 (4H, m), 3.98 (1H, d, J = 15.0 Hz), 4.21 (1H, d, J = 13.7 Hz), 4.40-4.49 (2H, m), 4.62 (1H, d, J = 6.6 Hz), 4.64-4.69 (1H, m), 7.39 (2H, d, J = 7.5 Hz), 7.43 (2H, d, J = 8.4 Hz), 7.58 (1H, t, J = 5.3 Hz), 7.64 (2H, d, J = 7.9 Hz), 7.76 (2H, d, J = 8.4 Hz). |
| 104 | 656 (M + H). | 1H-NMR (CDCl₃, 300 MHz) δ: 2.34-2.59 (5H, m), 2.83-3.04 (7H, m), 3.05-3.27 (2H, m), 3.53 (1H, d, J = 13.9 Hz), 3.59-3.84 (5H, m), 4.23-4.43 (4H, m), 4.77 (1H, d, J = 13.9 Hz), 6.52-6.60 (1H, m), 6.69 (2H, d, J = 8.7 Hz), 7.04 (2H, d, J = 8.7 Hz), 7.52 (2H, d, J = 8.3 Hz), 7.88 (2H, d, J = 8.7 Hz). |
| 105 | 676 (M + H). | 1H-NMR (CDCl₃, 300 MHz) δ: 2.39-2.55 (1H, m), 2.80 (1H, dd, J = 13.6, 4.1 Hz), 2.94 (6H, s), 3.04-3.21 (1H, m), 3.42 (1H, d, J = 16.6 Hz), 3.65-3.88 (4H, m), 4.18-4.61 (5H, m), 6.57-6.74 (3H, m), 7.05 (2H, d, J = 8.7 Hz), 7.28-7.36 (4H, m), 7.51 (2H, d, J = 8.7 Hz), 7.87 (2H, d, J = 8.3 Hz). |
| 106 | 528 (M + H). | 1H-NMR (CDCl₃, 300 MHz) δ: 2.12 (3H, s), 2.35 (1H, ddd, J = 14.6, 11.2, 2.9 Hz), 2.78 (1H, dd, J = 13.8, 4.3 Hz), 3.19 (1H, ddd, J = 14.7, 11.7, 3.2 Hz), 3.87 (1H, dt, J = 14.7, 3.2 Hz), 3.98 (3H, s), 4.28-4.62 (5H, m), 7.01 (1H, t, J = 5.8 Hz), 7.33 (2H, d, J = 8.3 Hz), 7.61 (2H, d, J = 7.9 Hz), 7.93 (2H, d, J = 8.3 Hz), 8.22 (2H, d, J = 8.7 Hz). |
| 107 | 514 (M + H). | 1H-NMR (CDCl₃, 300 MHz) δ: 2.14 (3H, s), 2.39 (1H, ddd, J = 14.4, 11.8, 2.7 Hz), 2.83 (1H, dd, J = 13.9, 4.5 Hz), 3.22 (1H, ddd, J = 14.8, 11.8, 3.1 Hz), 3.88 (1H, dt, J = 14.7, 2.8 Hz), 4.33 (1H, dt, J = 13.1, 2.5 Hz), 4.44-4.61 (4H, m), 7.02 (1H, t, J = 6.4 Hz), 7.34 (2H, d, J = 7.9 Hz), 7.61 (2H, d, J = 8.3 Hz), 7.96 (2H, d, J = 8.7 Hz), 8.26 (2H, d, J = 8.3 Hz), 9.50 (1H, br s). |

TABLE 250

| Example No. | MS ESI m/e: | NMR |
|---|---|---|
| 108 | 524 (M + H). | 1H-NMR (CDCl₃, 400 MHz) δ: 1.28 (6H, d, J = 6.8 Hz), 2.15 (3H, s), 2.36-2.45 (1H, m), 2.82 (1H, dd, J = 13.7, 4.6 Hz), 2.94-3.04 (1H, m), 3.10-3.19 (1H, m), 3.82 (1H, d, J = 13.2 Hz), 3.95 (3H, s), 4.28 (1H, d, J = 13.5 Hz), 4.37-4.54 (4H, m), 6.95 (1H, br s), 7.20 (2H, d, J = 7.9 Hz), 7.39 (2H, d, J = 8.4 Hz), 7.44 (2H, d, J = 8.2 Hz), 7.60 (1H, s), 7.75 (1H, s), 7.76 (2H, d, J = 7.7 Hz). |
| 109 | 527 (M + H). | 1H-NMR (CDCl₃, 400 MHz) δ: 1.28 (6H, d, J = 6.8 Hz), 1.57-1.61 (2H, m), 1.67-1.74 (4H, m), 2.15 (3H, s), 2.35-2.44 (1H, m), 2.81 (1H, dd, J = 13.3, 3.9 Hz), 2.95-3.03 (1H, m), 3.07-3.16 (1H, m), 3.13-3.18 (4H, m), 3.80 (1H, d, J = 14.8 Hz), 4.24-4.42 (3H, m), 4.45-4.53 (2H, m), 6.78 (1H, br s), 6.89 (2H, d, J = 8.8 Hz), 7.08 (2H, d, J = 8.6 Hz), 7.38 (2H, d, J = 8.4 Hz), 7.74 (2H, d, J = 8.4 Hz). |
| 110 | 670 (M + H). | 1H-NMR (CDCl₃, 300 MHz) δ: 0.82 (6H, t, J = 7.3 Hz), 1.34-1.52 (4H, m), 2.26-2.56 (4H, m), 2.83-3.03 (7H, m), 3.06-3.22 (2H, m), 3.66-3.82 (2H, m), 4.05-4.68 (5H, m), 4.82 (1H, d, J = 14.3 Hz), 6.51-6.61 (1H, m), 6.70 (2H, d, J = 8.7 Hz), 7.00-7.13 (2H, m), 7.52 (2H, d, J = 7.5 Hz), 7.86 (2H, d, J = 8.3 Hz). |
| 111 | 529 (M + H). | 1H-NMR (CDCl₃, 400 MHz) δ: 1.29 (6H, d, J = 7.1 Hz), 2.69 (2H, dd, J = 13.8, 3.4 Hz), 2.98-3.05 (1H, m), 3.12-3.19 (1H, m), 3.95 (1H, d, J = 14.8 Hz), 4.46-4.63 (4H, m), 4.98 (1H, d, J = 15.2 Hz), 6.31 (2H, br s), 7.34 (2H, d, J = 7.9 Hz), 7.43 (2H, d, J = 8.2 Hz), 7.63 (2H, d, J = 7.9 Hz), 7.77 (2H, d, J = 8.4 Hz). |
| 112 | 555 (M + H). | 1H-NMR (CDCl₃, 400 MHz) δ: 1.28 (6H, d, J = 6.8 Hz), 2.82-3.04 (3H, m), 3.20-3.40 (3H, m), 3.82 (2H, d, J = 14.1 Hz), 3.89-3.97 (2H, m), 4.42-4.63 (4H, m), 7.38 (4H, d, J = 8.4 Hz), 7.59 (2H, d, J = 7.7 Hz), 7.76 (2H, d, J = 8.6 Hz). |

TABLE 251

| Example No. | MS ESI m/e: | NMR |
|---|---|---|
| 113 | 670 (M + H). | 1H-NMR (CDCl₃, 300 MHz) δ: 2.34-2.57 (6H, m), 2.59-2.71 (2H, m), 2.76-2.90 (2H, m), 2.96 (6H, s), 3.04-3.19 (1H, m), 3.62-3.73 (4H, m), 3.79 (1H, d, J = 13.2 Hz), 4.20-4.39 (3H, m), 4.40-4.49 (1H, m), 4.58 (1H, d, J = 12.8 Hz), 6.50-6.61 (1H, m), 6.70 (2H, d, J = 8.7 Hz), 7.05 (2H, d, J = 8.7 Hz), 7.52 (2H, d, J = 8.7 Hz), 7.87 (2H, d, J = 8.3 Hz). |
| 114 | 684 (M + H). | 1H-NMR (CDCl₃, 300 MHz) δ: 0.88 (6H, t, J = 7.3 Hz), 1.41-1.59 (4H, m), 2.37-2.56 (5H, m), 2.56-2.92 (5H, m), 2.96 (6H, s), 3.06-3.22 (1H, m), 3.78 (1H, d, J = 14.3 Hz), 4.18-4.36 (3H, m), 4.41-4.47 (1H, m), 4.57 (1H, d, J = 13.9 Hz), 6.55-6.65 (1H, m), 6.70 (2H, d, J = 8.7 Hz), 7.06 (2H, d, J = 8.7 Hz), 7.52 (2H, d, J = 8.7 Hz), 7.88 (2H, d, J = 8.3 Hz). |
| 115 | 567 (M + H). | 1H-NMR (CDCl₃, 400 MHz) δ: 1.27 (6H, d, J = 6.8 Hz), 2.18 (3H, d, J = 1.1 Hz), 2.77-2.90 (2H, m), 2.93-3.03 (1H, m), 3.37-3.47 (1H, m), 3.78-3.93 (2H, m), 4.39 (1H, d, J = 12.8 Hz), 4.53 (2H, d, J = 6.2 Hz), 4.55-4.59 (1H, m), 6.13 (1H, d, J = 1.1 Hz), 7.17 (1H, t, J = 6.2 Hz), 7.34 (2H, d, J = 7.9 Hz), 7.38 (2H, d, J = 8.2 Hz), 7.56 (2H, d, J = 8.2 Hz), 7.77 (2H, d, J = 8.4 Hz). |
| 116 | 554 (M + H). | 1H-NMR (CDCl₃, 400 MHz) δ: 1.28 (6H, d, J = 7.0 Hz), 1.91 (0H, s), 2.15 (3H, s), 2.36-2.44 (1H, m), 2.81 (1H, dd, J = 13.7, 4.2 Hz), 2.94-3.04 (1H, m), 3.13-3.23 (1H, m), 3.83 (1H, d, J = 14.4 Hz), 4.28 (1H, d, J = 13.4 Hz), 4.46-4.54 (4H, m), 7.05 (1H, t, J = 5.7 Hz), 7.29 (2H, d, J = 7.9 Hz), 7.40 (2H, d, J = 8.6 Hz), 7.52 (4H, t, J = 8.2 Hz), 7.77 (2H, d, J = 8.3 Hz). |
| 117 | 486 (M + H). | 1H-NMR (CDCl₃, 400MHz) δ: 1.25-1.28 (12H, m), 1.91 (0.3H, s), 2.15 (2.7H, s), 2.35-2.43 (1H, m), 2.81 (1H, dd, J = 14.1, 4.9 Hz), 2.87-2.94 (1H, m), 2.96-3.03 (1H, m), 3.11-3.18 (1H, m), 3.82 (1H, d, J = 14.4 Hz), 4.28 (1H, d, J = 13.4 Hz), 4.36-4.52 (4H, m), 6.88-6.91 (1H, br m), 7.13 (2H, d, J = 8.1 Hz), 7.21 (2H, d, J = 8.1 Hz), 7.39 (2H, d, J = 8.3 Hz), 7.76 (2H, d, J = 8.3 Hz). |

TABLE 252

| Example No. | MS ESI m/e: | NMR |
|---|---|---|
| 118 | 458 (M + H). | 1H-NMR (CDCl₃, 400 MHz) δ: 1.28 (6H, d, J = 7.0 Hz), 1.89 (0.3H, s), 2.12 (2.7H, s), 2.24-2.32 (1H, m), 2.70-2.89 (4H, m), 2.95-3.04 (1H, m), 3.42-3.61 (2H, m), 3.69 (1H, d, J = 14.4 Hz), 4.18 (1H, d, J = 13.4 Hz), 4.39-4.46 (2H, m), 6.62-6.65 (1H, br m), 7.16-7.24 (3H, m), 7.32 (2H, t, J = 7.3 Hz), 7.39 (2H, d, J = 8.1 Hz), 7.72 (2H, d, J = 8.1 Hz). |
| 119 | 512 (M + H). | 1H-NMR (CDCl₃, 300 MHz) δ: 1.30 (6.2H, d, J = 7.2 Hz), 1.92 (0.3H, s), 2.15 (2.6H, s), 2.35-2.49 (0.9H, m), 2.83 (0.9H, dd, J = 13.8, 4.3 Hz), 2.95-3.08 (1.0H, m), 3.12-3.22 (0.9H, m), 3.85 (0.8H, d, J = 13.9 Hz), 4.29 (0.9H, d, J = 12.8 Hz), 4.43-4.63 (3.9H, m), 7.08-7.17 (0.9H, m), 7.37-7.60 (6.0H, m), 7.78 (2.0H, d, J = 8.3 Hz). |
| 120 | 512 (M + H). | 1H-NMR (CDCl₃, 300 MHz) δ: 1.28 (6.5H, d, J = 7.2 Hz), 1.90 (0.3H, s), 2.13 (2.7H, s), 2.37-2.49 (0.9H, m), 2.87 (0.9H, dd, J = 13.8, 4.3 Hz), 2.93-3.16 (2.0H, m), 3.80 (0.9H, d, J = 14.3 Hz), 4.27 (0.9H, d, J = 13.2 Hz), 4.45-4.53 (1.9H, m), 4.63 (2.2H, d, J = 6.0 Hz), 6.92-7.01 (0.8H, m), 7.35-7.46 (4.0H, m), 7.53 (1.0H, d, J = 7.2 Hz), 7.66 (1.1H, d, J = 7.9 Hz), 7.73-7.79 (2.0H, m). |
| 121 | 528 M + H). | 1H-NMR (CDCl₃, 300 MHz) δ: 1.28 (6.3H, d, J = 7.2 Hz), 1.91 (0.3H, s), 2.13 (2.6H, s), 2.33-2.46 (0.9H, m), 2.81 (0.9H, dd, J = 13.9, 4.5 Hz), 2.94-3.06 (1.0H, m), 3.08-3.22 (0.9H, m), 3.84 (0.8H, d, J = 14.3 Hz), 4.27 (0.9H, d, J = 14.3 Hz), 4.39-4.57 (3.9H, m), 7.02-7.19 (3.8H, m), 7.33-7.44 (3.0H, m), 7.77 (2.0H, d, J = 8.3 Hz). |
| 122 | 653 (M + H). | 1H-NMR (CDCl₃, 300 MHz) δ: 0.81-1.36 (5H, m), 1.60-1.78 (6H, m), 2.26-2.35 (2H, m), 2.39-2.52 (1H, m), 2.80-2.91 (1H, m), 2.95 (6H, s), 3.05-3.20 (1H, m), 3.66-3.83 (1H, m), 4.18-4.47 (4H, m), 4.52-4.66 (1H, m), 6.54-6.62 (1H, m), 6.65-6.74 (2H, m), 6.96-7.14 (2H, m), 7.47-7.60 (2H, m), 7.81-7.93 (2H, m). |

TABLE 253

| Example No. | MS ESI m/e: | NMR |
|---|---|---|
| 123 | 574 (M + H). | 1H-NMR (CDCl₃, 400 MHz) δ: 1.28 (6H, d, J = 7.1 Hz), 2.86-3.07 (4H, m), 3.31-3.46 (1H, m), 3.57-4.20 (2H, m), 4.27-4.59 (2H, m), 4.52 (2H, d, J = 6.0 Hz), 7.13 (1H, br s), 7.28-7.45 (9H, m), 7.61 (2H, d, J = 7.9 Hz), 7.76 (2H, d, J = 8.4 Hz). |
| 124 | 588 (M + H). | 1H-NMR (CDCl₃, 400 MHz) δ: 1.27 (6H, d, J = 6.8 Hz), 2.38-2.49 (1H, m), 2.70 (1H, dd, J = 13.9, 4.2 Hz), 2.94-3.03 (1H, m), 3.15-3.26 (1H, m), 3.76-3.93 (3H, m), 4.32 (1H, d, J = 13.0 Hz), 4.42-4.64 (4H, m), 7.11-7.30 (6H, m), 7.37 (4H, t, J = 9.0 Hz), 7.61 (2H, d, J = 8.2 Hz), 7.74 (2H, d, J = 8.4 Hz). |
| 125 | 604 (M + H). | 1H-NMR. (CDCl₃, 400 MHz) δ: 1.28 (6H, d, J = 6.8 Hz), 2.45-2.54 (1H, m), 2.88 (1H, dd, J = 13.6, 3.9 Hz), 2.96-3.05 (1H, m), 3.16-3.26 (1H, m), 3.84 (1H, d, J = 15.0 Hz), 4.28 (1H, d, J = 13.7 Hz), 4.47-4.64 (4H, m), 4.78 (1H, d, J = 13.9 Hz), 4.93 (1H, d, J = 13.7 Hz), 6.90-6.97 (3H, m), 7.15 (1H, t, J = 5.8 Hz), 7.21-7.28 (2H, m), 7.34 (2H, d, J = 7.9 Hz), 7.41 (2H, d, J = 8.4 Hz), 7.61 (2H, d, J = 8.2 Hz), 7.76 (2H, d, J = 8.4 Hz). |
| 126 | 536 (M + H). | 1H-NMR (CDCl₃, 300 MHz) δ: 1.28 (6.2H, d, J = 7.2 Hz), 1.91 (0.3H, s), 2.15 (2.7H, s), 2.32-2.46 (0.9H, m), 2.80 (0.9H, dd, J = 13.6, 4.5 Hz), 2.96-3.05 (1.1H, m), 3.09-3.22 (1.0H, m), 3.83 (0.9H, d, J = 15.1 Hz), 4.27 (0.9H, d, J = 13.2 Hz), 4.38-4.54 (4.0H, m), 6.90-7.06 (4.7H, m), 7.08-7.14 (0.9H, m), 7.18 (1.9H, d, J = 8.3 Hz), 7.30-7.44 (3.9H, m), 7.76 (2.0H, d, 3 = 8.3 Hz). |
| 127 | 502 (M + H). | 1H-NMR (CDCl₃, 300 MHz) δ: 1.28 (6.3H, d, J = 6.8 Hz), 1.33 (6.2H, d, J = 6.0 Hz), 1.91 (0.3H, s), 2.15 (2.8H, s), 2.34-2.44 (0.9H, m), 2.81 (0.9H, dd, J = 14.1, 4.7 Hz), 2.95-3.04 (1.0H, m), 3.07-3.17 (1.0H, m), 3.81 (0.9H, d, J = 13.9 Hz), 4.21-4.40 (3.0H, m), 4.45-4.59 (3.0H, m), 6.79-6.88 (2.9H, m), 7.11 (1.9H, d, J = 8.7 Hz), 7.39 (2.0H, d, J = 8.3 Hz), 7.75 (2.0H, d, J = 8.3 Hz). |

TABLE 254

| Example No. | MS ESI m/e: | NMR |
|---|---|---|
| 128 | 487 (M + H). | 1H-NMR (CDCl₃, 300 MHz) δ: 1.28 (6.3H, d, J = 7.2 Hz), 1.90 (0.2H, s), 2.15 (2.8H, s), 2.35-2.45 (0.9H, m), 2.81 (1.0H, dd, J = 13.6, 4.5 Hz), 2.90-3.06 (7.0H, m), 3.08-3.22 (1.0H, m), 3.81 (0.9H, d, J = 14.3 Hz), 4.21-4.56 (4.8H, m), 6.50-6.60 (1.9H, m), 6.61-6.69 (1.0H, in), 6.86-6.94 (0.8H, m), 7.20 (1.0H, t, J = 7.9 Hz), 7.38 (2.0H, d, J = 8.7 Hz), 7.75 (2.0H, d, J = 8.3 Hz). |
| 129 | 487 (M + H). | 1H-NMR (CDCl₃, 300 MHz) 5: 1.28 (6.4H, d, J = 6.4 Hz), 1.88 (0.2H, s), 2.12 (2.7H, s), 2.23-2.37 (0.9H, m), 2.64-2.81 (7.1H, m), 2.91-3.05 (1.1H, m), 3.10-3.19 (0.9H, m), 3.86 (0.9H, d, J = 14.3 Hz), 4.23 (0.9H, d, J = 13.6 Hz), 4.41-4.67 (4.1H, m), 6.99-7.09 (1.1H, m), 7.17 (2.0H, d, J = 7.9 Hz), 7.34-7.43 (2.0H, m), 7.70-7.79 (2.0H, m). |
| 130 | 585 (M + H). | 1H-NMR (CDCl₃, 300 MHz) δ: 1.09 (3H, t, J = 7.3 Hz), 2.11-2.51 (2H, m), 2.52-2.69 (1H, m), 2.83 (1H, dd, J = 13.8, 4.3 Hz), 2.96 (6H, s), 3.05-3.20 (1H, m), 3.79 (1H, d, J = 14.3 Hz), 4.19-4.39 (3H, m), 4.40-4.47 (1H, m), 4.58 (1H, d, J = 13.6 Hz), 6.53-6.63 (1H, m), 6.70 (2H, d, J = 8.7 Hz), 7.06 (2H, d, J = 8.7 Hz), 7.52 (2H, d, J = 8.3 Hz), 7.87 (2H, d, J = 8.3 Hz). |
| 131 | 647 (M + H). | 1H-NMR (CDCl₃, 300 MHz) 8: 2.31-2.50 (0.9H, m), 2.74 (0.8H, dd, J = 13.9, 3.8 Hz), 2.96 (6.4H, s), 3.07-3.22 (1.211, m), 3.59-4.02 (3.0H, m), 4.24-4.55 (4.0H, m), 4.64 (0.811, d, J = 13.9 Hz), 6.54-6.65 (1.0H, m), 6.71 (2.1H, d, J = 8.7 Hz), 7.08 (2.2H, d, J = 8.7 Hz), 7.17-7.35 (5.0H, m), 7.49 (2.1H, d, J = 8.3 Hz), 7.85 (2.0H, d, J = 8.3 Hz). |
| 132 | 500 (M + H). | 1H-NMR (CDCl₃, 400 MHz) 5: 2.01 (1H, br s), 2.12 (3H, s), 2.40 (1H, ddd, J = 14.3, 11.4, 3.3 Hz), 2.82 (1H, dd, J = 13.3, 4.3 Hz), 3.18 (1H, ddd, J = 14.7, 11.8, 3.1 Hz), 3.84 (1H, dt, J = 14.8, 3.0 Hz), 4.26 (1H, dt, J = 13.0, 3.0 Hz), 4.43-4.59 (4H, m), 4.82 (2H, s), 7.10 (1H, t, J = 5.3 Hz), 7.34 (2H, d, J = 8.2 Hz), 7.57 (2H, d, J = 8.4 Hz), 7.61 (2H, d, J = 7.9 Hz), 7.85 (2H, d, J = 8.4 Hz). |

TABLE 255

| Example No. | MS ESI m/e: | NMR |
|---|---|---|
| 133 | 539 (M + H). | 1H-NMR (CDCl₃, 400 MHz) δ: 1.28 (6H, d, J = 6.8 Hz), 2.69-2.80 (2H, m), 2.94-3.03 (1H, m), 3.29-3.38 (1H, m), 3.64-3.73 (3H, m), 3.80 (1H, dt, J = 14.1, 3.1 Hz), 4.25 (2H, td, J = 17.1, 8.0 Hz), 4.45-4.61 (4H, m), 7.16 (1H, t, J = 5.5 Hz), 7.38 (4H, d, J = 8.4 Hz), 7.59 (2H, d, J = 7.9 Hz), 7.76 (2H, d, J = 8.4 Hz). |
| 134 | 603 (M + H). | 1H-NMR (CDCl₃, 400 MHz) 8: 1.25 (6H, dd, J = 6.9, 1.9 Hz), 2.90-3.08 (2H, m), 3.11 (1H, dd, J = 13.1, 4.5 Hz), 3.41-3.50 (1H, m), 3.92 (1H, dt, J = 13.8, 3.2 Hz), 4.07 (1H, d, J = 12.6 Hz), 4.47-4.58 (3H, m), 4.60-4.64 (1H, m), 7.08-7.12 (1H, m), 7.21 (1H, br s), 7.27-7.32 (3H, m), 7.39 (2H, d, J = 8.4 Hz), 7.46 (2H, d, J = 7.9 Hz), 7.52 (1H, d, J = 8.2 Hz), 7.56 (1H, dd, J = 7.9, 0.7 Hz), 7.79 (2H, d, S= 8.6 Hz). |
| 135 | 629 (M + H). | 1H-NMR (CDCl₃, 400 MHz) δ: 1.26 (6H, d, J = 6.8 Hz), 2.85-3.04 (3H, m), 3.40-3.50 (1H, m), 3.89-4.03 (2H, m), 4.48 (1H, d, J = 12.8 Hz), 4.53 (2H, d, J = 6.2 Hz), 4.61 (1H, d, J = 2.6 Hz), 6.77 (1H, s), 7.18 (1H, t, J = 5.3 Hz), 7.23-7.29 (1H, m), 7.30-7.37 (4H, m), 7.39 (2H, d, J = 8.4 Hz), 7.53 (2H, d, J = 8.2 Hz), 7.74-7.81 (4H, m). |
| 136 | 530 (M + H). | 1H-NMR (CDCl₃, 400 MHz) δ: 2.15 (3H, s), 2.47 (1H, ddd, J = 13.9, 11.5, 3.0 Hz), 2.85 (1H, dd, J = 13.3, 4.1 Hz), 3.19 (1H, ddd, J = 14.5, 11.6, 3.4 Hz), 3.85 (1H, dt, J = 13.3, 3.1 Hz), 3.93 (3H, s), 3.97 (3H, s), 4.30 (1H, dt, J = 13.6, 3.1 Hz), 4.46-4.60 (4H, m), 6.98 (1H, d, J = 8.3 Hz), 7.14 (1H, t, J = 6.6 Hz), 7.27 (1H, d, J = 2.3 Hz), 7.35 (2H, d, J = 8.1 Hz), 7.48 (1H, dd, J = 8.5, 2.2 Hz), 7.62 (2H, d, J = 7.9 Hz). |

TABLE 256

| Example No. | MS ESI m/e: | NMR |
|---|---|---|
| 137 | 486 (M + H). | 1H-NMR (CDCl₃, 400 MHz) δ: 1.25 (6H, d, J = 7.1 Hz), 1.28 (6H, d, J = 6.8 Hz), 2.14 (3H, s), 2.34-2.46 (1H, m), 2.81 (1H, dd, J = 13.8, 4.5 Hz), 2.86-2.95 (1H, m), 2.95-3.04 (1H, m), 3.10-3.19 (1H, m), 3.82 (1H, d, J = 14.3 Hz), 4.28 (1H, d, J = 13.7 Hz), 4.35-4.47 |

TABLE 256-continued

| Example No. | MS ESI m/e: | NMR |
|---|---|---|
| | | (2H, m), 4.50 (2H, d, J = 12.1 Hz), 6.90 (1H, t, J = 5.4 Hz), 7.13 (2H, d, J = 8.2 Hz), 7.20 (2H, d, J = 8.2 Hz), 7.39 (2H, d, J = 8.4 Hz), 7.75 (2H, d, J = 8.4 Hz). |
| 138 | 492 (M + H). | 1H-NMR (CDCl₃, 400 MHz) δ: 1.29 (6H, d, J = 7.1 Hz), 2.12 (3H, s), 2.25-2.36 (1H, m), 2.70-2.95 (4H, m), 2.95-3.07 (1H, m), 3.49 (2H, q, J = 6.7 Hz), 3.72 (1H, d, J = 14.3 Hz), 4.21 (1H, d, J = 13.7 Hz), 4.39 (1H, d, J = 3.7 Hz), 4.43 (1H, d, J = 13.5 Hz), 6.69 (1H, t, J = 5.5 Hz), 7.10 (2H, d, J =8.2 Hz), 7.29 (2H, d, J = 8.4 Hz), 7.41 (2H, d, J = 8.4 Hz), 7.73 (2H, d, J = 8.4 Hz). |
| 139 | 512 (M + H). | 1H-NMR (CDCl₃, 400 MHz) δ: 1.28 (6H, d, J = 6.8 Hz), 1.54-1.65 (2H, m), 1.65-1.74 (2H, m), 1.75-1.86 (2H, m), 2.01-2.11 (2H, m), 2.15 (3H, s), 2.35-2.45 (1H, m), 2.81 (1H, dd, J = 13.5, 4.2 Hz), 2.93-3.04 (2H, m), 3.10-3.19 (1H, m), 3.82 (1H, d, J = 14.3 Hz), 4.28 (1H, d, J = 13.7 Hz), 4.34-4.54 (4H, m), 6.88 (1H, br s), 7.12 (2H, d, J = 8.2 Hz), 7.22 (2H, d, J = 8.2 Hz), 7.39 (2H, d, J = 8.2 Hz), 7.75 (2H, d, J = 8.4 Hz). |
| 140 | 542 (M + H). | 1H-NMR (CDCl₃, 400 MHz) δ: 0.84 (6H, t, J = 7.4 Hz), 1.09-1.26 (4H, m), 1.29 (6H, d, J = 6.8 Hz), 1.45-1.65 (4H, m), 2.15 (3H, s), 2.33-2.44 (1H, m), 2.46-2.57 (1H, m), 2.81 (1H, dd, J = 13.8, 4.5 Hz), 2.95-3.05 (1H, m), 3.11-3.20 (1H, m), 3.84 (1H, d, J = 14.3 Hz), 4.29 (1H, d, J = 13.9 Hz), 4.36-4.55 (4H, m), 6.89 (1H, br s), 7.11(4H, s), 7.39 (2H, d, J = 8.2 Hz), 7.76 (2H, d, J = 8.4 Hz). |

TABLE 257

| Example No. | MS EST m/e: | NMR |
|---|---|---|
| 141 | 554 (M + H). | 1H-NMR (CDCl₃, 400 MHz) δ: 1.28 (6H, d, J = 7.1 Hz), 1.92 (0.3H, s), 2.15 (2.7H, s), 2.37-2.45 (1H, m), 2.82 (1H, dd, J = 13.7, 4.2 Hz), 2.96-3.03 (1H, m), 3.14-3.21 (1H, m), 3.83 (1H, d, J = 14.1 Hz), 4.29 (1H, d, J = 13.5 Hz), 4.45-4.54 (4H, m), 7.02-7.05 (1H, br m), 7.29-7.47 (7H, m), 7.55 (3H, t, J = 6.9 Hz), 7.76-7.78 (2H, m). |
| 142 | 554 (M + H). | 1H-NMR (CDCl₃, 400 MHz) δ: 1.28 (6.0H, d, J = 6.8 Hz), 1.92 (0.3H, s), 2.15 (2.6H, s), 2.38-2.45 (0.8H, m), 2.83 (0.9H, dd, J = 13.6, 4.5 Hz), 2.96-3.03 (1.1H, m), 3.15-3.22 (0.9H, m), 3.85 (0.8H, d, J = 14.3 Hz), 4.30 (0.9H, d, J = 13.2 Hz), 4.46-4.56 (3.8H, m), 7.00-7.02 (0.8H, br m), 7.26-7.33 (5.0H, m), 7.41-7.46 (5.0H, m), 7.77 (1.9H, d, J = 8.2 Hz). |
| 143 | 514 (M + H). | 1H-NMR (CDCl₃, 300 MHz) δ: 2.13 (3H, s), 2.38 (1H, ddd, J = 13.8, 11.0, 2.7 Hz), 2.80 (1H, dd, J = 13.8, 4.3 Hz), 3.17 (1H, ddd, J = 14.8, 11.6, 3.5 Hz), 3.47 (3H, s), 3.84 (1H, dt, J = 14.8, 3.2 Hz), 4.29 (1H, dt, J = 13.9, 3.2 Hz), 4.44-4.56 (6H, m), 7.07 (1H, t, J = 5.7 Hz), 7.33 (2H, d, J = 7.9 Hz), 7.53 (2H, d, J = 8.3 Hz), 7.61 (2H, d, J = 7.9 Hz), 7.84 (2H, d, J = 8.3 Hz). |
| 144 | 472 (M + H). | 1H-NMR (CDCl₃, 400 MHz) δ: 1.22-1.29 (8.8H, m), 1.91 (0.2H, s), 2.15 (2.6H, s), 2.36-2.43 (0.9H, m), 2.64 (2.0H, q, J = 7.6 Hz), 2.82 (0.9H, dd, J = 13.1, 3.9 Hz), 2.96-3.03 (1.1H, m), 3.10-3.17 (1.0H, m), 3.82 (0.9H, d, J = 14.3 Hz), 4.28 (0.9H, d, J = 13.5 Hz), 4.36-4.52 (4.0H, m), 6.87-6.90 (0.8H, br m), 7.12 (1.7H, d, J = 7.9 Hz), 7.18 (2.2H, d, J = 7.9 Hz), 7.39 (2.1H, d, J = 8.4 Hz), 7.75 (2.0H, d, J = 8.2 Hz). |

TABLE 258

| Example No. | MS EST m/e: | NMR |
|---|---|---|
| 145 | 472 (M + H). | 1H-NMR (CDCl₃, 400 MHz) δ: 1.28 (5.9H, d, J = 6.8 Hz), 1.79-1.86 (1.9H, m), 1.92 (0.3H, s), 2.13 (2.6H, s), 2.34-2.42 (0.8H, m), 2.63 (1.9H, t, J = 7.6 Hz), 2.78 (0.8H, dd, J = 13.1, 3.9 Hz), 2.96-3.03 (1.0H, m), 3.08-3.15 (0.9H, m), 3.22-3.34 (2.0H, m), 3.82 |

TABLE 258-continued

| Example No. | MS ESI m/e | NMR |
|---|---|---|
|  |  | (0.8H, d, J = 14.3 Hz), 4.27 (0.8H, d, J = 13.5 Hz), 4.40-4.48 (1.8H, m), 6.65-6.66 (0.8H, br m), 7.19 (2.9H, t, J = 10.0 Hz), 7.27-7.31 (2.0H, m), 7.42 (2.1H, d, J = 8.2 Hz), 7.78 (2.0H, d, J = 8.2 Hz). |
| 146 | 527 (M + H). | 1H-NMR (CDCl$_3$, 300 MHz) δ: 1.26 (6H, d, J = 6.8 Hz), 1.76 (1H, dd, J = 11.7, 3.4 Hz), 1.98-2.10 (1H, m), 2.61 (1H, d, J = 11.7 Hz), 2.79 (1H, d, J = 17.0 Hz), 2.86-2.97 (1H, m), 3.04 (1H, d, J = 17.0 Hz), 3.27-3.40 (1H, m), 3.52 (1H, d, J = 11.7 Hz), 3.87-3.96 (1H, m), 4.38-4.53 (3H, m), 5.39 (1H, s), 6.93-6.96 (1H, m), 7.18 (2H, d, J = 4.1 Hz), 7.23 (2H, d, J = 4.1 Hz), 7.55 (1H, s), 7.81 (2H, d, J = 8.3 Hz), 7.96 (2H, d, J = 8.3 Hz). |
| 147 | 567 (M + H). | 1H-NMR (CDCl$_3$, 300 MHz) δ: 1.22-1.28 (6H, m), 2.02-2.09 (0.5H, m), 2.12-2.23 (0.5H, m), 2.54-2.97 (5H, m), 3.17-3.34 (1H, m), 3.36-3.47 (1H, m), 3.70 (1H, ddd, J = 17.2, 9.3, 5.6 Hz), 3.79-3.92 (1H, m), 4.36-4.56 (2H, m), 4.46-4.49 (0.5H, br m), 4.53-4.56 (0.5H, br m), 6.87 (0.5H, t, J = 5.5 Hz), 7.10-7.20(4.5H, m), 7.75-7.84 (2H, m), 7.84-8.05 (3H, m). |
| 148 | 641 (M + H). | 1H-NMR (CDCl$_3$, 300 MHz) δ: 1.25 (6H, d, J = 6.8 Hz), 2.72-2.97 (2H, m), 3.09-3.24 (1H, m), 3.37-3.54 (1H, m), 3.58-3.74 (2H, m), 4.28-4.56 (4H, m), 6.68-6.79 (1H, m), 6.89-6.99 (1H, m), 7.08-7.36 (9H, m), 7.76 (2H, d, J = 8.3 Hz), 7.91 (2H, d, J = 8.7 Hz). |

TABLE 259

| Example No. | MS ESI m/e: | NMR |
|---|---|---|
| 149 | 492 (M + H). | 1H-NMR (CDCl$_3$, 300 MHz) δ: 1.29 (6H, d, J = 6.8 Hz), 2.12 (3H, s), 2.30 (1H, td, J = 12.7, 3.5 Hz), 2.74 (1H, dd, J = 13.2, 4.1 Hz), 2.87-3.06 (4H, m), 3.55 (2H, ddd, J = 12.9, 6.9, 1.6 Hz), 3.76 (1H, d, J = 15.1 Hz), 4.22 (1H, d, J = 13.2 Hz), 4.40 (1H, d, J = 4.1 Hz), 4.45 (1H, d, J = 13.2 Hz), 6.63 (1H, br s), 7.12-7.25 (3H, m), 7.32-7.43 (3H, m), 7.73 (2H, d, J = 8.3 Hz). |
| 150 | 492 (M + H). | 1H-NMR (CDCl$_3$, 300 MHz) δ: 1.29 (6H, d, J = 7.2 Hz), 2.12 (3H, s), 2.26-2.38 (1H, m), 2.70-3.07 (5H, m), 3.42-3.59 (2H, m), 3.75 (1H, d, J = 15.1 Hz), 4.22 (1H, d, J = 13.9 Hz), 4.39 (1H, d, J = 3.4 Hz), 4.44 (1H, d, J = 13.6 Hz), 6.64 (1H, br s), 7.05 (1H, dt, J = 6.8, 1.7 Hz), 7.18 (1H, s), 7.25 (2H, d, J = 7.5 Hz), 7.41 (2H, d, J = 8.3 Hz), 7.73 (2H, d, J = 8.3 Hz). |
| 151 | 513 (M + H). | 1H-NMR (CDCl$_3$, 300 MHz) δ: 1.29 (6.5H, d, J = 6.8 Hz), 1.90 (0.4H, s), 2.12 (2.7H, s), 2.35-2.50 (0.9H, m), 2.81 (0.9H, dd, J = 13.9, 4.5 Hz), 2.95-3.08 (1.3H, m), 3.11-3.26 (1.0H, m), 3.83 (0.9H, d, J = 14.3 Hz), 4.26 (0.9H, d, J = 12.8 Hz), 4.39-4.56 (3.3H, m), 4.58-4.74 (1.1H, m), 7.27-7.34 (1.0H, m), 7.42 (2.1H, d, J = 8.7 Hz), 7.67 (1.2H, d, J = 7.9 Hz), 7.72-7.82 (3.1H, m). |
| 152 | 445 (M + H). | 1H-NMR (CDCl$_3$, 300 MHz) δ: 1.27 (6.5H, d, J = 7.2 Hz), 1.93 (0.3H, s), 2.12 (2.8H, s), 2.41-2.55 (0.9H, m), 2.85-3.06 (2.2H, m), 3.22-3.32 (1.0H, m), 3.86 (0.9H, d, J = 14.7 Hz), 4.32 (0.9H, d, J = 13.9 Hz), 4.45-4.67 (4.2H, m), 7.15-7.23 (2.1H, m), 7.40 (1.9H, d, J = 8.3 Hz), 7.62-7.71 (1.1H, m), 7.72-7.79 (1.1H, m), 7.83 (1.9H, d, J = 8.7 Hz), 8.50-8.55 (1.0H, m). |
| 153 | 648 (M + H). | 1H-NMR (CDC$_3$, 300 MHz) δ: 2.38-2.58 (1H, m), 2.78-2.87 (1H, m), 2.96 (6H, s), 3.06-3.26 (1H, m), 3.81 (1H, d, 3 = 17.3 Hz), 3.93 (1H, d, J = 15.1 Hz), 4.21 (1H, d, J = 15.4 Hz), 4.26-4.55 (3H, m), 4.73 (1H, d, J = 14.7 Hz), 6.55-6.77 (3H, m), 7.02-7.20 (3H, m), 7.46-7.66 (3H, m), 7.80-7.92 (2H, m), 8.41-8.55 (1H, m). |

TABLE 260

| Example No. | MS ESI m/e: | NMR |
|---|---|---|
| 154 | 648 (M + H). | 1H-NMR (CDCl$_3$, 300 MHz) δ: 2.33-2.50 (1H, m), 2.82 (1H, dd, J = 13.6, 3.8 Hz), 2.96 (6H, s), 3.06-3.22 (1H, m), 3.72-3.88 (2H, m), 3.95 (1H, d, J = 15.8 Hz), 4.22-4.42 (3H, m), 4.45-4.53 (1H, m), 4.66 (1H, d, 3 = 13.2 Hz), 6.60-6.66 (1H, m), 6.70 (2H, d, J = 8.7 Hz), 7.07 (2H, d, J = 8.7 Hz), 7.18-7.25 (1H, m), 7.47-7.59 (3H, m), 7.87 (2H, d, J = 8.3 Hz), 8.42-8.53 (2H, m). |
| 155 | 641 (M + H). | 1H-NMR (CDCl$_3$, 400 MHz) δ: 1.26 (6H, d, J = 6.6 Hz), 2.88-3.02 (3H, m), 3.42-3.51 (1H, m), 3.66 (2H, s), 3.89-4.03 (2H, m), 4.48 (1H, d, J = 12.8 Hz), 4.53 (2H, d, J = 6.0 Hz), 4.60-4.63 (1H, m), |

TABLE 260-continued

| Example No. | MS ESI m/e: | NMR |
|---|---|---|
| | | 7.14-7.22 (2H, m), 7.28-7.35 (3H, m), 7.39 (2H, d, J = 8.4 Hz), 7.42 (1H, d, J = 7.5 Hz), 7.52 (2H, d, J = 8.4 Hz), 7.54 (1H, d, J = 8.4 Hz), 7.80 (2H, d, J = 8.4 Hz). |
| 156 | 607 (M + H). | 1H-NMR (CDCl$_3$, 400 MHz) δ: 1.27 (6H, d, J = 6.8 Hz), 1.72-1.81 (4H, m), 2.47-2.58 (4H, m), 2.72-2.85 (2H, m), 2.94-3.02 (1H, m), 3.34-3.44 (1H, m), 3.77-3.91 (2H, m), 4.35 (1H, d, J = 12.8 Hz), 4.53 (2H, d, J = 6.0 Hz), 4.55-4.58 (1H, m), 7.15 (1H, t, J = 5.8 Hz), 7.34 (2H, d, J = 7.9 Hz), 7.38 (2H, d, J = 8.2 Hz), 7.56 (2H, d, J = 7.9 Hz), 7.77 (2H, d, J = 8.6 Hz). |
| 157 | 586 (M + H). | 1H-NMR (DMSO-d$_6$, 400 MHz) δ: 2.97-4.00 (10H, m), 3.57 (6H, s), 4.08-4.23 (2H, m), 4.49-4.64 (2H, m), 7.18-7.28 (2H, m), 7.50 (1H, d, J = 8.6 Hz), 7.61 (1H, d, J = 8.4 Hz), 7.91 (1H, d, J = 8.6 Hz), 7.96 (1H, d, J = 8.4 Hz), 8.11-8.18 (2H, m), 8.60-8.76 (1H, m). |
| 158 | 654 (M + H). | 1H-NMR (CDCl$_3$, 400 MHz) δ: 1.36-1.82 (10H, m), 2.40-2.56 (1H, m), 2.62-2.85 (2H, m), 2.89-2.93 (1H, m), 2.95 (6H, s), 3.14 (1H, ddd, J = 13.7, 11.2, 3.7 Hz), 3.63-3.72 (1H, m), 3.78 (1H, d, J = 14.6 Hz), 4.20-4.68 (4H, m), 6.64 (1H, t, J = 5.2 Hz), 6.69 (2H, d, J = 8.8 Hz), 7.05 (2H, d, J = 9.3 Hz), 7.52 (2H, d, J = 8.2 Hz), 7.88 (2H, d, J = 8.8 Hz). |

TABLE 261

| Example No. | MS ESI m/e: | NMR |
|---|---|---|
| 159 | 640 (M + H). | 1H-NMR (CDCl$_3$, 400 MHz) δ: 1.56-1.89 (8H, m), 2.49 (1H, td, J = 13.1, 3.8 Hz), 2.62-2.75 (2H, m), 2.86-2.95 (1H, m), 2.95 (6H, s), 3.14 (1H, dt, J = 16.5, 6.2 Hz), 3.76 (1H, t, J = 14.3 Hz), 4.10-4.70 (5H, m), 6.66 (1H, t, J = 6.5 Hz), 6.69 (2H, d, J = 8.8 Hz), 7.05 (2H, d, J = 8.6 Hz), 7.52 (2H, d, J = 8.2 Hz), 7.88 (2H, d, J = 8.2 Hz). |
| 160 | 656 (M + H). | 1H-NMR (CDCl$_3$, 400 MHz) δ: 2.37-2.59 (5H, m), 2.87-2.93 (1H, m), 2.96 (6H, s), 3.13 (1H, t, J = 11.2 Hz), 3.49-3.82 (7H, m), 4.14-4.77 (5H, m), 6.57 (1H, t, J = 5.1 Hz), 6.69 (2H, d, J = 8.6 Hz), 7.04 (2H, d, J = 9.7 Hz), 7.52 (2H, d, J = 8.2 Hz), 7.88 (2H, d, J = 9.0 Hz). |
| 161 | 538 (M + H). | 1H-NMR (CDCl$_3$, 400 MHz) δ: 2.19 (3H, s), 2.58 (1H, td, J = 13.0, 3.7 Hz), 3.12 (1H, td, J = 13.3, 3.5 Hz), 3.24 (1H, dd, J = 13.5, 4.6 Hz), 3.77 (1H, dt, J = 13.7, 2.4 Hz), 4.38-4.68 (5H, m), 6.98 (1H, t, J = 5.2 Hz), 7.30 (2H, d, J = 8.2 Hz), 7.45 (1H, dd, J = 8.7, 1.7 Hz), 7.49 (1H, d, J = 2.2 Hz), 7.60 (2H, d, J = 7.9 Hz), 8.07 (1H, d, J = 8.6 Hz). |
| 162 | 540 (M + H). | 1H-NMR (CDCl$_3$, 400 MHz) δ: 0.76 (6H, t, J = 7.4 Hz), 1.51-1.60 (2H, m), 1.69-1.80 (2H, m), 2.13 (3H, s), 2.36-2.49 (2H, m), 2.78 (1H, dd, J = 13.7, 4.4 Hz), 3.18 (1H, ddd, J = 14.4, 11.4, 3.5 Hz), 3.83 (1H, dt, J = 14.5, 3.0 Hz), 4.28 (1H, dt, J = 13.4, 3.2 Hz), 4.45-4.58 (4H, m), 7.13 (1H, t, J = 6.1 Hz), 7.34 (2H, d, J = 8.4 Hz), 7.35 (2H, d, J = 7.5 Hz), 7.61 (2H, d, J = 7.9 Hz), 7.77 (2H, d, J = 8.4 Hz). |
| 163 | 514 (M + H). | 1H-NMR (CDCl$_3$, 400 MHz) δ: 0.77 (6H, t, J = 7.4 Hz), 1.28 (6H, d, J = 6.8 Hz), 1.48-1.59 (2H, m), 1.62-1.74 (2H, m), 2.15 (3H, s), 2.27-2.35 (1H, m), 2.35-2.45 (1H, m), 2.82 (1H, dd, J = 13.7, 4.4 Hz), 2.93-3.04 (1H, m), 3.11-3.21 (1H, m), 3.83 (1H, d, J = 13.9 Hz), 4.29 (1H, d, J = 13.2 Hz), 4.37-4.54 (4H, m), 6.89 (1H, br s), 7.11 (4H, s), 7.39 (2H, d, 3 = 8.4 Hz), 7.76 (2H, d, J = 8.6 Hz). |

TABLE 262

| Example No. | MS ESI m/e: | NMR |
|---|---|---|
| 164 | 500 (M + H). | 1H-NMR (CDCl$_3$, 400 MHz) δ: 2.10 (3H, s), 2.42 (1H, ddd, J = 14.0, 11.4, 2.9 Hz), 2.81 (1H, dd, J = 13.5, 4.2 Hz), 3.20 (1H, ddd, J = 14.3, 11.3, 3.4 Hz), 3.94 (1H, dt, J = 14.0, 3.2 Hz), 4.32 (1H, dt, J = 13.6, 3.1 Hz), 4.41-4.59 (4H, m), 7.06 (1H, t, J = 5.0 Hz), 7.29 |

953 954

TABLE 262-continued

| Example No. | MS ESI m/e: | NMR |
|---|---|---|
| | | (2H, d, J = 8.2 Hz), 7.56 (2H, d, J = 8.2 Hz), 7.65-7.74 (2H, m), 7.78 (1H, dd, J = 8.8, 1.8 Hz), 7.92-8.02 (3H, m), 8.44 (1H, d, J = 1.5 Hz). |
| 165 | 548, 550 (M + H). | 1H-NMR (CDCl$_3$, 400 MHz) δ: 2.14 (3H, s), 2.42 (1H, ddd, J = 14.1, 11.5, 3.3 Hz), 2.85 (1H, dd, J = 13.2, 4.0 Hz), 3.19 (1H, ddd, J = 14.6, 11.2, 3.3 Hz), 3.85 (1H, dt, J = 13.7, 2.9 Hz), 4.34 (1H, dt, J = 14.3, 2.9 Hz), 4.44-4.60 (4H, m), 6.98 (1H, t, J = 5.8 Hz), 7.34 (2H, d, J = 8.2 Hz), 7.45 (1H, t, J = 7.9 Hz), 7.61 (2H, d, J = 8.2 Hz), 7.78 (2H, dd, J = 7.7, 1.1 Hz), 8.00 (1H, t, J = 1.9 Hz). |
| 166 | 556 (M + H). | 1H-NMR (CDCl$_3$, 400 MHz) δ: 2.13 (3H, s), 2.39 (1H, ddd, J = 14.0, 11.1, 3.2 Hz), 2.67 (2H, t, J = 7.5 Hz), 2.80 (1H, dd, J = 13.9, 4.6 Hz), 3.05 (2H, t, J = 7.5 Hz), 3.17 (1H, ddd, J = 14.6, 11.5, 3.6 Hz), 3.67 (3H, s), 3.82 (1H, dt, J = 14.6, 2.7 Hz), 4.28 (1H, dt, J = 13.6, 2.8 Hz), 4.45-4.59 (4H, m), 7.10 (1H, t, J = 5.7 Hz), 7.34 (2H, d, J = 8.2 Hz), 7.41 (2H, d, J = 8.2 Hz), 7.61 (2H, d, J = 7.9 Hz), 7.78 (2H, d, J = 8.4 Hz). |
| 167 | 552 (M + H). | 1H-NMR (CDCl$_3$, 400 MHz) δ: 1.23-1.32 (1H, m), 1.41 (4H, t, J = 10.0 Hz), 1.79 (1H, d, J = 13.0 Hz), 1.88 (4H, d, J = 8.6 Hz), 2.13 (3H, s), 2.41 (1H, ddd, J = 14.0, 11.4, 3.3 Hz), 2.56-2.63 (1H, m), 2.81 (1H, dd, J = 13.7, 4.2 Hz), 3.16 (1H, ddd, J = 14.8, 11.6, 3.5 Hz), 3.82 (1H, dt, J = 14.6, 2.9 Hz), 4.28 (1H, dt, J = 14.2, 3.4 Hz), 4.44-4.58 (4H, m), 7.11 (1H, t, J = 5.6 Hz), 7.34 (2H, d, J = 7.5 Hz), 7.39 (2H, d, J = 8.2 Hz), 7.61 (2H, d, J = 7.9 Hz), 7.76 (2H, d, J = 8.4 Hz). |

TABLE 263

| Example No. | MS ESI m/e: | NMR |
|---|---|---|
| 168 | 514 (M + H). | 1H-NMR (DMSO-d$_6$, 300 MHz) δ: 1.71 (1.7H, s), 1.89 (1.3H, s), 2.83-3.87 (4H, m), 3.95-4.66 (5H, m), 7.40 (2H, d, J = 7.5 Hz), 7.54-7.72 (3H, m), 7.80-7.98 (1H, m), 8.10-8.20 (1H, m), 8.21-8.33 (1H, m), 8.63-8.84 (1H, m). |
| 169 | 516 (M + H). | 1H-NMR (CDCl$_3$, 300 MHz) δ: 1.29 (6.3H, d, J = 6.8 Hz), 1.33 (6.2H, s), 1.91 (0.2H, s), 2.08 (2.7H, s), 2.34-2.44 (0.9H, m), 2.79 (0.9H, dd, J = 13.8, 4.3 Hz), 2.96-3.05 (1.1H, m), 3.12-3.22 (1.0H, m), 3.61 (2.0H, s), 3.78 (0.9H, d, J = 14.3 Hz), 4.20 (0.9H, d, J = 13.6 Hz), 4.28-4.55 (4.0H, m), 6.96-7.05 (0.9H, m), 7.20 (2.0H, d, J = 8.3 Hz), 7.32-7.44 (4.0H, m), 7.76 (2.0H, d, J = 8.3 Hz). |
| 170 | 625 (M + H). | 1H-NMR (CDCl$_3$, 400 MHz) δ: 1.27 (6H, d, J = 6.8 Hz), 1.34 (3H, t, J = 7.2 Hz), 2.81-3.03 (3H, m), 3.35-3.44 (1H, m), 3.87-3.93 (1H, m), 4.04-4.10 (1H, m), 4.32 (2H, q, J = 7.1 Hz), 4.33-4.37 (1H, m), 4.52 (2H, d, J = 6.2 Hz), 4.58-4.61 (1H, m), 7.15 (1H, t, J = 6.3 Hz), 7.33 (2H, d, J = 8.2 Hz), 7.39 (2H, d, J = 8.4 Hz), 7.44 (1H, s), 7.56 (2H, d, J = 8.2 Hz), 7.77 (2H, d, J = 8.6 Hz). |
| 171 | 597 (M + H). | 1H-NMR (CDCl$_3$, 400 MHz) δ: 1.26 (6H, d, J = 7.1 Hz), 2.83-3.05 (3H, m), 3.34-3.50 (1H, m), 3.73-3.97 (2H, m), 4.36-4.66 (4H, m), 7.27-7.35 (2H, m), 7.38 (2H, d, J = 7.9 Hz), 7.43-7.65 (3H, m), 7.76 (2H, d, J = 7.9 Hz). |
| 172 | 588 (M + H). | 1H-NMR (CDCl$_3$, 400 MHz) δ: 1.26 (6.0H, d, J = 7.0 Hz), 2.36-2.46 (1.0H, m), 2.70 (1.0H, dd, J = 13.6, 4.1 Hz), 2.85-3.05 (1.4H, m), 3.14-3.28 (1.0H, m), 3.51-3.76 (0.9H, m), 3.80-3.95 (2.4H, m), 4.22-4.50 (3.4H, m), 4.65 (1.0H, d, J = 13.9 Hz), 4.98 (0.2H, d, J = 13.4 Hz), 6.73-6.76 (0.9H, br m), 7.09-7.32 (9.0H, m), 7.71-7.81 (2.0H, m), 7.92-7.99 (2.0H, m). |

TABLE 264

| Example No. | MS ESI m/e: | NMR |
|---|---|---|
| 173 | 584 (M + H). | 1H-NMR (CDCl$_3$, 400 MHz) δ: 1.25 (6.0H, d, J = 6.7 Hz), 2.36-2.53 (2.6H, m), 2.60-2.74 (2.2H, m), 2.79-2.95 (2.9H, m), 3.00-3.07 (0.3H, m), 3.15-3.23 (0.7H, m), 3.29-3.37 (0.2H, m), 3.66 (3.0H, s), 3.85 (1.2H, d, J = 14.1 Hz), 4.27-4.38 (2.9H, m), 4.41 (2.9H, d, J = 5.6 Hz), 4.50-4.52 (0.8H, br m), 4.60 (0.9H, d, J = 13.4 Hz), 6.71-6.76 (0.9H, br m), 7.13 (1.9H, d, J = 8.1 Hz), 7.21 |

TABLE 264-continued

| Example No. | MS ESI m/e: | NMR |
|---|---|---|
| | | (2.0H, d, J = 7.9 Hz), 7.73-7.78 (0.4H, br m), 7.82 (1.6H, d, J = 8.3 Hz), 7.98 (2.0H, d, J = 8.1 Hz). |
| 174 | 598 (M + H). | 1H-NMR (CDCl$_3$, 400 MHz) δ: 1.25 (6.4H, d, J = 7.0 Hz), 1.78-1.93 (2.1H, m), 2.23-2.45 (4.4H, m), 2.55-2.63 (0.8H, m), 2.81 (0.8H, dd, J = 13.4, 3.9 Hz), 2.91 (1.0H, h, J = 7.0 Hz), 2.96-3.03 (0.2H, m), 3.16-3.26 (1.4H, m), 3.26-3.35 (1.4H, m), 3.65 (3.1H, s), 3.70-3.79 (1.4H, m), 3.80-3.87 (1.4H, m), 4.27-4.43 (3.1H, m), 4.47-4.50 (0.9H, br m), 4.58 (1.1H, d, J = 13.4 Hz), 4.90 (0.2H, d, J = 14.6 Hz), 6.69-6.76 (1.0H, br m), 7.12 (2.0H, d, J = 8.1 Hz), 7.21 (2.0H, t, J = 4.1 Hz), 7.74 (0.3H, d, J = 7.9 Hz), 7.81 (1.6H, d, J = 8.3 Hz), 7.97 (2.0H, d, J = 8.3 Hz). |
| 175 | 589 (M + H). | 1H-NMR (CDCl$_3$, 400 MHz) δ: 1.25 (6.0H, d, J = 7.0 Hz), 2.37-2.44 (1.0H, m), 2.80 (0.9H, dd, J = 13.6, 4.1 Hz), 2.88-2.95 (1.0H, m), 3.16-3.28 (1.2H, m), 3.56-3.70 (0.5H, m), 3.71-3.98 (3.0H, m), 4.26-4.33 (0.3H, br m), 4.38-4.47 (0.2H, m), 4.53 (0.9H, s), 4.61 (0.2H, br s), 4.68 (0.9H, d, J = 13.4 Hz), 4.91-4.99 (0.1H, m), 7.69-7.78 (1.7H, m), 7.81 (1.7H, d, J = 8.3 Hz), 7.97 (2.0H, d, J = 8.3 Hz), 8.36-8.41 (0.2H, m), 8.43-8.47 (0.8H, m), 8.47-8.51 (1.0H, m). |
| 176 | 512 (M + H). | 1H-NMR (CDCl$_3$, 400 MHz) δ: 1.25 (6H, d, J = 6.8 Hz), 2.16 (3H, s), 2.37-2.40 (1H, m), 2.79-2.96 (2H, m), 3.17-3.20 (1H, m), 3.85 (1H, d, J = 15.2 Hz), 4.26-4.66 (5H, m), 6.70 (1H, t, J = 5.7 Hz), 7.12 (2H, d, J = 8.2 Hz), 7.21 (2H, d, J = 7.9 Hz), 7.81 (2H, d, J = 8.4 Hz), 7.98 (2H, d, J= 8.2 Hz). |

TABLE 265

| Example No. | MS ESI m/e: | NMR |
|---|---|---|
| 177 | 541 (M + H). | 1H-NMR (CDCl$_3$, 400 MHz) δ: 1.10 (3H, t, J = 7.3 Hz), 1.25 (6H, d, J = 6.8 Hz), 2.39 (1H, dt, J = 18.4, 6.6 Hz), 2.61 (1H, dd, J = 14.2, 3.9 Hz), 2.85-2.96 (1H, m), 3.06-3.22 (3H, m), 3.85 (1H, d, J = 14.3 Hz), 4.07 (1H, d, J = 13.7 Hz), 4.27-4.54 (4H, m), 5.39 (1H, t, J = 5.0 Hz), 6.90 (1H, t, J = 5.3 Hz), 7.14 (2H, d, J = 8.2 Hz), 7.21 (2H, d, J = 8.4 Hz), 7.81 (2H, d, J = 8.2 Hz), 7.98 (2H, d, J = 8.4 Hz). |
| 178 | 589 (M + H). | 1H-NMR (CDCl$_3$, 400 MHz) δ: 1.24 (6H, d, J = 7.1 Hz), 2.46 (1H, td, J = 13.1, 3.2 Hz), 2.71 (1H, dd, J = 14.3, 3.3 Hz), 2.84-2.95 (1H, m), 3.11 (1H, ddd, J = 15.3, 12.2, 3.0 Hz), 3.92 (1H, d, J = 13.9 Hz), 4.17 (1H, d, J = 13.0 Hz), 4.45-4.62 (4H, m), 6.92-7.02 (2H, m), 7.13-7.22 (4H, m), 7.24-7.33 (4H, m), 7.83 (2H, d, J = 8.6 Hz), 8.00 (2H, d, J = 8.2 Hz), 8.07 (1H, s). |
| 179 | 555 (M + H). | 1H-NMR (CDCl$_3$, 400 MHz) δ: 1.24 (6H, d, J = 6.8 Hz), 2.84-3.35 (6H, m), 3.69-3.91 (4H, m), 4.29-4.60 (4H, m), 7.03 (1H, t, J = 5.2 Hz), 7.13-7.21 (4H, m), 7.78 (2H, d, J = 8.4 Hz), 8.01 (2H, d, J = 8.2 Hz). |
| 180 | 597 (M + H). | 1H-NMR (CDCl$_3$, 400 MHz) δ: 1.25 (6H, d, J = 6.8 Hz), 2.30-2.61 (5H, m), 2.82-3.27 (4H, m), 3.46-3.90 (6H, m), 4.09-4.98 (5H, m), 6.51-6.74 (1H, m), 7.07-7.24 (4H, m), 7.72-8.02 (4H, m). |
| 181 | 517 (M + H). | 1H-NMR (CDCl$_3$, 400 MHz) δ: 1.30 (6H, d, J = 7.0 Hz), 2.16 (3H, s), 2.34-2.43 (1H, m), 2.80 (1H, dd, J = 13.3, 4.1 Hz), 2.96-3.05 (1H, m), 2.99 (3H, s), 3.08-3.17 (1H, m), 3.49 (2H, t, J = 5.7 Hz), 3.77-3.86 (3H, m), 4.21-4.32 (2H, m), 4.37-4.53 (3H, m), 6.77 (2H, d, J = 8.8 Hz), 6.83 (1H, br s), 7.10 (2H, d, J = 8.8 Hz), 7.41 (2H, d, J = 8.1 Hz), 7.76 (2H, d, J = 8.3 Hz). |
| 182 | 556, 558, (M + H). | 1H-NMR (CDCl$_3$, 300 MHz) δ: 1.29 (6H, d, J = 7.2 Hz), 2.10 (3H, s), 2.35-2.48 (1H, m), 2.83 (1H, dd, J = 13.8, 4.3 Hz), 2.93-3.07 (1H, m), 3.08-3.20 (1H, m), 3.82 (1H, d, J = 14.3 Hz), 4.28 (1H, d, J = 13.9 Hz), 4.40-4.52 (4H, m), 7.08-7.19 (2H, m), 7.34-7.44 (3H, m), 7.54 (1H, d, J = 1.9 Hz), 7.76 (2H, d, J = 8.3 Hz). |

TABLE 266

| Example No. | MS ESI m/e: | NMR |
|---|---|---|
| 183 | 520 (M + H). | 1H-NMR (CDCl$_3$, 300 MHz) δ: 1.24 (6H, d, J = 6.8 Hz), 1.28 (6H, d, J = 6.8 Hz), 2.11 (3H, s), 2.40 (1H, td, J = 12.6, 3.0 Hz), 2.79-3.06 (3H, m), 3.07-3.21 (1H, m), 3.82 (1H, d, J = 14.3 Hz), 4.29 (1H, d, J = 13.9 Hz), 4.39-4.56 (4H, m), 7.01 (1H, t, J = 5.8 |

TABLE 266-continued

| Example No. | MS ESI m/e: | NMR |
|---|---|---|
| | | Hz), 7.10 (1H, dd, J = 7.9, 1.5 Hz), 7.16-7.27 (2H, m), 7.40 (2H, d, J = 8.3 Hz), 7.77 (2H, d, J = 8.7 Hz). |
| 184 | 567 (M + H). | 1H-NMR (CDCl$_3$, 400 MHz) δ: 1.25 (6H, d, J = 6.8 Hz), 2.16 (3H, d, J = 1.1 Hz), 2.84-3.02 (3H, m), 3.38-3.48 (1H, m), 3.78-3.95 (2H, m), 4.37-4.48 (3H, m), 4.58-4.65 (1H, br m), 6.13 (1H, d, J = 1.1 Hz), 6.79 (1H, t, J = 5.7 Hz), 7.12 (4H, d, J = 8.2 Hz), 7.18 (4H, d, J = 8.2 Hz), 7.77 (2H, d, J = 8.4 Hz), 7.99 (2H, d, J = 8.4 Hz). |
| 185 | 569 (M + H). | 1H-NMR (CDCl$_3$, 300 MHz) δ: 1.25 (6.0H, d, J = 6.8 Hz), 2.01 (3.0H, s), 2.46-2.58 (0.8H, m), 2.82-3.00 (2.0H, m), 3.13-3.30 (0.9H, m), 3.34-3.49 (0.3H, m), 3.56-3.68 (0.3H, m), 3.70-3.81 (0.3H, m), 3.82-3.96 (1.1H, m), 4.21 (1.4H, d, J = 4.1 Hz), 4.32-4.45 (3.4H, m), 4.53-4.56 (1.0H, m), 4.91 (0.2H, d, J = 12.8 Hz), 6.23-6.42 (0.9H, br m), 6.51-6.58 (0.2H, br m), 6.67-6.75 (0.6H, br m), 7.12 (2.0H, d, J = 8.3 Hz), 7.21 (2.0H, d, J = 7.9 Hz), 7.72-7.84 (2.1H, m), 7.97 (2.0H, d, J = 7.9 Hz). |
| 186 | 641 (M + H). | 1H-NMR (CDCl$_3$, 300 MHz) δ: 1.25 (6.3H, d, J = 6.8 Hz), 1.39 (9.0H, s), 2.34-2.55 (2.3H, m), 2.75-2.98 (3.0H, m), 3.12-3.50 (0.3H, m), 3.57-3.76 (0.9H, m), 3.81-3.90 (1.0H, m), 4.26-4.43 (3.1H, m), 4.46-4.61 (1.9H, m), 4.87-5.07 (0.4H, m), 5.08-5.21 (0.7H, m), 6.60-6.74 (1.0H, m), 7.07-7.18 (2.6H, m), 7.21 (2.6H, d, J = 8.3 Hz), 7.72-7.77 (0.6H, m), 7.81 (1.6H, d, J = 8.3 Hz), 7.97 (2.0H, d, J = 8.3 Hz). |

TABLE 267

| Example No. | MS ESI m/e: | NMR |
|---|---|---|
| 187 | 570 (M + H). | 1H-NMR (CDCl$_3$, 300 MHz) δ: 1.25 (6.4H, d, J = 7.2 Hz), 2.37-2.76 (4.4H, m), 2.79-3.05 (3.0H, m), 3.13-3.25 (0.9H, m), 3.68-3.92 (1.4H, m), 4.24-4.44 (3.0H, m), 4.49-4.62 (2.0H, m), 4.82-4.91 (0.2H, br m), 6.75 (1.0H, t, J = 5.8 Hz), 7.12 (2.0H, d, J = 7.9 Hz), 7.21 (2.0H, d, J = 8.3 Hz), 7.72-7.75 (0.3H, br m), 7.81 (1.6H, d, J = 8.7 Hz), 7.97 (2.0H, d, J = 8.3 Hz). |
| 188 | 583 (M + H). | 1H-NMR (CDCl$_3$, 300 MHz) δ: 1.25 (6.0H, d, J = 6.8 Hz), 1.83 (0.6H, s), 1.89 (2.7H, s), 2.32-2.56 (2.8H, br m), 2.76-2.98 (3.8H, br m), 3.17-3.27 (1.5H, m), 3.33-3.48 (2.2H, m), 3.55-3.77 (1.9H, m), 3.87 (1.3H, d, J = 13.2 Hz), 4.24-4.43 (4.0H, m), 4.44-4.53 (2.6H, m), 4.95 (0.5H, d, J = 13.9 Hz), 6.12-6.25 (1.5H, br m), 6.50-6.61 (0.5H, br m), 6.68-6.77 (0.9H, br m), 7.08-7.18 (2.7H, m), 7.21 (2.7H, d, J = 7.9 Hz), 7.73 (0.5H, br m), 7.81 (2.0H, d, J = 8.3 Hz), 7.93-7.99 (2.6H, m). |
| 189 | 541 (M + H). | 1H-NMR (CDCl$_3$, 300 MHz) δ: 1.21-1.25 (6H, m), 2.38-3.38 (6H, br m), 3.56-3.89 (1H, br m), 4.13-4.58 (3H, br m), 7.01-7.23 (4H, br m), 7.72-8.00 (6H, br m). |
| 190 | 584 (M + H). | 1H-NMR (CDCl$_3$, 300 MHz) δ: 1.25 (6H, d, J = 7.2 Hz), 1.91-1.93 (2H, m), 2.36-2.41 (4H, m), 2.61-2.67 (1H, m), 2.82-2.92 (2H, m), 3.16-3.26 (1H, m), 3.78-3.84 (1H, m), 4.31-4.39 (3H, m), 4.52-4.56 (2H, m), 6.70-6.74 (1H, m), 7.12 (2H, d, J = 7.9 Hz), 7.21 (2H, d, J = 7.9 Hz), 7.73 (1H, d, J = 9.0 Hz), 7.81 (2H, d, J = 8.3 Hz), 7.97 (2H, d, J = 8.7 Hz). |
| 191 | 603 (M + H). | 1H-NMR (CDCl$_3$, 400 MHz) δ: 1.21 (6H, d, J = 7.1 Hz), 2.78-2.90 (1H, m), 3.08-3.30 (2H, m), 3.44-3.54 (1H, m), 3.88-4.15 (2H, br m), 4.37 (2H, d, J = 6.0 Hz), 4.68 (1H, br s), 6.89 (1H, br s), 7.05-7.16 (5H, m), 7.28-7.34 (1H, m), 7.50-7.59 (2H, m), 7.76 (2H, d, J = 8.4 Hz), 8.00 (2H, d, J = 7.9 Hz). |

TABLE 268

| Example No. | MS ESI m/e: | NMR |
|---|---|---|
| 192 | 488 (M + H). | 1H-NMR (CDCl$_3$, 400 MHz) δ: 1.25 (6H, d, J = 7.1 Hz), 1.46 (3H, t, J = 6.9 Hz), 2.15 (3H, s), 2.40 (1H, dt, J = 18.5, 6.3 Hz), 2.81 (1H, dd, J = 13.1, 4.7 Hz), 2.86-2.94 (1H, m), 3.13 (1H, ddd, J = |

TABLE 268-continued

| Example No. | MS ESI m/e: | NMR |
|---|---|---|
|  |  | 14.7, 11.3, 3.5 Hz), 3.80 (1H, dt, J = 14.6, 2.9 Hz), 4.10 (2H, q, J = 7.1 Hz), 4.28 (1H, dt, J = 14.3, 3.1 Hz), 4.39-4.53 (4H, m), 6.90 (1H, t, J = 5.2 Hz), 6.98 (2H, d, J = 8.8 Hz), 7.13 (2H, d, J = 7.9 Hz), 7.20 (2H, d, J = 7.9 Hz), 7.75 (2H, d, J = 8.8 Hz). |
| 193 | 502 (M + H). | 1H-NMR (CDCl$_3$, 400 MHz) δ: 1.07 (3H, t, J = 7.5 Hz), 1.25 (6H, d, J = 7.1 Hz), 1.85 (2H, q, J = 7.3 Hz), 2.15 (3H, s), 2.40 (1H, dt, J = 18.1, 6.8 Hz), 2.82 (1H, dd, J = 13.6, 4.5 Hz), 2.86-2.95 (1H, m), 3.13 (1H, ddd, J = 14.3, 11.2, 3.0 Hz), 3.80(1H, dt, J = 14.5, 2.5 Hz), 3.99 (2H, t, J = 6.1 Hz), 4.27 (1H, dt, J = 13.5, 3.0 Hz), 4.37-4.53 (4H, m), 6.90 (1H, t, J = 5.6 Hz), 6.98 (2H, d, J = 9.0 Hz), 7.13 (2H, d, J = 8.4 Hz), 7.20 (2H, d, J = 8.2 Hz), 7.75 (2H, d, J = 8.8 Hz). |
| 194 | 500 (M + H). | 1H-NMR (CDCl$_3$, 400 MHz) δ: 0.91 (6H, d, J = 6.6 Hz), 1.25 (6H, d, J = 6.8 Hz), 1.85-1.94 (1H, m), 2.15 (3H, s), 2.38 (1H, ddd, J = 14.2, 11.3, 3.4 Hz), 2.56 (2H, d, J = 7.1 Hz), 2.79 (1H, dd, J = 12.7, 3.9 Hz), 2.86-2.94 (1H, m), 3.14 (1H, ddd, J = 14.8, 11.5, 3.7 Hz), 3.83(1H, dt, J = 15.1, 3.4 Hz), 4.29 (1H, dt, J = 14.3, 2.8 Hz), 4.35-4.53 (4H, m), 6.88 (1H, t, J = 5.8 Hz), 7.13 (2H, d, 3 = 8.2 Hz), 7.21 (2H, d, J = 8.2 Hz), 7.31 (2H, d, J = 8.2 Hz), 7.74 (2H, d, J = 8.4 Hz). |
| 195 | 578 (M + H). | 1H-NMR (CDCl$_3$, 300 MHz) δ: 1.25 (5.8H, d, J = 6.8 Hz), 2.46-2.50 (0.8H, m), 2.88-2.95 (2.0H, m), 3.16-3.27 (1.4H, m), 3.60-4.02 (3.3H, m), 4.27-4.39 (2.7H, m), 4.55-4.59 (1.0H, m), 4.75 (0.7H, d, J = 14.3 Hz), 4.94-4.97 (0.3H, br m), 6.79-6.91 (2.1H, m), 7.13 (2.0H, d, J = 7.9 Hz), 7.21 (2.0H, d, J = 7.9 Hz), 7.43 (0.3H, br s), 7.51 (0.8H, s), 7.74-7.80 (2.1H, m), 7.97 (2.0H, d, J = 8.3 Hz). |

TABLE 269

| Example No. | MS ESI m/e: | NMR |
|---|---|---|
| 196 | 476 (M + H). | 1H-NMR (DMSO-d$_6$, 300 MHz) δ: 1.02-1.35 (6.1H, m), 1.58-1.65 (3.1H, m), 1.85-1.99 (2.9H, m), 2.10 (2.1H, s), 2.73-3.14 (3.5H, m), 3.36-3.53 (1.8H, m), 3.83 (0.7H, d, J = 12.4 Hz), 4.11-4.15 (0.9H, m), 4.40-4.43 (2.3H, m), 4.64-4.67 (0.3H, br m), 5.02-5.03 (0.7H, br m), 7.47-7.50 (2.0H, m), 7.66 (2.0H, d, J = 7.9 Hz), 8.58-8.60 (0.7H, br m), 8.77-8.80 (0.3H, br m). |
| 197 | 504 (M + H). | 1H-NMR (CDCl$_3$, 300 MHz) δ: 1.28 (6.2H, d, J = 7.2 Hz), 1.88 (0.2H, s), 2.13 (2.8H, s), 2.24-2.39 (1.0H, m), 2.75 (0.9H, dd, J = 13.2, 4.1 Hz), 2.92-3.16 (2.0H, m), 3.74-3.89 (7.1H, m), 4.18-4.51 (4.9H, m), 6.37-6.49 (2.0H, m), 7.10 (1.0H, d, J = 8.3 Hz), 7.14-7.20 (0.9H, m), 7.38 (1.9H, d, 3 = 8.3 Hz), 7.74 (2.0H, d, J = 8.3 Hz). |
| 198 | 504 (M + H). | 1H-NMR (CDCl$_3$, 300 MHz) δ: 1.28 (6.2H, d, J = 6.8 Hz), 1.89 (0.3H, s), 2.15 (2.7H, s), 2.33-2.46 (0.9H, m), 2.80 (0.9H, dd, J = 13.6, 4.5 Hz), 2.95-3.05 (1.1H, m), 3.09-3.19 (1.0H, m), 3.79 (0.9H, d, J = 13.6 Hz), 3.88 (6.1H, s), 4.26 (0.9H, d, J = 13.2 Hz), 4.32-4.54 (4.0H, m), 6.74-6.87 (3.2H, m), 6.93-7.00 (0.8H, m), 7.40 (2.0H, d, J = 8.3 Hz), 7.76 (2.0H, d, J = 8.3 Hz). |
| 199 | 599 (M + H). | 1H-NMR (CDCl$_3$, 400 MHz) δ: 1.25 (6H, d, J = 6.8 Hz), 1.76-1.89 (2H, m), 2.29-2.52 (3H, m), 2.65 (1H, dd, J = 14.2, 3.6 Hz), 2.85-2.96 (1H, m), 3.08-3.34 (3H, m), 3.84 (1H, d, J = 13.7 Hz), 4.05 (1H, d, J = 13.5 Hz), 4.25-4.56 (4H, m), 5.63 (1H, t, J = 5.5 Hz), 6.96 (1H, t, J = 5.2 Hz), 7.12-7.24 (4H, m), 7.81 (2H, d, J = 8.8 Hz), 7.97 (2H, d, J = 9.5 Hz). |
| 200 | 632 (M + H). | 1H-NMR (CDCl$_3$, 400 MHz) δ: 1.25 (6H, d, J = 7.0 Hz), 2.44 (1H, dt, J = 18.3, 6.6 Hz), 2.69 (1H, dd, J = 14.6, 3.5 Hz), 2.83-2.95 (7H, m), 3.12 (1H, ddd, J = 15.0, 11.9, 2.7 Hz), 3.90 (1H, d, J = 13.9 Hz), 4.14 (1H, d, J = 13.2 Hz), 4.44-4.53 (3H, m), 4.58 (1H, br s), 6.69 (2H, d, J = 9.0 Hz), 6.94 (1H, t, J = 5.9 Hz), 7.13-7.23 (6H, m), 7.66 (1H, s), 7.83 (2H, d, J = 8.3 Hz), 8.00 (2H, d, J = 8.1 Hz). |

TABLE 270

| Example No. | MS ESI m/e: | NMR |
|---|---|---|
| 201 | 575 (M + H). | 1H-NMR (CDCl$_3$, 400 MHz) δ: 1.24-1.27 (6H, m), 2.70-3.33 (4H, m), 3.38-3.55 (1H, m), 3.80-3.99 (1H, m), 4.17-4.53 (4H, br m), 6.63 (1H, t, J = 4.9 Hz), 7.07-7.25 (5H, m), 7.28-7.36 (1H, m), 7.71-7.84 (2H, br m), 7.95 (2H, d, J = 8.3 Hz), 8.67 (2H, d, J = 5.6 Hz). |
| 202 | 515 (M + H). | 1H-NMR (CDCl$_3$, 400 MHz) δ: 0.93 (3H, t, J = 7.4 Hz), 1.28 (6H, d, J = 6.8 Hz), 1.54-1.66 (2H, m), 2.16 (3H, s), 2.35-2.44 (1H, m), 2.81 (1H, dd, J = 13.5, 4.2 Hz), 2.93 (3H, s), 2.94-3.04 (1H, m), 3.06-3.17 (1H, m), 3.27 (2H, t, J = 7.4 Hz), 3.80 (1H, d, J = 14.6 Hz), 4.23-4.40 (3H, m), 4.44-4.54 (2H, m), 6.64 (2H, d, J = 8.8 Hz), 6.73 (1H, br s), 7.05 (2H, d, J = 8.6 Hz), 7.38 (2H, d, J = 8.2 Hz), 7.74 (2H, d, J = 8.4 Hz). |
| 203 | 498 (M + H). | 1H-NMR (CDCl$_3$, 400 MHz) δ: 1.25 (6H, d, J = 6.8 Hz), 1.80-1.86 (4H, m), 2.15 (3H, s), 2.42 (1H, td, J = 12.2, 3.3 Hz), 2.76-2.94 (6H, m), 3.13 (1H, ddd, J = 14.5, 11.4, 3.5 Hz), 3.83 (1H, dt, J = 14.4, 2.6 Hz), 4.28 (1H, dt, J = 13.9, 2.9 Hz), 4.41 (2H, dd, J = 5.2, 4.7 Hz), 4.46-4.53 (2H, m), 6.88 (1H, t, J = 5.8 Hz), 7.13 (2H, d, J = 8.2 Hz), 7.20 (1H, d, J = 8.2 Hz), 7.20 (2H, d, J = 7.9 Hz), 7.51 (1H, d, J = 8.4 Hz), 7.53 (1H, s). |
| 204 | 484 (M + H). | 1H-NMR (CDCl$_3$, 400 MHz) δ: 1.25 (6H, d, J = 7.1 Hz), 2.12-2.20 (2H, m), 2.15 (3H, s), 2.41 (1H, td, J = 12.8, 3.4 Hz), 2.79-3.01 (6H, m), 3.13 (1H, ddd, J = 14.4, 11.6, 3.3 Hz), 3.83 (1H, dt, J = 14.5, 2.9 Hz), 4.28 (1H, dt, J = 14.3, 2.9 Hz), 4.35-4.42 (2H, m), 4.46-4.52 (2H, m), 6.87 (1H, t, J = 5.2 Hz), 7.12 (2H, d, J = 7.9 Hz), 7.20 (2H, d, J = 8.2 Hz), 7.34 (1H, d, J = 7.7 Hz), 7.61 (1H, dd, J = 7.9, 1.1 Hz), 7.67 (1H, d, J = 0.9 Hz). |

TABLE 271

| Example No. | MS ESI m/e: | NMR |
|---|---|---|
| 205 | 486 (M + H). | 1H-NMR (CDCl$_3$, 400 MHz) δ: 0.96 (3H, t, J = 7.4 Hz), 1.25 (6H, d, J = 6.8 Hz), 1.62-1.72 (2H, m), 2.15 (3H, s), 2.38 (1H, ddd, J = 14.2, 11.6, 3.3 Hz), 2.67 (2H, t, J = 7.6 Hz), 2.79 (1H, dd, J = 14.3, 4.4 Hz), 2.86-2.94 (1H, m), 3.14 (1H, ddd, J = 14.8, 11.7, 3.4 Hz), 3.83 (1H, dt, J = 14.3, 2.9 Hz), 4.28 (1H, dt, J = 14.1, 3.0 Hz), 4.35-4.43 (2H, m), 4.46-4.53 (2H, m), 6.88 (1H, t, J = 6.2 Hz), 7.13 (2H, d, J = 7.9 Hz), 7.21 (2H, d, J = 8.2 Hz), 7.34 (2H, d, J = 8.2 Hz), 7.74 (2H, d, J = 8.4 Hz). |
| 206 | 520 (M + H). | 1H-NMR (CDCl$_3$, 400 MHz) δ: 1.23 (6H, d, J = 7.1 Hz), 2.15 (3H, s), 2.45 (1H, ddd, J = 14.1, 11.2, 3.1 Hz), 2.84-2.92 (2H, m), 3.18 (1H, ddd, J = 14.4, 11.1, 3.5 Hz), 3.89 (1H, dt, J = 14.3, 3.0 Hz), 4.33 (1H, dt, J = 13.8, 3.2 Hz), 4.37-4.44 (2H, m), 4.50-4.56 (2H, m), 6.85 (1H, t, J = 4.7 Hz), 7.12 (2H, d, J = 7.9 Hz), 7.18 (2H, d, J = 8.2 Hz), 7.43-7.53 (3H, m), 7.61 (2H, d, J = 6.8 Hz), 7.75 (2H, d, J = 8.4 Hz), 7.90 (2H, d, J = 8.4 Hz). |
| 207 | 528 M + H). | 1H-NMR (CDCl$_3$, 400 MHz) δ: 1.25 (6H, d, J = 6.8 Hz), 2.16 (3H, s), 2.42 (1H, ddd, J = 15.1, 11.9, 3.6 Hz), 2.83-2.95 (2H, m), 3.18 (1H, ddd, J = 14.6, 11.8, 3.1 Hz), 3.82 (1H, dt, J = 14.6, 3.1 Hz), 4.30-4.57 (5H, m), 6.75 (1H, t, J = 5.5 Hz), 7.12 (2H, d, J = 7.9 Hz), 7.21 (2H, d, J = 7.9 Hz), 7.35 (2H, d, J = 8.4 Hz), 7.89 (2H, d, J = 8.8 Hz). |
| 208 | 500 (M + H). | 1H-NMR (CDCl$_3$, 400 MHz) δ: 1.25 (6H, d, J = 6.8 Hz), 1.35 (9H, s), 2.15 (3H, s), 2.40 (1H, ddd, J = 13.7, 11.2, 3.1 Hz), 2.81 (1H, dd, J = 13.2, 4.4 Hz), 2.86-2.94 (1H, m), 3.15 (1H, ddd, J = 14.7, 11.4, 3.5 Hz), 3.83 (1H, dt, J = 14.1, 3.1 Hz), 4.28 (1H, dt, J = 14.1, 3.1 Hz), 4.36-4.53 (4H, m), 6.91 (1H, t, J = 5.2 Hz), 7.14 (2H, d, J = 7.9 Hz), 7.21 (2H, d, J = 8.2 Hz), 7.55 (2H, d, J = 8.6 Hz), 7.76 (2H, d, J = 8.6 Hz). |

TABLE 272

| Example No. | MS ESI m/e: | NMR |
|---|---|---|
| 209 | 470 (M − 2HCl + H). | 1H-NMR (DMSO-d$_6$, 300 MHz) δ: 2.68-2.89 (1H, m), 2.90-3.14 (1H, m), 3.22 (1H, d, J = 12.4 Hz), 3.52-3.73 (2H, m), 3.91 (1H, d, |

TABLE 272-continued

| Example No. | MS ESI m/e: | NMR |
|---|---|---|
| | | J = 13.6 Hz), 4.15 (2H, d, J = 4.9 Hz), 4.75 (1H, d, J = 3.8 Hz), 4.95 (1H, br s), 7.24 (3H, br s), 7.96 (2H, d, J = 8.7 Hz), 8.05 (2H, d, J = 7.9 Hz), 8.46 (1H, br s), 8.81 (1H, br s), 9.70 (1H, br s). |
| 210 | 458 (M + H). | 1H-NMR (CDCl$_3$, 400 MHz) δ: 1.28 (6H, d, J = 7.0 Hz), 2.15 (3H, s), 2.34-2.43 (4H, m), 2.81 (1H, dd, J = 13.1, 3.8 Hz), 2.94-3.03 (1H, m), 3.09-3.16 (1H, m), 3.81 (1H, d, J = 14.4 Hz), 4.28 (1H, d, J = 13.7 Hz), 4.35-4.52 (4H, m), 6.88-6.90 (1H, br m), 7.10 (2H, d, J = 8.1 Hz), 7.15 (2H, d, J = 7.9 Hz), 7.39 (2H, d, J = 8.3 Hz), 7.75 (2H, d, J = 8.3 Hz). |
| 211 | 590 (M + H). | 1H-NMR (CDCl$_3$, 400 MHz) δ: 1.24 (6H, d, J = 6.8 Hz), 2.48 (1H, td, J = 13.2, 3.0 Hz), 2.73 (1H, dd, J = 15.0, 3.3 Hz), 2.83-2.96 (1H, m), 3.11 (1H, ddd, J = 15.2, 12.2, 2.7 Hz), 3.94 (1H, d, J = 13.2 Hz), 4.18 (1H, d, J = 14.3 Hz), 4.43-4.64 (4H, m), 7.00 (1H, t, J = 5.3 Hz), 7.11-7.22 (4H, m), 7.72-7.87 (3H, m), 8.01 (2H, d, J = 8.4 Hz), 8.22-8.33 (2H, m), 8.51 (1H, d, J = 2.4 Hz). |
| 212 | 612 (M + H). | 1H-NMR (CDCl$_3$, 300 MHz) δ: 1.25 (6H, d, J = 6.8 Hz), 1.59-1.63 (4H, br m), 2.20-2.44 (4H, m), 2.57-2.61 (1H, m), 2.80 (1H, dd, J = 13.4, 4.0 Hz), 2.86-2.95 (1H, m), 3.18-3.22 (1H, m), 3.64 (3H, s), 3.84 (1H, d, J = 13.9 Hz), 4.37-4.45 (3H, m), 4.57 (2H, d, J = 13.6 Hz), 6.71-6.72 (1H, m), 7.12 (2H, d, J = 7.9 Hz), 7.21 (2H, d, J = 8.3 Hz), 7.73-7.77 (1H, br m), 7.81 (2H, d, J = 8.3 Hz), 7.98 (2H, d, J = 8.3 Hz). |
| 213 | 598 (M + H). | 1H-NMR (CDCl$_3$, 300 MHz) δ: 1.25 (6H, d, J = 7.2 Hz), 2.23-2.64 (4H, m), 2.83-2.90 (2H, m), 3.19-3.23 (1H, m), 3.67-3.83 (2H, m), 4.32-4.40 (3H, m), 4.53-4.57 (2H, m), 6.74-6.77 (1H, br m), 7.12 (2H, d, J = 8.3 Hz), 7.21 (2H, d, J = 8.3 Hz), 7.73-7.75 (0H, br m), 7.81 (2H, d, J = 8.3 Hz), 7.97 (2H, d, J = 8.3 Hz). |

TABLE 273

| Example No. | MS ESI m/e: | NMR |
|---|---|---|
| 214 | 474 (M + H). | 1H-NMR (CDCl$_3$, 400 MHz) δ: 1.25 (6H, d, J = 7.1 Hz), 2.15 (3H, s), 2.39 (1H, dt, J = 18.5, 6.6 Hz), 2.81 (1H, dd, J = 14.1, 4.0 Hz), 2.86-2.94 (1H, m), 3.14 (1H, ddd, J = 14.7, 11.7, 3.3 Hz), 3.81 (1H, dt, J = 14.5, 2.6 Hz), 3.89 (3H, s), 4.28 (1H, dt, J = 13.3, 2.6 Hz), 4.37-4.53 (4H, m), 6.88 (1H, t, J = 5.4 Hz), 7.00 (2H, d, J = 9.0 Hz), 7.13 (2H, d, J = 7.9 Hz), 7.20 (2H, d, J = 7.9 Hz), 7.77 (2H, d, J = 9.0 Hz). |
| 215 | 516 (M + H). | 1H-NMR (CDCl$_3$, 400 MHz) δ: 1.20 (6H, d, J = 6.8 Hz), 1.25 (6H, d, J = 7.1 Hz), 2.15 (3H, s), 2.34 (1H, td, J = 12.7, 3.7 Hz), 2.76 (1H, dd, J = 13.2, 4.0 Hz), 2.86-2.94 (1H, m), 3.13 (1H, ddd, J = 14.8, 11.7, 3.4 Hz), 3.29-3.37 (1H, m), 3.82 (1H, dt, J = 14.3, 3.0 Hz), 3.92 (3H, s), 4.28 (1H, dt, J = 13.0, 2.8 Hz), 4.36-4.53 (4H, m), 6.90-6.95 (1H, m), 6.92 (1H, d, J = 8.6 Hz), 7.13 (2H, d, J = 8.2 Hz), 7.20 (2H, d, J = 8.2 Hz), 7.62-7.69 (2H, m). |
| 216 | 508 (M + H). | 1H-NMR (CDCl$_3$, 400 MHz) δ: 1.25 (6H, d, J = 7.1 Hz), 2.16 (3H, s), 2.42 (1H, ddd, J = 14.1, 11.4, 3.2 Hz), 2.82-2.96 (2H, m), 3.16 (1H, ddd, J = 14.6, 11.3, 3.3 Hz), 3.81 (1H, dt, J = 15.3, 2.8 Hz), 3.99 (3H, s), 4.32 (1H, dt, J = 14.0, 3.4 Hz), 4.39-4.55 (4H, m), 6.83 (1H, t, J = 5.0 Hz), 7.02 (1H, d, J = 8.6 Hz), 7.13 (2H, d, J = 8.2 Hz), 7.21 (2H, d, J = 8.2 Hz), 7.73 (1H, dd, J = 8.5, 2.5 Hz), 7.85 (1H, d, J = 2.4 Hz). |
| 217 | 546 (M + H). | 1H-NMR (CDCl$_3$, 400 MHz) δ: 1.25 (6H, d, J = 7.1 Hz), 2.22 (3H, s), 2.62 (1H, td, J = 12.7, 3.0 Hz), 2.86-2.96 (1H, m), 3.05 (1H, ddd, J = 15.0, 12.0, 3.2 Hz), 3.15 (1H, dd, J = 13.6, 4.3 Hz), 3.63 (3H, s), 3.64 (3H, s), 3.72 (3H, s), 3.85 (1H, dt, J = 14.2, 2.1 Hz), 4.36 (2H, d, J = 5.7 Hz), 4.46-4.67 (3H, m), 6.83 (1H, d, J = 8.6 Hz), 6.93 (1H, t, J = 5.3 Hz), 7.08 (2H, d, J = 7.9 Hz), 7.19 (2H, d, J = 8.2 Hz), 7.48 (1H, dd, J = 8.5, 2.3 Hz), 7.84 (1H, d, J = 2.2 Hz). |

TABLE 274

| Example No. | MS ESI m/e: | NMR |
|---|---|---|
| 218 | 560 (M + H). | 1H-NMR (CDCl₃, 400 MHz) δ: 1.25 (6H, d, J = 6.8 Hz), 2.15 (3H, s), 2.39 (1H, ddd, J = 14.1, 11.5, 2.9 Hz), 2.62 (2H, t, J = 7.4 Hz), 2.83 (1H, dd, J = 13.9, 4.6 Hz), 2.85-2.92 (1H, m), 2.95 (2H, t, J = 7.1 Hz), 3.13 (1H, ddd, J = 14.4, 11.5, 3.3 Hz), 3.64 (3H, s), 3.79 (1H, dt, J = 13.4, 2.9 Hz), 3.92 (3H, s), 4.26 (1H, dt, J = 13.2, 2.6 Hz), 4.37-4.52 (4H, m), 6.92 (1H, d, J = 8.6 Hz), 6.95 (1H, t, J = 5.3 Hz), 7.13 (2H, d, J = 8.2 Hz), 7.20 (2H, d, J = 8.2 Hz), 7.66 (1H, d, J = 2.4 Hz), 7.71 (1H, dd, J = 8.8, 2.4 Hz). |
| 219 | 578 (M + H). | 1H-NMR (CDCl₃, 300 MHz) δ: 1.25 (6H, d, J = 6.8 Hz), 2.39-2.45 (1H, m), 2.86-2.93 (2H, m), 3.13-3.23 (1H, m), 3.91 (1H, d, J = 13.9 Hz), 4.43-4.48 (4H, m), 4.55-4.58 (1H, br m), 4.75 (1H, d, J = 16.6 Hz), 5.26 (1H, d, J = 16.6 Hz), 6.80-6.83 (1H, br m), 6.89 (1H, s), 7.06 (1H, s), 7.12 (2H, d, J = 7.9 Hz), 7.22 (2H, d, J = 7.9 Hz), 7.46 (1H, s), 7.82 (2H, d, J = 8.3 Hz), 7.99 (2H, d, J = 8.3 Hz). |
| 220 | 579 (M + H). | 1H-NMR (CDCl₃, 300 MHz) δ: 1.26 (6H, d, J = 6.8 Hz), 2.39-2.49 (1H, m), 2.87-2.96 (2H, m), 3.19-3.23 (1H, m), 3.93 (1H, d, J = 13.6 Hz), 4.39-4.43 (3H, m), 4.57-4.61 (2H, m), 5.44 (1H, d, J = 16.2 Hz), 5.53 (1H, d, J = 16.2 Hz), 6.82-6.83 (1H, br m), 7.14 (2H, d, J = 8.3 Hz), 7.23 (2H, d, J = 8.3 Hz), 7.63 (1H, s), 7.71 (1H, s), 7.83 (2H, d, J = 8.3 Hz), 7.99 (2H, d, J = 8.3 Hz). |
| 221 | 532 (M + H). | 1H-NMR (CDCl₃, 400 MHz) δ: 1.25 (6H, d, J = 6.8 Hz), 2.22 (3H, s), 2.60 (1H, td, J = 13.2, 2.8 Hz), 2.86-2.94 (1H, m), 3.05 (1H, ddd, J = 14.5, 12.0, 2.8 Hz), 3.14 (1H, dd, J = 12.8, 4.2 Hz), 3.64 (3H, s), 3.65 (2H, s), 3.82 (1H, dt, J = 13.7, 2.4 Hz), 4.35 (1H, d, J = 2.9 Hz), 4.36 (1H, d, J = 2.6 Hz), 4.46 (1H, dt, J = 13.0, 2.7 Hz), 4.57 (1H, d, J = 3.7 Hz), 4.63 (1H, d, J = 13.7 Hz), 6.84 (1H, d, J = 8.6 Hz), 6.96 (1H, t, J = 5.0 Hz), 7.09 (2H, d, J = 8.2 Hz), 7.19 (2H, d, J = 7.9 Hz), 7.48 (1H, dd, J = 9.0, 2.2 Hz), 7.86 (1H, d, J = 2.0 Hz), 9.50 (1H, br s). |

TABLE 275

| Example No. | MS ESI m/e: | NMR |
|---|---|---|
| 222 | 546 (M + H). | 1H-NMR (CDCl₃, 400 MHz) δ: 1.24 (6H, d, J = 7.1 Hz), 2.11 (3H, s), 2.49 (1H, ddd, J = 13.7, 10.8, 3.3 Hz), 2.67 (2H, t, J = 6.7 Hz), 2.81-2.99 (4H, m), 3.16 (1H, ddd, J = 14.7, 11.3, 3.4 Hz), 3.76 (1H, dt, J = 14.7, 3.4 Hz), 3.92 (3H, s), 4.13 (1H, dt, J = 13.5, 3.0 Hz), 4.37-4.48 (4H, m), 6.91 (1H, d, J = 8.6 Hz), 7.03 (1H, t, J = 6.1 Hz), 7.14 (2H, d, J = 8.2 Hz), 7.19-7.22 (1H, m), 7.20 (2H, d, J = 7.7 Hz), 7.71 (2H, d, J = 7.9 Hz). |
| 223 | 544 (M + H). | 1H-NMR (CDCl₃, 300 MHz) δ: 1.29 (6.3H, d, J = 6.8 Hz), 1.58 (8.7H, s), 1.90 (0.3H, s), 2.14 (2.8H, s), 2.33-2.45 (0.9H, m), 2.79 (0.9H, dd, J = 13.6, 4.5 Hz), 2.96-3.05 (1.0H, m), 3.11-3.21 (1.0H, m), 3.66 (3.0H, s), 3.84 (1.0H, d, J = 14.3 Hz), 4.28 (0.9H, d, J = 13.2 Hz), 4.38-4.54 (4.1H, m), 6.91-6.99 (0.9H, m), 7.17 (2.0H, d, J = 8.3 Hz), 7.32 (2.1H, d, J = 8.7 Hz), 7.40 (2.0H, d, J = 8.3 Hz), 7.76 (2.0H, d, J = 8.3 Hz). |
| 224 | 488 (M + H). | 1H-NMR (CDC₃, 300 MHz) δ: 1.29 (6.2H, d, J = 7.2 Hz), 1.79 (0.8H, t, J = 5.5 Hz), 1.91 (0.2H, s), 2.09 (2.7H, s), 2.34-2.44 (0.9H, m), 2.79 (0.9H, dd, J = 13.8, 4.3 Hz), 2.85 (2.1H, t, J = 6.4 Hz), 2.96-3.05 (1.0H, m), 3.10-3.20 (1.0H, m), 3.72-3.82 (0.9H, m), 3.82-3.92 (2.0H, m), 4.20 (0.9H, d, J = 14.3 Hz), 4.29-4.55 (3.9H, m), 6.95-7.03 (0.8H, m), 7.15-7.24 (4.1H, m), 7.40 (1.9H, d, J = 8.3 Hz), 7.76 (2.0H, d, J = 8.3 Hz). |
| 225 | 527 (M + H). | 1H-NMR (CDCl₃, 400 MHz) δ: 1.04-1.24 (6H, m), 2.50-3.80 (6H, m), 3.92-4.87 (6H, m), 6.99-7.16 (4H, br m), 7.52-7.63 (2H, br m), 7.81 (2H, br s), 8.06-8.32 (3H, m). |
| 226 | 474 (M + H). | 1H-NMR (CDCl₃, 400 MHz) δ: 1.28 (6H, d, J = 6.8 Hz), 1.80 (1H, br s), 2.13 (3H, s), 2.38 (1H, dt, J = 17.3, 6.9 Hz), 2.80 (1H, dd, J = 13.9, 4.9 Hz), 2.93-3.20 (2H, m), 3.80 (1H, dt, J = 14.3, 3.3 Hz), 4.24 (1H, d, J = 13.7 Hz), 4.36-4.54 (4H, m), 4.68 (2H, d, J = 4.6 Hz), 6.99 (1H, t, J = 5.1 Hz), 7.22 (2H, d, J = 8.2 Hz), 7.32-7.43 (4H, m), 7.76 (2H, d, J = 8.4 Hz). |

TABLE 276

| Example No. | MS ESI m/e: | NMR |
|---|---|---|
| 227 | 490 (M + H). | 1H-NMR (CDCl$_3$, 300 MHz) δ: 1.28 (6H, d, J = 7.2 Hz), 2.15 (3H, s), 2.37-2.43 (1H, m), 2.48 (3H, s), 2.81 (1H, dd, J = 13.9, 4.5 Hz), 2.96-3.05 (1H, m), 3.10-3.16 (1H, m), 3.82 (1H, d, J =13.9 Hz), 4.28 (1H, d, J = 13.2 Hz), 4.39-4.48 (4H, m), 6.92 (1H, t, J = 4.1 Hz), 7.14 (2H, d, J = 8.3 Hz), 7.23 (2H, d, J = 8.3 Hz), 7.40 (2H, d, J = 8.3 Hz), 7.75 (2H, d, J = 8.3 Hz). |
| 228 | 578 (M + H). | 1H-NMR (CDCl$_3$, 300 MHz) δ: 1.26 (6H, d, J = 6.8 Hz), 2.40-2.45 (1H, m), 2.85-2.93 (2H, m), 3.15-3.25 (1H, m), 3.89 (1H, d, J = 14.7 Hz), 4.28-4.61 (5H, m), 4.90 (1H, br s), 5.19 (2H, abq, J = 24.9, 16.2 Hz), 6.28-6.29 (1H, br m), 6.77-6.80 (1H, br m), 7.14 (2H, d, J = 7.9 Hz), 7.22 (2H, d, J = 8.3 Hz), 7.44 (1H, s), 7.51 (1H, s), 7.81 (2H, d, J = 8.3 Hz), 7.97 (2H, d, J = 8.7 Hz). |
| 229 | 579 (M + H). | 1H-NMR (CDCl$_3$, 300 MHz) δ: 1.26 (6H, d, J = 6.8 Hz), 2.40-2.48 (1H, m), 2.87-2.96 (2H, m), 3.14-3.24 (1H, m), 3.92 (1H, d, J = 13.9 Hz), 4.38-4.58 (5H, m), 5.16 (1H, d, J = 16.6 Hz), 5.39 (1H, d, J = 16.6 Hz), 6.79-6.81 (1H, br m), 7.13 (2H, d, J = 7.9 Hz), 7.22 (2H, d, J = 7.9 Hz), 7.83 (2H, d, J = 8.3 Hz), 7.93 (1H, s), 7.99 (2H, d, J = 8.3 Hz), 8.13 (1H, s). |
| 230 | 579 (M + H). | 1H-NMR (CDCl$_3$, 300 MHz) δ: 1.25 (6H, d, J = 7.2 Hz), 2.42-2.49 (1H, m), 2.87-2.96 (2H, m), 3.14-3.18 (1H, m), 3.93 (1H, d, J = 12.8 Hz), 4.42 (4H, dt, J = 21.0, 7.9 Hz), 4.57-4.61 (1H, br m), 4.69 (1H, d, J = 16.6 Hz), 5.52 (1H, d, J = 16.6 Hz), 6.81-6.84 (1H, br m), 7.11 (2H, d, J = 8.3 Hz), 7.21 (2H, d, J = 7.9 Hz), 7.83 (2H, d, J = 8.3 Hz), 8.00 (2H, d, J = 8.3 Hz), 8.15 (2H, s). |

TABLE 277

| Example No. | MS ESI m/e: | NMR |
|---|---|---|
| 231 | 530 M + H). | 1H-NMR (CDCl$_3$, 300 MHz) δ: 1.28 (6.3H, d, J = 7.2 Hz), 1.60 (6.0H, s), 1.90 (0.3H, s), 2.11 (2.7H, s), 2.33-2.46 (1.1H, m), 2.79 (1.3H, dd, J = 13.6, 4.1 Hz), 2.95-3.04 (1.3H, m), 3.10-3.20 (1.1H, m), 3.80 (0.8H, d, J = 14.7 Hz), 4.22 (0.9H, d, J = 12.8 Hz), 4.34-4.52 (4.0H, m), 7.00-7.08 (0.9H, m), 7.19 (2.0H, d, J = 7.9 Hz), 7.34-7.43 (4.1H, m), 7.75 (2.0H, d, J = 8.3 Hz). |
| 232 | 472 (M + H) . | 1H-NMR (CDCl$_3$, 300 MHz) δ: 1.19-1.32 (9.4H, m), 1.91 (0.2H, s), 2.15 (2.7H, s), 2.33-2.45 (0.9H, m), 2.64 (2.1H, q, J = 7.5 Hz), 2.81 (0.9H, dd, J = 13.9, 4.5 Hz), 2.95-3.04 (1.0H, m), 3.09-3.18 (0.9H, m), 3.82 (0.9H, d, J = 14.7 Hz), 4.28 (0.9H, d, J = 13.6 Hz), 4.33-4.55 (4.0H, m), 6.85-6.93 (0.9H, m), 7.09-7.22 (4.2H, m), 7.39 (2.0H, d, J = 8.3 Hz), 7.75 (2.0H, d, J = 8.3 Hz). |
| 233 | 557 (M + H). | 1H-NMR (CDCl$_3$, 300 MHz) δ: 1.29 (6.3H, d, J = 6.8 Hz), 1.54 (6.2H, s), 1.91 (0.3H, s), 2.14 (2.7H, s), 2.30-3.08 (8.8H, br m), 3.12-3.22 (1.3H, m), 3.83 (0.9H, d, J = 14.3 Hz), 4.27 (0.9H, d, J = 13.9 Hz), 4.39-4.54 (4.0H, m), 6.96-7.04 (0.9H, m), 7.15-7.23 (4.2H, m), 7.42 (2.0H, d, J = 8.3 Hz), 7.77 (2.0H, d, J = 8.3 Hz). |
| 234 | 514 (M + H). | 1H-NMR (CDCl$_3$, 300 MHz) δ: 0.86 (4.1H, d, J = 4.1 Hz), 1.29 (6.3H, d, J = 6.8 Hz), 1.83-1.90 (0.8H, m), 1.91 (0.2H, s), 2.09 (2.7H, s), 2.32-2.45 (0.9H, m), 2.79 (0.9H, dd, J = 13.8, 4.3 Hz), 2.93-3.06 (1.1H, m), 3.10-3.20 (1.0H, m), 3.66 (2.1H, d, J = 5.3 Hz), 3.78 (0.9H, d, J = 13.9 Hz), 4.20 (0.9H, d, J = 12.8 Hz), 4.29-4.53 (4.0H, m), 6.93-7.04 (0.8H, m), 7.18 (2.1H, d, J = 8.3 Hz), 7.34 (2.1H, d, J = 7.9 Hz), 7.41 (1.9H, d, J = 8.7 Hz), 7.76 (2.0H, d, J = 8.3 Hz). |

TABLE 278

| Example No. | MS ESI m/e: | NMR |
|---|---|---|
| 235 | 532 (M + H). | 1H-NMR (CDCl$_3$, 400 MHz) δ: 1.25 (6H, d, J = 6.8 Hz), 2.15 (3H, s), 2.41 (1H, ddd, J = 1.41, 11.3, 2.9 Hz), 2.81 (1H, dd, J = 13.9, 4.4 Hz), 2.86-2.94 (1H, m), 3.17 (1H, ddd, J = 14.4, 11.5, 3.3 Hz), 3.82 (1H, dt, J = 14.0, 3.3 Hz), 3.92 (3H, s), 4.00 (3H, s), 4.31 (1H, dt, J = 13.3, 2.6 Hz), 4.36-4.54 (4H, m), 6.89 (1H, t, J = 5.0 Hz), 7.09 (1H, d, J = 8.8 Hz), 7.13 (2H, d, J = 8.2 Hz), 7.21 (2H, d, J = 7.9 Hz), 7.93 (1H, dd, J = 8.0, 2.5 Hz), 8.26 (1H, d, J = 2.2 Hz). |
| 236 | 502 (M + H). | 1H-NMR (CDCl$_3$, 400 MHz) δ: 1.18 (3H, t, J = 7.5 Hz), 1.25 (6H, d, J = 7.1 Hz), 2.15 (3H, s), 2.38 (1H, td, J = 12.6, 3.2 Hz), 2.65 |

TABLE 278-continued

| Example No. | MS ESI m/e: | NMR |
|---|---|---|
|  |  | (2H, q, J = 7.5 Hz), 2.80 (1H, dd, J = 13.5, 4.4 Hz), 2.86-2.94 (1H, m), 3.13 (1H, ddd, J = 14.7, 11.6, 3.4 Hz), 3.82 (1H, dt, J = 14.4, 2.8 Hz), 3.91 (3H, s), 4.27 (1H, dt, J = 13.1, 2.6 Hz), 4.36-4.53 (4H, m), 6.91 (2H, d, J = 8.6 Hz), 7.13 (2H, d, J = 8.2 Hz), 7.20 (2H, d, J = 8.2 Hz), 7.59 (1H, d, J = 2.6 Hz), 7.68 (1H, dd, J = 8.9, 2.8 Hz). |
| 237 | 514 (M + H). | 1H-NMR (CDCl$_3$, 400 MHz) δ: 0.91 (9H, s), 1.25 (6H, d, J = 7.1 Hz), 2.15 (3H, s), 2.37 (1H, ddd, J = 14.2, 11.4, 3.2 Hz), 2.58 (2H, s), 2.78 (1H, dd, J = 13.6, 4.7 Hz), 2.86-2.94 (1H, m), 3.15 (1H, ddd, J = 14.5, 11.5, 3.4 Hz), 3.84 (1H, dt, J = 14.8, 3.2 Hz), 4.29 (1H, dt, J = 13.5, 2.8 Hz), 4.35-4.53 (4H, m), 6.88 (1H, t, J = 5.2 Hz), 7.13 (2H, d, J = 7.9 Hz), 7.21 (2H, d, J = 7.9 Hz), 7.29 (2H, d, J = 8.4 Hz), 7.74 (2H, d, J = 8.2 Hz). |
| 238 | 532 (M + H). | 1H-NMR (CDCl$_3$, 400 MHz) δ: 1.25 (6H, d, J = 7.1 Hz), 2.15 (3H, s), 2.41 (1H, ddd, J = 13.9, 11.4, 3.2 Hz), 2.82 (1H, dd, J = 13.6, 3.9 Hz), 2.86-2.94 (1H, ddd, J = 14.4, 11.5, 3.3 Hz), 3.80 (1H, dt, J = 13.7, 3.0 Hz), 3.83 (3H, s), 4.29 (1H, dt, J = 13.5, 2.5 Hz), 4.35-4.53 (4H, m), 4.71 (2H, s), 6.87 (1H, t, J = 5.3 Hz), 7.01 (2H, d, J = 9.0 Hz), 7.13 (2H, d, J = 7.9 Hz), 7.21 (2H, d, J = 8.2 Hz), 7.79 (2H, d, J = 9.0 Hz). |

TABLE 279

| Example No. | MS ESI m/e: | NMR |
|---|---|---|
| 239 | 499 (M + H). | 1H-NMR (CDCl$_3$, 400 MHz) δ: 1.25 (6H, d, J = 6.8 Hz), 2.15 (3H, s), 2.41 (1H, ddd, J = 14.2, 11.0, 2.8 Hz), 2.84-2.95 (2H, m), 3.19 (1H, ddd, J = 14.7, 11.1, 3.5 Hz), 3.78 (1H, dt, J = 14.6, 2.8 Hz), 4.05 (3H, s), 4.29-4.59 (5H, m), 6.75 (1H, t, J = 5.1 Hz), 7.08-7.24 (5H, m), 7.99 (1H, dd, J = 8.9, 2.1 Hz), 8.05 (1H, d, J = 2.4 Hz). |
| 240 | 530 (M + H). | 1H-NMR (CDCl$_3$, 400 MHz) δ: 1.25 (6H, d, J = 6.8 Hz), 1.37 (9H, s), 2.16 (3H, s), 2.35 (1H, ddd, J = 14.3, 11.6, 3.2 Hz), 2.77 (1H, dd, J = 13.3, 4.3 Hz), 2.86-2.94 (1H, m), 3.13 (1H, ddd, J = 14.9, 11.6, 3.5 Hz), 3.81 (1H, dt, J = 14.5, 3.1 Hz), 3.93 (3H, s), 4.29 (1H, dt, J = 13.6, 2.7 Hz), 4.35-4.53 (4H, m), 6.95 (1H, d, J = 8.8 Hz), 6.95 (1H, t, J = 4.4 Hz), 7.13 (2H, d, J = 8.2 Hz), 7.20 (2H, d, J = 8.2 Hz), 7.68-7.72 (2H, m). |
| 241 | 542 (M + H). | 1H-NMR (CDCl$_3$, 400 MHz) δ: 1.25 (6H, d, J = 7.1 Hz), 1.45-1.54 (2H, m), 1.66-1.83 (4H, m), 1.98-2.07 (2H, m), 2.15 (3H, s), 2.34 (1H, ddd, J = 14.6, 11.6, 3.4 Hz), 2.77 (1H, dd, J = 13.1, 4.3 Hz), 2.86-2.94 (1H, m), 3.13 (1H, ddd, J = 14.4, 11.6, 3.2 Hz), 3.31 (1H, ddd, J = 9.6, 7.1, 2.3 Hz), 3.82 (1H, dt, J = 14.3, 2.5 Hz), 3.91 (3H, s), 4.27 (1H, dt, J = 13.8, 2.9 Hz), 4.35-4.53 (4H, m), 6.91 (1H, d, J = 8.4 Hz), 6.93 (1H, t, J = 5.2 Hz), 7.13 (2H, d, J = 8.2 Hz), 7.20 (2H, d, J = 8.2 Hz), 7.64-7.69 (2H, m). |
| 242 | (M + H). | 1H-NMR (CDCl$_3$, 300 MHz) δ: 1.26 (6H, d, J = 7.2 Hz), 2.40-2.46 (1H, m), 2.86-2.93 (2H, m), 3.16-3.20 (1H, m), 3.90 (1H, d, J = 15.8 Hz), 4.42-4.53 (4H, m), 5.45 (1H, d, J = 15.8 Hz), 5.68 (1H, d, J = 16.2 Hz), 6.70-6.74 (1H, br m), 7.15 (2H, d, J = 8.3 Hz), 7.23 (2H, d, J = 8.3 Hz), 7.65 (2H, s), 7.81 (2H, d, J = 8.3 Hz), 7.98 (2H, d, J = 8.7 Hz). |

TABLE 280

| Example No. | MS ESI m/e: | NMR |
|---|---|---|
| 243 | 603 (M + H). | 1H-NMR (CDCl$_3$, 400 MHz) δ: 1.25 (6H, d, J = 6.8 Hz), 2.42 (1H, dt, J = 18.2, 6.8 Hz), 2.64 (1H, dd, J = 14.1, 4.2 Hz), 2.85-2.97 (1H, m), 3.12 (1H, ddd, J = 15.3, 11.7, 2.6 Hz), 4.10 (1H, d, J = 13.2 Hz), 4.21-4.54 (7H, m), 5.90 (1H, t, J = 5.3 Hz), 6.89 (1H, t, J = 5.7 Hz), 7.12 (2H, d, J = 8.2 Hz), 7.18-7.24 (3H, m), 7.27-7.31 (4H, m), 7.81 (2H, d, J = 8.8 Hz), 7.98 (2H, d, J = 8.4 Hz). |
| 244 | 597 (M + H). | 1H-NMR (CDCl$_3$, 400 MHz) δ: 1.21 (6H, d, J = 6.6 Hz), 2.74-3.11 (3H, m), 3.36-3.92 (3H, m), 4.20-4.70 (4H, m), 6.94-7.20 (4H, br m), 7.63-7.79 (2H, br m), 7.86-8.01 (2H, br m). |
| 245 | 691 (M + H). | 1H-NMR (CDCl$_3$, 400 MHz) δ: 1.22-1.31 (9H, m), 2.40-2.50 (1H, m), 2.70 (1H, dd, J = 14.8, 3.5 Hz), 2.85-2.96 (1H, m), 3.06-3.16 (1H, m), 3.91 (1H, d, J = 14.6 Hz), 4.16 (1H, d, J = 13.0 Hz), 4.25 (2H, q, J = 7.0 Hz), 4.44-4.61 (6H, m), 6.84 (2H, d, J = 9.0 Hz), 6.95 (1H, t, J = 5.7 Hz), 7.12-7.24 (6H, m), 7.83 (2H, d, J = 8.2 Hz), 7.93 (1H, s), 8.00 (2H, d, J = 7.9 Hz). |
| 246 | 663 (M + H). | 1H-NMR (CD$_3$OD, 400 MHz) δ: 1.20 (6H, d, J = 6.8 Hz), 2.79-2.89 (1H, m), 3.02 (1H, ddd, J = 14.4, 10.2, 2.9 Hz), 3.19 (1H, dd, J = 14.3, 4.2 Hz), 3.64-3.84 (2H, m), 4.03 (1H, d, J = 13.2 Hz), 4.23 (2H, s), 4.39-4.50 (3H, m), 4.59 (1H, br s), 6.85 (2H, d, J = 9.0 Hz), 7.09-7.20 |

TABLE 280-continued

| Example No. | MS ESI m/e: | NMR |
|---|---|---|
| | | (6H, m), 7.80 (2H, d, J = 8.2 Hz), 8.00 (2H, d, J = 8.2 Hz). |
| 247 | 472 (M + H). | 1H-NMR (CDCl₃, 300 MHz) δ: 0.95 (3.2H, t, J = 7.3 Hz), 1.24 (3.3H, t, J = 7.5 Hz), 1.67 (2.2H, td, J = 15.0, 7.4 Hz), 1.92 (0.3H, s), 2.15 (2.7H, s), 2.33-2.42 (0.9H, m), 2.60-2.70 (4.2H, m), 2.79 (0.9H, dd, J = 13.6, 4.5 Hz), 3.08-3.18 (1.0H, m), 3.83 (0.9H, d, J = 14.3 Hz), 4.28 (0.9H, d, J = 13.9 Hz), 4.33-4.55 (4.1H, m), 6.83-6.90 (0.9H, m), 7.08-7.21 (4.2H, m), 7.34 (2.0H, d, J = 8.3 Hz), 7.74 (2.0H, d, J = 8.3 Hz). |

TABLE 281

| Example No. | MS ESI m/e: | NMR |
|---|---|---|
| 248 | 518 (M + H). | 1H-NMR (DMSO-d₆, 400 MHz, 120° C.) δ: 1.20 (6H, d, J = 7.1 Hz), 1.82 (3H, s), 2.83-2.91 (2H, m), 3.07-3.15 (1H, m), 3.52-3.61 (2H, m), 3.90 (3H, s), 3.93-4.02 (1H, m), 4.12-4.23 (3H, m), 4.44 (1H, dd, J = 4.4, 2.2 Hz), 7.12 (2H, d, J = 8.2 Hz), 7.15 (2H, d, J = 8.4 Hz), 7.20 (1H, d, J = 9.0 Hz), 7.83 (1H, dd, J = 8.8, 1.8 Hz), 7.98 (1H, d, J = 2.2 Hz), 8.04 (1H, t, J = 5.7 Hz), 10.03 (1H, br s). |
| 249 | 518 (M + H). | 1H-NMR (DMSO-d₆, 400 MHz, 120° C.) δ: 1.20 (6H, d, J = 6.8 Hz), 1.83 (3H, s), 2.83-2.91 (1H, m), 2.98-3.11 (2H, m), 3.49-3.59 (2H, m), 3.87-3.98 (1H, m), 4.18-4.24 (1H, m), 4.20 (2H, d, J = 6.4 Hz), 4.30-4.33 (2H, m), 4.40 (1H, dd, J = 5.0, 2.3 Hz), 6.96 (2H, d, J = 9.0 Hz), 7.12-7.17 (4H, m), 7.67 (2H, d, J = 8.8 Hz), 7.97 (1H, t, J = 5.0 Hz), 10.13 (1H, br s). |
| 250 | 546 (M + H). | 1H-NMR (CDCl₃, 400 MHz) δ: 1.25 (6H, d, J = 6.8 Hz), 2.15 (3H, s), 2.39 (1H, ddd, J = 13.8, 11.2, 3.2 Hz), 2.80 (1H, dd, J = 13.6, 4.3 Hz), 2.85 (2H, t, J = 6.2 Hz), 2.87-2.94 (1H, m), 3.14 (1H, ddd, J = 14.7, 11.5, 3.2 Hz), 3.75 (3H, s), 3.80 (1H, dt, J = 14.1, 2.9 Hz), 4.25-4.53 (5H, m), 4.32 (2H, t, J = 6.2 Hz), 6.89 (1H, t, J = 5.3 Hz), 7.00 (2H, d, J = 8.8 Hz), 7.13 (2H, d, J = 7.9 Hz), 7.21 (2H, d, J = 7.9 Hz), 7.76 (2H, d, J = 8.8 Hz). |
| 251 | 460 (M + H). | 1H-NMR (CDCl₃, 400 MHz) δ: 1.24 (6H, d, J = 6.8 Hz), 2.17 (3H, s), 2.40 (1H, ddd, J = 14.2, 11.3, 3.6 Hz), 2.82 (1H, dd, J = 13.5, 5.1 Hz), 2.85-2.94 (1H, m), 3.15 (1H, ddd, J = 14.8, 11.7, 3.4 Hz), 3.82 (1H, dt, J = 14.6, 3.1 Hz), 4.23 (1H, dt, J = 14.3, 3.4 Hz), 4.36-4.49 (4H, m), 6.95-7.00 (1H, m), 6.95 (2H, d, J = 8.8 Hz), 7.14 (2H, d, J = 7.9 Hz), 7.21 (2H, d, J = 8.4 Hz), 7.70 (2H, d, J = 8.6 Hz), 7.88 (1H, br s). |

TABLE 282

| Example No. | MS ESI m/e: | NMR |
|---|---|---|
| 252 | 641 (M + H). | 1H-NMR (CDCl₃, 400 MHz) δ: 1.25 (6.0H, d, J = 6.8 Hz), 2.54 (2.8H, t, J = 6.7 Hz), 2.65 (2.0H, t, J = 6.8 Hz), 2.81-2.95 (1.7H, m), 3.17-3.25 (0.8H, m), 3.67 (3.1H, s), 3.85-3.95 (1.0H, m), 4.21-4.23 (1.5H, m), 4.31-4.40 (3.5H, m), 4.49-4.56 (1.0H, m), 6.40-6.54 (1.1H, m), 6.67-6.71 (0.7H, m), 7.12 (2.0H, d, J = 7.9 Hz), 7.21 (2.1H, d, J = 8.2 Hz), 7.74-7.82 (2.0H, m), 7.97 (2.0H, d, J = 8.2 Hz). |

TABLE 282-continued

| Example No. | MS ESI m/e: | NMR |
|---|---|---|
| 253 | 500 (M + H). | 1H-NMR (CDCl₃, 300 MHz) δ: 1.28 (6H, d, J = 7.2 Hz), 1.32 (9H, s), 2.15 (3H, s), 2.32-2.45 (1H, m), 2.80 (1H, dd, J = 13.9, 4.5 Hz), 2.93-3.07 (1H, m), 3.08-3.23 (1H, m), 3.83 (1H, d, J = 14.7 Hz), 4.29 (1H, d, J = 13.6 Hz), 4.34-4.55 (4H, m), 6.89 (1H, br s), 7.15 (2H, d, J = 7.9 Hz), 7.32-7.43 (4H, m), 7.76 (2H, d, J = 8.3 Hz). |
| 254 | 625 (M + H). | 1H-NMR (CDCl₃, 300 MHz) δ: 1.24 (6H, d, J = 6.8 Hz), 2.45 (3H, s), 2.89 (1H, h J = 6.8 Hz), 3.01-3.07 (1H, m), 3.15 (1H, dd, J = 13.4, 4.7 Hz), 3.39-3.49 (1H, m), 3.77 (3H, s), 3.88 (2H, d, J = 10.2 Hz), 4.38-4.39 (2H, m), 4.51 (1H, d, J = 13.2 Hz), 4.61-4.64 (1H, br m), 6.75 (1H, t, J = 5.5 Hz), 7.11 (2H, d, J = 8.3 Hz), 7.18 (2H, d, J = 8.3 Hz), 7.78 (2H, d, J = 9.0 Hz), 7.99 (2H, d, J = 7.9 Hz). |
| 255 | 625 (M + H). | 1H-NMR (CDCl₃, 300 MHz) δ: 1.25 (6H, d, J = 7.2 Hz), 2.82-3.02 (3H, m), 3.40-3.46 (1H, m), 3.52 (2H, s), 3.69 (3H, s), 3.85-3.90 (2H, m), 4.41-4.43 (3H, br m), 4.60-4.63 (1H, br m), 6.41 (1H, s), 6.76-6.78 (1H, m), 7.13 (2H, d, J = 8.3 Hz), 7.19 (2H, d, J = 8.3 Hz), 7.78 (2H, d, J = 8.3 Hz), 7.98 (2H, d, J = 8.3 Hz). |

TABLE 283

| Example No. | MS ESI m/e: | NMR |
|---|---|---|
| 256 | 691 (M + H). | 1H-NMR (CDCl₃, 300 MHz) δ: 1.23-1.32 (9H, m), 2.41-2.50 (1H, m), 2.69 (1H, dd, J = 14.3, 3.4 Hz), 2.85-2.95 (1H, m), 3.05-3.15 (1H, m), 3.93 (1H, d, J = 13.6 Hz), 4.17-4.26 (4H, m), 4.47-4.50 (3H, m), 4.57-4.58 (4H, m), 6.29-6.32 (1H, m), 6.56 (1H, dd, J = 8.3, 1.9 Hz), 6.93 (2H, t, J = 8.5 Hz), 7.03 (1H, t, J = 2.3 Hz), 7.15 (1H, d, J = 9.0 Hz), 7.20 (2H, d, J = 6.2 Hz), 7.83 (2H, d, J = 8.3 Hz), 8.00 (2H, d, J = 8.3 Hz), 8.15 (1H, s). |
| 257 | 580 (M + H). | 1H-NMR (CDCl₃, 300 MHz) δ: 1.26 (7H, d, J = 7.2 Hz), 2.39-2.53 (1H, m), 2.86-3.01 (0H, m), 3.16-3.22 (1H, m), 3.95 (1H, d, J = 15.1 Hz), 4.38-4.51 (4H, m), 4.60 (1H, s), 5.42 (1H, d, J = 16.6 Hz), 5.72 (1H, d, J = 16.6 Hz), 6.83-6.85 (1H, br m), 7.13 (2H, d, J = 8.3 Hz), 7.23 (2H, d, J = 8.3 Hz), 7.84 (2H, d, J = 8.3 Hz), 8.01 (2H, d, J = 8.3 Hz), 8.69 (1H, s). |
| 258 | 537 (M + H). | 1H-NMR (CDCl₃, 300 MHz) δ: 1.26 (7H, d, J = 7.2 Hz), 2.37-2.47 (1H, m), 2.88-2.96 (2H, m), 3.09-3.19 (1H, m), 3.81 (2H, s), 3.92 (1H, d, J = 14.3 Hz), 4.34-4.42 (4H, m), 4.52-4.55 (1H, br m), 6.75-6.78 (1H, br m), 7.11 (2H, d, J = 8.3 Hz), 7.22 (2H, d, J = 8.3 Hz), 7.83 (2H, d, J = 8.7 Hz), 7.98 (2H, d, J = 8.3 Hz). |
| 259 | 611 (M + H). | 1H-NMR (CDCl₃, 300 MHz) δ: 1.24 (6H, d, J = 7.0 Hz), 2.84-3.01 (4H, m), 3.46-3.50 (3H, m), 3.72 (1H, d, J = 13.2 Hz), 3.91 (1H, d, J = 13.6 Hz), 4.38-4.41 (2H, m), 4.49 (1H, d, J = 13.6 Hz), 4.60 (1H, s), 6.28 (1H, s), 6.81- 6.85 (1H, br m), 7.09-7.19 (4H, m), 7.76 (2H, d, J = 7.9 Hz), 7.96 (2H, d, J = 8.3 Hz). |

TABLE 284

| Example No. | MS ESI m/e: | NMR |
|---|---|---|
| 260 | 663 (M + H). | 1H-NMR (CD₃OD, 300 MHz) δ: 1.23 (6H, d, J = 6.8 Hz), 2.87 (1H, h, J = 6.8 |

TABLE 284-continued

| Example No. | MS ESI m/e: | NMR |
|---|---|---|
| | | Hz), 3.01-3.11 (1H, m), 3.23 (1H, dd, J = 14.1, 4.3 Hz), 3.70-3.78 (1H, m), 3.84-3.86 (1H, m), 4.10 (1H, J = 13.6 Hz), 4.27 (2H, s), 4.44 (2H, s), 4.51 (1H, d, J = 14.3 Hz), 4.62-4.64 (1H, br m), 6.65 (1H, dd, J = 7.9, 4.0 Hz), 6.92 (1H, t, J = 2.1 Hz), 6.99 (1H, d, J = 4.5 Hz), 7.13-7.17 (5H, m), 7.84 (2H, d, J = 8.3 Hz), 8.05 (2H, d, J = 7.9 Hz), 8.55-8.58 (1H, br m). |
| 261 | 580 (M + H). | 1H-NMR (CD$_3$OD, 300 MHz) δ: 1.23-1.27 (6.3H, m), 2.79-2.90 (2.1H, m), 3.12-3.17 (0.6H, m), 3.29-3.32 (0.4H, m), 3.55-3.59 (0.7H, m), 3.84-4.08 (5.0H, m), 4.33-4.37 (2.6H, m), 4.63-4.66 (1.2H, m), 4.79-4.83 (0.5H, m), 7.19-7.23 (4.0H, m), 7.78 (0.7H, d, J = 8.3 Hz), 7.87 (1.0H, d, J = 8.3 Hz), 7.97 (0.6H, d, J = 7.5 Hz), 8.07 (1.0H, d, J = 8.3 Hz). |
| 262 | 527 (M − 2HCl + H). | 1H-NMR (DMSO-d$_6$, 300 MHz) δ: 2.55-3.54 (9H, m), 3.58-4.28 (6H, m), 4.53-4.69 (2H, m), 7.21 (3H, br s), 7.84-7.99 (4H, m), 8.00-8.22 (4H, m), 8.59-8.83 (1H, m). |
| 263 | 512 (M + H). | 1H-NMR (CDCl$_3$, 400 MHz) δ: 1.25 (6H, d, J = 6.8 Hz), 2.15 (3H, s), 2.36 (1H, td, J = 12.6, 3.5 Hz), 2.82 (1H, dd, J = 13.5, 4.6 Hz), 2.87-2.94 (1H, m), 3.19 (1H, ddd, J = 14.4, 11.9, 3.4 Hz), 3.85 (1H, dt, J = 14.6, 2.4 Hz), 4.27-4.60 (5H, m), 6.71 (1H, t, J = 5.0 Hz), 7.12 (2H, d, J = 8.2 Hz), 7.21 (2H, d, J = 7.9 Hz), 7.70 (1H, t, J = 7.5 Hz), 7.90 (1H, d, J = 8.4 Hz), 8.04 (1H, d, J = 7.7 Hz), 8.11 (1H, s). |
| 264 | 512 (M + H). | 1H-NMR (CDCl$_3$, 400 MHz) δ: 1.25 (6H, d, J = 7.1 Hz), 1.60-1.70 (4H, m), 1.83-1.90 (2H, m), 2.15 (3H, s), 2.39 (1H, ddd, J = 14.5, 11.5, 3.4 Hz), 2.78-2.94 (6H, m), 3.13 (1H, ddd, J = 14.4, 11.6, 3.3 Hz), 3.83 (1H, dt, J = 14.1, 2.6 Hz), 4.28 (1H, dt, J = 14.0, 3.3 Hz), 4.40 (1H, d, J = 5.7 Hz), 4.42 (1H, d, J = 5.7 Hz), 4.47-4.53 (2H, m), 6.88 (1H, t, J = 5.8 Hz), 7.13 (2H, d, J = 7.9 Hz), 7.20 (2H, d, J = 8.2 Hz), 7.22 (1H, d, J = 8.8 Hz), 7.53-7.57 (2H, m). |

TABLE 285

| Example No. | MS ESI m/e: | NMR |
|---|---|---|
| 265 | 653 (M + H). | 1H-NMR (CD$_3$OD, 400 MHz) δ: 1.23 (6H, d, J = 7.1 Hz), 2.80-2.96 (2H, m), 3.04-3.13 (1H, m), 3.50-3.62 (1H, m), 3.68 (1H, d, J = 12.1 Hz), 4.00 (1H, d, J = 13.9 Hz), 4.10 (1H, d, J = 15.0 Hz), 4.19 (1H, d, J = 11.9 Hz), 4.42-4.56 (2H, m), 7.11 (2H, d, J = 8.4 Hz), 7.16 (2H, d, J = 7.9 Hz), 7.39-7.50 (3H, m), 7.75 (2H, d, J = 8.4 Hz), 7.89 (2H, d, J = 7.3 Hz), 7.94 (2H, d, J = 8.4 Hz). |
| 266 | 618 (M + H). | 1H-NMR (CDCl$_3$, 400 MHz) δ: 1.26 (6H, d, J = 7.1 Hz), 2.32-2.47 (1H, m), 2.72 (1H, dd, J = 12.7, 4.7 Hz), 2.84-2.97 (1H, m), 3.14-3.28 (1H, m), 3.48-3.93 (6H, m), 4.21-5.02 (5H, m), 6.71-6.86 (3H, m), 6.99-7.24 (6H, m), 7.69-8.04 (4H, m). |
| 267 | 618 (M + H). | 1H-NMR (CDCl$_3$, 400 MHz) δ: 1.26 (6H, d, J = 6.8 Hz), 2.44-2.56 (1H, m), 2.77-3.33 (3H, m), 3.52-4.04 (6H, m), 4.14-5.00 (5H, m), 6.65-6.92 (3H, m), 7.06-7.25 (6H, m), 7.71-8.05 (4H, m). |
| 268 | 618 (M + H). | 1H-NMR (CDCl$_3$, 400 MHz) δ: 1.26 (6H, d, J = 6.8 Hz), 2.34-2.47 (1H, m), 2.65-2.76 |

TABLE 285-continued

| Example No. | MS ESI m/e: | NMR |
|---|---|---|
| | | (1H, m), 2.85-2.99 (1H, m), 3.16-3.29 (1H, m), 3.69-3.97 (6H, m), 4.34-4.68 (5H, m), 6.64-6.82 (4H, m), 7.10-7.25 (5H, m), 7.70-8.00 (4H, m). |
| 269 | 623 (M + H). | 1H-NMR (CDCl$_3$, 400 MHz) δ: 1.25 (6H, d, J = 6.8 Hz), 2.49-2.56 (1H, m), 2.75 (1H, dd, J = 14.3, 3.5 Hz), 2.87-2.93 (1H, m), 3.15-3.22 (1H, m), 3.94 (1H, d, J = 14.6 Hz), 4.13 (1H, d, J = 11.7 Hz), 4.41-4.60 (4H, m), 6.84-6.87 (1H, br m), 6.95 (1H, t, J = 7.6 Hz), 7.16-7.21 (5H, m), 7.33 (1H, d, J = 7.9 Hz), 7.82 (2H, d, J = 8.2 Hz), 7.89 (1H, d, J = 8.4 Hz), 8.01 (3H, t, J = 8.5 Hz). |
| 270 | 623 (M + H). | 1H-NMR (CDCl$_3$, 400 MHz) δ: 1.24 (6H, d, J = 7.1 Hz), 2.45 (1H, td, J = 13.2, 3.2 Hz), 2.70 (1H, dd, J = 14.6, 3.3 Hz), 2.86-2.93 (1H, m), 3.06-3.14 (1H, m), 3.93 (1H, d, J = 14.8 Hz), 4.17 (1H, d, J = 13.7 Hz), 4.47-4.50 (3H, m), 4.59 (1H, s), 6.95-6.98 (2H, m), 7.14-7.22 (6H, m), 7.38 (1H, s), 7.84 (2H, d, J = 8.4 Hz), 8.00 (2H, d, J = 8.4 Hz), 8.21 (1H, s). |

TABLE 286

| Example No. | MS ESI m/e: | NMR |
|---|---|---|
| 271 | 623 (M + H). | 1H-NMR (CDCl$_3$, 400 MHz) δ: 1.24 (6H, d, J = 6.8 Hz), 2.45 (1H, td, J = 13.0, 2.9 Hz), 2.70 (1H, dd, J = 14.6, 3.3 Hz), 2.86-2.93 (1H, m), 3.06-3.14 (1H, m), 3.93 (1H, d, J = 14.6 Hz), 4.17 (1H, d, J = 13.2 Hz), 4.46-4.51 (3H, m), 4.59 (1H, s), 6.96 (1H, t, J = 5.2 Hz), 7.10-7.25 (8H, m), 7.83 (2H, d, J = 8.2 Hz), 8.00 (2H, d, J = 8.4 Hz), 8.16 (1H, s). |
| 272 | 619 (M + H). | 1H-NMR (CDCl$_3$, 400 MHz) δ: 1.24 (6H, d, J = 7.1 Hz), 2.56 (1H, td, J = 12.7, 3.2 Hz), 2.77 (1H, dd, J = 13.8, 3.2 Hz), 2.86-2.93 (1H, m), 3.16-3.23 (1H, m), 3.88-3.92 (4H, m), 4.08 (1H, d, J = 11.9 Hz), 4.46 (2H, d, J = 5.5 Hz), 4.54-4.58 (2H, m), 6.84-6.97 (4H, m), 7.15-7.20 (4H, m), 7.81 (2H, d, J = 8.2 Hz), 7.87 (1H, d, J = 7.9 Hz), 7.94 (1H, s), 8.00 (2H, d, J = 8.2 Hz). |
| 273 | 619 (M + H). | 1H-NMR (CDCl$_3$, 400 MHz) δ: 1.24 (6H, d, J = 6.8 Hz), 2.45 (1H, td, J = 13.2, 3.1 Hz), 2.70 (1H, dd, J = 14.4, 3.4 Hz), 2.86-2.93 (1H, m), 3.06-3.15 (1H, m), 3.77 (3H, s), 3.92 (1H, d, J = 14.3 Hz), 4.16 (1H, d, J = 14.3 Hz), 4.47-4.52 (3H, m), 4.59 (1H, s), 6.56 (1H, d, J = 8.2 Hz), 6.85 (1H, d, J = 7.9 Hz), 6.94 (1H, t, J = 5.3 Hz), 7.02 (1H, t, J = 2.2 Hz), 7.13-7.21 (5H, m), 7.83 (2H, d, J = 8.4 Hz), 8.00 (2H, d, J = 8.2 Hz), 8.09 (1H, s). |
| 274 | 627 (M + H). | 1H-NMR (CDCl$_3$, 400 MHz) δ: 1.25 (6.0H, d, J = 6.8 Hz), 2.52-2.65 (4.8H, m), 2.87-2.99 (1.9H, m), 3.24-3.32 (0.7H, m), 3.84 (1.0H, d, J = 13.7 Hz), 3.95-3.97 (0.3H, m), 4.21 (1.6H, d, J = 3.3 Hz), 4.29-4.37 (3.7H, m), 4.55-4.60 (1.0H, m), 4.89 (0.2H, d, J = 13.9 Hz), 6.73-6.79 (1.0H, br m), 6.96-7.02 (0.8H, br m), 7.12 (2.0H, d, J = 7.7 Hz), 7.21 (2.1H, d, J = 8.2 Hz), 7.75 (2.0H, d, J = 8.2 Hz), 7.93 (2.0H, d, J = 8.2 Hz). |

TABLE 287

| Example No. | MS ESI m/e: | NMR |
|---|---|---|
| 275 | 647 (M + H). | 1H-NMR (CDCl$_3$, 300 MHz) δ: 1.24 (6H, d, J = 7.2 Hz), 2.45-2.49 (1H, m), 2.71 (1H, dd, |

TABLE 287-continued

| Example No. | MS ESI m/e: | NMR |
|---|---|---|
| | | J = 14.7, 3.4 Hz), 2.89 (1H, t, J = 7.0 Hz), 3.06-3.17 (1H, m), 3.90-3.94 (4H, m), 4.18 (1H, d, J = 13.9 Hz), 4.49-4.52 (3H, m), 4.60 (1H, br s), 6.96 (1H, t, J = 6.0 Hz), 7.16 (2H, d, J = 8.3 Hz), 7.21 (2H, d, J = 8.3 Hz), 7.33 (1H, t, J = 7.9 Hz), 7.54 (1H, d, J = 9.0 Hz), 7.68 (1H, d, J = 7.5 Hz), 7.84 (2H, d, J = 8.7 Hz), 7.93-7.93 (1H, br m), 8.01 (2H, d, J = 8.7 Hz), 8.24 (1H, s). |
| 276 | 647 (M + H). | 1H-NMR (CDCl$_3$, 300 MHz) δ: 1.24 (6H, d, J = 7.2 Hz), 2.45-2.49 (1H, m), 2.71 (1H, dd, J = 14.7, 3.4 Hz), 2.90 (1H, h, J = 7.2 Hz), 3.05-3.15 (1H, m), 3.88 (3H, s), 3.95 (1H, d, J = 13.2 Hz), 4.18 (1H, d, J = 13.9 Hz), 4.49-4.52 (3H, m), 4.60 (1H, s), 6.97 (1H, t, J = 5.3 Hz), 7.15 (2H, d, J = 8.7 Hz), 7.21 (2H, d, J = 8.3 Hz), 7.37 (2H, d, J = 4.3 Hz), 7.84 (2H, d, J = 8.3 Hz), 7.94 (2H, d, J = 6.4 Hz), 8.01 (2H, d, J = 8.3 Hz), 8.47 (1H, br s). |
| 277 | 619 (M + H). | 1H-NMR (CDCl$_3$, 400 MHz) δ: 1.24 (6H, d, J = 6.8 Hz), 2.45 (1H, dt, J = 18.1, 6.5 Hz), 2.70 (1H, dd, J = 14.8, 3.5 Hz), 2.86-2.94 (1H, m), 3.07-3.15 (1H, m), 3.76 (3H, s), 3.91 (1H, d, J = 14.1 Hz), 4.16 (1H, d, J = 12.4 Hz), 4.47-4.52 (3H, m), 4.58 (1H, s), 6.82 (2H, d, J = 9.0 Hz), 6.94 (1H, t, J = 5.4 Hz), 7.14-7.22 (6H, m), 7.82-7.84 (3H, m), 8.00 (2H, d, J = 8.2 Hz). |
| 278 | 580 (M + H). | 1H-NMR (CDCl$_3$, 300 MHz) δ: 1.26 (6H, d, J = 7.2 Hz), 2.43-2.46 (1H, m), 2.91-2.95 (2H, m), 3.12-3.22 (1H, m), 3.93 (1H, d, J = 14.3 Hz), 4.43-4.54 (5H, m), 5.59-5.65 (1H, m), 6.01 (1H, d, J = 16.2 Hz), 6.76 (1H, br s), 7.15 (2H, d, J = 8.3 Hz), 7.23 (2H, d, J = 8.3 Hz), 7.83 (2H, d, J = 8.3 Hz), 7.99 (2H, d, J = 8.3 Hz), 8.54 (1H, s). |
| 279 | 542 (M + H). | 1H-NMR (CDCl$_3$, 300 MHz) δ: 1.25 (6H, d, J = 6.8 Hz), 2.45-2.49 (1H, m), 2.88-2.92 (2H, m), 3.21-3.34 (4H, m), 3.83-3.88 (1H, m), 4.22-4.45 (6H, m), 6.75 (1H, br s), 7.12 (2H, d, J = 7.9 Hz), 7.21 (2H, d, J = 7.9 Hz), 7.81 (2H, d, J = 8.7 Hz), 7.98 (2H, d, J = 8.3 Hz). |

TABLE 288

| Example No. | MS ESI m/e: | NMR |
|---|---|---|
| 280 | 484 (M + H). | 1H-NMR (CDCl$_3$, 400 MHz) δ: 0.66-0.71 (2H, m), 0.92-0.99 (2H, m), 1.28 (6H, d, J = 7.1 Hz), 1.84-1.93 (1H, m), 2.15 (3H, s), 2.35-2.44 (1H, m), 2.77-2.84 (1H, m), 2.94-3.05 (1H, m), 3.08-3.17 (1H, m), 3.81 (1H, d, J = 14.1 Hz), 4.28 (5H, d, J = 13.9 Hz), 4.32-4.53 (4H, m), 6.86 (1H, br s), 7.04 (4H, d, J = 8.4 Hz), 7.09 (4H, d, J = 8.4 Hz), 7.38 (2H, d, J = 8.2 Hz), 7.75 (2H, d, J = 8.4 Hz). |
| 281 | 665 (M + H). | 1H-NMR (CDCl$_3$, 300 MHz) δ: 0.96 (3H, t, J = 7.3 Hz), 1.21-1.32 (9H, m), 1.68 (2H, td, J = 15.0, 7.4 Hz), 2.39-2.48 (1H, m), 2.63-2.70 (3H, m), 2.85-2.94 (1H, m), 2.99-3.11 (1H, m), 3.91 (1H, d, J = 13.9 Hz), 4.08 (1H, d, J = 12.8 Hz), 4.25 (2H, q, J = 7.2 Hz), 4.37-4.50 (3H, m), 4.54-4.60 (3H, m), 6.51-6.59 (1H, m), 6.87-6.94 (1H, m), 7.03-7.08 (2H, m), 7.12-7.21 (5H, m), 7.36 (2H, d, J = 8.3 Hz), 7.76 (2H, d, J = 8.3 Hz), 8.19 (1H, s). |
| 282 | 637 (M + H). | 1H-NMR (CDCl$_3$, 300 MHz) δ: 0.94 (3H, t, J = 7.3 Hz), 1.22 (6H, d, J = 7.2 Hz), 1.66 (2H, td, J = 14.6, 6.9 Hz), 2.16-2.30 (1H, m), 2.53 (1H, d, J = 14.3 Hz), 2.65 (2H, t, J = 7.5 Hz), 2.80-2.92 (1H, m), 2.94-3.07 (1H, m), 3.66 (1H, d, J = 14.7 Hz), 3.77 (1H, d, J = |

TABLE 288-continued

| Example No. | MS ESI m/e: | NMR |
|---|---|---|
| | | 13.2 Hz), 4.25-4.58 (6H, m), 6.47 (1H, d, J = 7.9 Hz), 6.68 (1H, d, J = 8.3 Hz), 6.93 (1H, s), 7.01-7.17 (5H, m), 7.28-7.35 (3H, m), 7.70 (2H, d, J = 8.3 Hz), 8.12 (1H, s). |
| 283 | 522 (M + H). | 1H-NMR (CDCl$_3$, 400 MHz) δ: 1.24 (6H, d, J = 7.1 Hz), 2.15 (3H, s), 2.53 (1H, ddd, J = 14.1, 10.8, 3.6 Hz), 2.73 (1H, t, J = 6.6 Hz), 2.86-2.93 (1H, m), 2.96 (1H, dd, J = 14.2, 5.2 Hz), 3.17 (2H, t, J = 6.7 Hz), 3.18-3.25 (1H, m), 3.83 (1H, dt, J = 14.3, 2.9 Hz), 4.20 (1H, dt, J = 13.7, 3.0 Hz), 4.37-4.50 (4H, m), 6.88 (1H, d, J = 3.5 Hz), 6.91 (1H, t, J = 4.6 Hz), 7.14 (2H, d, J = 7.7 Hz), 7.20 (2H, d, J = 8.2 Hz), 7.47 (1H, d, J = 3.3 Hz), 11.25 (1H, br s). |

TABLE 289

| Example No. | MS ESI m/e: | NMR |
|---|---|---|
| 284 | 542 (M+ H). | 1H-NMR (CDCl$_3$, 400 MHz) δ: 1.25 (6H, d, J = 6.8 Hz), 2.15 (3H, s), 2.39 (1H, ddd, J = 13.7, 11.0, 3.1 Hz), 2.83 (1H, dd, J = 13.2, 4.2 Hz), 2.86-2.94 (1H, m), 3.15 (1H, ddd, J = 14.7, 11.5, 3.5 Hz), 3.81 (1H, dt, J = 13.8, 2.9 Hz), 4.31 (1H, dt, J = 13.7, 2.9 Hz), 4.37-4.55 (6H, m), 6.82 (1H, t, J = 4.9 Hz), 7.05 (2H, d, J = 9.0 Hz), 7.13 (2H, d, J = 7.9 Hz), 7.21 (2H, d, J = 8.2 Hz), 7.82 (2H, d, J = 8.8 Hz). |
| 285 | 633 (M + H). | 1H-NMR (CD$_3$OD, 300 MHz) δ: 1.21 (6H, d, J = 6.8 Hz), 2.80-2.89 (1H, h, J = 6.8 Hz), 3.03-3.13 (1H, m), 3.25 (1H, dd, J = 14.1, 4.3 Hz), 3.71-3.77 (1H, m), 3.85-3.90 (1H, m), 4.13 (1H, d, J = 13.9 Hz), 4.25 (2H, d, J = 3.4 Hz), 4.54 (1H, d, J = 14.3 Hz), 4.65 (1H, br s), 7.10 (2H, d, J = 8.3 Hz), 7.15 (2H, d, J = 8.3 Hz), 7.43 (2H, d, J = 7.0 Hz), 7.85 (2H, d, J = 8.3 Hz), 7.94 (2H, d, J = 6.8 Hz), 8.06 (2H, d, J = 7.9 Hz). |
| 286 | 633 (M + H). | 1H-NMR (CD$_3$OD, 300 MHz) δ: 1.21 (6H, d, J = 6.8 Hz), 2.84 (1H, h, J = 6.8 Hz), 3.04-3.13 (1H, m), 3.26 (1H, dd, J = 14.1, 4.3 Hz), 3.73-3.78 (1H, m), 3.86-3.88 (1H, m), 4.13 (1H, d, J = 13.6 Hz), 4.26 (2H, d, J = 3.0 Hz), 4.53 (1H, d, J = 14.7 Hz), 4.63-4.64 (1H, br m), 7.10 (2H, d, J = 8.3 Hz), 7.16 (2H, d, J = 8.7 Hz), 7.38 (1H, t, J = 7.9 Hz), 7.60 (1H, d, J = 8.3 Hz), 7.71 (1H, d, J = 7.5 Hz), 7.85 (2H, d, 3 = 8.3 Hz), 8.00 (1H, t, J = 1.9 Hz), 8.05 (2H, d, J = 8.3 Hz). |
| 287 | 492 (M + H). | 1H-NMR (CDCl$_3$, 300 MHz) δ: 0.99 (3H, t, J = 7.3 Hz), 1.25 (6H, d, J = 6.8 Hz), 1.65-1.78 (2H, m), 2.17 (3H, s), 2.57 (1H, ddd, J = 13.9, 11.3, 3.2 Hz), 2.82 (2H, t, J = 7.5 Hz), 2.91 (1H, dd, J = 13.9, 6.8 Hz), 2.96 (1H, dd, J = 13.6, 4.1 Hz), 3.19 (1H, ddd, J = 14.7, 11.3, 3.4 Hz), 3.84 (1H, dt, J = 14.4, 3.1 Hz), 4.29 (1H, dt, J = 13.7, 2.9 Hz), 4.42 (1H, d, J = 5.3 Hz), 4.43 (1H, d, J = 5.3 Hz), 4.47-4.57 (4H, m), 6.81 (1H, d, J = 3.8 Hz), 6.87 (1H, t, J = 5.7 Hz), 7.14 (2H, d, J = 7.9 Hz), 7.21 (2H, d, J = 7.9 Hz), 7.48 (1H, d, J = 3.8 Hz). |

TABLE 290

| Example No. | MS ESI m/e: | NMR |
|---|---|---|
| 288 | 542 (M + H). | 1H-NMR (DMSO-d$_6$, 400 MHz, 120° C.) δ: 1.19 (6H, d, J = 6.8 Hz), 1.81 (3H, s), 2.76-3.20 (3H, m), 3.56-3.68 (2H, m), 3.96-4.26 (2H, m), 4.04 (3H, s), 4.10 (1H, d, J = 5.5 |

TABLE 290-continued

| Example No. | MS ESI m/e: | NMR |
|---|---|---|
| | | Hz), 4.12 (1H, d, J = 6.0 Hz), 4.48 (1H, dd, J = 5.0, 2.3 Hz), 7.08 (2H, d, J = 8.4 Hz), 7.12 (2H, d, J = 8.2 Hz), 7.37 (1H, d, J = 8.8 Hz), 7.94 (1H, dd, J = 8.8, 2.4 Hz), 8.08 (1H, t, J = 5.2 Hz), 8.42 (1H, d, J = 2.4 Hz), 12.05 (1H, br s). |
| 289 | 508 (M + H). | 1H-NMR (CDCl$_3$, 400 MHz) δ: 1.24 (6H, d, J = 6.8 Hz), 2.15 (3H, s), 2.61 (1H, ddd, J = 13.6, 10.6, 3.3 Hz), 2.86-2.93 (1H, m), 2.98 (1H, dd, J = 14.0, 4.3 Hz), 3.21 (1H, ddd, J = 14.9, 11.6, 3.5 Hz), 3.84 (1H, dt, J = 14.8, 3.3 Hz), 3.89 (2H, s), 4.20 (1H, dt, J = 13.7, 2.9 Hz), 4.39-4.52 (4H, m), 6.92 (1H, t, J = 5.5 Hz), 6.95 (1H, d, J = 3.7 Hz), 7.14 (2H, d, J = 8.2 Hz), 7.20 (2H, d, J = 8.2 Hz), 7.49 (1H, d, J = 3.1 Hz), 10.15 (1H, br s). |
| 290 | 570 (M + H). | 1H-NMR (CDCl$_3$, 400 MHz) δ: 1.18 (6.0H, d, J = 6.8 Hz), 1.25-1.33 (3.1H, m), 2.54-2.62 (0.7H, m), 2.80-2.88 (1.0H, m), 2.92-3.01 (1.0H, m), 3.15-3.22 (1.0H, m), 3.36-3.44 (0.3H, m), 3.66-3.73 (0.5H, m), 3.81 (0.7H, d, J = 14.8 Hz), 4.14-4.40 (5.5H, m), 4.56 (1.0H, d, J = 14.1 Hz), 4.80 (0.3H, d, J = 13.9 Hz), 6.35-6.39 (0.2H, br m), 6.57-6.62 (0.7H, br m), 7.05-7.09 (1.9H, m), 7.14 (2.0H, d, J = 8.2 Hz), 7.67-7.75 (1.9H, m), 7.88-7.92 (2.1H, m). |
| 291 | 500 (M + H). | 1H-NMR (CDCl$_3$, 400 MHz) δ: 1.22-1.31 (12H, m), 2.15 (3H, s), 2.27 (3H, s), 2.39 (1H, J = 17.7, 6.4 Hz), 2.76-3.19 (5H, m), 3.82 (1H, d, J = 14.1 Hz), 4.24-4.56 (5H, m), 6.72 (1H, s), 7.02-7.10 (3H, m), 7.38 (2H, d, J = 8.4 Hz), 7.74 (2H, d, J = 8.6 Hz). |
| 292 | 504 (M + H). | 1H-NMR (CDCl$_3$, 400 MHz) δ: 1.21-1.31 (12H, m), 2.12 (3H, s), 2.34-2.45 (1H, m), 2.77-3.18 (4H, m), 3.83 (1H, d, J = 14.3 Hz), 4.29 (1H, d, J = 13.2 Hz), 4.38-4.54 (4H, m), 6.85-7.00 (3H, m), 7.14 (1H, t, J = 7.8 Hz), 7.40 (2H, d, J = 8.4 Hz), 7.76 (2H, d, J = 8.6 Hz). |

TABLE 291

| Example No. | MS ESI m/e: | NMR |
|---|---|---|
| 293 | 508 (M + H). | 1H-NMR (CDCl$_3$, 400 MHz) δ: 1.28 (6H, d, J = 6.8 Hz), 1.92 (3H, t, J = 18.2 Hz), 2.14 (3H, s), 2.34-2.46 (1H, m), 2.81 (1H, dd, J = 13.7, 4.6 Hz), 2.94-3.05 (1H, m), 3.10-3.22 (1H, m), 3.83 (1H, d, J = 14.3 Hz), 4.28 (1H, d, J = 13.7 Hz), 4.42-4.56 (4H, m), 7.03 (1H, t, J = 5.4 Hz), 7.25-7.30 (2H, m), 7.37-7.52 (4H, m), 7.76 (2H, d, J = 8.2 Hz). |
| 294 | 486 (M + H). | 1H-NMR (CDCl$_3$, 400 MHz) δ: 1.28 (6H, d, J = 6.8 Hz), 1.64 (2H, d, J = 15.0, 7.5 Hz), 2.15 (3H, s), 2.34-2.46 (1H, m), 2.57 (2H, t, J = 7.6 Hz), 2.81 (1H, dd, J = 13.8, 4.5 Hz), 2.94-3.04 (2H, m), 3.08-3.19 (1H, m), 3.82 (1H, d, J = 14.3 Hz), 4.24-4.55 (6H, m), 6.88 (1H, t, J = 5.3 Hz), 7.09-7.18 (4H, m), 7.39 (2H, d, J = 8.4 Hz), 7.75 (2H, d, J = 8.4 Hz). |
| 295 | 564 (M + H). | 1H-NMR (CDCl$_3$, 300 MHz) δ: 0.96 (3H, t, J = 7.2 Hz), 1.24 (6H, d, J = 7.2 Hz), 1.68 (2H, td, J = 15.1, 7.5 Hz), 2.40-2.52 (1H, m), 2.68 (3H, t, J = 7.5 Hz), 2.83-2.95 (1H, m), 2.99-3.12 (1H, m), 3.94 (1H, d, J = 14.7 Hz), 4.10 (1H, d, J = 12.8 Hz), 4.39-4.50 (3H, m), 4.59 (1H, br s), 7.06-7.22 (5H, m), 7.23-7.29 (2H, m), 7.36 (2H, d, J = 8.3 Hz), 7.76 (2H, d, J = 8.3 Hz), 8.39 (2H, d, J = 6.4 Hz), 8.58 (1H, s). |

TABLE 291-continued

| Example No. | MS ESI m/e: | NMR |
|---|---|---|
| 296 | 599 (M + H). | 1H-NMR (CDCl$_3$, 300 MHz) δ: 0.95 (3H, t, J = 7.3 Hz), 1.25 (6H, d, J = 6.8 Hz), 1.44 (3H, t, J = 7.2 Hz), 1.66 (2H, td, J = 15.1, 7.5 Hz), 2.65 (2H, t, J = 7.7 Hz), 2.84-2.96 (1H, m), 3.30-3.46 (2H, m), 3.49-3.61 (1H, m), 4.02 (1H, d, J = 13.9 Hz), 4.23-4.50 (4H, m), 4.59 (1H, br s), 4.80 (1H, br s), 5.20 (1H, br s), 7.02-7.11 (1H, m), 7.12-7.23 (4H, m), 7.32 (2H, d, J = 8.7 Hz), 7.45 (1H, s), 7.73 (2H, d, J = 8.3 Hz). |
| 297 | 599 (M + H). | 1H-NMR (CDCl$_3$, 300 MHz) δ: 0.94 (3H, t, J = 7.3 Hz), 1.25 (6H, d, J = 6.8 Hz), 1.66 (2H, td, J = 14.9, 7.0 Hz), 2.49 (3H, s), 2.65 (2H, t, J = 7.7 Hz), 2.84-3.01 (3H, m), 3.34-3.46 (1H, m), 3.76 (3H, s), 3.83-3.93 (2H, m), 4.34-4.49 (3H, m), 4.54-4.58 (1H, m), 6.86-6.92 (1H, m), 7.09-7.22 (4H, m), 7.32 (2H, d, J = 8.3 Hz), 7.75 (2H, d, J = 8.3 Hz). |

TABLE 292

| Example No. | MS ESI m/e: | NMR |
|---|---|---|
| 298 | 571 (M + H). | 1H-NMR (CD$_3$OD, 300 MHz) δ: 0.95 (3H, t, J = 7.5 Hz), 1.22 (6H, d, J = 6.8 Hz), 1.66 (2H, td, J = 14.8, 7.7 Hz), 2.67 (2H, t, J = 7.5 Hz), 2.80-2.93 (1H, m), 2.94-3.12 (1H, m), 3.35-3.45 (1H, m), 3.67-3.93 (3H, m), 4.24-4.36 (3H, m), 4.67 (1H, br s), 7.12 (4H, br s), 7.35 (2H, d, J = 7.9 Hz), 7.44 (1H, br s), 7.78 (2H, d, J = 8.3 Hz), 8.50-8.62 (1H, br m). |
| 299 | 585 (M + H). | 1H-NMR (CD$_3$OD, 300 MHz) δ: 0.96 (3H, t, J = 7.3 Hz), 1.23 (7H, d, J = 6.8 Hz), 1.68 (2H, td, J = 15.0, 7.4 Hz), 2.45 (3H, s), 2.69 (2H, t, J = 7.7 Hz), 2.82-2.94 (1H, m), 3.08-3.21 (1H, m), 3.40 (1H, dd, J = 13.9, 4.9 Hz), 3.73-3.88 (3H, m), 4.26-4.40 (3H, m), 4.58-4.63 (1H, m), 7.14 (4H, s), 7.38 (2H, d, J = 8.7 Hz), 7.78 (2H, d, J = 8.3 Hz), 8.51-8.58 (1H, m). |
| 300 | 591 (M + H). | 1H-NMR (CDCl$_3$, 400 MHz) δ: 1.24 (6H, d, J = 7.1 Hz), 2.54 (1H, dt, J = 18.2, 7.1 Hz), 2.75 (1H, dd, J = 14.7, 3.4 Hz), 2.84-2.98 (1H, m), 3.07-3.19 (1H, m), 3.97 (1H, d, J = 13.7 Hz), 4.17 (1H, d, J = 13.7 Hz), 4.44-4.64 (4H, m), 6.85 (1H, s), 7.12-7.21 (4H, m), 7.70 (1H, dd, J = 5.8, 1.4 Hz), 7.83 (2H, d, J = 8.4 Hz), 8.00 (2H, d, J = 8.2 Hz), 8.48 (1H, d, J = 6.0 Hz), 8.83 (1H, d, J = 1.1 Hz), 9.01 (1H, s). |
| 301 | 690 (M + H). | 1H-NMR (CDCl$_3$, 400 MHz) δ: 1.24 (6H, d, J = 6.8 Hz), 1.63 (9H, s), 2.49 (1H, td, J = 13.2, 3.1 Hz), 2.72 (1H, dd, J = 14.7, 3.6 Hz), 2.84-2.94 (1H, m), 3.04-3.16 (1H, m), 3.95 (1H, d, J = 13.2 Hz), 4.17 (1H, d, J = 12.8 Hz), 4.41-4.54 (3H, m), 4.60 (1H, s), 7.00 (1H, t, J = 5.5 Hz), 7.12-7.23 (4H, m), 7.49 (1H, dd, J = 5.5, 2.2 Hz), 7.84 (2H, d, J = 8.6 Hz), 7.90 (1H, d, J = 2.2 Hz), 8.00 (2H, d, J = 8.2 Hz), 8.51 (1H, d, J = 5.7 Hz), 8.72 (1H, s). |
| 302 | 611 (M+H). | 1H-NMR (CDCl$_3$, 400 MHz) δ: 1.25 (6H, d, J = 7.1 Hz), 2.84-2.95 (1H, m), 3.03-3.12 (1H, m), 3.18 (1H, dd, J = 13.5, 4.6 Hz), 3.42-3.52 (1H, m), 3.81 (3H, s), 3.90 (2H, d, J = 10.1 Hz), 4.38 (2H, dd, J = 5.7, 1.8 Hz), 4.53 (1H, dd, J = 13.7, 2.2 Hz), 4.59-4.65 (1H, m), 6.71 (1H, s), 7.08-7.20 (4H, m), 7.75-7.80 (3H, m), 7.98 (2H, d, J = 8.2 Hz). |

TABLE 293

| Example No. | MS ESI m/e: | NMR |
|---|---|---|
| 303 | 605 (M + H). | 1H-NMR (CDCl₃, 400 MHz) δ: 1.23 (6H, d, J = 6.8 Hz), 2.83-2.92 (1H, m), 2.94-3.04 (1H, m), 3.13 (1H, dd, J = 13.7, 4.4 Hz), 3.37-3.46 (1H, m), 3.82-3.91 (1H, m), 3.86 (3H, s), 4.15-4.24 (1H, m), 4.36 (2H, ddd, J = 24.4, 14.9, 5.7 Hz), 4.59-4.66 (1H, m), 4.79 (1H, d, J = 13.9 Hz), 6.60 (1H, d, J = 9.0 Hz), 6.93 (1H, t, J = 5.2 Hz), 7.05 (2H, d, J = 8.2 Hz), 7.13 (2H, d, J = 7.9 Hz), 7.76 (2H, d, J = 8.2 Hz), 7.99 (1H, d, J = 9.2 Hz), 8.00 (2H, d, J = 8.8 Hz), 8.66 (1H, d, J = 1.8 Hz). |
| 304 | 575 (M + H). | 1H-NMR (CDCl₃, 400 MHz) δ: 1.24 (6H, d, J = 7.1 Hz), 1.92-2.03 (2H, m), 2.55 (2H, t, J = 7.1 Hz), 2.63-2.75 (3H, m), 2.85-2.92 (1H, m), 3.15-3.26 (1H, m), 3.53 (1H, d, J = 11.9 Hz), 3.82 (1H, d, J = 13.5 Hz), 4.27 (1H, dd, J = 14.8, 5.7 Hz), 4.36 (1H, dd, J = 14.9, 5.8 Hz), 4.54 (1H, s), 7.04 (2H, d, J = 8.2 Hz), 7.09 (3H, d, J = 6.0 Hz), 7.15 (2H, d, J = 7.9 Hz), 7.77 (2H, d, J = 8.2 Hz), 7.98 (2H, d, J = 8.2 Hz), 8.45 (2H, dd, J = 4.5, 1.4 Hz). |
| 305 | 572 (M + H). | 1H-NMR (DMSO-d₆, 400 MHz, 120° C.) δ: 1.19 (6H, d, J = 6.8 Hz), 1.81 (3H, s), 2.77-2.94 (2H, m), 3.14-3.24 (1H, m), 3.59-3.69 (2H, m), 3.93-4.31 (4H, m), 4.49 (1H, dd, J = 4.4, 2.4 Hz), 7.11 (1H, d, J = 8.2 Hz), 7.15 (2H, d, J = 8.2 Hz), 7.52 (1H, dd, J = 8.5, 1.4 Hz), 7.98 (1H, dd, J = 8.7, 2.1 Hz), 8.12 (1H, t, J = 4.9 Hz), 8.21 (1H, d, J = 2.6 Hz), 10.25 (1H, br s). |
| 306 | 574 (M + H). | 1H-NMR (CDCl₃, 400 MHz) δ: 1.25 (6H, d, J = 6.8 Hz), 2.16 (3H, s), 2.46 (1H, ddd, J = 14.1, 12.1, 2.4 Hz), 2.87-2.96 (2H, m), 3.20 (1H, ddd, J = 14.7, 11.2, 3.0 Hz), 3.81 (1H, dt, J = 14.3, 2.6 Hz), 4.29-4.60 (5H, m), 6.68 (1H, t, J = 6.3 Hz), 7.12 (2H, d, J = 7.7 Hz), 7.21 (2H, d, J = 7.7 Hz), 7.28 (1H, d, J = 8.8 Hz), 7.65 (1H, dd, J = 8.7, 2.3 Hz), 7.69 (1H, d, J = 1.8 Hz). |

TABLE 294

| Example No. | MS ESI m/e: | NMR |
|---|---|---|
| 307 | 513 (M + H). | 1H-NMR (CDCl₃, 400 MHz) δ: 1.25 (6H, d, J = 6.8 Hz), 1.94-2.02 (2H, m), 2.16 (3H, s), 2.47 (1H, td, J = 12.8, 3.7 Hz), 2.78 (2H, t, J = 6.2 Hz), 2.84-2.92 (2H, m), 2.90 (3H, s), 3.11 (1H, ddd, J = 14.8, 11.5, 3.5 Hz), 3.31 (2H, t, J = 5.8 Hz), 3.87 (1H, dt, J = 13.8, 2.8 Hz), 4.27 (1H, dt, J = 13.4, 2.7 Hz), 4.39 (1H, d, J = 6.0 Hz), 4.41 (1H, d, J = 6.4 Hz), 4.46-4.52 (2H, m), 6.87 (1H, d, J = 1.5 Hz), 6.90 (1H, t, J = 5.0 Hz), 6.97 (1H, dd, J = 7.8, 1.7 Hz), 7.02 (1H, d, J = 7.9 Hz), 7.13 (2H, d, J = 7.9 Hz), 7.20 (2H, d, J = 8.2 Hz). |
| 308 | 541 (M + H). | 1H-NMR (CDCl₃, 400 MHz) δ: 1.25 (6H, d, J = 7.1 Hz), 2.78-3.00 (2H, m), 3.27 (1H, dd, J = 14.2, 4.1 Hz), 3.36 (1H, dt, J = 17.9, 6.6 Hz), 3.43-3.52 (0H, m), 3.75-3.85 (1H, m), 4.23 (1H, d, J = 13.7 Hz), 4.29-4.41 (2H, m), 4.50 (1H, s), 4.61 (0H, s), 4.76 (0H, d, J = 13.0 Hz), 4.86 (0H, d, J = 13.5 Hz), 5.21 (1H, d, J = 14.3 Hz), 5.45-5.55 (1H, m), 6.62-6.65 (0H, br m), 6.89-6.98 (2H, br m), 7.13-7.22 (4H, m), 7.74-7.79 (2H, m), 7.94-7.99 (2H, m). |
| 309 | 666 (M + H). | 1H-NMR (CDCl₃, 300 MHz) δ: 1.23-1.28 (9H, m), 2.42-2.46 (1H, m), 2.87-2.96 (2H, m), 3.13-3.20 (1H, m), 3.92 (1H, d, J = 15.4 Hz), 3.98 (2H, s), 4.19 (2H, q, J = 7.2 Hz), 4.41-4.50 (4H, m), 4.58 (1H, br s), 5.60 (1H, d, J = 16.2 Hz), 5.92 (1H, d, J = 16.2 Hz), 6.72-6.74 (1H, br m), 7.15 (2H, d, J = 8.3 Hz), 7.23 (2H, d, J = 8.3 Hz), 7.82 (2H, d, J = 8.7 Hz), 7.99 (2H, d, J = 8.7 Hz). |
| 310 | 636 (M + H). | 1H-NMR (DMSO-d₆, 300 MHz) δ: 1.17-1.19 (6.3H, m), 2.67-2.79 (2.0H, m), 3.00-3.07 (0.7H, m), 3.71-4.22 (5.9H, m), 4.58-4.66 (1.5H, m), 5.22-5.27 (0.5H, m), 5.69-5.79 (1.3H, m), 7.02-7.20 (4.4H, m), 7.87-7.94 (3.2H, m), 8.05 (1.0H, d, J = 8.7 Hz), 8.60-8.62 (0.5H, br m), 8.89-8.91 (0.4H, br m). |

TABLE 295

| Example No. | MS ESI m/e: | NMR |
|---|---|---|
| 311 | 666 (M + H). | 1H-NMR (CDCl₃, 300 MHz) δ: 1.22 (3H, t, J = 7.0 Hz), 1.26 (6H, d, J = 6.8 Hz), 2.43-2.47 (1H, m), 2.89-2.95 (2H, m), 3.16-3.20 (1H, m), 3.89-4.09 (3H, m), 4.14-4.19 (2H, m), 4.33-4.48 (4H, m), 4.57 (1H, br s), 6.79 (1H, br s), 7.12 (2H, d, J = 8.3 Hz), 7.22 (2H, d, J = 7.9 Hz), 7.83 (2H, d, J = 8.3 Hz), 8.00 (2H, d, J = 8.3 Hz). |
| 312 | 638 (M + H). | 1H-NMR (DMSO-d₆, 300 MHz) δ: 1.18 (5.9H, d, J = 7.2 Hz), 2.65-2.70 (0.7H, m), 2.80-2.89 (1.0H, m), 3.00-3.04 (0.5H, m), 3.17-3.46 (7.1H, m), 3.68-4.20 (6.7H, m), 4.34 (0.4H, s), 4.51-4.73 (0.4H, m), 5.14-5.25 (0.5H, m), 5.49-5.69 (1.4H, m), 7.04 (1.0H, d, J = 8.3 Hz), 7.11-7.20 (2.8H, m), 7.86-7.97 (2.9H, m), 8.06 (0.8H, d, J = 7.9 Hz), 8.58-8.60 (0.4H, m), 8.71-8.73 (0.4H, m). |
| 313 | 512 (M + H). | 1H-NMR (CDCl₃, 300 MHz) δ: 1.25 (6H, d, J = 6.8 Hz), 2.82-2.99 (3H, br m), 3.20 (1H, br s), 3.94-4.07 (2H, m), 4.30-4.50 (3H, m), 4.61 (1H, br s), 7.14 (3H, d, J = 7.9 Hz), 7.23 (2H, d, J = 7.9 Hz), 7.59 (3H, br s), 7.80 (2H, d, J = 8.3 Hz), 7.96 (2H, d, J = 8.7 Hz). |
| 314 | 634 (M + H). | 1H-NMR (CD₃OD, 400 MHz) δ: 1.19 (6H, d, J = 7.1 Hz), 2.77-2.89 (1H, m), 3.06-3.19 (1H, m), 3.25-3.32 (1H, m), 3.67-3.92 (2H, m), 4.09-4.25 (3H, m), 4.49-4.69 (2H, m), 7.11 (4H, s), 7.80 (2H, d, J = 8.2 Hz), 8.01 (3H, d, J = 8.6 Hz), 8.29 (1H, d, J = 2.2 Hz), 8.41 (1H, d, J = 6.8 Hz), 8.64 (1H, t, J = 5.5 Hz). |
| 315 | 597 (M + H). | 1H-NMR (CD₃OD, 400 MHz) δ: 1.21 (6H, d, J = 6.8 Hz), 2.80-2.91 (1H, m), 3.19-3.28 (1H, m), 3.48 (1H, dd, J = 13.7, 4.6 Hz), 3.76-3.97 (3H, m), 4.19 (2H, dd, J = 19.8, 15.2 Hz), 4.40 (1H, d, J = 11.9 Hz), 4.62-4.68 (1H, m), 7.07-7.16 (4H, m), 7.66 (1H, s), 7.78 (2H, d, J = 8.4 Hz), 7.99 (2H, d, J = 8.4 Hz). |
| 316 | 640 (M + H). | 1H-NMR (CDCl₃, 400 MHz) δ: 1.19-1.69 (15H, m), 2.12-2.60 (5H, m), 2.74-3.89 (5H, m), 4.10 (2H, dd, J = 14.3, 7.1 Hz), |

TABLE 295-continued

| Example No. | MS ESI m/e: | NMR |
|---|---|---|
| | | 4.22-4.95 (5H, m), 6.74 (1H, t, J = 5.3 Hz), 7.09-7.24 (4H, m), 7.69-7.85 (2H, m), 7.97 (2H, d, J = 8.4 Hz). |

TABLE 296

| Example No. | MS ESI m/e: | NMR |
|---|---|---|
| 317 | 612 (M + H). | 1H-NMR (CD$_3$OD, 400 MHz) δ: 1.14-1.68 (0H, m), 2.08-2.37 (4H, m), 2.67-3.30 (4H, m), 3.48-4.82 (6H, m), 7.11-7.25 (4H, m), 7.68-8.09 (4H, m). |
| 318 | 606 (M + H). | 1H-NMR (CDCl$_3$, 400 MHz) δ: 1.24 (6H, d, J = 6.8 Hz), 2.50 (1H, td, J = 3.2, 3.3 Hz), 2.74 (1H, dd, J = 14.7, 3.4 Hz), 2.86-2.93 (1H, m), 3.04-3.12 (1H, m), 3.93 (1H, d, J = 14.6 Hz), 4.17 (1H, d, J = 13.2 Hz), 4.46-4.50 (3H, m), 4.59 (1H, s), 7.02 (1H, t, J = 6.2 Hz), 7.14-7.20 (4H, m), 7.23-7.25 (4H, m), 7.38 (2H, d, J = 8.4 Hz), 7.92 (2H, d, J = 8.8 Hz), 8.40 (2H, d, J = 6.2 Hz), 8.56 (1H, s). |
| 319 | 641 (M + H). | 1H-NMR (CDCl$_3$, 300 MHz) δ: 0.94 (3H, t, J = 7.3 Hz), 1.25 (6H, d, J = 7.2 Hz), 1.51 (9H, s), 1.66 (2H, td, J = 15.1, 7.7 Hz), 2.46 (3H, s), 2.65 (2H, t, J = 7.7 Hz), 2.81-2.96 (3H, m), 3.32-3.46 (1H, m), 3.83-3.93 (2H, m), 4.34-4.50 (3H, m), 4.53-4.57 (1H, m), 6.86-6.92 (1H, m), 7.11-7.21 (4H, m), 7.32 (2H, d, J = 8.3 Hz), 7.75 (2H, d, J = 8.3 Hz). |
| 320 | 683 (M + H). | 1H-NMR (CDCl$_3$, 300 MHz) δ: 1.25 (6H, d, J = 6.8 Hz), 1.51 (9H, s), 2.43 (3H, s), 2.85-3.12 (3H, m), 3.37-3.47 (1H, m), 3.81-3.93 (2H, m), 4.40 (2H, d, J = 6.0 Hz), 4.47 (1H, d, J = 13.2 Hz), 4.59 (1H, br s), 6.75-6.82 (1H, m), 7.08-7.21 (4H, m), 7.33 (2H, d, J = 7.9 Hz), 7.88-7.95 (2H, m). |
| 321 | 486 (M + H). | 1H-NMR (CDCl$_3$, 400 MHz) δ: 1.20-1.32 (9H, m), 2.15 (3H, s), 2.26 (3H, s), 2.35-2.45 (1H, m), 2.61 (2H, q, J = 7.4 Hz), 2.81 (1H, dd, J = 13.3, 4.1 Hz), 2.93-3.17 (2H, m), 3.81 (1H, d, J = 14.6 Hz), 4.24-4.55 (5H, m), 6.72 (1H, t, J = 5.4 Hz), 6.99-7.09 (3H, m), 7.38 (2H, d, J = 8.4 Hz), 7.74 (2H, d, J = 8.4 Hz). |
| 322 | 627 (M + H). | 1H-NMR (CDCl$_3$, 300 MHz) δ: 1.24 (6H, d, J = 6.8 Hz), 2.46 (3H, s), 2.84-2.98 (1H, m), 3.02-3.20 (2H, m), 3.41-3.50 (1H, m), 3.81-3.93 (2H, m), 4.32-4.47 (2H, m), 4.53 (1H, d, J = 13.6 Hz), 4.61 (1H, br s), 6.75-6.84 (1H, m), 7.08-7.21 (4H, m), 7.33 (2H, d, J = 7.9 Hz), 7.91 (2H, d, J = 9.0 Hz). |

TABLE 297

| Example No. | MS ESI m/e: | NMR |
|---|---|---|
| 323 | 498 (M + H). | 1H-NMR (CDCl$_3$, 400 MHz) δ: 0.65-0.71 (2H, m), 0.95 (2H, ddd, J = 9.7, 5.2, 3.2 Hz), 1.28 (6H, d, J = 7.1 Hz), 1.80-1.90 (1H, m), 2.14 (3H, s), 2.24 (3H, s), 2.34-2.45 (1H, m), 2.81 (1H, dd, J = 13.3, 4.1 Hz), 2.93-3.15 (2H, m), 3.80 (1H, d, J = 14.1 Hz), 4.23-4.55 (5H, m), 6.69 (1H, t, J = 5.5 Hz), 6.85-6.91 (2H, m), 7.03 (1H, d, J = 7.5 Hz), 7.37 (2H, d, J = 8.4 Hz), 7.73 (2H, d, J = 8.4 Hz). |
| 324 | 600 (M + H). | 1H-NMR (CDCl$_3$, 300 MHz) δ: 1.25 (6H, d, J = 7.2 Hz), 2.12 (3H, s), 2.53 (1H, ddd, J = 14.0, 11.0, 3.3 Hz), 2.71 (2H, t, J = 6.4 Hz), 2.85-2.96 (2H, m), 3.05 (2H, t, J = 6.4 Hz), 3.20 (1H, ddd, J = 14.8, 10.8, 3.7 Hz), 3.76 (1H, dt, J = 15.1, 2.9 Hz), 4.18 (1H, dt, J = 14.9, 2.6 Hz), 4.36-4.48 (4H, m), 6.89 (1H, t, J = 5.5 Hz), 7.13 (2H, d, J = 7.9 Hz), 7.20 (2H, d, J = 6.8 Hz), 7.36 (1H, dd, J = 8.3, 1.5 Hz), 7.76 (1H, dd, J = 8.1, 2.4 Hz), 7.89 (1H, d, J = 1.9 Hz), 11.26 (1H, br s). |
| 325 | 636 (M + H). | 1H-NMR (CDCl$_3$, 300 MHz) δ: 1.23 (6H, d, J = 6.8 Hz), 1.39 (3H, t, J = 7.2 Hz), 2.83-2.92 (1H, m), 3.38-3.46 (3H, m), 3.82-3.84 (1H, m), 4.24-4.45 (6H, m), 4.64 (1H, br s), 6.84 (1H, br s), 7.08 (2H, d, J = 8.3 Hz), 7.14 (2H, d, J = 8.3 Hz), 7.73 (2H, d, J = 7.9 Hz), 7.99 (2H, d, J = 8.3 Hz), 8.53 (1H, s), 11.75 (1H, br s). |
| 326 | 647 (M + H). | 1H-NMR (CDCl$_3$, 400 MHz) δ: 1.23 (6H, d, J = 7.1 Hz), 1.56 (9H, s), 2.82-2.92 (1H, m), 2.93-3.04 (1H, m), 3.11-3.19 (1H, m), 3.36-3.47 (1H, m), 3.86 (1H, d, J = 13.7 Hz), 4.16 (1H, d, J = 13.7 Hz), 4.32 (1H, dd, J = 14.8, 5.3 Hz), 4.41 (1H, dd, J = 14.8, 6.0 Hz), 4.61 (1H, s), 4.75 (1H, d, J = 15.0 Hz), 6.57 (1H, d, J = 9.3 Hz), 6.93 (1H, br s), 7.06 (2H, d, J = 7.9 Hz), 7.13 (2H, d, J = 7.9 Hz), |

TABLE 297-continued

| Example No. | MS ESI m/e: | NMR |
|---|---|---|
| | | 7.75 (2H, d, J = 8.4 Hz), 7.95 (1H, dd, J = 8.8, 2.2 Hz), 8.00 (2H, d, J = 8.4 Hz), 8.64 (1H, d, J = 2.0 Hz). |

TABLE 298

| Example No. | MS ESI m/e: | NMR |
|---|---|---|
| 327 | 591 (M + H). | 1H-NMR (CD$_3$OD, 400 MHz) δ: 1.20 (6H, d, J = 7.1 Hz), 2.77-2.90 (1H, m), 3.12-3.23 (1H, m), 3.44 (1H, dd, J = 14.2, 4.5 Hz), 3.71-3.90 (2H, m), 4.12-4.27 (3H, m), 4.60-4.65 (1H, m), 4.77 (1H, d, J = 14.1 Hz), 6.62 (1H, d, J = 9.0 Hz), 7.06 (4H, dd, J = 13.3, 8.3 Hz), 7.78 (2H, d, J = 8.4 Hz), 7.95 (1H, dd, J = 8.9, 2.3 Hz), 8.01 (2H, d, J = 8.2 Hz), 8.60-8.62 (1H, m). |
| 328 | 613 (M + H). | 1H-NMR (CD$_3$OD, 300 MHz) δ: 1.24 (6H, d, J = 6.8 Hz), 2.82-2.96 (1H, m), 3.23-3.32 (1H, m), 3.51 (1H, dd, J = 13.8, 4.7 Hz), 3.81-3.90 (2H, m), 3.92-4.01 (1H, m), 4.14-4.31 (2H, m), 4.43 (1H, d, J = 13.6 Hz), 4.62-4.67 (1H, m), 7.10-7.17 (4H, m), 7.41 (2H, d, J = 8.3 Hz), 7.73 (1H, s), 7.92-7.98 (2H, m), 8.57-8.64 (1H, m). |
| 329 | 571 (M + H). | 1H-NMR (CD$_3$OD, 300 MHz) δ: 0.96 (3H, t, J = 7.3 Hz), 1.23 (6H, d, J = 7.2 Hz), 1.67 (2H, td, J = 15.0, 7.4 Hz), 2.68 (2H, t, J = 7.5 Hz), 2.80-2.93 (1H, m), 3.08-3.26 (1H, m), 3.43 (1H, dd, J = 13.8, 4.7 Hz), 3.73-3.90 (3H, m), 4.27 (2H, d, J = 6.0 Hz), 4.31-4.38 (1H, m), 4.58-4.64 (1H, m), 7.10-7.18 (4H, m), 7.37 (2H, d, J = 8.3 Hz), 7.78 (2H, d, J = 8.3 Hz), 8.52-8.59 (1H, m). |
| 330 | 655 (M + H). | 1H-NMR (CDCl$_3$, 400 MHz) δ: 0.94 (3H, t, J = 7.3 Hz), 1.24 (6H, d, J = 7.1 Hz), 1.51 (9H, s), 1.65 (2H, q, J = 7.6 Hz), 2.26 (3H, s), 2.45 (3H, s), 2.65 (2H, t, J = 7.7 Hz), 2.85-2.96 (3H, m), 3.35-3.41 (1H, m), 3.85-3.92 (2H, m), 4.35-4.43 (3H, m), 4.53-4.56 (1H, m), 6.71-6.74 (1H, m), 6.99-7.03 (2H, m), 7.09 (1H, d, J = 8.4 Hz), 7.31 (2H, d, J = 8.2 Hz), 7.74 (2H, d, J = 8.4 Hz). |
| 331 | 599 (M + H). | 1H-NMR (CD$_3$OD, 400 MHz) δ: 0.93 (3H, t, J = 7.3 Hz), 1.20 (6H, d, J = 6.8 Hz), 1.58-1.69 (2H, m), 2.24 (3H, s), 2.42 (3H, s), 2.65 (2H, t, J = 7.5 Hz), 2.78-2.85 (1H, m), 3.09-3.17 (1H, m), 3.40 (1H, dd, J = 13.7, 4.6 Hz), 3.74-3.84 (3H, m), 4.18-4.29 (3H, m), 4.58-4.59 (1H, m), 6.93-7.06 (3H, m), 7.34 (2H, d, J = 8.2 Hz), 7.75 (2H, d, J = 8.2 Hz), 8.29 (1H, t, J = 5.3 Hz). |

TABLE 299

| Example No. | MS ESI m/e: | NMR |
|---|---|---|
| 332 | 597 (M + H). | 1H-NMR (CDCl$_3$, 400 MHz) δ: 1.22 (6H, d, 3 = 6.8 Hz), 2.76-3.07 (3H, m), 3.27-3.39 (1H, m), 3.91 (1H, d, J = 15.4 Hz), 4.23 (1H, d, J = 13.9 Hz), 4.36 (2H, d, J = 5.7 Hz), 4.61-4.71 (2H, m), 7.06-7.16 (4H, m), 7.79 (2H, d, J = 8.4 Hz), 7.99 (2H, d, J = 8.4 Hz), 8.64 (1H, s). |
| 333 | 584 (M + H). | 1H-NMR (CDCl$_3$, 300 MHz) δ: 0.94 (3H, t, J = 7.7 Hz), 1.25 (7H, d, J = 6.4 Hz), 1.63-1.68 (2H, m), 2.48 (3H, s), 2.66 (2H, t, J = 7.5 Hz), 2.88-2.93 (3H, m), 3.39 (1H, td, J = 12.6, 3.6 Hz), 3.87-3.92 (2H, m), 4.39-4.41 (3H, m), 4.56 (1H, br s), 5.31 (2H, s), 6.89 (1H, s), 7.16 (4H, q, J = 8.4 Hz), 7.33 (2H, d, J = 8.3 Hz), 7.75 (2H, d, J = 8.7 Hz). |
| 334 | 653 (M + H). | 1H-NMR (DMSO-d$_6$, 400 MHz, 90° C.) δ: 1.14 (6H, d, J = 7.0 Hz), 1.28 (3H, t, J = 7.1 Hz), 2.69-2.92 (2H, m), 3.15 (1H, d, J = 12.1 Hz), 3.50-3.65 (2H, br m), 3.96-4.37 (5H, m), 4.48 (1H, br s), 4.73 (1H, br s), 7.06 (4H, dd, J = 9.8, 8.8 Hz), 7.82 (2H, d, J = 8.0 Hz), 7.95 (2H, d, J = 8.7 Hz), 8.21 (1H, br s). |
| 335 | 625 (M + H). | 1H-NMR (CD$_3$OD, 400 MHz) δ: 1.21 (6H, d, J = 6.8 Hz), 2.23 (3H, s), 2.42 (3H, s), 2.77-2.89 (1H, m), 3.24 (1H, dq, J = 14.1, 4.3 Hz), 3.49 (1H, dd, J = 13.9, 4.6 Hz), 3.77-3.99 (3H, m), 4.19 (2H, ddd, J = 23.2, 14.9, 5.4 Hz), 4.38 (1H, d, J = 13.2 Hz), 4.66 (1H, dd, J = 4.3, 2.5 Hz), 6.93-7.09 (3H, m), 7.81 (2H, d, J = 8.4 Hz), 8.00 (2H, d, J = 8.2 Hz), 8.38 (1H, t, J = 5.3 Hz). |
| 336 | 696 (M + H). | 1H-NMR (CDCl$_3$, 300 MHz) δ: 1.21 (6H, d, J = 6.8 Hz), 2.54 (3H, s), 2.83 (1H, h, J = 6.8 Hz), 3.25-3.36 (3H, m), 3.83 (1H, d, J = 13.2 |

TABLE 299-continued

| Example No. | MS ESI m/e: | NMR |
|---|---|---|
| | | Hz), 4.31 (5H, ddd, J = 25.4, 14.7, 5.5 Hz), 4.53 (5H, d, J = 12.8 Hz), 4.66 (5H, s), 5.17 (3H, d, J = 12.1 Hz), 5.28 (3H, s), 6.86 (1H, br s), 7.07 (4H, dd, J = 22.0, 8.1 Hz), 7.34-7.38 (5H, m), 7.73 (2H, d, J = 8.7 Hz), 8.01 (2H, d, J = 7.9 Hz), 8.76 (1H, br s). |

TABLE 300

| Example No. | MS ESI m/e: | NMR |
|---|---|---|
| 337 | 620 (M + H). | 1H-NMR (CDCl₃, 300 MHz) δ: 1.23 (6H, d, J = 6.8 Hz), 2.55 (3H, br s), 2.86 (1H, h, J = 6.8 Hz), 3.24-3.36 (3H, m), 3.84 (4H, s), 4.31 (2H, ddd, J = 30.3, 14.7, 5.8 Hz), 4.54 (1H, d, J = 12.4 Hz), 4.67 (1H, s), 5.17 (1H, d, J = 12.8 Hz), 6.89 (1H, br s), 7.08 (4H, dd, J = 25.6, 8.3 Hz), 7.74 (2H, d, J = 8.7 Hz), 8.02 (2H, d, J = 8.3 Hz), 8.68 (1H, s). |
| 338 | 606 (M + H). | 1H-NMR (CD₃OD, 300 MHz) δ: 1.21 (6H, d, J = 6.8 Hz), 2.54 (3H, s), 2.85 (1H, h, J = 6.8 Hz), 3.19-3.23 (1H, m), 3.44 (1H, dd, J = 13.9, 4.9 Hz), 3.73-3.81 (2H, m), 4.11 (2H, dd, J = 33.3, 14.9 Hz), 4.61 (1H, s), 4.70 (1H, d, J = 12.8 Hz), 5.15 (1H, d, J = 13.9 Hz), 7.07 (4H, q, J = 8.2 Hz), 7.74 (2H, d, J = 8.3 Hz), 7.95 (2H, d, J = 8.3 Hz), 8.67 (1H, s). |
| 339 | 611 (M + H). | 1H-NMR (CD₃OD, 300 MHz) δ: 0.92 (3H, t, J = 7.3 Hz), 1.54-1.69 (2H, m), 2.42 (3H, s), 2.55 (2H, t, J = 7.5 Hz), 3.17-3.29 (1H, m), 3.48 (1H, dd, J = 13.8, 4.7 Hz), 3.75-3.99 (3H, m), 4.12-4.30 (2H, m), 4.39 (1H, d, J = 14.3 Hz), 4.61-4.69 (1H, m), 7.05-7.13 (4H, m), 7.80 (2H, d, J = 8.7 Hz), 8.00 (2H, d, J = 8.3 Hz), 8.59 (1H, t, J = 5.8 Hz). |
| 340 | 626 (M + H). | 1H-NMR (CDCl₃, 300 MHz) δ: 1.25 (6H, d, J = 7.2 Hz), 2.45 (3H, s), 2.88-3.10 (3H, m), 3.41-3.45 (1H, m), 3.89 (2H, t, J = 13.4 Hz), 4.40 (2H, d, J = 5.7 Hz), 4.47 (1H, d, J = 12.4 Hz), 4.59 (1H, br s), 5.34 (2H, br s), 6.79 (1H, br s), 7.12 (4H, d, J = 7.9 Hz), 7.19 (4H, d, J = 8.3 Hz), 7.34 (2H, d, J = 9.0 Hz), 7.91 (2H, d, J = 8.7 Hz). |
| 341 | 641 (M + H). | 1H-NMR (CD₃OD, 400 MHz) δ: 0.90 (3H, t, J = 7.4 Hz), 1.55-1.64 (2H, m), 2.22 (3H, s), 2.42 (3H, s), 2.51 (2H, t, J = 7.6 Hz), 3.17-3.26 (1H, m), 3.46 (1H, dd, J = 13.7, 4.6 Hz), 3.81-3.84 (2H, m), 3.92 (1H, d, J = 12.8 Hz), 4.13-4.26 (2H, m), 4.36 (1H, d, J = 13.5 Hz), 4.61 (1H, br s), 6.89-6.95 (2H, m), 7.04 (1H, d, J = 7.7 Hz), 7.38 (2H, d, J = 8.6 Hz), 7.92 (2H, d, J = 8.8 Hz), 8.34 (1H, t, J = 5.4 Hz). |

TABLE 301

| Example No. | MS ESI m/e: | NMR |
|---|---|---|
| 342 | 592 (M + H). | 1H-NMR (CD₃OD, 400 MHz) δ: 1.23 (6H, d, J = 6.8 Hz), 2.78-2.94 (1H, m), 3.18-3.28 (1H, m), 3.49 (1H, dd, J = 14.3, 4.6 Hz), 3.71-3.90 (2H, m), 4.12 (2H, ddd, J = 44.4, 14.8, 4.5 Hz), 4.56-4.74 (2H, m), 5.14 (1H, d, J = 13.0 Hz), 7.06-7.15 (4H, m), 7.76 (2H, d, J = 8.2 Hz), 7.97 (2H, d, J = 8.2 Hz), 8.62 (1H, t, J = 5.5 Hz), 8.72 (2H, s). |
| 343 | 612 (M + H). | 1H-NMR (CD3OD, 400 MHz) δ: 2.42 (3H, s), 2.89 (6H, s), 3.22 (1H, dq, J = 14.0, 4.3 Hz), 3.47 (1H, dd, J = 13.5, 4.6 Hz), 3.76-3.98 (3H, m), 4.13 (2H, ddd, J = 31.2, 14.5, 3.9 Hz), 4.37 (1H, d, J = 13.9 Hz), 4.63 (1H, dd, J = 4.5, 2.3 Hz), 6.67 (2H, d, J = 8.8 Hz), 7.04 (2H, d, J = 8.6 Hz), 7.80 (2H, d, J = 8.2 Hz), 7.99 (2H, d, J = 8.2 Hz), 8.46 (1H, t, J = 5.4 Hz). |
| 344 | 585 (M + H). | 1H-NMR (DMSO-d₆, 300 MHz) δ: 1.16-1.21 (12H, m), 2.37 (3H, s), 2.79-2.88 (1H, m), 2.92-3.12 (2H, m), 3.33-3.40 (1H, m), 3.66-3.86 (3H, m), 4.01-4.25 (3H, m), 4.55-4.58 (1H, br m), 7.10 (4H, dd, J = 14.3, 8.3 Hz), 7.42 (2H, d, J = 8.3 Hz), 7.72 (2H, d, J = 8.3 Hz), 8.58 (1H, t, J = 5.8 Hz), 12.50 (1H, br s). |
| 345 | 553 (M + H). | 1H-NMR (CDCl₃, 300 MHz) δ: 1.18-1.29 (6H, m), 1.96-3.87 (12H, m), 4.31-4.50 (2H, m), 4.50-4.55 (0.3H, bs), 4.62 (0.7H, bs), 5.74 (0.3H, s), 5.89 (0.7H, s), 7.12 (2.8H, s), 7.15 (1.2H, s), 7.37 (0.3H, t, J = 5.7 Hz), 7.77 (2H, d, J = 8.3 Hz), 7.99 (0.6H, d, J = 8.3 Hz), 8.10 (1.4H, d, J = 8.3 Hz), 8.41 (0.7H, t, J = 5.7 Hz). |

TABLE 301-continued

| Example No. | MS ESI m/e: | NMR |
|---|---|---|
| 346 | 669 (M + H). | 1H-NMR (CDCl₃, 300 MHz) δ: 2.22-2.72 (11H, m), 2.80-2.89 (1H, m), 2.96 (5H, s), 3.03-3.39 (3H, m), 3.52 (1H, d, J = 15.8 Hz), 3.77 (1H, d, J = 15.8 Hz), 4.19-4.37 (3H, m), 4.38-4.56 (1H, m), 4.69-4.81 (1H, m), 6.50-6.61 (1H, m), 6.69 (2H, d, J = 8.7 Hz), 6.97-7.13 (2H, m), 7.46-7.60 (2H, m), 7.87 (2H, d, J = 8.7 Hz). |

TABLE 302

| Example No. | MS ESI m/e: | NMR |
|---|---|---|
| 348 | 581 (M + H). | 1H-NMR (CDCl₃, 400 MHz) δ: 1.23 (6H, d, J = 7.1 Hz), 2.09 (1H, dd, J = 13.7, 5.1 Hz), 2.31-2.44 (1H, m), 2.84-2.97 (1H, m), 3.13-3.27 (1H, m), 3.81 (1H, d, J = 13.7 Hz), 4.26-4.64 (4H, m), 5.14 (1H, d, J = 13.7 Hz), 6.98 (1H, t, J = 5.5 Hz), 7.21 (4H, dd, J = 9.0, 4.5 Hz), 7.35 (2H, d, J = 9.0 Hz), 7.55-7.69 (3H, m). |
| 349 | 591 (M + H). | 1H-NMR (CD₃OD, 400 MHz) δ: 1.20 (6H, d, J = 6.8 Hz), 2.79-2.88 (1H, m), 3.03-3.14 (1H, m), 3.36-3.43 (1H, m), 3.72-3.80 (1H, m), 3.82-3.89 (1H, m), 4.12 (1H, d, J = 13.0 Hz), 4.20 (2H, s), 4.60-4.69 (2H, m), 7.07 (4H, s), 7.11 (1H, d, J = 5.3 Hz), 7.18 (1H, s), 7.76 (2H, d, J = 8.2 Hz), 8.00 (2H, d, J = 8.4 Hz), 8.11 (1H, d, J = 5.1 Hz). |
| 350 | 513 (M + H). | 1H-NMR (CDCl₃, 400 MHz) δ: 1.28 (6H, d, J = 6.8 Hz), 2.43 (1H, dt, J = 18.0, 6.5 Hz), 2.68 (1H, dd, J = 13.6, 3.9 Hz), 2.95-3.05 (1H, m), 3.11 (1H, ddd, J = 15.7, 11.7, 3.6 Hz), 3.90 (1H, t, J = 12.0 Hz), 4.29 (1H, d, J = 15.4 Hz), 4.47-4.69 (4H, m), 7.15 (1H, t, J = 5.4 Hz), 7.34-7.45 (4H, m), 7.58-7.64 (2H, m), 7.70-7.78 (2H, m), 8.66 (1H, br s), 10.95 (1H, br s). |
| 351 | 538 (M + H). | 1H-NMR (CDCl₃, 400 MHz) δ: 1.99 (0.9H, s), 2.15 (2.1H, s), 2.46 (0.7H, ddd, J = 14.3, 11.5, 3.6 Hz), 2.63-2.79 (0.3H, m), 2.91 (0.7H, dd, J = 12.7, 4.7 Hz), 2.95-3.11 (0.3H, m), 3.21 (0.7H, ddd, J +32 14.5, 11.7, 3.1 Hz), 3.33 (0.3H, d, J = 9.5 Hz), 3.70-3.79 (0.3H, m), 3.85 (0.7H, dt, J = 14.3, 3.4 Hz), 4.33-4.61 (5H, m), 6.79-6.84 (0.3H, m), 6.89 (0.7H, t, J = 5.8 Hz), 7.31-7.39 (2H, m), 7.56-7.64 (3H, m), 7.71-7.73 (2H, m). |
| 352 | 550 (M + H). | 1H-NMR (CDCl₃, 300 MHz) δ: 1.25 (6H, d, J = 7.2 Hz), 2.42 (1H, dd, J = 11.9, 4.0 Hz), 2.74-2.78 (1H, m), 2.91 (1H, h, J = 7.2 Hz), 3.05 (1H, d, J = 12.4 Hz), 3.43-3.48 (1H, m), 3.49 (3H, s), 3.90 (1H, d, J = 12.1 Hz), 4.01 (1H, d, J = 14.3 Hz), 4.41 (1H, dd, J = 14.9, 5.5 Hz), 4.55 (1H, br s), 4.61 (1H, dd, J = 15.1, 6.4 Hz), 6.63 (1H, d, J = 1.5 Hz), 6.69 (1H, d, J = 1.5 Hz), 6.96 (1H, br s), 7.22 (4H, s), 7.80 (2H, d, J = 8.3 Hz), 7.98 (2H, d, J = 8.3 Hz). |

TABLE 303

| Example No. | MS ESI m/e: | NMR |
|---|---|---|
| 353 | 536 (M + H). | 1H-NMR (CDCl₃, 300 MHz) δ: 1.24 (6H, t, J = 7.2 Hz), 2.61-2.71 (2H, m), 2.90 (1H, h, J = 7.2 Hz), 3.30-3.36 (1H, m), 3.77 (1H, d, J = 12.8 Hz), 3.94 (1H, d, J = 13.2 Hz), 4.21 (1H, d, J = 13.2 Hz), 4.45 (2H, abq, J = 31.6, 14.7, 5.8 Hz), 4.56 (1H, br s), 6.64 (2H, s), 6.96 (1H, br s), 7.11 (2H, d, J = 8.3 Hz), 7.20 (2H, d, J = 7.9 Hz), 7.81 (2H, d, J = 8.3 Hz), 7.99 (2H, d, J = 8.3 Hz). |
| 354 | 640 (M + H). | 1H-NMR (CDCl₃, 300 MHz) δ: 1.24 (6H, d, J = 7.2 Hz), 2.44 (3H, s), 2.86-2.90 (4H, m), 2.94-3.08 (2H, m), 3.37-3.47 (1H, m), 3.89 (2H, t, J = 12.8 Hz), 4.40 (3H, d, J = 5.7 Hz), 4.45 (3H, d, J = 13.2 Hz), 4.59 (1H, br s), 5.42-5.44 (1H, br m), 6.79 (1H, t, J = 5.3 Hz), 7.11 (4H, d, J = 8.3 Hz), 7.18 (4H, d, J = 8.3 Hz), 7.34 (2H, d, J = 8.3 Hz), 7.89-7.93 (2H, m). |
| 355 | 654 (M + H). | 1H-NMR (CDCl₃, 300 MHz) δ: 1.25 (6H, d, J = 6.8 Hz), 2.19 (3H, s), 2.89-2.96 (3H, m), 3.03 (6H, s), 3.40-3.46 (1H, m), 3.82-3.87 (2H, m), 4.41 (2H, d, J = 5.7 Hz), 4.46 (1H, d, J = 12.8 Hz), 4.59 (1H, br s), 6.80-6.82 (1H, br m), 7.13 (2H, d, J = 8.3 Hz), 7.19 (2H, d, J = 8.3 Hz), 7.34 (2H, d, J = 7.9 Hz), 7.91 (2H, d, J = 6.8 Hz). |
| 356 | 639 (M + H). | 1H-NMR (CD₃OD, 400 MHz) δ: 0.59-0.65 (2H, m), 0.91 (2H, ddd, J = 9.5, 5.2, 3.0 Hz), 1.83 (1H, tt, J = 8.4, 4.0 Hz), 2.21 (3H, s), 2.43 (3H, s), 3.23 (1H, ddd, J = 13.9, 8.3, 4.2 Hz), 3.47 (1H, dd, J = 13.7, |

TABLE 303-continued

| Example No. | MS ESI m/e: | NMR |
|---|---|---|
| | | 4.4 Hz), 3.75-3.98 (3H, m), 4.18 (2H, ddd, J = 29.4, 14.8, 5.4 Hz), 4.36 (1H, d, J = 13.2 Hz), 4.62 (1H, dd, J = 4.5, 2.5 Hz), 6.78 (1H, dd, J = 7.8, 1.4 Hz), 6.86 (1H, s), 7.01 (1H, d, J = 7.7 Hz), 7.39 (2H, d, J = 8.4 Hz), 7.92 (2H, d, J 8.6 Hz), 8.34 (1H, t, J 5.5 Hz). |
| 357 | 608 (M + H). | 1H-NMR (CD₃OD, 300 MHz) δ: 1.26 (7H, d, J = 6.8 Hz), 2.86-2.95 (1H, m), 3.25-3.35 (2H, br m), 3.49-3.51 (1H, br m), 3.76-3.90 (2H, br m), 4.21 (2H, dt, J = 25.1, 7.2 Hz), 4.40 (1H, br s), 4.68 (0H, br s), 7.13-7.18 (5H, m), 7.83 (2H, d, J = 8.3 Hz), 8.03 (2H, d, J = 8.3 Hz), 8.47 (1H, br s). |

TABLE 304

| Example No. | MS EST m/e: | NMR |
|---|---|---|
| 358 | 740 (M + H). | 1H-NMR (CDCl₃, 300 MHz) δ: 1.24 (6H, d, J = 6.8 Hz), 1.49 (9H, s), 2.46 (3H, s), 2.83-3.12 (3H, m), 3.36-3.48 (1H, m), 3.86 (2H, d, J = 10.2 Hz), 4.01-4.06 (2H, m), 4.40 (2H, d, J = 5.7 Hz), 4.45-4.53 (1H, m), 4.59 (1H, br s), 5.97-6.02 (1H, m), 6.75-6.81 (1H, m), 7.08-7.21 (4H, m), 7.33 (2H, d, J = 8.7 Hz), 7.91 (2H, d, J = 8.7 Hz). |
| 359 | 754 (M + H). | 1H-NMR (CDCl₃, 300 MHz) δ: 1.25 (6H, d, J = 6.8 Hz), 1.45 (9H, s), 2.42 (3H, s), 2.49 (2H, t, J = 6.0 Hz), 2.83-3.09 (3H, m), 3.35-3.48 (1H, m), 3.53-3.62 (2H, m), 3.85 (2H, d, J = 9.8 Hz), 4.39 (2H, d, J = 5.7 Hz), 4.48 (1H, d, J = 12.4 Hz), 4.59 (1H, br s), 6.19-6.26 (1H, m), 6.74-6.81 (1H, m), 7.07-7.21 (4H, m), 7.33 (2H, d, J = 8.3 Hz), 7.91 (2H, d, J = 8.7 Hz). |
| 360 | 684 (M + H). | 1H-NMR (CD₃OD, 300 MHz) δ: 1.22 (6H, d, J = 6.8 Hz), 2.43 (3H, s), 2.81-2.93 (1H, m), 3.14-3.28 (1H, m), 3.42 (1H, dd, J = 13.8, 4.7 Hz), 3.75-3.94 (3H, m), 3.98 (2H, s), 4.18-4.28 (2H, m), 4.40 (1H, d, J = 13.9 Hz), 4.61-4.65 (1H, m), 7.08-7.17 (4H, m), 7.39 (2H, d, J = 8.3 Hz), 7.93 (2H, d, J = 9.0 Hz), 8.53-8.59 (1H, m). |
| 361 | 698 (M + H). | 1H-NMR (CD₃OD, 300 MHz) δ: 1.22 (6H, d, J = 6.8 Hz), 2.39 (3H, s), 2.56 (2H, t, J = 6.8 Hz), 2.81-2.93 (1H, m), 3.15-3.26 (1H, m), 3.41 (1H, dd, J = 13.8, 4.7 Hz), 3.53 (2H, t, J = 6.8 Hz), 3.74-3.92 (3H, m), 4.16-4.29 (2H, m), 4.35-4.42 (1H, m), 4.60-4.65 (1H, m), 7.09-7.16 (4H, m), 7.38 (2H, d, J = 7.9 Hz), 7.90-7.97 (2H, m), 8.53-8.59 (1H, m). |
| 362 | 582 (M + H). | 1H-NMR (CDCl₃, 400 MHz) δ: 1.23 (6H, d, J = 6.8 Hz), 2.52-2.98 (3H, m), 3.25-3.80 (2H, m), 3.86-4.15 (2H, m), 4.34-4.81 (3H, m), 7.02-7.22 (4H, m), 7.77 (2H, d, J = 7.7 Hz), 7.96 (2H, d, J = 7.7 Hz). |

TABLE 305

| Example No. | MS ESI m/e: | NMR |
|---|---|---|
| 363 | 655 (M + H). | 1H-NMR (CD₃OD, 400 MHz) δ: 0.90 (3H, t, J = 7.4 Hz), 1.14 (3H, t, J = 7.5 Hz), 1.55-1.64 (2H, m), 2.22 (3H, s), 2.51 (2H, t, J = 7.5 Hz), 2.83-2.93 (2H, m), 3.17-3.24 (1H, m), 3.46 (1H, dd, J = 14.2, 5.4 Hz), 3.81-3.84 (2H, m), 3.94 (1H, d, J = 13.9 Hz), 4.14-4.25 (2H, m), 4.38 (1H, d, J = 13.7 Hz), 4.62 (1H, s), 6.89-6.95 (2H, m), 7.04 (1H, d, 3 = 7.7 Hz), 7.38 (2H, d, J = 8.4 Hz), 7.92 (2H, d, J = 8.8 Hz), 8.34-8.37 (1H, br m). |
| 364 | 641 (M + H). | 1H-NMR (CD₃OD, 400 MHz) δ: 1.22 (6H, d, J = 7.0 Hz), 2.24 (3H, s), 2.44 (3H, s), 2.79-2.88 (1H, m), 3.19-3.28 (1H, m), 3.48 (1H, dd, J = 13.8, 4.8 Hz), 3.80-3.87 (2H, m), 3.94 (1H, d, J = 12.8 Hz), 4.14-4.27 (2H, m), 4.38 (1H, d, J = 13.7 Hz), 4.61-4.65 (1H, m), 6.91-7.09 (3H, m), 7.40 (2H, d, J = 8.1 Hz), 7.92-7.96 (2H, m), 8.35-8.42 (1H, m). |
| 365 | 669 (M + H). | 1H-NMR (CD₃OD, 400 MHz) δ: 2.43 (3H, s), 3.18-3.27 (1H, m), 3.44-3.51 (1H, m), 3.77-3.94 (3H, m), 4.22-4.41 (2H, m), 4.61-4.65 (1H, m), 7.14-7.19 (2H, m), 7.27-7.32 (2H, m), 7.41-7.45 (2H, m), 7.94-7.99 (2H, m). |
| 366 | 613 (M + H). | 1H-NMR (CD₃OD, 400 MHz) δ: 1.19 (3H, t, J = 7.6 Hz), 2.43 (3H, s), 2.60 (2H, q, J = 7.6 Hz), 3.21-3.27 (1H, m), 3.47 (1H, dd, J = |

TABLE 305-continued

| Example No. | MS ESI m/e: | NMR |
|---|---|---|
| | | 13.8, 4.5 Hz), 3.76-3.93 (3H, m), 4.15-4.26 (2H, m), 4.36 (1H, d, J = 13.7 Hz), 4.62-4.63 (1H, m), 7.07-7.10 (4H, m), 7.39 (2H, d, J = 7.9 Hz), 7.93 (2H, d, J. = 8.8 Hz), 8.57-8.60 (1H, br m). |
| 367 | 641 (M + H). | 1H-NMR (CD$_3$OD, 300 MHz) δ: 1.29 (9H, s), 2.44 (3H, s), 3.18-3.28 (1H, m), 3.48 (1H, dd, J = 13.8, 4.7 Hz), 3.75-3.89 (2H, m), 3.94 (1H, d, J = 12.8 Hz), 4.15-4.31 (2H, m), 4.41 (1H, d, J = 13.9 Hz), 4.63 (1H, dd, J = 4.3, 2.4 Hz), 7.10 (2H, d, J = 8.3 Hz), 7.29 (2H, d, J = 8.3 Hz), 7.36-7.43 (2H, m), 7.90-7.98 (2H, m), 8.61 (1H, t, J = 5.7 Hz). |

TABLE 306

| Example No. | MS ESI m/e: | NMR |
|---|---|---|
| 368 | 552 (M + H). | 1H-NMR (CD$_3$OD, 400 MHz) δ: 1.23 (6H, d, J = 7.1 Hz), 2.74-2.93 (2H, m), 3.01 (1H, dd, J = 13.1, 4.5 Hz), 3.67-3.88 (3H, m), 4.16-4.27 (3H, br m), 4.62 (1H, br s), 7.08-7.20 (4H, m), 7.76 (2H, d, J = 8.2 Hz), 7.97 (2H, d, J = 8.2 Hz), 8.45 (1H, t, J = 5.8 Hz). |
| 369 | 698 (M + H). | 1H-NMR (CD$_3$OD, 300 MHz) δ: 1.22 (6H, d, J = 7.2 Hz), 1.45 (3H, d, J = 7.2 Hz), 2.42 (3H, s), 2.79-2.95 (1H, m), 3.14-3.27 (1H, m), 3.42 (1H, dd, J = 13.6, 4.5 Hz), 3.74-3.94 (3H, m), 4.16-4.29 (2H, m), 4.35-4.43 (2H, m), 4.47 (2H, q, J = 7.3 Hz), 4.61-4.65 (1H, m), 7.08-7.18 (4H, m), 7.39 (2H, d, J = 8.3 Hz), 7.90-7.97 (2H, m), 8.53-8.61 (1H, m). |
| 370 | 698 (M + H). | 1H-NMR (CD$_3$OD, 300 MHz) δ: 1.22 (6H, d, J = 6.8 Hz), 1.45 (3H, d, J = 7.5 Hz), 2.42 (3H, s), 2.81-2.93 (1H, m), 3.16-3.28 (1H, m), 3.41 (1H, dd, J = 13.6, 4.5 Hz), 3.75-3.93 (3H, m), 4.16-4.29 (2H, m), 4.38-4.53 (2H, m), 4.61-4.65 (1H, m), 7.09-7.17 (4H, m), 7.39 (2H, d, J = 8.3 Hz), 7.90-7.97 (2H, m), 8.53-8.61 (1H, m). |
| 371 | 595 (M + H). | 1H-NMR (CD$_3$OD, 400 MHz) δ: 1.22 (6H, d, J = 6.8 Hz), 2.27 (3H, s), 2.82-2.91 (1H, m), 3.18-3.26 (1H, m), 3.45 (1H, dd, J = 13.9, 4.4 Hz), 3.74-3.87 (2H, m), 4.04-4.18 (3H, m), 4.44 (1H, d, J = 13.9 Hz), 4.64 (1H, dd, J = 4.3, 1.9 Hz), 7.10 (2H, d, J = 8.2 Hz), 7.15 (2H, d, J = 8.2 Hz), 7.73 (2H, d, J = 8.6 Hz), 7.94 (2H, d, J = 8.2 Hz). |
| 372 | 615, 617 (M + H). | 1H-NMR (CDCl$_3$, 300 MHz) δ: 1.24 (6H, d, J = 7.2 Hz), 2.69-2.95 (3H, m), 3.25-3.33 (1H, m), 3.90-3.99 (2H, m), 4.29-4.52 (3H, m), 4.69 (1H, br s), 6.92-6.96 (1H, br m), 7.06 (2H, d, J = 4.1 Hz), 7.20 (2H, d, J = 8.3 Hz), 7.78 (2H, d, J = 8.3 Hz), 7.97 (2H, d, J = 8.3 Hz), 11.32 (1H, br s). |

TABLE 307

| Example No. | MS ESI m/e: | NMR |
|---|---|---|
| 373 | 537 (M + H). | 1H-NMR (CDCl$_3$, 300 MHz) δ: 1.24 (6H, d, J = 6.8 Hz), 2.78-2.85 (3H, m), 3.43-3.48 (1H, m), 3.93 (2H, d, J = 13.2 Hz), 4.40-4.42 (2H, m), 4.52 (1H, d, J = 13.6 Hz), 4.65 (1H, br s), 6.98-7.01 (1H, br m), 7.10 (2H, d, J = 8.3 Hz), 7.18 (2H, d, J = 8.3 Hz), 7.69 (1H, s), 7.77 (2H, d, J = 8.3 Hz), 7.99 (2H, d, J = 8.3 Hz). |
| 374 | 608 (M + H). | 1H-NMR (CD$_3$OD, 300 MHz) δ: 0.91 (3H, t, J = 7.3 Hz), 1.53-1.67 (2H, m), 2.54 (2H, t, J = 7.5 Hz), 3.21-3.30 (1H, m), 3.43 (1H, dd, J = 13.9, 4.5 Hz), 3.71-3.92 (2H, m), 4.14-4.21 (2H, m), 4.27-4.37 (1H, m), 4.59-4.65 (1H, m), 4.81-4.86 (1H, m), 6.99-7.07 (4H, m), 7.36-7.44 (2H, m), 7.92-7.99 (2H, m), 8.08-8.12 (1H, m), 8.59-8.67 (2H, m). |
| 375 | 493 (M + H). | 1H-NMR (CDCl$_3$, 400 MHz) δ: 1.04 (3H, t, J = 7.3 Hz), 1.25 (6H, d, J = 6.8 Hz), 1.80-1.90 (2H, m), 2.18 (3H, s), 2.59 (1H, ddd, J = 14.2, 11.5, 3.5 Hz), 2.86-2.94 (1H, m), 2.98-3.02 (1H, m), 3.03 (2H, t, J = 7.6 Hz), 3.24 (1H, ddd, J = 14.3, 11.4, 3.3 Hz), 3.83 (1H, dt, J = 14.3, 2.8 Hz), 4.31-4.59 (5H, m), 6.79 (1H, t, J = 5.7 Hz), 7.14 (2H, d, J = 7.9 Hz), 7.21 (2H, d, J = 8.2 Hz), 8.12 (1H, s). |
| 376 | 592 (M + H). | 1H-NMR (CD$_3$OD, 300 MHz) δ: 1.25 (6H, d, J = 7.2 Hz), 2.84-2.93 (1H, m), 3.24-3.29 (1H, m), 3.49-3.54 (1H, m), 3.78-3.97 (2H, m), 4.22-4.24 (2H, m), 4.39 (1H, d, J = 13.6 Hz), 4.73 (1H, br |

TABLE 307-continued

| Example No. | MS ESI m/e: | NMR |
|---|---|---|
| | | s), 4.85 (1H, br s), 7.08 (2H, d, J = 8.3 Hz), 7.13 (1H, s), 7.13 (2H, d, J = 4.1 Hz), 7.83 (2H, d, J = 8.3 Hz), 7.84 (3H, s), 7.89 (2H, d, J = 9.8 Hz), 8.06 (2H, d, J = 8.3 Hz), 8.68-8.70 (1H, br m). |
| 377 | 591 (M + H). | 1H-NMR (CDCl₃, 400 MHz) δ: 1.24 (6H, d, J = 6.8 Hz), 2.83-2.98 (2H, m), 3.09 (1H, dd, J = 13.5, 4.4 Hz), 3.39-3.49 (1H, m), 3.91 (1H, d, J = 14.1 Hz), 4.28-4.43 (3H, m), 4.63 (1H, s), 4.84 (1H, d, J = 14.1 Hz), 5.39 (1H, s), 6.81 (1H, t, J = 5.4 Hz), 7.06 (2H, d, J = 7.9 Hz), 7.16 (2H, d, J = 7.9 Hz), 7.33 (1H, s), 7.79 (2H, d, J = 8.2 Hz), 7.97-8.08 (3H, m), 8.77 (1H, d, J = 1.3 Hz). |

TABLE 308

| Example No. | MS ESI m/e: | NMR |
|---|---|---|
| 378 | 627 (M + H). | 1H-NMR (DMSO-d₆, 400 MHz) δ: 0.87 (3H, t, J = 7.4 Hz), 1.49-1.60 (2H, m), 2.37 (3H, s), 2.46-2.54 (2H, m), 3.11-3.20 (1H, m), 3.44 (1H, dd, J = 13.5, 4.4 Hz), 3.71-3.78 (2H, m), 3.82-3.91 (1H, m), 3.98-4.16 (2H, m), 4.23-4.29 (1H, m), 4.54-4.58 (1H, m), 7.06 (4H, br s), 7.50 (2H, d, J = 8.8 Hz), 7.90 (2H, d, J = 8.8 Hz), 8.62 (1H, br t, J = 5.8 Hz), 12.49 (1H, br s). |
| 379 | 662 (M − H). | 1H-NMR (CD₃OD, 400 MHz) δ: 2.48 (3H, s), 3.26-3.29 (7H, br m), 3.48-3.55 (1H, m), 3.73-3.83 (1H, m), 3.85-3.94 (2H, m), 4.28-4.37 (2H, m), 4.39-4.46 (1H, m), 4.68-4.73 (1H, m), 7.45-7.51 (4H, m), 7.55 (2H, d, J = 8.8 Hz), 8.02 (2H, d, J = 8.8 Hz), 8.80 (1H, br t, J 6.2 Hz). |
| 380 | 591 (M + H). | 1H-NMR (DMSO-d₆, 300 MHz) δ: 0.90 (3H, t, J = 7.3 Hz), 1.16 (6H, d, J = 6.8 Hz), 1.62 (2H, q, J = 7.3 Hz), 2.39 (3H, s), 2.75-2.88 (3H, m), 3.08-3.20 (1H, m), 3.41 (1H, dd, J = 13.6, 4.5 Hz), 3.65-3.88 (3H, m), 4.05-4.27 (3H, m), 4.49-4.54 (1H, br m), 6.93 (1H, d, J = 3.8 Hz), 7.08-7.12 (4H, m), 7.50 (1H, d, J = 3.8 Hz), 8.63 (1H, t, J = 5.8 Hz), 12.51 (1H, br s). |
| 381 | 6H (M + H). | 1H-NMR (DMSO-d₆, 300 MHz) δ: 1.17 (6H, d, J = 7.2 Hz), 1.49-1.58 (4H, br m), 1.74-1.83 (2H, br m), 2.37 (3H, s), 2.79-2.86 (5H, m), 3.01-3.07 (1H, m), 3.34-3.40 (1H, m), 3.71-3.78 (3H, m), 4.02-4.24 (3H, m), 4.53-4.56 (1H, m), 7.05-7.15 (4H, m), 7.28 (1H, d, J = 7.9 Hz), 7.50-7.56 (2H, m), 8.58 (1H, t, J = 5.7 Hz), 12.49 (1H, br s). |
| 382 | 641 (M + H). | 1H-NMR (DMSO-d₆, 400 MHz) δ: 1.17 (6H, d, J = 6.8 Hz), 2.46-2.53 (2H, m), 2.64-2.71 (2H, m), 2.79-2.89 (1H, m), 2.92-3.02 (1H, m), 3.18-3.24 (1H, m), 3.71-3.79 (3H, m), 4.00-4.19 (2H, m), 4.23-4.30 (1H, m), 4.55-4.59 (1H, m), 6.43 (1H, s), 7.07 (2H, d, J = 8.4 Hz), 7.13 (2H, d, J = 8.4 Hz), 7.50 (2H, d, J = 8.8 Hz), 7.90 (2H, d, J = 8.8 Hz), 8.58 (1H, br t, J = 5.7 Hz), 12.11 (1H, br s). |

TABLE 309

| Example No. | MS ESI m/e: | NMR |
|---|---|---|
| 383 | 625 (M + H). | 1H-NMR (DMSO-d₆, 400 MHz) δ: 0.57-0.63 (2H, m), 0.88-0.95 (2H, m), 1.82-1.90 (1H, m), 2.37 (3H, s), 3.10-3.20 (1H, m), 3.40-3.47 (1H, m), 3.71-3.78 (2H, m), 3.83-3.90 (1H, m), 3.97-4.14 (2H, m), 4.21-4.29 (1H, m), 4.53-4.57 (1H, m), 6.95 (2H, d, J = 8.2 Hz), 7.02 (2H, d, J = 8.2 Hz), 7.50 (2H, d, J = 8.8 Hz), 7.89 (2H, d, J = 8.8 Hz), 8.61 (1H, br t, J = 5.7 Hz), 12.51 (1H, br s). |
| 384 | 585 (M + H). | 1H-NMR (DMSO-d₆, 300 MHz) δ: 1.19 (6H, d, J = 6.8 Hz), 2.62-2.74 (1H, m), 2.82-3.80 (8H, m), 3.96-4.29 (4H, m), 4.50-4.64 (2H, m), 7.07-7.24 (4H, m), 7.83-7.99 (4H, m), 8.57-8.74 (1H, br m). |
| 385 | 608 (M + H). | 1H-NMR (DMSO-d₆, 400 MHz) δ: 1.16 (6H, d, J = 6.8 Hz), 2.76-2.88 (1H, m), 3.16-3.27 (1H, m), 3.37-3.45 (1H, m), 3.68-3.78 (2H, m), 3.94-4.10 (2H, m), 4.30-4.38 (1H, m), 4.55-4.60 (1H, m), 4.74-4.82 (1H, m), 6.99 (2H, d, J = 7.9 Hz), 7.07 (2H, d, J = 7.9 Hz), 7.48 (2H, d, J = 8.8 Hz), 7.90 (2H, d, J = 8.8 Hz), 8.23 (1H, d, J = 1.1 Hz), 8.56 (1H, d, J = 1.1 Hz), 8.66 (1H, br t, J = 5.7 Hz), 12.74 (1H, br s). |

TABLE 309-continued

| Example No. | MS ESI m/e: | NMR |
|---|---|---|
| 386 | 650 (M + H). | 1H-NMR (DMSO-d$_6$, 400 MHz) δ: 3.18-3.25 (1H, m), 3.42 (1H, dd, J = 13.9, 4.4 Hz), 3.68-3.80 (2H, m), 4.04-4.15 (2H, m), 4.32 (1H, d, J = 13.7 Hz), 4.57-4.61 (1H, br m), 4.77 (1H, d, J = 14.4 Hz), 7.20-7.22 (4H, br m), 7.49 (2H, d, J = 8.1 Hz), 7.92 (2H, d, J = 8.1 Hz), 8.23 (1H, s), 8.55 (1H, s), 8.78 (1H, t, J = 5.8 Hz), 12.75 (1H, br s). |
| 387 | 629 (M + H). | 1H-NMR (DMSO-d$_6$, 400 MHz) δ: 2.37 (3H, s), 2.98 (6H, s), 3.09-3.16 (1H, m), 3.37-3.44 (1H, m), 3.69-3.77 (2H, m), 3.81-3.88 (1H, m), 3.88-4.05 (2H, m), 4.19-4.26 (1H, m), 4.50-4.54 (1H, m), 6.50 (1H, d, J = 8.8 Hz), 7.26 (1H, dd, J = 8.8, 2.6 Hz), 7.53 (2H, d, J = 9.0 Hz), 7.88 (2H, d, J = 9.0 Hz), 7.91 (1H, d, J = 2.6 Hz), 8.55 (1H, br t, 3 = 5.8 Hz), 12.50 (1H, br s). |

TABLE 310

| Example No. | MS ESI m/e: | NMR |
|---|---|---|
| 388 | 628 (M + H). | 1H-NMR (DMSO-d$_6$, 400 MHz) δ: 0.88 (3H, t, J = 7.4 Hz), 1.65 (2H, tq, J = 7.4, 7.4 Hz), 2.37 (3H, s), 2.65 (2H, t, J = 7.4 Hz), 3.09-3.19 (1H, m), 3.38-3.45 (1H, m), 3.67-3.87 (3H, m), 4.03-4.20 (2H, m), 4.22-4.30 (1H, m), 4.54-4.59 (1H, m), 7.10 (1H, d, J = 7.9 Hz), 7.42 (1H, dd, J = 7.9, 2.3 Hz), 7.52 (2H, d, J = 9.0 Hz), 7.90 (2H, d, J = 9.0 Hz), 8.30 (1H, d, J = 2.3 Hz), 8.72 (1H, br t, J = 5.9 Hz), 12.51 (1H, br s). |
| 389 | 641 (M + H). | 1H-NMR (DMSO-d$_6$, 400 MHz) δ: 2.24-2.34 (2H, m), 2.37 (3H, s), 3.08-3.16 (1H, m), 3.36-3.43 (1H, m), 3.67-3.76 (2H, m), 3.80-4.05 (7H, m), 4.18-4.25 (1H, m), 4.50-4.54 (1H, m), 6.22 (1H, d, J = 8.6 Hz), 7.26 (1H, dd, J = 8.6, 2.3 Hz), 7.54 (2H, d, J = 9.0 Hz), 7.86-7.92 (3H, m), 8.56 (1H, br t, J = 5.8 Hz), 12.51 (1H, br s). |
| 390 | 655 (M + H). | 1H-NMR (DMSO-d$_6$, 400 MHz) δ: 1.88-1.96 (4H, m), 2.36 (3H, s), 3.09-3.16 (1H, m), 3.29-3.36 (4H, m), 3.36-3.43 (1H, m), 3.67-3.77 (2H, m), 3.80-4.04 (3H, m), 4.18-4.25 (1H, m), 4.49-4.53 (1H, m), 6.29 (1H, d, J = 8.7 Hz), 7.23 (1H, dd, J = 8.7, 2.4 Hz), 7.53 (2H, dd, J = 8.8, 0.9 Hz), 7.86-7.92 (3H, m), 8.54 (1H, br t, J = 5.8 Hz), 12.50 (1H, br s). |
| 391 | 599 (M + H). | 1H-NMR (DMSO-d$_6$, 300 MHz) δ: 1.19 (6H, d, J = 6.8 Hz), 2.16-2.30 (2H, br m), 2.55-2.73 (2H, m), 2.82-2.91 (1H, m), 2.97-3.86 (6H, m), 4.00-4.28 (4H, m), 4.49-4.64 (2H, m), 7.06-7.14 (2H, m), 7.20 (2H, d, J = 7.9 Hz), 7.83-7.99 (4H, m), 8.55-8.70 (1H, m). |
| 392 | 488 (M + H). | 1H-NMR (CDCl$_3$, 400 MHz) δ: 1.29 (6H, d, J = 6.8 Hz), 2.13 (3H, s), 2.23-2.33 (1H, m), 2.67-2.89 (4H, m), 2.96-3.05 (1H, m), 3.38-3.58 (2H, m), 3.67-3.75 (1H, m), 3.80 (3H, s), 4.15-4.24 (1H, m), 4.37-4.49 (2H, m), 6.56-6.63 (1H, br), 6.86 (2H, d, J = 8.8 Hz), 7.07 (2H, d, J = 8.8 Hz), 7.40 (2H, d, J = 8.4 Hz), 7.72 (2H, d, J = 8.4 Hz). |

TABLE 311

| Example No. | MS ESI m/e: | NMR |
|---|---|---|
| 393 | 502 (M + H). | 1H-NMR (DMSO-d$_6$, 400 MHz) δ: 1.13-1.24 (6H, m), 1.77 (1.8H, s), 1.86 (1.2H, s), 2.36-2.55 (1H, m), 2.61-2.78 (2H, m), 2.81-3.33 (5H, m), 3.51-4.42 (4H, m), 7.26-7.35 (2H, m), 7.39-7.47 (2H, m), 7.64 (0.8H, d, J = 8.2 Hz), 7.72 (1.2H, d, J = 8.4 Hz), 7.83-7.89 (2H, m), 8.08-8.17 (1H, br m), 12.81 (1H, br s). |
| 394 | 615 (M + H). | 1H-NMR (CD$_3$OD, 400 MHz) δ: 0.93 (3H, t, J = 7.4 Hz), 1.21 (6H, d, J = 7.1 Hz), 1.60-1.70 (2H, m), 2.65 (2H, t, J = 7.6 Hz), 2.81-2.88 (1H, m), 3.09-3.16 (1H, m), 3.35 (3H, s), 3.41 (1H, dd, J = 14.0, 5.0 Hz), 3.71-3.89 (3H, m), 4.25 (2H, s), 4.32 (1H, d, J = 11.9 Hz), 4.58-4.69 (3H, m), 7.09-7.14 (4H, m), 7.34 (2H, d, J = 8.2 Hz), 7.76 (2H, d, J = 8.2 Hz). |
| 395 | 459 (M + H). | 1H-NMR (CDCl$_3$, 400 MHz) δ: 1.29 (6H, d, J = 6.8 Hz), 1.89 (0.3H, s), 2.13 (2.7H, s), 2.26-2.33 (1H, m), 2.73 (1H, dd, J = 13.5, 4.0 Hz), 2.79-2.95 (3H, m), 2.98-3.05 (1H, m), 3.52-3.59 (2H, m), 3.73 (1H, d, J = 13.7 Hz), 4.22 (1H, d, J = 12.4 Hz), 4.39-4.45 (2H, m), 6.75 (1H, t, J = 5.6 Hz), 7.12 (2H, d, J = 6.0 Hz), 7.42 (2H, d, J = 8.4 Hz), 7.74 (2H, d, J = 8.2 Hz), 8.55 (2H, d, J = 5.7 Hz). |

TABLE 311-continued

| Example No. | MS ESI m/e: | NMR |
|---|---|---|
| 396 | 459 (M + H). | 1H-NMR (CDCl$_3$, 300 MHz) δ: 1.28 (6H, d, J = 6.8 Hz), 2.12 (3H, s), 2.25-2.37 (1H, m), 2.79 (1H, dd, J = 13.0, 4.0 Hz), 2.88-3.09 (4H, m), 3.51-3.64 (1H, m), 3.67-3.77 (1H, m), 3.81 (1H, d, J = 15.1 Hz), 4.22 (1H, d, J = 13.2 Hz), 4.40-4.52 (2H, m), 7.11-7.21 (2H, m), 7.39 (1H, d, J = 8.3 Hz), 7.63 (1H, td, J = 7.6, 1.8 Hz), 7.78 (2H, d, J = 8.3 Hz), 8.11 (1H, br s), 8.55 (1H, d, J = 4.1 Hz). |
| 397 | 459 (M + H). | 1H-NMR (CDCl$_3$, 300 MHz) δ: 1.29 (6H, d, J = 7.2 Hz), 2.12 (3H, s), 2.24-2.37 (1H, m), 2.73 (1H, dd, J = 13.4, 4.0 Hz), 2.78-3.10 (4H, m), 3.49-3.59 (2H, m), 3.76 (1H, d, J = 14.7 Hz), 4.22 (1H, d, J = 13.9 Hz), 4.36-4.48 (2H, m), 6.75 (1H, t, J = 6.0 Hz), 7.23-7.31 (1H, m), 7.42 (2H, d, J = 8.7 Hz), 7.53 (1H, d, J = 7.9 Hz), 7.75 (2H, d, J = 8.3 Hz), 8.42-8.54 (3H, m). |

TABLE 312

| Example No. | MS ESI m/e: | NMR |
|---|---|---|
| 398 | 640 (M + H). | 1H-NMR (CD$_3$OD, 300 MHz) δ: 2.28-2.40 (2H, m), 2.43 (3H, s), 3.15-3.27 (1H, m), 3.44 (1H, dd, J = 13.8, 4.7 Hz), 3.77-3.87 (6H, m), 3.92 (1H, d, J = 12.8 Hz), 4.04-4.21 (2H, m), 4.36 (1H, d, J = 12.8 Hz), 4.56-4.63 (1H, m), 6.33-6.41 (2H, m), 6.99-7.06 (2H, m), 7.36-7.46 (2H, m), 7.88-7.97 (2H, m), 8.42-8.48 (1H, m). |
| 399 | 609 (M + H). | 1H-NMR (CD$_3$OD, 300 MHz) δ: 2.89 (6H, s), 3.19-3.29 (1H, m), 3.41 (1H, dd, J = 14.1, 4.3 Hz), 3.71-3.88 (2H, m), 4.03-4.17 (2H, m), 4.27-4.37 (1H, m), 4.58-4.64 (1H, m), 4.80-4.87 (1H, m), 6.62 (2H, dd, J = 6.8, 1.9 Hz), 6.97 (2H, d, J = 8.7 Hz), 7.40 (2H, dd, J = 8.9, 0.9 Hz), 7.92-7.98 (2H, m), 8.08 (1H, d, J = 1.5 Hz), 8.46-8.53 (1H, m), 8.61 (1H, d, J = 1.5 Hz). |
| 400 | 484 (M + H). | 1H-NMR (CDCl$_3$, 400 MHz) δ: 0.78-0.82 (2H, m), 1.11-1.16 (2H, m), 1.25 (6H, d, J = 7.1 Hz), 1.91-1.99 (1H, m), 2.15 (3H, s), 2.33-2.41 (1H, m), 2.79 (1H, dd, J = 12.5, 3.2 Hz), 2.87-2.94 (1H, m), 3.10-3.17 (1H, m), 3.82 (1H, d, J = 14.3 Hz), 4.28 (1H, d, J 13.5 Hz), 4.36-4.51 (4H, m), 6.87-6.90 (1H, br m), 7.12-7.22 (6H, m), 7.70 (2H, d, J = 8.2 Hz). |
| 401 | 585 (M + H). | 1H-NMR (CD$_3$OD, 400 MHz) δ: 2.43 (3H, s), 3.22 (1H, dq, J = 13.6, 4.3 Hz), 3.47 (1H, dd, J = 13.9, 4.9 Hz), 3.75-3.96 (3H, m), 4.18-4.42 (3H, m), 4.63 (1H, dd, J = 4.6, 2.4 Hz), 7.18-7.30 (5H, m), 7.40 (2H, d, J = 7.9 Hz), 7.94 (2H, d, J = 8.8 Hz), 8.62 (1H, t, J = 6.0 Hz). |
| 402 | 465 (M + H). | 1H-NMR (CDCl$_3$, 300 MHz) δ: 1.19-1.30 (8H, m), 1.41-1.48 (2H, m), 1.54-1.62 (2H, m), 2.13 (3H, s), 2.24 (1H, d, J = 4.9 Hz), 2.33-2.44 (6H, m), 2.83 (1H, dd, J = 13.0, 4.0 Hz), 2.94-3.05 (1H, m), 3.15-3.42 (3H, m), 3.86 (1H, d, J = 14.7 Hz), 4.29 (1H, d, J = 13.2 Hz), 4.44-4.50 (2H, m), 7.29-7.34 (1H, br m), 7.41 (2H, d, J = 8.3 Hz), 7.79 (2H, d, J = 8.3 Hz). |

TABLE 313

| Example No. | MS ESI m/e: | NMR |
|---|---|---|
| 403 | 467 (M + H). | 1H-NMR (CDCl$_3$, 300 MHz) δ: 1.29 (6H, d, J = 6.8 Hz), 2.13 (3H, s), 2.30-2.52 (7H, m), 2.80 (1H, dd, J = 13.9, 4.5 Hz), 2.96-3.06 (1H, m), 3.16-3.43 (3H, m), 3.65-3.85 (5H, m), 4.28 (1H, d, J = 13.2 Hz), 4.46-4.50 (2H, m), 7.25-7.31 (1H, br m), 7.42 (2H, d, J = 8.3 Hz), 7.78 (2H, d, J = 8.3 Hz). |
| 404 | 481 (M + H). | 1H-NMR (CDCl$_3$, 300 MHz) δ: 1.29 (6H, d, J = 6.8 Hz), 1.66-1.75 (2H, m), 2.12 (3H, s), 2.31-2.48 (7H, m), 2.71 (1H, dd, J = 13.4, 4.0 Hz), 2.97-3.06 (1H, m), 3.13-3.23 (1H, m), 3.29-3.41 (2H, m), 3.70-3.88 (5H, m), 4.25 (1H, d, J = 13.2 Hz), 4.40-4.47 (2H, m), 7.14 (1H, t, J = 5.1 Hz), 7.43 (2H, d, J = 8.3 Hz), 7.78 (2H, d, J = 8.3 Hz). |
| 405 | 465 (M + H). | 1H-NMR (CDCl$_3$, 300 MHz) δ: 1.29 (6H, d, J = 7.2 Hz), 1.68-2.01 (6H, m), 2.11 (3H, s), 2.32-2.42 (1H, m), 2.49-2.76 (7H, m), 2.96-3.06 (1H, m), 3.16-3.26 (1H, m), 3.36 (2H, q, J = 5.8 Hz), 3.89 (1H, d, J = 14.3 Hz), 4.24 (1H, d, J = 13.9 Hz), 4.37-4.45 (2H, m), 7.42 (2H, d, J = 8.7 Hz), 7.75-7.81 (3H, m). |
| 406 | 626 (M + H). | 1H-NMR (DMSO-d$_6$, 400 MHz) δ: 0.87 (3H, t, J = 7.3 Hz), 1.49-1.61 (2H, m), 2.34 (3H, s), 2.45-2.54 (2H, m), 3.05-3.15 (1H, m), 3.31-3.39 (1H, m), 3.70-3.84 (3H, m), 4.00-4.17 (2H, m), |

TABLE 313-continued

| Example No. | MS ESI m/e: | NMR |
|---|---|---|
| 407 | 610 (M + H). | 4.23-4.30 (1H, m), 4.54-4.59 (1H, m), 7.03-7.11 (6H, m), 7.51 (2H, d, J = 8.6 Hz), 7.90 (2H, d, J = 8.6 Hz), 8.62 (1H, br t, J = 5.8 Hz). 1H-NMR (DMSO-$d_6$, 400 MHz) δ: 2.97 (6H, s), 3.07-3.17 (1H, m), 3.27-3.35 (1H, m), 3.65-3.76 (2H, m), 3.84-3.98 (2H, m), 4.24-4.31 (1H, m), 4.50-4.55 (1H, m), 4.68-4.75 (1H, m), 6.46 (1H, d, J = 8.7 Hz), 7.17 (1H, dd, J = 8.7, 2.3 Hz), 7.51 (2H, d, J = 8.8 Hz), 7.88 (1H, d, J = 2.3 Hz), 7.89 (2H, d, J = 8.8 Hz), 8.12 (1H, d, J = 1.1 Hz), 8.53 (1H, d, J = 1.1 Hz), 8.61 (1H, br t, J = 5.5 Hz). |

TABLE 314

| Example No. | MS ESI m/e: | NMR |
|---|---|---|
| 408 | 609 (M + H). | 1H-NMR (DMSO-$d_6$, 400 MHz) δ: 1.19 (6H, d, J = 7.1 Hz), 2.90-3.00 (1H, m), 3.11-3.21 (1H, m), 3.31-3.39 (1H, m), 3.64-3.78 (2H, m), 3.99-4.13 (2H, m), 4.25-4.32 (1H, m), 4.55-4.60 (1H, m), 4.71-4.78 (1H, m), 7.10 (1H, d, J = 8.2 Hz), 7.36 (1H, dd, J = 8.2, 2.2 Hz), 7.50 (2H, d, J = 8.8 Hz), 7.91 (2H, d, J = 8.8 Hz), 8.17 (1H, d, J = 0.9 Hz), 8.28 (1H, d, J = 2.2 Hz), 8.53 (1H, d, J = 0.9 Hz), 8.78 (1H, br t, J = 6.0 Hz). |
| 409 | 647 (M + H). | 1H-NMR (CDCl$_3$, 300 MHz) δ: 2.37-2.46 (1H, m), 2.76 (1H, dd, J = 13.8, 4.0 Hz), 3.16-3.26 (1H, m), 3.79-3.94 (3H, m), 4.38-4.61 (5H, m), 7.01 (1H, t, J = 6.0 Hz), 7.13 (2H, d, J = 5.7 Hz), 7.20 (2H, d, J = 8.3 Hz), 7.25-7.28 (2H, m), 7.38 (2H, d, J = 8.3 Hz), 7.90 (2H, d, J = 9.0 Hz), 8.52 (2H, d, J = 5.7 Hz). |
| 410 | 606 (M + H). | 1H-NMR (CDCl$_3$, 300 MHz) δ: 2.39-2.49 (1H, m), 2.81 (1H, dd, J = 13.2, 4.1 Hz), 2.95 (6H, s), 3.11-3.20 (1H, m), 3.80-3.98 (3H, m), 4.25-4.49 (4H, m), 4.62 (1H, d, J = 13.9 Hz), 6.62-6.70 (3H, m), 7.07 (2H, d, J = 8.3 Hz), 7.14 (2H, d, J = 5.7 Hz), 7.34 (2H, d, J = 8.3 Hz), 7.87 (2H, d, J = 9.0 Hz), 8.52 (2H, d, J = 5.7 Hz). |
| 411 | 605 (M + H). | 1H-NMR (CDCl$_3$, 300 MHz) δ: 0.95 (3H, t, J = 7.3 Hz), 1.60-1.68 (2H, m), 2.38-2.47 (1H, m), 2.58 (2H, t, J = 7.5 Hz), 2.79 (1H, dd, J = 13.8, 4.0 Hz), 3.14-3.23 (1H, m), 3.79-3.97 (3H, m), 4.37-4.46 (3H, m), 4.50 (1H, d, J = 3.0 Hz), 4.61 (1H, d, J = 13.6 Hz), 6.81 (1H, t, J = 5.5 Hz), 7.10-7.18 (6H, m), 7.35 (2H, d, J = 8.3 Hz), 7.89 (2H, d, J = 9.0 Hz), 8.52 (2H, br s). |
| 412 | 603 (M + H). | 1H-NMR (CDCl$_3$, 300 MHz) δ: 0.66-0.72 (2H, m), 0.94-1.01 (2H, m), 1.85-1.94 (1H, m), 2.38-2.48 (1H, m), 2.79 (1H, dd, J = 13.8, 4.0 Hz), 3.12-3.22 (1H, m), 3.79-3.96 (3H, m), 4.38-4.44 (3H, m), 4.48-4.51 (1H, br m), 4.60 (1H, d, J = 13.6 Hz), 6.79 (1H, t, J = 5.7 Hz), 7.03-7.14 (6H, m), 7.35 (2H, d, J = 8.3 Hz), 7.88 (2H, d, J = 9.0 Hz), 8.48-8.57 (2H, br m). |

TABLE 315

| Example No. | MS ESI m/e: | NMR |
|---|---|---|
| 413 | 606 (M + H). | 1H-NMR (DMSO-$d_6$, 400 MHz) δ: 0.86 (3H, t, J = 7.4 Hz), 1.48-1.59 (2H, m), 2.45-2.53 (2H, m), 2.80-2.90 (1H, m), 3.04-3.12 (1H, m), 3.63-3.81 (3H, m), 4.05-4.23 (3H, m), 4.54-4.60 (1H, m), 6.77 (2H, d, J = 9.0 Hz), 7.02 (4H, br s), 7.51 (2H, d, J = 8.8 Hz), 7.71 (2H, d, J = 9.0 Hz), 7.95 (2H, d, J = 8.8 Hz), 8.60 (1H, br t, J = 5.8 Hz), 12.29 (1H, br s). |
| 414 | 571 (M + H). | 1H-NMR (DMSO-$d_6$, 300 MHz) δ: 0.87 (3H, t, J = 7.5 Hz), 1.18 (3H, t, J = 7.5 Hz), 1.47-1.63 (2H, m), 2.34-2.50 (1H, m), 2.37 (3H, s), 2.40-2.66 (2H, m), 2.67 (2H, q, J = 7.7 Hz), 2.95-3.13 (1H, m), 3.63-3.86 (3H, m), 3.97-4.28 (3H, m), 4.46-4.61 (1H, m), 7.06 (4H, s), 7.38 (2H, d, J = 8.3 Hz), 7.71 (2H, d, J = 8.3 Hz), 8.59 (1H, t, J = 5.7 Hz), 12.51 (1H, bs). |
| 415 | 552 (M + H). | 1H-NMR (DMSO-$d_6$, 300 MHz) δ: 0.86 (3H, t, J = 7.5 Hz), 1.16 (3H, t, J = 7.5 Hz), 1.46-1.61 (2H, m), 2.40-2.55 (1H, m), 2.50-2.80 (2H, m), 3.10-3.20 (1H, m), 3.20-3.40 (2H, m), 3.60-3.76 (2H, m), 3.99-4.23 (3H, m), 4.50-4.80 (2H, m), 7.01 (4H, s), 7.35 (2H, d, J = 8.3 Hz), 7.71 (2H, d, J = 8.3 Hz), 8.11 (1H, d, J = 1.1 Hz), 8.53 (1H, d, J = 1.1 Hz), 8.64 (1H, t, J = 5.7 Hz). |
| 416 | 654 (M + H). | 1H-NMR (CD$_3$OD, 300 MHz) δ: 1.94-2.07 (4H, m), 2.42 (3H, s), 3.16-3.28 (5H, m), 3.44 (1H, dd, J = 13.6, 4.5 Hz), 3.77-3.85 (2H, m), 3.88-3.97 (1H, m), 4.03-4.21 (3H, m), 4.36 (1H, d, J = 14.3 Hz), 4.57-4.62 (1H, m), 6.42-6.51 (2H, m), 7.00 (2H, d, J = 8.7 Hz), 7.39 (2H, d, J = 7.9 Hz), 7.89-7.95 (2H, m), 8.36-8.44 (1H, m). |

TABLE 315-continued

| Example No. | MS ESI m/e: | NMR |
|---|---|---|
| 417 | 608 (M + H). | 1H-NMR (CD$_3$OD, 300 MHz) δ: 0.95 (3H, t, J = 7.3 Hz), 1.63 (2H, td, J = 15.0, 7.4 Hz), 2.57 (2H, t, J = 7.7 Hz), 3.26-3.28 (1H, m), 3.49-3.54 (1H, m), 3.81-3.92 (2H, m), 4.23-4.24 (2H, m), 4.40 (1H, d, J = 13.2 Hz), 4.69 (1H, s), 4.84 (1H, s), 7.06 (4H, s), 7.12 (1H, d, J = 9.4 Hz), 7.44 (2H, d, J = 7.9 Hz), 7.88 (1H, d, J = 9.8 Hz), 8.00 (2H, d, J = 8.7 Hz), 8.67-8.70 (1H, br m). |

TABLE 316

| Example No. | MS ESI m/e: | NMR |
|---|---|---|
| 418 | 599 (M + H). | 1H-NMR. (CD$_3$OD, 400 MHz) δ: 2.43 (3H, s), 2.67-2.77 (2H, m), 3.09-3.16 (1H, m), 3.33-3.39 (2H, m), 3.60-3.66 (1H, m), 3.80-3.86 (2H, m), 4.26 (1H, d, J = 14.6 Hz), 4.54 (1H, s), 4.82 (1H, s), 7.17-7.19 (3H, m), 7.23-7.27 (2H, m), 7.42 (2H, d, J = 8.2 Hz), 7.93 (2H, d, J = 8.6 Hz), 8.09-8.13 (1H, br m). |
| 419 | 540, 542 (M + H). | 1H-NMR (CDCl$_3$, 400 MHz) δ: 1.26 (6.0H, d, J = 7.1 Hz), 1.99 (0.5H, s), 2.20 (2.4H, s), 2.45-2.53 (0.8H, m), 2.86-2.95 (1.1H, m), 3.05 (0.9H, dd, J = 13.3, 3.9 Hz), 3.12-3.19 (0.9H, m), 3.83 (0.9H, d, J = 14.1 Hz), 4.42 (1.7H, d, J = 5.1 Hz), 4.46-4.53 (2.0H, m), 4.62 (0.9H, d, J = 13.2 Hz), 6.71-6.74 (0.8H, br m), 7.13 (2.0H, d, J = 8.2 Hz), 7.18-7.23 (2.1H, m), 7.36 (1.2H, d, J = 9.7 Hz), 7.48 (0.9H, d, J = 8.4 Hz), 7.79 (1.0H, t, J = 7.9 Hz). |
| 420 | 655 (M + H). | 1H-NMR (CDCl$_3$, 400 MHz) δ: 1.24 (6H, d, J = 7.1 Hz), 2.84-3.02 (2H, m), 3.23 (1H, dd, J = 14.2, 5.6 Hz), 3.58 (1H, dt, J = 17.5, 6.0 Hz), 3.82-3.94 (4H, m), 4.05 (1H, d, J = 12.6 Hz), 4.28 (1H, dd, J = 14.8, 5.1 Hz), 4.46-4.65 (3H, m), 6.83 (1H, t, J = 5.7 Hz), 7.11-7.21 (4H, m), 7.76 (2H, d, J = 8.4 Hz), 7.97 (2H, d, J = 8.4 Hz). |
| 421 | 718, 720 (M + H). | 1H-NMR (CDCl$_3$, 400 MHz) δ: 1.25 (6H, d, J = 6.8 Hz), 2.85-3.07 (2H, m), 3.22 (1H, dd, J = 14.0, 4.3 Hz), 3.56-3.68 (1H, m), 3.82-3.98 (4H, m), 4.11-4.28 (2H, m), 4.40-4.60 (2H, m), 4.90 (1H, d, J = 14.3 Hz), 6.73 (1H, t, J = 5.7 Hz), 7.10 (2H, d, J = 8.4 Hz), 7.21 (2H, d, J = 8.2 Hz), 7.79 (2H, d, J = 8.2 Hz), 7.97 (2H, d, J = 8.6 Hz). |
| 422 | 620 (M + H). | 1H-NMR (CD$_3$OD, 400 MHz) δ: 1.20 (6H, d, J = 6.8 Hz), 2.47 (3H, s), 2.63-2.96 (5H, m), 3.16 (1H, d, J = 10.8 Hz), 3.75-3.97 (3H, m), 4.07-4.34 (3H, m), 4.68 (1H, s), 6.98-7.13 (4H, m), 7.79 (2H, d, J = 8.4 Hz), 8.01 (2H, d, J = 8.2 Hz), 8.52 (1H, s). |

TABLE 317

| Example No. | MS ESI m/e: | NMR |
|---|---|---|
| 423 | 621 (M + H). | 1H-NMR (CDCl$_3$, 400 MHz) δ: 1.24 (6H, d, J = 6.8 Hz), 2.83-2.94 (1H, m), 3.01-3.19 (2H, m), 3.37-3.50 (1H, m), 3.78-3.95 (4H, m), 4.06 (1H, d, J = 13.0 Hz), 4.30-4.46 (2H, m), 4.59 (1H, t, J = 3.5 Hz), 4.76 (1H, dd, J = 14.3, 2.6 Hz), 6.84 (1H, t, J = 5.2 Hz), 7.07-7.19 (4H, m), 7.51 (1H, s), 7.77 (2H, d, J = 8.6 Hz), 7.99 (2H, d, J = 8.4 Hz). |
| 424 | 642 (M + H). | 1H-NMR (CD$_3$OD, 300 MHz) δ: 1.07 (3H, t, J = 7.0 Hz), 2.43 (3H, s), 2.87 (3H, s), 3.16-3.28 (1H, m), 3.33-3.50 (3H, m), 3.76-3.86 (2H, m), 3.87-3.99 (1H, m), 4.05-4.20 (2H, m), 4.37 (1H, d, J = 13.6 Hz), 4.57-4.63 (1H, m), 6.65 (2H, d, J = 8.7 Hz), 7.03 (2H, d, J = 8.7 Hz), 7.40 (2H, d, J = 8.3 Hz), 7.89-7.96 (2H, m), 8.40-8.48 (1H, m). |
| 425 | 656 (M + H). | 1H-NMR (CD$_3$OD, 300 MHz) δ: 1.11 (6H, t, J = 7.0 Hz), 2.44 (3H, s), 3.17-3.28 (1H, m), 3.33-3.39 (2H, m), 3.45 (1H, dd, J = 13.6, 4.5 Hz), 3.78-3.85 (2H, m), 3.88-3.98 (1H, m), 4.05-4.19 (2H, m), 4.38 (1H, d, J = 13.6 Hz), 4.57-4.63 (1H, m), 6.59-6.65 (2H, m), 7.01 (2H, d, J = 8.7 Hz), 7.39 (2H, d, J = 8.3 Hz), 7.89-7.96 (2H, m), 8.38-8.47 (1H, m). |
| 426 | 580 (M + H). | 1H-NMR (CD$_3$OD, 300 MHz) δ: 1.25 (6H, d, J = 6.8 Hz), 2.71-2.79 (1H, m), 2.88-2.95 (2H, m), 3.67 (1H, d, J = 12.8 Hz), 3.74-3.82 (1H, m), 3.93 (1H, d, J = 12.4 Hz), 4.13 (1H, d, J = 13.6 Hz), 4.26-4.35 (2H, m), 4.71 (1H, br s), 6.22 (1H, s), 7.16 (4H, s), 7.84 (2H, d, J = 8.7 Hz), 8.05 (2H, d, J = 8.3 Hz), 8.48-8.50 (1H, br m). |

TABLE 317-continued

| Example No. | MS ESI m/e: | NMR |
|---|---|---|
| 427 | 614 (M + H). | 1H-NMR (CD$_3$OD, 300 MHz) δ: 1.26 (6H, d, J = 6.8 Hz), 2.80-2.95 (3H, m), 3.60 (1H, d, J = 11.3 Hz), 3.81-3.89 (1H, m), 3.95 (1H, d, J = 10.2 Hz), 4.09 (1H, d, J = 12.4 Hz), 4.31 (2H, d, J = 6.0 Hz), 4.70 (1H, br s), 7.18 (4H, s), 7.84 (2H, d, J = 8.3 Hz), 8.05 (2H, d, J = 8.3 Hz), 8.49-8.51 (1H, br m). |

TABLE 318

| Example No. | MS ESI m/e: | NMR |
|---|---|---|
| 428 | 498 (M + H). | 1H-NMR (CDCl$_3$, 400 MHz) δ: 0.22-0.26 (1.8H, m), 0.58-0.62 (1.9H, m), 0.94-1.02 (1.0H, m), 1.25 (6H, d, J = 6.8 Hz), 1.92 (0.4H, s), 2.15 (2.8H, s), 2.35-2.42 (0.9H, m), 2.63 (2.0H, d, J = 7.1 Hz), 2.80 (0.9H, dd, J = 13.9, 4.6 Hz), 2.87-2.94 (1.1H, m), 3.11-3.18 (0.9H, m), 3.84 (1.0H, d, J = 14.3 Hz), 4.28 (0.9H, d, J = 13.7 Hz), 4.36-4.52 (4.0H, m), 6.87-6.90 (0.9H, br m), 7.13 (2.0H, d, J = 8.2 Hz), 7.21 (2.4H, d, J = 8.2 Hz), 7.44 (2.0H, d, J = 8.2 Hz), 7.76 (2.0H, d, J = 8.2 Hz). |
| 429 | 504 (M + H). | 1H-NMR (CDCl$_3$, 400 MHz) δ: 0.96 (2.9H, t, J = 7.3 Hz), 1.25 (6.1H, d, J = 7.0 Hz), 1.61-1.72 (3.3H, m), 1.99 (0.3H, s), 2.20 (2.7H, s), 2.44-2.52 (1.0H, m), 2.66 (2.0H, t, J = 7.7 Hz), 2.87-2.94 (1.1H, m), 3.03 (0.9H, dd, J = 13.4, 4.2 Hz), 3.10-3.17 (1.0H, m), 3.83 (1.1H, d, J = 14.4 Hz), 4.33-4.45 (3.0H, m), 4.55-4.62 (1.9H, m), 6.87-6.90 (0.9H, br m), 7.00 (1.0H, d, J = 11.6 Hz), 7.10-7.15 (2.9H, m), 7.21 (2.0H, d, J = 8.1 Hz), 7.81 (1.0H, t, J = 7.8 Hz). |
| 430 | 522, 524 (M + H). | 1H-NMR (CDCl$_3$, 400 MHz) δ: 1.26 (6.0H, d, J = 7.0Hz), 1.96 (0.4H, s), 2.16 (2.5H, s), 2.35-2.43 (1.0H, m), 2.82-2.95 (2.0H, m), 3.12-3.19 (0.9H, m), 3.80-3.85 (0.9H, m), 4.33-4.37 (1.2H, m), 4.41 (1.7H, d, J = 5.8 Hz), 4.46 (0.9H, d, J = 3.9 Hz), 4.53 (1.0H, d, J = 13.4 Hz), 6.73-6.76 (1.1H, br m), 7.12 (1.9H, d, J = 8.3 Hz), 7.22 (1.9H, d, J = 8.1 Hz), 7.66-7.71 (3.8H, m). |
| 431 | 620 (M + H). | 1H-NMR (CDCl$_3$, 400 MHz) δ: 1.25 (6H, d, J = 6.7 Hz), 2.59 (3H, s), 2.76 (1H, td, J = 12.6, 3.6 Hz), 2.81-2.95 (2H, m), 3.58 (1H, ddd, J = 14.6, 11.2, 2.8 Hz), 3.69 (1H, d, J = 12.8 Hz), 3.90-4.00 (4H, m), 4.29 (1H, dd, J = 14.8, 5.6 Hz), 4.41-4.53 (2H, m), 4.59 (1H, br s), 6.81 (1H, t, J = 5.9 Hz), 7.11 (2H, d, J = 8.3 Hz), 7.19 (2H, d, J = 8.1 Hz), 7.80 (2H, d, J = 8.1 Hz), 7.99 (2H, d, J = 8.1 Hz), 8.66 (1H, s). |

TABLE 319

| Example No. | MS ESI m/e: | NMR |
|---|---|---|
| 432 | 622 (M + H). | 1H-NMR (CD$_3$OD, 300 MHz) δ: 0.91 (3H, t, J = 7.3 Hz), 1.52-1.66 (2H, m), 2.20 (3H, s), 2.51 (2H, t, J = 7.7 Hz), 3.21-3.30 (1H, m), 3.45 (1H, dd, J = 14.3, 4.5 Hz), 3.72-3.92 (2H, m), 4.09-4.24 (2H, m), 4.28-4.38 (1H, m), 4.61-4.66 (1H, m), 4.79-4.86 (1H, m), 6.86 (1H, d, J = 7.9 Hz), 6.93 (1H, br s), 6.99 (2H, d, J = 7.9 Hz), 7.39 (2H, d, J = 7.9 Hz), 7.92-7.98 (2H, m), 8.11 (1H, d, J = 1.1 Hz), 8.42 (1H, t, J = 5.8 Hz), 8.61 (1H, d, J = 1.1 Hz). |
| 433 | 448 (M + H). | 1H-NMR (CDCl$_3$, 400 MHz) δ: 1.23-1.28 (6H, m), 2.04 (3H, br s), 2.43-2.53 (0.5H, br m), 2.77-3.08 (4H, br m), 3.15-3.34 (1.5H, br m), 3.53-3.62 (1H, br m), 3.65-3.91 (2.5H, br m), 4.10-4.19 (0.5H, br m), 4.26-4.34 (0.5H, br m), 4.57 (0.5H, br s), 4.69 (0.5H, br m), 4.75-4.84 (0.5H, br m), 7.14 (0.5H, br s), 7.23 (0.5H, br s), 7.32-7.43 (2H, br m), 7.69-7.82 (2H, br m), 8.02 (0.5H, br s), 8.30 (0.5H, br s), 8.66 (0.5H, br s), 8.80 (0.5H, br s). |

TABLE 320

| Example No. | MS ESI m/e: | NMR |
|---|---|---|
| 434 | 585 (M + H). | 1H-NMR (CD₃OD, 300 MHz) δ: 0.94 (3H, t, J = 7.3 Hz), 1.21 (6H, d, J = 6.8 Hz), 1.59-1.73 (2H, m), 2.55 (3H, s), 2.66 (2H, t, J = 7.5 Hz), 2.81-2.90 (1H, m), 2.92-3.03 (1H, m), 3.16-3.27 (1H, m), 3.60-3.91 (3H, m), 4.22-4.33 (3H, m), 4.63 (1H, br s), 7.12 (4H, br s), 7.35 (2H, d, J = 8.3 Hz), 7.77 (2H, d, J = 7.9 Hz), 8.55 (1H, br s). |
| 435 | 592 (M + H). | 1H-NMR (CD₃OD, 300 MHz) δ: 0.91 (3H, t, J = 7.3 Hz), 1.51-1.69 (6H, m), 1.79-1.92 (2H, m), 2.53 (2H, t, J = 7.5 Hz), 2.78-2.92 (4H, m), 3.19-3.39 (1H, m), 3.53 (1H, dd, J = 14.5, 5.5 Hz), 3.67-3.78 (1H, m), 3.82-3.92 (1H, m), 4.03-4.13 (1H, m), 4.24-4.30 (2H, m), 4.54-4.64 (2H, m), 7.02 (2H, d, J = 8.3 Hz), 7.06 (2H, d, J = 8.3 Hz), 7.23 (1H, d, J = 8.7 Hz), 7.55-7.62 (2H, m), 8.00 (1H, s), 8.55-8.65 (2H, m). |
| 436 | 606 (M + H). | 1H-NMR (CDCl₃, 400 MHz) δ: 0.94 (3H, t, J = 7.4 Hz), 1.57-1.68 (2H, m), 2.44-2.79 (4H, m), 3.07 (1H, ddd, J = 15.5, 11.9, 2.9 Hz), 3.92 (1H, d, J = 14.8 Hz), 4.17 (1H, d, J = 13.7 Hz), 4.43-4.62 (4H, m), 7.02 (1H, t, J = 5.5 Hz), 7.13 (4H, dd, J = 10.9, 8.5 Hz), 7.25 (2H, d, J = 6.2 Hz), 7.39 (2H, d, J = 8.8 Hz), 7.92 (2H, dt, J = 9.4, 2.4 Hz), 8.40 (2H, dd, J = 4.9, 1.5 Hz), 8.56 (1H, s). |
| 437 | 613 (M + H). | 1H-NMR (CDCl₃, 400 MHz) δ: 0.93 (3H, t, J = 7.4 Hz), 1.55-1.66 (2H, m), 2.53 (2H, t, J = 7.7 Hz), 2.79-3.10 (2H, m), 3.34 (1H, t, J = 12.2 Hz), 3.89 (1H, d, J = 15.0 Hz), 4.22 (1H, d, J = 13.5 Hz), 4.36 (2H, d, J = 5.7 Hz), 4.61-4.71 (2H, m), 7.05-7.18 (5H, m), 7.34 (2H, d, J = 8.8 Hz), 7.91 (2H, d, J = 8.8 Hz), 8.65 (1H, s). |
| 438 | 572 (M + H). | 1H-NMR (CDCl₃, 300 MHz) δ: 0.85-1.04 (6H, m), 1.55-1.76 (4H, m), 2.55 (2H, t, J = 7.7 Hz), 2.80 (2H, t, J = 7.5 Hz), 3.07-3.23 (2H, m), 3.38-3.50 (1H, m), 3.89 (1H, d, J = 13.2 Hz), 4.26-4.47 (3H, m), 4.61 (1H, br s), 4.83 (1H, d, J = 13.6 Hz), 6.80 (1H, d, J = 3.8 Hz), 6.97 (1H, t, J = 5.7 Hz), 7.06 (4H, dd, J = 13.2, 7.9 Hz), 7.50 (1H, d, J = 3.8 Hz), 8.13 (1H, br s), 8.81 (1H, br s). |

TABLE 321

| Example No. | MS ESI m/e: | NMR |
|---|---|---|
| 439 | 594 (M + H). | 1H-NMR (CD₃OD, 300 MHz) δ: 1.23 (6H, d, J = 6.8 Hz), 2.64-2.78 (2H, m), 2.84-2.93 (1H, m), 3.06 (1H, d, J = 10.5 Hz), 3.50 (3H, s), 3.52-3.58 (1H, m), 3.72-3.80 (1H, m), 3.97 (1H, d, J = 13.6 Hz), 4.27-4.33 (2H, m), 4.69 (1H, s), 6.30 (1H, s), 7.16 (4H, s), 7.84 (2H, d, J = 8.7 Hz), 8.04 (2H, d, J = 7.9 Hz), 8.47-8.54 (1H, m). |
| 440 | 566 (M + H). | 1H-NMR (CD₃OD, 300 MHz) δ: 0.88-0.98 (6H, m), 1.55-1.72 (4H, m), 2.53 (2H, t, J = 7.5 Hz), 2.65 (2H, t, J = 7.7 Hz), 3.16-3.25 (1H, m), 3.38-3.48 (1H, m), 3.66-3.91 (2H, m), 4.10-4.29 (3H, m), 4.55-4.61 (1H, m), 4.64-4.75 (1H, m), 6.99-7.09 (4H, m), 7.34 (2H, d, J = 8.3 Hz), 7.78 (2H, d, J = 8.3 Hz), 8.03 (1H, s), 8.54-8.67 (2H, m). |
| 441 | 580 (M + H). | 1H-NMR (CD₃OD, 300 MHz) δ: 0.88-0.99 (6H, m), 1.52-1.72 (4H, m), 2.21 (3H, s), 2.51 (2H, t, J = 7.5 Hz), 2.64 (2H, t, J = 7.7 Hz), 3.19-3.27 (1H, m), 3.43-3.53 (1H, m), 3.70-3.91 (2H, m), 4.12-4.29 (3H, m), 4.58-4.72 (2H, m), 6.86 (1H, d, J = 7.9 Hz), 6.94 (1H, s), 7.00 (1H, d, J = 7.5 Hz), 7.33 (2H, d, J = 8.3 Hz), 7.77 (2H, d, J = 8.3 Hz), 8.05 (1H, d, J = 1.1 Hz), 8.37 (1H, t, J = 5.3 Hz), 8.62 (1H, d, J = 1.5 Hz). |
| 442 | 629 (M + H). | 1H-NMR (CD₃OD, 400 MHz) δ: 1.37 (3H, t, J = 7.1 Hz), 2.43 (3H, s), 3.17-3.25 (1H, m), 3.46 (1H, dd, J = 13.7, 4.6 Hz), 3.78-4.03 (5H, m), 4.17 (2H, ddd, J = 31.4, 14.5, 5.8 Hz), 4.36 (1H, d, 3 =13.5 Hz), 4.60 (1H, dd, J = 4.4, 2.4 Hz), 6.78 (2H, d, J = 8.8 Hz), 7.10 (2H, d, J = 8.8 Hz), 7.41 (2H, d, J = 7.9 Hz), 7.94 (2H, d, J = 9.0 Hz), 8.53 (1H, t, J = 5.8 Hz). |
| 443 | 607 (M + H). | |

TABLE 322

| Example No. | MS ESI m/e: | NMR |
|---|---|---|
| 444 | 709 (M + H). | (1H-NMR (CDCl₃, 400 MHz) δ: 0.95 (3H, t, J = 7.4 Hz), 1.34 (3H, t, J = 7.2 Hz), 1.60-1.69 (2H, m), 2.58 (2H, t, J = 7.7 Hz), 2.97-3.04 |

TABLE 322-continued

| Example No. | MS ESI m/e: | NMR |
|---|---|---|
| | | (1H, m), 3.14 (1H, dd, J = 13.2, 4.4 Hz), 3.41-3.48 (1H, m), 3.90 1H, d, J = 14.1 Hz), 4.08 (1H, d, J = 13.0 Hz), 4.30 (2H, q, J = 7.1 Hz), 4.39-4.45 (3H, m), 4.61 (1H, br s), 6.72 (1H, t, J = 5.7 Hz), 7.13 (4H, q, J = 8.1 Hz), 7.35 (2H, d, J = 8.1 Hz), 7.91 (2H, d, J = 9.0 Hz). |
| 445 | 594 (M + H). | 1H-NMR (CD$_3$OD, 300 MHz) δ: 1.24 (6H, d, J = 7.2 Hz), 2.63-2.71 (1H, m), 2.83-2.93 (2H, m), 3.58-3.67 (1H, m), 3.69-3.78 (1H, m), 3.86-3.94 (1H, m), 3.96 (3H, s), 4.11 (1H, d, J = 12.4 Hz), 4.20-4.34 (2H, m), 4.68 (1H, s), 6.21 (1H, s), 7.13-7.15 (4H, m), 7.81 (2H, d, J = 8.3 Hz), 8.02 (2H, d, J = 8.3 Hz), 8.44-8.50 (1H, m). |
| 446 | 688 (M + H). | 1H-NMR (DMSO-d$_6$, 300 MHz) δ: 1.17 (6H, d, J =6.8 Hz), 2.37 (3H, s), 2.79 (3H, br s), 2.81-2.88 (1H, m), 2.96-3.06 (1H, m), 3.24-3.31 (1H, m), 3.70-3.78 (2H, m), 3.83 (1H, d, J = 12.1 Hz), 4.01-4.16 (2H, m), 4.28 (1H, d, J = 13.7 Hz), 4.57 (1H, br s), 6.80 (1H, br s), 7.08 (2H, d, J = 8.2 Hz), 7.15 (2H, d, J = 8.2 Hz), 7.87 (2H, d, J = 8.4 Hz), 7.96 (2H, d, J = 8.4 Hz), 8.61 (1H, t, J = 5.7 Hz). |
| 447 | 704 (M + H). | 1H-NMR (DMSO-d$_6$, 300 MHz) δ: 0.87 (3H, t, J = 7.3 Hz), 1.51-1.58 (2H, m), 2.36 (3H, s), 2.51-2.54 (2H, m), 2.79 (3H, br s), 2.94-3.04 (1H, m), 3.22-3.29 (1H, m), 3.70-3.76 (2H, m), 3.82 (1H, d, J = 12.1 Hz), 4.02-4.18 (2H, m), 4.26 (1H, d, J = 13.2 Hz), 4.53-4.57 (1H, m), 6.80 (1H, br s), 7.07 (2H, d, J = 8.6 Hz), 7.10 (2H, d, J = 8.4 Hz), 7.50 (2H, d, J = 8.2 Hz), 7.89 (2H, d, J = 9.0 Hz), 8.59 (1H, t, J = 5.8 Hz). |
| 448 | 663 (M + H). | 1H-NMR (CD$_3$OD, 400 MHz) δ: 0.93 (3H, t, J = 7.4 Hz), 2.06-2.21 (2H, m), 2.44 (3H, s), 3.20-3.28 (1H, m), 3.48 (1H, dd, J = 13.9, 4.6 Hz), 3.79-3.94 (3H, m), 4.25-4.43 (3H, m), 4.64 (1H, dd, J = 4.5, 2.7 Hz), 7.28 (2H, d, J = 8.1 Hz), 7.37 (2H, d, J = 8.1 Hz), 7.43 (2H, d, J = 8.1 Hz), 7.97 (2H, d, J = 8.8 Hz). |

TABLE 323

| Example No. | MS ESI m/e: | NMR |
|---|---|---|
| 449 | 622 (M + H). | 1H-NMR (CD$_3$OD, 400 MHz) δ: 0.91 (3H, s), 1.59 (2H, td, J = 15.2, 7.6 Hz), 2.49-2.62 (5H, m), 3.36-3.46 (1H, m), 3.72-3.87 (2H, m), 4.16-4.36 (3H, m), 4.62 (1H, s), 4.78-4.85 (2H, m), 7.02 (4H, t, J = 8.6 Hz), 7.39 (2H, d, J = 8.4 Hz), 7.88-7.99 (3H, m), 8.61 (1H, s). |
| 450 | 528 (M + H). | 1H-NMR (CDCl$_3$, 400 MHz) δ: 0.95 (3H, t, J = 7.4 Hz), 1.63 (2H, t, J = 7.5 Hz), 1.94-2.19 (3H, m), 2.36-2.62 (3H, m), 2.81-3.05 (1H, m), 3.10-3.42 (1H, m), 3.61-3.88 (1H, m), 4.29-4.90 (5H, m), 6.75 (1H, s), 7.08-7.19 (4H, m), 7.28-7.39 (2H, m), 7.86-7.95 (2H, m). |
| 451 | 629 (M + H). | 1H-NMR (DMSO-d$_6$, 400 MHz) δ: 2.37 (3H, s), 3.10-3.19 (1H, m), 3.25 (3H, s), 3.40-3.47 (1H, m), 3.71-3.78 (2H, m), 3.82-3.89 (1H, m), 4.02-4.20 (2H, m), 4.22-4.31 (1H, m), 4.36 (2H, s), 4.55-4.59 (1H, m), 7.13 (2H, d, J = 8.12 Hz), 7.20 (2H, d, J = 8.12 Hz), 7.51 (2H, d, J = 9.04 Hz), 7.90 (2H, d, J = 9.04 Hz), 8.68 (1H, t, J = 5.91 Hz), 12.52 (1H, br s). |
| 452 | 613 (M + H). | 1H-NMR (DMSO-d$_6$, 400 MHz) δ: 0.87 (3H, t, J = 7.39 Hz), 1.50-1.61 (2H, m), 2.05 (3H, s), 2.48-2.54 (2H, m), 2.88-2.98 (1H, m), 3.13-3.21 (1H, m), 3.70-3.80 (3H, m), 4.06 (1H, dd, J = 15.11, 5.40 Hz), 4.15 (1H, dd, J = 15.11, 6.06 Hz), 4.19-4.26 (1H, m), 4.40 (2H, d, J = 5.51 Hz), 4.54-4.59 (1H, m), 5.11 (1H, t, J = 5.51 Hz), 7.04-7.12 (4H, m), 7.51 (2H, d, J = 8.82 Hz), 7.90 (2H, d, 3 =8.82 Hz), 8.57 (1H, t, J = 5.84 Hz). |
| 453 | 681 (M + H). | 1H-NMR (CDCl$_3$, 300 MHz) δ: 0.93 (3H, t, J = 7.2 Hz), 1.56-1.68 (2H, m), 2.56 (2H, t, J = 7.3 Hz), 2.92-3.16 (2H, m), 3.38-3.51 (1H, m), 3.80-3.91 (1H, m), 3.97-4.08 (1H, m), 4.32-4.47 (3H, m), 4.60 (1H, br s), 6.80 (1H, br s), 7.04-7.16 (4H, m), 7.32 (2H, d, J = 8.3 Hz), 7.88 (2H, d, J = 8.3 Hz). |
| 454 | 594 (M + H). | 1H-NMR (CDCl$_3$, 300 MHz) δ: 0.94 (3H, t, J = 7.3 Hz), 1.60-1.70 (2H, m), 2.18 (3H, s), 2.39-2.53 (2H, m), 2.58 (2H, t, J = 7.7 Hz), 3.28-3.41 (1H, m), 3.57 (1H, d, J = 13.2 Hz), 3.93 (1H, d, J = 13.9 Hz), 4.31 (1H, d, J = 12.8 Hz), 4.38-4.51 (2H, m), 4.54 (1H, s), 6.80-6.86 (1H, m), 7.11 (1H, s), 7.14 (4H, s), 7.35 (2H, d, J = 7.9 Hz), 7.90 (2H, d, J = 8.7 Hz), 9.65 (1H, br s). |

TABLE 324

| Example No. | MS ESI m/e: | NMR |
|---|---|---|
| 455 | 682 (M + H). | 1H-NMR (CDCl₃, 300 MHz) δ: 0.95 (3H, t, J = 7.3 Hz), 1.26 (3H, t, J = 7.2 Hz), 1.64 (2H, q, J = 7.5 Hz), 2.45 (1H, td, J = 13.4, 3.6 Hz), 2.59 (2H, t, J = 7.7 Hz), 2.94 (1H, dd, J = 13.6, 3.8 Hz), 3.14 (1H, ddd, J = 15.5, 12.0, 3.1 Hz), 3.89 (1H, d, J = 14.3 Hz), 3.98 (2H, s), 4.19 (2H, q, J = 7.2 Hz), 4.32-4.59 (5H, m), 5.60 (1H, d, J = 15.8 Hz), 5.93 (1H, d, J = 16.2 Hz), 6.77 (1H, t, J = 5.7 Hz), 7.13 (2H, d, J = 8.3 Hz), 7.17 (2H, d, J = 8.3 Hz), 7.37 (2H, d, J = 8.7 Hz), 7.90 (2H, d, J = 8.7 Hz). |
| 456 | 610 (M + H). | 1H-NMR (CDCl₃, 400 MHz) δ: 0.95 (3H, t, J = 7.3 Hz), 1.64 (2H, q, J = 7.7 Hz), 2.44-2.50 (1H, m), 2.44 (3H, s), 2.58 (2H, t, J = 7.6 Hz), 2.92-2.99 (1H, m), 3.15 (1H, ddd, J = 15.5, 12.5, 3.2 Hz), 3.90 (1H, d, J = 15.2 Hz), 4.33-4.43 (2H, m), 4.44-4.52 (2H, m), 4.59 (1H, s), 5.33 (1H, d, J = 16.8 Hz), 5.62 (1H, d, J = 16.5 Hz), 6.91 (1H, t, J = 5.0 Hz), 7.10 (2H, d, J = 7.9 Hz), 7.16 (2H, d, J = 7.9 Hz), 7.39 (2H, d, J = 8.8 Hz), 7.92 (2H, d, J = 8.6 Hz). |
| 457 | 610 (M + H). | 1H-NMR (CDCl₃, 400 MHz) δ: 0.95 (3H, t, J = 7.4 Hz), 1.64 (2H, q, J = 7.4 Hz), 2.40-2.50 (1H, m), 2.55 (3H, s), 2.59 (2H, t, J = 7.6 Hz), 2.94 (1H, dd, J = 13.1, 3.4 Hz), 3.09-3.19 (1H, m), 3.89 (1H, d, J = 15.0 Hz), 4.34-4.52 (4H, m), 4.56 (1H, s), 5.54 (1H, d, J = 15.9 Hz), 5.88 (1H, d, J = 15.9 Hz), 6.76 (1H, t, J = 6.7 Hz), 7.13 (2H, d, J = 7.9 Hz), 7.17 (2H, d, J = 7.7 Hz), 7.37 (2H, d, J = 8.4 Hz), 7.90 (2H, d, J = 8.8 Hz). |
| 458 | 578 (M + H). | 1H-NMR (CD₃OD, 400 MHz) δ: 0.92 (3H, t, J = 7.3 Hz), 1.61 (2H, td, J = 14.9, 7.6 Hz), 2.55 (2H, t, J = 7.5 Hz), 2.72 (1H, td, J = 11.8, 3.7 Hz), 2.94 (1H, dd, J = 13.0, 4.2 Hz), 3.63-3.90 (3H, m), 4.27 (3H, dd, J = 27.7, 14.9 Hz), 4.61 (1H, t, J = 3.2 Hz), 6.61 (1H, dd, J = 8.8, 0.7 Hz), 7.03-7.13 (5H, m), 7.40 (2H, dd, J = 8.9, 1.0 Hz), 7.65 (1H, dd, J = 2.9, 0.7 Hz), 7.95 (2H, dt, J = 9.5, 2.5 Hz). |

TABLE 325

| Example No. | MS ESI m/e: | NMR |
|---|---|---|
| 459 | 564 (M + H). | 1H-NMR (CDCl₃, 400 MHz) δ: 1.00 (3H, t, J = 7.4 Hz), 2.08-2.23 (2H, m), 2.16 (3H, s), 2.37-2.47 (1H, m), 2.85 (1H, dd, J = 13.4, 4.2 Hz), 3.17-3.26 (1H, m), 3.84 (1H, d, J = 14.4 Hz), 4.32-4.58 (5H, m), 6.96 (1H, br s), 7.28 (2H, d, J = 6.0 Hz), 7.40 (2H, d, J = 8.1 Hz), 7.46 (2H, d, J = 8.1 Hz), 7.93 (2H, d, J = 9.0 Hz). |
| 460 | 596 (M + H). | 1H-NMR (CDCl₃, 400 MHz) δ: 0.95 (3H, t, J = 7.3 Hz), 1.64 (2H, dd, J = 14.6, 7.1 Hz), 2.37-2.51 (1H, m), 2.58 (2H, t, J = 7.5 Hz), 2.86 (1H, dd, J = 13.5, 4.0 Hz), 3.11-3.22 (1H, m), 3.82 (1H, d, J = 14.1 Hz), 4.31-4.58 (5H, m), 5.63 (1H, d, J = 15.9 Hz), 6.02 (1H, d, J = 15.9 Hz), 6.73 (1H, br s), 7.11 (2H, d, J = 8.6 Hz), 7.16 (2H, d, J = 6.8 Hz), 7.35 (2H, d, J = 7.7 Hz), 7.89 (2H, d, J = 8.2 Hz), 8.55 (1H, s). |
| 461 | 596 (M + H). | 1H-NMR (CDCl₃, 400 MHz) δ: 0.93-0.97 (3H, m), 1.60-1.67 (2H, m), 2.43-2.53 (1H, m), 2.59 (2H, t, J = 7.5 Hz), 2.98 (1H, dd, J = 13.6, 3.4 Hz), 3.16 (1H, t, J = 13.6 Hz), 3.91 (1H, d, J = 14.1 Hz), 4.37-4.50 (4H, m), 4.58 (1H, br s), 5.43 (1H, d, J = 16.5 Hz), 5.72 (1H, d, J = 16.5 Hz), 6.86 (1H, br s), 7.11 (2H, d, J = 8.4 Hz), 7.17 (2H, d, J = 7.7 Hz), 7.39 (2H, d, J = 8.2 Hz), 7.92 (2H, d, J = 8.4 Hz), 8.68 (1H, s). |
| 462 | 594 (M + H). | 1H-NMR (CDCl₃, 400 MHz) δ: 0.93-0.97 (3H, m), 1.62-1.66 (2H, m), 2.44 (1H, t, J = 11.7 Hz), 2.58 (2H, t, J = 7.6 Hz), 2.84-2.93 (1H, m), 3.15 (1H, t, J = 12.0 Hz), 3.89 (1H, d, J = 15.0 Hz), 4.39-4.59 (5H, m), 4.76 (1H, d, J = 16.5 Hz), 5.27 (1H, d, J = 16.5 Hz), 6.82 (1H, br s), 6.89 (1H, s), 7.06 (1H, s), 7.10 (2H, d, J = 7.9 Hz), 7.16 (2H, d, J = 6.8 Hz), 7.37 (2H, d, J = 8.4 Hz), 7.47 (1H, s), 7.90 (2H, d, J = 8.6 Hz). |
| 463 | 620 (M + H). | 1H-NMR (CDCl₃, 300 MHz) δ: 0.95 (3H, t, J = 7.3 Hz), 1.59-1.68 (2H, m), 2.59 (2H, t, J = 7.5 Hz), 2.70-2.77 (2H, m), 3.20 (3H, s), 3.26-3.35 (1H, m), 3.65 (2H, t, J = 14.7 Hz), 4.24 (1H, d, J = 13.9 Hz), 4.34-4.47 (3H, m), 6.81-6.86 (3H, m), 7.16 (4H, dd, J = 11.3, 8.3 Hz), 7.33 (2H, d, J = 7.9 Hz), 7.86 (2H, d, J = 8.7 Hz), 8.39 (2H, d, J = 6.4 Hz). |

TABLE 326

| Example No. | MS ESI m/e: | NMR |
|---|---|---|
| 464 | 632 (M + H). | 1H-NMR (CDCl₃, 300 MHz) δ: 0.99 (3H, t, J = 7.4 Hz), 2.10-2.09 (2H, m), 2.13 (1H, t, J = 8.5 Hz), 2.91-2.96 (1H, m), 3.08-3.21 (1H, m), 3.85-3.96 (1H, m), 4.36-6.40 (5H, m), 5.41 (1H, d, J = 13.7 Hz), 5.72 (1H, d, J = 13.7 Hz), 7.03 (1H, br s), 7.28 (2H, d, J = 8.8 Hz), 7.41 (2H, d, J = 8.2 Hz), 7.46 (2H, d, J = 8.1 Hz), 7.93 (2H, d, J = 8.8 Hz), 8.71 (1H, s). |
| 465 | 654 (M + H). | 1H-NMR (CDCl₃, 400 MHz) δ: 0.94 (3H, t, J = 7.3 Hz), 1.63 (2H, q, J = 7.6 Hz), 2.46 (1H, t, J = 11.7 Hz), 2.58 (2H, t, J = 7.6 Hz), 2.91-2.98 (1H, m), 3.15 (1H, t, J = 13.2 Hz), 3.86 (1H, d, J = 13.7 Hz), 3.99 (2H, s), 4.26-4.52 (4H, m), 4.57 (1H, s), 5.57 (1H, d, J = 14.3 Hz), 5.92 (1H, d, J = 15.2 Hz), 6.85 (1H, t, J = 5.5 Hz), 7.11 (2H, d, J = 7.7 Hz), 7.15 (2H, d, J = 7.9 Hz), 7.35 (2H, d, J = 8.6 Hz), 7.89 (2H, d, J = 8.4 Hz). |
| 466 | 718 (M + H). | 1H-NMR (CDCl₃, 300 MHz) δ: 0.99 (3H, t, J = 7.5 Hz), 1.25 (3H, t, J = 7.0 Hz), 2.15 (2H, td, J = 16.1, 7.7 Hz), 2.43 (1H, dt, J = 18.8, 7.0 Hz), 2.91 (1H, dd, J = 13.6, 3.8 Hz), 3.17 (1H, ddd, J = 15.1, 12.2, 2.8 Hz), 3.90 (1H, d, J = 15.4 Hz), 3.98 (2H, s), 4.19 (2H, q, J = 7.2 Hz), 4.31-4.62 (5H, m), 5.58 (1H, d, J = 16.2 Hz), 5.92 (1H, d, J = 15.8 Hz), 6.98 (1H, t, J = 5.7 Hz), 7.29 (2H, d, J = 8.3 Hz), 7.40 (2H, d, J = 8.3 Hz), 7.46 (2H, d, J = 7.9 Hz), 7.92 (2H, d, J = 8.7 Hz). |
| 467 | 646 (M + H). | 1H-NMR (CDCl₃, 400 MHz) δ: 0.99 (3H, t, J = 7.4 Hz), 2.08-2.20 (2H, m), 2.44-2.49 (1H, m), 2.44 (3H, s), 2.88-2.97 (1H, m), 3.18 (1H, t, J = 13.5 Hz), 3.92 (1H, d, J = 15.0 Hz), 4.36 (1H, d, J = 12.8 Hz), 4.44-4.54 (3H, m), 4.60 (1H, s), 5.32 (1H, d, J = 16.5 Hz), 5.60 (1H, d, J = 16.1 Hz), 7.08 (1H, t, J = 4.9 Hz), 7.28 (2H, d, J = 7.3 Hz), 7.42 (2H, d, J = 8.2 Hz), 7.46 (2H, d, J = 7.5 Hz), 7.94 (2H, d, J = 8.8 Hz). |

TABLE 327

| Example No. | MS ESI m/e: | NMR |
|---|---|---|
| 468 | MS ESI(−) m/e: 644 (M − H). | 1H-NMR (CDCl₃, 300 MHz) δ: 0.99 (3H, t, J = 7.5 Hz), 2.05-2.24 (2H, m), 2.43 (1H, td, J = 12.8, 3.9 Hz), 2.54 (3H, s), 2.91 (1H, dd, J = 13.6, 3.8 Hz), 3.17 (1H, ddd, J = 14.8, 11.6, 2.5 Hz), 3.91 (1H, d, J = 14.7 Hz), 4.37 (1H, d, J = 12.1 Hz), 4.43-4.61 (4H, m), 5.53 (1H, d, J = 16.2 Hz), 5.88 (1H, d, J = 16.2 Hz), 6.97 (1H, t, J = 5.7 Hz), 7.29 (2H, d, J = 8.3 Hz), 7.40 (2H, d, J = 8.3 Hz), 7.46 (2H, d, J = 7.9 Hz), 7.92 (2H, d, J = 8.7 Hz). |
| 469 | 540 (M + H). | 1H-NMR (CDCl₃, 400 MHz) δ: 1.24-1.25 (6H, m), 1.98 (1H, s), 2.16 (2H, s), 2.41-2.43 (1H, m), 2.87-2.91 (2H, m), 3.15-3.22 (1H, m), 3.82 (1H, d, J = 14.4 Hz), 4.32-4.40 (3H, m), 4.47 (1H, d, J = 3.7 Hz), 4.54 (1H, d, J = 13.4 Hz), 6.72 (1H, s), 7.12 (2H, d, J = 8.1 Hz), 7.21 (2H, d, J = 8.1 Hz), 7.50 (1H, dd, J = 8.3, 2.1 Hz), 7.60 (1H, dd, J = 7.4, 1.9 Hz), 7.74 (1H, dd, J = 8.3, 6.5 Hz). |
| 470 | 698 (M + H). | 1H-NMR (CDCl₃, 400 MHz) δ: 0.94 (3H, t, J = 7.4 Hz), 1.25-1.29 (3H, m), 1.57-1.69 (2H, m), 2.53-2.65 (3H, m), 2.79 (1H, dd, J = 14.0, 3.4 Hz), 3.09-3.16 (1H, m), 3.68 (2H, s), 3.91 (1H, d, J = 14.3 Hz), 4.13-4.21 (3H, m), 4.36-4.52 (3H, m), 4.56 (1H, s), 6.68 (1H, s), 6.86 (1H, br s), 7.10 (2H, d, J = 8.6 Hz), 7.13 (2H, d, J = 8.8 Hz), 7.37 (2H, d, J = 8.4 Hz), 7.91 (2H, d, J = 8.8 Hz), 9.28 (1H, s). |
| 471 | 563 (M + H). | 1H-NMR (CD₃OD, 400 MHz) δ: 1.22 (6H, d, J = 7.1 Hz), 2.74-3.01 (3H, m), 3.67-3.93 (3H, m), 4.17-4.41 (3H, m), 4.66 (1H, t, J = 3.2 Hz), 7.11 (4H, s), 7.54 (1H, d, J = 1.5 Hz), 7.63 (1H, d, J = 1.5 Hz), 7.79 (2H, d, J = 8.4 Hz), 8.01 (2H, d, J = 8.2 Hz). |
| 472 | 564 (M + H). | 1H-NMR (CDCl₃, 400 MHz) δ: 0.91-0.99 (3H, m), 1.59-1.69 (2H, m), 2.57 (2H, t, J = 7.7 Hz), 2.85-3.06 (2H, m), 3.39-3.52 (1H, m), 3.83-4.10 (2H, m), 4.39 (1H, dd, J = 8.5, 5.6 Hz), 4.56-4.82 (2H, m), 6.85 (1H, s), 7.05-7.15 (4H, m), 7.33 (2H, d, J = 9.0 Hz), 7.86-8.00 (4H, m), 8.16 (1H, s). |

TABLE 328

| Example No. | MS ESI m/e: | NMR |
|---|---|---|
| 473 | 610 (M + H). | 1H-NMR (DMSO-d₆, 400 MHz) δ: 3.17-3.27 (1H, m), 3.25 (3H, s), 3.37-3.45 (1H, m), 3.67-3.79 (2H, m), 3.98-4.14 (2H, m), 4.28-4.36 (1H, m), 4.35 (2H, s), 4.56-4.60 (1H, m), 4.72-4.79 (1H, m), 7.08 (2H, d, J = 8.16 Hz), 7.16 (2H, d, J = 8.16 Hz), 7.49 (2H, d, J = 9.04 |

TABLE 328-continued

| Example No. | MS ESI m/e: | NMR |
|---|---|---|
| | | Hz), 7.91 (2H, d, J = 9.04 Hz), 8.21 (1H, d, J = 1.32 Hz), 8.53 (1H, d, J = 1.32 Hz), 8.69 (1H, t, J = 5.73 Hz), 12.72 (1H, br s). |
| 474 | 642 (M + H). | 1H-NMR (DMSO-d$_6$, 400 MHz) δ: 0.85 (3H, t, J = 7.28 Hz), 1.47-1.60 (2H, m), 2.46-2.53 (2H, m), 3.14-3.26 (1H, m), 3.36-3.44 (1H, m), 3.67-3.81 (2H, m), 3.99-4.17 (2H, m), 4.27-4.38 (1H, m), 4.60-4.65 (1H, m), 4.74-4.83 (1H, m), 6.95 (1H, dd, J = 7.94, 1.54 Hz), 7.01 (1H, d, J = 7.94 Hz), 7.21 (1H, d, J = 1.54 Hz), 7.49 (2H, d, J = 8.82 Hz), 7.92 (2H, d, J = 8.82 Hz), 8.20 (1H, d, J = 1.32 Hz), 8.53 (1H, d, J = 1.32 Hz), 8.70 (1H, s), 12.74 (1H, br s). |
| 475 | 739 (M + H). | 1H-NMR (CDCl$_3$, 400 MHz) δ: 0.94 (3H, t, J = 7.3 Hz), 1.54-1.69 (2H, m), 2.53-2.64 (3H, m), 2.79 (1H, dd, J = 14.3, 3.5 Hz), 3.08-3.16 (1H, m), 3.52-3.77 (10H, m), 3.91 (1H, d, J = 14.1 Hz), 4.12-4.20 (1H, m), 4.38-4.49 (3H, m), 4.57 (1H, s), 6.65 (1H, s), 6.90 (1H, br s), 7.10 (2H, d, J = 8.2 Hz), 7.13 (2H, d, J = 8.2 Hz), 7.37 (2H, d, J = 8.8 Hz), 7.91 (2H, d, J = 8.8 Hz). |
| 476 | 656 (M + H). | 1H-NMR (CDCl$_3$, 400 MHz) δ: 0.93 (3H, td, J = 7.3, 4.7 Hz), 1.53-1.69 (2H, m), 2.53-2.63 (3H, m), 2.75-2.88 (3H, m), 3.12 (1H, t, J = 13.3 Hz), 3.85-3.94 (3H, m), 4.16 (1H, d, J = 13.7 Hz), 4.40-4.52 (3H, m), 4.56 (1H, s), 6.48 (1H, s), 6.88 (1H, s), 7.08-7.15 (4H, m), 7.36 (2H, d, J = 6.2 Hz), 7.91 (2H, d, J = 8.8 Hz). |
| 477 | 721 (M + H). | 1H-NMR (CDCl$_3$, 400 MHz) δ: 0.93 (3H, t, J = 7.4 Hz), 1.42 (3H, t, J = 7.2 Hz), 1.98-2.14 (2H, m), 2.97 (1H, br s), 3.17 (1H, dd, J = 13.7, 3.7 Hz), 3.55 (1H, t, J = 11.2 Hz), 3.89 (1H, d, J = 13.5 Hz), 4.21-4.35 (2H, m), 4.41-4.48 (3H, m), 4.69-4.79 (2H, m), 7.16 (2H, d, J = 7.9 Hz), 7.26 (2H, d, J = 6.8 Hz), 7.34 (2H, d, J = 8.4 Hz), 7.48 (1H, s), 7.94 (2H, d, J = 8.8 Hz), 11.17 (1H, br s). |

TABLE 329

| Example No. | MS ESI m/e: | NMR |
|---|---|---|
| 478 | 538 (M + H). | 1H-NMR (DMSO-d$_6$, 300 MHz) δ: 0.87 (3H, t, J = 7.4 Hz), 1.17 (3H, t, J = 7.6 Hz), 1.48-1.61 (2H, m), 2.47-2.52 (2H, m), 2.62-2.70 (2H, m), 2.80-3.00 (1H, m), 3.09-3.13 (1H, m), 3.68-3.69 (2H, m), 4.01-4.13 (3H, m), 4.26 (2H, d, J = 5.0 Hz), 4.52-4.59 (2H, m), 5.23 (1H, t, J = 5.4 Hz), 7.04 (4H, m), 7.36 (2H, d, J = 8.3 Hz), 7.72 (2H, d, J = 8.3 Hz), 8.04 (1H, s), 8.06 (1H, s), 8.55 (1H, t, J = 5.9 Hz). |
| 479 | 708 (M + H). | 1H-NMR (CDCl$_3$, 300 MHz) δ: 0.99 (3H, t, J = 7.5 Hz), 2.05-2.24 (2H, m), 2.44 (1H, ddd, J = 14.1, 11.9, 2.4 Hz), 2.93 (1H, dd, J = 13.6, 3.4 Hz), 3.19 (1H, ddd, J = 15.1, 12.2, 3.0 Hz), 3.91 (1H, d, J = 15.1 Hz), 4.39 (1H, d, J = 13.6 Hz), 4.47-4.61 (4H, m), 5.65 (1H, d, J = 15.8 Hz), 5.96 (1H, d, J = 15.8 Hz), 6.99 (1H, t, J = 5.7 Hz), 7.31 (2H, d, J = 7.9 Hz), 7.40 (2H, d, J = 8.3 Hz), 7.44-7.50 (5H, m), 7.93 (2H, d, J = 8.3 Hz), 8.13 (2H, d, J = 3.8 Hz). |
| 480 | 645 (M + H). | 1H-NMR (CDCl$_3$, 300 MHz) δ: 0.99 (3H, t, J = 7.3 Hz), 2.04-2.23 (2H, m), 2.25 (3H, s), 2.43 (1H, td, J = 13.0, 2.9 Hz), 2.88 (1H, dd, J = 13.8, 4.0 Hz), 3.21 (1H, ddd, J = 15.7, 12.2, 3.3 Hz), 3.82-3.97 (2H, m), 4.11 (1H, d, J = 16.2 Hz), 4.36-4.64 (5H, m), 6.01 (1H, s), 6.99 (1H, t, J = 5.5 Hz), 7.28 (2H, d, J = 7.2 Hz), 7.39 (2H, d, J = 7.9 Hz), 7.46 (2H, d, J = 7.5 Hz), 7.91 (2H, d, J = 8.7 Hz). |
| 481 | 510 (M + H). | 1H-NMR (CDCl$_3$, 400 MHz) δ: 1.28 (6H, d, J = 6.8 Hz), 2.15 (3H, s), 2.34-2.45 (1H, m), 2.82 (1H, dd, J = 13.8, 4.5 Hz), 2.98-3.00 (1H, m), 3.14-3.17 (1H, m), 3.82 (1H, d, J = 14.3 Hz), 4.29 (1H, d, J = 13.5 Hz), 4.44-4.50 (4H, m), 6.70 (1H, s), 6.98 (1H, t, J = 5.8 Hz), 7.22 (2H, d, J = 8.2 Hz), 7.39 (2H, d, J = 8.4 Hz), 7.46-7.48 (3H, m), 7.74-7.76 (3H, m). |
| 482 | 679 (M + H). | 1H-NMR (CDCl$_3$, 400 MHz) δ: 0.94-0.97 (3H, m), 2.01-2.18 (2H, m), 2.83 (1H, br s), 3.02 (1H, d, J = 14.1 Hz), 3.32 (1H, br s), 3.85 (1H, d, J = 12.4 Hz), 4.16 (1H, d, J = 13.9 Hz), 4.39-4.64 (4H, m), 4.90 (2H, s), 7.17-7.39 (6H, m), 7.93 (2H, t, J = 4.4 Hz). |

TABLE 330

| Example No. | MS ESI m/e: | NMR |
|---|---|---|
| 483 | 691 (M + H). | 1H-NMR (CDCl₃, 400 MHz) δ: 0.97 (3H, td, J = 7.4, 1.8 Hz), 2.03-2.19 (2H, m), 2.66-2.81 (1H, m), 2.69 (3H, s), 2.94 (1H, d, J = 12.1 Hz), 3.26 (1H, t, J = 12.2 Hz), 3.93 (1H, d, J = 13.5 Hz), 4.20 (1H, d, J = 13.0 Hz), 4.40-4.64 (4H, m), 7.14-7.19 (1H, m), 7.24 (2H, d, J = 7.9 Hz), 7.35-7.41 (4H, m), 7.94 (2H, dd, J = 8.8, 1.8 Hz), 10.50 (1H, br s). |
| 484 | 707 (M + H). | 1H-NMR (CDCl₃, 400 MHz) δ: 0.96 (3H, t, J = 7.5 Hz), 1.67 (6H, s), 2.05-2.13 (2H, m), 2.75-2.88 (2H, m), 3.01 (1H, d, J = 11.0 Hz), 3.24-3.35 (1H, m), 3.88 (1H, d, J = 14.8 Hz), 4.18 (1H, d, J = 12.1 Hz), 4.42-4.65 (4H, m), 7.23 (2H, d, J = 7.9 Hz), 7.35 (2H, d, J = 7.1 Hz), 7.37 (2H, d, J = 7.3 Hz), 7.94 (2H, d, J = 8.8 Hz). |
| 485 | 586 (M + H). | 1H-NMR (DMSO-d₆, 400 MHz) δ: 0.85 (3H, t, J = 7.28 Hz), 1.16 (3H, t, J = 7.61 Hz), 1.48-1.60 (2H, m), 2.46-2.52 (2H, m), 2.60-2.70 (2H, m), 3.07-3.18 (1H, m), 3.30-3.39 (1H, m), 3.66-3.77 (2H, m), 4.05-4.25 (3H, m), 4.56-4.70 (2H, m), 6.95 (1H, dd, J = 7.94, 1.10 Hz), 7.03 (1H, d, J = 7.94 Hz), 7.21 (1H, d, J = 1.10 Hz), 7.35 (2H, d, J = 8.16 Hz), 7.72 (2H, d, J = 8.16 Hz), 8.13 (1H, s), 8.53 (1H, s), 8.67 (1H, t, J = 5.84 Hz), 12.92 (1H, br s). |
| 486 | 636 (M + H). | 1H-NMR (CDCl₃, 300 MHz) δ: 0.93 (3H, t, J = 7.3 Hz), 1.57-1.68 (2H, m), 2.51 (3H, s), 2.55 (2H, t, J = 7.7 Hz), 2.92-3.06 (2H, m), 3.38-3.47 (1H, m), 3.85-3.94 (1H, m), 3.96 (3H, s), 4.28-4.44 (2H, m), 4.57-4.66 (2H, m), 4.67-4.75 (1H, m), 6.78 (1H, s), 6.86-6.93 (1H, m), 7.03 (2H, d, J = 8.3 Hz), 7.09 (2H, d, J = 7.9 Hz), 7.34 (2H, d, J = 7.9 Hz), 7.93 (2H, d, J = 8.7 Hz). |
| 487 | 622 (M + H). | 1H-NMR (CDCl₃, 300 MHz) δ: 0.93 (3H, t, J = 7.3 Hz), 1.55-1.65 (2H, m), 2.56 (2H, t, J = 7.7 Hz), 2.64 (3H, s), 2.97-3.10 (2H, m), 3.39-3.50 (1H, m), 3.86-3.95 (1H, m), 4.28-4.43 (2H, m), 4.50-4.59 (1H, m), 4.61 (1H, s), 4.74 (1H, d, J = 13.2 Hz), 6.82-6.90 (2H, m), 7.03 (2H, d, J = 8.3 Hz), 7.09 (2H, d, J = 7.9 Hz), 7.36 (2H, d, J = 8.3 Hz), 7.94 (2H, d, J = 8.7 Hz). |

TABLE 331

| Example No. | MS ESI m/e: | NMR |
|---|---|---|
| 488 | 663 (M + H). | 1H-NMR (CDCl₃, 400 MHz) δ: 0.95 (3H, t, J = 7.3 Hz), 2.00-2.17 (2H, m), 2.60 (3H, s), 2.78-2.88 (1H, m), 3.04 (1H, d, J = 11.5 Hz), 3.29-3.38 (1H, m), 3.85 (1H, d, J = 13.2 Hz), 4.23 (1H, d, J = 11.9 Hz), 4.30-4.37 (1H, m), 4.48 (1H, dd, J = 14.8, 5.5 Hz), 4.60-4.68 (2H, m), 7.18 (2H, d, J = 7.7 Hz), 7.24-7.29 (2H, m), 7.35 (2H, d, J = 7.7 Hz), 7.61 (1H, s), 7.93 (2H, d, J = 7.7 Hz). |
| 489 | 717 (M + H). | 1H-NMR (CDCl₃, 400 MHz) δ: 0.97 (3H, t, J = 7.4 Hz), 2.04-2.19 (2H, m), 2.77 (1H, br s), 2.93 (1H, d, J = 10.4 Hz), 3.21-3.33 (1H, m), 3.95 (1H, d, J = 15.4 Hz), 4.18 (1H, d, J = 14.3 Hz), 4.41-4.61 (4H, m), 7.09 (1H, br s), 7.23-7.28 (4H, m), 7.39 (2H, d, J = 7.9 Hz), 7.94 (2H, d, J = 8.8 Hz). |
| 490 | 672 (M + H). | 1H-NMR (CD₃OD, 400 MHz) δ: 0.91 (3H, t, J = 7.5 Hz), 2.01-2.16 (2H, m), 3.00-3.09 (1H, m), 3.21 (1H, dt, J = 14.3, 4.3 Hz), 3.78-3.94 (1H, m), 3.85 (3H, s), 4.05 (1H, d, J = 13.0 Hz), 4.27 (2H, d, J = 14.8 Hz), 4.35 (2H, d, J = 15.3 Hz), 4.48 (1H, d, J = 14.6 Hz), 6.89-6.94 (2H, m), 7.28 (2H, d, J = 8.1 Hz), 7.33 (2H, d, J = 8.6 Hz), 7.44 (2H, d, J = 7.9 Hz), 7.88 (1H, d, J = 6.0 Hz), 7.97 (2H, dd, J = 6.7, 2.1 Hz). |
| 491 | 742 (M + H). | 1H-NMR (CDCl₃, 400 MHz) δ: 0.99 (3H, t, J = 7.5 Hz), 1.64 (9H, s), 2.06-2.21 (2H, m), 2.46-2.55 (1H, m), 2.73 (1H, dd, J = 14.5, 3.4 Hz), 3.06-3.15 (1H, m), 3.96 (1H, d, J = 13.9 Hz), 4.18 (1H, d, J = 17.2 Hz), 4.46-4.64 (4H, m), 7.18 (1H, br s), 7.31 (2H, d, J = 8.3 Hz), 7.42 (2H, d, J = 7.9 Hz), 7.46 (2H, d, J = 8.6 Hz), 7.50-7.53 (1H, m), 7.90 (1H, d, J = 1.6 Hz), 7.95 (2H, d, J = 8.8 Hz), 8.53 (1H, d, J = 5.6 Hz), 8.70 (1H, s). |
| 492 | 528 (M + H). | 1H-NMR (CDCl₃, 400 MHz) δ: 1.28 (6H, d, J = 7.0 Hz), 2.16 (3H, s), 2.39-2.42 (1H, m), 2.82 (1H, dd, J = 13.6, 4.3 Hz), 2.97-3.01 (1H, m), 3.17-3.19 (1H, m), 3.84 (1H, d, J = 14.4 Hz), 4.29 (1H, d, J = 13.4 Hz), 4.51-4.53 (4H, m), 7.10 (1H, s), 7.38-7.41 (4H, m), 7.77 (2H, d, J = 8.6 Hz), 8.04 (2H, d, J = 8.3 Hz), 8.66 (1H, s). |

TABLE 332

| Example No. | MS ESI m/e: | NMR |
|---|---|---|
| 493 | 610 (M + H). | 1H-NMR (CD₃OD, 300 MHz) δ: 1.22 (6H, d, J = 6.8 Hz), 2.40-2.51 (1H, m), 2.64 (1H, dd, J = 12.1, 4.1 Hz), 2.81-2.92 (1H, m), 3.21 (1H, d, J = 12.1 Hz), 3.62-3.77 (2H, m), 3.89 (1H, d, J = 13.6 Hz), 4.21-4.41 (2H, m), 4.64 (1H, br s), 4.79 (2H, s), 7.15 (4H, s), 7.21 (1H, s), 7.26 (1H, s), 7.41 (2H, d, J = 7.9 Hz), 7.93-7.98 (2H, m), 8.38 (1H, t, J = 5.7 Hz). |
| 494 | 621 (M + H). | 1H-NMR (CDCl₃, 300 MHz) δ: 0.93 (3H, t, J = 7.3 Hz), 1.58-1.69 (2H, m), 2.56 (2H, t, J = 7.5 Hz), 2.63 (3H, s), 2.93-3.06 (2H, m), 3.40-3.50 (1H, m), 3.85-3.95 (1H, m), 4.30-4.45 (2H, m), 4.45-4.53 (1H, m), 4.60 (1H, s), 4.71 (1H, d, J = 13.6 Hz), 5.37 (1H, br s), 6.80 (1H, s), 6.84-6.90 (1H, m), 7.04 (2H, d, J = 8.3 Hz), 7.09 (2H, d, J = 8.3 Hz), 7.35 (2H, d, J = 7.9 Hz), 7.71-7.77 (1H, m), 7.93 (2H, d, J = 8.7 Hz). |
| 495 | 762 (M + H). | 1H-NMR (CD₃OD, 400 MHz) δ: 0.81 (3H, t, J = 7.5 Hz), 1.87-2.07 (4H, m), 2.98-3.09 (1H, m), 3.21-3.25 (1H, m), 3.56-3.72 (4H, m), 3.88-4.24 (5H, m), 4.33-4.58 (3H, m), 7.18 (2H, d, J = 8.2 Hz), 7.25 (2H, d, J = 8.4 Hz), 7.31 (2H, d, J = 8.2 Hz), 7.84 (2H, d, J = 8.6 Hz). |
| 496 | 776 (M + H). | 1H-NMR (CD₃OD, 400 MHz) δ: 0.91 (3H, t, J = 7.4 Hz), 1.48-1.66 (2H, m), 1.89-1.98 (2H, m), 2.02-2.18 (2H, m), 3.05-3.17 (1H, m), 3.34-3.43 (3H, m), 3.65-3.81 (3H, m), 3.90-3.94 (1H, m), 4.09-4.35 (4H, m), 4.49-4.68 (3H, m), 7.27 (2H, d, J = 8.2 Hz), 7.34 (2H, d, J = 8.2 Hz), 7.40 (2H, d, J = 7.9 Hz), 7.93 (2H, d, J = 8.6 Hz). |
| 497 | 762 (M + H). | 1H-NMR (CD₃OD, 400 MHz) δ: 0.82 (3H, t, J = 7.4 Hz), 1.94-2.09 (2H, m), 3.00-3.09 (2H, m), 3.58-3.73 (8H, m), 4.04-4.25 (5H, m), 4.46-4.57 (2H, m), 7.18 (2H, d, J = 8.2 Hz), 7.25 (2H, d, J = 8.4 Hz), 7.31 (2H, d, J = 8.2 Hz), 7.84 (2H, d, J = 8.6 Hz). |

TABLE 333

| Example No. | MS ESI m/e: | NMR |
|---|---|---|
| 498 | 644 (M + H). | 1H-NMR (DMSO-d₆, 400 MHz, 120° C.) δ: 0.92 (3H, t, J = 7.4 Hz), 2.11-2.24 (2H, m), 2.77-3.01 (1H, m), 3.18 (1H, d, J = 16.5 Hz), 3.35 (1H, d, J = 15.2 Hz), 3.46 (1H, d, J = 15.2 Hz), 3.55 (3H, s), 3.57-3.63 (2H, m), 4.05 (1H, d, J = 12.4 Hz), 4.24 (2H, d, J = 5.5 Hz), 4.41-4.51 (2H, m), 6.75 (1H, s), 7.28-7.35 (3H, m), 7.40 (2H, d, J = 8.4 Hz), 7.44 (2H, d, J = 8.4 Hz), 7.90 (2H, d, J = 8.8 Hz), 8.20 (1H, s). |
| 499 | 669 (M + H). | 1H-NMR (CD₃OD, 400 MHz) δ: 0.91 (3H, t, J = 7.3 Hz), 0.97 (3H, t, J = 7.3 Hz), 1.58-1.65 (4H, m), 2.43 (3H, s), 2.54 (2H, t, J = 7.4 Hz), 2.69 (2H, t, J = 7.4 Hz), 3.17-3.20 (1H, m), 3.48 (1H, d, J = 13.7 Hz), 3.82-3.86 (3H, m), 4.23-4.32 (3H, m), 4.63 (1H, s), 7.09-7.10 (4H, m), 7.40 (1H, d, J = 8.6 Hz), 7.78 (1H, d, J = 8.6 Hz), 7.83 (1H, s), 8.57 (1H, s). |
| 500 | 619 (M + H). | 1H-NMR (CDCl₃, 300 MHz) δ: 1.33 (9H, s), 2.36-2.49 (1H, m), 2.79 (1H, dd, J = 13.8, 4.0 Hz), 3.14-3.28 (1H, m), 3.78-4.00 (3H, m), 4.30-4.54 (4H, m), 4.61 (1H, d, J = 13.9 Hz), 6.81 (1H, t, J = 5.7 Hz), 7.11-7.18 (4H, m), 7.35 (2H, d, J = 7.9 Hz), 7.38 (2H, d, J = 7.9 Hz), 7.89 (2H, d, J = 9.0 Hz), 8.52 (2H, d, J = 4.5 Hz). |
| 501 | 622 (M + H). | 1H-NMR (CD₃OD, 300 MHz) δ: 1.28 (9H, s), 3.22-3.34 (1H, m), 3.44 (1H, dd, J = 14.3, 4.5 Hz), 3.72-3.91 (2H, m), 4.16-4.21 (2H, m), 4.29-4.39 (1H, m), 4.60-4.65 (1H, m), 4.84-4.92 (1H, m), 7.04 (2H, d, J = 8.3 Hz), 7.25 (2H, d, J = 8.3 Hz), 7.39 (2H, d, J = 8.3 Hz), 7.95 (2H, d, J = 8.7 Hz), 8.13 (1H, d, J = 1.5 Hz), 8.64 (1H, t, J = 5.7 Hz), 8.66 (1H, d, J = 1.5 Hz). |
| 502 | 686 (M + H). | 1H-NMR (CD₃OD, 400 MHz) δ: 0.92 (3H, t, J = 7.5 Hz), 2.03-2.19 (2H, m), 3.27 (1H, dd, J = 14.0, 4.1 Hz), 3.67-3.71 (1H, m), 3.72-3.77 (1H, m), 3.88 (1H, d, J = 12.3 Hz), 4.14 (1H, d, J = 14.1 Hz), 4.19-4.36 (2H, m), 4.54 (1H, d, J = 13.9 Hz), 4.65 (1H, br s), 7.29 (2H, d, J = 8.6 Hz), 7.34 (2H, d, J = 8.6 Hz), 7.46 (2H, d, J = 8.1 Hz), 7.99 (2H, d, J = 9.0 Hz), 8.34 (1H, s), 8.43 (1H, d, J = 7.0 Hz), 8.80 (1H, br s). |

TABLE 334

| Example No. | MS ESI m/e: | NMR |
|---|---|---|
| 503 | 685 (M + H). | 1H-NMR (CDCl₃, 400 MHz) δ: 0.98 (3H, t, J = 7.4 Hz), 2.05-2.20 (2H, m), 2.56 (1H, t, J = 11.4 Hz), 2.77 (1H, d, J = 11.4 Hz), 3.16 (1H, t, J = 11.6 Hz), 3.94 (1H, d, J = 14.1 Hz), 4.18 (1H, d, J = 13.2 Hz), 4.46-4.63 (4H, m), 5.76 (1H, s), 7.22 (1H, s), 7.30 (1H, d, J = 7.9 Hz), 7.42 (2H, d, J = 9.0 Hz), 7.44 (2H, d, J = 8.6 Hz), 7.71 (1H, dd, J = 5.6, 2.1 Hz), 7.87 (1H, d, J = 4.2 Hz), 7.94 (2H, d, J = 9.0 Hz), 7.98 (1H, d, J = 1.9 Hz), 8.37 (1H, d, J = 5.6 Hz), 8.77 (1H, s). |
| 504 | 713 (M + H). | 1H-NMR (CDCl₃, 400 MHz) δ: 0.99 (3H, t, J = 7.5 Hz), 2.07-2.22 (2H, m), 2.51 (1H, t, J = 11.6 Hz), 2.73 (1H, dd, J = 14.5, 3.4 Hz), 3.06 (3H, s), 3.12 (3H, s), 3.96 (1H, d, J = 13.9 Hz), 4.17 (1H, d, J = 14.4 Hz), 4.42-4.64 (5H, m), 7.20 (1H, br s), 7.30 (2H, d, J = 8.3 Hz), 7.40-7.48 (6H, m), 7.95 (2H, d, J = 8.8 Hz), 8.38 (1H, d, J = 5.8 Hz), 8.71 (1H, s). |
| 505 | 640 (M + H). | 1H-NMR (DMSO-d₆, 400 MHz) δ: 0.87 (3H, t, J = 7.39 Hz), 1.49-1.60 (2H, m), 2.05 (3H, s), 2.13 (6H, br s), 2.46-2.53 (2H, m), 2.87-2.98 (1H, m), 3.14-3.22 (1H, m), 3.34 (2H, br s), 3.70-3.79 (3H, m), 4.00-4.25 (3H, m), 4.55-4.59 (1H, m), 7.06 (4H, br s), 7.51 (2H, d, J = 8.80 Hz), 7.90 (2H, d, J = 8.80 Hz), 8.59 (1H, t, J = 5.84 Hz). |
| 506 | 626 (M + H). | 1H-NMR (DMSO-d₆, 400 MHz) δ: 0.88 (3H, t, J = 7.42 Hz), 1.50-1.62 (2H, m), 2.06 (3H, s), 2.09 (1H, br s), 2.23 (3H, s), 2.48-2.55 (2H, m), 2.87-2.96 (1H, m), 3.12-3.19 (1H, m), 3.59 (2H, s), 3.69-3.80 (3H, m), 4.02-4.26 (3H, m), 4.55-4.60 (1H, m), 7.08 (4H, br s), 7.52 (2H, d, J = 8.93 Hz), 7.91 (2H, d, J = 8.93 Hz), 8.60 (1H, t, J = 5.91 Hz). |
| 507 | 637 (M + H). | 1H-NMR (CDCl₃, 300 MHz) δ: 0.93 (3H, t, J = 7.3 Hz), 1.58-1.66 (2H, m), 2.56 (2H, t, J = 7.5 Hz), 3.05-3.19 (2H, m), 3.40-3.47 (1H, m), 3.78-3.83 (1H, m), 3.91 (3H, s), 4.01-4.06 (1H, m), 4.30-4.46 (2H, m), 4.56 (1H, br s), 4.71-4.76 (1H, m), 6.84-6.87 (1H, br m), 7.06-7.12 (4H, m), 7.31 (2H, d, J = 8.3 Hz), 7.50 (1H, s), 7.90 (2H, d, J = 7.9 Hz) |

TABLE 335

| Example No. | MS ESI m/e: | NMR |
|---|---|---|
| 508 | 641 (M + H). | 1H-NMR (CDCl₃, 400 MHz) δ: 0.99 (3H, t, J = 7.5 Hz), 2.07-2.21 (2H, m), 2.39-2.48 (1H, m), 2.81 (1H, dd, J = 13.7, 3.7 Hz), 3.22 (1H, ddd, J = 15.4, 11.9, 3.7 Hz), 3.81 (1H, d, J = 15.9 Hz), 3.87 (1H, d, J = 14.1 Hz), 4.02 (1H, d, J = 15.7 Hz), 4.41 (1H, d, J = 13.9 Hz), 4.44-4.62 (4H, m), 7.05 (1H, t, J = 5.7 Hz), 7.25-7.29 (4H, m), 7.38 (2H, d, J = 8.6 Hz), 7.45 (2H, d, J = 7.9 Hz), 7.91 (2H, d, J = 8.6 Hz), 8.53 (2H, s). |
| 509 | 644 (M + H). | 1H-NMR (CD₃OD, 400 MHz) δ: 0.90 (3H, t, J = 7.3 Hz), 1.58-1.61 (2H, m), 2.42 (3H, s), 2.54 (2H, t, J = 7.6 Hz), 3.22-3.28 (1H, m), 3.51 (1H, dd, J = 13.9, 4.6 Hz), 3.83-3.94 (3H, m), 4.14 (1H, dd, J = 14.9, 3.9 Hz), 4.25 (1H, dd, J = 14.9, 4.7 Hz), 4.39 (1H, d, J = 13.9 Hz), 4.64 (1H, s), 7.06-7.09 (4H, m), 7.55 (1H, t, J = 7.8 Hz), 7.72 (1H, d, J = 8.6 Hz), 7.85 (1H, dd, J = 9.7, 2.0 Hz), 8.58 (1H, t, J = 5.8 Hz). |
| 510 | 599 (M + H). | 1H-NMR (CDCl₃, 300 MHz) δ: 0.94 (3H, t, J = 7.3 Hz), 1.63 (2H, td, J = 14.9, 7.3 Hz), 2.09 (1H, br s), 2.57 (2H, t, J = 7.7 Hz), 2.84-2.96 (1H, m), 2.98 (1H, dd, J = 13.0, 4.3 Hz), 3.37-3.49 (1H, m), 3.81-3.93 (2H, m), 4.41 (2H, d, J = 5.7 Hz), 4.43-4.51 (3H, m), 4.59 (1H, br s), 6.44 (1H, s), 6.81 (1H, t, J = 5.5 Hz), 7.10 (2H, d, J = 9.0 Hz), 7.13 (2H, d, J = 9.0 Hz), 7.33 (2H, d, J = 8.3 Hz), 7.91 (2H, d, J = 8.7 Hz). |
| 511 | 672 (M + H). | 1H-NMR (CDCl₃, 400 MHz) δ: 0.99 (3H, t, J = 7.5 Hz), 2.07-2.18 (2H, m), 2.50 (1H, t, J = 11.4 Hz), 2.74 (1H, dd, J = 14.6, 3.5 Hz), 3.07-3.16 (1H, m), 3.96 (1H, d, J = 14.6 Hz), 4.18 (1H, d, J = 13.9 Hz), 4.46-4.64 (4H, m), 4.69 (2H, d, J = 2.1 Hz), 7.18 (1H, br s), 7.21 (2H, d, J = 8.8 Hz), 7.30 (2H, d, J = 8.1 Hz), 7.42 (2H, d, J = 7.9 Hz), 7.46 (2H, d, J = 8.6 Hz), 7.95 (2H, d, J = 8.6 Hz), 8.35 (1H, d, J = 5.6 Hz), 8.59 (1H, s). |

TABLE 336

| Example No. | MS ESI m/e: | NMR |
|---|---|---|
| 512 | 725 (M + H). | 1H-NMR (CDCl₃, 400 MHz) δ: 0.64-0.68 (2H, m), 0.84-0.89 (2H, m), 0.99 (3H, t, J = 7.4 Hz), 2.06-2.20 (2H, m), 2.47-2.56 (1H, m), 2.73 (1H, dd, J = 14.6, 3.5 Hz), 2.90-2.97 (1H, m), 3.07-3.17 (1H, m), 3.96 (1H, d, J = 14.1 Hz), 4.18 (1H, d, J = 13.7 Hz), 4.45-4.62 (4H, m), 7.18 (1H, br s), 7.31 (2H, d, J = 8.3 Hz), 7.42 (2H, d, J = 8.1 Hz), 7.45 (2H, d, J = 8.6 Hz), 7.67 (1H, dd, J = 5.6, 2.3 Hz), 7.89 (1H, d, J = 1.9 Hz), 7.95 (2H, d, J = 8.8 Hz), 8.04 (1H, d, J = 3.7 Hz), 8.31 (1H, d, J = 5.6 Hz), 8.75 (1H, s). |
| 513 | 755 (M + H). | 1H-NMR (CDCl₃, 400 MHz) δ: 0.99 (3H, t, J = 7.5 Hz), 2.06-2.22 (2H, m), 2.46-2.56 (1H, m), 2.73 (1H, dd, J = 14.7, 3.4 Hz), 3.04-3.15 (1H, m), 3.58-3.71 (4H, m), 3.78-3.82 (4H, m), 3.97 (1H, d, J = 14.4 Hz), 4.18 (1H, d, J = 14.1 Hz), 4.43-4.64 (4H, m), 7.19 (1H, br s), 7.30 (1H, d, J = 8.3 Hz), 7.40-7.52 (6H, m), 7.95 (2H, d, J = 8.8 Hz), 8.38 (1H, d, J = 5.6 Hz), 8.73 (1H, s). |
| 514 | 739 (M + H). | 1H-NMR (CDCl₃, 400 MHz) δ: 0.99 (3H, t, J = 7.5 Hz), 1.85-1.98 (4H, m), 2.06-2.22 (2H, m), 2.46-2.55 (1H, m), 2.73 (1H, d, J = 11.4 Hz), 3.06-3.16 (1H, m), 3.60-3.75 (4H, m), 3.96 (1H, d, J = 13.4 Hz), 4.17 (1H, d, J = 13.7 Hz), 4.43-4.62 (4H, m), 7.19 (1H, br s), 7.30 (2H, d, J = 8.3 Hz), 7.41-7.49 (5H, m), 7.58 (1H, d, J = 1.9 Hz), 7.95 (2H, d, J = 8.8 Hz), 8.38 (1H, d, J = 5.6 Hz), 8.69 (1H, s). |
| 515 | 679 (M + H). | 1H-NMR (CDCl₃, 300 MHz) δ: 0.91 (3H, t, J = 7.3 Hz), 1.49-1.63 (2H, m), 2.20 (3H, s), 2.46 (2H, t, J = 7.7 Hz), 3.17-3.37 (3H, m), 3.80-3.89 (1H, m), 3.92-4.04 (4H, m), 4.11-4.19 (1H, m), 4.54-4.66 (1H, m), 4.83 (1H, s), 5.19-5.33 (1H, m), 6.85 (2H, d, J = 7.9 Hz), 6.91 (2H, d, J = 7.9 Hz), 7.33 (2H, d, J = 9.0 Hz), 7.52-7.64 (1H, m), 7.78 (1H, s), 8.01 (2H, d, J = 8.7 Hz), 10.71 (1H, s). |

TABLE 337

| Example No. | MS ESI m/e: | NMR |
|---|---|---|
| 516 | 586 (M + H). | 1H-NMR (CDCl₃, 300 MHz) δ: 0.95 (3H, t, J = 7.3 Hz), 1.57-1.71 (2H, m), 2.58 (2H, t, J = 7.7 Hz), 2.69-2.82 (2H, m), 3.35-3.43 (1H, m), 3.54 (1H, d, J = 12.4 Hz), 3.89 (1H, d, J = 13.6 Hz), 4.24 (1H, d, J = 12.8 Hz), 4.42 (2H, d, J = 5.7 Hz), 4.52 (1H, br s), 6.69 (1H, s), 7.12 (2H, d, J = 8.7 Hz), 7.16 (2H, d, J = 8.7 Hz), 7.34 (2H, d, J = 8.3 Hz), 7.88 (2H, d, J = 8.7 Hz), 8.26 (1H, br s). |
| 517 | 676 (M + H). | 1H-NMR (CDCl₃, 400 MHz) δ: 0.99 (3H, t, J = 7.5 Hz), 2.06-2.21 (2H, m), 2.45-2.55 (1H, m), 2.73 (1H, dd, J = 14.7, 3.4 Hz), 3.05-3.14 (1H, m), 3.96 (1H, d, J = 13.0 Hz), 4.18 (1H, d, J = 13.7 Hz), 4.42-4.64 (4H, m), 7.17-7.20 (2H, m), 7.30 (2H, d, J = 8.6 Hz), 7.35 (1H, d, J = 1.9 Hz), 7.43 (2H, d, J = 8.1 Hz), 7.47 (2H, d, J = 8.1 Hz), 7.95 (2H, d, J = 8.8 Hz), 8.17 (1H, d, J = 5.8 Hz), 8.70 (1H, s). |
| 518 | 646 (M + H). | 1H-NMR (CDCl₃, 400 MHz) δ: 0.99 (3H, t, J = 7.5 Hz), 2.07-2.22 (2H, m), 2.45 (1H, t, J = 12.2 Hz), 2.90 (1H, dd, J = 13.7, 3.5 Hz), 3.22 (1H, t, J = 12.7 Hz), 3.83-3.92 (1H, m), 4.16 (1H, d, J = 15.9 Hz), 4.24 (1H, d, J = 16.3 Hz), 4.30 (3H, s), 4.38 (1H, d, J = 14.1 Hz), 4.45-4.58 (3H, m), 4.70 (1H, d, J = 13.9 Hz), 6.96 (1H, t, J = 6.0 Hz), 7.29 (2H, d, J = 7.9 Hz), 7.39 (2H, d, J = 8.2 Hz), 7.46 (2H, d, J = 7.9 Hz), 7.91 (2H, d, J = 8.6 Hz). |
| 519 | 646 (M + H). | 1H-NMR (CDCl₃, 400 MHz) δ: 0.99 (3H, t, J = 7.4 Hz), 2.07-2.21 (2H, m), 2.43 (1H, t, J = 13.0 Hz), 2.91 (1H, d, J = 13.7 Hz), 3.21 (1H, t, J = 13.1 Hz), 3.86-3.99 (1H, m), 3.94 (3H, s), 4.18 (1H, dd, J = 16.4, 3.6 Hz), 4.30-4.39 (2H, m), 4.47-4.64 (4H, m), 7.10 (1H, s), 7.28 (2H, d, J = 8.6 Hz), 7.40 (2H, d, J = 7.7 Hz), 7.46 (2H, d, J = 7.1 Hz), 7.92 (2H, d, J = 8.6 Hz). |
| 520 | 633 (M + H). | 1H-NMR (DMSO-d₆, 400 MHz, 120° C.) δ: 0.92 (3H, t, J = 7.5 Hz), 2.09-2.26 (2H, m), 3.09-3.19 (1H, m), 3.37-3.45 (1H, m), 3.65-3.80 (2H, m), 4.07-4.21 (2H, m), 4.28-4.36 (1H, m), 4.50-4.56 (1H, m), 4.69-4.75 (1H, m), 7.24 (2H, d, J = 8.2 Hz), 7.38 (2H, d, J = 8.2 Hz), 7.42 (2H, d, J = 7.9 Hz), 7.89 (2H, d, J = 9.0 Hz), 7.97 (1H, d, J = 2.0 Hz), 9.02 (1H, d, J = 2.0 Hz). |

TABLE 338

| Example No. | MS ESI m/e: | NMR |
|---|---|---|
| 521 | 631 (M + H). | 1H-NMR (DMSO-d$_6$, 400 MHz, 120° C.) δ: 0.92 (3H, t, J = 7.5 Hz), 2.11-2.26 (2H, m), 2.39 (3H, s), 3.67-3.77 (3H, m), 4.11-4.27 (4H, m), 4.49-4.64 (2H, m), 6.23 (1H, s), 7.26 (2H, d, J = 7.9 Hz), 7.37-7.46 (4H, m), 7.89 (2H, d, J = 9.0 Hz). |
| 522 | 558 (M + H). | 1H-NMR (CD$_3$OD, 300 MHz) δ: 0.91 (3H, t, J = 7.3 Hz), 1.30 (3H, t, J = 7.5 Hz), 1.59 (2H, td, J = 15.0, 7.4 Hz), 2.52 (2H, t, J = 7.5 Hz), 2.87 (2H, dt, J = 20.6, 6.0 Hz), 3.39 (1H, dd, J = 13.2, 7.2 Hz), 3.52 (1H, dd, J = 14.1, 4.7 Hz), 3.78-3.85 (2H, m), 4.11-4.33 (3H, m), 4.55 (1H, t, J = 3.8 Hz), 4.73 (1H, dd, J = 14.3, 3.0 Hz), 6.86 (1H, d, J = 3.8 Hz), 7.00 (2H, d, J = 8.3 Hz), 7.05 (2H, d, J = 8.3 Hz), 7.51 (1H, d, J = 3.8 Hz), 8.07 (1H, d, J = 1.1 Hz), 8.65 (1H, d, J = 1.1 Hz), 8.66 (1H, t, J = 6.0 Hz). |
| 523 | 566 (M + H). | 1H-NMR (CDCl$_3$, 300 MHz) δ: 1.24 (6H, d, J = 6.8 Hz), 2.20 (3H, s), 2.44-2.61 (2H, m), 2.84-2.96 (1H, m), 3.34-3.47 (1H, m), 3.51 (1H, d, J = 12.8 Hz), 3.91 (1H, d, J = 14.3 Hz), 4.21 (1H, d, J = 12.1 Hz), 4.43 (2H, d, J = 5.7 Hz), 4.56 (1H, br s), 5.54 (1H, s), 6.88 (1H, t, J = 4.9 Hz), 7.10-7.21 (4H, m), 7.31 (2H, d, J = 7.9 Hz), 7.91 (2H, d, J = 8.7 Hz). |
| 524 | 566 (M + H). | 1H-NMR (CD$_3$OD, 300 MHz) δ: 1.24 (3H, t, J = 7.7 Hz), 1.28 (9H, s), 2.70 (2H, q, J = 7.5 Hz), 3.18-3.29 (1H, m), 3.44 (1H, dd, J = 14.1, 4.7 Hz), 3.67-3.79 (1H, m), 3.85 (1H, td, J = 8.8, 4.4 Hz), 4.13-4.33 (3H, m), 4.59 (1H, t, J = 3.8 Hz), 4.72 (1H, dd, J = 14.1, 2.8 Hz), 7.04 (2H, d, J = 8.3 Hz), 7.23 (2H, d, J = 8.3 Hz), 7.36 (2H, d, J = 8.3 Hz), 7.78 (2H, d, J = 8.3 Hz), 8.07 (1H, d, J = 1.5 Hz), 8.60 (1H, t, J = 5.7 Hz), 8.65 (1H, d, J = 1.5 Hz). |

TABLE 339

| Example No. | MS ESI m/e: | NMR |
|---|---|---|
| 525 | 648 (M + H). | 1H-NMR (CDCl$_3$, 400 MHz) δ: 0.98 (3H, t, J = 7.5 Hz), 2.05-2.21 (2H, m), 2.56 (1H, td, J = 12.8, 3.2 Hz), 2.77 (1H, dd, J = 14.3, 3.5 Hz), 3.11-3.19 (1H, m), 3.92 (1H, d, J = 14.6 Hz), 4.14 (1H, d, J = 13.5 Hz), 4.46-4.64 (4H, m), 7.07 (1H, br s), 7.27 (2H, d, J = 9.3 Hz), 7.39 (2H, d, J = 7.7 Hz), 7.41 (2H, d, J = 7.7 Hz), 7.93 (2H, d, J = 8.8 Hz), 8.57 (1H, d, J = 2.2 Hz), 8.75 (1H, s). |
| 526 | 646 (M + H). | 1H-NMR (CDCl$_3$, 400 MHz) δ: 0.98 (3H, t, J = 7.6 Hz), 2.04-2.21 (2H, m), 2.35 (3H, s), 2.49-2.59 (1H, m), 2.74 (1H, dd, J = 14.2, 3.4 Hz), 3.09-3.16 (1H, m), 3.92 (1H, d, J = 14.1 Hz), 4.11 (1H, d, J = 14.8 Hz), 4.40-4.59 (4H, m), 6.37 (1H, s), 7.05 (1H, br s), 7.28 (1H, d, J = 7.7 Hz), 7.39 (2H, d, J = 8.4 Hz), 7.43 (2H, d, J = 8.2 Hz), 7.92 (2H, d, J = 8.6 Hz), 8.56 (1H, s). |
| 527 | 663 (M + H). | 1H-NMR (CDCl$_3$, 400 MHz) δ: 1.00 (3H, t, J = 7.4 Hz), 2.06-2.22 (2H, m), 2.52 (3H, s), 2.56-2.66 (1H, m), 2.81 (1H, dd, J = 14.4, 3.5 Hz), 3.11-3.20 (1H, m), 3.98 (1H, d, J = 14.6 Hz), 4.21 (1H, d, J = 13.7 Hz), 4.42-4.50 (2H, m), 4.55-4.63 (2H, m), 7.06-7.12 (1H, m), 7.27 (2H, d, J = 7.4 Hz), 7.42 (2H, d, J = 9.3 Hz), 7.44 (2H, d, J = 8.6 Hz), 7.94 (2H, d, J = 8.6 Hz), 9.80 (1H, br s). |
| 528 | 579 (M + H). | 1H-NMR (CDCl$_3$, 400 MHz) δ: 1.00 (3H, t, J = 7.5 Hz), 2.15 (2H, td, J = 16.1, 7.6 Hz), 2.24 (3H, s), 2.47-2.58 (1H, m), 2.73 (1H, dd, J = 14.4, 3.5 Hz), 3.06-3.15 (1H, m), 3.96 (1H, d, J = 14.6 Hz), 4.16 (1H, d, J = 13.2 Hz), 4.40-4.60 (4H, m), 5.90 (1H, s), 7.10-7.14 (1H, m), 7.30 (2H, d, J = 7.4 Hz), 7.42 (2H, d, J = 9.3 Hz), 7.46 (2H, d, J = 8.6 Hz), 7.94 (2H, d, J = 8.6 Hz), 9.01 (1H, s). |
| 529 | 542 (M + H). | 1H-NMR (CDCl$_3$, 300 MHz) δ: 1.32 (9H, s), 2.16 (3H, s), 2.34-2.48 (1H, m), 2.85 (1H, dd, J = 13.6, 4.1 Hz), 3.11-3.25 (1H, m), 3.83 (1H, d, J = 14.7 Hz), 4.36 (1H, d, J = 13.9 Hz), 4.42 (2H, d, J = 5.7 Hz), 4.48 (1H, d, J = 3.8 Hz), 4.54 (1H, d, J = 13.6 Hz), 6.70-6.79 (1H, m), 7.14 (2H, d, J = 8.3 Hz), 7.33-7.40 (4H, m), 7.90 (2H, d, J = 8.7 Hz). |

TABLE 340

| Example No. | MS ESI m/e: | NMR |
|---|---|---|
| 530 | 579 (M + H). | 1H-NMR (CDCl$_3$, 400 MHz) δ: 0.94 (3H, t, J = 7.3 Hz), 1.57-1.69 (2H, m), 2.54-2.74 (4H, m), 3.42 (1H, ddd, J = 14.4, 11.1, 3.0 Hz), |

TABLE 340-continued

| Example No. | MS ESI m/e: | NMR |
|---|---|---|
| | | 3.73 (1H, d, J = 12.5 Hz), 3.91 (1H, dt, J = 13.8, 2.6 Hz), 4.09 (2H, s), 4.36-4.61 (4H, m), 6.87 (1H, t, J = 5.4 Hz), 7.13 (4H, t, J = 7.3 Hz), 7.33 (2H, d, J = 8.1 Hz), 7.57 (1H, d, J = 1.4 Hz), 7.69 (1H, d, J = 1.4 Hz), 7.92 (2H, dt, J = 9.4, 2.4 Hz). |
| 531 | 666 (M + H). | 1H-NMR (CDCl$_3$, 300 MHz) δ: 0.94 (3H, t, J = 7.2 Hz), 1.60-1.70 (2H, m), 1.77 (4H, br s), 2.12 (3H, s), 2.47-2.62 (6H, m), 2.79-2.86 (1H, m), 2.92 (1H, dd, J = 13.0, 4.3 Hz), 3.35-3.45 (1H, m), 3.59 (2H, br s), 3.76 (1H, d, J = 12.4 Hz), 3.86 (1H, d, J = 14.3 Hz), 4.37-4.49 (3H, m), 4.59 (1H, s), 6.77-6.85 (1H, br m), 7.12 (4H, s), 7.32 (2H, d, J = 8.3 Hz), 7.91 (2H, d, J = 8.7 Hz). |
| 532 | 718 (M + H). | 1H-NMR (CDCl$_3$, 400 MHz) δ: 0.99 (3H, t, J = 7.4 Hz), 1.28 (3H, t, J = 7.2 Hz), 2.08-2.21 (2H, m), 2.46 (1H, t, J = 12.0 Hz), 2.90 (1H, dd, J = 13.7, 3.7 Hz), 3.22 (1H, t, J = 12.2 Hz), 3.86 (1H, d, J = 14.3 Hz), 4.17-4.38 (5H, m), 4.45-4.57 (3H, m), 4.66 (1H, d, J = 13.7 Hz), 5.36 (2H, s), 6.97 (1H, t, J = 5.3 Hz), 7.29 (2H, d, J = 7.5 Hz), 7.38 (2H, d, J = 8.2 Hz), 7.46 (2H, d, J = 7.7 Hz), 7.91 (2H, d, J = 8.6 Hz). |
| 533 | 718 (M + H). | 1H-NMR (CDCl$_3$, 400 MHz) δ: 0.99 (3H, t, J = 7.5 Hz), 1.24 (3H, t, J = 6.9 Hz), 2.08-2.20 (2H, m), 2.44 (1H, ddd, J = 15.0, 10.9, 3.5 Hz), 2.89 (1H, dd, J = 13.8, 3.6 Hz), 3.20 (1H, ddd, J = 14.5, 12.1, 2.8 Hz), 3.86 (1H, d, J = 14.1 Hz), 4.16-4.33 (4H, m), 4.43-4.62 (5H, m), 5.20 (2H, d, J = 6.0 Hz), 7.02 (1H, t, J = 6.0 Hz), 7.28 (2H, d, J = 7.3 Hz), 7.39 (2H, d, J = 8.8 Hz), 7.46 (2H, d, J = 7.9 Hz), 7.90 (2H, d, J = 8.6 Hz). |
| 534 | 758 (M + H). | 1H-NMR (CDCl$_3$, 300 MHz) δ: 0.94 (3H, t, J = 7.3 Hz), 1.59-1.69 (2H, m), 2.52-2.66 (4H, m), 2.79-2.89 (1H, m), 2.93 (1H, dd, J = 12.8, 4.5 Hz), 3.33-3.47 (1H, m), 3.66-3.95 (4H, m), 4.34-4.44 (3H, m), 4.49 (2H, br s), 4.57 (1H, s), 5.15 (2H, s), 6.78 (1H, t, J = 6.0 Hz), 7.12 (4H, s), 7.30-7.37 (7H, m), 7.90 (2H, d, J = 8.7 Hz). |

TABLE 341

| Example No. | MS ESI m/e: | NMR |
|---|---|---|
| 535 | 601 (M + H). | 1H-NMR (CD$_3$OD, 300 MHz) δ: 0.94 (3H, t, J = 7.3 Hz), 1.22 (6H, d, J = 7.2 Hz), 1.66 (2H, td, J = 15.0, 7.4 Hz), 2.67 (2H, t, J = 7.5 Hz), 2.81-2.91 (1H, m), 2.93-3.05 (1H, m), 3.22 (1H, dd, J = 13.6, 4.5 Hz), 3.64-3.76 (1H, m), 3.79-3.88 (2H, m), 4.25-4.34 (3H, m), 4.60-4.65 (1H, m), 4.91-4.94 (2H, m), 7.08-7.17 (4H, m), 7.36 (2H, d, J = 8.3 Hz), 7.78 (2H, d, J = 8.3 Hz), 8.48 (1H, t, J = 5.8 Hz). |
| 536 | 657 (M + H). | 1H-NMR (CD$_3$OD, 300 MHz) δ: 0.92 (3H, t, J = 7.3 Hz), 1.53-1.67 (2H, m), 2.54 (2H, t, J = 7.3 Hz), 3.04-3.19 (1H, m), 3.39 (3H, s), 3.43-3.52 (1H, m), 3.68-3.91 (3H, m), 4.25 (2H, dd, J = 25.1, 14.9 Hz), 4.34-4.46 (1H, m), 4.73 (1H, br s), 4.83-4.89 (2H, m), 7.01-7.10 (4H, m), 7.40 (2H, d, J = 8.7 Hz), 7.97 (2H, d, J = 9.0 Hz). |
| 537 | 643 (M + H). | 1H-NMR (CD$_3$OD, 300 MHz) δ: 0.92 (3H, t, J = 7.3 Hz), 1.61 (2H, td, J = 15.0, 7.4 Hz), 2.55 (2H, t, J = 7.5 Hz), 2.99-3.14 (1H, m), 3.32-3.37 (1H, m), 3.65-3.92 (3H, m), 4.14-4.30 (2H, m), 4.38 (1H, d, J = 14.3 Hz), 4.66 (1H, br s), 4.87-4.92 (2H, m), 7.02-7.12 (4H, m), 7.39 (2H, d, J = 9.0 Hz), 7.90-7.97 (2H, m). |
| 538 | 565 (M + H). | 1H-NMR (CDCl$_3$, 400 MHz) δ: 0.94 (3H, t, J = 7.3 Hz), 1.25 (3H, t, J = 7.7 Hz), 1.63 (2H, td, J = 15.2, 7.7 Hz), 2.26 (6H, s), 2.56 (2H, t, J = 7.8 Hz), 2.68-2.86 (4H, m), 3.39-3.51 (3H, m), 3.92 (2H, ddt, J = 42.6, 13.2, 3.4 Hz), 4.41 (2H, ddd, J = 34.1, 14.6, 5.7 Hz), 4.56 (1H, s), 4.72 (1H, d, J = 12.8 Hz), 6.98 (1H, t, J = 5.8 Hz), 7.10 (4H, dd, J = 9.6, 8.7 Hz), 7.34 (2H, d, J = 8.6 Hz), 7.77 (2H, dt, J = 8.5, 1.9 Hz), 8.00 (1H, d, J = 1.4 Hz), 8.12 (1H, d, J = 1.6 Hz). |
| 539 | 632 (M + H). | 1H-NMR (CDCl$_3$, 400 MHz) δ: 1.00 (3H, t, J = 7.5 Hz), 2.07-2.24 (2H, m), 2.54 (1H, td, J = 13.0, 2.9 Hz), 2.77 (1H, dd, J = 14.6, 3.5 Hz), 3.09-3.21 (1H, m), 3.97 (1H, d, J = 13.7 Hz), 4.19 (1H, d, J = 13.0 Hz), 4.37-4.65 (4H, m), 7.30 (2H, d, J = 7.9 Hz), 7.42 (2H, d, J = 8.8 Hz), 7.49 (2H, d, J = 7.9 Hz), 7.94 (2H, d, J = 8.8 Hz), 8.11 (2H, s), 9.21 (1H, s). |

TABLE 342

| Example No. | MS ESI m/e: | NMR |
|---|---|---|
| 540 | 632 (M + H). | 1H-NMR (CDCl₃, 400 MHz) δ: 0.99 (3H, t, J = 7.5 Hz), 2.05-2.22 (2H, m), 3.07-3.19 (2H, m), 3.29-3.51 (2H, m), 3.82 (1H, d, J = 14.1 Hz), 4.38 (1H, dd, J = 15.0, 5.3 Hz), 4.51 (1H, dd, J = 14.7, 5.8 Hz), 4.61 (1H, s), 5.89 (1H, s), 7.27 (2H, d, J = 9.3 Hz), 7.33 (2H, d, J = 8.6 Hz), 7.43 (2H, d, J = 8.2 Hz), 7.95 (2H, d, J = 8.6 Hz). |
| 541 | 674 (M + H). | 1H-NMR (CDCl₃, 400 MHz) δ: 0.99 (3H, t, J = 7.5 Hz), 1.36 (6H, d, J = 6.8 Hz), 2.07-2.22 (2H, m), 2.44 (1H, ddd, J = 14.9, 11.1, 1.9 Hz), 2.94 (1H, dd, J = 13.8, 3.6 Hz), 3.01-3.08 (1H, m), 3.17 (1H, ddd, J = 14.7, 12.2, 2.8 Hz), 3.91 (1H, d, J = 14.1 Hz), 4.36 (1H, d, J = 13.5 Hz), 4.47-4.62 (4H, m), 5.33 (1H, d, J = 16.5 Hz), 5.61 (1H, d, J = 16.5 Hz), 7.06 (1H, t, J = 5.7 Hz), 7.28 (2H, d, J = 7.7 Hz), 7.42 (2H, d, J = 8.4 Hz), 7.46 (2H, d, J = 7.9 Hz), 7.94 (2H, d, J = 8.6 Hz). |
| 542 | 674 (M + H). | 1H-NMR (CDCl₃, 400 MHz) δ: 1.00 (3H, t, J = 6.5 Hz), 1.39 (6H, dd, J = 7.1, 2.2 Hz), 2.15 (2H, ddd, J = 30.7, 14.9, 7.3 Hz), 2.44 (1H, t, J = 12.9 Hz), 2.91 (1H, d, J = 12.4 Hz), 3.13-3.30 (2H, m), 3.90 (1H, d, J = 13.2 Hz), 4.37 (1H, d, J = 13.2 Hz), 4.45-4.61 (4H, m), 5.55 (1H, d, J = 16.3 Hz), 5.84 (1H, d, J = 16.1 Hz), 6.96 (1H, t, J = 4.6 Hz), 7.30 (2H, d, J = 7.3 Hz), 7.40 (2H, d, J = 8.2 Hz), 7.47 (2H, d, J = 6.8 Hz), 7.93 (2H, d, J = 6.8 Hz). |
| 543 | 759 (M + H). | 1H-NMR (CDCl₃, 400 MHz) δ: 0.99 (3H, t, J = 7.5 Hz), 2.15 (2H, td, J = 15.5, 7.2 Hz), 2.45 (1H, ddd, J = 13.9, 11.7, 2.2 Hz), 2.93 (1H, dd, J = 14.3, 5.1 Hz), 3.17 (1H, ddd, J = 15.2, 13.2, 2.3 Hz), 3.51-3.68 (8H, m), 3.90 (1H, d, J = 12.8 Hz), 4.02 (2H, s), 4.35 (1H, d, J = 13.0 Hz), 4.44-4.60 (4H, m), 5.56 (1H, d, J = 16.1 Hz), 5.93 (1H, d, J = 15.9 Hz), 6.98 (1H, t, J = 5.2 Hz), 7.29 (2H, d, J = 8.2 Hz), 7.40 (2H, d, J = 8.2 Hz), 7.46 (2H, d, J = 7.9 Hz), 7.92 (2H, d, J = 8.6 Hz). |

TABLE 343

| Example No. | MS ESI m/e: | NMR |
|---|---|---|
| 544 | 657 (M + H). | 1H-NMR (CDCl₃, 400 MHz) δ: 0.94 (3H, t, J = 7.3 Hz), 1.59-1.68 (2H, m), 2.57 (2H, t, J = 7.7 Hz), 2.74-2.93 (2H, m), 3.08 (3H, s), 3.43 (1H, ddd, J = 28.8, 14.4, 7.2 Hz), 3.89 (1H, dt, J = 13.7, 3.0 Hz), 4.08 (1H, dt, J = 13.2, 3.1 Hz), 4.35-4.45 (2H, m), 4.59 (1H, br s), 4.72 (1H, d, J = 13.2 Hz), 6.85 (1H, t, J = 5.9 Hz), 6.98-7.20 (5H, m), 7.35 (2H, d, J = 9.0 Hz), 7.89-7.96 (3H, m), 8.10 (1H, d, J = 1.6 Hz). |
| 545 | 608 (M + H). | 1H-NMR (CDCl₃, 400 MHz) δ: 1.31 (9H, s), 2.60 (1H, t, J = 5.7 Hz), 2.82-3.01 (2H, m), 3.40-3.52 (1H, m), 3.89 (1H, d, J = 14.1 Hz), 4.07 (1H, d, J = 13.4 Hz), 4.35-4.45 (2H, m), 4.56-4.68 (3H, m), 4.75 (1H, d, J = 13.4 Hz), 6.86 (1H, t, J = 5.3 Hz), 7.11 (2H, d, J = 8.6 Hz), 7.33 (4H, d, J = 8.2 Hz), 7.92 (2H, dt, J = 9.4, 2.4 Hz), 8.00-8.01 (1H, m), 8.14 (1H, d, J = 1.4 Hz). |
| 546 | 580 (M + H). | 1H-NMR (CDCl₃, 300 MHz) δ: 0.94 (3H, t, J = 7.3 Hz), 1.57-1.70 (2H, m), 2.41-2.62 (4H, m), 3.27-3.41 (1H, m), 3.63 (1H, d, J = 13.2 Hz), 3.92 (1H, d, J = 14.7 Hz), 4.32 (1H, d, J = 13.2 Hz), 4.35-4.50 (2H, m), 4.52 (1H, br s), 6.79-6.85 (1H, m), 6.85 (1H, d, J = 10.2 Hz), 7.11 (2H, d, J = 8.3 Hz), 7.15 (2H, d, J = 8.7 Hz), 7.32 (1H, d, J = 11.7 Hz), 7.35 (2H, d, J = 9.0 Hz), 7.90 (2H, d, J = 8.7 Hz), 10.18 (1H, s). |
| 547 | 607 (M + H). | 1H-NMR (CDCl₃, 300 MHz) δ: 0.93 (3H, t, J = 7.3 Hz), 1.55-1.68 (2H, m), 2.55 (2H, t, J = 7.7 Hz), 2.93-3.10 (2H, m), 3.38-3.51 (1H, m), 3.91 (1H, d, J = 14.3 Hz), 4.28-4.45 (2H, m), 4.58 (2H, d, J = 17.7 Hz), 4.72 (1H, d, J = 13.2 Hz), 5.49 (1H, br s), 6.82-6.88 (1H, m), 7.02 (2H, d, J = 8.3 Hz), 7.09 (2H, d, J = 8.3 Hz), 7.12 (1H, d, J = 9.8 Hz), 7.36 (2H, d, J = 8.7 Hz), 7.66 (1H, br s), 7.94 (2H, d, J = 8.7 Hz), 8.01 (1H, d, J = 9.4 Hz). |

TABLE 344

| Example No. | MS ESI m/e: | NMR |
|---|---|---|
| 548 | 638 (M + H). | 1H-NMR (CDCl₃, 300 MHz) δ: 0.94 (3H, t, J = 7.3 Hz), 1.56-1.71 (2H, m), 2.45 (3H, s), 2.57 (2H, t, J = 7.7 Hz), 2.62-2.67 (2H, m), 2.69-2.76 (2H, m), 2.79-2.87 (1H, m), 2.92 (1H, dd, J = 13.0, 4.3 |

TABLE 344-continued

| Example No. | MS ESI m/e: | NMR |
|---|---|---|
| | | Hz), 3.34-3.45 (1H, m), 3.47 (2H, s), 3.76-3.92 (2H, m), 4.35-4.44 (3H, m), 4.57 (1H, s), 6.80 (1H, t, J = 5.8 Hz), 7.12 (4H, s), 7.33 (2H, d, J = 8.3 Hz), 7.90 (2H, d, J = 8.7 Hz). |
| 549 | 609 (M + H). | 1H-NMR (CDCl$_3$, 300 MHz) δ: 0.94 (3H, t, J = 7.3 Hz), 1.57-1.70 (2H, m), 2.57 (2H, t, J = 7.5 Hz), 2.81-2.92 (1H, m), 2.97 (1H, dd, J = 13.4, 4.3 Hz), 3.35-3.48 (1H, m), 3.77-3.93 (2H, m), 4.32-4.48 (2H, m), 4.52-4.71 (6H, m), 6.86-6.94 (1H, m), 7.09 (2H, d, J = 8.3 Hz), 7.12 (2H, d, J = 8.7 Hz), 7.32 (2H, d, J = 8.7 Hz), 7.33 (1H, s), 7.92 (2H, d, J = 8.7 Hz). |
| 550 | 604 (M + H). | 1H-NMR (DMSO-d$_6$, 400 MHz, 120° C.) δ: 1.82 (3H, s), 3.18 (1H, d, J = 15.7 Hz), 3.54-3.68 (3H, m), 3.94-4.01 (2H, m), 4.28 (2H, d, J = 6.0 Hz), 4.49 (1H, s), 7.44 (4H, d, J = 8.2 Hz), 7.58 (2H, d, J = 8.2 Hz), 7.91 (2H, d, J = 8.8 Hz), 8.28 (1H, br s). |
| 551 | 686 (M + H). | 1H-NMR (CDCl$_3$, 400 MHz) δ: 2.44 (1H, t, J = 11.4 Hz), 2.54 (3H, s), 2.91 (1H, d, J = 10.4 Hz), 3.18 (1H, t, J = 14.3 Hz), 3.92 (1H, d, J = 14.1 Hz), 4.36-4.68 (5H, m), 5.53 (1H, d, J = 16.1 Hz), 5.87 (1H, d, J = 15.9 Hz), 7.05 (1H, br s), 7.39 (2H, d, J = 8.4 Hz), 7.41 (2H, d, J = 9.7 Hz), 7.61 (2H, d, J = 8.2 Hz), 7.94 (2H, d, J = 8.8 Hz). |
| 552 | 703 (M + H). | 1H-NMR (CDCl$_3$, 400 MHz) δ: 2.83-2.96 (3H, m), 3.11 (1H, d, J = 10.6 Hz), 3.39 (1H, t, J = 11.2 Hz), 3.84 (1H, d, J = 13.2 Hz), 4.25 (1H, d, J = 13.7 Hz), 4.34 (1H, dd, J = 15.1, 6.1 Hz), 4.47-4.75 (5H, m), 7.27 (2H, d, J = 8.4 Hz), 7.35 (2H, d, J = 8.4 Hz), 7.39 (2H, d, J = 8.2 Hz), 7.79 (1H, s), 7.93 (2H, d, J = 8.8 Hz). |

TABLE 345

| Example No. | MS ESI m/e: | NMR |
|---|---|---|
| 553 | 662 (M + H). | 1H-NMR (CDCl$_3$, 400 MHz) δ: 1.00 (3H, t, J = 7.4 Hz), 2.05-2.22 (2H, m), 2.38 (3H, s), 2.54 (1H, td, J = 11.6, 5.8 Hz), 2.77 (1H, dd, J = 14.6, 3.5 Hz), 3.08-3.17 (1H, m), 3.94 (1H, d, J = 14.1 Hz), 4.20 (1H, d, J = 13.7 Hz), 4.40-4.62 (4H, m), 6.57 (1H, s), 7.13-7.19 (1H, m), 7.27 (2H, d, J = 7.9 Hz), 7.42 (2H, d, J = 8.6 Hz), 7.45 (2H, d, J = 8.3 Hz), 7.94 (2H, d, J = 8.6 Hz), 9.10 (1H, s). |
| 554 | 648 (M + H). | 1H-NMR (CDCl$_3$, 300 MHz) δ: 0.98 (3H, t, J = 7.5 Hz), 2.03-2.23 (2H, m), 2.60 (1H, t, J = 11.3 Hz), 2.80 (1H, dd, J = 14.5, 3.6 Hz), 3.09-3.19 (1H, m), 3.93 (1H, d, J = 14.7 Hz), 4.18 (1H, d, J = 13.6 Hz), 4.48 (3H, dt, J = 19.0, 6.2 Hz), 4.59 (1H, s), 6.84 (1H, d, J = 3.8 Hz), 7.08 (1H, br s), 7.26 (2H, d, J = 7.5 Hz), 7.35 (1H, d, J = 3.4 Hz), 7.40 (2H, d, J = 7.5 Hz), 7.41 (2H, d, J = 7.9 Hz), 7.93 (2H, d, J = 8.7 Hz). |
| 555 | 710 (M + H). | 1H-NMR (CDCl$_3$, 400 MHz) δ: 0.99 (3H, t, J = 7.9 Hz), 2.06-2.20 (2H, m), 2.52 (1H, td, J = 13.0, 3.2 Hz), 2.75 (1H, dd, J = 14.6, 3.5 Hz), 3.07-3.15 (1H, m), 3.97 (1H, d, J = 14.6 Hz), 4.20 (1H, d, J = 13.9 Hz), 4.44-4.65 (4H, m), 7.21 (1H, t, J = 6.3 Hz), 7.30 (2H, d, J = 8.6 Hz), 7.40-7.50 (5H, m), 7.66 (1H, d, J = 1.9 Hz), 7.95 (2H, d, J = 9.0 Hz), 8.51 (1H, d, J = 5.6 Hz), 8.86 (1H, s). |
| 556 | 635 (M + H). | 1H-NMR (CDCl$_3$, 300 MHz) δ: 0.94 (3H, t, J = 7.3 Hz), 1.59-1.69 (2H, m), 2.57 (2H, t, J = 7.7 Hz), 2.87-2.99 (2H, m), 3.42-3.49 (1H, m), 3.79-3.90 (1H, m), 3.93-4.03 (1H, m), 4.39 (2H, d, J = 6.0 Hz), 4.56 (1H, s), 4.73 (1H, d, J = 13.2 Hz), 5.28 (2H, s), 6.79-6.87 (1H, m), 7.06-7.14 (5H, m), 7.34 (2H, d, J = 9.0 Hz), 7.72 (1H, s), 7.91 (2H, d, J = 9.0 Hz). |
| 557 | 624 (M + H). | 1H-NMR (CDCl$_3$, 300 MHz) δ: 0.94 (3H, t, J = 7.2 Hz), 1.60-1.70 (2H, m), 2.47-2.62 (4H, m), 2.79-2.99 (2H, m), 3.09 (2H, br s), 3.36-3.46 (1H, m), 3.75-3.93 (5H, m), 4.37-4.45 (3H, m), 4.57 (1H, s), 6.77-6.85 (1H, br m), 7.13 (4H, s), 7.33 (2H, d, J = 8.7 Hz), 7.91 (2H, d, J = 9.0 Hz). |

TABLE 346

| Example No. | MS ESI m/e: | NMR |
|---|---|---|
| 558 | 661 (M + H). | 1H-NMR (CDCl$_3$, 400 MHz) δ: 1.32 (9H, s), 1.84 (4H, s), 2.51-2.97 (6H, m), 3.40-3.50 (1H, m), 3.66-3.93 (3H, m), 4.08 |

TABLE 346-continued

| Example No. | MS ESI m/e: | NMR |
|---|---|---|
| | | (1H, d, J = 12.3 Hz), 4.40 (2H, ddd, J = 19.6, 13.9, 4.9 Hz), 4.59 (1H, s), 4.76 (1H, d, J = 13.4 Hz), 6.87 (1H, t, J = 5.3 Hz), 7.12 (2H, d, J = 8.3 Hz), 7.32-7.35 (4H, m), 7.92 (2H, dt, J = 9.4, 2.5 Hz), 8.05-8.15 (2H, m). |
| 559 | 644 (M + H). | 1H-NMR (CD$_3$OD, 400 MHz) δ: 0.93 (3H, t, J = 7.5 Hz), 2.13 (2H, dq, J = 31.2, 7.6 Hz), 3.20-3.32 (1H, m), 3.43 (1H, d, J = 13.4 Hz), 3.71-3.91 (2H, m), 4.20-4.34 (3H, m), 4.64 (1H, s), 4.85 (1H, d, J = 11.6 Hz), 7.22 (2H, d, J = 8.1 Hz), 7.33 (2H, d, J = 7.9 Hz), 7.41 (2H, d, J = 8.1 Hz), 7.97 (2H, d, J = 8.8 Hz), 8.13 (1H, s), 8.65 (1H, s), 8.75 (1H, m). |
| 560 | 630 (M + H). | 1H-NMR (CDCl$_3$, 400 MHz) δ: 0.98 (3H, t, J = 7.4 Hz), 2.06-2.20 (2H, m), 2.58 (1H, t, J = 5.7 Hz), 2.82-3.00 (2H, m), 3.39-3.51 (1H, m), 3.88 (1H, dt, J = 13.7, 3.5 Hz), 4.06 (1H, dt, J = 12.8, 3.5 Hz), 4.40-4.53 (2H, m), 4.57-4.67 (3H, m), 4.75 (1H, d, J = 13.2 Hz), 7.03 (1H, t, J = 5.6 Hz), 7.23 (2H, d, J = 8.1 Hz), 7.37 (4H, dd, J = 12.2, 8.0 Hz), 7.94 (2H, dt, J = 9.4, 2.6 Hz), 7.99 (1H, d, J = 1.4 Hz), 8.12 (1H, d, J = 1.4 Hz). |
| 561 | 714 (M + H). | 1H-NMR (CDCl$_3$, 300 MHz) δ: 0.94 (3H, t, J = 7.3 Hz), 1.55-1.71 (2H, m), 2.53-2.67 (4H, m), 2.79-2.95 (4H, m), 3.36-3.45 (1H, m), 3.49 (2H, s), 3.68 (2H, s), 3.74-3.91 (2H, m), 4.36-4.47 (3H, m), 4.56 (1H, s), 6.80 (1H, t, J = 5.8 Hz), 7.08-7.16 (4H, m), 7.27-7.38 (7H, m), 7.90 (2H, d, J = 8.7 Hz). |
| 562 | 629 (M + H). | 1H-NMR (CDCl$_3$, 300 MHz) δ: 0.94 (3H, t, J = 7.3 Hz), 1.61-1.70 (2H, m), 2.16 (1H, br s), 2.45 (1H, br s), 2.57 (2H, t, J = 7.5 Hz), 2.82-2.99 (2H, m), 3.35-3.47 (1H, m), 3.78-3.93 (2H, m), 4.38-4.51 (5H, m), 4.57 (1H, br s), 4.64 (2H, br s), 6.80 (1H, t, J = 5.8 Hz), 7.08-7.17 (4H, m), 7.33 (2H, d, J = 7.9 Hz), 7.87-7.93 (2H, m). |

TABLE 347

| Example No. | MS ESI m/e: | NMR |
|---|---|---|
| 563 | 584 (M + H). | 1H-NMR (CDCl$_3$, 400 MHz) δ: 0.94 (3H, t, J = 7.3 Hz), 1.59-1.68 (2H, m), 2.35 (3H, s), 2.57 (2H, t, J = 7.7 Hz), 3.02-3.18 (2H, m), 3.41-3.49 (1H, m), 3.76-3.91 (2H, m), 4.32-4.45 (3H, m), 4.59 (1H, d, J = 2.6 Hz), 6.73 (1H, t, J = 5.4 Hz), 7.12 (4H, ddd, J = 15.1, 6.1, 2.1 Hz), 7.34 (2H, d, J = 8.1 Hz), 7.90 (2H, dt, J = 9.4, 2.5 Hz). |
| 564 | 588 (M + H). | 1H-NMR (CD$_3$OD, 300 MHz) δ: 0.93 (3H, t, J = 7.3 Hz), 1.23 (3H, t, J = 7.7 Hz), 2.02-2.23 (2H, m), 2.70 (2H, q, J = 7.5 Hz), 3.19-3.29 (1H, m), 3.47 (1H, dd, J = 14.1, 4.7 Hz), 3.77 (1H, dd, J = 9.6, 4.0 Hz), 3.87 (1H, td, J = 9.0, 4.5 Hz), 4.16 (1H, dt, J = 12.8, 4.0 Hz), 4.33 (2H, d, J = 5.7 Hz), 4.60 (1H, t, J = 4.0 Hz), 4.68 (1H, dd, J = 13.9, 3.4 Hz), 7.23 (2H, d, J = 8.3 Hz), 7.33 (2H, d, J = 8.3 Hz), 7.36 (2H, d, J = 8.7 Hz), 7.79 (2H, d, J = 8.7 Hz), 8.05 (1H, d, J = 1.1 Hz), 8.64 (1H, d, J = 1.1 Hz), 8.74 (1H, t, J = 6.0 Hz). |
| 565 | 632 (M + H). | 1H-NMR (CDCl$_3$, 400 MHz) δ: 0.94-1.01 (3H, m), 2.03-2.21 (2H, m), 2.58-2.70 (1H, m), 2.83 (1H, d, J = 14.1 Hz), 3.18 (1H, t, J = 13.2 Hz), 3.94 (1H, d, J = 14.6 Hz), 4.15 (1H, d, J = 12.8 Hz), 4.39-4.61 (4H, m), 7.13 (1H, s), 7.26 (2H, d, J = 8.6 Hz), 7.39 (2H, d, J = 8.2 Hz), 7.41 (2H, d, J = 8.6 Hz), 7.68 (1H, s), 7.93 (2H, d, J = 8.6 Hz). |
| 566 | 633 (M + H). | 1H-NMR (CD$_3$OD, 400 MHz) δ: 0.91 (3H, t, J = 7.5 Hz), 2.02-2.18 (2H, m), 3.12 (1H, s), 3.31-3.39 (1H, m), 3.66-3.75 (1H, m), 3.77-3.84 (1H, m), 4.06 (1H, d, J = 11.5 Hz), 4.28 (2H, s), 4.49 (1H, d, J = 14.8 Hz), 4.58 (1H, s), 7.28 (2H, d, J = 7.9 Hz), 7.35 (2H, d, J = 8.4 Hz), 7.40 (2H, d, J = 7.9 Hz), 7.94 (2H, d, J = 8.8 Hz). |
| 567 | 662 (M + H). | 1H-NMR (CDCl$_3$, 400 MHz) δ: 0.98 (3H, t, J = 7.4 Hz), 2.05-2.21 (2H, m), 2.50-2.60 (1H, m), 2.62 (3H, s), 2.77 (1H, dd, J = 14.3, 3.5 Hz), 3.12-3.19 (1H, m), 3.90 (1H, d, J = 14.1 Hz), 4.11 (1H, d, J = 14.6 Hz), 4.44-4.60 (4H, m), 6.99-7.06 (2H, m), 7.27 (2H, d, J = 8.6 Hz), 7.39 (2H, d, J = 8.8 Hz), 7.42 (2H, d, J = 8.2 Hz), 7.93 (2H, d, J = 8.6 Hz), 8.44 (1H, s). |

TABLE 348

| Example No. | MS ESI m/e: | NMR |
|---|---|---|
| 568 | 646 (M + H). | 1H-NMR (CDCl₃, 400 MHz) δ: 0.99 (3H, t, J = 7.4 Hz), 2.07 (3H, s), 2.09-2.21 (2H, m), 3.06-3.15 (1H, m), 3.27-3.45 (2H, m), 3.81 (1H, d, J = 13.9 Hz), 4.14-4.30 (1H, m), 4.39 (1H, dd, J = 15.0, 6.0 Hz), 4.56 (1H, dd, J = 15.0, 6.0 Hz), 4.65 (1H, br s), 5.18 (1H, br s), 5.90 (2H, s), 7.28 (2H, d, J = 7.9 Hz), 7.36 (2H, d, J = 8.3 Hz), 7.43 (2H, d, J = 8.3 Hz), 7.98 (2H, d, J = 8.6 Hz). |
| 569 | 645 (M + H). | 1H-NMR (CDCl₃, 400 MHz) δ: 1.00 (3H, t, J = 7.5 Hz), 2.07-2.22 (2H, m), 2.49-2.58 (1H, m), 2.75 (1H, dd, J = 14.3, 3.6 Hz), 3.12-3.19 (1H, m), 3.78 (3H, s), 3.90 (1H, d, J = 14.6 Hz), 4.11 (1H, d, J = 13.4 Hz), 4.45-4.61 (4H, m), 6.37 (1H, d, J = 2.3 Hz), 7.06 (1H, t, J = 5.9 Hz), 7.19 (1H, d, J = 2.3 Hz), 7.29 (2H, d, J = 8.1 Hz), 7.40 (2H, d, J = 8.1 Hz), 7.44 (2H, d, J = 8.1 Hz), 7.94 (2H, d, J = 8.8 Hz), 8.07 (1H, s). |
| 570 | 613 (M + H). | 1H-NMR (CDCl₃, 300 MHz) δ: 1.32 (9H, s), 1.63 (1H, br s), 2.85-3.02 (2H, m), 3.44 (1H, dt, J = 18.3, 6.4 Hz), 3.81-3.95 (2H, m), 4.39-4.50 (3H, m), 4.59 (1H, br s), 4.65 (2H, br s), 6.78 (1H, t, J = 5.5 Hz), 6.99 (1H, s), 7.14 (2H, d, J = 8.3 Hz), 7.30-7.38 (4H, m), 7.87-7.94 (2H, m). |
| 571 | 598 (M + H). | 1H-NMR (CDCl₃, 400 MHz) δ: 0.94 (3H, t, J = 7.3 Hz), 1.58-1.68 (2H, m), 2.57 (2H, t, J = 7.7 Hz), 2.91-3.06 (2H, m), 3.34-3.45 (1H, m), 3.81 (1H, dt, J = 13.6, 3.7 Hz), 4.19 (1H, d, J = 13.2 Hz), 4.37 (2H, ddd, J = 24.1, 14.8, 5.5 Hz), 4.57 (1H, dd, J = 3.7, 2.3 Hz), 4.72 (1H, d, J = 13.4 Hz), 6.56 (1H, s), 6.82 (1H, t, J = 5.7 Hz), 7.09 (4H, dd, J = 19.6, 4.1 Hz), 7.35 (2H, d, J = 8.1 Hz), 7.92 (2H, dt, J = 9.5, 2.4 Hz), 8.30 (1H, d, J = 0.7 Hz). |
| 572 | 564 (M + H). | 1H-NMR (CDCl₃, 400 MHz) δ: 0.94 (3H, t, J = 7.3 Hz), 1.60-1.68 (2H, m), 2.56 (2H, t, J = 7.8 Hz), 2.86-3.05 (2H, m), 3.32-3.42 (1H, m), 3.83 (1H, dt, J = 13.5, 3.4 Hz), 4.22-4.44 (3H, m), 4.58 (1H, s), 4.75 (1H, d, J = 13.7 Hz), 6.57 (1H, d, J = 6.5 Hz), 6.86 (1H, t, J = 5.7 Hz), 7.07 (4H, dd, J = 21.8, 8.1 Hz), 7.34 (2H, d, J = 7.9 Hz), 7.92 (2H, dt, J = 9.5, 2.4 Hz), 8.22 (1H, d, J = 6.0 Hz), 8.52 (1H, s). |

TABLE 349

| Example No. | MS ESI m/e: | NMR |
|---|---|---|
| 573 | 652 (M + H). | 1H-NMR (CDCl₃, 400 MHz) δ: 1.32 (9H, s), 3.14 (1H, ddd, J = 14.0, 10.4, 3.0 Hz), 3.23 (1H, dd, J = 13.2, 4.4 Hz), 3.49 (1H, ddd, J = 14.5, 10.8, 3.1 Hz), 3.90 (1H, dt, J = 14.3, 3.1 Hz), 4.18 (1H, d, J = 13.5 Hz), 4.39 (2H, ddd, J = 19.1, 13.4, 4.5 Hz), 4.50 (1H, d, J = 12.8 Hz), 4.60-4.64 (1H, m), 6.72 (1H, t, J = 5.7 Hz), 6.99 (1H, s), 7.12 (2H, d, J = 8.4 Hz), 7.32-7.38 (4H, m), 7.91 (2H, d, J = 9.0 Hz). |
| 574 | 616 (M + H). | 1H-NMR (CDCl₃, 300 MHz) δ: 0.91 (3H, t, J = 7.2 Hz), 1.51-1.65 (2H, m), 2.50 (2H, t, J = 7.5 Hz), 2.93-3.07 (1H, m), 3.20 (1H, dd, J = 13.9, 3.8 Hz), 3.35-3.49 (1H, m), 3.95 (1H, d, J = 14.3 Hz), 4.24-4.39 (2H, m), 4.66 (1H, s), 4.83 (1H, d, J = 12.8 Hz), 5.08 (1H, d, J = 13.9 Hz), 6.83 (1H, t, J = 5.7 Hz), 6.96 (2H, d, J = 8.7 Hz), 7.00 (2H, d, J = 8.3 Hz), 7.37 (2H, d, J = 7.9 Hz), 7.95 (2H, d, J = 8.7 Hz), 8.78 (1H, s), 9.22 (1H, s), 9.26 (1H, s). |
| 575 | 623 (M + H). | 1H-NMR (CDCl₃, 400 MHz) δ: 1.31 (9H, s), 2.48 (1H, t, J = 5.2 Hz), 2.81-3.01 (2H, m), 3.38-3.47 (1H, m), 3.79-3.94 (2H, m), 4.41 (2H, ddd, J = 30.8, 14.6, 5.6 Hz), 4.53-4.69 (6H, m), 6.91 (1H, t, J = 5.8 Hz), 7.13 (2H, d, J = 13.2 Hz), 7.29-7.36 (5H, m), 7.92 (2H, dt, J = 9.4, 2.5 Hz). |
| 576 | 619 (M + H). | 1H-NMR (CDCl₃, 400 MHz) δ: 0.99 (3H, t, J = 7.5 Hz), 2.07-2.20 (2H, m), 2.35 (3H, s), 3.01-3.18 (2H, m), 3.41-3.51 (1H, m), 3.76-3.93 (2H, m), 4.32-4.62 (4H, m), 6.90 (1H, t, J = 6.0 Hz), 7.25 (2H, d, J = 5.0 Hz), 7.39 (4H, dd, J = 22.2, 8.0 Hz), 7.92 (2H, dt, J = 9.4, 2.5 Hz). |
| 577 | 622 (M + H). | 1H-NMR (CDCl₃, 300 MHz) δ: 1.32 (9H, s), 2.32 (3H, s), 2.97-3.14 (2H, m), 3.39-3.49 (1H, m), 3.83-3.97 (2H, m), 4.34-4.48 (3H, m), 4.59 (1H, br s), 6.73 (1H, t, J = 6.2 Hz), 7.12 (2H, d, J = 8.3 Hz), 7.31-7.38 (4H, m), 7.87-7.94 (2H, m). |
| 578 | 652 (M + H). | 1H-NMR (CDCl₃, 400 MHz) δ: 1.32 (9H, s), 2.84-3.02 (2H, m), 3.39-3.50 (3H, m), 3.85-3.95 (2H, m), 4.35-4.46 (5H, m), 4.58 (1H, br s), 6.00 (1H, s), 6.78 (1H, t, J = 5.7 Hz), 7.14 (2H, d, J = 8.6 Hz), 7.31-7.38 (4H, m), 7.91 (2H, dt, J = 9.5, 2.4 Hz). |

TABLE 350

| Example No. | MS ESI m/e: | NMR |
|---|---|---|
| 579 | 649 (M + H). | 1H-NMR (CDCl$_3$, 400 MHz) δ: 1.29 (9H, s), 2.86-3.00 (2H, m), 3.42-3.52 (1H, m), 3.86 (1H, dt, J = 13.7, 3.5 Hz), 3.99 (1H, dt, J = 12.9, 3.5 Hz), 4.41 (2H, d, J = 5.7 Hz), 4.56 (1H, dd, J = 3.6, 2.8 Hz), 4.73 (1H, d, J = 13.2 Hz), 5.29 (2H, s), 6.83 (1H, t, J = 5.4 Hz), 7.09-7.15 (3H, m), 7.34 (4H, d, J = 8.4 Hz), 7.73 (1H, s), 7.91 (2H, dt, J = 9.4, 2.4 Hz). |
| 580 | 600 (M + H). | 1H-NMR (CDCl$_3$, 400 MHz) δ: 0.98 (3H, t, J = 7.5 Hz), 2.06-2.20 (2H, m), 2.85-3.06 (2H, m), 3.34-3.45 (1H, m), 3.84 (1H, dt, J = 13.9, 3.6 Hz), 4.25 (1H, d, J = 13.2 Hz), 4.38-4.51 (2H, m), 4.59 (1H, t, J = 3.1 Hz), 4.74 (1H, d, J = 14.1 Hz), 6.56 (1H, dd, J = 6.2, 1.1 Hz), 7.02 (1H, t, J = 5.5 Hz), 7.20 (2H, d, J = 8.2 Hz), 7.37 (4H, t, J = 7.6 Hz), 7.94 (2H, dt, J = 9.5, 2.4 Hz), 8.22 (1H, d, J = 6.4 Hz), 8.53 (1H, s). |
| 581 | 594 (M + H). | 1H-NMR (CDCl$_3$, 400 MHz) δ: 1.29 (9H, s), 2.63-3.45 (3H, m), 3.82 (1H, d, J = 13.7 Hz), 4.29-4.99 (5H, m), 5.98 (1H, br s), 6.88 (1H, br s), 7.09 (2H, d, J = 8.4 Hz), 7.29-7.39 (5H, m), 7.91 (2H, dt, J = 9.4, 2.5 Hz), 11.44-11.83 (1H, m). |
| 582 | 670 (M + H). | 1H-NMR (CDCl$_3$, 300 MHz) δ: 1.25-1.33 (12H, m), 2.96-3.16 (2H, m), 3.36-3.47 (1H, m), 3.74-3.88 (2H, m), 4.20 (2H, q, J = 7.0 Hz), 4.40 (2H, d, J = 5.7 Hz), 4.47 (1H, d, J = 13.6 Hz), 4.57 (1H, br s), 5.67 (2H, br s), 6.76 (1H, t, J = 5.3 Hz), 7.13 (2H, d, J = 8.3 Hz), 7.31-7.37 (4H, m), 7.88-7.94 (2H, m). |
| 583 | 665 (M + H). | 1H-NMR (CD$_3$OD, 300 MHz) δ: 1.23 (9H, s), 2.48 (3H, s), 3.16-3.25 (1H, m), 3.44 (1H, dd, J = 13.8, 4.7 Hz), 3.81-3.97 (3H, m), 4.17-4.32 (2H, m), 4.40 (1H, d, J = 13.2 Hz), 4.66 (1H, br s), 7.11 (2H, d, J = 8.3 Hz), 7.27 (2H, d, J = 8.3 Hz), 7.39 (2H, d, J = 9.0 Hz), 7.95 (2H, d, J = 9.0 Hz), 8.59 (1H, t, J = 6.4 Hz). |

TABLE 351

| Example No. | MS ESI m/e: | NMR |
|---|---|---|
| 584 | 615 (M + H). | 1H-NMR (CDCl$_3$, 400 MHz) δ: 0.98 (3H, t, J = 7.5 Hz), 2.05-2.20 (2H, m), 2.83-3.07 (2H, m), 3.31-3.41 (1H, m), 3.78 (1H, dt, J = 13.6, 3.5 Hz), 4.07 (1H, d, J = 12.6 Hz), 4.37-4.73 (6H, m), 5.93 (1H, d, J = 6.0 Hz), 7.08 (1H, t, J = 5.4 Hz), 7.21 (2H, d, J = 8.2 Hz), 7.38 (4H, dd, J = 14.6, 8.6 Hz), 7.87 (1H, d, J = 6.2 Hz), 7.93 (2H, dt, J = 9.6, 2.5 Hz). |
| 585 | 615 (M + H). | 1H-NMR (CDCl$_3$, 400 MHz) δ: 0.97 (3H, t, J = 7.5 Hz), 2.12 (2H, dq, J = 31.5, 7.8 Hz), 3.01-3.30 (3H, m), 3.74 (1H, dt, J = 13.3, 3.0 Hz), 4.30-4.69 (6H, m), 5.03 (1H, d, J = 14.3 Hz), 5.67 (1H, d, J = 5.7 Hz), 7.18 (2H, d, J = 8.2 Hz), 7.29-7.38 (5H, m), 7.70 (1H, d, J = 5.7 Hz), 7.99 (2H, dt, J = 9.6, 2.5 Hz). |
| 586 | 643 (M + H). | 1H-NMR (CDCl$_3$, 400 MHz) δ: 0.98 (3H, t, J = 7.5 Hz), 2.03-2.20 (2H, m), 2.92-2.99 (1H, m), 3.09 (1H, dd, J = 13.5, 4.2 Hz), 3.41-3.49 (1H, m), 3.89 (1H, dt, J = 13.7, 3.4 Hz), 4.31 (1H, d, J = 13.2 Hz), 4.44 (2H, d, J = 6.0 Hz), 4.60-4.62 (1H, br m), 4.82 (1H, d, J = 13.9 Hz), 5.41 (1H, s), 7.02 (1H, t, J = 6.1 Hz), 7.20 (2H, d, J = 8.2 Hz), 7.31-7.42 (5H, m), 7.93 (2H, d, J = 9.0 Hz), 8.05 (1H, d, J = 1.3 Hz), 8.79 (1H, d, J = 1.5 Hz). |
| 587 | 738 (M + H). | 1H-NMR (CDCl$_3$, 300 MHz) δ: 1.32 (9H, s), 1.46 (9H, s), 2.58 (2H, s), 2.79-2.97 (2H, m), 3.35-3.49 (1H, m), 3.56-3.73 (2H, m), 3.76-3.95 (2H, m), 4.32-4.47 (5H, m), 4.58 (1H, s), 6.80 (1H, s), 7.14 (2H, d, J = 8.3 Hz), 7.30-7.38 (4H, m), 7.91 (2H, d, J = 8.7 Hz). |
| 588 | 638 (M + H). | 1H-NMR (CDCl$_3$, 300 MHz) δ: 1.32 (9H, s), 2.50-2.58 (2H, m), 2.79-2.90 (1H, m), 2.93 (1H, dd, J = 13.0, 4.3 Hz), 3.10 (2H, td, J = 5.7, 1.3 Hz), 3.36-3.48 (1H, m), 3.75-3.93 (4H, m), 4.36-4.44 (3H, m), 4.58 (1H, s), 6.81 (1H, t, J = 5.7 Hz), 7.14 (2H, d, J = 7.9 Hz), 7.30-7.38 (4H, m), 7.91 (2H, d, J = 9.0 Hz). |
| 589 | 680 (M + H). | 1H-NMR (CDCl$_3$, 300 MHz) δ: 1.32 (9H, s), 2.13 (1H, s), 2.16 (2H, s), 2.58-2.70 (2H, m), 2.80-2.99 (2H, m), 3.36-3.49 (1H, m), 3.63-3.70 (1H, m), 3.73-3.94 (3H, m), 4.36-4.51 (4H, m), 4.53-4.67 (2H, m), 6.74-6.83 (1H, m), 7.15 (2H, d, J = 8.3 Hz), 7.29-7.38 (4H, m), 7.90 (2H, d, J = 8.7 Hz). |

TABLE 352

| Example No. | MS ESI m/e: | NMR |
|---|---|---|
| 590 | 642 (M + H). | 1H-NMR (CDCl₃, 400 MHz) δ: 1.00 (3H, t, J = 7.5 Hz), 2.15 (2H, td, J = 16.0, 7.6 Hz), 2.47 (1H, ddd, J = 14.7, 11.7, 3.1 Hz), 2.85 (1H, dd, J = 13.9, 4.0 Hz), 3.23 (1H, ddd, J = 14.1, 11.5, 2.9 Hz), 3.87 (1H, d, J = 14.3 Hz), 3.96 (1H, d, J = 15.7 Hz), 4.12 (1H, d, J = 15.7 Hz), 4.38 (1H, d, J = 14.1 Hz), 4.46-4.57 (3H, m), 4.68 (1H, d, J = 13.9 Hz), 6.98 (1H, t, J = 5.3 Hz), 7.26-7.30 (3H, m), 7.39 (2H, d, J = 8.6 Hz), 7.46 (2H, d, J = 8.2 Hz), 7.91 (2H, d, J = 8.8 Hz), 8.63 (1H, d, J = 5.3 Hz), 9.10 (1H, s). |
| 591 | 625 (M + H). | 1H-NMR (CDCl₃, 400 MHz) δ: 0.99 (3H, dd, J = 8.5, 6.5 Hz), 2.07-2.19 (2H, m), 2.95-3.07 (2H, m), 3.40-3.47 (1H, m), 3.88 (1H, dt, J = 14.0, 3.7 Hz), 4.28 (1H, d, J = 13.7 Hz), 4.44 (2H, d, J = 6.0 Hz), 4.58-4.60 (1H, br m), 4.83 (1H, d, J = 13.9 Hz), 6.96 (1H, t, J = 6.1 Hz), 7.22 (2H, d, J = 7.9 Hz), 7.35-7.42 (4H, m), 7.93 (2H, d, J = 9.0 Hz), 8.20 (1H, d, J = 1.3 Hz), 8.26 (1H, d, J = 1.5 Hz). |
| 592 | 668 (M + H). | 1H-NMR (DMSO-d₆, 400 MHz) δ: 0.80 (3H, t, J = 7.5 Hz), 2.01-2.17 (2H, m), 3.01-3.13 (1H, br m), 3.24-3.38 (1H, m), 3.74-3.76 (2H, m), 4.05-4.18 (3H, m), 4.55-4.68 (2H, m), 7.18 (2H, d, J = 7.9 Hz), 7.33 (2H, d, J = 8.2 Hz), 7.45 (2H, d, J = 8.4 Hz), 7.91 (3H, m), 8.69 (1H, s), 8.75 (1H, t, J = 5.8 Hz). |
| 593 | 677 (M + H). | 1H-NMR (CDCl₃, 400 MHz) δ: 1.31 (9H, s), 2.47 (4H, s), 2.85-2.96 (2H, m), 3.43-3.52 (3H, m), 3.70 (4H, t, J = 4.5 Hz), 3.88 (1H, d, J = 13.9 Hz), 4.04 (1H, d, J = 13.0 Hz), 4.35-4.45 (2H, m), 4.59 (1H, s), 4.76 (1H, d, J = 12.4 Hz), 6.87 (1H, t, J = 5.7 Hz), 7.12 (2H, d, J = 8.4 Hz), 7.31-7.36 (4H, m), 7.92 (2H, d, J = 9.0 Hz), 8.01 (1H, d, J = 1.3 Hz), 8.14 (1H, d, J = 1.5 Hz). |
| 594 | 690 (M + H). | 1H-NMR (CDCl₃, 400 MHz) δ: 1.32 (9H, s), 2.28 (3H, s), 2.35-2.59 (8H, m), 2.82-2.96 (2H, m), 3.37-3.51 (1H, m), 3.53 (2H, s), 3.88 (1H, d, J = 13.9 Hz), 4.02 (1H, d, J = 13.0 Hz), 4.34-4.47 (2H, m), 4.59 (1H, s), 4.76 (1H, d, J = 13.5 Hz), 6.86 (1H, t, J = 5.8 Hz), 7.12 (2H, d, J = 8.6 Hz), 7.31-7.36 (4H, m), 7.92 (2H, d, J = 9.0 Hz), 8.00 (1H, d, J = 1.3 Hz), 8.13 (1H, d, J = 1.5 Hz). |

TABLE 353

| Example No. | MS ESI m/e: | NMR |
|---|---|---|
| 595 | 657 (M + H). | 1H-NMR (CDCl₃, 400 MHz) δ: 0.98 (3H, t, J = 7.5 Hz), 2.05-2.20 (2H, m), 2.25 (6H, s), 2.83-2.99 (2H, m), 3.40-3.51 (3H, m), 3.88 (1H, d, J = 13.7 Hz), 4.02 (1H, d, J = 12.8 Hz), 4.47 (2H, d, J = 5.5 Hz), 4.60 (1H, s), 4.75 (1H, d, J = 13.7 Hz), 7.02 (1H, t, J = 5.8 Hz), 7.24 (2H, d, J = 8.2 Hz), 7.32-7.42 (4H, m), 7.90-7.96 (2H, m), 7.99 (1H, s), 8.12 (1H, d, J = 1.3 Hz). |
| 596 | 663 (M + H). | 1H-NMR (CDCl₃, 400 MHz) δ: 0.98 (3H, t, J = 7.5 Hz), 2.04-2.45 (5H, m), 3.01-3.16 (2H, m), 3.41-3.51 (1H, m), 3.72 (1H, d, J = 11.7 Hz), 3.88 (1H, dt, J = 14.0, 3.0 Hz), 4.30-4.63 (4H, m), 6.96 (1H, t, J = 5.6 Hz), 7.25 (2H, d, J = 8.4 Hz), 7.39 (4H, dd, J = 19.4, 8.2 Hz), 7.92 (3H, dt, J = 9.4, 2.5 Hz). |
| 597 | 650 (M + H). | 1H-NMR (CDCl₃, 400 MHz) δ: 1.29 (9H, s), 3.07-3.32 (2H, m), 3.50 (1H, t, J = 12.2 Hz), 3.90 (1H, d, J = 14.3 Hz), 4.01-4.65 (5H, m), 6.53 (1H, s), 6.94 (1H, s), 7.10 (2H, d, J = 8.4 Hz), 7.28-7.35 (4H, m), 7.51 (1H, s), 7.90 (2H, d, J = 8.8 Hz). |
| 598 | 569 (M + H). | 1H-NMR (CDCl₃, 400 MHz) δ: 2.17 (3H, s), 2.43 (1H, ddd, J = 14.1, 11.4, 2.4 Hz), 2.88 (1H, dd, J = 13.5, 4.2 Hz), 3.18 (1H, ddd, J = 14.2, 11.4, 2.7 Hz), 3.85 (1H, d, J = 14.6 Hz), 4.37 (1H, d, J = 13.5 Hz), 4.47-4.65 (4H, m), 6.88 (1H, t, J = 5.4 Hz), 6.94 (1H, d, J = 3.7 Hz), 7.17 (1H, t, J = 5.4 Hz), 7.37 (2H, d, J = 9.3 Hz), 7.41-7.47 (1H, m), 7.63 (1H, d, J = 7.7 Hz), 7.69 (1H, d, J = 7.5 Hz), 7.91 (2H, d, J = 8.8 Hz), 8.56 (1H, d, J = 4.6 Hz). |
| 599 | 575 (M + H). | 1H-NMR (CDCl₃, 400 MHz) δ: 2.14 (3H, s), 2.48 (1H, ddd, J = 14.2, 11.1, 2.0 Hz), 2.94 (1H, dd, J = 13.7, 4.4 Hz), 3.29 (1H, ddd, J = 14.8, 11.7, 3.4 Hz), 3.87 (1H, d, J = 14.6 Hz), 4.37 (1H, d, J = 13.7 Hz), 4.45-4.60 (4H, m), 7.01 (1H, s), 7.09 (1H, dd, J = 5.1, 3.7 Hz), 7.18 (1H, t, J = 5.2 Hz), 7.34 (2H, d, J = 7.9 Hz), 7.41 (1H, d, J = 5.1 Hz), 7.52 (1H, d, J = 3.5 Hz), 7.94 (2H, d, J = 9.0 Hz). |

TABLE 354

| Example No. | MS ESI m/e: | NMR |
|---|---|---|
| 600 | 716 (M + H). | 1H-NMR (CDCl$_3$, 300 MHz) δ: 1.32 (9H, s), 2.68-2.75 (2H, m), 2.83 (3H, s), 2.85-2.98 (2H, m), 3.37-3.49 (1H, m), 3.60 (2H, t, J = 5.8 Hz), 3.80-3.95 (2H, m), 4.33-4.45 (5H, m), 4.56-4.60 (1H, m), 6.75-6.82 (1H, m), 7.15 (2H, d, J = 8.3 Hz), 7.30-7.38 (4H, m), 7.91 (2H, d, J = 9.0 Hz). |
| 601 | 709 (M + H). | 1H-NMR (CDCl$_3$, 300 MHz) δ: 1.15 (3H, t, J = 7.2 Hz), 1.32 (9H, s), 2.63 (2H, s), 2.79-2.90 (1H, m), 2.93 (1H, dd, J = 13.0, 4.3 Hz), 3.29 (2H, dt, J = 13.8, 6.3 Hz), 3.36-3.49 (1H, m), 3.61 (2H, t, J = 5.5 Hz), 3.79-3.93 (2H, m), 4.35-4.45 (6H, m), 4.58 (1H, s), 6.77-6.83 (1H, m), 7.14 (2H, d, J = 8.3 Hz), 7.30-7.38 (4H, m), 7.90 (2H, d, J = 8.7 Hz). |
| 602 | 651 (M + H). | 1H-NMR (DMSO-d$_6$, 300 MHz) δ: 1.21 (9H, s), 3.60 (1H, dd, J = 13.9, 4.5 Hz), 3.74-3.83 (2H, br m), 3.96-4.15 (3H, m), 4.35-4.47 (1H, br m), 4.59-4.63 (1H, m), 7.05 (2H, d, J = 8.3 Hz), 7.22 (2H, d, J = 8.3 Hz), 7.50 (2H, d, J = 7.9 Hz), 7.91 (2H, d, J = 8.7 Hz), 8.10 (1H, s), 8.70 (1H, t, J = 6.0 Hz), 12.45 (1H, br s). |
| 603 | 657 (M + H). | 1H-NMR (DMSO-d$_6$, 400 MHz) δ: 1.27 (9H, s), 3.17 (1H, d, J = 5.1 Hz), 3.71-3.78 (2H, m), 4.03-4.12 (2H, m), 4.16 (2H, d, J = 5.5 Hz), 4.20 (2H, s), 4.37 (1H, d, J = 13.5 Hz), 4.59-4.66 (1H, m), 7.16 (2H, d, J = 8.2 Hz), 7.37 (2H, d, J = 8.4 Hz), 7.52 (2H, d, J = 7.9 Hz), 7.85 (1H, br s), 7.92 (2H, d, J = 8.8 Hz), 8.63 (1H, t, J = 5.7 Hz), 8.99 (1H, br s). |
| 604 | 645 (M + H). | 1H-NMR (CDCl$_3$, 300 MHz) δ: 0.98 (3H, t, J = 7.5 Hz), 2.02-2.22 (2H, m), 2.84-2.91 (1H, m), 2.97 (1H, dd, J = 13.4, 4.0 Hz), 3.39-3.47 (1H, m), 3.78-3.96 (2H, m), 4.48 (2H, t, J = 5.5 Hz), 4.54-4.71 (6H, m), 7.01-7.07 (1H, m), 7.23 (2H, d, J = 8.3 Hz), 7.33 (1H, s), 7.33-7.35 (4H, m), 7.39 (2H, d, J = 8.3 Hz), 7.93 (2H, d, J = 9.0 Hz). |

TABLE 355

| Example No. | MS ESI m/e: | NMR |
|---|---|---|
| 605 | 615 (M + H). | 1H-NMR (CD$_3$OD, 400 MHz) δ: 0.93 (3H, t, J = 7.5 Hz), 2.14 (2H, dq, J = 31.6, 7.9 Hz), 3.10 (1H, dq, J = 13.3, 4.4 Hz), 3.26-3.36 (1H, m), 3.70-3.83 (2H, m), 3.96 (1H, dt, J = 12.9, 3.9 Hz), 4.33 (2H, s), 4.55 (1H, dd, J = 4.5, 3.1 Hz), 4.64 (1H, dd, J = 13.8, 2.7 Hz), 5.58 (1H, d, J = 0.7 Hz), 7.26 (2H, d, J = 8.6 Hz), 7.36 (2H, d, J = 8.6 Hz), 7.43 (2H, d, J = 8.4 Hz), 7.90 (1H, d, J = 0.9 Hz), 7.97 (2H, dt, J = 9.5, 2.4 Hz). |
| 606 | 614 (M + H). | 1H-NMR (CDCl$_3$, 400 MHz) δ: 1.32 (9H, s), 3.02-3.19 (2H, m), 3.40-3.51 (1H, m), 3.80-3.91 (2H, m), 3.95 (3H, s), 4.23 (1H, d, J = 13.0 Hz), 4.40 (2H, d, J = 5.5 Hz), 4.58 (1H, br s), 6.69 (1H, t, J = 5.6 Hz), 7.13 (2H, d, J = 8.2 Hz), 7.31-7.38 (4H, m), 7.89 (2H, dt, J = 9.4, 2.4 Hz). |
| 607 | 648 (M + H). | 1H-NMR (CDCl$_3$, 400 MHz) δ: 0.98 (3H, t, J = 7.5 Hz), 2.05-2.21 (2H, m), 2.47-2.57 (1H, m), 2.75 (1H, dd, J = 14.6, 3.5 Hz), 3.06-3.16 (1H, m), 3.93 (1H, d, J = 14.6 Hz), 4.17 (1H, d, J = 13.7 Hz), 4.44-4.56 (3H, m), 4.59 (1H, s), 7.16 (1H, t, J = 5.7 Hz), 7.27 (2H, d, J = 8.7 Hz), 7.41 (2H, d, J = 8.7 Hz), 7.43 (2H, d, J = 8.6 Hz), 7.55 (1H, s), 7.93 (2H, d, J = 8.6 Hz), 8.36 (1H, s), 8.75 (1H, s). |
| 608 | 516 (M + H). | 1H-NMR (CDCl$_3$, 400 MHz) δ: 2.16 (3H, s), 2.41 (1H, ddd, J = 14.3, 11.0, 2.8 Hz), 2.86 (1H, dd, J = 13.5, 4.2 Hz), 3.15 (1H, ddd, J = 14.8, 11.6, 2.9 Hz), 3.79-3.83 (1H, m), 3.81 (3H, s), 4.27-4.40 (3H, m), 4.46 (1H, d, J = 3.3 Hz), 4.54 (1H, d, J = 13.5 Hz), 6.72 (1H, t, J = 5.7 Hz), 6.87 (2H, d, J = 8.6 Hz), 7.13 (2H, d, J = 8.6 Hz), 7.36 (2H, d, J = 8.2 Hz), 7.89 (2H, d, J = 8.8 Hz). |
| 609 | 592 (M + H). | 1H-NMR (DMSO-d$_6$, 400 MHz, 120° C.) δ: 0.87-0.95 (9H, m), 2.12-2.25 (3H, m), 2.64-2.71 (2H, m), 2.92-3.01 (1H, m), 3.15-3.21 (1H, m), 3.61-3.66 (1H, m), 4.02 (1H, d, J = 12.8 Hz), 4.21 (2H, d, J = 5.5 Hz), 4.35-4.42 (1H, m), 4.47-4.51 (1H, m), 7.29 (2H, d, J = 7.9 Hz), 7.41 (2H, d, J = 7.9 Hz), 7.45 (1H, d, J = 8.4 Hz), 7.90 (2H, dd, J = 9.4, 2.5 Hz), 8.23 (1H, br s). |

TABLE 356

| Example No. | MS ESI m/e: | NMR |
|---|---|---|
| 610 | 590 (M + H). | 1H-NMR (DMSO-d<sub>6</sub>, 400 MHz) δ: 0.53-0.67 (4H, m), 0.92 (3H, t, J = 7.5 Hz), 1.67-1.76 (1H, m), 2.11-2.26 (2H, m), 2.97-3.06 (1H, m), 3.22-3.29 (1H, m), 3.65 (2H, s), 4.09-4.16 (1H, m), 4.23 (2H, d, J = 5.7 Hz), 4.51 (2H, d, J = 4.0 Hz), 7.29 (2H, d, J = 7.7 Hz), 7.41 (2H, d, J = 8.2 Hz), 7.44 (2H, d, J = 7.9 Hz), 7.90 (2H, d, J = 8.6 Hz), 8.23 (1H, br s). |
| 611 | 606 (M + H). | 1H-NMR (CDCl<sub>3</sub>, 400 MHz) δ: 0.98 (3H, t, J = 7.5 Hz), 1.14 (9H, s), 2.04-2.20 (2H, m), 3.06 (1H, dd, J = 14.1, 4.2 Hz), 3.21-3.31 (2H, m), 3.58-3.68 (1H, m), 3.93-4.04 (1H, m), 4.36 (1H, dd, J = 14.8, 5.7 Hz), 4.49 (1H, dd, J = 14.8, 6.2 Hz), 4.57 (1H, s), 4.85 (1H, d, J = 13.7 Hz), 7.19 (1H, t, J = 5.6 Hz), 7.30 (2H, d, J = 8.2 Hz), 7.35 (2H, d, J = 8.2 Hz), 7.42 (2H, d, J = 8.2 Hz), 7.96 (2H, d, J = 8.6 Hz). |
| 612 | 706 (M + H). | 1H-NMR (CDCl<sub>3</sub>, 400 MHz) δ: 0.98 (3H, t, J = 7.5 Hz), 1.55 (6H, s), 2.05-2.20 (2H, m), 2.56-2.65 (1H, m), 2.81 (1H, dd, J = 14.3, 3.5 Hz), 3.16 (1H, dt, J = 19.0, 6.6 Hz), 3.91 (1H, d, J = 14.1 Hz), 4.16 (1H, d, J = 13.5 Hz), 4.46-4.57 (3H, m), 4.59 (1H, s), 6.57 (1H, s), 7.08 (1H, t, J = 6.0 Hz), 7.27 (2H, d, J = 7.7 Hz), 7.40 (2H, d, J = 9.3 Hz), 7.42 (2H, d, J = 8.4 Hz), 7.93 (2H, d, J = 8.4 Hz). |
| 613 | 502 (M + H). | 1H-NMR (CDCl<sub>3</sub>, 400 MHz) δ: 2.16 (3H, s), 2.42 (1H, ddd, J = 14.9, 10.4, 2.9 Hz), 2.85 (1H, dd, J = 13.5, 4.2 Hz), 3.15 (1H, ddd, J = 14.3, 11.9, 3.1 Hz), 3.79 (1H, dt, J = 14.6, 2.3 Hz), 4.24-4.44 (3H, m), 4.46 (1H, d, J = 4.0 Hz), 4.53 (1H, d, J = 13.5 Hz), 5.40 (1H, s), 6.75-6.80 (3H, m), 7.07 (2H, d, J = 8.6 Hz), 7.37 (2H, d, J = 8.8 Hz), 7.89 (2H, d, J = 8.8 Hz). |
| 614 | 568 (M + H). | 1H-NMR (CDCl<sub>3</sub>, 400 MHz) δ: 2.18 (3H, s), 2.41 (1H, ddd, J = 14.5, 11.6, 3.1 Hz), 2.87 (1H, dd, J = 13.5, 4.2 Hz), 3.19 (1H, ddd, J = 15.3, 11.1, 3.0 Hz), 3.84 (1H, d, J = 14.1 Hz), 4.37 (1H, d, 14.1 Hz), 4.48-4.63 (4H, m), 6.87 (1H, t, J = 4.7 Hz), 6.90 (1H, d, J = 3.7 Hz), 7.14 (1H, d, J = 3.5 Hz), 7.29 (1H, d, J = 7.5 Hz), 7.34-7.40 (4H, m), 7.57 (2H, d, J = 7.5 Hz), 7.91 (2H, d, J = 9.0 Hz). |

TABLE 357

| Example No. | MS ESI m/e: | NMR |
|---|---|---|
| 615 | 652 (M + H). | 1H-NMR (CDCl<sub>3</sub>, 300 MHz) δ: 0.95 (3H, t, J = 7.5 Hz), 1.99-2.18 (2H, m), 2.95-3.07 (1H, m), 3.20 (1H, dd, J = 14.3, 3.4 Hz), 3.41-3.50 (1H, m), 3.96 (1H, d, J = 14.3 Hz), 4.40 (2H, d, J = 6.0 Hz), 4.67 (1H, s), 4.81 (1H, d, J = 13.6 Hz), 5.07 (1H, d, J = 13.6 Hz), 7.00 (1H, t, J = 6.0 Hz), 7.14 (2H, d, J = 7.9 Hz), 7.31 (2H, d, J = 7.9 Hz), 7.39 (2H, d, J = 8.3 Hz), 7.96 (2H, d, 3 = 8.7 Hz), 8.77 (1H, s), 9.23 (1H, s), 9.27 (1H, s). |
| 616 | 671 (M + H). | 1H-NMR (CDCl<sub>3</sub>, 300 MHz) δ: 0.98 (3H, t, J = 7.5 Hz), 2.05-2.20 (2H, m), 2.87-2.97 (2H, m), 3.40-3.53 (1H, m), 3.80-3.90 (1H, m), 3.92-4.02 (1H, m), 4.48 (2H, d, J = 5.7 Hz), 4.56 (1H, s), 4.67-4.75 (1H, m), 5.28 (2H, s), 7.00 (1H, t, J = 5.7 Hz), 7.11 (1H, s), 7.24 (2H, d, J = 8.3 Hz), 7.37 (2H, d, J = 8.7 Hz), 7.40 (2H, d, J = 8.3 Hz), 7.71 (1H, s), 7.93 (2H, d, J = 9.0 Hz). |
| 617 | 630 (M + H). | 1H-NMR (CDCl<sub>3</sub>, 300 MHz) δ: 1.27 (9H, s), 2.96-3.07 (1H, m), 3.20 (1H, dd, J = 14.1, 3.6 Hz), 3.40-3.49 (1H, m), 3.96 (1H, d, J = 15.1 Hz), 4.24-4.41 (2H, m), 4.67 (1H, s), 4.85 (1H, d, J = 14.3 Hz), 5.09 (1H, d, J = 13.9 Hz), 6.82 (1H, t, J = 5.7 Hz), 6.99 (2H, d, J = 8.3 Hz), 7.23 (2H, d, J = 8.3 Hz), 7.37 (2H, d, J = 8.3 Hz), 7.95 (2H, d, J = 8.7 Hz), 8.80 (1H, s), 9.22 (1H, s), 9.27 (1H, s). |
| 618 | 652 (M + H). | 1H-NMR (CDCl<sub>3</sub>, 300 MHz) δ: 1.30 (9H, s), 3.14-3.35 (2H, m), 3.46-3.59 (1H, m), 3.95 (1H, d, J = 14.3 Hz), 4.21-4.46 (3H, br m), 4.55-4.70 (2H, br m), 6.78 (1H, t, J = 5.7 Hz), 7.11 (2H, d, J = 8.3 Hz), 7.30-7.39 (4H, m), 7.88-7.96 (2H, m). |
| 619 | 631 (M + H). | 1H-NMR (CDCl<sub>3</sub>, 300 MHz) δ: 1.08 (3H, t, J = 7.0 Hz), 2.85 (3H, s), 2.94-3.07 (1H, m), 3.21 (1H, dd, J = 14.1, 3.6 Hz), 3.27-3.51 (3H, m), 3.93 (1H, d, J = 14.3 Hz), 4.13-4.31 (2H, m), 4.65 (1H, br s), 4.79-4.90 (1H, br m), 5.10 (1H, d, J = 13.9 Hz), 6.49 (2H, d, J = 8.7 Hz), 6.67 (1H, t, J = 5.1 Hz), 6.89 (2H, d, J = 8.7 Hz), 7.36 (2H, d, J = 8.3 Hz), 7.90-7.97 (2H, m), 8.79 (1H, s), 9.21 (1H, s), 9.25 (1H, s). |

TABLE 358

| Example No. | MS ESI m/e: | NMR |
|---|---|---|
| 620 | 621 (M + H). | 1H-NMR (CD₃OD, 300 MHz) δ: 1.27 (9H, s), 3.02-3.14 (1H, m), 3.21-3.28 (1H, m), 3.74-3.92 (3H, br m), 4.24-4.31 (3H, m), 4.64 (1H, br s), 7.06 (2H, d, J = 7.9 Hz), 7.18-7.28 (3H, m), 7.41 (2H, d, J = 8.3 Hz), 7.89-8.02 (3H, m), 8.14 (1H, s), 8.58 (1H, br s). |
| 621 | 508 (M + H). | 1H-NMR (CDCl₃, 400 MHz) δ: 1.19-1.64 (10.0H, m), 1.73 (0.8H, s), 2.03 (0.6H, s), 2.13 (2.4H, s), 2.43-2.53 (0.8H, m), 2.62 (0.2H, s), 2.89-3.08 (1.2H, m), 3.17-3.44 (3.0H, m), 3.69-3.87 (1.0H, m), 4.32-4.58 (2.6H, m), 4.67 (0.2H, s), 4.95 (0.2H, d, J = 14.3 Hz), 6.60 (0.2H, br s), 6.86 (0.8H, br s), 7.33 (0.4H, d, J = 8.6 Hz), 7.41 (1.6H, d, J = 8.2 Hz), 7.94 (2.0H, d, J = 9.0 Hz). |
| 622 | 574 (M + H). | 1H-NMR (CDCl₃, 400 MHz) δ: 2.17 (3H, s), 2.35-2.44 (1H, m), 2.85 (1H, dd, J = 13.5, 4.2 Hz), 3.15-3.23 (1H, m), 3.83 (1H, d, J = 14.3 Hz), 4.36 (1H, d, J = 13.9 Hz), 4.45-4.64 (4H, m), 6.83 (1H, d, J = 3.7 Hz), 6.94 (1H, br s), 6.98-7.03 (2H, m), 7.16 (1H, d, J = 4.2 Hz), 7.21 (1H, dd, J = 5.1, 1.1 Hz), 7.37 (2H, d, J = 8.2 Hz), 7.91 (2H, d, J = 8.8 Hz). |
| 623 | 568 (M + H). | 1H-NMR (CDCl₃, 400 MHz) δ: 2.15 (3H, s), 2.36-2.46 (1H, m), 2.85 (1H, dd, J = 13.5, 4.2 Hz), 3.16-3.24 (1H, m), 3.82 (1H, d, J = 14.3 Hz), 4.35 (1H, d, J = 13.7 Hz), 4.42-4.64 (4H, m), 6.92 (1H, br s), 7.08 (1H, dd, J = 5.1, 3.5 Hz), 7.22 (2H, d, J = 8.4 Hz), 7.27-7.33 (2H, m), 7.37 (2H, d, J = 8.2 Hz), 7.59 (2H, d, J = 8.4 Hz), 7.90 (2H, d, J = 8.8 Hz). |
| 624 | 544 (M + H). | 1H-NMR (CDCl₃, 300 MHz) δ: 0.95 (3H, t, J = 7.3 Hz), 1.62 (2H, dd, J = 15.8, 7.9 Hz), 2.21 (3H, s), 2.56 (2H, dt, J = 11.2, 3.7 Hz), 2.69 (1H, ddd, J = 13.9, 9.8, 3.6 Hz), 3.06 (1H, dd, J = 13.6, 3.8 Hz), 3.40 (1H, ddd, J = 14.2, 9.9, 3.7 Hz), 3.63 (1H, td, J = 8.7, 3.9 Hz), 3.94 (1H, dd, J = 15.6, 4.0 Hz), 4.34 (1H, dt, J = 14.4, 4.0 Hz), 4.54-4.67 (2H, m), 4.99 (1H, dd, J = 15.4, 8.7 Hz), 6.08 (1H, s), 6.62 (1H, d, J = 6.8 Hz), 6.96 (1H, t, J = 5.8 Hz), 7.03 (1H, d, J = 7.9 Hz), 7.10 (1H, s), 7.42 (2H, d, J = 8.7 Hz), 7.93 (2H, d, J = 8.7 Hz). |

TABLE 359

| Example No. | MS ESI m/e: | NMR |
|---|---|---|
| 625 | 636 (M + H). | 1H-NMR (CDCl₃, 400 MHz) δ: 0.98 (3H, t, J = 7.5 Hz), 2.13 (2H, dq, J = 31.5, 7.8 Hz), 3.01-3.19 (2H, m), 3.40-3.51 (1H, m), 3.76-3.99 (5H, m), 4.25 (1H, d, J = 12.6 Hz), 4.40-4.63 (3H, m), 6.88 (1H, t, J = 5.3 Hz), 7.25 (2H, d, J = 8.8 Hz), 7.39 (4H, dd, J = 24.6, 8.3 Hz), 7.91 (2H, dt, J = 9.3, 2.4 Hz). |
| 626 | 640(M + H). | 1H-NMR (CDCl₃, 400 MHz) δ: 0.96 (3H, t, J = 7.5 Hz), 2.02-2.18 (2H, m), 2.85-2.97 (1H, m), 3.08 (1H, dd, J = 13.7, 3.7 Hz), 3.36-3.47 (1H, m), 3.90 (1H, dt, J = 14.0, 2.9 Hz), 4.36-4.49 (2H, m), 4.57-4.69 (2H, m), 4.79 (1H, d, J = 14.3 Hz), 6.62 (1H, d, J = 7.9 Hz), 7.06-7.20 (3H, m), 7.35 (4H, dd, J = 23.5, 8.0 Hz), 7.95 (2H, dt, J = 9.4, 2.4 Hz), 8.15 (1H, s), 8.35 (1H, d, J = 7.7 Hz). |
| 627 | 658 (M + H). | 1H-NMR (CDCl₃, 300 MHz) δ: 2.94-3.08 (1H, m), 3.19 (1H, dd, J = 13.8, 4.0 Hz), 3.42-3.50 (1H, m), 3.96 (1H, d, J = 15.1 Hz), 4.30-4.43 (2H, m), 4.65 (1H, s), 4.80 (1H, d, 3 = 11.7 Hz), 5.05 (1H, d, J = 14.3 Hz), 7.00 (1H, t, J = 5.7 Hz), 7.05 (2H, d, J = 8.7 Hz), 7.14 (2H, d, J = 8.3 Hz), 7.39 (2H, d, J = 8.7 Hz), 7.96 (2H, d, J = 8.7 Hz), 8.76 (1H, s), 9.23 (1H, s), 9.27 (1H, s). |
| 628 | 620 (M + H). | 1H-NMR (CD₃OD, 300 MHz) δ: 0.91 (3H, t, J = 7.3 Hz), 1.53-1.66 (2H, m), 2.54 (2H, t, J = 7.7 Hz), 2.92-3.04 (1H, m), 3.19 (1H, dd, J = 13.6, 4.1 Hz), 3.69-3.91 (2H, m), 3.97 (1H, d, J = 12.1 Hz), 4.25 (2H, dd, J = 19.4, 14.9 Hz), 4.53 (1H, d, J = 13.9 Hz), 4.61 (1H, t, J = 3.4 Hz), 7.01 (2H, d, J = 8.3 Hz), 7.07 (2H, d, J = 7.9 Hz), 7.35 (1H, s), 7.40 (2H, d, J = 7.9 Hz), 7.97 (2H, d, J = 8.7 Hz). |
| 629 | 608 (M + H). | 1H-NMR (CDCl₃, 400 MHz) δ: 2.92-3.26 (2H, m), 3.38-3.50 (1H, m), 3.94 (1H, dt, J = 14.0, 3.2 Hz), 4.32 (2H, ddd, 3 = 19.0, 13.0, 4.3 Hz), 4.61-4.84 (2H, m), 5.06 (1H, d, J = 14.6 Hz), 6.99-7.16 (5H, m), 7.39 (2H, d, J = 8.2 Hz), 7.96 (2H, dt, J = 9.5, 2.4 Hz), 8.74 (1H, s), 9.25 (2H, d, J = 16.8 Hz). |

TABLE 360

| Example No. | MS ESI m/e: | NMR |
|---|---|---|
| 630 | 618 (M + H). | 1H-NMR (CDCl₃, 400 MHz) δ: 3.02 (7H, s), 3.19 (1H, dd, J = 13.9, 3.5 Hz), 3.32-3.44 (1H, m), 3.93 (1H, dt, J = 14.2, 2.8 Hz), 4.14-4.26 (2H, m), 4.64 (1H, s), 4.79 (1H, d, J = 12.6 Hz), 5.08 (1H, d, J = 14.8 Hz), 6.24 (1H, d, J = 8.6 Hz), 6.78 (1H, t, J = 5.7 Hz), 7.11 (1H, dd, J = 8.8, 2.4 Hz), 7.38 (2H, d, J = 8.2 Hz), 7.90-7.97 (3H, m), 8.77 (1H, s), 9.23 (2H, d, J = 21.4 Hz). |
| 631 | 607 (M + H). | 1H-NMR (CD₃OD, 300 MHz) δ: 0.88 (3H, t, J = 7.3 Hz), 1.49-1.63 (2H, m), 2.49 (2H, t, J = 7.5 Hz), 2.96-3.12 (1H, m), 3.17-3.28 (1H, m), 3.70-3.89 (3H, m), 4.19-4.35 (3H, m), 4.66 (1H, br s), 6.95-7.07 (4H, m), 7.32-7.41 (3H, m), 7.92-8.17 (4H, m). |
| 632 | 650 (M + H). | 1H-NMR (CDCl₃, 300 MHz) δ: 0.94 (3H, t, J = 7.3 Hz), 1.96-2.17 (2H, m), 2.91-3.01 (1H, m), 3.11 (1H, dd, J = 13.6, 4.1 Hz), 3.42-3.51 (1H, m), 3.94 (1H, d, J = 13.9 Hz), 4.31-4.56 (3H, m), 4.66 (1H, s), 4.97 (1H, d, J = 13.2 Hz), 7.06-7.12 (1H, m), 7.13 (2H, d, J = 8.3 Hz), 7.26 (2H, d, J = 7.9 Hz), 7.35 (2H, d, J = 8.3 Hz), 7.41-7.46 (1H, m), 7.55-7.62 (2H, m), 7.90 (1H, d, J = 8.3 Hz), 7.96 (2H, d, J = 8.7 Hz), 8.62 (1H, s). |
| 633 | 673 (M + H). | 1H-NMR (DMSO-d₆, 300 MHz) δ: 0.85 (3H, t, J = 7.5 Hz), 2.03-2.23 (2H, m), 3.53-3.66 (1H, m), 3.73-3.87 (2H, m), 3.97 (1H, d, J = 12.8 Hz), 4.06-4.25 (2H, m), 4.45 (1H, d, J = 13.9 Hz), 4.61-4.66 (1H, m), 7.23 (2H, d, J = 8.3 Hz), 7.35 (2H, d, J = 8.3 Hz), 7.52 (2H, d, J = 8.3 Hz), 7.93 (2H, d, J = 8.7 Hz), 8.09 (1H, s), 8.82 (1H, t, J = 5.7 Hz). |
| 634 | 545 (M + H). | 1H-NMR (CDCl₃, 300 MHz) δ: 0.96 (3.0H, t, J = 7.3 Hz), 1.77 (2.0H, td, J = 14.6, 7.2 Hz), 2.06 (0.7H, s), 2.13 (2.3H, s), 2.42 (1.0H, ddd, J = 14.5, 11.5, 2.8 Hz), 2.83 (1.0H, dd, J = 13.8, 4.3 Hz), 3.04 (0.3H, dd, J = 14.5, 4.3 Hz), 3.22 (1.0H, ddd, J = 14.6, 11.2, 2.9 Hz), 3.33 (0.7H, d, J = 9.8 Hz), 3.69-3.91 (3.0H, m), 4.13-4.40 (2.0H, m), 4.44-4.97 (2.0H, m), 5.98 (0.7H, dd, J = 7.0, 2.1 Hz), 6.01-6.05 (0.3H, m), 6.27 (0.3H, s), 6.39 (0.7H, s), 7.05 (1.0H, t, J = 6.0 Hz), 7.19 (0.3H, d, J = 6.4 Hz), 7.22 (0.7H, d, J = 6.8 Hz), 7.34 (0.5H, d, J = 7.9 Hz), 7.42 (1.5H, d, J = 8.3 Hz), 7.94 (2.0H, d, J = 9.0 Hz). |

TABLE 361

| Example No. | MS ESI m/e: | NMR |
|---|---|---|
| 635 | 543 (M + H). | 1H-NMR (CDCl₃, 400 MHz) δ: 0.99 (3H, t, J = 7.4 Hz), 1.64 (2H, dd, J = 15.2, 7.5 Hz), 2.18 (3H, s), 2.41-2.53 (3H, m), 2.92 (1H, dd, J = 13.5, 4.0 Hz), 3.23 (1H, ddd, J = 14.8, 11.9, 3.7 Hz), 3.76 (1H, dt, J = 14.3, 2.5 Hz), 3.79 (2H, br s), 4.16 (1H, dd, J = 15.1, 4.7 Hz), 4.36 (1H, dt, 3= 13.0, 3.0 Hz), 4.49-4.60 (3H, m), 6.37 (1H, d, J = 1.5 Hz), 6.52 (1H, dd, J = 7.5, 1.3 Hz), 6.75 (1H, t, J = 5.4 Hz), 6.98 (1H, d, J = 7.7 Hz), 7.38 (2H, d, J = 8.2 Hz), 7.90 (2H, d, J = 8.8 Hz). |
| 636 | 516 (M + H). | 1H-NMR (CDCl₃, 400 MHz) δ: 2.16 (3H, s), 2.43 (1H, ddd, J = 14.6, 11.2, 2.0 Hz), 2.86 (1H, dd, J = 13.6, 4.1 Hz), 3.18 (1H, ddd, J = 14.9, 11.4, 3.1 Hz), 3.80-3.85 (1H, m), 3.80 (3H, s), 4.32-4.60 (5H, m), 6.76-6.84 (4H, m), 7.24-7.28 (1H, m), 7.37 (2H, d, J = 8.2 Hz), 7.90 (2H, d, J = 8.8 Hz). |
| 637 | 502 (M + H). | 1H-NMR (DMSO-d₆, 400 MHz) δ: 1.75 (3H, s), 2.57 (1H, ddd, J = 15.3, 11.8, 2.6 Hz), 3.26 (1H, dd, J = 14.4, 5.2 Hz), 3.40-3.48 (1H, m), 3.57-3.70 (2H, m), 3.97-4.06 (2H, m), 4.24 (1H, d, J = 12.1 Hz), 4.43-4.58 (1H, m), 6.59-6.66 (3H, m), 7.08 (1H, d, J = 7.9 Hz), 7.52 (2H, d, J = 8.4 Hz), 7.90 (2H, d, J = 9.0 Hz), 8.61 (1H, t, J = 5.4 Hz), 9.35 (1H, s). |
| 638 | 644 (M + H). | 1H-NMR (CDCl₃, 300 MHz) δ: 0.98 (3H, t, J = 7.5 Hz), 2.04-2.19 (2H, m), 2.77-2.89 (1H, m), 2.95 (1H, dd, J = 13.2, 4.1 Hz), 3.37-3.46 (1H, m), 3.81-3.88 (2H, m), 3.90 (2H, s), 4.39-4.54 (2H, m), 4.55-4.60 (1H, m), 4.60-4.68 (1H, m), 5.29 (2H, s), 7.06 (1H, t, J = 6.0 Hz), 7.22 (1H, s), 7.26 (2H, d, J = 5.3 Hz), 7.34 (2H, d, J = 7.9 Hz), 7.39 (2H, d, 3= 7.9 Hz), 7.93 (2H, d, J = 8.7 Hz). |
| 639 | 615 (M + H). | 1H-NMR (CDCl₃, 400 MHz) δ: 3.03-3.16 (1H, m), 3.27 (1H, dd, J = 13.9, 3.9 Hz), 3.63-3.70 (1H, m), 4.00 (1H, d, J = 14.4 Hz), 4.58 (1H, dd, J = 17.2, 6.1 Hz), 4.71 (1H, dd, J = 17.2, 6.1 Hz), 4.80 (1H, br s), 4.90-4.93 (1H, br m), 5.11 (1H, d, J = 13.7 Hz), 7.22-7.29 (1H, m), 7.35-7.42 (3H, m), 7.48-7.54 (2H, m), 8.03 (2H, d, J = 9.0 Hz), 8.75 (1H, s), 9.17 (1H, s), 9.17 (1H, s). |

TABLE 362

| Example No. | MS ESI m/e: | NMR |
|---|---|---|
| 640 | 674 (M + H). | 1H-NMR (DMSO-d$_6$, 300 MHz) δ: 0.85 (3H, t, J = 7.3 Hz), 2.01-2.23 (2H, m), 3.36-3.49 (1H, m), 3.62-3.87 (3H, m), 3.96-4.28 (3H, m), 4.45 (1H, br s), 4.67 (1H, br s), 7.24 (2H, d, J = 8.3 Hz), 7.34 (2H, d, J = 8.3 Hz), 7.52 (2H, d, J = 8.3 Hz), 7.94 (2H, d, J = 8.7 Hz), 8.84 (1H, t, J = 5.5 Hz). |
| 641 | 553 (M + H). | 1H-NMR (CDCl$_3$, 400 MHz) δ: 1.73 (6H, s), 2.15 (3H, s), 2.40 (1H, ddd, J = 14.4, 10.8, 2.3 Hz), 2.83 (1H, dd, J = 13.5, 4.2 Hz), 3.20 (1H, ddd, J = 14.8, 12.0, 3.5 Hz), 3.83 (1H, dt, J = 14.6, 2.6 Hz), 4.34 (1H, d, J = 14.1 Hz), 4.45-4.49 (3H, m), 4.53 (1H, d, J = 13.5 Hz), 6.92 (1H, t, J = 5.8 Hz), 7.25 (2H, d, J = 7.7 Hz), 7.39 (2H, d, J = 8.2 Hz), 7.46 (2H, d, J = 8.2 Hz), 7.92 (2H, d, J = 8.8 Hz). |
| 642 | 562 (M + H). | 1H-NMR (CDCl$_3$, 300 MHz) δ: 2.10 (3H, s), 2.33 (1H, ddd, J = 13.9, 10.9, 1.9 Hz), 2.76 (1H, dd, J = 13.6, 4.1 Hz), 2.93 (1H, ddd, J = 14.3, 11.7, 2.8 Hz), 3.73 (1H, dt, J = 14.4, 2.7 Hz), 4.22-4.47 (5H, m), 6.54 (1H, t, J = 5.8 Hz), 7.26-7.47 (11H, m), 7.86 (2H, d, J = 8.7 Hz). |
| 643 | 492 (M + H). | 1H-NMR (CDCl$_3$, 300 MHz) δ: 0.90 (2H, dd, J = 24.1, 12.4 Hz), 1.12-1.25 (4H, m), 1.37-1.50 (1H, m), 1.60-1.77 (4H, m), 2.14 (3H, s), 2.39 (1H, ddd, J = 13.9, 11.5, 2.6 Hz), 2.81 (1H, dd, J = 13.6, 4.1 Hz), 3.04-3.23 (3H, m), 3.85 (1H, d, J = 14.3 Hz), 4.31-4.43 (2H, m), 4.52 (1H, d, J = 13.6 Hz), 6.57 (1H, t, J = 6.0 Hz), 7.41 (2H, d, J = 8.7 Hz), 7.94 (2H, d, J = 8.7 Hz). |
| 644 | 593 (M + H). | 1H-NMR (CDCl$_3$, 300 MHz) δ: 1.08-1.15 (2H, m), 1.46 (9H, s), 1.63 (2H, d, J = 12.8 Hz), 2.14 (3H, s), 2.38 (1H, ddd, J = 13.8, 11.4, 2.5 Hz), 2.68 (2H, t, J = 12.8 Hz), 2.79 (1H, dd, J = 13.6, 4.1 Hz), 3.07-3.29 (4H, m), 3.83 (1H, dt, J = 14.7, 3.2 Hz), 4.03-4.20 (2H, m), 4.31-4.52 (3H, m), 6.70 (1H, t, J = 5.8 Hz), 7.42 (2H, d, J = 8.3 Hz), 7.94 (2H, d, J = 8.7 Hz). |

TABLE 363

| Example No. | MS ESI m/e: | NMR |
|---|---|---|
| 645 | 532 (M + H). | 1H-NMR (CDCl$_3$, 300 MHz) δ: 2.01 (0.6H, s), 2.17 (2.4H, s), 2.47 (1.0H, ddd, J = 14.2, 11.0, 2.7 Hz), 2.90 (0.8H, dd, J = 13.8, 4.3 Hz), 3.01 (0.2H, dd, J = 14.1, 4.7 Hz), 3.19 (0.8H, ddd, J = 14.3, 12.1, 3.4 Hz), 3.36 (0.2H, dd, J = 28.6, 11.3 Hz), 3.71 (0.2H, d, J = 12.1 Hz), 3.79 (0.8H, d, J = 14.3 Hz), 3.87 (0.6H, s), 3.89 (2.4H, s), 4.26 (1.0H, dd, J = 14.5, 5.8 Hz), 4.35 (0.8H, d, J = 13.9 Hz), 4.43 (1.0H, dd, J = 14.5, 6.2 Hz), 4.49 (1.0H, d, J = 4.9 Hz), 4.55 (1.0H, d, J = 13.9 Hz), 4.89 (0.2H, d, J = 15.1 Hz), 5.97 (0.2H, s), 6.01 (0.8H, s), 6.63-6.83 (4.0H, m), 7.32 (0.4H, d, J = 9.0 Hz), 7.37 (1.6H, d, J = 8.3 Hz), 7.90 (2.0H, d, J = 9.0 Hz). |
| 646 | 545 (M + H). | 1H-NMR (CDCl$_3$, 300 MHz) δ: 0.99 (3.0H, t, J = 7.3 Hz), 1.71 (2.0H, dtd, J = 14.6, 7.3, 7.3 Hz), 1.99 (0.6H, s), 2.08 (2.4H, s), 2.48 (1.0H, ddd, J = 13.8, 12.4, 4.0 Hz), 2.54 (2.0H, t, J = 7.2 Hz), 2.96 (0.8H, dd, J = 13.8, 4.3 Hz), 3.03 (0.2H, dd, J = 12.4, 3.0 Hz), 3.25 (0.8H, ddd, J = 14.7, 11.3, 3.0 Hz), 3.64 (0.2H, td, J = 13.8, 4.0 Hz), 3.72 (0.2H, d, J = 12.1 Hz), 3.81 (0.8H, d, J = 14.3 Hz), 4.14 (0.4H, d, J = 5.3 Hz), 4.26 (1.6H, d, J = 6.0 Hz), 4.36 (1.0H, d, J = 13.6 Hz), 4.45 (0.8H, d, J = 8.7 Hz), 4.47 (0.8H, d, J = 8.7 Hz), 4.56 (0.2H, s), 4.88 (0.2H, d, J = 13.9 Hz), 6.02 (1.0H, d, J = 7.2 Hz), 7.32 (1.0H, d, J = 7.2 Hz), 7.37 (2.0H, d, J = 8.7 Hz), 7.66-7.76 (1.0H, m), 7.85 (0.4H, d, J = 8.7 Hz), 7.94 (1.6H, d, J = 8.7 Hz), 10.89 (1.0H, br s). |
| 647 | 674 (M + H). | 1H-NMR (CDCl$_3$, 400 MHz) δ: 0.97 (3H, t, J = 7.5 Hz), 2.03-2.20 (2H, m), 3.10-3.41 (2H, m), 3.60-3.86 (2H, m), 4.34-4.65 (4H, m), 5.50 (1H, br s), 7.10 (1H, t, J = 5.8 Hz), 7.19 (2H, d, J = 8.2 Hz), 7.35 (4H, d, J = 8.4 Hz), 7.93 (2H, dt, J = 9.4, 2.4 Hz), 9.76 (1H, s). |

TABLE 364

| Example No. | MS ESI m/e: | NMR |
|---|---|---|
| 648 | 651 (M + H). | 1H-NMR (CDCl$_3$, 400 MHz) δ: 0.95 (3H, t, J = 7.5 Hz), 2.04-2.12 (2H, m), 2.97-3.04 (1H, m), 3.15 (1H, dd, J = 13.8, 4.1 Hz), |

TABLE 364-continued

| Example No. | MS ESI m/e: | NMR |
|---|---|---|
| | | 3.43-3.50 (1H, m), 3.94 (1H, dt, J = 13.8, 3.5 Hz), 4.39 (1H, dd, J = 15.0, 5.9 Hz), 4.47 (1H, dd, J = 15.2, 6.4 Hz), 4.50-4.56 (1H, m), 4.64-4.67 (1H, m), 5.02 (1H, d, J = 13.7 Hz), 7.07 (1H, t, J = 5.9 Hz), 7.15 (2H, d, J = 8.1 Hz), 7.29 (2H, d, J = 8.1 Hz), 7.35-7.41 (3H, m), 7.96 (2H, d, J = 9.4 Hz), 8.57 (1H, d, J = 5.8 Hz), 8.68 (1H, s), 9.18 (1H, s). |
| 649 | 531 (M + H). | 1H-NMR (CDCl₃, 400 MHz) δ: 2.15 (3H, s), 2.18 (3H, s), 2.27-2.37 (1H, m), 2.79 (1H, dd, 3 = 13.7, 4.4 Hz), 3.27-3.36 (1H, m), 3.90 (1H, d, J = 13.5 Hz), 3.98 (3H, s), 4.31-4.58 (5H, m), 6.69 (1H, d, J = 7.1 Hz), 7.36 (1H, d, J = 8.2 Hz), 7.38 (2H, d, J = 9.0 Hz), 7.88 (1H, br s), 7.93 (2H, d, J = 8.6 Hz). |
| 650 | 706 (M + H). | 1H-NMR (CD₃OD, 300 MHz) δ: 0.95 (3H, t, J = 7.5 Hz), 2.06-2.27 (2H, m), 3.06-3.16 (1H, m), 3.37 (1H, d, J = 5.3 Hz), 3.71-3.88 (2H, m), 4.05-4.15 (1H, m), 4.32 (2H, s), 4.36 (2H, s), 4.55-4.65 (2H, m), 7.27 (2H, d, J = 8.3 Hz), 7.36-7.45 (4H, m), 7.57 (1H, s), 7.96 (2H, d, J = 8.7 Hz). |
| 651 | 618 (M + H). | 1H-NMR (CDCl₃, 400 MHz) δ: 1.41 (3H, t, J = 7.1 Hz), 2.90-3.08 (1H, m), 3.14-3.26 (1H, m), 3.36-3.48 (1H, m), 3.90-4.00 (3H, m), 4.22-4.33 (2H, m), 4.65 (1H, s), 4.81 (1H, br s), 5.09 (1H, d, J = 13.9 Hz), 6.70 (2H, d, J = 8.6 Hz), 6.79 (1H, t, J = 5.1 Hz), 6.98 (2H, d, J = 8.6 Hz), 7.38 (2H, d, J = 8.3 Hz), 7.95 (2H, d, J = 8.8 Hz), 8.78 (1H, s), 9.22 (1H, s), 9.27 (1H, s). |
| 652 | 656 (M + H). | 1H-NMR (CDCl₃, 400 MHz) δ: 2.98-3.08 (1H, m), 3.18-3.25 (1H, m), 3.41-3.51 (1H, m), 3.96 (1H, d, J = 14.8 Hz), 4.31-4.42 (2H, m), 4.68 (1H, br s), 4.78-4.87 (1H, m), 5.10 (1H, d, J = 13.7 Hz), 6.97 (1H, t, J = 6.5 Hz), 7.05-7.11 (3H, m), 7.25 (1H, d, J = 3.5 Hz), 7.29 (1H, d, J = 5.1 Hz), 7.39-7.43 (4H, m), 7.98 (2H, d, J = 8.8 Hz), 8.77 (1H, s), 9.19 (1H, s), 9.24 (1H, s). |

TABLE 365

| Example No. | MS ESI m/e: | NMR |
|---|---|---|
| 653 | 654 (M + H). | 1H-NMR (CDCl₃, 400 MHz) δ: 2.95-3.10 (1H, m), 3.16-3.25 (1H, m), 3.39-3.50 (1H, m), 3.95 (1H, d, J = 13.9 Hz), 4.26-4.38 (2H, m), 4.65 (1H, s), 4.74-4.86 (1H, m), 5.06 (1H, d, J = 13.4 Hz), 6.96-7.03 (3H, m), 7.30 (2H, d, J = 8.6 Hz), 7.40 (2H, d, J = 8.6 Hz), 7.97 (2H, d, J = 8.8 Hz), 8.75 (1H, s), 9.24 (1H, s), 9.28 (1H, s). |
| 654 | 493 (M − HCl + H). | 1H-NMR (DMSO-d₆, 400 MHz, 120° C.) δ: 1.28-1.40 (2H, m), 1.64-1.80 (3H, m), 1.88 (3H, s), 2.80 (2H, t, J = 8.7 Hz), 2.94 (2H, t, J = 8.3 Hz), 3.06-3.32 (4H, m), 3.57-3.65 (2H, m), 3.94 (1H, br s), 4.27 (1H, br s), 4.40-4.43 (1H, m), 7.50 (2H, d, J = 9.0 Hz), 7.81 (1H, t, J = 6.2 Hz), 7.92 (2H, d, J = 8.8 Hz), 8.45 (1H, br s), 8.72 (1H, br s). |
| 655 | 564, 566 (M + H). | 1H-NMR (CDCl₃, 300 MHz) δ: 2.14 (3H, s), 2.40 (1H, ddd, J = 14.0, 11.2, 2.9 Hz), 2.83 (1H, dd, J = 13.4, 4.0 Hz), 3.18 (1H, ddd, J = 14.3, 11.7, 3.0 Hz), 3.82 (1H, dt, J = 14.6, 2.6 Hz), 4.28-4.55 (5H, m), 6.91 (1H, t, J = 5.8 Hz), 7.10 (2H, d, J = 8.3 Hz), 7.39 (2H, d, J = 8.3 Hz), 7.47 (2H, d, J = 8.3 Hz), 7.91 (2H, d, J = 8.7 Hz). |
| 656 | 614 (M + H). | 1H-NMR (CDCl₃, 300 MHz) δ: 0.59-0.64 (2H, m), 0.91-0.97 (2H, m), 1.75-1.84 (1H, m), 2.94-3.07 (1H, m), 3.20 (1H, dd, J = 13.8, 4.0 Hz), 3.36-3.46 (1H, m), 3.94 (1H, d, J = 13.9 Hz), 4.22-4.36 (2H, m), 4.65 (1H, br s), 4.78-4.87 (1H, m), 5.08 (1H, d, J = 13.6 Hz), 6.79-6.95 (5H, m), 7.37 (2H, d, J = 8.3 Hz), 7.94 (2H, d, J = 8.7 Hz), 8.77 (1H, s), 9.22 (1H, s), 9.26 (1H, s). |
| 657 | 618 (M + H). | 1H-NMR (CDCl₃, 300 MHz) δ: 2.95-3.07 (1H, m), 3.19 (1H, dd, J = 13.9, 3.8 Hz), 3.37-3.47 (4H, m), 3.94 (1H, d, J = 14.3 Hz), 4.34-4.37 (4H, m), 4.66 (1H, br s), 4.77-4.85 (1H, m), 5.07 (1H, d, J = 13.9 Hz), 6.89 (1H, t, J = 5.5 Hz), 7.06 (2H, d, J = 8.3 Hz), 7.16 (2H, d, J = 8.3 Hz), 7.38 (2H, d, J = 8.3 Hz), 7.95 (2H, d, J = 9.0 Hz), 8.77 (1H, s), 9.22 (1H, s), 9.26 (1H, s). |

TABLE 366

| Example No. | MS ESI m/e: | NMR |
|---|---|---|
| 658 | 604 (M + H). | 1H-NMR (CDCl₃, 300 MHz) δ: 2.96-3.06 (1H, m), 3.20 (1H, dd, J = 13.4, 3.6 Hz), 3.36-3.46 (1H, m), 3.74 (3H, s), 3.94 (1H, d, J = 14.3 Hz), 4.27 (2H, dd, J = 5.7, 2.6 Hz), 4.64 (1H, br s), 4.76-4.86 (1H, m), 5.08 (1H, d, J = 13.9 Hz), 6.70 (2H, d, J = 8.3 Hz), 6.80 (1H, t, J = 5.8 Hz), 6.99 (2H, d, J = 8.7 Hz), 7.37 (2H, d, J = 8.3 Hz), 7.95 (2H, d, J = 9.0 Hz), 8.77 (1H, s), 9.21 (1H, s), 9.26 (1H, s). |
| 659 | 662 (M + H). | 1H-NMR (DMSO-d₆, 300 MHz) δ: 3.47 (1H, dd, J = 14.5, 4.7 Hz), 3.64-3.91 (2H, m), 4.21 (2H, d, J = 6.0 Hz), 4.53-4.63 (1H, m), 4.69 (1H, br s), 4.85-5.01 (1H, m), 6.77 (1H, d, J = 3.8 Hz), 6.88 (1H, d, J = 3.8 Hz), 6.94 (1H, d, J = 3.0 Hz), 6.97-7.00 (1H, m), 7.41 (1H, d, J = 4.1 Hz), 7.52 (2H, d, J = 8.3 Hz), 7.98 (2H, d, J = 9.0 Hz), 8.80 (1H, s), 8.94 (1H, t, J = 6.0 Hz), 9.03 (1H, s), 9.08 (1H, s). |
| 660 | 642 (M + H). | 1H-NMR (CDCl₃, 400 MHz) δ: 2.99-3.08 (1H, m), 3.20 (1H, dd, J = 13.6, 3.2 Hz), 3.45-3.52 (1H, m), 3.95 (1H, d, J = 14.1 Hz), 4.35-4.51 (2H, m), 4.67 (1H, s), 4.73-4.84 (1H, m), 5.06 (1H, d, J = 13.9 Hz), 7.11-7.19 (1H, br m), 7.22 (2H, d, J = 7.9 Hz), 7.39 (2H, d, J = 8.8 Hz), 7.45 (2H, d, J = 7.9 Hz), 7.97 (2H, d, J = 8.6 Hz), 8.75 (1H, s), 9.23 (1H, s), 9.26 (1H, s). |
| 661 | 620 (M + H). | 1H-NMR (CDCl₃, 400 MHz) δ: 2.43 (3H, s), 2.97-3.08 (1H, br m), 3.19 (1H, dd, J = 13.3, 3.2 Hz), 3.39-3.47 (1H, m), 3.94 (1H, d, J = 13.9 Hz), 4.30 (2H, d, J = 6.2 Hz), 4.66 (1H, s), 4.73-4.85 (1H, m), 5.08 (1H, d, J = 14.1 Hz), 6.93 (1H, t, J = 5.7 Hz), 6.98 (2H, d, J = 8.4 Hz), 7.04 (2H, d, J = 8.4 Hz), 7.38 (2H, d, J = 7.9 Hz), 7.95 (2H, d, J = 9.0 Hz), 8.76 (1H, s), 9.22 (1H, s), 9.27 (1H, s). |
| 662 | 621 (M + H). | 1H-NMR (CDCl₃, 400 MHz) δ: 0.90 (3H, t, J = 7.6 Hz), 1.51-1.54 (2H, m), 1.96-1.98 (2H, br m), 2.35 (2H, t, J = 7.6 Hz), 2.44-2.49 (2H, m), 2.89-2.91 (2H, br m), 3.01 (1H, t, J = 12.2 Hz), 3.19 (1H, dd, J = 13.6, 3.2 Hz), 3.45-3.52 (1H, m), 3.74 (2H, d, J = 5.3 Hz), 3.96 (1H, d, J = 14.8 Hz), 4.62 (1H, br s), 4.83 (1H, d, J = 13.7 Hz), 5.04 (1H, d, J = 13.7 Hz), 5.43 (1H, br s), 6.71 (1H, t, J = 6.2 Hz), 7.42 (2H, d, J = 8.2 Hz), 7.98 (2H, d, J = 8.8 Hz), 8.77 (1H, s), 9.20 (1H, s), 9.25 (1H, s) |

TABLE 367

| Example No. | MS ESI m/e: | NMR |
|---|---|---|
| 663 | 650 (M + H). | 1H-NMR (CDCl₃, 400 MHz) δ: 3.03 (1H, t, J = 11.2 Hz), 3.21 (1H, dd, J = 13.8, 3.6 Hz), 3.43-3.50 (1H, m), 3.95 (1H, dt, J = 14.0, 2.9 Hz), 4.37 (1H, dd, J = 13.5, 4.4 Hz), 4.42 (1H, dd, J = 13.6, 4.3 Hz), 4.69 (1H, br s), 4.81 (1H, d, J = 12.4 Hz), 5.09 (1H, d, J = 13.7 Hz), 7.02 (1H, t, J = 5.7 Hz), 7.14 (2H, d, J = 8.4 Hz), 7.32-7.46 (7H, m), 7.48-7.53 (2H, m), 7.96 (2H, d, J = 9.0 Hz), 8.77 (1H, s), 9.16 (1H, s), 9.23 (1H, s). |
| 664 | 673 (M + H). | 1H-NMR (CDCl₃, 400 MHz) δ: 0.96 (3H, t, J = 7.5 Hz), 2.11 (2H, dq, J = 31.7, 7.9 Hz), 3.08-3.18 (1H, m), 3.28 (1H, dd, J = 13.3, 4.3 Hz), 3.44-3.54 (1H, m), 3.91 (1H, d, J = 14.1 Hz), 4.32 (1H, d, J = 12.8 Hz), 4.43 (2H, ddd, J = 37.6, 15.2, 6.0 Hz), 4.55 (1H, d, J = 13.2 Hz), 4.67 (1H, s), 7.09 (1H, br s), 7.22 (2H, d, J = 8.2 Hz), 7.36 (4H, dd, J = 7.9, 6.0 Hz), 7.93 (2H, d, J = 9.0 Hz), 8.05 (1H, s), 10.58 (1H, br s). |
| 665 | 598 (M + H). | 1H-NMR (CDCl₃, 400 MHz) δ: 1.32-1.34 (9H, m), 2.56-2.75 (1H, m), 2.94-3.09 (1H, m), 3.18-3.45 (1H, m), 3.64-3.76 (1H, m), 3.90-3.99 (1H, m), 4.20-4.29 (1H, m), 4.39-4.68 (4H, m), 6.05 (0.3H, d, J = 11.8 Hz), 6.22 (0.3H, d, J = 11.4 Hz), 6.38 (0.7H, d, J = 12.8 Hz), 6.78 (1H, br s), 6.98 (0.7H, d, J = 13.2 Hz), 7.11-7.20 (2H, m), 7.34-7.40 (3H, m), 7.83-7.95 (2H, m). |
| 666 | 620 (M + H). | 1H-NMR (CDCl₃, 400 MHz) δ: 0.99 (3H, t, J = 7.5 Hz), 2.06-2.22 (2H, m), 2.55-2.80 (1H, m), 2.91-3.13 (1H, m), 3.19-3.46 (1H, m), 3.64-3.76 (1H, m), 3.88-3.98 (1H, m), 4.33-4.64 (4H, m), 6.08 (0.3H, d, J = 11.9 Hz), 6.25 (0.3H, d, J = 11.7 Hz), 6.35 (0.7H, d, J = 12.8 Hz), 6.77 (0.3H, br s), 6.90-6.97 (1.3H, m), 7.23-7.34 (2H, m), 7.38-7.48 (4H, m), 7.86-7.95 (2H, m). |
| 667 | 620 (M + H). | 1H-NMR (CDCl₃, 400 MHz) δ: 0.98 (3H, t, 3 = 7.6 Hz), 2.04-2.21 (2H, m), 2.52-2.64 (1H, m), 2.88-2.98 (1H, m), 3.19-3.32 (1H, m), 3.80-3.91 (1H, m), 4.30-4.66 (5H, m), 6.69 (1H, d, J = 18.1 Hz), 6.99 (1H, br s), 7.21-7.25 (2H, m), 7.33-7.46 (4H, m), 7.51 (1H, d, J = 15.9 Hz), 7.91 (2H, d, J = 8.8 Hz). |

TABLE 368

| Example No. | MS ESI m/e: | NMR |
|---|---|---|
| 668 | 598 (M + H). | 1H-NMR (CDCl$_3$, 400 MHz) δ: 1.31 (9H, s), 2.52-2.66 (1H, m), 2.91-2.99 (1H, m), 3.19-3.31 (1H, m), 3.80-3.90 (1H, m), 4.29-4.71 (5H, m), 6.69 (1H, d, J = 17.2 Hz), 6.86 (1H, br s), 7.11 (2H, d, J = 7.9 Hz), 7.35 (3H, d, J = 7.9 Hz), 7.52 (1H, d, J = 15.2 Hz), 7.90 (2H, d, J = 8.8 Hz). |
| 669 | 536 (M + H). | 1H-NMR (CDCl$_3$, 400 MHz) δ: 0.92-1.06 (2H, m), 1.36-1.55 (3H, m), 2.00-2.10 (2H, m), 2.14 (3H, s), 2.22-2.32 (1H, m), 2.35-2.44 (1H, m), 2.80 (1H, dd, J = 13.5, 4.2 Hz), 2.97-3.37 (3H, m), 3.83 (1H, d, J = 14.1 Hz), 4.35 (1H, d, J = 14.3 Hz), 4.42 (1H, d, J = 3.5 Hz), 4.50 (1H, d, J = 13.7 Hz), 6.66 (1H, t, J = 6.4 Hz), 7.42 (2H, d, J = 8.4 Hz), 7.94 (2H, d, J = 8.8 Hz). |
| 670 | 535 (M + H). | 1H-NMR (CDCl$_3$, 400 MHz) δ: 1.11-1.17 (2H, m), 1.65-1.79 (3H, m), 2.09 (3H, s), 2.14 (3H, s), 2.40 (1H, ddd, J = 13.5, 10.6, 2.9 Hz), 2.54 (1H, dt, J = 19.3, 6.0 Hz), 2.80 (1H, dd, J = 12.5, 4.7 Hz), 3.02 (1H, t, J = 12.6 Hz), 3.09-3.32 (3H, m), 3.79-3.83 (2H, m), 4.33 (1H, d, J = 13.0 Hz), 4.39-4.42 (1H, m), 4.49 (1H, d, J = 13.5 Hz), 4.62 (1H, t, J = 14.2 Hz), 6.75 (1H, t, J = 5.6 Hz), 7.42 (2H, d, J = 8.2 Hz), 7.94 (2H, d, J = 9.0 Hz). |
| 671 | 530 (M + H). | 1H-NMR (CDCl$_3$, 400 MHz) δ: 2.11 (3H, s), 2.30 (1H, ddd, J = 15.2, 11.2, 2.0 Hz), 2.73 (1H, dd, J = 13.1, 3.9 Hz), 2.86 (2H, t, J = 6.6 Hz), 2.90-2.94 (1H, m), 3.41-3.59 (2H, m), 3.73 (1H, d, J = 14.6 Hz), 3.88 (3H, s), 4.25 (1H, d, J = 13.5 Hz), 4.35 (1H, d, J = 2.9 Hz), 4.46 (1H, d, J = 13.5 Hz), 6.64 (1H, t, J = 5.0 Hz), 6.89-6.94 (2H, m), 7.08 (1H, d, J = 7.3 Hz), 7.23 (1H, d, J = 7.9 Hz), 7.36 (2H, d, J = 8.6 Hz), 7.85 (2H, d, J = 8.8 Hz). |
| 672 | 530 (M + H). | 1H-NMR (CDCl$_3$, 400 MHz) δ: 2.14 (3H, s), 2.33 (1H, ddd, J = 14.4, 10.8, 2.2 Hz), 2.73-2.85 (3H, m), 2.86-2.95 (1H, m), 3.43-3.61 (2H, m), 3.70 (1H, d, J = 14.8 Hz), 3.82 (3H, s), 4.26 (1H, d, J = 13.0 Hz), 4.38 (1H, s), 4.48 (1H, d, J = 13.5 Hz), 6.50 (1H, t, J = 3.7 Hz), 6.72-6.81 (3H, m), 7.23 (1H, d, J = 7.9 Hz), 7.37 (2H, d, J = 8.4 Hz), 7.85 (2H, d, J = 9.0 Hz). |

TABLE 369

| Example No. | MS ESI m/e: | NMR |
|---|---|---|
| 673 | 530 (M + H). | 1H-NMR (CDCl$_3$, 400 MHz) δ: 2.14 (3H, s), 2.30 (1H, ddd, J = 14.7, 10.9, 2.2 Hz), 2.69-2.81 (3H, m), 2.86 (1H, ddd, J = 14.3, 11.2, 3.1 Hz), 3.39-3.58 (2H, m), 3.69 (1H, dt, J = 14.1, 2.6 Hz), 3.80 (3H, s), 4.26 (1H, d, J = 12.6 Hz), 4.39 (1H, s), 4.48 (1H, d, J = 13.5 Hz), 6.48 (1H, t, J = 4.9 Hz), 6.87 (2H, d, J = 8.6 Hz), 7.08 (2H, d, J = 8.6 Hz), 7.38 (2H, d, J = 7.9 Hz), 7.86 (2H, d, J = 9.0 Hz). |
| 674 | 516 (M + H). | 1H-NMR (CDCl$_3$, 400 MHz) δ: 2.27-2.33 (1H, m), 2.27 (3H, s), 2.63-2.67 (1H, m), 2.72 (1H, dt, J = 13.5, 3.6 Hz), 2.80 (1H, dd, J = 13.6, 4.1 Hz), 2.93-3.01 (1H, m), 3.06-3.15 (1H, m), 3.55 (1H, dt, J = 15.1, 2.6 Hz), 3.85 (1H, ddd, J = 13.2, 9.4, 4.6 Hz), 4.28 (1H, d, J = 13.7 Hz), 4.44 (1H, d, J = 3.1 Hz), 4.60 (1H, d, J = 13.5 Hz), 6.14 (1H, t, J = 2.1 Hz), 6.39 (1H, t, J = 5.3 Hz), 6.67-6.75 (2H, m), 7.20 (1H, t, J = 7.8 Hz), 7.37-7.43 (3H, m), 7.86 (2H, d, J = 8.6 Hz). |
| 675 | 516 (M + H). | 1H-NMR (CDCl$_3$, 400 MHz) δ: 2.12 (3H, s), 2.18-2.27 (1H, m), 2.63-2.73 (3H, m), 2.85 (1H, dt, J = 14.3, 6.0 Hz), 3.37 (1H, dt, J = 17.9, 5.3 Hz), 3.61-3.75 (2H, m), 4.19 (1H, d, J = 13.5 Hz), 4.36 (1H, d, J = 4.4 Hz), 4.46 (1H, d, J = 13.7 Hz), 5.50 (1H, s), 6.43 (1H, t, J = 5.6 Hz), 6.77 (2H, d, J = 8.6 Hz), 7.01 (2H, d, J = 8.6 Hz), 7.38 (2H, d, J = 8.2 Hz), 7.86 (2H, d, J = 8.8 Hz). |
| 676 | 640 (M + H). | 1H-NMR (CD$_3$OD, 400 MHz) δ: 0.88 (3H, t, J = 7.5 Hz), 2.00-2.16 (2H, m), 3.15 (1H, ddd, J = 13.6, 9.3, 3.4 Hz), 3.35 (1H, dd, J = 14.0, 4.3 Hz), 3.76-3.94 (2H, m), 4.19 (1H, td, J = 8.4, 4.6 Hz), 4.31 (2H, dd, J = 17.3, 15.4 Hz), 4.63-4.76 (2H, m), 7.20 (4H, dt, J = 10.0, 4.5 Hz), 7.37-7.43 (2H, m), 7.96-8.01 (3H, m), 8.23 (1H, s). |
| 677 | 623 (M + H). | 1H-NMR (DMSO-d$_6$, 400 MHz) δ: 0.89 (3H, t, J = 7.4 Hz), 2.11-2.27 (2H, m), 2.78-2.88 (1H, m), 3.00 (1H, dd, J = 13.7, 4.4 Hz), 3.52-3.64 (4H, m), 3.81 (1H, d, J = 13.0 Hz), 4.12-4.31 (3H, m), 4.44 (1H, br s), 6.85 (1H, t, J = 5.8 Hz), 7.28 (2H, d, J = 8.1 Hz), 7.43 (2H, d, J = 8.3 Hz), 7.49 (2H, d, J = 8.1 Hz), 7.88 (2H, d, J = 8.6 Hz), 12.32 (1H, br s). |

TABLE 370

| Example No. | MS ESI m/e: | NMR |
|---|---|---|
| 678 | 608 (M + H). | 1H-NMR (CDCl$_3$, 400 MHz) δ: 1.00 (3H, t, J = 7.4 Hz), 2.07-2.23 (2H, m), 2.48-2.59 (1H, m), 2.87 (1H, dd, J = 13.7, 3.9 Hz), 3.14-3.24 (1H, m), 3.37 (1H, d, J = 19.5 Hz), 3.91 (1H, d, J = 19.2 Hz), 3.91 (1H, d, J = 11.8 Hz), 4.35-4.59 (5H, m), 6.94 (1H, t, J = 5.1 Hz), 7.26 (2H, d, J = 7.9 Hz), 7.40 (2H, d, J = 8.3 Hz), 7.46 (2H, d, J = 8.1 Hz), 7.93 (2H, d, J = 8.3 Hz). |
| 679 | 594 (M + H). | 1H-NMR (CDCl$_3$, 400 MHz) δ: 0.96-1.02 (3H, m), 2.06-2.22 (2H, m), 2.74-2.89 (1H, m), 3.16-3.53 (2H, m), 3.75-3.88 (1H, m), 4.24 (1H, d, J = 13.2 Hz), 4.35-4.66 (3H, m), 4.82-5.10 (1H, m), 6.82-7.05 (1H, m), 7.23-7.30 (2H, m), 7.34-7.40 (2H, m), 7.41-7.48 (2H, m), 7.88-7.91 (2H, m). |
| 680 | 633 (M + H). | 1H-NMR (CDCl$_3$, 300 MHz) δ: 0.93 (3H, t, J = 7.3 Hz), 1.72 (2H, ddt, J = 14.8, 7.5, 7.5 Hz), 3.06 (1H, t, J = 12.1 Hz), 3.22 (1H, dd, J = 13.8, 4.0 Hz), 3.51 (1H, ddd, J = 14.6, 10.6, 3.3 Hz), 3.81 (2H, t, J = 7.2 Hz), 3.98 (1H, dt, J = 14.4, 3.4 Hz), 4.16 (1H, dd, J = 16.4, 6.2 Hz), 4.24 (1H, dd, J = 16.2, 6.4 Hz), 4.71 (1H, br s), 4.79 (1H, d, J = 13.9 Hz), 5.03 (1H, d, J = 14.3 Hz), 5.85 (1H, dd, J = 7.2, 1.9 Hz), 6.33 (1H, d, J = 1.4 Hz), 7.06 (1H, d, J = 7.2 Hz), 7.22-7.29 (1H, m), 7.41 (2H, d, J = 7.9 Hz), 7.99 (2H, d, J = 8.7 Hz), 8.75 (1H, s), 9.21 (1H, s), 9.26 (1H, s). |
| 681 | 535 (M + H). | 1H-NMR (DMSO-d$_6$, 400 MHz, 120° C.) δ: 0.91 (3H, t, J = 7.3 Hz), 1.21 (1H, t, J = 6.4 Hz), 1.34-1.46 (2H, m), 1.57-1.79 (6H, m), 1.88 (3H, s), 2.58-3.30 (8H, m), 3.54-3.66 (2H, m), 3.88-4.01 (1H, m), 4.21-4.33 (1H, m), 4.41 (1H, s), 7.50 (2H, d, J = 9.0 Hz), 7.77 (1H, br s), 7.92 (2H, d, J = 8.2 Hz). |
| 682 | 516 (M + H). | 1H-NMR (CDCl$_3$, 300 MHz) δ: 2.11-2.17 (1H, m), 2.12 (3H, s), 2.72 (1H, dd, J = 13.6, 4.1 Hz), 2.83-3.00 (3H, m), 3.36-3.57 (2H, m), 3.71 (1H, d, J = 14.3 Hz), 4.24 (1H, d, J = 13.9 Hz), 4.41-4.53 (2H, m), 4.68-5.01 (1H, m), 6.21 (1H, s), 6.81 (1H, d, J = 7.5 Hz), 6.90 (1H, t, J = 7.2 Hz), 7.08-7.16 (2H, m), 7.40 (2H, d, J = 8.3 Hz), 7.90 (2H, d, J = 8.7 Hz). |

TABLE 371

| Example No. | MS ESI m/e: | NMR |
|---|---|---|
| 683 | 647 (M + H). | 1H-NMR (CDCl$_3$, 300 MHz) δ: 0.96 (3H, t, J = 7.5 Hz), 1.99-2.19 (2H, m), 2.97-3.09 (1H, m), 3.18-3.27 (1H, m), 3.38-3.52 (1H, m), 3.92-4.02 (1H, m), 4.40 (2H, d, J = 6.0 Hz), 4.65 (1H, br s), 4.71-4.82 (1H, m), 5.00 (1H, d, J = 13.9 Hz), 6.99 (1H, t, J = 6.0 Hz), 7.15 (2H, d, J = 7.9 Hz), 7.32 (2H, d, J = 8.3 Hz), 7.65-7.79 (4H, m), 8.75 (1H, s), 9.22 (1H, s), 9.27 (1H, s). |
| 684 | 728, 730 (M + H). | 1H-NMR (CDCl$_3$, 300 MHz) δ: 0.95 (3H, t, J = 7.3 Hz), 1.97-2.18 (2H, m), 2.89-2.98 (1H, m), 3.09 (1H, dd, J = 13.6, 4.1 Hz), 3.38-3.52 (1H, m), 3.94 (1H, d, J = 14.3 Hz), 4.33-4.55 (3H, m), 4.64 (1H, s), 4.95 (1H, d, J = 13.6 Hz), 7.05 (1H, t, J = 5.7 Hz), 7.13 (2H, d, J = 8.3 Hz), 7.27 (2H, d, J = 7.9 Hz), 7.35-7.37 (2H, m), 7.46 (1H, d, J = 9.0 Hz), 7.64 (1H, dd, J = 8.9, 2.1 Hz), 7.95 (2H, d, J = 8.7 Hz), 8.05 (1H, d, J = 2.3 Hz), 8.62 (1H, s). |
| 685 | 728, 730 (M + H). | 1H-NMR (CDCl$_3$, 300 MHz) δ: 0.95 (3H, t, J = 7.5 Hz), 2.01-2.17 (2H, m), 2.89-3.00 (1H, m), 3.11 (1H, dd, J = 13.6, 4.1 Hz), 3.41-3.50 (1H, m), 3.87-3.98 (1H, m), 4.32-4.53 (3H, m), 4.64 (1H, s), 4.96 (1H, d, J = 13.9 Hz), 7.00-7.07 (1H, m), 7.12 (2H, d, J = 7.9 Hz), 7.27 (2H, d, J = 7.9 Hz), 7.36 (2H, d, J = 7.9 Hz), 7.50 (1H, dd, J = 8.7, 2.3 Hz), 7.74 (1H, d, J = 8.7 Hz), 7.80 (1H, d, J = 1.9 Hz), 7.96 (2H, d, J = 8.7 Hz), 8.61 (1H, s). |
| 686 | 636 (M + H). | 1H-NMR (CDCl$_3$, 400 MHz) δ: 0.95 (3H, t, J = 7.4 Hz), 2.01-2.16 (2H, m), 2.93-3.06 (1H, m), 3.14-3.24 (1H, m), 3.44-3.52 (1H, m), 3.95-4.02 (1H, m), 4.35-4.45 (2H, m), 4.70 (1H, s), 4.75-4.86 (1H, br m), 5.07 (1H, d, J = 13.7 Hz), 7.01 (1H, t, J = 5.6 Hz), 7.14 (2H, d, J = 8.1 Hz), 7.30 (2H, d, J = 8.3 Hz), 7.84 (2H, d, J = 8.3 Hz), 8.05 (2H, d, J = 8.3 Hz), 8.76 (1H, s), 9.22 (1H, s), 9.27 (1H, s). |

TABLE 372

| Example No. | MS ESI m/e: | NMR |
|---|---|---|
| 687 | 602, 604 (M + H). | 1H-NMR (CD$_3$OD, 300 MHz) δ: 0.92 (3H, t, J = 7.3 Hz), 1.60 (2H, td, J = 15.0, 7.4 Hz), 2.54 (2H, t, J = 7.7 Hz), 3.20-3.30 (1H, m), 3.45 (1H, dd, J = 14.1, 4.7 Hz), 3.69-3.92 (2H, m), 4.16-4.22 (2H, m), 4.26 (1H, d, J = 13.2 Hz), 4.60 (1H, t, J = 3.6 Hz), 4.78 (1H, dd, J = 13.6, 1.9 Hz), 7.04 (4H, s), 7.66 (2H, d, J = 9.0 Hz), 7.75 (2H, d, J = 8.7 Hz), 8.08 (1H, d, J = 1.1 Hz), 8.58 (1H, t, J = 5.7 Hz), 8.62 (1H, d, J = 1.1 Hz). |
| 688 | 684 (M + H). | 1H-NMR (CDCl$_3$, 300 MHz) δ: 0.95 (3H, t, J = 7.5 Hz), 1.98-2.17 (2H, m), 2.89-2.98 (1H, m), 3.08 (1H, dd, J = 13.6, 4.1 Hz), 3.39-3.53 (1H, m), 3.93 (1H, d, J = 14.3 Hz), 4.32-4.54 (3H, m), 4.64 (1H, br s), 4.95 (1H, d, J = 13.6 Hz), 7.05-7.17 (3H, m), 7.26 (2H, d, J = 8.3 Hz), 7.36 (2H, d, 3 = 8.5 Hz), 7.52 (2H, s), 7.88 (1H, s), 7.95 (2H, d, J = 8.5 Hz), 8.62 (1H, s). |
| 689 | 629 (M + H). | 1H-NMR (CDCl$_3$, 300 MHz) δ: 1.27 (9H, s), 2.97-3.06 (1H, m), 3.16 (1H, dd, J = 13.9, 4.1 Hz), 3.42-3.51 (1H, m), 3.94 (1H, d, J = 14.3 Hz), 4.30 (1H, dd, J = 14.9, 5.5 Hz), 4.41 (1H, dd, J = 14.7, 6.0 Hz), 4.55 (1H, d, J = 13.6 Hz), 4.65 (1H, br s), 5.04 (1H, d, J = 13.6 Hz), 6.90 (1H, t, J = 5.7 Hz), 7.01 (2H, d, J = 8.3 Hz), 7.21 (2H, d, J = 8.3 Hz), 7.32-7.43 (3H, m), 7.95 (2H, d, J = 9.0 Hz), 8.57 (1H, d, J = 6.0 Hz), 8.69 (1H, s), 9.18 (1H, s). |
| 690 | 652 (M + H). | 1H-NMR (CDCl$_3$, 400 MHz) δ: 0.95 (3H, t, J = 7.4 Hz), 2.01-2.15 (2H, m), 2.99-3.24 (2H, m), 3.45-3.55 (1H, m), 3.96 (1H, dt, J = 14.4, 3.0 Hz), 4.41 (2H, ddd, J = 19.9, 14.1, 4.9 Hz), 4.64-4.76 (2H, m), 5.06 (1H, d, J = 13.7 Hz), 7.03 (1H, t, J = 5.9 Hz), 7.15 (2H, d, J = 8.1 Hz), 7.29 (2H, d, J = 8.1 Hz), 7.39 (2H, d, J = 8.1 Hz), 7.97 (2H, dt, J = 9.4, 2.4 Hz), 8.73 (1H, d, J = 2.1 Hz), 8.81 (1H, d, J = 1.9 Hz), 8.93 (1H, s). |

TABLE 373

| Example No. | MS ESI m/e: | NMR |
|---|---|---|
| 691 | 658 (M + H). | 1H-NMR (CDCl$_3$, 400 MHz) δ: 0.96 (3H, t, J = 7.5 Hz), 2.10 (2H, dq, J = 31.7, 7.9 Hz), 2.92-3.03 (1H, m), 3.18 (1H, dd, J = 14.0, 4.0 Hz), 3.42-3.53 (1H, m), 3.95 (1H, dt, J = 14.1, 3.0 Hz), 4.41 (2H, d, J = 6.0 Hz), 4.58-4.69 (2H, m), 5.01 (1H, d, J = 13.9 Hz), 7.01 (1H, t, J = 5.8 Hz), 7.16 (2H, d, J = 8.1 Hz), 7.36 (4H, dd, J = 28.6, 8.2 Hz), 7.96 (2H, dt, J = 9.4, 2.4 Hz), 8.88 (1H, s). |
| 692 | 666 (M + H). | 1H-NMR (CDCl$_3$, 300 MHz) δ: 0.95 (3H, t, J = 7.3 Hz), 1.98-2.17 (2H, m), 2.87 (3H, s), 2.94-3.09 (1H, m), 3.15-3.25 (1H, m), 3.39-3.52 (1H, m), 3.89-3.98 (1H, m), 4.39 (2H, d, J = 5.7 Hz), 4.65 (1H, s), 4.71-4.83 (1H, m), 5.05 (1H, d, J = 13.9 Hz), 6.99 (1H, t, J = 5.8 Hz), 7.12 (2H, d, J = 8.3 Hz), 7.29 (2H, d, J = 7.9 Hz), 7.38 (2H, d, J = 7.9 Hz), 7.95-7.97 (2H, m), 8.69 (1H, s), 9.18 (1H, s). |
| 693 | 722 (M + H). | 1H-NMR (CDCl$_3$, 300 MHz) δ: 0.94 (3H, t, J = 7.3 Hz), 1.42 (3H, t, J = 7.2 Hz), 1.96-2.16 (2H, m), 2.93-3.05 (1H, m), 3.14 (1H, dd, J = 13.8, 4.0 Hz), 3.41-3.53 (1H, m), 3.89-3.99 (1H, m), 4.33-4.48 (4H, m), 4.50 (1H, d, J = 4.9 Hz), 4.65 (1H, s), 5.01 (1H, d, J = 13.6 Hz), 7.07 (1H, t, J = 5.8 Hz), 7.13 (2H, d, J = 8.3 Hz), 7.26 (2H, d, J = 7.5 Hz), 7.36 (2H, d, J = 8.7 Hz), 7.60 (1H, d, J = 9.0 Hz), 7.96 (2H, d, J = 8.7 Hz), 8.19 (1H, dd, J = 8.7, 1.9 Hz), 8.60 (1H, d, J = 1.9 Hz), 8.68 (1H, s). |
| 694 | 657 (M + H). | 1H-NMR (CDCl$_3$, 400 MHz) δ: 0.97 (3H, t, J = 7.5 Hz), 2.12 (2H, dq, J = 31.5, 7.9 Hz), 3.13-3.23 (1H, m), 3.28 (1H, dd, J = 13.2, 4.2 Hz), 3.46-3.56 (1H, m), 3.97 (1H, d, J = 14.4 Hz), 4.25 (1H, d, J = 12.5 Hz), 4.46 (2H, ddd, J = 35.7, 15.1, 5.9 Hz), 4.63 (1H, d, J = 13.5 Hz), 4.67 (1H, d, J = 2.3 Hz), 7.01 (1H, t, 3 = 5.5 Hz), 7.23 (2H, d, J = 8.1 Hz), 7.38 (4H, d, J = 8.4 Hz), 7.95 (2H, d, J = 9.0 Hz), 9.28 (1H, s), 9.33 (1H, s). |

TABLE 374

| Example No. | MS ESI m/e: | NMR |
|---|---|---|
| 695 | 624 (M + H). | 1H-NMR (CDCl$_3$, 400 MHz) δ: 0.95 (3H, t, J = 7.5 Hz), 1.34 (9H, s), 2.01-2.16 (2H, m), 2.88-3.02 (1H, br m), 3.13 (1H, dd, J = 13.2, |

TABLE 374-continued

| Example No. | MS ESI m/e: | NMR |
|---|---|---|
| | | 3.7 Hz), 3.37-3.48 (1H, m), 3.97 (1H, d, J = 14.4 Hz), 4.41 (2H, d, J = 6.0 Hz), 4.67 (1H, s), 4.73-4.84 (1H, br m), 5.01 (1H, d, J = 13.4 Hz), 7.11 (1H, t, J = 6.0 Hz), 7.15 (2H, d, J = 8.3 Hz), 7.31 (2H, d, J = 8.3 Hz), 7.59 (2H, d, J = 8.6 Hz), 7.82 (2H, d, J = 8.6 Hz), 8.78 (1H, s), 9.21 (1H, s), 9.25 (1H, s). |
| 696 | 644 (M + H). | 1H-NMR (CDCl$_3$, 400 MHz) δ: 0.95 (3H, t, J = 7.4 Hz), 2.00-2.15 (2H, m), 3.04-3.06 (1H, br m), 3.20-3.31 (1H, br m), 3.41-3.51 (1H, br m), 4.04 (1H, d, J = 14.4 Hz), 4.42 (2H, d, J = 6.0 Hz), 4.68-4.82 (2H, m), 4.98 (1H, d, J = 13.7 Hz), 7.09 (1H, t, J = 6.1 Hz), 7.16 (2H, d, J = 8.3 Hz), 7.31 (2H, d, J = 8.1 Hz), 7.42-7.53 (3H, m), 7.58 (2H, d, J = 8.1 Hz), 7.76 (2H, d, J = 8.3 Hz), 7.96 (2H, d, J = 8.6 Hz), 8.75 (1H, s), 9.20-9.21 (2H, m). |
| 697 | 602 (M + H). | 1H-NMR (CDCl$_3$, 400 MHz) δ: 0.96 (3H, t, J = 7.4 Hz), 2.01-2.18 (2H, m), 3.00-3.02 (1H, br m), 3.22 (1H, d, J = 12.3 Hz), 3.39-3.49 (1H, m), 3.97 (1H, d, J = 14.6 Hz), 4.40 (2H, d, J = 5.3 Hz), 4.65 (1H, br s), 4.71-4.83 (1H, br m), 5.01 (1H, d, J = 13.9 Hz), 7.00 (1H, t, J = 6.3 Hz), 7.15 (2H, d, J = 8.3 Hz), 7.32 (2H, d, J = 8.3 Hz), 7.53 (2H, d, J = 8.6 Hz), 7.84 (2H, d, J = 8.6 Hz), 8.75 (1H, s), 9.22 (1H, s), 9.27 (1H, s). |
| 698 | 613 (M + H). | 1H-NMR (CDCl$_3$, 400 MHz) δ: 0.95 (3H, t, J = 7.4 Hz), 2.02-2.13 (2H, m), 3.08 (1H, s), 3.21-3.30 (1H, br m), 3.44-3.55 (1H, m), 3.99-4.02 (1H, m), 4.29-4.46 (2H, m), 4.69-4.83 (2H, m), 5.13 (1H, d, J = 13.2 Hz), 6.98 (1H, t, J = 5.4 Hz), 7.13 (2H, d, J = 8.1 Hz), 7.29 (2H, d, J = 8.1 Hz), 8.09 (2H, d, J = 9.0 Hz), 8.39 (2H, d, J = 8.8 Hz), 8.72 (1H, s), 9.22 (1H, s), 9.27 (1H, s). |

TABLE 375

| Example No. | MS ESI m/e: | NMR |
|---|---|---|
| 699 | 608, 610 (M + H). | 1H-NMR (CD$_3$OD, 300 MHz) δ: 0.91 (3H, t, J = 7.3 Hz), 1.52-1.66 (2H, m), 2.53 (2H, t, J = 7.5 Hz), 3.33-3.45 (1H, m), 3.54 (1H, dd, J = 13.9, 4.5 Hz), 3.79-3.87 (2H, m), 4.22 (2H, d, J = 5.7 Hz), 4.23-4.31 (1H, m), 4.58 (1H, s), 4.76-4.85 (1H, m), 6.98-7.08 (4H, m), 7.16 (2H, d, J = 3.8 Hz), 7.45 (1H, d, J = 3.8 Hz), 8.10 (1H, s), 8.64 (1H, s), 8.66 (1H, t, J = 5.3 Hz). |
| 700 | 580 (M + H). | 1H-NMR (CD$_3$OD, 300 MHz) δ: 0.91 (3H, t, J = 7.3 Hz), 1.59 (2H, td, J = 15.4, 7.4 Hz), 2.53 (2H, t, J = 7.7 Hz), 3.16-3.28 (1H, m), 3.40 (1H, dd, J = 13.9, 4.5 Hz), 3.68-3.87 (2H, m), 4.14-4.30 (3H, m), 4.59 (1H, t, J = 3.6 Hz), 4.75 (1H, dd, J = 14.1, 2.8 Hz), 6.98-7.07 (4H, m), 7.59 (2H, d, J = 8.7 Hz), 7.80 (2H, d, J = 8.3 Hz), 8.05 (1H, d, J = 1.1 Hz), 8.57 (1H, t, J = 5.5 Hz), 8.62 (1H, d, J = 1.1 Hz). |
| 701 | 600 (M + H). | 1H-NMR (CD$_3$OD, 300 MHz) δ: 0.90 (3H, t, J = 7.3 Hz), 1.57 (2H, td, J = 15.0, 7.4 Hz), 2.51 (2H, t, J = 7.5 Hz), 3.25-3.38 (1H, m), 3.50 (1H, dd, J = 13.9, 4.5 Hz), 3.69-3.96 (2H, m), 4.16-4.26 (3H, m), 4.64 (1H, t, J = 3.8 Hz), 4.73 (1H, dd, J = 14.3, 3.0 Hz), 6.99 (2H, d, J = 8.3 Hz), 7.04 (4H, d, J = 8.3 Hz), 7.38-7.51 (3H, m), 7.60-7.66 (2H, m), 7.75 (2H, d, J = 8.7 Hz), 7.93 (2H, d, J = 8.3 Hz), 8.06 (1H, d, J = 1.5 Hz), 8.56-8.63 (2H, m). |
| 702 | 544 (M + H). | 1H-NMR (CDCl$_3$, 300 MHz) δ: 1.89 (2H, tt, J = 7.5, 6.5 Hz), 2.15 (3H, s), 2.40 (1H, td, J = 12.6, 3.4 Hz), 2.71 (2H, t, J = 7.5 Hz), 2.84 (1H, dd, J = 13.6, 4.1 Hz), 3.16 (1H, ddd, J = 14.6, 11.0, 3.5 Hz), 3.67 (2H, t, J = 6.2 Hz), 3.81 (1H, d, J = 13.6 Hz), 4.28-4.38 (1H, m), 4.38 (1H, dd, J = 13.2, 3.8 Hz), 4.45 (1H, dd, J = 13.2, 3.4 Hz), 4.47 (1H, d, J = 3.0 Hz), 4.54 (1H, d, J = 13.6 Hz), 6.78 (1H, t, J = 5.7 Hz), 7.13 (2H, d, J = 8.3 Hz), 7.17 (1H, br s), 7.19 (2H, d, J = 7.9 Hz), 7.37 (2H, d, J = 7.9 Hz), 7.90 (2H, d, J = 8.7 Hz). |

TABLE 376

| Example No. | MS EST m/e: | NMR |
|---|---|---|
| 703 | 518 (M + H). | 1H-NMR (CDCl$_3$, 300 MHz) δ: 0.92 (3.0H, t, J = 7.3 Hz), 1.88 (2.0H, ddt, J = 14.6, 7.3, 7.3 Hz), 1.97 (0.6H, s), 2.16 (2.4H, s), 2.38 (1.0H, ddd, J = 13.7, 10.8, 2.7 Hz), 2.82 (0.8H, dd, J = 13.4, 4.0 Hz), 2.94-3.04 (0.2H, m), 3.14 (0.8H, ddd, J = 14.0, 10.8, 3.4 Hz), 3.24-3.31 (0.2H, m), 3.62-3.71 (0.2H, m), 3.80 (0.8H, d, J = 14.7 Hz), 4.04 (0.4H, t, J = 7.0 Hz), 4.05 (1.6H, t, J = 7.0 Hz), 4.18-4.36 (1.0H, m), 4.31 (2.0H, d, J = 6.4 Hz), 4.43 (0.8H, d, J = 3.4 Hz), 4.51 (0.8H, d, J = 13.9 Hz), 4.55 (0.2H, s), 4.84 (0.2H, d, J = 13.6 Hz), 6.71 (1.0H, t, J = 5.7 Hz), 7.31 (1.0H, s), 7.34 (0.4H, d, J = 7.9 Hz), 7.39 (1.6H, d, J = 7.5 Hz), 7.41 (1.0H, s), 7.91 (1.6H, d, J = 9.0 Hz), 7.94 (0.4H, d, J = 9.0 Hz). |
| 704 | 621 (M + H). | 1H-NMR (DMSO-d$_6$, 400 MHz) δ: 0.88 (3H, t, J = 7.4 Hz), 2.08-2.26 (2H, m), 3.56-3.83 (3H, m), 3.85-4.07 (3H, m), 4.08-4.22 (1H, m), 4.38-4.82 (2H, m), 7.28 (2H, d, J = 8.3 Hz), 7.43-7.53 (4H, m), 7.83-7.92 (2H, m), 8.72-8.79 (1H, m). |
| 705 | 649 (M + H). | 1H-NMR (CDCl$_3$, 400 MHz) δ: 0.98 (3H, t, J = 7.5 Hz), 2.06-2.21 (2H, m), 2.67-2.76 (1H, m), 2.83 (1H, dd, J = 13.6, 4.3 Hz), 3.23-3.38 (2H, m), 3.63 (1H, d, J = 13.0 Hz), 3.74 (1H, d, J = 13.7 Hz), 4.09-4.20 (4H, m), 4.24 (1H, d, J = 13.2 Hz), 4.41-4.54 (3H, m), 7.17 (1H, t, J = 6.0 Hz), 7.29 (2H, d, J = 7.9 Hz), 7.35 (2H, d, J = 7.9 Hz), 7.44 (2H, d, J = 8.4 Hz), 7.90 (2H, d, J = 8.6 Hz). |
| 706 | 677 (M + H). | 1H-NMR (CDCl$_3$, 400 MHz) δ: 0.98 (3H, t, J = 7.4 Hz), 1.59-1.74 (2H, m), 1.84-1.95 (2H, m), 2.06-2.21 (2H, m), 2.44-2.54 (1H, m), 2.63-2.87 (4H, m), 3.26-3.43 (2H, m), 3.60-3.81 (3H, m), 4.17 (1H, d, J = 13.2 Hz), 4.40-4.58 (3H, m), 7.27-7.38 (4H, m), 7.43 (2H, d, J = 8.2 Hz), 7.92 (2H, d, J = 8.8 Hz). |

TABLE 377

| Example No. | MS ESI m/e: | NMR |
|---|---|---|
| 707 | 652 (M + H). | 1H-NMR (CDCl$_3$, 300 MHz) δ: 0.96 (3H, t, 3 = 7.5 Hz), 1.99-2.19 (2H, m), 2.91-3.03 (1H, m), 3.11 (1H, dd, J = 13.8, 4.0 Hz), 3.42-3.52 (1H, m), 3.97 (1H, d, J = 14.7 Hz), 4.43 (2H, d, J = 6.4 Hz), 4.52 (1H, d, J = 13.9 Hz), 4.64 (1H, br s), 5.00 (1H, d, J = 13.6 Hz), 7.01 (1H, t, J = 5.8 Hz), 7.18 (2H, d, J = 8.7 Hz), 7.33 (2H, d, J = 8.7 Hz), 7.39 (2H, d, J = 8.7 Hz), 7.96 (2H, d, J = 8.7 Hz), 9.02 (1H, s), 9.20 (1H, s), 9.25 (1H, s). |
| 708 | 694 (M + H). | 1H-NMR (CDCl$_3$, 300 MHz) δ: 0.96 (3H, t, J = 7.5 Hz), 2.00-2.18 (2H, m), 2.95-3.08 (1H, m), 3.18-3.28 (1H, m), 3.38-3.50 (1H, m), 3.97 (1H, d, J = 14.7 Hz), 4.40 (2H, d, J = 6.0 Hz), 4.64 (1H, br s), 4.71-4.81 (1H, m), 4.99 (1H, d, J = 14.3 Hz), 6.99 (1H, t, J = 6.0 Hz), 7.15 (2H, d, J = 7.9 Hz), 7.32 (2H, d, J = 7.9 Hz), 7.60 (2H, d, J = 8.7 Hz), 7.91 (2H, d, J = 8.7 Hz), 8.75 (1H, s), 9.23 (1H, s), 9.27 (1H, s). |
| 709 | 650 (M + H). | 1H-NMR (CDCl$_3$, 300 MHz) δ: 0.95 (3H, t, J = 7.3 Hz), 2.00-2.15 (2H, m), 3.01-3.15 (1H, m), 3.23-3.37 (1H, m), 3.37-3.52 (1H, m), 4.03 (1H, d, J = 15.1 Hz), 4.42 (2H, d, J = 6.0 Hz), 4.65-4.76 (2H, m), 4.88-4.95 (1H, m), 7.06 (1H, t, J = 5.7 Hz), 7.12-7.19 (3H, m), 7.31 (2H, d, J = 7.5 Hz), 7.42-7.44 (2H, m), 7.74 (2H, d, J = 8.3 Hz), 7.88 (2H, d, J = 8.7 Hz), 8.73 (1H, s), 9.19 (2H, s). |
| 710 | 722 (M + H). | 1H-NMR (CDCl$_3$, 300 MHz) δ: 0.93 (3H, t, J = 7.3 Hz), 1.44 (3H, t, J = 7.2 Hz), 1.96-2.12 (2H, m), 2.91-3.00 (1H, m), 3.11 (1H, dd, J = 13.8, 4.3 Hz), 3.41-3.53 (1H, m), 3.89-4.00 (1H, m), 4.32-4.54 (5H, m), 4.64 (1H, s), 4.98 (1H, d, J = 13.9 Hz), 7.03 (1H, t, J = 5.8 Hz), 7.11 (2H, d, J = 8.3 Hz), 7.25 (2H, d, J = 8.7 Hz), 7.36 (2H, d, J = 8.3 Hz), 7.91-7.98 (3H, m), 8.04 (1H, dd, J = 8.7, 1.9 Hz), 8.35 (1H, d, J = 1.5 Hz), 8.70 (1H, s). |

TABLE 378

| Example No. | MS ESI m/e: | NMR |
|---|---|---|
| 711 | 694 (M + H). | 1H-NMR (CDCl$_3$, 300 MHz) δ: 0.94 (3H, t, J = 7.5 Hz), 1.99-2.15 (2H, m), 2.90-3.04 (1H, m), 3.12 (1H, dd, J = 13.9, 4.1 Hz), 3.50 (1H, t, J = 10.9 Hz), 3.95 (1H, d, J = 13.9 Hz), 4.35-4.53 (3H, m), |

TABLE 378-continued

| Example No. | MS ESI m/e: | NMR |
|---|---|---|
| | | 4.67 (1H, s), 5.00 (1H, d, J = 13.2 Hz), 7.07-7.17 (3H, m), 7.26 (2H, d, J = 7.9 Hz), 7.37 (2H, d, J = 8.7 Hz), 7.89-8.07 (4H, m), 8.38 (1H, br s), 8.72 (1H, br s). |
| 712 | 694 (M + H). | 1H-NMR (CDCl$_3$, 300 MHz) δ: 0.93 (3H, t, J = 7.5 Hz), 1.93-2.20 (2H, m), 2.92-3.20 (2H, m), 3.42-3.56 (1H, m), 3.92 (1H, d, J = 15.8 Hz), 4.34-4.53 (3H, m), 4.66 (1H, br s), 5.00 (1H, d, J = 13.6 Hz), 7.09-7.18 (3H, m), 7.27 (2H, d, J = 8.7 Hz), 7.35 (2H, d, J = 8.3 Hz), 7.56 (1H, br s), 7.95 (2H, d, J = 8.7 Hz), 8.15 (1H, br s), 8.61 (1H, br s), 8.69 (1H, br s). |
| 713 | 601 (M + H). | 1H-NMR (CDCl$_3$, 400 MHz) δ: 0.95 (3H, t, J = 7.5 Hz), 2.02-2.16 (2H, m), 2.97-3.04 (1H, m), 3.18 (1H, dd, J = 13.7, 4.2 Hz), 3.41-3.48 (1H, m), 3.95 (1H, dt, J = 13.9, 3.7 Hz), 4.37-4.52 (3H, m), 4.63 (1H, br s), 4.94 (1H, d, J = 12.8 Hz), 7.05 (1H, t, J = 5.0 Hz), 7.15 (2H, d, J = 8.2 Hz), 7.30 (2H, d, J = 8.2 Hz), 7.40 (1H, d, J = 5.8 Hz), 7.50 (2H, d, J = 8.7 Hz), 7.83 (2H, d, J = 8.7 Hz), 8.57 (1H, d, J = 5.8 Hz), 8.66 (1H, s), 9.18 (1H, s). |
| 714 | 623 (M + H). | 1H-NMR (CDCl$_3$, 400 MHz) δ: 0.95 (3H, t, J = 7.5 Hz), 1.33 (9H, s), 2.00-2.15 (2H, m), 2.94-3.01 (1H, m), 3.12 (1H, dd, J = 13.6, 4.1 Hz), 3.41-3.48 (1H, m), 3.95 (1H, dt, J = 14.3, 3.6 Hz), 4.39 (1H, dd, J = 15.1, 6.1 Hz), 4.44-4.52 (2H, m), 4.65 (1H, br s), 4.95 (1H, d, J = 13.5 Hz), 7.15-7.17 (3H, m), 7.29 (2H, d, J = 8.4 Hz), 7.41 (1H, dd, J = 5.8, 0.8 Hz), 7.56 (2H, d, J = 8.7 Hz), 7.81 (2H, d, J = 8.7 Hz), 8.56 (1H, d, J = 5.8 Hz), 8.67 (1H, s), 9.16 (1H, s). |
| 715 | 656 (M + H). | 1H-NMR (CDCl$_3$, 300 MHz) δ: 0.96 (3H, t, J = 7.3 Hz), 1.99-2.20 (2H, m), 3.10-3.30 (2H, m), 3.42-3.55 (1H, m), 3.87-3.97 (1H, m), 4.14 (1H, d, J = 12.8 Hz), 4.38-4.53 (2H, m), 4.58-4.67 (2H, m), 6.97 (1H, t, J = 5.8 Hz), 7.21 (2H, d, J = 8.3 Hz), 7.32-7.40 (5H, m), 7.91-7.98 (2H, m), 8.43 (1H, d, J = 5.7 Hz), 8.76 (1H, s). |

TABLE 379

| Example No. | MS ESI m/e: | NMR |
|---|---|---|
| 716 | 530 (M + H). | 1H-NMR (CDCl$_3$, 400 MHz) δ: 1.83-1.90 (2H, m), 2.17 (3H, s), 2.36-2.45 (1H, m), 2.49 (1H, dd, J = 16.4, 7.2 Hz), 2.62-2.69 (1H, m), 2.85 (1H, dd, J = 13.7, 4.0 Hz), 3.03-3.13 (1H, m), 3.19 (1H, ddd, J = 14.6, 10.8, 3.4 Hz), 3.37-3.46 (1H, m), 3.82 (1H, dt, J = 14.5, 2.9 Hz), 4.39-4.46 (2H, m), 4.56 (1H, d, J = 13.7 Hz), 6.40 (1H, s), 6.53 (1H, t, J = 5.2 Hz), 6.67-6.71 (2H, m), 6.98 (1H, s), 7.15 (1H, t, J = 7.8 Hz), 7.43 (2H, d, J = 8.2 Hz), 7.94 (2H, d, J = 8.8 Hz). |
| 717 | 530 (M + H). | 1H-NMR (CDCl$_3$, 400 MHz) δ: 1.74-1.85 (2H, m), 2.14 (3H, s), 2.35 (1H, ddd, J = 15.2, 10.7, 2.3 Hz), 2.58 (2H, t, J = 6.7 Hz), 2.76 (1H, dd, J = 13.5, 4.2 Hz), 3.04 (1H, ddd, J = 15.3, 11.2, 3.9 Hz), 3.30 (2H, q, J = 7.1 Hz), 3.78 (1H, dt, J = 14.5, 2.0 Hz), 4.29 (1H, d, J = 12.8 Hz), 4.37 (1H, dd, J = 4.0 Hz), 4.48 (1H, d, J = 13.5 Hz), 5.20 (1H, br s), 6.51 (1H, t, J = 6.0 Hz), 6.75 (2H, d, J = 8.4 Hz), 7.03 (2H, d, J = 8.4 Hz), 7.41 (2H, d, J = 8.2 Hz), 7.92 (2H, d, J = 8.8 Hz). |
| 718 | 529 (M + H). | 1H-NMR (CDCl$_3$, 400 MHz) δ: 0.97 (3H, t, J = 7.4 Hz), 1.71-1.78 (2H, m), 2.13 (3H, s), 2.40 (1H, ddd, J = 14.3, 11.3, 3.5 Hz), 2.72-2.79 (2H, m), 2.83 (1H, dd, J = 13.6, 4.1 Hz), 3.19 (1H, ddd, J = 14.8, 11.7, 3.0 Hz), 3.82 (1H, d, J = 14.3 Hz), 4.29-4.53 (5H, m), 7.00 (1H, t, J = 4.5 Hz), 7.14 (1H, d, J = 7.9 Hz), 7.39 (2H, d, J = 8.6 Hz), 7.47 (1H, dd, J = 7.9, 4.0 Hz), 7.91 (2H, d, J = 8.8 Hz), 8.43 (1H, d, J = 2.0 Hz). |
| 719 | 502 (M + H). | 1H-NMR (CDCl$_3$, 400 MHz) δ: 2.11 (3H, s), 2.46 (1H, ddd, J = 14.1, 11.7, 2.2 Hz), 2.57 (3H, s), 2.92 (1H, dd, J = 13.9, 4.6 Hz), 3.28 (1H, ddd, J = 14.4, 11.5, 3.0 Hz), 3.85 (1H, d, J = 13.9 Hz), 4.37 (1H, d, J = 13.5 Hz), 4.46-4.64 (4H, m), 7.39 (2H, d, J = 8.2 Hz), 7.45 (1H, t, J = 5.2 Hz), 7.96 (2H, d, J = 8.8 Hz), 8.36 (1H, s), 8.43 (1H, s). |

TABLE 380

| Example No. | MS ESI m/e: | NMR |
|---|---|---|
| 720 | 617 (M + H). | 1H-NMR (CDCl$_3$, 400 MHz) δ: 0.94 (3H, t, J = 7.4 Hz), 1.67-1.74 (2H, m), 2.69 (2H, t, J = 7.6 Hz), 3.02 (1H, dt, J = 16.2, 6.1 Hz), 3.20 (1H, dd, J = 15.2, 3.5 Hz), 3.44 (1H, ddd, J = 14.6, 11.3, 4.1 Hz), 3.95 (1H, d, J = 14.1 Hz), 4.35 (2H, t, J = 6.0 Hz), 4.65 (1H, s), 4.77 (1H, d, J = 14.1 Hz), 5.05 (1H, d, J = 13.5 Hz), 6.95 (1H, d, J = 7.9 Hz), 7.03 (1H, t, J = 6.1 Hz), 7.32 (1H, dd, J = 7.8, 2.3 Hz), 7.39 (2H, d, J = 8.2 Hz), 7.96 (2H, dd, J = 9.6, 0.8 Hz), 8.33 (1H, d, J = 2.9 Hz), 8.76 (1H, s), 9.22 (1H, s), 9.27 (1H, s). |
| 721 | 590 (M + H). | 1H-NMR (CDCl$_3$, 400 MHz) δ: 2.46 (3H, s), 3.05 (1H, dt, J = 16.6, 6.0 Hz), 3.25 (1H, dd, J = 13.6, 3.6 Hz), 3.56 (1H, ddd, J = 14.2, 11.7, 2.6 Hz), 3.97 (1H, d, J = 14.1 Hz), 4.40 (1H, dd, J = 16.8, 5.7 Hz), 4.52 (1H, dd, J = 16.3, 6.2 Hz), 4.72 (1H, d, J = 2.9 Hz), 4.88 (1H, d, J = 11.5 Hz), 5.07 (1H, d, J = 13.9 Hz), 7.40 (2H, d, J = 8.4 Hz), 7.48 (1H, t, J = 6.0 Hz), 8.00 (2H, d, J = 8.8 Hz), 8.23 (1H, s), 8.30 (1H, s), 8.75 (1H, s), 9.20 (1H, s), 9.24 (1H, s). |
| 722 | 631 (M + H). | 1H-NMR (CDCl$_3$, 400 MHz) δ: 0.97 (3H, t, J = 7.3 Hz), 1.59 (2H, dd, J = 15.3, 7.6 Hz), 1.91 (2H, br s), 2.39 (2H, t, J = 7.6 Hz), 3.07 (1H, ddd, J = 14.1, 10.7, 3.0 Hz), 3.23 (1H, d, J = 12.4 Hz), 3.48 (1H, dt, J = 17.2, 6.0 Hz), 3.92 (1H, dt, J = 14.0, 3.1 Hz), 4.17 (1H, dd, J = 15.0, 5.5 Hz), 4.27 (1H, dd, J = 15.0, 5.5 Hz), 4.66 (1H, t, J = 2.9 Hz), 4.80 (1H, d, J = 11.9 Hz), 5.09 (1H, d, J = 13.5 Hz), 6.40-6.43 (2H, m), 6.79 (1H, t, J = 4.4 Hz), 6.86 (1H, d, J = 7.9 Hz), 7.37 (2H, d, J = 8.4 Hz), 7.94 (2H, d, J = 8.8 Hz), 8.77 (1H, s), 9.20 (1H, s), 9.25 (1H, s). |
| 723 | 632 (M + H). | 1H-NMR (CDCl$_3$, 300 MHz) δ: 0.98 (3H, t, J = 7.3 Hz), 1.59-1.72 (2H, m), 2.60 (2H, t, J = 7.7 Hz), 3.33-4.60 (9H, m), 5.35 (1H, br s), 6.28-6.48 (1H, m), 6.56 (1H, d, J = 7.5 Hz), 6.75-6.91 (1H, m), 6.99 (1H, d, J = 7.5 Hz), 7.37 (2H, d, J = 8.7 Hz), 7.90 (2H, d, J = 8.7 Hz), 8.71 (1H, s), 9.21 (1H, s), 9.28 (1H, s). |

TABLE 381

| Example No. | MS ESI m/e: | NMR |
|---|---|---|
| 724 | 660 (M + H). | 1H-NMR (CDCl$_3$, 300 MHz) δ: 0.94 (3H, t, J = 7.3 Hz), 1.98-2.14 (2H, m), 3.02-3.13 (1H, m), 3.27-3.35 (1H, m), 3.39-3.50 (1H, m), 4.01 (1H, d, J = 13.9 Hz), 4.41 (2H, d, J = 6.0 Hz), 4.71 (2H, br s), 4.96 (1H, d, J = 14.3 Hz), 5.65 (1H, br s), 6.95 (1H, d, J = 8.3 Hz), 7.01-7.09 (2H, m), 7.15 (2H, d, J = 8.3 Hz), 7.26-7.31 (4H, m), 7.75 (2H, d, J = 8.7 Hz), 7.93 (2H, d, J = 8.3 Hz), 8.73 (1H, s), 9.19 (1H, s), 9.20 (1H, s). |
| 725 | 660 (M + H). | 1H-NMR (CDCl$_3$, 300 MHz) δ: 0.95 (3H, t, J = 7.5 Hz), 1.99-2.17 (2H, m), 3.01-3.12 (1H, m), 3.26-3.34 (1H, m), 3.39-3.50 (1H, m), 4.02 (1H, d, J = 13.9 Hz), 4.42 (2H, d, J = 6.0 Hz), 4.70 (2H, br s), 4.94 (1H, d, J = 14.3 Hz), 5.47 (1H, br s), 6.91 (1H, dd, J = 7.9, 2.3 Hz), 6.99-7.01 (1H, m), 7.06 (1H, t, J = 5.8 Hz), 7.11-7.17 (3H, m), 7.30-7.37 (3H, m), 7.70 (2H, d, J = 8.7 Hz), 7.92 (2H, d, J = 8.7 Hz), 8.73 (1H, s), 9.19-9.22 (2H, m). |
| 726 | 612 (M + H). | 1H-NMR (CDCl$_3$, 400 MHz) δ: 0.95 (3H, t, J = 7.5 Hz), 2.06-2.11 (2H, m), 3.03-3.10 (1H, m), 3.21 (1H, dd, J = 14.0, 4.1 Hz), 3.43-3.51 (1H, m), 3.99 (1H, dt, J = 13.8, 3.1 Hz), 4.34-4.45 (2H, m), 4.51 (1H, d, J = 14.3 Hz), 4.71 (1H, br s), 5.05 (1H, d, J = 13.7 Hz), 7.05 (1H, t, J = 6.0 Hz), 7.13 (2H, d, J = 8.4 Hz), 7.29 (2H, d, J = 8.4 Hz), 7.33 (1H, dd, J = 5.7, 0.7 Hz), 8.09 (2H, dt, J = 9.2, 2.2 Hz), 8.36 (2H, dt, J = 9.2, 2.2 Hz), 8.56 (1H, d, J = 5.7 Hz), 8.64 (1H, s), 9.17 (1H, d, J = 0.7 Hz). |
| 727 | 643 (M + H). | 1H-NMR (CDCl$_3$, 400 MHz) δ: 0.95 (3H, t, J = 7.5 Hz), 2.03-2.11 (2H, m), 3.01-3.08 (1H, m), 3.23 (1H, dd, J = 13.7, 4.2 Hz), 3.43-3.51 (1H, m), 4.02 (1H, dt, J = 13.7, 3.2 Hz), 4.41-4.49 (3H, m), 4.69 (1H, br s), 4.92 (1H, d, J = 13.7 Hz), 7.11 (1H, t, J = 6.1 Hz), 7.16 (2H, d, J = 8.2 Hz), 7.29 (2H, d, J = 8.2 Hz), 7.40 (1H, d, J = 5.8 Hz), 7.41-7.52 (3H, m), 7.53-7.57 (2H, m), 7.73 (2H, d, J = 8.2 Hz), 7.95 (2H, d, J = 8.2 Hz), 8.55 (1H, d, J = 5.8 Hz), 8.65 (1H, s), 9.12 (1H, s). |

TABLE 382

| Example No. | MS ESI m/e: | NMR |
|---|---|---|
| 728 | 668 (M + H). | 1H-NMR (CDCl₃, 400 MHz) δ: 0.94 (3H, t, J = 7.3 Hz), 1.52 (9H, s), 1.61-1.68 (2H, m), 2.57 (2H, t, J = 7.6 Hz), 2.68-2.78 (2H, m), 3.32 (1H, d, J = 12.6 Hz), 3.42-3.49 (1H, m), 3.90 (1H, d, J = 14.6 Hz), 4.26 (1H, d, J = 12.6 Hz), 4.37-4.49 (2H, m), 4.54-4.57 (1H, br m), 6.04 (1H, d, J = 4.2 Hz), 6.73 (1H, t, J = 5.6 Hz), 7.11-7.13 (4H, m), 7.33 (2H, d, J = 7.9 Hz), 7.42 (1H, d, J = 4.2 Hz), 7.89 (2H, d, J = 9.0 Hz). |
| 729 | 694 (M + H). | 1H-NMR (CDCl₃, 400 MHz) δ: 0.95 (3H, t, J = 7.5 Hz), 1.12-1.23 (2H, m), 2.03-2.17 (4H, m), 2.19-2.27 (2H, m), 2.29 (2H, d, J = 6.2 Hz), 2.81-2.96 (4H, m), 3.00-3.23 (2H, m), 3.40 (1H, m), 3.95 (1H, m), 4.42 (2H, d, J = 6.0 Hz), 4.65-4.68 (2H, br m), 4.93 (1H, d, J = 13.0 Hz), 7.13 (1H, m), 7.17 (2H, d, J = 7.9 Hz), 7.32 (2H, d, J = 7.9 Hz), 7.58-7.65 (2H, m), 8.75 (1H, d, J = 7.9 Hz), 9.21 (1H, s), 9.25 (1H, s). |
| 730 | 657 (M + H). | 1H-NMR (CDCl₃, 300 MHz) δ: 3.05 (1H, dq, J = 13.8, 4.7 Hz), 3.23 (1H, dd, J = 13.6, 3.8 Hz), 3.44 (1H, ddd, J = 14.1, 11.7, 3.2 Hz), 3.95 (1H, dt, J = 14.3, 2.4 Hz), 4.53 (2H, d, J = 5.7 Hz), 4.69 (1H, d, J = 1.9 Hz), 4.79 (1H, d, J = 12.8 Hz), 5.11 (1H, d, J = 13.2 Hz), 6.80 (1H, d, J = 3.8 Hz), 7.03 (1H, t, J = 5.1 Hz), 7.14 (1H, dd, J = 6.8, 5.7 Hz), 7.21 (1H, d, J = 3.8 Hz), 7.39 (2H, d, J = 7.9 Hz), 7.48 (1H, d, J = 7.9 Hz), 7.65 (1H, td, J = 7.7, 1.6 Hz), 7.97 (2H, d, J = 9.0 Hz), 8.49 (1H, d, J = 4.1 Hz), 8.76 (1H, s), 9.16 (2H, d, J = 11.7 Hz). |
| 731 | 718 (M + H). | 1H-NMR (CDCl₃, 300 MHz) δ: 0.95 (3H, t, J = 7.5 Hz), 2.01-2.17 (2H, m), 3.00-3.10 (1H, m), 3.18 (1H, dd, J = 13.9, 3.8 Hz), 3.44-3.54 (1H, m), 3.92-4.00 (1H, m), 4.42-4.50 (3H, m), 4.59 (2H, s), 4.69 (1H, br s), 4.87 (1H, d, J = 13.6 Hz), 6.95 (1H, d, J = 8.3 Hz), 7.12 (1H, t, J = 7.7 Hz), 7.18-7.23 (3H, m), 7.30-7.41 (4H, m), 7.76 (2H, d, J = 8.3 Hz), 7.92 (2H, d, J = 8.3 Hz), 8.70 (1H, s), 9.12 (1H, s), 9.15 (1H, s). |

TABLE 383

| Example No. | MS ESI m/e: | NMR |
|---|---|---|
| 732 | 718 (M + H). | 1H-NMR (CDCl₃, 300 MHz) δ: 0.96 (3H, t, J = 7.3 Hz), 2.01-2.16 (2H, m), 3.19-3.30 (1H, m), 3.44-3.58 (2H, m), 4.00-4.09 (1H, m), 4.30-4.47 (3H, m), 4.63-4.75 (4H, m), 6.83 (1H, br s), 6.96 (1H, d, J = 7.9 Hz), 7.15-7.26 (4H, m), 7.33-7.42 (3H, m), 7.62 (2H, d, J = 8.3 Hz), 7.89 (2H, d, J = 8.7 Hz), 8.61 (1H, s), 9.08 (1H, s), 9.15 (1H, s). |
| 733 | 656 (M + H). | 1H-NMR (CDCl₃, 300 MHz) δ: 0.98 (3H, t, J = 7.3 Hz), 2.13 (2H, tq, J = 15.6, 7.8 Hz), 2.51 (1H, td, J = 12.7, 3.3 Hz), 2.87 (1H, dd, J = 13.2, 3.8 Hz), 3.22 (1H, ddd, J 15.1, 11.3, 3.4 Hz), 3.81 (1H, dd, J = 16.8, 4.7 Hz), 3.89 (1H, d, J = 15.1 Hz), 4.28-4.61 (6H, m), 4.72 (1H, t, J = 4.5 Hz), 6.90 (1H, dd, J = 8.3, 2.3 Hz), 6.96 (1H, t, J = 5.5 Hz), 7.07 (1H, dd, J = 8.1, 5.1 Hz), 7.25 (2H, d, J = 8.7 Hz), 7.39 (2H, d, J = 8.7 Hz), 7.43 (2H, d, J = 9.0 Hz), 7.93 (2H, d, J = 9.0 Hz), 7.97 (1H, d, J = 4.9 Hz), 8.06 (1H, d, J = 2.3 Hz). |
| 734 | 659 (M + H). | 1H-NMR (CDCl₃, 300 MHz) δ: 0.98 (3.0H, t, J = 7.5 Hz), 2.14 (2.0H, tq, J = 15.8, 7.9 Hz), 2.56 (1.0H, ddd, J = 13.7, 10.5, 3.1 Hz), 2.88 (0.7H, dd, J = 13.4, 4.3 Hz), 3.03 (0.3H, dd, J = 14.1, 3.6 Hz), 3.16-3.40 (1.0H, m), 3.68 (3.0H, s), 3.72-4.05 (2.0H, m), 4.15-5.00 (6.0H, m), 5.54 (1.0H, d, J = 1.9 Hz), 6.86 (0.3H, br s), 6.93 (0.7H, t, J = 4.9 Hz), 7.05 (1.0H, d, J = 2.3 Hz), 7.25 (2.0H, d, J = 7.5 Hz), 7.29-7.48 (4.0H, m), 7.91 (2.0H, d, J = 9.0 Hz). |
| 735 | 635 (M + H). | 1H-NMR (CDCl₃, 400 MHz) δ: 0.95 (3H, t, J = 7.5 Hz), 2.01-2.15 (2H, m), 2.97-3.01 (1H, m), 3.14 (1H, dd, J = 13.9, 4.2 Hz), 3.43-3.51 (1H, m), 3.97 (1H, dt, J = 14.3, 3.3 Hz), 4.39 (1H, dd, J = 15.2, 6.0 Hz), 4.46 (1H, dd, J = 15.2, 6.0 Hz), 4.54 (1H, d, J = 13.5 Hz), 4.68 (1H, br s), 5.02 (1H, d, J = 14.1 Hz), 7.03 (1H, t, J = 6.1 Hz), 7.14 (2H, d, J = 8.4 Hz), 7.29 (2H, d, J = 8.4 Hz), 7.38 (1H, dd, J = 5.8, 0.7 Hz), 7.82 (2H, d, J = 8.3 Hz), 8.04 (2H, d, J = 8.3 Hz), 8.57 (1H, d, J = 5.8 Hz), 8.67 (1H, s), 9.18 (1H, d, J = 0.7 Hz). |

TABLE 384

| Example No. | MS ESI m/e: | NMR |
|---|---|---|
| 736 | 610 (M + H). | 1H-NMR (CDCl₃, 300 MHz) δ: 0.95 (3H, t, J = 7.5 Hz), 2.03-2.13 (2H, m), 2.97 (6H, s), 3.03-3.19 (1H, m), 3.33-3.46 (2H, m), 3.96 (1H, dt, J = 14.4, 3.5 Hz), 4.29 (1H, d, J = 13.9 Hz), 4.38-4.53 (2H, m), 4.61 (1H, t, J = 4.0 Hz), 4.74 (1H, dd, J = 13.4, 3.2 Hz), 6.58 (2H, d, J = 9.0 Hz), 7.18 (2H, d, J = 8.1 Hz), 7.31 (2H, d, J = 8.1 Hz), 7.41 (1H, d, J = 5.8 Hz), 7.65 (2H, d, J = 9.0 Hz), 8.55 (1H, d, J = 5.8 Hz), 8.60 (1H, s), 9.15 (1H, s). |
| 737 | 652, 654 (M + H). | 1H-NMR (CDCl₃, 300 MHz) δ: 0.95 (3H, t, J = 7.5 Hz), 2.09 (2H, tt, J = 19.8, 7.0 Hz), 3.12-3.29 (1H, m), 3.31-3.60 (2H, m), 3.92-4.02 (1H, m), 4.41 (2H, d, J = 5.7 Hz), 4.66 (1H, s), 4.69-4.82 (1H, m), 5.05 (1H, d, J = 13.9 Hz), 6.96 (1H, t, J = 5.8 Hz), 7.11 (1H, d, J = 3.8 Hz), 7.16 (2H, d, J = 8.3 Hz), 7.32 (2H, d, J = 8.3 Hz), 7.46 (1H, d, J = 3.8 Hz), 8.78 (1H, s), 9.23 (1H, s), 9.28 (1H, s). |
| 738 | 624 (M + H). | 1H-NMR (CDCl₃, 300 MHz) δ: 0.96 (3H, t, J = 7.3 Hz), 1.99-2.19 (2H, m), 3.20-3.40 (1H, m), 3.40-3.60 (2H, m), 4.06-4.16 (1H, m), 4.43 (2H, d, J = 6.0 Hz), 4.60-4.75 (1H, m), 4.78 (1H, t, J = 3.0 Hz), 4.90 (1H, d, J = 13.2 Hz), 7.05 (1H, t, J = 6.0 Hz), 7.16 (2H, d, J = 7.9 Hz), 7.31 (2H, d, J = 8.3 Hz), 7.41-7.53 (2H, m), 7.78-7.87 (2H, m), 7.96 (1H, s), 8.71 (1H, s), 9.19 (1H, s). |
| 739 | 656 (M + H). | 1H-NMR (CDCl₃, 400 MHz) δ: 0.96 (3H, t, J = 7.4 Hz), 2.10 (2H, dq, J = 31.8, 7.8 Hz), 3.09-3.25 (2H, m), 3.43-3.54 (1H, m), 3.86-4.07 (2H, m), 4.46 (2H, ddd, J = 19.2, 13.4, 4.2 Hz), 4.61-4.69 (2H, m), 7.00 (1H, t, J = 5.8 Hz), 7.18-7.25 (3H, m), 7.34 (4H, d, J = 8.1 Hz), 7.64 (1H, dd, J = 8.0, 1.5 Hz), 7.94 (2H, dt, J = 9.4, 2.4 Hz), 8.21 (1H, dd, J = 4.8, 1.5 Hz). |
| 740 | 650 (M + H). | 1H-NMR (CDCl₃, 400 MHz) δ: 0.94 (3H, t, J = 7.4 Hz), 1.99-2.13 (2H, m), 3.01 (1H, ddd, J = 13.9, 10.6, 2.9 Hz), 3.14 (1H, dd, J = 13.7, 3.9 Hz), 3.36-3.46 (1H, m), 3.90 (1H, dt, J = 13.9, 2.9 Hz), 4.34-4.55 (3H, m), 4.67 (1H, s), 4.97 (1H, d, J = 13.7 Hz), 7.04-7.14 (3H, m), 7.21-7.26 (3H, m), 7.32-7.39 (3H, m), 7.92-8.00 (3H, m), 8.51 (1H, d, J = 6.0 Hz), 8.90 (1H, s). |

TABLE 385

| Example No. | MS ESI m/e: | NMR |
|---|---|---|
| 741 | 684, 686 (M + H). | 1H-NMR (CDCl₃, 300 MHz) δ: 0.95 (3H, t, J = 7.3 Hz), 2.01-2.17 (2H, m), 2.96-3.05 (1H, m), 3.14 (1H, dd, J = 13.6, 4.1 Hz), 3.43-3.52 (1H, m), 3.89-3.99 (1H, m), 4.33-4.54 (3H, m), 4.65 (1H, br s), 4.97 (1H, d, J = 14.3 Hz), 7.04 (1H, t, J = 5.8 Hz), 7.14 (2H, d, J = 7.9 Hz), 7.28 (2H, d, J = 8.7 Hz), 7.35 (2H, d, J = 9.0 Hz), 7.48-7.53 (3H, m), 7.94-7.97 (2H, m), 8.69 (1H, s). |
| 742 | 684, 686 (M + H). | 1H-NMR (CDCl₃, 300 MHz) δ: 0.94 (3H, t, J = 7.5 Hz), 1.95-2.17 (2H, m), 3.00-3.12 (1H, m), 3.17 (1H, dd, J = 13.9, 4.1 Hz), 3.37-3.49 (1H, m), 3.95 (1H, d, J = 14.3 Hz), 4.42 (2H, d, J = 6.0 Hz), 4.52 (1H, d, J = 13.2 Hz), 4.72 (1H, s), 5.10 (1H, d, J = 13.9 Hz), 7.09 (2H, d, J = 8.7 Hz), 7.22 (3H, m, J = 8.7 Hz), 7.30-7.39 (3H, m), 7.68 (1H, dd, J = 7.5, 1.5 Hz), 7.81 (1H, dd, J = 8.3, 1.1 Hz), 7.98 (2H, d, J = 8.7 Hz), 8.65 (1H, s). |
| 743 | 636 (M + H). | 1H-NMR (CDCl₃, 400 MHz) δ: 0.95 (3H, t, J = 7.5 Hz), 2.04-2.13 (6H, m), 3.09-3.16 (1H, m), 3.19-3.29 (4H, m), 3.32-3.44 (2H, m), 3.96 (1H, dt, J = 14.0, 4.0 Hz), 4.27 (1H, d, J = 12.8 Hz), 4.42 (1H, dd, J = 15.0, 5.7 Hz), 4.49 (1H, dd, J = 15.1, 6.1 Hz), 4.60 (1H, t, J = 3.7 Hz), 4.72 (1H, dd, J = 13.3, 3.2 Hz), 6.44 (2H, d, J = 8.9 Hz), 7.19 (2H, d, J = 8.0 Hz), 7.31 (2H, d, J = 8.0 Hz), 7.40 (1H, d, J = 5.8 Hz), 7.63 (2H, d, J = 8.9 Hz), 8.55 (1H, d, J = 5.8 Hz), 8.59 (1H, s), 9.14 (1H, s). |
| 744 | 708 (M + H). | 1H-NMR (CDCl₃, 400 MHz) δ: 0.96 (4H, t, J = 7.4 Hz), 1.15-1.28 (2H, m), 1.45-1.56 (2H, m), 1.87-2.01 (3H, m), 2.03-2.18 (2H, m), 2.32 (2H, d, J = 7.0 Hz), 2.51-2.61 (2H, m), 2.97 (1H, m), 3.16 (1H, m), 3.43 (1H, m), 3.97 (1H, dd, J = 14.1, 0.7 Hz), 4.41 (2H, d, J = 6.0 Hz), 4.67 (1H, m), 4.76 (1H, m), 4.99 (1H, m), 7.11 (1H, t, J = 5.9 Hz), 7.16 (2H, d, J = 8.0 Hz), 7.32 (2H, d, J = 8.0 Hz), 7.39 (2H, d, J = 8.3 Hz), 7.82 (2H, d, J = 8.3 Hz), 8.77 (1H, br s), 9.22 (1H, s), 9.26 (1H, s). |

TABLE 386

| Example No. | MS ESI m/e: | NMR |
|---|---|---|
| 745 | 657 (M + H). | 1H-NMR (CDCl₃, 300 MHz) δ: 2.95-3.07 (1H, m), 3.15 (1H, dd, J = 13.6, 4.1 Hz), 3.36-3.52 (1H, m), 3.87-3.99 (1H, m), 4.33-4.47 (2H, m), 4.51 (1H, d, J = 13.6 Hz), 4.63 (1H, br s), 5.00 (1H, d, J = 13.6 Hz), 6.99-7.09 (3H, m), 7.14 (2H, d, J = 8.7 Hz), 7.34-7.41 (3H, m), 7.94-7.98 (2H, m), 8.57 (1H, d, J = 6.0 Hz), 8.67 (1H, s), 9.19 (1H, s). |
| 746 | 652 (M + H). | 1H-NMR (CDCl₃, 400 MHz) δ: 0.95 (3H, t, J = 7.5 Hz), 2.06-2.11 (2H, m), 3.02-3.09 (1H, m), 3.20-3.32 (5H, m), 3.38-3.46 (1H, m), 3.83 (4H, t, J = 4.9 Hz), 3.94 (1H, dt, J = 14.4, 3.7 Hz), 4.34-4.51 (3H, m), 4.61 (1H, t, J = 3.4 Hz), 4.84 (1H, dd, J = 13.7, 2.4 Hz), 6.83 (2H, d, J = 9.2 Hz), 7.17-7.20 (3H, m), 7.30 (2H, d, J = 8.2 Hz), 7.41 (1H, d, J = 5.7 Hz), 7.71 (2H, d, J = 9.2 Hz), 8.56 (1H, d, J = 5.7 Hz), 8.63 (1H, s), 9.16 (1H, s). |
| 747 | 598 (M + H). | 1H-NMR (CDCl₃, 400 MHz) δ: 0.95 (3H, t, J = 7.5 Hz), 2.02-2.14 (2H, m), 2.93-3.06 (1H, br m), 3.15-3.24 (1H, br m), 3.36-3.46 (1H, m), 3.86 (3H, s), 3.92-4.00 (1H, m), 4.41 (2H, d, J = 6.0 Hz), 4.62-4.78 (2H, m), 4.96 (1H, d, J = 13.0 Hz), 7.00 (2H, d, J = 8.8 Hz), 7.10 (1H, t, J = 5.9 Hz), 7.15 (2H, d, J = 7.9 Hz), 7.32 (2H, d, J = 8.1 Hz), 7.82 (2H, d, J = 8.8 Hz), 8.76 (1H, s), 9.21 (1H, s), 9.25 (1H, s). |
| 748 | 651 (M + H). | 1H-NMR (CDCl₃, 400 MHz) δ: 0.94 (3H, t, J = 7.5 Hz), 2.06 (2H, dq, J = 31.7, 7.9 Hz), 2.98-3.19 (2H, m), 3.41-3.51 (1H, m), 3.92 (1H, dt, J = 13.8, 3.1 Hz), 4.42 (2H, d, J = 6.0 Hz), 4.63-4.73 (2H, m), 4.96 (1H, d, J = 13.7 Hz), 7.09-7.18 (3H, m), 7.23 (2H, d, J = 8.3 Hz), 7.32-7.39 (3H, m), 7.97 (2H, dt, J = 9.4, 2.5 Hz), 8.11 (1H, d, J = 9.5 Hz), 8.57 (1H, d, J = 2.1 Hz), 8.74 (1H, d, J = 2.1 Hz). |
| 749 | 658 (M + H). | 1H-NMR (CDCl₃, 400 MHz) δ: 2.98-3.09 (1H, m), 3.19 (1H, dd, J = 13.8, 4.1 Hz), 3.44-3.54 (1H, m), 3.95 (1H, dt, J = 14.1, 3.2 Hz), 4.37 (2H, d, J = 6.3 Hz), 4.63-4.74 (2H, m), 5.04 (1H, d, J = 13.4 Hz), 7.00-7.07 (3H, m), 7.14 (2H, dt, J = 9.0, 2.3 Hz), 7.39 (2H, d, J = 8.1 Hz), 7.97 (2H, dt, J = 9.4, 2.4 Hz), 8.73 (1H, d, J = 1.9 Hz), 8.81 (1H, d, J = 2.1 Hz), 8.92 (1H, s). |

TABLE 387

| Example No. | MS ESI m/e: | NMR |
|---|---|---|
| 750 | 646 (M + H). | 1H-NMR (CDCl₃, 400 MHz) δ: 2.85-3.13 (2H, m), 3.36-3.46 (1H, m), 3.90 (1H, dt, J = 14.1, 3.2 Hz), 4.39 (2H, ddd, J = 30.1, 15.2, 6.1 Hz), 4.57-4.67 (2H, m), 4.78 (1H, d, J = 13.9 Hz), 6.62 (1H, d, J = 7.9 Hz), 7.05-7.18 (5H, m), 7.38 (2H, d, J = 7.9 Hz), 7.95 (2H, dt, J = 9.6, 2.8 Hz), 8.15 (1H, s), 8.35 (1H, d, J = 7.7 Hz). |
| 751 | 650 (M + H). | 1H-NMR (CDCl₃, 400 MHz) δ: 0.95 (3H, t, J = 7.5 Hz), 2.06-2.18 (4H, m), 2.64 (2H, t, J = 8.0 Hz), 3.02-3.09 (1H, m), 3.27 (1H, dd, J = 13.7, 4.4 Hz), 3.40-3.47 (1H, m), 3.76-3.82 (2H, m), 3.98 (1H, dt, J = 14.2, 3.4 Hz), 4.33-4.51 (3H, m), 4.64 (1H, t, J = 3.4 Hz), 4.81 (1H, dd, J = 13.8, 2.3 Hz), 7.11 (1H, br s), 7.17 (2H, d, J = 8.0 Hz), 7.31 (2H, d, J = 8.0 Hz), 7.40 (1H, d, J = 5.8 Hz), 7.81 (2H, d, J = 9.3 Hz), 7.85 (2H, d, J = 9.3 Hz), 8.56 (1H, d, J = 5.8 Hz), 8.62 (1H, s), 9.16 (1H, s). |
| 752 | 607 (M + H). | 1H-NMR (CDCl₃, 400 MHz) δ: 2.97-3.05 (1H, m), 3.18 (1H, dd, J = 13.8, 4.3 Hz), 3.40-3.48 (1H, m), 3.95 (1H, dt, J = 13.8, 3.5 Hz), 4.40 (2H, d, J = 6.0 Hz), 4.46 (1H, d, J = 13.9 Hz), 4.62 (1H, br s), 4.93 (1H, d, J = 13.7 Hz), 7.02-7.08 (3H, m), 7.15 (2H, d, J = 8.6 Hz), 7.39 (1H, dd, J = 5.8, 0.6 Hz), 7.50 (2H, dt, J = 9.0, 2.3 Hz), 7.83 (2H, dt, J = 9.0, 2.3 Hz), 8.57 (1H, d, J = 5.8 Hz), 8.65 (1H, s), 9.19 (1H, d, J = 0.6 Hz). |
| 753 | 688 (M + H). | 1H-NMR (CDCl₃, 300 MHz) δ: 0.95 (3H, t, J = 7.5 Hz), 1.99-2.17 (2H, m), 3.04-3.15 (1H, m), 3.26-3.36 (1H, m), 3.44-3.54 (1H, m), 4.05 (1H, d, J = 13.6 Hz), 4.43 (2H, d, J = 6.0 Hz), 4.68-4.75 (2H, m), 4.96 (1H, d, J = 12.8 Hz), 7.12 (1H, t, J = 5.8 Hz), 7.17 (2H, d, J = 8.3 Hz), 7.32 (2H, d, J = 7.9 Hz), 7.61 (1H, t, J = 7.7 Hz), 7.78-7.83 (3H, m), 7.99 (2H, d, J = 8.3 Hz), 8.17 (1H, d, J = 7.9 Hz), 8.30 (1H, s), 8.75 (1H, s), 9.20 (1H, s), 9.21 (1H, s). |

TABLE 388

| Example No. | MS ESI m/e: | NMR |
|---|---|---|
| 754 | 618 (M + H). | 1H-NMR (CDCl₃, 300 MHz) δ: 3.02-3.11 (1H, m), 3.21 (1H, dd, J = 13.9, 4.1 Hz), 3.40-3.51 (1H, m), 3.94-4.04 (1H, m), 4.37 (2H, d, J = 6.0 Hz), 4.50 (1H, d, J = 13.2 Hz), 4.70 (1H, s), 5.04 (1H, d, J = 13.6 Hz), 6.99-7.08 (3H, m), 7.13 (2H, d, J = 8.7 Hz), 7.33 (1H, d, J = 5.7 Hz), 8.09 (2H, d, J = 9.0 Hz), 8.37 (2H, d, J = 8.7 Hz), 8.57 (1H, d, J = 5.7 Hz), 8.64 (1H, s), 9.18 (1H, s). |
| 755 | 642 (M + H). | 1H-NMR (CDCl₃, 300 MHz) δ: 1.95-2.10 (4H, m), 3.06-3.31 (5H, m), 3.32-3.49 (2H, m), 3.96 (1H, dt, J = 14.6, 3.8 Hz), 4.25 (1H, d, J = 12.8 Hz), 4.36-4.49 (2H, m), 4.59 (1H, t, J = 4.0 Hz), 4.69 (1H, dd, J = 13.8, 3.2 Hz), 6.44 (2H, d, J = 9.0 Hz), 7.06 (2H, d, J = 8.5 Hz), 7.19 (2H, d, J = 8.5 Hz), 7.31 (1H, t, J = 6.2 Hz), 7.40 (1H, d, J = 5.8 Hz), 7.63 (2H, d, J = 9.0 Hz), 8.55 (1H, d, J = 5.8 Hz), 8.58 (1H, s), 9.14 (1H, s). |
| 756 | 639 (M + H). | 1H-NMR (CDCl₃, 300 MHz) δ: 0.94 (3H, t, J = 7.5 Hz), 1.94-2.17 (2H, m), 2.88-3.04 (1H, m), 3.04-3.15 (1H, m), 3.22-3.36 (1H, m), 3.93 (1H, d, J = 13.6 Hz), 4.31-4.53 (3H, m), 4.60-4.71 (2H, m), 7.12 (2H, d, J = 7.9 Hz), 7.19 (1H, d, J = 5.7 Hz), 7.27-7.35 (3H, m), 7.39 (2H, d, J = 8.7 Hz), 7.97 (2H, d, J = 8.7 Hz), 8.09 (1H, d, J = 5.7 Hz), 8.39 (1H, s). |
| 757 | 641 (M + H). | 1H-NMR (CDCl₃, 300 MHz) δ: 2.94-3.03 (1H, m), 3.14 (1H, dd, J = 13.8, 4.3 Hz), 3.40-3.52 (1H, m), 3.92-4.02 (1H, m), 4.40 (2H, d, J = 6.0 Hz), 4.53 (1H, d, J = 13.2 Hz), 4.66 (1H, br s), 5.01 (1H, d, J = 14.3 Hz), 6.96-7.09 (3H, m), 7.11-7.18 (2H, m), 7.36-7.40 (1H, m), 7.82 (2H, d, J = 8.3 Hz), 8.04 (2H, d, J = 7.9 Hz), 8.57 (1H, d, J = 6.0 Hz), 8.67 (1H, s), 9.18 (1H, s). |
| 758 | 638 (M + H). | 1H-NMR (CDCl₃, 300 MHz) δ: 0.95 (3H, t, J = 7.5 Hz), 1.97-2.18 (2H, m), 2.72-2.87 (1H, m), 2.93 (1H, dd, J = 13.9, 3.8 Hz), 3.20-3.34 (1H, m), 3.93 (1H, d, J = 14.7 Hz), 4.24 (1H, d, J = 11.7 Hz), 4.36-4.57 (3H, m), 4.59-4.64 (1H, m), 7.01-7.19 (5H, m), 7.24-7.33 (4H, m), 7.40 (2H, d, J = 8.3 Hz), 7.90-7.99 (2H, m). |

TABLE 389

| Example No. | MS ESI m/e: | NMR |
|---|---|---|
| 759 | 652 (M + H). | 1H-NMR (CD₃OD, 400 MHz) δ: 0.88 (3H, t, J = 7.4 Hz), 2.01-2.12 (2H, m), 3.42 (1H, m), 3.60 (1H, m), 3.81 (1H, m), 4.06 (1H, m), 4.29 (2H, s), 4.51 (1H, m), 4.78 (1H, m), 4.95 (1H, m), 7.19 (4H, s), 7.95 (2H, d, J = 8.2 Hz), 8.03 (2H, d, J = 8.2 Hz), 8.74 (1H, s), 9.06 (1H, s), 9.13 (1H, s). |
| 760 | 651 (M + H). | 1H-NMR (CDCl₃, 400 MHz) δ: 0.94 (3H, t, J = 7.4 Hz), 2.07 (2H, dq, J = 31.7, 7.9 Hz), 2.96-3.05 (1H, m), 3.19 (1H, dd, J = 13.8, 4.1 Hz), 3.44-3.54 (1H, m), 3.94 (1H, dt, J = 14.1, 3.1 Hz), 4.34-4.47 (2H, m), 4.63-4.71 (2H, m), 5.03 (1H, d, J = 13.7 Hz), 7.03-7.14 (3H, m), 7.25 (2H, d, J = 8.8 Hz), 7.34-7.41 (3H, m), 7.96 (2H, dt, J = 9.5, 2.4 Hz), 8.22 (1H, dd, J = 8.1, 2.1 Hz), 8.71 (1H, s), 8.86 (1H, dd, J = 4.3, 2.0 Hz). |
| 761 | 651 (M + H). | 1H-NMR (CDCl₃, 400 MHz) δ: 0.95 (3H, t, J = 7.5 Hz), 2.08 (2H, dq, J = 31.7, 7.8 Hz), 2.95-3.15 (2H, m), 3.43-3.53 (1H, m), 3.94 (1H, dt, J = 14.0, 3.4 Hz), 4.34-4.53 (3H, m), 4.65 (1H, br s), 5.00 (1H, d, J = 13.7 Hz), 7.06 (1H, t, J = 5.6 Hz), 7.17 (2H, d, J = 7.7 Hz), 7.33 (4H, dd, J = 27.9, 8.5 Hz), 7.51 (1H, dd, J = 8.2, 4.2 Hz), 7.91-7.99 (3H, m), 8.78-8.84 (2H, m). |
| 762 | 657 (M + H). | 1H-NMR (CDCl₃, 400 MHz) δ: 2.99-3.20 (2H, m), 3.41-3.51 (1H, m), 3.92 (1H, dt, J = 13.9, 3.2 Hz), 4.38 (2H, d, J = 6.0 Hz), 4.62-4.71 (2H, m), 4.95 (1H, d, J = 14.6 Hz), 6.98 (2H, d, J = 8.4 Hz), 7.08-7.19 (3H, m), 7.31-7.40 (3H, m), 7.97 (2H, dt, J = 9.5, 2.4 Hz), 8.11 (1H, d, J = 9.3 Hz), 8.58 (1H, d, J = 2.1 Hz), 8.74 (1H, d, J = 2.1 Hz). |
| 763 | 672 (M + H). | 1H-NMR (CDCl₃, 400 MHz) δ: 2.95-3.06 (1H, m), 3.15-3.23 (1H, m), 3.36-3.46 (1H, m), 3.92-3.95 (1H, m), 4.25-4.32 (4H, m), 4.65 (1H, s), 4.72-4.84 (1H, m), 5.07 (1H, d, J = 13.7 Hz), 6.75 (2H, d, J = 8.6 Hz), 6.90 (1H, t, J = 6.1 Hz), 7.04 (2H, d, J = 8.8 Hz), 7.38 (2H, d, J = 8.1 Hz), 7.96 (2H, d, J = 9.0 Hz), 8.76 (1H, s), 9.22 (1H, s), 9.27 (1H, s). |

TABLE 390

| Example No. | MS ESI m/e: | NMR |
|---|---|---|
| 764 | 688 (M + H). | 1H-NMR (CDCl$_3$, 300 MHz) δ: 1.25 (3H, t, J = 7.2 Hz), 3.02-3.14 (1H, m), 3.07 (3H, s), 3.27 (1H, dd, J = 13.6, 4.5 Hz), 3.36-3.45 (1H, m), 3.93 (1H, dt, J = 14.1, 3.7 Hz), 4.04 (2H, s), 4.19 (2H, q, J = 7.2 Hz), 4.28-4.48 (3H, m), 4.58 (1H, t, J = 3.6 Hz), 4.79 (1H, dd, J = 13.4, 2.4 Hz), 6.62 (2H, d, J = 9.0 Hz), 7.05 (2H, d, J = 7.9 Hz), 7.17 (2H, d, J = 7.9 Hz), 7.23 (1H, t, J = 5.8 Hz), 7.40 (1H, d, J 5.8 Hz), 7.68 (2H, d, J = 9.0 Hz), 8.56 (1H, d, J = 5.8 Hz), 8.62 (1H, s), 9.16 (1H, s). |
| 765 | 660 (M + H). | 1H-NMR (CD$_3$OD, 300 MHz) δ: 3.02 (3H, s), 3.21-3.39 (1H, m), 3.48-3.72 (2H, m), 3.90 (1H, dt, J = 13.9, 3.9 Hz), 4.03 (1H, d, J = 18.3 Hz), 4.10 (1H, d, J = 18.3 Hz), 4.22-4.38 (3H, m), 4.59 (1H, t, J = 4.0 Hz), 4.71 (1H, dd, J = 14.1, 3.6 Hz), 6.69 (2H, d, J = 9.0 Hz), 6.93 (2H, d, J = 8.5 Hz), 7.19 (2H, d, J = 8.5 Hz), 7.46 (1H, d, J = 6.0 Hz), 7.69 (2H, d, J = 9.0 Hz), 8.44 (1H, d, J = 6.0 Hz), 8.61 (1H, s), 8.97 (1H, s). |
| 766 | 690, 692 (M + H). | 1H-NMR (CDCl$_3$, 300 MHz) δ: 2.96-3.04 (1H, m), 3.14 (1H, dd, J = 13.6, 4.1 Hz), 3.41-3.52 (1H, m), 3.89-3.98 (1H, m), 4.30-4.50 (3H, m), 4.63 (1H, s), 4.96 (1H, d, J = 12.4 Hz), 7.01-7.04 (3H, m), 7.13 (2H, d, J = 9.0 Hz), 7.35 (2H, d, J = 9.0 Hz), 7.48-7.53 (3H, m), 7.95 (2H, d, J = 9.0 Hz), 8.68 (1H, s). |
| 767 | 672 (M + H). | 1H-NMR (CDCl$_3$, 300 MHz) δ: 2.86 (3H, s), 2.95-3.09 (1H, m), 3.20 (1H, dd, J = 13.2, 3.8 Hz), 3.41-3.50 (1H, m), 3.93 (1H, d, J = 14.3 Hz), 4.36 (2H, d, J = 6.0 Hz), 4.63 (1H, s), 4.76 (1H, d, J = 13.2 Hz), 5.03 (1H, d, J = 13.6 Hz), 6.96-7.07 (3H, m), 7.13 (2H, d, J = 8.7 Hz), 7.39 (2H, d, J = 7.9 Hz), 7.96 (2H, d, J = 9.0 Hz), 8.67 (1H, s), 9.18 (1H, s). |
| 768 | 662 (M + H). | 1H-NMR (CDCl$_3$, 300 MHz) δ: 3.11-3.31 (2H, m), 3.42-3.56 (1H, m), 3.92 (1H, d, J = 13.9 Hz), 4.13 (1H, d, J = 12.8 Hz), 4.34-4.51 (2H, m), 4.57-4.68 (2H, m), 7.01 (1H, t, J = 5.7 Hz), 7.09 (2H, d, J = 7.9 Hz), 7.20 (2H, d, J = 8.7 Hz), 7.31-7.40 (3H, m), 7.90-7.97 (2H, m), 8.43 (1H, d, J = 5.3 Hz), 8.76 (1H, s). |

TABLE 391

| Example No. | MS ESI m/e: | NMR |
|---|---|---|
| 769 | 657 (M + H). | 1H-NMR (CDCl$_3$, 400 MHz) δ: 2.95-3.15 (2H, m), 3.43-3.53 (1H, m), 3.94 (1H, dt, J = 17.6, 3.6 Hz), 4.33-4.48 (3H, m), 4.64 (1H, br s), 4.99 (1H, d, J = 13.9 Hz), 7.01-7.12 (3H, m), 7.15 (2H, dt, J = 9.0, 2.4 Hz), 7.37 (2H, d, J = 8.9 Hz), 7.51 (1H, dd, J = 8.4, 4.2 Hz), 7.91-7.99 (3H, m), 8.78-8.83 (2H, m). |
| 770 | 657 (M + H). | 1H-NMR (CDCl$_3$, 400 MHz) δ: 2.96-3.23 (2H, m), 3.44-3.53 (1H, m), 3.94 (1H, dt, J = 13.8, 3.1 Hz), 4.37 (2H, dd, J = 6.1, 2.3 Hz), 4.61-4.69 (2H, m), 5.02 (1H, d, J = 13.7 Hz), 6.99 (2H, d, J = 9.0 Hz), 7.03-7.13 (3H, m), 7.34-7.41 (3H, m), 7.96 (2H, dt, J = 9.5, 2.4 Hz), 8.22 (1H, dd, J = 8.2, 2.0 Hz), 8.70 (1H, s), 8.86 (1H, dd, J = 4.3, 1.9 Hz). |
| 771 | 656 (M + H). | 1H-NMR (CDCl$_3$, 400 MHz) δ: 2.97-3.19 (2H, m), 3.35-3.45 (1H, m), 3.90 (1H, dt, J = 13.7, 3.1 Hz), 4.33-4.52 (3H, m), 4.66 (1H, br s), 4.96 (1H, d, J = 13.2 Hz), 6.99 (2H, d, J = 7.9 Hz), 7.03-7.13 (3H, m), 7.22-7.25 (1H, m), 7.33-7.38 (3H, m), 7.93-8.00 (3H, m), 8.51 (1H, d, J = 6.0 Hz), 8.90 (1H, s). |
| 772 | 674 (M + H). | 1H-NMR (CDCl$_3$, 400 MHz) δ: 2.96-3.08 (1H, br m), 3.16-3.24 (1H, m), 3.44-3.51 (1H, m), 3.93-4.00 (1H, m), 4.38-4.44 (2H, m), 4.67 (1H, s), 4.75-4.84 (1H, m), 5.05 (1H, d, J = 13.7 Hz), 7.09 (1H, t, J = 6.1 Hz), 7.16 (2H, d, J = 8.1 Hz), 7.40 (2H, d, J = 8.3 Hz), 7.49 (2H, d, J = 8.3 Hz), 7.97 (2H, d, J = 8.8 Hz), 8.75 (1H, s), 9.23 (1H, s), 9.27 (1H, s). |
| 773 | 702 (M + H). | 1H-NMR (CD$_3$OD, 300 MHz) δ: 0.90 (3H, t, J = 7.3 Hz), 1.46-1.61 (2H, m), 1.86-2.00 (2H, m), 2.35 (2H, t, J = 7.2 Hz), 2.44 (2H, t, J = 7.7 Hz), 2.79 (2H, t, J = 7.9 Hz), 3.36-3.44 (1H, m), 3.50-3.62 (1H, m), 3.73-3.87 (1H, br m), 4.01 (1H, d, J = 12.8 Hz), 4.21 (2H, s), 4.56-4.70 (1H, br m), 4.77-4.80 (1H, m), 4.99-5.12 (1H, br m), 6.89 (2H, d, J = 7.9 Hz), 7.02 (2H, d, J = 7.9 Hz), 7.44 (1H, d, J = 8.3 Hz), 7.83-7.98 (2H, m), 8.78 (1H, s), 9.11 (1H, s), 9.19 (1H, s). |

TABLE 392

| Example No. | MS ESI m/e: | NMR |
|---|---|---|
| 774 | 649 (M + H). | 1H-NMR (CD$_3$OD, 300 MHz) δ: 3.17-3.29 (1H, m), 3.47 (1H, dd, J = 13.9, 4.5 Hz), 3.74-3.92 (2H, m), 4.17 (1H, d, J = 13.6 Hz), 4.24-4.39 (2H, m), 4.62 (1H, t, J = 4.0 Hz), 4.79 (1H, dd, J = 14.5, 3.2 Hz), 6.66 (1H, d, J = 9.0 Hz), 7.12 (2H, d, J = 7.9 Hz), 7.27 (2H, d, J = 8.7 Hz), 7.44 (2H, d, J = 8.3 Hz), 7.95-8.04 (3H, m), 8.66 (1H, d, J = 1.9 Hz). |
| 775 | 658 (M + H). | 1H-NMR (CDCl$_3$, 300 MHz) δ: 3.12-3.27 (1H, m), 3.35 (1H, dd, J = 13.8, 4.3 Hz), 3.44-3.57 (1H, m), 3.92-4.01 (1H, m), 4.38-4.52 (3H, m), 4.62 (1H, s), 4.96 (1H, d, J = 13.9 Hz), 6.96-7.12 (4H, m), 7.16 (2H, d, J = 8.7 Hz), 7.38-7.48 (2H, m), 8.58 (1H, d, J = 5.7 Hz), 8.68 (1H, s), 9.20 (1H, s). |
| 776 | 662 (M + H). | 1H-NMR (CDCl$_3$, 400 MHz) δ: 3.10-3.26 (2H, m), 3.42-3.54 (1H, m), 3.86-4.07 (2H, m), 4.43 (2H, ddd, J = 24.1, 15.1, 5.8 Hz), 4.60-4.70 (2H, m), 7.01 (1H, t, J = 5.8 Hz), 7.08 (2H, d, J = 7.9 Hz), 7.18-7.24 (3H, m), 7.35 (2H, d, J = 7.9 Hz), 7.64 (1H, dd, J = 7.9, 1.5 Hz), 7.94 (2H, dt, J = 9.4, 2.4 Hz), 8.21 (1H, dd, J = 4.7, 1.4 Hz). |
| 777 | 657 (M + H). | 1H-NMR (CDCl$_3$, 300 MHz) δ: 0.92 (3H, t, J = 7.3 Hz), 1.56-1.63 (2H, m), 2.50-2.53 (2H, m), 2.96-3.05 (1H, m), 3.19 (1H, dd, J = 13.6, 4.1 Hz), 3.37-3.47 (1H, m), 3.94 (1H, d, J = 14.3 Hz), 4.27-4.42 (2H, m), 4.47 (1H, d, J = 12.4 Hz), 4.62 (1H, br s), 4.95 (1H, d, J = 13.2 Hz), 6.87 (1H, t, J = 5.7 Hz), 7.00 (4H, s), 7.39 (1H, d, J = 5.7 Hz), 7.58 (2H, d, J = 8.7 Hz), 7.86 (2H, d, J = 8.7 Hz), 8.56 (1H, d, J = 5.7 Hz), 8.66 (1H, s), 9.18 (1H, s). |
| 778 | 623 (M + H). | 1H-NMR (CDCl$_3$, 300 MHz) δ: 0.91 (3H, t, J = 7.3 Hz), 1.52-1.64 (2H, m), 2.51 (2H, t, J = 7.7 Hz), 3.08-3.17 (1H, m), 3.34-3.51 (2H, m), 4.03 (1H, d, J = 14.3 Hz), 4.31-4.46 (3H, m), 4.67 (1H, t, J = 3.8 Hz), 4.79 (1H, dd, J = 13.9, 3.0 Hz), 6.85 (1H, br s), 6.90 (1H, dd, J = 7.9, 2.3 Hz), 6.99-7.08 (6H, m), 7.32 (1H, t, J = 7.9 Hz), 7.40 (1H, d, J = 5.7 Hz), 7.63 (2H, d, J = 8.3 Hz), 7.89 (2H, d, J = 8.3 Hz), 8.54 (1H, d, J = 5.7 Hz), 8.60 (1H, s), 9.10 (1H, s). |

TABLE 393

| Example No. | MS ESI m/e: | NMR |
|---|---|---|
| 779 | 681 (M + H). | 1H-NMR (CDCl$_3$, 300 MHz) δ: 0.94 (3H, t, J = 7.3 Hz), 1.56-1.68 (2H, m), 2.56 (2H, t, J = 7.7 Hz), 3.51-3.63 (2H, m), 3.76-3.82 (1H, m), 4.04-4.25 (3H, m), 4.47 (2H, d, J = 5.7 Hz), 4.65 (1H, t, J = 6.8 Hz), 4.75 (2H, s), 6.14 (1H, br s), 6.89-6.93 (1H, m), 7.07-7.23 (6H, m), 7.33-7.43 (4H, m), 7.81 (2H, d, J = 8.3 Hz), 8.35-8.40 (2H, m), 8.73 (1H, s). |
| 780 | 700 (M + H). | 1H-NMR (CDCl$_3$, 300 MHz) δ: 2.86-2.95 (1H, m), 3.09 (1H, dd, J = 13.8, 4.0 Hz), 3.38-3.49 (1H, m), 3.99 (1H, d, J = 13.6 Hz), 4.40 (2H, d, J = 6.0 Hz), 4.57 (1H, d, J = 13.6 Hz), 4.63 (1H, s), 4.94 (1H, d, J = 13.9 Hz), 7.02-7.05 (3H, m), 7.14 (2H, d, J = 8.7 Hz), 7.40 (2H, d, J = 9.0 Hz), 7.75 (1H, t, J = 7.9 Hz), 7.85 (1H, dd, J = 8.3, 1.5 Hz), 7.97 (2H, d, J = 9.0 Hz), 8.44 (1H, dd, J = 7.2, 1.5 Hz), 8.66 (1H, s), 14.69 (1H, s). |
| 781 | 700 (M + H). | 1H-NMR (CDCl$_3$, 300 MHz) δ: 3.17-3.25 (2H, m), 3.57-3.65 (1H, m), 3.89-3.99 (1H, m), 4.05-4.15 (1H, m), 4.33-4.52 (2H, m), 4.64 (1H, s), 4.93 (1H, d, J = 13.6 Hz), 7.06-7.09 (3H, m), 7.18-7.21 (2H, m), 7.39 (2H, d, J = 8.3 Hz), 7.56-7.62 (1H, m), 7.96 (2H, d, J = 9.0 Hz), 8.12-8.17 (1H, m), 8.60-8.64 (1H, m), 8.79 (1H, s), 14.87 (1H, s). |
| 782 | 656 (M + H). | 1H-NMR (CDCl$_3$, 400 MHz) δ: 2.72-2.83 (2H, m), 3.47-3.60 (2H, m), 3.95-4.04 (1H, m), 4.48-4.62 (4H, m), 7.03-7.15 (4H, m), 7.25 (2H, d, J = 7.6 Hz), 7.37 (2H, d, J = 7.9 Hz), 7.56 (1H, dd, J = 9.3, 2.6 Hz), 7.92-7.98 (3H, m), 8.63 (1H, d, J = 1.6 Hz), 8.70 (1H, d, J = 2.0 Hz). |
| 783 | 528 (M + H). | 1H-NMR (CDCl$_3$, 300 MHz) δ: 2.45-2.58 (2H, m), 2.86 (1H, d, J = 13.2 Hz), 3.16 (1H, dt, J = 3.3, 6.8 Hz), 3.54 (1H, d, J = 12.9 Hz), 3.76 (1H, d, J = 13.7 Hz), 4.35 (1H, d, J = 3.9 Hz), 4.40-4.55 (2H, m), 7.18 (2H, d, J = 8.1 Hz), 7.20 (1H, m), 7.28 (2H, d, J = 8.9 Hz), 7.35 (2H, d, J = 8.1 Hz), 7.90 (2H, d, J = 8.9 Hz). |

TABLE 394

| Example No. | MS ESI m/e: | NMR |
|---|---|---|
| 784 | 679 (M + H). | 1H-NMR (DMSO-d$_6$, 300 MHz) δ: 3.35-3.41 (1H, m), 3.55-3.65 (1H, m), 3.74-3.84 (2H, m), 3.91-4.00 (1H, m), 4.03-4.23 (2H, m), 4.45 (1H, d, J = 13.9 Hz), 4.59-4.65 (1H, m), 7.17-7.30 (4H, m), 7.51 (2H, d, J = 7.9 Hz), 7.92 (2H, d, J = 9.0 Hz), 8.09 (1H, s), 8.80 (1H, t, J = 5.8 Hz), 12.43 (1H, br s). |
| 785 | 680 (M + H). | 1H-NMR (CDCl$_3$, 300 MHz) δ: 3.14-3.33 (2H, m), 3.45-3.56 (1H, m), 3.90-3.98 (1H, m), 4.18-4.61 (4H, m), 4.62-4.67 (1H, m), 6.91 (1H, t, J = 5.5 Hz), 7.16 (2H, d, J = 8.7 Hz), 7.21-7.26 (2H, m), 7.38 (2H, d, J = 8.3 Hz), 7.90-7.97 (2H, m). |
| 786 | 594 (M + H). | 1H-NMR (CD$_3$OD, 400 MHz) δ: 1.24 (3H, t, J = 7.7 Hz), 2.70 (2H, q, J = 7.6 Hz), 3.24 (1H, dq, J = 13.7, 4.5 Hz), 3.48 (1H, dd, J = 13.7, 4.5 Hz), 3.74 (1H, m), 3.87 (1H, td, J = 8.9, 4.5 Hz), 4.13 (1H, m), 4.31 (2H, s), 4.57-4.67 (2H, m), 7.13 (2H, d, J = 8.8 Hz), 7.28 (2H, d, J = 8.8 Hz), 7.37 (2H, d, J = 8.5 Hz), 7.79 (2H, d, J = 8.5 Hz), 8.03 (1H, d, J = 1.4 Hz), 8.63 (1H, d, J = 1.4 Hz). |
| 787 | 650 (M + H). | 1H-NMR (CD$_3$OD, 400 MHz) δ: 3.38 (1H, m), 3.51 (1H, m), 3.72-3.86 (2H, m), 4.17-4.28 (3H, m), 4.59 (1H, m), 4.70 (1H, m), 7.11 (1H, d, J = 3.8 Hz), 7.14 (2H, d, J = 8.3 Hz), 7.25 (2H, d, J = 6.5 Hz), 7.43 (1H, d, J = 3.8 Hz), 7.90 (1H, br s), 8.81 (1H, br s). |
| 788 | 635 (M + H). | 1H-NMR (CD$_3$OD, 400 MHz) δ: 1.99-2.04 (4H, m), 3.21-3.29 (4H, m), 3.32-40 (2H, m), 3.60 (1H, m), 3.78 (1H, m), 3.95 (1H, m), 4.27 (2H, s), 4.44 (1H, m), 4.54 (1H, m), 6.49 (2H, d, J = 8.8 Hz), 7.11 (2H, d, J = 8.6 Hz), 7.23 (2H, d, J = 8.6 Hz), 7.60 (2H, d, J = 8.8 Hz), 7.84 (1H, br s), 8.72 (1H, br s). |
| 789 | 658, 660 (M + H). | 1H-NMR (CDCl$_3$, 300 MHz) δ: 3.14-3.27 (1H, m), 3.38 (1H, dd, J = 13.6, 4.1 Hz), 3.46-3.55 (1H, m), 3.92-4.02 (1H, m), 4.31-4.45 (2H, m), 4.64 (1H, s), 4.74 (1H, t, J = 7.5 Hz), 5.03 (1H, d, J = 13.2 Hz), 6.98 (1H, t, J = 5.5 Hz), 7.07 (2H, d, J = 7.9 Hz), 7.11 (1H, d, J = 3.8 Hz), 7.15 (2H, dd, J = 6.6, 4.3 Hz), 7.46 (1H, d, J = 4.1 Hz), 8.77 (1H, s), 9.24 (1H, s), 9.28 (1H, s). |

TABLE 395

| Example No. | MS ESI m/e: | NMR |
|---|---|---|
| 790 | 619 (M + H). | 1H-NMR (CDCl$_3$, 300 MHz) δ: 3.02-3.17 (1H, m), 3.20-3.31 (1H, m), 3.43-3.57 (1H, m), 4.00 (1H, d, J = 14.3 Hz), 4.25-4.45 (2H, m), 4.68-4.81 (2H, m), 5.12 (1H, d, J = 12.8 Hz), 6.97-7.02 (1H, m), 7.03 (2H, d, J = 7.9 Hz), 7.13 (2H, d, J = 8.7 Hz), 8.09 (2H, d, J = 8.7 Hz), 8.39 (2H, d, J = 9.0 Hz), 8.71 (1H, s), 9.22 (1H, s), 9.27 (1H, s). |
| 791 | 642 (M + H). | 1H-NMR (CDCl$_3$, 300 MHz) δ: 2.94-3.09 (1H, m), 3.20 (1H, d, J = 13.6 Hz), 3.41-3.54 (1H, m), 3.99 (1H, d, J = 14.7 Hz), 4.29-4.44 (2H, m), 4.68 (1H, s), 4.79 (1H, d, J = 12.8 Hz), 5.06 (1H, d, J = 13.6 Hz), 7.00 (1H, t, J = 5.8 Hz), 7.06 (2H, d, J = 8.3 Hz), 7.14 (2H, d, J = 8.7 Hz), 7.84 (2H, d, J = 8.3 Hz), 8.05 (2H, d, J = 8.3 Hz), 8.74 (1H, s), 9.22 (1H, s), 9.27 (1H, s). |
| 792 | 614, 616 (M + H). | 1H-NMR (CDCl$_3$, 300 MHz) δ: 3.14-3.27 (1H, m), 3.34-3.42 (1H, m), 3.43-3.56 (1H, m), 3.92-4.02 (1H, m), 4.31-4.46 (2H, m), 4.64 (1H, s), 4.75 (1H, d, J = 13.2 Hz), 5.05 (1H, d, J = 14.3 Hz), 6.92-7.00 (2H, m), 7.07 (2H, d, J = 7.9 Hz), 7.15 (2H, d, J = 8.7 Hz), 7.50 (1H, d, J = 4.1 Hz), 8.78 (1H, s), 9.24 (1H, s), 9.28 (1H, s). |
| 793 | 656 (M + H). | 1H-NMR (CDCl$_3$, 400 MHz) δ: 2.92-3.14 (2H, m), 3.36-3.46 (1H, m), 3.91 (1H, dt, J = 14.1, 3.2 Hz), 4.32-4.49 (3H, m), 4.65 (1H, br s), 4.94 (1H, d, J = 13.2 Hz), 6.99 (2H, d, J = 8.6 Hz), 7.11 (2H, d, J = 8.8 Hz), 7.21-7.29 (2H, m), 7.32-7.46 (3H, m), 7.84 (1H, dq, J = 8.5, 0.8 Hz), 7.97 (1H, dt, J = 9.5, 2.4 Hz), 8.11 (1H, d, J = 9.3 Hz), 8.65 (1H, dd, J = 4.2, 1.6 Hz). |
| 794 | 663 (M + H). | 1H-NMR (CDCl$_3$, 400 MHz) δ: 3.17-3.56 (3H, m), 3.93 (1H, dt, J = 14.0, 2.8 Hz), 4.20-4.53 (3H, m), 4.67 (2H, br s), 6.96-7.12 (3H, m), 7.20 (2H, d, J = 8.4 Hz), 7.35 (2H, d, J = 9.0 Hz), 7.94 (2H, d, J = 8.6 Hz), 8.09 (1H, d, J = 2.9 Hz), 8.30 (1H, d, J = 2.6 Hz). |
| 795 | 714 (M + H). | 1H-NMR (CDCl$_3$, 400 MHz) δ: 3.00-3.12 (1H, m), 3.17-3.28 (1H, m), 3.36-3.48 (1H, m), 3.97 (1H, d, J = 14.4 Hz), 4.47-4.65 (3H, m), 4.72-4.83 (1H, m), 5.01 (1H, d, J = 13.7 Hz), 7.16-7.23 (1H, m), 7.41 (2H, d, J = 8.3 Hz), 7.98 (2H, d, J = 8.6 Hz), 8.73 (1H, s), 9.22 (1H, s), 9.28 (1H, s). |

TABLE 396

| Example No. | MS ESI m/e: | NMR |
|---|---|---|
| 796 | 580 (M + H). | 1H-NMR (CDCl₃, 400 MHz) δ: 1.26 (3H, dd, J = 8.0, 7.6 Hz), 2.73 (2H, q, J = 7.6 Hz), 2.82 (1H, tt, J = 10.1, 3.2 Hz), 2.89 (1H, dt, J = 9.0, 4.2 Hz), 3.44 (1H, ddd, J = 14.5, 9.6, 2.9 Hz), 3.88 (1H, ddd, J = 13.6, 5.2, 2.3 Hz), 4.01 (1H, m), 4.40-4.51 (2H, m), 4.57 (1H, m), 4.64 (2H, s), 4.69 (1H, dd, J = 13.2, 0.9 Hz), 7.14 (2H, d, J = 8.8 Hz), 7.16-7.19 (1H, m), 7.22 (2H, d, J = 8.8 Hz), 7.36 (2H, d, J = 8.6 Hz), 7.78 (2H, d, J = 8.6 Hz), 8.01 (1H, s), 8.10 (1H, s). |
| 797 | 678 (M + H). | 1H-NMR (CDCl₃, 400 MHz) δ: 2.97-3.10 (1H, m), 3.24 (1H, dd, J = 13.8, 4.1 Hz), 3.32-3.41 (1H, m), 3.92 (1H, d, J = 14.3 Hz), 4.53 (1H, dd, J = 14.2, 5.4 Hz), 4.60-4.68 (2H, m), 4.75-4.85 (1H, m), 5.08 (1H, d, J = 13.7 Hz), 6.81 (1H, t, J = 5.5 Hz), 7.18 (2H, s), 7.38 (2H, d, J = 8.2 Hz), 7.95-7.97 (2H, m), 8.74 (1H, s), 9.21 (1H, s), 9.27 (1H, s). |
| 798 | 726 (M + H). | 1H-NMR (CDCl₃, 300 MHz) δ: 2.92-3.09 (1H, m), 3.21 (1H, d, J = 11.3 Hz), 3.36-3.51 (1H, m), 3.91-4.02 (1H, m), 4.26-4.44 (2H, m), 4.66 (1H, s), 4.82-4.98 (1H, m), 5.08 (1H, d, J = 14.3 Hz), 6.98 (1H, t, J = 6.2 Hz), 7.06 (2H, d, J = 7.9 Hz), 7.14 (2H, d, J = 8.7 Hz), 7.40 (2H, d, J = 8.3 Hz), 7.97 (2H, d, J = 8.7 Hz), 8.86 (1H, br s), 9.35 (1H, s). |
| 799 | 635, 637 (M + H). | 1H-NMR (CDCl₃, 300 MHz) δ: 3.01-3.24 (2H, m), 3.37-3.50 (1H, m), 3.93-4.03 (1H, m), 4.29-4.47 (2H, m), 4.62-4.74 (2H, m), 5.10 (1H, d, J = 14.3 Hz), 7.03 (2H, d, J = 7.9 Hz), 7.09-7.15 (3H, m), 7.38 (2H, d, J = 9.0 Hz), 7.98 (2H, d, J = 8.3 Hz), 8.68 (1H, br s), 8.78 (1H, s), 9.07 (1H, s). |
| 800 | 731 (M + H). | 1H-NMR (CDCl₃, 400 MHz) δ: 3.12-3.55 (3H, m), 3.96 (1H, d, J = 13.7 Hz), 4.28-4.71 (5H, m), 6.88 (1H, s), 7.12-7.25 (4H, m), 7.38 (2H, d, J = 7.7 Hz), 7.93 (2H, dt, J = 9.6, 2.4 Hz). |
| 801 | 663 (M + H). | 1H-NMR (CDCl₃, 400 MHz) δ: 3.16-3.57 (3H, m), 3.94 (1H, d, J = 14.4 Hz), 4.26-4.73 (5H, m), 6.98-7.14 (3H, m), 7.20 (2H, d, J = 8.8 Hz), 7.36 (2H, d, J = 8.3 Hz), 7.94 (2H, d, J = 8.9 Hz), 8.79 (1H, s), 8.95 (1H, s). |

TABLE 397

| Example No. | MS ESI m/e: | NMR |
|---|---|---|
| 802 | 697 (M + H). | 1H-NMR (CDCl₃, 400 MHz) δ: 3.14-3.55 (3H, m), 3.95 (1H, d, J = 13.9 Hz), 4.27-4.71 (5H, m), 6.95 (1H, t, J = 6.6 Hz), 7.13 (2H, d, J = 8.1 Hz), 7.21 (2H, d, J = 8.6 Hz), 7.37 (2H, d, J = 8.3 Hz), 7.93 (2H, d, J = 8.7 Hz), 8.60 (1H, s). |
| 803 | 695 (M + H). | 1H-NMR (DMSO-d₆, 300 MHz) δ: 3.28-3.39 (1H, m), 3.52-3.63 (1H, m), 3.76-3.85 (2H, m), 3.96 (1H, d, J = 13.6 Hz), 4.03-4.23 (2H, m), 4.44 (1H, d, J = 13.6 Hz), 4.60-4.67 (1H, m), 7.17-7.32 (4H, m), 7.51 (2H, d, J = 8.3 Hz), 7.92 (2H, d, J = 9.0 Hz), 8.79 (1H, t, J = 5.8 Hz). |
| 804 | 632 (M + H). | 1H-NMR (CDCl₃, 400 MHz) δ: 1.27 (6H, dd, J = 20.7, 12.6 Hz), 1.43-1.80 (9H, m), 2.75-3.22 (4H, m), 3.44-3.54 (1H, m), 3.98 (1H, dt, J = 14.1, 2.7 Hz), 4.61 (1H, br s), 4.91 (1H, d, J = 13.7 Hz), 5.07 (1H, d, J = 14.1 Hz), 6.60 (1H, t, J = 6.4 Hz), 7.43 (2H, d, J = 7.9 Hz), 8.00 (2H, dt, J = 9.4, 2.5 Hz), 8.78 (1H, s), 9.19 (1H, s), 9.24 (1H, s). |
| 805 | 679 (M + H). | 1H-NMR (DMSO-d₆, 400 MHz) δ: 3.33-3.40 (1H, m), 3.60-3.85 (3H, m), 3.95-4.20 (3H, m), 4.39 (1H, d, J = 13.0 Hz), 4.64 (1H, dd, J = 4.8, 2.4 Hz), 7.23 (4H, dd, J = 22.3, 8.6 Hz), 7.50 (2H, d, J = 8.6 Hz), 7.93 (2H, dt, J = 9.7, 2.5 Hz), 8.13 (1H, s), 8.81 (1H, t, J = 5.9 Hz), 12.87 (1H, s). |
| 806 | 701 (M + H). | 1H-NMR (CDCl₃, 300 MHz) δ: 3.17-3.31 (2H, m), 3.50-3.64 (1H, m), 3.92-3.99 (1H, m), 4.18-4.27 (1H, m), 4.28-4.51 (2H, m), 4.66 (1H, s), 5.01 (1H, d, J = 13.9 Hz), 7.05 (1H, t, J = 5.3 Hz), 7.11 (2H, d, J = 7.9 Hz), 7.21 (3H, d, J = 8.7 Hz), 7.41 (2H, d, J = 7.9 Hz), 7.96 (2H, d, J = 8.7 Hz), 8.85 (1H, br s), 9.35 (1H, s), 9.47 (1H, s). |
| 807 | 700 (M + H). | 1H-NMR (CDCl₃, 300 MHz) δ: 3.10-3.26 (2H, m), 3.52-3.59 (1H, m), 3.92-4.01 (1H, m), 4.15-4.25 (1H, m), 4.32-4.51 (2H, m), 4.65 (1H, s), 5.12 (1H, d, J = 13.9 Hz), 6.04 (1H, br s), 7.07-7.10 (3H, m), 7.19 (2H, d, J = 8.7 Hz), 7.40 (2H, d, J = 8.3 Hz), 7.96 (2H, d, J = 8.7 Hz), 8.72 (1H, br s), 9.24-9.31 (2H, br m), 9.49 (1H, s). |

TABLE 398

| Example No. | MS ESI m/e: | NMR |
|---|---|---|
| 808 | 729 (M + H). | 1H-NMR (CDCl₃, 300 MHz) δ: 2.64-2.75 (2H, m), 3.09-3.23 (1H, br m), 3.24-3.35 (2H, m), 3.35-3.49 (1H, m), 3.52-3.64 (1H, m), 3.91-4.00 (1H, m), 4.19-4.32 (1H, br m), 4.33-4.51 (2H, m), 4.73 (1H, br s), 4.89-4.99 (1H, m), 7.05 (3H, m), 7.17 (2H, d, J = 8.7 Hz), 7.30 (2H, d, J = 8.7 Hz), 7.94 (2H, d, J = 8.7 Hz), 8.48 (2H, br s), 9.05 (1H, br s). |
| 809 | 664 (M + H). | 1H-NMR (CD₃OD, 400 MHz) δ: 2.71 (3H, s), 3.05-3.17 (1H, m), 3.62-3.72 (1H, m), 3.76-3.84 (1H, m), 4.09-4.23 (2H, m), 4.25-4.35 (1H, m), 4.64 (1H, m), 4.76 (1H, m), 4.90 (1H, m), 7.03-7.08 (2H, m), 7.14-7.17 (2H, m), 7.37 (2H, d, J = 8.5 Hz), 7.81 (1H, brs), 7.94 (2H, d, J = 8.5 Hz). |
| 810 | 728 (M + H). | 1H-NMR (CDCl₃, 300 MHz) δ: 2.49-2.72 (2H, m), 3.21-3.29 (4H, m), 3.54-3.66 (1H, m), 3.87-3.97 (1H, m), 4.24-4.33 (1H, m), 4.37 (2H, d, J = 6.0 Hz), 4.70 (1H, br s), 5.22-5.35 (2H, m), 6.00 (1H, s), 7.00 (2H, d, J = 8.7 Hz), 7.12 (2H, d, J = 8.7 Hz), 7.31-7.44 (3H, m), 7.94 (2H, d, J = 8.7 Hz), 8.48 (1H, s), 8.56 (1H, s), 9.09 (1H, s). |
| 811 | 602 (M + H). | 1H-NMR (CDCl₃, 400 MHz) δ: 1.70-1.78 (2H, m), 2.53 (2H, t, J = 7.6 Hz), 2.98 (1H, t, J = 12.5 Hz), 3.10-3.32 (3H, m), 3.39-3.46 (1H, m), 3.95 (1H, d, J = 14.1 Hz), 4.57 (1H, br s), 4.80 (1H, d, J = 12.1 Hz), 5.01 (1H, d, J = 13.7 Hz), 6.62 (1H, t, J = 5.8 Hz), 7.04-7.09 (2H, m), 7.14-7.20 (1H, m), 7.23 (2H, dt, J = 7.9, 1.7 Hz), 7.41 (2H, d, J = 8.2 Hz), 7.98 (2H, dt, J = 9.4, 2.4 Hz), 8.77 (1H, s), 9.17 (1H, s), 9.24 (1H, s). |
| 812 | 581 (M + H). | 1H-NMR (CDCl₃, 400 MHz) δ: 0.94 (3H, t, J = 7.3 Hz), 1.25 (3H, t, J = 7.7 Hz), 1.59-1.68 (2H, m), 2.56 (2H, t, J = 7.7 Hz), 2.72 (2H, q, J = 7.7 Hz), 3.06-3.18 (2H, m), 3.40-3.51 (1H, m), 3.88-4.00 (2H, m), 4.40 (2H, d, J = 5.8 Hz), 4.53-4.63 (2H, m), 6.90 (1H, t, J = 5.6 Hz), 7.11 (4H, s), 7.35 (2H, d, J = 8.1 Hz), 7.77 (2H, dt, J = 8.4, 1.9 Hz), 8.05 (1H, s), 10.18 (1H, s). |

TABLE 399

| Example No. | MS ESI m/e: | NMR |
|---|---|---|
| 813 | 637, 639 (M + H). | 1H-NMR (CDCl₃, 300 MHz) δ: 0.89-0.94 (3H, m), 1.25 (3H, t, J = 7.5 Hz), 1.51-1.65 (2H, m), 2.47-2.54 (2H, m), 2.70 (2H, q, J = 7.5 Hz), 2.92-3.05 (1H, m), 3.13 (1H, dd, J = 13.6, 4.1 Hz), 3.35-3.46 (1H, m), 3.94-4.03 (1H, m), 4.26-4.44 (2H, m), 4.58-4.70 (2H, br m), 4.98 (1H, d, J = 13.6 Hz), 6.97-7.01 (5H, m), 7.36 (2H, d, J = 8.3 Hz), 7.80 (2H, d, J = 8.7 Hz), 8.69 (1H, br s), 8.77 (1H, s), 9.06 (1H, s). |
| 814 | 602 (M + H). | 1H-NMR (CDCl₃, 300 MHz) δ: 0.91 (3H, t, J = 7.2 Hz), 1.25 (3H, t, J = 7.5 Hz), 1.51-1.63 (2H, m), 2.49 (2H, t, J = 7.5 Hz), 2.71 (2H, q, J = 7.7 Hz), 2.83-2.93 (1H, m), 3.08 (1H, dd, J = 13.9, 4.1 Hz), 3.34-3.44 (1H, m), 3.94-4.03 (1H, m), 4.29 (1H, dd, J = 15.1, 5.7 Hz), 4.40 (1H, dd, J = 15.1, 6.0 Hz), 4.51 (1H, d, J = 12.8 Hz), 4.64 (1H, s), 4.88 (1H, d, J = 13.9 Hz), 6.91-7.04 (5H, m), 7.36 (2H, d, J = 8.3 Hz), 7.73 (1H, t, J = 7.7 Hz), 7.80 (2H, d, J = 8.3 Hz), 7.85 (1H, dd, J = 8.3, 1.5 Hz), 8.41 (1H, dd, J = 7.3, 1.3 Hz), 8.65 (1H, s), 14.75 (1H, s). |
| 815 | 603 (M + H). | 1H-NMR (CDCl₃, 300 MHz) δ: 0.91 (3H, t, J = 7.3 Hz), 1.26 (3H, t, J = 7.7 Hz), 1.52-1.61 (2H, m), 2.50 (2H, t, J = 7.7 Hz), 2.71 (2H, q, J = 7.5 Hz), 3.14-3.27 (2H, m), 3.43-3.57 (1H, m), 3.89-3.99 (1H, m), 4.08-4.17 (1H, m), 4.26-4.44 (2H, m), 4.67 (1H, br s), 4.97 (1H, d, J = 14.3 Hz), 6.99-7.01 (5H, m), 7.39 (2H, d, J = 8.3 Hz), 7.80 (2H, d, J = 8.3 Hz), 8.84 (1H, br s), 9.33 (1H, s), 9.46 (1H, s), 13.92 (1H, br s). |
| 816 | 602 (M + H). | 1H-NMR (CDCl₃, 300 MHz) δ: 0.91 (3H, t, J = 7.3 Hz), 1.24 (3H, t, J = 7.5 Hz), 1.49-1.65 (2H, m), 2.50 (2H, t, J = 7.7 Hz), 2.68 (2H, q, J = 7.5 Hz), 3.12-3.23 (2H, m), 3.47-3.59 (1H, m), 3.87-4.05 (2H, m), 4.31 (1H, dd, J = 14.7, 5.7 Hz), 4.43 (1H, dd, J = 14.7, 6.4 Hz), 4.65 (1H, s), 4.88 (1H, dd, J = 13.6, 1.9 Hz), 6.98-7.08 (5H, m), 7.37 (2H, d, J = 8.3 Hz), 7.56 (1H, t, J = 7.7 Hz), 7.79 (2H, d, J = 8.3 Hz), 8.13 (1H, dd, J = 8.3, 1.5 Hz), 8.60 (1H, dd, J = 7.5, 1.5 Hz), 8.79 (1H, s), 14.95 (1H, s). |

TABLE 400

| Example No. | MS ESI m/e: | NMR |
|---|---|---|
| 817 | 658 (M + H). | 1H-NMR (CDCl₃, 300 MHz) δ: 0.91 (3H, t, J =7.3 Hz), 1.49-1.70 (2H, m), 2.49 (2H, t, J = 7.5 Hz), 2.86-2.98 (1H, m), 3.12 (1H, dd, J = 13.8, 4.0 Hz), 3.36-3.49 (1H, m), 3.91-4.02 (1H, m), 4.30 (1H, dd, J = 14.9, 5.8 Hz), 4.38 (1H, dd, J = 14.7, 6.0 Hz), 4.59 (1H, d, J = 13.9 Hz), 4.65 (1H, s), 4.97 (1H, d, J = 13.9 Hz), 6.87 (1H, t, J = 5.7 Hz), 6.98 (4H, s), 7.37 (2H, d, J = 7.9 Hz), 7.74 (1H, t, J = 7.9 Hz), 7.85 (1H, dd, J = 8.3, 1.5 Hz), 7.96 (2H, d, J = 8.7 Hz), 8.43 (1H, dd, J = 7.3, 1.3 Hz), 8.67 (1H, s), 14.71 (1H, s). |
| 818 | 607 (M + H). | 1H-NMR (CDCl₃, 400 MHz) δ: 0.93 (3H, t, J =7.3 Hz), 1.25 (3H, t, J =7.5 Hz), 1.59-1.67 (2H, m), 2.55 (2H, t, J =7.5 Hz), 2.70 (2H, q, J =7.5 Hz), 3.12-3.24 (2H, m), 3.48 (1H, m), 3.92-4.08 (2H, m), 4.34-4.52 (3H, m), 4.65 (1H, m), 6.94 (1H, t, J=5.8 Hz), 7.06-7.12 (4H, m), 7.24 (1H, t, J =7.8 Hz), 7.36 (2H, d, J =8.5 Hz), 7.75 (1H, dd, J = 7.8, 1.2 Hz), 7.78 (2H, dt, J =8.5, 2.0 Hz), 8.14 (1H, dd, J = 7.8, 1.2 Hz), 13.32 (1H, d, J = 1.8 Hz). |
| 819 | 637 (M + H). | 1H-NMR (CDCl₃, 300 MHz) δ: 0.93 (3H, t, J = 7.3 Hz), 1.58-1.68 (2H, m), 2.56 (2H, t, J = 7.7 Hz), 3.17-3.28 (2H, m), 3.44-3.56 (1H, m), 3.86-3.96 (1H, m), 3.97-4.07 (1H, m), 4.30-4.44 (2H, m), 4.60-4.70 (2H, m), 6.72-6.80 (1H, m), 7.08 (2H, d, J = 8.7 Hz), 7.11 (2H, d, J = 8.7 Hz), 7.34 (2H, d, J = 8.3 Hz), 7.91 (2H, d, J = 8.7 Hz), 8.03 (1H, s), 10.10 (1H, br s). |
| 820 | 621 (M + H). | 1H-NMR (CDCl₃, 300 MHz) 5: 0.93 (3H, t, J = 7.3 Hz), 1.56-1.69 (2H, m), 2.56 (2H, t, J = 7.5 Hz), 3.14-3.31 (2H, m), 3.46-3.58 (1H, m), 3.89-4.07 (2H, m), 4.28-4.45 (2H, m), 4.61-4.70 (2H, m), 6.69-6.79 (1H, m), 7.07 (2H, d, J = 8.3 Hz), 7.11 (2H, d, J = 8.3 Hz), 7.78 (2H, d, J = 8.3 Hz), 7.99 (2H, d, J = 8.3 Hz), 8.01 (1H, s), 10.12 (1H, br s). |

TABLE 401

| Example No. | MS ESI m/e: | NMR |
|---|---|---|
| 821 | 673 (M + H). | 1H-NMR (CDCl₃, 300 MHz) δ: 0.98 (3H, t, J = 7.3 Hz), 2.01-2.23 (2H, m), 3.11-3.27 (2H, m), 3.46-3.57 (1H, m), 3.88-3.98 (1H, m), 3.98-4.08 (1H, m), 4.37-4.55 (2H, m), 4.57-4.67 (2H, m), 6.93 (1H, t, J = 6.2 Hz), 7.25 (2H, d, J = 7.9 Hz), 7.37 (2H, d, J = 9.4 Hz), 7.40 (2H, d, J = 7.9 Hz), 7.93 (2H, d, J = 8.7 Hz), 8.04 (1H, s), 9.96 (1H, br s). |
| 822 | 621( M + H). | 1H-NMR (CD₃OD, 400 MHz) δ: 0.91 (3H, t, J = 7.4 Hz), 1.59 (2H, td, J = 14.9, 7.5 Hz), 2.50-2.59 (5H, m), 3.13 (1H, ddd, J = 13.7, 9.5, 3.6 Hz), 3.38 (1H, dd, J = 13.9, 4.6 Hz), 3.67-3.85 (2H, m), 4.15-4.28 (3H, m), 4.59 (1H, dd, J = 4.2, 3.1 Hz), 4.76-4.81 (1H, m), 6.44 (1H, d, J = 9.0 Hz), 7.01 (4H, ddd, J = 11.5, 6.0, 2.5 Hz), 7.38 (2H, d, J = 8.8 Hz), 7.92-8.00 (3H, m), 8.55 (1H, t, J = 6.0 Hz). |
| 823 | 639 (M + H). | 1H-NMR (CD₃OD, 400 MHz) δ: 0.91 (3H, t, J = 7.4 Hz), 1.60 (2H, td, J = 14.9, 7.4 Hz), 2.51-2.59 (5H, m), 3.10-3.20 (1H, m), 3.41 (1H, dd, J = 14.1, 4.4 Hz), 3.74-3.88 (2H, m), 4.11-4.39 (3H, m), 4.59 (1H, dd, J = 4.1, 3.0 Hz), 4.74 (1H, d, J = 13.9 Hz), 7.03 (4H, s), 7.36 (2H, d, J = 8.2 Hz), 7.71 (1H, d, J = 14.3 Hz), 7.92 (2H, dt, J = 9.4, 2.4 Hz), 8.56 (1H, t, J = 5.7 Hz). |
| 824 | 659 (M + H). | 1H-NMR (CDCl₃, 300 MHz) δ: 0.91 (3H, t, J = 7.3 Hz), 1.50-1.65 (2H, m), 2.50 (2H, t, J = 7.7 Hz), 3.19-3.31 (2H, m), 3.48-3.61 (1H, m), 3.94 (1H, d, J = 14.3 Hz), 4.20-4.40 (3H, m), 4.68 (1H, s), 5.05 (1H, d, J = 13.9 Hz), 6.84-6.94 (1H, m), 7.01 (4H, s), 7.38 (2H, d, J = 8.7 Hz), 7.94 (2H, d, J = 8.7 Hz), 8.85 (1H, br s), 9.34 (1H, s), 9.45 (1H, s). |
| 825 | 598 (M + H). | 1H-NMR (CDCl₃, 300 MHz) δ: 0.92 (3H, t, J = 7.3 Hz), 1.51-1.63 (2H, m), 2.54 (2H, t, J = 7.7 Hz), 3.24-3.38 (1H, m), 3.38-3.49 (1H, m), 3.53-3.68 (1H, m), 3.92-4.15 (2H, m), 4.19-4.40 (2H, m), 4.63-4.77 (2H, m), 6.91 (1H, t, J = 5.7 Hz), 6.99-7.10 (4H, m), 7.96-8.06 (3H, m), 8.21-8.35 (2H, m), 10.64 (1H, s). |

TABLE 402

| Example No. | MS ESI m/e: | NMR |
|---|---|---|
| 826 | 655 (M + H). | 1H-NMR (CD$_3$OD, 300 MHz) δ: 0.94 (3H, t, J = 7.2 Hz), 1.60-1.69 (2H, m), 2.11 (3H, s), 2.51 (2H, t, J = 7.2 Hz), 2.58 (2H, t, J = 7.7 Hz), 2.89 (2H, t, J = 7.5 Hz), 3.01-3.09 (1H, m), 3.23-3.30 (2H, m), 3.72-3.91 (3H, m), 4.22-4.33 (3H, m), 4.64 (1H, s), 7.11 (4H, t, J = 5.1 Hz), 7.40 (2H, d, J = 7.9 Hz), 7.95 (2H, d, J = 9.0 Hz), 8.52 (1H, t, J = 6.2 Hz). |
| 827 | 662 (M + H). | 1H-NMR (CDCl$_3$, 400 MHz) δ: 0.94 (3H, t, J = 7.5 Hz), 1.58-1.70 (2H, m), 2.40 (3H, s), 2.58 (2H, t, J = 7.5 Hz), 2.98 (1H, ddd, J = 14.2, 10.1, 3.1 Hz), 3.05 (1H, dd, J = 13.2, 4.4 Hz), 3.39-3.48 (1H, m), 3.83-3.92 (2H, m), 4.34-4.45 (3H, m), 4.58 (1H, br s), 4.86 (2H, s), 6.75 (1H, t, J = 5.8 Hz), 7.10 (2H, d, J = 8.3 Hz), 7.14 (2H, d, J = 8.3 Hz), 7.34 (2H, d, J = 9.2 Hz), 7.90 (2H, dt, J = 9.2, 2.4 Hz). |
| 828 | 676 (M + H). | 1H-NMR (CDCl$_3$, 400 MHz) δ: 0.94 (3H, t, J = 7.4 Hz), 1.61-1.66 (2H, m), 2.40 (3H, s), 2.58 (2H, t, J = 7.6 Hz), 2.70 (3H, d, J = 5.5 Hz), 2.94-3.03 (1H, m), 3.03 (1H, dd, J = 13.0, 4.4 Hz), 3.38-3.48 (1H, m), 3.83-3.91 (2H, m), 4.34 (1H, q, J = 5.1 Hz), 4.40 (2H, d, J = 5.5 Hz), 4.45 (1H, d, J = 12.6 Hz), 4.58 (1H, d, J = 2.2 Hz), 6.75 (1H, t, J = 5.5 Hz), 7.11 (2H, d, J = 8.4 Hz), 7.14 (2H, d, J = 8.2 Hz), 7.35 (2H, d, J = 8.8 Hz), 7.90 (2H, dt, J = 9.5, 2.4 Hz). |
| 829 | 690 (M + H). | 1H-NMR (CDCl$_3$, 400 MHz) δ: 0.94 (3H, t, J = 7.4 Hz), 1.58-1.69 (2H, m), 2.41 (3H, s), 2.58 (2H, t, J = 7.6 Hz), 2.77 (6H, s), 2.94-3.06 (2H, m), 3.39-3.49 (1H, m), 3.81-3.91 (2H, m), 4.38 (1H, dd, J = 13.0, 4.0 Hz), 4.42 (1H, dd, J = 13.0, 4.0 Hz), 4.47 (1H, d, J = 13.9 Hz), 4.59 (1H, d, J = 3.3 Hz), 6.74 (1H, t, J = 5.7 Hz), 7.11 (2H, d, J = 8.2 Hz), 7.14 (2H, d, J = 8.2 Hz), 7.34 (2H, d, J = 9.0 Hz), 7.90 (2H, dt, J = 9.5, 2.5 Hz). |

TABLE 403

| Example No. | MS ESI m/e: | NMR |
|---|---|---|
| 830 | 605 (M +H). | 1H-NMR (CDCl$_3$, 400 MHz) δ: 0.94 (3H, t, J = 7.4 Hz), 1.60-1.67 (2H, m), 2.47 (1H, td, J = 12.8, 10.1 Hz), 2.56 (2H, t, J = 7.7 Hz), 2.73 (1H, dd, J = 14.4, 3.4 Hz), 3.08 (1H, td, J = 19.1, 8.0 Hz), 3.89 (1H, d, J = 14.6 Hz), 4.16 (1H, d, J = 13.9 Hz), 4.47 (2H, d, J = 5.7 Hz), 4.51 (1H, d, J = 14.3 Hz), 4.58 (1H, s), 6.99 (2H, m, J = 9.9, 4.2 Hz), 7.29-7.34 (9H, m), 7.91 (2H, d, J = 11.9 Hz), 7.91 (1H, s). |
| 831 | 663 (M +H). | 1H-NMR (CDCl$_3$, 400 MHz) δ: 0.93 (3H, t, J = 7.4 Hz), 1.59-1.62 (2H, m), 2.54 (2H, t, J = 7.7 Hz), 2.98-3.01 (1H, m), 3.10 (1H, dd, J = 13.7, 4.2 Hz), 3.36-3.43 (1H, m), 3.81 (1H, d, J = 14.1 Hz), 3.90 (3H, s), 3.99 (1H, d, J = 13.9 Hz), 4.41 (2H, dd, J = 5.6, 2.3 Hz), 4.60-4.64 (2H, m), 6.85 (1H, t, J = 10.0 Hz), 6.96-7.00 (1H, m), 7.11 (4H, d, J = 8.1 Hz), 7.32 (2H, d, J = 7.9 Hz), 7.45-7.50 (1H, m), 7.92 (2H, dt, J = 9.5, 2.4 Hz), 7.98 (1H, dd, J = 7.9, 1.5 Hz), 8.45 (1H, dd, J = 8.7, 1.0 Hz), 10.71 (1H, s). |
| 832 | 704 (M +H). | 1H-NMR (CDCl$_3$, 400 MHz) δ: 0.95 (3H, t, J = 7.2 Hz), 1.59-1.70 (2H, m), 2.07 (3H, s), 2.48 (3H, s), 2.59 (2H, t, J = 7.2 Hz), 2.98-3.08 (2H, m), 3.39-3.51 (1H, m), 3.88 (2H, t, J = 14.7 Hz), 4.34-4.47 (3H, m), 4.61 (1H, s), 6.79 (1H, br s), 7.11 (2H, d, J = 6.7 Hz), 7.16 (2H, d, J = 6.5 Hz), 7.35 (2H, d, J = 7.9 Hz), 7.90 (2H, d, J = 8.6 Hz), 8.26 (1H, s). |
| 833 | 711 (M +H). | 1H-NMR (CDCl$_3$, 400 MHz) δ: 0.94 (3H, t, J = 7.4 Hz), 1.63 (2H, td, J = 15.0, 7.4 Hz), 2.55-2.57 (1H, m), 2.56 (2H, dd, J = 14.3, 6.6 Hz), 2.74 (1H, dd, J = 13.8, 3.4 Hz), 3.12-3.20 (1H, m), 3.85 (1H, d, J = 14.3 Hz), 4.04 (1H, d, J = 13.5 Hz), 4.36 (2H, dd, J = 5.7, 2.2 Hz), 4.46-4.50 (2H, m), 5.15 (2H, dd, J = 30.9, 12.1 Hz), 6.83 (1H, t, J = 10.0 Hz), 6.89-6.92 (3H, m), 7.12 (4H, dt, J = 10.8, 8.6 Hz), 7.30-7.33 (4H, m), 7.48 (2H, dd, J = 4.1, 2.0 Hz), 7.89-7.92 (1H, m), 7.90 (2H, d, J = 8.7 Hz), 8.02 (1H, s). |

TABLE 404

| Example No. | MS ESI m/e: | NMR |
|---|---|---|
| 834 | 621 (M + H). | 1H-NMR (CDCl$_3$, 400 M Hz) δ: 0.93 (3H, t, J = 7.4 Hz), 1.61-1.64 (2H, m), 2.48-2.50 (2H, m), 2.49-2.58 (1H, m), 2.81 (1H, dd, J = |

TABLE 404-continued

| Example No. | MS ESI m/e: | NMR |
|---|---|---|
| | | 14.7, 3.4 Hz), 3.06-3.14 (1H, m), 3.90 (1H, d, J = 14.6 Hz), 4.18 (1H, d, J = 13.7 Hz), 4.47 (2H, d, J = 5.7 Hz), 4.52-4.60 (2H, m), 6.84 (1H, t, J = 7.5 Hz), 6.97-7.06 (4H, m), 7.12-7.17 (2H, m), 7.38 (2H, d, J = 7.9 Hz), 7.91 (2H, d, J = 11.9 Hz), 8.20 (1H, s), 8.65 (1H, s). |
| 835 | 640 (M + H). | 1H-NMR (CDCl$_3$, 300 MHz) δ: 3.16-3.36 (2H, m), 3.50-3.64 (1H, m), 3.92-4.10 (2H, m), 4.29-4.51 (2H, m), 4.60-4.74 (2H, m), 6.98 (1H, t, J = 5.8 Hz), 7.13 (2H, d, J = 8.7 Hz), 7.21 (2H, d, J = 8.7 Hz), 7.95-8.11 (3H, m), 8.36 (2H, d, J = 9.0 Hz), 10.27 (1H, s). |
| 836 | 695 (M + H). | 1H-NMR (DMSO-d6, 300 MHz) δ: 0.82 (3H, t, J = 7.3 Hz), 1.99-2.18 (2H, m), 3.23-3.44 (1H, m), 3.55-3.90 (3H, m), 4.03-4.16 (2H, m), 4.36-4.53 (1H, m), 4.71-4.87 (2H, m), 7.15-7.25 (4H, m), 7.48 (2H, d, J = 7.9 Hz), 7.97 (2H, d, J = 8.7 Hz), 8.84-8.91 (2H, m), 8.99 (1H, s), 9.16 (1H, s), 13.74 (1H, br s). |
| 837 | 739 (M + H). | 1H-NMR (CDCl$_3$, 400 MHz) δ: 0.92 (3H, t, J = 7.4 Hz), 1.58-1.62 (2H, m), 2.53 (2H, t, J = 7.7 Hz), 3.00 (1H, t, J = 10.1 Hz), 3.10 (1H, dd, J = 13.5, 4.0 Hz), 3.39 (1H, dt, J = 17.6, 6.2 Hz), 3.81 (1H, d, J = 13.9 Hz), 3.98 (1H, d, J = 13.5 Hz), 4.41 (2H, d, J = 5.7 Hz), 4.59-4.62 (2H, m), 5.34 (2H, s), 6.86 (1H, t, J = 5.6 Hz), 6.95-6.99 (1H, m), 7.11 (4H, d, J = 8.5 Hz), 7.30-7.50 (8H, m), 7.92 (2H, dt, J = 9.5, 2.5 Hz), 8.03 (1H, dd, J = 8.0, 1.4 Hz), 8.45 (1H, dd, J = 8.6, 0.9 Hz), 10.68 (1H, s). |
| 838 | 649 (M + H). | 1H-NMR (CDCl$_3$, 400 MHz) δ: 0.91 (3H, t, J = 7.4 Hz), 1.58 (2H, td, J = 14.9, 7.5 Hz), 2.51 (2H, t, J = 7.6 Hz), 2.92 (1H, d, J = 11.0 Hz), 3.03 (1H, dd, J = 13.9, 4.4 Hz), 3.46 (1H, t, J = 10.7 Hz), 3.79 (1H, d, J = 12.6 Hz), 4.04 (1H, d, J = 13.2 Hz), 4.38 (2H, d, J = 5.5 Hz), 4.64-4.67 (2H, m), 6.87 (1H, t, J = 7.2 Hz), 7.07-7.09 (6H, m), 7.31 (2H, d, J = 8.2 Hz), 7.42-7.47 (1H, m), 7.84 (1H, dd, J = 7.9, 1.5 Hz), 7.91 (2H, d, J = 8.8 Hz), 8.40 (1H, d, J = 7.7 Hz), 10.80 (1H, s). |

TABLE 405

| Example No. | MS ESI m/e: | NMR |
|---|---|---|
| 839 | 693 (M + H). | 1H-NMR (DMSO-d$_6$, 300 MHz) δ: 2.32 (3H, s), 3.33-3.40 (1H, m), 3.62 (1H, dd, J = 13.9, 4.5 Hz), 3.71-3.87 (2H, m), 3.98-4.20 (3H, m), 4.30-4.45 (1H, m), 4.62-4.68 (1H, m), 7.17 (2H, d, J = 8.3 Hz), 7.25 (2H, d, J = 8.7 Hz), 7.49 (2H, d, J = 8.3 Hz), 7.92 (2H, d, J = 8.7 Hz), 8.82 (1H, t, J = 5.8 Hz), 12.59 (1H, s). |
| 840 | 665 (M + H). | 1H-NMR (CD$_3$OD, 400 MHz) δ: 0.62 (3H, dq, J = 10.5, 2.6 Hz), 1.22 (3H, s), 1.23 (3H, s), 1.56-1.65 (2H, m), 3.37 (1H, m), 3.45 (1H, m), 3.64 (1H, m), 3.83-3.95 (2H, m), 4.11 (1H, m), 4.15-4.27 (2H, m), 4.59 (1H, m), 4.70 (1H, m), 7.08-7.11 (2H, m), 7.16-7.19 (2H, m), 7.40-7.43 (2H, m), 7.94-8.00 (2H, m), 8.11 (1H, d, J = 3.9 Hz). |
| 841 | 651 (M + H). | 1H-NMR (CD$_3$OD, 300 MHz) δ: 0.91 (3H, t, J = 7.2 Hz), 1.28-1.38 (2H, m), 1.47-1.58 (2H, m), 2.53 (2H, t, J = 7.5 Hz), 3.36-3.49 (1H, m), 3.57-3.67 (1H, m), 3.83-3.91 (2H, m), 4.02-4.26 (3H, m), 4.55 (1H, d, J = 14.3 Hz), 4.64-4.69 (1H, m), 6.98-7.10 (4H, m), 7.39 (2H, d, J = 7.9 Hz), 7.92-7.96 (2H, m), 8.07 (1H, s). |
| 842 | 643 (M + H). | 1H-NMR (DMSO-d$_6$, 300 MHz) δ: 0.82 (3H, t, J = 7.3 Hz), 1.40-1.52 (2H, m), 2.39 (2H, t, J = 7.5 Hz), 3.31-3.43 (1H, m), 3.57-4.06 (5H, m), 4.37-4.51 (1H, m), 4.74-4.83 (2H, m), 6.89 (2H, d, J = 7.5 Hz), 6.96 (2H, d, J = 7.5 Hz), 7.85 (2H, d, J = 8.7 Hz), 8.02 (2H, d, J = 7.5 Hz), 8.77 (1H, t, J = 6.2 Hz), 8.89 (1H, s), 9.00 (1H, s), 9.17 (1H, s), 13.72 (1H, br s). |
| 843 | 620 (M + H). | 1H-NMR (DMSO-d$_6$, 300 MHz) δ: 0.82 (3H, t, J = 7.3 Hz), 1.43-1.50 (2H, m), 2.39 (2H, t, J = 7.5 Hz), 3.27-3.39 (1H, m), 3.58-3.80 (2H, m), 3.87-4.05 (3H, m), 4.37-4.50 (1H, m), 4.72-4.83 (2H, m), 6.87-6.97 (4H, m), 8.07 (2H, d, J = 8.7 Hz), 8.26 (2H, d, J = 8.7 Hz), 8.78 (1H, t, J = 5.3 Hz), 8.88 (1H, s), 8.96 (1H, s), 9.15 (1H, s). |

TABLE 406

| Example No. | MS ESI m/e: | NMR |
|---|---|---|
| 844 | 631 (M + H). | 1H-NMR (DMSO-d₆, 300 MHz) δ: 0.81 (3H, t, J = 7.2 Hz), 1.23 (9H, s), 1.38-1.51 (2H, m), 2.37 (2H, t, J = 7.5 Hz), 3.31-3.38 (1H, m), 3.47-3.58 (1H, m), 3.70-3.84 (2H, m), 3.97-4.08 (2H, m), 4.22-4.43 (1H, m), 4.67-4.76 (2H, m), 6.87 (2H, d, J = 7.9 Hz), 6.97 (2H, d, J = 7.9 Hz), 7.54 (2H, d, J = 8.3 Hz), 7.77 (2H, d, J = 7.9 Hz), 8.72 (1H, t, J = 5.7 Hz), 8.88 (1H, s), 9.01 (1H, s), 9.17 (1H, s), 13.79 (1H, br s). |
| 845 | 609 (M + H). | 1H-NMR (DMSO-d₆, 300 MHz) δ: 0.82 (3H, t, J = 7.2 Hz), 1.40-1.53 (2H, m), 2.39 (2H, t, J = 7.5 Hz), 3.31-3.44 (1H, m), 3.52-3.90 (3H, m), 4.00-4.08 (2H, m), 4.27-4.43 (1H, m), 4.67-4.77 (2H, m), 6.89 (2H, d, J = 7.9 Hz), 6.97 (2H, d, J = 7.5 Hz), 7.54 (2H, d, J = 8.7 Hz), 7.83 (2H, d, J = 8.3 Hz), 8.74 (1H, t, J = 5.8 Hz), 8.89 (1H, s), 9.01 (1H, s), 9.18 (1H, s), 13.75 (1H, br s). |
| 846 | 683 (M + H). | 1H-NMR (CDCl₃, 300 MHz) δ: 0.94 (3H, t, J = 7.3 Hz), 1.39 (3H, t, J = 7.2 Hz), 1.58-1.70 (2H, m), 2.54 (3H, s), 2.57 (2H, t, J = 7.3 Hz), 3.11-3.28 (2H, m), 3.41-3.52 (1H, m), 3.86 (1H, dt, J = 13.3, 3.7 Hz), 3.97 (1H, d, J = 12.8 Hz), 4.30-4.45 (4H, m), 4.57-4.65 (2H, m), 6.73 (1H, t, J = 6.0 Hz), 7.09 (2H, d, J = 8.3 Hz), 7.12 (2H, d, J = 8.3 Hz), 7.33 (2H, d, J = 7.9 Hz), 7.91 (2H, d, J = 8.7 Hz). |
| 847 | 647 (M + H). | 1H-NMR (CD₃OD, 400 MHz) δ: 0.91 (3H, t, J = 7.5 Hz), 1.58-1.62 (2H, m), 2.54 (2H, t, J = 7.5 Hz), 3.21-3.33 (1H, m), 3.47 (1H, dd, J = 13.7, 4.6 Hz), 3.75-3.94 (3H, m), 4.16 (1H, d, J = 14.9 Hz), 4.23 (1H, d, J = 14.9 Hz), 4.37 (1H, d, J = 13.9 Hz), 4.61 (1H, dd, J = 4.6, 2.4 Hz), 7.08 (2H, d, J = 8.5 Hz), 7.10 (2H, d, J = 8.5 Hz), 7.39 (2H, d, J = 8.6 Hz), 7.92 (2H, d, J = 8.6 Hz). |
| 848 | 655 (M + H). | 1H-NMR (CD₃OD, 400 MHz) δ: 0.91 (3H, t, J = 7.4 Hz), 1.54-1.65 (2H, m), 2.51 (3H, s), 2.54 (2H, t, J = 7.4 Hz), 3.43-3.52 (1H, m), 3.58 (1H, dd, J = 13.9, 4.6 Hz), 3.81-3.89 (2H, m), 4.05 (1H, d, J = 13.5 Hz), 4.15 (1H, d, J = 14.6 Hz), 4.22 (1H, d, J = 14.8 Hz), 4.50 (1H, d, J = 13.7 Hz), 4.64 (1H, dd, J = 4.5, 2.5 Hz), 7.06 (2H, d, J = 8.4 Hz), 7.10 (2H, d, J = 7.9 Hz), 7.39 (2H, d, J = 8.2 Hz), 7.93 (2H, d, J = 8.8 Hz). |

TABLE 407

| Example No. | MS ESI m/e: | NMR |
|---|---|---|
| 849 | 614 (M + H). | 1H-NMR (CDCl₃, 400 MHz) δ: 0.74-0.91 (2H, m), 1.16-1.18 (1H, m), 1.70-1.77 (1H, m), 2.90-3.06 (1H, m), 3.20-3.26 (3H, m), 3.41 (1H, t, J = 12.6 Hz), 3.95 (1H, t, J = 13.5 Hz), 4.62 (1H, d, J = 11.0 Hz), 4.79 (1H, t, J = 10.0 Hz), 5.04 (1H, d, J = 13.9 Hz), 6.78 (1H, t, J = 10.0 Hz), 6.89-6.96 (2H, m), 7.09-7.21 (3H, m), 7.36 (1H, d, J = 8.8 Hz), 7.94-7.97 (2H, m), 8.77 (1H, d, J = 15.4 Hz), 9.20 (1H, d, J = 4.2 Hz), 9.25 (1H, d, J 2.4 Hz). |
| 850 | 635 (M + H). | 1H-NMR (DMSO-d₆, 300 MHz) δ: 3.36-3.49 (1H, m), 3.68 (1H, dd, J = 13.8, 4.7 Hz), 3.73-3.90 (2H, m), 3.94-4.05 (1H, m), 4.16 (1H, dd, J = 15.1, 5.7 Hz), 4.24 (1H, dd, J = 15.6, 6.2 Hz), 4.39 (1H, d, J = 14.3 Hz), 4.59-4.66 (1H, m), 7.20 (2H, d, J = 7.9 Hz), 7.25 (1H, d, J = 4.1 Hz), 7.29 (2H, d, J = 8.7 Hz), 7.59 (1H, d, J = 4.1 Hz), 8.15 (1H, s), 8.85 (1H, t, J = 5.8 Hz), 12.89 (1H, s). |
| 851 | 681 (M + H). | 1H-NMR (CD₃OD, 300 MHz) δ: 1.24 (6H, s), 3.25 (3H, s), 3.35 (2H, s), 3.39-3.50 (1H, m), 3.59-3.68 (1H, m), 3.84-3.92 (2H, m), 4.04-4.26 (3H, m), 4.58 (1H, d, J = 13.2 Hz), 4.65-4.70 (1H, m), 7.09 (2H, d, J = 8.3 Hz), 7.22 (2H, d, J = 8.7 Hz), 7.39 (2H, d, J = 8.3 Hz), 7.91-7.95 (2H, m), 8.10 (1H, s). |
| 852 | 677 (M + H). | 1H-NMR (CD₃OD, 400 MHz) δ: 1.21 (3H, t, J = 7.3 Hz), 3.25 (1H, m), 3.38-3.47 (3H, m), 3.78 (1H, m), 3.88 (1H, td, J = 8.5, 4.3 Hz), 4.22-4.31 (3H, m), 4.63 (1H, dd, J = 4.2, 3.0 Hz), 4.80 (1H, m), 7.11 (2H, dd, J = 8.8, 0.8 Hz), 7.24 (2H, d, J = 8.8 Hz), 7.42 (2H, dd, J = 9.0, 1.0 Hz), 7.98 (2H, d, J = 9.0 Hz), 8.04 (1H, d, J = 1.4 Hz), 8.59 (1H, d, J = 1.4 Hz). |
| 853 | 705 (M + H). | 1H-NMR (CD₃OD, 400 MHz) δ: 1.46 (9H, s), 3.25 (1H, m), 3.46 (1H, dd, J = 14.1, 4.6 Hz), 3.78 (1H, m), 3.88 (1H, td, J = 8.6, 4.5 Hz), 4.21-4.32 (3H, m), 4.63 (1H, t, J = 3.7 Hz), 4.77 (1H, m), 7.11 (2H, dd, J = 8.8, 0.8 Hz), 7.24 (2H, d, J = 8.8 Hz), 7.42 (2H, dd, J = 9.0, 0.9 Hz), 7.95-8.01 (3H, m), 8.57 (1H, d, J = 1.4 Hz). |

TABLE 408

| Example No. | MS ESI m/e: | NMR |
|---|---|---|
| 854 | 631 (M + H). | 1H-NMR (CD₃OD, 400 MHz) δ: 0.57 (3H, t, J = 7.5 Hz), 1.16 (6H, s), 1.21 (3H, t, J = 7.5 Hz), 1.53 (2H, t, J = 7.5 Hz), 2.65 (2H, q, J = 7.5 Hz), 3.47 (1H, m), 3.56 (1H, dd, J = 14.1, 4.4 Hz), 3.80 (1H, m), 3.95 (1H, m), 4.06 (1H, m), 4.18 (1H, d, J = 14.8 Hz), 4.31 (1H, m), 4.76 (1H, t, J = 3.6 Hz), 4.82 (1H, m), 7.01 (2H, d, J = 8.5 Hz), 7.05 (2H, d, J = 8.5 Hz), 7.38 (2H, d, J = 8.1 Hz), 7.84 (2H, d, J = 8.1 Hz), 8.85 (1H, s), 9.15 (1H, s), 9.16 (1H, s). |
| 855 | 617 (M + H). | 1H-NMR (CD₃OD, 400 MHz) δ: 0.91 (3H, t, J = 7.3 Hz), 1.22 (3H, t, J = 7.7 Hz), 1.26-1.33 (2H, m), 1.41-1.48 (2H, m), 2.39 (2H, td, J = 7.5, 0.5 Hz), 2.66 (2H, q, J = 7.7 Hz), 3.40 (1H, m), 3.52 (1H, dd, J = 14.4, 4.4 Hz), 3.81 (1H, m), 3.91 (1H, m), 4.06 (1H, m), 4.15 (1H, d, J = 14.4 Hz), 4.30 (1H, m), 4.73 (1H, m), 4.78 (1H, m), 6.82 (2H, d, J = 7.9 Hz), 6.99 (2H, d, J = 7.9 Hz), 7.39 (2H, d, J = 8.3 Hz), 7.84 (2H, d, J = 8.3 Hz), 8.80 (1H, s), 9.13 (1H, s), 9.15 (1H, s). |
| 856 | 685 (M + H). | 1H-NMR (CDCl₃, 400 MHz) δ: 0.94 (3.0H, t, J = 7.3 Hz), 1.25 (1.5H, t, J = 7.2 Hz), 1.26 (1.5H, t, J = 7.1 Hz), 1.62-1.65 (2.0H, m), 2.18 (1.5H, s), 2.19 (1.5H, s), 2.57 (2.0H, t, J = 7.6 Hz), 2.82-2.94 (2.0H, m), 3.24 (0.5H, d, J = 5.1 Hz), 3.31 (0.5H, d, J = 4.6 Hz), 3.36-3.44 (1.0H, m), 3.73 (0.5H, d, J = 13.0 Hz), 3.80 (0.5H, d, J = 13.2 Hz), 3.86 (1.0H, d, J = 13.9 Hz), 4.14-4.31 (2.0H, m), 4.35-4.50 (3.0H, m), 4.57 (1.0H, s), 5.23 (0.5H, d, J = 2.4 Hz), 5.24 (0.5H, d, J = 2.6 Hz), 6.75 (0.5H, t, J = 5.3 Hz), 6.79 (0.5H, t, J = 5.1 Hz), 7.11-7.14 (4.0H, m), 7.32 (2.0H, d, J = 7.9 Hz), 7.89 (1.0H, d, J = 3.5 Hz), 7.91 (1.0H, d, J = 3.3 Hz). |
| 857 | 622 (M + H). | 1H-NMR (CDCl₃, 400 MHz) δ: 0.90 (3H, t, J = 7.3 Hz), 1.53 (2H, td, J = 14.8, 7.4 Hz), 2.55 (2H, td, J = 7.4, 2.6 Hz), 2.98-3.00 (1H, m), 3.20 (1H, d, J= 10.2 Hz), 3.42 (1H, t, J = 11.1 Hz), 3.95 (1H, d, J = 14.4 Hz), 4.45 (2H, dd, J = 61.5, 15.1 Hz), 4.67 (1H, s), 4.83 (1H, s), 5.10 (1H, d, J = 13.7 Hz), 6.43 (1H, d, J = 3.5 Hz), 6.59 (1H, d, J = 3.5 Hz), 6.93 (1H, t, J = 10.0 Hz), 7.39 (2H, d, J = 8.1 Hz), 7.97 (2H, dt, J = 9.5, 2.4 Hz), 8.80 (1H, s), 9.21 (1H, s), 9.26 (1H, s). |

TABLE 409

| Example No. | MS EST m/e: | NMR |
|---|---|---|
| 858 | 643 (M + H). | 1H-NMR (CD₃OD, 400 MHz) δ: 0.56 (3H, t, J = 7.4 Hz), 1.15 (6H, s), 1.53 (2H, q, J = 7.4 Hz), 3.61 (1H, m), 3.62 (1H, m), 3.84-3.98 (2H, m), 4.18 (1H, d, J = 14.8 Hz), 4.29 (1H, m), 4.42 (1H, m), 4.73 (1H, m), 4.95 (1H, m), 6.96-7.09 (5H, m), 7.55 (1H, m), 8.89 (1H, s), 9.13 (1H, s), 9.15 (1H, s). |
| 859 | 668 (M + H). | 1H-NMR (CDCl₃, 300 MHz) δ: 0.94 (3H, t, J = 7.5 Hz), 1.54-1.69 (2H, m), 2.56 (2H, t, J = 7.5 Hz), 2.57 (3H, s), 2.92 (3H, d, J = 5.3 Hz), 3.17-3.29 (1H, m), 3.30 (1H, dd, J = 13.0, 4.3 Hz), 3.42-3.54 (1H, m), 3.79-3.95 (2H, m), 4.30-4.44 (2H, m), 4.59-4.64 (1H, m), 4.68 (1H, d, J = 14.3 Hz), 6.76 (1H, t, J = 4.7 Hz), 7.08 (2H, d, J = 8.3 Hz), 7.12 (2H, d, J = 8.3 Hz), 7.32 (2H, d, J = 8.7 Hz), 7.39-7.47 (1H, m), 7.91 (2H, d, J = 8.7 Hz). |
| 860 | 615 (M + H). | 1H-NMR (DMSO-d₆, 300 MHz) δ: 0.81 (3H, t, J = 7.3 Hz), 1.38-1.51 (2H, m), 2.37 (2H, t, J = 7.5 Hz), 3.44-3.58 (1H, m), 3.63-3.87 (3H, m), 4.01-4.14 (2H, m), 4.29-4.47 (1H, m), 4.69-4.84 (2H, m), 6.87 (2H, d, J = 7.9 Hz), 6.98 (2H, d, J = 7.9 Hz), 7.21 (1H, d, J = 3.8 Hz), 7.59-7.64 (1H, m), 8.79 (1H, t, J = 5.7 Hz), 8.93 (1H, s), 9.02 (1H, s), 9.19 (1H, s), 13.77 (1H, br s). |
| 861 | 657 (M + H). | 1H-NMR (DMSO-d₆, 300 MHz) δ: 3.44-3.56 (1H, m), 3.64-3.85 (3H, m), 4.12-4.17 (2H, m), 4.29-4.44 (1H, m), 4.70 (1H, br s), 4.75-4.83 (1H, m), 7.07 (2H, d, J = 8.7 Hz), 7.21-7.23 (3H, m), 7.63 (1H, d, J = 4.1 Hz), 8.88-8.92 (2H, m), 9.00 (1H, s), 9.18 (1H, s). |
| 862 | 653 (M + H). | 1H-NMR (CDCl₃, 300 MHz) δ: 0.93 (3H, t, J = 7.3 Hz), 1.26 (3H, t, J = 7.5 Hz), 1.43 (3H, t, J = 7.2 Hz), 1.58-1.69 (2H, m), 2.56 (2H, t, J = 7.5 Hz), 2.73 (2H, q, J = 7.7 Hz), 3.04-3.19 (2H, m), 3.37-3.51 (1H, m), 3.94 (1H, d, J = 13.6 Hz), 4.17 (1H, br s), 4.31-4.66 (6H, m), 6.93 (1H, t, J = 5.3 Hz), 7.03-7.16 (4H, m), 7.36 (2H, d, J = 7.9 Hz), 7.78 (2H, d, J = 8.3 Hz), 10.34 (1H, s). |

TABLE 410

| Example No. | MS ESI m/e: | NMR |
|---|---|---|
| 863 | 625 (M + H). | 1H-NMR (DMSO-d6, 300 MHz) δ: 0.84 (3H, t, J = 7.3 Hz), 1.17 (3H, t, J = 7.5 Hz), 1.52 (2H, dt, J = 23.0, 7.8 Hz), 2.38-2.47 (2H, m), 2.66 (2H, q, J = 7.5 Hz), 3.47-3.61 (1H, m), 3.77 (2H, br s), 3.93-4.41 (4H, m), 4.62 (1H, br s), 6.99-7.09 (4H, m), 7.37 (2H, d, J = 8.3 Hz), 7.72 (2H, d, J = 8.3 Hz), 8.66 (1H, t, J = 5.7 Hz), 13.07 (1H, br s). |
| 864 | 613 (M + H). | 1H-NMR (DMSO-d6, 300 MHz) δ: 3.24-3.39 (1H, m), 3.57 (1H, dd, J = 13.9, 4.5 Hz), 3.69-3.84 (2H, m), 3.98 (1H, d, J = 12.8 Hz), 4.12 (1H, dd, J = 15.1, 5.7 Hz), 4.20 (1H, dd, J = 15.3, 6.2 Hz), 4.37 (1H, d, J = 13.2 Hz), 4.61-4.65 (1H, m), 7.20 (2H, d, J = 8.7 Hz), 7.27 (2H, d, J = 8.7 Hz), 7.38 (2H, t, J = 8.7 Hz), 7.88 (2H, dd, J = 8.9, 5.1 Hz), 8.13 (1H, s), 8.79 (1H, t, J = 5.8 Hz), 12.88 (1H, s). |
| 865 | 714 (M + H). | 1H-NMR (CDCl3, 300 MHz) δ: 3.08-3.15 (4H, m), 3.18-3.27 (1H, m), 3.50-3.59 (1H, m), 3.99 (1H, d, J = 14.3 Hz), 4.17 (1H, d, J = 13.2 Hz), 4.33-4.50 (2H, m), 4.65 (1H, br s), 5.17 (1H, d, J = 13.9 Hz), 7.06-7.09 (3H, m), 7.18 (2H, d, J = 8.7 Hz), 7.41 (2H, d, J = 8.3 Hz), 7.98 (2H, d, J = 9.0 Hz), 8.66 (1H, s), 9.24 (1H, s), 9.36-9.41 (1H, m), 9.48 (1H, s). |
| 866 | 728 (M + H). | 1H-NMR. (CDCl3, 300 MHz) δ: 2.82 (3H, s), 2.98-3.14 (2H, m), 3.20 (3H, s), 3.35-3.44 (1H, m), 3.92 (1H, d, J = 13.9 Hz), 4.31 (1H, dd, J = 15.1, 5.7 Hz), 4.41-4.51 (2H, m), 4.66 (1H, br s), 5.06 (1H, d, J = 13.9 Hz), 7.02-7.18 (5H, m), 7.37 (2H, d, J = 8.3 Hz), 7.96 (2H, d, J = 8.7 Hz), 8.55 (1H, s), 8.67 (1H, s), 9.17 (1H, s). |
| 867 | 629 (M + H). | 1H-NMR (CDCl3, 400 MHz) δ: 2.76-2.79 (1H, m), 2.96-2.99 (1H, m), 3.18 (1H, d, J = 13.7 Hz), 3.43-3.55 (6H, m), 3.81-3.93 (3H, m), 4.60 (1H, d, J = 15.3 Hz), 4.69-4.72 (1H, m), 5.03 (1H, d, J = 13.7 Hz), 6.32 (1H, dd, J = 8.5, 1.0 Hz), 6.74 (1H, dd, J = 17.0, 9.6 Hz), 7.04 (1H, t, J = 5.8 Hz), 7.15-7.20 (2H, m), 7.39 (2H, d, J = 8.1 Hz), 7.95 (2H, d, J = 14.6 Hz), 8.77 (1H, s), 9.22 (1H, s), 9.28 (1H, s). |

TABLE 411

| Example No. | MS ESI m/e: | NMR |
|---|---|---|
| 868 | 591 (M + H). | 1H-NMR (CD3OD, 400 MHz) δ: 0.91 (3H, t, J = 7.4 Hz), 1.25 (3H, t, J = 7.6 Hz), 1.59-1.63 (2H, m), 2.55 (2H, t, J = 7.5 Hz), 2.73 (2H, q, J = 7.6 Hz), 3.12-3.21 (1H, m), 3.41 (1H, dd, J = 13.9, 4.9 Hz), 3.72-3.85 (3H, m), 4.23-4.31 (1H, m), 4.25 (2H, s), 4.59 (1H, dd, J = 4.5, 3.0 Hz), 7.08 (2H, d, J = 8.4 Hz), 7.12 (2H, d, J = 8.4 Hz), 7.38 (2H, d, J = 8.4 Hz), 7.77 (2H, d, J = 8.4 Hz). |
| 869 | 697 (M + H ). | 1H-NMR (CDCl3, 300 MHz) δ: 3.12-3.19 (1H, m), 3.26 (1H, dd, J = 13.2, 4.1 Hz), 3.43-3.52 (1H, m), 3.97 (1H, d, J = 13.9 Hz), 4.25 (1H, d, J = 13.9 Hz), 4.37 (1H, dd, J = 14.7, 5.3 Hz), 4.50 (1H, dd, J = 15.1, 6.0 Hz), 4.58 (1H, d, J = 12.8 Hz), 4.64 (1H, s), 6.92 (1H, br s), 7.15 (2H, d, J = 8.7 Hz), 7.23 (2H, d, J = 8.7 Hz), 7.38 (2H, d, J = 8.7 Hz), 7.94 (2H, d, J = 9.0 Hz), 9.16 (1H, s). |
| 870 | 709 (M + H). | 1H-NMR (CD3OD, 300 MHz) δ: 3.34-3.46 (1H, m), 3.63 (1H, dd, J = 13.9, 4.5 Hz), 3.76-3.98 (2H, m), 4.05-4.16 (1H, m), 4.26 (2H, dd, J = 22.0, 15.3 Hz), 4.55 (1H, d, J = 15.8 Hz), 4.69 (3H, br s), 7.09 (2H, d, J =7.9 Hz), 7.27 (2H, d, J =8.7 Hz), 7.41 (2H, d, J = 8.3 Hz), 7.97 (2H, d, J = 9.0 Hz). |
| 871 | 742 (M + H). | 1H-NMR (CDCl3, 300 MHz) δ: 1.27-1.30 (6H, m), 3.17-3.29 (2H, m), 3.53-3.63 (1H, m), 3.95 (1H, d, J = 13.6 Hz), 4.19 (1H, d, J = 13.6 Hz), 4.33-4.49 (3H, m), 4.62 (1H, br s), 5.01 (1H, d, J = 12.4 Hz), 7.06-7.10 (3H, m), 7.19 (2H, d, J = 8.7 Hz), 7.40 (2H, d, J = 8.3 Hz), 7.97 (2H, d, J = 8.7 Hz), 8.70 (1H, s), 9.25 (1H, s), 9.31 (1H, d, J = 7.5 Hz), 9.49 (1H, s). |
| 872 | 682 (M + H). | 1H-NMR (CDCl3, 300 MHz) δ: 2.94-3.20 (2H, m), 3.41-3.49 (1H, m), 3.99 (1H, d, J = 14.7 Hz), 4.29-4.47 (2H, m), 4.69 (1H, br s), 4.74-4.86 (1H, m), 5.05-5.13 (1H, m), 7.00-7.08 (3H, m), 7.16 (2H, d, J = 8.7 Hz), 7.39 (2H, d, J = 8.7 Hz), 7.96 (2H, d, J = 8.7 Hz), 8.79 (1H, s), 8.87 (1H, s), 9.26 (1H, s). |

TABLE 412

| Example No. | MS ESI m/e: | NMR |
|---|---|---|
| 873 | 629 (M + H). | 1H-NMR (DMSO-d<sub>6,</sub> 300 MHz) δ: 3.26-3.40 (1H, m), 3.60 (1H, dd, J = 13.9, 4.9 Hz), 3.69-3.84 (2H, m), 3.98 (1H, d, J = 12.4 Hz), 4.12 (1H, dd, J = 15.3, 5.8 Hz), 4.20 (1H, dd, J = 15.4, 6.0 Hz), 4.37 (1H, d, J = 13.2 Hz), 4.60-4.66 (1H, m), 7.21 (2H, d, J = 8.7 Hz), 7.27 (2H, d, J = 8.7 Hz), 7.60 (2H, d, J = 8.7 Hz), 7.81 (2H, d, J = 8.7 Hz), 8.13 (1H, s), 8.80 (1H, t, J = 6.0 Hz), 12.88 (1H, s). |
| 874 | 723 (M + H). | 1H-NMR (DMSO-d<sub>6</sub>, 300 MHz) δ: 3.57-3.70 (1H, m), 3.76-3.89 (2H, m), 3.98-4.22 (3H, br m), 4.40 (1H, br s), 4.66 (1H, br s), 7.16-7.30 (4H, m), 7.50 (2H, d, J = 8.3 Hz), 7.92 (2H, d, J = 8.7 Hz), 8.82 (1H, t, J = 5.7 Hz), 13.17 (1H, br s). |
| 875 | 736 (M + H). | 1H-NMR (DMSO-d<sub>6</sub>, 300 MHz) δ: 2.81 (3H, d, J = 4.9 Hz), 3.57-3.70 (1H, m), 3.70-3.87 (2H, m), 3.96-4.17 (3H, br m), 4.41 (1H, br s), 4.66 (1H, br s), 7.14-7.31 (4H, m), 7.50 (2H, d, J = 8.7 Hz), 7.94 (2H, d, J = 8.7 Hz), 8.66 (1H, q, J = 4.8 Hz), 8.84 (1H, t, J = 5.7 Hz), 13.21 (1H, br s). |
| 876 | 722 (M + H). | 1H-NMR (DMSO-d<sub>6</sub>, 300 MHz) δ: 3.36-3.44 (1H, m), 3.60-3.70 (1H, m), 3.74-3.87 (2H, m), 3.95-4.15 (3H, br m), 4.38 (1H, br s), 4.66 (1H, br s), 7.14-7.31 (4H, m), 7.49 (2H, d, J = 8.7 Hz), 7.85 (1H, br s), 7.93 (2H, d, J = 8.7 Hz), 8.24 (1H, br s), 8.84 (1H, t, J = 6.0 Hz), 13.24 (1H, br s). |
| 877 | 663 (M + H). | 1H-NMR (CD<sub>3</sub>OD, 400 MHz) δ: 3.41 (1H, ddd, 3= 14.0, 9.5, 3.5 Hz), 3.63 (1H, dd, J = 13.9, 4.6 Hz), 3.82-3.98 (2H, m), 4.07 (1H, d, J = 13.7 Hz), 4.25 (2H, dd, J = 31.9, 15.1 Hz), 4.53 (1H, d, J = 14.3 Hz), 4.72 (1H, dd, J = 4.5, 2.5 Hz), 7.11 (2H, d, J = 7.9 Hz), 7.28 (2H, d, J = 8.8 Hz), 7.83 (2H, d, J = 8.4 Hz), 8.02-8.09 (3H, m). |
| 878 | 679 (M + H). | 1H-NMR (DMSO-d<sub>6,</sub> 400 MHz) δ: 3.07-4.78 (9H, m), 7.27 (4H, s), 7.53 (2H, d, J = 8.8 Hz), 7.93 (2H, d, J = 6.6 Hz), 8.35 (1H, br s), 8.88 (1H, s). |

TABLE 413

| Example No. | MS EST m/e: | NMR |
|---|---|---|
| 879 | 663 (M + H). | 1H-NMR (CDCl<sub>3</sub>, 400 MHz) δ: 3.13-3.20 (1H, m), 3.26 (1H, dd, J = 13.3, 4.3 Hz), 3.46-3.53 (1H, m), 3.96 (1H, dt, J = 14.2, 3.0 Hz), 4.24 (1H, d, J = 13.7 Hz), 4.37 (1H, dd, J = 15.0, 5.7 Hz), 4.49 (1H, dd, J = 15.0, 6.2 Hz), 4.61 (1H, d, J = 13.5 Hz), 4.64 (1H, d, J = 4.0 Hz), 6.99 (1H, br s), 7.13 (2H, d, J = 8.6 Hz), 7.22 (2H, dt, J = 9.0, 2.3 Hz), 7.37 (2H, d, J = 8.8 Hz), 7.94 (2H, dt, J = 9.5, 2.5 Hz), 9.27 (1H, d, J = 1.2 Hz), 9.33 (1H, d, J = 1.2 Hz). |
| 880 | 671 (M + H). | 1H-NMR (CDCl<sub>3</sub>, 300 MHz) δ: 0.93 (3H, t, J = 7.3 Hz), 1.27 (3H, t, J = 7.5 Hz), 1.46 (3H, t, J = 7.2 Hz), 1.58-1.68 (2H, m), 2.55 (2H, t, J = 7.5 Hz), 2.73 (2H, q, J = 7.5 Hz), 3.03-3.24 (2H, m), 3.33-3.44 (1H, m), 3.99 (1H, d, J = 14.3 Hz), 4.30-4.57 (6H, m), 4.65-4.69 (1H, m), 6.86-6.91 (1H, m), 7.09 (4H, s), 7.37 (2H, d, J = 8.3 Hz), 7.78 (2H, d, J = 8.7 Hz). |
| 881 | 673, 675 (M + H). | 1H-NMR (DMSO-d<sub>6</sub>, 300 MHz) δ: 3.26-3.39 (1H, m), 3.60 (1H, dd, J = 13.8, 4.3 Hz), 3.69-3.84 (2H, m), 3.98 (1H, d, J = 11.3 Hz), 4.12 (1H, dd, J = 15.4, 5.7 Hz), 4.20 (1H, dd, J = 15.6, 6.2 Hz), 4.36 (1H, d, J = 13.9 Hz), 4.61-4.65 (1H, m), 7.21 (2H, d, J = 8.3 Hz), 7.27 (2H, d, J = 8.7 Hz), 7.72 (2H, d, J = 9.8 Hz), 7.75 (2H, d, J = 9.4 Hz), 8.13 (1H, s), 8.80 (1H, t, J = 6.0 Hz), 12.88 (1H, s). |
| 882 | 679 (M + H). | 1H-NMR (CD<sub>3</sub>OD, 300 MHz) δ: 0.75-0.88 (4H, m), 3.27 (3H, s), 3.37-3.49 (3H, m), 3.62 (1H, dd, J = 13.9, 4.5 Hz), 3.83-3.92 (2H, m), 4.03-4.26 (3H, m), 4.56 (1H, d, J = 13.2 Hz), 4.65-4.70 (1H, m), 7.08 (2H, d, J = 8.3 Hz), 7.17 (2H, d, J = 8.3 Hz), 7.39 (2H, d, J = 8.3 Hz), 7.91-7.95 (2H, m), 8.09 (1H, s). |
| 883 | 652 (M + H). | 1H-NMR (DMSO-d<sub>6</sub>, 300 MHz) δ: 0.96 (3H, t, J = 7.0 Hz), 2.78 (3H, s), 3.25-3.40 (3H, m), 3.63 (1H, dd, J = 13.9, 4.5 Hz), 3.77-4.08 (5H, m), 4.32-4.40 (1H, m), 4.58-4.61 (1H, m), 6.52 (2H, d, 3 = 8.7 Hz), 6.93 (2H, d, J = 8.7 Hz), 7.52 (2H, d, J = 7.9 Hz), 7.91 (2H, d, J = 9.0 Hz), 8.14 (1H, s), 8.56 (1H, t, J = 5.7 Hz), 12.88 (1H, s). |

TABLE 414

| Example No. | MS ESI m/e: | NMR |
|---|---|---|
| 884 | 625 (M + H). | 1H-NMR (DMSO-d$_6$, 300 MHz) δ: 3.20-3.35 (1H, m), 3.51 (1H, dd, J = 13.8, 4.7 Hz), 3.69-3.78 (2H, m), 3.81 (3H, s), 3.93 (1H, d, J = 13.2 Hz), 4.15 (1H, dd, J = 15.3, 5.5 Hz), 4.23 (1H, dd, J = 16.0, 5.8 Hz), 4.32 (1H, d, J = 13.6 Hz), 4.57-4.62 (1H, m), 7.05 (2H, d, J = 8.7 Hz), 7.20 (2H, d, J = 8.3 Hz), 7.28 (2H, d, J = 8.7 Hz), 7.76 (2H, d, J = 8.7 Hz), 8.13 (1H, s), 8.77 (1H, t, J = 5.8 Hz), 12.87 (1H, s). |
| 885 | 663 (M + H). | 1H-NMR (CDCl$_3$, 400 MHz) δ: 3.09-3.19 (1H, m), 3.22 (1H, dd, J = 13.7, 4.6 Hz), 3.44-3.54 (1H, m), 3.95 (1H, d, J = 13.9 Hz), 4.13 (1H, d, J = 12.8 Hz), 4.39 (1H, dd, J = 15.0, 5.7 Hz), 4.49 (1H, dd, J = 15.1, 6.3 Hz), 4.59-4.67 (2H, m), 6.99 (1H, br s), 7.12 (2H, d, J = 8.1 Hz), 7.23 (2H, d, J = 8.6 Hz), 7.37 (2H, d, J = 8.8 Hz), 7.94 (2H, d, J = 9.0 Hz), 8.70 (1H, s), 8.79 (1H, s). |
| 886 | 647 (M + H). | 1H-NMR (CDCl$_3$, 400 MHz) δ: 3.14-3.39 (2H, m), 3.51 (1H, t, J = 12.6 Hz), 3.97 (1H, dt, J = 13.7, 2.7 Hz), 4.24-4.52 (3H, m), 4.58-4.75 (2H, m), 6.96-7.13 (3H, m), 7.19 (2H, d, J = 8.6 Hz), 7.81 (2H, d, J = 8.3 Hz), 8.01 (2H, d, J = 8.3 Hz), 8.79 (1H, s), 8.95 (1H, s). |
| 887 | 681 (M + H). | 1H-NMR (CDCl$_3$, 400 MHz) δ: 3.11-3.58 (3H, m), 3.98 (1H, d, J = 14.1 Hz), 4.24-4.74 (5H, m), 6.94 (1H, t, J = 5.9 Hz), 7.13 (2H, d, J = 7.9 Hz), 7.21 (2H, dt, J = 9.0, 2.4 Hz), 7.82 (2H, d, J = 8.3 Hz), 8.01 (2H, d, J = 8.3 Hz), 8.60 (1H, s). |
| 888 | 695 (M + H). | 1H-NMR (DMSO-d$_6$, 400 MHz) δ: 3.25-3.30 (1H, m), 3.59 (1H, dd, J = 13.9, 4.6 Hz), 3.69-3.97 (3H, m), 4.14 (3H, d, J = 5.8 Hz), 4.61 (1H, dd, J = 4.2, 2.1 Hz), 7.25 (4H, t, J = 9.6 Hz), 7.51 (2H, d, J = 8.1 Hz), 7.92 (2H, dt, J = 9.4, 2.6 Hz), 8.80 (1H, t, J = 6.0 Hz), 10.91 (1H, s), 11.83 (1H, s). |

TABLE 415

| Example No. | MS ESI m/e: | NMR |
|---|---|---|
| 889 | 568 (M + H). | 1H-NMR (CDCl$_3$, 300 MHz) δ: 0.97 (3H, t, J = 7.3 Hz), 1.32 (3H, t, J = 7.5 Hz), 1.67 (2H, dd, J = 14.9, 7.3 Hz), 2.51 (1H, td, J = 11.6, 2.3 Hz), 2.60 (2H, dd, J = 7.9, 7.2 Hz), 2.74-2.88 (4H, m), 3.48 (1H, ddd, J = 14.7, 11.1, 3.0 Hz), 3.76 (1H, d, J = 12.1 Hz), 4.04 (1H, d, J = 13.2 Hz), 4.40 (1H, dd, J = 13.9, 6.0 Hz), 4.49 (1H, dd, J = 13.9, 6.0 Hz), 4.69 (1H, d, J = 1.1 Hz), 6.66-6.75 (2H, m), 7.05 (1H, t, J = 8.1 Hz), 7.17-7.19 (4H, m), 7.41 (2H, d, J = 7.9 Hz), 7.79 (2H, d, J = 8.3 Hz), 8.23 (1H, t, J = 7.0 Hz), 13.00 (1H, br s). |
| 890 | 675 (M + H). | 1H-NMR (CD$_3$OD, 400 MHz) δ: 0.64 (3H, t, J = 7.5 Hz), 1.25 (6H, s), 1.64 (2H, q, J = 7.5 Hz), 3.21-3.34 (1H, m), 3.43-3.51 (1H, m), 3.82-3.85 (2H, m), 3.91 (1H, d, J = 12.1 Hz), 4.17-4.28 (2H, m), 4.41 (1H, d, J = 13.7 Hz), 4.63 (1H, dd, J = 4.4, 2.2 Hz), 7.11 (2H, d, J = 8.2 Hz), 7.25 (2H, d, J = 8.2 Hz), 7.41 (2H, d, J = 8.6 Hz), 7.94 (2H, d, J = 8.8 Hz). |
| 891 | 637 (M + H). | 1H-NMR (CDCl$_3$, 300 MHz) δ: 0.93 (3H, t, J = 7.3 Hz), 1.26 (3H, t, J = 7.7 Hz), 1.48 (3H, t, J = 7.2 Hz), 1.57-1.68 (2H, m), 2.55 (2H, t, J = 7.7 Hz), 2.72 (2H, q, J = 7.5 Hz), 3.02-3.13 (1H, m), 3.16-3.22 (1H, m), 3.35-3.44 (1H, m), 3.99 (1H, d, J = 13.9 Hz), 4.31-4.59 (6H, m), 4.65-4.68 (1H, m), 6.87-6.92 (1H, m), 7.08 (4H, s), 7.37 (2H, d, J = 8.3 Hz), 7.78 (2H, d, J = 8.3 Hz), 9.39 (1H, s). |
| 892 | 609 (M + H). | 1H-NMR (DMSO-d$_6$, 300 MHz) δ: 0.81 (3H, t, J = 7.0 Hz), 1.15 (3H, t, J = 7.5 Hz), 1.44-1.55 (2H, m), 2.41-2.46 (2H, m), 2.64 (2H, q, J = 7.5 Hz), 3.20-3.37 (1H, m), 3.50-3.64 (1H, m), 3.80 (2H, br s), 3.98-4.25 (4H, m), 4.64 (1H, br s), 7.04 (4H, s), 7.36 (2H, d, J = 8.3 Hz), 7.73 (2H, d, J = 7.9 Hz), 8.63-8.69 (1H, m), 9.35 (1H, br s). |
| 893 | 677 (M + H). | 1H-NMR (DMSO-d$_6$, 300 MHz) δ: 2.31 (3H, s), 3.32-3.41 (1H, m), 3.63 (1H, dd, J = 13.8, 4.3 Hz), 3.71-3.90 (2H, m), 3.96-4.11 (1H, m), 4.10-4.17 (2H, m), 4.32-4.46 (1H, m), 4.66-4.72 (1H, m), 7.17 (2H, d, J = 8.3 Hz), 7.25 (2H, d, J = 8.7 Hz), 7.88 (2H, d, J = 8.7 Hz), 8.00 (2H, d, J = 8.3 Hz), 8.85 (1H, t, J = 5.8 Hz), 12.59 (1H, s). |

TABLE 416

| Example No. | MS ESI m/e: | NMR |
|---|---|---|
| 894 | 657 (M + H). | 1H-NMR (CDCl₃) δ: 0.96 (3H, t, J = 7.4 Hz), 2.10 (2H, dq, J = 31.7, 7.9 Hz), 3.14-3.57 (3H, m), 3.94 (1H, dt, J = 14.0, 3.0 Hz), 4.26-4.74 (5H, m), 7.04 (1H, t, J = 5.6 Hz), 7.20 (2H, d, J = 8.1 Hz), 7.35 (4H, t, J = 8.3 Hz), 7.94 (2H, dt, J = 9.5, 2.6 Hz), 8.79 (1H, s), 8.95 (1H, s). |
| 895 | 691 (M + H). | 1H-NMR (CDCl₃, 400 Mhz) δ: 0.97 (3H, t, J = 7.4 Hz), 2.11 (2H, dq, J = 31.7, 7.8 Hz), 3.13-3.56 (3H, m), 3.95 (1H, d, J = 14.6 Hz), 4.29-4.73 (5H, m), 6.95 (1H, t, J = 5.7 Hz), 7.21 (2H, d, J = 8.1 Hz), 7.37 (4H, d, J = 8.1 Hz), 7.93 (2H, dt, J = 9.4, 2.4 Hz), 8.60 (1H, s). |
| 896 | 681 (M + H). | 1H-NMR (CDCl₃, 400 MHz) δ: 3.11-3.18 (1H, m), 3.25 (1H, dd, J = 13.3, 4.3 Hz), 3.46-3.53 (1H, m), 4.00 (1H, dd, J = 14.2, 2.8 Hz), 4.24(1H, d, J = 11.7 Hz), 4.37 (1H, dd, J = 15.0, 5.5 Hz), 4.50(1H, dd, J = 15.1, 6.3 Hz), 4.58 (1H, d, J = 13.5 Hz), 4.67 (1H, s), 6.92 (1H, t, J = 6.0 Hz), 7.15 (2H, d, J = 8.8 Hz), 7.23 (2H, d, J = 8.8 Hz), 7.84 (2H, d, J = 8.4 Hz), 8.02 (2H, d, J = 8.2 Hz), 9.15 (1H, s). |
| 897 | 647 (M + H). | 1H-NMR (CDCl₃, 300 MHz) δ: 3.12-3.18 (1H, m), 3.26 (1H, dd, J = 13.4, 4.3 Hz), 3.46-3.56 (1H, m), 3.99 (1H, d, J = 13.9 Hz), 4.24 (1H, d, J = 12.8 Hz), 4.36 (1H, dd, J = 14.7, 5.7 Hz), 4.49 (1H, dd, J = 15.1, 6.4 Hz), 4.62 (1H, d, J = 13.9 Hz), 4.67 (1H, d, J = 3.4 Hz), 6.98 (1H, t, J = 5.8 Hz), 7.13 (2H, d, J = 8.3 Hz), 7.22 (2H, d, J = 8.7 Hz), 7.82 (2H, d, J = 8.3 Hz), 8.02 (2H, d, J = 8.3 Hz), 9.27 (1H, d, J = 1.1 Hz), 9.33 (1H, d, J = 1.1 Hz). |
| 898 | 711 (M + H). | 1H-NMR (CDCl₃, 400 MHz) δ: 3.15-3.27 (2H, m), 3.50-3.57 (1H, m), 3.92 (1H, dt, J = 13.8, 3.3 Hz), 4.03 (1H, d, J = 12.8 Hz), 4.42 (2H, dd, J = 33.7, 15.0 Hz), 4.61-4.63 (2H, m), 5.91 (1H, t, J = 111.8 Hz), 7.01 (1H, t, J = 6.0 Hz), 7.13 (2H, d, J = 8.6 Hz), 7.22 (2H, d, J = 11.2 Hz), 7.36 (2H, d, J = 4.4 Hz), 7.92 (2H, d, J = 9.5 Hz), 8.04 (1H, s), 10.41 (1H, s). |

TABLE 417

| Example No. | MS ESI m/e: | NMR |
|---|---|---|
| 899 | 649 (M + H). | 1H-NMR (CDCl₃, 400 MHz) δ: 1.73-1.79 (1H, m), 2.05-2.15 (1H, m), 2.24-2.27 (1H, m), 2.40-2.48 (2H, m), 3.09-3.63 (6H, m), 3.91-4.04 (2H, m), 4.60-4.61 (2H, m), 6.68 (1H, t, J = 14.6 Hz), 7.14-7.20 (3H, m), 7.26-7.32 (2H, m), 7.40 (2H, d, J = 8.6 Hz), 7.95 (2H, d, J = 12.3 Hz), 8.06 (1H, s), 10.69 (1H, s). |
| 900 | 657 (M + H). | 1H-NMR (CDCl₃, 300 MHz) δ: 0.97 (3H, t, J = 7.5 Hz), 2.12 (2H, tq, J = 14.8, 7.9 Hz), 3.17 (1H, ddd, J = 13.7, 9.3, 2.5 Hz), 3.24 (1H, dd, J = 13.0, 4.3 Hz), 3.54 (1H, ddd, J = 14.4, 10.6, 2.9 Hz), 3.95 (1H, dt, J = 14.2, 3.4 Hz), 4.03 (1H, d, J = 13.2 Hz), 4.41 (1H, dd, J = 15.1, 5.7 Hz), 4.50 (1H, dd, J = 14.5, 5.8 Hz), 4.63 (1H, d, J = 13.6 Hz), 4.67 (1H, d, J = 3.8 Hz), 6.98 (1H, t, J = 5.8 Hz), 7.24 (2H, d, J = 7.9 Hz), 7.39 (2H, d, J = 8.3 Hz), 7.81 (2H, d, J = 8.7 Hz), 8.01 (2H, d, J = 7.9 Hz), 8.03 (1H, s), 10.18 (1H, br s). |
| 901 | 645 (M + H). | 1H-NMR (CDCl₃, 300 MHz) δ: 3.16-3.31 (2H, m), 3.50-3.61 (1H, m), 3.88 (1H, dt, J = 13.3, 3.4 Hz), 4.00 (1H, d, J = 13.2 Hz), 4.48-4.70 (4H, m), 7.14 (1H, t, J = 5.8 Hz), 7.24 (1H, dd, J = 7.9, 1.5 Hz), 7.30 (2H, d, J = 8.7 Hz), 7.42-7.48 (2H, m), 7.62 (1H, s), 7.69-7.80 (2H, m), 7.72 (1H, d, J = 9.0 Hz), 7.91 (2H, d, J = 9.0 Hz), 7.97 (1H, s), 10.59 (1H, s). |
| 902 | 675 (M + H). | 1H-NMR (CDCl₃, 300 MHz) δ: 0.96 (3H, t, J = 7.5 Hz), 2.11 (2H, tq, J = 15.6, 7.8 Hz), 3.09-3.44 (2H, m), 3.54 (1H, t, J = 12.4 Hz), 3.97 (1H, d, J = 14.7 Hz), 4.18-4.44 (1H, m), 4.34 (1H, dd, J = 15.6, 5.1 Hz), 4.49 (1H, dd, J = 15.1, 6.0 Hz), 4.55-4.80 (1H, m), 4.72 (1H, d, J = 3.0 Hz), 7.03 (1H, t, J = 5.8 Hz), 7.20 (2H, d, J = 8.3 Hz), 7.35 (2H, d, J = 7.9 Hz), 7.81 (2H, d, J = 8.7 Hz), 8.01 (2H, d, J = 8.3 Hz), 8.60 (1H, s). |

TABLE 418

| Example No. | MS ESI m/e: | NMR |
|---|---|---|
| 903 | 641 (M + H). | 1H-NMR (CDCl₃, 300 MHz) δ: 0.96 (3H, t, J = 7.5 Hz), 2.10 (2H, tq, J = 15.8, 7.9 Hz), 3.20 (1H, td, J = 12.2, 3.4 Hz), 3.31 (1H, dd, J = |

TABLE 418-continued

| Example No. | MS ESI m/e: | NMR |
|---|---|---|
| | | 13.9, 3.8 Hz), 3.53 (1H, ddd, J = 14.5, 10.5, 3.2 Hz), 3.96 (1H, dt, J = 13.9, 3.2 Hz), 4.21-4.42 (1H, m), 4.36 (1H, dd, J = 15.4, 4.9 Hz), 4.49 (1H, dd, J = 14.7, 6.0 Hz), 4.66 (1H, d, J = 13.9 Hz), 4.73 (1H, d, J = 2.3 Hz), 7.07 (1H, t, J = 5.8 Hz), 7.20 (2H, d, J = 8.3 Hz), 7.34 (2H, d, J = 7.9 Hz), 7.81 (2H, d, J = 7.9 Hz), 8.02 (2H, d, J = 8.7 Hz), 8.78 (1H, s), 8.95 (1H, s). |
| 904 | 693 (M + H). | 1H-NMR (CDCl$_3$, 300 MHz) δ: 3.16 (1H, ddd, J = 13.4, 10.0, 2.6 Hz), 3.21 (1H, dd, J = 13.4, 5.1 Hz), 3.50 (1H, ddd, J = 13.8, 10.6, 3.3 Hz), 3.83 (3H, s), 3.92 (1H, dt, J = 14.2, 3.6 Hz), 4.00 (1H, dt, J = 12.7, 3.4 Hz), 4.38 (1H, dd, J = 14.7, 5.7 Hz), 4.49 (1H, dd, J = 14.7, 6.4 Hz), 4.60 (1H, d, J = 9.0 Hz), 4.62 (1H, s), 6.95 (1H, t, J = 6.0 Hz), 7.14 (2H, d, J = 7.9 Hz), 7.23 (2H, d, J = 8.7 Hz), 7.36 (2H, d, J = 9.0 Hz), 7.93 (2H, d, J = 9.0 Hz), 8.00 (1H, s). |
| 905 | 677 (M + H). | 1H-NMR (CDCl$_3$, 400 MHz) δ: 3.15-3.55 (3H, m), 3.91-4.05 (4H, m), 4.22-4.72 (5H, m), 6.92-7.23 (5H, m), 7.81 (2H, d, J = 8.4 Hz), 8.01 (2H, d, J = 8.2 Hz), 8.53 (1H, s). |
| 906 | 711 (M + H). | 1H-NMR (CDCl$_3$, 300 MHz) δ: 2.77 (3H, s), 3.08-3.18 (1H, m), 3.24 (1H, dd, J = 13.2, 4.1 Hz), 3.44-3.53 (1H, m), 3.98 (1H, d, J = 13.9 Hz), 4.22-4.31 (1H, m), 4.38 (1H, dd, J = 15.1, 5.7 Hz), 4.47-4.58 (2H, m), 4.65 (1H, br s), 6.99 (1H, t, J = 6.2 Hz), 7.15 (2H, d, J = 8.3 Hz), 7.24 (2H, d, J = 8.7 Hz), 7.38 (2H, d, J = 9.0 Hz), 7.94 (2H, d, J = 8.7 Hz). |
| 907 | 712 (M + H). | 1H-NMR (CDCl$_3$, 300 MHz) δ: 2.70 (3H, s), 3.06-3.38 (2H, m), 3.38-3.56 (1H, m), 3.94 (1H, d, J = 14.3 Hz), 4.23-4.69 (5H, m), 6.92 (1H, t, J = 6.6 Hz), 7.12 (2H, d, J = 8.7 Hz), 7.22 (2H, d, J = 8.7 Hz), 7.37 (2H, d, J = 8.7 Hz), 7.88-7.98 (2H, m). |

TABLE 419

| Example No. | MS ESI m/e: | NMR |
|---|---|---|
| 908 | 677 (M + H). | 1H-NMR (CDCl$_3$, 300 MHz) δ: 2.72 (3H, s), 3.12-3.37 (2H, m), 3.42-3.55 (1H, m), 3.86-3.99 (1H, m), 4.24-4.53 (3H, m), 4.58-4.69 (2H, m), 6.97 (1H, t, J = 5.7 Hz), 7.09 (2H, d, J = 8.3 Hz), 7.19 (2H, d, J = 8.7 Hz), 7.36 (2H, d, J = 8.3 Hz), 7.90-7.97 (2H, m), 8.69 (1H, s). |
| 909 | 658 (M + H). | 1H-NMR (CDCl$_3$, 300 MHz) δ: 0.98 (3H, t, J = 7.3 Hz), 1.67-1.78 (2H, m), 2.34 (3H, s), 2.85 (2H, t, J = 7.5 Hz), 3.10-3.25 (2H, m), 3.49 (1H, ddd, J = 13.9, 10.9, 3.2 Hz), 3.91 (1H, dt, J = 14.6, 2.8 Hz), 4.03 (1H, d, J = 12.4 Hz), 4.49 (2H, dd, J = 5.1, 4.0 Hz), 4.58-4.66 (2H, m), 6.96 (1H, t, J = 5.1 Hz), 7.38 (2H, d, J = 8.7 Hz), 7.93 (2H, d, J = 9.0 Hz), 8.05 (1H, s), 10.18 (1H, s). |
| 910 | 693 (M + H). | 1H-NMR (DMSO-d$_6$, 300 MHz) δ: 2.30 (3H, s), 3.24-3.33 (1H, m), 3.54-3.62 (1H, m), 3.75-3.83 (2H, m), 3.85-3.96 (1H, m), 3.99-4.25 (2H, m), 4.41-4.55 (1H, m), 4.60 (1H, br s), 7.23 (2H, d, J = 8.7 Hz), 7.28 (2H, d, J = 9.0 Hz), 7.52 (2H, d, J = 7.9 Hz), 7.91 (2H, d, J = 8.7 Hz), 8.80 (1H, t, J = 5.7 Hz), 12.33 (1H, br s). |
| 911 | 687 (M + H). | 1H-NMR (DMSO-d$_6$, 300 MHz) δ: 0.85 (3H, t, J = 7.3 Hz), 2.02-2.21 (2H, m), 2.30 (3H, s), 3.23-3.30 (1H, m), 3.58 (1H, dd, J = 14.1, 4.3 Hz), 3.75-3.82 (2H, m), 3.87-3.96 (1H, m), 4.02-4.27 (2H, m), 4.42-4.56 (1H, m), 4.61 (1H, s), 7.24 (2H, d, J = 7.5 Hz), 7.37 (2H, d, J = 8.3 Hz), 7.53 (2H, d, J = 9.0 Hz), 7.92 (2H, d, J = 8.7 Hz), 8.81 (1H, t, J = 6.0 Hz), 12.33 (1H, br s). |
| 912 | 741, 743 (M + H). | 1H-NMR (CDCl$_3$, 400 MHz) δ: 3.11-3.53 (3H, m), 3.95 (1H, d, J = 13.9 Hz), 4.27-4.70 (5H, m), 6.92 (1H, t, J = 5.2 Hz), 7.11-7.23 (4H, m), 7.38 (2H, d, J = 8.6 Hz), 7.93 (2H, dt, J = 9.5, 2.4 Hz), 8.56 (1H, s). |
| 913 | 655 (M + H). | 1H-NMR (CDCl$_3$, 400 MHz) δ: 0.89-0.99 (3H, m), 1.58-1.62 (2H, m), 2.53 (2H, t, J = 7.7 Hz), 3.30-3.44 (3H, m), 3.93 (1H, d, J = 13.9 Hz), 4.32-4.40 (3H, m), 4.56 (1H, br s), 4.69 (1H, s), 6.89 (1H, br s), 7.04-7.07 (4H, m), 7.32 (2H, d, J = 8.9 Hz), 7.91 (2H, d, J = 9.2 Hz), 8.60 (1H, s). |

TABLE 420

| Example No. | MS ESI m/e: | NMR |
|---|---|---|
| 914 | 621 (M + H). | 1H-NMR (CDCl₃, 400 MHz) δ: 0.92 (3H, t, J = 7.4 Hz), 1.59 (2H, td, J = 14.9, 7.5 Hz), 2.52 (2H, t, J = 7.6 Hz), 3.24-3.33 (2H, m), 3.53 (1H, t, J = 11.7 Hz), 3.92 (1H, d, J = 13.9 Hz), 4.30-4.37 (3H, m), 4.70 (1H, br s), 4.70 (1H, s), 7.01-7.04 (1H, m), 7.02-7.05 (4H, m), 7.32 (2H, d, J = 8.6 Hz), 7.91 (2H, d, J = 8.8 Hz), 8.78 (1H, s), 8.92 (1H, s). |
| 915 | 706 (M + H). | 1H-NMR (DMSO-d₆, 300 MHz) δ: 3.37-3.52 (1H, m), 3.66-3.88 (3H, m), 4.02-4.20 (4H, m), 4.67 (1H, br s), 7.19-7.26 (4H, m), 7.49 (2H, d, J = 8.7 Hz), 7.82 (1H, br s), 7.92 (2H, d, J = 8.7 Hz), 8.28 (1H, br s), 8.85 (1H, t, J = 5.8 Hz), 9.59 (1H, s). |
| 916 | 720 (M + H). | 1H-NMR (DMSO-d₆, 300 MHz) δ: 2.85 (3H, d, J = 4.9 Hz), 3.39-3.51 (1H, m), 3.65-3.88 (3H, m), 4.01-4.20 (4H, m), 4.67 (1H, br s), 7.18-7.26 (4H, m), 7.50 (2H, d, J = 8.7 Hz), 7.93 (2H, d, J = 8.7 Hz), 8.77-8.87 (2H, m), 9.59 (1H, s). |
| 917 | 677 (M + H). | 1H-NMR (CDCl₃, 300 MHz) δ: 2.82 (3H, s), 3.09-3.18 (1H, m), 3.25 (1H, dd, J = 13.2, 4.1 Hz), 3.46-3.56 (1H, m), 3.97 (1H, d, J = 13.9 Hz), 4.26 (1H, d, J = 12.8 Hz), 4.37 (1H, dd, J = 15.1, 5.7 Hz), 4.50 (1H, dd, J = 15.1, 6.4 Hz), 4.58-4.66 (2H, m), 7.05-7.14 (3H, m), 7.23 (2H, d, J = 8.7 Hz), 7.37 (2H, d, J = 8.7 Hz), 7.94 (2H, d, J = 9.0 Hz), 9.21 (1H, s). |
| 918 | 679 (M + H). | 1H-NMR (CDCl₃, 400 MHz) δ: 3.12-3.37 (2H, m), 3.46 (1H, t, J = 11.9 Hz), 3.96 (1H, d, J = 14.1 Hz), 4.26-4.63 (2H, m), 4.34 (1H, dd, J = 14.9, 5.4 Hz), 4.49 (1H, dd, J = 15.0, 6.2 Hz), 4.66 (1H, s), 6.62 (1H, t, J = 72.0 Hz), 6.98 (1H, br s), 7.14 (2H, d, J = 8.4 Hz), 7.22 (2H, d, J = 8.6 Hz), 7.27 (2H, d, J = 9.0 Hz), 7.89 (2H, dt, J = 9.5, 2.4 Hz), 8.60 (1H, s). |

TABLE 421

| Example No. | MS ESI m/e: | NMR |
|---|---|---|
| 919 | 645 (M + H). | 1H-NMR (CDCl₃, 400 MHz) δ: 3.16-3.22 (1H, m), 3.30 (1H, dd, J = 13.2, 4.2 Hz), 3.45-3.50 (1H, m), 3.95 (1H, d, J = 14.1 Hz), 4.28-4.43 (1H, m), 4.35 (1H, dd, J = 14.9, 5.6 Hz), 4.48 (1H, dd, J = 15.0, 6.2 Hz), 4.58 (1H, d, J = 13.7 Hz), 4.66 (1H, br s), 6.61 (1H, t, J = 72.1 Hz), 7.02 (1H, br s), 7.11 (2H, d, J = 8.2 Hz), 7.21 (2H, dt, J = 9.1, 2.4 Hz), 7.27 (2H, d, J = 8.8 Hz), 7.89 (2H, dt, J = 9.4, 2.4 Hz), 8.79 (1H, s), 8.95 (1H, s). |
| 920 | 693 (M + H). | 1H-NMR (CDCl₃, 300 MHz) δ: 2.30 (3H, s), 3.03 (1H, ddd, J = 14.2, 11.2, 2.5 Hz), 3.14 (1H, dd, J = 13.2, 4.1 Hz), 3.45 (1H, ddd, J = 14.1, 11.3, 3.0 Hz), 3.91 (1H, dt, J = 14.6, 3.0 Hz), 4.07 (1H, dt, J = 13.1, 2.5 Hz), 4.29 (1H, d, J = 13.2 Hz), 4.37 (1H, dd, J = 15.1, 5.7 Hz), 4.49 (1H, dd, J = 14.9, 6.2 Hz), 4.60 (1H, d, J = 3.0 Hz), 6.21 (1H, s), 7.03 (1H, t, J = 5.1 Hz), 7.15 (2H, d, J = 8.3 Hz), 7.24 (2H, d, J = 8.3 Hz), 7.37 (2H, d, J = 8.3 Hz), 7.92 (2H, d, J = 9.0 Hz). |
| 921 | 677 (M + H). | 1H-NMR (CDCl₃, 400 MHz) δ: 2.74 (3H, s), 3.09-3.24 (2H, m), 3.44-3.52 (1H, m), 3.94 (1H, d, J = 13.9 Hz), 4.07 (1H, d, J = 13.4 Hz), 4.39 (1H, dd, J = 15.0, 5.7 Hz), 4.50 (1H, dd, J = 14.8, 6.3 Hz), 4.59-4.65 (2H, m), 6.97 (1H, br s), 7.12 (2H, d, J = 7.9 Hz), 7.23 (2H, d, J = 8.8 Hz), 7.37 (2H, d, J = 7.9 Hz), 7.93-7.95 (2H, m), 8.61 (1H, s). |
| 922 | 652 (M + H). | 1H-NMR (CDCl₃, 400 MHz) δ: 2.95-3.06 (2H, m), 3.42-3.51 (1H, m), 3.82 (1H, d, J = 13.2 Hz), 3.96 (1H, d, J = 14.1 Hz), 4.34-4.45 (2H, m), 4.52 (1H, dd, J = 15.1, 6.3 Hz), 4.60 (1H, br s), 6.96 (1H, br s), 7.18 (2H, d, J = 7.9 Hz), 7.27 (2H, d, J = 8.3 Hz), 7.39 (2H, d, J = 7.9 Hz), 7.93 (2H, d, J = 9.3 Hz), 8.57 (1H, s). |

TABLE 422

| Example No. | MS ESI m/e: | NMR |
|---|---|---|
| 923 | 625 (M + H). | 1H-NMR (CDCl₃, 300 MHz) δ: 1.64-1.90 (2.0H, m), 1.91-2.12 (2.0H, m), 2.17-2.56 (2.0H, m), 2.57-2.78 (2.0H, m), 3.09-3.35 (3.0H, m), 3.54 (0.5H, dt, J = 11.8, 2.1 Hz), 3.59 (0.5H, dt, J = 11.7, 1.9 Hz), 3.83 (0.5H, q, J = 2.3 Hz), 3.88 (0.5H, q, J = 2.8 Hz), |

TABLE 422-continued

| Example No. | MS ESI m/e: | NMR |
|---|---|---|
| | | 4.38-4.53 (3.0H, m), 5.61 (1.0H, br s), 7.02 (0.5H, t, J = 6.2 Hz), 7.11 (0.5H, t, J = 5.8 Hz), 7.17 (1.0H, d, J = 7.9 Hz), 7.17 (1.0H, d, J = 8.7 Hz), 7.25 (1.0H, d, J = 9.8 Hz), 7.25 (1.0H, d, J = 7.9 Hz), 7.36 (2.0H, d, J = 8.3 Hz), 7.90 (1.0H, d, J = 7.9 Hz), 7.90 (1.0H, d, J = 9.8 Hz). |
| 924 | 621 (M − HCl + H). | 1H-NMR (DMSO-d$_6$, 300 MHz) δ: 2.41 (1H, td, J = 11.6, 3.3 Hz), 2.60 (1H, dd, J = 12.4, 4.1 Hz), 3.20 (1H, d, J = 10.9 Hz), 3.60 (1H, td, J = 12.4, 3.4 Hz), 3.69 (1H, d, J = 12.4 Hz), 3.76 (1H, d, J = 12.1 Hz), 4.20 (1H, dd, J = 15.4, 6.0 Hz), 4.30 (1H, dd, J = 15.3, 5.8 Hz), 4.59 (1H, br s), 6.44 (1H, d, J = 9.8 Hz), 6.87 (1H, d, J = 3.0 Hz), 7.26 (2H, d, J = 9.4 Hz), 7.30 (2H, d, J = 9.0 Hz), 7.32 (1H, dd, J = 9.8, 3.4 Hz), 7.52 (2H, d, J = 8.3 Hz), 7.95 (2H, d, J = 9.0 Hz), 8.61 (1H, t, J = 5.8 Hz). |
| 925 | 661 (M + H). | 1H-NMR (CDCl$_3$, 300 MHz) δ: 2.72 (3H, s), 3.19-3.35 (2H, m), 3.44-3.55 (1H, m), 3.96 (1H, d, J = 13.9 Hz), 4.20-4.53 (3H, m), 4.61-4.72 (2H, m), 6.93-7.01 (1H, br m), 7.09 (2H, d, J = 8.7 Hz), 7.19 (2H, d, J = 8.7 Hz), 7.81 (2H, d, J = 8.3 Hz), 8.01 (2H, d, J = 8.7 Hz), 8.69 (1H, s). |
| 926 | 671 (M + H). | 1H-NMR (CDCl$_3$, 300 MHz) δ: 0.96 (3H, t, J = 7.5 Hz), 2.01-2.20 (2H, m), 2.73 (3H, s), 3.21-3.34 (2H, m), 3.42-3.55 (1H, m), 3.93 (1H, d, J = 13.6 Hz), 4.26-4.55 (3H, m), 4.57-4.70 (2H, m), 6.97 (1H, t, J = 6.0 Hz), 7.20 (2H, d, J = 8.3 Hz), 7.34 (2H, d, J = 6.4 Hz), 7.36 (2H, d, J = 6.8 Hz), 7.93 (2H, d, J = 9.0 Hz), 8.69 (1H, s). |
| 927 | 695, 697 (M + H). | 1H-NMR (CDCl$_3$, 300 MHz) δ: 2.70 (3H, s), 3.13-3.37 (2H, m), 3.43-3.55 (1H, m), 3.97 (1H, d, J = 14.3 Hz), 4.28-4.53 (3H, m), 4.54-4.65 (1H, m), 4.68 (1H, s), 6.85-6.94 (1H, br m), 7.12 (2H, d, J = 8.3 Hz), 7.21 (2H, d, J = 8.7 Hz), 7.82 (2H, d, J = 8.3 Hz), 8.01 (2H, d, J = 8.3 Hz). |

TABLE 423

| Example No. | MS ESI m/e: | NMR |
|---|---|---|
| 928 | 705, 707 (M + H). | 1H-NMR (CDCl$_3$, 300 MHz) δ: 0.97 (3H, t, J = 7.5 Hz), 2.04-2.20 (2H, m), 2.70 (3H, s), 3.15-3.34 (2H, m), 3.42-3.55 (1H, m), 3.94 (1H, d, J = 13.9 Hz), 4.28-4.63 (4H, m), 4.67 (1H, s), 6.92 (1H, t, J = 5.7 Hz), 7.22 (2H, d, J = 8.3 Hz), 7.36-7.39 (4H, m), 7.93 (2H, d, J = 8.7 Hz). |
| 929 | 693 (m + H). | 1H-NMR (CDCl$_3$, 400 MHz) δ: 3.14-3.39 (2H, m), 3.43-3.57 (1H, m), 3.92 (1H, dt, J = 13.8, 2.8 Hz), 4.03 (3H, s), 4.24-4.70 (5H, m), 6.99-7.14 (3H, m), 7.20 (2H, d, J = 8.8 Hz), 7.36 (2H, d, J = 8.2 Hz), 7.93 (2H, dt, J = 9.5, 2.4 Hz), 8.53 (1H, s). |
| 930 | 734 (M + H). | 1H-NMR (DMSO-d$_6$, 300 MHz) δ: 2.72 (3H, s), 3.07 (3H, s), 3.36-3.44 (1H, m), 3.59-3.88 (3H, m), 3.98-4.50 (4H, m), 4.66 (1H, br s), 7.23 (4H, s), 7.50 (2H, d, J = 8.7 Hz), 7.93 (2H, d, J = 9.0 Hz), 8.83 (1H, t, J = 5.8 Hz), 9.56 (1H, s). |
| 931 | 679 (M + H). | 1H-NMR (CDCl$_3$, 300 MHz) δ: 3.18-3.37 (2H, m), 3.44-3.55 (1H, m), 3.94 (1H, d, J = 13.9 Hz), 4.25-4.49 (3H, m), 4.56-4.72 (2H, m), 6.49 (1H, t, J = 73.7 Hz), 6.96 (1H, t, J = 6.0 Hz), 7.02 (2H, d, J = 8.3 Hz), 7.17 (2H, d, J = 8.7 Hz), 7.37 (2H, d, J = 8.3 Hz), 7.93 (2H, d, J = 9.0 Hz), 8.60 (1H, s). |
| 932 | 645 (M + H). | 1H-NMR (CDCl$_3$, 300 MHz) δ: 3.16-3.34 (2H, m), 3.45-3.56 (1H, m), 3.93 (1H, d, J = 13.6 Hz), 4.28-4.47 (3H, m), 4.60-4.71 (2H, m), 6.47 (1H, t, J = 73.7 Hz), 6.99 (2H, d, J = 8.3 Hz), 7.03-7.09 (1H, m), 7.15 (2H, d, J = 8.7 Hz), 7.36 (2H, d, J = 8.3 Hz), 7.93 (2H, d, J = 8.7 Hz), 8.79 (1H, s), 8.94 (1H, s). |
| 933 | 666 (M + H). | 1H-NMR (CDCl$_3$, 400 MHz) δ: 2.56 (3H, s), 2.93-3.05 (2H, m), 3.42-3.52 (1H, m), 3.82 (1H, d, J = 13.2 Hz), 3.95 (1H, d, J = 14.4 Hz), 4.34-4.54 (3H, m), 4.60 (1H, br s), 7.00 (1H, br s), 7.18 (2H, d, J = 8.1 Hz), 7.27 (2H, d, J = 8.6 Hz), 7.39 (2H, d, J = 8.1 Hz), 7.93 (2H, d, J = 8.8 Hz). |

TABLE 424

| Example No. | MS ESI m/e: | NMR |
|---|---|---|
| 934 | 689 (M + H). | 1H-NMR (CDCl₃, 300 MHz) δ: 0.97 (3H, t, J = 7.5 Hz), 2.11 (2H, tq, J = 15.8, 7.9 Hz), 2.70 (3H, s), 3.10-3.40 (2H, m), 3.51 (1H, ddd, J = 14.9, 10.4, 3.4 Hz), 3.96 (1H, dt, J = 14.3, 3.1 Hz), 4.15-4.45 (1H, m), 4.38 (1H, dd, J = 14.3, 4.9 Hz), 4.50 (1H, dd, J = 15.4, 5.7 Hz), 4.55-4.68 (1H, m), 4.70 (1H, d, J = 2.3 Hz), 6.96 (1H, t, J = 6.0 Hz), 7.21 (2H, d, J = 8.3 Hz), 7.37 (2H, d, J = 8.3 Hz), 7.81 (2H, d, J = 8.7 Hz), 8.01 (2H, d, J = 8.3 Hz). |
| 935 | 655 (M + H). | 1H-NMR (CDCl₃, 300 MHz) δ: 0.95 (3H, t, J = 7.5 Hz), 2.09 (2H, tq, J = 15.8, 7.9 Hz), 2.72 (3H, s), 3.22 (1H, td, J = 12.0, 3.4 Hz), 3.33 (1H, dd, J = 14.3, 4.5 Hz), 3.53 (1H, ddd, J = 14.3, 10.4, 2.8 Hz), 3.95 (1H, dt, J = 14.1, 3.1 Hz), 4.15-4.42 (1H, m), 4.35 (1H, dd, J = 14.7, 6.0 Hz), 4.48 (1H, dd, J = 14.7, 6.4 Hz), 4.59-4.77 (1H, m), 4.71 (1H, d, J = 2.3 Hz), 7.09 (1H, t, J = 5.7 Hz), 7.18 (2H, d, J = 7.9 Hz), 7.32 (2H, d, J = 7.9 Hz), 7.80 (2H, d, J = 7.9 Hz), 8.01 (2H, d, J = 8.3 Hz), 8.68 (1H, s). |
| 936 | 732, 734 (M + H). | 1H-NMR (CDCl₃, 300 MHz) δ: 2.72-2.86 (1H, m), 2.96 (1H, dd, J = 14.3, 3.8 Hz), 3.30 (1H, ddd, J = 14.3, 12.1, 3.0 Hz), 3.91 (1H, dd, J = 12.6, 3.6 Hz), 4.15 (1H, dt, J = 13.7, 2.5 Hz), 4.37 (1H, dd, J = 14.7, 5.7 Hz), 4.44-4.63 (3H, m), 7.13 (2H, d, J = 8.3 Hz), 7.16 (1H, t, J = 4.5 Hz), 7.23 (2H, d, J = 8.7 Hz), 7.39 (2H, d, J = 8.7 Hz), 7.93 (2H, d, J = 8.7 Hz), 10.50 (1H, br s). |
| 937 | 679 (M + H). | 1H-NMR (CDCl₃, 300 MHz) δ: 3.14 (1H, ddd, J = 13.8, 10.6, 3.1 Hz), 3.27 (1H, dd, J = 13.2, 4.1 Hz), 3.50 (1H, ddd, J = 14.0, 11.2, 2.9 Hz), 3.91 (1H, dt, J = 14.1, 2.7 Hz), 4.25-4.34 (1H, m), 4.34 (1H, dd, J = 14.9, 6.2 Hz), 4.47 (1H, dd, J = 14.9, 6.2 Hz), 4.57 (1H, d, J = 13.6 Hz), 4.66 (1H, d, J = 1.9 Hz), 7.12 (2H, d, J = 8.3 Hz), 7.13 (1H, t, J = 3.4 Hz), 7.22 (2H, d, J = 8.7 Hz), 7.36 (2H, d, J = 8.7 Hz), 7.93 (2H, d, J = 8.7 Hz), 8.05 (1H, s), 10.62 (1H, s). |

TABLE 425

| Example No. | MS ESI m/e: | NMR |
|---|---|---|
| 938 | MS ESI(−) m/e: 673 (M − H). | 1H-NMR (CDCl₃, 400 MHz) δ: 3.17-3.29 (2H, m), 3.55 (1H, t, J = 11.0 Hz), 3.71 (3H, s), 3.91 (1H, d, J = 6.8 Hz), 4.04 (1H, d, J = 13.0 Hz), 4.40-4.53 (2H, m), 4.62-4.65 (2H, m), 7.25 (2H, d, J = 8.6 Hz), 7.35 (2H, d, J = 8.1 Hz), 7.52 (2H, d, J = 8.1 Hz), 7.92 (2H, d, J = 11.0 Hz), 8.05 (1H, s), 10.66 (1H, s). |
| 939 | 639 (M + H). | 1H-NMR (CDCl₃, 400 MHz) δ: 3.20-3.26 (2H, m), 3.38 (3H, s), 3.54 (1H, t, J = 11.1 Hz), 3.91 (1H, dd, J = 7.4, 6.5 Hz), 3.91 (2H, s), 4.03 (1H, d, J = 13.0 Hz), 4.40-4.42 (3H, m), 4.63-4.65 (2H, m), 6.94-6.97 (1H, m), 7.18 (1H, d, J = 10.2 Hz), 7.25 (2H, d, J = 7.9 Hz), 7.35 (2H, d, J = 8.8 Hz), 7.93 (2H, d, J = 13.4 Hz), 8.06 (1H, s), 10.61 (1H, br s). |
| 940 | 693 (M + H). | 1H-NMR (CDCl₃, 300 MHz) δ: 3.10-3.19 (1H, m), 3.25 (1H, dd, J = 13.2, 4.1 Hz), 3.45-3.54 (1H, m), 3.97 (1H, d, J = 14.3 Hz), 4.08-4.17 (1H, m), 4.23-4.39 (2H, m), 4.50 (1H, dd, J = 15.1, 6.4 Hz), 4.56-4.67 (2H, m), 5.14 (2H, s), 7.04 (1H, t, J = 5.8 Hz), 7.13 (2H, d, J = 8.3 Hz), 7.23 (2H, d, J = 8.7 Hz), 7.38 (2H, d, J = 8.3 Hz), 7.94 (2H, d, J = 9.0 Hz), 9.27 (1H, s). |
| 941 | 693 (M + H). | 1H-NMR (CDCl₃, 300 MHz) δ: 2.70 (3H, s), 3.13-3.37 (2H, m), 3.40-3.52 (1H, m), 3.88-3.98 (1H, m), 4.24-4.40 (2H, m), 4.46 (1H, dd, J = 14.7, 6.0 Hz), 4.52-4.63 (1H, m), 4.63-4.68 (1H, m), 6.48 (1H, t, J = 73.7 Hz), 6.89 (1H, t, J = 5.3 Hz), 7.02 (2H, d, J = 8.3 Hz), 7.18 (2H, d, J = 8.7 Hz), 7.37 (2H, d, J = 8.3 Hz), 7.93 (2H, d, J = 8.7 Hz). |
| 942 | 659 (M + H). | 1H-NMR (CDCl₃, 300 MHz) δ: 2.72 (3H, s), 3.15-3.36 (2H, m), 3.41-3.53 (1H, m), 3.92 (1H, dt, J = 13.9, 2.8 Hz), 4.24-4.38 (2H, m), 4.44 (1H, dd, J = 14.7, 6.0 Hz), 4.57-4.69 (2H, m), 6.47 (1H, t, J = 73.7 Hz), 6.96 (1H, t, J = 6.0 Hz), 6.98 (2H, d, J = 8.3 Hz), 7.15 (2H, d, J = 8.7 Hz), 7.36 (2H, d, J = 7.9 Hz), 7.93 (2H, d, J = 9.0 Hz), 8.69 (1H, s). |

TABLE 426

| Example No. | MS ESI m/e: | NMR |
|---|---|---|
| 943 | 678 (M + H). | 1H-NMR. (DMSO-d$_6$, 400 MHz) δ: 3.28-3.41 (2H, m), 3.61 (1H, dd, J = 13.7, 4.6 Hz), 3.70-4.19 (5H, m), 4.62 (1H, dd, J = 4.6, 2.1 Hz), 6.32 (2H, s), 7.25 (4H, dd, J = 16.6, 8.7 Hz), 7.51 (2H, d, J = 8.1 Hz), 7.91 (2H, dt, J = 9.4, 2.5 Hz), 8.40 (1H, s), 8.81 (1H, t, J = 5.7 Hz). |
| 944 | 693 (M + H). | 1H-NMR (CDCl$_3$, 300 MHz) δ: 3.16 (1H, ddd, J = 13.9, 10.4, 3.0 Hz), 3.27 (1H, dd, J = 13.2, 4.5 Hz), 3.50 (1H, ddd, J = 14.4, 10.3, 2.9 Hz), 3.94 (1H, dt, J = 14.8, 3.4 Hz), 4.14 (1H, dt, J = 13.1, 3.5 Hz), 4.22 (3H, s), 4.36 (1H, dd, J = 15.4, 5.7 Hz), 4.49 (1H, dd, J = 15.3, 5.8 Hz), 4.60 (1H, d, J = 13.6 Hz), 4.64 (1H, d, J = 4.5 Hz), 7.00 (1H, t, J = 6.0 Hz), 7.12 (2H, d, J = 7.9 Hz), 7.22 (2H, d, J = 8.7 Hz), 7.36 (2H, d, J = 9.0 Hz), 7.93 (2H, d, J = 9.4 Hz), 8.98 (1H, s). |
| 945 | 706 (M + H). | 1H-NMR (CDCl$_3$, 300 MHz) δ: 3.12-3.25 (7H, m), 3.25-3.34 (1H, m), 3.39-3.52 (1H, m), 3.88 (1H, d, J = 13.6 Hz), 4.25 (1H, d, J = 13.2 Hz), 4.32-4.52 (2H, m), 4.53-4.66 (2H, m), 6.96 (1H, t, J = 6.8 Hz), 7.09 (2H, d, J = 8.3 Hz), 7.20 (2H, d, J = 8.7 Hz), 7.35 (2H, d, J = 8.7 Hz), 7.93 (2H, d, J = 9.0 Hz), 8.37 (1H, s). |
| 946 | 722 (M + H). | 1H-NMR (CDCl$_3$, 300 MHz) δ: 3.14-3.36 (2H, m), 3.42-3.58 (1H, m), 3.58-3.67 (2H, m), 3.78-3.92 (3H, m), 4.05-4.27 (1H, m), 4.27-4.51 (2H, m), 4.56-4.74 (2H, m), 5.60 (1H, t, J = 5.8 Hz), 7.04-7.22 (5H, m), 7.35 (2H, d, J = 7.9 Hz), 7.89-7.96 (2H, m), 8.31 (1H, s). |
| 947 | 687, 689 (M + H). | 1H-NMR (CDCl$_3$, 300 MHz) δ: 3.32-3.52 (2H, m), 3.63 (1H, t, J = 12.2 Hz), 3.99 (1H, dt, J = 13.8, 3.0 Hz), 4.24-4.75 (5H, m), 7.03 (1H, t, J = 5.3 Hz), 7.11 (2H, d, J = 8.3 Hz), 7.21 (2H, d, J = 8.7 Hz), 7.43 (1H, d, J = 3.8 Hz), 7.61 (1H, d, J = 3.0 Hz), 8.62 (1H, s). |

TABLE 427

| Example No. | MS ESI m/e: | NMR |
|---|---|---|
| 948 | 737 (M + H). | 1H-NMR (CDCl$_3$, 300 MHz) δ: 2.96 (1H, td, J = 12.3, 3.3 Hz), 3.07 (1H, dd, J = 13.2, 4.1 Hz), 3.39-3.51 (1H, m), 3.83-3.95 (2H, m), 3.96 (3H, s), 4.24 (1H, d, J = 12.8 Hz), 4.40 (1H, dd, J = 15.1, 6.0 Hz), 4.48 (1H, dd, J = 15.1, 6.4 Hz), 4.61 (1H, d, J = 2.3 Hz), 6.61 (1H, s), 7.15 (1H, t, J = 4.9 Hz), 7.18 (2H, d, J = 8.3 Hz), 7.26 (2H, d, J = 8.7 Hz), 7.37 (2H, d, J = 8.7 Hz), 7.90 (2H, d, J = 9.0 Hz). |
| 949 | 691 (M + H). | 1H-NMR (CDCl$_3$, 300 MHz) δ: 1.39 (3H, t, J = 7.5 Hz), 2.95-3.02 (2H, m), 3.13-3.36 (2H, m), 3.42-3.52 (1H, m), 3.93 (1H, d, J = 13.9 Hz), 4.29-4.54 (3H, m), 4.54-4.67 (2H, m), 6.93 (1H, t, J = 6.0 Hz), 7.09 (2H, d, J = 8.3 Hz), 7.20 (2H, d, J = 8.7 Hz), 7.37 (2H, d, J = 7.9 Hz), 7.94 (2H, d, J = 9.0 Hz), 8.71 (1H, s). |
| 950 | 675 (M + H). | 1H-NMR (CDCl$_3$, 300 MHz) δ: 1.38 (3H, t, J = 7.5 Hz), 2.98 (2H, q, J = 7.5 Hz), 3.14-3.39 (2H, m), 3.44-3.53 (1H, m), 3.96 (1H, d, J = 13.9 Hz), 4.23-4.54 (3H, m), 4.59-4.71 (2H, m), 6.92-6.95 (1H, br m), 7.09 (2H, d, J = 8.7 Hz), 7.19 (2H, d, J = 8.7 Hz), 7.81 (2H, d, J = 8.3 Hz), 8.02 (2H, d, J = 8.7 Hz), 8.71 (1H, s). |
| 951 | 720 (M + H). | 1H-NMR (CDCl$_3$, 400 MHz) δ: 2.98-3.12 (2H, m), 3.41-3.50 (1H, m), 3.91-4.02 (2H, m), 4.30 (1H, d, J = 13.0 Hz), 4.40 (1H, dd, J = 14.9, 5.8 Hz), 4.51 (1H, dd, J = 15.0, 6.2 Hz), 4.60 (1H, br s), 6.94 (1H, br s), 7.18 (2H, d, J = 8.8 Hz), 7.26 (2H, d, J = 8.4 Hz), 7.39 (2H, d, J = 8.6 Hz), 7.92 (2H, d, J = 8.4 Hz). |
| 952 | 692 (M + H). | 1H-NMR (CDCl$_3$, 300 MHz) δ: 3.02 (3H, d, J = 4.9 Hz), 3.13-3.35 (2H, m), 3.43-3.57 (1H, m), 3.88 (1H, d, J = 14.3 Hz), 4.14-4.27 (1H, m), 4.28-4.50 (2H, m), 4.53-4.77 (2H, m), 5.07-5.18 (1H, m), 7.04-7.13 (3H, m), 7.18 (2H, d, J = 8.7 Hz), 7.35 (2H, d, J = 8.7 Hz), 7.87-7.97 (2H, m), 8.33 (1H, s). |

TABLE 428

| Example No. | MS ESI m/e: | NMR |
|---|---|---|
| 953 | 636 (M + H). | 1H-NMR (CDCl$_3$, 400 MHz) δ: 2.94-3.05 (2H, m), 3.44-3.53 (1H, m), 3.83 (1H, d, J = 12.8 Hz), 3.98 (1H, d, J = 14.4 Hz), 4.37 (1H, |

TABLE 428-continued

| Example No. | MS ESI m/e: | NMR |
|---|---|---|
| | | d, J = 13.0 Hz), 4.42 (1H, dd, J = 14.8, 6.3 Hz), 4.52 (1H, dd, J = 14.8, 6.3 Hz), 4.63 (1H, br s), 6.94 (1H, br s), 7.18 (2H, d, J = 7.9 Hz), 7.27 (2H, d, J = 8.6 Hz), 7.85 (2H, d, J = 8.3 Hz), 8.01 (2H, d, J = 8.3 Hz), 8.56 (1H, s). |
| 954 | (M + H). | 1H-NMR (CDCl$_3$, 400 MHz) δ: 2.97-3.08 (2H, m), 3.42-3.53 (1H, m), 3.82 (1H, d, J = 13.2 Hz), 3.94 (1H, d, J = 14.6 Hz), 4.36 (1H, d, J = 13.2 Hz), 4.40 (1H, dd, J = 14.7, 6.1 Hz), 4.47 (1H, dd, J = 14.7, 6.1 Hz), 4.60 (1H, br s), 6.52 (1H, t, J = 73.6 Hz), 6.95 (1H, br s), 7.07 (2H, d, J = 8.6 Hz), 7.23 (2H, d, J = 8.6 Hz), 7.39 (2H, d, J = 8.1 Hz), 7.93 (2H, d, J = 8.8 Hz), 8.56 (1H, s). |
| 955 | 661 (M + H). | 1H-NMR (CDCl$_3$, 400 MHz) δ: 3.11-3.36 (2H, m), 3.44 (1H, t, J = 12.8 Hz), 3.95 (1H, d, J = 14.3 Hz), 4.24-4.70 (2H, br m), 4.32 (1H, dd, J = 14.8, 5.5 Hz), 4.46 (1H, dd, J = 14.8, 6.2 Hz), 4.65 (1H, d, J = 2.6 Hz), 6.50 (1H, t, J = 73.6 Hz), 6.62 (1H, t, J = 72.0 Hz), 6.90 (1H, br s), 7.03 (2H, d, J = 8.6 Hz), 7.18 (2H, d, J = 8.6 Hz), 7.27 (2H, d, J = 8.4 Hz), 7.89 (2H, dt, J = 9.6, 2.5 Hz), 8.60 (1H, s). |
| 956 | 627 (M + H). | 1H-NMR (CDCl$_3$, 400 MHz) δ: 3.18-3.20 (1H, m), 3.29 (1H, dd, J = 13.7, 4.2 Hz), 3.46 (1H, t, J = 11.0 Hz), 3.94 (1H, d, J = 14.1 Hz), 4.27-4.40 (1H, m), 4.34 (1H, dd, J = 14.9, 5.6 Hz), 4.45 (1H, dd, J = 14.9, 6.1 Hz), 4.58 (1H, d, J = 12.6 Hz), 4.66 (1H, br s), 6.48 (1H, t, J = 73.8 Hz), 6.61 (1H, t, J = 72.1 Hz), 6.94-7.06 (3H, m), 7.17 (2H, d, J = 8.6 Hz), 7.26 (2H, d, J = 8.6 Hz), 7.89 (2H, d, J = 8.8 Hz), 8.79 (1H, s), 8.95 (1H, s). |
| 957 | 693 (M + H). | 1H-NMR (CDCl$_3$, 300 MHz) δ: 3.12 (1H, ddd, J = 14.5, 11.1, 3.2 Hz), 3.25 (1H, dd, J = 13.4, 4.3 Hz), 3.47 (1H, ddd, J = 14.4, 10.6, 3.1 Hz), 3.85 (3H, s), 3.86-3.95 (1H, m), 4.31-4.54 (4H, m), 4.65 (1H, d, J = 3.0 Hz), 7.05 (1H, t, J = 5.8 Hz), 7.12 (2H, d, J = 8.3 Hz), 7.21 (2H, d, J = 8.3 Hz), 7.36 (2H, d, J = 8.7 Hz), 7.93 (2H, d, J = 8.7 Hz), 7.98 (1H, s). |

TABLE 429

| Example No. | MS ESI m/e: | NMR |
|---|---|---|
| 958 | 670 (M + H). | 1H-NMR (CDCl$_3$, 300 MHz) δ: 1.10 (3H, t, J = 7.0 Hz), 2.88 (3H, s), 3.09-3.53 (3H, m), 3.37 (2H, q, J = 7.0 Hz), 3.92 (1H, d, J = 13.6 Hz), 4.14-4.79 (5H, m), 6.51-6.64 (3H, m), 6.97 (2H, d, J = 8.7 Hz), 7.34 (2H, d, J = 8.3 Hz), 7.91 (2H, d, J = 8.7 Hz), 8.58 (1H, s). |
| 959 | 729 (M + H). | 1H-NMR (CDCl$_3$, 400 MHz) δ: 3.31-3.45 (3H, m), 3.96 (1H, d, J = 14.1 Hz), 4.29-4.49 (3H, m), 4.63 (1H, br s), 4.68 (1H, s), 5.94 (1H, t, J = 55.4 Hz), 7.02 (1H, br s), 7.12 (2H, d, J = 7.5 Hz), 7.21 (2H, d, J = 7.8 Hz), 7.38 (2H, d, J = 8.2 Hz), 7.91 (2H, d, J = 4.4 Hz), 8.60 (1H, s). |
| 960 | 695 (M + H). | 1H-NMR (CDCl$_3$, 400 MHz) δ: 3.25-3.31 (2H, m), 3.55 (1H, t, J = 10.0 Hz), 3.94 (1H, d, J = 13.9 Hz), 4.30-4.47 (3H, m), 4.66-4.72 (2H, m), 5.94 (1H, t, J = 52.8 Hz), 7.08 (2H, t, J = 7.3 Hz), 7.18 (3H, d, J = 4.2 Hz), 7.36 (2H, d, J = 8.6 Hz), 7.91 (2H, d, J = 8.8 Hz), 8.78 (1H, s), 8.94 (1H, s). |
| 961 | 731 (M + H). | 1H-NMR (CDCl$_3$, 400 MHz) δ: 3.28-3.46 (3H, m), 3.96 (1H, d, J = 13.9 Hz), 4.30-4.51 (3H, m), 4.64 (1H, br s), 4.68 (1H, s), 6.97 (1H, t, J = 5.7 Hz), 7.11 (2H, d, J = 8.2 Hz), 7.20 (2H, d, J = 6.6 Hz), 7.37 (2H, d, J = 8.4 Hz), 7.95 (2H, d, J = 15.6 Hz), 8.87 (1H, s). |
| 962 | 713 (M + H). | 1H-NMR (CD$_3$OD, 300 MHz) δ: 3.41-3.62 (2H, m), 3.83-4.04 (3H, m), 4.14-4.35 (2H, m), 4.56-4.70 (2H, m), 7.10 (2H, d, J = 8.7 Hz), 7.27 (2H, d, J = 8.7 Hz), 7.41 (2H, d, J = 8.7 Hz), 7.96 (2H, d, J = 9.0 Hz). |
| 963 | 730 (M + NH4). | 1H-NMR (DMSO-d$_6$, 400 MHz) δ: 3.30-3.40 (2H, m), 3.61 (1H, dd, J = 13.8, 4.5 Hz), 3.72-3.83 (2H, m), 3.90 (1H, m), 4.06 (1H, dd, J = 15.5, 5.6 Hz), 4.19 (1H, dd, J = 15.5, 6.4 Hz), 4.47 (1H, m), 4.63 (1H, m), 7.22 (2H, d, J = 8.6 Hz), 7.27 (2H, d, J = 8.6 Hz), 7.52 (2H, d, J = 8.8 Hz), 7.92 (2H, d, J = 8.8 Hz), 8.81 (1H, t, J = 5.8 Hz). |
| 964 | 688 (M + H). | 1H-NMR (CDCl$_3$, 400 MHz) δ: 3.08-3.39 (3H, m), 3.50 (1H, m), 3.98 (1H, m), 4.33 (1H, m), 4.50 (1H, dd, J = 14.7, 6.4 Hz), 4.60 (1H, m), 4.68 (1H, m), 6.97 (1H, br s), 7.14 (2H, d, J = 8.6 Hz), 7.22 (2H, d, J = 8.6 Hz), 7.39 (2H, d, J = 8.6 Hz), 7.95 (2H, d, J = 8.6 Hz), 8.81 (1H, s). |

TABLE 430

| Example No. | MS ESI m/e: | NMR |
|---|---|---|
| 965 | 643 (M + H). | 1H-NMR (CDCl$_3$, 300 MHz) δ: 3.17-3.51 (3H, m), 3.78 (3H, s), 3.93 (1H, d, J = 13.9 Hz), 4.20-4.71 (5H, m), 6.73-6.80 (3H, m), 7.05 (2H, d, J = 8.7 Hz), 7.35 (2H, d, J = 8.7 Hz), 7.92 (2H, d, J = 8.7 Hz), 8.59 (1H, s). |
| 966 | 661 (M + H). | 1H-NMR (CDCl$_3$, 300 MHz) δ: 3.16-3.55 (3H, m), 3.93 (1H, d, J = 13.6 Hz), 4.22-4.46 (3H, m), 4.55-4.69 (2H, m), 5.69 (2H, d, J = 54.6 Hz), 6.87-6.97 (3H, m), 7.12 (2H, d, J = 8.7 Hz), 7.36 (2H, d, J = 8.7 Hz), 7.93 (2H, d, J = 8.7 Hz), 8.59 (1H, s). |
| 967 | 627 (M + H). | 1H-NMR (CDCl$_3$, 300 MHz) δ: 3.16-3.35 (2H, m), 3.44-3.55 (1H, m), 3.91 (1H, d, J = 13.9 Hz), 4.25-4.44 (3H, m), 4.59-4.73 (2H, m), 5.67 (2H, d, J = 54.6 Hz), 6.91-7.12 (5H, m), 7.36 (2H, d, J = 8.7 Hz), 7.93 (2H, d, J = 9.0 Hz), 8.78 (1H, s), 8.94 (1H, s). |
| 968 | 663 (M + H). | 1H-NMR (CDCl$_3$, 300 MHz) δ: 3.17-3.39 (2H, m), 3.46-3.61 (1H, m), 3.97 (1H, d, J = 13.6 Hz), 4.22-4.49 (3H, m), 4.57-4.78 (2H, m), 6.49 (1H, t, J = 73.7 Hz), 6.95-7.06 (3H, m), 7.16 (2H, d, J = 8.3 Hz), 7.81 (2H, d, J = 8.3 Hz), 8.01 (2H, d, J = 8.3 Hz), 8.60 (1H, s). |
| 969 | 629 (M + H). | 1H-NMR (CDCl$_3$, 300 MHz) δ: 3.16-3.36 (2H, m), 3.47-3.59 (1H, m), 3.95 (1H, d, J = 13.9 Hz), 4.25-4.36 (2H, m), 4.44 (1H, dd, J = 15.1, 6.0 Hz), 4.63-4.75 (2H, m), 6.47 (1H, t, J = 73.7 Hz), 6.98 (2H, d, J = 8.3 Hz), 7.03-7.11 (1H, m), 7.15 (2H, d, J = 8.7 Hz), 7.81 (2H, d, J = 8.7 Hz), 8.01 (2H, d, J = 8.3 Hz), 8.79 (1H, s), 8.94 (1H, s). |
| 970 | 643 (M + H). | 1H-NMR (CDCl$_3$, 300 MHz) δ: 2.72 (3H, s), 3.15-3.37 (2H, m), 3.43-3.55 (1H, m), 3.90-4.00 (1H, m), 4.20-4.36 (2H, m), 4.45 (1H, dd, J = 14.9, 6.2 Hz), 4.61-4.73 (2H, m), 6.47 (1H, t, J = 73.7 Hz), 6.93-7.01 (3H, m), 7.15 (2H, d, J = 8.7 Hz), 7.81 (2H, d, J = 8.3 Hz), 8.01 (2H, d, J = 8.3 Hz), 8.68 (1H, s). |
| 971 | 653 (M + H). | 1H-NMR (CDCl$_3$, 300 MHz) δ: 0.62-0.69 (2H, m), 0.93-1.00 (2H, m), 1.80-1.89 (1H, m), 3.14-3.52 (3H, m), 3.88-3.98 (1H, m), 4.22-4.44 (3H, m), 4.52-4.70 (2H, m), 6.75 (1H, t, J = 5.7 Hz), 6.95 (2H, d, J = 8.3 Hz), 7.02 (2H, d, J = 8.3 Hz), 7.34 (2H, d, J = 8.7 Hz), 7.91 (2H, d, J = 9.0 Hz), 8.59 (1H, s). |

TABLE 431

| Example No. | MS ESI m/e: | NMR |
|---|---|---|
| 972 | 681 (M + H). | 1H-NMR (CDCl$_3$, 400 MHz) δ: 3.26 (2H, d, J = 31.1 Hz), 3.49 (1H, t, J = 11.9 Hz), 3.96 (1H, d, J = 14.1 Hz), 4.25-4.71 (5H, m), 6.96 (1H, t, J = 5.8 Hz), 7.13 (2H, d, J = 8.1 Hz), 7.21 (2H, dt, J = 9.1, 2.4 Hz), 7.37 (2H, d, J = 8.3 Hz), 7.94 (2H, dt, J = 9.5, 2.4 Hz), 8.57 (1H, d, J = 1.4 Hz). |
| 973 | 720 (M + H). | 1H-NMR (CDCl$_3$, 400 MHz) δ: 1.22 (3H, d, J = 1.8 Hz), 1.24 (3H, d, J = 1.8 Hz), 3.16-3.33 (2H, m), 3.49 (1H, t, J = 12.1 Hz), 3.88 (1H, d, J = 14.1 Hz), 4.08-4.49 (4H, m), 4.55-4.76 (2H, m), 4.98 (1H, br s), 7.09 (2H, d, J = 7.9 Hz), 7.18 (2H, d, J = 8.2 Hz), 7.34 (2H, d, J = 8.6 Hz), 7.92 (2H, d, J = 8.8 Hz), 8.31 (1H, s). |
| 974 | 796 (M + H). 798 (M + H). | 1H-NMR (CDCl$_3$, 400 MHz) δ: 1.25 (6H, t, J = 7.1 Hz), 3.22-3.37 (2H, m), 3.52-3.75 (5H, m), 3.91 (1H, d, J = 13.7 Hz), 3.94 (1H, br s), 4.20 (1H, br s), 4.35 (1H, br s), 4.71 (1H, s), 4.96 (1H, br s), 6.98 (1H, br s), 7.09 (2H, br s), 7.74 (2H, d, J = 8.2 Hz), 7.98 (2H, d, J = 8.2 Hz). |
| 975 | 703 (M + H). | 1H-NMR (CDCl$_3$, 300 MHz) δ: 1.01-1.09 (2H, m), 1.16-1.21 (2H, m), 2.21-2.30 (1H, m), 3.12-3.36 (2H, m), 3.42-3.51 (1H, m), 3.91 (1H, d, J = 13.6 Hz), 4.24-4.52 (3H, m), |

TABLE 431-continued

| Example No. | MS ESI m/e: | NMR |
|---|---|---|
| | | 4.55-4.67 (2H, m), 6.90-6.98 (1H, m), 7.09 (2H, d, J = 9.0 Hz), 7.19 (2H, d, J = 8.7 Hz), 7.36 (2H, d, J = 8.7 Hz), 7.93 (2H, d, J = 8.7 Hz), 8.61 (1H, s). |
| 976 | 619 (M + H). | 1H-NMR (CDCl$_3$, 300 MHz) δ: 0.62-0.67 (2H, m), 0.92-0.99 (2H, m), 1.79-1.88 (1H, m), 3.14-3.26 (1H, m), 3.27-3.36 (1H, m), 3.39-3.51 (1H, m), 3.88-3.97 (1H, m), 4.26-4.45 (3H, m), 4.57-4.70 (2H, m), 6.78 (1H, t, J = 5.5 Hz), 6.93 (2H, d, J = 8.3 Hz), 7.02 (2H, d, J = 7.9 Hz), 7.34 (2H, d, J = 8.3 Hz), 7.91 (2H, d, J = 9.0 Hz), 8.78 (1H, s), 8.95 (1H, s). |

TABLE 432

| Example No. | MS ESI m/e: | NMR |
|---|---|---|
| 977 | 679 (M + H). | 1H-NMR (CDCl$_3$, 300 MHz) δ: 2.92-3.03 (1H, m), 3.07 (1H, dd, J = 13.2, 4.1 Hz), 3.49 (1H, ddd, J = 15.0, 11.2, 3.5 Hz), 3.79 (1H, dt, J = 13.1, 2.5 Hz), 3.94 (1H, dt, J = 14.2, 3.2 Hz), 4.28 (1H, dt, J = 13.4, 1.5 Hz), 4.38 (1H, dd, J = 15.4, 6.4 Hz), 4.48 (1H, dd, J = 14.5, 5.5 Hz), 4.61 (1H, d, J = 3.8 Hz), 6.24 (1H, d, J = 7.5 Hz), 7.17 (2H, d, J = 8.3 Hz), 7.19 (1H, t, J = 4.0 Hz), 7.26 (2H, d, J = 8.7 Hz), 7.36 (2H, d, J = 8.3 Hz), 7.74 (1H, d, J = 7.5 Hz), 7.90 (2H, d, J = 9.0 Hz). |
| 978 | 667 (M + H). | 1H-NMR (CDCl$_3$, 400 MHz) δ: 2.40 (3H, s), 2.48 (3H, s), 3.04 (1H, m), 3.12 (1H, dd, J = 13.3, 4.5 Hz), 3.45 (1H, m), 3.84-3.95 (2H, m), 4.41 (1H, dd, J = 15.0, 5.9 Hz), 4.46-4.54 (2H, m), 4.61(1H, m), 6.97 (1H, m), 7.17 (2H, d, J = 8.3 Hz), 7.25 (2H, d, J = 8.3 Hz), 7.37 (2H, d, J = 8.8 Hz), 7.93 (2H, d, J = 8.8 Hz). |
| 979 | 706 (M + H). | 1H-NMR (CD$_3$OD, 400 MHz) δ: 3.35 (1H, br s), 3.49 (1H, br s), 3.69 (1H, dd, J = 13.9, 4.4 Hz), 3.92-3.95 (2H, m), 4.23-4.27 (3H, m), 4.74 (1H, m), 7.09-7.11 (2H, m), 7.29 (2H, d, J = 8.8 Hz), 7.43 (2H, d, J = 7.9 Hz), 7.98 (2H, d, J = 8.8 Hz), 8.95 (1H, s). |
| 980 | 679 (M + H). | 1H-NMR (CDCl$_3$, 400 MHz) δ: 2.30 (3H, s), 2.96-3.05 (1H, m), 3.08 (1H, dd, J = 13.3, 4.5 Hz), 3.42-3.51 (1H, m), 3.82 (3H, s), 3.85-3.94 (2H, m), 4.40-4.54 (3H, m), 4.61 (1H, br s), 6.97 (1H, t, J = 6.1 Hz), 7.13 (2H, d, J = 7.9 Hz), 7.23 (2H, d, J = 8.8 Hz), 7.36 (2H, d, J = 7.9 Hz), 7.94 (2H, d, J = 8.8 Hz). |
| 981 | 715 (M + H) | 1H-NMR (CDCl$_3$, 400 MHz) δ: 3.15-3.58 (3H, m), 4.00 (1H, d, J = 13.9 Hz), 4.33-4.52 (3H, m), 4.65 (1H, br s), 4.71 (1H, s), 6.91 (1H, t, J = 10.0 Hz), 7.12 (2H, d, J = 8.1 Hz), 7.21 (2H, d, J = 8.6 Hz), 7.84 (2H, d, J = 8.3 Hz), 8.03 (2H, d, J = 8.1 Hz), 8.88 (1H, s). |
| 982 | 692 (M + H). | 1H-NMR (CD$_3$OD, 300 MHz) δ: 2.42 (3H, s), 3.34-3.47 (1H, m), 3.50-3.64 (1H, m), 3.81-4.06 (3H, m), 4.26 (2H, dd, J = 24.7, 14.9 Hz), 4.55-4.71 (2H, m), 7.06 (2H, d, J = 7.5 Hz), 7.25 (2H, d, J = 8.7 Hz), 7.41 (2H, d, J = 8.7 Hz), 7.90-8.02 (2H, m). |

TABLE 433

| Example No. | MS ESI m/e: | NMR |
|---|---|---|
| 983 | 687 (M + H). | 1H-NMR (CDCl$_3$, 300 MHz) δ: 1.03-1.08 (2H, m), 1.17-1.21 (2H, m), 2.22-2.29 (1H, m), 3.21 (1H, t, J = 10.9 Hz), 3.32 (1H, d, J = 11.6 Hz), 3.46-3.53 (1H, m), 3.90-3.98 (1H, m), 4.22-4.52 (3H, m), 4.59-4.73 (2H, m), 7.00 (1H, t, J = 5.9 Hz), 7.09 (2H, d, J = 8.1 Hz), |

TABLE 433-continued

| Example No. | MS ESI m/e: | NMR |
|---|---|---|
| 984 | 705 (M + H). | 7.19 (2H, d, J = 8.1 Hz), 7.81 (2H, d, J = 8.3 Hz), 8.01 (2H, d, J = 8.3 Hz), 8.62 (1H, s). 1H-NMR (CDCl₃, 300 MHz) δ: 1.37 (6H, d, J = 6.7 Hz), 3.16-3.36 (3H, m), 3.43-3.53 (1H, m), 3.88-3.97 (1H, m), 4.27-4.53 (3H, m), 4.57-4.69 (2H, m), 6.98 (1H, t, J = 6.0 Hz), 7.09 (2H, d, J = 8.1 Hz), 7.20 (2H, d, J = 8.6 Hz), 7.37 (2H, d, J = 8.1 Hz), 7.94 (2H, d, J = 9.3 Hz), 8.73 (1H, s). |
| 985 | 697 (M + H). | 1H-NMR (CDCl₃, 300 MHz) δ: 3.17 (1H, ddd, J = 14.2, 10.3, 2.7 Hz), 3.27 (1H, dd, J = 13.0, 4.3 Hz), 3.48 (1H, ddd, J = 14.6, 10.8, 2.9 Hz), 3.98 (1H, dt, J = 14.6, 2.8 Hz), 4.29-4.44 (1H, m), 4.35 (1H, dd, J = 15.1, 5.7 Hz), 4.50 (1H, dd, J = 15.1, 6.4 Hz), 4.57 (1H, d, J = 13.2 Hz), 4.66 (1H, d, J = 3.0 Hz), 6.96 (1H, t, J = 6.0 Hz), 7.14 (2H, d, J = 7.9 Hz), 7.23 (2H, d, J = 8.7 Hz), 7.38 (2H, d, J = 8.7 Hz), 7.94 (2H, d, J = 9.0 Hz), 9.22 (1H, s). |
| 986 | 694 (M + H). | 1H-NMR (CDCl₃, 300 MHz) δ: 2.55 (3H, s), 3.05 (1H, ddd, J = 14.2, 10.6, 2.7 Hz), 3.17 (1H, dd, J = 13.0, 4.3 Hz), 3.44 (1H, ddd, J = 14.8, 11.2, 2.7 Hz), 3.93 (1H, dt, J = 14.2, 3.2 Hz), 4.15 (1H, dt, J = 13.4, 2.7 Hz), 4.25 (1H, d, J = 13.2 Hz), 4.39 (1H, dd, J = 15.1, 5.7 Hz), 4.49 (1H, dd, J = 14.9, 6.2 Hz), 4.59 (1H, dd, J = 2.1, 1.3 Hz), 6.91 (1H, t, J = 5.8 Hz), 7.17 (2H, d, J = 7.9 Hz), 7.25 (2H, d, J = 8.7 Hz), 7.39 (2H, d, J = 8.3 Hz), 7.92 (2H, d, J = 9.0 Hz). |
| 987 | 664 (M + H). | 1H-NMR (CDCl₃, 400 MHz) δ: 3.14-3.58 (3H, m), 4.00 (1H, d, J = 13.7 Hz), 4.26-4.74 (5H, m), 6.98 (1H, t, J = 5.9 Hz), 7.13 (2H, d, J = 8.3 Hz), 7.21 (2H, d, J = 8.6 Hz), 7.39 (2H, d, J = 8.6 Hz), 7.95 (2H, dt, J = 9.4, 2.4 Hz), 9.15 (1H, s). |

TABLE 434

| Example No. | MS ESI m/e: | NMR |
|---|---|---|
| 988 | 774, 776 (M + H). | 1H-NMR (CDCl₃, 300 MHz) δ: 2.47 (1H, ddd, J = 14.9, 10.7, 2.1 Hz), 2.90 (1H, dd, J = 13.9, 4.1 Hz), 3.19 (1H, ddd, J = 15.9, 12.2, 3.5 Hz), 3.53 (1H, d, J = 17.7 Hz), 3.92 (1H, dt, J = 13.8, 2.7 Hz), 4.07 (1H, d, J = 17.3 Hz), 4.34-4.62 (5H, m), 7.02 (1H, t, J = 5.7 Hz), 7.19 (2H, d, J = 8.3 Hz), 7.27 (2H, d, J = 8.7 Hz), 7.40 (2H, d, J = 8.3 Hz), 7.93 (2H, d, J = 9.0 Hz), 11.87 (1H, br s). |
| 989 | 618 (M + H). | 1H-NMR (CDCl₃, 300 MHz) δ: 3.15-3.26 (1H, m), 3.32 (1H, dd, J = 13.8, 4.3 Hz), 3.47 (1H, ddd, J = 14.6, 10.8, 2.9 Hz), 3.92 (1H, dt, J = 13.9, 2.7 Hz), 4.35-4.50 (1H, m), 4.42 (1H, dd, J = 15.3, 5.8 Hz), 4.49 (1H, dd, J = 15.3, 6.6 Hz), 4.59-4.69 (2H, m), 6.17 (1H, s), 6.43 (1H, t, J = 6.4 Hz), 6.63 (1H, dd, J = 8.7, 6.8 Hz), 6.77 (1H, t, J = 5.5 Hz), 7.13 (1H, s), 7.21 (1H, d, J = 9.0 Hz), 7.33 (2H, d, J = 8.7 Hz), 7.77 (1H, d, J = 7.2 Hz), 7.93 (2H, d, J = 9.0 Hz), 8.75 (1H, s), 8.93 (1H, s). |
| 990 | 736 (M + H). | 1H-NMR (CDCl₃, 300 MHz) δ: 3.00 (3H, d, J = 4.9 Hz), 3.07-3.16 (2H, m), 3.49 (1H, ddd, J = 14.5, 11.1, 3.2 Hz), 3.66 (1H, d, J = 13.2 Hz), 3.98 (1H, d, J = 14.3 Hz), 4.31-4.53 (3H, m), 4.65 (1H, d, J = 2.6 Hz), 6.78 (1H, s), 7.15 (2H, d, J = 8.3 Hz), 7.24 (2H, d, J = 7.5 Hz), 7.30 (1H, t, J = 5.8 Hz), 7.37 (2H, d, J = 8.3 Hz), 7.92 (2H, d, J = 8.7 Hz), 8.33 (1H, d, J = 4.5 Hz). |
| 991 | 689 (M + H). | 1H-NMR (CDCl₃, 300 MHz) δ: 1.37 (6H, d, J = 7.2 Hz), 3.12-3.39 (3H, m), 3.42-3.54 (1H, m), 3.95 (1H, d, J = 14.3 Hz), 4.28-4.54 (3H, m), 4.59-4.71 (2H, m), 6.88-6.96 (1H, br m), 7.09 (2H, d, J = 7.9 Hz), 7.19 (2H, d, J = 8.7 Hz), 7.81 (2H, d, J = 8.3 Hz), 8.02 (2H, d, J = 7.9 Hz), 8.72 (1H, s). |
| 992 | 717 (M + H). | 1H-NMR (CDCl₃, 300 MHz) δ: 0.26-0.31 (2H, m), 0.48-0.54 (2H, m), 1.26-1.35 (1H, m), |

TABLE 434-continued

| Example No. | MS ESI m/e: | NMR |
|---|---|---|
| | | 2.85 (2H, d, J = 7.2 Hz), 3.16-3.35 (2H, m), 3.43-3.52 (1H, m), 3.93 (1H, d, J = 14.3 Hz), 4.28-4.38 (2H, m), 4.48 (1H, dd, J = 14.9, 6.2 Hz), 4.59-4.67 (2H, m), 6.97 (1H, t, J = 5.8 Hz), 7.09 (2H, d, J = 8.3 Hz), 7.20 (2H, d, J = 8.7 Hz), 7.36 (2H, d, J = 7.9 Hz), 7.94 (2H, d, J = 8.7 Hz), 8.73 (1H, s). |

TABLE 435

| Example No. | MS ESI m/e: | NMR |
|---|---|---|
| 993 | 768 (M + H). | 1H-NMR (CDCl₃, 400 MHz) δ: 1.27 (6H, t, J = 8.5 Hz), 3.08-3.22 (2H, m), 3.41-3.48 (1H, m), 3.57-3.59 (4H, br m), 3.78-3.87 (1H, m), 4.25 (1H, d, J = 13.5 Hz), 4.38-4.49 (2H, m), 4.61 (1H, t, J = 2.9 Hz), 4.87 (1H, d, J = 13.7 Hz), 7.11 (2H, d, J = 6.1 Hz), 7.15 (2H, d, J = 7.9 Hz), 7.22 (2H, d, J = 4.4 Hz), 7.34 (2H, d, J = 4.4 Hz), 7.92 (2H, d, J = 9.4 Hz). |
| 994 | 745 (M + H). | 1H-NMR (CD₃OD, 400 MHz) δ: 1.59 (6H, s), 3.55 (1H, m), 3.68 (1H, dt, J = 14.8, 4.6 Hz), 3.83-3.99 (2H, m), 4.09-4.20 (2H, m), 4.29 (1H, d, J = 14.8 Hz), 4.70 (1H, m), 4.90 (1H, m), 7.11 (2H, d, J = 8.3 Hz), 7.29 (2H, d, J = 8.3 Hz), 7.43 (2H, d, J = 8.8 Hz), 7.97 (2H, d, J = 8.8 Hz), 8.77 (1H, s). |
| 995 | 687 (M + H). | 1H-NMR (CD₃OD, 400 MHz) δ: 3.38 (1H, m), 3.55 (1H, m), 3.68 (1H, dd, J = 15.1, 4.3 Hz), 3.74 (1H, s), 3.83-3.99 (2H, m), 4.16 (1H, m), 4.29 (1H, d, J = 15.1 Hz), 4.71 (1H, m), 4.90 (1H, m), 7.12 (2H, d, J = 8.5 Hz), 7.29 (2H, d, J = 8.5 Hz), 7.43 (2H, d, J = 8.3 Hz), 7.97 (2H, d, J = 8.3 Hz), 8.79 (1H, s). |
| 996 | 705 (M + H). | 1H-NMR (CDCl₃, 400 MHz) δ: 3.23 (1H, t, J = 12.0 Hz), 3.32 (1H, dd, J = 14.4, 3.0 Hz), 3.51 (1H, ddd, J = 14.3, 10.8, 2.9 Hz), 3.95 (1H, dt, J = 14.3, 2.7 Hz), 4.29-4.38 (1H, m), 4.37 (1H, dd, J = 15.1, 5.2 Hz), 4.55 (1H, dd, J = 15.3, 6.3 Hz), 4.60-4.70 (2H, m), 7.13 (1H, t, J = 5.6 Hz), 7.27 (2H, d, J = 6.6 Hz), 7.38 (2H, d, J = 8.4 Hz), 7.64 (2H, d, J = 8.8 Hz), 7.95 (2H, d, J = 9.0 Hz), 8.79 (1H, s), 8.96 (1H, s). |
| 997 | 697 (M + H). | 1H-NMR (CDCl₃, 400 MHz) δ: 3.14-3.53 (3H, m), 3.94 (1H, d, J = 14.8 Hz), 4.28-4.72 (3H, br m), 4.36 (1H, dd, J = 14.4, 4.7 Hz), 4.46 (1H, dd, J = 15.0, 6.2 Hz), 4.64 (1H, d, J = 2.6 Hz), 6.50 (1H, t, J = 73.0 Hz), 6.82 (2H, d, J = 8.4 Hz), 6.88 (1H, br s), 7.21 (1H, t, J = 8.4 Hz), 7.38 (2H, d, J = 8.2 Hz), 7.93 (2H, dt, J = 9.4, 2.4 Hz), 8.59 (1H, s). |

TABLE 436

| Example No. | MS ESI m/e: | NMR |
|---|---|---|
| 998 | 663 (M + H). | 1H-NMR (CDCl₃, 300 MHz) δ: 3.15-3.55 (3H, m), 3.93 (1H, d, J = 15.1 Hz), 4.27-4.70 (5H, m), 6.48 (1H, t, J = 73.1 Hz), 6.77-6.81 (2H, m), 6.96 (1H, br s), 7.20 (1H, t, J = 8.7 Hz), 7.37 (2H, d, J = 9.0 Hz), 7.94 (2H, d, J = 8.7 Hz), 8.78 (1H, s), 8.94 (1H, s). |
| 999 | 713 (M + H). | 1H-NMR (CDCl₃, 300 MHz) δ: 3.10-3.55 (3H, m), 3.97 (1H, d, J = 14.3 Hz), 4.23-4.75 (3H, m), 4.33 (1H, dd, J = 15.6, 5.5 Hz), 4.49 (1H, dd, J = 15.1, 6.4 Hz), 6.61 (1H, t, J = 72.0 Hz), 6.94 (1H, br s), 7.13 (2H, d, J = 8.3 Hz), 7.21 (2H, d, J = 9.0 Hz), 7.28 (2H, d, J = 9.0 Hz), 7.90 (2H, d, J = 9.0 Hz), 8.87 (1H, s). |
| 1000 | 713 (M + H). | 1H-NMR (CDCl₃, 400 MHz) δ: 3.15-3.55 (3H, m), 3.97 (1H, d, J = 14.4 Hz), 4.26-4.36 (1H, m), 4.47 (1H, dd, J = 15.0, 6.4 Hz), 4.61 (2H, br s), 4.68 |

TABLE 436-continued

| Example No. | MS ESI m/e: | NMR |
|---|---|---|
| | | (1H, br s), 6.48 (1H, t, J = 73.6 Hz), 6.88 (1H, br s), 7.02 (2H, d, J = 8.3 Hz), 7.17 (2H, d, J = 8.6 Hz), 7.39 (2H, d, J = 8.6 Hz), 7.94 (2H, d, J = 8.3 Hz), 8.88 (1H, s). |
| 1001 | 697 (M + H). | 1H-NMR (CDCl₃, 300 MHz) δ: 3.09-3.42 (2H, m), 3.49 (1H, t, J = 11.5 Hz), 3.99 (1H, dt, J = 14.4, 3.4 Hz), 4.18-4.53 (1H, m), 4.28 (1H, dd, J = 14.9, 4.7 Hz), 4.47 (1H, dd, J = 14.3, 6.4 Hz), 4.54-4.76 (1H, m), 4.70 (1H, d, J = 2.6 Hz), 6.48 (1H, t, J = 73.8 Hz), 6.84 (1H, t, J = 6.0 Hz), 7.01 (2H, d, J = 8.7 Hz), 7.16 (2H, d, J = 8.7 Hz), 7.83 (2H, d, J = 8.7 Hz), 8.02 (2H, d, J = 8.3 Hz), 8.87 (1H, s). |
| 1002 | 723 (M + H). | 1H-NMR (CD₃OD, 400 MHz) δ: 3.42-4.32 (12H, m), 4.71 (1H, dd, J = 4.4, 2.1 Hz), 7.09 (2H, d, J = 8.1 Hz), 7.28 (2H, dt, J = 9.3, 2.4 Hz), 7.43 (2H, d, J = 8.1 Hz), 7.98 (2H, dt, J = 9.3, 2.3 Hz). |
| 1003 | 747 (M + H). | 1H-NMR (CD₃OD, 400 MHz) δ: 3.42-3.48 (1H, m), 3.61 (1H, dd, J = 14.0, 3.0 Hz), 3.89-3.90 (2H, m), 4.01 (1H, d, J = 10.0 Hz), 4.17-4.31 (2H, m), 4.67-4.68 (2H, m), 7.10 (2H, d, J = 7.7 Hz), 7.29 (2H, d, J = 6.6 Hz), 7.42 (2H, d, J = 8.2 Hz), 7.96 (2H, d, J = 8.8 Hz). |

TABLE 437

| Example No. | MS ESI m/e: | NMR |
|---|---|---|
| 1004 | 763 (M + H). | 1H-NMR (CDCl₃, 400 MHz) δ: 3.30-3.42 (3H, m), 3.98 (1H, d, J = 14.3 Hz), 4.31-4.51 (3H, m), 4.67 (1H, br s), 4.67 (1H, s), 5.94 (1H, t, J = 52.8 Hz), 6.92 (1H, t, J = 10.0 Hz), 7.12 (2H, d, J = 8.2 Hz), 7.20 (2H, d, J = 8.6 Hz), 7.39 (2H, d, J = 8.6 Hz), 7.92 (2H, d, J = 6.8 Hz), 8.87 (1H, s). |
| 1005 | 695 (M + H). | 1H-NMR (CDCl₃, 300 MHz) δ: 3.13-3.53 (3H, m), 3.92-4.01 (1H, m), 4.31 (1H, dd, J = 14.9, 5.1 Hz), 4.46 (1H, dd, J = 14.9, 6.2 Hz), 4.51-4.64 (2H, m), 4.66 (1H, d, J = 1.9 Hz), 6.48 (1H, t, J = 73.7 Hz), 6.61 (1H, t, J = 72.0 Hz), 6.87-6.95 (1H, m), 7.02 (2H, d, J = 8.7 Hz), 7.17 (2H, d, J = 8.7 Hz), 7.28 (2H, d, J = 9.0 Hz), 7.89 (2H, d, J = 9.0 Hz), 8.87 (1H, s). |
| 1006 | 648 (M + H). | 1H-NMR (CDCl₃, 400 MHz) δ: 3.11-3.64 (3H, m), 3.96-4.80 (6H, m), 7.02-7.24 (5H, m), 7.83 (2H, d, J = 8.3 Hz), 8.03 (2H, d, J = 8.3 Hz), 9.15 (1H, s). |
| 1007 | 735 (M + H). | 1H-NMR (CD₃OD, 300 MHz) δ: 1.43 (3H, t, J = 7.0 Hz), 3.46-3.75 (2H, m), 3.85-3.98 (2H, m), 3.99-4.33 (3H, m), 4.42-4.52 (3H, m), 4.71 (1H, br s), 7.11 (2H, d, J = 7.5 Hz), 7.28 (2H, d, J = 8.7 Hz), 7.43 (2H, d, J = 8.7 Hz), 7.97 (2H, d, J = 8.3 Hz), 8.95 (1H, s). |
| 1008 | 693 (M + H). | 1H-NMR (CD₃OD, 300 MHz) δ: 3.45-3.57 (1H, m), 3.62-3.75 (1H, m), 3.84-3.99 (2H, m), 4.12-4.35 (3H, m), 4.72 (4H, m), 7.10 (2H, d, J = 8.3 Hz), 7.28 (2H, d, J = 8.7 Hz), 7.41 (2H, d, J = 8.3 Hz), 7.96 (2H, d, J = 8.7 Hz), 8.81 (1H, s). |
| 1009 | 693 (M + H). | 1H-NMR (CDCl₃, 300 MHz) δ: 3.13 (1H, ddd, J = 14.1, 10.5, 3.0 Hz), 3.24 (1H, dd, J = 13.2, 4.1 Hz), 3.47 (1H, ddd, J = 14.8, 10.8, 3.1 Hz), 3.93 (1H, dt, J = 13.8, 3.3 Hz), 4.26 (3H, s), 4.32 (1H, d, J = 12.8 Hz), 4.38 (1H, dd, J = 15.3, 6.2 Hz), 4.47 (1H, dd, J = 15.4, 6.8 Hz), 4.54 (1H, d, J = 13.6 Hz), 4.63 (1H, d, J = 2.6 Hz), 6.96 (1H, t, J = 5.3 Hz), 7.13 (2H, d, J = 8.3 Hz), 7.21 (2H, d, J = 8.7 Hz), 7.37 (2H, d, J = 8.7 Hz), 7.93 (2H, d, J = 9.0 Hz), 9.02 (1H, s). |

TABLE 438

| Example No. | MS ESI m/e: | NMR |
|---|---|---|
| 1010 | 672 (M + H). | 1H-NMR (CDCl₃, 300 MHz) δ: 3.13-3.59 (3H, m), 4.01 (1H, d, J = 14.3 Hz), 4.27-4.71 (5H, m), 6.88-6.96 (1H, m), 7.13 (2H, d, J = 7.9 Hz), 7.21 (2H, d, J = 8.7 Hz), 7.83 (2H, d, J = 8.7 Hz), 8.02 (2H, d, J = 8.3 Hz), 8.80 (1H, s). |
| 1011 | 654 (M + H). | 1H-NMR (CDCl₃, 300 MHz) δ: 3.14-3.57 (3H, m), 4.00 (1H, d, J = 13.9 Hz), 4.24-4.72 (5H, m), 6.49 (1H, t, J = 73.7 Hz), 6.88 (1H, t, J = 5.7 Hz), 7.02 (2H, d, J = 8.3 Hz), 7.17 (2H, d, J = 8.7 Hz), 7.83 (2H, d, J = 8.3 Hz), 8.02 (2H, d, J = 8.3 Hz), 8.80 (1H, s). |
| 1012 | 701 (M + H). | 1H-NMR (CDCl₃, 300 MHz) δ: 0.26-0.31 (2H, m), 0.48-0.54 (2H, m), 1.26-1.34 (1H, m), 2.85 (2H, d, J = 7.2 Hz), 3.16-3.37 (2H, m), 3.44-3.54 (1H, m), 3.95 (1H, d, J = 13.9 Hz), 4.24-4.36 (2H, m), 4.48 (1H, dd, J = 14.9, 6.2 Hz), 4.61-4.71 (2H, m), 6.97 (1H, t, J = 5.8 Hz), 7.08 (2H, d, J = 7.9 Hz), 7.19 (2H, d, J = 8.7 Hz), 7.81 (2H, d, J = 8.3 Hz), 8.01 (2H, d, J = 8.3 Hz), 8.73 (1H, s). |
| 1013 | 690 (M + H). | 1H-NMR (CD₃OD, 400 MHz) δ: 3.48 (1H, br s), 3.69 (1H, d, J = 9.5 Hz), 3.89-3.96 (3H, m), 4.22-4.26 (3H, m), 4.75 (1H, s), 7.09 (2H, d, J = 8.4 Hz), 7.28 (2H, d, J = 8.6 Hz), 7.83 (2H, d, J = 8.4 Hz), 8.04 (2H, d, J = 8.4 Hz), 8.94 (1H, s). |
| 1014 | 667 (M + H). | 1H-NMR (CDCl₃, 400 MHz) δ: 1.00-1.22 (4H, m), 2.20-2.30 (1H, m), 3.13-3.50 (3H, m), 3.90 (1H, d, J = 14.1 Hz), 4.20-4.66 (5H, m), 6.26-6.79 (2H, m), 6.89-7.03 (3H, m), 7.16 (2H, d, J = 8.1 Hz), 7.25 (2H, d, J = 8.3 Hz), 7.88 (2H, d, J = 8.3 Hz), 8.61 (1H, s). |
| 1015 | 745 (M + H). | 1H-NMR (CDCl₃, 300 MHz) δ: 3.12-3.59 (3H, br m), 3.97 (1H, d, J = 14.3 Hz), 4.22-4.73 (5H, m), 5.95 (1H, tt, J = 52.9, 2.7 Hz), 6.48 (1H, t, J = 73.7 Hz), 6.86 (1H, br s), 7.02 (2H, d, J = 8.7 Hz), 7.17 (2H, d, J = 8.7 Hz), 7.39 (2H, d, J = 8.9 Hz), 7.92 (2H, d, J = 8.9 Hz), 8.87 (1H, s). |

TABLE 439

| Example No. | MS ESI m/e: | NMR |
|---|---|---|
| 1016 | 685 (M + H). | 1H-NMR (CDCl₃, 400 MHz) δ: 1.01-1.08 (2H, m), 1.16-1.21 (2H, m), 2.21-2.30 (1H, m), 3.18 (1H, t, J = 10.0 Hz), 3.28 (1H, d, J = 10.0 Hz), 3.45 (1H, t, J = 11.1 Hz), 3.91 (1H, d, J = 14.1 Hz), 4.23-4.41 (1H, m), 4.36 (1H, dd, J = 14.9, 5.4 Hz), 4.47 (1H, dd, J = 15.1, 6.3 Hz), 4.55 (1H, d, J = 12.8 Hz), 4.63 (1H, s), 6.60 (1H, t, J = 72.1 Hz), 6.96 (1H, t, J = 5.3 Hz), 7.10 (2H, d, J = 8.4 Hz), 7.20 (2H, d, J = 8.4 Hz), 7.26 (2H, d, J = 8.6 Hz), 7.89 (2H, d, J = 8.6 Hz), 8.61 (1H, s). |
| 1017 | 685 (M + H). | 1H-NMR (CDCl₃, 300 MHz) δ: 1.02-1.08 (2H, m), 1.16-1.21 (2H, m), 2.21-2.29 (1H, m), 3.15-3.34 (2H, m), 3.41-3.51 (1H, m), 3.90 (1H, d, J = 13.9 Hz), 4.25-4.36 (2H, m), 4.44 (1H, dd, J = 14.9, 6.2 Hz), 4.56-4.66 (2H, m), 6.47 (1H, t, J = 73.7 Hz), 6.93-7.01 (3H, m), 7.15 (2H, d, J = 8.7 Hz), 7.36 (2H, d, J = 8.3 Hz), 7.93 (2H, d, J = 9.0 Hz), 8.61 (1H, s). |
| 1018 | 717 (M + H). | 1H-NMR (CDCl₃, 400 MHz) δ: 1.05 (2H, dt, J = 11.6, 3.3 Hz), 1.19 (2H, dt, J = 8.0, 3.3 Hz), 2.22-2.29 (1H, m), 3.20 (1H, td, J = 11.9, 2.1 Hz), 3.30 (1H, dd, J = 13.7, 3.5 Hz), 3.44 (1H, ddd, J = 14.3, 11.2, 3.1 Hz), 3.92 (1H, dt, J = 14.4, 3.0 Hz), 4.25-4.39 (1H, m), 4.33 (1H, d, J = 15.0 Hz), 4.44 (1H, d, J = 14.8 Hz), 4.58 (1H, d, J = 13.7 Hz), 4.63 (1H, d, J = 4.4 Hz), 5.94 (1H, tt, J = 52.9, 2.6 Hz), 6.47 (1H, t, J = 73.8 Hz), 6.90 (1H, t, J = 6.5 Hz), 6.99 (2H, d, J = 8.4 Hz), 7.16 (2H, d, J = 8.6 Hz), 7.38 (2H, d, J = 8.6 Hz), 7.91 (2H, dt, J = 9.4, 2.4 Hz), 8.61 (1H, s). |
| 1019 | 693 (M + H). | 1H-NMR (CDCl₃, 300 MHz) δ: 2.36 (3H, s), 3.01 (1H, td, J = 12.2, 3.1 Hz), 3.15 (1H, dd, J = 13.2, 4.1 Hz), 3.57 (1H, ddd, J = 13.8, 10.7, 2.4 Hz), |

TABLE 439-continued

| Example No. | MS ESI m/e: | NMR |
|---|---|---|
| | | 3.90 (2H, tt, J = 16.4, 3.0 Hz), 4.28 (1H, d, J = 13.2 Hz), 4.36 (1H, dd, J = 13.6, 5.3 Hz), 4.43 (1H, dd, J = 14.1, 5.5 Hz), 4.66 (1H, d, J = 1.9 Hz), 6.05 (1H, d, J = 0.8 Hz), 7.15 (2H, d, J = 7.9 Hz), 7.26 (2H, d, J = 8.7 Hz), 7.32 (2H, d, J = 8.3 Hz), 7.57 (1H, t, J = 5.7 Hz), 7.88 (2H, d, J = 8.7 Hz). |

TABLE 440

| Example No. | MS ESI m/e: | NMR |
|---|---|---|
| 1020 | 735 (M + H). | 1H-NMR (CD$_3$OD, 300 MHz) δ: 0.99-1.11 (2H, m), 1.16-1.21 (2H, m), 2.22-2.28 (1H, m), 3.07-3.36 (2H, m), 3.38-3.54 (1H, m), 3.92 (1H, d, J = 13.9 Hz), 4.24-4.68 (5H, m), 5.71-6.16 (1H, m), 6.93 (1H, t, J = 6.2 Hz), 7.10 (2H, d, J = 8.7 Hz), 7.19 (2H, d, J = 8.7 Hz), 7.38 (2H, d, J = 8.7 Hz), 7.91 (2H, d, J = 9.0 Hz), 8.61 (1H, s). |
| 1021 | 746 (M + H). | 1H-NMR (CD$_3$OD, 300 MHz) δ: 3.40-3.66 (2H, m), 3.81-4.09 (3H, m), 4.12-4.36 (2H, m), 4.58-4.76 (2H, m), 7.08 (2H, d, J = 8.3 Hz), 7.27 (2H, d, J = 8.7 Hz), 7.42 (2H, d, J = 8.7 Hz), 7.97 (2H, d, J = 9.0 Hz), 8.81 (1H, t, J = 5.5 Hz). |
| 1022 | 761 (M + H). | 1H-NMR (CDCl$_3$, 300 MHz) δ: 3.18-3.55 (3H, m), 3.93 (1H, d, J = 14.7 Hz), 4.14 (3H, s), 4.19-4.56 (3H, m), 4.57-4.70 (2H, br m), 6.94 (1H, t, J = 6.0 Hz), 7.08 (2H, d, J = 7.9 Hz), 7.19 (2H, d, J = 8.7 Hz), 7.36 (2H, d, J = 8.3 Hz), 7.94 (2H, d, J = 8.7 Hz). |
| 1023 | 669 (M + H). | 1H-NMR (CDCl$_3$, 400 MHz) δ: 1.02-1.09 (2H, m), 1.16-1.22 (2H, m), 2.22-2.30 (1H, m), 3.17-3.52 (3H, m), 3.94 (1H, d, J = 13.7 Hz), 4.23-4.36 (1H, m), 4.32 (1H, dd, J = 15.1, 5.1 Hz), 4.45 (1H, dd, J = 14.7, 6.6 Hz), 4.60-4.70 (2H, m), 6.48 (1H, t, J = 73.7 Hz), 6.88 (1H, br s), 6.99 (2H, d, J = 7.9 Hz), 7.15 (2H, d, J = 7.4 Hz), 7.81 (2H, d, J = 7.9 Hz), 8.02 (2H, d, J = 7.7 Hz), 8.62 (1H, d, J = 1.6 Hz). |
| 1024 | 719 (M + H). | 1H-NMR (CDCl$_3$, 300 MHz) δ: 1.44 (9H, s), 3.12-3.37 (2H, m), 3.40-3.52 (1H, m), 3.92 (1H, d, J = 14.3 Hz), 4.29-4.53 (3H, m), 4.56-4.68 (2H, m), 6.88-6.97 (1H, br m), 7.09 (2H, d, J = 8.3 Hz), 7.20 (2H, d, J = 8.7 Hz), 7.37 (2H, d, J = 8.3 Hz), 7.94 (2H, d, J = 9.0 Hz), 8.74 (1H, s). |
| 1025 | 703 (M + H). | 1H-NMR (CDCl$_3$, 300 MHz) δ: 1.44 (9H, s), 3.13-3.26 (1H, m), 3.27-3.38 (1H, m), 3.41-3.54 (1H, m), 3.95 (1H, d, J = 15.4 Hz), 4.29-4.53 (3H, m), 4.58-4.69 (2H, m), 6.86-6.94 (1H, br m), 7.09 (2H, d, J = 8.7 Hz), 7.19 (2H, d, J = 8.7 Hz), 7.81 (2H, d, J = 8.7 Hz), 8.02 (2H, d, J = 8.7 Hz), 8.74 (1H, d, J = 0.8 Hz). |

TABLE 441

| Example No. | MS ESI m/e: | NMR |
|---|---|---|
| 1026 | 727, 729 (M + H). | 1H-NMR (CDCl$_3$, 400 MHz) δ: 2.59 (3H, s), 3.00-3.09 (1H, m), 3.19 (1H, dd, J = 13.3, 4.1 Hz), 3.57 (1H, ddd, J = 14.0, 11.1, 2.4 Hz), 3.92 (2H, dd, J = 22.3, 14.4 Hz), 4.27 (1H, d, J = 13.4 Hz), 4.37 (1H, dd, J = 14.8, 5.8 Hz), 4.44 (1H, dd, J = 14.8, 5.8 Hz), 4.66 (1H, s), 7.16 (2H, d, J = 8.1 Hz), 7.26 (2H, d, J = 6.3 Hz), 7.34 (2H, d, J = 8.6 Hz), 7.43 (1H, t, J = 5.9 Hz), 7.90 (2H, d, J = 7.9 Hz). |
| 1027 | 675 (M + H). | 1H-NMR (CDCl$_3$, 300 MHz) δ: 2.36 (3H, s), 2.95-3.06 (1H, m), 3.14 (1H, dd, J = 13.4, 4.3 Hz), 3.56 (1H, ddd, J = 13.9, 10.4, 3.0 Hz), 3.90 (2H, tt, J = 15.6, 2.4 Hz), 4.28 (1H, d, J = 13.9 Hz), 4.31-4.45 (2H, m), 4.64 (1H, d, |

TABLE 441-continued

| Example No. | MS ESI m/e: | NMR |
|---|---|---|
| | | J = 2.3 Hz), 6.05 (1H, s), 6.50 (1H, t, J = 73.7 Hz), 7.05 (2H, d, J = 8.7 Hz), 7.22 (2H, d, J = 8.3 Hz), 7.34 (2H, d, J = 8.3 Hz), 7.42 (1H, t, J = 5.1 Hz), 7.89 (2H, d, J = 8.7 Hz). |
| 1028 | 677 (M + H). | 1H-NMR (CDCl$_3$, 300 MHz) δ: 2.37 (3H, s), 3.03 (1H, td, J = 12.5, 3.8 Hz), 3.21 (1H, dd, J = 13.4, 4.3 Hz), 3.64 (1H, ddd, J = 14.3, 10.9, 3.4 Hz), 3.93 (2H, t, J = 12.8 Hz), 4.28 (1H, d, J = 13.2 Hz), 4.37 (2H, d, J = 6.0 Hz), 4.71 (1H, d, J = 1.5 Hz), 6.06 (1H, d, J = 0.8 Hz), 7.14 (2H, d, J = 8.3 Hz), 7.24 (2H, s), 7.74 (2H, d, J = 8.3 Hz), 7.79 (1H, t, J = 5.8 Hz), 7.94 (2H, d, J = 8.3 Hz). |
| 1029 | 720 (M + H). | 1H-NMR (CD$_3$OD, 400 MHz) δ: 2.69 (3H, s), 3.48 (1H, br s), 3.71 (1H, d, J = 7.1 Hz), 3.90-3.93 (3H, m), 4.19-4.26 (3H, m), 4.69 (1H, s), 7.07 (2H, d, J = 7.7 Hz), 7.28 (2H, d, J = 8.4 Hz), 7.40 (2H, d, J = 8.4 Hz), 7.96 (2H, d, J = 8.6 Hz). |
| 1030 | 677 (M + H). | 1H-NMR (CDCl$_3$, 300 MHz) δ: 3.08-3.17 (1H, m), 3.27 (1H, dd, J = 13.4, 4.3 Hz), 3.45-3.55 (1H, m), 3.85 (3H, s), 3.93 (1H, d, J = 14.3 Hz), 4.25-4.37 (2H, m), 4.46 (1H, dd, J = 15.1, 6.4 Hz), 4.56 (1H, d, J = 13.6 Hz), 4.68 (1H, br s), 7.05-7.13 (3H, m), 7.20 (2H, d, J = 8.7 Hz), 7.80 (2H, d, J = 8.7 Hz), 7.98-8.02 (3H, m). |

TABLE 442

| Example No. | MS ESI m/e: | NMR |
|---|---|---|
| 1031 | 748 (M + H). | 1H-NMR (CDCl$_3$, 300 MHz) δ: 3.08 (1H, ddd, J = 14.6, 11.0, 2.5 Hz), 3.23 (1H, dd, J = 13.6, 4.1 Hz), 3.42 (1H, ddd, J = 14.9, 11.3, 2.6 Hz), 3.96 (1H, dt, J = 14.4, 2.6 Hz), 4.25 (2H, d, J = 13.9 Hz), 4.36 (1H, dd, J = 15.1, 5.7 Hz), 4.50 (1H, dd, J = 14.7, 6.0 Hz), 4.62 (1H, d, J = 3.4 Hz), 6.92 (1H, t, J = 5.8 Hz), 7.18 (2H, d, J = 8.7 Hz), 7.25 (2H, d, J = 8.3 Hz), 7.40 (2H, d, J = 7.9 Hz), 7.93 (2H, d, J = 9.0 Hz). |
| 1032 | 659 (M + H). | 1H-NMR (CDCl$_3$, 300 MHz) δ: 2.37 (3H, d, J = 0.8 Hz), 3.05 (1H, ddd, J = 14.6, 9.9, 2.7 Hz), 3.24 (1H, dd, J = 13.4, 4.3 Hz), 3.66 (1H, ddd, J = 14.2, 11.0, 2.5 Hz), 3.93 (2H, d, J = 10.2 Hz), 4.27 (1H, d, J = 13.2 Hz), 4.30 (1H, dd, J = 15.8, 5.3 Hz), 4.36 (1H, dd, J = 14.1, 6.2 Hz), 4.71 (1H, d, J = 2.6 Hz), 6.04 (1H, d, J = 1.1 Hz), 6.49 (1H, t, J = 73.7 Hz), 7.03 (2H, d, J = 9.0 Hz), 7.20 (2H, d, J = 8.3 Hz), 7.74 (2H, d, J = 9.4 Hz), 7.79 (1H, t, J = 5.3 Hz), 7.94 (2H, d, J = 8.3 Hz). |
| 1033 | 707 (M + H). | 1H-NMR (CD$_3$OD, 400 MHz) δ: 3.09-3.41 (2H, m), 3.42-3.59 (1H, m), 3.69 (1H, d, J = 13.9 Hz), 3.92 (2H, t, J = 14.5 Hz), 4.18 (1H, d, J = 15.5 Hz), 4.28 (1H, d, J = 15.1 Hz), 4.73 (1H, s), 7.12 (2H, d, J = 8.6 Hz), 7.29 (2H, d, J = 7.0 Hz), 7.42 (2H, d, J = 8.1 Hz), 7.97 (2H, d, J = 7.2 Hz), 8.91 (1H, s). |
| 1034 | 679 (M + H). | 1H-NMR (CD$_3$OD, 400 MHz) δ: 3.11-3.14 (0.2H, m), 3.25-3.29 (0.8H, m), 3.41-3.54 (1.0H, m), 3.59-3.69 (1.0H, m), 3.80-3.98 (2.0H, m), 4.00-4.15 (0.8H, br m), 4.20 (1.0H, d, J = 15.2 Hz), 4.28 (1.0H, d, J = 15.2 Hz), 4.35-4.42 (0.2H, m), 4.66 (0.2H, dd, J = 4.6, 2.6 Hz), 4.71 (0.8H, dd, J = 4.5, 2.3 Hz), 7.08-7.13 (2.0H, m), 7.23 (0.4H, d, J = 8.6 Hz), 7.28 (1.6H, d, J = 8.6 Hz), 7.38 (0.4H, d, J = 7.9 Hz), 7.42 (1.6H, d, J = 8.2 Hz), 7.94-7.98 (2.0H, m). |
| 1035 | 694 (M + H). | 1H-NMR (CDCl$_3$, 300 MHz) δ: 3.15-3.56 (3H, m), 3.97 (1H, d, J = 13.9 Hz), 4.24-4.73 (5H, m), 4.29 (3H, s), 6.99 (1H, br s), 7.11 (2H, d, J = 8.3 Hz), 7.20 (2H, d, J = 8.7 Hz), 7.37 (2H, d, J = 8.7 Hz), 7.94 (2H, d, J = 9.0 Hz). |

TABLE 443

| Example No. | MS ESI m/e: | NMR |
|---|---|---|
| 1036 | 670 (M + H). | 1H-NMR (CDCl$_3$, 400 MHz) δ: 3.10-3.56 (3H, m), 3.98 (1H, m), 4.31 (1H, m), 4.46 (2H, tt, J = 10.2, 3.3 Hz), 4.58 (1H, m), 4.68 (1H, td, J = 1.5, 0.6 Hz), 6.50 (1H, m), 6.91 (1H, m), 7.04 (2H, dt, J = 7.7, 1.5 Hz), 7.18 (2H, d, J = 7.7 Hz), 7.39 (2H, d, J = 8.1 Hz), 7.94 (2H, d, J = 8.1 Hz), 8.80 (1H, d, J = 1.4 Hz). |
| 1037 | 691 (M + H). | 1H-NMR (CDCl$_3$, 300 MHz) δ: 1.38 (3H, t, J = 7.2 Hz), 3.07-3.17 (1H, m), 3.27 (1H, dd, J = 13.4, 4.3 Hz), 3.44-3.54 (1H, m), 3.93 (1H, d, J = 13.9 Hz), 4.25-4.37 (4H, m), 4.46 (1H, dd, J = 14.9, 6.2 Hz), 4.56 (1H, d, J = 13.6 Hz), 4.68 (1H, br s), 7.03-7.14 (3H, m), 7.20 (2H, d, J = 8.7 Hz), 7.81 (2H, d, J = 8.3 Hz), 7.99-8.03 (3H, m). |
| 1038 | 747 (M + H). | 1H-NMR (CDCl$_3$, 300 MHz) δ: 3.06 (1H, ddd, J = 14.2, 10.8, 3.1 Hz), 3.19 (1H, dd, J = 13.9, 4.5 Hz), 3.45 (1H, ddd, J = 13.6, 11.1, 3.2 Hz), 3.93 (1H, d, J = 14.7 Hz), 4.17 (1H, d, J = 13.9 Hz), 4.27 (1H, d, J = 13.2 Hz), 4.37 (1H, dd, J = 15.1, 5.7 Hz), 4.49 (1H, dd, J = 14.9, 6.6 Hz), 4.60 (1H, d, J = 1.1 Hz), 6.74 (1H, s), 6.96 (1H, t, J = 5.8 Hz), 7.17 (2H, d, J = 8.3 Hz), 7.24 (2H, d, J = 7.5 Hz), 7.39 (2H, d, J = 8.3 Hz), 7.92 (2H, d, J = 8.7 Hz). |
| 1039 | 691 (M + H). | 1H-NMR (CDCl$_3$, 300 MHz) δ: 2.72 (3H, s), 3.16-3.35 (2H, m), 3.42-3.52 (1H, m), 3.93 (1H, d, J = 14.3 Hz), 4.27-4.37 (2H, m), 4.44 (1H, dd, J = 14.9, 6.2 Hz), 4.57-4.66 (2H, m), 5.94 (1H, tt, J = 52.7, 2.6 Hz), 6.47 (1H, t, J = 73.7 Hz), 6.95-7.01 (3H, m), 7.15 (2H, d, J = 8.7 Hz), 7.38 (2H, d, J = 9.0 Hz), 7.91 (2H, d, J = 8.7 Hz), 8.68 (1H, s). |
| 1040 | 687 (M + H). | 1H-NMR (CDCl$_3$, 300 MHz) δ: 1.01-1.08 (2H, m), 1.15-1.20 (2H, m), 2.20-2.29 (1H, m), 3.17-3.37 (2H, m), 3.41-3.50 (1H, m), 3.93 (1H, d, J = 13.9 Hz), 4.23-4.39 (2H, m), 4.47 (1H, dd, J = 14.9, 6.2 Hz), 4.57-4.67 (2H, m), 6.47 (1H, t, J = 73.1 Hz), 6.74-6.81 (2H, m), 6.92 (1H, t, J = 5.7 Hz), 7.18 (1H, dd, J = 10.5, 6.4 Hz), 7.81 (2H, d, J = 8.3 Hz), 8.01 (2H, d, J = 8.3 Hz), 8.60 (1H, s). |

TABLE 444

| Example No. | MS ESI m/e: | NMR |
|---|---|---|
| 1041 | 734 (M + H). | 1H-NMR (CDCl$_3$, 400 MHz) δ: 2.95 (3H, s), 3.13 (3H, s), 3.18-3.39 (2H, m), 3.56 (1H, m), 3.93 (1H, m), 4.24-4.48 (3H, m), 4.62 (1H, m), 4.70 (1H, m), 7.09 (2H, d, J = 8.3 Hz), 7.19 (2H, d, J = 8.3 Hz), 7.22 (1H, m), 7.35 (2H, d, J = 8.7 Hz), 7.93 (2H, d, J = 8.7 Hz), 8.81 (1H, s). |
| 1042 | 715 (M + H). | 1H-NMR (CDCl$_3$, 400 MHz) δ: 3.14-3.55 (3H, m), 3.98 (1H, d, J = 14.1 Hz), 4.29-4.78 (5H, m), 6.47 (1H, t, J = 72.9 Hz), 6.77-6.86 (3H, m), 7.21 (1H, t, J = 8.5 Hz), 7.83 (2H, d, J = 8.2 Hz), 8.02 (2H, d, J = 8.2 Hz), 8.86 (1H, s). |
| 1043 | 707 (M + H). | 1H-NMR (CDCl$_3$, 300 MHz) δ: 3.15-3.39 (2H, m), 3.50-3.60 (4H, m), 3.93 (1H, d, J = 13.9 Hz), 4.27-4.53 (3H, m), 4.60-4.76 (4H, m), 7.02-7.13 (3H, m), 7.19 (2H, d, J = 8.7 Hz), 7.36 (2H, d, J = 8.3 Hz), 7.87-7.98 (2H, m), 8.80 (1H, s). |
| 1044 | 731 (M + H). | 1H-NMR (CDCl$_3$, 400 MHz) δ: 3.17-3.52 (3H, br m), 3.95 (1H, d, J = 14.4 Hz), 4.35 (1H, d, J = 15.3 Hz), 4.44 (1H, dd, J = 15.1, 6.3 Hz), 4.58 (2H, br s), 4.64 (1H, s), 6.47 (1H, t, J = 74.0 Hz), 6.75-6.93 (3H, m), 7.20 (1H, t, J = 7.7 Hz), 7.38 (2H, d, J = 7.9 Hz), 7.93 (2H, t, J = 4.5 Hz), 8.86 (1H, d, J = 1.9 Hz). |
| 1045 | 703 (M + H). | 1H-NMR (CDCl$_3$, 400 MHz) δ: 1.01-1.07 (2H, m), 1.15-1.20 (2H, m), 2.19-2.29 (1H, m), 3.17-3.49 (3H, m), 3.90 (1H, d, J = 14.1 Hz), 4.25-4.40 (1H, br m), 4.36 (1H, dd, J = 15.0, 5.5 Hz), 4.46 (1H, dd, J = 15.1, 6.3 Hz), |

TABLE 444-continued

| Example No. | MS ESI m/e: | NMR |
|---|---|---|
|  |  | 4.54-4.65 (1H, br m), 4.62 (1H, d, J = 3.3 Hz), 6.47 (1H, t, J = 73.1 Hz), 6.78 (2H, t, J = 8.7 Hz), 6.92 (1H, t, J = 5.6 Hz), 7.19 (1H, t, J = 8.5 Hz), 7.36 (2H, d, J = 8.2 Hz), 7.93 (2H, d, J = 8.8 Hz), 8.60 (1H, s). |
| 1046 | 720 (M + H). | 1H-NMR (CD$_3$OD, 400 MHz) δ: 2.99 (3H, s), 3.21-3.42 (2H, m), 3.46-3.58 (1H, m), 3.67-3.71 (1H, m), 3.86-3.98 (2H, m), 4.17 (1H, d, J = 13.0 Hz), 4.28 (1H, d, J = 15.1 Hz), 4.71-4.73 (1H, m), 7.10 (2H, d, J = 8.1 Hz), 7.29 (2H, d, J = 8.6 Hz), 7.43 (2H, d, J = 8.1 Hz), 7.98 (2H, d, J = 8.8 Hz), 8.94 (1H, s). |

TABLE 445

| Example No. | MS ESI m/e: | NMR |
|---|---|---|
| 1047 | 721 (M + H). | 1H-NMR (CDCl$_3$, 400 MHz) δ: 1.63 (6H, s), 3.43-3.53 (1H, m), 3.95 (1H, d, J = 14.4 Hz), 4.32-4.68 (2H, br m), 3.17-3.37 (2H, m), 4.36 (1H, dd, J = 15.1, 5.6 Hz), 4.49 (1H, dd, J = 15.0, 6.4 Hz), 4.66 (1H, br s), 4.76 (1H, s), 6.92 (1H, br s), 7.12 (2H, d, J = 7.9 Hz), 7.21 (2H, d, J = 8.8 Hz), 7.38 (2H, d, J = 7.9 Hz), 7.95 (2H, d, J = 8.8 Hz), 8.75 (1H, s). |
| 1048 | 705 (M + H). | 1H-NMR (CDCl$_3$, 400 MHz) δ: 2.83 (3H, s), 3.20-3.41 (2H, m), 3.57 (1H, br s), 3.96 (1H, d, J = 14.1 Hz), 4.22-4.83 (2H, m), 4.32 (1H, dd, J = 15.1, 5.6 Hz), 4.45 (1H, dd, J = 15.2, 5.9 Hz), 4.69 (1H, d, J = 2.6 Hz), 7.08 (1H, d, J = 7.9 Hz), 7.19 (2H, d, J = 8.3 Hz), 7.38 (2H, d, J = 8.6 Hz), 7.95 (2H, d, J = 8.8 Hz), 8.95 (1H, s). |
| 1049 | 747 (M + H). | 1H-NMR (CDCl$_3$, 300 MHz) δ: 2.96 (1H, ddd, J = 14.1, 11.3, 2.3 Hz), 3.07 (1H, dd, J = 13.2, 4.1 Hz), 3.42 (1H, ddd, J = 15.0, 11.0, 3.7 Hz), 3.93 (2H, t, J = 14.7 Hz), 4.21 (1H, d, J = 13.2 Hz), 4.41 (1H, dd, J = 15.1, 5.7 Hz), 4.51 (1H, dd, J = 14.7, 6.0 Hz), 4.59 (1H, d, J = 2.3 Hz), 6.60 (1H, s), 6.98 (1H, t, J = 5.5 Hz), 7.18 (2H, d, J = 7.9 Hz), 7.27 (2H, d, J = 8.7 Hz), 7.39 (2H, d, J = 7.9 Hz), 7.92 (2H, d, J = 9.0 Hz). |
| 1050 | 692 (M + H). | 1H-NMR (CDCl$_3$, 300 MHz) δ: 3.06 (1H, ddd, J = 14.5, 10.5, 2.8 Hz), 3.14 (1H, dd, J = 13.0, 3.6 Hz), 3.45 (1H, ddd, J = 15.8, 10.0, 3.4 Hz), 3.85-3.99 (2H, m), 3.92 (3H, s), 4.41 (1H, dd, J = 15.3, 6.2 Hz), 4.48 (1H, dd, J = 15.1, 6.4 Hz), 4.59 (1H, d, J = 13.2 Hz), 4.62 (1H, d, J = 3.8 Hz), 6.67 (1H, d, J = 8.7 Hz), 7.01 (1H, t, J = 5.7 Hz), 7.09 (2H, d, J = 7.9 Hz), 7.21 (2H, d, J = 8.7 Hz), 7.35 (1H, dd, J = 8.9, 0.9 Hz), 7.58 (1H, d, J = 8.7 Hz), 7.94 (2H, d, J = 8.7 Hz). |
| 1051 | 709 (M + H). | 1H-NMR (CDCl$_3$, 400 MHz) δ: 2.73 (3H, s), 3.24-3.30 (2H, m), 3.50 (1H, t, J = 10.8 Hz), 3.95 (1H, d, J = 14.1 Hz), 4.35-4.47 (3H, m), 4.66-4.68 (2H, m), 5.95 (1H, t, J = 68.0 Hz), 7.01 (1H, t, J = 6.7 Hz), 7.10 (2H, d, J = 8.1 Hz), 7.20 (2H, d, J = 8.8 Hz), 7.38 (2H, d, J = 8.8 Hz), 7.92 (2H, d, J = 9.4 Hz), 8.69 (1H, s). |

TABLE 446

| Example No. | MS ESI m/e: | NMR |
|---|---|---|
| 1052 | 677 (M + H). | 1H-NMR (CD$_3$OD, 300 MHz) δ: 3.42-3.56 (1H, m), 3.64-3.73 (1H, m), 3.82-4.01 (2H, m), 4.06-4.33 (3H, m), 4.64-4.77 (4H, m), 7.10 (2H, d, J = 8.3 Hz), 7.28 (2H, d, J = 9.0 Hz), 7.82 (2H, d, J = 8.3 Hz), 8.04 (2H, d, J = 7.9 Hz), 8.81 (1H, s). |

TABLE 446-continued

| Example No. | MS ESI m/e: | NMR |
|---|---|---|
| 1053 | 660 (M + H). | 1H-NMR (CDCl₃, 400 MHz) δ: 2.95-3.04 (1H, m), 3.10 (1H, dd, J = 13.2, 4.2 Hz), 3.46-3.56 (1H, m), 3.81 (1H, d, J = 13.2 Hz), 3.93 (1H, d, J = 13.9 Hz), 4.28 (1H, d, J = 13.2 Hz), 4.37 (1H, dd, J = 14.5, 5.7 Hz), 4.44 (1H, dd, J = 15.0, 6.1 Hz), 4.62 (1H, d, J = 2.8 Hz), 6.24 (1H, d, J = 7.9 Hz), 6.52 (1H, t, J = 73.7 Hz), 7.08 (2H, d, J = 8.6 Hz), 7.19-7.26 (3H, m), 7.36 (2H, d, J = 7.9 Hz), 7.74 (1H, d, J = 7.9 Hz), 7.90 (2H, d, J = 8.8 Hz). |
| 1054 | 750 (M + H). | 1H-NMR (CD₃OD, 400 MHz) δ: 3.22-3.35 (2H, m), 3.37 (3H, br s), 3.62-3.74 (4H, m), 3.82-3.99 (3H, m), 4.04-4.22 (1H, m), 4.29 (1H, d, J = 14.6 Hz), 4.71 (1H, br s), 7.15 (2H, d, J = 8.1 Hz), 7.31 (2H, d, J = 8.6 Hz), 7.36-7.47 (3H, m), 7.97 (2H, d, J = 9.5 Hz), 8.90 (1H, s). |
| 1055 | 722 (M + H). | 1H-NMR (CD₃OD, 300 MHz) δ: 3.44 (4H, m), 3.53-3.65 (1H, m), 3.81-4.09 (3H, m), 4.25 (2H, dd, J = 26.7, 15.1 Hz), 4.39 (2H, s), 4.58-4.73 (1H, m), 7.07 (2H, d, J = 8.3 Hz), 7.26 (2H, d, J = 8.7 Hz), 7.42 (2H, d, J = 8.7 Hz), 7.93-8.01 (2H, m). |
| 1056 | 746 (M + H). | 1H-NMR (CDCl₃, 400 MHz) δ: 1.79-1.87 (4H, m), 2.66-2.76 (4H, m), 3.21 (1H, m), 3.31 (1H, m), 3.50 (1H, m), 3.89-4.00 (3H, m), 4.26-4.39 (2H, m), 4.47 (1H, dd, J = 15.0, 6.4 Hz), 4.57-4.70 (2H, m), 7.04 (1H, t, J = 6.0 Hz), 7.11 (2H, d, J = 7.9 Hz), 7.21 (2H, d, J = 8.7 Hz), 7.37 (2H, dd, J = 8.7, 0.7 Hz), 7.94 (2H, dt, J = 9.5, 2.6 Hz), 8.80 (1H, s). |

TABLE 447

| Example No. | MS ESI m/e: | NMR |
|---|---|---|
| 1057 | 645 (M + H). | 1H-NMR (CDCl₃, 300 MHz) δ: 2.96 (1H, ddd, J = 14.1, 10.7, 2.8 Hz), 3.07 (1H, dd, J = 13.6, 4.1 Hz), 3.51 (1H, ddd, J = 14.6, 11.2, 2.7 Hz), 3.80 (1H, d, J = 13.2 Hz), 3.95 (1H, dt, J = 13.9, 3.0 Hz), 4.27 (1H, d, J = 12.4 Hz), 4.36 (1H, dd, J = 14.7, 5.7 Hz), 4.44 (1H, dd, J = 14.7, 6.0 Hz), 4.63 (1H, d, J = 2.6 Hz), 6.24 (1H, d, J = 7.5 Hz), 6.51 (1H, t, J = 73.7 Hz), 7.07 (2H, d, J = 8.7 Hz), 7.14 (1H, t, J = 5.8 Hz), 7.23 (2H, d, J = 8.7 Hz), 7.73 (1H, d, J = 7.5 Hz), 7.81 (2H, d, J = 8.3 Hz), 7.98 (2H, d, J = 8.3 Hz). |
| 1058 | 661 (M + H). | 1H-NMR (CDCl₃, 400 MHz) δ: 2.87-2.96 (1H, m), 3.00 (1H, dd, J = 13.2, 4.5 Hz), 3.35-3.47 (1H, m), 3.74 (1H, d, J = 13.2 Hz), 3.95 (1H, d, J = 13.9 Hz), 4.27 (1H, d, J = 12.8 Hz), 4.36-4.55 (2H, m), 4.58 (1H, s), 6.24 (1H, d, J = 7.9 Hz), 6.63 (1H, t, J = 72.0 Hz), 6.99-7.07 (1H, br m), 7.18 (2H, d, J = 7.9 Hz), 7.26-7.30 (4H, m), 7.73 (1H, d, J = 7.9 Hz), 7.87 (2H, d, J = 8.7 Hz). |
| 1059 | 663 (M + H). | 1H-NMR (CDCl₃, 400 MHz) δ: 2.95-3.04 (1H, m), 3.11 (1H, dd, J = 13.3, 4.3 Hz), 3.51-3.60 (1H, m), 3.83 (1H, d, J = 13.4 Hz), 3.96 (1H, d, J = 13.9 Hz), 4.28 (1H, d, J = 13.2 Hz), 4.39 (1H, dd, J = 15.2, 6.1 Hz), 4.45 (1H, dd, J = 15.1, 6.0 Hz), 4.67 (1H, d, J = 2.6 Hz), 6.25 (1H, d, J = 7.7 Hz), 7.18 (2H, d, J = 7.9 Hz), 7.27 (2H, d, J = 8.8 Hz), 7.38 (1H, t, J = 5.9 Hz), 7.75 (1H, d, J = 7.9 Hz), 7.80 (2H, d, J = 8.1 Hz), 7.97 (2H, d, J = 8.3 Hz). |
| 1060 | 707 (M + H). | 1H-NMR (CDCl₃, 400 MHz) δ: 1.57-1.62 (3H, m), 3.16-3.37 (2H, m), 3.49 (1H, J = 11.2 Hz), 3.96 (1H, d, J = 14.4 Hz), 4.13 (1H, dd, J = 9.3, 5.6 Hz), 4.36 (1H, dd, J = 15.3, 5.6 Hz), 4.50 (1H, dd, J = 15.0, 6.4 Hz), 4.63 (1H, br s), 4.67 (1H, s), 4.92-4.98 (1H, m), 6.93 (1H, t, J = 5.9 Hz), 7.12 (2H, d, J = 8.6 Hz), 7.21 |

TABLE 447-continued

| Example No. | MS ESI m/e: | NMR |
|---|---|---|
| | | (2H, d, J = 8.8 Hz), 7.38 (2H, d, J = 7.9 Hz), 7.95 (2H, d, J = 8.8 Hz), 8.76 (1H, s). |

TABLE 448

| Example No. | MS ESI m/e: | NMR |
|---|---|---|
| 1061 | 731 (M + H). | 1H-NMR (CDCl₃, 400 MHz) δ: 3.16-3.42 (2H, m), 3.47 (1H, t, J = 12.4 Hz), 3.97 (1H, d, J = 14.3 Hz), 4.22-4.77 (2H, br m), 4.28 (1H, dd, J = 15.1, 5.4 Hz), 4.48 (1H, dd, J = 15.1, 6.7 Hz), 4.68 (1H, d, J = 2.4 Hz), 6.51 (1H, t, J = 73.3 Hz), 6.93-7.00 (3H, m), 7.13 (1H, t, J = 8.0 Hz), 7.39 (2H, d, J = 8.2 Hz), 7.95 (2H, dt, J = 9.4, 2.4 Hz), 8.88 (1H, s). |
| 1062 | 678 (M + H). | 1H-NMR (CDCl₃, 300 MHz) δ: 3.04 (1H, ddd, J = 14.5, 9.8, 2.8 Hz), 3.12 (1H, dd, J = 13.2, 4.5 Hz), 3.46 (1H, ddd, J = 15.4, 10.6, 3.3 Hz), 3.93 (2H, tt, J = 15.1, 3.5 Hz), 4.40 (1H, dd, J = 15.1, 6.0 Hz), 4.48 (1H, dd, J = 16.0, 6.6 Hz), 4.54 (1H, d, J = 13.2 Hz), 4.61(1H, br s), 6.70 (1H, d, J = 8.7 Hz), 6.99 (1H, t, J = 6.0 Hz), 7.11 (2H, d, J = 7.9 Hz), 7.22 (2H, d, J = 8.7 Hz), 7.35 (2H, d, J = 8.7 Hz), 7.66 (1H, d, J = 8.7 Hz), 7.93 (2H, d, J = 9.0 Hz). |
| 1063 | 643 (M + H). | 1H-NMR (CDCl₃, 300 MHz) δ: 2.94 (1H, ddd, J = 14.4, 10.8, 2.9 Hz), 3.01 (1H, dd, J = 13.6, 4.5 Hz), 3.41 (1H, ddd, J = 14.5, 11.1, 3.0 Hz), 3.74 (1H, d, J = 12.8 Hz), 3.94 (1H, d, J = 13.6 Hz), 4.27 (1H, d, J = 13.2 Hz), 4.39 (1H, dd, J = 14.7, 6.0 Hz), 4.47 (1H, dd, J = 14.7, 6.0 Hz), 4.57 (1H, d, J = 3.4 Hz), 6.24 (1H, d, J = 7.9 Hz), 6.51 (1H, t, J = 73.7 Hz), 6.63 (1H, t, J = 72.0 Hz), 6.96 (1H, t, J = 5.7 Hz), 7.09 (2H, d, J = 8.7 Hz), 7.23 (2H, d, J = 8.7 Hz), 7.28 (2H, d, J = 9.0 Hz), 7.73 (1H, d, J = 7.5 Hz), 7.87 (2H, d, J = 8.7 Hz). |
| 1064 | 636 (M + H). | 1H-NMR (CDCl₃, 400 MHz) δ: 0.94 (3H, t, J = 7.3 Hz), 1.27 (3H, t, J = 7.7 Hz), 1.43 (3H, t, J = 7.2 Hz), 1.57-1.66 (2H, m), 2.54 (2H, t, J = 7.7 Hz), 2.72 (2H, q, J = 7.6 Hz), 3.10-3.14 (2H, m), 3.41 (1H, dt, J = 18.3, 6.6 Hz), 3.98 (1H, d, J = 14.6 Hz), 4.33-4.46 (5H, m), 4.67 (1H, br s), 4.67 (1H, s), 6.96 (1H, br s), 7.08 (4H, s), 7.37 (2H, d, J = 8.6 Hz), 7.79 (2H, d, J = 8.3 Hz), 8.81 (1H, s), 8.98 (1H, s). |

TABLE 449

| Example No. | MS ESI m/e: | NMR |
|---|---|---|
| 1065 | 608 (M + H). | 1H-NMR (CDCl₃, 400 MHz) δ: 0.92 (3H, t, J = 7.3 Hz), 1.26 (3H, t, J = 7.7 Hz), 1.59-1.63 (2H, m), 2.55 (2H, t, J = 7.7 Hz), 2.72 (2H, q, J = 7.6 Hz), 3.24-3.27 (2H, m), 3.47 (1H, t, J = 10.8 Hz), 3.99 (1H, d, J = 14.1 Hz), 4.14 (1H, br s), 4.40 (2H, d, J = 5.8 Hz), 4.50 (1H, br s), 4.67 (1H, d, J = 2.1 Hz), 6.93 (1H, t, J = 5.6 Hz), 7.08 (4H, s), 7.38 (2H, d, J = 8.3 Hz), 7.79 (2H, d, J = 8.3 Hz), 8.86 (1H, s), 9.17 (1H, s), 12.46 (1H, br s). |
| 1066 | 729 (M + H). | 1H-NMR (CDCl₃, 300 MHz) δ: 2.96 (1H, ddd, J = 14.0, 11.0, 2.4 Hz), 3.08 (1H, dd, J = 13.2, 4.1 Hz), 3.42 (1H, ddd, J = 14.5, 10.9, 3.0 Hz), 3.93 (2H, t, J = 12.8 Hz), 4.21 (1H, d, J = 12.8 Hz), 4.38 (1H, dd, J = 14.7, 5.7 Hz), 4.48 (1H, dd, J = 14.7, 6.0 Hz), 4.59 (1H, d, J = 3.4 Hz), 6.51 (1H, t, J = 73.7 Hz), 6.60 (1H, s), 6.94 (1H, t, J = 5.8 Hz), 7.09 (2H, d, J = 8.7 Hz), 7.23 (2H, d, J = 8.7 Hz), 7.38 (2H, d, J = 8.3 Hz), 7.91 (2H, d, J = 8.7 Hz). |
| 1067 | 731 (M + H). | 1H-NMR (CDCl₃, 300 MHz) δ: 2.98 (1H, ddd, J = 14.1, 10.5, 2.1 Hz), 3.09 (1H, dd, J = 13.2, 4.1 Hz), 3.48 (1H, ddd, J = 14.4, 11.6, 2.9 Hz), |

TABLE 449-continued

| Example No. | MS ESI m/e: | NMR |
|---|---|---|
| | | 3.89-4.05 (2H, m), 4.24 (1H, d, J = 13.2 Hz), 4.43 (1H, dd, J = 15.1, 5.7 Hz), 4.54 (1H, dd, J = 14.9, 6.2 Hz), 4.65 (1H, d, J = 1.1 Hz), 6.63 (1H, s), 7.02 (1H, t, J = 5.8 Hz), 7.21 (2H, d, J = 8.3 Hz), 7.30 (2H, d, J = 7.5 Hz), 7.86 (2H, d, J = 8.3 Hz), 8.02 (2H, d, J = 7.9 Hz). |
| 1068 | 713 (M + H). | 1H-NMR (CDCl$_3$, 300 MHz) δ: 2.90-3.02 (1H, m), 3.08 (1H, dd, J = 13.2, 4.1 Hz), 3.45 (1H, ddd, J = 14.2, 11.6, 2.7 Hz), 3.94 (2H, t, J = 16.4 Hz), 4.21 (1H, d, J = 13.2 Hz), 4.38 (1H, dd, J = 14.9, 5.8 Hz), 4.47 (1H, dd, J = 15.1, 6.0 Hz), 4.62 (1H, d, J = 2.6 Hz), 6.51 (1H, t, J = 73.5 Hz), 6.60 (1H, s), 6.97 (1H, t, J = 5.7 Hz), 7.09 (2H, d, J = 8.3 Hz), 7.23 (2H, d, J = 8.7 Hz), 7.83 (2H, d, J = 8.3 Hz), 7.99 (2H, d, J = 8.3 Hz). |
| 1069 | 717 (M + H). | 1H-NMR (CDCl$_3$, 400 MHz) δ: 1.86-2.15 (2H, m), 2.32-2.58 (4H, m), 3.15-3.54 (3H, m), 3.76-3.96 (2H, m), 4.27-4.70 (5H, m), 6.95 (1H, t, J = 6.0 Hz), 7.09 (2H, d, J = 7.9 Hz), 7.19 (2H, dt, J = 9.0, 2.3 Hz), 7.36 (2H, d, J = 7.9 Hz), 7.94 (2H, dt, J = 9.5, 2.4 Hz), 8.72 (1H, s). |

TABLE 450

| Example No. | MS ESI m/e: | NMR |
|---|---|---|
| 1070 | 721 (M + H). | 1H-NMR (CDCl$_3$, 300 MHz) δ: 3.16-3.40 (2H, m), 3.27 (2H, t, J = 6.8 Hz), 3.39 (3H, s), 3.44-3.55 (1H, m), 3.90-4.00 (1H, m), 3.95 (2H, t, J = 6.8 Hz), 4.27-4.72 (3H, m), 4.36 (1H, dd, J = 15.1, 5.5 Hz), 4.51 (1H, dd, J = 15.1, 6.2 Hz), 6.98 (1H, t, J = 5.3 Hz), 7.12 (2H, d, J = 7.9 Hz), 7.22 (2H, d, J = 8.7 Hz), 7.39 (2H, d, J = 8.3 Hz), 7.96 (2H, dt, J = 9.4, 2.4 Hz), 8.75 (1H, s). |
| 1071 | 737 (M + H). | 1H-NMR (CDCl$_3$, 300 MHz) δ: 3.06-3.15 (1H, m), 3.25 (1H, dd, J = 13.4, 4.3 Hz), 3.34 (3H, s), 3.40-3.50 (1H, m), 3.80 (2H, t, J = 5.5 Hz), 3.91 (1H, d, J = 13.9 Hz), 4.28-4.39 (2H, m), 4.42-4.56 (4H, m), 4.64 (1H, br s), 7.02 (1H, t, J = 6.2 Hz), 7.13 (2H, d, J = 8.3 Hz), 7.21 (2H, d, J = 8.7 Hz), 7.37 (2H, d, J = 8.3 Hz), 7.93 (2H, d, J = 8.7 Hz), 8.03 (1H, s). |
| 1072 | 701 (M + H). | 1H-NMR (CDCl$_3$, 300 MHz) δ: 1.86-2.15 (2H, m), 2.32-2.58 (4H, m), 3.16-3.27 (1H, m), 3.29-3.37 (1H, m), 3.44-3.54 (1H, m), 3.76-3.88 (1H, m), 3.95 (1H, d, J = 13.9 Hz), 4.29-4.38 (2H, m), 4.47 (1H, dd, J = 15.1, 6.4 Hz), 4.61-4.70 (2H, m), 6.95 (1H, t, J = 5.8 Hz), 7.08 (1H, d, J = 8.3 Hz), 7.19 (2H, d, J = 8.7 Hz), 7.81 (2H, d, J = 8.3 Hz), 8.01 (2H, d, J = 8.3 Hz), 8.72 (1H, s). |
| 1073 | 703 (M + H). | 1H-NMR (CDCl$_3$, 400 MHz) δ: 1.03-1.08 (2H, m), 1.16-1.21 (2H, m), 2.22-2.29 (1H, m), 3.17-3.36 (2H, m), 3.42-3.51 (1H, m), 3.93 (1H, d, J = 14.1 Hz), 4.30 (2H, dd, J = 15.2, 5.4 Hz), 4.48 (1H, dd, J = 5.1, 6.5 Hz), 4.57-4.68 (1H, m), 4.66 (1H, s), 6.51 (1H, t, J = 73.3 Hz), 6.93 (1H, d, J = 8.3 Hz), 7.00 (1H, dd, J = 10.9, 2.1 Hz), 7.04 (1H, t, J = 6.0 Hz), 7.10 (1H, t, J = 8.1 Hz), 7.38 (2H, d, J = 8.1 Hz), 7.95 (2H, d, J = 8.8 Hz), 8.62 (1H, s). |

TABLE 451

| Example No. | MS ESI m/e: | NMR |
|---|---|---|
| 1074 | 687 (M + H). | 1H-NMR (CDCl$_3$, 400 MHz) δ: 1.02-1.08 (2H, m), 1.15-1.20 (2H, m), 2.21-2.28 (1H, m), 3.17-3.39 (2H, m), 3.43-3.52 (1H, m), 3.94 (1H, d, J = 14.1 Hz), 4.20-4.30 (1H, m), 4.27 (1H, dd, J = 15.1, 5.4 Hz), 4.48 (1H, dd, J = 15.1, 6.5 Hz), 4.61-4.71 (1H, m), 4.69 (1H, s), 6.50 (1H, t, J = 73.3 Hz), 6.92 (1H, d, J = 8.4 Hz), 6.98 (1H, dd, J = 10.7, 2.3 Hz), 7.03 (1H, t, J = 6.2 Hz), 7.08 (1H, t, J = 8.2 Hz), 7.82 (2H, d, J = 8.2 Hz), 8.02 (2H, d, J = 8.2 Hz), 8.61 (1H, s). |
| 1075 | 705 (M + H). | 1H-NMR (CDCl$_3$, 400 MHz) δ: 1.63 (6H, s), 3.16-3.38 (2H, m), 3.45-3.55 (1H, m), 3.98 (1H, d, J = 14.1 Hz), 4.32-4.41 (1H, m), 4.35 (1H, dd, J = 14.8, 5.6 Hz), 4.49 (1H, dd, J = 14.8, 6.3 Hz), 4.62 (1H, br s), 4.69 (1H, s), 4.75 (1H, s), 6.90 (1H, t, J = 5.7 Hz), 7.12 (2H, d, J = 8.1 Hz), 7.21 (2H, d, J = 8.8 Hz), 7.83 (2H, d, J = 8.3 Hz), 8.03 (2H, d, J = 8.1 Hz), 8.75 (1H, s). |
| 1076 | 747 (M + H). | 1H-NMR (CDCl$_3$, 400 MHz) δ: 1.09 (2H, dd, J = 7.2, 4.2 Hz), 1.41-1.48 (2H, m), 3.12-3.34 (2H, m), 3.40-3.49 (4H, m), 3.87-3.98 (3H, m), 4.28-4.66 (5H, m), 6.93 (1H, t, J = 6.0 Hz), 7.10 (2H, d, J = 8.1 Hz), 7.20 (2H, dt, J = 9.1, 2.4 Hz), 7.37 (2H, d, J = 8.1 Hz), 7.93 (2H, dt, J = 9.4, 2.5 Hz), 8.68 (1H, s). |
| 1077 | 733 (M + H). | 1H-NMR (CDCl$_3$, 400 MHz) δ: 1.04 (2H, dd, J = 6.6, 3.8 Hz), 1.46 (2H, dd, J = 6.6, 3.8 Hz), 3.13-3.53 (3H, m), 3.82-3.97 (3H, m), 4.27-4.68 (6H, m), 6.94 (1H, t, J = 5.8 Hz), 7.10 (2H, d, J = 8.1 Hz), 7.20 (2H, d, J = 8.8 Hz), 7.37 (2H, d, J = 8.8 Hz), 7.94 (2H, dt, J = 9.4, 2.6 Hz), 8.63 (1H, s). |
| 1078 | 723 (M + H). | 1H-NMR (CDCl$_3$, 300 MHz) δ: 3.08-3.30 (3H, m), 3.44-3.52 (1H, m), 3.90 (1H, d, J = 13.6 Hz), 4.04 (2H, q, J = 5.0 Hz), 4.26-4.38 (2H, m), 4.42-4.58 (4H, m), 4.66 (1H, br s), 7.03-7.14 (3H, m), 7.21 (2H, d, J = 8.7 Hz), 7.36 (2H, d, J = 8.7 Hz), 7.93 (2H, d, J = 9.0 Hz), 8.05 (1H, s). |

TABLE 452

| Example No. | MS ESI m/e: | NMR |
|---|---|---|
| 1079 | 733 (M + H). | 1H-NMR (CDCl$_3$, 400 MHz) δ: 1.31-1.38 (2H, m), 1.47-1.53 (2H, m), 3.13-3.37 (2H, m), 3.39-3.51 (1H, m), 3.52 (3H, s), 3.87-3.96 (1H, m), 4.29-4.52 (3H, m), 4.53-4.66 (2H, m), 6.92 (1H, t, J = 6.0 Hz), 7.10 (2H, d, J = 8.3 Hz), 7.20 (2H, d, J = 8.7 Hz), 7.37 (2H, d, J = 7.9 Hz), 7.93 (2H, d, J = 8.3 Hz), 8.75 (1H, s). |
| 1080 | 719 (M + H). | 1H-NMR (CDCl$_3$, 300 MHz) δ: 1.32-1.39 (2H, m), 1.45-1.52 (2H, m), 3.15-3.36 (2H, m), 3.40-3.55 (1H, m), 3.88-3.97 (1H, m), 4.30-4.53 (4H, m), 4.55-4.68 (2H, m), 6.93 (1H, t, J = 5.8 Hz), 7.10 (2H, d, J = 7.9 Hz), 7.20 (2H, d, J = 8.7 Hz), 7.37 (2H, d, J = 7.9 Hz), 7.93 (2H, d, J = 8.7 Hz), 8.68 (1H, s). |
| 1081 | 720 (M + H). | 1H-NMR (CDCl$_3$, 400 MHz) δ: 0.92 (3H, t, J = 7.4 Hz), 1.57-1.63 (2H, m), 1.66 (9H, s), 2.53 (2H, t, J = 7.7 Hz), 3.18-3.27 (2H, m), 3.45-3.50 (1H, m), 3.93 (1H, d, J = 13.9 Hz), 4.19 (1H, d, J = 13.5 Hz), 4.32-4.42 (2H, m), 4.61-4.64 (2H, m), 6.79 (1H, t, J = 5.6 Hz), 7.05 (4H, s), 7.34 (2H, d, J = 4.5 Hz), 7.92 (2H, d, J = 9.5 Hz), 8.10 (1H, s), 8.84 (1H, s). |
| 1082 | 664 (M + H). | 1H-NMR (CDCl$_3$, 400 MHz) δ: 0.91 (3H, t, J = 15.3 Hz), 1.56-1.64 (2H, m), 2.53 (2H, t, J = 7.6 Hz), 3.18-3.29 (2H, m), 3.48 (1H, s), 3.95 (1H, d, J = 11.7 Hz), 4.31-4.37 (3H, m), 4.64-4.67 (2H, m), 6.79 (1H, br s), 7.02 (4H, s), 7.32 (2H, d, J = 16.0 Hz), 7.92 (2H, d, J = 8.4 Hz), 8.18 (1H, s), 8.69 (1H, s). |
| 1083 | 692 (M + H). | 1H-NMR (CDCl$_3$, 400 MHz) δ: 0.92 (3H, t, J = 7.4 Hz), 1.42 (3H, t, J = 7.2 Hz), 1.55-1.63 (2H, m), 2.50 (2H, t, J = 7.7 Hz), 3.29-3.49 (3H, m), 3.93 (1H, d, J = 14.1 Hz), 4.26-4.48 (5H, m), 4.70-4.72 (2H, m), 7.00-7.06 (5H, m), |

TABLE 452-continued

| Example No. | MS ESI m/e: | NMR |
|---|---|---|
| 1084 | 664 (M + H). | 7.34 (2H, d, J = 7.9 Hz), 7.95 (2H, d, J = 8.8 Hz), 8.80 (1H, s), 8.97 (1H, s). 1H-NMR (CDCl₃, 400 MHz) δ: 0.91 (3H, t, J = 15.0 Hz), 1.58-1.62 (2H, m), 2.53 (2H, t, J = 7.6 Hz), 3.34-3.36 (2H, m), 3.52 (1H, br s), 3.97 (1H, d, J = 13.7 Hz), 4.35-4.37 (3H, m), 4.67-4.69 (2H, m), 6.84 (1H, br s), 7.07 (4H, s), 7.35 (2H, d, J = 8.6 Hz), 7.92 (2H, d, J = 9.0 Hz), 8.85 (1H, s), 9.16 (1H, s). |

TABLE 453

| Example No. | MS ESI m/e: | NMR |
|---|---|---|
| 1085 | 715 (M + H). | 1H-NMR (CDCl₃, 300 MHz) δ: 3.08-3.42 (2H, m), 3.50 (1H, t, J = 12.2 Hz), 4.00 (1H, dt, J = 14.3, 3.3 Hz), 4.21-4.54 (1H, m), 4.27 (1H, dd, J = 14.5, 6.2 Hz), 4.49 (1H, dd, J = 14.9, 7.0 Hz), 4.56-4.79 (1H, m), 4.71 (1H, d, J = 2.3 Hz), 6.51 (1H, t, J = 73.3 Hz), 6.89-7.03 (3H, m), 7.12 (1H, t, J = 7.9 Hz), 7.84 (2H, d, J = 8.7 Hz), 8.03 (2H, d, J = 8.3 Hz), 8.87 (1H, s). |
| 1086 | 662 (M + H). | 1H-NMR (CDCl₃, 300 MHz) δ: 3.03 (1H, ddd, J = 14.2, 10.5, 2.9 Hz), 3.12 (1H, dd, J = 13.4, 4.3 Hz), 3.47 (1H, ddd, J = 14.8, 10.8, 3.1 Hz), 3.88-4.01 (2H, m), 4.40 (1H, dd, J = 15.1, 6.0 Hz), 4.48 (1H, dd, J = 15.1, 6.0 Hz), 4.55 (1H, d, J = 14.3 Hz), 4.64 (1H, br s), 6.69 (1H, d, J = 8.7 Hz), 6.97 (1H, t, J = 5.7 Hz), 7.11 (2H, d, J = 7.9 Hz), 7.22 (2H, d, J = 8.7 Hz), 7.65 (1H, d, J = 9.0 Hz), 7.80 (2H, d, J = 8.7 Hz), 8.01 (2H, d, J = 8.3 Hz). |
| 1087 | 729 (M + H). | 1H-NMR (CDCl₃, 300 MHz) δ: 3.14-3.37 (2H, m), 3.49 (1H, t, J = 11.9 Hz), 3.94 (1H, dt, J = 13.8, 3.4 Hz), 4.27-4.48 (1H, m), 4.33 (1H, dd, J = 14.7, 4.9 Hz), 4.48 (1H, dd, J = 15.1, 6.0 Hz), 4.48-4.73 (1H, m), 4.66 (1H, d, J = 3.0 Hz), 6.97 (1H, t, J = 5.5 Hz), 7.12 (2H, d, J = 8.7 Hz), 7.21 (2H, d, J = 7.9 Hz), 7.37 (2H, d, J = 8.3 Hz), 7.48 (1H, t, J = 72.1 Hz), 7.93 (2H, d, J = 8.7 Hz), 8.56 (1H, s). |
| 1088 | 721 (M + H). | 1H-NMR (CDCl₃, 300 MHz) δ: 1.26 (6H, d, J = 6.8 Hz), 3.03 (1H, td, J = 12.5, 3.4 Hz), 3.13-3.27 (2H, m), 3.59 (1H, dd, J = 14.3, 10.9, 3.0 Hz), 3.90 (2H, dd, J = 22.6, 13.2 Hz), 4.30 (1H, d, J = 13.2 Hz), 4.33-4.48 (2H, m), 4.68 (1H, d, J = 1.5 Hz), 6.10 (1H, s), 7.15 (2H, d, J = 7.9 Hz), 7.26 (2H, d, J = 8.3 Hz), 7.31 (2H, d, J = 8.3 Hz), 7.68 (1H, t, J = 5.7 Hz), 7.88 (2H, d, J = 8.7 Hz). |

TABLE 454

| Example No. | MS ESI m/e: | NMR |
|---|---|---|
| 1089 | 703 (M + H). | 1H-NMR (CDCl₃, 300 MHz) δ: 1.26 (6H, d, J = 7.2 Hz), 3.03 (1H, td, J = 12.2, 3.5 Hz), 3.14-3.26 (2H, m), 3.60 (1H, ddd, J = 13.8, 10.6, 2.9 Hz), 3.90 (2H, t, J = 15.4 Hz), 4.29-4.45 (2H, m), 4.30 (1H, d, J = 12.1 Hz), 4.67 (1H, d, J = 3.0 Hz), 6.09 (1H, s), 6.50 (1H, t, J = 73.7 Hz), 7.04 (2H, d, J = 8.7 Hz), 7.22 (2H, d, J = 8.3 Hz), 7.32 (2H, d, J = 7.9 Hz), 7.61 (1H, t, J = 6.0 Hz), 7.88 (2H, d, J = 8.3 Hz). |
| 1090 | 718 (M + H). | 1H-NMR (CD₃OD, 300 MHz) δ: 0.85-0.97 (2H, m), 1.01-1.07 (2H, m), 1.89-1.99 (1H, m), 3.38-3.45 (1H, m), 3.51-3.61 (1H, m), 3.79-4.04 (3H, m), 4.26 (2H, dd, J = 24.3, 15.3 Hz), 4.54-4.72 (2H, m), 7.06 (2H, d, J = 8.7 Hz), 7.25 (2H, d, J = 8.7 Hz), 7.41 (2H, d, J = 9.0 Hz), 7.96 (2H, d, J = 8.7 Hz). |
| 1091 | 736 (M + H). | 1H-NMR (CD₃OD, 300 MHz) δ: 1.51 (6H, s), 3.37-3.48 (1H, m), 3.54-3.64 (1H, m), 3.85-3.92 (2H, m), 4.02 (1H, d, J = 13.6 Hz), 4.26 (2H, dd, J = 22.8, 15.3 Hz), 4.53-4.72 (2H, m), 7.07 (2H, d, J = 8.3 Hz), 7.27 (2H, d, J = 8.7 Hz), 7.38-7.45 (2H, m), 7.94-8.01 (2H, m). |
| 1092 | 657 (M + H). | 1H-NMR (CD₃OD, 400 MHz) δ: 0.92 (3H, t, J = 7.3 Hz), 1.56-1.67 (2H, m), 2.19 (3H, s), 2.56 (2H, t, J = 7.1 Hz), 3.04-3.14 (1H, m), 3.25-3.35 (1H, m), 3.71-3.88 (3H, m), 4.16-4.26 (2H, m), 4.29 (1H, d, J = 14.8 Hz), 4.61 (1H, s), 5.27 (1H, s), 7.11 (4H, br s), 7.37 (2H, d, J = 8.8 Hz), 7.92 (2H, dd, J = 8.8, 1.3 Hz). |
| 1093 | 662 (M + H). | 1H-NMR (CD₃OD, 400 MHz) δ: 1.07 (3H, t, J = 7.1 Hz), 2.87 (3H, s), 3.20-3.34 (1H, m), 3.38 (2H, q, J = 7.1 Hz), 3.42-3.50 (1H, m), 3.76-3.95 (3H, m), 4.05-4.22 (2H, m), 4.37 (1H, d, J = 13.0 Hz), 4.59-4.60 (1H, m), 6.67 (2H, d, J = 8.6 Hz), 7.03 (2H, d, J = 8.8 Hz), 7.40 (2H, d, J = 8.8 Hz), 7.92 (2H, d, J = 8.8 Hz). |

TABLE 455

| Example No. | MS ESI m/e: | NMR |
|---|---|---|
| 1094 | 624 (M + H). | 1H-NMR (CD₃OD, 300 MHz) δ: 1.24 (6H, d, J = 6.8 Hz), 2.17 (3H, s), 2.61 (1H, td, J = 11.9, 3.5 Hz), 2.77-2.95 (2H, m), 3.53 (1H, d, J = 12.1 Hz), 3.69 (1H, dt, J = 18.0, 6.0 Hz), 3.83-3.91 (1H, m), 4.02 (1H, d, J = 12.4 Hz), 4.22-4.39 (2H, m), 4.63 (1H, br s), 4.66 (1H, s), 5.56 (1H, s), 7.13-7.19 (4H, m), 7.41 (2H, d, J = 8.3 Hz), 7.92-7.98 (2H, m), 8.41 (1H, t, J = 6.0 Hz). |
| 1095 | 691 (M + H). | 1H-NMR (CDCl₃, 400 MHz) δ: 1.31 (9H, s), 1.42 (9H, t, J = 19.9 Hz), 2.89-2.99 (1H, m), 3.04 (1H, dd, J = 13.4, 3.9 Hz), 3.31 (6H, q, J = 7.3 Hz), 3.43-3.53 (1H, m), 3.89 (1H, dt, J = 13.8, 3.4 Hz), 4.24-4.48 (5H, m), 4.61 (1H, s), 4.79 (1H, d, J = 13.7 Hz), 7.01 (1H, t, J = 5.9 Hz), 7.12 (2H, dt, J = 8.5, 2.1 Hz), 7.30-7.37 (4H, m), 7.91 (2H, dt, J = 9.5, 2.4 Hz), 8.23 (2H, dd, J = 6.4, 1.3 Hz). |
| 1096 | MS ESI(−) m/e: 645 (M − H). | 1H-NMR (CDCl₃, 400 MHz) δ: 0.99 (3H, t, J = 7.5 Hz), 2.14 (2H, dt, J = 22.6, 7.4 Hz), 2.56 (1H, dt, J = 17.8, 6.5 Hz), 2.88 (1H, d, J = 13.5 Hz), 3.18 (1H, q, J = 9.9 Hz), 3.55 (1H, d, J = 12.4 Hz), 3.71-3.93 (2H, m), 4.30-4.59 (5H, m), 5.41 (1H, d, J = 15.9 Hz), 5.68 (1H, d, J = 15.9 Hz), 6.97 (1H, t, J = 7.2 Hz), 7.29 (2H, d, J = 7.9 Hz), 7.33-7.48 (4H, m), 7.91 (2H, d, J = 7.9 Hz). |
| 1097 | 647 (M + H). | 1H-NMR (CDCl₃, 400 MHz) δ: 0.98 (3H, t, J = 7.9 Hz), 2.14 (2H, dt, J = 23.4, 8.2 Hz), 2.46 (1H, t, J = 13.8 Hz), 2.95 (1H, d, J = 13.5 Hz), 3.20 (1H, t, J = 13.0 Hz), 3.89 (1H, ddd, J = 16.3 Hz), 4.32-4.61 (5H, m), 5.07-5.27 (4H, m), 7.18 (1H, t, J = 4.5 Hz), 7.27-7.33 (2H, m), 7.40 (2H, d, J = 9.0 Hz), 7.45 (2H, d, J = 7.7 Hz), 7.93 (2H, d, J = 8.8 Hz). |
| 1098 | 707 (M + H). | 1H-NMR (CDCl₃, 300 MHz) δ: 3.15-3.36 (2H, m), 3.21 (2H, t, J = 5.5 Hz), 3.42-3.54 (1H, m), 3.89-3.99 (2H, m), 4.08 (2H, q, J = 5.1 Hz), 4.27-4.42 (1H, m), 4.34 (1H, dd, J = 14.9, 5.5 Hz), 4.49 (1H, d, J = 14.9, 6.6 Hz), 4.55-4.68 (2H, m), 6.94 (1H, t, J = 5.8 Hz), 7.11 (2H, d, J = 7.9 Hz), 7.20 (2H, d, J = 8.7 Hz), 7.37 (2H, d, J = 8.3 Hz), 7.94 (2H, d, J = 9.0 Hz), 8.70 (1H, s). |

TABLE 456

| Example No. | MS ESI m/e: | NMR |
|---|---|---|
| 1099 | 659 (M + H). | 1H-NMR (CDCl₃, 400 MHz) δ: 0.76-0.80 (2H, m), 1.02-1.07 (2H, m), 1.10-1.16 (2H, m), 1.17-1.22 (2H, m), 1.89-1.97 (1H, m), 2.21-2.29 (1H, m), 3.06-3.14 (1H, m), 3.17-3.25 (1H, m), 3.37-3.45 (1H, m), 3.93 (1H, d, J = 14.1 Hz), 4.27-4.51 (4H, m), 4.62 (1H, br s), 7.05 (1H, br s), 7.12 (2H, d, J = 8.1 Hz), 7.19 (2H, d, J = 8.8 Hz), 7.21 (2H, d, J = 8.8 Hz), 7.73 (2H, d, J = 8.6 Hz), 8.61 (1H, s). |
| 1100 | 687 (M + H). | 1H-NMR (CDCl₃, 300 MHz) δ: 0.74-0.82 (2H, m), 1.07-1.18 (2H, m), 1.89-1.99 (1H, m), 3.07-3.30 (2H, m), 3.33-3.48 (1H, m), 3.98 (1H, d, J = 13.9 Hz), 4.30-4.54 (4H, m), 4.65 (1H, br s), 7.02 (1H, t, J = 5.8 Hz), 7.13 (2H, d, J = 8.3 Hz), 7.18-7.24 (4H, m), 7.74 (2H, d, J = 8.7 Hz), 8.85 (1H, s). |
| 1101 | 704 (M + H). | 1H-NMR (CDCl₃, 300 MHz) δ: 1.02-1.08 (2H, m), 1.15-1.20 (2H, m), 2.20-2.29 (1H, m), 3.16-3.27 (1H, m), 3.29-3.37 (1H, m), 3.44-3.54 (1H, m), 3.95 (1H, d, J = 13.9 Hz), 4.20-4.33 (2H, m), 4.50 (1H, dd, J = 15.3, 6.6 Hz), 4.59-4.71 (2H, m), 6.94-7.04 (2H, m), 7.08 (1H, t, J = 5.8 Hz), 7.16 (1H, t, J = 7.5 Hz), 7.82 (2H, d, J = 8.7 Hz), 8.02 (2H, d, J = 8.3 Hz), 8.61 (1H, s). |
| 1102 | 721 (M + H). | 1H-NMR (CDCl₃, 400 MHz) δ: 1.01-1.08 (2H, m), 1.15-1.21 (2H, m), 2.25 (1H, tt, J = 8.1, 3.9 Hz), 3.15-3.37 (2H, m), 3.43-3.53 (1H, m), 3.92 (1H, dt, J = 14.1, 3.1 Hz), 4.21-4.69 (5H, m), 6.96 (1H, d, J = 8.3 Hz), 7.03 (1H, dd, J = 10.3, 2.0 Hz), 7.08-7.21 (2H, m), 7.37 (2H, d, J = 8.1 Hz), 7.94 (2H, dt, J = 9.5, 2.4 Hz), 8.62 (1H, s). |
| 1103 | 588 (M + H). | 1H-NMR (CDCl₃, 400 MHz) δ: 1.96-2.16 (3H, m), 2.36-2.47 (1H, m), 2.78-3.36 (2H, m), 3.61-3.89 (1H, m), 4.26-4.93 (5H, m), 6.99-7.14 (3H, m), 7.25-7.44 (3H, m), 7.90-7.96 (2H, m). |
| 1104 | 706 (M + H). | 1H-NMR (CDCl₃, 400 MHz) δ: 3.24-3.35 (2H, m), 3.48-3.62 (1H, m), 3.96-4.04 (1H, m), 4.12-4.25 (1H, m), 4.32-4.40 (1H, m), 4.44-4.70 (3H, m), 6.94-7.00 (1H, m), 7.14 (2H, d, J = 8.6 Hz), 7.24 (2H, d, J = 8.6 Hz), 7.38 (2H, d, J = 8.6 Hz), 7.94 (2H, d, J = 8.6 Hz), 8.87 (1H, s), 9.18 (1H, s). |

TABLE 457

| Example No. | MS ESI m/e: | NMR |
|---|---|---|
| 1105 | 709 (M + H). | 1H-NMR (CDCl₃, 300 MHz) δ: 2.48-2.56 (1H, m), 2.99-3.09 (1H, m), 3.16 (1H, dd, J = 13.4, 4.0 Hz), 3.46 (1H, ddd, J = 14.5, 11.3, 2.8 Hz), 3.92 (1H, d, J = 14.3 Hz), 4.10 (1H, d, J = 13.2 Hz), 4.30 (1H, d, J = 12.8 Hz), 4.39 (1H, d, J = 5.7 Hz), 4.46 (1H, d, J = 6.4 Hz), 4.53 (2H, d, J = 4.9 Hz), 4.61 (1H, d, J = 2.6 Hz), 6.42 (1H, s), 7.05 (1H, t, J = 6.8 Hz), 7.15 (2H, d, J = 8.3 Hz), 7.25 (2H, d, J = 9.0 Hz), 7.38 (2H, d, J = 8.3 Hz), 7.92 (2H, d, J = 9.0 Hz). |
| 1106 | 737 (M + H). | 1H-NMR (DMSO-d₆, 300 MHz) δ: 3.26-3.41 (1H, m), 3.60 (1H, dd, J = 13.8, 4.3 Hz), 3.77-3.85 (2H, m), 3.93-4.20 (2H, m), 4.42-4.51 (1H, m), 4.63 (1H, br s), 4.78 (2H, br s), 7.24 (4H, s), 7.51 (2H, d, J = 8.3 Hz), 7.93 (2H, d, J = 9.0 Hz), 8.37 (1H, s), 8.81 (1H, t, J = 5.7 Hz), 13.04 (1H, br s). |
| 1107 | 703 (M + H). | 1H-NMR (CDCl₃, 400 MHz) δ: 1.09-1.16 (2H, m), 1.28-1.35 (2H, m), 1.86-1.94 (1H, m), 3.14-3.23 (1H, m), 3.30 (1H, dd, J = 13.7, 4.4 Hz), 3.50 (1H, dt, J = 17.6, 6.3 Hz), 3.88-3.95 (1H, m), 4.08-4.18 (1H, m), 4.37 (1H, d, J = 14.8, 5.6 Hz), 4.48 (1H, dd, J = 14.7, 6.1 Hz), 4.52-4.60 (1H, m), 4.63-4.68 (1H, m), 6.90 (1H, t, J = 6.0 Hz), 7.13 (2H, d, J = 7.9 Hz), 7.22 (2H, d, J = 7.9 Hz), 7.81 (2H, d, J = 8.3 Hz), 8.01 (2H, d, J = 8.1 Hz), 12.08 (1H, br s). |

TABLE 457-continued

| Example No. | MS ESI m/e: | NMR |
|---|---|---|
| 1108 | 719 (M + H). | 1H-NMR (CDCl₃, 300 MHz) δ: 1.08-1.16 (2H, m), 1.28-1.35 (2H, m), 1.87-1.95 (1H, m), 3.13-3.23 (1H, m), 3.27 (1H, dd, J = 13.3, 3.9 Hz), 3.44-3.52 (1H, m), 3.87 (1H, dt, J = 14.8, 3.6 Hz), 4.09-4.20 (1H, m), 4.38 (1H, dd, J = 15.3, 5.2 Hz), 4.47 (1H, dd, J = 14.1, 5.5 Hz), 4.50-4.58 (1H, m), 4.59-4.64 (1H, m), 6.92 (1H, t, J = 5.4 Hz), 7.12 (2H, d, J = 7.9 Hz), 7.21 (2H, d, J = 8.6 Hz), 7.35 (2H, d, J = 7.9 Hz), 7.89-7.95 (2H, m), 12.20 (1H, br s). |
| 1109 | 706 (M + H). | 1H-NMR (DMSO-d₆, 400 MHz) δ: 3.35-3.48 (1H, m), 3.68 (1H, dd, J = 13.6, 4.5 Hz), 3.73-3.90 (2H, m), 4.00-4.73 (2H, br m), 4.09 (2H, d, J = 5.5 Hz), 4.68 (1H, s), 6.95-7.32 (4H, m), 7.51 (2H, d, J = 7.9 Hz), 7.94 (2H, d, J = 8.8 Hz), 8.77 (1H, s), 8.86 (1H, t, J = 6.1 Hz), 8.97 (1H, s), 12.80 (1H, br s). |

TABLE 458

| Example No. | MS ESI m/e: | NMR |
|---|---|---|
| 1110 | 721 (M + H). | 1H-NMR (CDCl₃, 400 MHz) δ: 1.01-1.09 (2H, m), 1.16-1.22 (2H, m), 2.21-2.29 (1H, m), 3.21-3.31 (1H, m), 3.40-3.52 (2H, m), 3.96 (1H, d, J = 14.1 Hz), 4.27-4.52 (3H, m), 4.68-4.79 (2H, m), 6.89 (1H, t, J = 5.4 Hz), 7.04-7.11 (3H, m), 7.14-7.21 (3H, m), 7.99 (1H, t, J = 8.4 Hz), 8.62 (1H, s). |
| 1111 | 650 (M + H). | 1H-NMR (CD₃OD, 400 MHz) δ: 3.24-3.29 (1H, m), 3.45 (1H, dd, J = 14.1, 4.6 Hz), 3.74-3.91 (2H, m), 4.15-4.33 (3H, m), 4.62 (1H, t, J = 3.7 Hz), 4.82 (1H, d, J = 13.7 Hz), 6.61-7.16 (4H, m), 7.43 (2H, d, J = 7.9 Hz), 7.98 (2H, dt, J = 9.5, 2.4 Hz), 8.08 (1H, d, J = 1.2 Hz), 8.63 (1H, d, J = 1.2 Hz), 8.78 (1H, t, J = 5.8 Hz). |
| 1112 | 751 (M + H). | 1H-NMR (DMSO-d₆, 300 MHz) δ: 2.67 (2H, t, J = 7.2 Hz), 3.26-3.42 (1H, m), 3.59 (1H, dd, J = 13.8, 4.3 Hz), 3.76-3.84 (2H, m), 3.96 (1H, d, J = 13.9 Hz), 4.04-4.21 (2H, m), 4.30 (2H, t, J = 7.5 Hz), 4.47 (1H, d, J = 14.7 Hz), 4.61-4.65 (1H, m), 7.23 (4H, m), 7.38 (1H, dd, J = 13.2, 9.0 Hz), 7.52 (2H, d, J = 7.9 Hz), 7.93 (2H, d, J = 9.0 Hz), 8.36 (1H, s), 8.82 (1H, t, J = 6.2 Hz), 12.33 (1H, br s). |
| 1113 | 719 (M + H). | 1H-NMR (CDCl₃, 300 MHz) δ: 1.08-1.15 (2H, m), 1.27-1.34 (2H, m), 1.86-1.95 (1H, m), 3.14-3.24 (1H, m), 3.29 (1H, dd, J = 13.9, 4.0 Hz), 3.42-3.52 (1H, m), 3.88 (1H, dt, J = 15.0, 3.8 Hz), 4.06-4.17 (1H, m), 4.32 (1H, dd, J = 14.8, 5.7 Hz), 4.46 (1H, d, J = 14.8, 5.7 Hz), 4.55 (1H, dd, J = 13.9, 0.4 Hz), 4.60-4.65 (1H, m), 6.51 (1H, t, J = 73.4 Hz), 6.95 (1H, d, J = 8.6 Hz), 6.98-7.04 (2H, m), 7.13 (1H, t, J = 8.2 Hz), 7.36 (2H, d, J = 8.2 Hz), 7.93 (2H, d, J = 9.0 Hz), 12.16 (1H, br s). |
| 1114 | 703 (M + H). | 1H-NMR (CDCl₃, 300 MHz) δ: 1.08-1.15 (2H, m), 1.27-1.33 (2H, m), 1.84-1.92 (1H, m), 3.15-3.24 (1H, m), 3.31 (1H, dd, J = 13.8, 4.5 Hz), 3.42-3.53 (1H, m), 3.87-3.95 (1H, m), 4.03-4.15 (1H, m), 4.30 (1H, dd, J = 15.0, 5.5 Hz), 4.47 (1H, dd, J = 15.1, 6.5 Hz), 4.52-4.61 (1H, m), 4.64-4.68 (1H, m), 6.51 (1H, t, J = 73.3 Hz), 6.91-7.03 (3H, m), 7.13 (1H, t, J = 8.2 Hz), 7.81 (2H, d, J = 8.4 Hz), 8.01 (2H, d, J = 8.2 Hz), 11.89 (1H, br s). |

TABLE 459

| Example No. | MS ESI m/e: | NMR |
|---|---|---|
| 1115 | 512 (M + H). | 1H-NMR (CDCl$_3$, 400 MHz) δ: 1.30 (6H, d, J = 7.0 Hz), 2.15 (3H, s), 2.37-2.46 (1H, m), 2.82 (1H, dd, J = 13.7, 4.4 Hz), 2.96-3.06 (1H, m), 3.14-3.23 (1H, m), 3.84 (1H, d, J = 14.4 Hz), 4.29 (1H, d, J = 14.1 Hz), 4.46-4.53 (3H, m), 4.57 (1H, dd, J = 15.4, 6.1 Hz), 7.14 (1H, t, J = 6.3 Hz), 7.35 (2H, d, J = 7.9 Hz), 7.43 (2H, d, J = 8.3 Hz), 7.62 (2H, d, J = 8.1 Hz), 7.78 (2H, d, J = 8.3 Hz). |

The evaluation of the HCV polymerase inhibitory activity of the compound of the present invention is explained in the following. This polymerase is an enzyme coded for by the non-structural protein region called NS5B on the genome RNA of HCV.

Experimental Example

[I] Assay of Enzyme Inhibitory Activity i) Preparation of Enzyme (HCV Polymerase)

Using, as a template, a cDNA clone corresponding to the full length genome RNA of HCV BK strain (type 1b) obtained from the blood of a patient with hepatitis C, a region encoding NS5B (J Virol 1991 March, 65(3), 1105-13, 544 amino acids after deletion of 47 amino acids on the C-terminal) was amplified by PCR. The objective gene was prepared by adding a 6 His tag {base pair encoding 6 continuous histidine (His)} to the 3' end thereof and transformed to *Escherichia coli*. The *Escherichia coli* capable of producing the objective protein was cultured. The obtained cells were suspended in a buffer solution and crushed in a microfluidizer. The supernatant was obtained by centrifugation and applied to various column chromatographys {mono-S, Sephacryl S-200 (Pharmacia)}, inclusive of metal chelate chromatography, to give a standard enzyme product.

Standard enzyme products for type 1a (cloned from the blood of patients) were also obtained by a similar method.

The amino acids sequence (from N-terminal to 544 amino acids+GS+6H is tag) is shown below.

```
                                             (SEQ ID NO: 1)
SMSYSWTGALITPCAAEEQKLPINALSNSLLRHHNLVYSTTSRSACQRQK

KVTFDRLQVLDSHYQDVLKEVKAAASKVKANLLSVEEACSLTPPHSARSK

FGYGAKDVRCHARKAVNHINSVWKDLLEDSVTPIDTTIMAKNEVFCVQPE

KGGRKPARLIVFPDLGVRVCEKMALYDVVSKLPLAVMGSSYGFQYSPGQR

VEFLVQAWKSKRTPMGFSYDTRCFDSTVTESDIRTEEAIYQCCDLDPQAR

VAIKLSTERLYVGGPLTNSRGENCGYRRCRASGVLTTSCGNTLTCYIKAQ

AACRAAGLQDCTMLVCGDDLVVICESAGVQEDAASLRAFTEAMTRYSAPP

GDPPQPEYDLELITSCSSNVSVAHDGAGKRVYYLTRDPTTPLARAAWETA

RHTPVNSWLGNIIMFAPTLWVRMILLTHFFSVLIARDQLEQALDCEIYGA

CYSIEPLDLPPIIQRLHGLSAFSLHSYSPGEINRVAACLRKLGVPPLRAW

RHRARSVRAKLLSRGGRAAICGKYLFNWAVKTKLKLTPIAAAGQGSHHHH

HH
``` ii) Synthesis of Substrate RNA

Using a synthetic primer designed based on the sequence of HCV genomic 3' untranslated region, a DNA fragment (148 bp) containing polyU and 3'X sequence was entirely synthesized and cloned into plasmid pBluescript SK II(+) (Stratagene). The cDNA encoding full length NS5B, which was prepared in i) above, was digested with restriction enzyme KpnI to give a cDNA fragment containing the nucleotide sequence of from the restriction enzyme cleavage site to the termination codon. This cDNA fragment was inserted into the upstream of 3' untranslated region of the DNA in pBluescript SK II(+) and ligated. The about 450 bp inserted DNA sequence was used as a template in the preparation of substrate RNA. This plasmid was cleaved immediately after the 3'X sequence, linearized and purified by phenol-chloroform treatment and ethanol precipitation to give DNA.

RNA was synthesized (37° C., 4 hr) by run-off method using this purified DNA as a template, a promoter of pBluescript SK II(+), MEGAscript RNA synthesis kit (Ambion) and T7 RNA polymerase. DNase I was added and the mixture was incubated for 1 hr. The template DNA was removed by decomposition to give a crude RNA product. This crude product was treated with phenol-chloroform and purified by ethanol precipitation to give the objective substrate RNA.

This RNA was applied to urea denaturation polyacrylamide gel electrophoresis to confirm the quality thereof and preserved at −80° C.

iii) Assay of Enzyme (HCV Polymerase) inhibitory activity

A test substance (compound of the present invention) and a reaction mixture (30 μl) having the following composition were reacted at 25° C. for 60 min.

10% Trichloroacetic acid and 1% sodium pyrophosphate solution (150 μl) at 4° C. was added to this reaction mixture to stop the reaction. The reaction mixture was left standing at 4° C. for 15 min to insolubilize RNA. This RNA was trapped on a glass filter (PerkinElmer, GF/B) upon filtration by suction. This filter was washed with a solution containing 1% trichloroacetic acid and 0.1% sodium pyrophosphate, washed with 90% ethanol and dried. A liquid scintillation cocktail (PerkinElmer) was added and the radioactivity of RNA synthesized by the enzyme reaction was measured on a liquid scintillation counter.

The HCV polymerase inhibitory activity (IC$_{50}$) of the compound of the present invention was calculated from the values of radioactivity of the enzyme reaction with and without the test substance.

The results are shown in Tables 460-497. IC$_{50}$ shows the following ranges.

A: not less than 1 μM
B: not less than 0.1 μM and less than 1 μM
C: less than 0.1 μM A preferable compound of the present invention is a compound having an HCV polymerase inhibitory activity (IC$_{50}$) of less than 0.1 μM.

In addition, a compound showing high inhibitory activity for both type 1a and type 1b is preferable, and a compound showing a high inhibitory activity of less than 0.1 μM for both type 1a and type 1b enzymes is one of the most preferable embodiments.

Reaction mixture: HCV polymerase (type 1b 0.5 μg/ml or type 1a 1.5 μg/m) obtained in i), substrate RNA (5 μg/ml) obtained in ii), ATP (50 μM), GTP (50 μM), CTP (50 μM), UTP (2 μM), [5,6-$^3$H]UTP (30-60 Ci/mmol (Amersham Biosciences), 1 μCi) 20 mM Tris-HCl (pH 7.5), EDTA (1 mM), MgCl$_2$ (5 mM), NaCl (50 mM), DTT (1 mM), BSA (0.01%)

TABLE 460

| Example No. | 1a | 1b |
|---|---|---|
| 1 | A | A |
| 2 | B | B |
| 3 | C | C |
| 4 | B | B |
| 5 | A | A |
| 6 | C | C |
| 7 | C | C |
| 8 | C | C |
| 9 | C | C |
| 10 | C | C |
| 11 | C | C |
| 12 | C | C |
| 13 | C | C |
| 14 | C | C |
| 15 | A | A |
| 16 | A | A |
| 17 | A | A |
| 18 | B | B |
| 19 | A | A |
| 20 | A | A |
| 21 | A | A |
| 22 | A | A |
| 23 | A | A |
| 24 | A | A |
| 25 | A | A |
| 26 | A | A |
| 27 | A | A |
| 28 | A | A |
| 29 | A | A |
| 30 | A | A |

TABLE 461

| Example No. | 1a | 1b |
|---|---|---|
| 31 | A | A |
| 32 | A | A |
| 33 | A | A |
| 34 | A | A |
| 35 | A | A |
| 36 | B | A |
| 37 | B | B |
| 38 | A | A |
| 39 | A | A |
| 40 | A | A |
| 41 | A | A |
| 42 | A | A |
| 43 | A | A |
| 44 | A | A |
| 45 | A | A |
| 46 | A | A |
| 47 | A | A |
| 48 | A | A |
| 49 | A | A |
| 50 | A | A |
| 51 | A | A |
| 52 | A | A |
| 53 | B | B |
| 54 | A | A |
| 55 | A | A |
| 56 | A | A |
| 57 | A | A |
| 58 | A | A |
| 59 | A | A |
| 60 | A | A |

TABLE 462

| Example No. | 1a | 1b |
|---|---|---|
| 61 | A | A |
| 62 | A | A |
| 63 | A | A |
| 64 | A | A |
| 65 | A | A |
| 66 | A | A |
| 67 | A | A |
| 68 | B | B |
| 69 | A | A |
| 70 | A | A |
| 71 | A | A |
| 72 | A | B |
| 73 | A | A |
| 74 | A | A |
| 75 | A | A |
| 76 | A | A |
| 77 | A | A |
| 78 | A | A |
| 79 | A | A |
| 80 | A | A |
| 81 | A | A |
| 82 | A | A |
| 83 | A | A |
| 84 | A | A |
| 85 | B | A |
| 86 | A | A |
| 87 | A | A |
| 88 | A | A |
| 89 | A | A |
| 90 | A | A |

TABLE 463

| Example No. | 1a | 1b |
|---|---|---|
| 91 | A | A |
| 92 | A | A |
| 93 | A | A |
| 94 | A | A |
| 95 | A | A |
| 96 | A | A |
| 97 | A | A |
| 98 | A | A |
| 99 | A | A |
| 100 | A | A |
| 101 | A | A |
| 102 | A | A |
| 103 | A | A |
| 104 | A | A |
| 105 | A | A |
| 106 | A | A |
| 107 | A | A |
| 108 | A | A |
| 109 | A | A |
| 110 | A | A |
| 111 | A | A |
| 112 | A | A |
| 113 | A | A |
| 114 | A | A |
| 115 | A | A |
| 116 | A | A |
| 117 | B | B |
| 118 | A | A |
| 119 | A | A |
| 120 | A | A |

TABLE 464

| Example No. | 1a | 1b |
|---|---|---|
| 121 | A | A |
| 122 | A | A |
| 123 | A | A |
| 124 | A | A |
| 125 | A | A |
| 126 | A | A |
| 127 | A | A |
| 128 | A | A |
| 129 | A | A |
| 130 | A | A |
| 131 | A | B |
| 132 | A | A |
| 133 | A | A |
| 134 | A | A |
| 135 | A | A |
| 136 | A | A |
| 137 | C | C |
| 138 | A | A |
| 139 | B | B |
| 140 | A | A |
| 141 | A | A |
| 142 | A | A |
| 143 | A | A |
| 144 | B | B |
| 145 | A | A |
| 146 | A | B |
| 147 | A | B |
| 148 | A | A |
| 149 | A | A |
| 150 | A | A |

TABLE 465

| Example No. | 1a | 1b |
|---|---|---|
| 151 | A | A |
| 152 | A | A |
| 153 | A | A |
| 154 | B | B |
| 155 | A | A |
| 156 | A | A |
| 157 | A | A |
| 158 | A | A |
| 159 | A | A |
| 160 | B | B |
| 161 | A | A |
| 162 | A | A |
| 163 | B | B |
| 164 | A | A |
| 165 | A | A |
| 166 | A | A |
| 167 | A | A |
| 168 | A | A |
| 169 | A | A |
| 170 | A | A |
| 171 | A | A |
| 172 | A | B |
| 173 | B | B |
| 174 | B | B |
| 175 | B | B |
| 176 | B | B |
| 177 | B | B |
| 178 | B | B |
| 179 | B | B |
| 180 | A | B |

TABLE 466

| Example No. | 1a | 1b |
|---|---|---|
| 181 | A | A |
| 182 | B | B |
| 183 | B | B |
| 184 | B | B |
| 185 | A | B |
| 186 | A | B |
| 187 | A | A |
| 188 | B | B |
| 189 | A | A |
| 190 | A | B |
| 191 | B | B |
| 192 | B | B |
| 193 | B | B |
| 194 | C | C |
| 195 | B | B |
| 196 | A | A |
| 197 | A | A |
| 198 | A | A |
| 199 | A | B |
| 200 | A | B |
| 201 | A | A |
| 202 | A | B |
| 203 | B | C |
| 204 | B | B |
| 205 | C | C |
| 206 | B | B |
| 207 | C | C |
| 208 | C | C |
| 209 | A | A |
| 210 | A | A |

TABLE 467

| Example No. | 1a | 1b |
|---|---|---|
| 211 | B | B |
| 212 | B | C |
| 213 | B | B |
| 214 | B | B |
| 215 | B | C |
| 216 | B | B |
| 217 | A | A |
| 218 | B | B |
| 219 | C | C |
| 220 | C | C |
| 221 | A | A |
| 222 | B | B |
| 223 | B | B |
| 224 | A | A |
| 225 | B | B |
| 226 | A | A |
| 227 | B | B |
| 228 | B | B |
| 229 | C | C |
| 230 | C | C |
| 231 | A | A |
| 232 | B | B |
| 233 | A | A |
| 234 | A | A |
| 235 | A | A |
| 236 | B | B |
| 237 | C | C |
| 238 | A | B |
| 239 | A | B |
| 240 | B | C |

TABLE 468

| Example No. | 1a | 1b |
|---|---|---|
| 241 | B | B |
| 242 | B | B |
| 243 | A | A |
| 244 | B | B |
| 245 | A | B |
| 246 | A | B |
| 247 | B | C |
| 248 | A | B |
| 249 | A | A |
| 250 | B | B |
| 251 | A | A |
| 252 | B | B |
| 253 | C | C |
| 254 | B | C |
| 255 | C | C |
| 256 | B | B |
| 257 | C | C |
| 258 | C | C |
| 259 | B | C |
| 260 | B | B |
| 261 | A | B |
| 262 | A | A |
| 263 | B | B |
| 264 | C | C |
| 265 | A | A |
| 266 | B | B |
| 267 | A | B |
| 268 | A | B |
| 269 | A | A |
| 270 | A | B |

TABLE 469

| Example No. | 1a | 1b |
|---|---|---|
| 271 | A | A |
| 272 | A | B |
| 273 | A | B |
| 274 | A | B |
| 275 | B | B |
| 276 | B | B |
| 277 | A | B |
| 278 | C | C |
| 279 | B | B |
| 280 | B | B |
| 281 | B | C |
| 282 | B | C |
| 283 | A | A |
| 284 | B | C |
| 285 | B | C |
| 286 | B | B |
| 287 | C | C |
| 288 | B | B |
| 289 | A | A |
| 290 | A | B |
| 291 | C | C |
| 292 | B | C |
| 293 | B | B |
| 294 | C | C |
| 295 | C | C |
| 296 | C | C |
| 297 | C | C |
| 298 | B | B |
| 299 | C | C |
| 300 | C | C |

TABLE 470

| Example No. | 1a | 1b |
|---|---|---|
| 301 | C | C |
| 302 | B | C |
| 303 | C | C |
| 304 | B | B |
| 305 | B | C |
| 306 | B | B |
| 307 | B | C |
| 308 | A | A |
| 309 | C | C |
| 310 | B | C |
| 311 | B | B |
| 312 | A | B |
| 313 | C | C |
| 314 | B | B |
| 315 | B | C |
| 316 | B | B |
| 317 | B | B |
| 318 | C | C |
| 319 | A | B |
| 320 | A | A |
| 321 | C | C |
| 322 | C | C |
| 323 | C | C |
| 324 | C | B |
| 325 | A | B |
| 326 | B | B |
| 327 | C | C |
| 328 | C | C |
| 329 | C | C |
| 330 | A | B |

TABLE 471

| Example No. | 1a | 1b |
|---|---|---|
| 331 | C | C |
| 332 | B | C |
| 333 | C | C |
| 334 | A | A |
| 335 | C | C |
| 336 | A | A |
| 337 | A | B |
| 338 | A | B |
| 339 | C | C |
| 340 | C | C |
| 341 | C | C |
| 342 | A | B |
| 343 | C | C |
| 344 | C | C |
| 345 | A | B |
| 346 | A | A |
| 347 | B | B |
| 348 | B | B |
| 349 | A | B |
| 350 | A | A |
| 351 | A | A |
| 352 | A | B |
| 353 | B | B |
| 354 | C | C |
| 355 | C | C |
| 356 | C | C |
| 357 | A | B |
| 358 | C | C |
| 359 | C | C |
| 360 | C | C |

TABLE 472

| Example No. | 1a | 1b |
|---|---|---|
| 361 | C | C |
| 362 | A | B |
| 363 | C | C |
| 364 | C | C |
| 365 | C | C |
| 366 | C | C |
| 367 | C | C |
| 368 | A | B |
| 369 | C | C |
| 370 | B | C |
| 371 | B | B |
| 372 | B | C |
| 373 | A | B |
| 374 | C | C |
| 375 | C | C |
| 376 | C | C |
| 377 | C | C |
| 378 | C | C |
| 379 | C | C |
| 380 | C | C |
| 381 | C | C |
| 382 | B | B |
| 383 | C | C |
| 384 | B | B |
| 385 | C | C |
| 386 | C | C |
| 387 | C | C |
| 388 | B | C |
| 389 | B | C |
| 390 | B | C |

TABLE 473

| Example No. | 1a | 1b |
|---|---|---|
| 391 | B | B |
| 392 | A | A |
| 393 | A | A |
| 394 | C | C |
| 395 | A | A |
| 396 | A | A |
| 397 | A | A |
| 398 | B | C |
| 399 | C | C |
| 400 | C | C |
| 401 | A | B |
| 402 | A | A |
| 403 | A | A |
| 404 | A | A |
| 405 | A | A |
| 406 | C | C |
| 407 | B | C |
| 408 | C | C |
| 409 | B | B |
| 410 | C | B |
| 411 | C | C |
| 412 | C | B |
| 413 | B | C |
| 414 | C | C |
| 415 | C | C |
| 416 | B | C |
| 417 | C | C |
| 418 | A | A |
| 419 | B | B |
| 420 | A | A |

TABLE 474

| Example No. | 1a | 1b |
|---|---|---|
| 421 | A | A |
| 422 | A | A |
| 423 | C | C |
| 424 | C | C |
| 425 | C | C |
| 426 | A | B |
| 427 | A | A |
| 428 | C | C |
| 429 | C | C |
| 430 | B | B |
| 431 | B | B |
| 432 | C | C |
| 433 | A | A |
| 434 | C | C |
| 435 | C | C |
| 436 | C | C |
| 437 | C | C |
| 438 | C | C |
| 439 | A | B |
| 440 | C | C |
| 441 | C | C |
| 442 | B | C |
| 443 | B | C |
| 444 | B | B |
| 445 | B | C |
| 446 | B | C |
| 447 | B | C |
| 448 | C | C |
| 449 | C | C |
| 450 | C | C |

TABLE 475

| Example No. | 1a | 1b |
|---|---|---|
| 451 | C | C |
| 452 | C | C |
| 453 | C | C |
| 454 | C | C |
| 455 | C | C |
| 456 | C | C |
| 457 | C | C |
| 458 | C | C |
| 459 | C | C |
| 460 | C | C |
| 461 | C | C |
| 462 | C | C |
| 463 | A | A |
| 464 | C | C |
| 465 | C | C |
| 466 | C | C |
| 467 | C | B |
| 468 | C | C |
| 469 | B | B |
| 470 | B | B |
| 471 | B | C |
| 472 | C | C |
| 473 | C | C |
| 474 | C | C |
| 475 | B | C |
| 476 | B | B |
| 477 | A | A |
| 478 | C | C |
| 479 | C | C |
| 480 | C | C |

TABLE 476

| Example No. | 1a | 1b |
|---|---|---|
| 481 | B | B |
| 482 | B | C |
| 483 | A | A |
| 484 | B | C |
| 485 | C | C |
| 486 | C | C |
| 487 | C | C |
| 488 | B | C |
| 489 | A | A |
| 490 | C | B |
| 491 | C | C |
| 492 | A | B |
| 493 | B | B |
| 494 | C | C |
| 495 | A | B |
| 496 | A | A |
| 497 | A | A |
| 498 | B | B |
| 499 | C | C |
| 500 | C | C |
| 501 | C | C |
| 502 | B | B |
| 503 | B | C |
| 504 | C | C |
| 505 | C | C |
| 506 | C | C |
| 507 | C | C |
| 508 | C | C |
| 509 | C | C |
| 510 | C | C |

TABLE 477

| Example No. | 1a | 1b |
|---|---|---|
| 511 | C | C |
| 512 | C | C |
| 513 | C | C |
| 514 | C | C |
| 515 | C | C |
| 516 | C | C |
| 517 | C | C |
| 518 | C | C |
| 519 | B | B |
| 520 | A | B |
| 521 | A | B |
| 522 | C | C |
| 523 | B | B |
| 524 | C | C |
| 525 | C | C |
| 526 | B | B |
| 527 | B | B |
| 528 | B | C |
| 529 | C | C |
| 530 | B | C |
| 531 | C | C |
| 532 | C | C |
| 533 | A | A |
| 534 | C | C |
| 535 | C | C |
| 536 | B | C |
| 537 | C | C |
| 538 | C | C |
| 539 | B | B |
| 540 | A | A |

TABLE 478

| Example No. | 1a | 1b |
|---|---|---|
| 541 | B | B |
| 542 | C | C |
| 543 | C | C |
| 544 | C | C |
| 545 | C | C |
| 546 | C | C |
| 547 | C | C |
| 548 | C | C |
| 549 | C | C |
| 550 | B | B |
| 551 | B | B |
| 552 | A | B |
| 553 | C | C |
| 554 | B | C |
| 555 | B | B |
| 556 | C | C |
| 557 | C | C |
| 558 | B | C |
| 559 | C | C |
| 560 | C | C |
| 561 | C | C |
| 562 | C | C |
| 563 | C | C |
| 564 | C | C |
| 565 | B | C |
| 566 | B | C |
| 567 | B | C |
| 568 | A | A |
| 569 | B | C |
| 570 | C | C |

TABLE 479

| Example No. | 1a | 1b |
|---|---|---|
| 571 | C | C |
| 572 | C | C |
| 573 | C | C |
| 574 | C | C |
| 575 | C | C |
| 576 | C | C |
| 577 | C | C |
| 578 | C | C |
| 579 | C | C |
| 580 | C | C |
| 581 | C | C |
| 582 | B | B |
| 583 | C | C |
| 584 | C | C |
| 585 | B | B |
| 586 | C | C |
| 587 | B | C |
| 588 | C | C |
| 589 | C | C |
| 590 | C | C |
| 591 | C | C |
| 592 | C | C |
| 593 | C | C |
| 594 | C | C |
| 595 | C | C |
| 596 | C | C |
| 597 | C | C |
| 598 | B | B |
| 599 | B | A |
| 600 | C | C |

TABLE 480

| Example No. | 1a | 1b |
|---|---|---|
| 601 | C | C |
| 602 | C | C |
| 603 | B | B |
| 604 | B | C |
| 605 | C | C |
| 606 | C | C |
| 607 | B | B |
| 608 | B | B |
| 609 | A | B |
| 610 | B | B |
| 611 | A | A |
| 612 | A | B |
| 613 | A | A |
| 614 | B | B |
| 615 | C | C |
| 616 | C | C |
| 617 | C | C |
| 618 | C | C |
| 619 | C | C |
| 620 | C | C |
| 621 | A | A |
| 622 | C | B |
| 623 | C | B |
| 624 | A | B |
| 625 | C | C |
| 626 | C | C |
| 627 | C | C |
| 628 | B | C |
| 629 | B | C |
| 630 | C | C |

TABLE 481

| Example No. | 1a | 1b |
|---|---|---|
| 631 | C | C |
| 632 | C | C |
| 633 | C | C |
| 634 | B | A |
| 635 | A | B |
| 636 | A | A |
| 637 | A | A |
| 638 | C | C |
| 639 | A | B |
| 640 | C | C |
| 641 | B | B |
| 642 | A | A |
| 643 | A | A |
| 644 | A | A |
| 645 | A | A |
| 646 | A | A |
| 647 | A | B |
| 648 | C | C |
| 649 | A | A |
| 650 | B | C |
| 651 | C | C |
| 652 | C | C |
| 653 | C | C |
| 654 | A | A |
| 655 | B | B |
| 656 | C | C |
| 657 | C | C |
| 658 | C | C |
| 659 | C | C |
| 660 | C | C |

TABLE 482

| Example No. | 1a | 1b |
|---|---|---|
| 661 | C | C |
| 662 | A | B |
| 663 | C | C |

TABLE 482-continued

| Example No. | 1a | 1b |
|---|---|---|
| 664 | C | C |
| 665 | A | A |
| 666 | A | A |
| 667 | A | B |
| 668 | A | A |
| 669 | A | A |
| 670 | A | A |
| 671 | A | A |
| 672 | A | A |
| 673 | A | A |
| 674 | A | A |
| 675 | A | A |
| 676 | C | C |
| 677 | A | A |
| 678 | A | A |
| 679 | A | A |
| 680 | A | B |
| 681 | A | A |
| 682 | A | A |
| 683 | C | C |
| 684 | B | B |
| 685 | B | B |
| 686 | C | C |
| 687 | C | C |
| 688 | B | B |
| 689 | C | C |
| 690 | C | C |

TABLE 483

| Example No. | 1a | 1b |
|---|---|---|
| 691 | C | C |
| 692 | C | C |
| 693 | A | B |
| 694 | C | C |
| 695 | C | C |
| 696 | C | C |
| 697 | C | C |
| 698 | C | C |
| 699 | C | C |
| 700 | C | C |
| 701 | C | C |
| 702 | A | A |
| 703 | A | A |
| 704 | C | C |
| 705 | A | A |
| 706 | A | A |
| 707 | C | C |
| 708 | C | C |
| 709 | C | C |
| 710 | B | B |
| 711 | B | C |
| 712 | C | C |
| 713 | C | C |
| 714 | C | C |
| 715 | C | C |
| 716 | A | A |
| 717 | A | A |
| 718 | A | B |
| 719 | A | A |
| 720 | C | C |

TABLE 484

| Example No. | 1a | 1b |
|---|---|---|
| 721 | A | A |
| 722 | B | C |
| 723 | B | C |
| 724 | C | C |
| 725 | C | C |
| 726 | C | C |

TABLE 484-continued

| Example No. | 1a | 1b |
|---|---|---|
| 727 | C | C |
| 728 | B | B |
| 729 | C | C |
| 730 | C | C |
| 731 | C | C |
| 732 | C | C |
| 733 | B | B |
| 734 | B | B |
| 735 | C | C |
| 736 | C | C |
| 737 | C | C |
| 738 | C | C |
| 739 | C | C |
| 740 | C | C |
| 741 | B | C |
| 742 | B | C |
| 743 | C | C |
| 744 | C | C |
| 745 | C | C |
| 746 | C | C |
| 747 | C | C |
| 748 | C | C |
| 749 | C | C |
| 750 | C | C |

TABLE 485

| Example No. | 1a | 1b |
|---|---|---|
| 751 | C | C |
| 752 | C | C |
| 753 | C | C |
| 754 | C | C |
| 755 | C | C |
| 756 | C | C |
| 757 | C | C |
| 758 | C | C |
| 759 | C | C |
| 760 | C | C |
| 761 | C | C |
| 762 | C | C |
| 763 | C | C |
| 764 | C | C |
| 765 | C | C |
| 766 | B | C |
| 767 | C | C |
| 768 | C | C |
| 769 | C | C |
| 770 | C | C |
| 771 | C | C |
| 772 | C | C |
| 773 | C | C |
| 774 | C | C |
| 775 | C | C |
| 776 | C | C |
| 777 | C | C |
| 778 | C | C |
| 779 | C | C |
| 780 | B | C |

TABLE 486

| Example No. | 1a | 1b |
|---|---|---|
| 781 | C | C |
| 782 | C | C |
| 783 | A | A |
| 784 | C | C |
| 785 | C | C |
| 786 | C | C |
| 787 | C | C |

TABLE 486-continued

| Example No. | 1a | 1b |
|---|---|---|
| 788 | C | C |
| 789 | C | C |
| 790 | C | C |
| 791 | C | C |
| 792 | C | C |
| 793 | C | C |
| 794 | C | C |
| 795 | C | C |
| 796 | C | C |
| 797 | C | C |
| 798 | B | C |
| 799 | C | C |
| 800 | C | C |
| 801 | C | C |
| 802 | C | C |
| 803 | C | C |
| 804 | A | A |
| 805 | C | C |
| 806 | C | C |
| 807 | C | C |
| 808 | C | C |
| 809 | C | C |
| 810 | C | C |

TABLE 487

| Example No. | 1a | 1b |
|---|---|---|
| 811 | B | B |
| 812 | C | C |
| 813 | C | C |
| 814 | C | C |
| 815 | C | C |
| 816 | C | C |
| 817 | C | C |
| 818 | C | C |
| 819 | C | C |
| 820 | C | C |
| 821 | C | C |
| 822 | C | C |
| 823 | B | B |
| 824 | C | C |
| 825 | C | C |
| 826 | C | C |
| 827 | C | C |
| 828 | C | C |
| 829 | B | C |
| 830 | B | C |
| 831 | A | A |
| 832 | C | C |
| 833 | A | A |
| 834 | B | B |
| 835 | C | C |
| 836 | C | C |
| 837 | A | A |
| 838 | A | A |
| 839 | C | C |
| 840 | C | C |

TABLE 488

| Example No. | 1a | 1b |
|---|---|---|
| 841 | C | C |
| 842 | C | C |
| 843 | C | C |
| 844 | C | C |
| 845 | C | C |
| 846 | B | C |
| 847 | C | C |

TABLE 488-continued

| Example No. | 1a | 1b |
| --- | --- | --- |
| 848 | C | C |
| 849 | B | C |
| 850 | C | C |
| 851 | C | C |
| 852 | C | C |
| 853 | A | B |
| 854 | C | C |
| 855 | C | C |
| 856 | B | C |
| 857 | C | C |
| 858 | C | C |
| 859 | B | C |
| 860 | C | C |
| 861 | C | C |
| 862 | C | C |
| 863 | C | C |
| 864 | B | C |
| 865 | C | C |
| 866 | C | C |
| 867 | B | B |
| 868 | C | C |
| 869 | C | C |
| 870 | C | C |

TABLE 489

| Example No. | 1a | 1b |
| --- | --- | --- |
| 871 | C | C |
| 872 | C | C |
| 873 | C | C |
| 874 | C | C |
| 875 | C | C |
| 876 | C | C |
| 877 | C | C |
| 878 | C | C |
| 879 | C | C |
| 880 | C | C |
| 881 | C | C |
| 882 | B | C |
| 883 | C | C |
| 884 | C | C |
| 885 | C | C |
| 886 | C | C |
| 887 | C | C |
| 888 | C | C |
| 889 | A | A |
| 890 | C | C |
| 891 | C | C |
| 892 | C | C |
| 893 | C | C |
| 894 | C | C |
| 895 | C | C |
| 896 | C | C |
| 897 | C | C |
| 898 | C | C |
| 899 | A | B |
| 900 | C | C |

TABLE 490

| Example No. | 1a | 1b |
| --- | --- | --- |
| 901 | C | C |
| 902 | C | C |
| 903 | C | C |
| 904 | B | C |
| 905 | C | C |
| 906 | C | C |
| 907 | C | C |

TABLE 490-continued

| Example No. | 1a | 1b |
| --- | --- | --- |
| 908 | C | C |
| 909 | B | C |
| 910 | C | C |
| 911 | C | C |
| 912 | C | C |
| 913 | C | C |
| 914 | C | C |
| 915 | C | C |
| 916 | C | C |
| 917 | C | C |
| 918 | C | C |
| 919 | C | C |
| 920 | B | C |
| 921 | B | C |
| 922 | C | C |
| 923 | B | B |
| 924 | B | B |
| 925 | C | C |
| 926 | C | C |
| 927 | C | C |
| 928 | C | C |
| 929 | C | C |
| 930 | C | C |

TABLE 491

| Example No. | 1a | 1b |
| --- | --- | --- |
| 931 | C | C |
| 932 | C | C |
| 933 | C | C |
| 934 | C | C |
| 935 | C | C |
| 936 | A | A |
| 937 | C | C |
| 938 | B | C |
| 939 | C | C |
| 940 | C | C |
| 941 | C | C |
| 942 | C | C |
| 943 | C | C |
| 944 | C | C |
| 945 | C | C |
| 946 | C | C |
| 947 | C | C |
| 948 | C | C |
| 949 | C | C |
| 950 | C | C |
| 951 | C | C |
| 952 | C | C |
| 953 | C | C |
| 954 | C | C |
| 955 | C | C |
| 956 | C | C |
| 957 | C | C |
| 958 | C | C |
| 959 | C | C |
| 960 | C | C |

TABLE 492

| Example No. | 1a | 1b |
| --- | --- | --- |
| 961 | C | C |
| 962 | C | C |
| 963 | C | C |
| 964 | C | C |
| 965 | C | C |
| 966 | C | C |
| 967 | C | C |

TABLE 492-continued

| Example No. | 1a | 1b |
|---|---|---|
| 968 | C | C |
| 969 | C | C |
| 970 | C | C |
| 971 | C | C |
| 972 | C | C |
| 973 | C | C |
| 974 | A | A |
| 975 | C | C |
| 976 | C | C |
| 977 | C | C |
| 978 | C | C |
| 979 | C | C |
| 980 | C | C |
| 981 | C | C |
| 982 | C | C |
| 983 | C | C |
| 984 | C | C |
| 985 | C | C |
| 986 | C | C |
| 987 | C | C |
| 988 | A | A |
| 989 | C | C |
| 990 | C | C |

TABLE 493

| Example No. | 1a | 1b |
|---|---|---|
| 991 | C | C |
| 992 | C | C |
| 993 | A | A |
| 994 | C | C |
| 995 | C | C |
| 996 | C | C |
| 997 | C | C |
| 998 | C | C |
| 999 | C | C |
| 1000 | C | C |
| 1001 | C | C |
| 1002 | C | C |
| 1003 | C | C |
| 1004 | C | C |
| 1005 | C | C |
| 1006 | C | C |
| 1007 | C | C |
| 1008 | C | C |
| 1009 | C | C |
| 1010 | C | C |
| 1011 | C | C |
| 1012 | C | C |
| 1013 | C | C |
| 1014 | C | C |
| 1015 | C | C |
| 1016 | C | C |
| 1017 | C | C |
| 1018 | C | C |
| 1019 | C | C |
| 1020 | C | C |

TABLE 494

| Example No. | 1a | 1b |
|---|---|---|
| 1021 | C | C |
| 1022 | B | B |
| 1023 | C | C |
| 1024 | C | C |
| 1025 | C | C |
| 1026 | C | C |
| 1027 | C | C |

TABLE 494-continued

| Example No. | 1a | 1b |
|---|---|---|
| 1028 | C | C |
| 1029 | B | C |
| 1030 | C | C |
| 1031 | B | B |
| 1032 | C | C |
| 1033 | C | C |
| 1034 | C | C |
| 1035 | C | C |
| 1036 | C | C |
| 1037 | C | C |
| 1038 | B | B |
| 1039 | C | C |
| 1040 | C | C |
| 1041 | C | C |
| 1042 | C | C |
| 1043 | C | C |
| 1044 | C | C |
| 1045 | C | C |
| 1046 | C | C |
| 1047 | C | C |
| 1048 | C | C |
| 1049 | C | C |
| 1050 | B | B |

TABLE 495

| Example No. | 1a | 1b |
|---|---|---|
| 1051 | C | C |
| 1052 | C | C |
| 1053 | C | C |
| 1054 | C | C |
| 1055 | C | C |
| 1056 | C | C |
| 1057 | C | C |
| 1058 | C | C |
| 1059 | C | C |
| 1060 | C | C |
| 1061 | C | C |
| 1062 | C | C |
| 1063 | C | C |
| 1064 | C | C |
| 1065 | C | C |
| 1066 | C | C |
| 1067 | C | C |
| 1068 | C | C |
| 1069 | C | C |
| 1070 | C | C |
| 1071 | C | C |
| 1072 | C | C |
| 1073 | C | C |
| 1074 | C | C |
| 1075 | C | C |
| 1076 | C | C |
| 1077 | C | C |
| 1078 | C | C |
| 1079 | C | C |
| 1080 | C | C |

TABLE 496

| Example No. | 1a | 1b |
|---|---|---|
| 1081 | C | C |
| 1082 | C | C |
| 1083 | C | C |
| 1084 | C | C |
| 1085 | C | C |
| 1086 | C | C |
| 1087 | C | C |

TABLE 496-continued

| Example No. | 1a | 1b |
|---|---|---|
| 1088 | C | C |
| 1089 | C | C |
| 1090 | C | C |
| 1091 | C | C |
| 1092 | B | C |
| 1093 | C | C |
| 1094 | B | B |
| 1095 | B | B |
| 1096 | C | C |
| 1097 | B | B |
| 1098 | C | C |
| 1099 | C | C |
| 1100 | C | C |
| 1101 | C | C |
| 1102 | C | C |
| 1103 | B | B |
| 1104 | C | C |
| 1105 | B | C |
| 1106 | C | C |
| 1107 | B | C |
| 1108 | B | C |
| 1109 | C | C |
| 1110 | C | C |

TABLE 497

| Example No. | 1a | 1b |
|---|---|---|
| 1111 | C | C |
| 1112 | C | C |
| 1113 | C | C |
| 1114 | C | C |
| 1115 | B | A |
| 1116 | B | B |
| 1117 | A | A |
| 1121 | C | C |
| 1122 | C | C |
| 1123 | C | C |

Formulation Example is given in the following. This example is merely for the purpose of exemplification and does not limit the invention.

Formulation Example

| (a) compound of Example 1 | 10 g |
|---|---|
| (b) lactose | 50 g |
| (c) corn starch | 15 g |
| (d) sodium carboxymethylcellulose | 44 g |
| (e) magnesium stearate | 1 g |

The entire amounts of (a), (b) and (c) and 30 g of (d) are kneaded with water, dried in vacuo and granulated. The obtained granules are mixed with 14 g of (d) and 1 g of (e) and processed into tablets with a tableting machine to give 1000 tablets each containing 10 mg of (a).

INDUSTRIAL APPLICABILITY

As is evident from the above-mentioned results, the compound of the present invention shows a high inhibitory activity against HCV polymerase.

Therefore, the compound of the present invention can provide a pharmaceutical agent effective for the prophylaxis or treatment of hepatitis C, based on the anti-HCV effect afforded by the HCV polymerase inhibitory activity. When used concurrently with a different anti-HCV agent, such as interferon, and/or an anti-inflammatory agent and the like, it can provide a pharmaceutical agent more effective for the prophylaxis or treatment of hepatitis C. Its high inhibitory activity specific to HCV polymerase suggests the possibility of the compound being a pharmaceutical agent with slight side effects, which can be used safely for humans.

sequence listing free text
SEQ ID NO: 1: artificial HCV polymerase derived from HCV BK strain (type 1a)

This application is based on a patent application No. 2006-115008 filed in Japan, the contents of which are hereby incorporated by reference.

The invention claimed is:

1. A compound represented by the following formula [I-B] or a pharmaceutically acceptable salt thereof, or a solvate thereof:

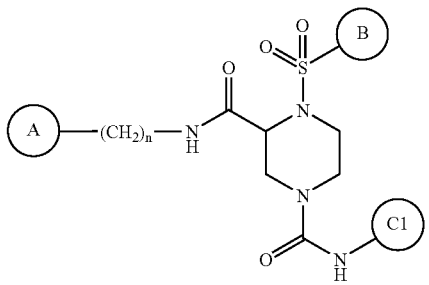

wherein
  ring A is
  a $C_{3-12}$ carbon ring group optionally substituted by 1 to 5 substituents selected from the following group A, or
  a heterocyclic group optionally substituted by 1 to 5 substituents selected from the following group A
  (wherein the heterocyclic group has, besides carbon atom, 1 to 6 hetero atoms selected from nitrogen atom, oxygen atom and sulfur atom),
  n is an integer of 1 to 6,
  ring B is
  a $C_{3-12}$ carbon ring group optionally substituted by 1 to 5 substituents selected from the following group A, or
  a heterocyclic group optionally substituted by 1 to 5 substituents selected from the following group A
  (wherein the heterocyclic group has, besides carbon atom, 1 to 6 hetero atoms selected from nitrogen atom, oxygen atom and sulfur atom),
  ring C1 is a heterocyclic group optionally substituted by 1 to 5 substituents selected from group A (wherein the heterocyclic group has, besides carbon atom, 1 to 6 hetero atoms selected from nitrogen atom, oxygen atom and sulfur atom
group A:
halogen atom, nitro group, cyano group,
—$OR^{a1}$,
—$SR^{a2}$,
—$NR^{a3}R^{a4}$,
—$NHCOR^{a5}$,
—$NHSO_2R^{a14}$,
—$COOR^{a6}$,
—$CONR^{a7}R^{a8}$,
—$SO_2NR^{a9}R^{a10}$,
—$SO_2NHCOR^{a15}$,
—$COR^{a11}$,
—$SO_2R^{a12}$,
—$CONHSO_2R^{a13}$,
—$COCOOR^{a16}$,
—$COCONR^{a17}R^{a18}$,
—$CONR^{a19}(OR^{a20})$,
—$SF_5$,
(wherein $R^{a1}$ to $R^{a20}$ are the same or different and each is a
  hydrogen atom,
  a $C_{1-10}$ alkyl group optionally substituted by 1 to 5 substituents selected from the following group B,
  a $C_{3-12}$ carbon ring group optionally substituted by 1 to 5 substituents selected from the following group C,
  a heterocyclic group optionally substituted by 1 to 5 substituents selected from the following group C
  (wherein the heterocyclic group has, besides carbon atom, 1 to 6 hetero atoms selected from nitrogen atom, oxygen atom and sulfur atom), or
  a $C_{6-12}$ aryl-$C_{1-4}$ alkyl group optionally substituted by 1 to 5 substituents selected from the following group C),
  a $C_{1-10}$ alkyl group optionally substituted by 1 to 5 substituents selected from the following group B,
  a $C_{2-10}$ alkynyl group optionally substituted by 1 to 5 substituents selected from the following group B,
  a $C_{3-12}$ carbon ring group optionally substituted by 1 to 5 substituents selected from the following group C,
  a heterocyclic group optionally substituted by 1 to 5 substituents selected from the following group C
  (wherein the heterocyclic group has, besides carbon atom, 1 to 6 hetero atoms selected from nitrogen atom, oxygen atom and sulfur atom),
  a $C_{6-12}$ aryl-$C_{1-4}$ alkyl group optionally substituted by 1 to 5 substituents selected from the following group C,
  a heterocyclyl-$C_{1-4}$ alkyl group optionally substituted by 1 to 5 substituents selected from the following group C
  (wherein the heterocyclyl moiety has, besides carbon atom, 1 to 6 hetero atoms selected from nitrogen atom, oxygen atom and sulfur atom), and
  a $C_{3-10}$ cycloalkyl-$C_{1-4}$ alkyl group optionally substituted by 1 to 5 substituents selected from the following group C,
group B:
halogen atom, cyano group, hydroxyl group,
$C_{1-4}$ alkoxy group,
amino group,
$C_{1-4}$ alkylamino group,
di($C_{1-4}$ alkyl)amino group,
carboxyl group,
$C_{1-4}$ alkoxy-carbonyl group,
carbamoyl group,
$C_{1-4}$ alkylamino-carbonyl group,
di($C_{1-4}$ alkyl)amino-carbonyl group,
heterocyclyl-carbonyl group, and
tri($C_{1-4}$ alkyl)ammoniumyl group
(wherein the heterocyclyl moiety has, besides carbon atom, 1 to 6 hetero atoms selected from nitrogen atom, oxygen atom and sulfur atom), group C:
halogen atom, cyano group, hydroxyl group,
carboxyl group,
$C_{1-4}$ alkyl group,
halogeno $C_{1-4}$ alkyl group,
hydroxy $C_{1-4}$ alkyl group,
carboxy $C_{1-4}$ alkyl group,
$C_{1-4}$ alkoxy $C_{1-4}$ alkyl group,
$C_{1-4}$ alkoxy group, and
carboxy $C_{1-4}$ alkoxy group.

2. A compound represented by the following formula [I-C] or a pharmaceutically acceptable salt thereof, or a solvate thereof:

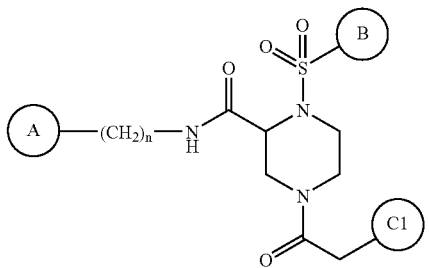

wherein
ring A is
a $C_{3-12}$ carbon ring group optionally substituted by 1 to 5 substituents selected from the following group A, or
a heterocyclic group optionally substituted by 1 to 5 substituents selected from the following group A
(wherein the heterocyclic group has, besides carbon atom, 1 to 6 hetero atoms selected from nitrogen atom, oxygen atom and sulfur atom),
n is an integer of 1 to 6,
ring B is
a $C_{3-12}$ carbon ring group optionally substituted by 1 to 5 substituents selected from the following group A, or
a heterocyclic group optionally substituted by 1 to 5 substituents selected from the following group A
(wherein the heterocyclic group has, besides carbon atom, 1 to 6 hetero atoms selected from nitrogen atom, oxygen atom and sulfur atom), and
ring C1 is a heterocyclic group optionally substituted by 1 to 5 substituents selected from group A (wherein the heterocyclic group has, besides carbon atom, 1 to 6 hetero atoms selected from nitrogen atom, oxygen atom and sulfur atom),
group A:
halogen atom, nitro group, cyano group,
—$OR^{a1}$,
—$SR^{a2}$,
—$NR^{a3}R^{a4}$,
—$NHCOR^{a5}$,
—$NHSO_2R^{a14}$,
—$COOR^{a6}$,
—$CONR^{a7}R^{a8}$,
—$SO_2NR^{a9}R^{a10}$,
—$SO_2NHCOR^{a15}$,
—$COR^{a11}$,
—$SO_2R^{a12}$,
—$CONHSO_2R^{a13}$,
—$COCOOR^{a16}$,
—$COCONR^{a17}R^{a18}$,
—$CONR^{a19}(OR^{a20})$,
—$SF_5$,
(wherein $R^{a1}$ to $R^{a20}$ are the same or different and each is
a hydrogen atom,
a $C_{1-10}$ alkyl group optionally substituted by 1 to 5 substituents selected from the following group B,
a $C_{3-12}$ carbon ring group optionally substituted by 1 to 5 substituents selected from the following group C,
a heterocyclic group optionally substituted by 1 to 5 substituents selected from the following group C
(wherein the heterocyclic group has, besides carbon atom, 1 to 6 hetero atoms selected from nitrogen atom, oxygen atom and sulfur atom), or
a $C_{6-12}$ aryl-$C_{1-4}$ alkyl group optionally substituted by 1 to 5 substituents selected from the following group C),
a $C_{1-10}$ alkyl group optionally substituted by 1 to 5 substituents selected from the following group B,
a $C_{2-10}$ alkynyl group optionally substituted by 1 to 5 substituents selected from the following group B,
a $C_{3-12}$ carbon ring group optionally substituted by 1 to 5 substituents selected from the following group C,
a heterocyclic group optionally substituted by 1 to 5 substituents selected from the following group C
(wherein the heterocyclic group has, besides carbon atom, 1 to 6 hetero atoms selected from nitrogen atom, oxygen atom and sulfur atom),
a $C_{6-12}$ aryl-$C_{1-4}$ alkyl group optionally substituted by 1 to 5 substituents selected from the following group C,
a heterocyclyl-$C_{1-4}$ alkyl group optionally substituted by 1 to 5 substituents selected from the following group C
(wherein the heterocyclyl moiety has, besides carbon atom, 1 to 6 hetero atoms selected from nitrogen atom, oxygen atom and sulfur atom), and
a $C_{3-10}$ cycloalkyl-$C_{1-4}$ alkyl group optionally substituted by 1 to 5 substituents selected from the following group C,
group B:
halogen atom, cyano group, hydroxyl group,
$C_{1-4}$alkoxy group,
amino group,
$C_{1-4}$ alkylamino group,
di($C_{1-4}$ alkyl)amino group,
carboxyl group,
$C_{1-4}$ alkoxy-carbonyl group,
carbamoyl group,
$C_{1-4}$ alkylamino-carbonyl group,
di($C_{1-4}$ alkyl)amino-carbonyl group,
heterocyclyl-carbonyl group, and
tri($C_{1-4}$ alkyl)ammoniumyl group
(wherein the heterocyclyl moiety has, besides carbon atom, 1 to 6 hetero atoms selected from nitrogen atom, oxygen atom and sulfur atom),
group C:
halogen atom, cyano group, hydroxyl group,
carboxyl group,
$C_{1-4}$ alkyl group,
halogeno $C_{1-4}$ alkyl group,
hydroxy $C_{1-4}$ alkyl group,
carboxy $C_{1-4}$ alkyl group,
$C_{1-4}$ alkoxy $C_{1-4}$ alkyl group,
$C_{1-4}$ alkoxy group, and
carboxy $C_{1-4}$ alkoxy group.

3. A compound represented by the following formula [I-D1] or a pharmaceutically acceptable salt thereof, or a solvate thereof:

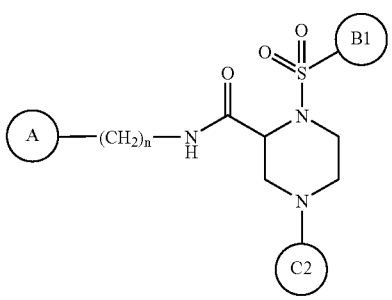

[I-D1]

wherein
ring A is
a $C_{3-12}$ carbon ring group optionally substituted by 1 to 5 substituents selected from the following group A, or
a heterocyclic group optionally substituted by 1 to 5 substituents selected from the following group A
(wherein the heterocyclic group has, besides carbon atom, 1 to 6 hetero atoms selected from nitrogen atom, oxygen atom and sulfur atom),
n is an integer of 1 to 6,
ring B is
a $C_{3-12}$ carbon ring group optionally substituted by 1 to 5 substituents selected from the following group A, or
a heterocyclic group optionally substituted by 1 to 5 substituents selected from the following group A
(wherein the heterocyclic group has, besides carbon atom, 1 to 6 hetero atoms selected from nitrogen atom, oxygen atom and sulfur atom),
ring B1 is a phenyl group optionally substituted by 1 to 5 substituents selected from group A, and
ring C2 is a heterocyclic group optionally substituted by 1 to 5 substituents selected from the following group A'
(wherein the heterocyclic group has, besides carbon atom, 1 to 6 hetero atoms selected from nitrogen atom, oxygen atom and sulfur atom),
group A':
halogen atom, nitro group, cyano group,
—$OR^{a1}$,
—$SR^{a2}$,
—$NR^{a3}R^{a4}$,
—$NHCOR^{a5}$,
—$NHSO_2R^{a14}$,
—$COOR^{a6}$,
—$CONR^{a7}R^{a8}$,
—$SO_2NR^{a9}R^{a10}$,
—$SO_2NHCOR^{a15}$,
—$COR^{a11}$,
—$SO_2R^{a12}$,
—$CONHSO_2R^{a13}$,
—$COCOOR^{a16}$,
—$COCONR^{a17}R^{a18}$,
—$CONR^{a19}(OR^{a20})$,
—$SF_5$,
(wherein $R^{a1}$ to $R^{a20}$ are the same or different and each is a hydrogen atom,
a $C_{1-10}$ alkyl group optionally substituted by 1 to 5 substituents selected from group B,
a $C_{3-12}$ carbon ring group optionally substituted by 1 to 5 substituents selected from group C,
a heterocyclic group optionally substituted by 1 to 5 substituents selected from group C (wherein the heterocyclic group has, besides carbon atom, 1 to 6 hetero atoms selected from nitrogen atom, oxygen atom and sulfur atom), or
a $C_{6-12}$ aryl-$C_{1-4}$ alkyl group optionally substituted by 1 to 5 substituents selected from group C),
a $C_{1-10}$ alkyl group optionally substituted by 1 to 5 substituents selected from group B,
a $C_{2-10}$ alkynyl group optionally substituted by 1 to 5 substituents selected from group B,
a $C_{3-12}$ carbon ring group optionally substituted by 1 to 5 substituents selected from group C,
a $C_{6-12}$ aryl-$C_{1-4}$ alkyl group optionally substituted by 1 to 5 substituents selected from group C,
a heterocyclyl-$C_{1-4}$ alkyl group optionally substituted by 1 to 5 substituents selected from group C
(wherein the heterocyclyl moiety has, besides carbon atom, 1 to 6 hetero atoms selected from nitrogen atom, oxygen atom and sulfur atom), and
a $C_{3-10}$ cycloalkyl-$C_{1-4}$ alkyl group optionally substituted by 1 to 5 substituents selected from group C,
group A:
halogen atom, nitro group, cyano group,
—$OR^{a1}$,
—$SR^{a2}$,
—$NR^{a3}R^{a4}$,
—$NHCOR^{a5}$,
—$NHSO_2R^{a14}$,
—$COOR^{a6}$,
—$CONR^{a7}R^{a8}$,
—$SO_2NR^{a9}R^{a10}$,
—$SO_2NHCOR^{a15}$,
—$COR^{a11}$,
—$SO_2R^{a12}$,
—$CONHSO_2R^{a13}$,
—$COCOOR^{a16}$,
—$COCONR^{a17}R^{a18}$,
—$CONR^{a19}(OR^{a20})$,
—$SF_5$,
(wherein $R^{a1}$ to $R^{a20}$ are the same or different and each is
a hydrogen atom,
a $C_{1-10}$ alkyl group optionally substituted by 1 to 5 substituents selected from the following group B,
a $C_{3-12}$ carbon ring group optionally substituted by 1 to 5 substituents selected from the following group C,
a heterocyclic group optionally substituted by 1 to 5 substituents selected from the following group C
(wherein the heterocyclic group has, besides carbon atom, 1 to 6 hetero atoms selected from nitrogen atom, oxygen atom and sulfur atom), or
a $C_{6-12}$ aryl-$C_{1-4}$ alkyl group optionally substituted by 1 to 5 substituents selected from the following group C),
a $C_{1-10}$ alkyl group optionally substituted by 1 to 5 substituents selected from the following group B,
a $C_{2-10}$ alkynyl group optionally substituted by 1 to 5 substituents selected from the following group B,
a $C_{3-12}$ carbon ring group optionally substituted by 1 to 5 substituents selected from the following group C,
a heterocyclic group optionally substituted by 1 to 5 substituents selected from the following group C
(wherein the heterocyclic group has, besides carbon atom, 1 to 6 hetero atoms selected from nitrogen atom, oxygen atom and sulfur atom),
a $C_{6-12}$ aryl-$C_{1-4}$ alkyl group optionally substituted by 1 to 5 substituents selected from the following group C,
a heterocyclyl-$C_{1-4}$ alkyl group optionally substituted by 1 to 5 substituents selected from the following group C (wherein the heterocyclyl moiety has, besides carbon atom, 1 to 6 hetero atoms selected from nitrogen atom, oxygen atom and sulfur atom), and a $C_{3\text{-}10}$ cycloalkyl-$C_{1\text{-}4}$ alkyl group optionally substituted by 1 to 5 substituents selected from the following group C, group B:
halogen atom, cyano group, hydroxyl group,
$C_{1\text{-}4}$ alkoxy group,
amino group,
$C_{1\text{-}4}$ alkylamino group,
di($C_{1\text{-}4}$ alkyl)amino group,
carboxyl group,
$C_{1\text{-}4}$ alkoxy-carbonyl group,
carbamoyl group,
$C_{1\text{-}4}$ alkylamino-carbonyl group,
di($C_{1\text{-}4}$ alkyl)amino-carbonyl group
heterocyclyl-carbonyl group, and
tri($C_{1\text{-}4}$ alkyl)ammoniumyl group
(wherein the heterocyclyl moiety has, besides carbon atom, 1 to 6 hetero atoms selected from nitrogen atom, oxygen atom and sulfur atom), group C:
halogen atom, cyano group, hydroxyl group,
carboxyl group,
$C_{1\text{-}4}$ alkyl group,
halogeno $C_{1\text{-}4}$ alkyl group,
hydroxy $C_{1\text{-}4}$ alkyl group,
carboxy $C_{1\text{-}4}$ alkyl group,
$C_{1\text{-}4}$ alkoxy $C_{1\text{-}4}$ alkyl group,
$C_{1\text{-}4}$ alkoxy group, and
carboxy $C_{1\text{-}4}$ alkoxy group.

4. The compound of any one of claims 1 to 3, wherein ring A is a phenyl group optionally substituted by 1 to 5 substituents selected from group A, or a pharmaceutically acceptable salt thereof, or a solvate thereof.

5. The compound of any one of claims 1 to 3, wherein n is 1, or a pharmaceutically acceptable salt thereof, or a solvate thereof.

6. The compound of claim 1 or claim 2, wherein the ring B is a phenyl group optionally substituted by 1 to 5 substituents selected from group A, or a pharmaceutically acceptable salt thereof, or a solvate thereof.

7. The compound of claim 1 or claim 2, wherein the ring C1 is a heterocyclic group optionally substituted by 1 to 5 substituents selected from group A, and the heterocyclic group is selected from the group consisting of piperidinyl group, morpholinyl group, pyrrolidinyl group, piperazinyl group, thiazolyl group, isothiazolyl group, pyrazolyl group, imidazolyl group, triazolyl group, tetrazolyl group, oxazolyl group, isoxazolyl group, thiadiazolyl group, oxadiazolyl group, pyridyl group and pyrimidinyl group, or a pharmaceutically acceptable salt thereof, or a solvate thereof.

8. The compound of claim 1, wherein the ring C1 is a heterocyclic group optionally substituted by 1 to 5 substituents selected from group A, and the heterocyclic group is selected from the group consisting of thiazolyl group, isothiazolyl group, isoxazolyl group, thiadiazolyl group, oxadiazolyl group, pyrazolyl group, triazolyl group, tetrazolyl group, pyridyl group and pyrimidinyl group, or a pharmaceutically acceptable salt thereof, or a solvate thereof.

9. The compound of claim 2, wherein the ring C1 is a heterocyclic group optionally substituted by 1 to 5 substituents selected from group A, and the heterocyclic group is selected from the group consisting of piperidinyl group, morpholinyl group, pyrrolidinyl group, piperazinyl group, pyrazolyl group, imidazolyl group, triazolyl group, tetrazolyl group, isoxazolyl group, pyridyl group and pyrimidinyl group, or a pharmaceutically acceptable salt thereof, or a solvate thereof.

10. The compound of claim 3, wherein the ring C2 is a heterocyclic group optionally substituted by 1 to 5 substituents selected from group A', and the heterocyclic group is selected from the group consisting of imidazolinyl group, thiazolinyl group, oxazolinyl group, thienyl group, dioxopyrrolidinyl group, dioxopyrrolinyl group, oxopyrrolidinyl group, oxothiadiazolinyl group, tetrahydrobenzothiazolyl group, thiazolyl group, thiadiazolyl group, pyrazolyl group, imidazolyl group, triazolyl group, oxazolyl group, pyridyl group, pyrimidinyl group, pyrazinyl group, pyridazinyl group,
quinolyl group,
[1,5]naphthyridinyl group,
[1,6]naphthyridinyl group,
oxopiperidinyl group,
oxodihydropyridinyl group,
[1,2,4]triazolo[1,5-a]pyrimidinyl group,
benzimidazolyl group,
imidazo[4,5-c]pyridinyl group,
quinoxalinyl group,
pyrido[2,3-b]pyrazinyl group,
pyrido[3,4-b]pyrazinyl group,
pteridinyl group,
pyrazino[2,3-b]pyrazinyl group,
imidazo[4,5-b]pyrazinyl group,
2,2-dioxo-1,2,3,4-tetrahydropyrazino[2,3-c][1,2,6]thiadiazinyl group,
2-oxo-1,4-dihydropyrazino[2,3-d][1,3]oxazinyl group,
2-oxo-2,3-dihydroimidazo[4,5-b]pyrazinyl group,
[1,2,5]thiadiazolo[3,4-b]pyrazinyl group,
benzothiazolyl group,
4,5,6,7-tetrahydrobenzothiazolyl group,
thiazolo[5,4-b]pyridinyl group,
thiazolo[5,4-c]pyridinyl group,
thiazolo[4,5-d]pyrimidinyl group,
thiazolo[5,4-d]pyrimidinyl group,
thiazolo[4,5-d]pyridazinyl group,
thiazolo[4,5-b]pyrazinyl group,
thiazolo[4,5-d][1,2,3]triazinyl group,
5-oxo-4,5-dihydrothiazolo[5,4-b]pyridinyl group,
pyrazolo[3,4-d]thiazolyl group,
4,6-dioxo-5,6-dihydropyrrolo[3,4-d]thiazolyl group,
4,5,6,7-tetrahydrothiazolo[5,4-c]pyridinyl group,
4-oxo-4,5,6,7-tetrahydrothiazolo[5,4-c]pyridinyl group,
4-oxo-4,5-dihydrothiazolo[5,4-c]pyridinyl group,
7-oxo-6,7-dihydrothiazolo[4,5-d]pyrimidinyl group,
4-oxo-4,5-dihydrothiazolo[4,5-d]pyridazinyl group,
7-oxo-6,7-dihydrothiazolo[4,5-d]pyridazinyl group,
4,7-dioxo-4,5,6,7-tetrahydrothiazolo[4,5-d]pyridazinyl group,
4-oxo-3,4-dihydrothiazolo[4,5-d][1,2,3]triazinyl group,
5-oxo-[1,3,4]thiadiazolo[3,2-a]pyrimidinyl group,
7-oxo-[1,3,4]thiadiazolo[3,2-a]pyrimidinyl group,
4-oxo-[1,3,4]thiadiazolo[2,3-c][1,2,4]triazinyl group,
[1,2,4]triazolo[3,4-b][1,3,4]thiadiazolyl group, and
indenothiazolyl group, or a pharmaceutically acceptable salt thereof, or a solvate thereof.

11. The compound of claim 10, wherein the ring C2 is a thiazol-2-yl group optionally substituted by 1 to 5 substituents selected from group A', or a pharmaceutically acceptable salt thereof, or a solvate thereof.

12. The compound of claim 10, wherein the ring C2 is a heterocyclic group optionally substituted by 1 to 5 substituents selected from group A', and the heterocyclic group is selected from the group consisting of
benzothiazol-2-yl group,
4,5,6,7-tetrahydrobenzothiazol-2-yl group,
thiazolo[5,4-b]pyridin-2-yl group,
thiazolo[5,4-c]pyridin-2-yl group,
thiazolo[4,5-d]pyrimidin-2-yl group,
thiazolo[5,4-d]pyrimidin-2-yl group,
thiazolo[4,5-d]pyridazin-2-yl group,
thiazolo[4,5-b]pyrazin-2-yl group,
thiazolo[4,5-d][1,2,3]triazin-6-yl group,
5-oxo-4,5-dihydrothiazolo[5,4-b]pyridin-2-yl group,
1H-pyrazolo[3,4-d]thiazol-5-yl group,
4,6-dioxo-5,6-dihydro-4H-pyrrolo[3,4-d]thiazol-2-yl group,
4,5,6,7-tetrahydrothiazolo[5,4-c]pyridin-2-yl group,
4-oxo-4,5,6,7-tetrahydrothiazolo[5,4-c]pyridin-2-yl group,
4-oxo-4,5-dihydrothiazolo[5,4-c]pyridin-2-yl group,
7-oxo-6,7-dihydrothiazolo[4,5-d]pyrimidin-2-yl group,
4-oxo-4,5-dihydrothiazolo[4,5-d]pyridazin-2-yl group,
7-oxo-6,7-dihydrothiazolo[4,5-d]pyridazin-2-yl group,
4,7-dioxo-4,5,6,7-tetrahydrothiazolo[4,5-d]pyridazin-2-yl group,
4-oxo-3,4-dihydrothiazolo[4,5-d][1,2,3]triazin-6-yl group,
5-oxo-5H-[1,3,4]thiadiazolo[3,2-a]pyrimidin-2-yl group,
7-oxo-7H-[1,3,4]thiadiazolo[3,2-a]pyrimidin-2-yl group,
4-oxo-4H-[1,3,4]thiadiazolo[2,3-c][1,2,4]triazin-7-yl group,
[1,2,4]triazolo[3,4-b][1,3,4]thiadiazol-6-yl group, and
indenothiazolyl group, or a pharmaceutically acceptable salt thereof, or a solvate thereof.

13. The compound of claim 10, wherein the ring C2 is a pyrazin-2-yl group optionally substituted by 1 to 5 substituents selected from group A', or a pharmaceutically acceptable salt thereof, or a solvate thereof.

14. The compound of claim 10, wherein the ring C2 is a heterocyclic group optionally substituted by 1 to 5 substituents selected from group A', and the heterocyclic group is selected from the group consisting of
quinoxalin-2-yl group,
pyrido[2,3-b]pyrazin-2-yl group,
pyrido[2,3-b]pyrazin-3-yl group,
pyrido[3,4-b]pyrazin-2-yl group,
pteridin-6-yl group,
pteridin-7-yl group,
pyrazino[2,3-b]pyrazin-2-yl group,
1H-imidazo[4,5-b]pyrazin-5-yl group,
2,2-dioxo-1,2,3,4-tetrahydropyrazino[2,3-c][1,2,6]thiadiazin-7-yl group,
2-oxo-1,4-dihydro-2H-pyrazino[2,3-d][1,3]oxazin-7-yl group,
2-oxo-2,3-dihydro-1H-imidazo[4,5-b]pyrazin-5-yl group, and
[1,2,5]thiadiazolo[3,4-b]pyrazinyl group, or a pharmaceutically acceptable salt thereof, or a solvate thereof.

15. A pharmaceutical composition comprising a compound of any one of claims 1 to 3 or a pharmaceutically acceptable salt thereof, or a solvate thereof, and a pharmaceutically acceptable carrier.

16. A method for treating hepatitis C in a mammal, which method comprises administering an effective amount of a compound of any one of claims 1 to 3 or a pharmaceutically acceptable salt thereof, or a solvate thereof to a mammal with hepatitis C thereby treating hepatitis C in the mammal.

17. The method of claim 16 further comprising administering an effective amount of at least one pharmaceutical agent selected from the group consisting of a different antiviral agent, an antiinflammatory agent and an immunostimulant to the mammal.

18. The method of claim 16 further comprising administering an effective amount of interferon to the mammal.

19. A method for inhibiting HCV polymerase in a mammal, which comprises administering an effective amount of a compound of any one of claims 1 to 3 or a pharmaceutically acceptable salt thereof, or a solvate thereof to a mammal, thereby inhibiting HCV polymerase in the mammal.

20. The method of claim 19 further comprising administering an effective amount of at least one pharmaceutical agent selected from the group consisting of a different antiviral agent, an antiinflammatory agent and an immunostimulant to the mammal.

21. The method of claim 19 further comprising administering an effective amount of interferon to the mammal.

22. A compound having the structural formula

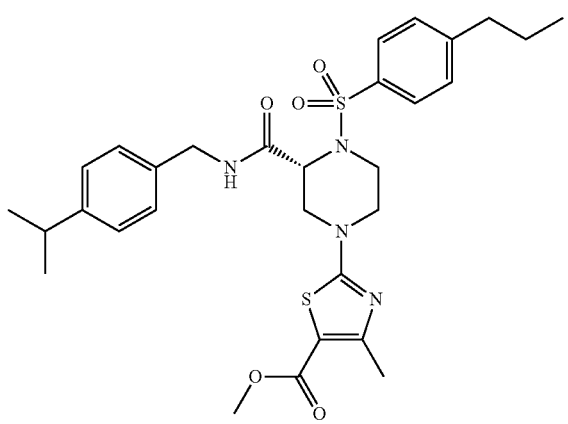

or a pharmaceutically acceptable salt thereof.

23. A compound having the structural formula

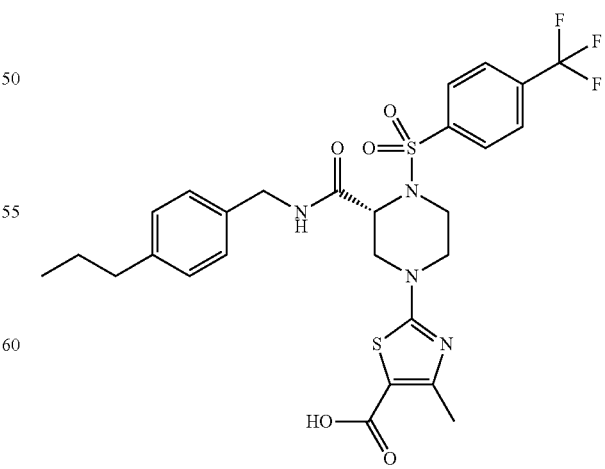

or a pharmaceutically acceptable salt thereof.

24. A compound having the structural formula

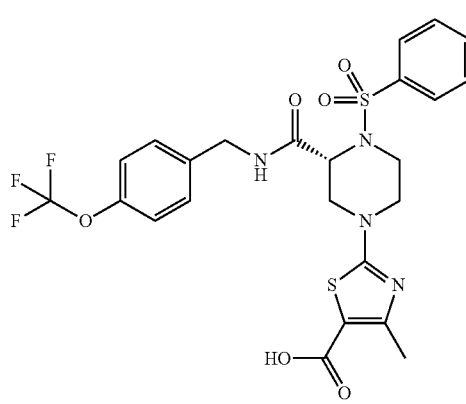

or a pharmaceutically acceptable salt thereof.

25. A compound having the structural formula

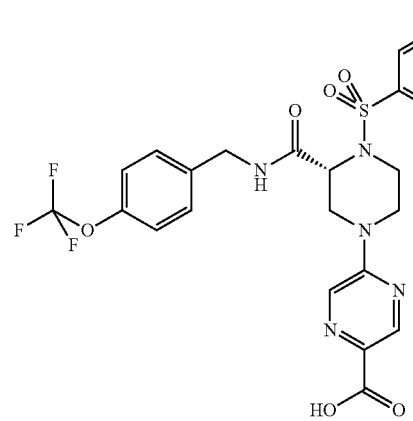

or a pharmaceutically acceptable salt thereof.

26. A compound having the structural formula

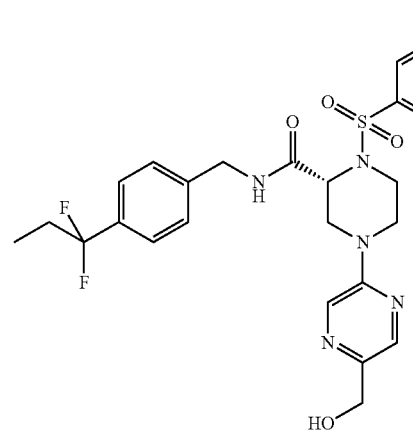

or a pharmaceutically acceptable salt thereof.

27. A compound having the structural formula

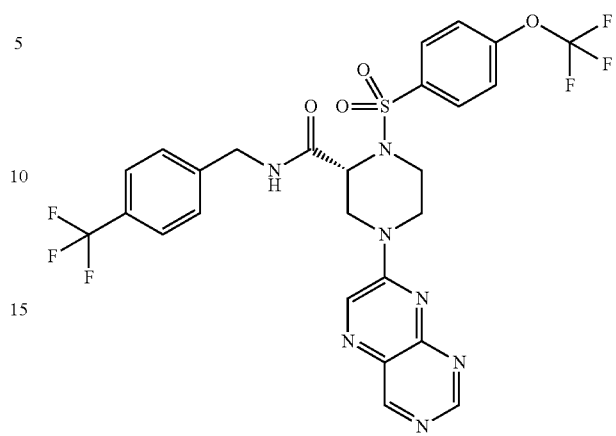

or a pharmaceutically acceptable salt thereof.

28. A compound having the structural formula

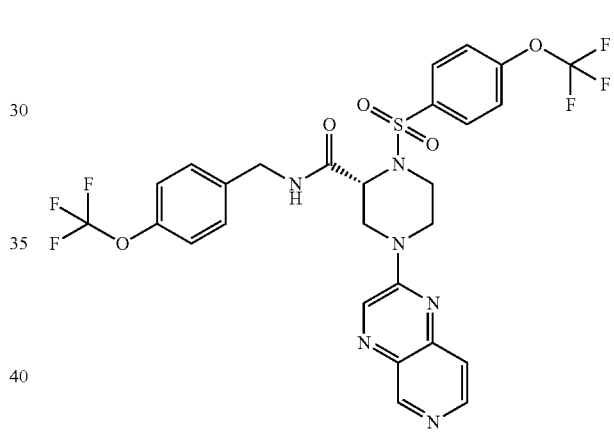

or a pharmaceutically acceptable salt thereof.

29. A compound having the structural formula

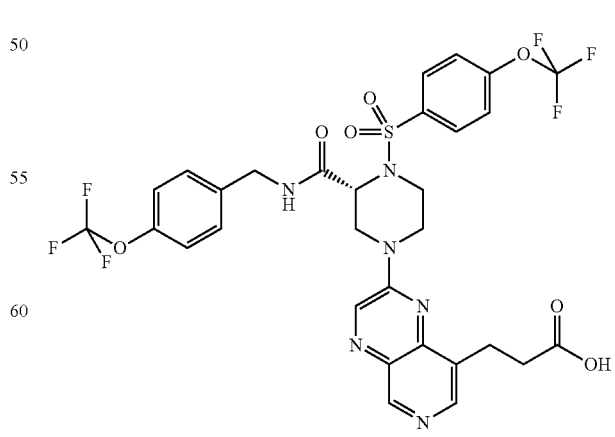

or a pharmaceutically acceptable salt thereof.

30. A compound having the structural formula

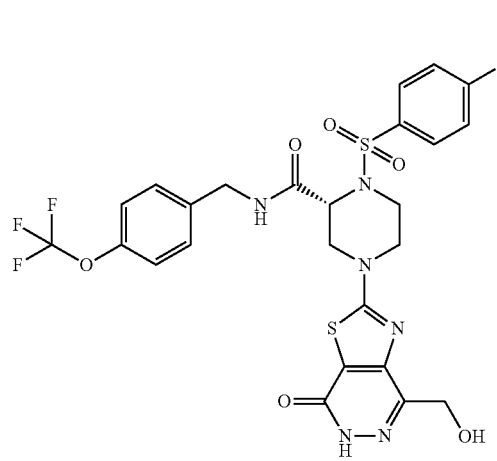

or a pharmaceutically acceptable salt thereof.

31. A compound having the structural formula

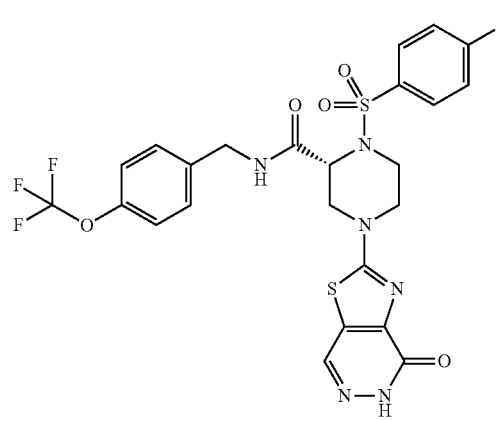

or a pharmaceutically acceptable salt thereof.

32. A compound having the structural formula

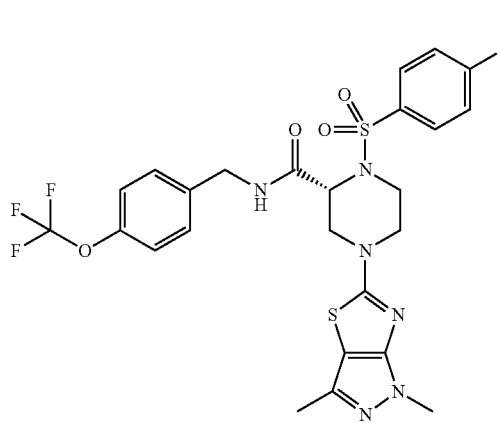

or a pharmaceutically acceptable salt thereof.

33. A compound having the structural formula

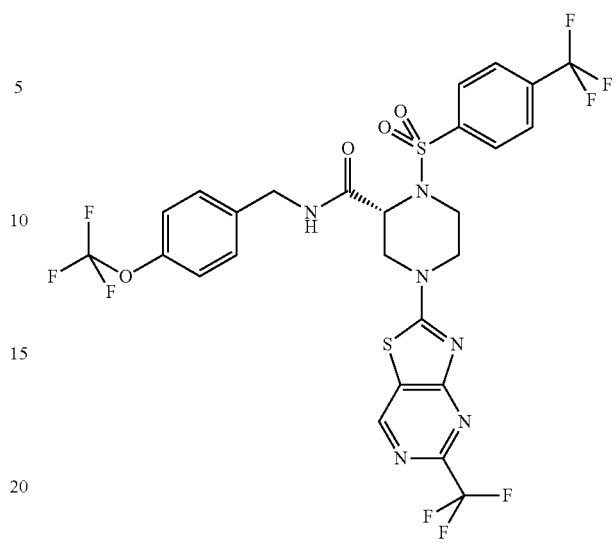

or a pharmaceutically acceptable salt thereof.

34. A compound having the structural formula

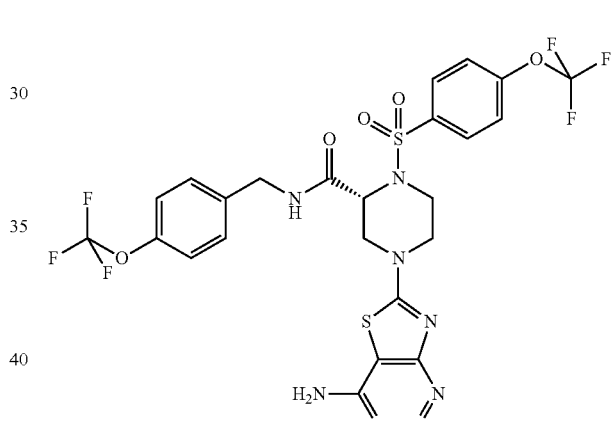

or a pharmaceutically acceptable salt thereof.

35. A compound having the structural formula

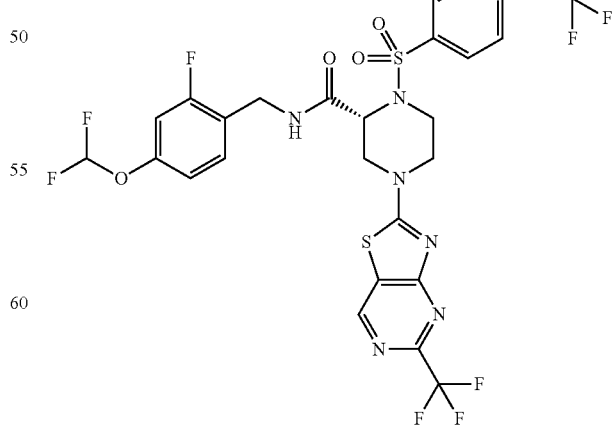

or a pharmaceutically acceptable salt thereof.

36. A compound having the structural formula

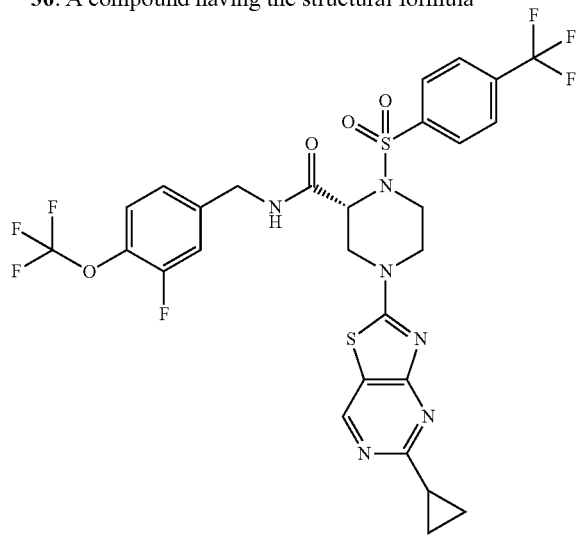

or a pharmaceutically acceptable salt thereof.

37. A pharmaceutical composition comprising a compound of any one of claims 22 to 36 or a pharmaceutically acceptable salt thereof and a pharmaceutically acceptable carrier.

38. A method for treating hepatitis C in a mammal, which method comprises administering an effective amount of a compound of any one of claims 22 to 36 or a pharmaceutically acceptable salt thereof to a mammal with hepatitis C, thereby treating hepatitis C in the mammal.

39. The method of claim 38 further comprising administering an effective amount of at least one pharmaceutical agent selected from the group consisting of a different antiviral agent, an antiinflammatory agent, and an immunostimulant to the mammal.

40. The method of claim 38 further comprising administering an effective amount of interferon to the mammal.

* * * * *

UNITED STATES PATENT AND TRADEMARK OFFICE
CERTIFICATE OF CORRECTION

| | | |
|---|---|---|
| PATENT NO. | : 8,017,612 B2 | Page 1 of 1 |
| APPLICATION NO. | : 11/736064 | |
| DATED | : September 13, 2011 | |
| INVENTOR(S) | : Abe et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1162 days.

Signed and Sealed this
Tenth Day of April, 2012

David J. Kappos
*Director of the United States Patent and Trademark Office*

SEQUENCE LISTING

```
<160> NUMBER OF SEQ ID NOS: 1

<210> SEQ ID NO 1
<211> LENGTH: 552
<212> TYPE: PRT
<213> ORGANISM: Artificial Sequence
<220> FEATURE:
<223> OTHER INFORMATION: Artificial HCV polymerase derived from HCV BK
      strain (1a type)

<400> SEQUENCE: 1

Ser Met Ser Tyr Ser Trp Thr Gly Ala Leu Ile Thr Pro Cys Ala Ala
1               5                   10                  15

Glu Glu Gln Lys Leu Pro Ile Asn Ala Leu Ser Asn Ser Leu Leu Arg
            20                  25                  30

His His Asn Leu Val Tyr Ser Thr Thr Ser Arg Ser Ala Cys Gln Arg
        35                  40                  45

Gln Lys Lys Val Thr Phe Asp Arg Leu Gln Val Leu Asp Ser His Tyr
    50                  55                  60

Gln Asp Val Leu Lys Glu Val Lys Ala Ala Ala Ser Lys Val Lys Ala
65                  70                  75                  80
```

```
Asn Leu Leu Ser Val Glu Glu Ala Cys Ser Leu Thr Pro Pro His Ser
                85                  90                  95

Ala Arg Ser Lys Phe Gly Tyr Gly Ala Lys Asp Val Arg Cys His Ala
            100                 105                 110

Arg Lys Ala Val Asn His Ile Asn Ser Val Trp Lys Asp Leu Leu Glu
        115                 120                 125

Asp Ser Val Thr Pro Ile Asp Thr Thr Ile Met Ala Lys Asn Glu Val
130                 135                 140

Phe Cys Val Gln Pro Glu Lys Gly Gly Arg Lys Pro Ala Arg Leu Ile
145                 150                 155                 160

Val Phe Pro Asp Leu Gly Val Arg Val Cys Glu Lys Met Ala Leu Tyr
                165                 170                 175

Asp Val Val Ser Lys Leu Pro Leu Ala Val Met Gly Ser Ser Tyr Gly
            180                 185                 190

Phe Gln Tyr Ser Pro Gly Gln Arg Val Glu Phe Leu Val Gln Ala Trp
        195                 200                 205

Lys Ser Lys Arg Thr Pro Met Gly Phe Ser Tyr Asp Thr Arg Cys Phe
    210                 215                 220

Asp Ser Thr Val Thr Glu Ser Asp Ile Arg Thr Glu Glu Ala Ile Tyr
225                 230                 235                 240

Gln Cys Cys Asp Leu Asp Pro Gln Ala Arg Val Ala Ile Lys Ser Leu
                245                 250                 255

Thr Glu Arg Leu Tyr Val Gly Gly Pro Leu Thr Asn Ser Arg Gly Glu
            260                 265                 270

Asn Cys Gly Tyr Arg Arg Cys Arg Ala Ser Gly Val Leu Thr Thr Ser
        275                 280                 285

Cys Gly Asn Thr Leu Thr Cys Tyr Ile Lys Ala Gln Ala Ala Cys Arg
    290                 295                 300

Ala Ala Gly Leu Gln Asp Cys Thr Met Leu Val Cys Gly Asp Asp Leu
305                 310                 315                 320

Val Val Ile Cys Glu Ser Ala Gly Val Gln Glu Asp Ala Ala Ser Leu
                325                 330                 335

Arg Ala Phe Thr Glu Ala Met Thr Arg Tyr Ser Ala Pro Pro Gly Asp
            340                 345                 350

Pro Pro Gln Pro Glu Tyr Asp Leu Glu Leu Ile Thr Ser Cys Ser Ser
        355                 360                 365

Asn Val Ser Val Ala His Asp Gly Ala Gly Lys Arg Val Tyr Tyr Leu
    370                 375                 380

Thr Arg Asp Pro Thr Thr Pro Leu Ala Arg Ala Ala Trp Glu Thr Ala
385                 390                 395                 400

Arg His Thr Pro Val Asn Ser Trp Leu Gly Asn Ile Ile Met Phe Ala
                405                 410                 415

Pro Thr Leu Trp Val Arg Met Ile Leu Leu Thr His Phe Phe Ser Val
            420                 425                 430

Leu Ile Ala Arg Asp Gln Leu Glu Gln Ala Leu Asp Cys Glu Ile Tyr
        435                 440                 445

Gly Ala Cys Tyr Ser Ile Glu Pro Leu Asp Leu Pro Pro Ile Ile Gln
    450                 455                 460

Arg Leu His Gly Leu Ser Ala Phe Ser Leu His Ser Tyr Ser Pro Gly
465                 470                 475                 480

Glu Ile Asn Arg Val Ala Ala Cys Leu Arg Lys Leu Gly Val Pro Pro
                485                 490                 495

Leu Arg Ala Trp Arg His Arg Ala Arg Ser Val Arg Ala Lys Leu Leu
```

-continued

```
                    500             505             510
Ser Arg Gly Gly Arg Ala Ala Ile Cys Gly Lys Tyr Leu Phe Asn Trp
        515                 520                 525

Ala Val Lys Thr Lys Leu Lys Leu Thr Pro Ile Ala Ala Ala Gly Gln
        530                 535                 540

Gly Ser His His His His His His
545             550
```